(12) United States Patent
Zhang et al.

(10) Patent No.: US 8,119,602 B2
(45) Date of Patent: Feb. 21, 2012

(54) ADMINISTRATION OF HCV PROTEASE INHIBITORS IN COMBINATION WITH FOOD TO IMPROVE BIOAVAILABILITY

(75) Inventors: Jenny Zhang, Cranbury, NJ (US); Samir K. Gupta, East Brunswick, NJ (US)

(73) Assignee: Schering Corporation, Kenilworth, NJ (US)

( * ) Notice: Subject to any disclaimer, the term of this patent is extended or adjusted under 35 U.S.C. 154(b) by 290 days.

(21) Appl. No.: 11/443,793

(22) Filed: May 31, 2006

(65) Prior Publication Data

US 2006/0281688 A1 Dec. 14, 2006

Related U.S. Application Data

(60) Provisional application No. 60/686,925, filed on Jun. 2, 2005.

(51) Int. Cl.
*A61K 38/05* (2006.01)

(52) U.S. Cl. .................. 514/20.3; 514/3.7; 424/85.4

(58) Field of Classification Search .................. None
See application file for complete search history.

(56) References Cited

U.S. PATENT DOCUMENTS

| | | | |
|---|---|---|---|
| 5,501,969 A | 3/1996 | Hastings et al. |
| 5,712,145 A | 1/1998 | Houghton et al. |
| 5,866,684 A | 2/1999 | Attwood et al. |
| 6,143,715 A | 11/2000 | Llinas-Burnet et al. |
| 6,265,380 B1 | 7/2001 | Tung et al. |
| 6,268,207 B1 | 7/2001 | Bailey |
| 6,323,180 B1 | 11/2001 | Llinas-Brunet et al. |
| 6,413,974 B1 | 7/2002 | Dumont et al. |
| 6,608,027 B1 | 8/2003 | Tsantrizos et al. |
| 6,617,309 B2 | 9/2003 | Tung et al. |
| 6,767,991 B1 | 7/2004 | Llinas-Brunet et al. |
| 6,800,434 B2 | 10/2004 | Saksena et al. |
| 6,894,072 B2 | 5/2005 | Arasappan et al. |
| 7,173,057 B2 | 2/2007 | Chen et al. |
| 7,186,747 B2 | 3/2007 | Arasappan et al. |
| 7,192,957 B2 | 3/2007 | Venkatraman et al. |
| 7,205,330 B2 | 4/2007 | Bogen et al. |
| 7,253,160 B2 | 8/2007 | Njoroge et al. |
| 2002/0010781 A1 | 1/2002 | Tuatini |
| 2002/0016294 A1 | 2/2002 | Venkatraman et al. |
| 2002/0068702 A1 | 6/2002 | Lim-Wilby et al. |
| 2002/0102235 A1 | 8/2002 | Arasappan et al. |
| 2002/0147139 A1 | 10/2002 | Zhu et al. |
| 2002/0160962 A1 | 10/2002 | Saksena et al. |
| 2003/0036501 A1 | 2/2003 | Saksena et al. |
| 2005/0020689 A1 | 1/2005 | Chen et al. |
| 2005/0059648 A1 | 3/2005 | Park et al. |
| 2005/0059800 A1 | 3/2005 | Sudhakar et al. |
| 2005/0085425 A1 | 4/2005 | Chen et al. |
| 2005/0119168 A1 | 6/2005 | Venkatraman et al. |
| 2005/0153900 A1 | 7/2005 | Velazquez et al. |
| 2005/0197301 A1 | 9/2005 | Njoroge et al. |
| 2005/0209164 A1 | 9/2005 | Bogen et al. |
| 2005/0272663 A1 | 12/2005 | Arasappan et al. |
| 2006/0046956 A1 | 3/2006 | Sannigrahi et al. |
| 2006/0105978 A1 | 5/2006 | Chu et al. |
| 2006/0252698 A1 | 11/2006 | Malcolm |
| 2006/0276404 A1 | 12/2006 | Ghosal et al. |
| 2006/0276405 A1 | 12/2006 | Albrecht |
| 2006/0276406 A1 | 12/2006 | Gupta et al. |
| 2006/0276407 A1 | 12/2006 | Albrecht et al. |
| 2006/0281689 A1 | 12/2006 | Malcolm |
| 2006/0287248 A1 | 12/2006 | Malcolm |
| 2007/0004635 A1 | 1/2007 | Albrecht et al. |
| 2007/0004653 A1 | 1/2007 | Arosio et al. |
| 2007/0010431 A1 | 1/2007 | Malcolm et al. |
| 2007/0021351 A1 | 1/2007 | White et al. |
| 2007/0042968 A1 | 2/2007 | Bennett et al. |
| 2007/0207949 A1 | 9/2007 | Ghosal et al. |
| 2007/0232527 A1 | 10/2007 | Ghosal et al. |
| 2007/0237818 A1 | 10/2007 | Malcolm et al. |

FOREIGN PATENT DOCUMENTS

| | | |
|---|---|---|
| EP | 0 423 358 A1 | 4/1991 |
| EP | 0 603 873 A1 | 6/1994 |
| EP | 0 381 216 B1 | 12/1995 |
| WO | WO 89/04669 A1 | 6/1989 |
| WO | WO 94/04172 A1 | 3/1994 |
| WO | WO 98/14181 A1 | 4/1998 |
| WO | WO 98/17679 A1 | 4/1998 |
| WO | WO 98/22496 A2 | 5/1998 |
| WO | WO 99/07734 A2 | 2/1999 |
| WO | WO 00/59929 A1 | 10/2000 |

(Continued)

OTHER PUBLICATIONS

Asselah et al., "BILN 2061: A Major Step Toward New Therapeutic Strategies in Hepatitis C", *Journal of Hepatology*, 41(1):178-181 (2004).

Baldwin et al., "Crystal structures of native and inhibited forms of human cathepsin D: implications for lysosomal targeting and drug design," *Proc Natl Acad Sci*, 90(14):6796-6800 (1993).

Berenguer and Wright, "Hepatitis B and C viruses: molecular identification and targeted antiviral therapies," *Proc Assoc Am Physicians*, 110(2):98-112 (1998).

(Continued)

*Primary Examiner* — Christopher R. Tate
*Assistant Examiner* — Roy Teller
(74) *Attorney, Agent, or Firm* — Julie M. Lake; Sheldon O. Heber

(57) ABSTRACT

Methods of treating, preventing or ameliorating one or more symptoms of hepatitis C in a subject comprising the step of administering at least one HCV protease inhibitor in combination with food are provided. Also provided are methods of increasing bioavailability of an HCV protease inhibitor and methods of increasing serum levels of an HCV protease inhibitor in a subject. All methods comprise adminstering at least one HCV protease inhibitor in combination with food, the at least one HCV protease inhibitor selected from the group consisting of compounds of Formulae I-XXVI, described herein. Administration of compounds of the present invention in combination with food provides improved bioavailability and increased peak serum levels of the compounds as compared to administration without food.

9 Claims, 1 Drawing Sheet

FOREIGN PATENT DOCUMENTS

| | | |
|---|---|---|
| WO | WO 02/08187 A1 | 1/2002 |
| WO | WO 02/08244 A2 | 1/2002 |
| WO | WO 02/08256 A2 | 1/2002 |
| WO | WO 02/18369 A2 | 3/2002 |
| WO | WO 03/062265 * | 7/2003 |
| WO | WO 03/062265 A2 | 7/2003 |
| WO | WO 03/066103 A1 | 8/2003 |
| WO | WO 2004/073747 A1 | 2/2004 |
| WO | WO 2004/073747 * | 9/2004 |
| WO | WO 2005/007681 A2 | 1/2005 |
| WO | WO 2005/107745 * | 11/2005 |
| WO | WO 2005/107745 A1 | 11/2005 |
| WO | WO 2005/123076 A2 | 12/2005 |

OTHER PUBLICATIONS

Bossard et al., "Proteolytic activity of human osteoclast cathepsin K," *J Biol Chem*, 271(21):12517-12524 (1996).

Bromme et al., "Human cathepsin O2, a matrix protein-degrading cysteine protease expressed in osteoclasts," *J. Biol. Chem*, 271(4):2126-2132 (1996).

Colella and Casey, "Decreased activity of cathepsins L+B and decreased invasive ability of PC3 prostate cancer cells," *Biotech Histochem*, 78(2):101-108 (2003).

Dimasi et al., "Characterization of engineered hepatitis C virus NS3 protease inhibitors affinity selected from human pancreatic secretory trypsin inhibitor and minibody repertoires," *J Virol*, 71(110):7461-7469 (1997).

Drake et al., "Cathepsin K, but not cathepsins B, L, or S, is abundantly expressed in human osteoclasts," *J Biol Chem*, 271(21):12511-12516 (1996).

Elzouki et al., "Serine protease inhibitors in patients with chronic viral hepatitis," *J Hepat*, 27(1):42-48 (1997).

Failla et al., "Redesigning the substrate specificity of the hepatitis C virus NS3 protease," *Fold Des*, 1(1):35-42 (1996).

Friedrich et al., "Cathepsins B, H, L and cysteine protease inhibitors in malignant prostate cell lines, primary cultured prostatic cells and prostatic tissue," *Eur J Cancer*, 35(1):138-144 (1999).

Frohlich et al., "Cathepsins in basal cell carcinomas: activity, immunoreactivity and mRNA staining of cathepsins B, D, H and L," *Arch Dermatol Res*, 295(10):411-421 (2004).

Hoofnagle and Di Bisceglie, "The treatment of chronic viral hepatitis," *N Engl J Med*, 336(5):347-356 (1997).

Huang et al., "Recent Development of Therapeutics for Chronic HCV Infection", *Antiviral Research*, 71(2-3):351-362 (2006).

Ingallinella et al., "Potent peptide inhibitors of human hepatitis C virus NS3 protease are obtained by optimizing the cleavage products," *Biochemistry*, 37(25):8906-8914 (1998).

Isahara et al., "Regulation of a novel pathway for cell death by lysosomal aspartic and cysteine proteinases," *Neuroscience*, 91(1):233-249 (1999).

Jones et al., "Cystatin A expression reduces bile salt-induced apoptosis in a rat hepatoma cell line," *Am J Physiol*, 275(4Pt1):G723-730 (1998).

Katunuma et al., "Structure-based design of specific cathepsin inhibitors and their application to protection of bone metastases of cancer cells," *Arch Biochem Biophys*, 397(2):305-311 (2002).

Keyszer et al., "Comparative analysis of cathepsin L, cathepsin D, and collagenase messenger RNA expression in synovial tissues of patients with rheumatoid arthritis and osteoarthritis, by in situ hybridization," *Arthritis Rheum*, 38(7):976-984 (1995).

Kolykhalov et al., "Specificity of the hepatitis C virus NS3 serine protease: effects of substitutions at the 3/4A, 4A/4B, 4B/5A, and 5A/5B cleavage sites on polyprotein processing," *J Virol*, 68(11):7525-7533 (1994).

Komoda et al., "Substrate requirements of hepatitis C virus serine proteinase for intermolecular polypeptide cleavage in *Escherichia coli*," *J Virol*, 68(11):7351-7357 (1994).

KOS and LAH, "Cysteine proteinases and their endogenous inhibitors: target proteins for prognosis, diagnosis and therapy in cancer (review)," *Oncol Rep*, 5(6):1349-136I (1998).

Krueger et al., "Cathepsin L antisense oligonucleotides in a human osteosarcoma cell line: Effects on the invasive phenotype," *Cancer Gene Ther*, 8(7):522-528 (2001).

Landro et al., "Mechanistic role of an NS4A peptide cofactor with the truncated NS3 protease of hepatitis C Virus: Elucidation of the NS4A stimulatory effect via kinetic analysis and inhibitor mapping," *Biochemistry*, 36(31):9340-9348 (1997).

Levicar et al., "Selective suppression of cathepsin L by antisense cDNA impairs human brain tumor cell invasion in vitro and promotes apoptosis," *Cancer Gene Ther*, 10(2):141-151 (2003).

Llinas-Brunet et al., "Peptide-based inhibitors of the hepatitis C virus serine protease," *Bioorg Med Chem Lett*, 8(13):1713-1718 (1998).

Martin et al., "Affinity selection of a camelized $V_H$ domain antibody inhibitor of hepatitis C virus NS3 protease," *Protein Eng*, 10(5):607-614 (1997).

Martin et al., "Design of selective eglin inhibitors of HCV NS3 proteinase," *Biochemistry*, 37(33):11459-11468 (1998).

Mizuochi et al., "Both cathepsin B and cathepsin D are necessary for processing of ovalbumin as well as for degradation of class II MHC invariant chain," *Immunol Lett*, 43(3):189-193 (1994).

Mort and Buttle, "Molecules in focus," *Int J Biolchem Cell Biol*, 29(5):715-720 (1997).

Osborne, R., Editor, "Other news to note. Ribozyme Pharmaceuticals Inc.," *BioWorld® Today*, 9(217):4 (Nov. 10, 1998); BioWorld® Publishing Group, Atlanta, Georgia.

Reesink et al., "Initial Results of a Phase 1B, Multiple-Dose Study of VX-950, A Hepatitis C Virus Protease Inhibitor", *Gastroenterology*, 128(4 suppl 2):A697 (2005).

Reesink et al., "Final Results of a Phase 1B, Multiple-Dose Study of VX-950, A Hepatitis C Virus Protease Inhibitor", *Hepatology*, 42(4 suppl 1):234A-235A (2005).

Pizzi et al., "Molecular model of the specificity pocket of the hepatitis C virus protease: implications for substrate recognition," *Proc Natl Acad Sci(USA)*, 91(3):888-892 (1994).

Potempa et al., "Host and *porphyromonas gingivalis* proteinases in periodontitis: a biochemical model of infection and tissue destruction," *Perspectives in Drug Discover and Design*, 2:445-458 (1994).

Roberts et al., "Cathepsin B contributes to bile salt-induced apoptosis of rat hepatocytes," *Gastroenterology*, 113(5):1714-1726 (1997).

Rousselet et al., "Inhibition of tumorigenicity and metastasis of human melanoma cells by anti-cathepsin L single chain variable fragment," *Cancer Res*, 64(1):146-151 (2004).

Shibata et al., "Participation of cathepsins B and D in Apoptosis of PC12 cells following serum deprivation," *Biochem Biophys Res Commun*, 251(1):199-203 (1998).

Sunesen et al., "Effect of Liquid Volume and Food Intake on the Absolute Bioavailability of Danazol, a Poorly Soluble Drug", *European Journal of Pharmaceutical Sciences*, 24(4):297-303 (2005).

Troy et al., "Expression of cathepsin B and L antigen and activity is associated with early colorectal cancer progression," *Eur J Cancer*, 40(10):1610-1616 (2004).

Wang et al., "Conserved C-terminal threonine of hepatitis C virus NS3 regulates autoproteolysis and prevents product inhibition," *J Virol*, 78(2):700-709 (2004).

Yan et al., "Cathepsin B and Human Tumor Progression," *Biol Chem*, 379(2):113-123 (1998).

Hinrichsen et al., "Short-term Antiviral Efficacy of BILN 2061, A Hepatitis C Virus Serine Protease Inhibitor, In Hepatitis C Genotype I Patients", *Gastroenterology*, 127(5)1347-1355 (2004).

Jackson A., "Evaluation of a Cmin and a normalized Cmin method for the confirmation of steady-state in bioequivalence studies," *Pharmaceutical Research*, 15(7)1077-1084 (1998).

Mycek, Harvez and Champe, "Lippincott's illustrated Reviews—Pharmacology," XP002423552, p. 6, chapter IV; Bioavailability, p. 11, end of paragraph 2; (1997) Lippincott-Raven Publishers, Philadelphia, USA.

Naveau et al., "Interleukin-I Receptor Antagonist Plasma Concentration is Specifically Increased by alpha-2A-interferon Treatment", *Journal of Hepatology*, 27(2):272-275 (1997).

Pang et al., "The Pharmacokinetics and Efficacy of Slow-Release Theophylline with Asymmetric Dosing in Asthmatic Chinese", *Chest*, 93(4):785-789 (1988).

Patel et al., "Week 12 Viral Load Reduction and the Effect of Intra-Assay Variability on Predicting Treatment Response to Combination Therapy in Patients with Chronic Hepatitis C", *Hepatology*, 34(4):604A (2001).

Reesink et al., "Initial Results of a Phase 1B, Multiple-Dose Study of VX-950, A Hepatitis C Virus Protease Inhibitor", *Gastroenterology*, 128(4, Suppl. 2):A-697 (2005).

Richards, P., "Pattern of asymmetric dosing and pain control in long-term use of controlled-release oxycodone for treatment of chronic noncancer pain", *Archives of Physical Medicine and Rehabilitation*, 85(9):E40 (2004).

Sacks et al., "Lessons from HIV and Hepatitis Viruses", *Antiviral Research*, 63S1:S1I-S18 (2004).

Tsuda et al., "Poststatin, A New Inhibitor of Prolyl Endopeptidase V. Endopeptidase Inhibitory, Activity of Poststatin Analogues", *Journal of Antibiotics*, 49(9):890-899 (1996).

Ulrich, J., "Lehrbuch der Klinischen Pharmazie," *Wissenschaftliche Verlagsgesellschaft MBH*, pp. 56-58, paragraphs 4.1.1, 4.1.2 and 4.1.3; p. 70, paragraph. 4.3.3, (1998) Stuttgart.

Ulrich, J., English Translation of "Lehrbuch der Klinisehen Pharmazie," *Wissensehaftliche Verlagsgesellschaft MBH*, pp. 56-58, paragraphs 4.1.1, 4.1.2 and 4.1.3; p. 70, paragraph. 4.3.3, (1998) Stuttgart.

Van Thiel et al., "1220 Potential Early Biomarkers of a Response to Interferon Therapy in Individuals with Chronic Hepatitis C Treated with Pegasys", *Hepatology*, 38:748A (2003).

Wong et al., "Update on Chronic Hepatitis C", *Clinical Gastroenierology and Hepatology*, 3(6):507-520 (2005).

Yip et al., "P4 and P1' optimization of bicycloproline P2 bearing tetrapeptidyl alpha-ketoamides as HCV protease inhibitors", *Bioorganic & Medicinal Chemistry Letters*, 14(19):5007-5011 (2004).

Yip et al., "Discovery of a novel bicycloproline P2 bearing peptidyl alpha-ketoamide LY514962 as HCV protease inhibitor", *Bioorganic & Medicinal Chemistry Letters*, 14:251-256 (2004).

M. Sulkowski et al., Orally available Hepatitis C Virus (HCV) Protease Inhibitor (BILN 2061, Boehringer Ingelheim Pharma) Demonstrates Potent Anti-Viral Activity in Persons Infected with HCV Genotype 1' Conference Reports for NATAP, Nov. 2, 2002, AASLD, Boston, MA.

D. Lamarre et al., "An NS3 Protease Inhibitor with Antiviral Effects in Humans Infected with Hepatitis C Virus", Nature, vol. 426, No. 6963, Nov. 13, 2003, Nature Publishing Group, London, GB, pp. 186-189.

* cited by examiner

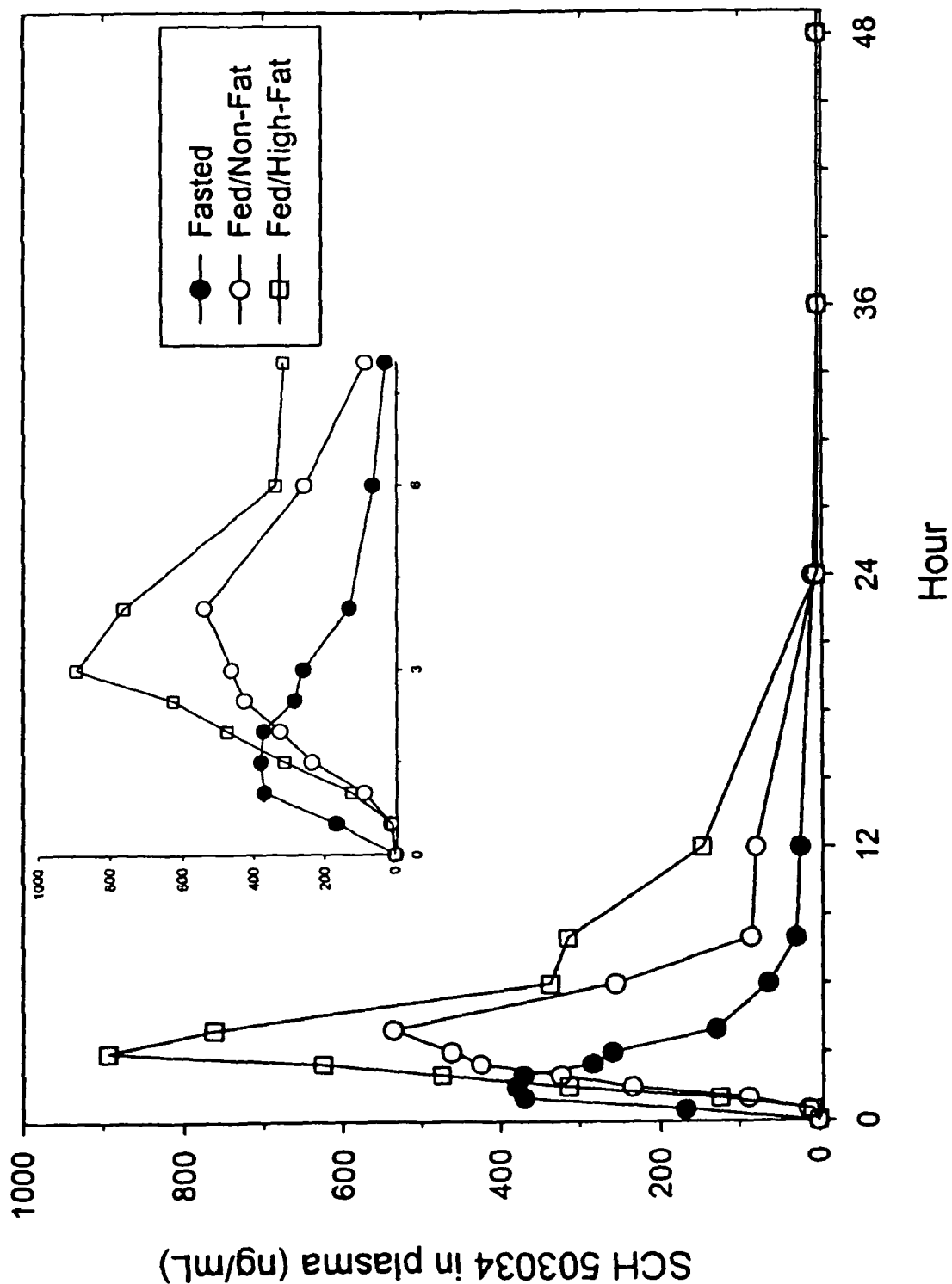

ADMINISTRATION OF HCV PROTEASE INHIBITORS IN COMBINATION WITH FOOD TO IMPROVE BIOAVAILABILITY

CROSS REFERENCE TO PRIORITY APPLICATION

This application claims priority from U.S. provisional patent application Ser. No. 60/686,925 filed Jun. 2, 2005.

FIELD OF THE INVENTION

The present invention relates to administering compounds that are useful for treating a wide variety of diseases or disorders associated with hepatitis C virus ("HCV") by inhibiting HCV protease (for example HCV NS3/NS4a serine protease), and/or diseases or disorders associated with cathepsin activity and inhibiting cathepsin activity. The compounds are administered in combination with food to enhance absorption of the compounds in the gastrointestinal tract and increase bioavailability of the compounds.

BACKGROUND OF THE INVENTION

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Current therapies for hepatitis C include interferon-α ($INF_\alpha$) and combination therapy with ribavirin and interferon. See, e.g., Beremguer et al. (1998) *Proc. Assoc. Am. Physicians* 110(2):98-112. These therapies suffer from a low sustained response rate and frequent side effects. See, e.g., Hoofnagle et al. (1997) *N. Engl. J. Med.* 336:347. Currently, no vaccine is available for HCV infection.

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci* (*USA*) 91:888-892, Failla et al. (1996) *Folding & Design* 1:35-42. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340-9348, Ingallinella et al. (1998) *Biochem.* 37:8906-8914, Llinàs-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPST1-C3) and minibody repertoires (MBip) (Dimasi et al. (1997) *J. Virol.* 71:7461-7469), $cV_HE2$ (a "camelized" variable domain antibody fragment) (Martin et al. (1997) *Protein Eng.* 10:607-614), and α1-antichymotrypsin (ACT) (Elzouki et al.) (1997) *J. Hepat.* 27:42-28). A ribozyme designed to selectively destroy hepatitis C virus RNA has recently been disclosed (see, *BioWorld Today* 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

Pending and copending U.S. patent applications, Ser. No. 60/194,607, filed Apr. 5, 2000, and Ser. No. 60/198,204, filed Apr. 19, 2000, Ser. No. 60/220,110, filed Jul. 21, 2000, Ser. No. 60/220,109, filed Jul. 21, 2000, Ser. No. 60/220,107, filed Jul. 21, 2000, Ser. No. 60/254,869, filed Dec. 12, 2000, Ser. No. 60/220,101, filed Jul. 21, 2000, Ser. No. 60/568,721 filed May 6, 2004, and WO 2003/062265, disclose various types of peptides and/or other compounds as NS-3 serine protease inhibitors of hepatitis C virus.

There is a need for new treatments and therapies for HCV infection to treat, prevent or ameliorate one or more symptoms of hepatitis C, methods for modulating the activity of serine proteases, particularly the HCV NS3/NS4a serine protease, and methods of modulating the processing of the HCV polypeptide using the compounds provided herein.

Another aspect of the present invention is directed to inhibiting cathepsin activity. Cathepsins (Cats) belong to the papain superfamily of lysosomal cysteine proteases. Cathepsins are involved in the normal proteolysis and turnover of target proteins and tissues as well as in initiating proteolytic cascades by proenzyme activation and in participating in MHC class II molecule expression. Baldwin (1993) Proc. Natl. Acad. Sci., 90: 6796-6800; Mixuochi (1994) Immunol. Lett., 43:189-193.

However, aberrant cathepsin expression has also been implicated in several serious human disease states. Cathepsins have been shown to be abundantly expressed in cancer cells, including breast, lung, prostate, glioblastoma and head/neck cancer cells, (Kos et al. (1998) Oncol. Rep., 5:1349-1361; Yan et al. (1998) Biol. Chem., 379:113-123; Mort et al. (1997) Int. J Biochem. Cell Biol., 29: 715-720; Friedrick et al. (1999) Eur. J Cancer, 35:138-144) and are associated with poor treatment outcome of patients with breast cancer, lung cancer, brain tumor and head/neck cancer. Kos et al, supra. Additionally, aberrant expression of cathepsin is evident in several inflammatory disease states, including rheumatoid arthritis and osteoarthritis. Keyszer (1995) Arthritis Rheum., 38:976-984.

The molecular mechanisms of cathepsin activity are not completely understood. Recently, it was shown that forced expression of cathepsin B rescued cells from serum deprivation-induced apoptotic death (Shibata et al. (1998) Biochem. Biophys. Res. Commun., 251: 199-203) and that treatment of cells with antisense oligonucleotides of cathepsin B induced apoptosis. Isahara et at. (1999) Neuroscience, 91:233-249. These reports suggest an anti-apoptotic role for the cathepsins that is contrary to earlier reports that cathepsins are mediators of apoptosis. Roberts et al (1997) Gastroenterology, 113: 1714-1726; Jones et al. (1998) Am. J Physiol., 275: G723-730.

Cathepsin K is a member of the family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J Biol. Chem.* 271, 12517-12524; Drake, F. H., et al., (1996) *J. Biol. Chem.* 271, 12511-12516; Bromme, D., et al., (1996) *J. Biol. Chem.* 271, 2126-2132.

Cathepsin K has been variously denoted as cathepsin O, cathepsin X or cathepsin O2 in the literature. The designation cathepsin K is considered to be the more appropriate one (name assigned by Nomenclature Committee of the International Union of Biochemistry and Molecular Biology).

Cathepsins of the papain superfamily of cysteine proteases function in the normal physiological process of protein degradation in animals, including humans, e.g., in the degradation of connective tissue. However, elevated levels of these enzymes in the body can result in pathological conditions leading to disease. Thus, cathepsins have been implicated in various disease states, including but not limited to, infections by *pneumocystis carinii, trypsanoma cruzi, trypsanoma brucei brucei*, and *Crithidia fusiculata*; as well as in schistosomiasis malaria, tumor metastasis, metachromatic leukodystrophy, muscular dystrophy, amytrophy, and the like. See International Publication Number WO 94/04172, published on Mar. 3, 1994, and references cited therein. See also European Patent Application EP 0 603 873 A1, and references cited therein. Two bacterial cysteine proteases from *P. gingivallis*, called gingipains, have been implicated in the pathogenesis of gingivitis. Potempa, J., et al. (1994) *Perspectives in Drug Discovery and Design*, 2, 445-458.

Cathepsin K is believed to play a causative role in diseases of excessive bone or cartilage loss. Bone is composed of a protein matrix in which spindle- or plate-shaped crystals of hydroxyapatite are incorporated. Type I Collagen represents the major structural protein of bone comprising approximately 90% of the structural protein. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodeling at discrete foci throughout life. These foci, or remodeling units, undergo a cycle consisting of a bone resorption phase followed by a phase of bone replacement. Bone resorption is carried out by osteoclasts, which are multinuclear cells of hematopoietic lineage. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

There are reports in the literature of the expression of Cathepsin B and L antigen and that activity is associated with early colorectal cancer progression. Troy et al., (2004) Eur J Cancer, 40(10):1610-6. The findings suggest that cysteine proteases play an important role in colorectal cancer progression.

Cathepsin L has been shown to be an important protein mediating the malignancy of gliomas and it has been suggested that its inhibition may diminish their invasion and lead to increased tumor cell apoptosis by reducing apoptotic threshold. Levicar et al., (2003) Cancer Gene Ther., 10(2): 141-51.

Katunama et al., (2002) Arch Biochem Biophys., 397(2): 305-11 reports on antihypercalcemic and antimetastatic effects of CLIK-148 in vivo, which is a specific inhibitor of cathepsin L. This reference also reports that CLIK-148 treatment reduced distant bone metastasis to the femur and tibia of melanoma A375 tumors implanted into the left ventricle of the heart.

Rousselet et al., (2004) Cancer Res., 64(1): 146-51 reports that anti-cathepsin L single chain variable fragment (ScFv) could be used to inhibit the tumorigenic and metastatic phenotype of human melanoma, depending on procathepsin L secretion, and the possible use of anti-cathepsin L ScFv as a molecular tool in a therapeutic cellular approach.

Colella et al., (2003) Biotech Histochem., 78(2):101-8 reports that the cysteine proteinases cathepsin L and B participate in the invasive ability of the PC3 prostrate cancer cell line, and the potential of using cystein protease inhibitiors such as cystatins as anti-metastatic agents.

Krueger et al., (2001) Cancer Gene Ther., 8(7):522-8 reports that in human osteosarcoma cell line MNNG/HOS, cathepsin L influences cellular malignancy by promoting migration and basement membrane degradation.

Frohlich et al., (2204) Arch Dermatol Res., 295(10):411-21 reports that cathepsins B and L are involved in invasion of basal cell carcinoma (BCC) cells.

U.S. Provisional Patent Application Serial No. Not Yet Assigned, entitled "Compounds for Inhibiting Cathepsin Activity", filed Apr. 20, 2005, discloses various types of peptides and/or other compounds as inhibitors of cathepsin.

Cathepsins therefore are attractive targets for the discovery of novel chemotherapeutics and methods of treatment effective against a variety of diseases. There is a need for compounds useful in the inhibition of cathepsin activity and in the treatment of these disorders.

Gastro-intestinal absorption of an oral dose of medication is influenced by many factors in the gastrointestinal tract. Attributes of the membrane, pH, blood supply, transit time, and surface area determine the particular location of absorption, such as the stomach, small intestine or large intestine. For example, the esophagus has a very thick membrane and virtually no absorption occurs while a drug is passing through the esophagus. The stomach has a thick mucous layer and the time that a drug resides there is usually relatively short, resulting in poor absorption despite the fact that it has a large epithelial surface. The small intestine has a very large surface area, and absorption of virtually all drugs is faster from the small intestine than from the stomach. Therefore, gastric emptying is a rate-limiting step in drug absorption.

It would be desirable to improve absorption, bioavailability and the effects of the drug in a treatment regimen.

SUMMARY OF THE INVENTION

In one aspect, the present invention provides a method of treating, preventing or ameliorating one or more symptoms of hepatitis C in a subject comprising the step of administering at least one compound of formulae I-XXVI in combination with food, wherein the at least one compound is at least one compound of formulae I-XXVI set forth below.

In an additional aspect, the present invention provides a method of increasing bioavailability of a compound of formulae I-XXVI in a subject comprising administering at least one compound in combination with food, wherein the at least one compound is at least one compound of formulae I-XXVI set forth below.

In a further aspect, the present invention provides a method of increasing the serum level of a compound in a subject comprising adminstering the at least one compound in combination with food, wherein the at least one compound is a compound of formulae I-XXVI set forth below.

In one embodiment, the compound is a compound of structural formula I:

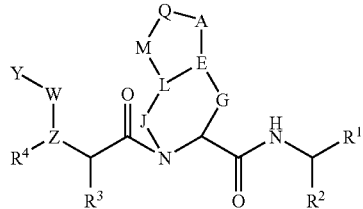

Formula I or a pharmaceutically acceptable salt, solvate or ester thereof; wherein:

Y is selected from the group consisting of the following moieties: alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe optionally substituted with $X^{11}$ or $X^{12}$;

$X^{11}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is $COR^5$, wherein $R^5$ is $COR^7$ wherein $R^7$ is $NHR^9$, wherein $R^9$ is selected from the group consisting of H, alkyl, aryl, heteroalkyl, heteroaryl, cycloalkyl, cycloalkyl, arylalkyl, heteroarylalkyl, $[CH(R^{1'})]_pCOOR^{11}$, $[CH(R^{1'})]_pCONR^{12}R^{13}$, $[CH(R^{1'})]_pSO_2R^{11}$, $[CH(R^{1'})]_pCOR^{11}$, $[CH(R^{1'})]_pCH(OH)R^{11}$, $CH(R^{1'})CONHCH(R^2)COOR^{11}$, $CH(R^{1'})CONHCH(R^2)CONR^{12}R^{13}$, $CH(R^{1'})CONHCH(R^2)R'$, $CH(R^{1'})CONHCH(R^2)CONHCH(R^{3'})COOR^{11}$, $CH(R^{1'})CONHCH(R^{2'})CONHCH(R^{3'})CONR^{12}R^{13}$, $CH(R^{1'})CONHCH(R^{2'})CONHCH(R^{3'})CONHCH(R^{4'})COOR^{11}$, $CH(R^{1'})CONHCH(R^{2'})CONHCH(R^{3'})CONHCH(R^{4'})CONR^{12}R^{13}$, $CH(R^{1'})CONHCH(R^{2'})CONHCH(R^{3'})CONHCH(R^{4'})CONHCH(R^{5'})COOR^{11}$ and $CH(R^{1'})CONHCH(R^{2'})CONHCH(R^{3'})CONHCH(R^{4'})CONHCH(R^{5'})CONR^{12}R^{13}$, wherein $R^{1'}$, $R^{2'}$, $R^{3'}$, $R^{4'}$, $R^{5'}$, $R^{11}$, $R^{12}$, $R^{13}$, and $R'$ are independently selected from the group consisting of H, alkyl, aryl, heteroalkyl, heteroaryl, cycloalkyl, alkyl-aryl, alkyl-heteroaryl, aryl-alkyl and heteroaralkyl;

Z is selected from O, N, CH or CR;

W maybe present or absent, and if W is present, W is selected from C=O, C=S, C(=N—CN), or $SO_2$;

Q maybe present or absent, and when Q is present, Q is CH, N, P, $(CH_2)_p$, $(CHR)_p$, $(CRR')_p$, O, NR, S, or $SO_2$; and when Q is absent, M may be present or absent; when Q and M are absent, A is directly linked to L;

A is O, $CH_2$, $(CHR)_p$, $(CHR—CHR')_p$, $(CRR')_p$, NR, S, $SO_2$ or a bond;

E is CH, N, CR, or a double bond towards A, L or G;

G may be present or absent, and when G is present, G is $(CH_2)_p$, $(CHR)_p$, or $(CRR')_p$; and when G is absent, J is present and E is directly connected to the carbon atom in Formula I as G is linked to;

J maybe present or absent, and when J is present, J is $(CH_2)_p$, $(CHR)_p$, or $(CRR')_p$, $SO_2$, NH, NR or O; and when J is absent, G is present and E is directly linked to N shown in Formula I as linked to J;

L may be present or absent, and when L is present, L is CH, CR, O, S or NR; and when L is absent, then M may be present or absent; and if M is present with L being absent, then M is directly and independently linked to E, and J is directly and independently linked to E;

M may be present or absent, and when M is present, M is O, NR, S, $SO_2$, $(CH_2)_p$, $(CHR)_p(CHR—CHR')_p$, or $(CRR')_p$;

p is a number from 0 to 6; and

R, R', $R^2$, $R^3$ and $R^4$ are independently selected from the group consisting of H; $C_1$-$C_{10}$ alkyl; $C_2$-$C_{10}$ alkenyl; $C_3$-$C_8$ cycloalkyl; $C_3$-$C_8$ heterocycloalkyl, alkoxy, aryloxy, alkylthio, arylthio, amino, amido, ester, carboxylic acid, carbamate, urea, ketone, aldehyde, cyano, nitro, halogen; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

wherein said alkyl, heteroalkyl, alkenyl, heteroalkenyl, aryl, heteroaryl, cycloalkyl and heterocycloalkyl moieties may be optionally and chemically-suitably substituted, with said term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate;

further wherein said unit N—C-G-E-L-J-N represents a five-membered or six-membered cyclic ring structure with the proviso that when said unit N—C-G-E-L-J-N represents a five-membered cyclic ring structure, or when the bicyclic ring structure in Formula I comprising N, C, G, E, L, J, N, A, Q, and M represents a five-membered cyclic ring structure, then said five-membered cyclic ring structure lacks a carbonyl group as part of the cyclic ring.

In another embodiment, the "at least one compound" is a compound of formula: II:

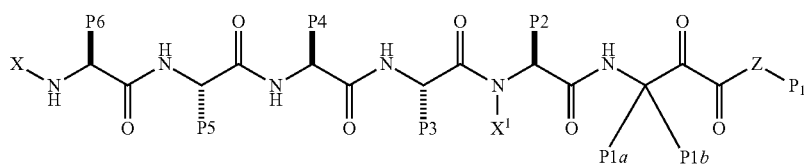

Formula II or a pharmaceutically acceptable salt, solvate or ester thereof; wherein:

Z is NH;

X is alkylsulfonyl, heterocyclylsulfonyl, heterocyclylalkylsulfonyl, arylsulfonyl, heteroarylsulfonyl, alkylcarbonyl, heterocyclylcarbonyl, heterocyclylalkylcarbonyl, arylcarbonyl, heteroarylcarbonyl, alkoxycarbonyl, heterocyclyloxycarbonyl, aryloxycarbonyl, heteroaryloxycarbonyl, alkyaminocarbonyl, heterocyclylaminocarbonyl, arylaminocarbonyl, or heteroarylaminocarbonyl moiety, with the proviso that X may be additionally optionally substituted with $R^{12}$ or $R^{13}$;

$X^1$ is H; $C_1$-$C_4$ straight chain alkyl; $C_1$-$C_4$ branched alkyl or; $CH_2$-aryl (substituted or unsubstituted);

$R^{12}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that $R^{12}$ may be additionally optionally substituted with $R^{13}$.

$R^{13}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro moiety, with the proviso that the alkyl, alkoxy, and aryl may be additionally optionally substituted with moieties independently selected from $R^{13}$.

P1a, P1b, P2, P3, P4, P5, and P6 are independently: H; C1-C10 straight or branched chain alkyl; C2-C10 straight or branched chain alkenyl; C3-C8 cycloalkyl, C3-C8 heterocyclic; (cycloalkyl)alkyl or (heterocyclyl)alkyl, wherein said cycloalkyl is made up of 3 to 8 carbon atoms, and zero to 6 oxygen, nitrogen, sulfur, or phosphorus atoms, and said alkyl is of 1 to 6 carbon atoms; aryl, heteroaryl, arylalkyl, or heteroarylalkyl, wherein said alkyl is of 1 to 6 carbon atoms;

wherein said alkyl, alkenyl, cycloalkyl, heterocyclyl; (cycloalkyl)alkyl and (heterocyclyl)alkyl moieties may be optionally substituted with $R^{13}$, and further wherein said P1a and P1b may optionally be joined to each other to form a spirocyclic or spiroheterocyclic ring, with said spirocyclic or spiroheterocyclic ring containing zero to six oxygen, nitrogen, sulfur, or phosphorus atoms, and may be additionally optionally substituted with $R^{13}$; and P1' is H, alkyl, alkenyl, alkynyl, cycloalkyl, cycloalkyl-alkyl, heterocyclyl, heterocyclyl-alkyl, aryl, aryl-alkyl, heteroaryl, or heteroaryl-alkyl; with the proviso that said P1' may be additionally optionally substituted with $R^{13}$.

In another embodiment, the "at least one compound" is a compound of formula III:

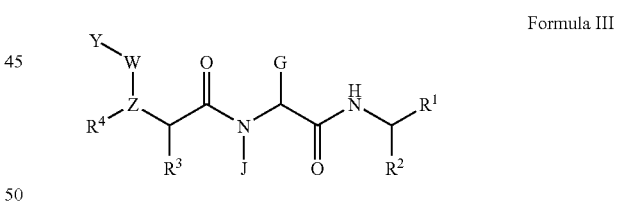

Formula III or a pharmaceutically acceptable salt, solvate or ester thereof; wherein:

G is carbonyl;

J and Y may be the same or different and are independently selected from the group consisting of the moieties: H, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe additionally optionally substituted with $X^{11}$ or $X^{12}$;

$X^{11}$ is selected from the group consisting of alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl moiety, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is $COR^5$ or $C(OR)_2$, wherein $R^5$ is selected from the group consisting of H, OH, $OR^8$, $NR^9R^{10}$, $CF_3$, $C_2F_5$, $C_3F_7$, $CF_2R^6$, $R^6$ and $COR^7$ wherein $R^7$ is selected from the group consisting of H, OH, $OR^8$, $CHR^9R^{10}$, and $NR^9R^{10}$, wherein $R^6$, $R^8$, $R^9$ and $R^{10}$ may be the same or different and are independently selected from the group consisting of H, alkyl, aryl, heteroalkyl, heteroaryl, cycloalkyl, cycloalkyl, arylalkyl, heteroarylalkyl, $CH(R^{1'})COOR^{11}$, $CH(R^{1'})CONR^{12}R^{13}$, $CH(R^{1'})CONHCH(R^{2'})COOR^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COOR^{11}$, $CH(R^{1'})CONHCH(R^{2'})CONHCH(R^{3'})CONR^{12}R^{13}$, $CH(R^{1'})CONHCH(R^{2'})CONHCH(R^{3'})CONHCH(R^{4'})COOR^{11}$, $CH(R^{1'})CONHCH(R^{2'})CONHCH(R^{3'})CONHCH(R^{4'})CONR^{12}R^{13}$, $CH(R^{1'})CONHCH(R^{2'})CONHCH(R^{3'})CONHCH(R^{4'})CONHCH(R^{5'})COOR^{11}$, and $CH(R^{1'})CONHCH(R^{2'})CONHCH(R^{3'})CONHCH(R^{4'})CONHCH(R^{5'})CONR^{12}R^{13}$, wherein $R^{1'}, R^{2'}, R^{3'}, R^{4'}, R^{5'}, R^{11}, R^{12}, R^{13}$, and R' may be the same or different and are independently selected from a group consisting of H, alkyl, aryl, heteroalkyl, heteroaryl, cycloalkyl, alkyl-aryl, alkyl-heteroaryl, aryl-alkyl and heteroaralkyl;

Z is selected from O, N, or CH;

W maybe present or absent, and if W is present, W is selected from C=O, C=S, or $SO_2$; and R, R', $R^2$, $R^3$ and $R^4$ are independently selected from the group consisting of H; C1-C10 alkyl; C2-C10 alkenyl; C3-C8 cycloalkyl; C3-C8 heterocycloalkyl, alkoxy, aryloxy, alkylthio, arylthio, amino, amido, ester, carboxylic acid, carbamate, urea, ketone, aldehyde, cyano, nitro; oxygen, nitrogen, sulfur, or phosphorus atoms (with said oxygen, nitrogen, sulfur, or phosphorus atoms numbering zero to six); (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkylaryl; and alkyl-heteroaryl;

wherein said alkyl, heteroalkyl, alkenyl, heteroalkenyl, aryl, heteroaryl, cycloalkyl and heterocycloalkyl moieties may be optionally substituted, with said term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamide, sulfoxide, sulfone, sulfonylurea, hydrazide, and hydroxamate.

In another embodiment, the inhibitor is a compound of Formula IV

Formula IV

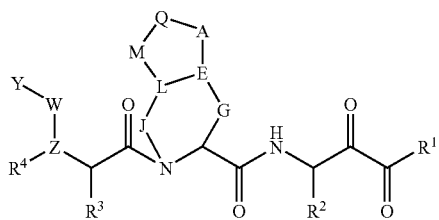

or a pharmaceutically acceptable salt, solvate or ester thereof;
wherein:

Y is selected from the group consisting of the following moieties: alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe optionally substituted with $X^{11}$ or $X^{12}$;

$X^{11}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxyl, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is selected from the following structures:

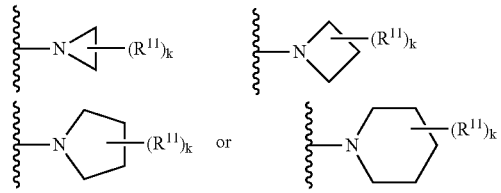

wherein k is a number from 0 to 5, which can be the same or different, $R^{11}$ denotes optional substituents, with each of said substituents being independently selected from the group consisting of alkyl, alkenyl, alkynyl, aryl, cycloalkyl, alkyl-aryl, heteroalkyl, heteroaryl, aryl-heteroaryl, alkyl-heteroaryl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino, heterocycloalkylamino, hydroxy, thio, alkylthio, arylthio, amino, alkylsulfonyl, arylsulfonyl, alkylsulfonamido, arylsulfonamido, carboxyl, carbalkoxy, carboxamido, alkoxycarbonylamino, alkoxycarbonyloxy, alkylureido, arylureido, halogen, cyano, and nitro, with the proviso that $R^{11}$ (when $R^{11}$≠H) maybe optionally substituted with $X^{11}$ or $X^{12}$;

Z is selected from O, N, CH or CR;

W may be present or absent, and if W is present, W is selected from C=O, C=S, C(=N—CN), or $S(O_2)$;

Q may be present or absent, and when Q is present, Q is CH, N, P, $(CH_2)_p$, $(CHR)_p$, $(CRR')_p$, O, N(R), S, or $S(O_2)$; and when Q is absent, M may be present or absent; when Q and M are absent, A is directly linked to L;

A is O, $CH_2$, $(CHR)_p$, $(CHR—CHR')_p$, $(CRR')_p$, N(R), S, $S(O_2)$ or a bond;

E is CH, N, CR, or a double bond towards A, L or G;

G may be present or absent, and when G is present, G is $(CH_2)_p$, $(CHR)_p$, or $(CRR')_p$; and when G is absent, J is present and E is directly connected to the carbon atom in Formula I as G is linked to;

J may be present or absent, and when J is present, J is $(CH_2)_p$, $(CHR)_p$, or $(CRR')_p$, $S(O_2)$, NH, N(R) or O; and when J is absent, G is present and E is directly linked to N shown in Formula I as linked to J;

L may be present or absent, and when L is present, L is CH, C(R), O, S or N(R); and when L is absent, then M may be present or absent; and if M is present with L being absent, then M is directly and independently linked to E, and J is directly and independently linked to E;

M may be present or absent, and when M is present, M is O, N(R), S, S(O₂), (CH₂)$_p$, (CHR)$_p$(CHR—CHR')$_p$, or (CRR')$_p$;

p is a number from 0 to 6; and

R, R', R², R³ and R⁴ can be the same or different, each being independently selected from the group consisting of H; $C_1$-$C_{10}$ alkyl; $C_2$-$C_{10}$ alkenyl; $C_3$-$C_8$ cycloalkyl; $C_3$-$C_8$ heterocycloalkyl, alkoxy, aryloxy, alkylthio, arylthio, amino, amido, ester, carboxylic acid, carbamate, urea, ketone, aldehyde, cyano, nitro, halogen, (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

wherein said alkyl, heteroalkyl, alkenyl, heteroalkenyl, aryl, heteroaryl, cycloalkyl and heterocycloalkyl moieties may be optionally substituted, with said term "substituted" referring to substitution with one or more moieties which can be the same or different, each being independently selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate;

further wherein said unit N—C-G-E-L-J-N represents a five-membered cyclic ring structure or six-membered cyclic ring structure with the proviso that when said unit N—C-G-E-L-J-N represents a five-membered cyclic ring structure, or when the bicyclic ring structure in Formula I comprising N, C, G, E, L, J, N, A, Q, and M represents a five-membered cyclic ring structure, then said five-membered cyclic ring structure lacks a carbonyl group as part of said five-membered cyclic ring.

In another embodiment, the inhibitor is a compound of Formula V

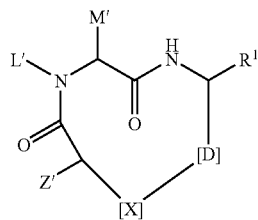

Formula V or a pharmaceutically acceptable salt, solvate or ester of said compound wherein:

(1) $R^1$ is —C(O)$R^5$ or —B(OR)₂;

(2) $R^5$ is H, —OH, —OR⁸, —NR⁹R¹⁰, —C(O)OR⁸, —C(O)NR⁹R¹⁰, —CF₃, —C₂F₅, C₃F₇, —CF₂R⁶, —R⁶, —C(O)R⁷ or NR⁷SO₂R⁸;

(3) $R^7$ is H, —OH, —OR⁸, or —CHR⁹R¹⁰;

(4) R⁶, R⁸, R⁹ and R¹⁰ are independently selected from the group consisting of H: alkyl, alkenyl, aryl, heteroalkyl, heteroaryl, cycloalkyl, arylalkyl, heteroarylalkyl, R¹⁴, —CH(R¹')CH(R¹')C(O)OR¹¹, [CH(R¹')]$_p$C(O)OR¹¹, —[CH(R¹')]$_p$C(O)NR¹²R¹³, —[CH(R¹')]$_p$S(O₂)R¹¹, —[CH(R¹')]$_p$C(O)R¹¹, —[CH(R¹')]$_p$S(O₂)NR¹²R¹³, CH(R¹')C(O)N(H)CH(R²')(R'), CH(R¹')CH(R¹')C(O)NR¹²R¹³, —CH(R¹')CH(R¹')S(O₂)R¹¹, —CH(R¹')CH(R¹')S(O₂)NR¹²R¹³, —CH(R¹')CH(R¹')C(O)R¹¹, —[CH(R¹')]$_p$CH(OH)R¹¹, —CH(R¹')C(O)N(H)CH(R²')C(O)OR¹¹, C(O)N(H)CH(R²')C(O)OR¹¹, —C(O)N(H)CH(R²')C(O)R¹¹, CH(R¹')C(O)N(H)CH(R²')C(O)NR¹²R¹³, —CH(R¹')C(O)N(H)CH(R²')R', CH(R¹')C(O)N(H)CH(R²')C(O)N(H)CH(R³')C(O)OR¹¹, CH(R¹')C(O)N(H)CH(R²')C(O)CH(R³')NR¹²R¹³, CH(R¹')C(O)N(H)CH(R²')C(O)N(H)CH(R³')C(O)NR¹²R¹³, CH(R¹')C(O)N(H)CH(R²')C(O)N(H)CH(R³')C(O)N(H)CH(R⁴')C(O)OR¹¹, H(R¹')C(O)N(H)CH(R²')C(O)N(H)CH(R³')C(O)N(H)CH(R⁴')C(O)NR¹²R¹³, CH(R¹')C(O)N(H)CH(R²')C(O)N(H)CH(R³')C(O)N(H)CH(R⁴')C(O)N(H)CH(R⁵')C(O)OR¹¹, and CH(R¹')C(O)N(H)CH(R²')C(O)N(H)CH(R³')C(O)N(H)CH(R⁴')C(O)N(H)CH(R⁵')C(O)NR¹²R¹³;

wherein R¹', R²', R³', R⁴', R⁵', R¹¹, R¹² and R¹³ can be the same or different, each being independently selected from the group consisting of: H, halogen, alkyl, aryl, heteroalkyl, heteroaryl, cycloalkyl, alkoxy, aryloxy, alkenyl, alkynyl, alkyl-aryl, alkyl-heteroaryl, heterocycloalkyl, aryl-alkyl and heteroaralkyl;

or

R¹² and R¹³ are linked together wherein the combination is cycloalkyl, heterocycloalkyl, ary or heteroaryl;

R¹⁴ is present or not and if present is selected from the group consisting of: H, alkyl, aryl, heteroalkyl, heteroaryl, cycloalkyl, alkyl-aryl, allyl, alkyl-heteroaryl, alkoxy, aryl-alkyl, alkenyl, alkynyl and heteroaralkyl;

(5) R and R' are present or not and if present can be the same or different, each being independently selected from the group consisting of: H, OH, $C_1$-$C_{10}$ alkyl, $C_2$-$C_{10}$ alkenyl, $C_3$-$C_8$ cycloalkyl, $C_3$-$C_8$ heterocycloalkyl, alkoxy, aryloxy, alkylthio, arylthio, alkylamino, arylamino, amino, amido, arylthioamino, arylcarbonylamino, arylaminocarboxy, alkylaminocarboxy, heteroalkyl, alkenyl, alkynyl, (aryl)alkyl, heteroarylalkyl, ester, carboxylic acid, carbamate, urea, ketone, aldehyde, cyano, nitro, halogen, (cycloalkyl)alkyl, aryl, heteroaryl, (alkyl)aryl, alkylheteroaryl, alkyl-heteroaryl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms;

(6) L' is H, OH, alkyl, heteroalkyl, aryl, heteroaryl, cycloalkyl, or heterocyclyl;

(7) M' is H, alkyl, heteroalkyl, aryl, heteroaryl, cycloalkyl, arylalkyl, heterocyclyl or an amino acid side chain;

or L' and M' are linked together to form a ring structure wherein the portion of structural Formula 1 represented by

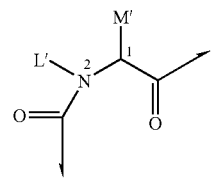

is represented by structural Formula 2:

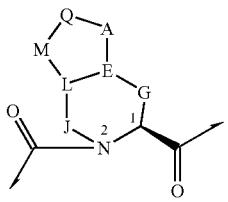

Formula 2 wherein in Formula 2:
E is present or absent and if present is C, CH, N or C(R);
J is present or absent, and when J is present, J is $(CH_2)_p$, $(CHR—CHR')_p$, $(CHR)_p$, $(CRR')_p$, $S(O_2)$, N(H), N(R) or O; when J is absent and G is present, L is directly linked to the nitrogen atom marked position 2;
p is a number from 0 to 6;
L is present or absent, and when L is present, L is C(H) or C(R); when L is absent, M is present or absent; if M is present with L being absent, then M is directly and independently linked to E, and J is directly and independently linked to E;
G is present or absent, and when G is present, G is $(CH_2)_p$, $(CHR)_p$, $(CHR—CHR')_p$ or $(CRR')_p$; when G is absent, J is present and E is directly connected to the carbon atom marked position 1;
Q is present or absent, and when Q is present, Q is NR, PR, (CR=CR), $(CH_2)_p$, $(CHR)_p$, $(CRR')_p$, $(CHR—CHR')_p$, O, NR, S, SO, or $SO_2$; when Q is absent, M is (i) either directly linked to A or (ii) an independent substituent on L, said independent substituent bing selected from —OR, —CH(R)(R'), $S(O)_{0-2}R$ or —NRR' or (iii) absent; when both Q and M are absent, A is either directly linked to L, or A is an independent substituent on E, said independent substituent bing selected from —OR, —CH(R)(R'), $S(O)_{0-2}R$ or —NRR' or A is absent;
A is present or absent and if present A is O, O(R), $(CH_2)_p$, $(CHR)_p$, $(CHR—CHR')_p$, $(CRR')_p$, N(R), NRR', S, $S(O_2)$, —OR, CH(R)(R') or NRR'; or A is linked to M to form an alicyclic, aliphatic or heteroalicyclic bridge;
M is present or absent, and when M is present, M is halogen, O, OR, N(R), S, $S(O_2)$, $(CH_2)_p$, $(CHR)_p$ $(CHR—CHR')_p$, or $(CRR')_p$; or M is linked to A to form an alicyclic, aliphatic or heteroalicyclic bridge;
(8) Z' is represented by the structural Formula 3:

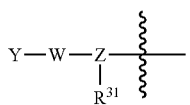

Formula 3 wherein in Formula 3, Y is selected from the group consisting of: H, aryl, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, heteroalkyl-heteroaryl, heteroalkyl-heterocycloalkyl, cycloalkyloxy, alkylamino, arylamino, alkyl-arylamino, arylamino, heteroarylamino, cycloalkylamino and heterocycloalkylamino, and Y is unsubstituted or optionally substituted with one or two substituents which are the same or different and are independently selected from $X^{11}$ or $X^{12}$;
$X^{11}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, and $X^{11}$ is unsubstituted or optionally substituted with one or more of $X^{12}$ moieties which are the same or different and are independently selected;
$X^{12}$ is hydroxy, alkoxy, alkyl, alkenyl, alkynyl, aryl, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkylcarbonyl, arylcarbonyl, heteroalkylcarbonyl, heteroarylcarbonyl, sulfonylurea, cycloalkylsulfonamido, heteroarylcycloalkylsulfonamido, heteroaryl-sulfonamido, alkoxycarbonylamino, alkoxycarbonyloxy, alkylureido, arylureido, halogen, cyano, or nitro, and said alkyl, alkoxy, and aryl are unsubstituted or optionally independently substituted with one or more moieties which are the same or different and are independently selected from alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl;
Z is O, N, C(H) or C(R);
$R^{31}$ is H, hydroxyl, aryl, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, heteroalkyl-heteroaryl, cycloalkyloxy, alkylamino, arylamino, alkyl-arylamino, arylamino, heteroarylamino, cycloalkylamino or heterocycloalkylamino, and $R^{31}$ is unsubstituted or optionally substituted with one or two substituents which are the same or different and are independently selected from $X^{13}$ or $X^{14}$;
$X^{13}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, and $X^{13}$ is unsubstituted or optionally substituted with one or more of $X^{14}$ moieties which are the same or different and are independently selected;
$X^{14}$ is hydroxy, alkoxy, alkyl, alkenyl, alkynyl, aryl, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkylcarbonyl, arylcarbonyl, heteroalkylcarbonyl, heteroarylcarbonyl, cycloalkylsulfonamido, heteroarylcycloalkylsulfonamido, heteroarylsulfonamido, alkoxycarbonylamino, alkoxycarbonyloxy, alkylureido, arylureido, halogen, cyano, or nitro, and said alkyl, alkoxy, and aryl are unsubstiuted or optionally independently substituted with one or more moieties which are the same or different and are independently selected from alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl;
W may be present or absent, and if W is present, W is C(=O), C(=S), C(=N—CN), or $S(O_2)$;
(9) X is represented by structural Formula 4:

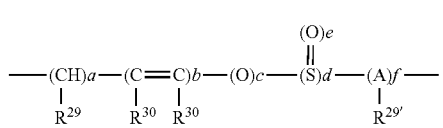

Formula 4 wherein in Formula 4, a is 2, 3, 4, 5, 6, 7, 8 or 9;
b, c, d, e and f are 0, 1, 2, 3, 4 or 5;
A is C, N, S or O;

$R^{29}$ and $R^{29'}$ are independently present or absent and if present can be the same or different, each being independently one or two substituents independently selected from the group consisting of: H, halo, alkyl, aryl, cycloalkyl, cycloalkylamino, cycloalkylaminocarbonyl, cyano, hydroxy, alkoxy, alkylthio, amino, —NH(alkyl), —NH(cycloalkyl), —N(alkyl)$_2$, carboxyl, C(O)O-alkyl, heteroaryl, aralkyl, alkylaryl, aralkenyl, heteroaralkyl, alkylheteroaryl, heteroaralkenyl, hydroxyalkyl, aryloxy, aralkoxy, acyl, aroyl, nitro, aryloxycarbonyl, aralkoxycarbonyl, alkylsulfonyl, arylsulfonyl, heteroarylsulfonyl, alkylsulfinyl, arylsulfinyl, heteroarylsulfinyl, arylthio, heteroarylthio, aralkylthio, heteroaralkylthio, cycloalkenyl, heterocyclyl, heterocyclenyl, $Y_1Y_2$N-alkyl-, $Y_1Y_2$NC(O)— and $Y_1Y_2$NSO$_2$—, wherein $Y_1$ and $Y_2$ can be the same or different and are independently selected from the group consisting of hydrogen, alkyl, aryl, and aralkyl; or $R^{29}$ and $R^{29'}$ are linked together such that the combination is an aliphatic or heteroaliphatic chain of 0 to 6 carbons;

$R^{30}$ is present or absent and if present is one or two substituents independently selected from the group consisting of: H, alkyl, aryl, heteroaryl and cylcoalkyl;

(10) D is represented by structural Formula 5:

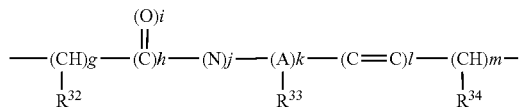

wherein in Formula 5, $R^{32}$, $R^{33}$ and $R^{34}$ are present or absent and if present are independently one or two substituents independently selected from the group consisting of: H, halo, alkyl, aryl, cycloalkyl, cycloalkylamino, spiroalkyl, cycloalkylaminocarbonyl, cyano, hydroxy, alkoxy, alkylthio, amino, —NH(alkyl), —NH(cycloalkyl), —N(alkyl)$_2$, carboxyl, —C(O)O-alkyl, heteroaryl, aralkyl, alkylaryl, aralkenyl, heteroaralkyl, alkylheteroaryl, heteroaralkenyl, hydroxyalkyl, aryloxy, aralkoxy, acyl, aroyl, nitro, aryloxycarbonyl, aralkoxycarbonyl, alkylsulfonyl, arylsulfonyl, heteroarylsulfonyl, alkylsulfinyl, arylsulfinyl, heteroarylsulfinyl, arylthio, heteroarylthio, aralkylthio, heteroaralkylthio, cycloalkenyl, heterocyclyl, heterocyclenyl, $Y_1Y_2$N-alkyl-, $Y_1Y_2$NC(O)— and $Y_1Y_2$NSO$_2$—, wherein $Y_1$ and $Y_2$ can be the same or different and are independently selected from the group consisting of hydrogen, alkyl, aryl, and aralkyl; or $R^{32}$ and $R^{34}$ are linked together such that the combination forms a portion of a cycloalkyl group;

g is 1, 2, 3, 4, 5, 6, 7, 8 or 9;

h, i, j, k, l and m are 0, 1, 2, 3, 4 or 5; and

A is C, N, S or O,

(11) provided that when structural Formula 2:

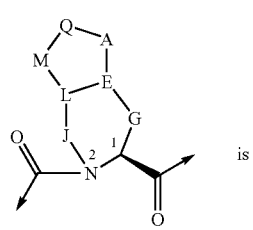

is

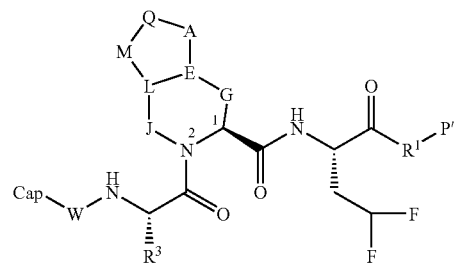

and

W' is CH or N, both the following conditional exclusions (i) and (ii) apply:

conditional exclusion (i): Z' is not —NH—$R^{36}$, wherein $R^{36}$ is H, $C_{6\,or\,10}$ aryl, heteroaryl, —C(O)—$R^{37}$, —C(O)O$R^{37}$ or —C(O)NHR$^{37}$, wherein $R^{37}$ is $C_{1-6}$ alkyl or $C_{3-6}$ cycloalkyl;

and conditional exclusion (ii): $R^1$ is not —C(O)OH, a pharmaceutically acceptable salt of —C(O)OH, an ester of —C(O)OH or —C(O)NHR$^{38}$ wherein $R^{38}$ is selected from the group consisting of $C_{1-8}$ alkyl, $C_{3-6}$ cycloalkyl, $C_{6\,to\,10}$ aryl or $C_{7-16}$ aralkyl.

In another embodiment, the "at least one compound" is a compound of formula VI:

Formula VI or a pharmaceutically acceptable salt, solvate or ester of said compound, wherein:

Cap is H, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arylalkyloxy or heterocyclylamino, wherein each of said alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arylalkyloxy or heterocyclylamino can be unsubstituted or optionally independently substituted with one or two substituents which can be the same or different and are independently selected from $X^1$ and $X^2$;

P' is —NHR;

$X^1$ is alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl, or heteroarylalkyl, and $X^1$ can be unsubstituted or optionally independently substituted with one or more of $X^2$ moieties which can be the same or different and are independently selected;

$X^2$ is hydroxy, alkyl, aryl, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, keto, ester or nitro, wherein each of said alkyl, alkoxy, and aryl can be unsubstituted or optionally independently substituted with one or more moieties which can be the same or different and are independently selected from alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl and heteroarylalkyl;

W may be present or absent, and when W is present W is C(=O), C(=S), C(=NH), C(=N—OH), C(=N—CN), S(O) or S($O_2$);

Q maybe present or absent, and when Q is present, Q is N(R), P(R), CR=CR', $(CH_2)_p$, $(CHR)_p$, $(CRR')_p$, (CHR—CHR')$_p$, O, S, S(O) or S($O_2$); when Q is absent, M is (i) either directly linked to A or (ii) M is an independent substituent on L and A is an independent substituent on E, with said independent substituent being selected from —OR, —CH(R), $S(O)_{0-2}R$ or —NRR'; when both Q and M are absent, A is either directly linked to L, or A is an independent substituent on E, selected from —OR, CH(R)(R'), —$S(O)_{0-2}R$ or —NRR';

A is present or absent and if present A is —O—, —O(R)$CH_2$—, —(CHR)$_p$—, —(CHR—CHR')$_p$—, (CRR')$_p$, N(R), NRR', S, or S($O_2$), and when Q is absent, A is —OR, —CH(R)(R') or —NRR'; and when A is absent, either Q and E are connected by a bond or Q is an independent substituent on M;

E is present or absent and if present E is CH, N, C(R);

G may be present or absent, and when G is present, G is (CH$_2$)$_p$, (CHR)$_p$, or (CRR')$_p$; when G is absent, J is present and E is directly connected to the carbon atom marked position 1;

J may be present or absent, and when J is present, J is (CH$_2$)$_p$, (CHR—CHR')$_p$, (CHR)$_p$, (CRR')$_p$, S(O$_2$), N(H), N(R) or O; when J is absent and G is present, L is directly linked to the nitrogen atom marked position 2;

L may be present or absent, and when L is present, L is CH, N, or CR; when L is absent, M is present or absent; if M is present with L being absent, then M is directly and independently linked to E, and J is directly and independently linked to E;

M may be present or absent, and when M is present, M is O, N(R), S, S(O$_2$), (CH$_2$)$_p$, (CHR)$_p$, (CHR—CHR')$_p$, or (CRR')$_p$;

p is a number from 0 to 6;

R, R' and $R^3$ can be the same or different, each being independently selected from the group consisting of: H, $C_1$-$C_{10}$ alkyl, $C_2$-$C_{10}$ alkenyl, $C_3$-$C_8$ cycloalkyl, $C_3$-$C_8$ heterocyclyl, alkoxy, aryloxy, alkylthio, arylthio, amino, amido, arylthioamino, arylcarbonylamino, arylaminocarboxy, alkylaminocarboxy, heteroalkyl, heteroalkenyl, alkenyl, alkynyl, aryl-alkyl, heteroarylalkyl, ester, carboxylic acid, carbamate, urea, ketone, aldehyde, cyano, nitro, halogen, (cycloalkyl)alkyl, aryl, heteroaryl, alkyl-aryl, alkylheteroaryl, alkyl-heteroaryl and (heterocyclyl)alkyl;

R and R' in (CRR') can be linked together such that the combination forms a cycloalkyl or heterocyclyl moiety; and $R^1$ is carbonyl.

In another embodiment, the inhibitor is a compound of Formula VII

Formula VII

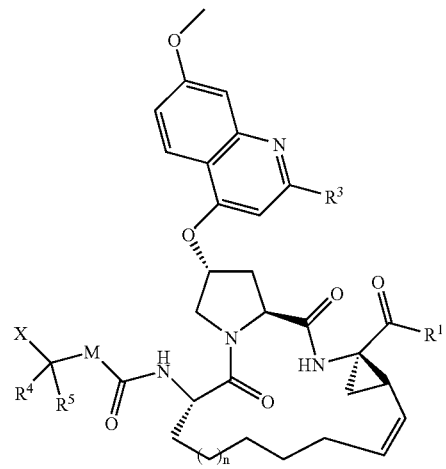

or a pharmaceutically acceptable salt, solvate or ester thereof, wherein,

M is O, N(H), or $CH_2$;

n is 0-4;

$R^1$ is —$OR^6$, —$NR^6R^7$ or

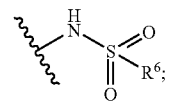

where $R^6$ and $R^7$ can be the same or different, each being independently selected from the group consisting of hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino and alkylamino;

$R^4$ and $R^5$ can be the same or different, each being independently selected from the group consisting of H, alkyl, aryl and cycloalkyl; or alternatively $R^4$ and $R^5$ together form part of a cyclic 5- to 7-membered ring such that the moiety

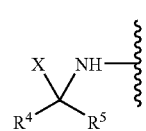

is represented by

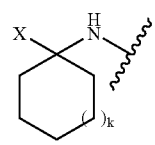

where k is 0 to 2;

X is selected from the group consisting of:

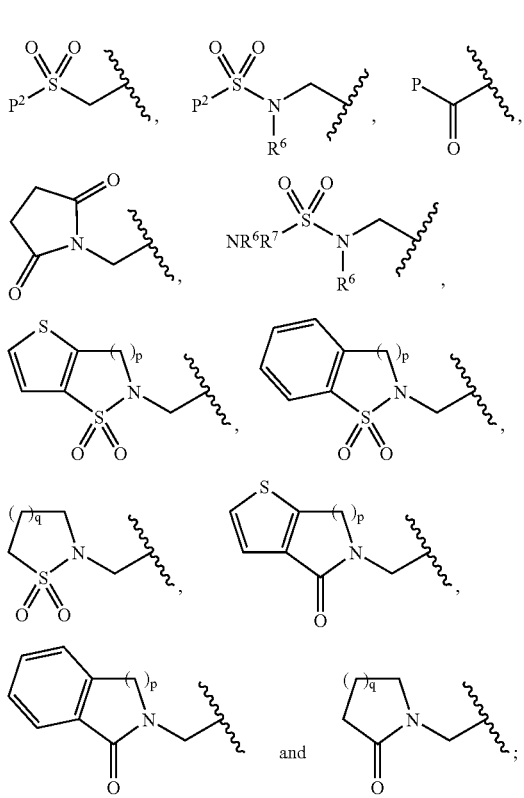

where p is 1 to 2, q is 1-3 and $P^2$ is alkyl, aryl, heteroaryl, heteroalkyl, cycloalkyl, dialkylamino, alkylamino, arylamino or cycloalkylamino; and $R^3$ is selected from the group consisting of: aryl, heterocyclyl, heteroaryl,

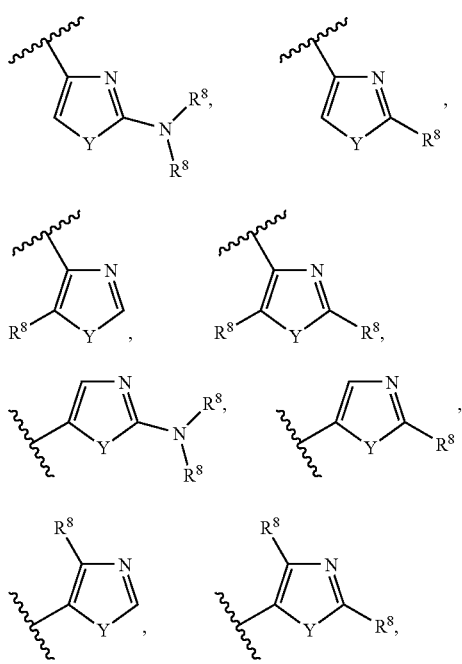

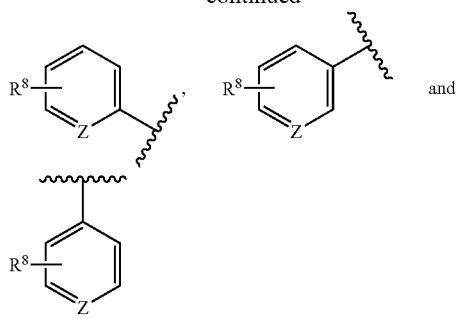

where Y is O, S or NH, and Z is CH or N, and the $R^8$ moieties can be the same or different, each $R^8$ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

In another embodiment, the "at least one compound" is a compound of formula formula VIII:

Formula VIII

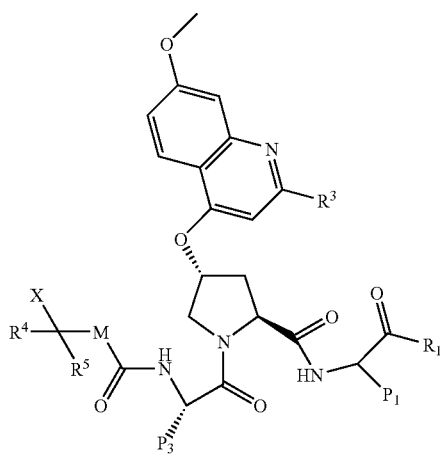

or a pharmaceutically acceptable salt, solvate or ester thereof, wherein,

M is O, N(H), or $CH_2$;

$R^1$ is —C(O)NHR$^6$, where $R^6$ is hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino or alkylamino;

$P_1$ is selected from the group consisting of alkyl, alkenyl, alkynyl, cycloalkyl haloalkyl;

$P_3$ is selected from the group consisting of alkyl, cycloalkyl, aryl and cycloalkyl fused with aryl;

$R^4$ and $R^5$ can be the same or different, each being independently selected from the group consisting of H, alkyl, aryl and cycloalkyl; or alternatively $R^4$ and $R^5$ together form part of a cyclic 5- to 7-membered ring such that the moiety

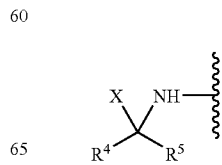

is represented by

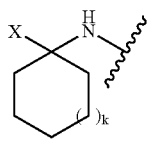

where k is 0 to 2;
X is selected from the group consisting of:

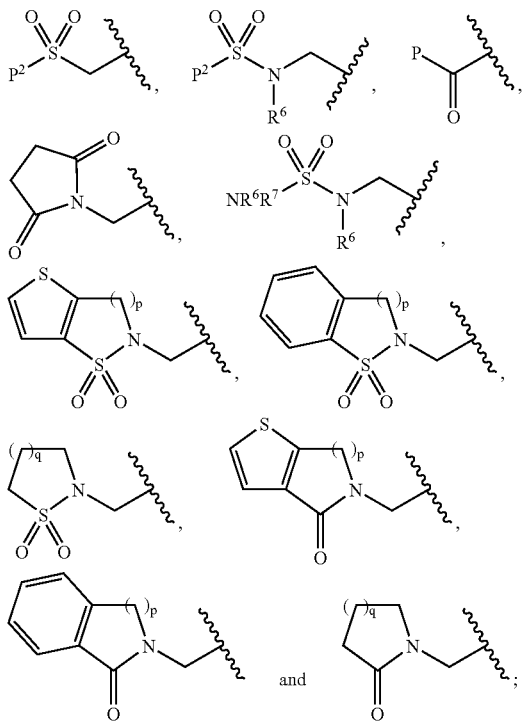

where p is 1 to 2, q is 1 to 3 and P² is alkyl, aryl, heteroaryl, heteroalkyl, cycloalkyl, dialkylamino, alkylamino, arylamino or cycloalkylamino; and R³ is selected from the group consisting of: aryl, heterocyclyl, heteroaryl,

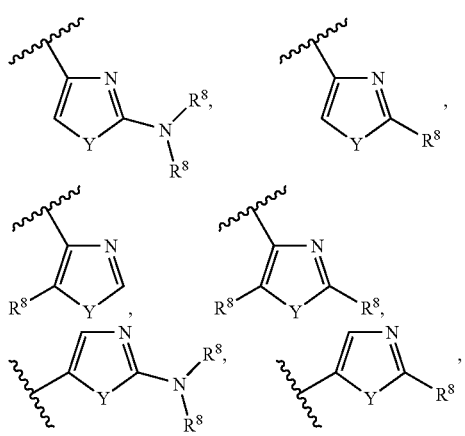

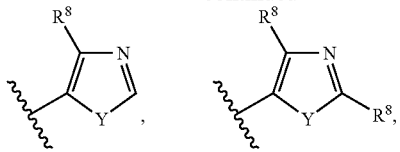

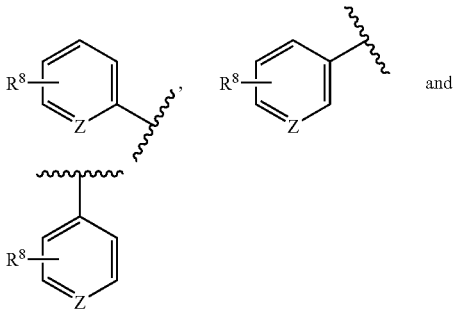

where Y is O, S or NH, and Z is CH or N, and the R⁸ moieties can be the same or different, each R⁸ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

In another embodiment, the "at least one compound" is a compound of formula IX:

Formula IX

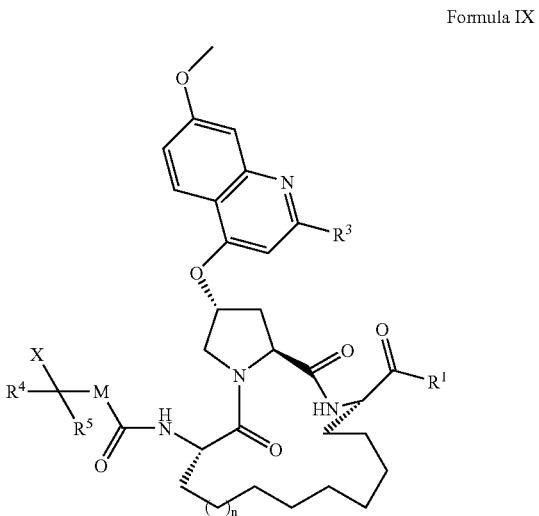

or a pharmaceutically acceptable salt, solvate or ester thereof, wherein,

M is O, N(H), or $CH_2$;
n is 0-4;
R¹ is —OR⁶, —NR⁶R⁷ or

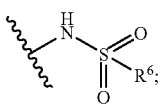

where R⁶ and R⁷ can be the same or different, each being independently selected from the group consisting of hydrogen, alkyl, alkenyl, alkynyl, heteroalkyl, cycloalkyl, cycloalkylalkyl, aryl, arylalkyl, heteroaryl, heteroarylalkyl, heterocyclyl, heterocyclylalkyl, hydroxyl, amino, arylamino and alkylamino;

$R^4$ and $R^5$ can be the same or different, each being independently selected from the group consisting of H, alkyl, aryl and cycloalkyl; or alternatively $R^4$ and $R^5$ together form part of a cyclic 5- to 7-membered ring such that the moiety

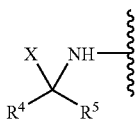

is represented by

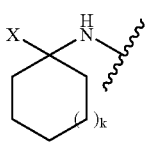

where k is 0 to 2;

X is selected from the group consisting of:

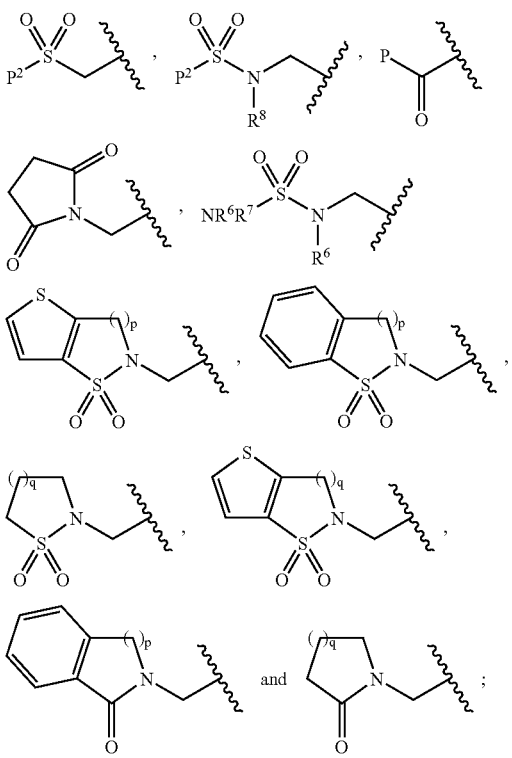

where p is 1 to 2, q is 1 to 3 and $P^2$ is alkyl, aryl, heteroaryl, heteroalkyl, cycloalkyl, dialkylamino, alkylamino, arylamino or cycloalkylamino; and $R^3$ is selected from the group consisting of: aryl, heterocyclyl, heteroaryl,

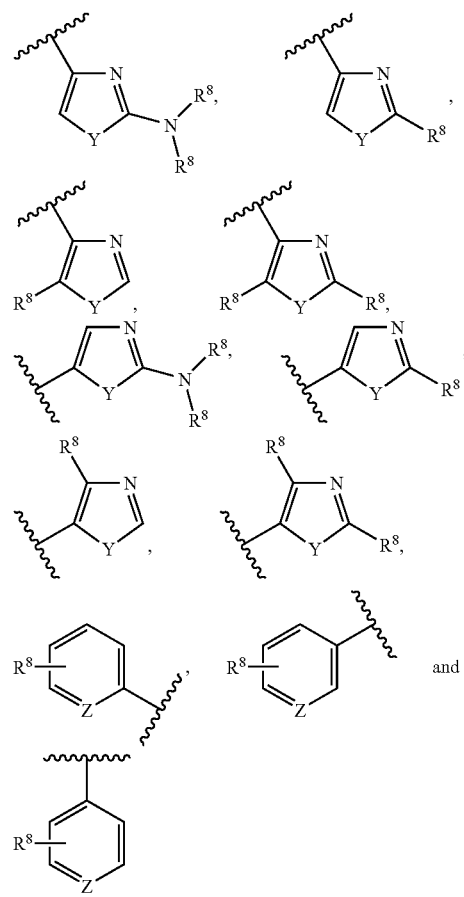

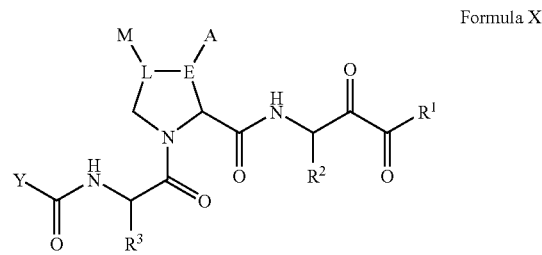

where Y is O, S or NH, and Z is CH or N, and the $R^8$ moieties can be the same or different, each $R^8$ being independently selected from the group consisting of hydrogen, alkyl, heteroalkyl, cycloalkyl, aryl, heteroaryl, heterocyclyl, hydroxyl, amino, arylamino, alkylamino, dialkylamino, halo, alkylthio, arylthio and alkyloxy.

In another embodiment, the "at least one compound" is a compound of formula X:

Formula X or a pharmaceutically acceptable salt, solvate or ester thereof; wherein:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, $SO_2R$, and halo; or A and M are connected to each other such that the moiety:

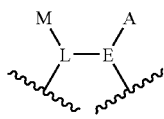

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), CH$_2$C(R), or C(R)CH$_2$;

R, R', R$^2$, and R$^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

and Y is selected from the following moieties:

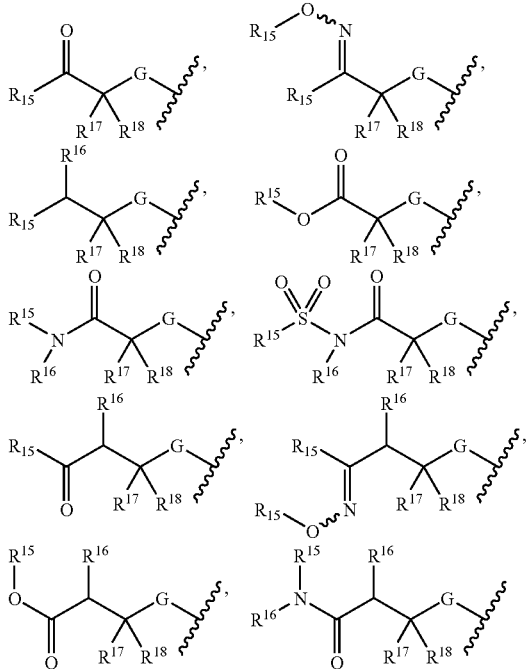

wherein G is NH or O; and R$^{15}$, R$^{16}$, R$^{17}$ and R$^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, R$^{15}$ and R$^{16}$ are connected to each other to form a four to eight-membered cycloalkyl, heteroaryl or heterocyclyl structure, and likewise, independently R$^{17}$ and R$^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In one embodiment, the "at least one compound" is a compound of Formula XI:

Formula XI

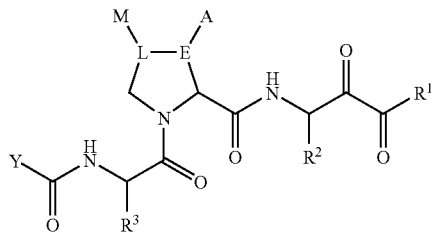

or a pharmaceutically acceptable salt, solvate or ester thereof; wherein:

R$^1$ is NHR$^9$, wherein R$^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, NR$^9$R$^{10}$, SR, SO$_2$R, and halo; or A and M are connected to each other (in other words, A-E-L-M taken together) such that the moiety:

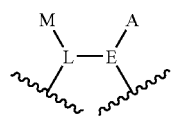

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), CH$_2$C(R), or C(R)CH$_2$;

R, R', R$^2$, and R$^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NR$^9$R$^{10}$ forms a four to eight-membered heterocyclyl;

Y is selected from the following moieties:

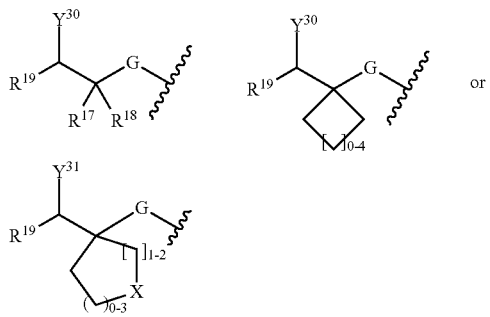

wherein $Y^{30}$ and $Y^{31}$ are selected from

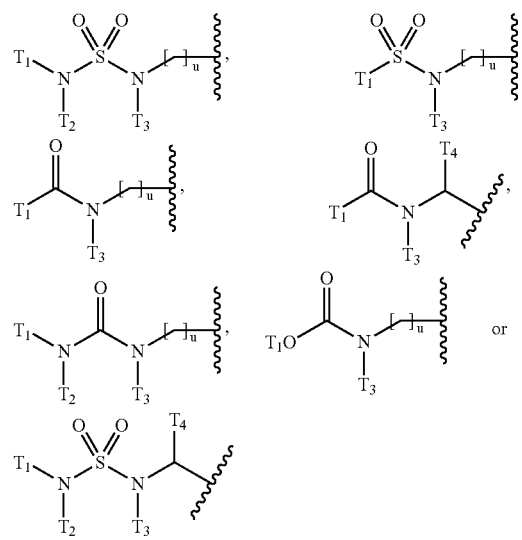

where u is a number 0-6;

where u is a number 0-6;

X is selected from O, $NR^{15}$, $NC(O)R^{16}$, S, S(O) and $SO_2$;

G is NH or O; and $R^{15}$, $R^{16}$, $R^{17}$, $R^{18}$, $R^{19}$, $T_1$, $T_2$, $T_3$ and $T_4$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the "at least one compound" is a compound of formula XII:

Formula XII

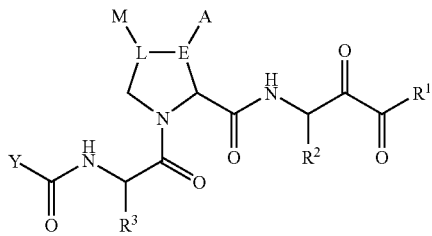

or a pharmaceutically acceptable salt, solvate or ester thereof; wherein:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, $SO_2R$, and halo; or A and M are connected to each other such that the moiety:

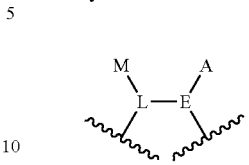

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

and Y is selected from the following moieties:

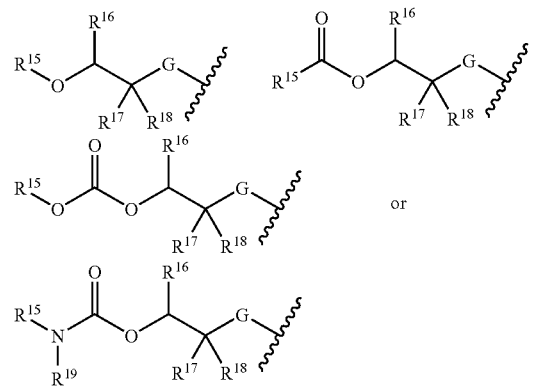

wherein G is NH or O; and $R^{15}$, $R^{16}$, $R^{17}$, $R^{18}$, and $R^{19}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, (i) either $R^{15}$ and $R^{16}$ are connected to each other to form a four to eight-membered cyclic structure, or $R^{15}$ and $R^{19}$ are connected to each other to form a four to eight-membered cyclic structure, and (ii) likewise, independently, $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, alkyl, aryl, heteroaryl, keto, carboxy, carbalkoxy, carboxamido, alkoxycarbonylamino, alkoxycarbonyloxy, alkylureido, arylureido, halo, cyano, and nitro.

In another embodiment, the "at least one compound" is a compound of Formula XIII:

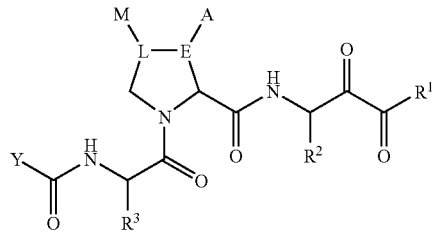

Formula XIII or a pharmaceutically acceptable salt, solvate or ester thereof; wherein:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, $SO_2R$, and halo; or A and M are connected to each other (in other words, A-E-L-M taken together) such that the moiety:

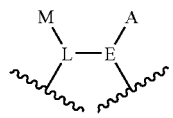

shown above in Formula I forms either a three, four, six, seven or eight-membered cycloalkyl, a four to eight-membered heterocyclyl, a six to ten-membered aryl, or a five to ten-membered heteroaryl;

E is C(H) or C(R);

L is C(H), C(R), $CH_2C(R)$, or $C(R)CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

and Y is selected from the following moieties:

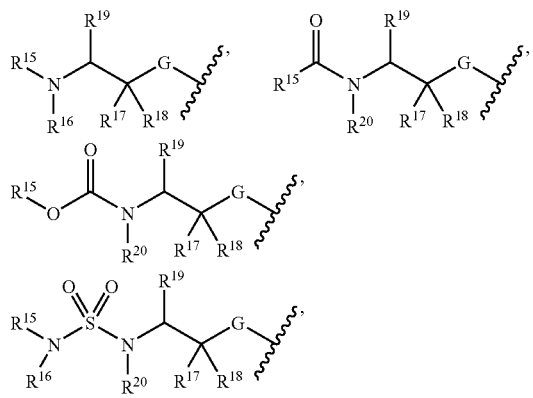

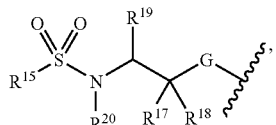

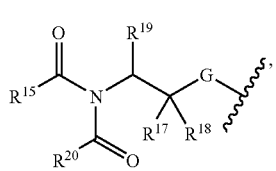

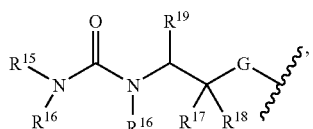

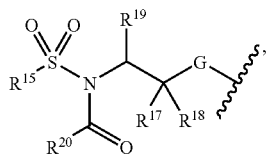

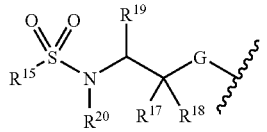

or

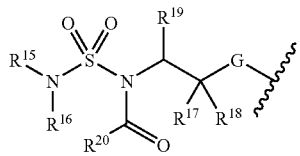

wherein G is NH or O, and $R^{15}$, $R^{16}$, $R^{17}R^{18}$, $R^{19}$ and $R^{20}$ can be the same or different, each being independently selected from the group consisting of H, $C_1$-$C_{10}$ alkyl, $C_1$-$C_{10}$ heteroalkyl, $C_2$-$C_{10}$ alkenyl, $C_2$-$C_{10}$ heteroalkenyl, $C_2$-$C_{10}$ alkynyl, $C_2$-$C_{10}$ heteroalkynyl, $C_3$-$C_8$ cycloalkyl, $C_3$-$C_8$ heterocyclyl, aryl, heteroaryl, or alternately: (i) either $R^{15}$ and $R^{16}$ can be connected to each other to form a four to eight-membered cycloalkyl or heterocyclyl, or $R^{15}$ and $R^{19}$ are connected to each other to form a five to eight-membered cycloalkyl or heterocyclyl, or $R^{15}$ and $R^{20}$ are connected to each other to form a five to eight-membered cycloalkyl or heterocyclyl, and (ii) likewise, independently, $R^{17}$ and $R^{18}$ are connected to each other to form a three to eight-membered cycloalkyl or heterocyclyl, wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the "at least one compound" is a compound of Formula XIV:

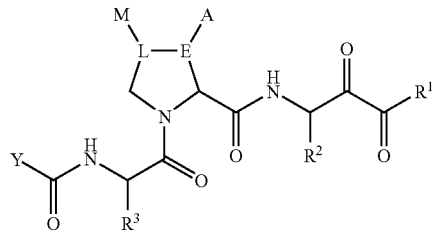

Formula XIV or a pharmaceutically acceptable salt, solvate or ester thereof; wherein:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, $SO_2R$, and halo;

or A and M are connected to each other such that the moiety:

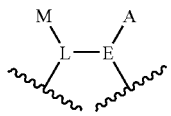

shown above in Formula I forms either a three, four, six, seven or eight-membered cycloalkyl, a four to eight-membered heterocyclyl, a six to ten-membered aryl, or a five to ten-membered heteroaryl;

E is C(H) or C=;

L is C(H), C=, $CH_2C$=, or C=$CH_2$;

R, R', $R^2$, and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately R and R' in NRR' are connected to each other such that NRR' forms a four to eight-membered heterocyclyl;

and Y is selected from the following moieties:

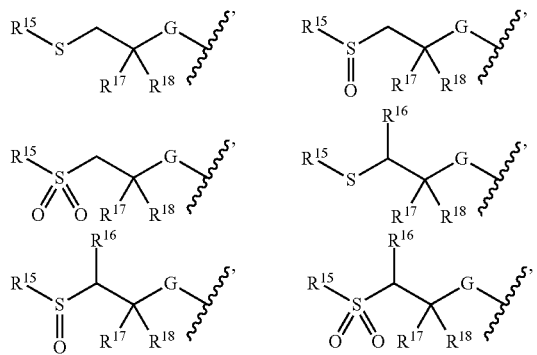

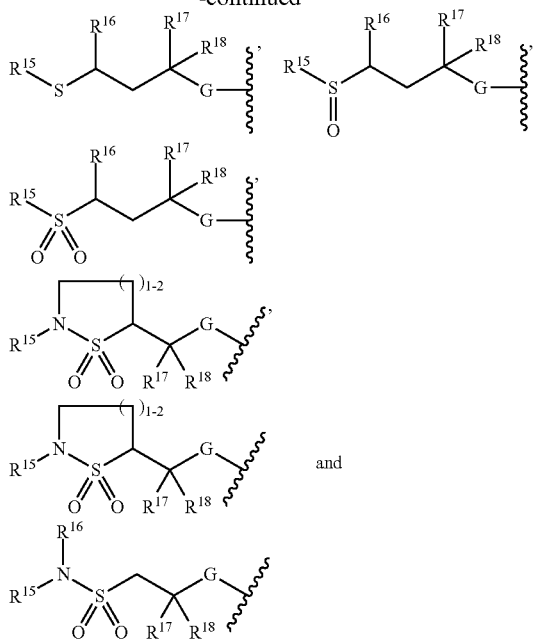

wherein G is NH or O; and $R^{15}$, $R^{16}$, $R^{17}$ and $R^{18}$ can be the same or different, each being independently selected from the group consisting of H, alkyl, heteroalkyl, alkenyl, heteroalkenyl, alkynyl, heteroalkynyl, cycloalkyl, heterocyclyl, aryl, and heteroaryl, or alternately, (i) $R^{15}$ and $R^{16}$ are connected to each other to form a four to eight-membered cyclic structure, and (ii) likewise, independently $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkylsulfonamido, arylsulfonamido, alkyl, aryl, heteroaryl, keto, carboxy, carbalkoxy, carboxamido, alkoxycarbonylamino, alkoxycarbonyloxy, alkylureido, arylureido, halo, cyano, and nitro.

In another embodiment, the "at least one compound" is a compound of Formula XV:

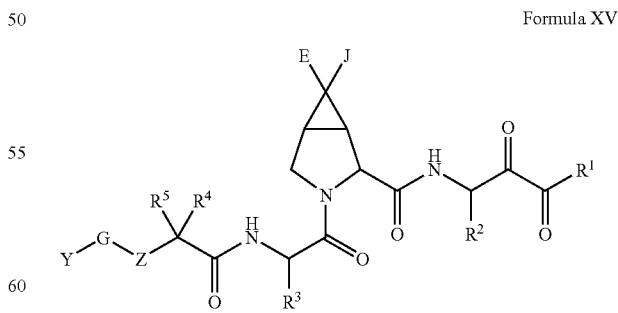

Formula XV or a pharmaceutically acceptable salt, solvate or ester thereof; wherein:

$R^1$ is $NHR^9$, wherein $R^9$ is H, alkyl-, aryl-, heteroalkyl-, heteroaryl-, cycloalkyl-, cycloalkyl-, arylalkyl-, or heteroarylalkyl;

E and J can be the same or different, each being independently selected from the group consisting of R, OR, NHR, NRR⁷, SR, halo, and S(O₂)R, or E and J can be directly connected to each other to form either a three to eight-membered cycloalkyl, or a three to eight-membered heterocyclyl moiety;

Z is N(H), N(R), or O, with the proviso that when Z is O, G is present or absent and if G is present with Z being O, then G is C(=O);

G maybe present or absent, and if G is present, G is C(=O) or S(O₂), and when G is absent, Z is directly connected to Y;

Y is selected from the group consisting of:

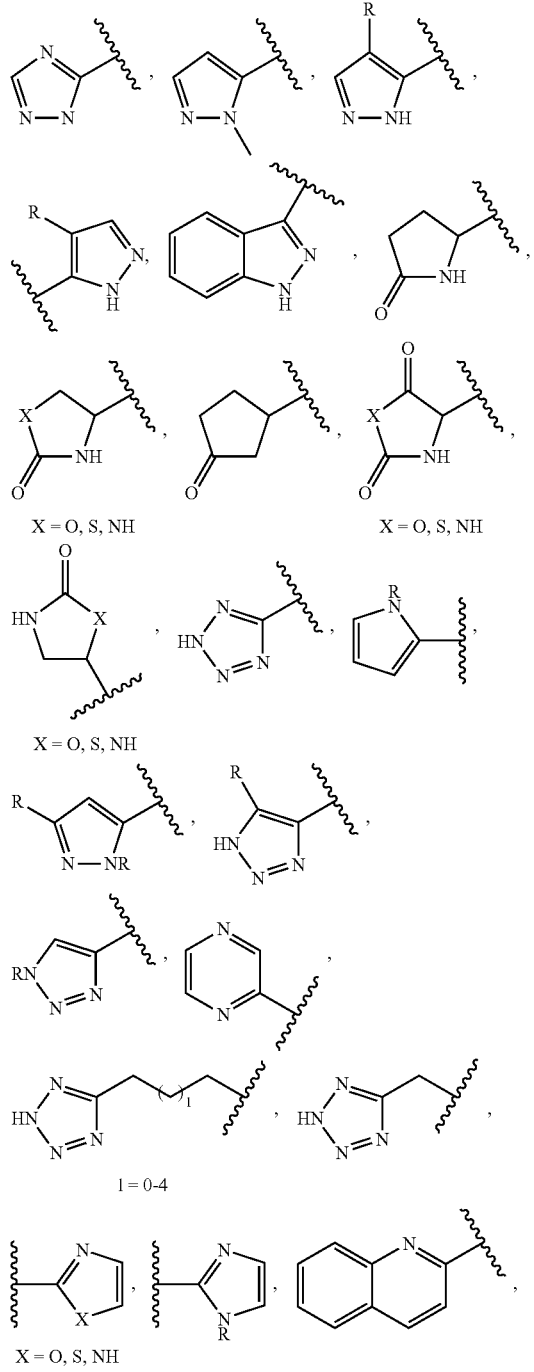

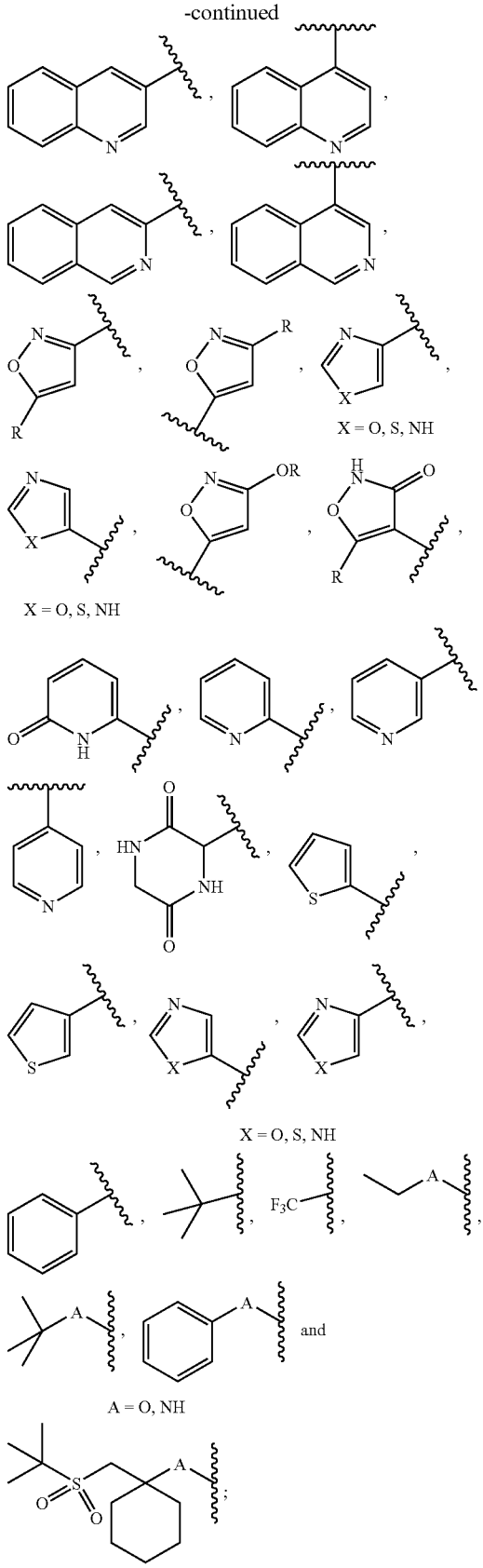

R, R⁷, R², R³, R⁴ and R⁵ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-, wherein each of said heteroalkyl, heteroaryl and heterocyclyl independently has one to six oxygen, nitrogen, sulfur, or phosphorus atoms;

wherein each of said alkyl, heteroalkyl, alkenyl, alkynyl, aryl, heteroaryl, cycloalkyl and heterocyclyl moieties can be unsubstituted or optionally independently substituted with one or more moieties selected from the group consisting of alkyl, alkenyl, alkynyl, aryl, aralkyl, cycloalkyl, heterocyclyl, halo, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate.

In another embodiment, the "at least one compound" is a compound of Formula XVI:

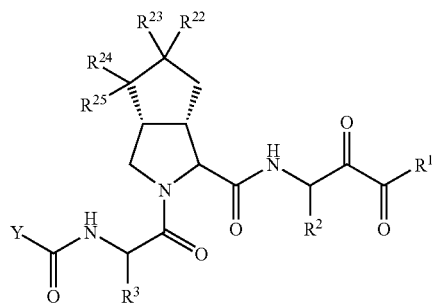

Formula XVI or a pharmaceutically acceptable salt, solvate or ester thereof; wherein:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

$R^2$ and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl;

Y is selected from the following moieties:

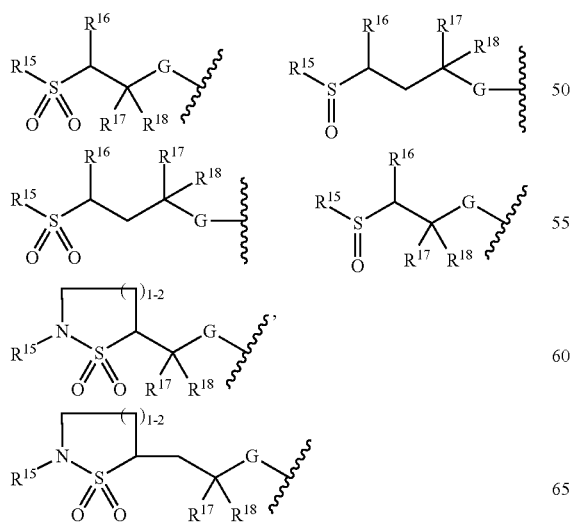

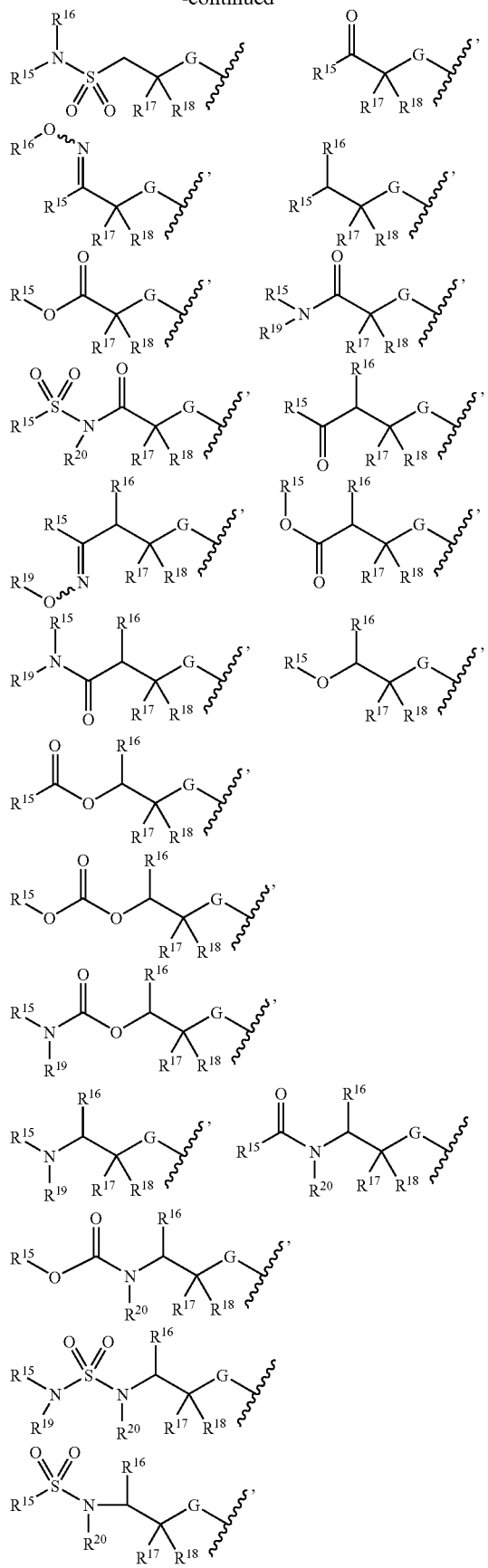

-continued

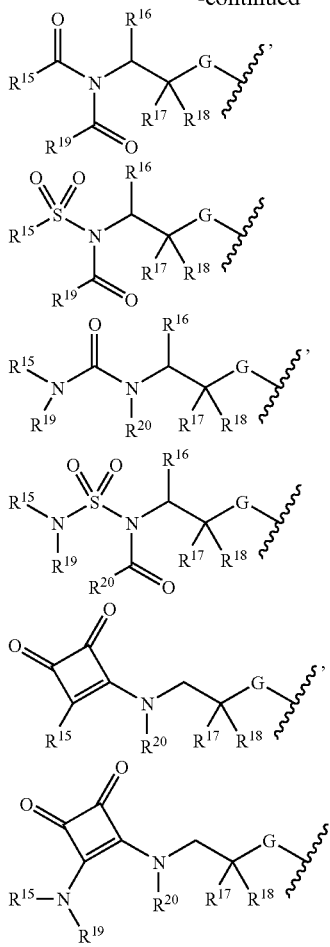

wherein G is NH or O; and $R^{15}$, $R^{16}$, $R^{17}$, $R^{18}$, $R^{19}$, $R^{20}$, $R^{21}$, $R^{22}$, $R^{23}$, $R^{24}$ and $R^{25}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; (iv) likewise independently $R^{15}$ and $R^{20}$ are connected to each other to form a four to eight-membered heterocyclyl; (v) likewise independently $R^{22}$ and $R^{23}$ are connected to each other to form a three to eight-membered cycloalkyl or a four to eight-membered heterocyclyl; and (vi) likewise independently $R^{24}$ and $R^{25}$ are connected to each other to form a three to eight-membered cycloalkyl or a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the "at least one compound" is a compound of Formula XVII:

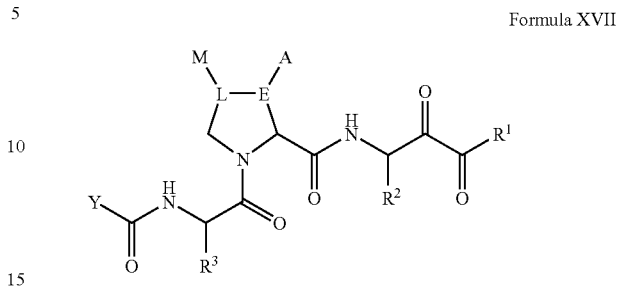

Formula XVII or a pharmaceutically acceptable salt, solvate or ester thereof; wherein:

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

A and M can be the same or different, each being independently selected from R, OR, NHR, NRR', SR, $SO_2R$, and halo; or A and M are connected to each other such that the moiety:

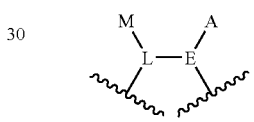

shown above in Formula I forms either a three, four, six, seven or eight-membered cycloalkyl, a four to eight-membered heterocyclyl, a six to ten-membered aryl, or a five to ten-membered heteroaryl;

E is C(H) or C=;

L is C(H), C=, $CH_2C=$, or $C=CH_2$;

R, R', $R^2$, and $R^3$ can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in NRR' are connected to each other such that NRR' forms a four to eight-membered heterocyclyl;

Y is selected from the following moieties:

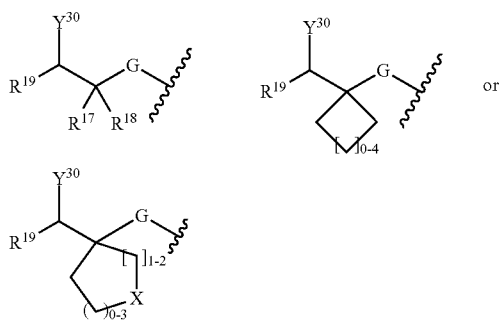

wherein $Y^{30}$ is selected from

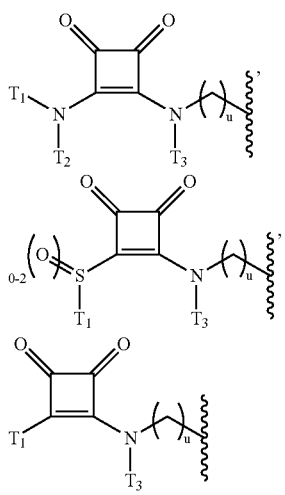

where u is a number 0-1;
X is selected from O, $NR^{15}$, $NC(O)R^{16}$, S, S(O) and $SO_2$;
G is NH or O; and
$R^{15}$, $R^{16}$, $R^{17}$, $R^{18}$, $R^{19}$, $T_1$, $T_2$, and $T_3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately, $R^{17}$ and $R^{18}$ are connected to each other to form a three to eight-membered cycloalkyl or heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the inhibitor is a compound of Formula XVIII:

Formula XVIII

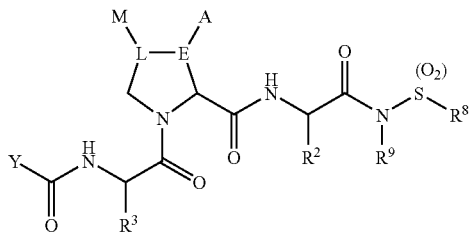

or a pharmaceutically acceptable salt, solvate or ester thereof, wherein:
$R^8$ is selected from the group consisting of alkyl-, aryl-, heteroalkyl-, heteroaryl-, cycloalkyl-, heterocyclyl-, arylalkyl-, heteroarylalkyl-, and heterocyclylalkyl;
$R^9$ is selected from the group consisting of H, alkyl, alkenyl, alkynyl, aryl and cycloalkyl;
A and M can be the same or different, each being independently selected from R, OR, N(H)R, N(RR'), SR, $S(O_2)R$, and halo; or A and M are connected to each other (in other words, A-E-L-M taken together) such that the moiety:

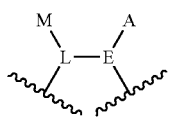

shown above in Formula I forms either a three, four, five, six, seven or eight-membered cycloalkyl, a four to eight-membered heterocyclyl, a six to ten-membered aryl, or a five to ten-membered heteroaryl;
E is C(H) or C(R);
L is C(H), C(R), $CH_2C(R)$, or $C(R)CH_2$;
R and R' can be the same or different, each being independently selected from the group consisting of H, alkyl-, alkenyl-, alkynyl-, cycloalkyl-, heteroalkyl-, heterocyclyl-, aryl-, heteroaryl-, (cycloalkyl)alkyl-, (heterocyclyl)alkyl-, aryl-alkyl-, and heteroaryl-alkyl-; or alternately R and R' in N(RR') are connected to each other such that N(RR') forms a four to eight-membered heterocyclyl;
$R^2$ and $R^3$ can be the same or different, each being independently selected from the group consisting of H, alkyl, heteroalkyl, alkenyl, heteroalkenyl, alkynyl, heteroalkynyl, cycloalkyl, spiro-linked cycloalkyl, heterocyclyl, aryl, arylalkyl, heteroaryl, and heteroarylalkyl;
Y is selected from the following moieties:

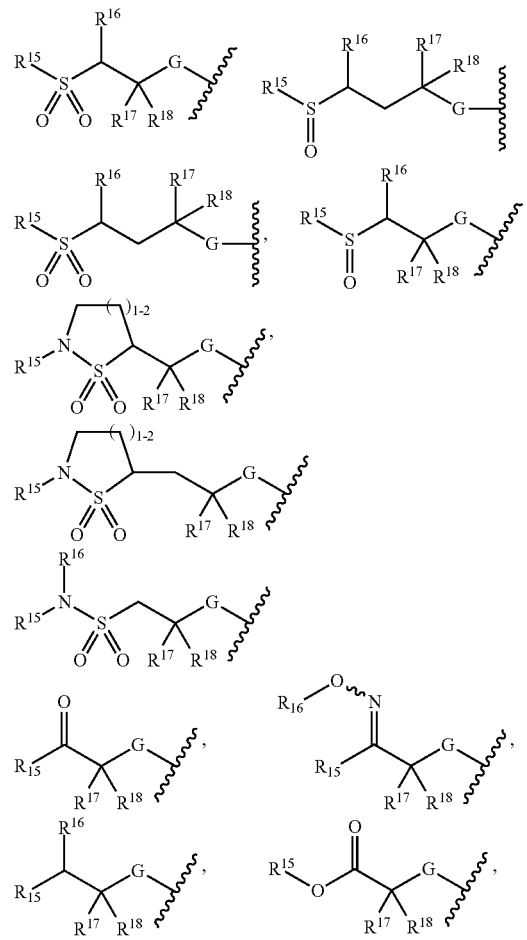

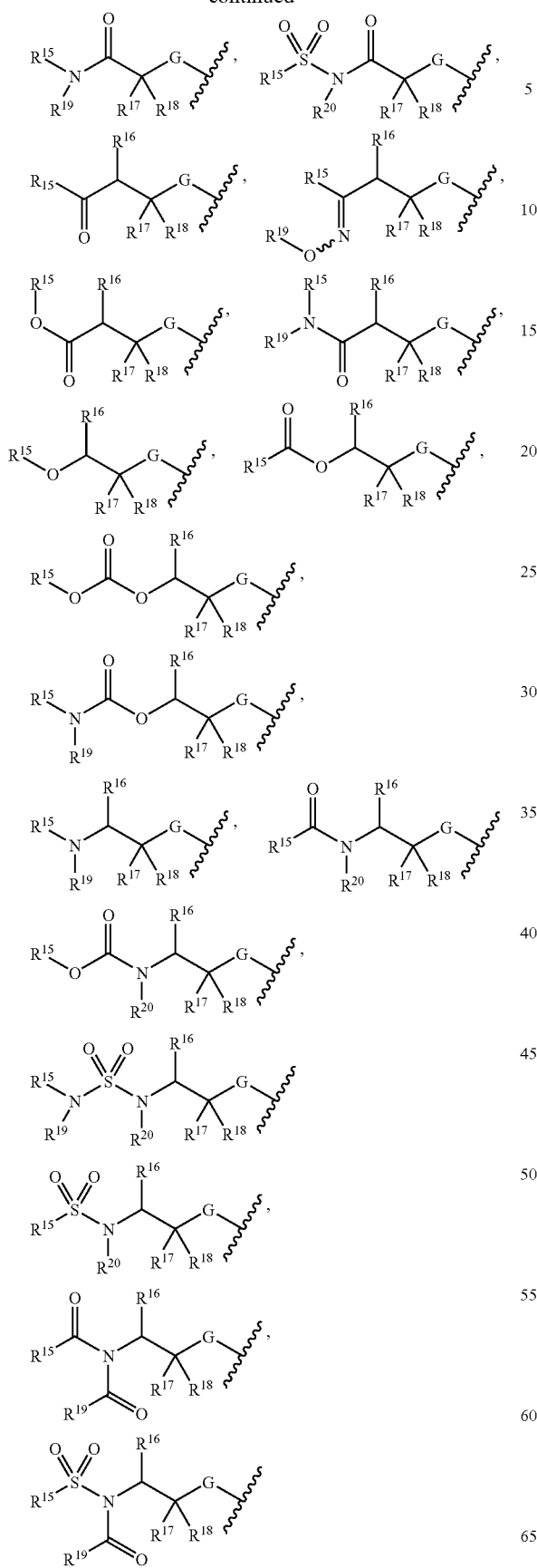

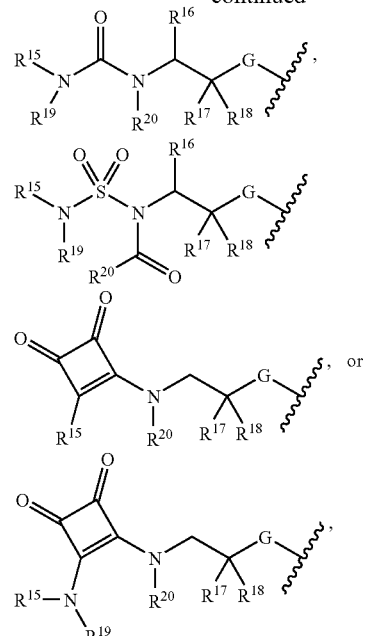

wherein G is NH or O; and $R^{15}$, $R^{16}$, $R^{17}$, $R^{18}$, $R^{19}$ and $R^{20}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl, spirolinked cycloalkyl, and heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, alkenyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, the "at least one compound" is a compound of Formula XIX:

Formula XIX

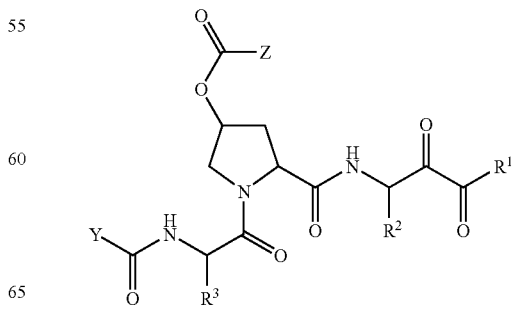

wherein:

Z is selected from the group consisting of a heterocyclyl moiety, N(H)(alkyl), —N(alkyl)$_2$, —N(H)(cycloalkyl), —N(cycloalkyl)$_2$, —N(H)(aryl, —N(aryl)$_2$, —N(H)(heterocyclyl), —N(heterocyclyl)$_2$, —N(H)(heteroaryl), and —N(heteroaryl)$_2$;

$R^1$ is $NHR^9$, wherein $R^9$ is H, alkyl-, alkenyl-, alkynyl-, aryl-, heteroalkyl-, heteroaryl-, cycloalkyl-, heterocyclyl-, arylalkyl-, or heteroarylalkyl;

$R^2$ and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl;

Y is selected from the following moieties:

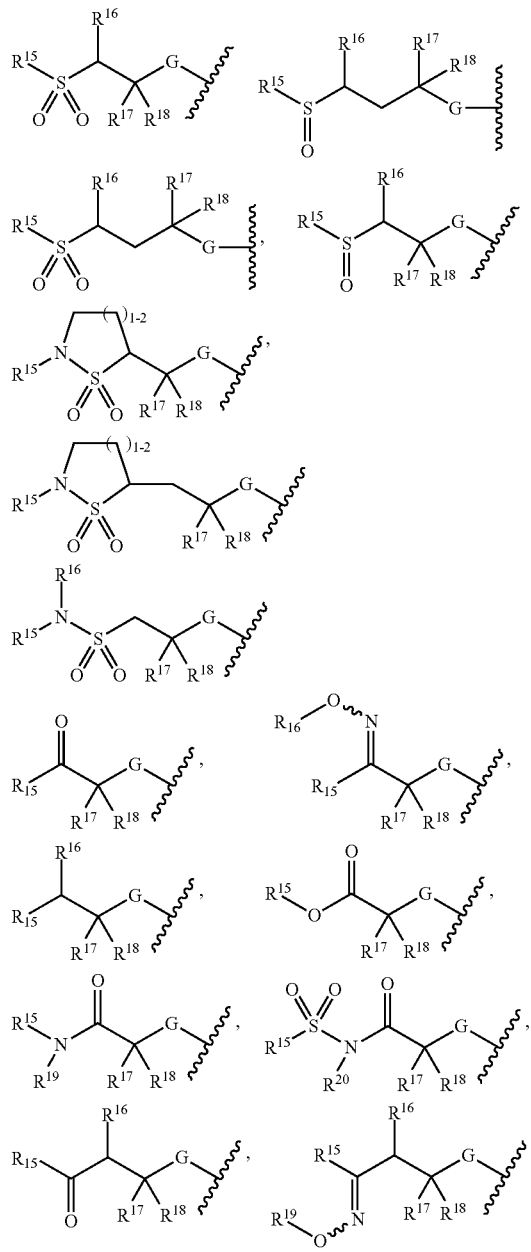

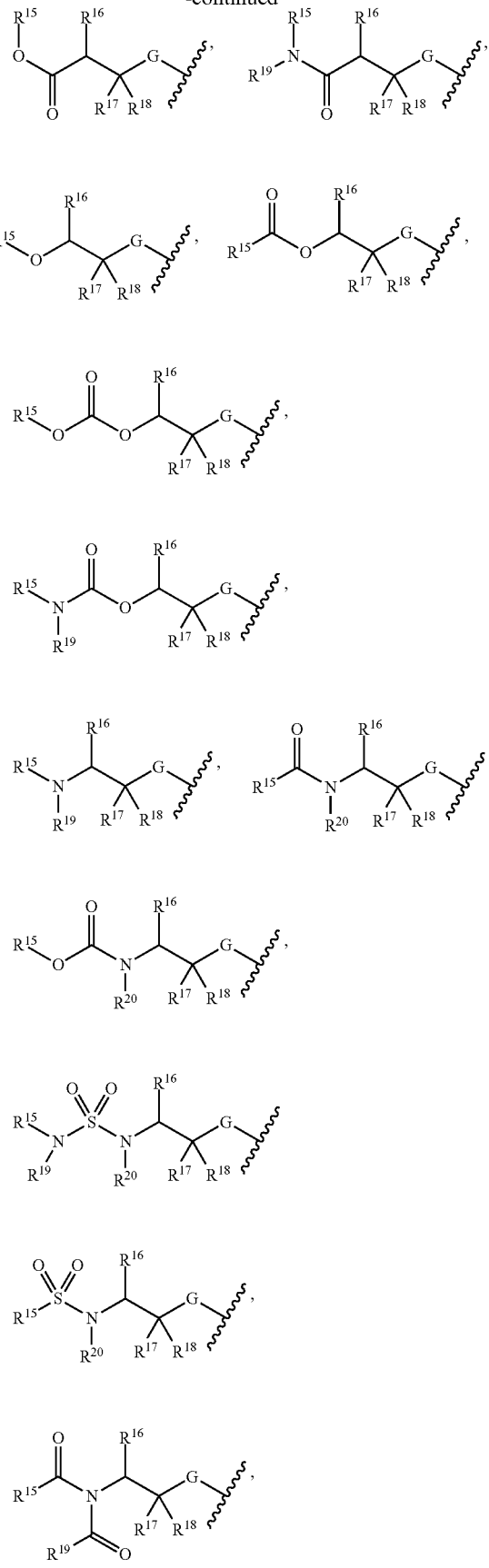

45

-continued

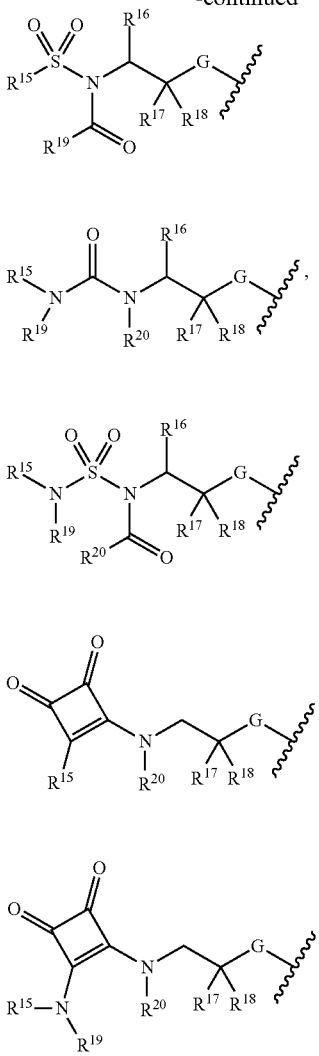

wherein G is NH or O; and $R^{15}, R^{16}, R^{17}, R^{18}, R^{19}, R^{20}$ and $R^{21}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are indenpendently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

46

In another embodiment, the inhibitor is a compound of Formula XX

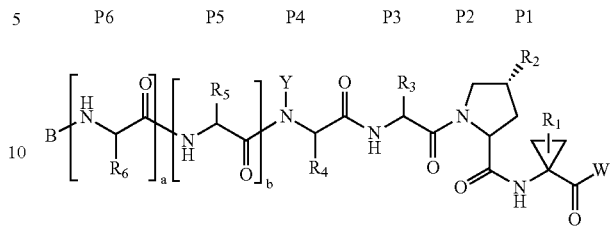

or a pharmaceutically acceptable salt, solvate or ester thereof; wherein: a is 0 or 1; b is 0 or 1; Y is H or $C_{1-6}$ alkyl;

B is H, an acyl derivative of formula $R_7$—C(O)— or a sulfonyl of formula $R_7$—SO2 wherein R7 is (i) $C_{I-10}$ alkyl optionally substituted with carboxyl, $C_{1-6}$ alkanoyloxy or $C_{1-6}$ alkoxy;

(ii) $C_{3-7}$ cycloalkyl optionally substituted with carboxyl, ($C_{I-6}$ alkoxy)carbonyl or phenylmethoxycarbonyl;

(iii) $C_6$ or $C_{10}$ aryl or $C_{7-16}$ aralkyl optionally substituted with $C_{1-6}$ alkyl, hydroxy, or amino optionally substituted with $C_{1-6}$ alkyl; or (iv) Het optionally substituted with $C_{1-6}$ alkyl, hydroxy, amino optionally substituted with $C_{1-6}$ alkyl, or amido optionally substituted with $C_{1-6}$ alkyl;

$R_6$, when present, is $C_{1-6}$ alkyl substituted with carboxyl;

$R_5$, when present, is $C_{1-6}$ alkyl optionally substituted with carboxyl;

$R_4$ is $C_{1-10}$ alkyl, $C_{3-7}$ cycloalkyl or $C_{4-10}$ (alkylcycloalkyl);

$R_3$ is $C_{1-10}$ alkyl, $C_{3-7}$ cycloalkyl or $C_{4-10}$ (alkylcycloalkyl);

$R_2$ is $CH_2$—$R_{20}$, NH—$R_{20}$, O—$R_{20}$ or S—$R_{20}$, wherein $R_{20}$ is a saturated or unsaturated $C_{3-7}$ cycloalkyl or $C_{4-10}$ (alkyl cycloalkyl) being optionally mono-, di- or tri-substituted with $R_{21}$, or $R_{20}$ is a $C_6$ or $C_{10}$ aryl or $C_{7-16}$ aralkyl optionally mono-, di- or tri-substituted with $R_{21}$, or $R_{20}$ is Het or (lower alkyl)-Het optionally mono-, di- or tri-substituted with $R_{21}$, wherein each $R_{21}$ is independently $C_{1-6}$ alkyl; $C_{1-6}$alkoxy; amino optionally mono- or di-substituted with $C_{1-6}$ alkyl; sulfonyl; $NO_2$; OH; SH; halo; haloalkyl; amido optionally mono-substituted with $C_{1-6}$ alkyl, $C_6$ or $C_{10}$ aryl, $C_{7-16}$ aralkyl, Het or (lower alkyl)-Het; carboxyl; carboxy(lower alkyl); $C_6$ or $C_{10}$ aryl, $C_{7-16}$ aralkyl or Het, said aryl, aralkyl or Het being optionally substituted with $R_{22}$;

wherein $R_{22}$ is $C_{1-6}$alkyl; $C_{1-6}$ alkoxy; amino optionally mono- or di-substituted with $C_{1-6}$ alkyl; sulfonyl; $N0_2$; OH; SH; halo; haloalkyl; carboxyl; amide or (lower alkyl)amide;

$R_1$ is $C_{1-6}$ alkyl or $C_{2-6}$ alkenyl optionally substituted with halogen; and W is hydroxy or a N-substituted amino.

In the above-shown structure of the compound of Formula XX, the terms P6, P5, P4, P3, P2 and P1 denote the respective amino acid moieties as is conventionally known to those skilled in the art.

In another embodiment, the inhibitor is a compound of Formula XXI

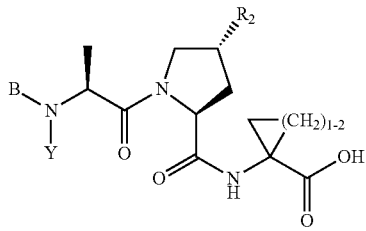

Formula XXI or a pharmaceutically acceptable salt, solvate or ester thereof; wherein:

B is H, a $C_6$ or $C_{10}$ aryl, $C_{7-16}$ aralkyl; Het or (lower alkyl)-Het, all of which optionally substituted with $C_{1-6}$ alkyl; $C_{1-6}$ alkoxy; $C_{1-6}$ alkanoyl; hydroxy; hydroxyalkyl; halo; haloalkyl; nitro; cyano; cyanoalkyl; amino optionally substituted with $C_{1-6}$ alkyl; amido; or (lower alkyl)amide;

or B is an acyl derivative of formula $R_4$—C(O)—; a carboxyl of formula $R_4$-0-C(O)—; an amide of formula $R_4$—N($R_5$)—C(O)—; a thioamide of formula $R_4$—N($R_5$)—C(S)—; or a sulfonyl of formula $R_4$—SO2 wherein $R_4$ is (i) $C_{1-10}$ alkyl optionally substituted with carboxyl, $C_{1-6}$ alkanoyl, hydroxy, $C_{1-6}$ alkoxy, amino optionally mono- or di-substituted with $C_{1-6}$ alkyl, amido, or (lower alkyl)amide;

(ii) $C_{3-7}$ cycloalkyl, $C_{3-7}$ cycloalkoxy, or $C_{4-10}$ alkylcycloalkyl, all optionally substituted with hydroxy, carboxyl, ($C_{1-6}$ alkoxy)carbonyl, amino optionally mono- or di-substituted with $C_{1-6}$ alkyl, amido, or (lower alkyl) amide;

(iii) amino optionally mono- or di-substituted with $C_{1-6}$ alkyl; amido; or (lower alkyl)amide;

(iv) $C_6$ or $C_{10}$ aryl or $C_{7-16}$ aralkyl, all optionally substituted with $C_{1-6}$ alkyl, hydroxy, amido, (lower alkyl)amide, or amino optionally mono- or di-substituted with $C_{1-6}$ alkyl; or (v) Het or (lower alkyl)-Het, both optionally substituted with $C_{1-6}$ alkyl, hydroxy, amido, (lower alkyl) amide, or amino optionally mono- or di-substituted with $C_{1-6}$ alkyl;

$R_5$ is H or $C_{1-6}$ alkyl;

with the proviso that when $R_4$ is an amide or a thioamide, $R_4$ is not (ii) a cycloalkoxy;

Y is H or $C_{1-6}$ alkyl;

$R_3$ is $C_{1-8}$ alkyl, $C_{3-7}$ cycloalkyl, or $C_{4-10}$ alkylcycloalkyl, all optionally substituted with hydroxy, $C_{1-6}$ alkoxy, $C_{1-6}$ thioalkyl, amido, (lower alkyl)amide, $C_6$ or $C_{10}$ aryl, or $C_{7-16}$ aralkyl;

$R_2$ is $CH_2$—$R_{20}$, NH—$R_{20}$, O—$R_{20}$ or S—$R_{20}$, wherein $R_{20}$ is a saturated or unsaturated $C_{3-7}$ cycloalkyl or $C_{4-10}$ (alkylcycloalkyl), all of which being optionally mono-, di- or tri-substituted with $R_{21}$, or $R_{20}$ is a $C_6$ or $C_{10}$ aryl or $C_{7-14}$ aralkyl, all optionally mono-, di- or tri-substituted with $R_{21}$, or $R_{20}$ is Het or (lower alkyl)-Het, both optionally mono-, di- or tri-substituted with $R_{21}$, wherein each $R_{21}$ is independently $C_{1-6}$ alkyl; $C_{1-6}$ alkoxy; lower thioalkyl; sulfonyl; $NO_2$; OH; SH; halo; haloalkyl; amino optionally mono- or di-substituted with $C_{1-6}$ alkyl, $C_6$ or $C_{10}$ aryl, $C_{7-14}$ aralkyl, Het or (lower alkyl)-Het; amido optionally mono-substituted with $C_{1-6}$ alkyl, $C_6$ or $C_{10}$ aryl, $C_{7-14}$ aralkyl, Het or (lower alkyl)-Het; carboxyl; carboxy (lower alkyl); $C_6$ or $C_{10}$ aryl, $C_{7-14}$ aralkyl or Het, said aryl, aralkyl or Het being optionally substituted with $R_{22}$;

wherein $R_{22}$ is $C_{1-6}$ alkyl; $C_{3-7}$ cycloalkyl; $C_{1-6}$ alkoxy; amino optionally mono- or di-substituted with $C_{1-6}$ alkyl; sulfonyl; (lower alkyl)sulfonyl; $NO_2$; OH; SH; halo; haloalkyl; carboxyl; amide; (lower alkyl)amide; or Het optionally substituted with $C_{1-6}$ alkyl;

R1 is H; $C_{1-6}$ alkyl, $C_{3-7}$ cycloalkyl, $C_{2-6}$ alkenyl, or $C_{2-6}$ alkynyl, all optionally substituted with halogen.

In another embodiment, the inhibitor is a compound of Formula XXII

(XXII)

or a pharmaceutically acceptable salt, solvate or ester thereof; wherein

W is CH or N, $R^{21}$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl;

$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_{6\ or\ 10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^{24}$, wherein $R^{24}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{25})_2$, NH—C(O)—$R^{25}$ or NH—C(O)—NH—$R^{25}$, wherein each $R^{25}$ is independently: H, $C_{1-6}$ alkyl or $C_{3-6}$ cycloalkyl; or $R^{24}$ is NH—C(O)—$OR^{26}$ wherein $R^{26}$ is $C_{1-6}$ alkyl or $C_{3-6}$ cycloalkyl;

$R^3$ is hydroxy, $NH_2$, or a group of formula —NH—$R^{31}$, wherein $R^{31}$ is $C_{6\ or\ 10}$ aryl, heteroaryl, —C(O)—$R^{32}$, —C(O)—$NHR^{32}$ or —C(O)—$OR^{32}$, wherein $R^{32}$ is $C_{1-6}$ alkyl or $C_{3-6}$ cycloalkyl;

D is a 5 to 10-atom saturated or unsaturated alkylene chain optionally containing one to three heteroatoms independently selected from: O, S, or N—$R^{41}$, wherein $R^{41}$ is H, $C_{1-6}$ alkyl, $C_{3-6}$ cycloalkyl or —C(O)—$R^{42}$, wherein $R^{42}$ is $C_{1-6}$ alkyl, $C_{3-6}$ cycloalkyl or $C_{6\ or\ 10}$ aryl; $R^4$ is H or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio and $C_{1-6}$ thioalkyl, and A is an amide of formula —C(O)—NH—$R^5$, wherein $R^5$ is selected from the group consisting of: $C_{1-8}$ alkyl, $C_{3-6}$ cycloalkyl, $C_{6\ or\ 10}$ aryl and $C_{7-16}$ aralkyl;

or A is a carboxylic acid.

In another embodiment, the "at least one compound" is a compound of formula XXIII:

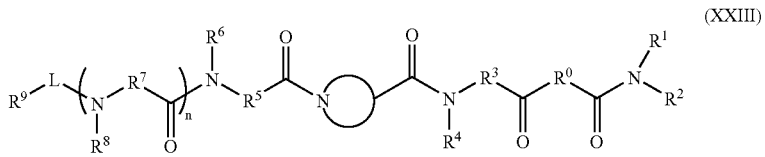

a pharmaceutically acceptable salt, solvate or ester thereof; wherein:
$R^0$ is a bond or difluoromethylene;
$R^1$ is hydrogen;
$R^2$ and $R^9$ are each independently optionally substituted aliphatic group, optionally substituted cyclic group or optionally substituted aromatic group;
R3, R5 and R7 are each independently:
optionally substituted (1,1- or 1,2-)cycloalkylene; or
optionally substituted (1,1- or 1,2-)heterocyclylene; or
methylene or ethylene), substituted with one substituent selected from the group consisting of an optionally substituted aliphatic group, an optionally substituted cyclic group or an optionally substituted aromatic group, and wherein the methylene or ethylene is further optionally substituted with an aliphatic group substituent; or; R4, R6, R8 and $R^{10}$ are each independently hydrogen or optionally substituted aliphatic group;

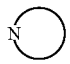

is substituted monocyclic azaheterocyclyl or optionally substituted multicyclic azaheterocyclyl, or optionally substituted multicyclic azaheterocyclenyl wherein the unsaturatation is in the ring distal to the ring bearing the $R^9$-L-(N($R^8$)—$R^7$—C(O)—)$_n$N($R^6$)—$R^5$—C(O)—N moiety and to which the —C(O)—N($R^4$)—$R^3$—C(O)C(O)N$R^2R^1$ moiety is attached;
L is —C(O)—, —OC(O)—, —N$R^{10}$C(O)—, —S(0)$_2$—, or —N$R^{10}$S(0)$_2$—; and n is 0 or 1,
provided
when

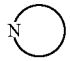

is substituted

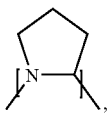

then L is —OC(O)— and $R^9$ is optionally substituted aliphatic; or at least one of $R^3$, $R^5$ and $R^7$ is ethylene, substituted with one substituent selected from the group consisting of an optionally substituted aliphatic group, an optionally substituted cyclic group or an optionally substituted aromatic group and wherein the ethylene is further optionally substituted with an aliphatic group substituent; or $R^4$ is optionally substituted aliphatic.

In another embodiment, the "at least one compound" is a compound of formula (XXIV):

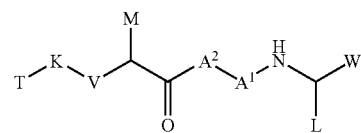

or a pharmaceutically acceptable salt, solvate or ester thereof; wherein:
W is:

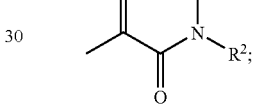

m is 0 or 1;
$R^2$ is hydrogen, alkyl, alkenyl, aryl, aralkyl, aralkenyl, cycloalkyl, cycloalkylalkyl, cycloalkenyl, cycloalkenylalkyl, heterocyclyl, heterocyclylalkyl, heterocyclylalkenyl, heteroaryl, or heteroaralkyl; wherein any $R^2$ carbon atom is optionally substituted with J;
J is alkyl, aryl, aralkyl, alkoxy, aryloxy, aralkoxy, cycloalkyl, cycloalkoxy, heterocyclyl, heterocyclyloxy, heterocyclylalkyl, keto, hydroxy, amino, alkylamino, alkanoylamino, aroylamino, aralkanoylamino, carboxy, carboxyalkyl, carboxamidoalkyl, halo, cyano, nitro, formyl, acyl, sulfonyl, or sulfonamido and is optionally substituted with 1-3 $J^1$ groups;
$J^1$ is alkyl, aryl, aralkyl, alkoxy, aryloxy, heterocyclyl, heterocyclyloxy, keto, hydroxy, amino, alkanoylamino, aroylamino, carboxy, carboxyalkyl, carboxamidoalkyl, halo, cyano, nitro, formyl, sulfonyl, or sulfonamido;
L is alkyl, alkenyl, or alkynyl, wherein any hydrogen is optionally substituted with halogen, and wherein any hydrogen or halogen atom bound to any terminal carbon atom is optionally substituted with sulfhydryl or hydroxy;
$A^1$ is a bond;
$R^4$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups;
$R^5$ and $R^6$ are independently hydrogen, alkyl, alkenyl, aryl, aralkyl, aralkenyl, cycloalkyl, cycloalkylalkyl, cycloalkenyl, heterocyclyl, heterocyclylalkyl, heteroaryl, or heteroaralkyl, and is optionally substituted with 1-3 J groups;
X is a bond, —C(H)(R7)-, -0-, —S—, or —N(R8)-;
$R^7$ is hydrogen, alkyl, alkenyl, aryl, aralkyl, heterocyclyl, heterocyclylalkyl, heteroaryl, or heteroaralkyl, and is optionally substitued with 1-3 J groups;

$R^8$ is hydrogen alkyl, aryl, aralkyl, heterocyclyl, heterocyclylalkyl, heteroaryl, heteroaralkyl, aralkanoyl, heterocyclanoyl, heteroaralkanoyl, —C(O)R$^{14}$, —SO$_2$R$^{14}$, or carboxamido, and is optionally substitiued with 1-3 J groups; or $R^8$ and Z, together with the atoms to which they are bound, form a nitrogen containing mono- or bicyclic ring system optionally substituted with 1-3 J groups;

$R^{14}$ is alkyl, aryl, aralkyl, heterocyclyl, heterocyclylalkyl, heteroaryl, or heteroaralkyl;

Y is a bond, —CH$_2$—, —C(O)—, —C(O)C(O)—, —S(O)—, —S(0)$_2$—, or —S(O)(NR$^7$)—, wherein $R^7$ is as defined above;

Z is alkyl, aryl, aralkyl, cycloalkyl, cycloalkylalkyl, heterocyclyl, heterocyclylalkyl, heteroaryl, heteroaralkyl, —OR$^2$, or —N(R$^2$)$_2$, wherein any carbon atom is optionally substituted with J, wherein $R^2$ is as defined above;

$A^2$ is a bond or

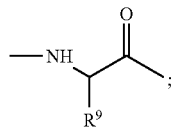

$R^9$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups;

M is alkyl, cycloalkyl, aryl, aralkyl, heterocyclyl, heterocyclylalkyl, heteroaryl, or heteroaralkyl, optionally substituted by 1-3 J groups, wherein any alkyl carbon atom may be replaced by a heteroatom;

V is a bond, —CH$_2$—, —C(H)(R$^{11}$)—, -O-, —S—, or —N(R$^{11}$)—;

$R^{11}$ is hydrogen or $C_{1-3}$ alkyl;

K is a bond, -O-, —S—, —C(O)—, —S(O)—, —S(0)$_2$—, or —S(O)(NR$^{11}$)—, wherein $R^{11}$ is as defined above;

T is —R$^{12}$, -alkyl-R$^{12}$, -alkenyl-R$^{12}$-alkynyl-R$^{12}$, —OR$^{12}$, —N(R$^{12}$)2, —C(O)R$^{12}$, —C(=NOalkyl)R$^{12}$, or

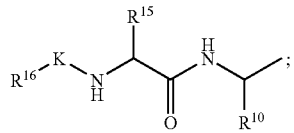

$R^{12}$ is hydrogen, aryl, heteroaryl, cycloalkyl, heterocyclyl, cycloalkylidenyl, or heterocycloalkylidenyl, and is optionally substituted with 1-3 J groups, or a first R$^{12}$ and a second R$^{12}$, together with the nitrogen to which they are bound, form a mono- or bicyclic ring system optionally substituted by 1-3 J groups;

$R^{10}$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 hydrogens J groups;

$R^{15}$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1-3 J groups; and $R^{16}$ is hydrogen, alkyl, aryl, heteroaryl, cycloalkyl, or heterocyclyl.

In another embodiment, the inhibitor is a compound of Formula XXV

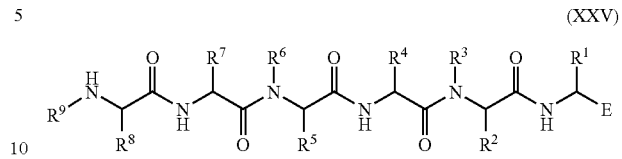

or a pharmaceutically acceptable salt, solvate or ester thereof; wherein

E represents CHO or B(OH)$_2$;

$R^1$ represents lower alkyl, halo-lower alkyl, cyano-lower alkyl, lower alkylthio-lower alkyl, aryl-lower alkylthio-lower alkyl, aryl-lower alkyl, heteroaryllower alkyl, lower alkenyl or lower alkynyl;

$R^2$ represents lower alkyl, hydroxy-lower alkyl, carboxy-lower alkyl, aryl-lower alkyl, aminocarbonyl-lower alkyl or lower cycloalkyl-lower alkyl; and $R^3$ represents hydrogen or lower alkyl;

or $R^2$ and $R^3$ together represent di- or trimethylene optionally substituted by hydroxy;

$R^4$ represents lower alkyl, hydroxy-lower alkyl, lower cycloalkyl-lower alkyl, carboxy-lower alkyl, aryllower alkyl, lower alkylthio-lower alkyl, cyano-lower alkylthio-lower alkyl, aryl-lower alkylthio-lower alkyl, lower alkenyl, aryl or lower cycloalkyl;

$R^5$ represents lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;

$R^6$ represents hydrogen or lower alkyl;

$R^7$ represent lower alkyl, hydroxydower alkyl, carboxy-lower alkyl, aryl-iower alkyl, lower cycloalkyl-lower alkyl or lower cycloalkyl;

$R^8$ represents lower alkyl, hydroxy-lower alkyl, carboxy-lower alkyl or aryl-lower alkyl; and $R^9$ represents lower alkylcarbonyl, carboxy-lower alkylcarbonyl, arylcarbonyl, lower alkylsulphonyl, arylsulphonyl, lower alkoxycarbonyl or aryl-lower alkoxycarbonyl.

In another embodiment, the "at least one compound" is a compound of formula XXVI:

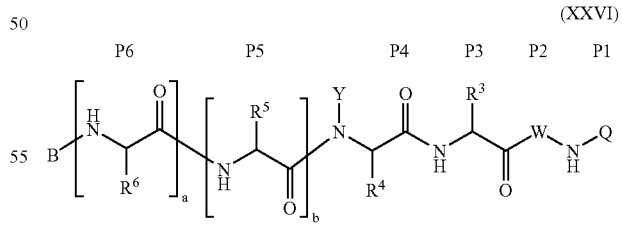

or a pharmaceutically acceptable salt, solvate or ester thereof; wherein

B is an acyl derivative of formula R$_{11}$—C(O)— wherein R$_{11}$ is Cl-10 alkyl optionally substituted with carboxyl; or R$_{11}$ is $C_6$ or $C_{10}$ aryl or $C_{7-16}$ aralkyl optionally substituted with a $C_{1-6}$ alkyl;

a is 0 or 1;

$R_6$, when present, is carboxy(lower)alkyl;

b is 0 or 1;

$R_5$, when present, is $C_{1-6}$ alkyl, or carboxy(lower)alkyl;

Y is H or $C_{1-6}$ alkyl;

$R_4$ is $C_{1-10}$ alkyl; $C_{3-10}$ cycloalkyl;

$R_3$ is C1-10 alkyl; $C_{3-10}$ cycloalkyl;

W is a group of formula:

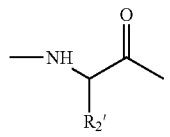

wherein $R_2$ is $C_{1-10}$ alkyl or $C_{3-7}$ cycloalkyl optionally substituted with carboxyl; $C_6$ or $C_{10}$ aryl; or $C_{7-16}$ aralkyl; or W is a group of formula:

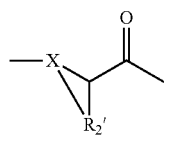

wherein X is CH or N; and $R_2'$ is $C_{3-4}$ alkylene that joins X to form a 5- or 6-membered ring, said ring optionally substituted with OH; SH; NH2; carboxyl; $R_{12}$; $OR_{12}$, $SR_{12}$, $NHR_{12}$ or $NR_{12}R_{12}'$ wherein $R_{12}$ and $R_{12}'$ are independently:

cyclic $C_{3-16}$ alkyl or acyclic $C_{1-16}$ alkyl or cyclic $C_{3-16}$ alkenyl or acyclic $C_{2-16}$ alkenyl, said alkyl or alkenyl optionally substituted with $NH_2$, OH, SH, halo, or carboxyl; said alkyl or alkenyl optionally containing at least one heteroatom selected independently from the group consisting of: O, S, and N; or $R_{12}$ and $R_{12}'$ are independently $C_6$ or $C_{10}$ aryl or $C_{7-16}$ aralkyl optionally substituted with $C_{1-6}$alkyl, $NH_2$, OH, SH, halo, carboxyl or carboxy(lower)alkyl; said aryl or aralkyl optionally containing at least one heteroatom selected independently from the group consisting of: O, S, and N;

said cyclic alkyl, cyclic alkenyl, aryl or aralkyl being optionally fused with a second 5-, 6-, or 7-membered ring to form a cyclic system or heterocycle, said second ring being optionally substituted with $NH_2$. OH, SH, halo, carboxyl or carboxy(lower)alkyl; $C_6$ or $C_{10}$ aryl, or heterocycle; said second ring optionally containing at least one heteroatom selected independently from the group consisting of: O, S, and N;

Q is a group of the formula:

wherein Z is CH;

X is O or S;

$R_1$ is H, $C_{1-6}$ alkyl or $C_{1-6}$ alkenyl both optionally substituted with thio or halo;

and $R_{13}$ is C0-NH—$R_{14}$ wherein $R_{14}$ is hydrogen, cyclic $C_{3-10}$ alkyl or acyclic $C_{1-10}$ alkyl or cyclic $C_{3-10}$ alkenyl or acyclic $C_{2-10}$ alkenyl, said alkyl or alkenyl optionally substituted with $NH_2$, OH, SH, halo or carboxyl; said alkyl or alkenyl optionally containing at least one heteroatom selected independently from the group consisting of: O, S, and N; or $R_{14}$ is $C_6$ or $C_{10}$ aryl or $C_{7-16}$ aralkyl optionally substituted with $C_{1-6}$ alkyl, $NH_2$, OH, SH, halo, carboxyl or carboxy (lower)alkyl or substituted with a further $C_{3-7}$ cycloalkyl, $C_6$ or $C_{10}$ aryl, or heterocycle; said aryl or aralkyl optionally containing at least one heteroatom selected independently from the group consisting of: O, S, and N;

said cyclic alkyl, cyclic alkenyl, aryl or aralkyl being optionally fused with a second 5-, 6-, or 7-membered ring to form a cyclic system or heterocycle, said second ring being optionally substituted with $NH_2$, OH, SH, halo, carboxyl or carboxy(lower)alkyl or substituted with a further $C_{3-7}$ cycloalkyl, $C_6$ or $C_{10}$ aryl, or heterocycle; said second ring optionally containing at least one heteroatom selected independently from the group consisting of: O, S, and N;

with the proviso that when Z is CH, then $R_{13}$ is not an α-amino acid or an ester thereof;

Q is a phosphonate group of the formula:

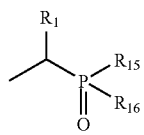

wherein $R_{15}$ and $R_{16}$ are independently $C_{6-20}$ aryloxy; and $R_1$ is as defined above.

In the above-shown structure of the compound of Formula XXVI, the terms P6, P5, P4, P3, P2 and P1 denote the respective amino acid moieties as is conventionally known to those skilled in the art. Thus, the actual structure of the compound of Formula XXVI is:

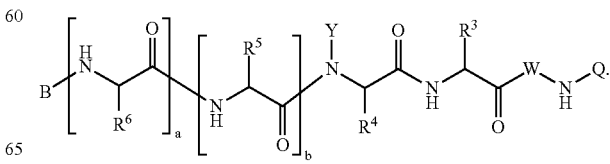

In another embodiment, the compound is selected from the group consisting of:
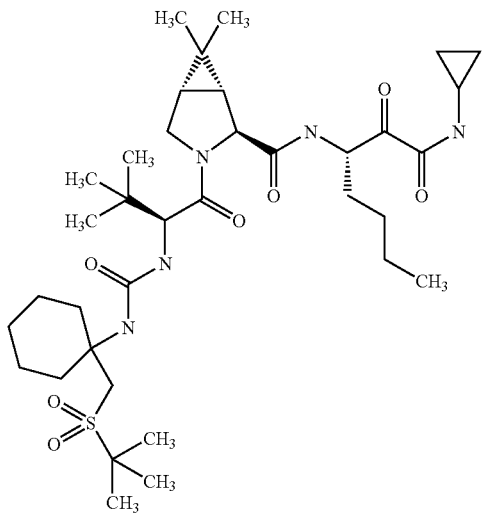
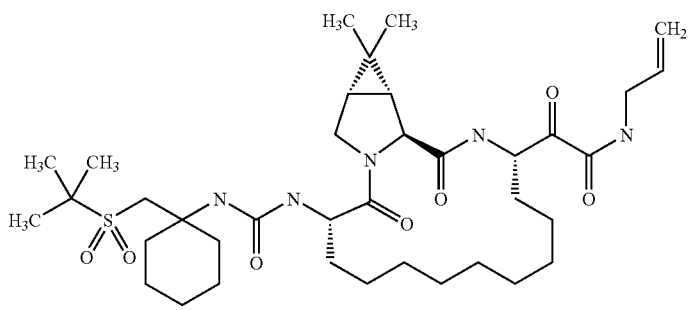
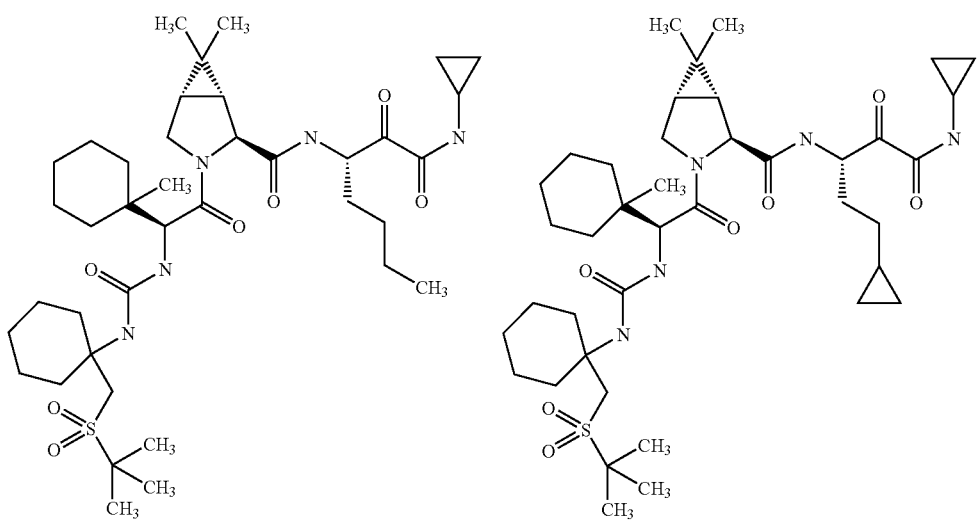

-continued
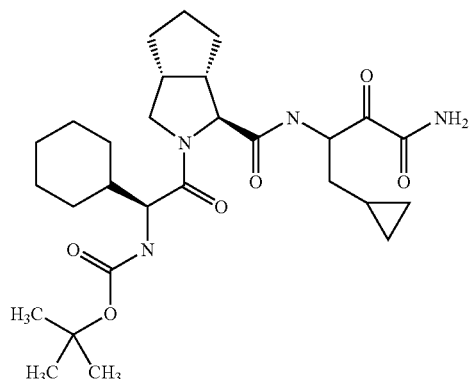
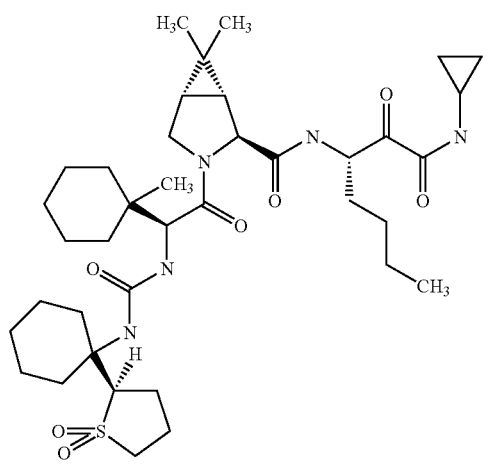
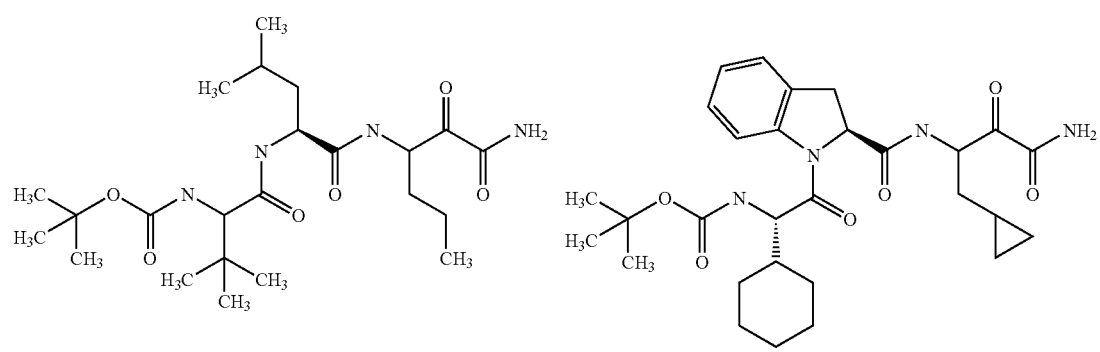
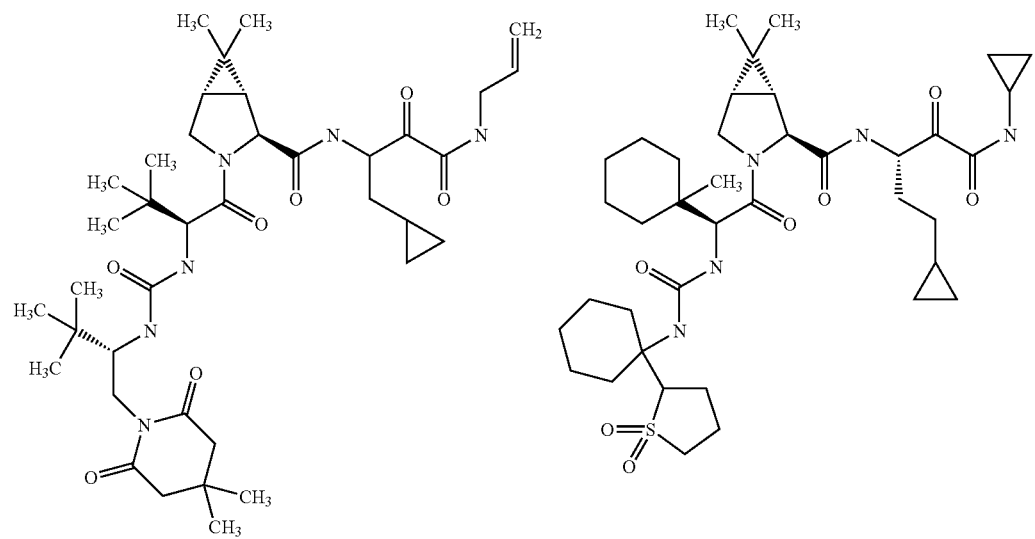

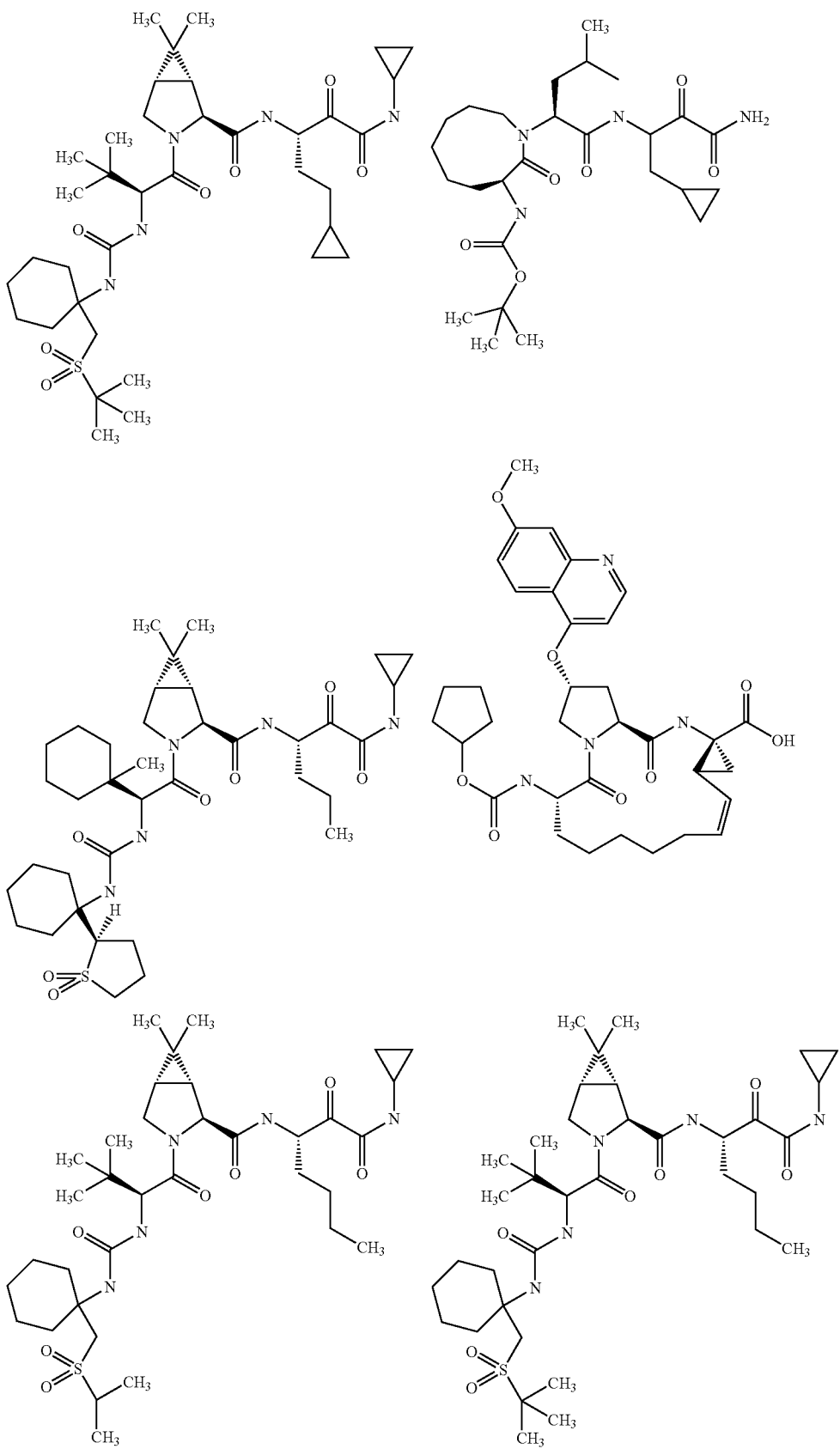

-continued
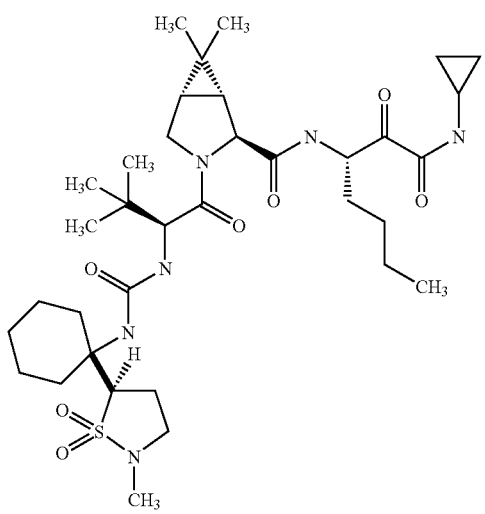
61
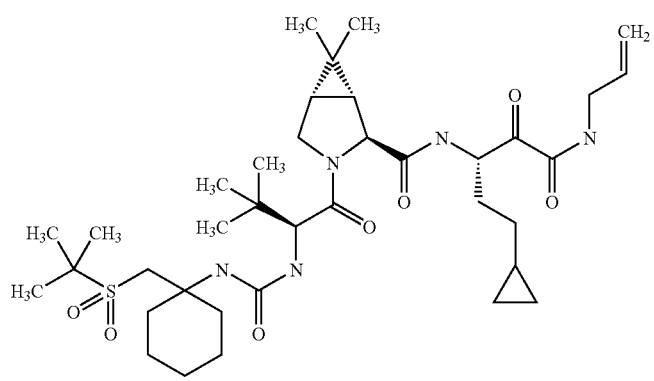
62
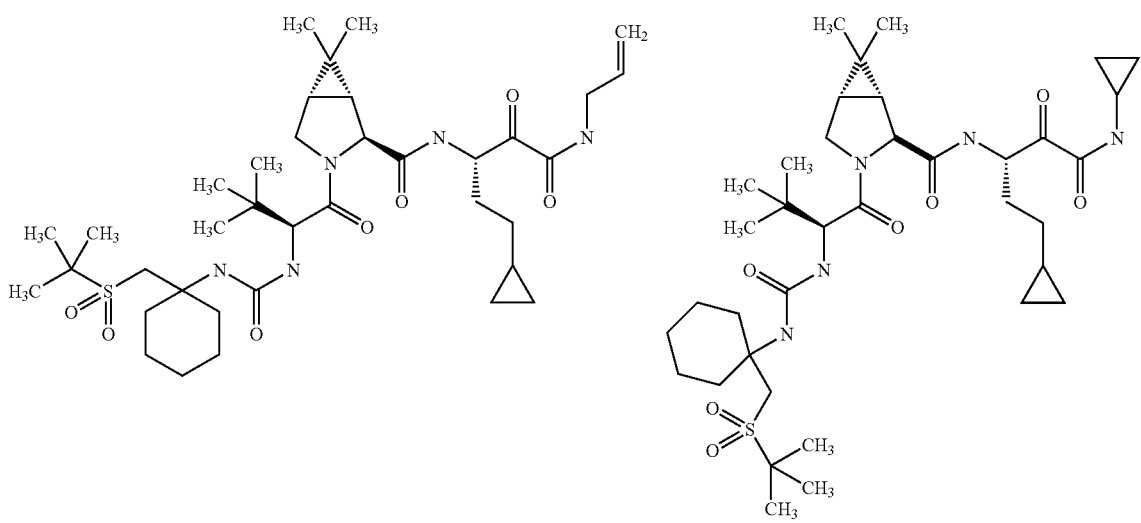
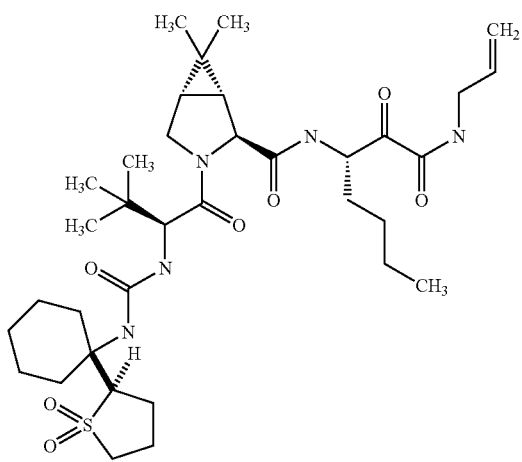
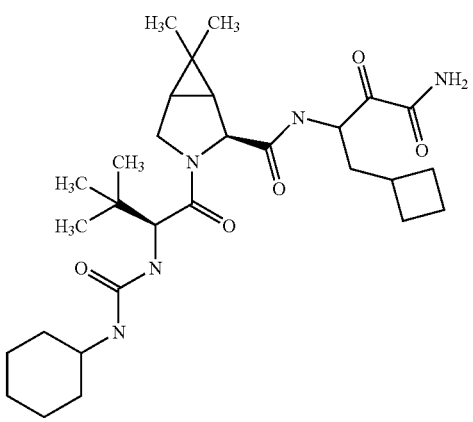

-continued
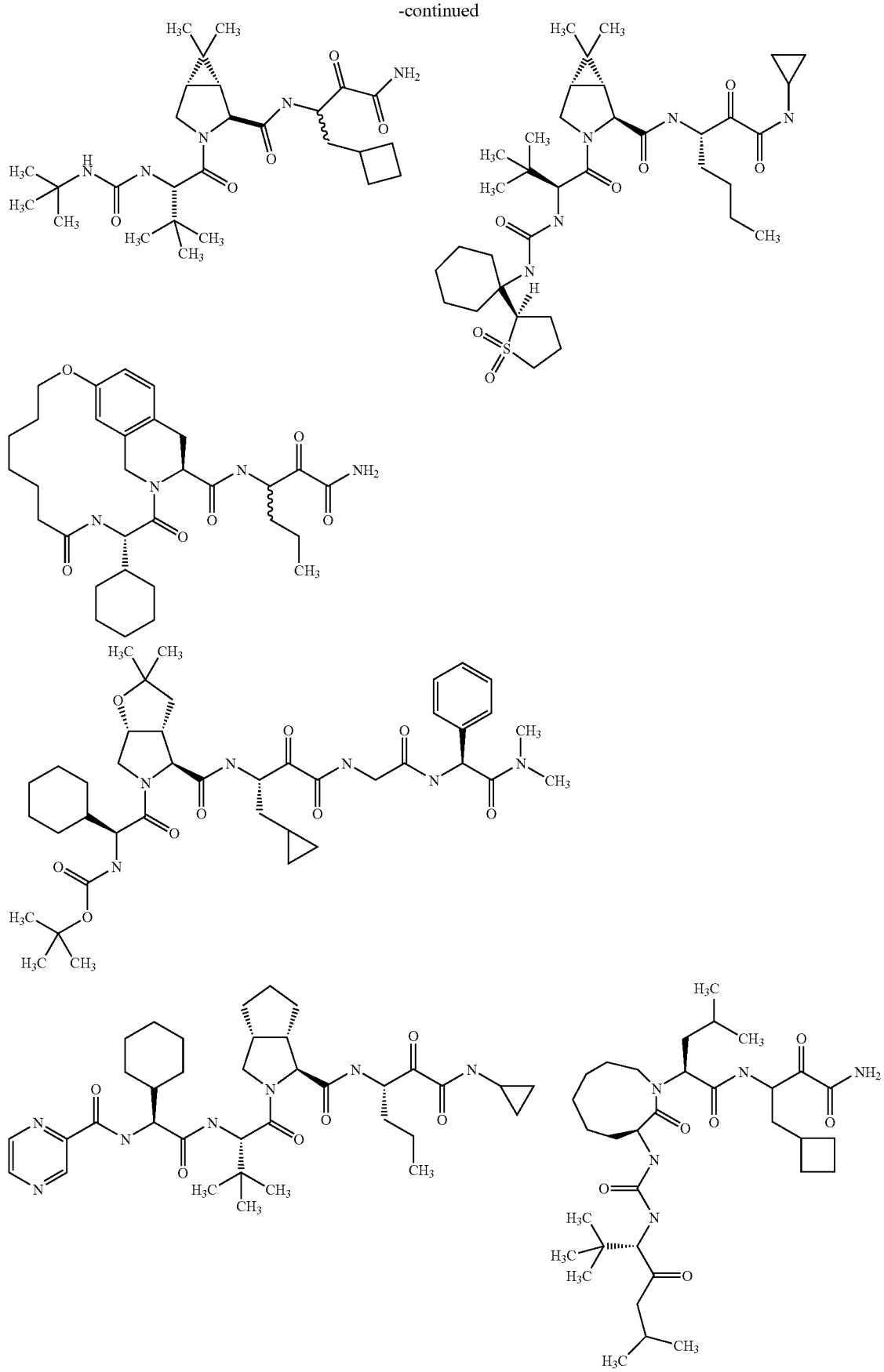

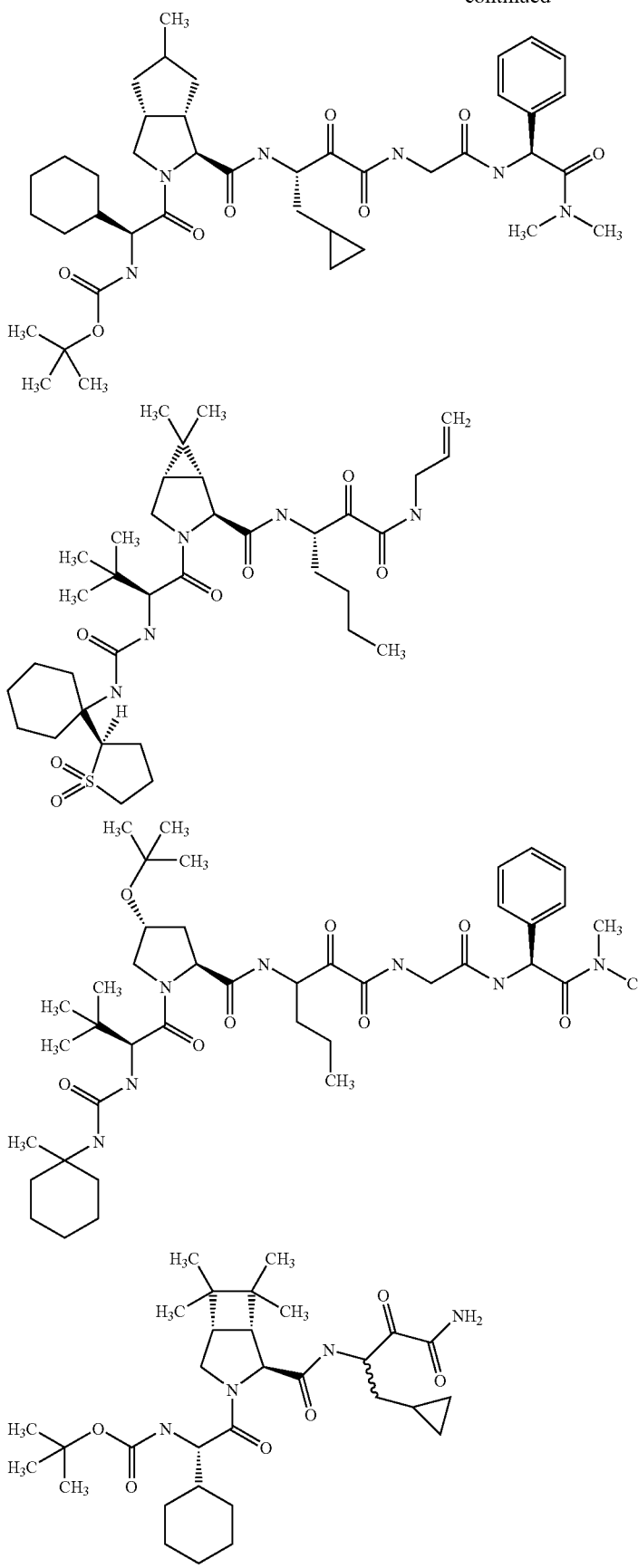

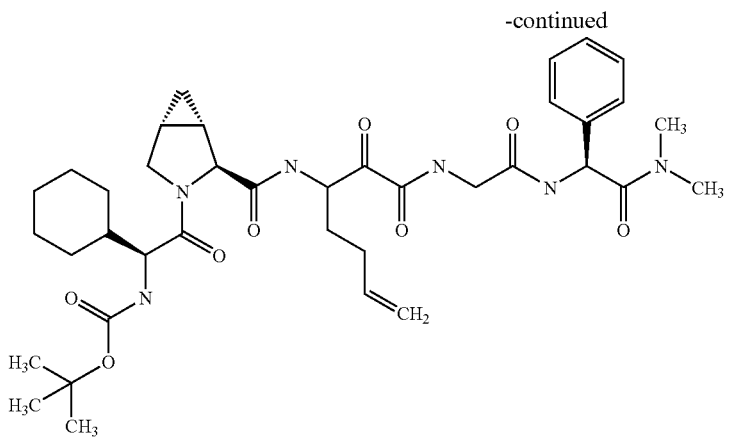
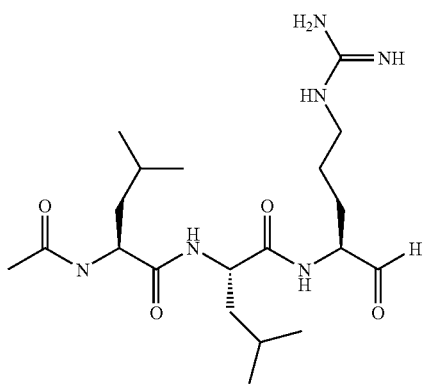
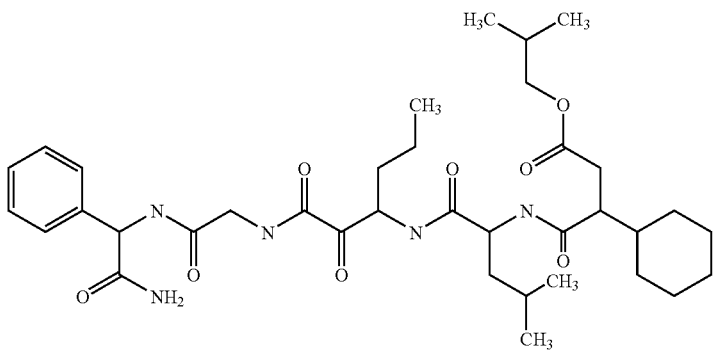
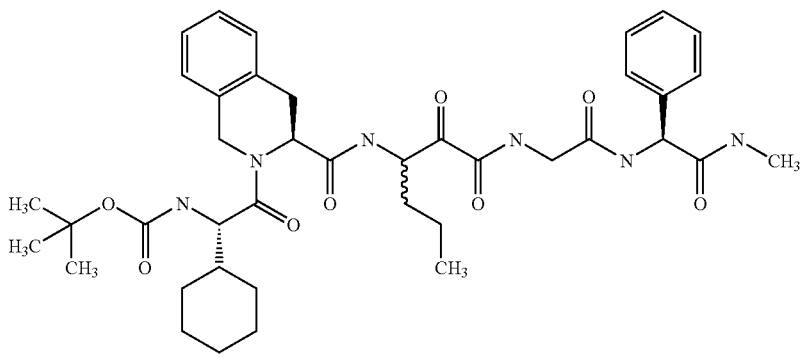

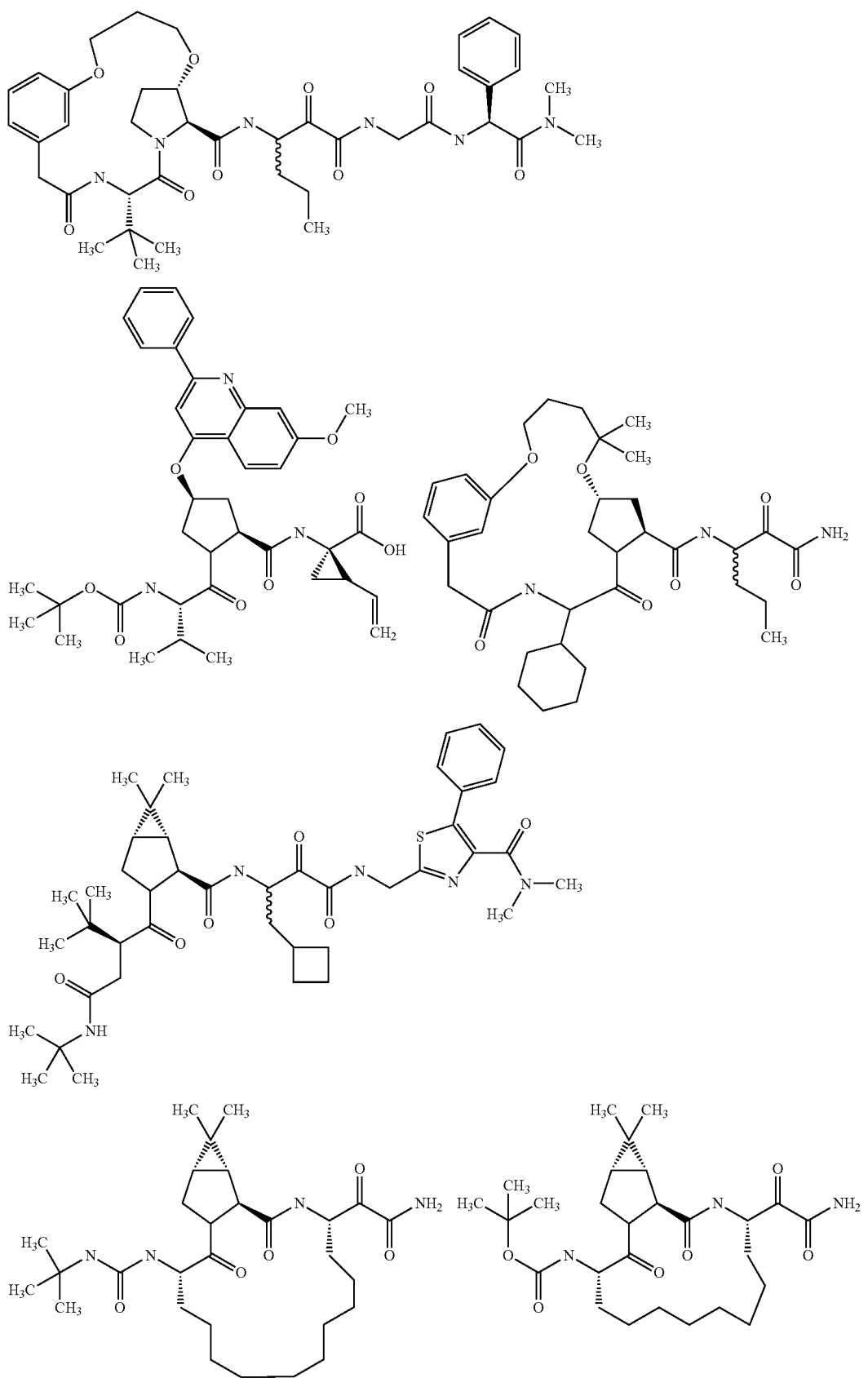

71          72
-continued
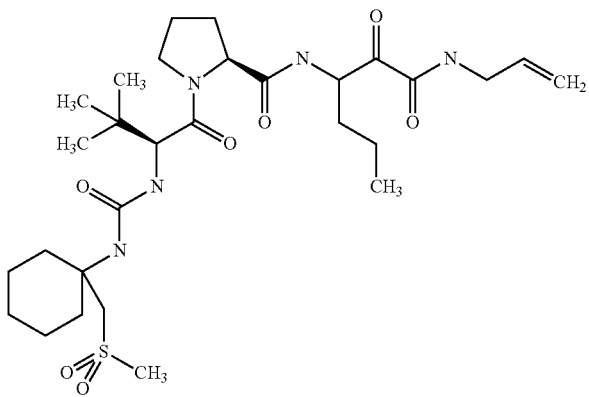
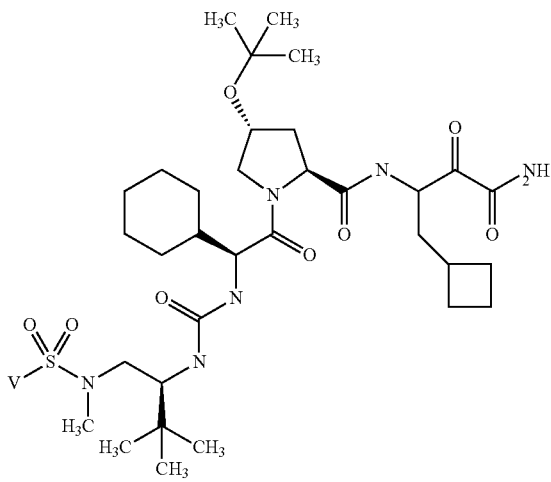
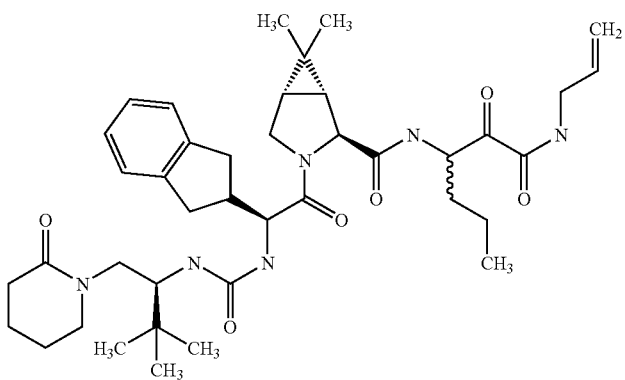
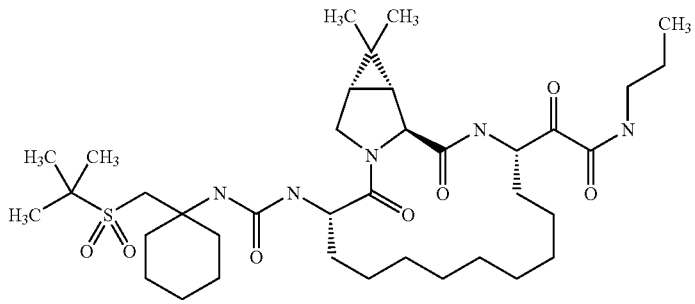
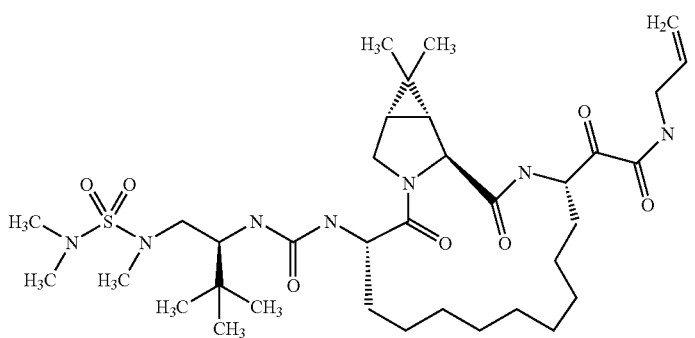

-continued
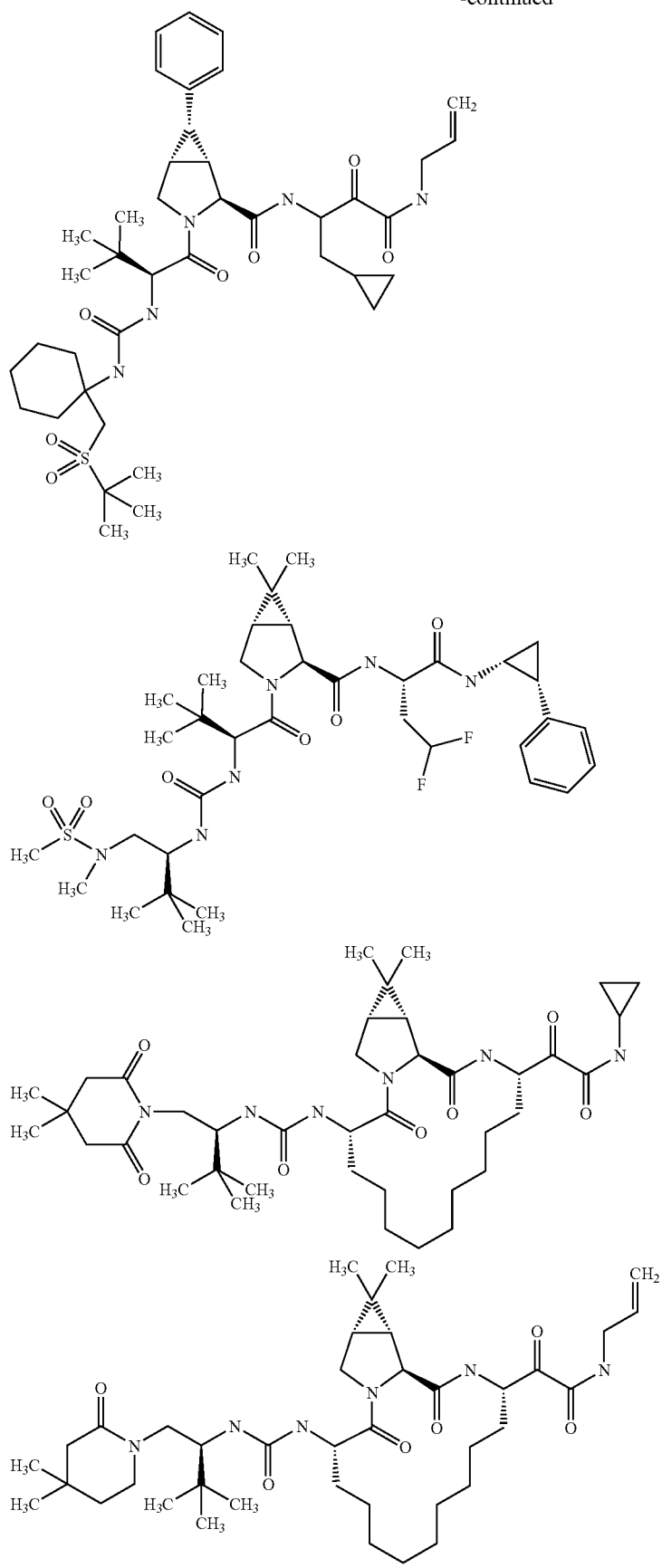

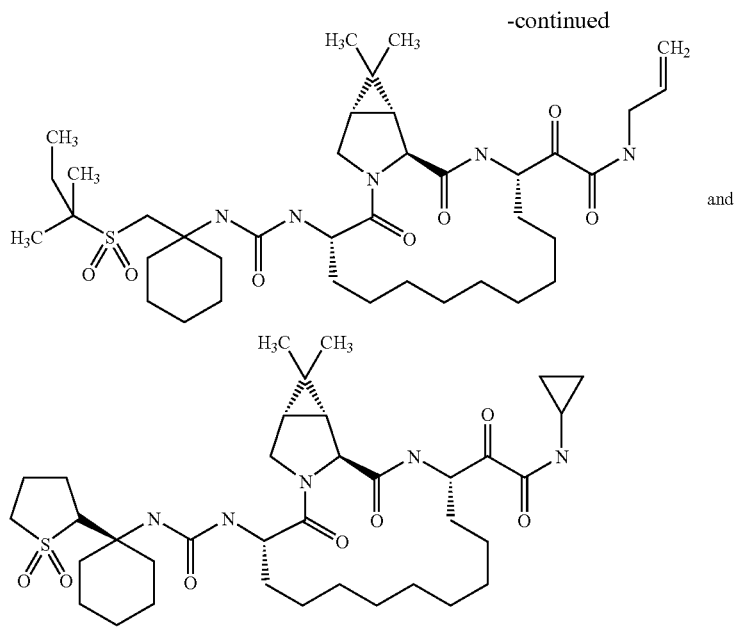

or a pharmaceutically acceptable salt, solvate or ester thereof.

Methods of treating a wide variety of diseases/disorders associated with cathepsin activity and/or for inhibiting cathepsin activity in a subject comprising administering to a subject in need of such treatment an effective amount of at least one of the inventive compounds also are provided.

One example of such disorders is proliferative diseases, such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974, the disclosure of which is incorporated herein.

Another example of a disease that can be treated by the present compounds is an inflammatory disease, such as organ transplant rejection, graft v. host disease, arthritis, rheumatoid arthritis, inflammatory bowel disease, atopic dermatitis, psoriasis, asthma, allergies, multiple sclerosis, fixed drug eruptions, cutaneous delayed-type hypersentitivity responses, tuberculoid leprosy, type I diabetes, and viral meningitis.

Another example of a disease that can be treated by the present compounds is a cardiovascular disease.

Another example of a disease that can be treated by the present compounds is a central nervous system disease, such as depression, cognitive function disease, neurodegenerative disease such as Parkinson's disease, senile dementia such as Alzheimer's disease, and psychosis of organic origin.

Other examples of diseases that can be treated by the present compounds are diseases characterized by bone loss, such as osteoporosis; gingival diseases, such as gingivitis and periodontitis; and diseases characterized by excessive cartilage or matrix degradation, such as osteoarthritis and rheumatoid arthritis.

Other than in the operating examples, or where otherwise indicated, all numbers expressing quantities of ingredients, reaction conditions, and so forth used in the specification and claims are to be understood as being modified in all instances by the term "about."

BRIEF DESCRIPTION OF THE DRAWING

The invention is further illustrated by the following drawing in which FIG. 1 is a graph comparing plasma levels of compound 1a (SCH 503034) measured over time in fasted versus fed (with high fat and low fat diet) subjects.

DETAILED DESCRIPTION

In one embodiment, the present invention provides a method of treating, preventing or ameliorating one or more symptoms of hepatitis C in a subject comprising the step of administering at least one compound selected from the group consisting of compounds of Formulae I-XXVI in combination with food, as described above.

In another embodiment, the present invention provides a method of increasing bioavailability of a compound of Formulae I-XXVI in a subject comprising administering the at least one compound of Formulae I-XXVI in combination with food. As used herein, the term "increasing bioavailability" means that more of the compound of Formulae I-XXVI is present in the blood when taken with food as compared to no food, as determined by measurement of serum levels of the compound of Formulae I-XXVI after administration. Administration of the compound in combination with food results in higher serum levels of the compound.

As used herein, the term "in combination with food" means that the compound is administered within about ninety minutes of consumption of food, e.g., no more than about 90 minutes after food is eaten and no more than about 90 minutes prior to eating food.

In another embodiment, a method of increasing the serum level of a compound of Formulae I-XXVI in a subject is provided. The method comprises administering at least one compound in combination with food.

Preferably, the at least one compound(s) are administered in one or more discrete dosages over twenty-four hours, and the total amount of the at least one compound of Formulae I-XXVI administered over twenty-four hours is between 50 mg and 3,000 mg. More preferably, the total amount of the at least one compound of Formulae I-XXVI administered over twenty-four hours is between 50 mg and 2,400 mg, and even more preferably, the total amount of the at least one compound of Formulae I-XXVI administered over twenty-four hours is between 50 mg and 1,200 mg.

In some embodiments, the one or more discrete dosages is between one and six doses over twenty-four hours. In an embodiment, the one or more discrete dosages are three or four doses in twenty-four hours.

In one embodiment, the one or more discrete dosages are in oral dosage form. The oral dosage form is selected from the group consisting of tablets, capsules, caplets, suspensions, emulsions, troches, lozenges, effervescent tablets, lollipops and reconstitutable powders.

In one embodiment, the at least one compound is administered in oral dosage form and is administered concurrently with consumption of food. In another embodiment, the at least one compound of Formulae I-XXVI is administered in oral dosage form and is administered up to ninety minutes after consumption of food. In another embodiment, the at least one compound of Formulae I-XXVI is administered in oral dosage form and is administered up to thirty minutes before or up to thirty minutes after consumption of food.

Preferably, the at least one compound is administered in combination with a high-fat meal. Although not required, and any type of food (high fat or low fat) is thought to aid absorption of the compounds of the present invention, a high-fat meal may provide additional improved absorption as compared to administration of the compounds with lower fat meals. The term "food" is to be considered to have the ordinary meaning as is commonly understood in the society and community in general, with non-limiting examples being low fat, high fat, non-fat, snack, solid material, liquid material, high solid, low solid and the like. AS used herein, "high fat" means food in which over about 30% of the calories are provided by fat. As will be understood by one skilled in the art, an increase in bioavailability will occur in a dose dependent fashion, so that any amount of food will provide at least some improvement, as compared to administration with no food. Accordingly, administration of the drug in combination with food having at least about 50-100 calories up to about 1,000 calories can provide improved bioavailability.

Optionally, the at least one compound of Formulae I-XXVI is administered in combination with a pharmaceutical selected from the group consisting of interferon alpha-2a, pegylated interferon alpha-2a, interferon alpha-2b pegylated interferon alpha-2b, interferon alphacon-1, and ribavirin.

Also optionally, the at least one compound of Formulae I-XXVI is administered in combination with at least one antiviral agent which is different from the compound of Formulae I-XXVI and/or an immunomodulatory agent.

As used herein, the term "in combination with" means that a treatment regimen incorporating additional pharmaceuticals, antiviral agents and/or immunomodulatory agents is used in combination with administration of the protease inhibitor. Each additional pharmaceutical or agent is administered according to an optimal regimen determined for each pharmaceutical or agent. For example, interferon or pegylated interferon is usually administered once per week. Typically, these other pharmaceuticals or agents are administered in dosage forms separate from the protease inhibitor, although a combined dosage form, where appropriate, is also within the scope of the present invention.

Suitable compounds of formula I are disclosed in PCT International publication WO03/062265 published Jul. 31, 2003. Non-limiting examples of certain compounds disclosed in this publication include:

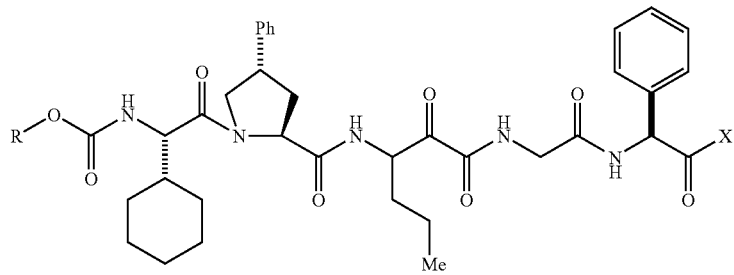

(R = t-butyl, X = NH$_2$)
(R = Isobutyl, X = NH$_2$)
(R = t-butyl, X = OH)
(R = Trichloroethyl, X = OH)

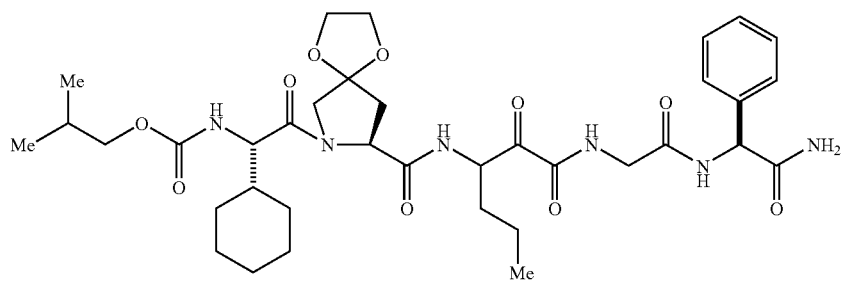

-continued
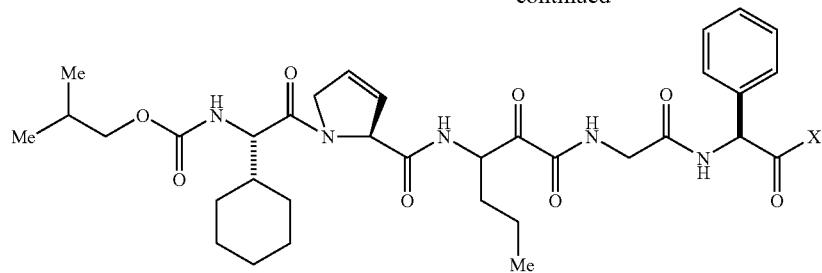
(X = O^tBu)
(X = OH)
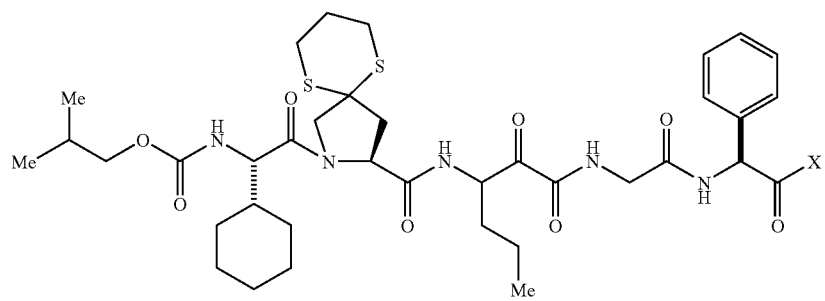
(X = OH)
(X = O^tBu)
(X = NH$_2$)
(X = NHMe)
(X = NMe$_2$)
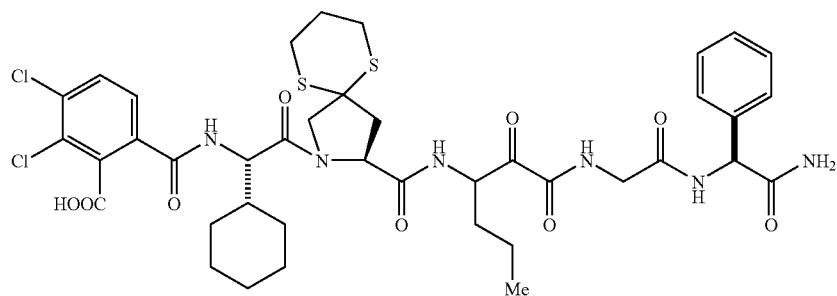
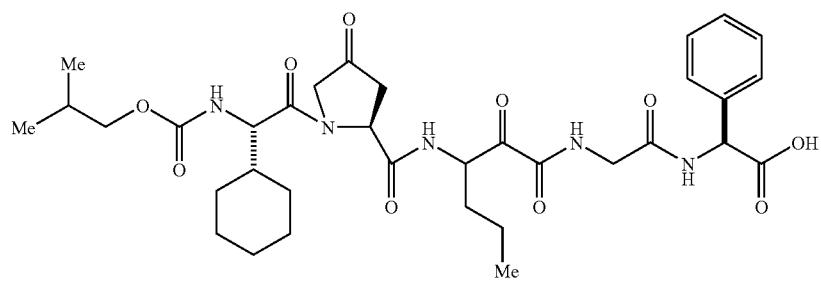
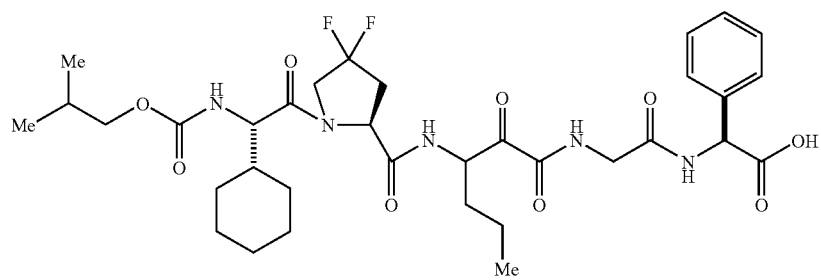

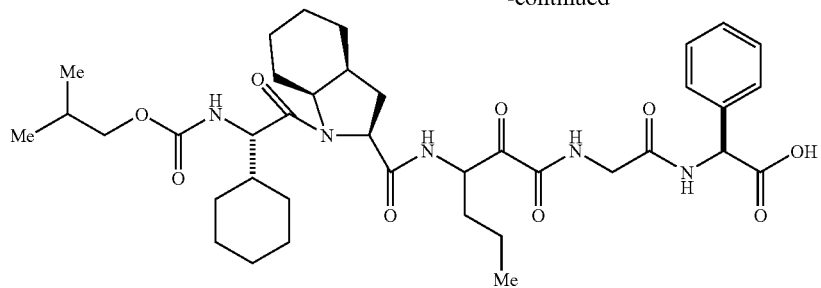
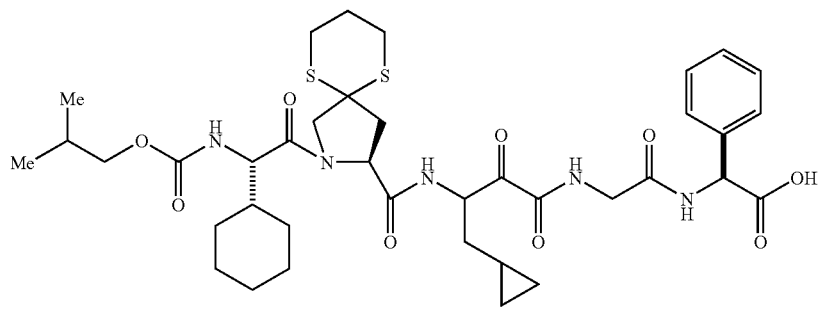
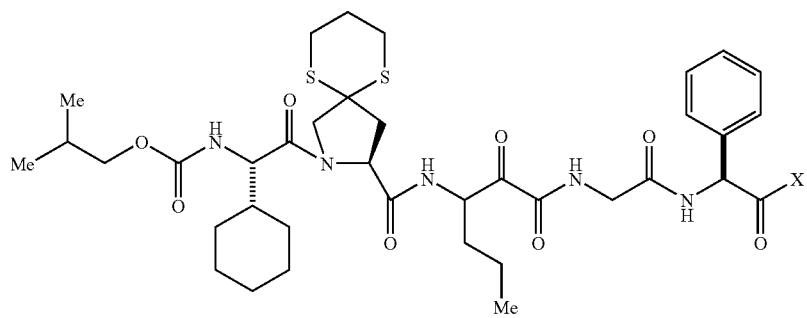
(X = NH₂)
(X = NMe₂)
(X = NHMe)
(X = OH)
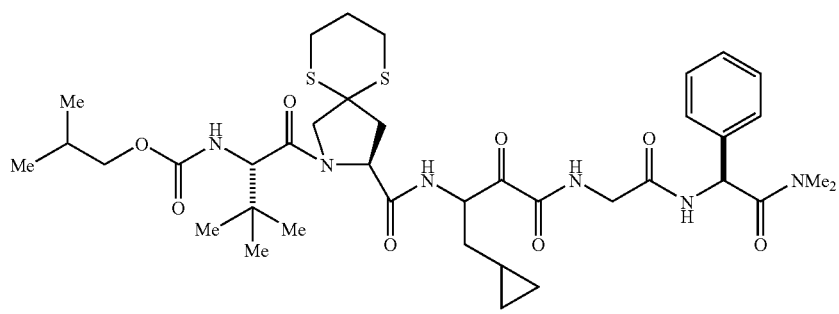
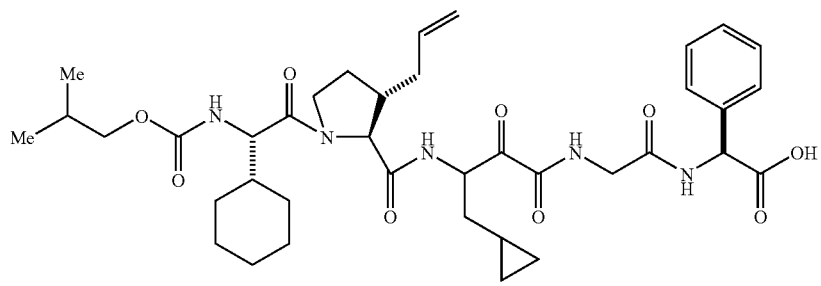

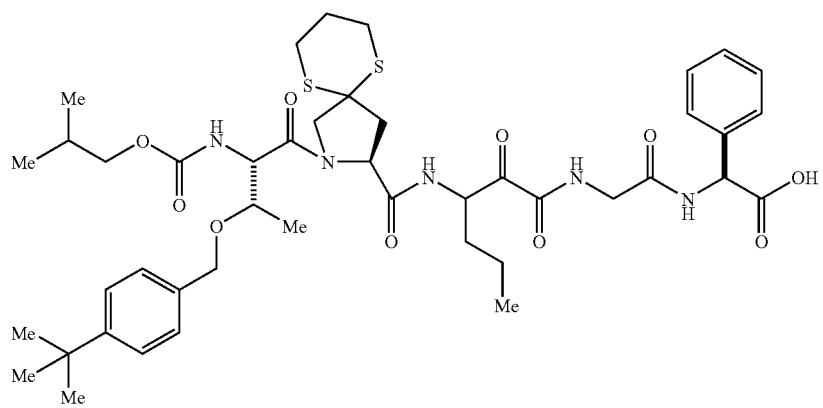
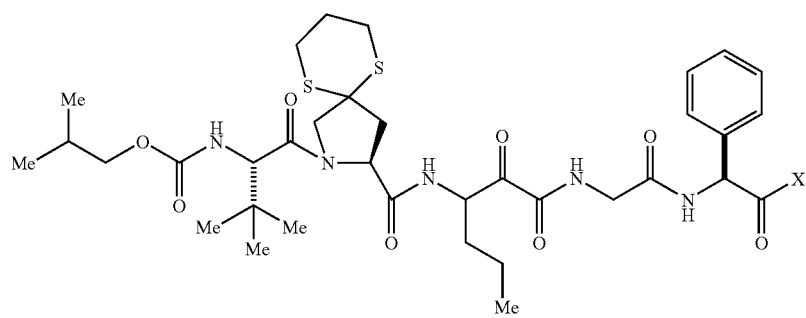
(X = O^tBu)
(X = OH)
(X = NH_2)
(X = NMe_2)
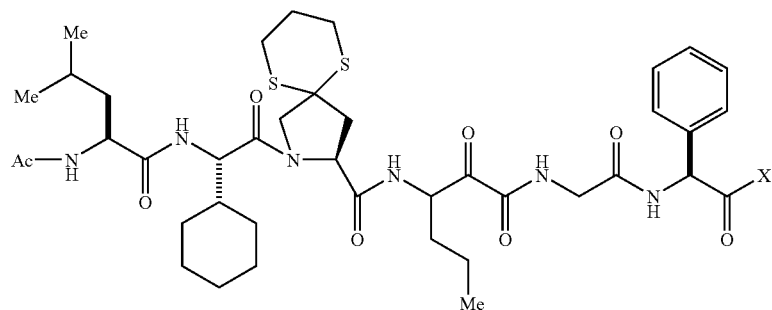
(X = O^tBu)
(X = OH)
(X = NH_2)
(X = NMe_2)
(X = NMeOMe)
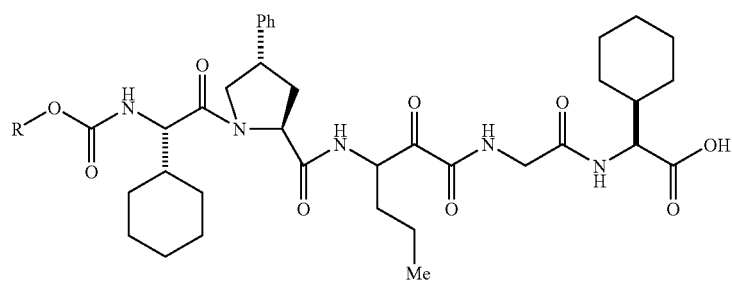
(R = t-butyl)
(R = Isobutyl)

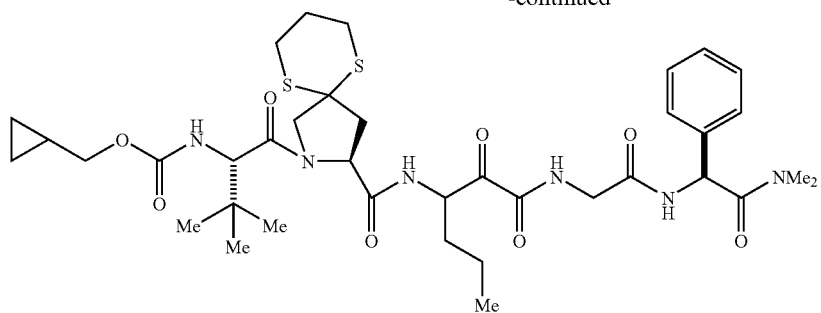
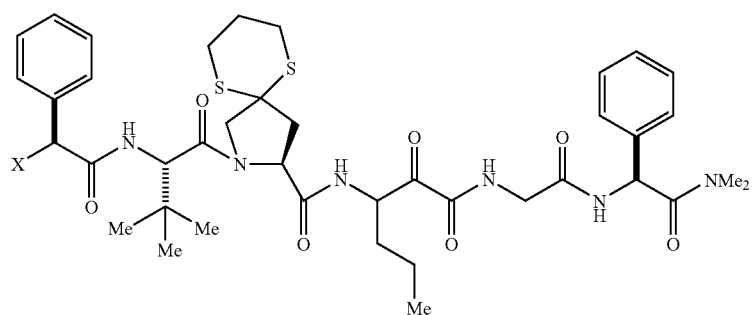
(X = Me, Y = CH₂Me)
(X = OAc, Y = Me)
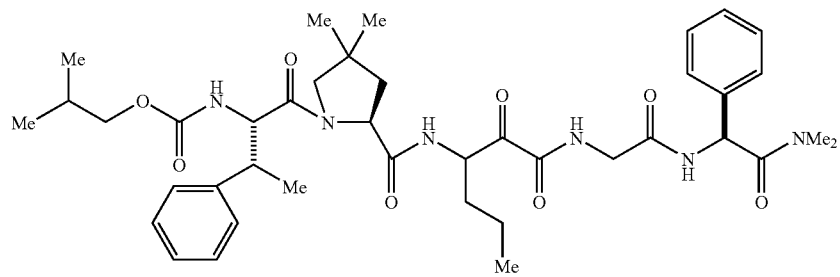
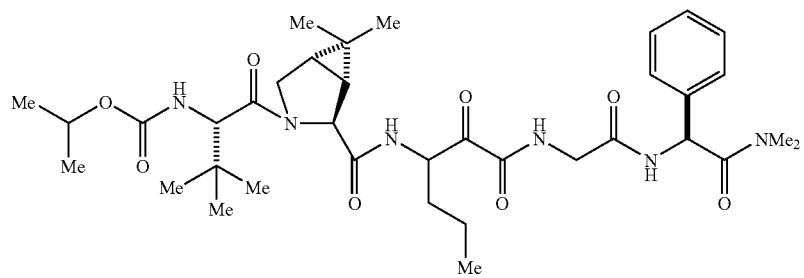
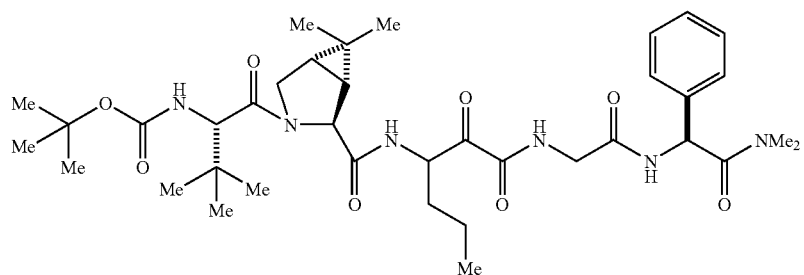

-continued
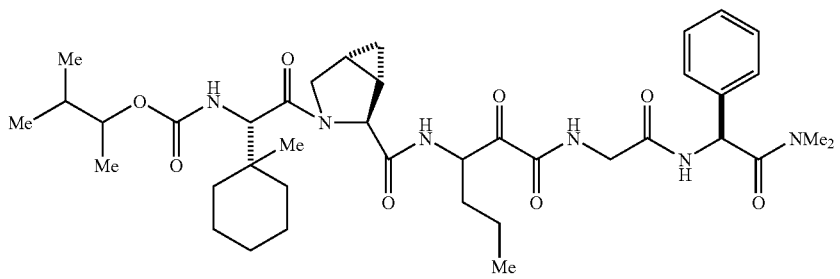
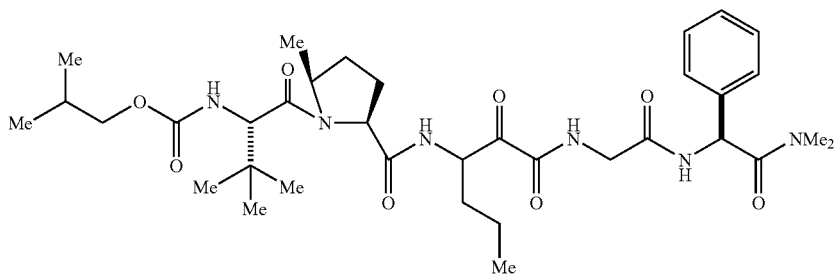
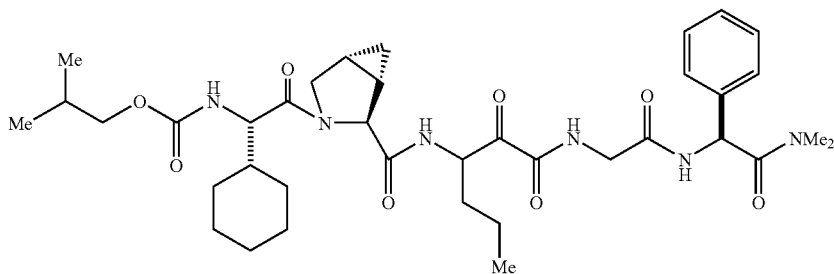
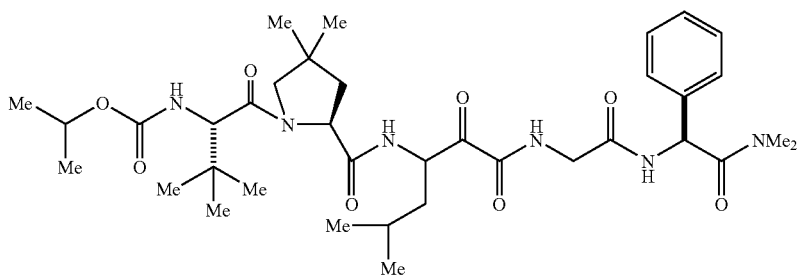
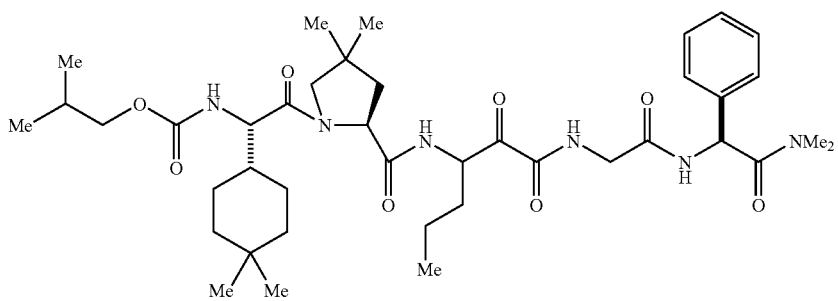

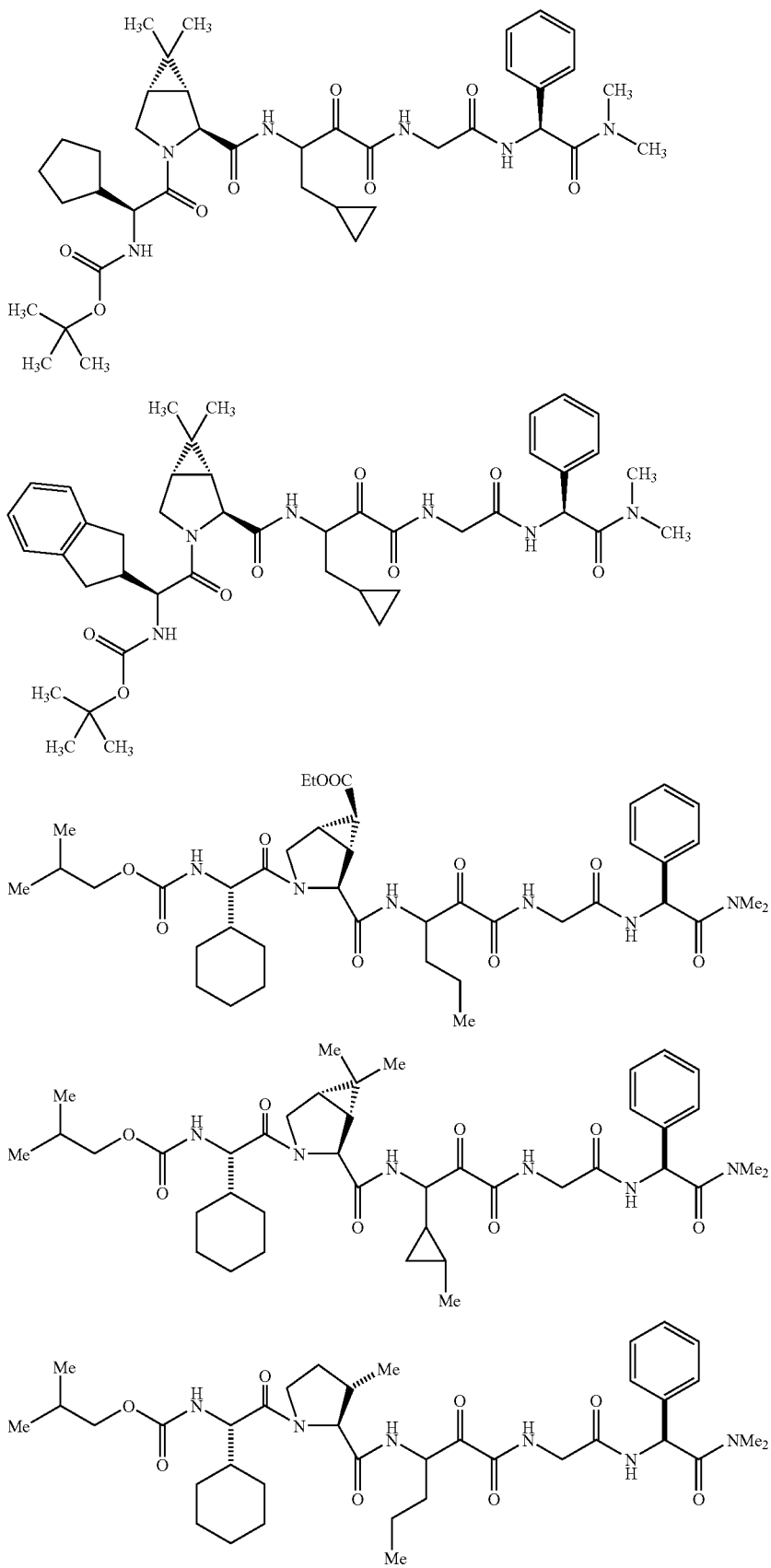

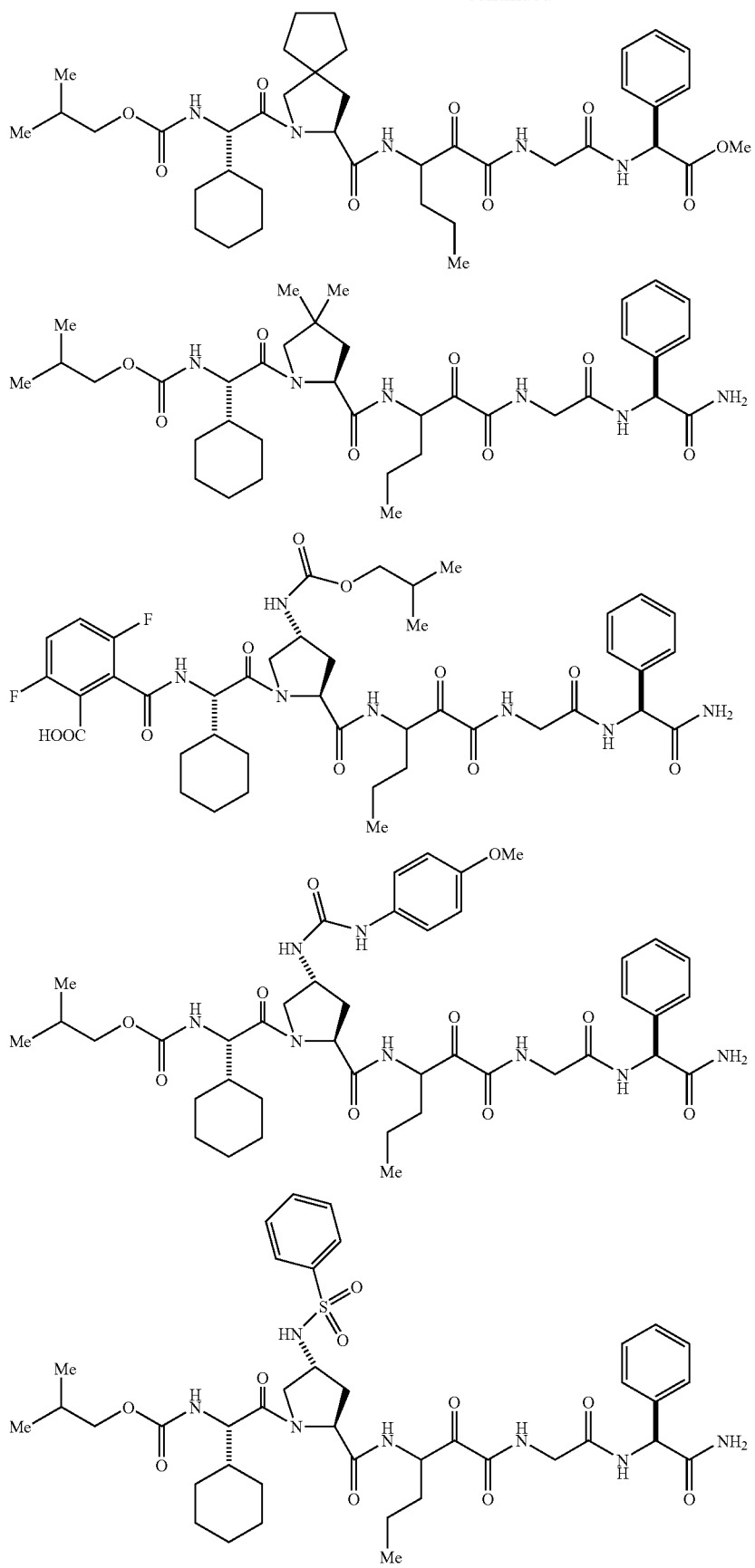

-continued
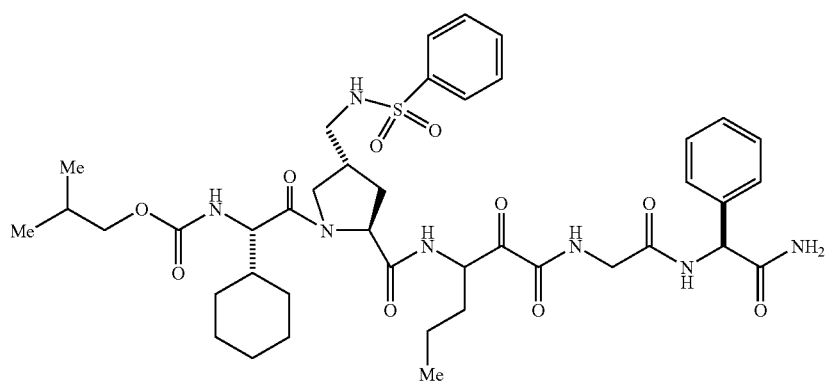
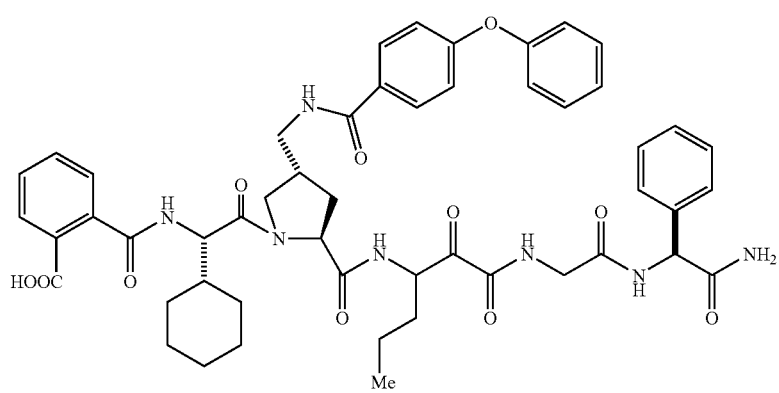
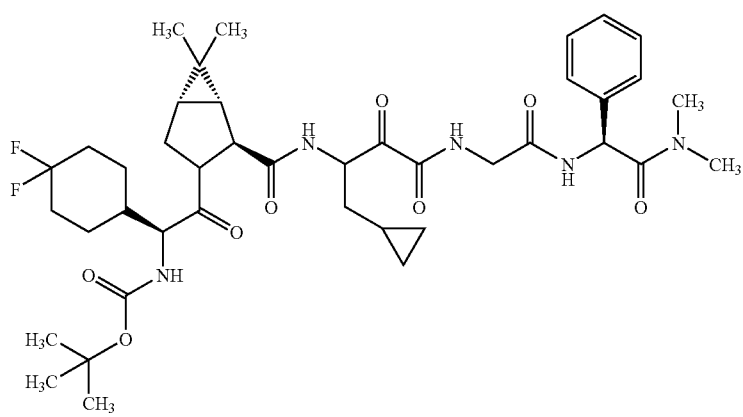
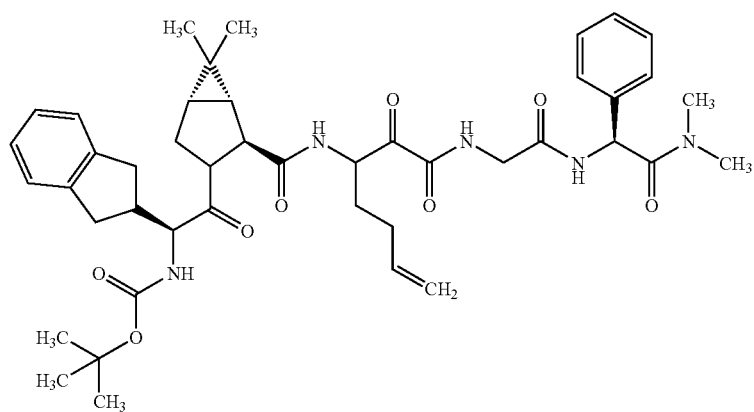

-continued
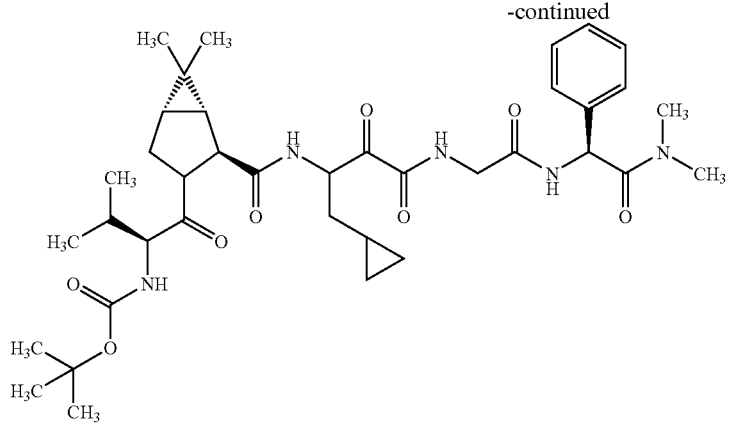
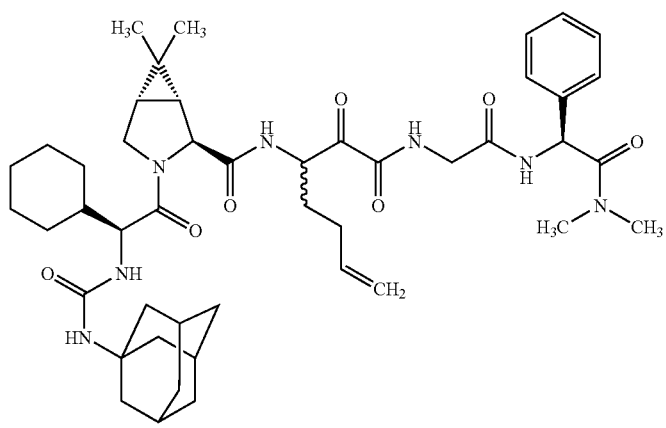
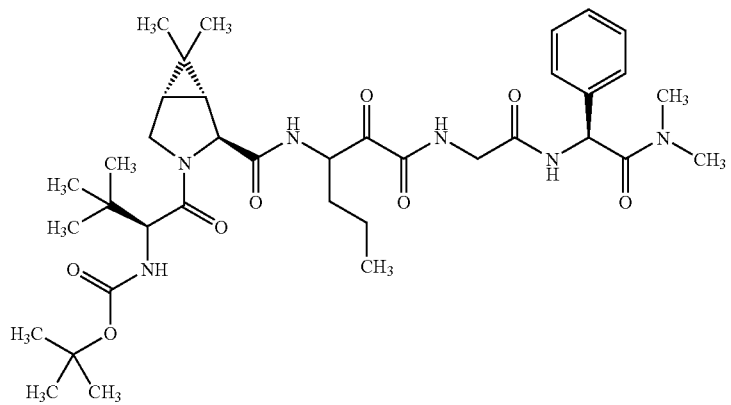
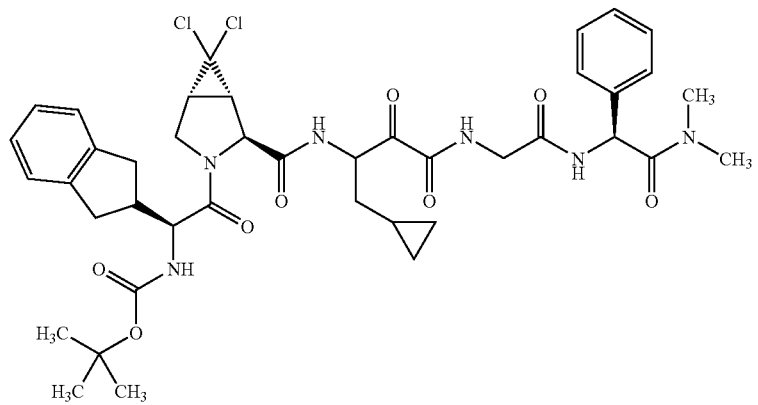

-continued
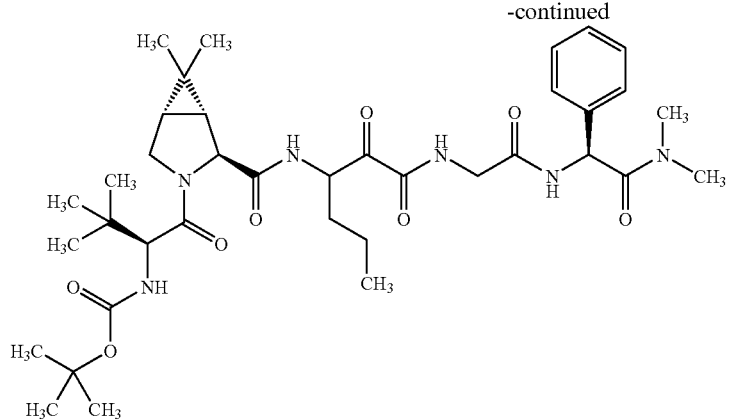
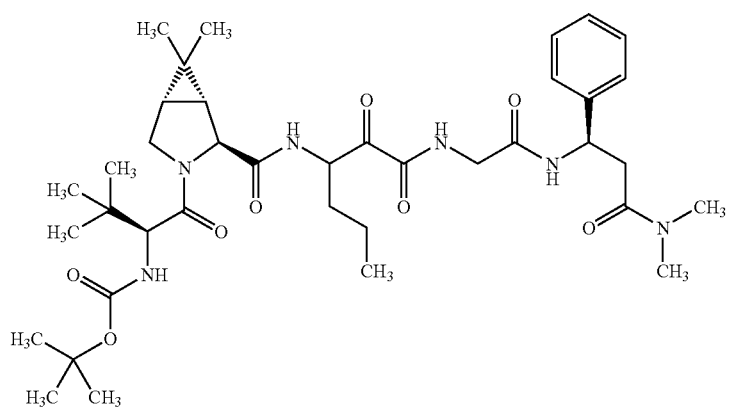
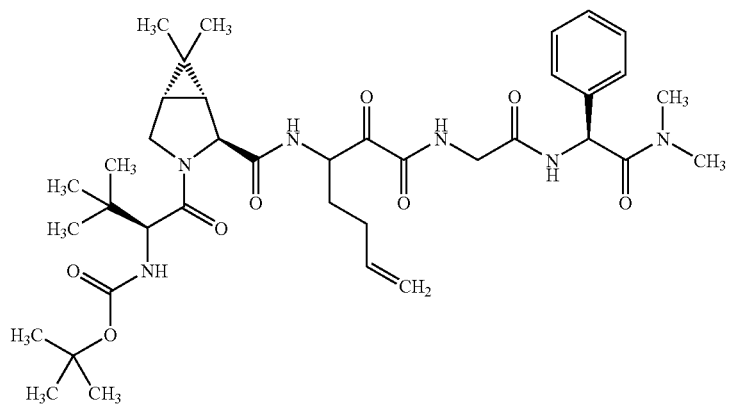
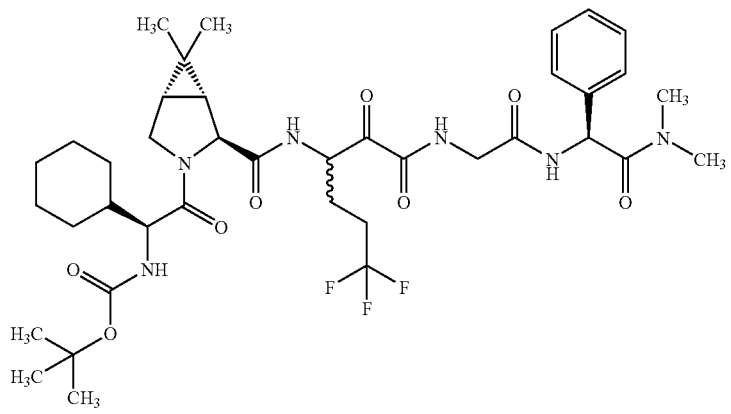

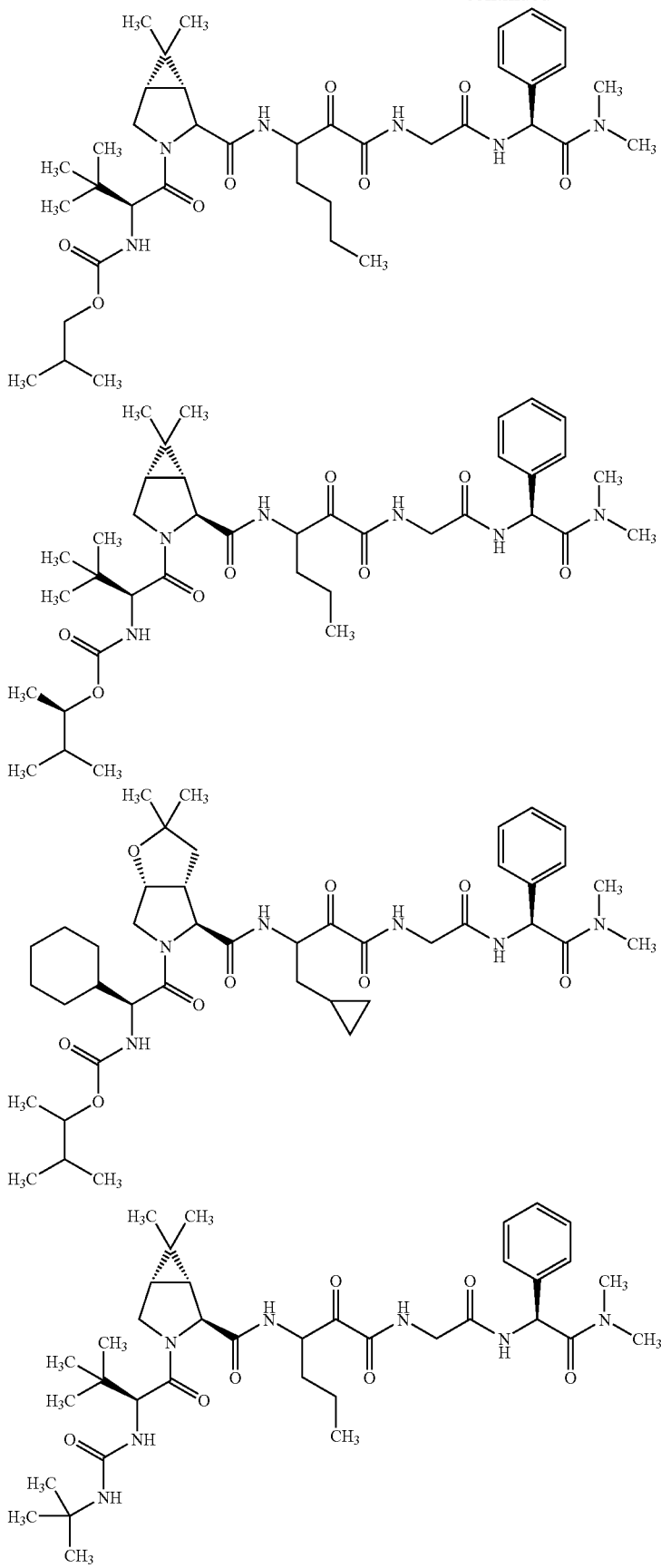

-continued
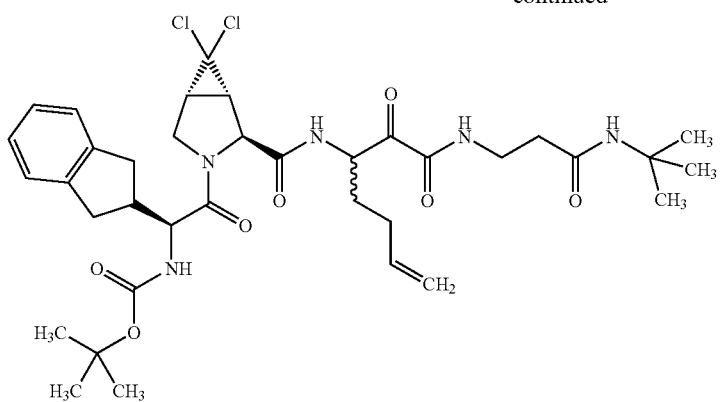
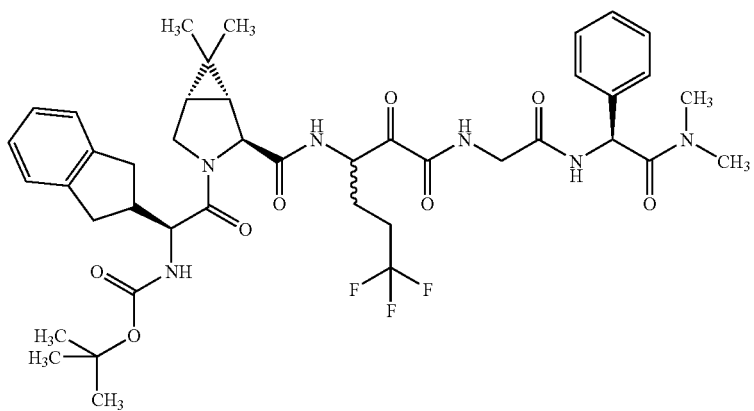
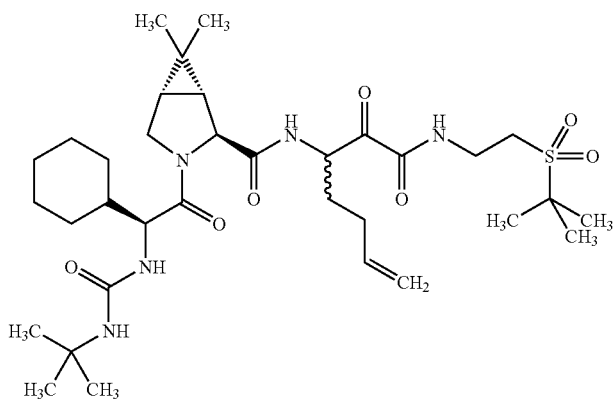
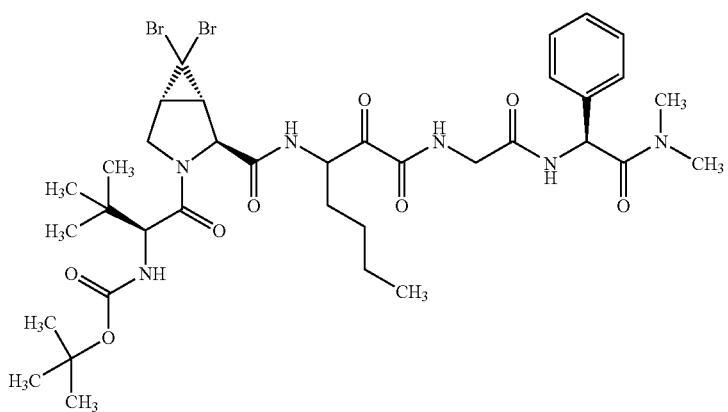

-continued
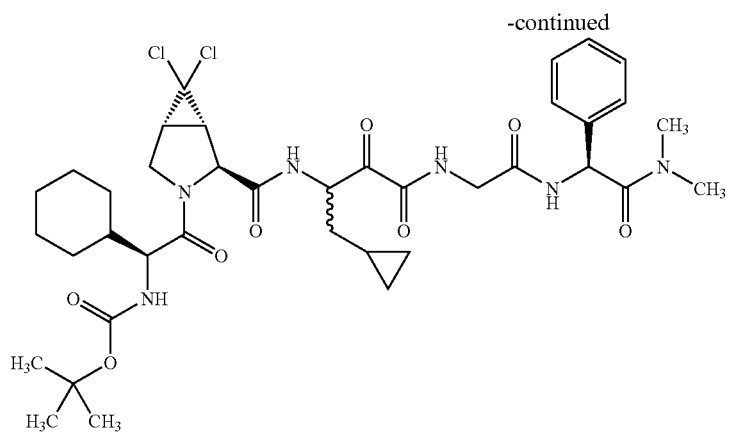
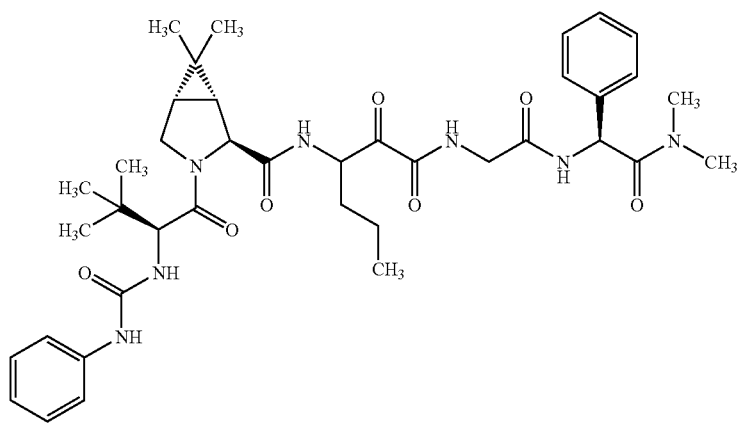
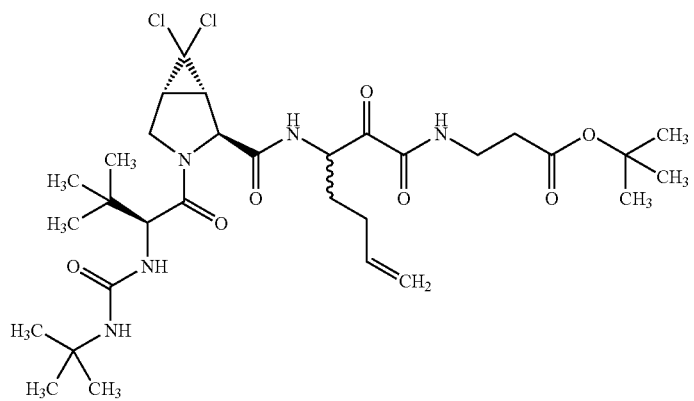
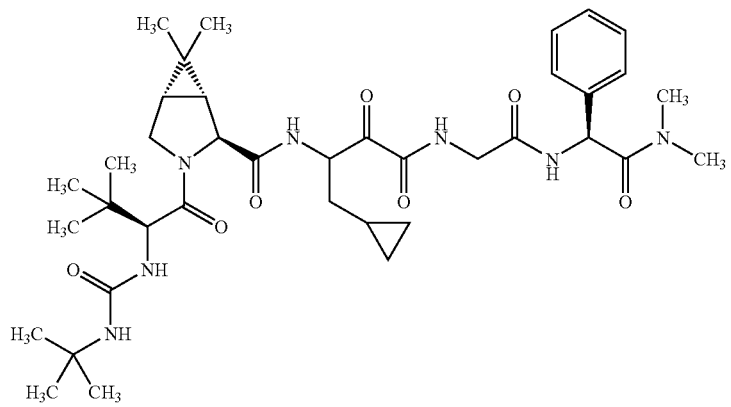

105
-continued
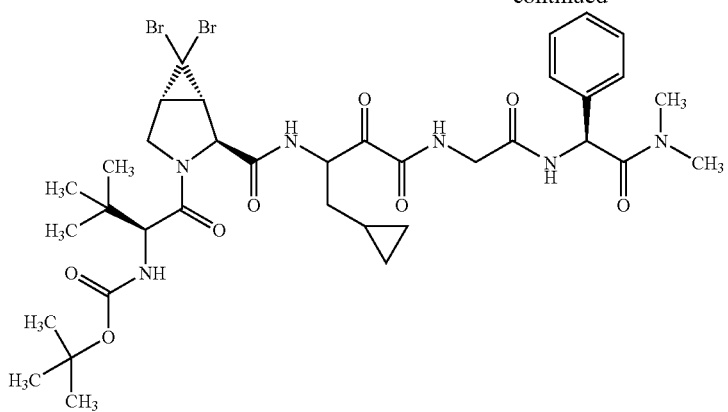
106
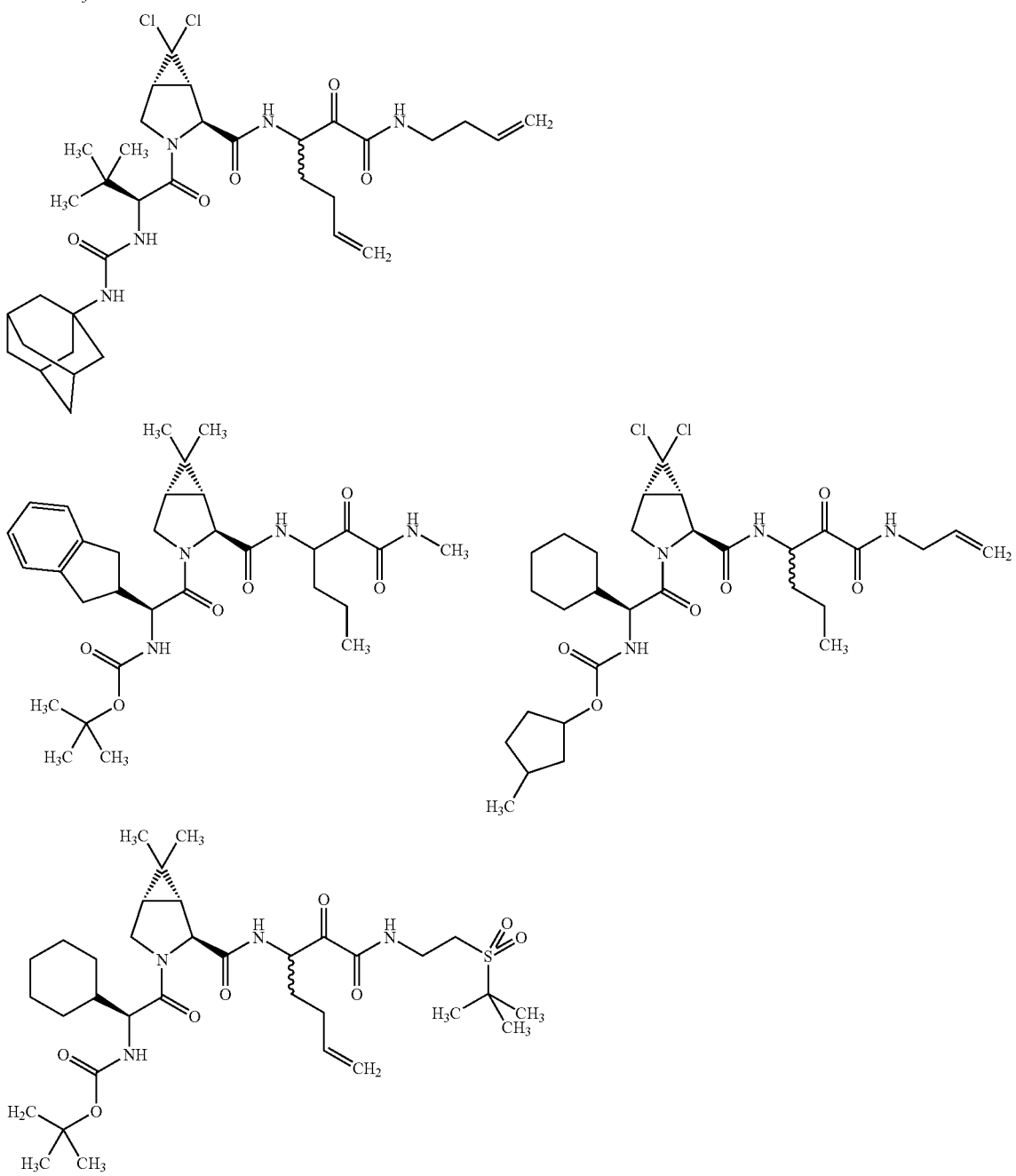

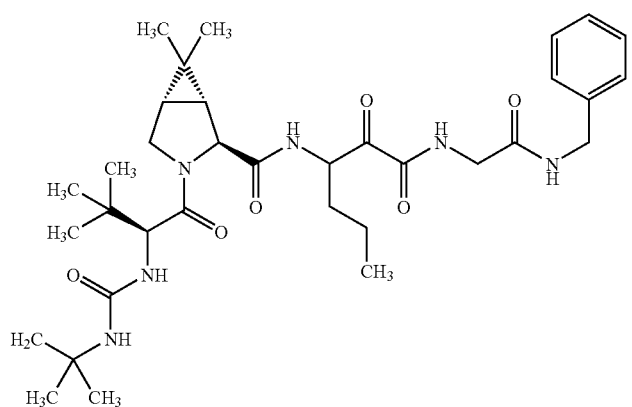
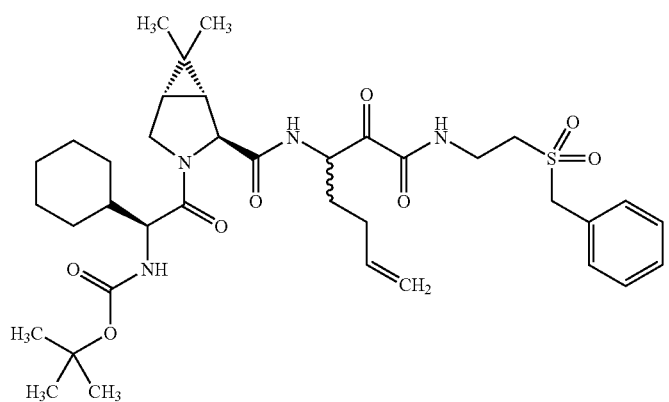
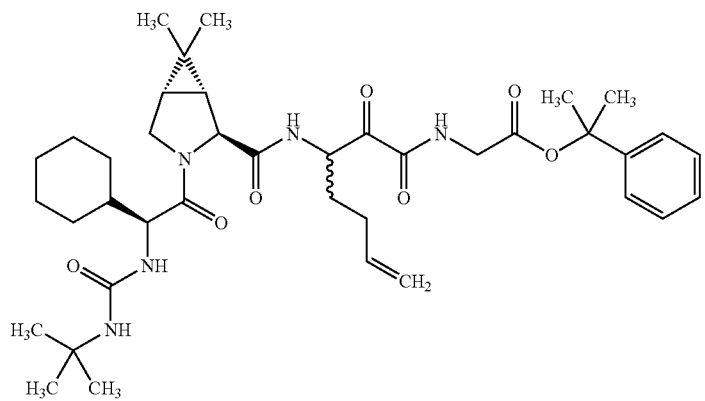
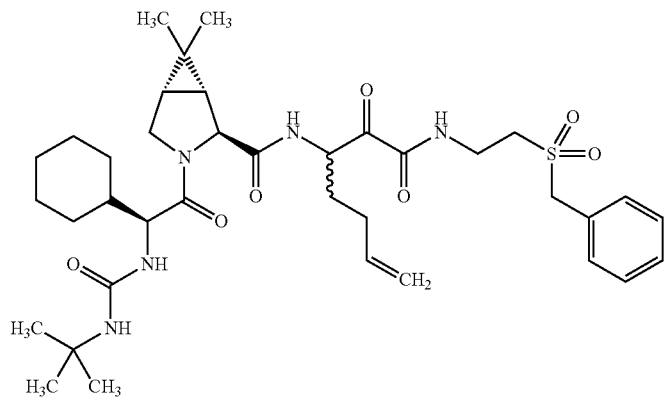

-continued
| 109 | 110 |
|---|---|
| 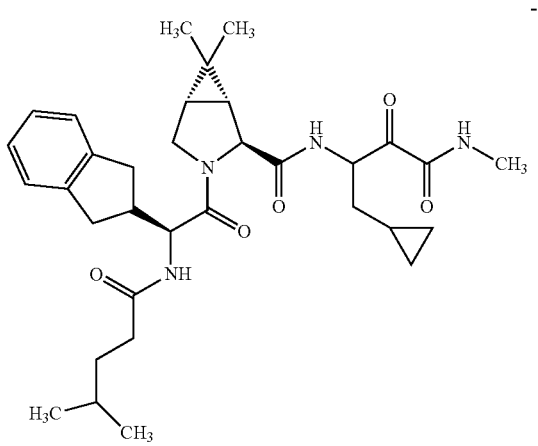 | 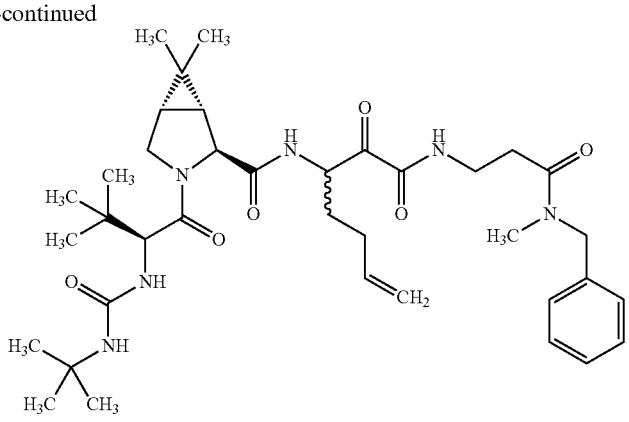 |
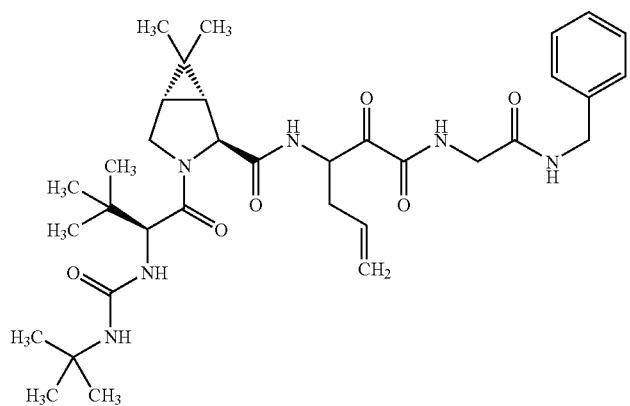
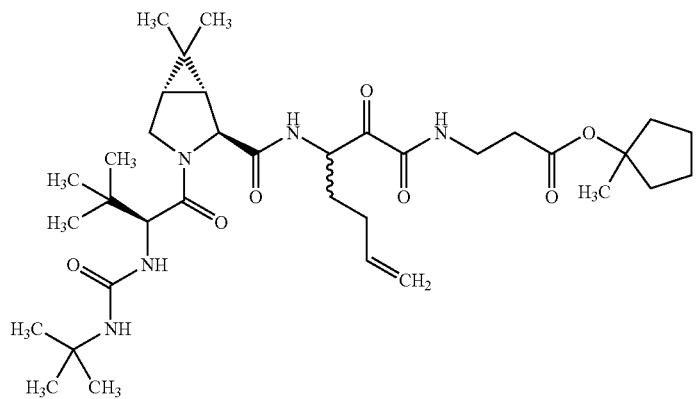
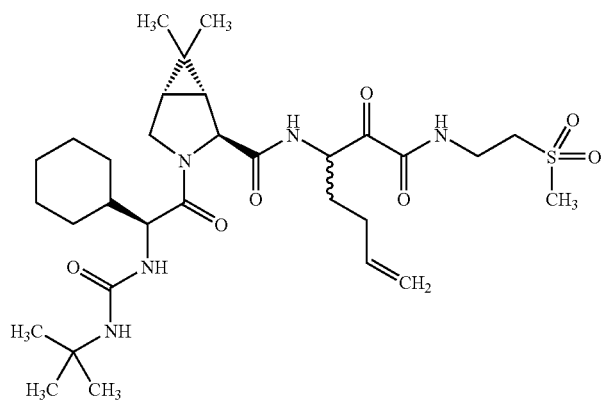

-continued
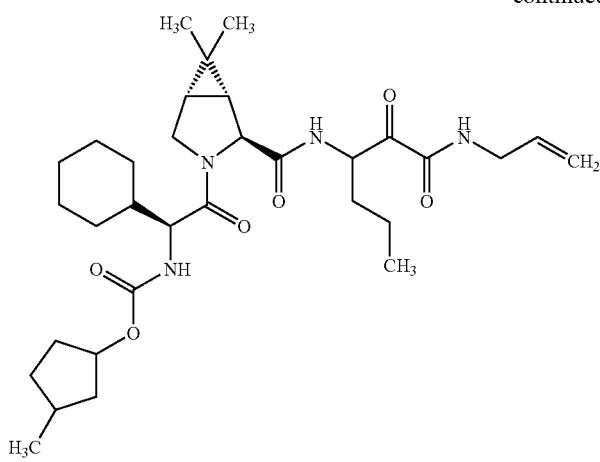
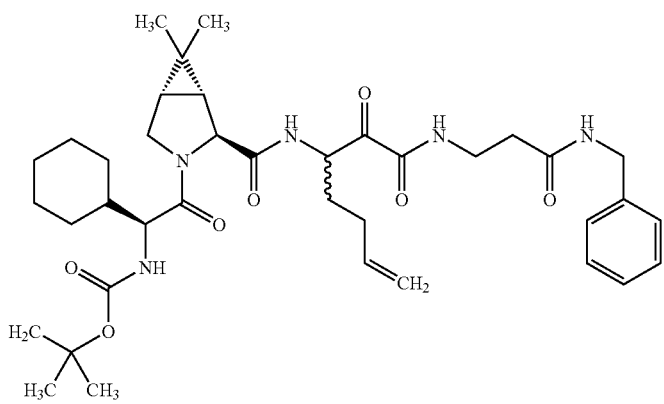
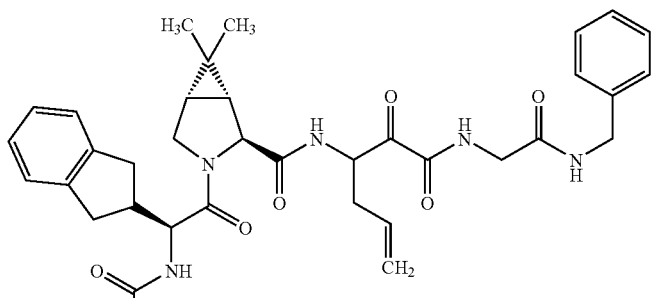
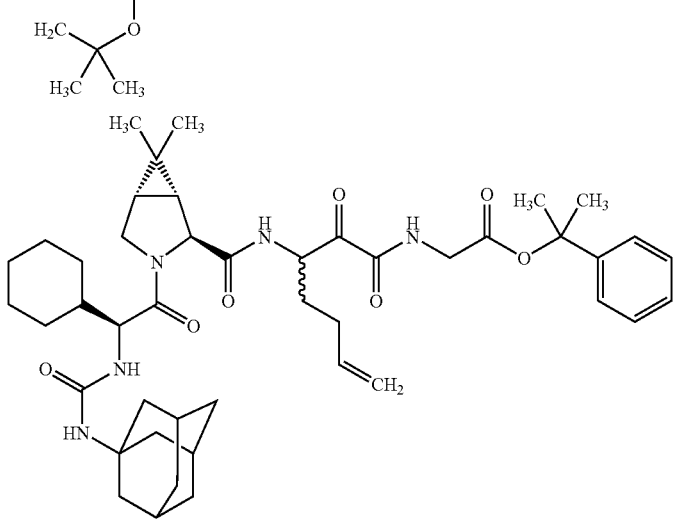

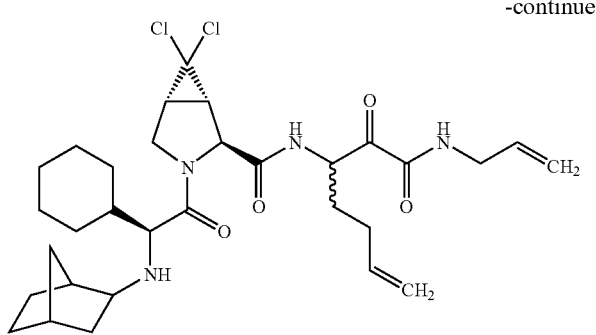
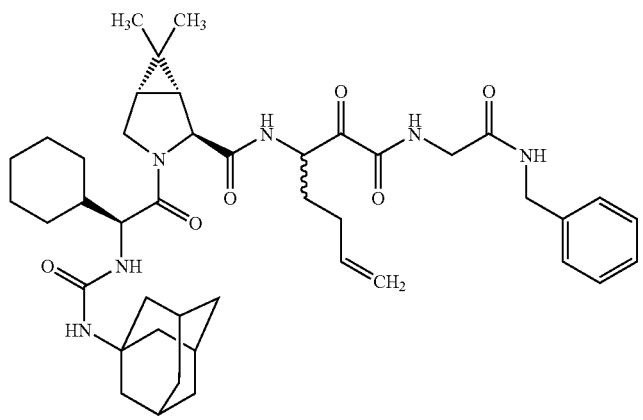
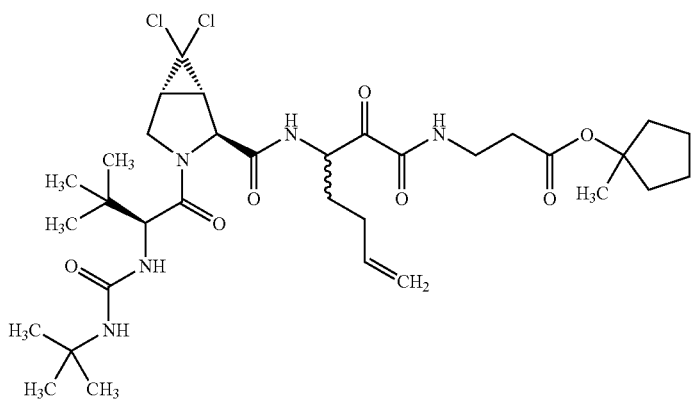
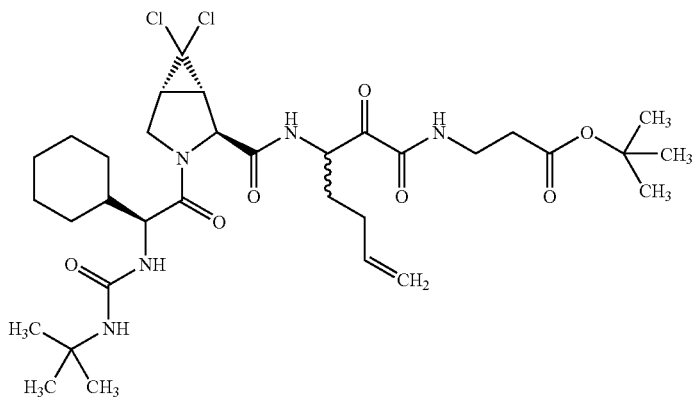

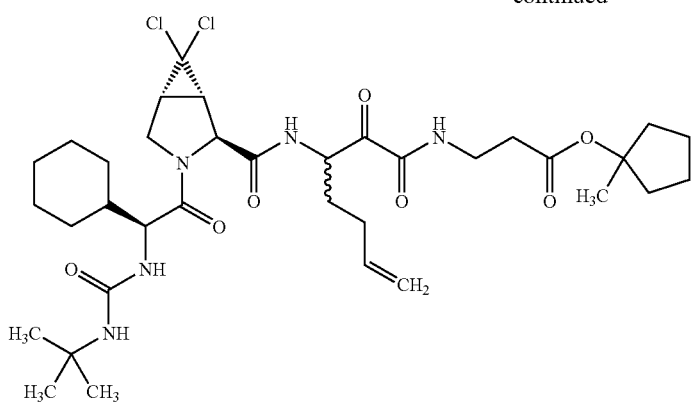
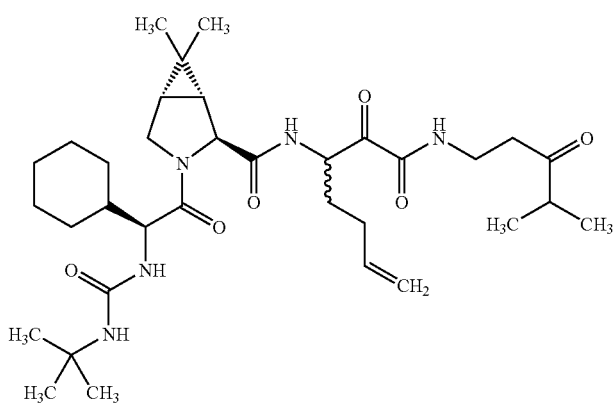
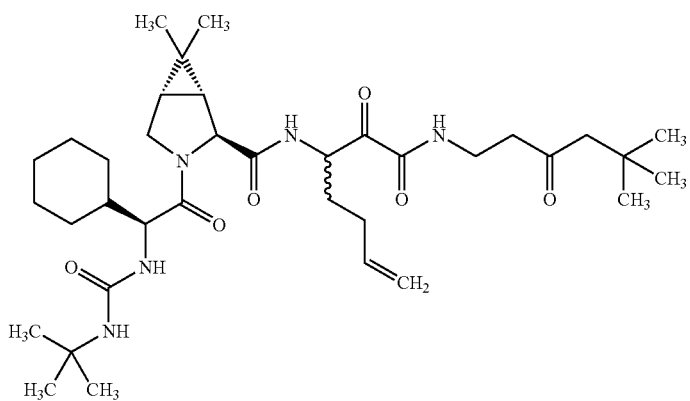
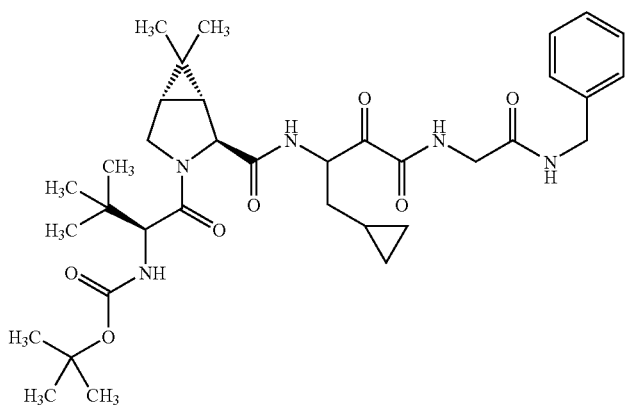

-continued
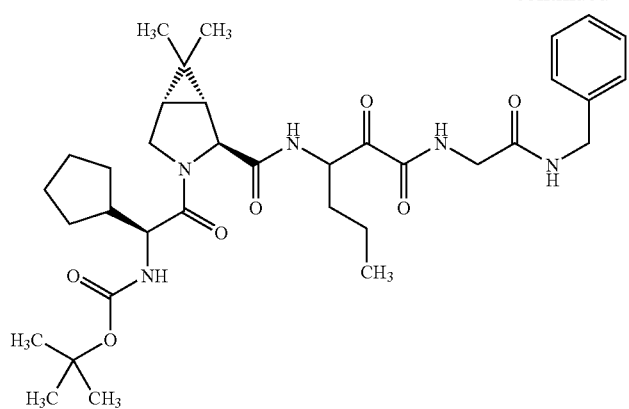
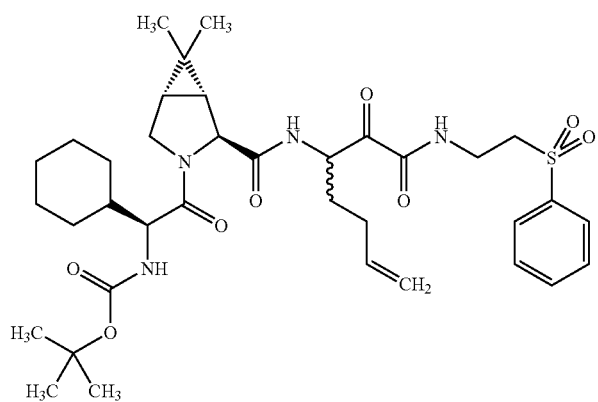
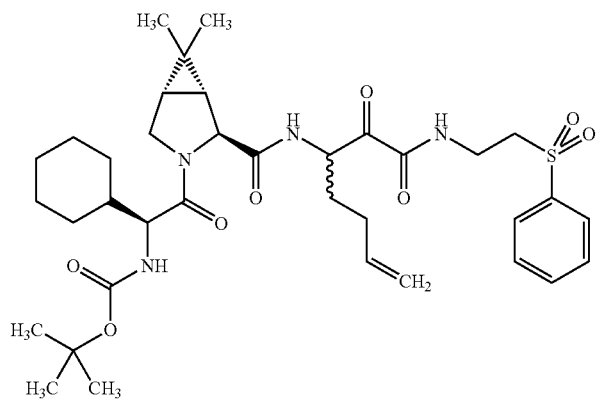
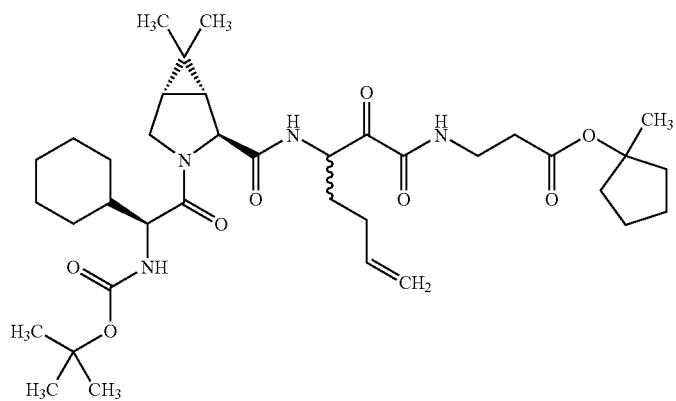

-continued
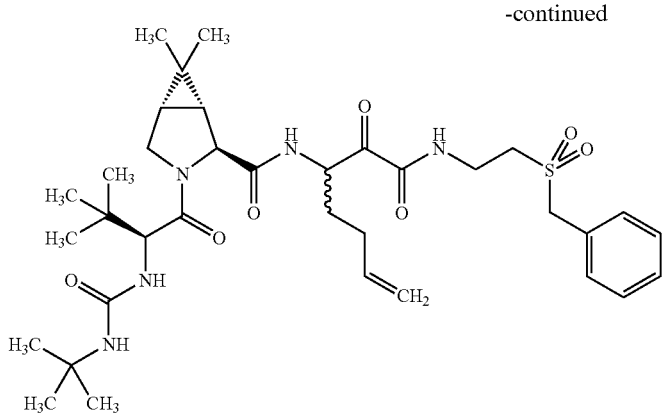
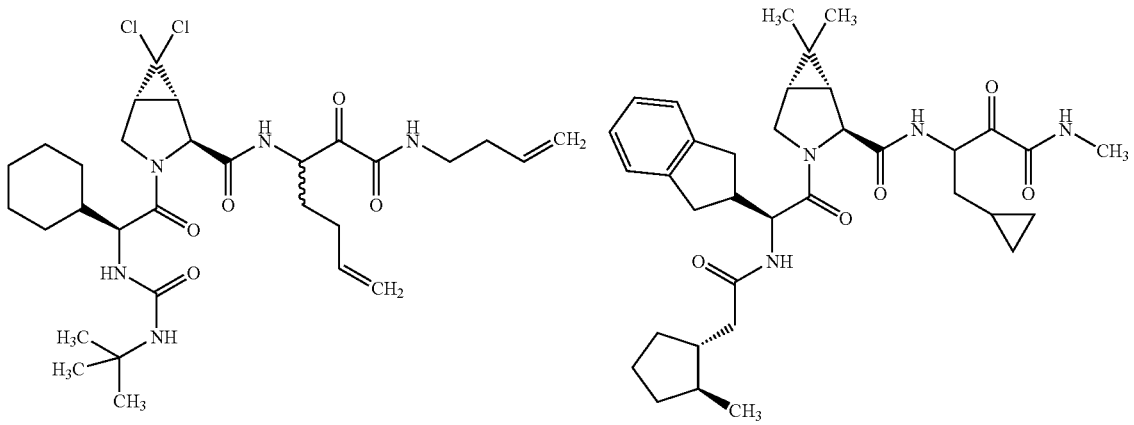
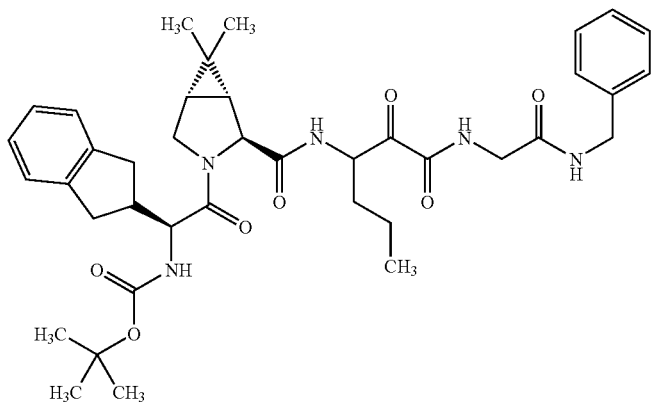
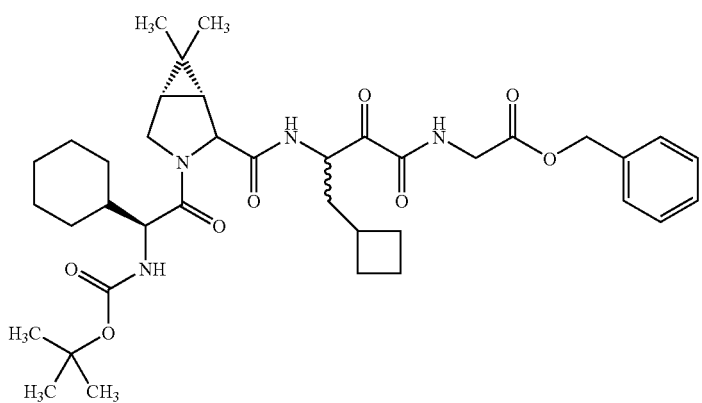

-continued
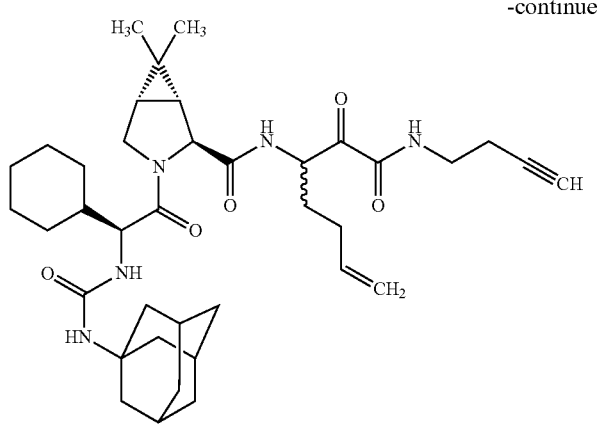
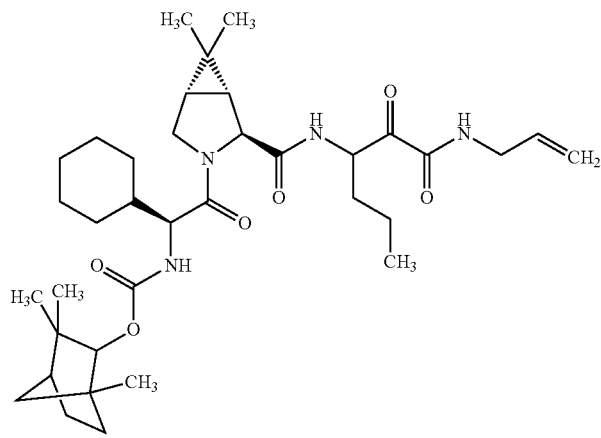
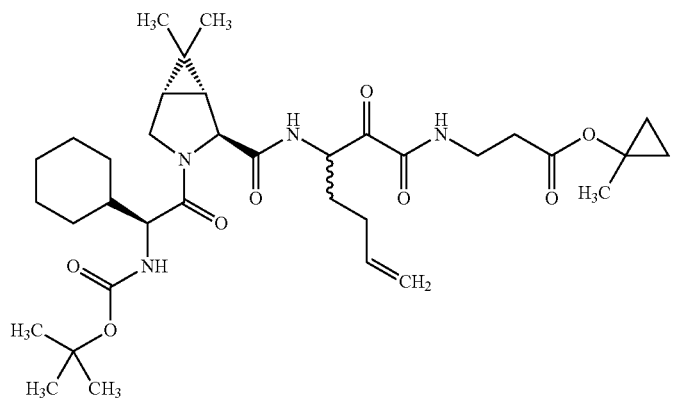
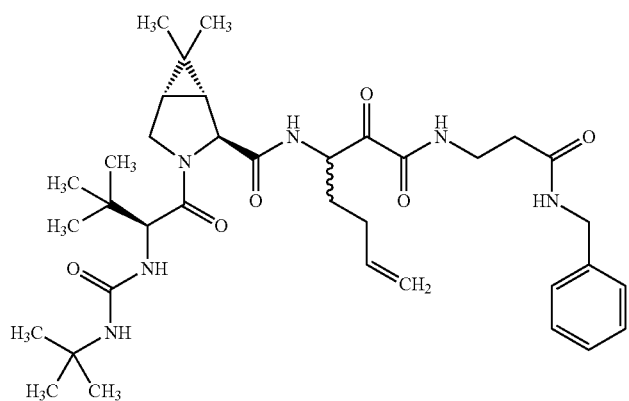

-continued
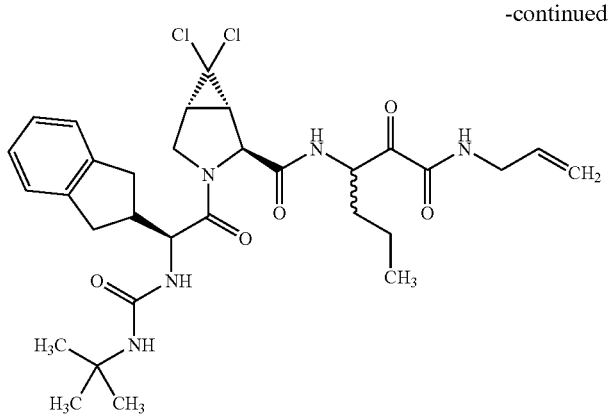
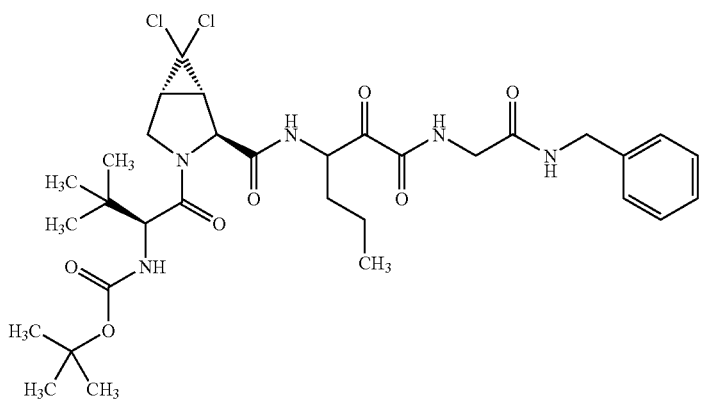
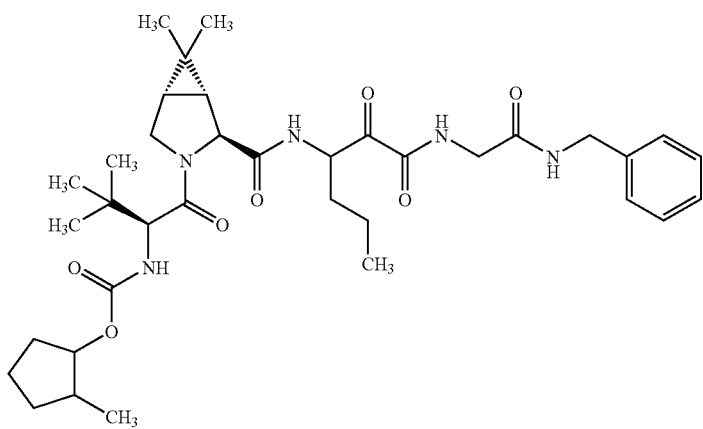
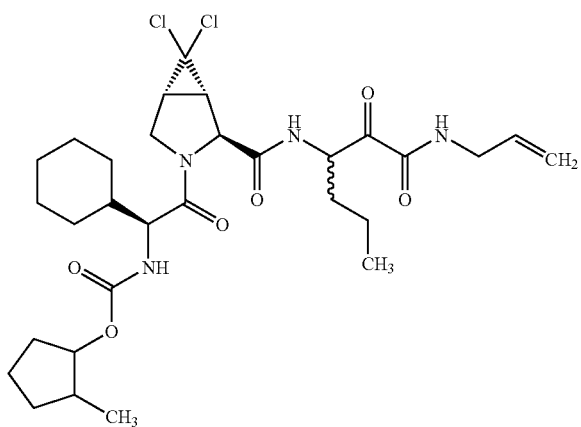

-continued
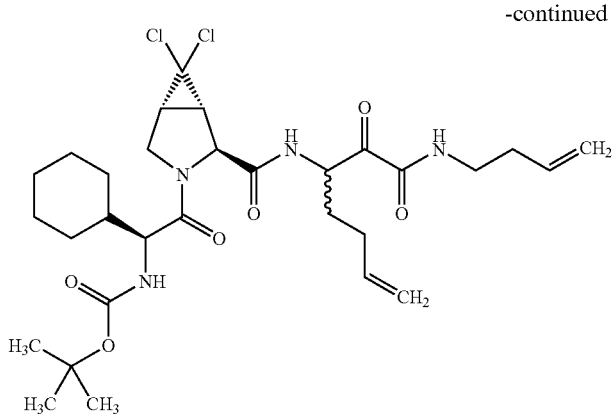
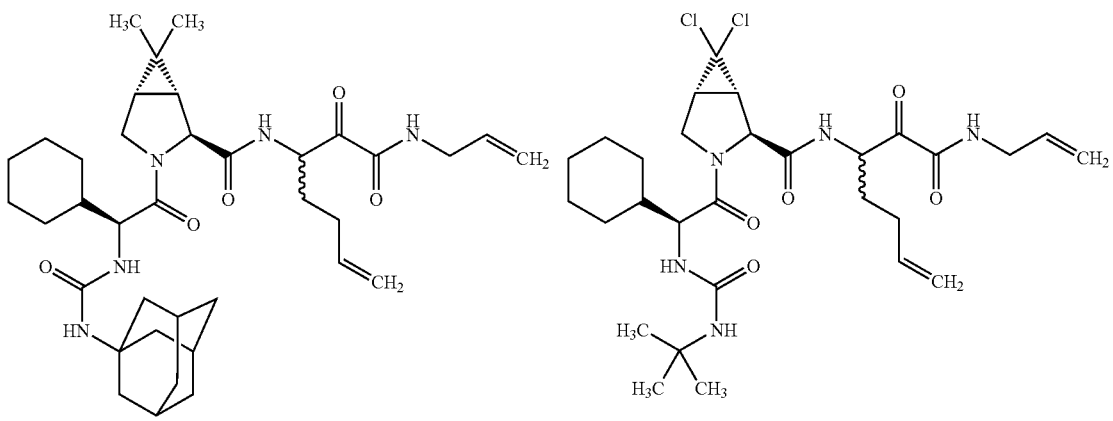
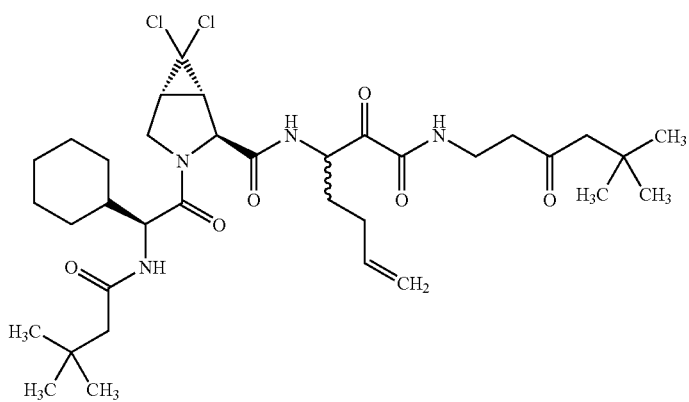
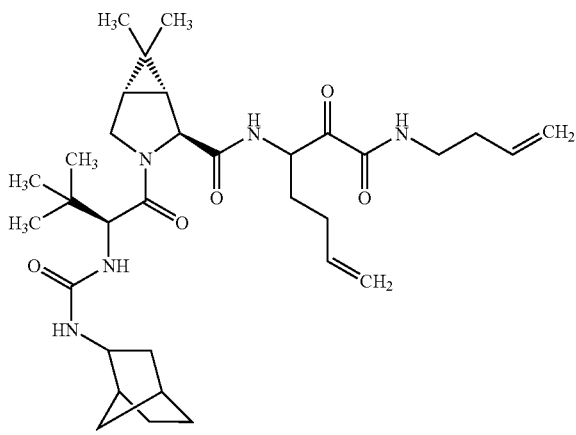

-continued
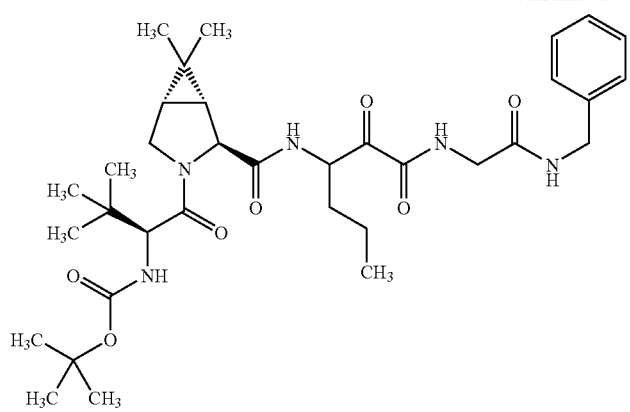
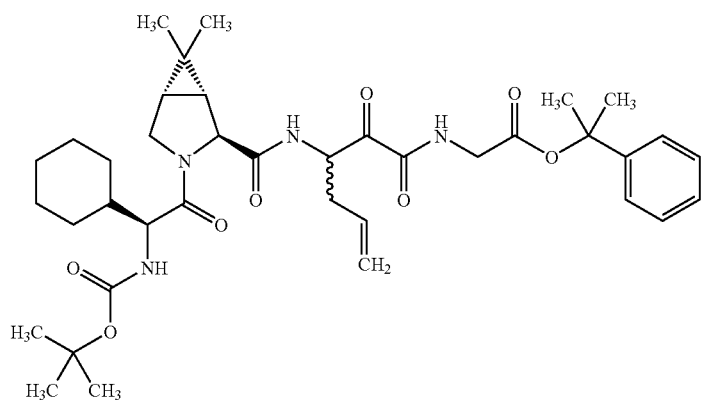
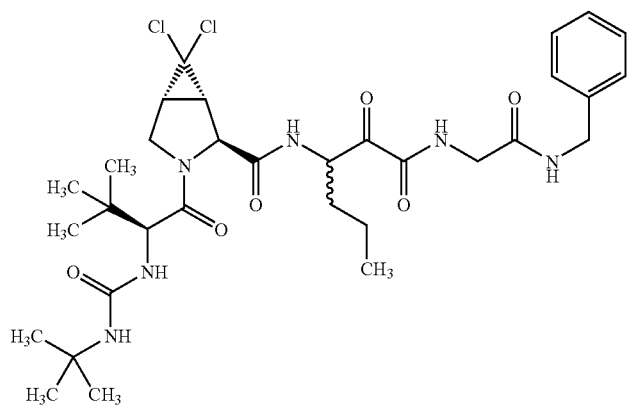
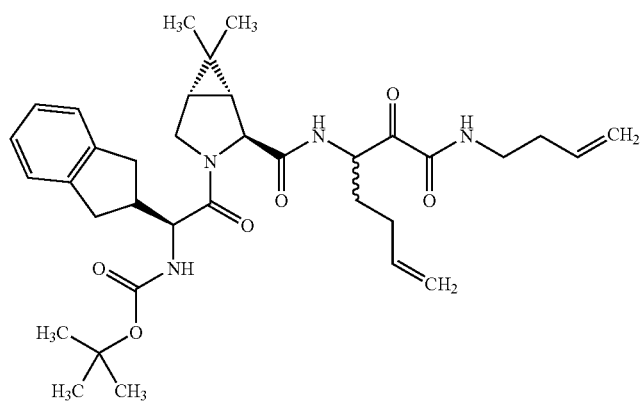

-continued
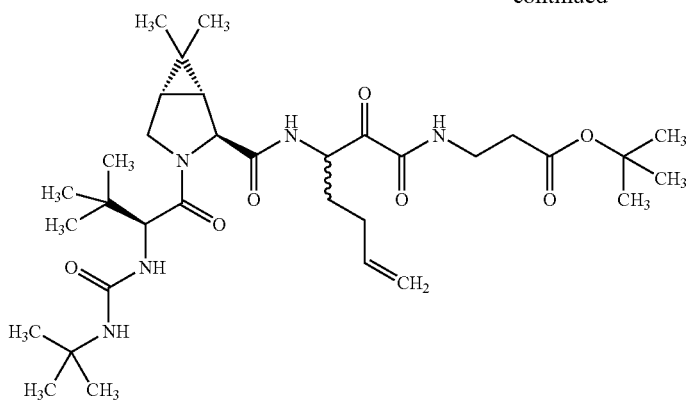
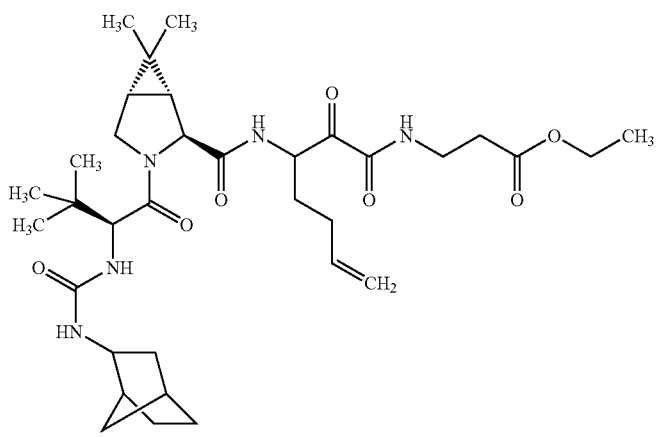
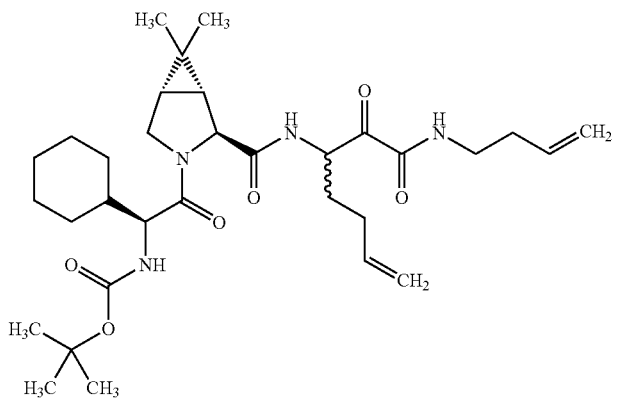
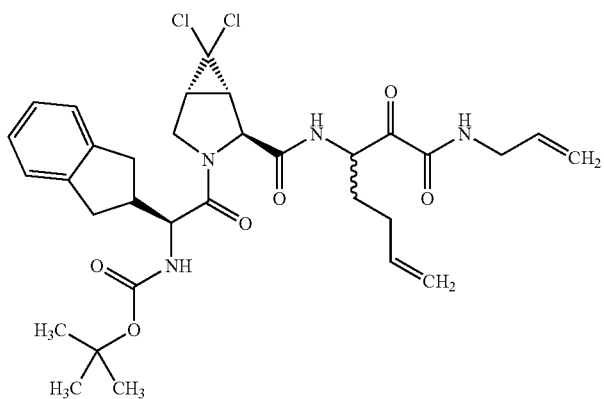

-continued
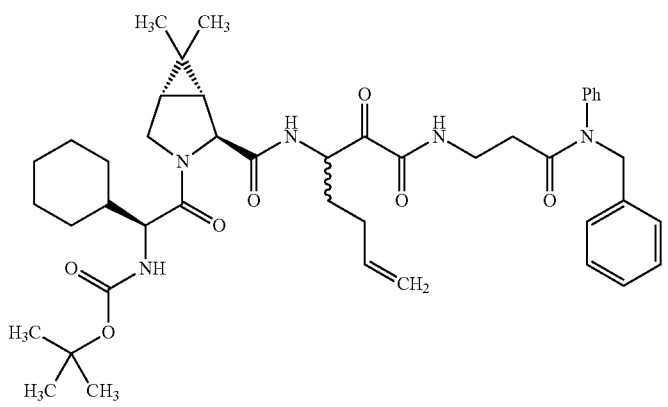
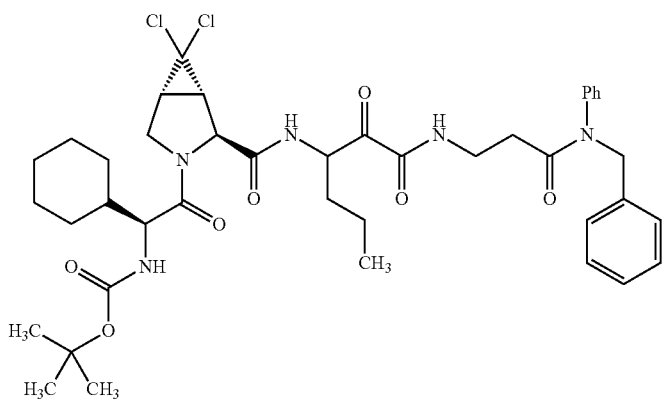
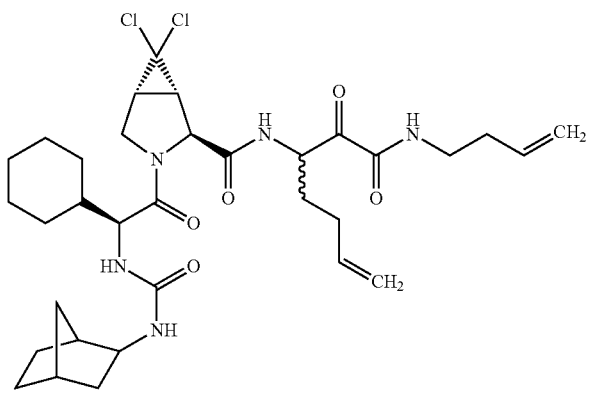
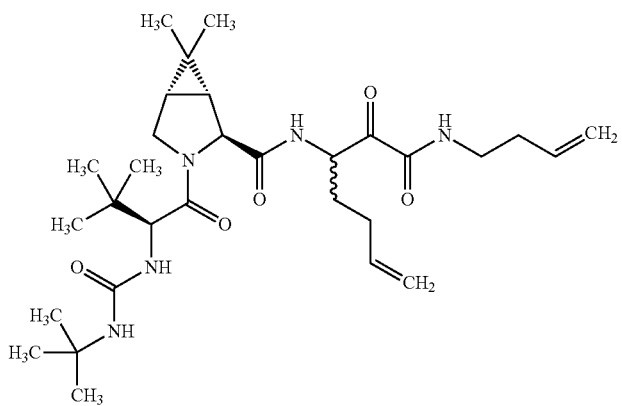

-continued
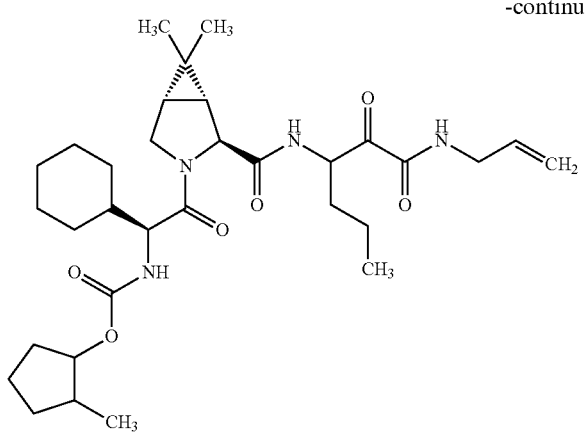
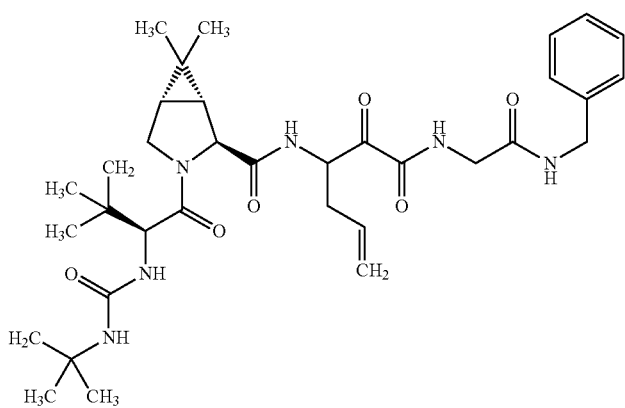
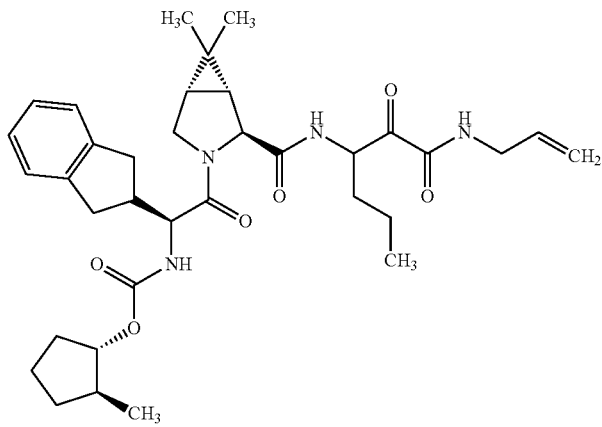
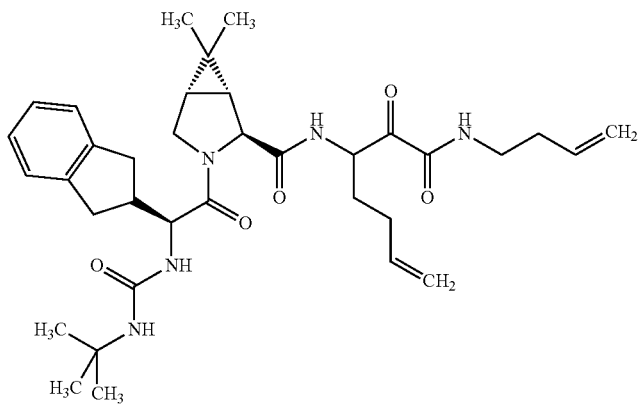

135 136
-continued
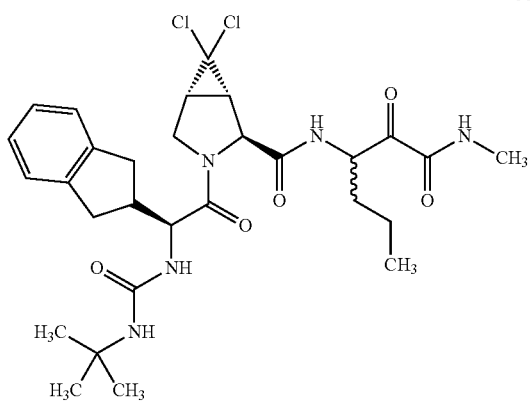
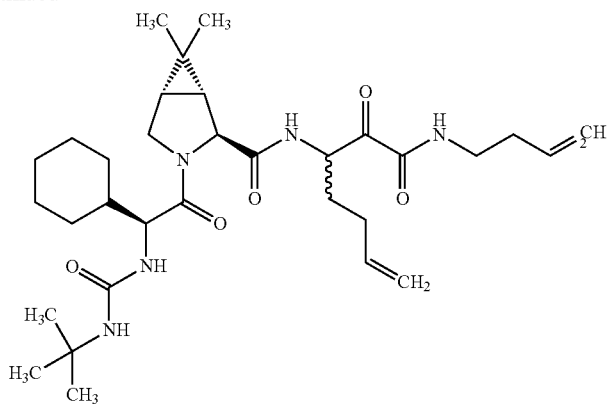
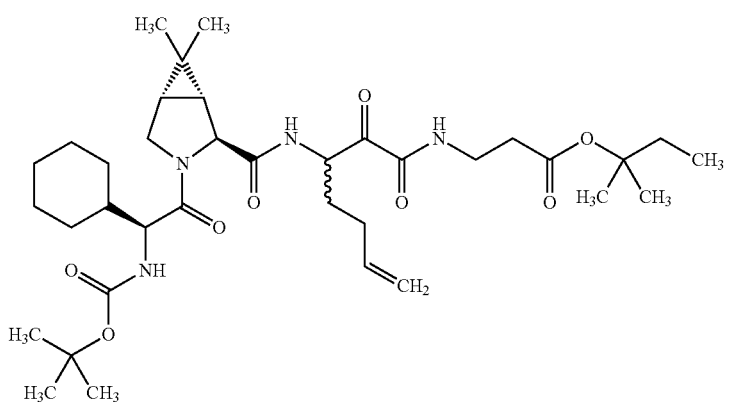
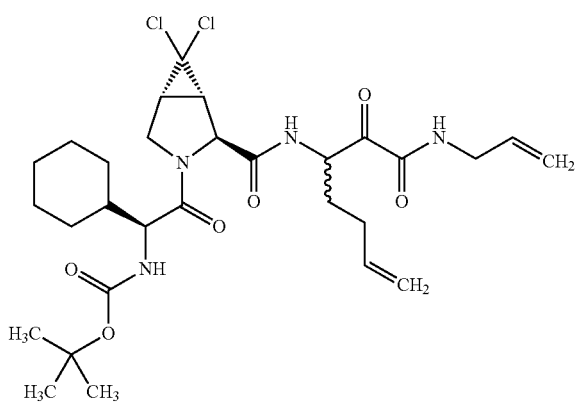
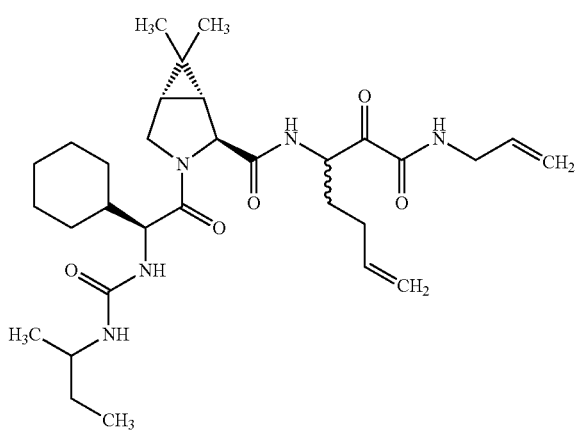

-continued
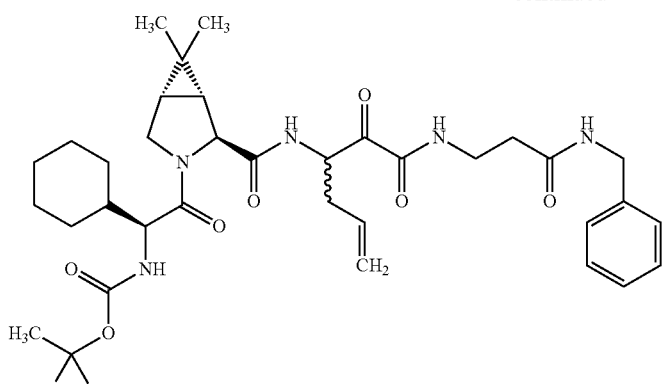
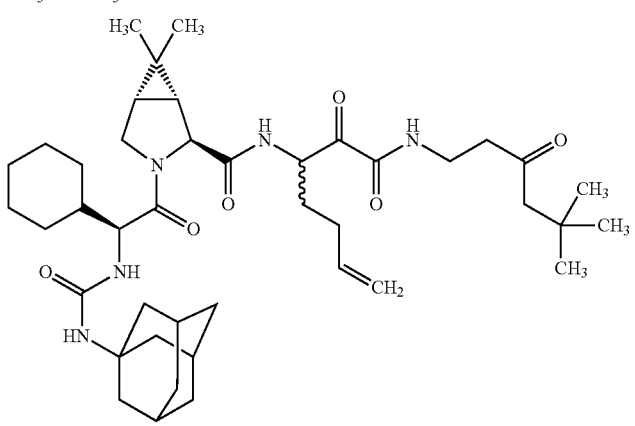
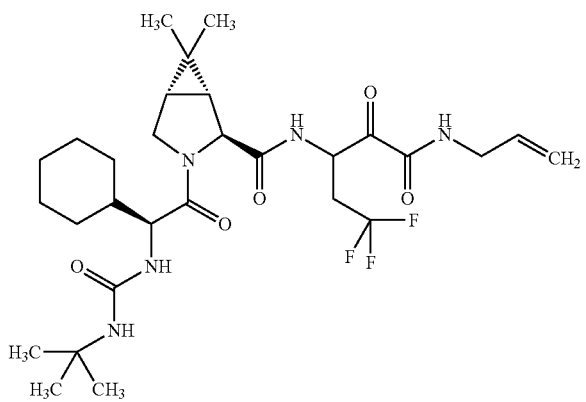
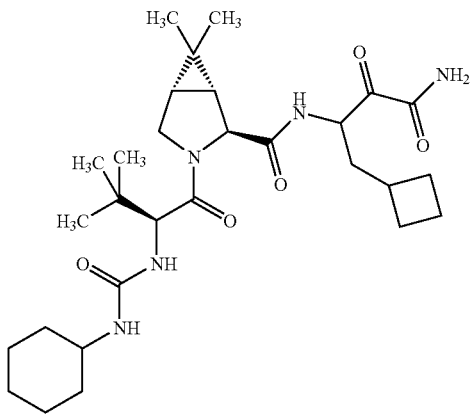
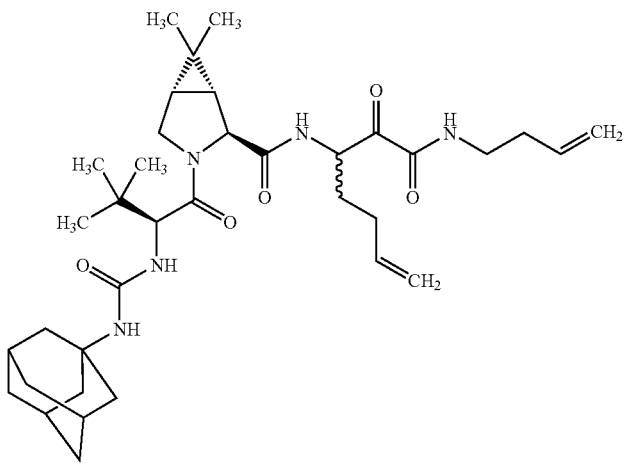

-continued
| 139 | 140 |
|---|---|
| 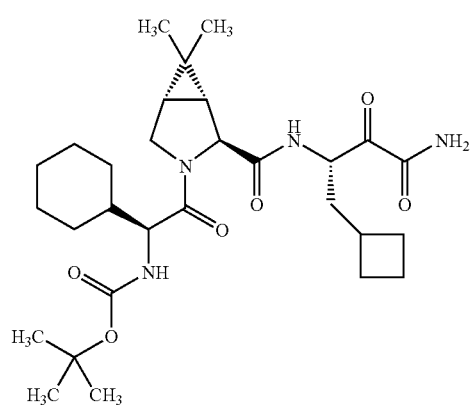 | 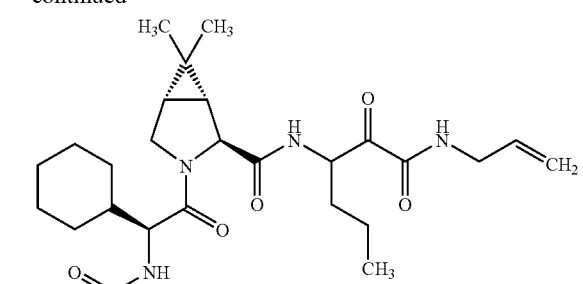 |
| 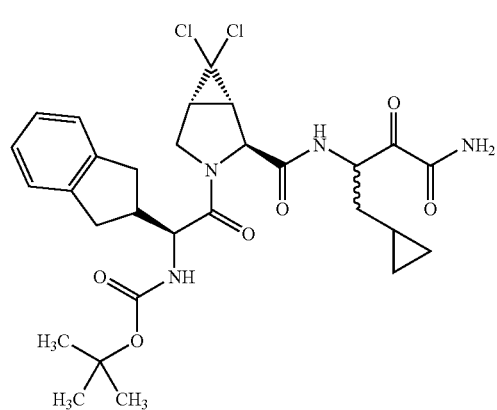 | 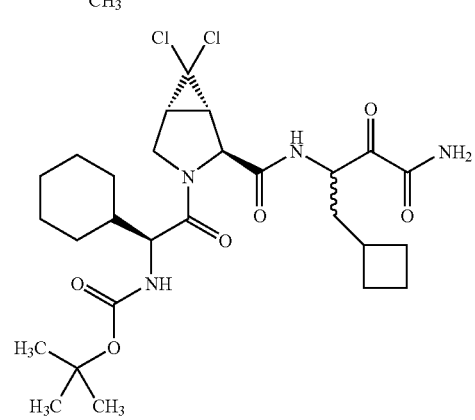 |
| 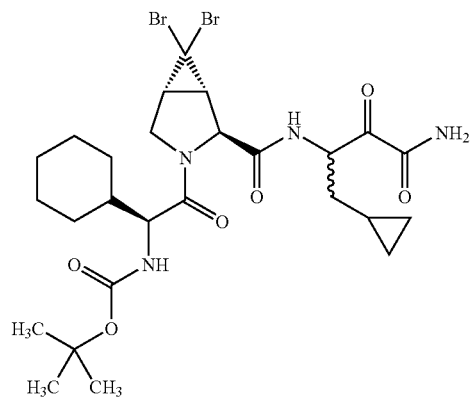 | 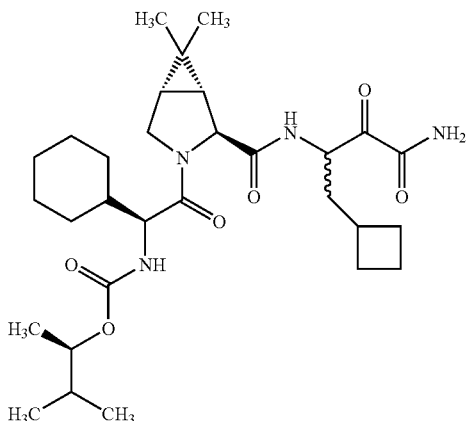 |
| 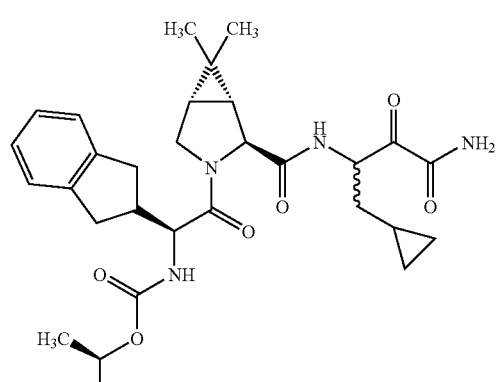 | 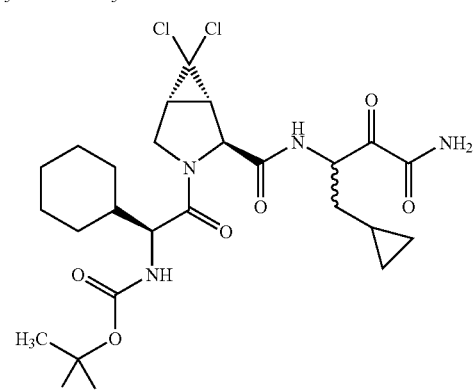 |

-continued
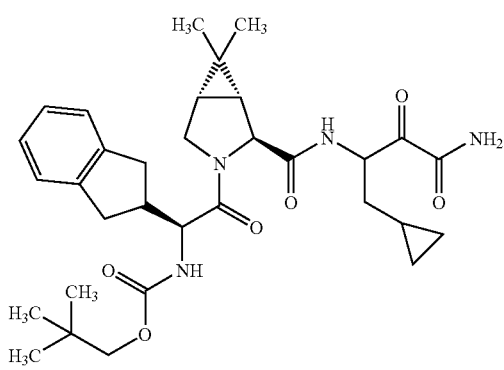
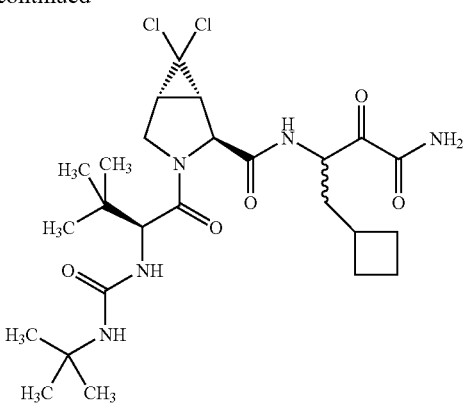
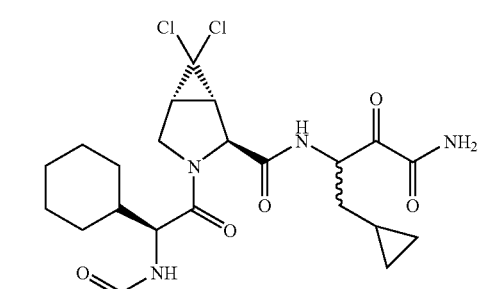
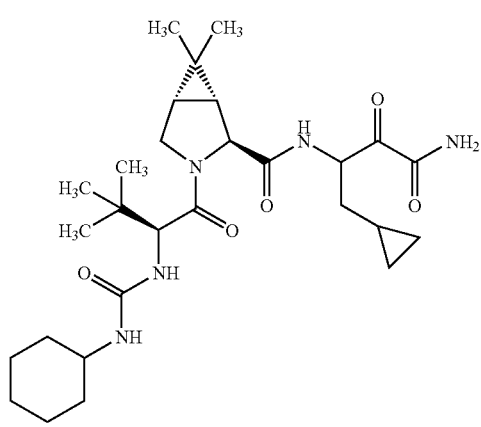
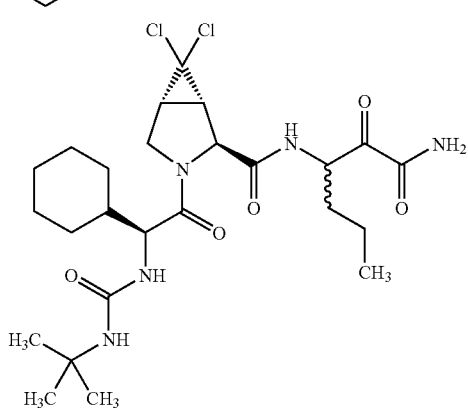
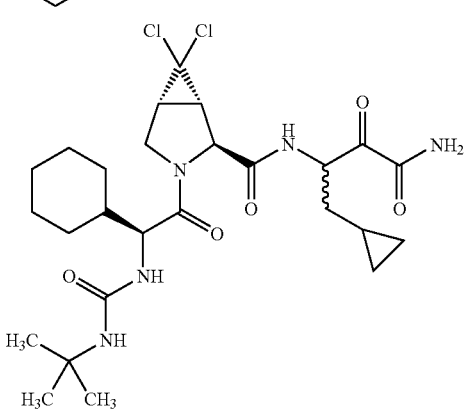
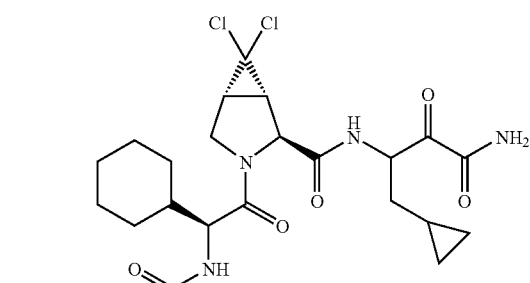
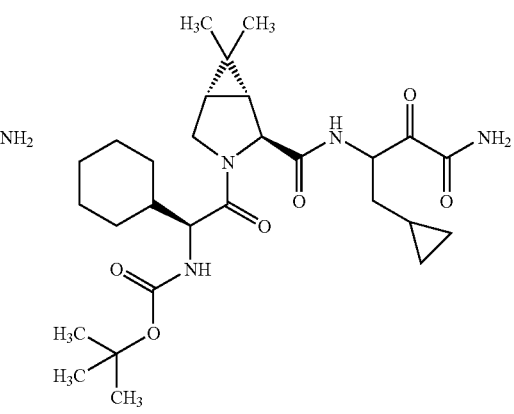

-continued
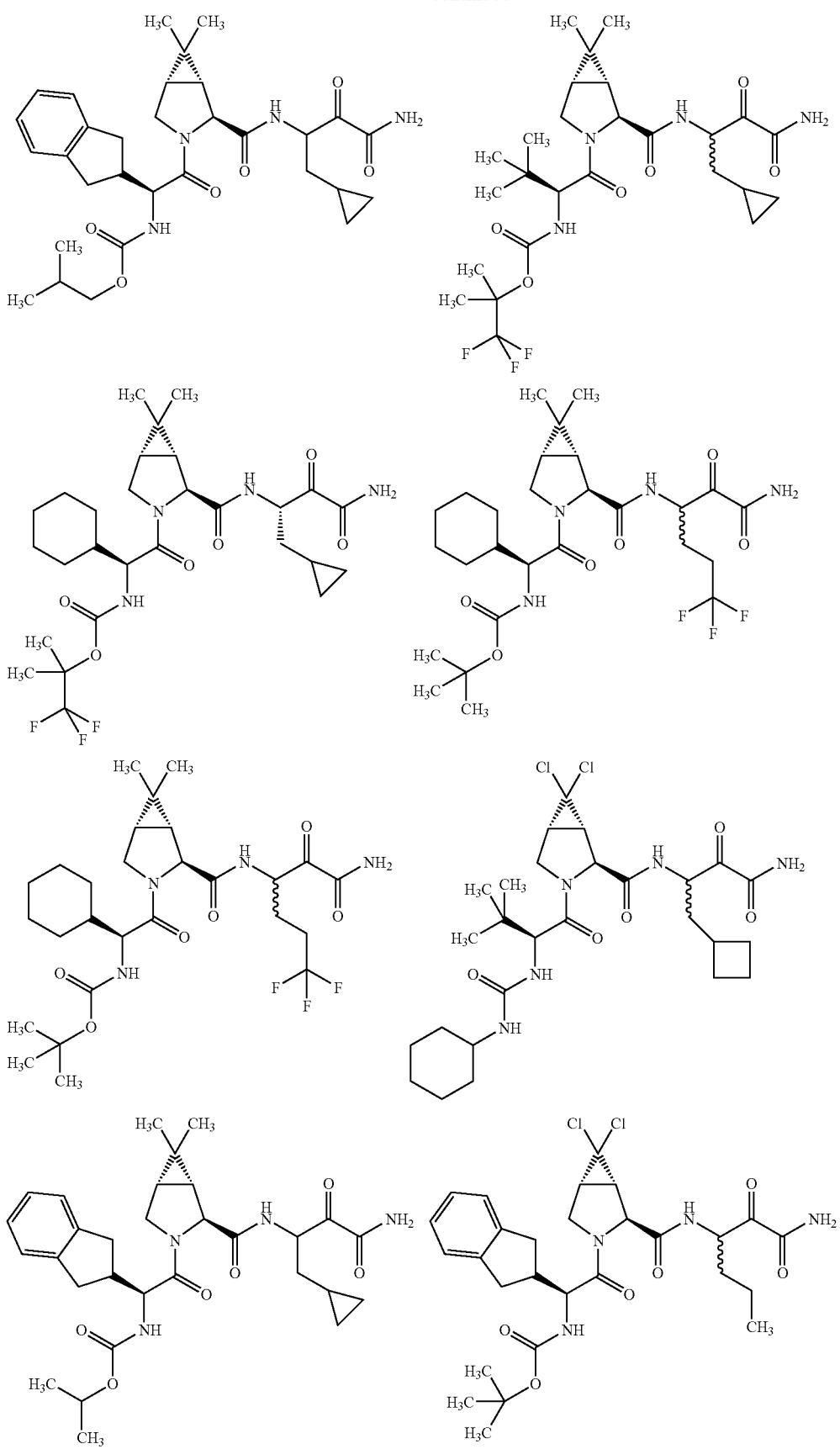

-continued
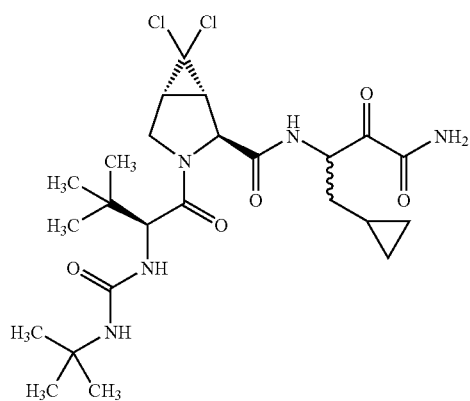
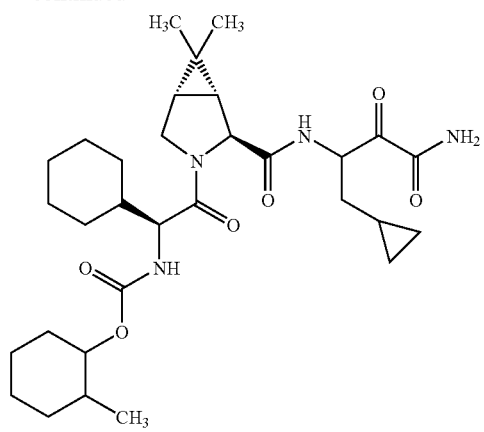
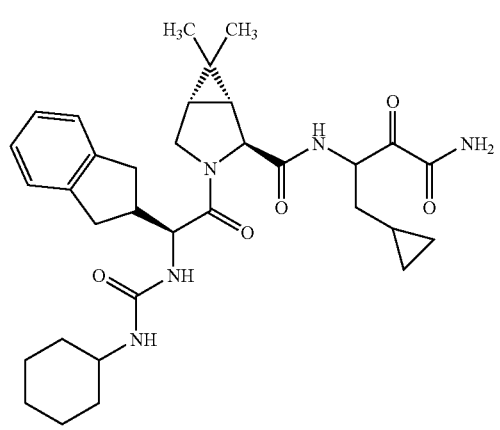
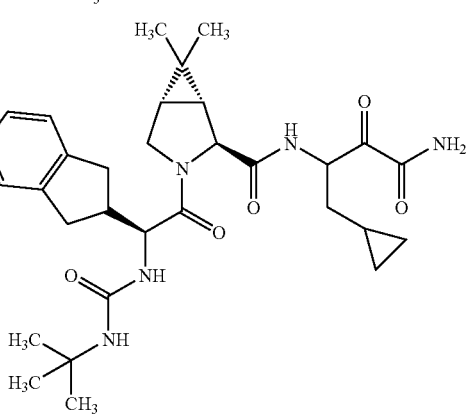
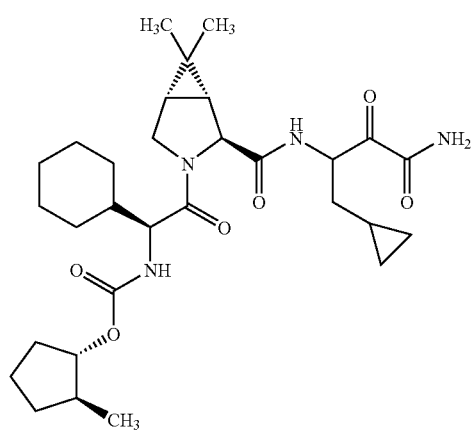
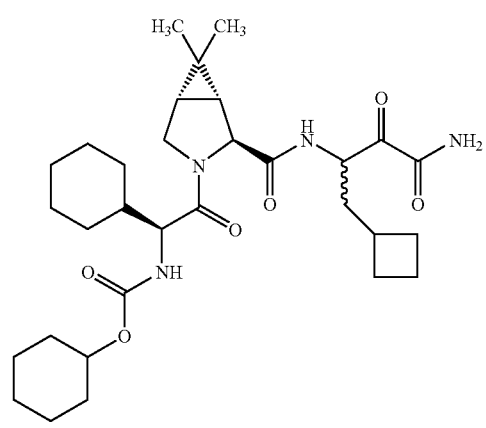
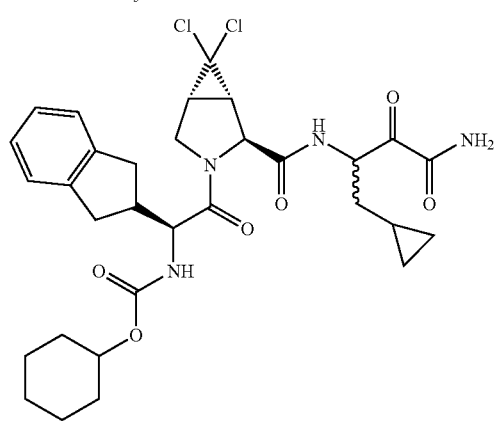
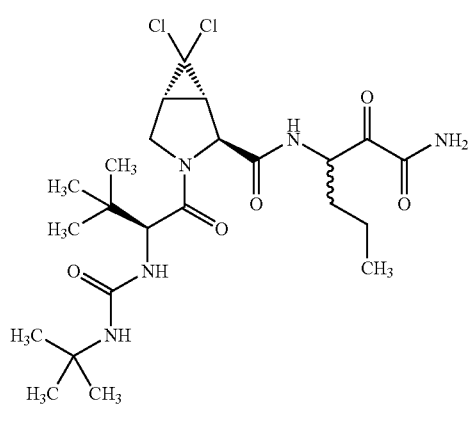

147 148
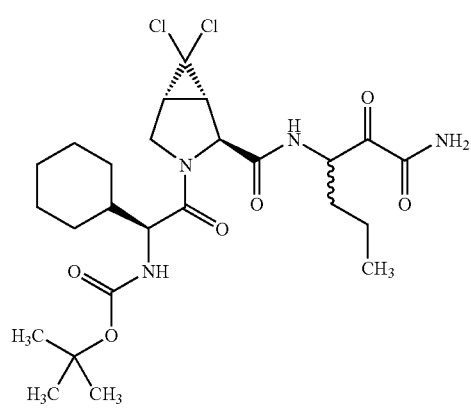
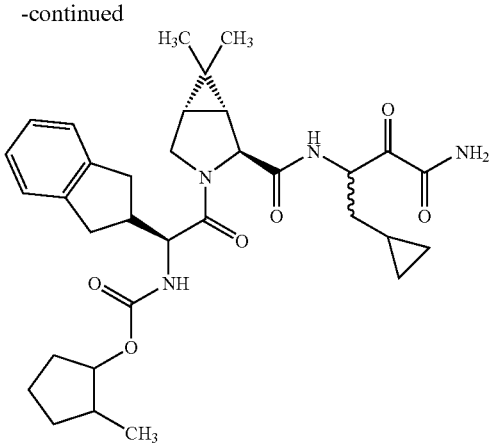
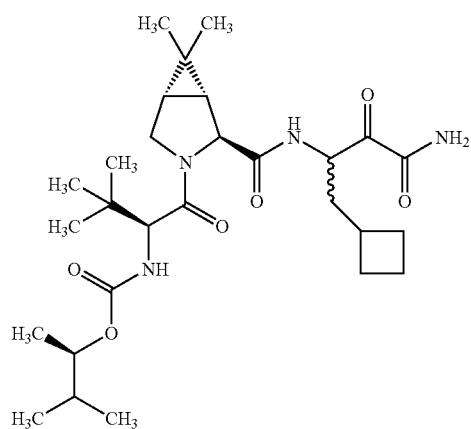
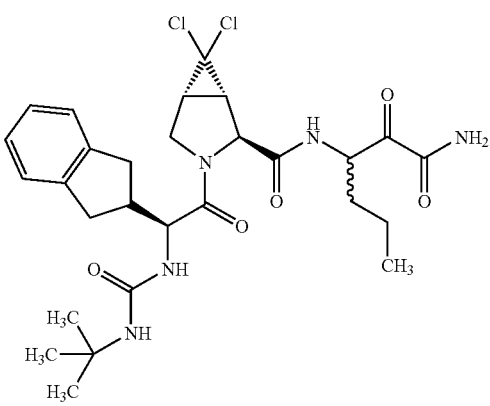
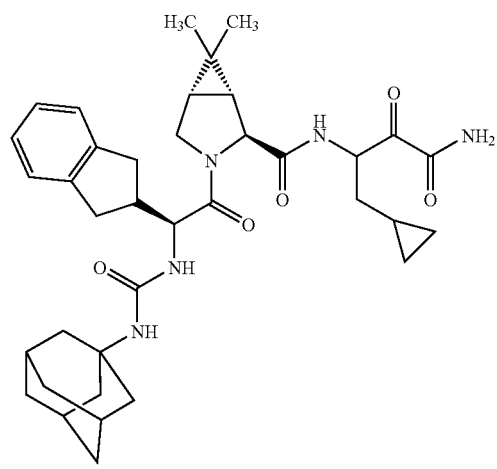
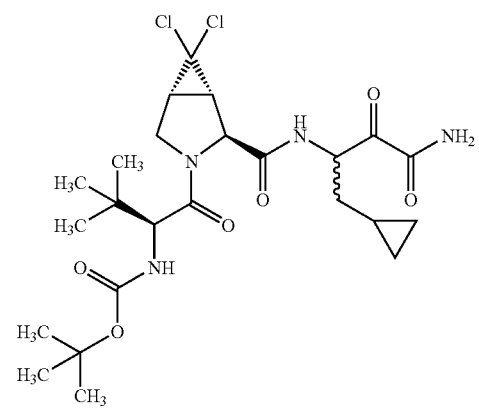
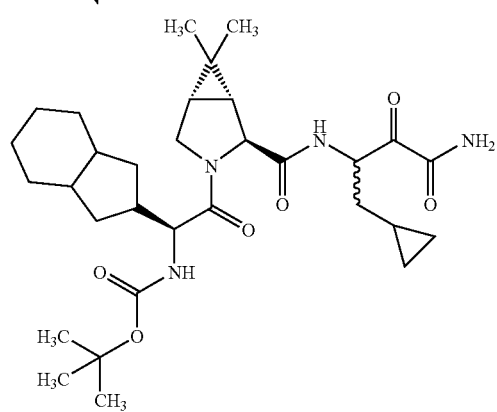
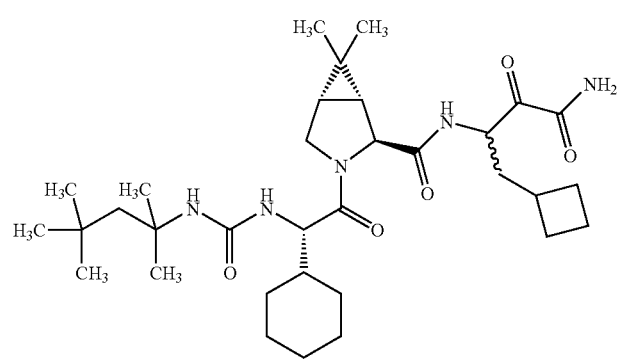

-continued
| 149 | 150 |
|---|---|
| 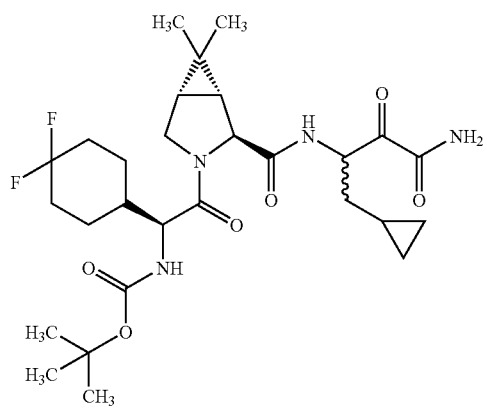 | 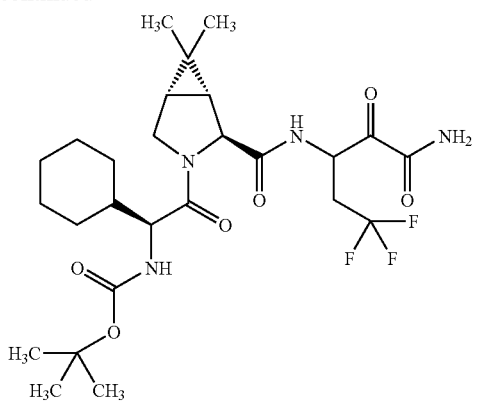 |
| 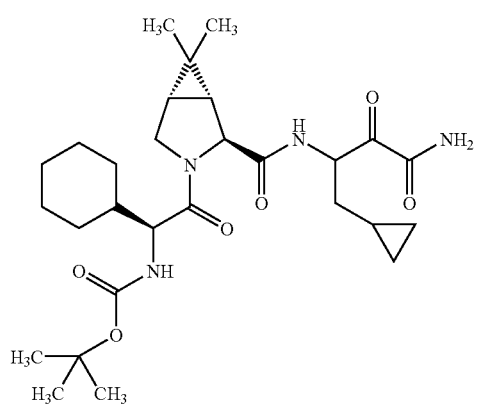 | 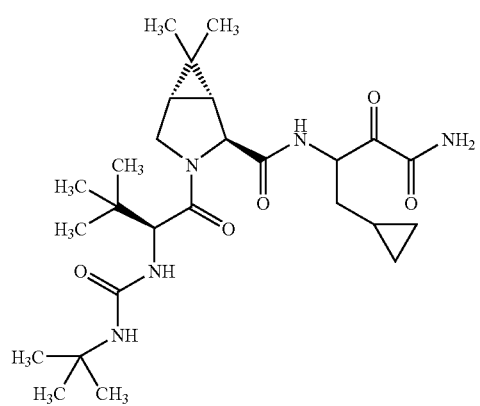 |
| 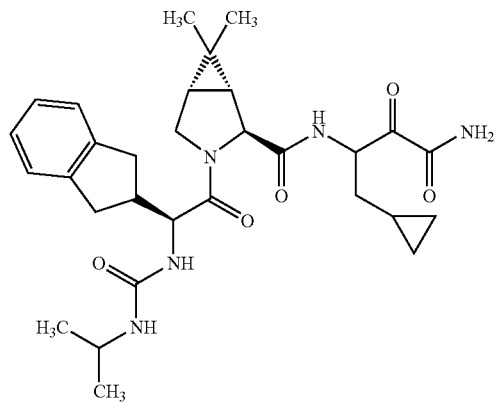 | 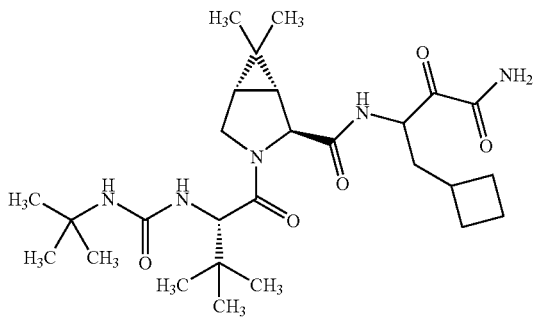 |
| 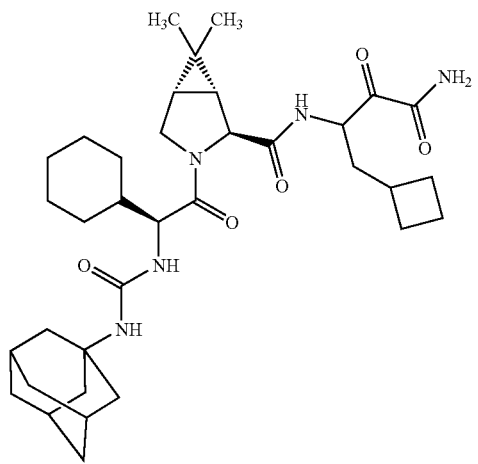 | 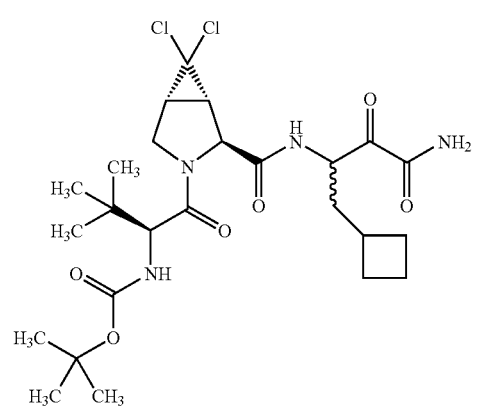 |

-continued
| 151 | 152 |
|---|---|
| 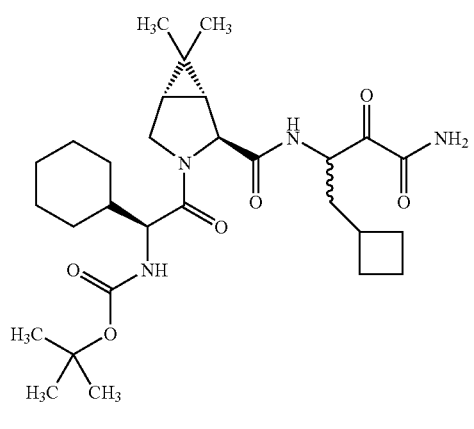 | 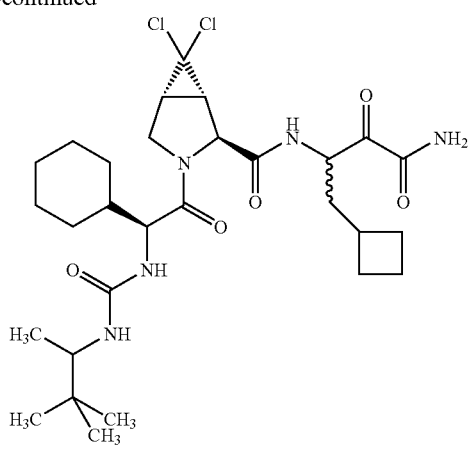 |
| 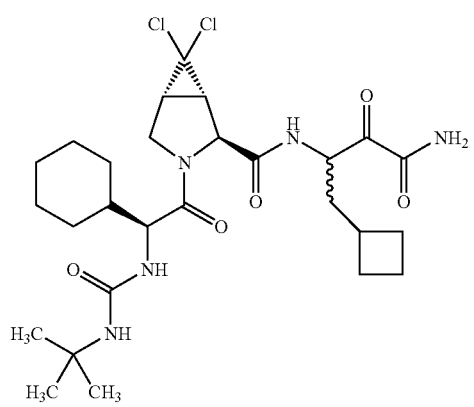 | 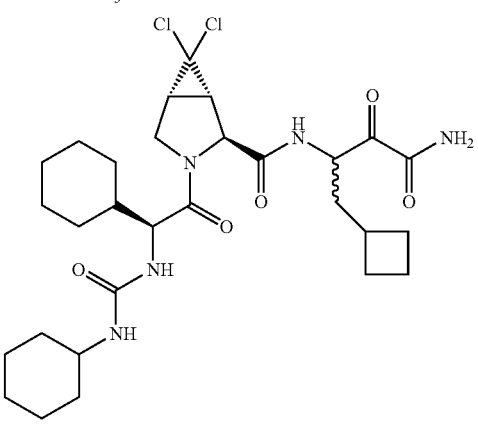 |
| 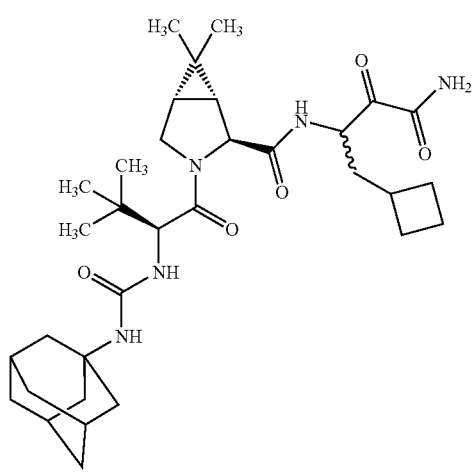 | 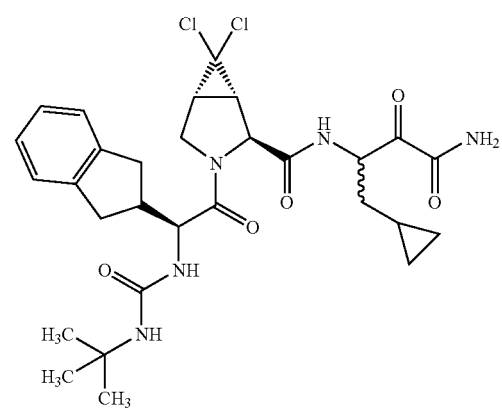 |
| 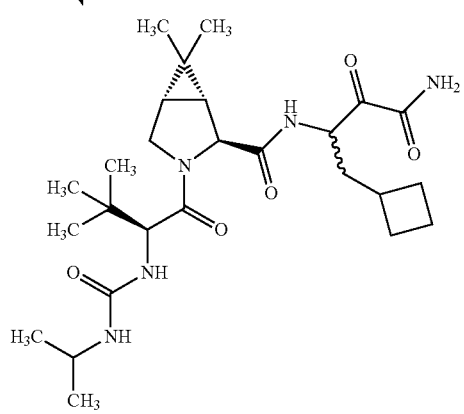 | 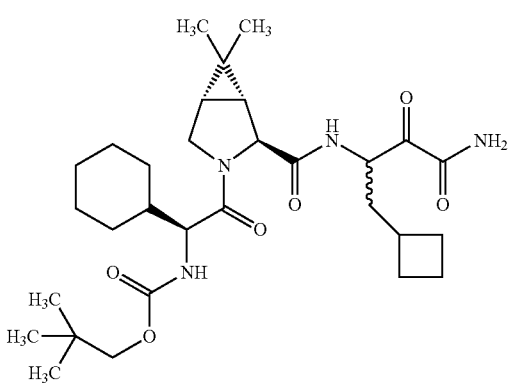 |

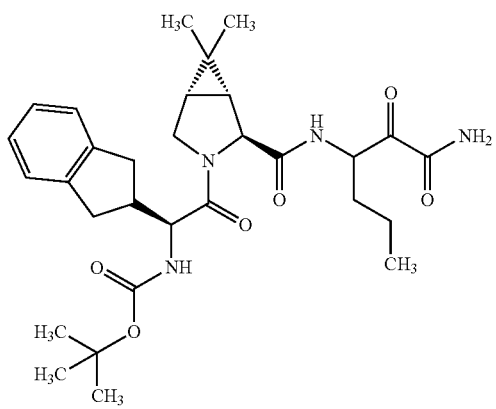
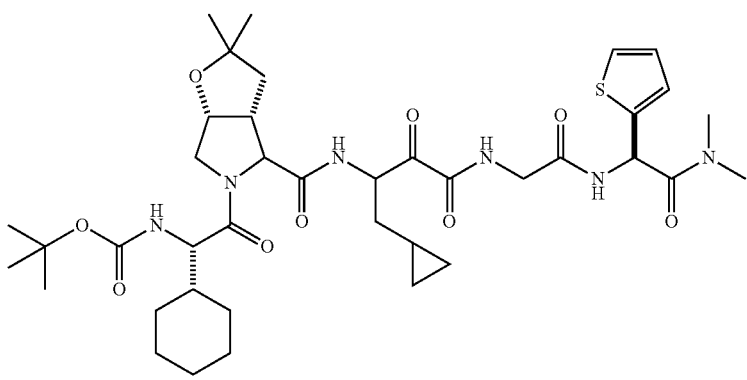
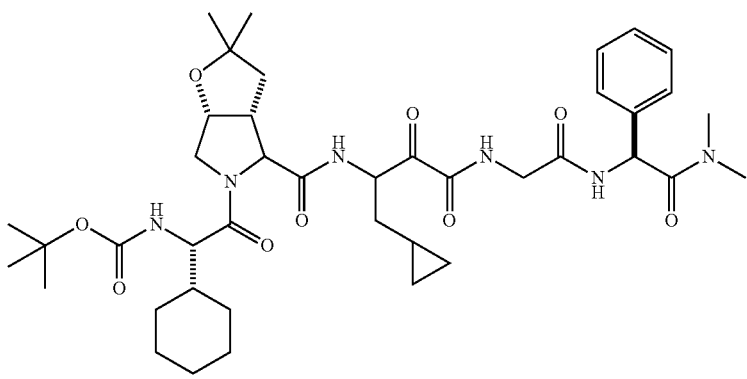
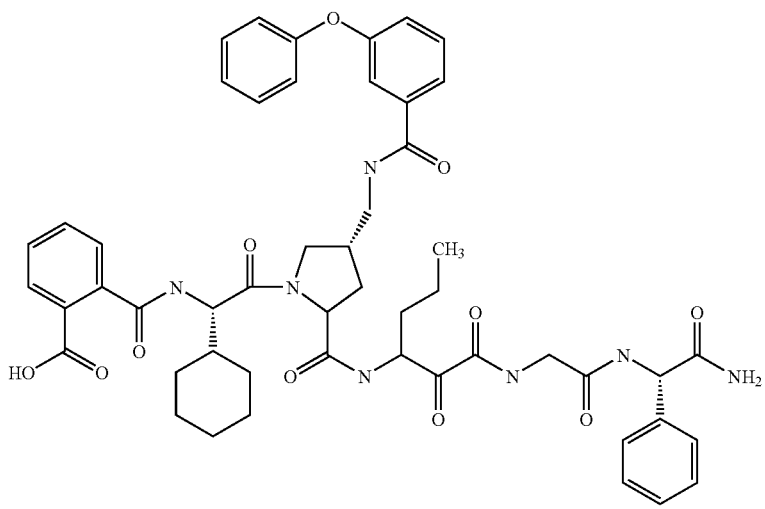

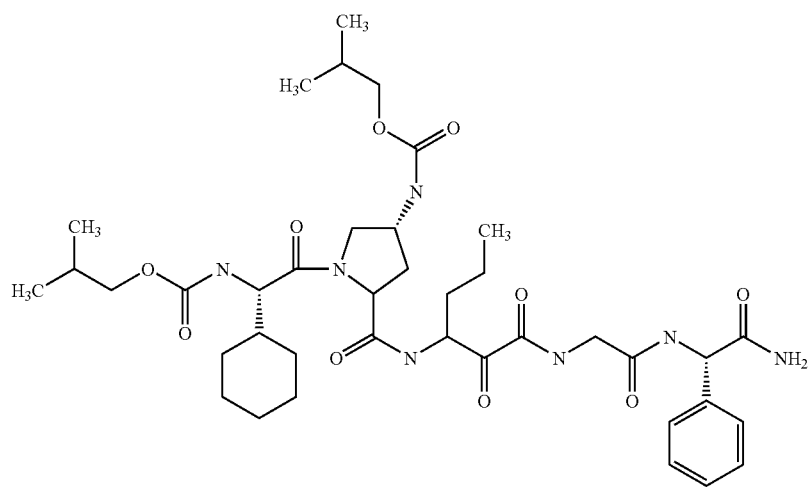
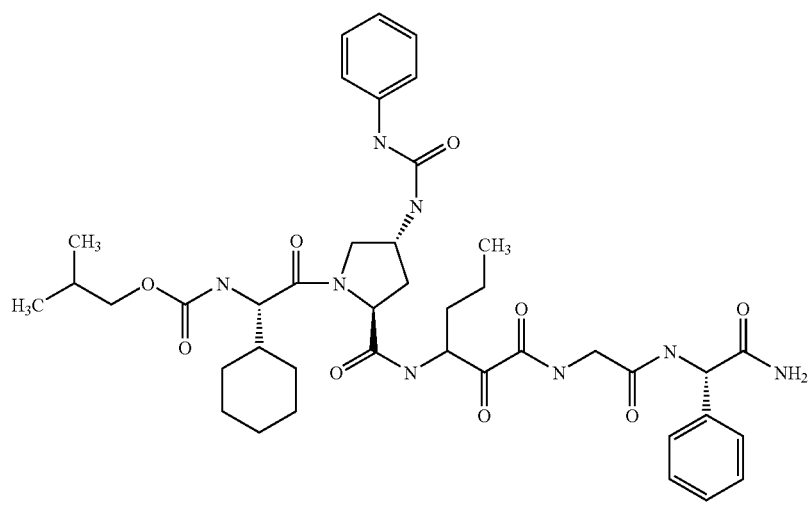
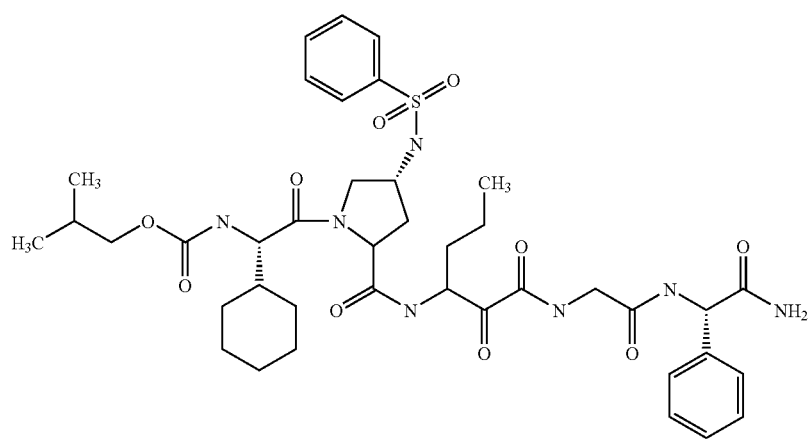

-continued
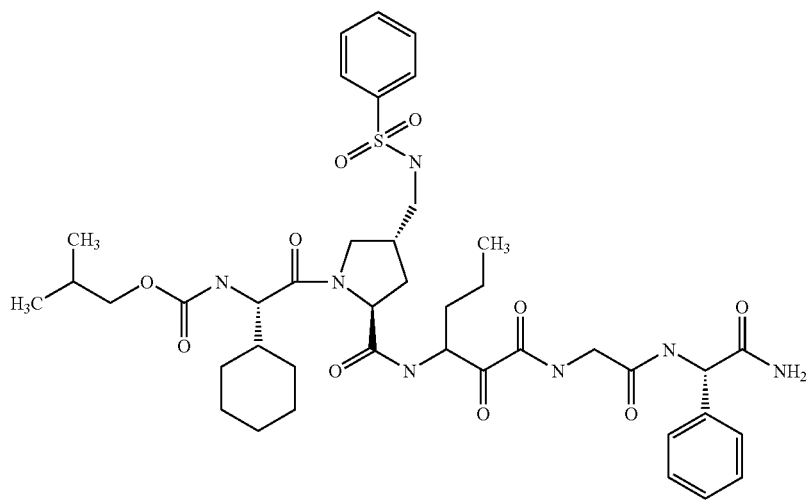
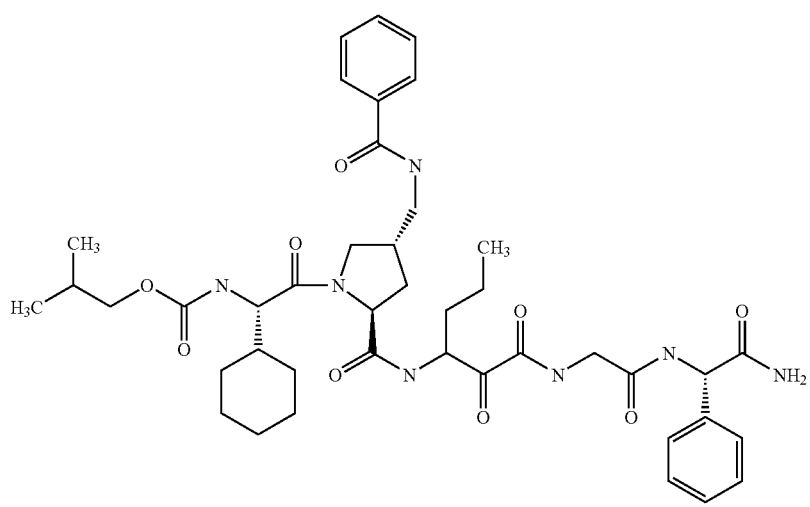
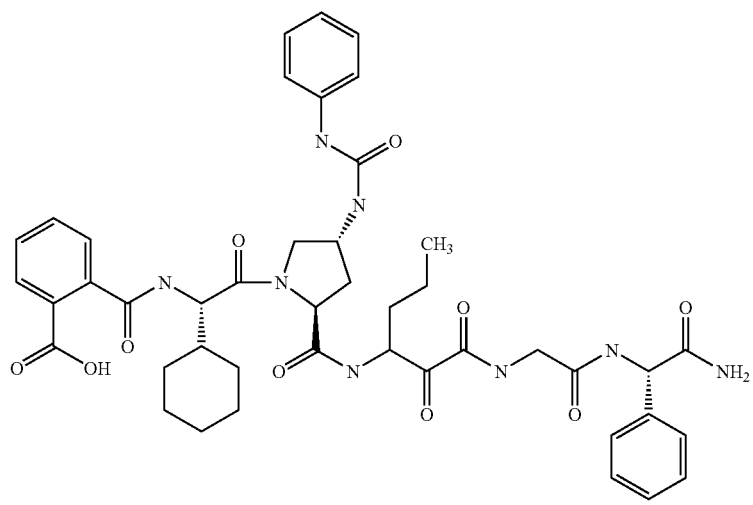

-continued
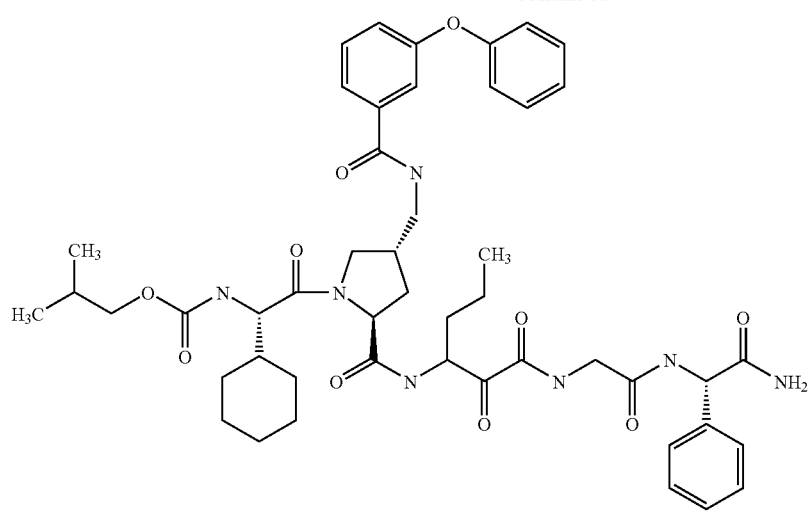
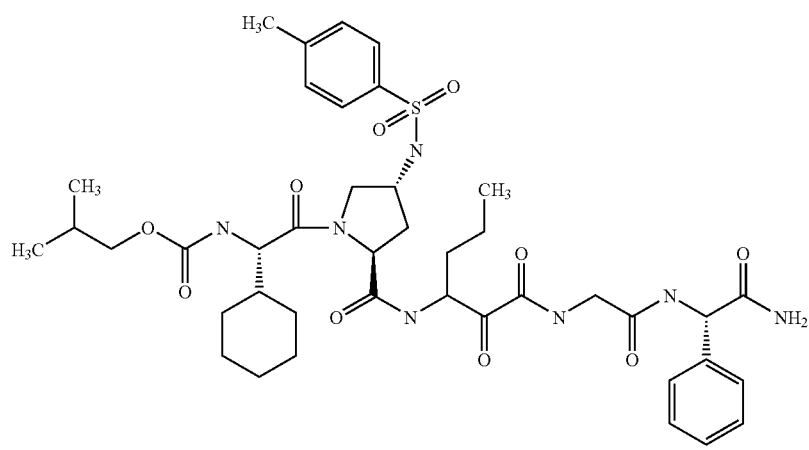

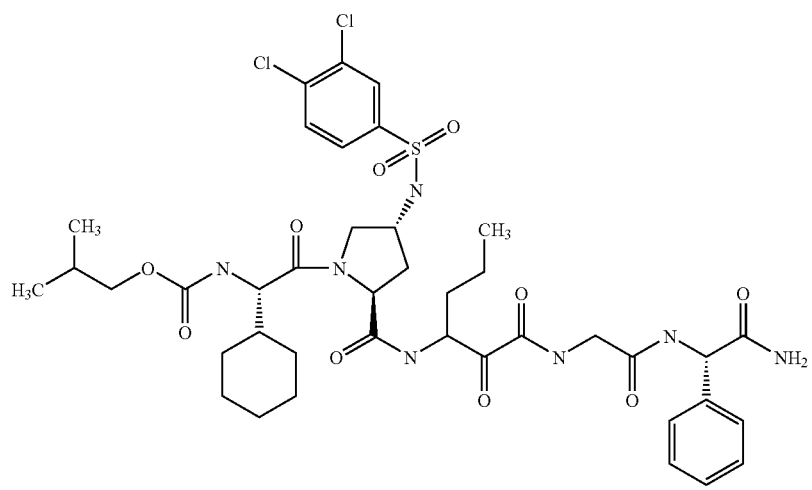
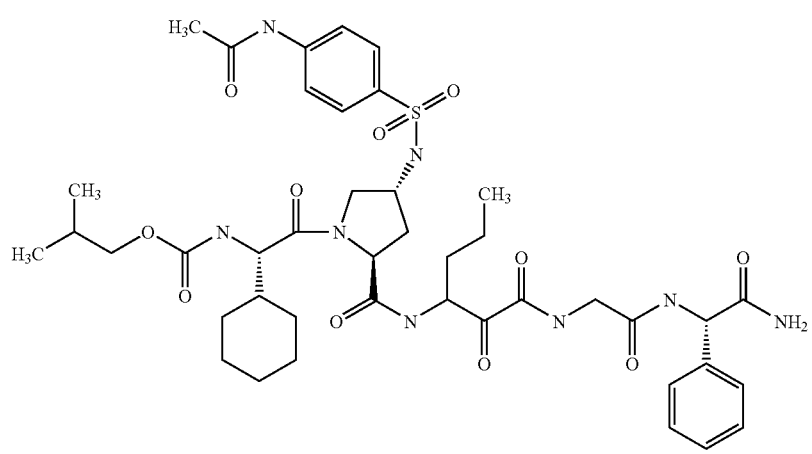
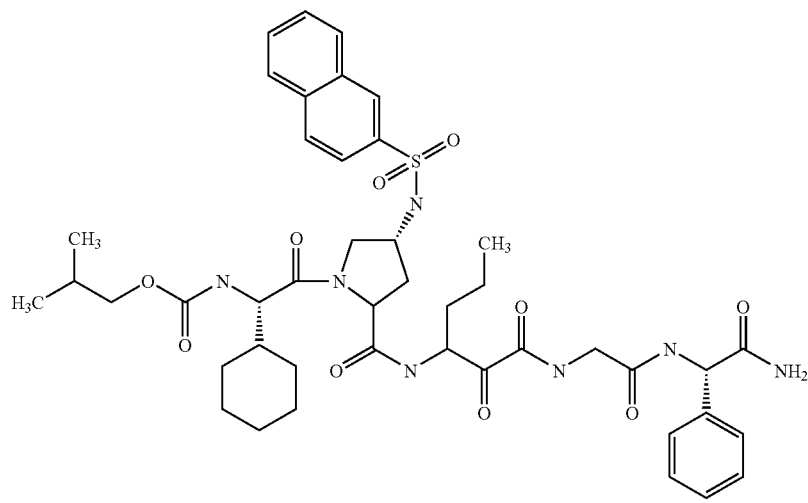

-continued
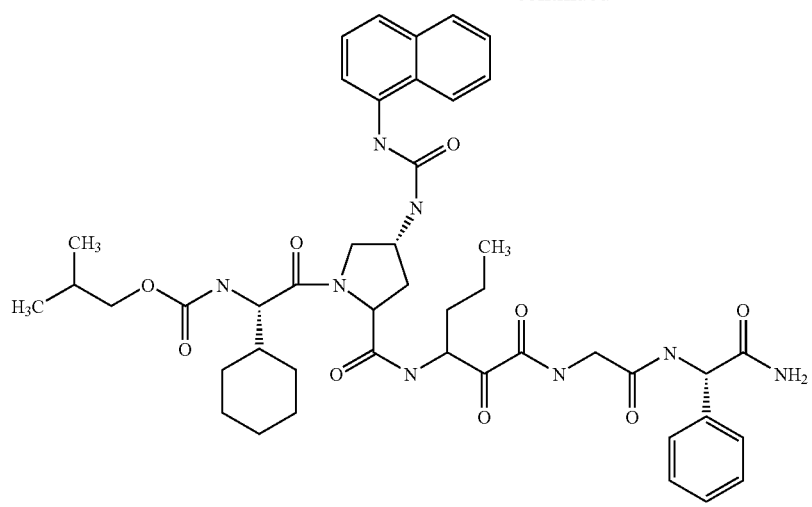
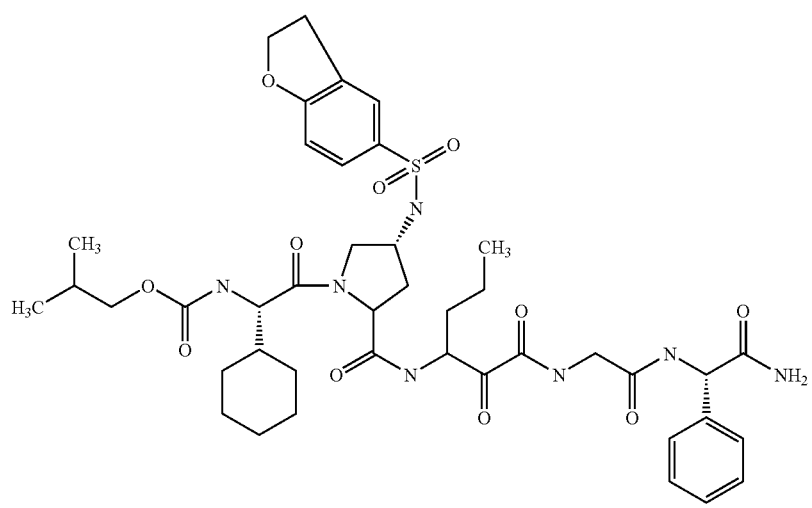
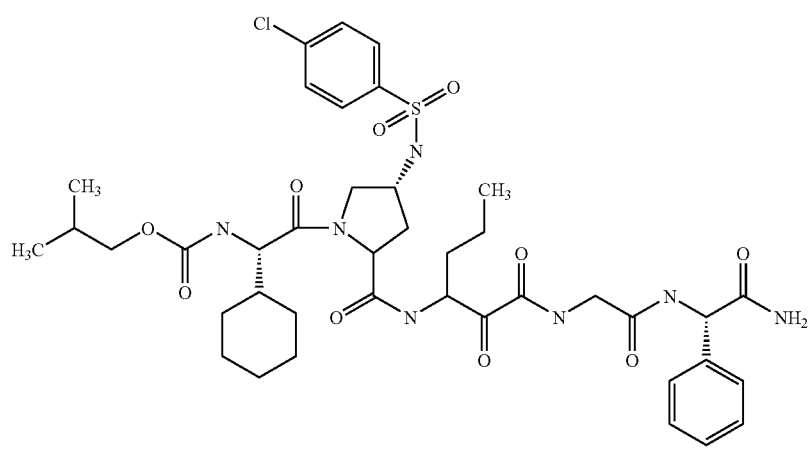

-continued
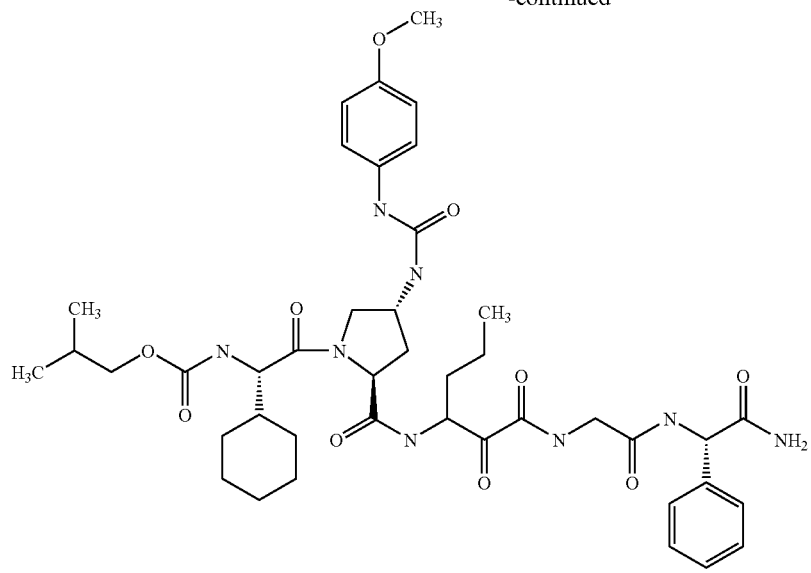
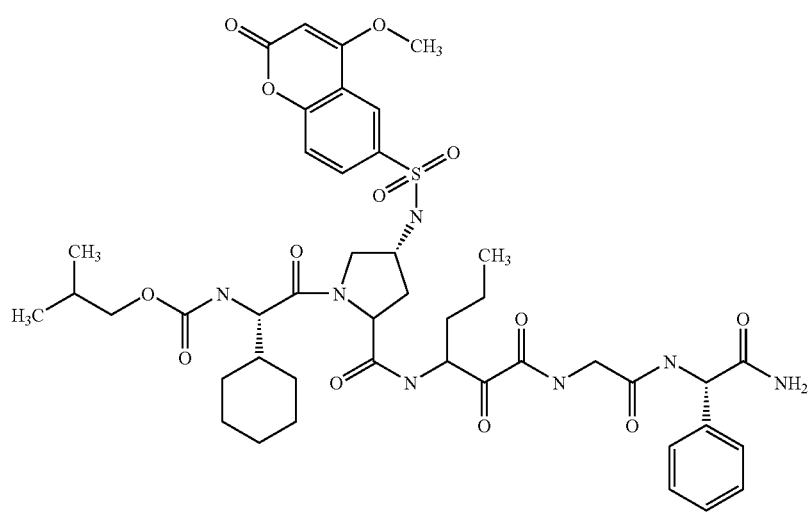
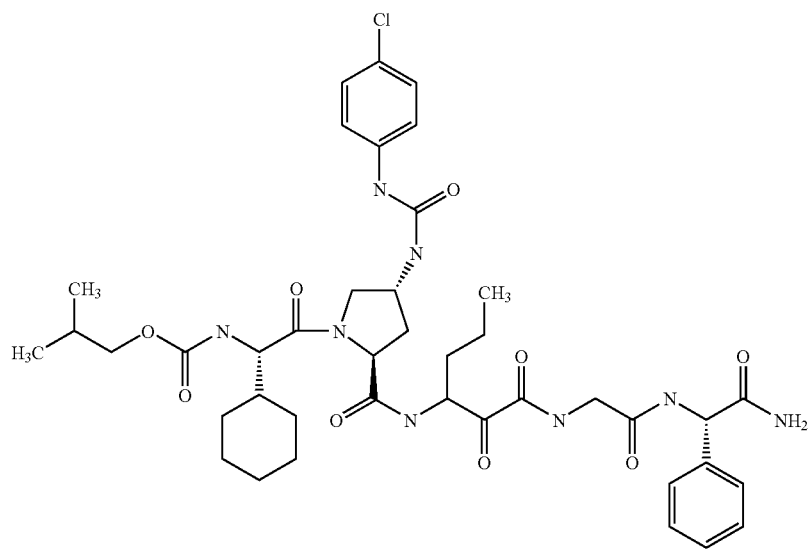

-continued
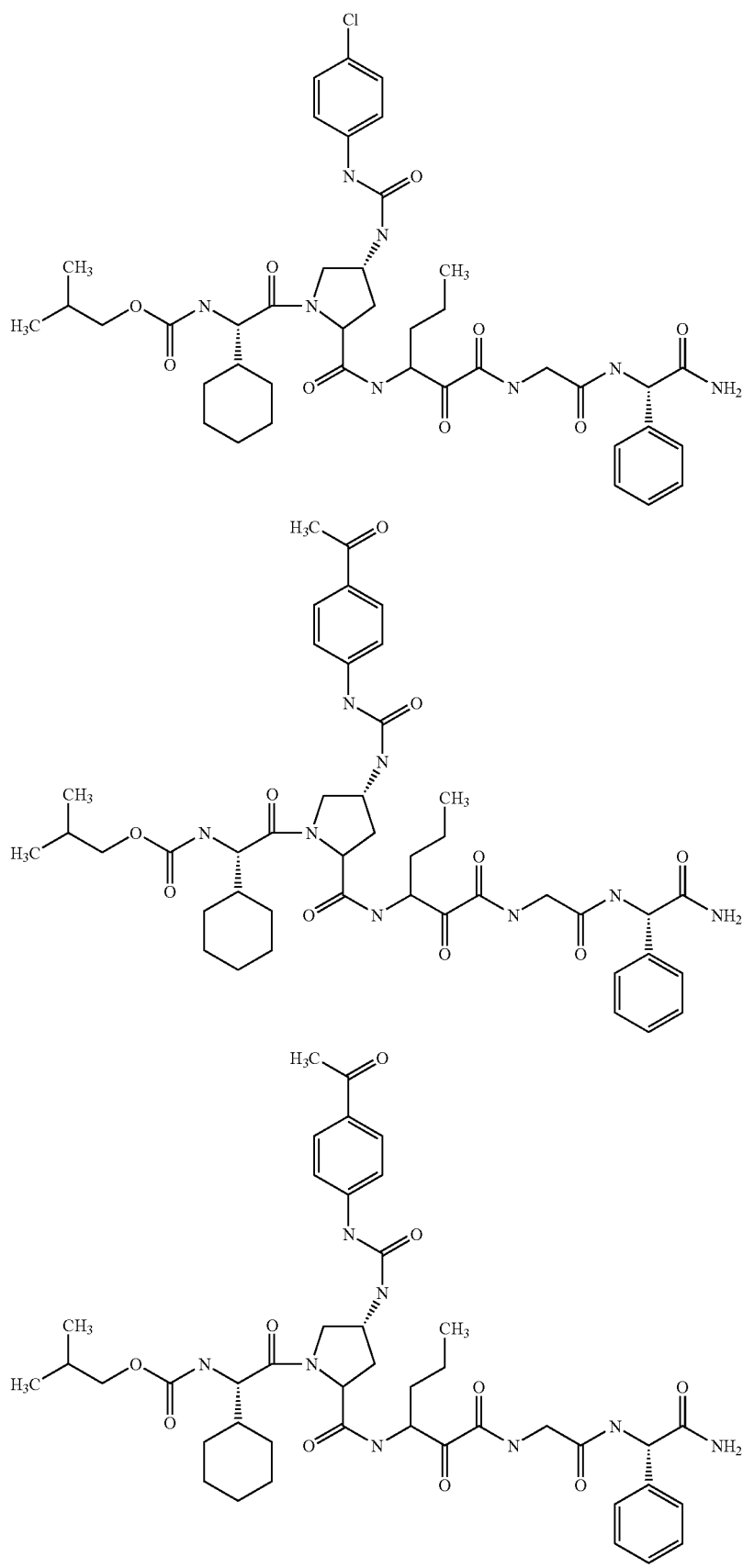

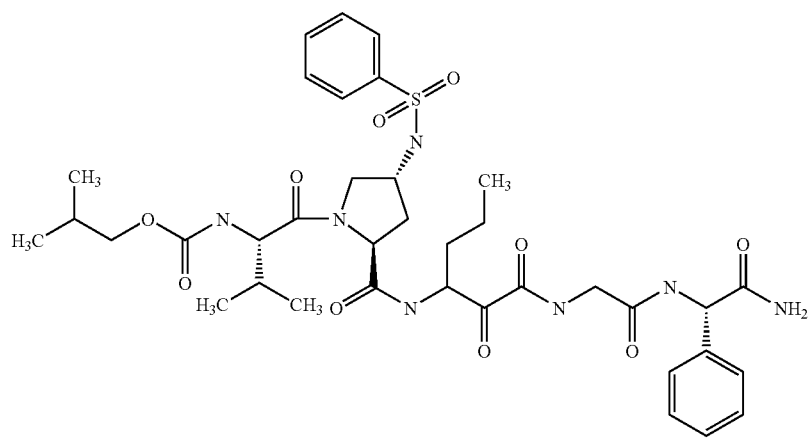
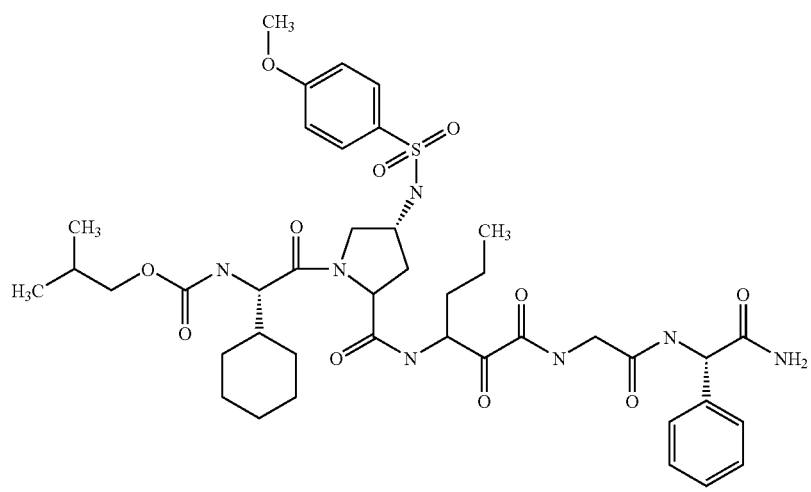
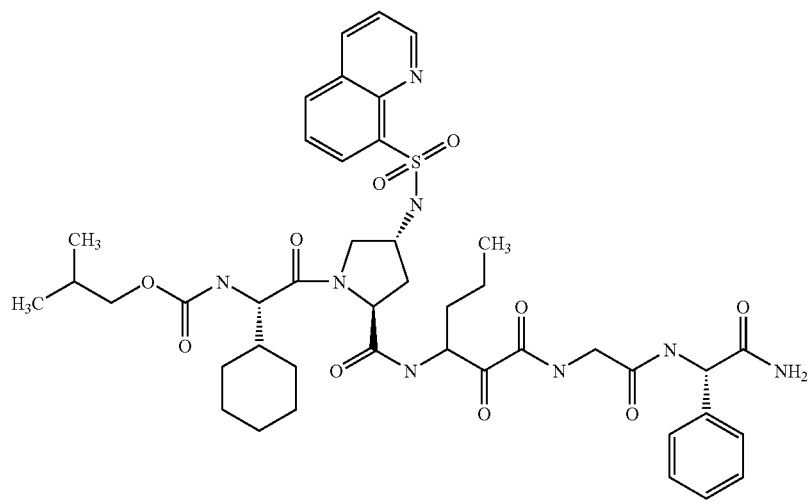

-continued
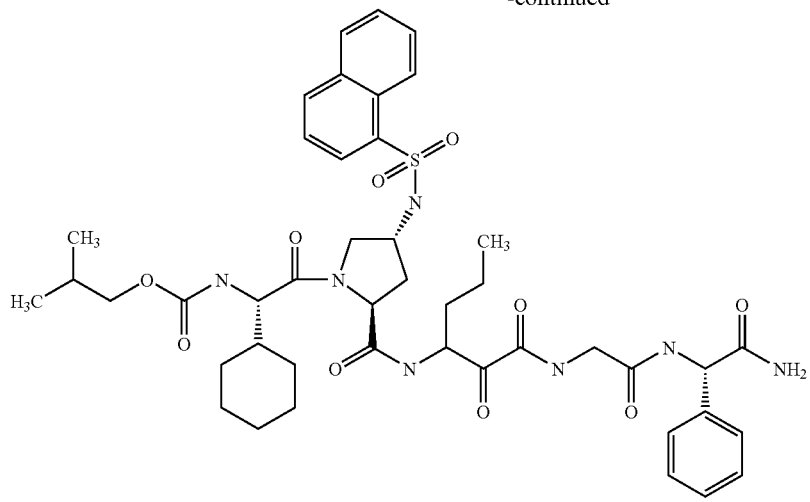
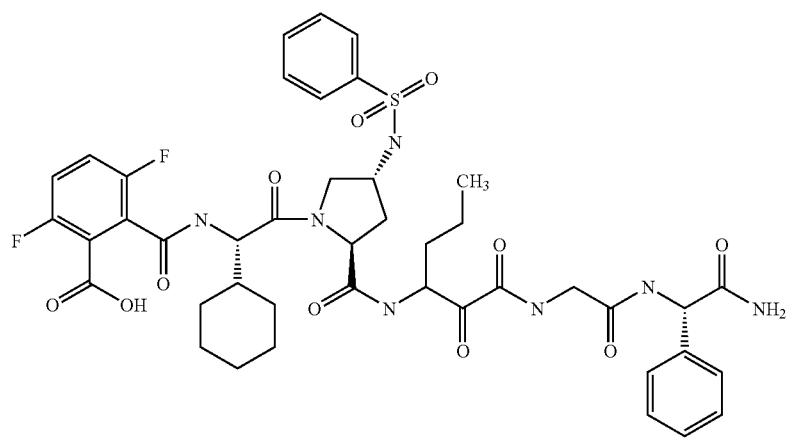
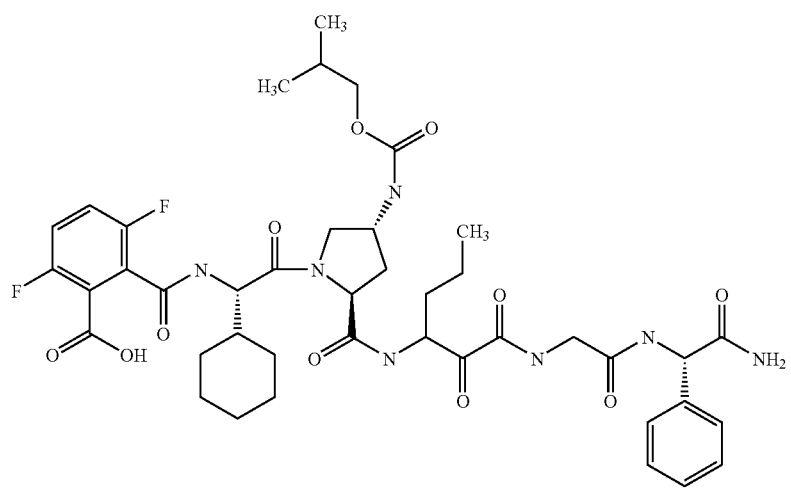

-continued
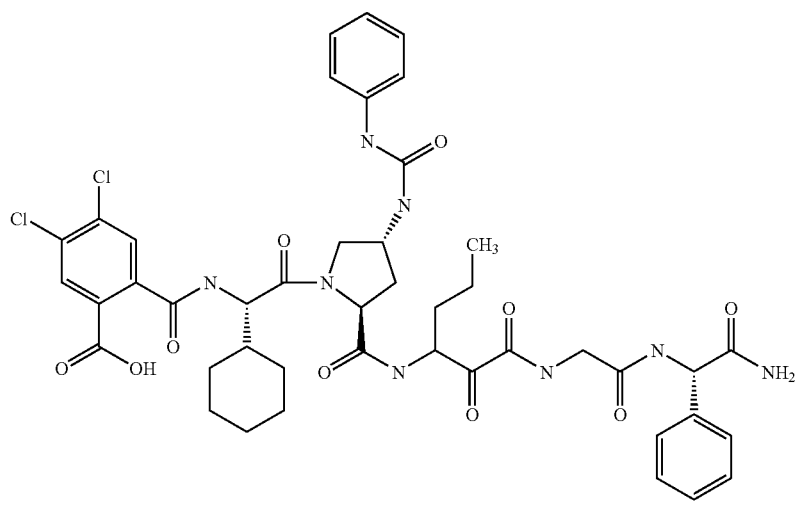
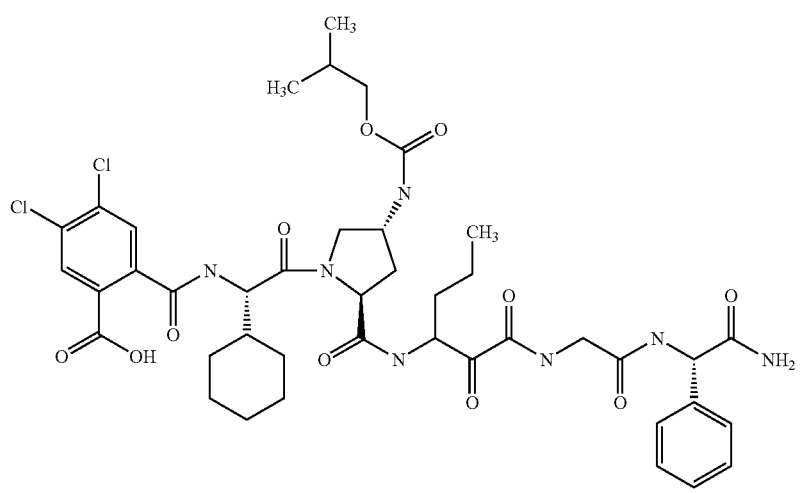
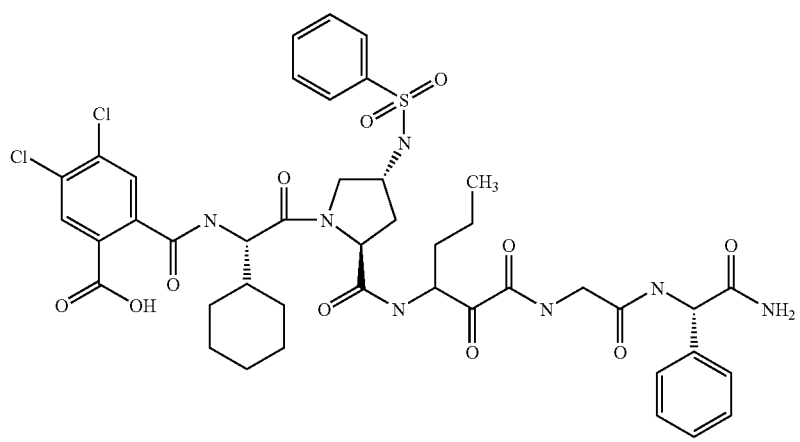

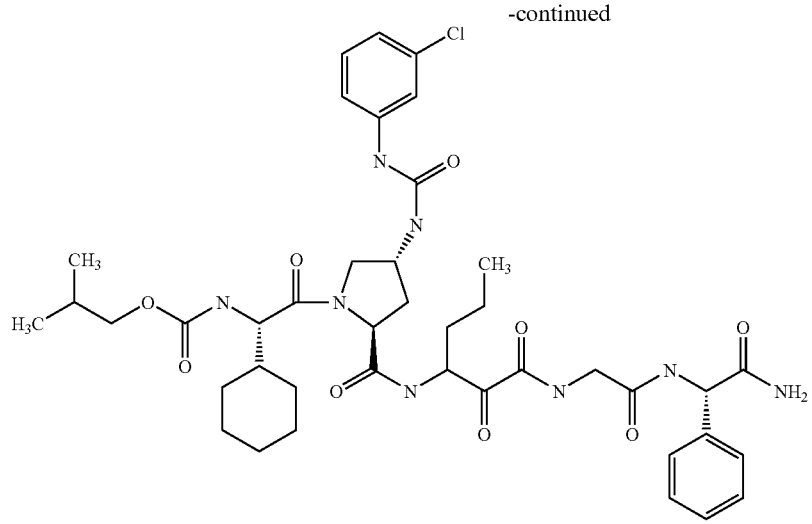
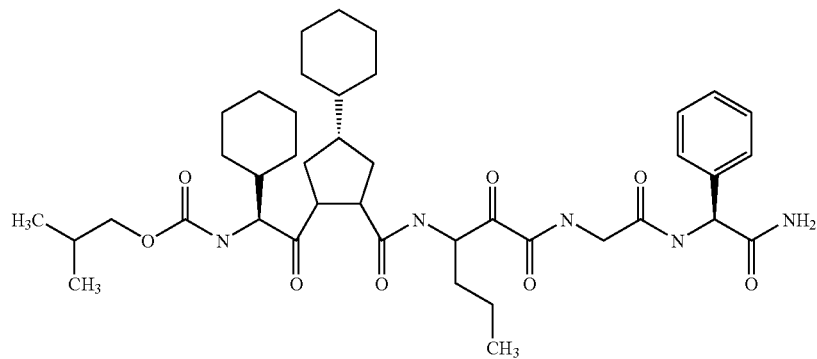
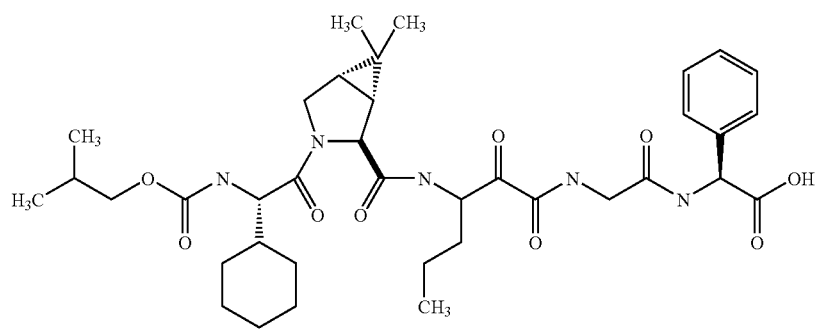
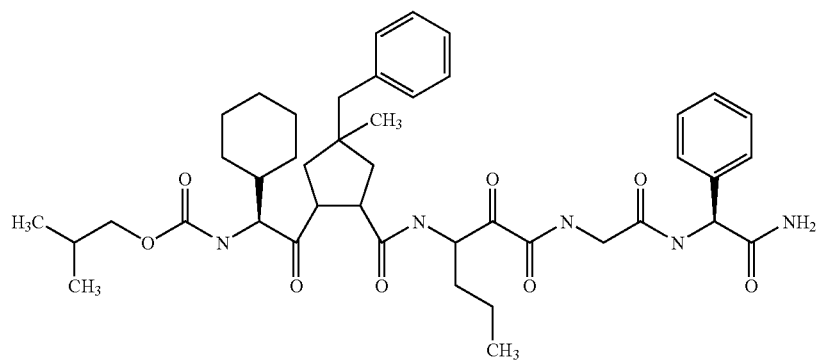

-continued
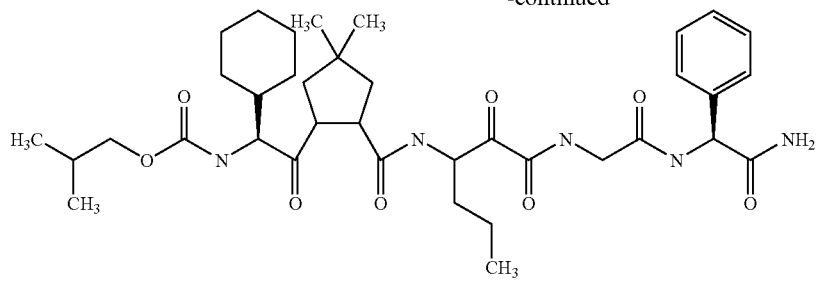
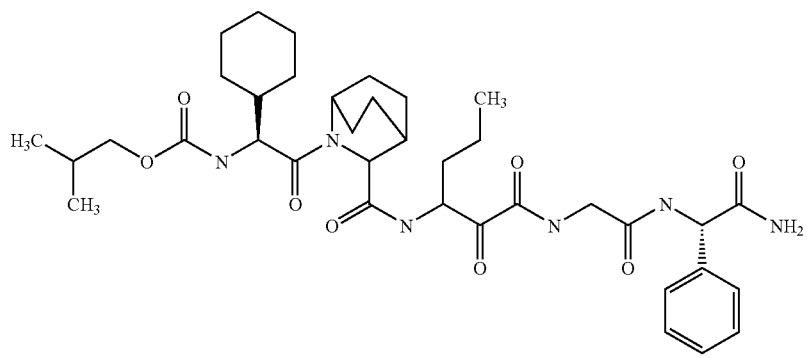
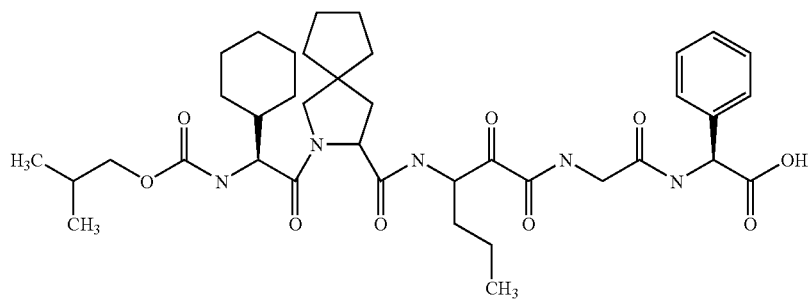
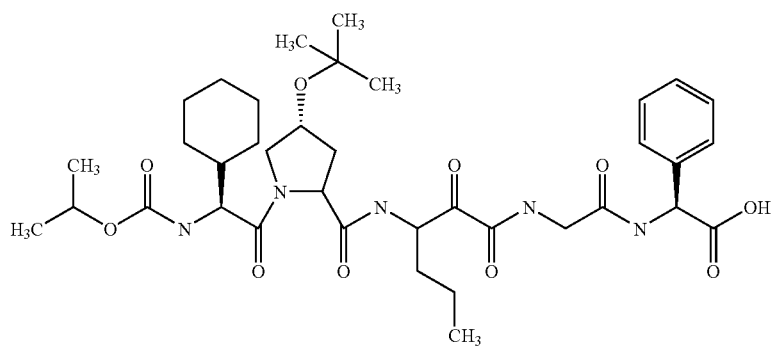
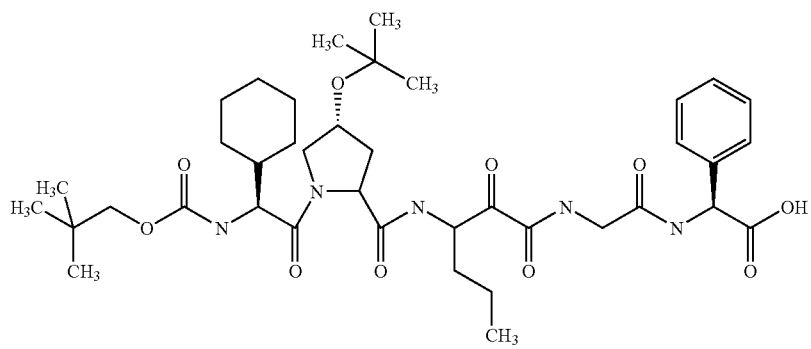

-continued
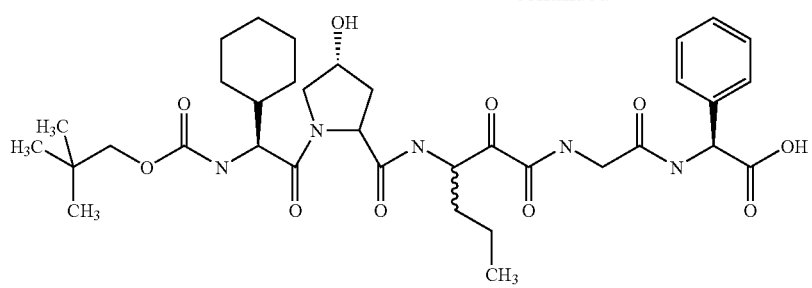
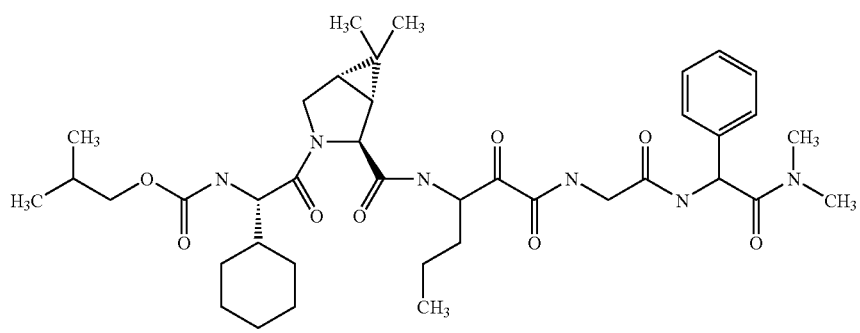
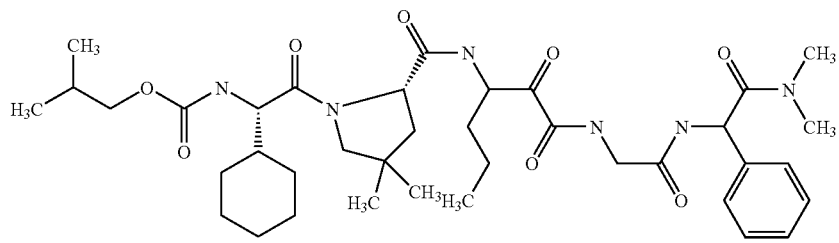
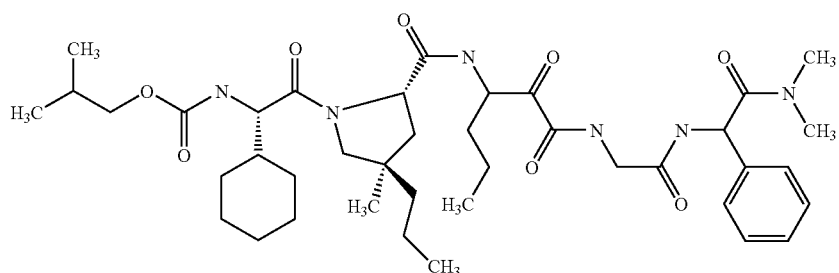
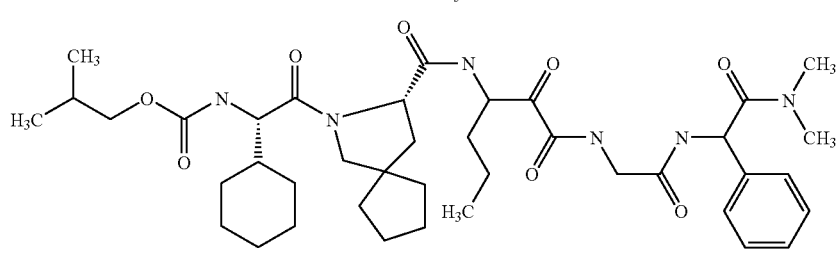

-continued
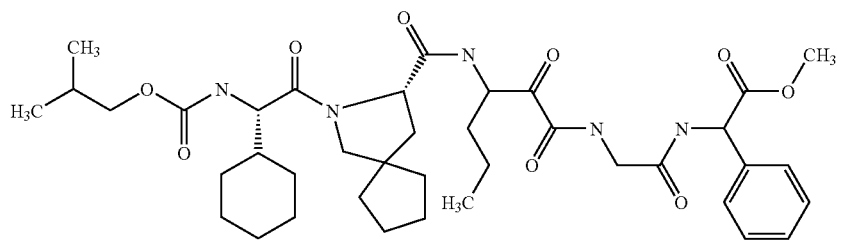
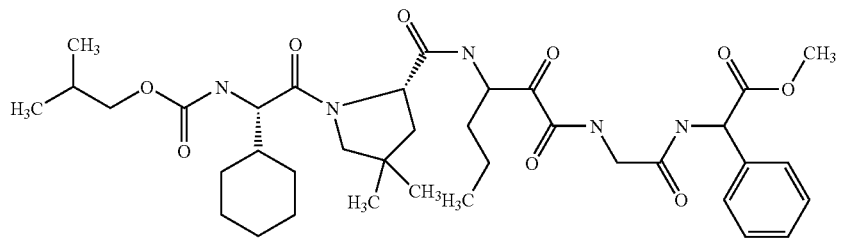
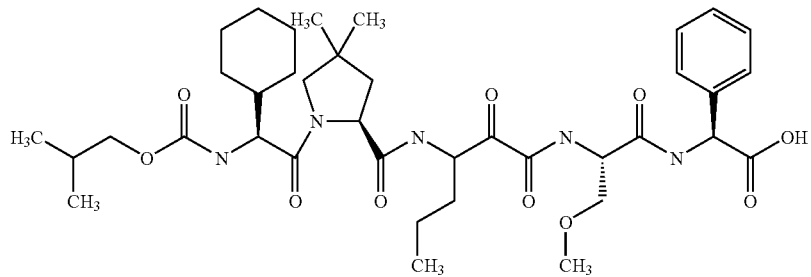
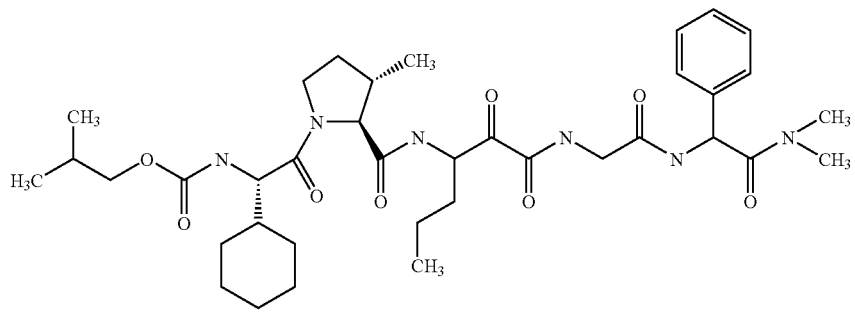
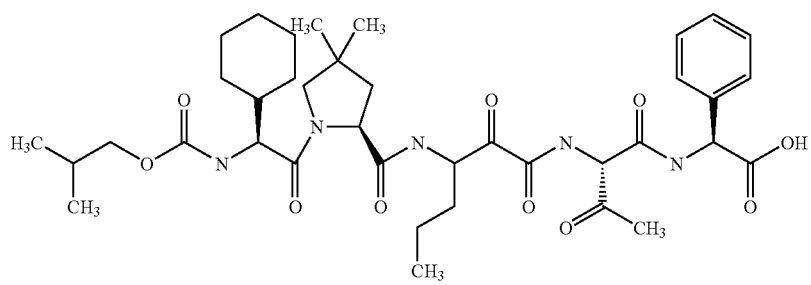
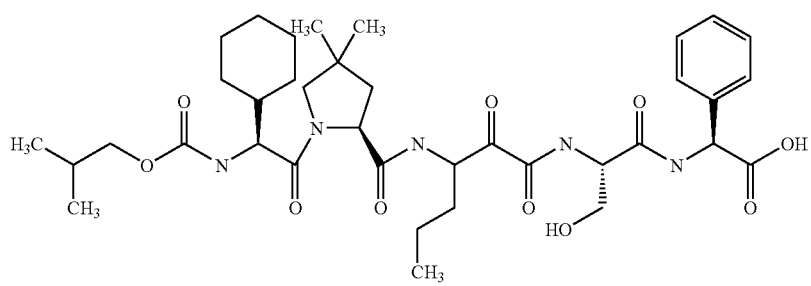

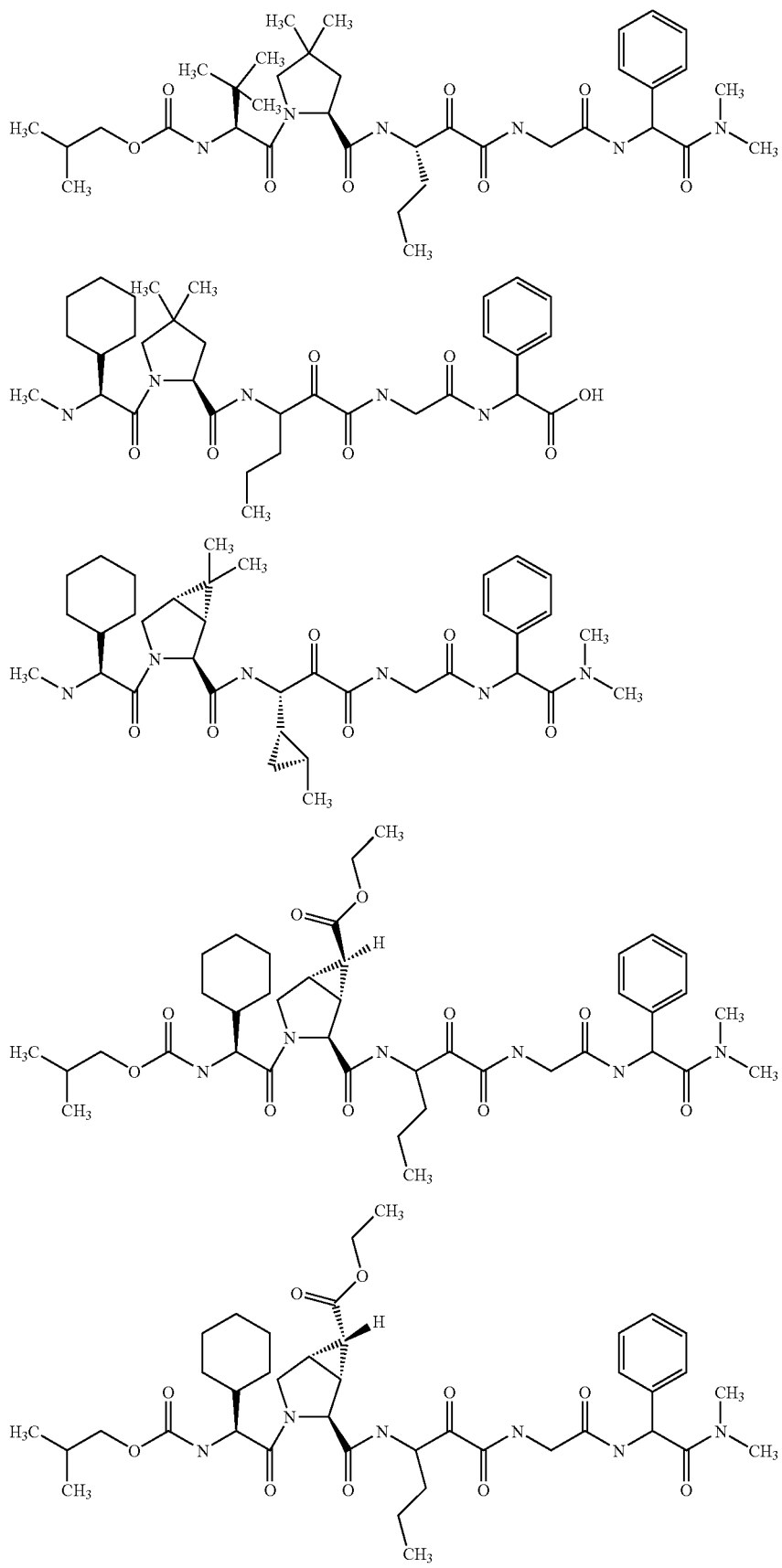

-continued
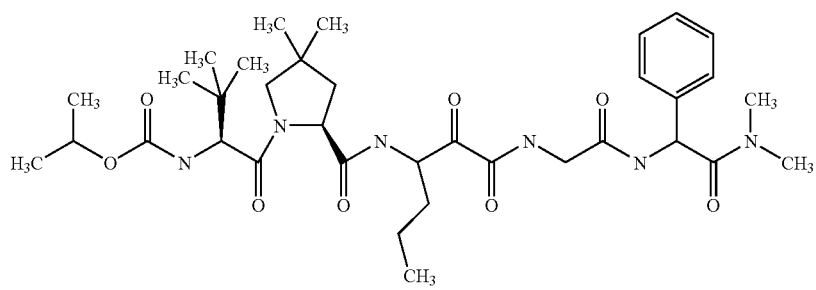
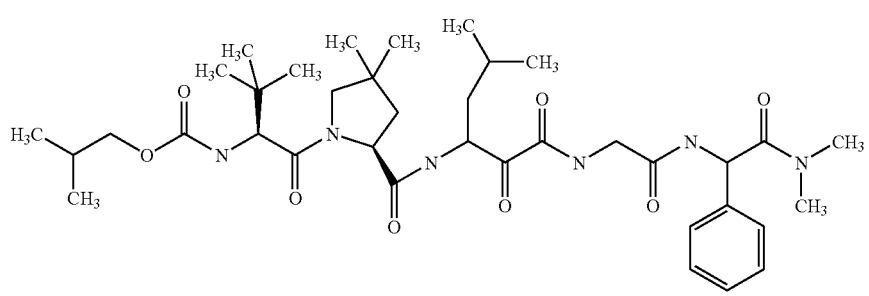
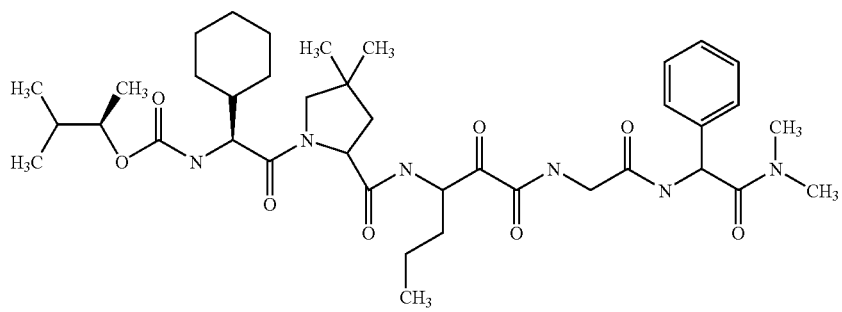
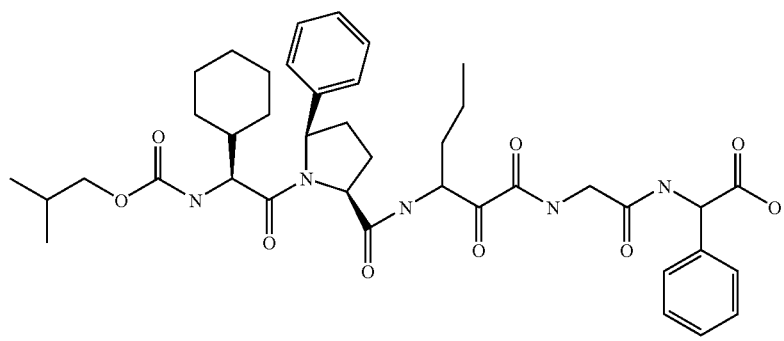
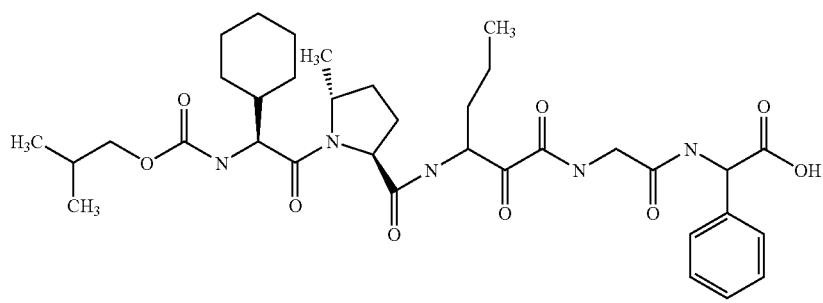

-continued
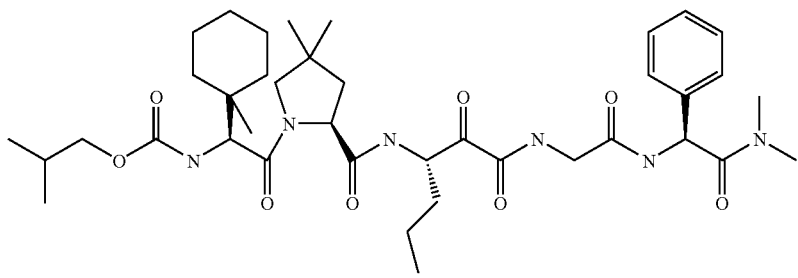
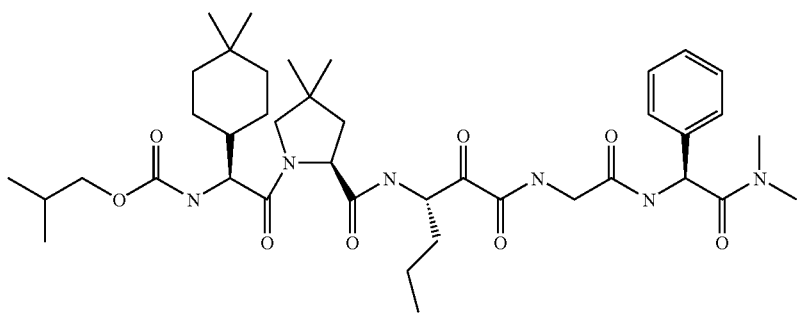
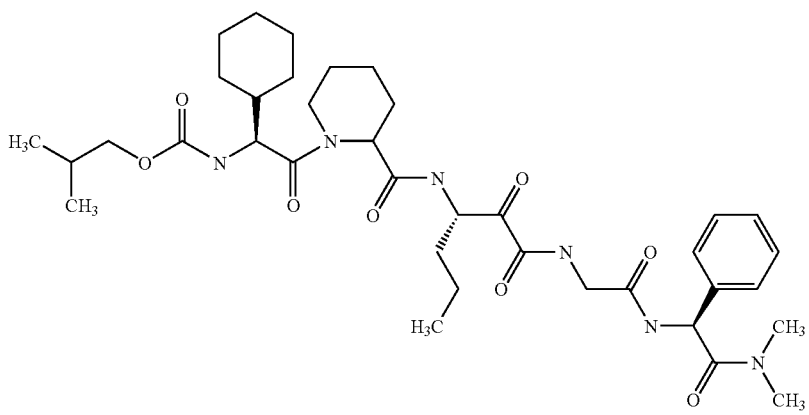
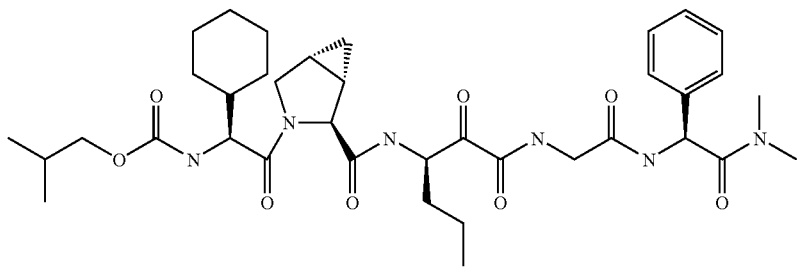
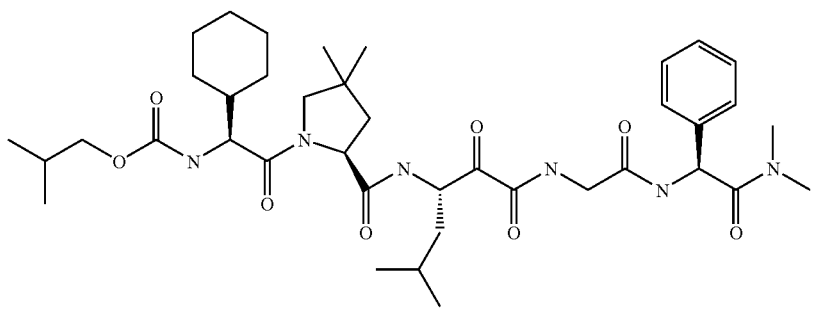

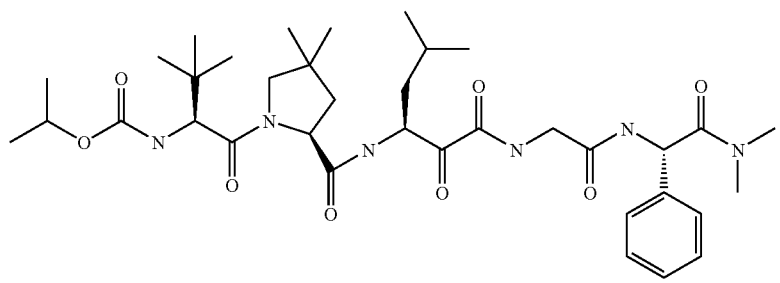
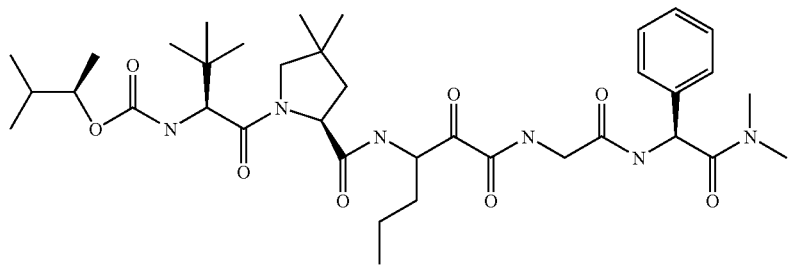
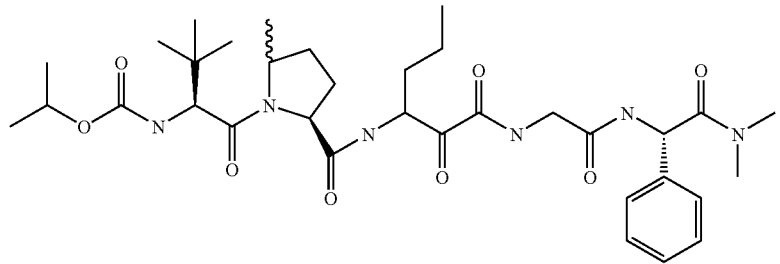
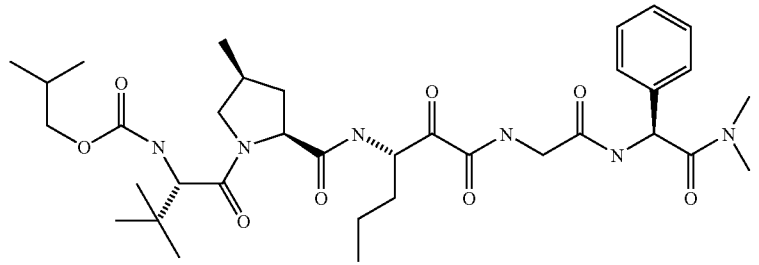
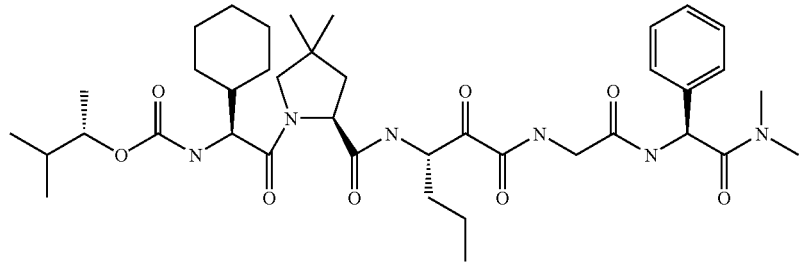
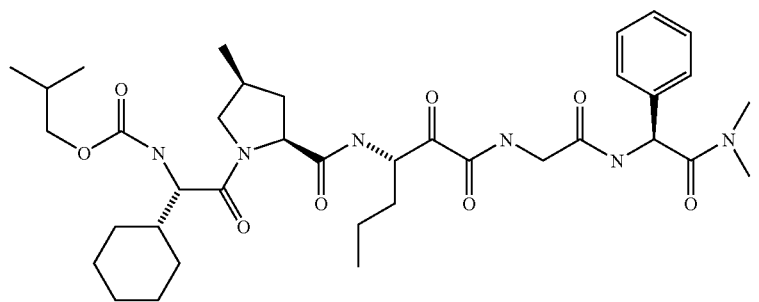

-continued
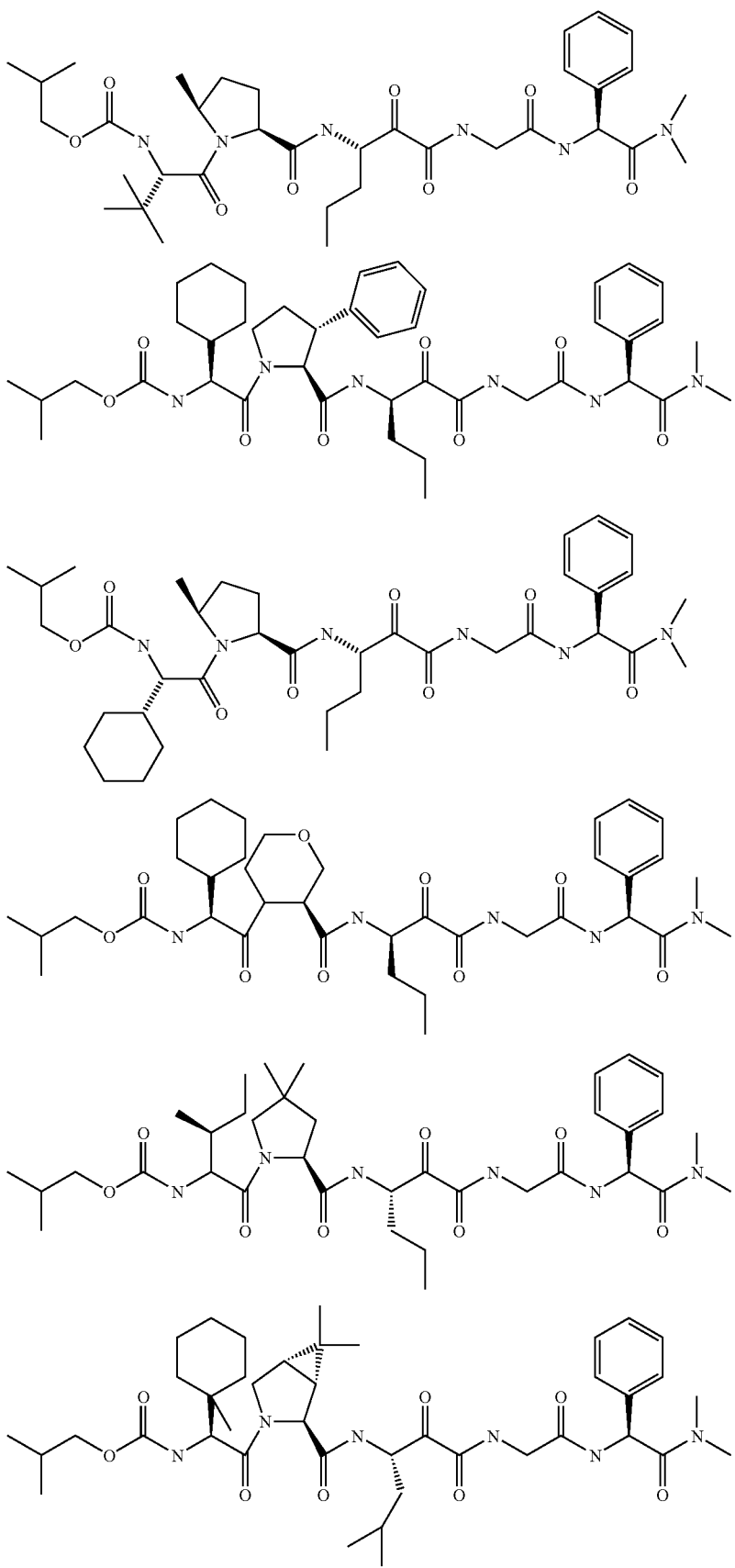

-continued
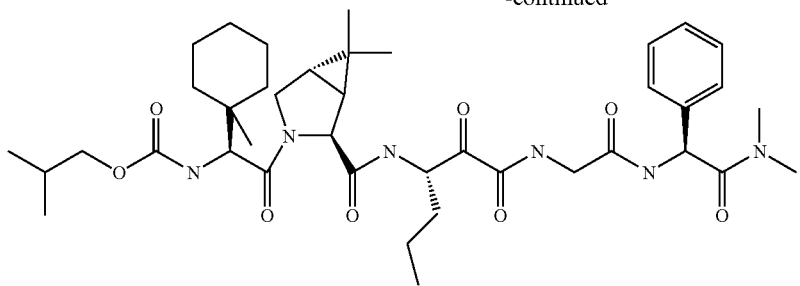
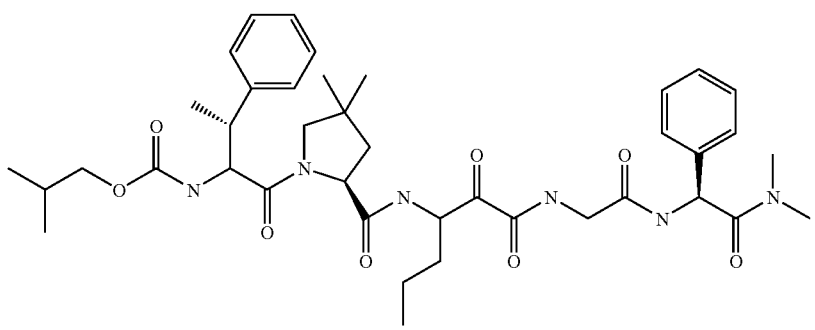
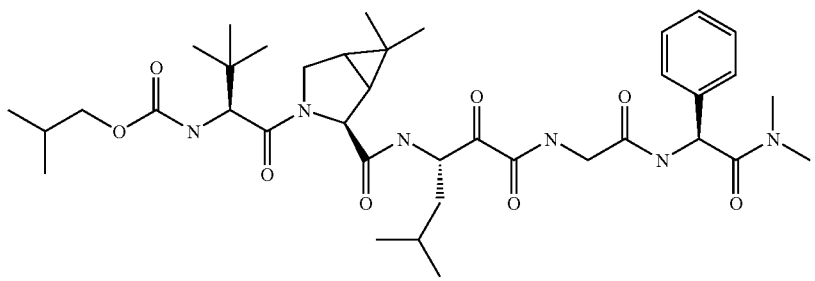
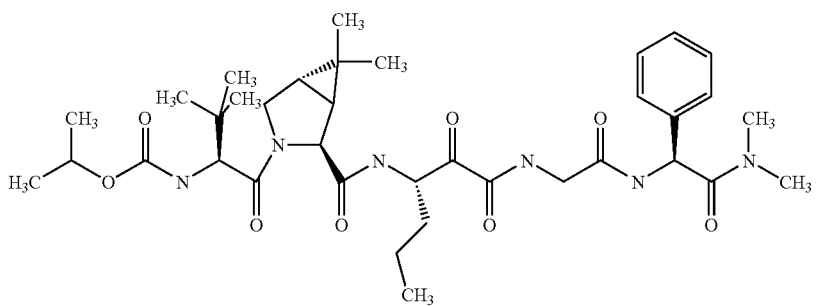
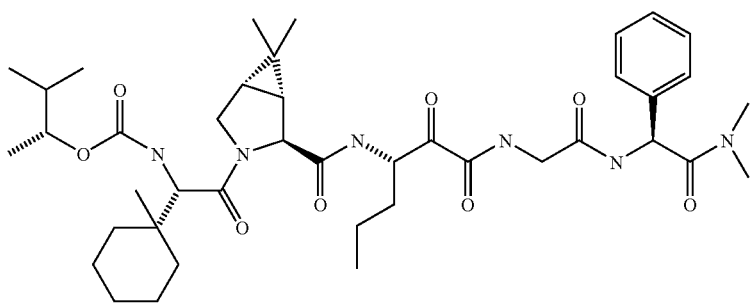

-continued
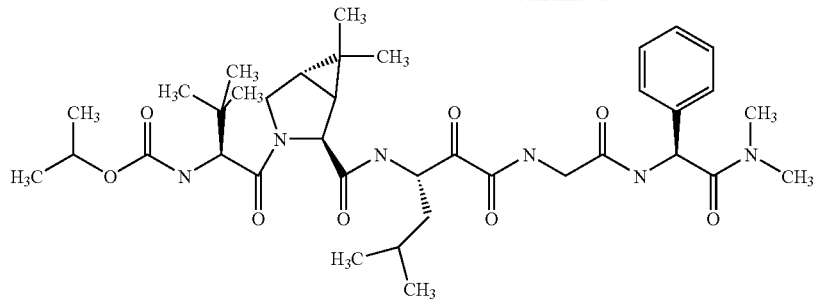
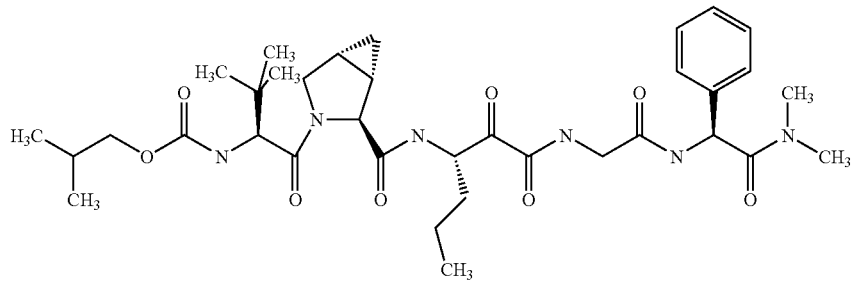
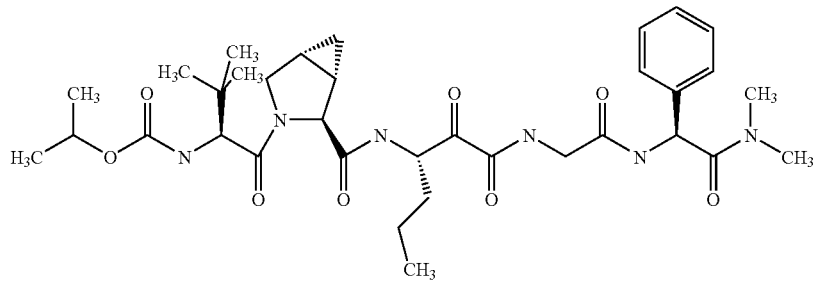
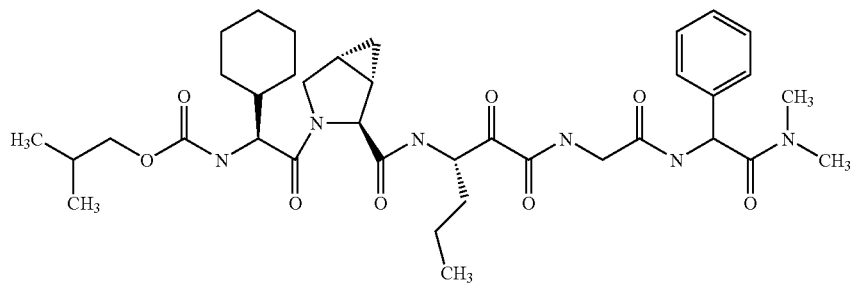
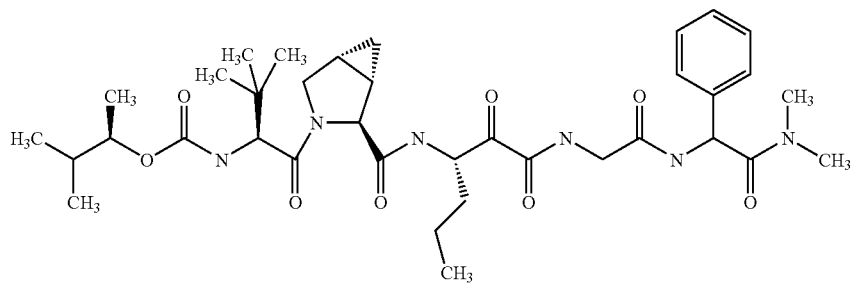
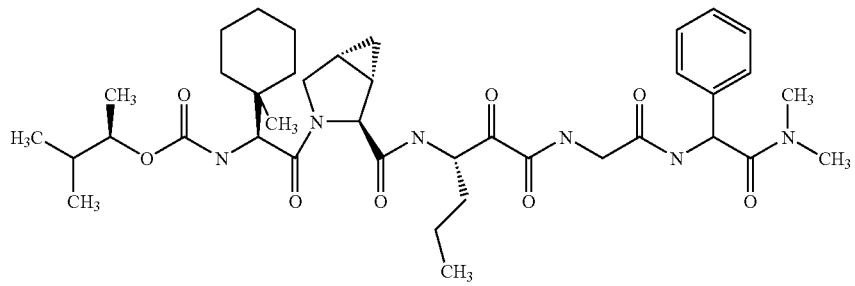

-continued
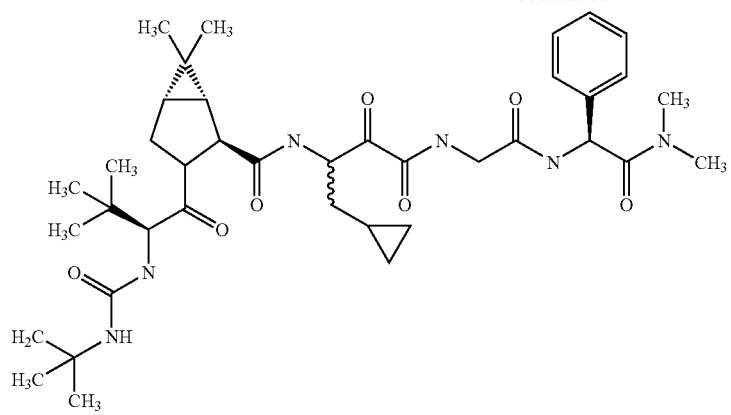
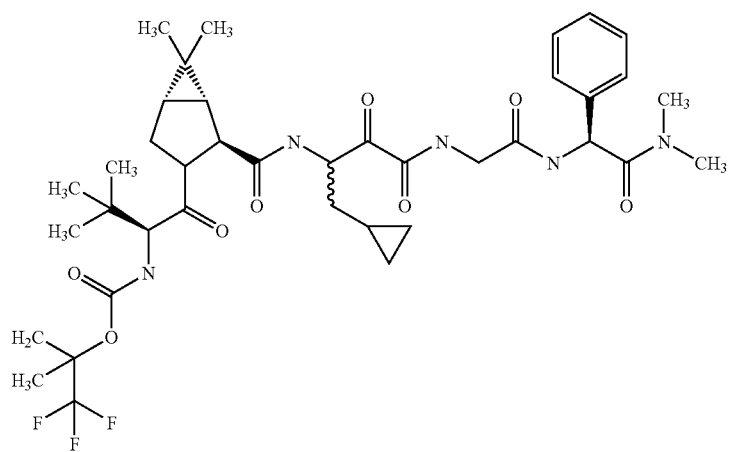
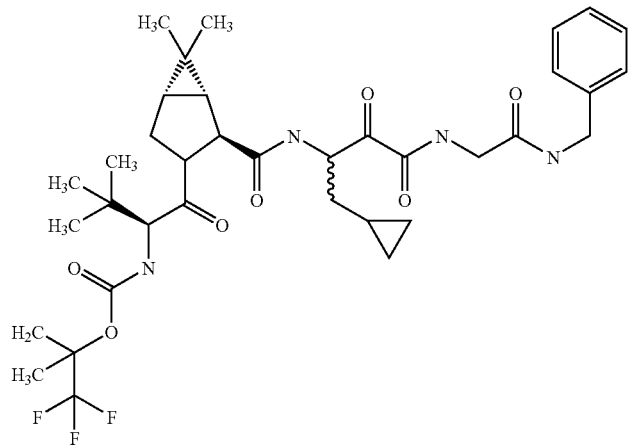
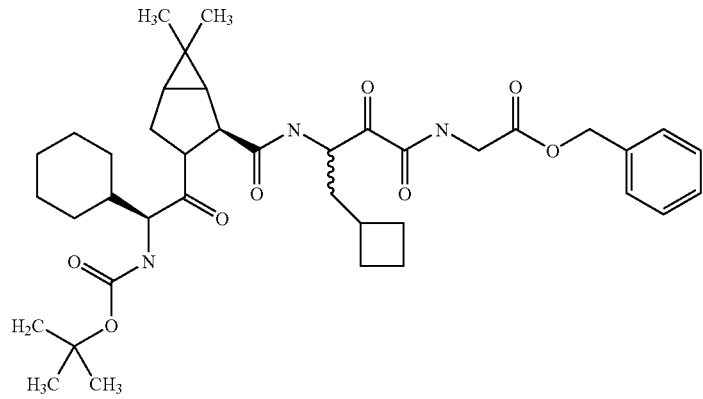

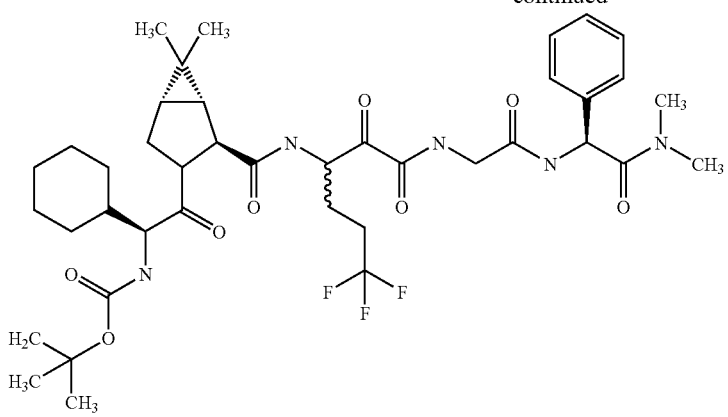
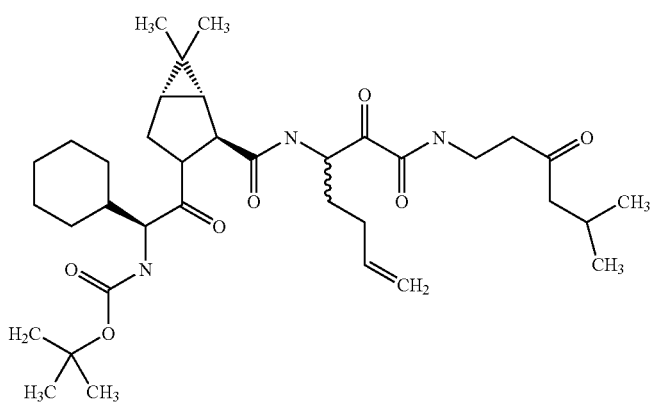
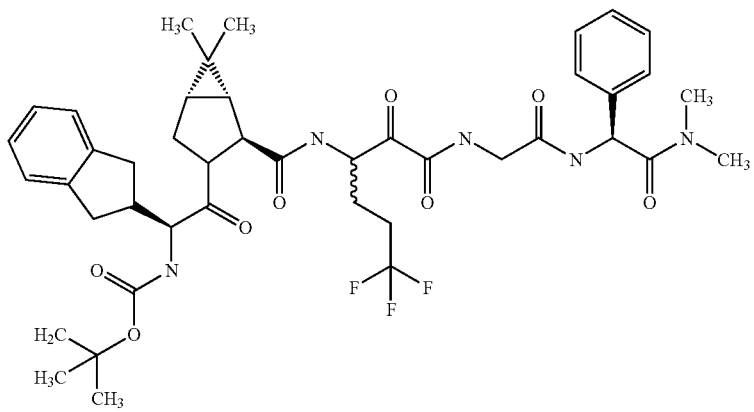
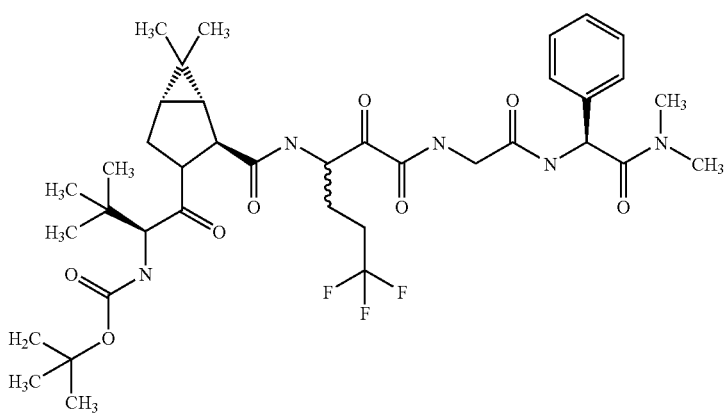

-continued
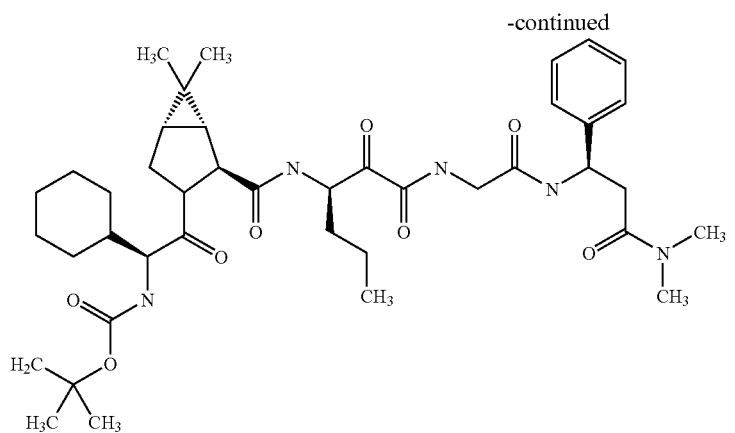
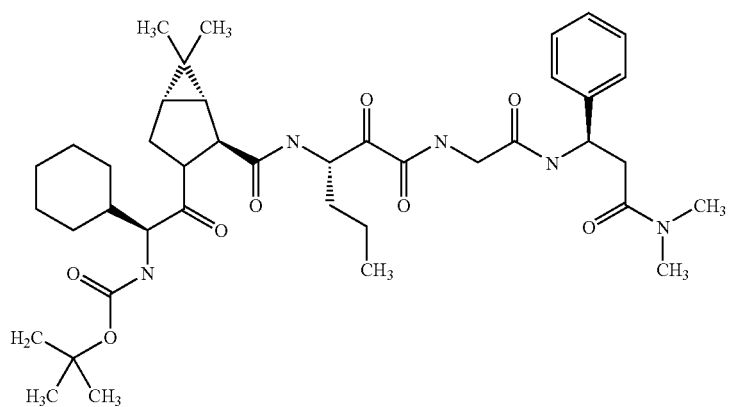
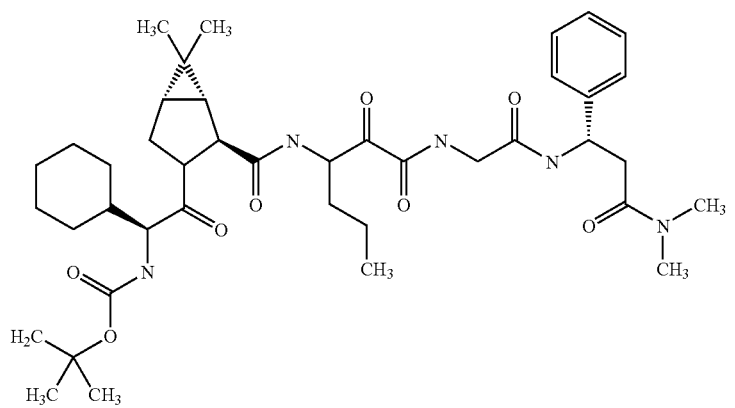
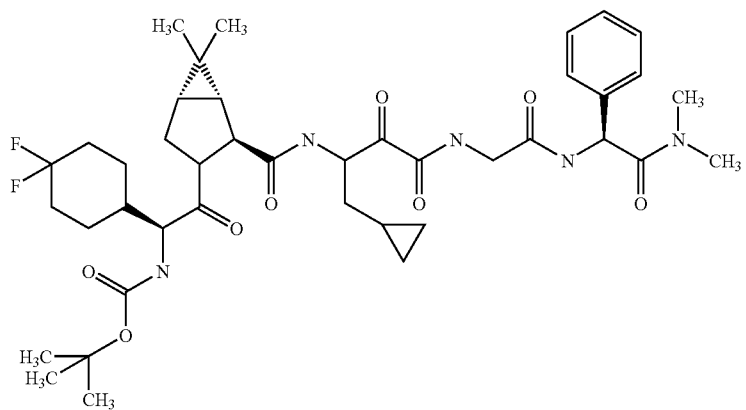

-continued
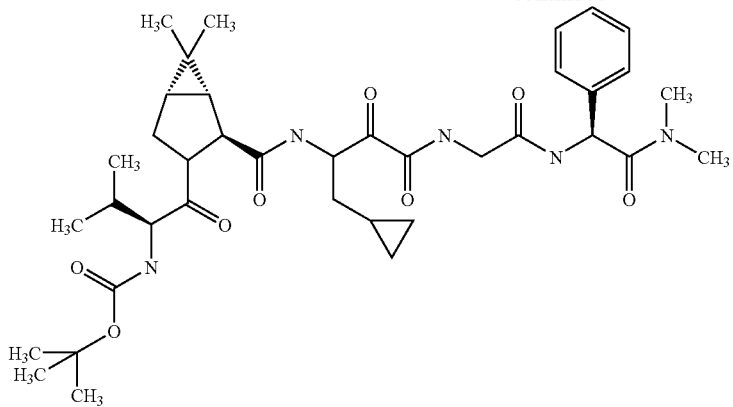
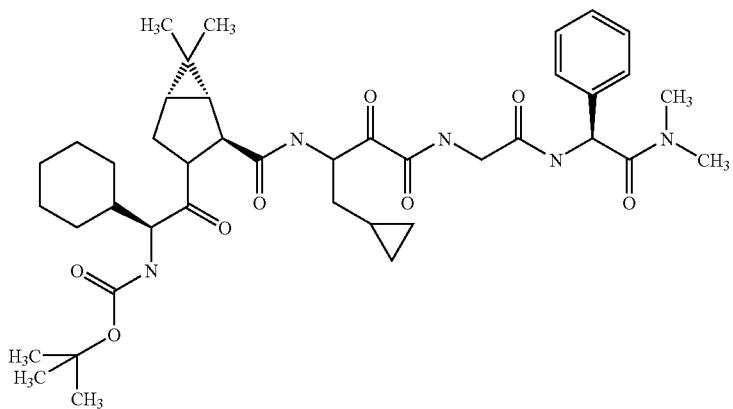
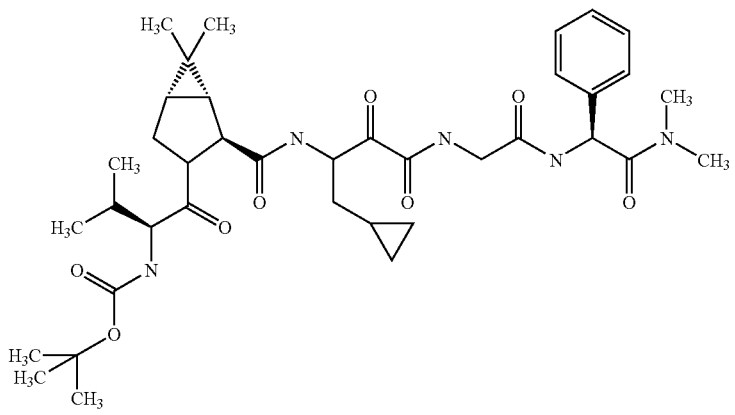
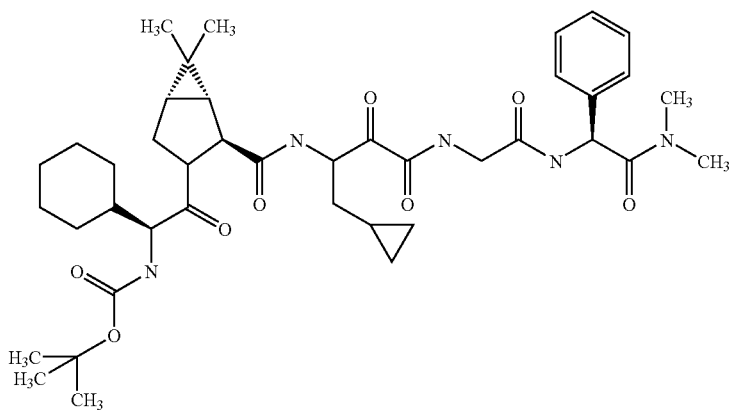

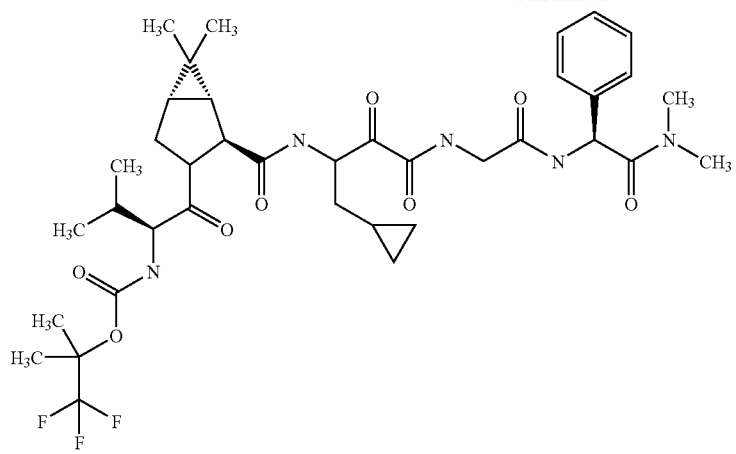
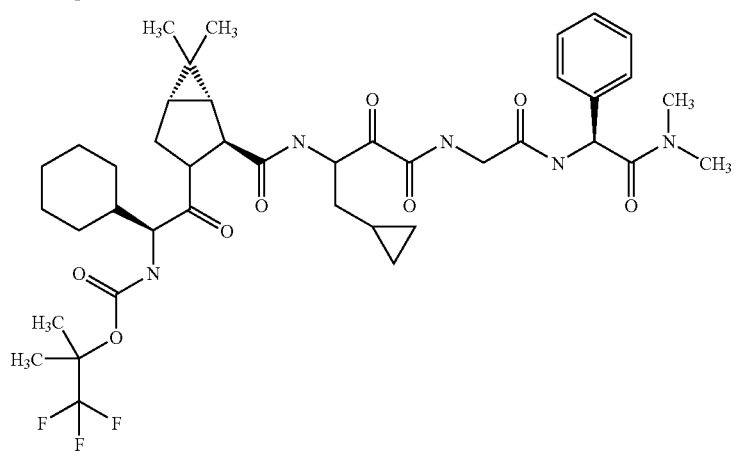
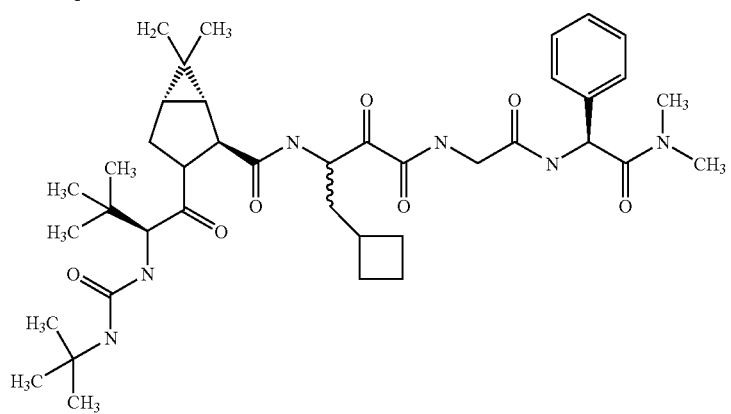
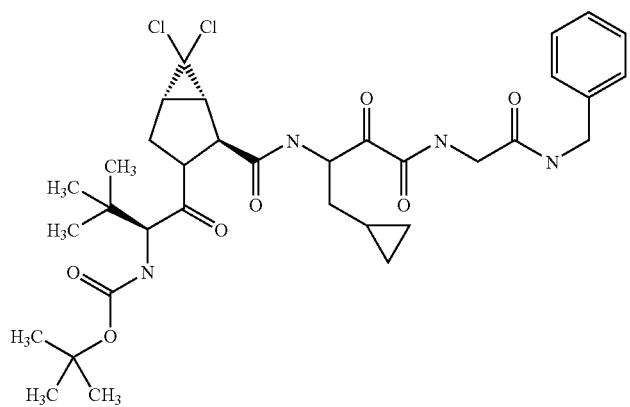

-continued
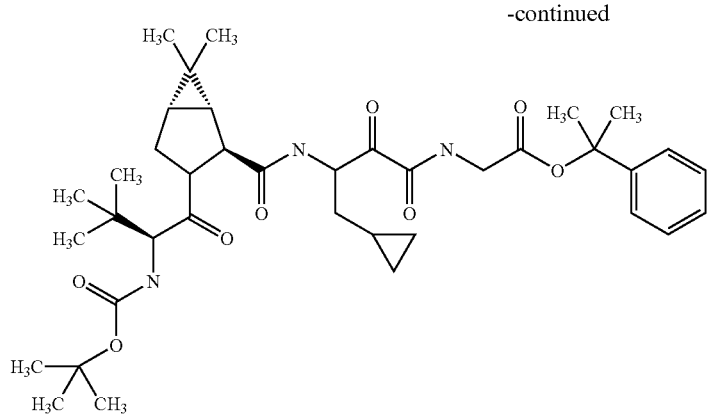
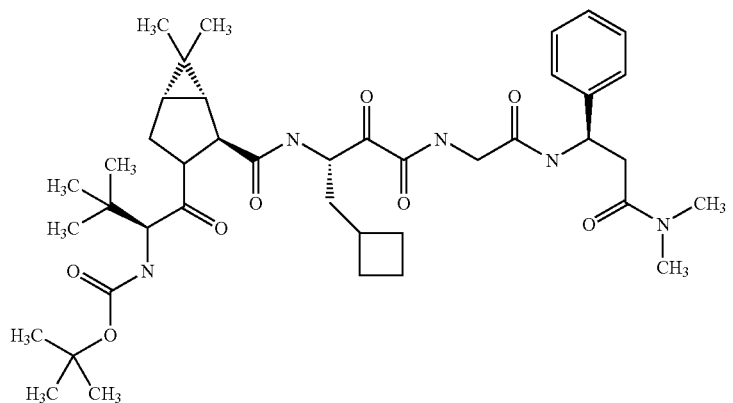
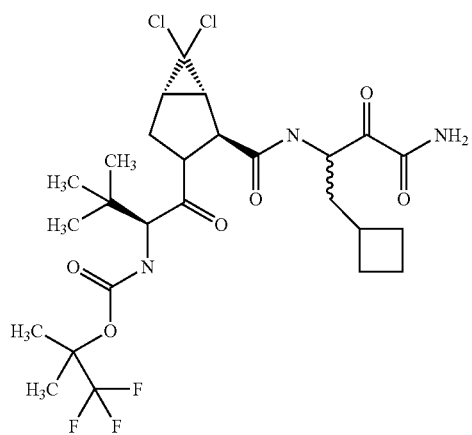
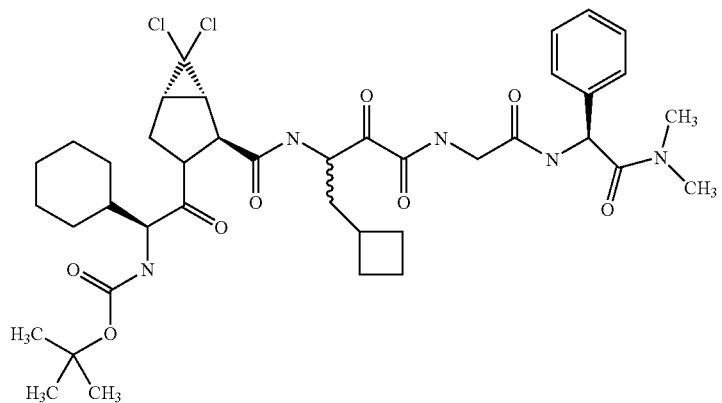

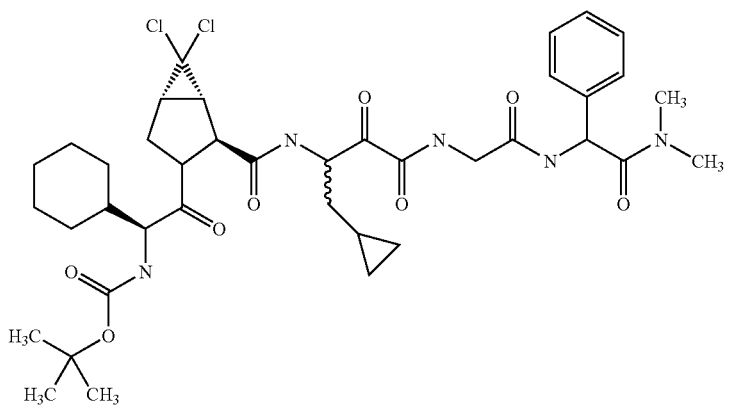
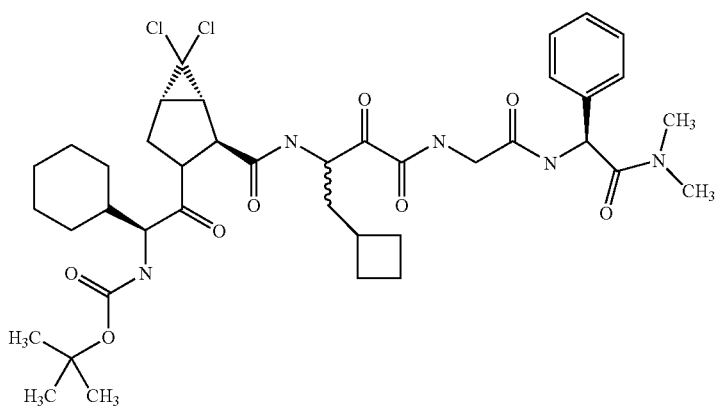
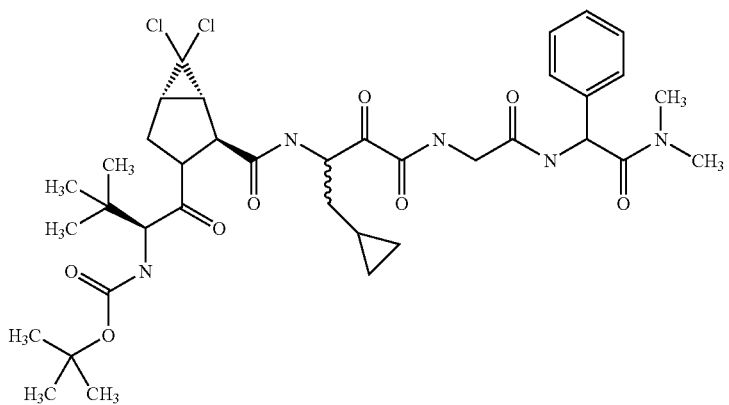
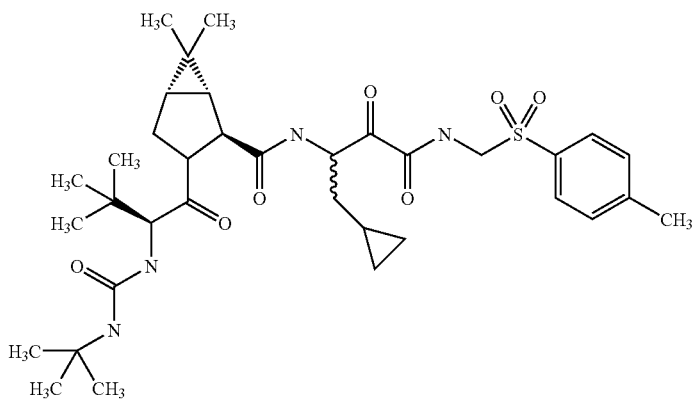

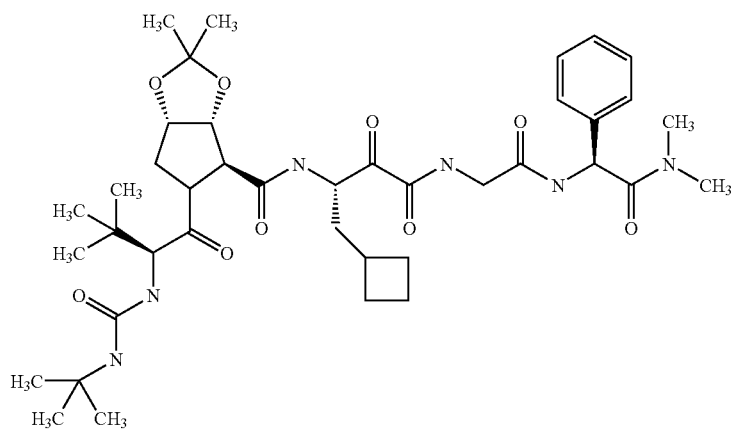
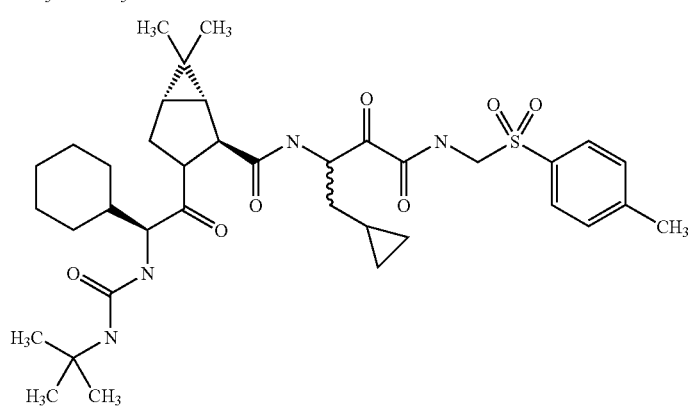
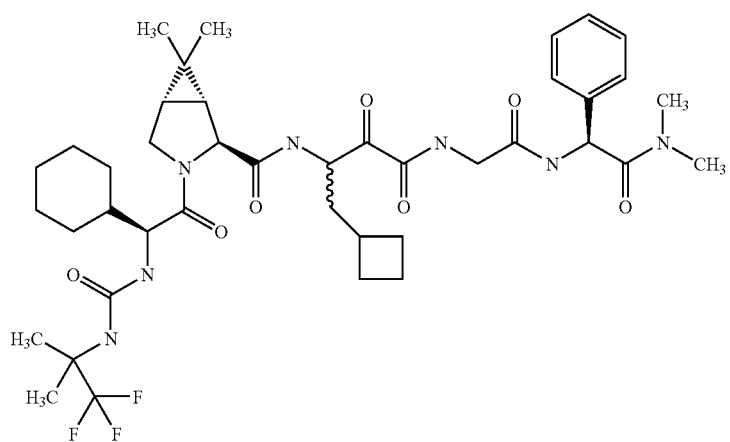
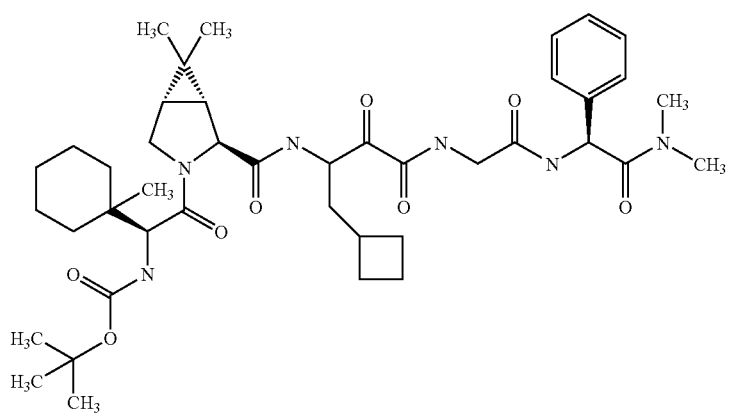

-continued
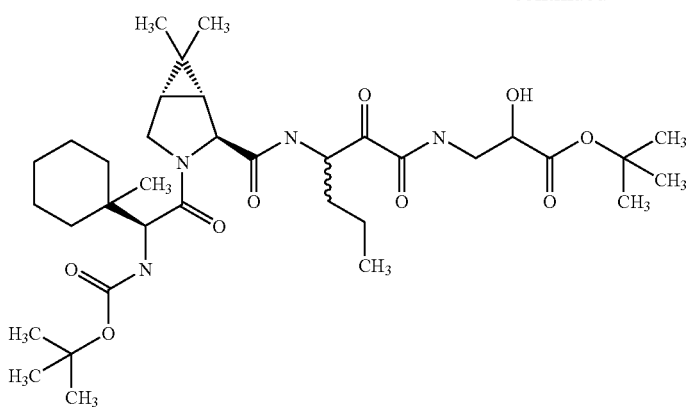
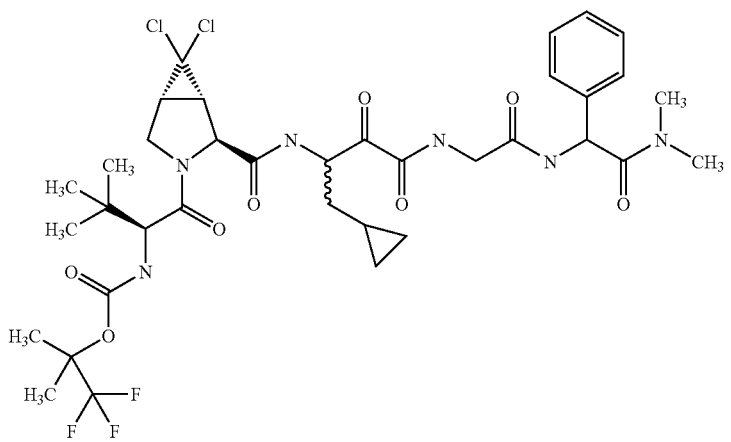
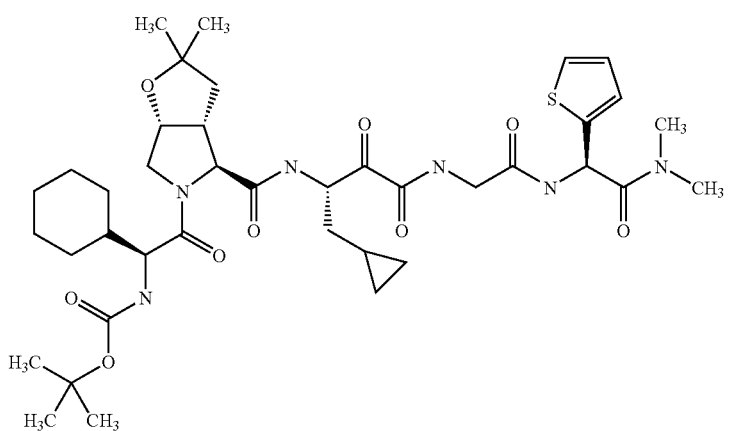
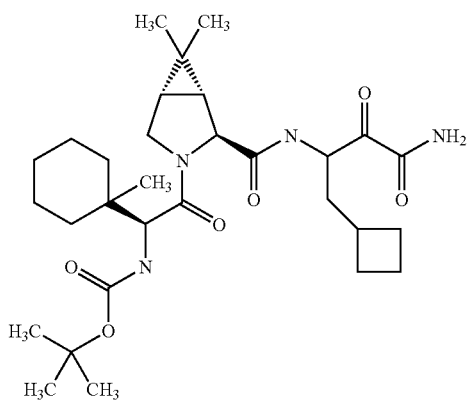

-continued
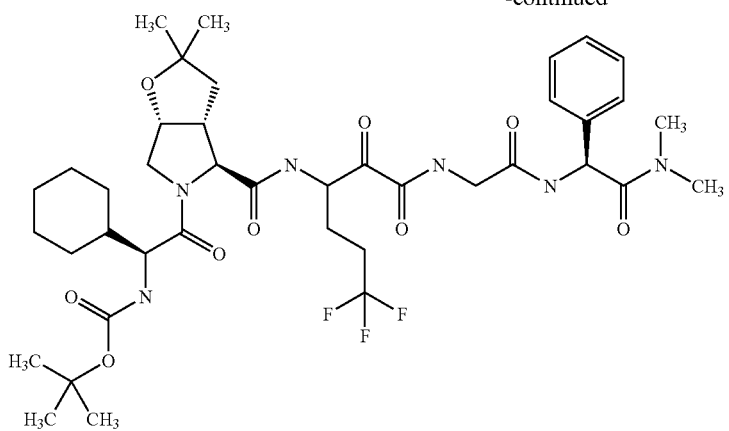
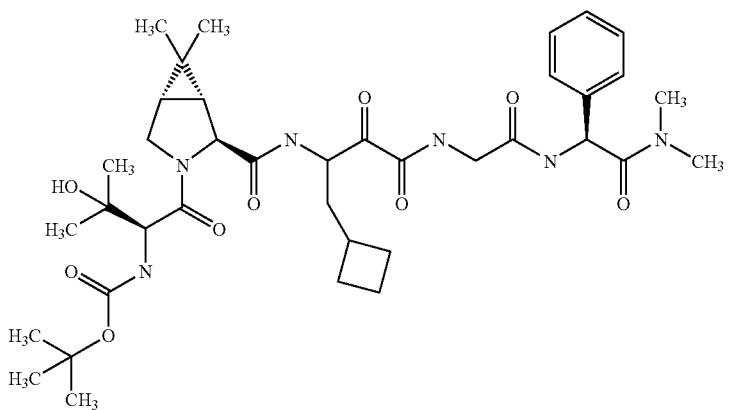
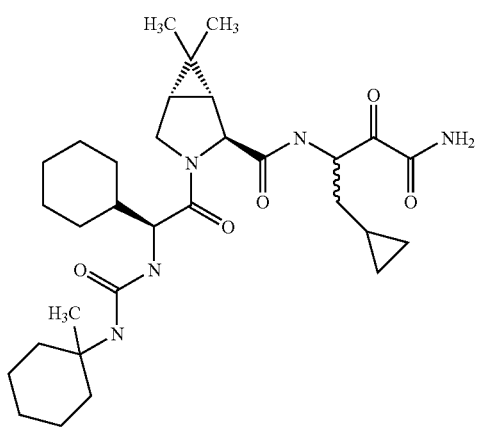
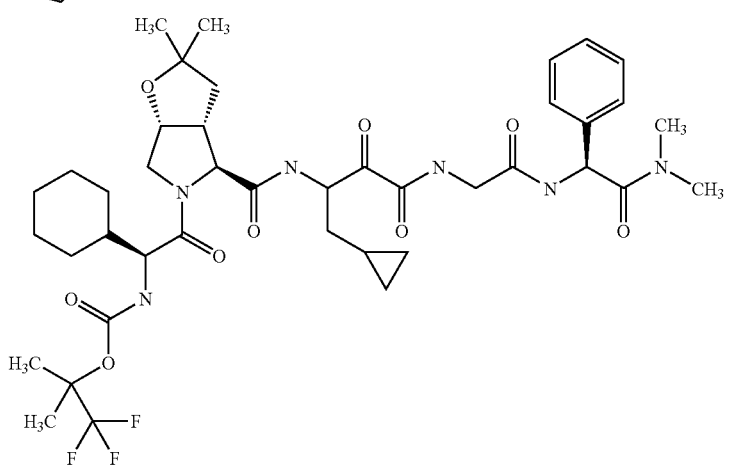

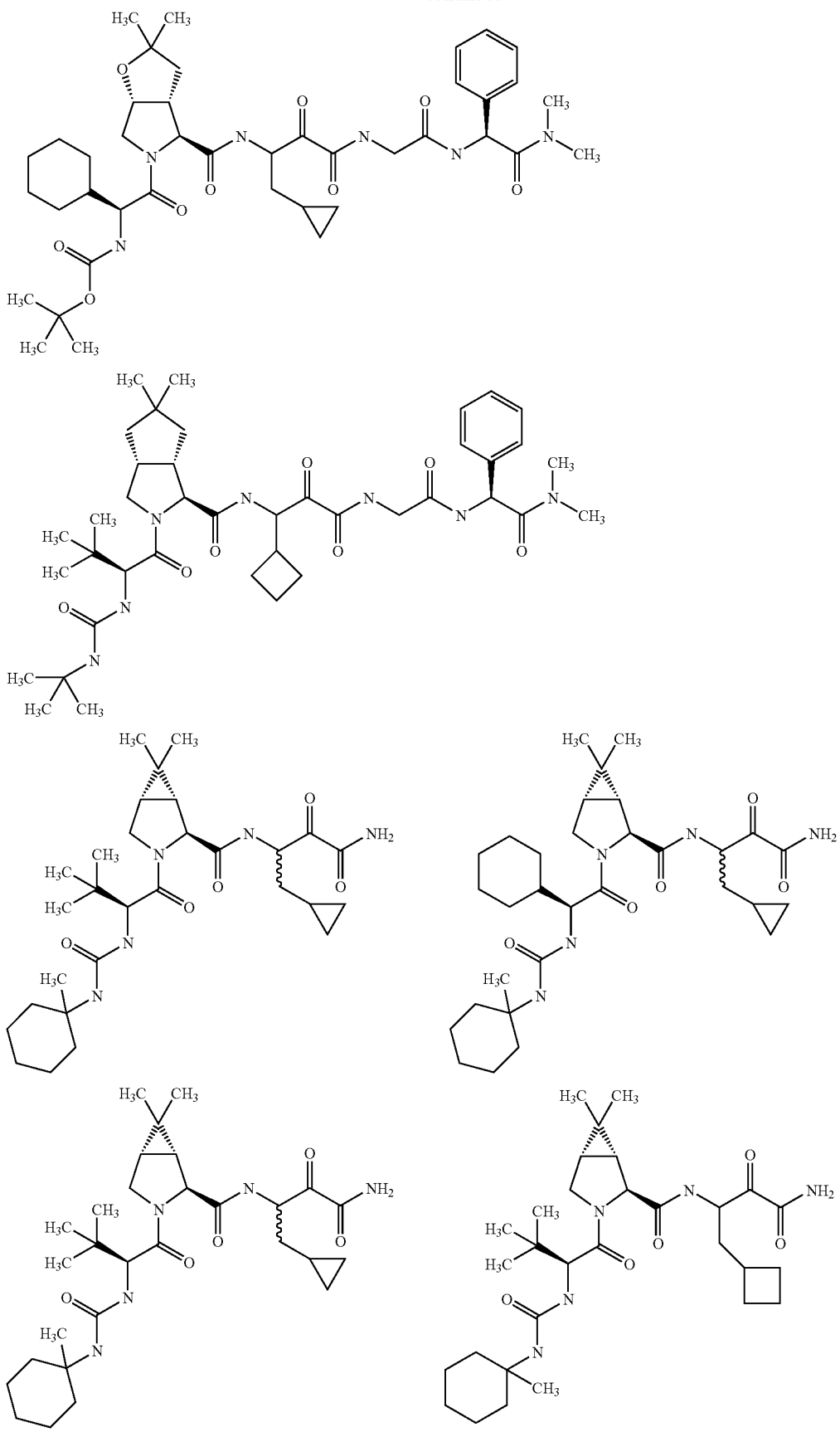

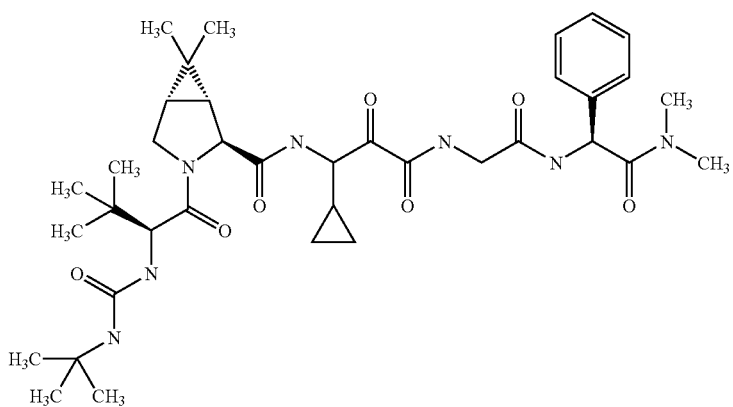
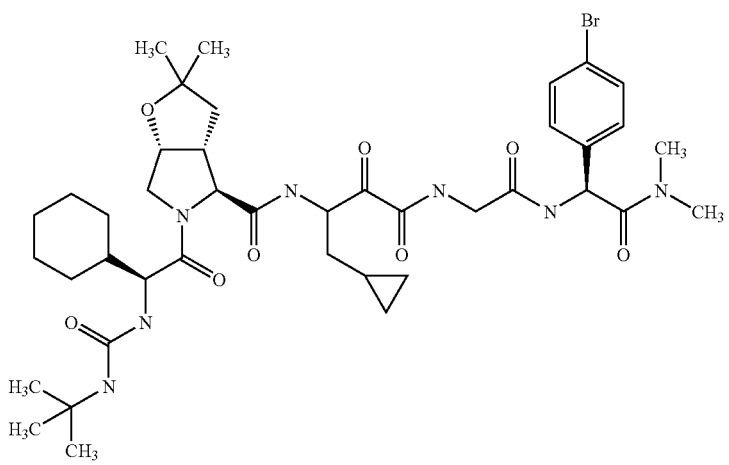
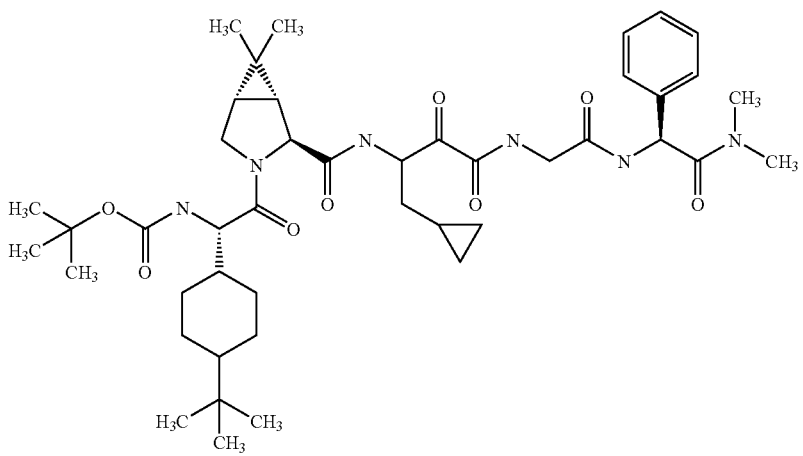

221 222
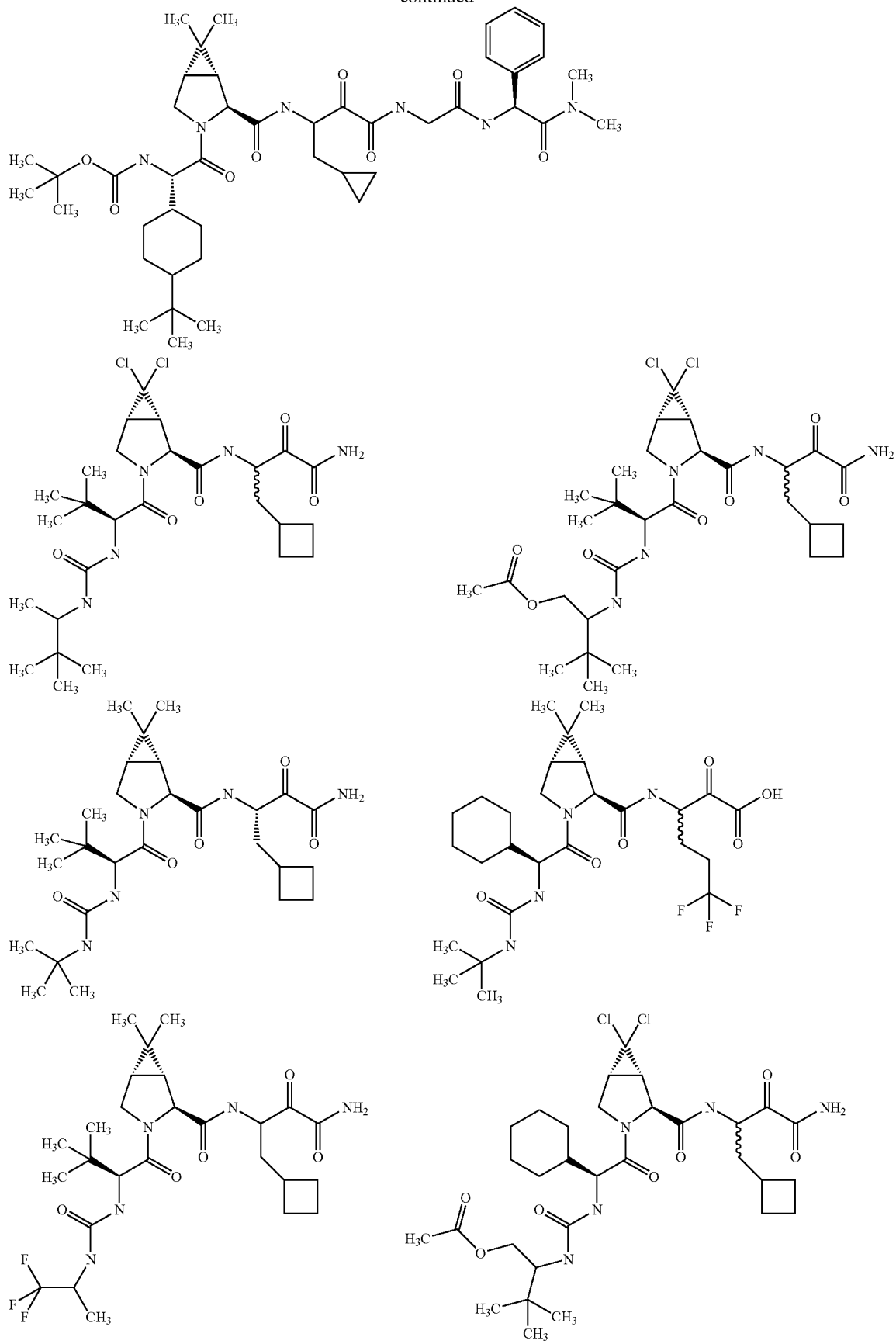
-continued

223
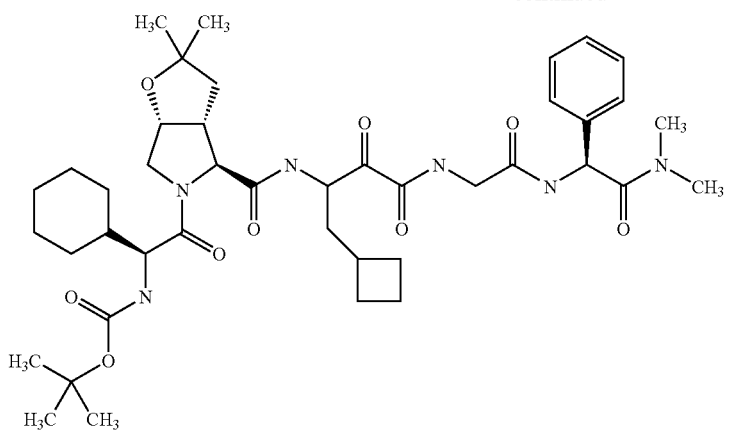
224
-continued
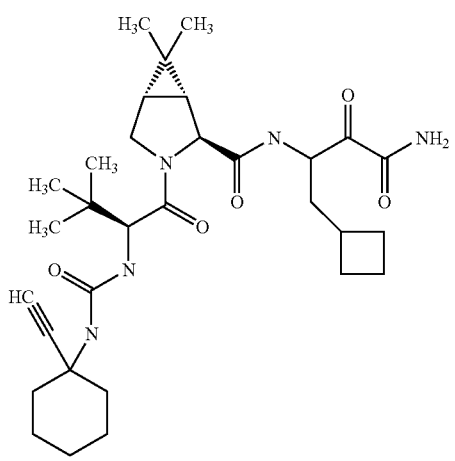
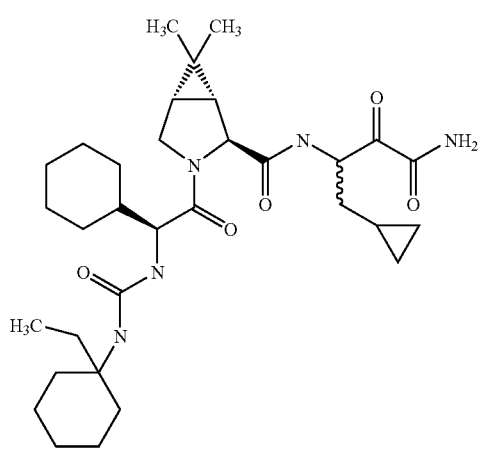
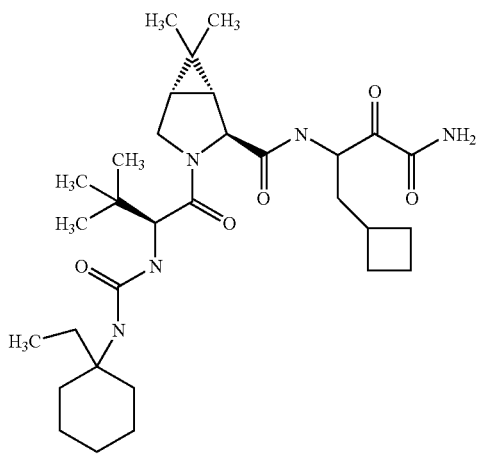
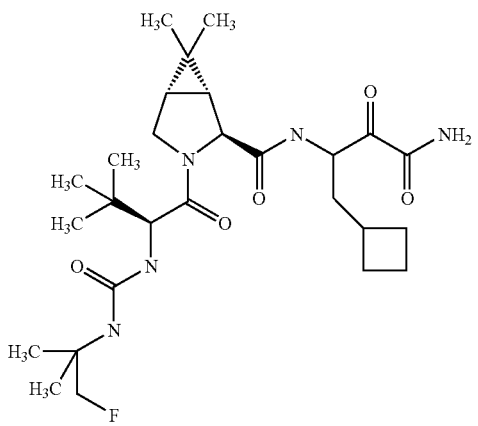

-continued
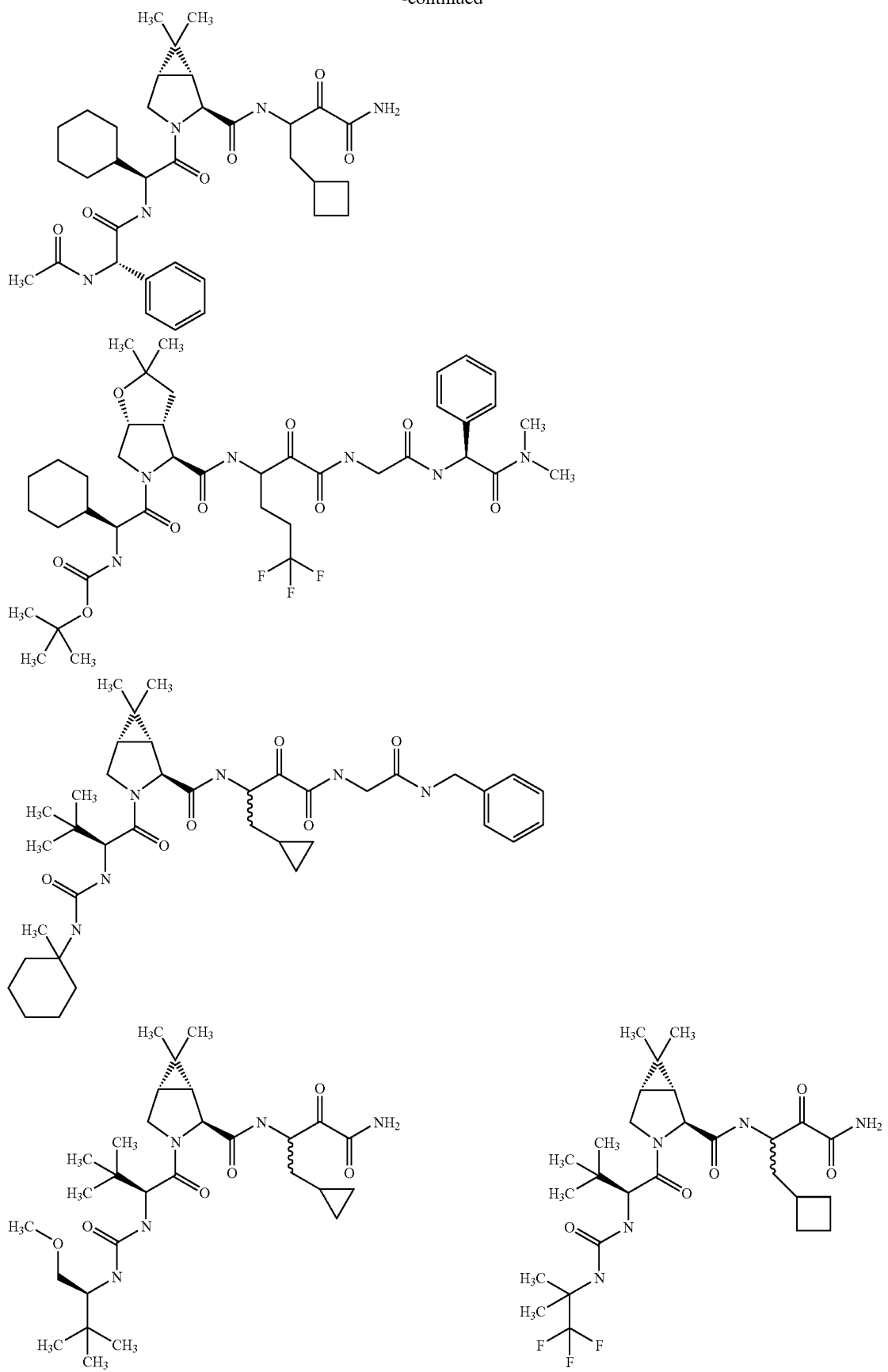

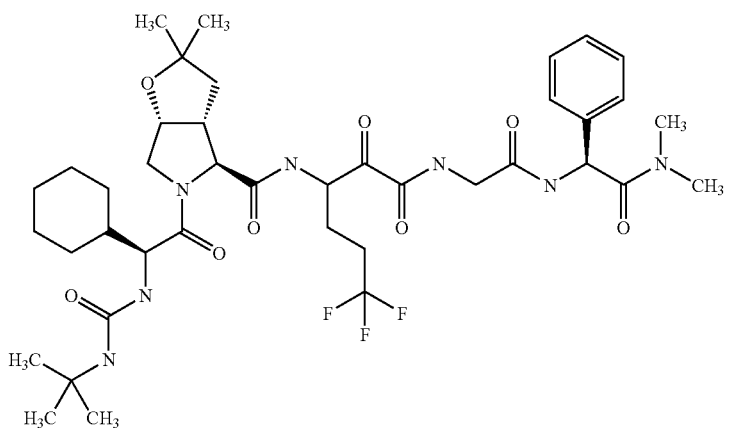
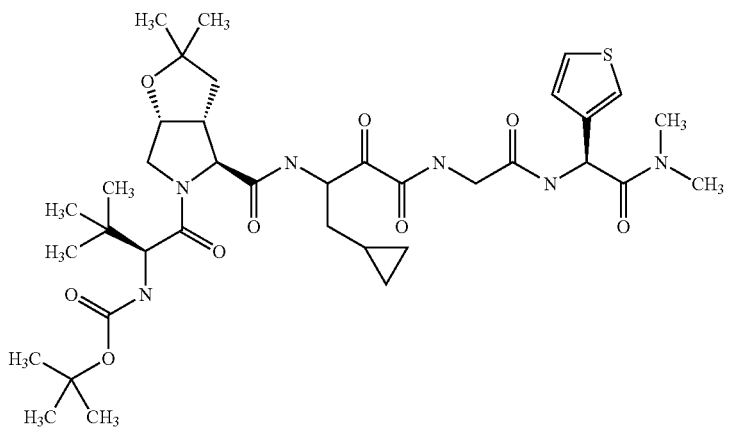
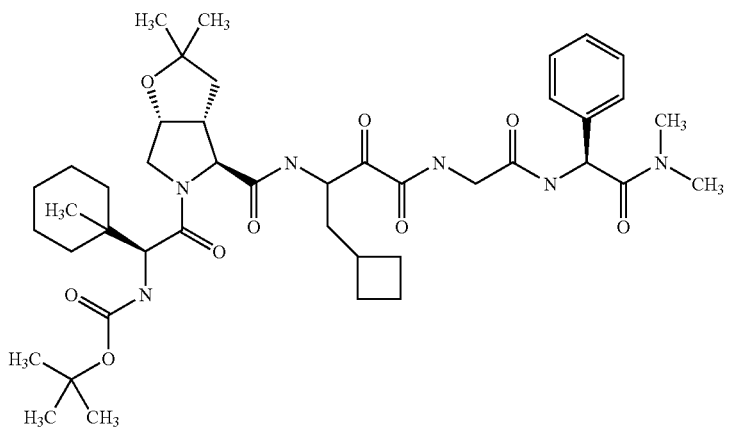
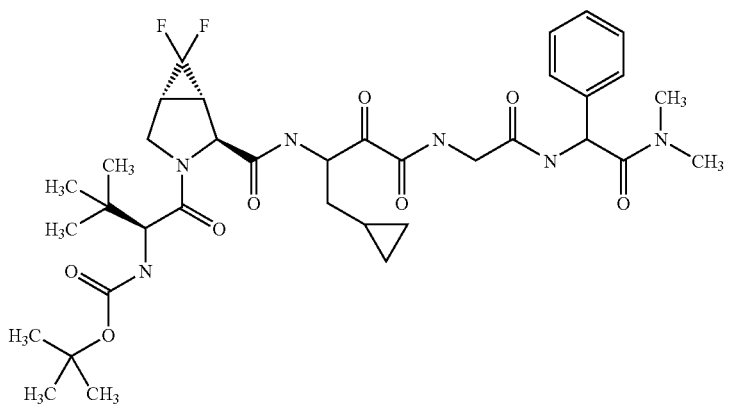

-continued
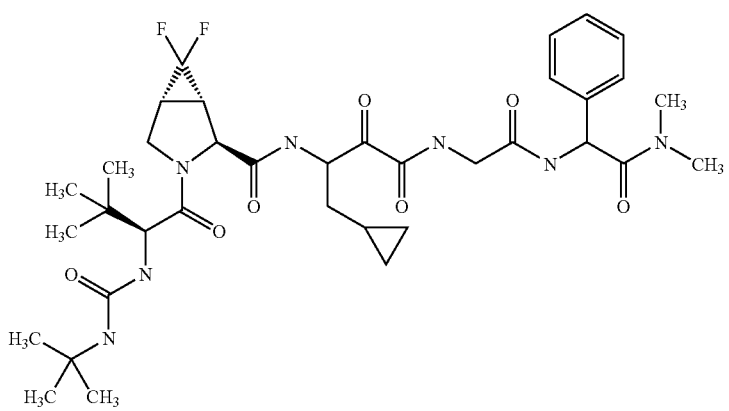
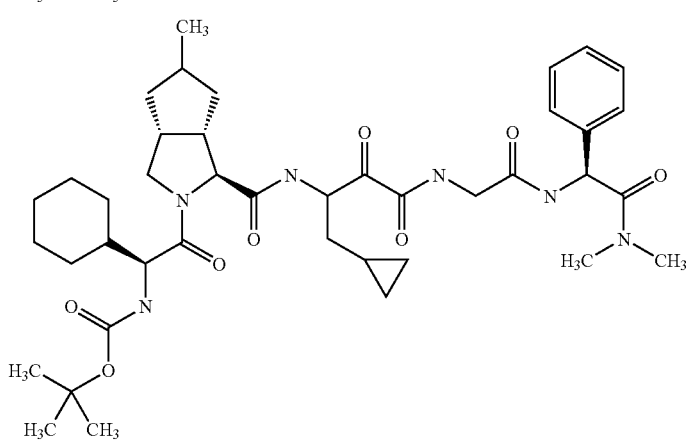
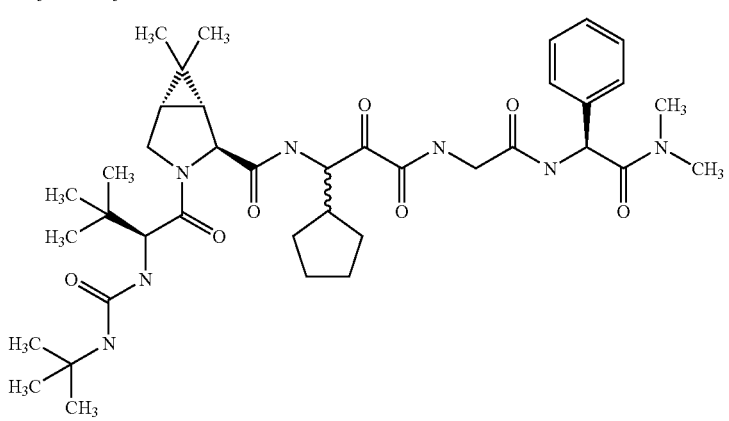
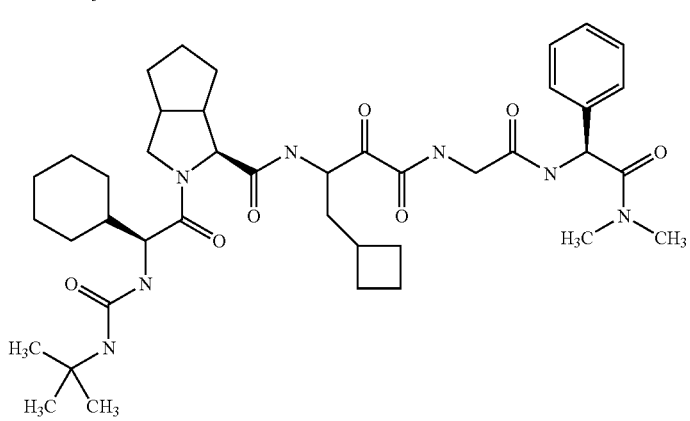

-continued
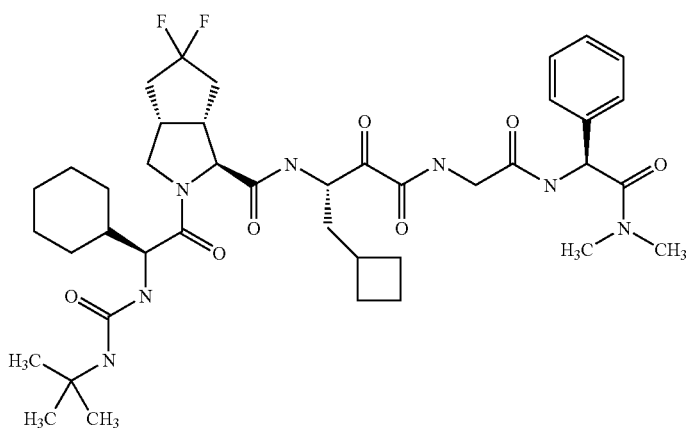
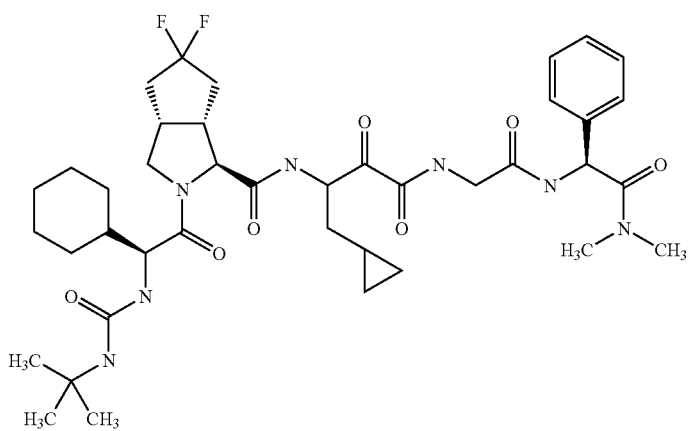
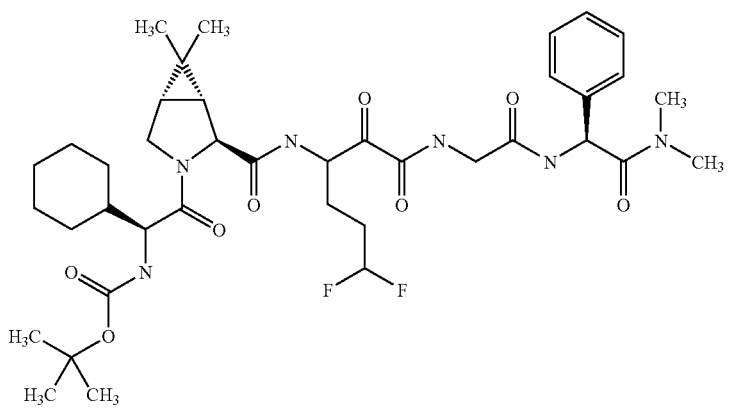
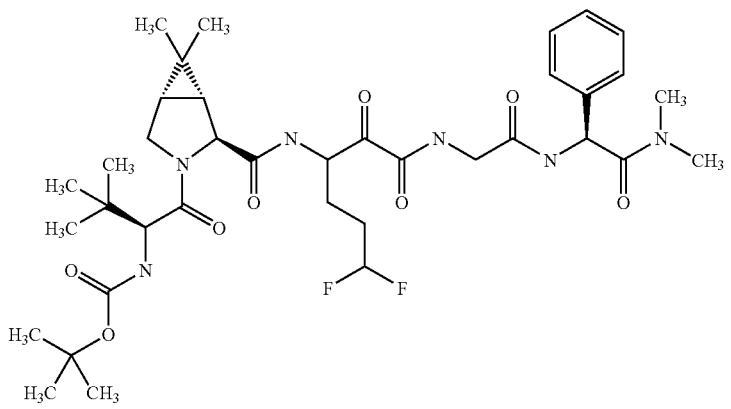

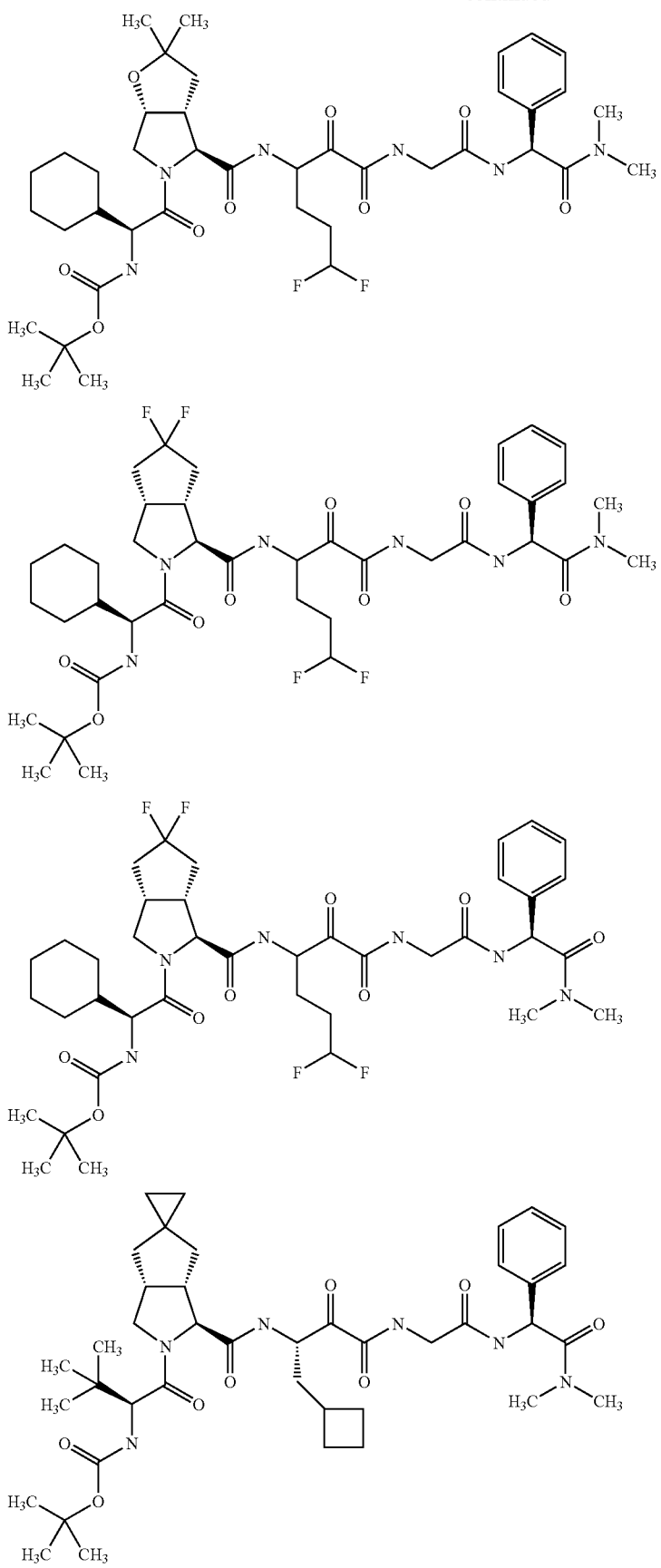

-continued
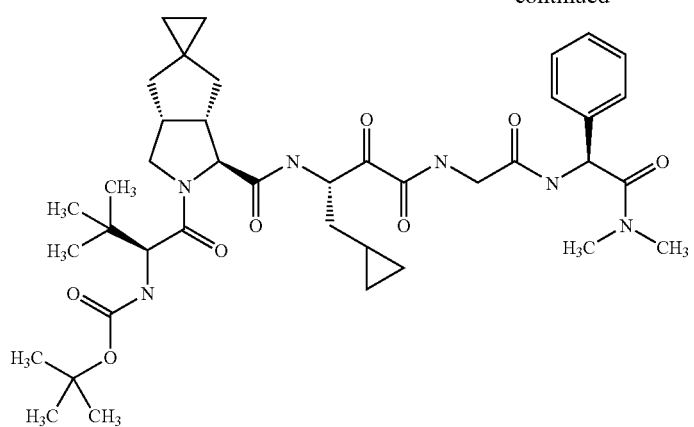
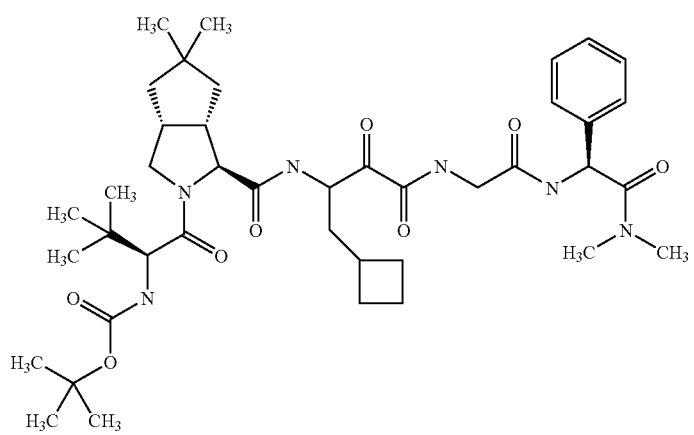
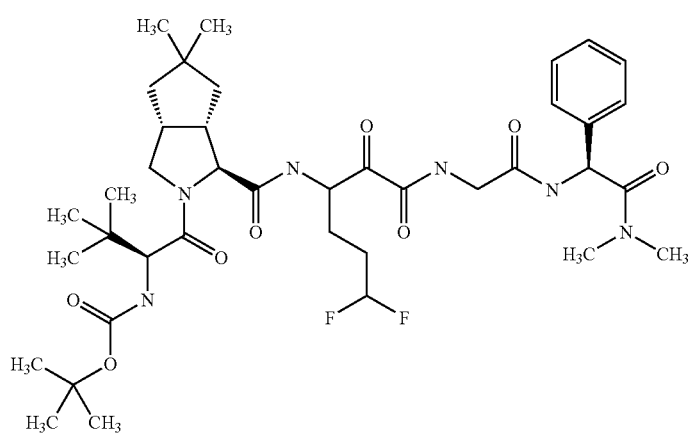
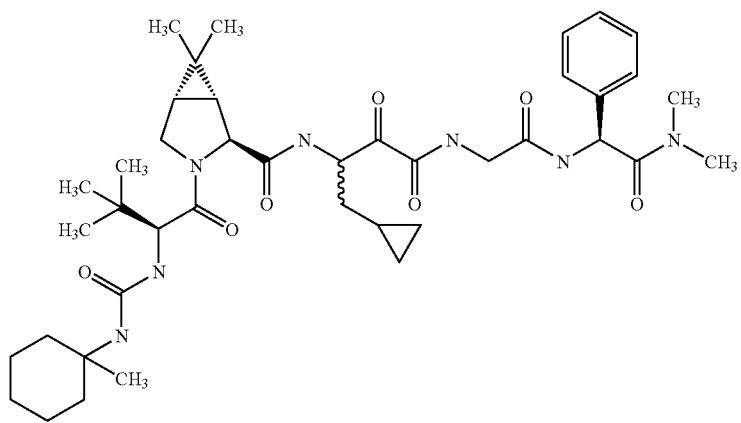

-continued
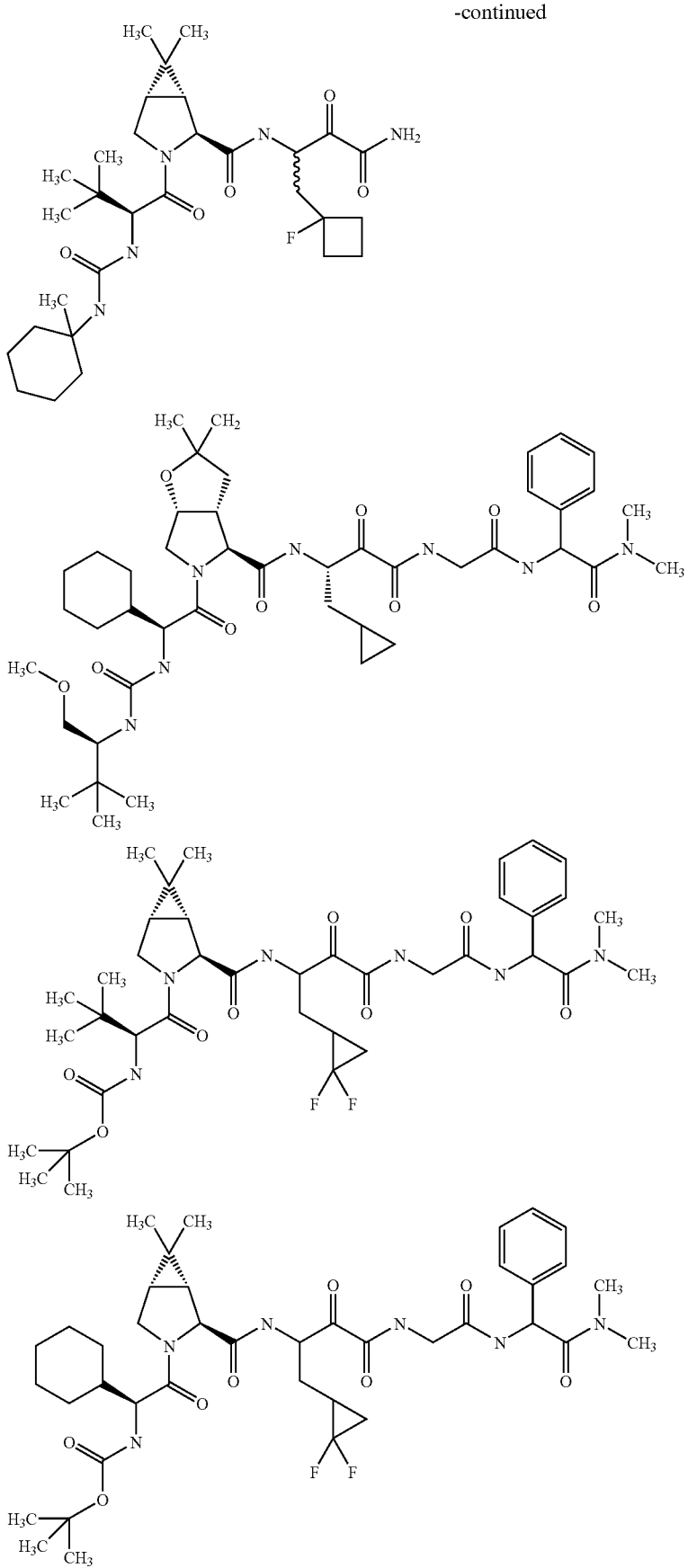

-continued
| 239 | 240 |
|---|---|
| 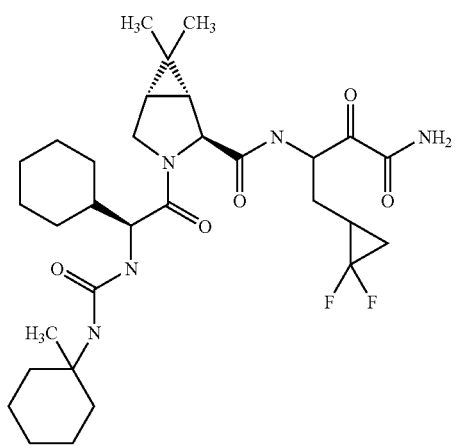 | 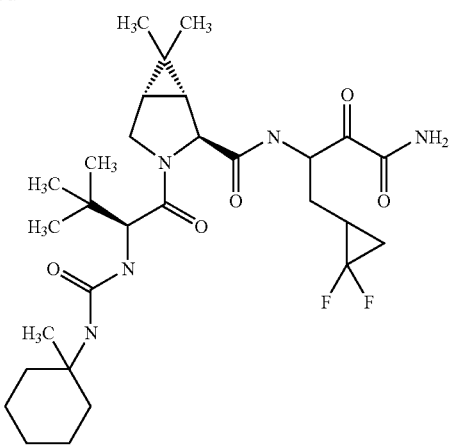 |
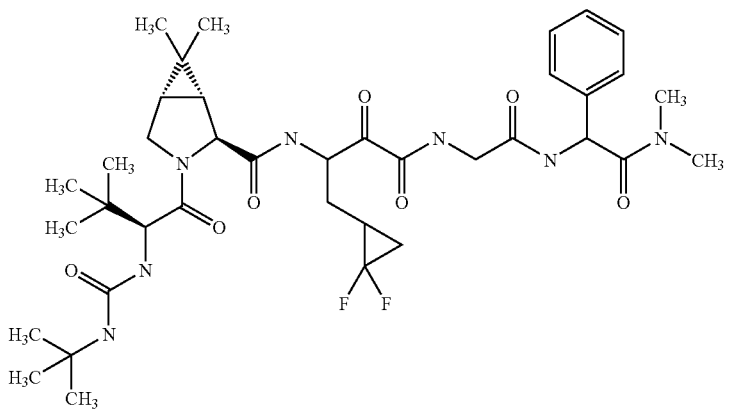
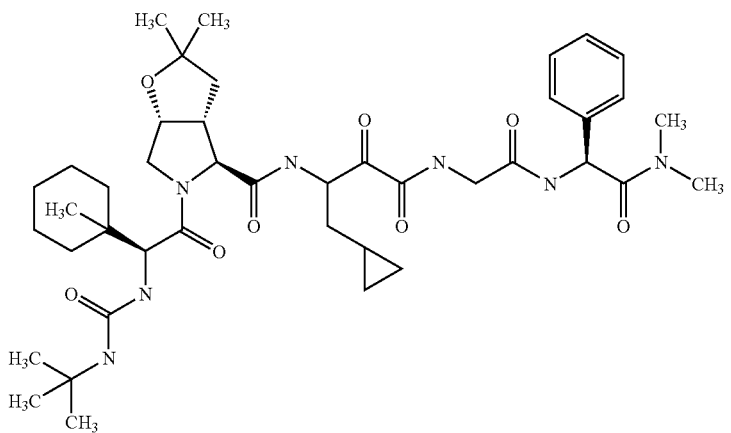
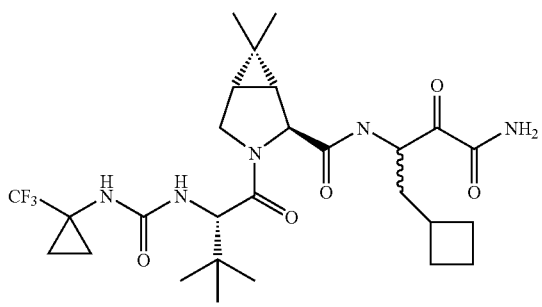

or a pharmaceutically acceptable salt, solvate or ester thereof.
In one embodiment, the HCV protease inhibitor is selected from the group consisting of Formula Ia

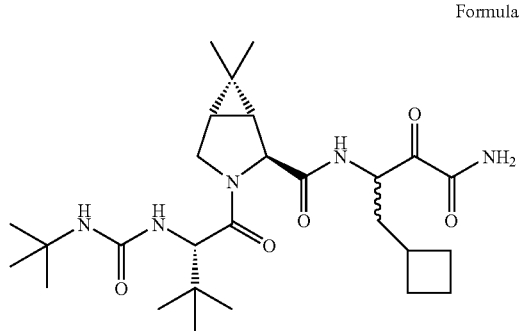

and pharmaceutically acceptable salts or solvates thereof.

The compound of formula Ia has recently been separated into its isomer/diastereomers of Formulas Ib and Ic. In one embodiment, the HCV protease inhibitor is selected from the group consisting of the compound of Formula Ic and pharmaceutically acceptable salts or solvates thereof as a potent inhibitor of HCV NS3 serine protease.

Formula Ib

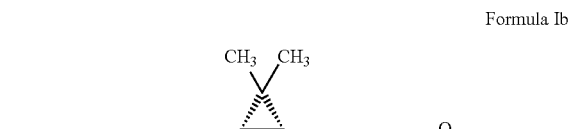

Formula Ic

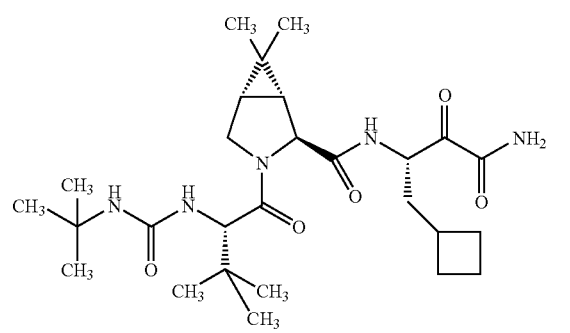

The chemical name of the compound of Formula Ic is (1R, 2S,5S)-N-[(1S)-3-amino-1-(cyclobutylmethyl)-2,3-dioxopropyl]-3-[(2S)-2-[[[(1,1-dimethylethyl)amino]carbonyl]amino]-3,3-dimethyl-1-oxobutyl]-6,6-dimethyl-3-azabicyclo[3.1.0]hexane-2-carboxamide.

Processes for making compounds of Formula I are disclosed in U.S. Patent Publication Nos. 2005/0059648, 2005/0020689 and 2005/0059800, incorporated by reference herein.

Non-limiting examples of suitable compounds of formula II and methods of making the same are disclosed in WO02/08256 and in U.S. Pat. No. 6,800,434, at col. 5 through col. 247, incorporated herein by reference.

Non-limiting examples of suitable compounds of formula III and methods of making the same are disclosed in International Patent Publication WO02/08187 and in U.S. Patent Publication 2002/0160962 at page 3, paragraph 22 through page 132, incorporated herein by reference.

Non-limiting examples of suitable compounds of formula IV and methods of making the same are disclosed in International Patent Publication WO03/062228 and in U.S. Patent Publication 2003/0207861 at page 3, paragraph 25 through page 26, incorporated herein by reference.

Non-limiting examples of suitable compounds of formula V and methods of making the same are disclosed in U.S. patent application Ser. No. 10/948,367 filed Sep. 23, 2004, and the preparation of the compounds are detailed in the experimental section of this application set forth hereinbelow.

Non-limiting examples of suitable compounds of formula VI and methods of making the same are disclosed in U.S. Patent Publication Ser. No. 2005/0085425 at page 3, paragraph 0023 through page 139, incorporated herein by reference.

Compounds of formula VII-IX are disclosed in U.S. patent application Ser. No. 10/993,394 filed Nov. 19, 2004, and the preparation of the compounds are detailed in the experimental section of this application set forth hereinbelow.

Non-limiting examples of certain compounds of formula VII disclosed in U.S. patent application Ser. No. 10/993,394 are:

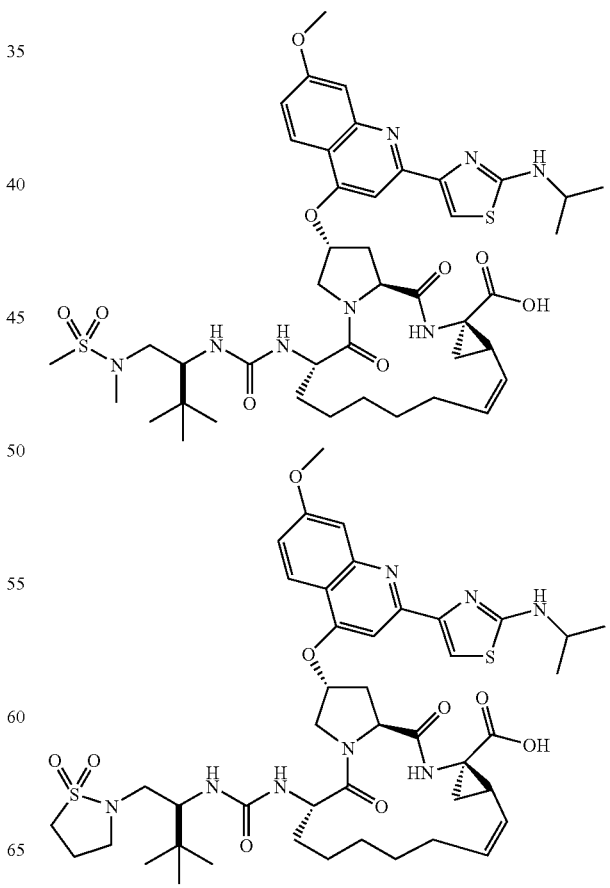

243
-continued
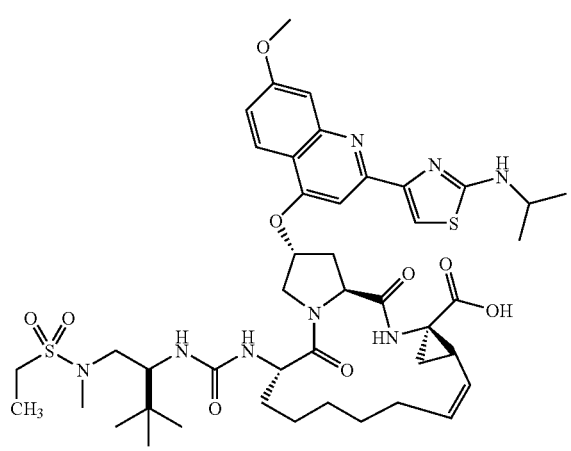
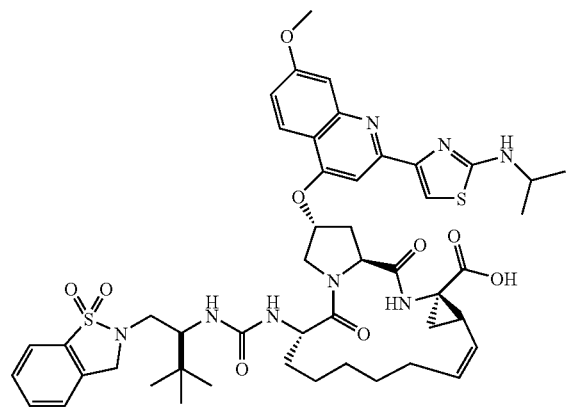
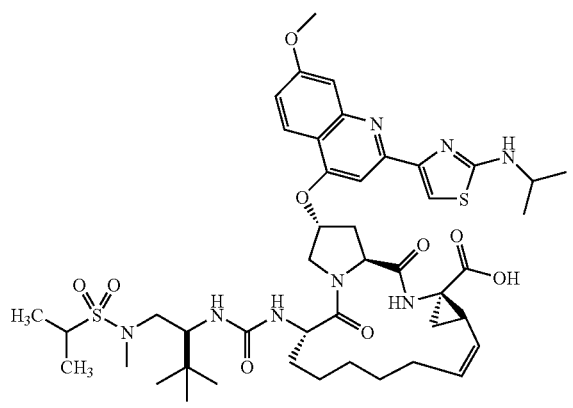
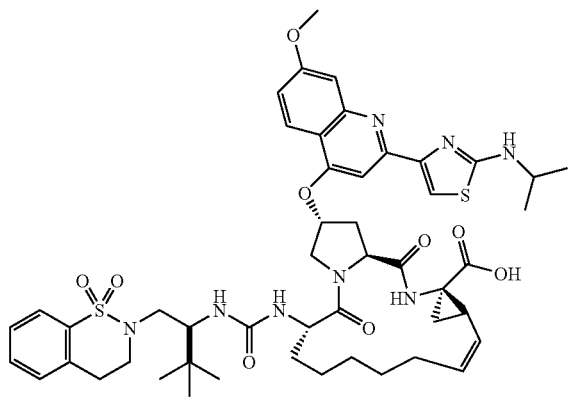
244
-continued
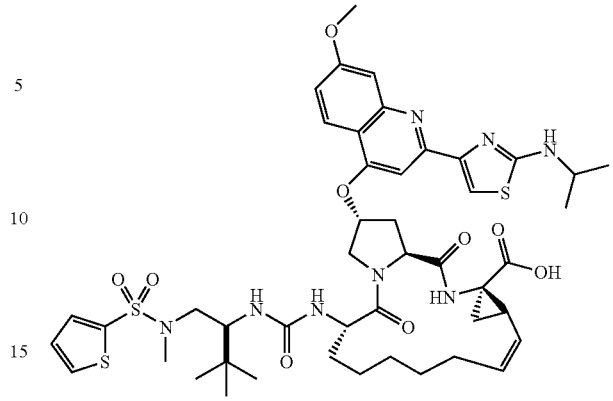

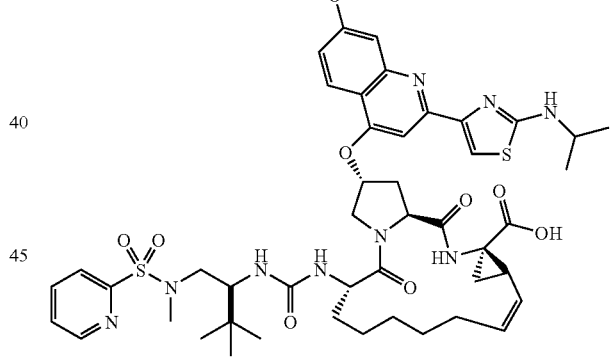
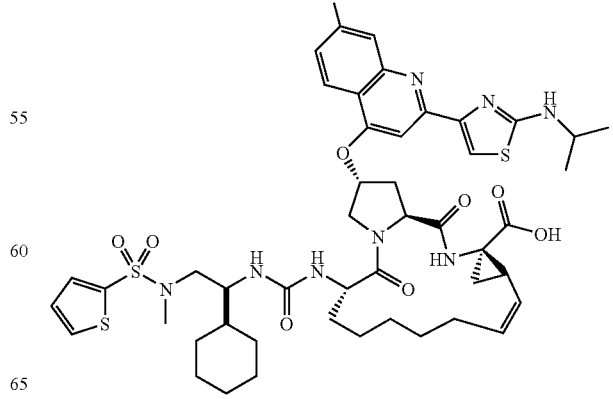

245
-continued
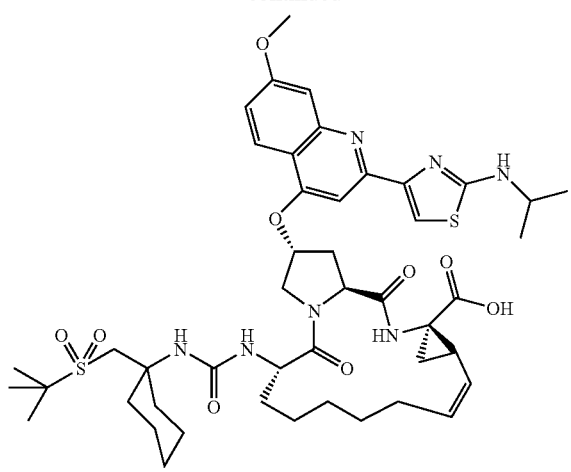
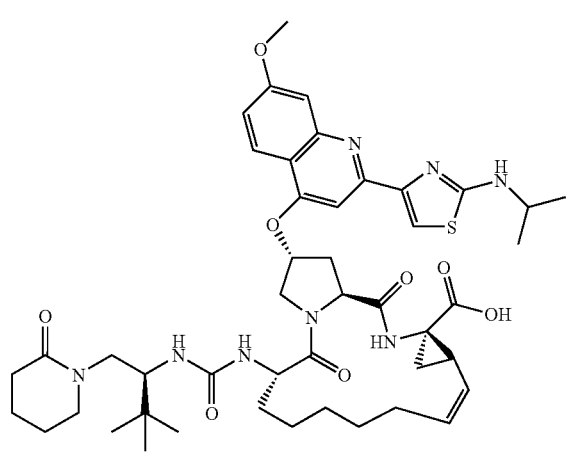
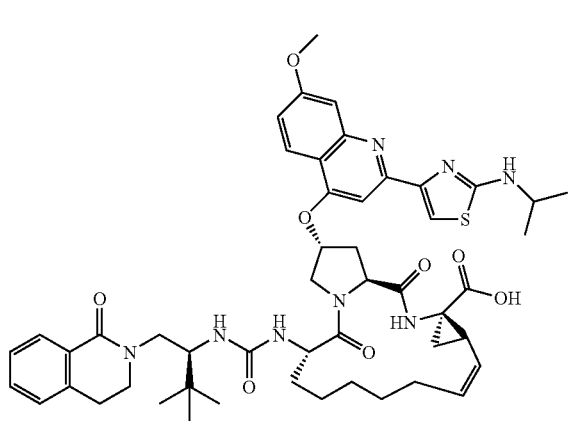
246
-continued
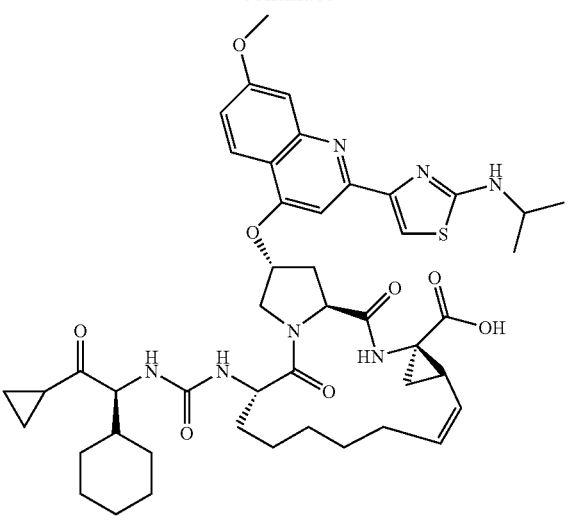
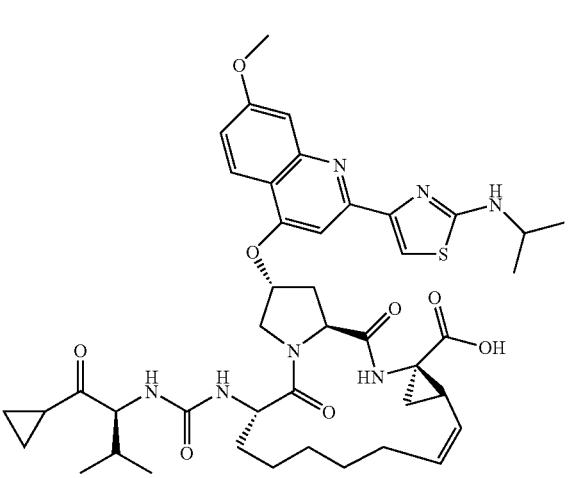
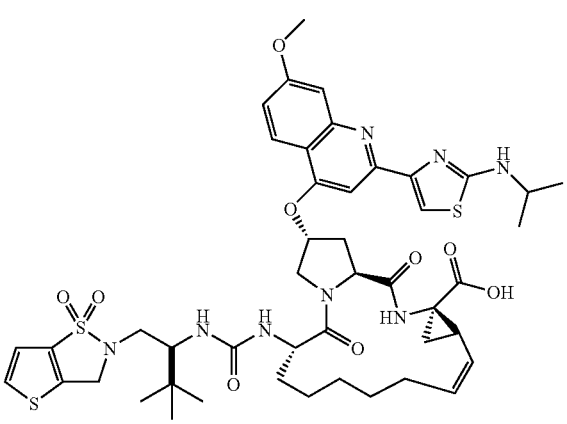

247
-continued
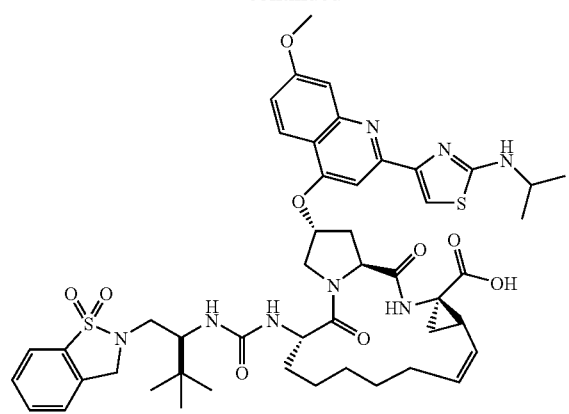
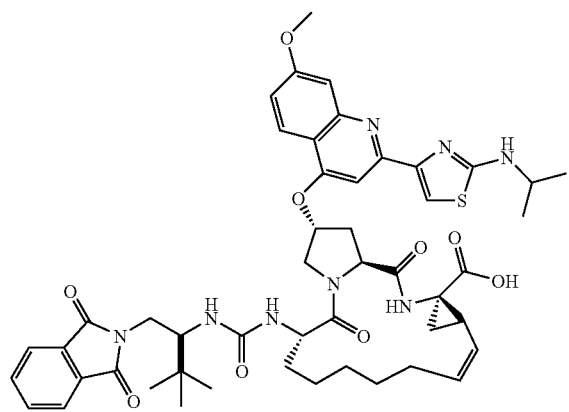
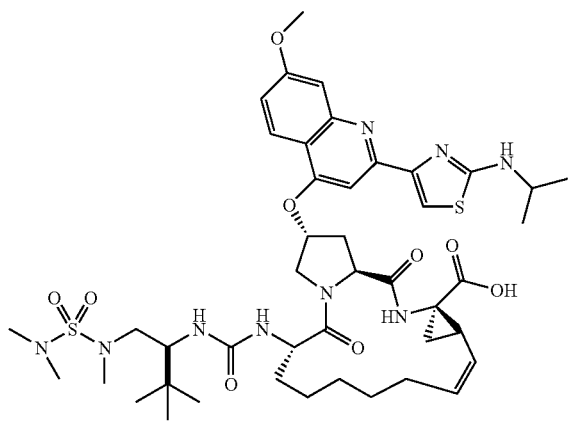
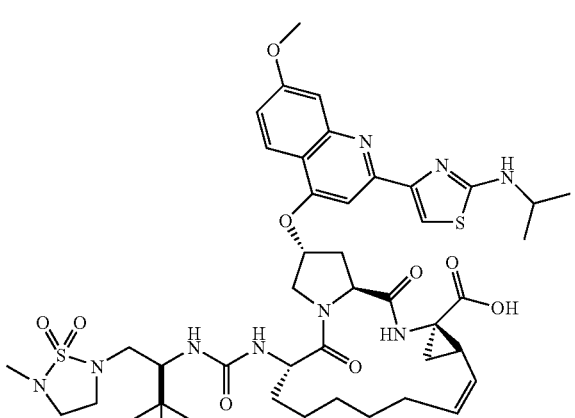
248
-continued
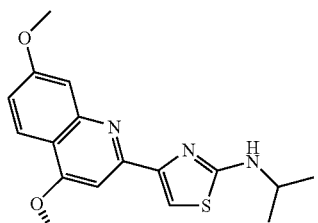

249
-continued
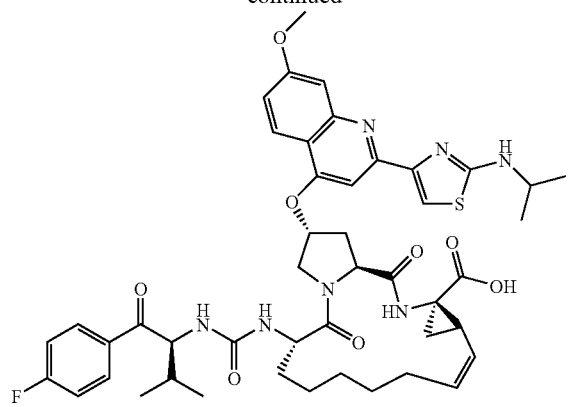
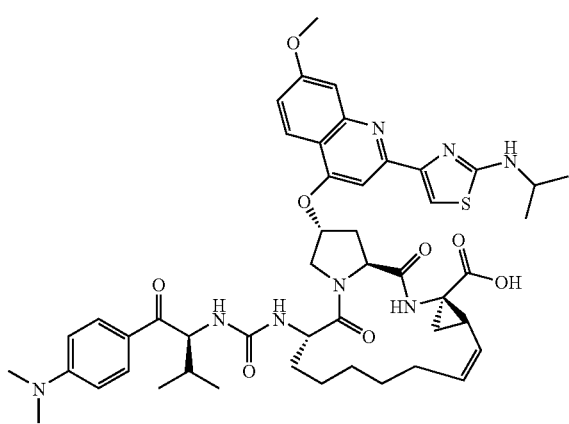
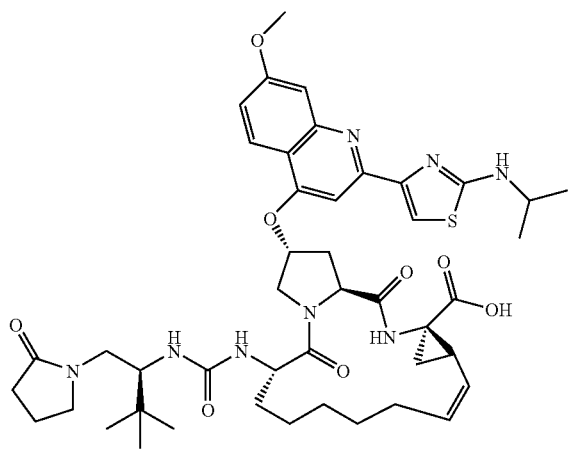
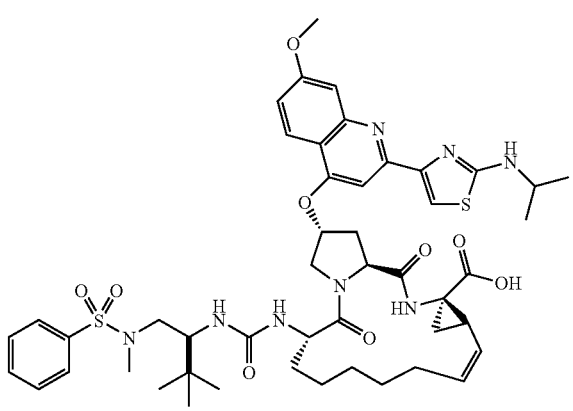
250
-continued
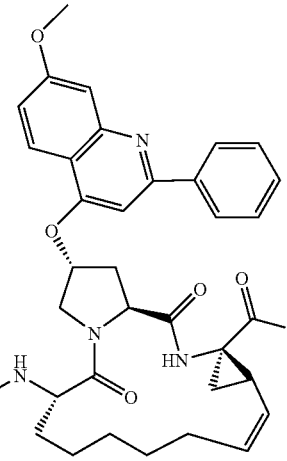
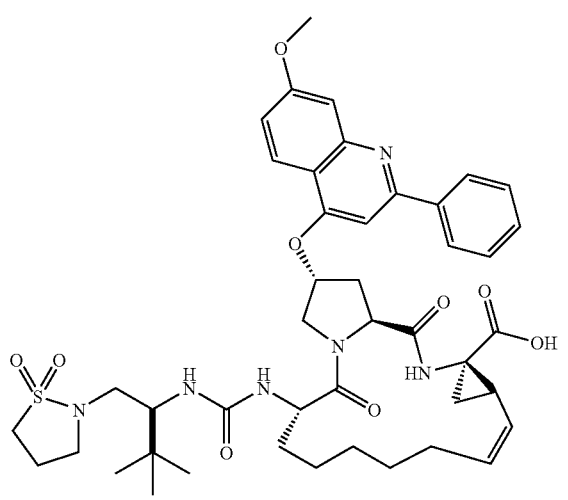

251
-continued
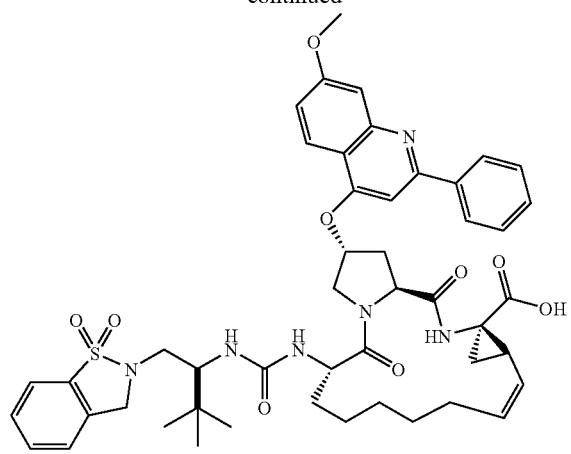
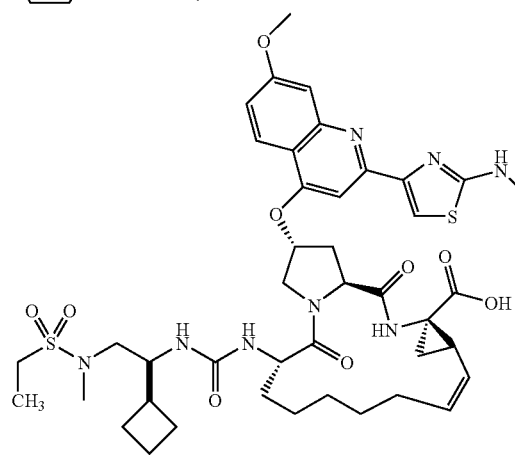
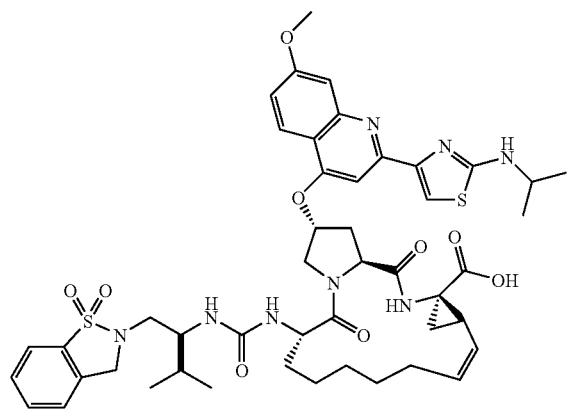
252
-continued
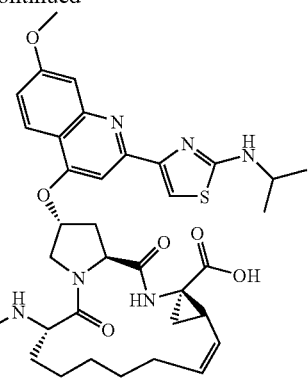
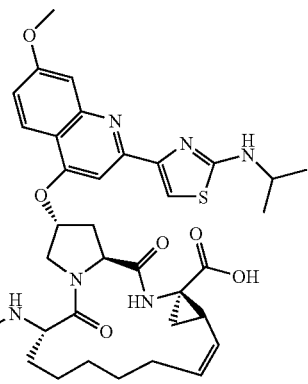
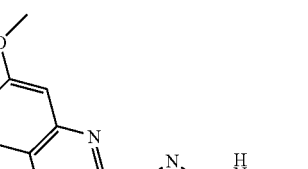
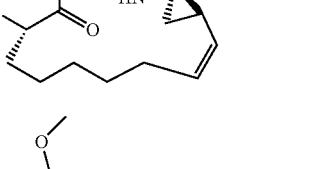
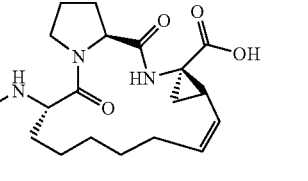

253
-continued
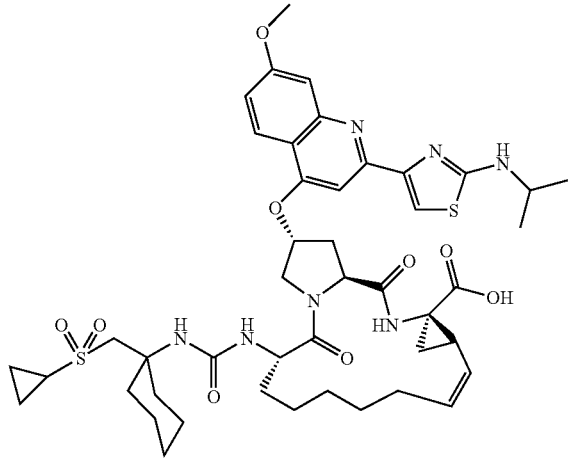
254
-continued
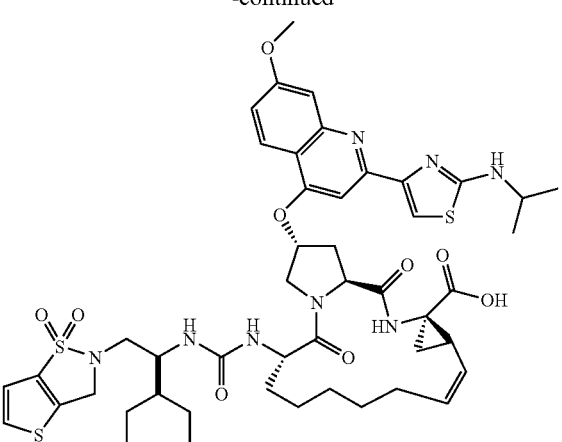
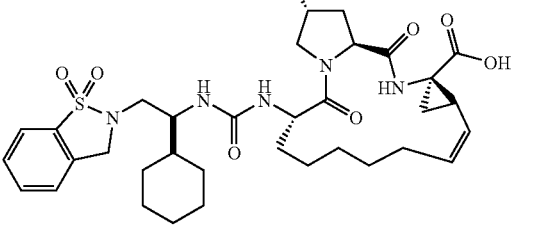
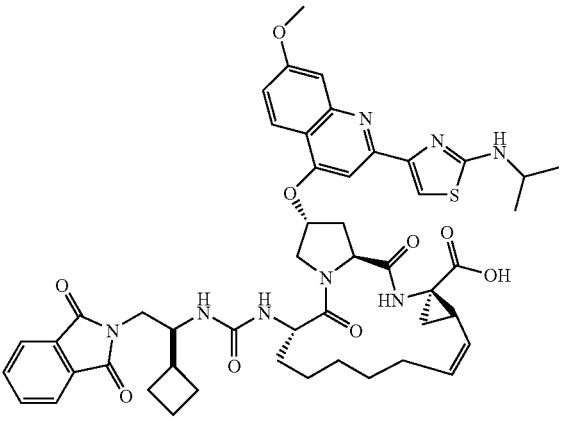

255
-continued
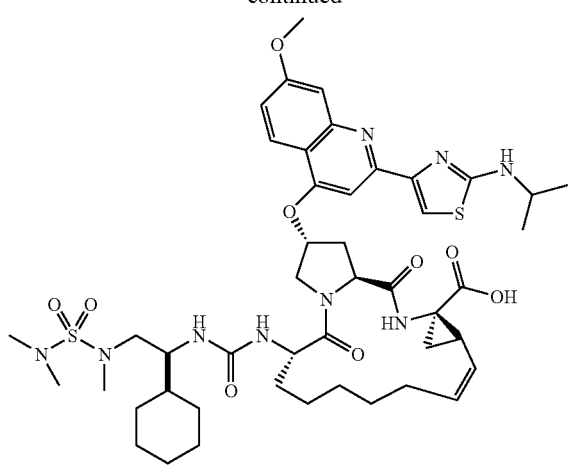
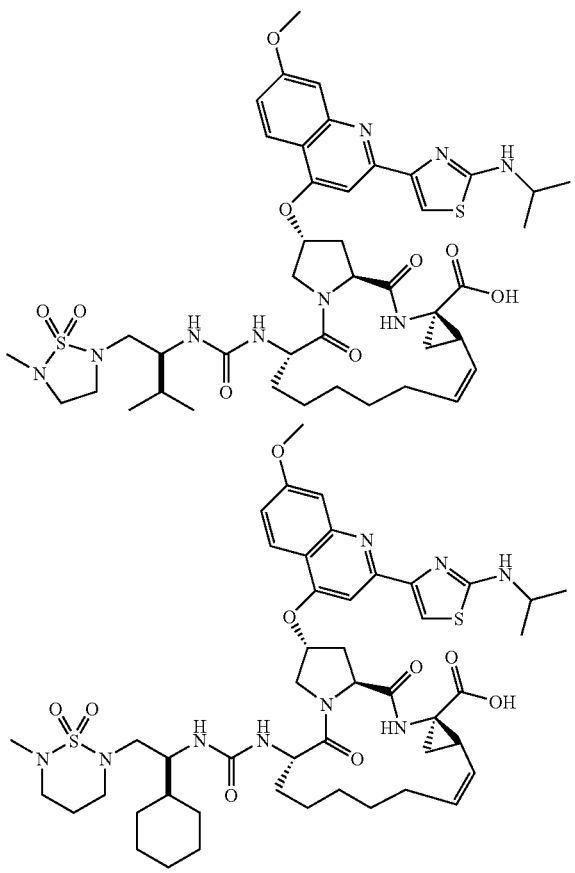
256
-continued
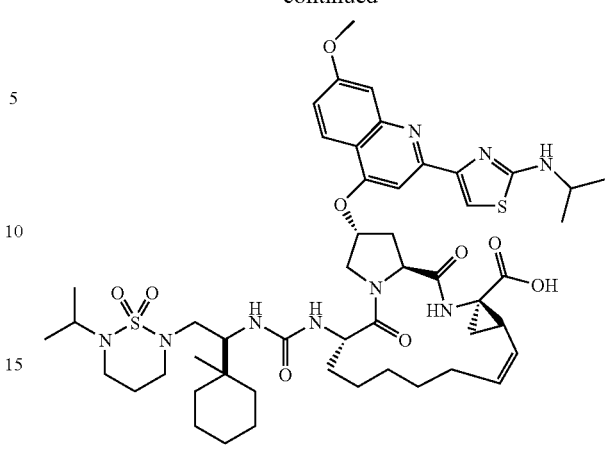
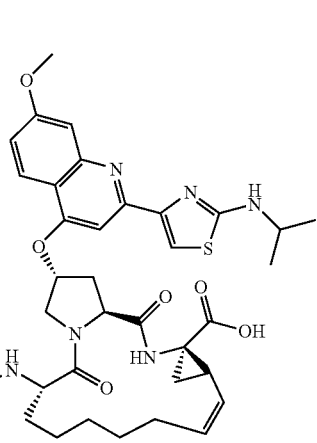
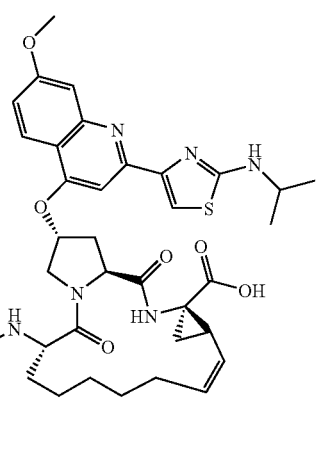

257
-continued
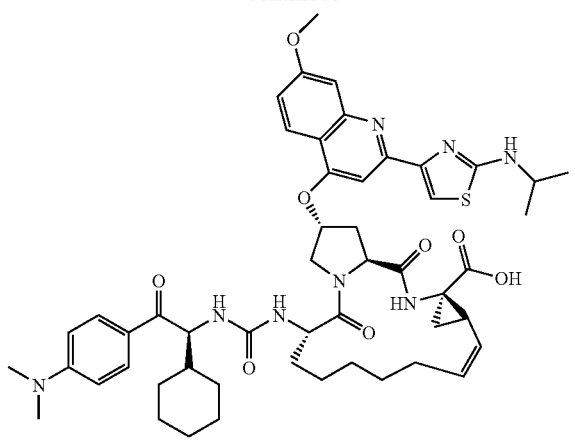
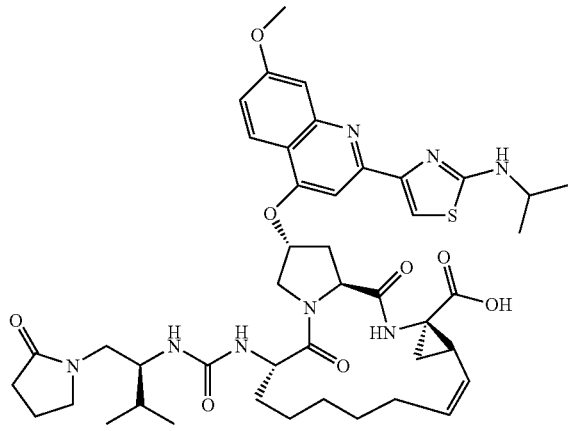
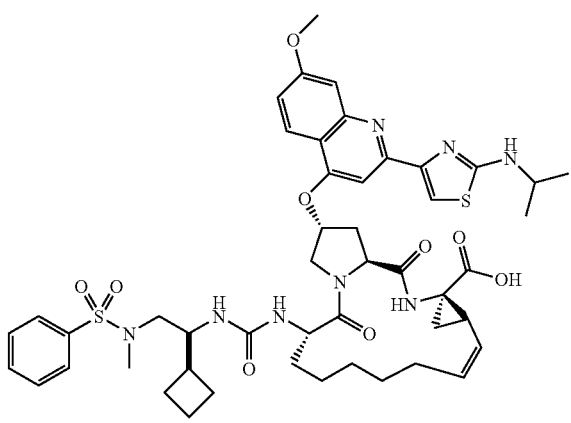
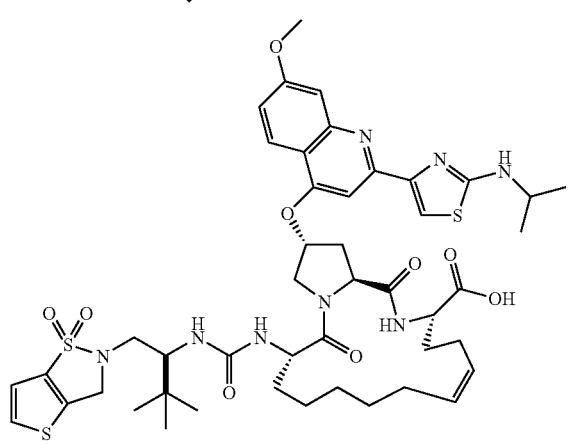
258
-continued
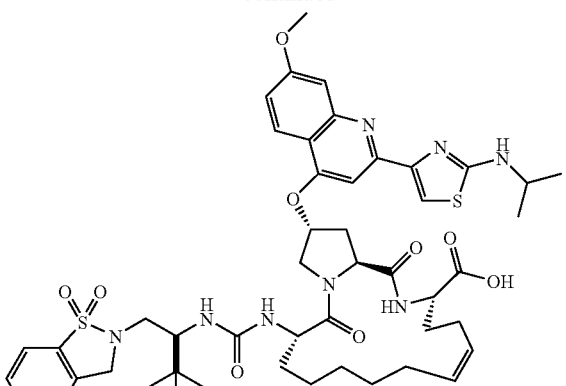
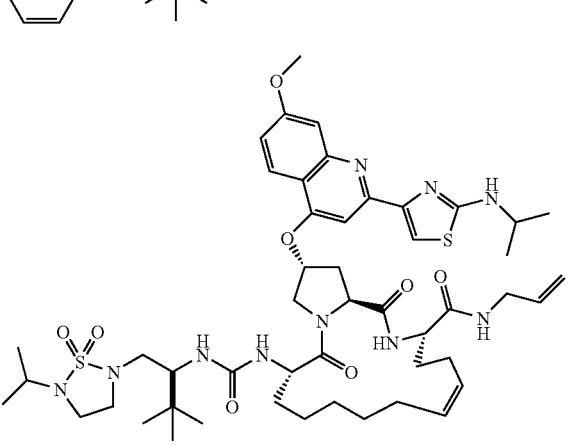
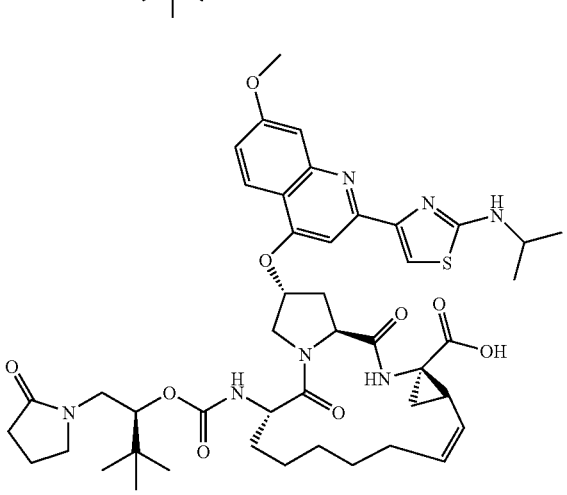
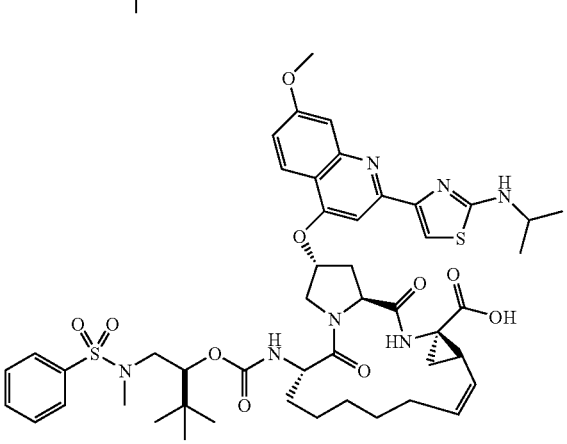

259
-continued
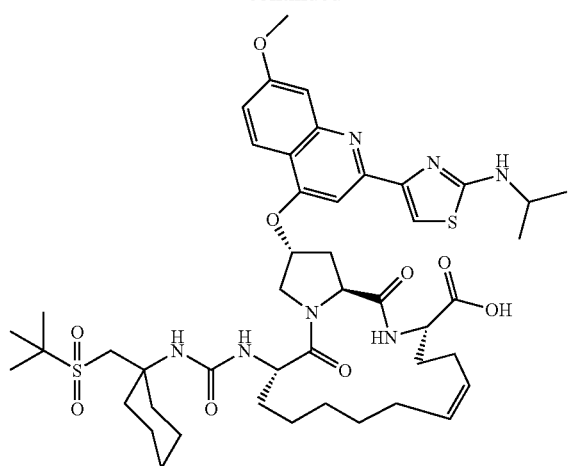

260
-continued
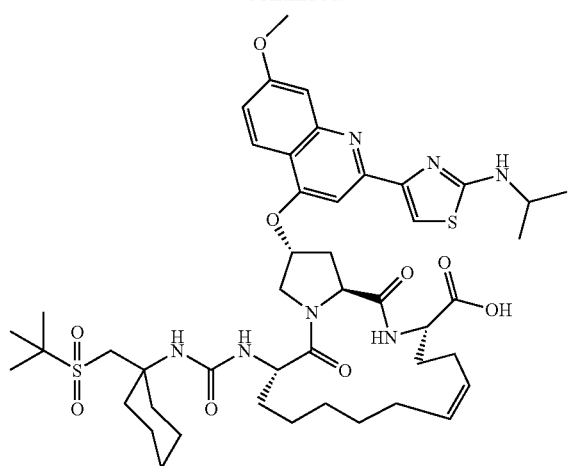
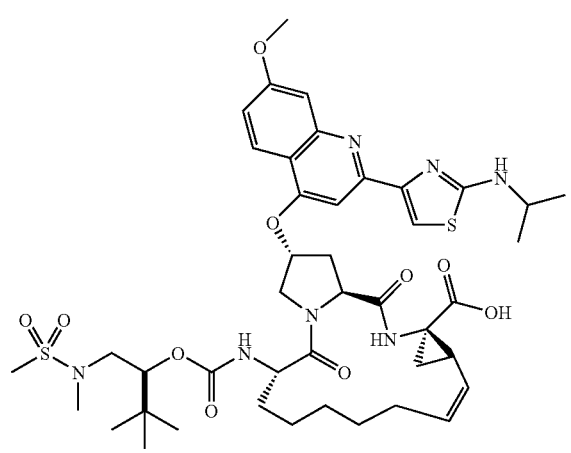

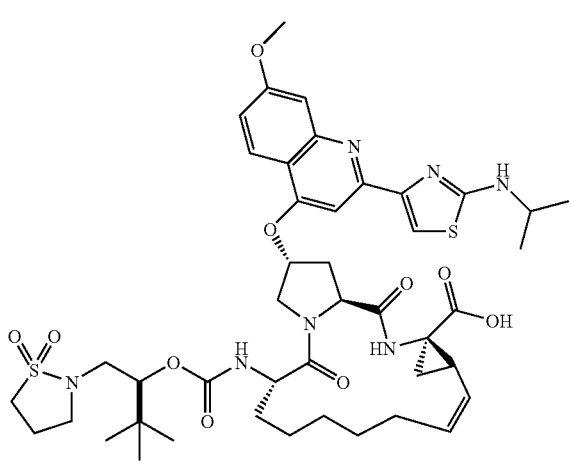

261
-continued
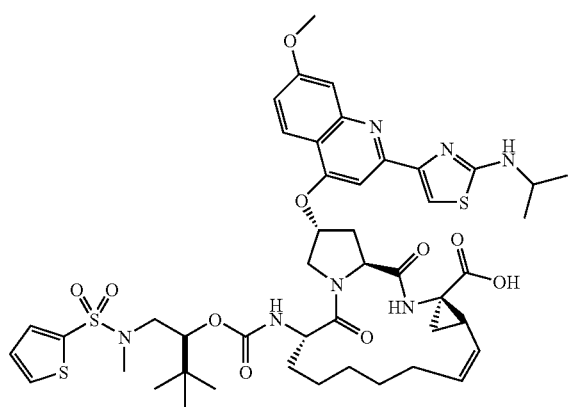
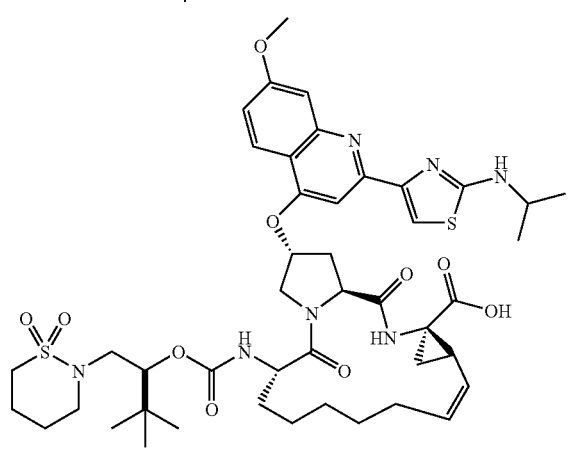
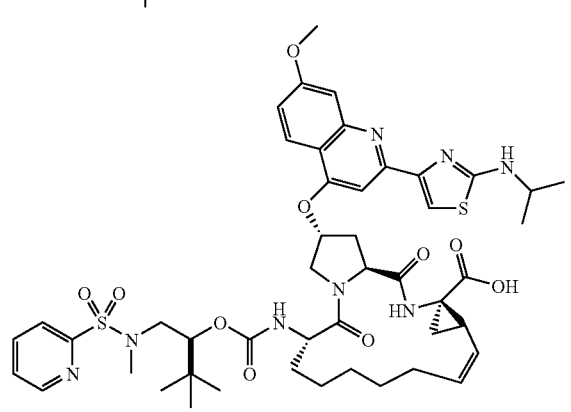
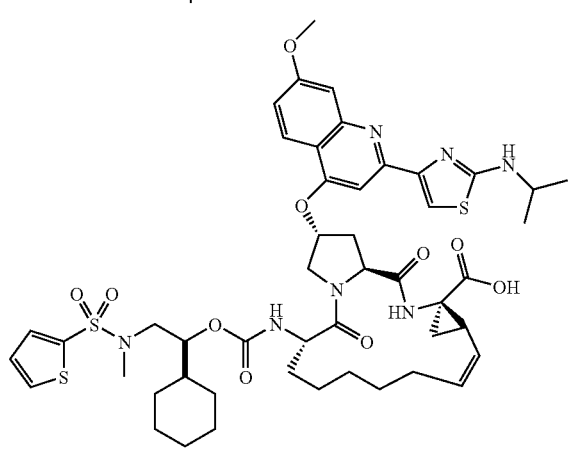
262
-continued
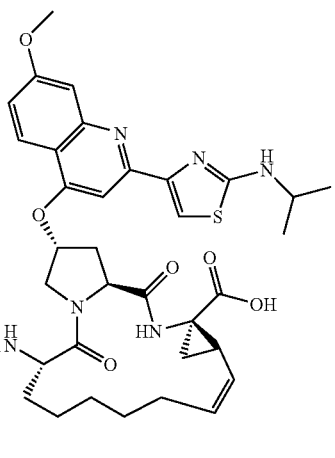
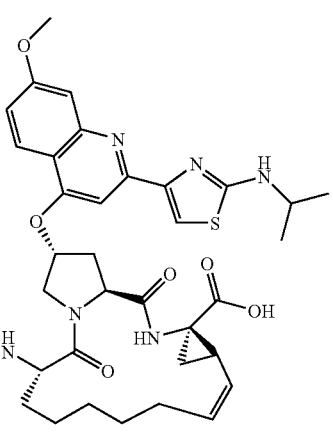
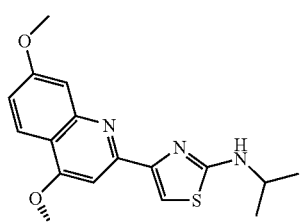

263
-continued
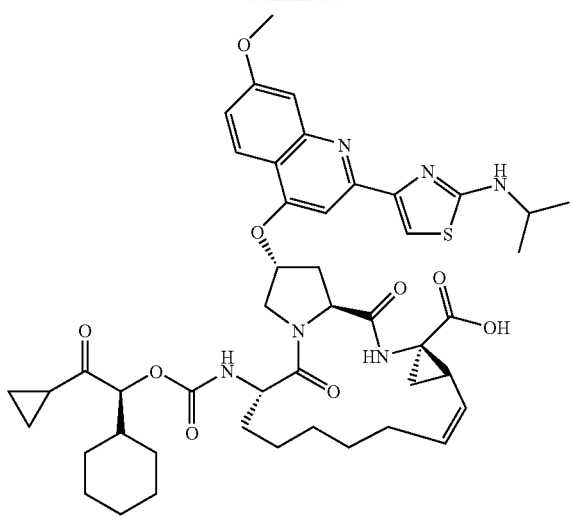
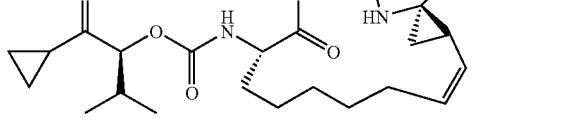
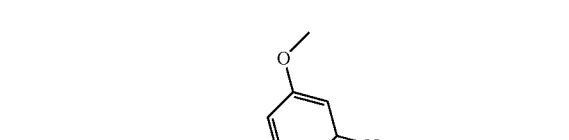
264
-continued
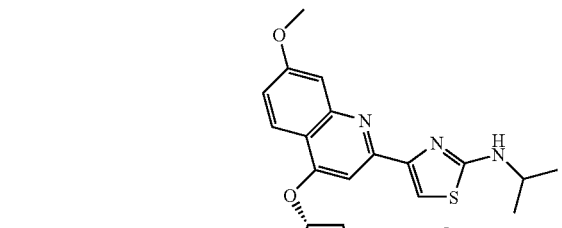
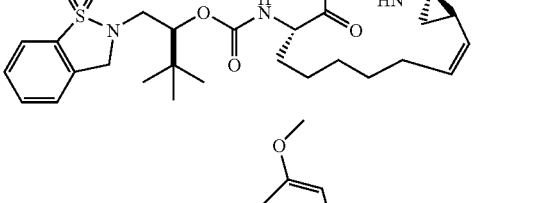
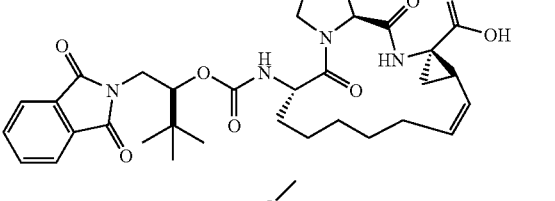
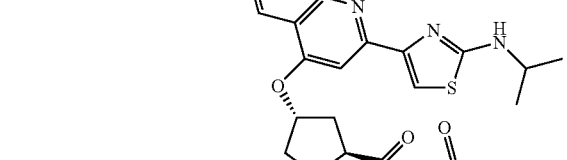
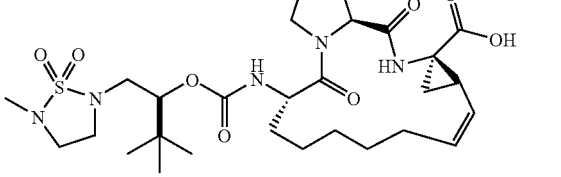

265
-continued
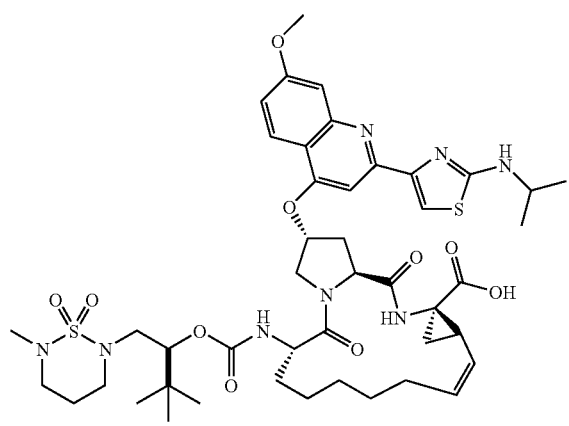
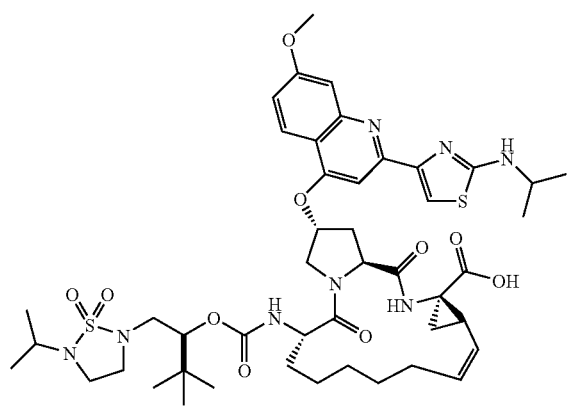
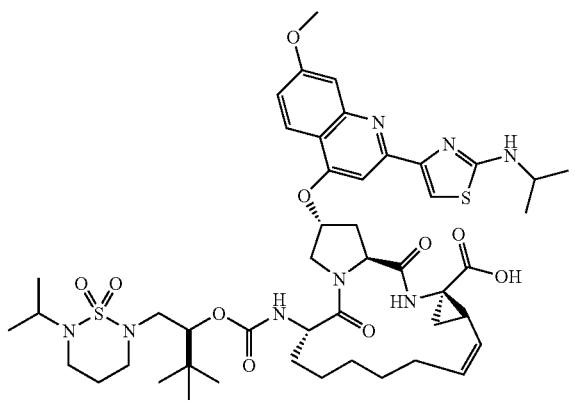
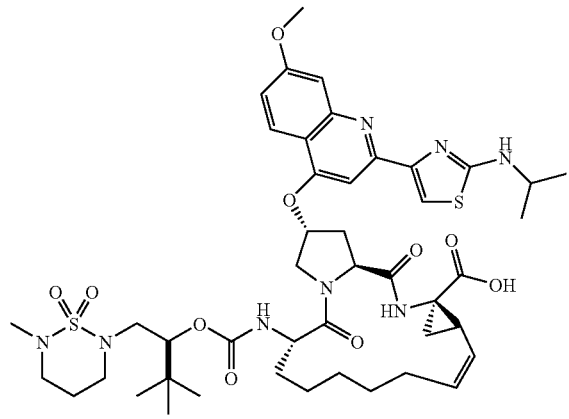
266
-continued
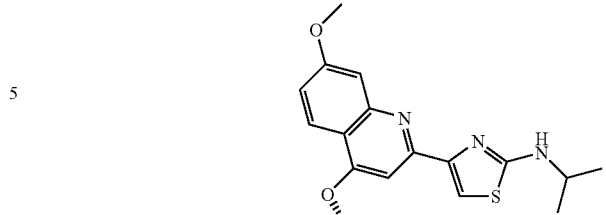
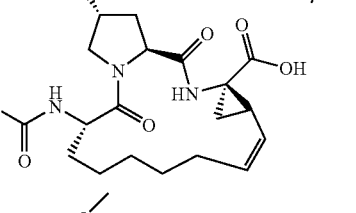
and
or a pharmaceutically acceptable salt, solvate or ester thereof.

Nonlimiting examples of certain compounds of formula VIII disclosed in U.S. patent application Ser. No. 10/993,394 are:
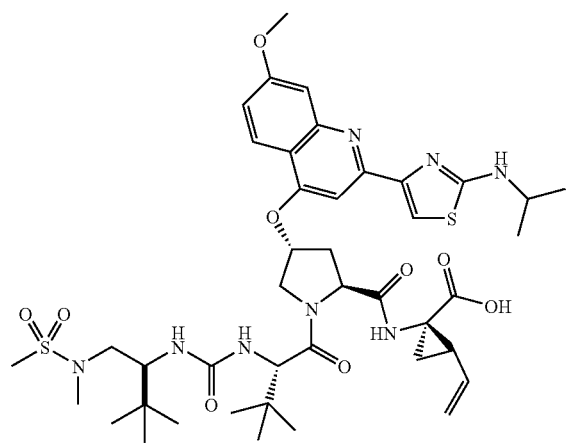
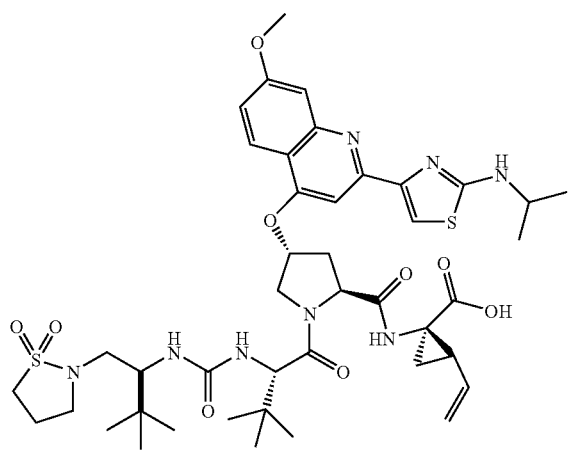
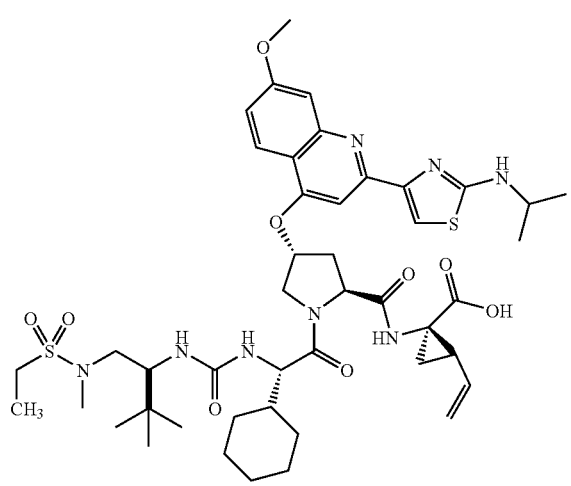
-continued
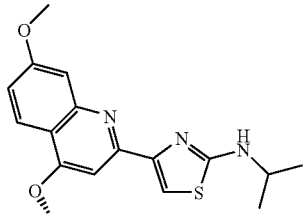
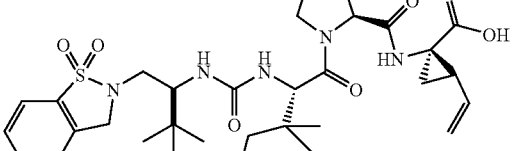
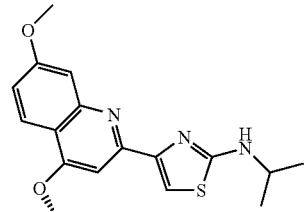
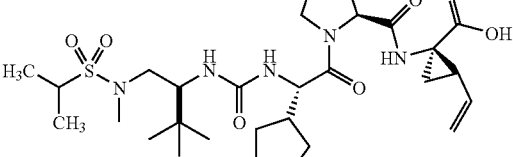
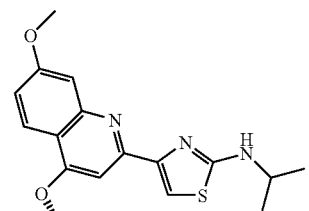
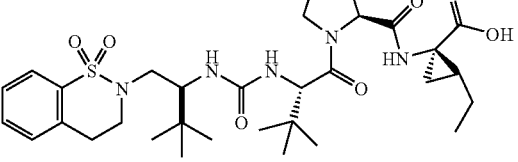
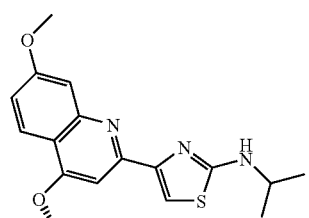
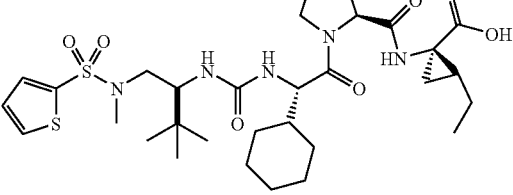

269
-continued
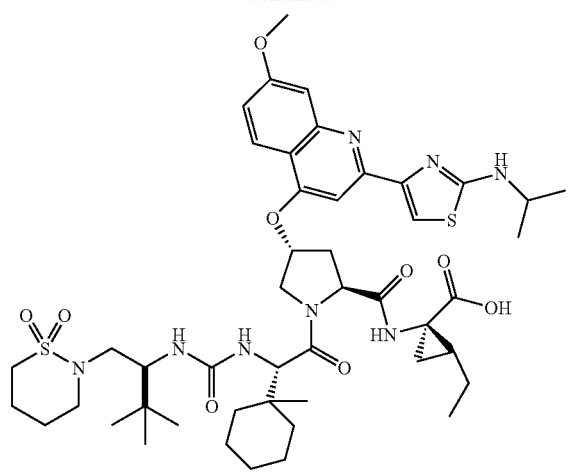
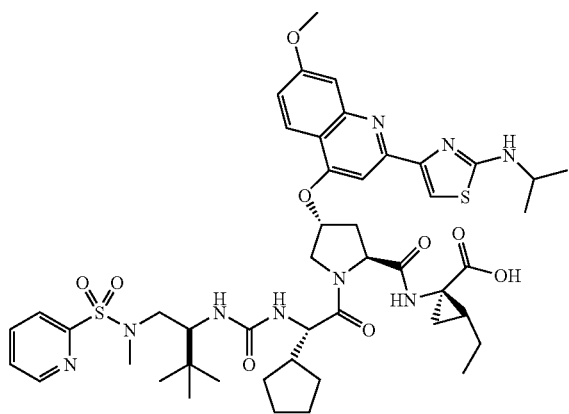
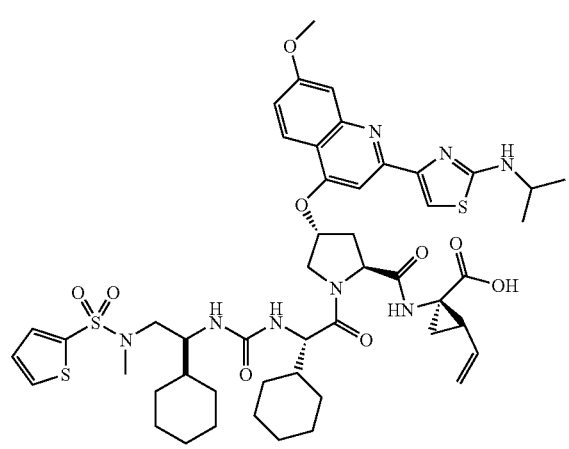
270
-continued
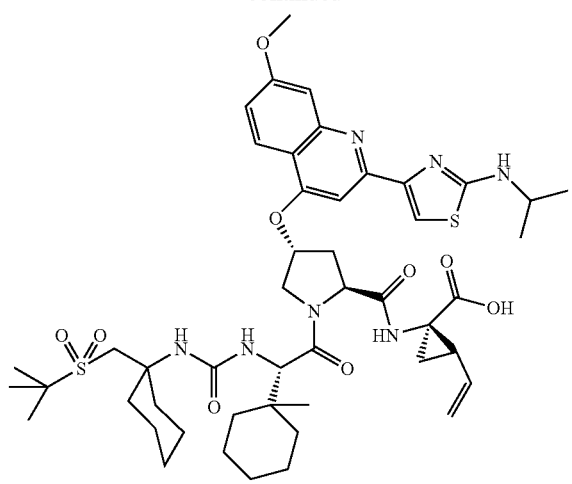
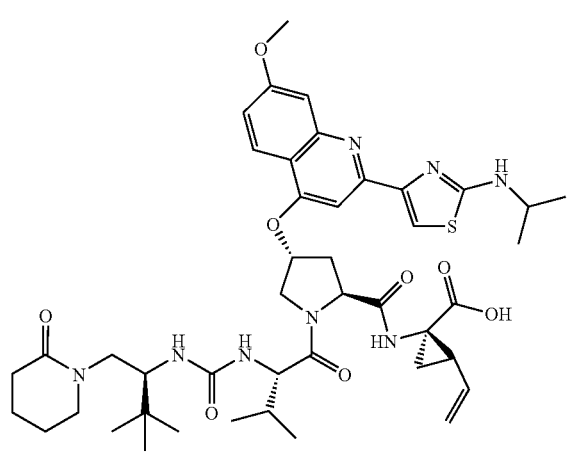
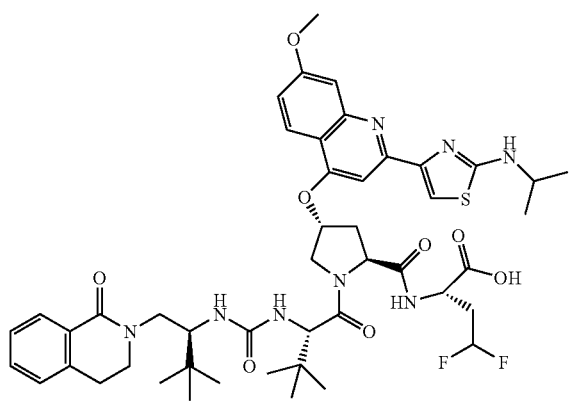

271
-continued
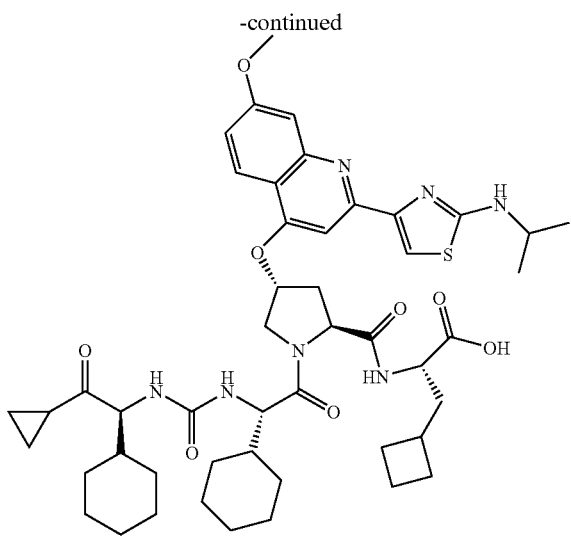
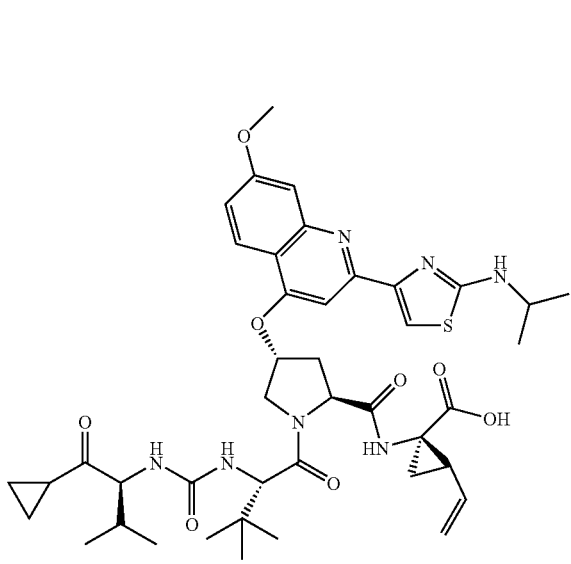
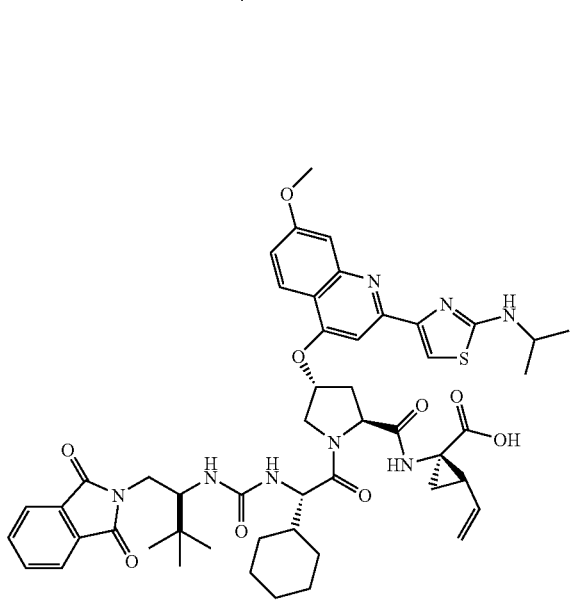
272
-continued
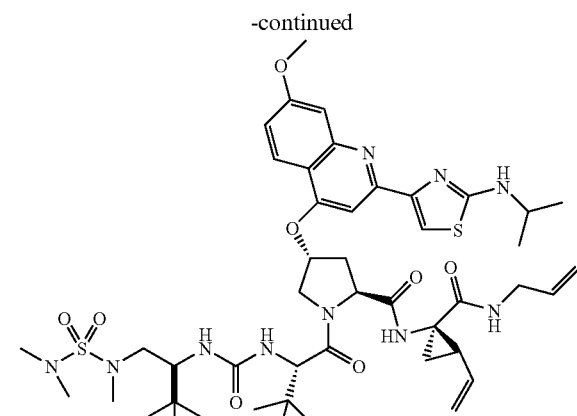
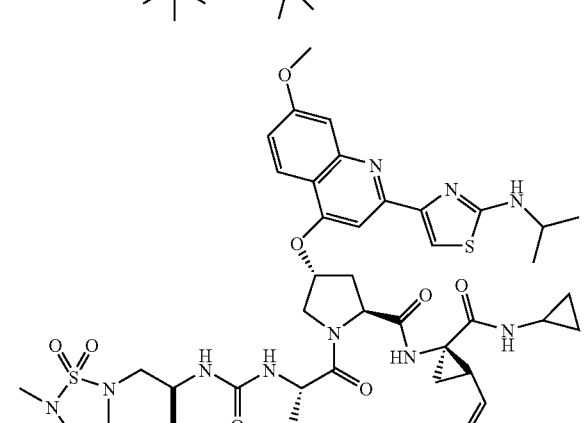
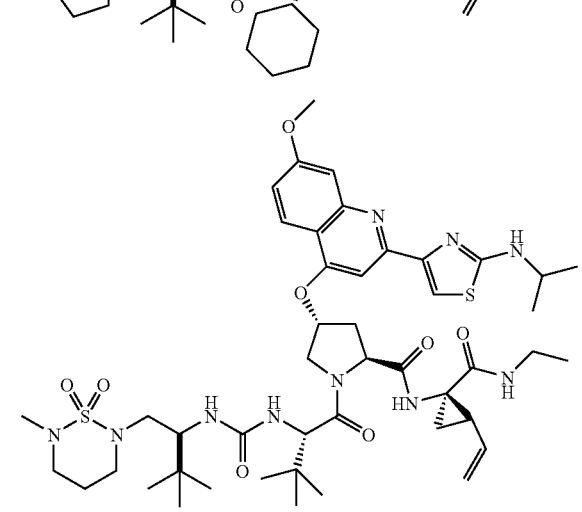
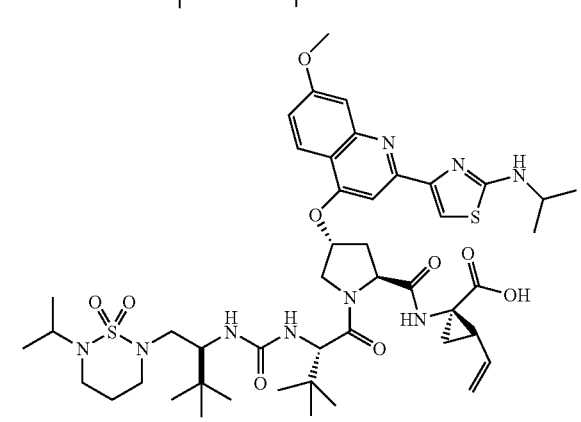

273
-continued
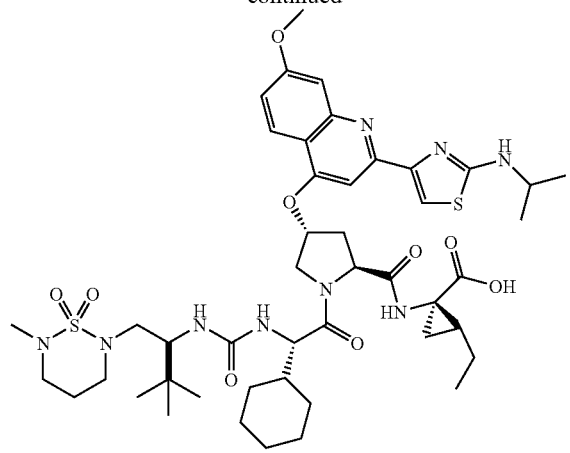
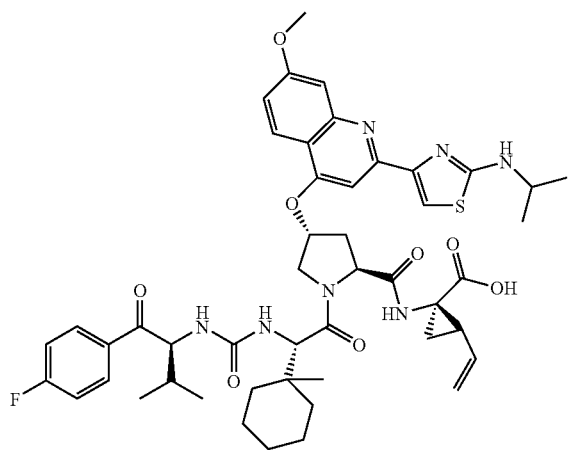
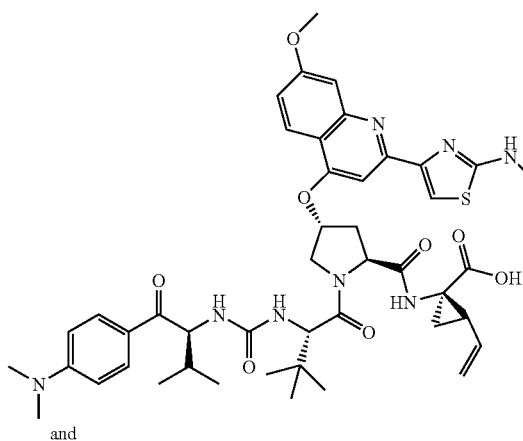
and
274
-continued
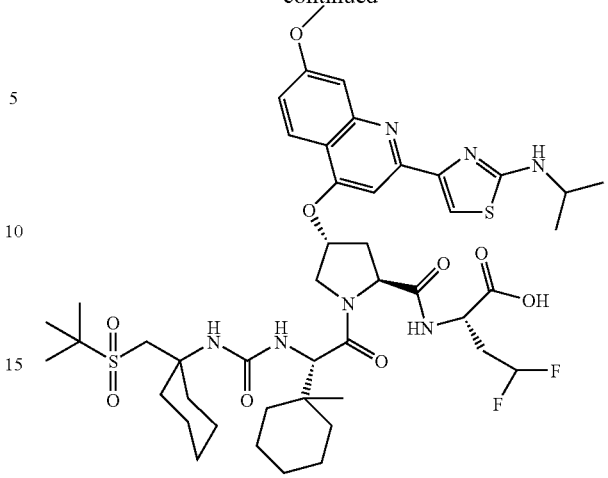
or a pharmaceutically acceptable salt, solvate or ester thereof.
Nonlimiting examples of certain compounds of formula IX disclosed in U.S. patent application Ser. No. 10/993,394 are:
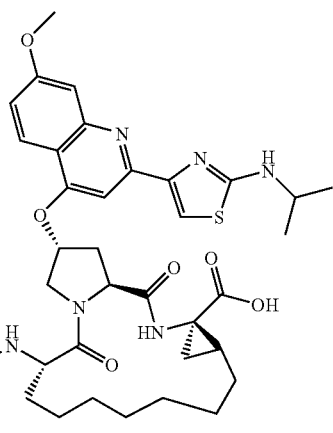
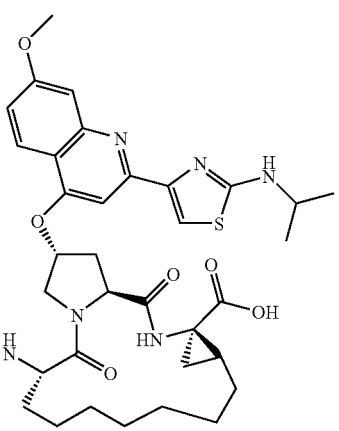

275
-continued
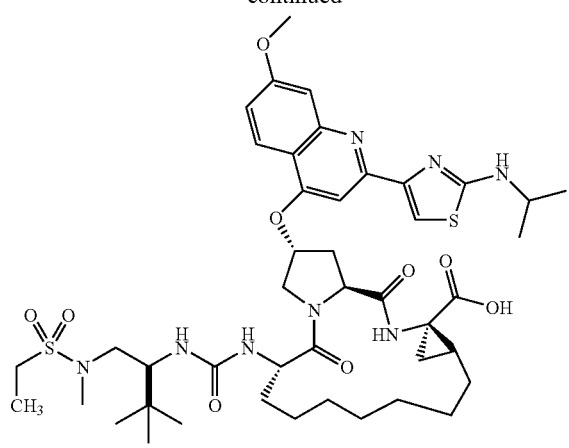
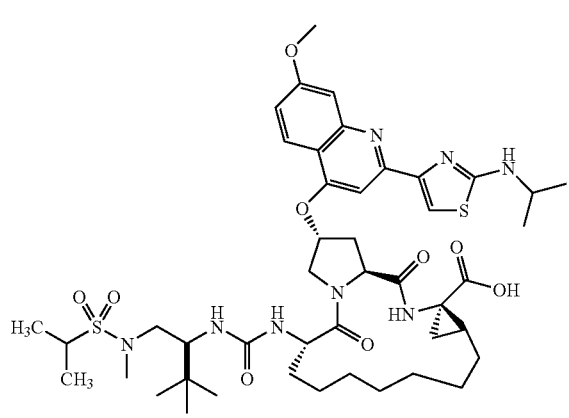
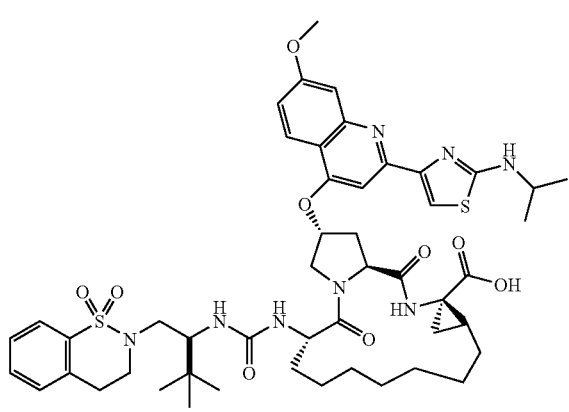
276
-continued
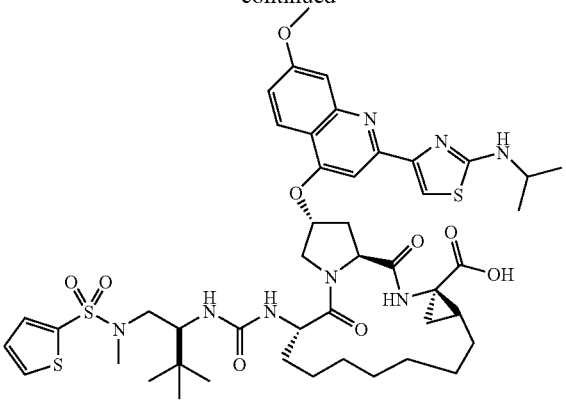
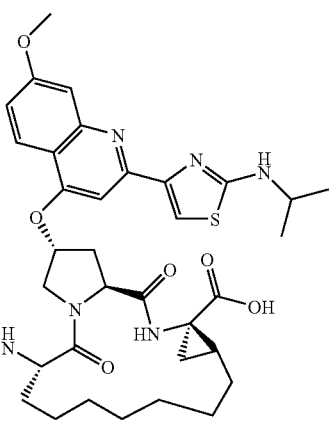
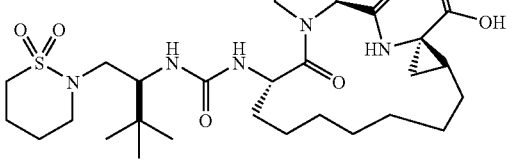
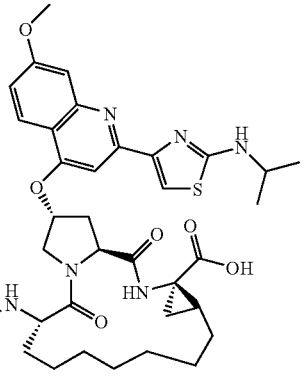
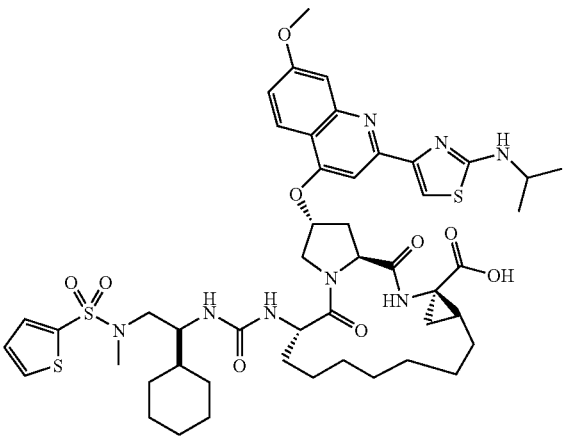

277
-continued
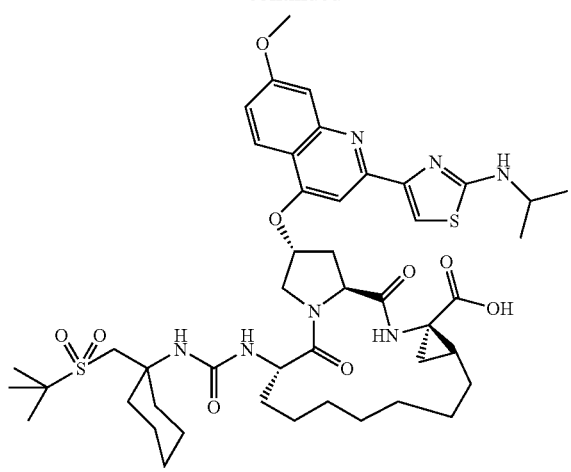
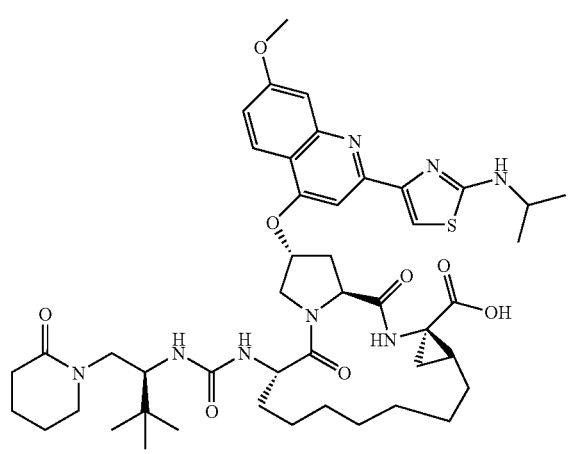
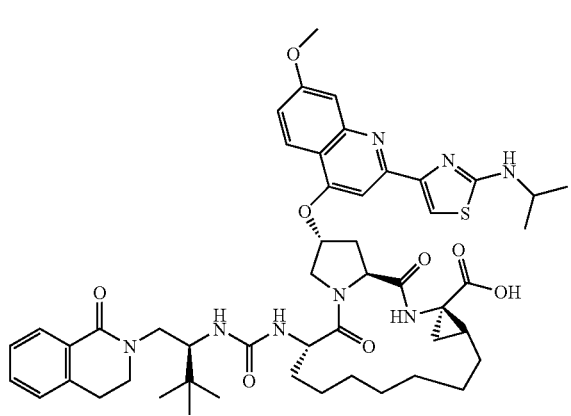
278
-continued
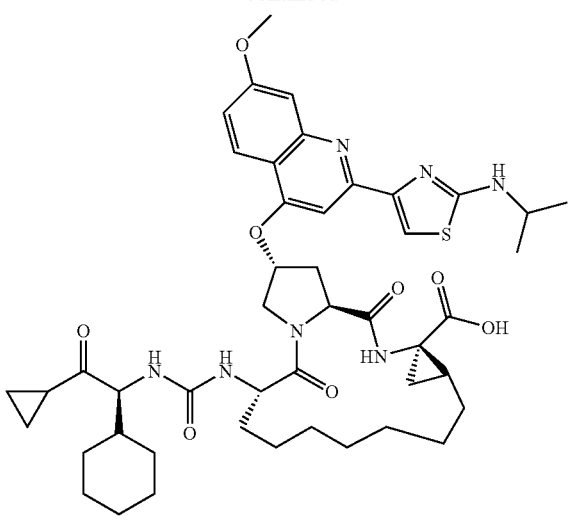
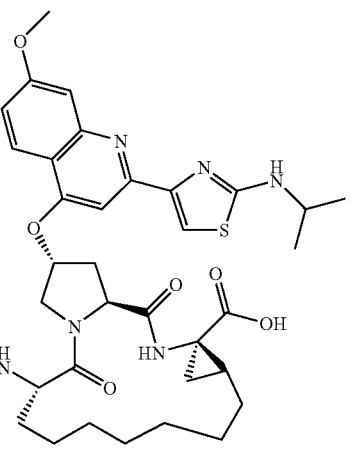
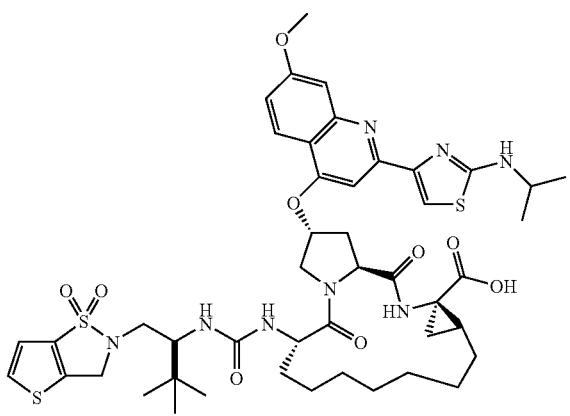

279
-continued
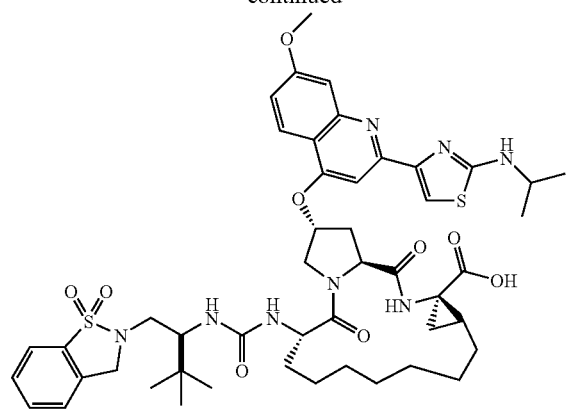
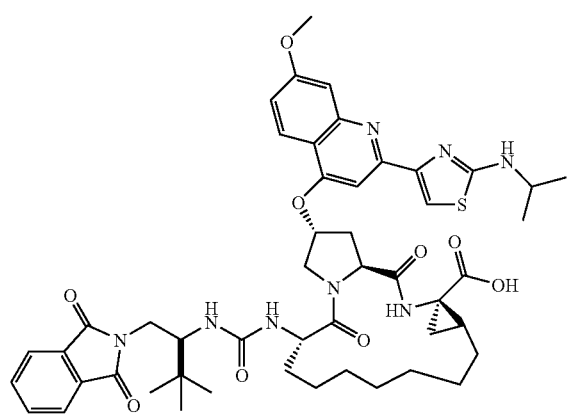
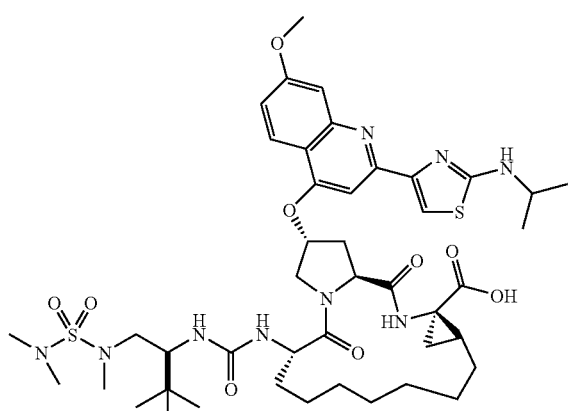
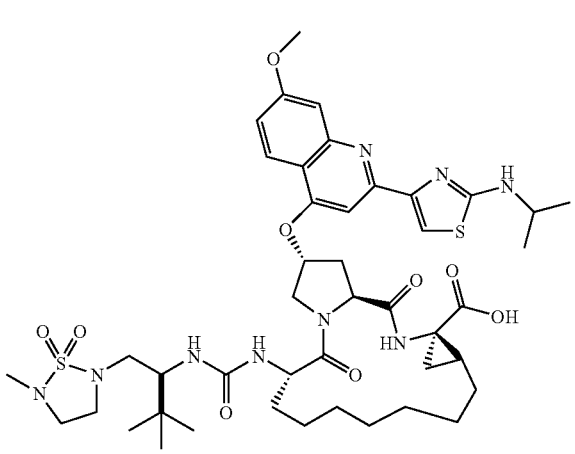
280
-continued
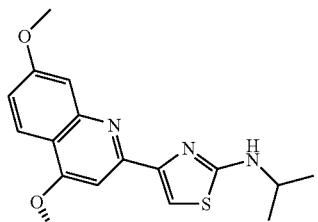
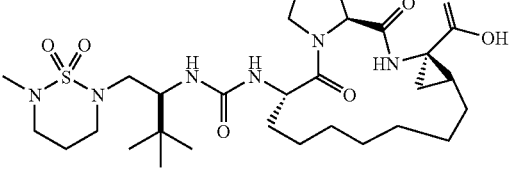
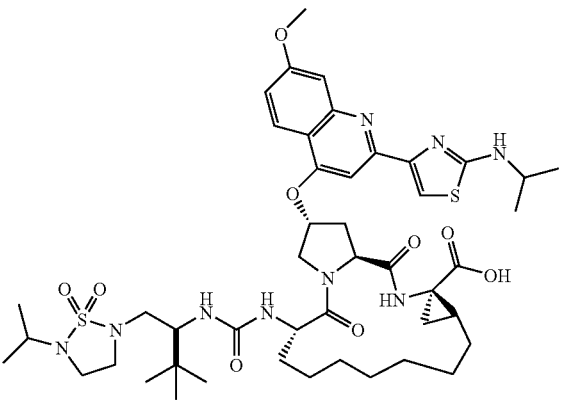
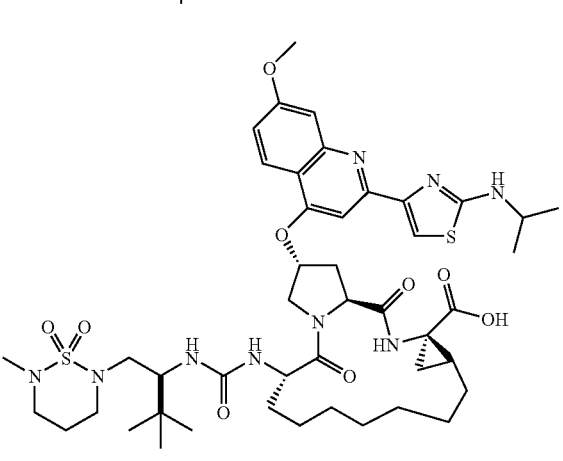

281
-continued
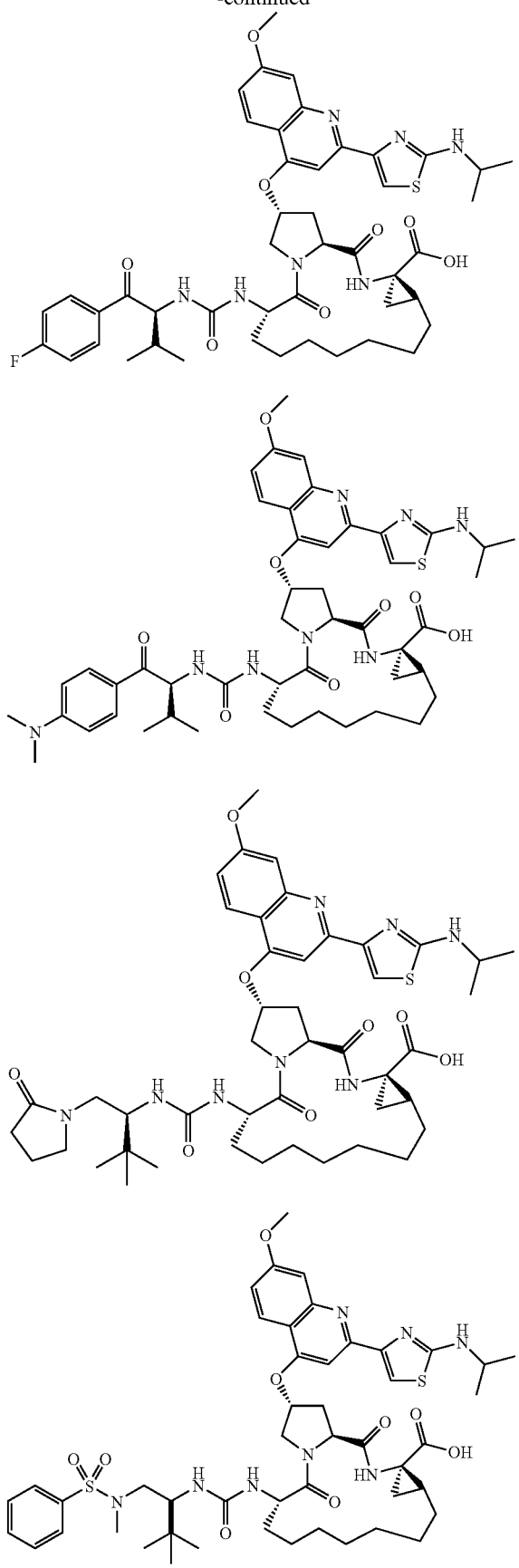
282
-continued
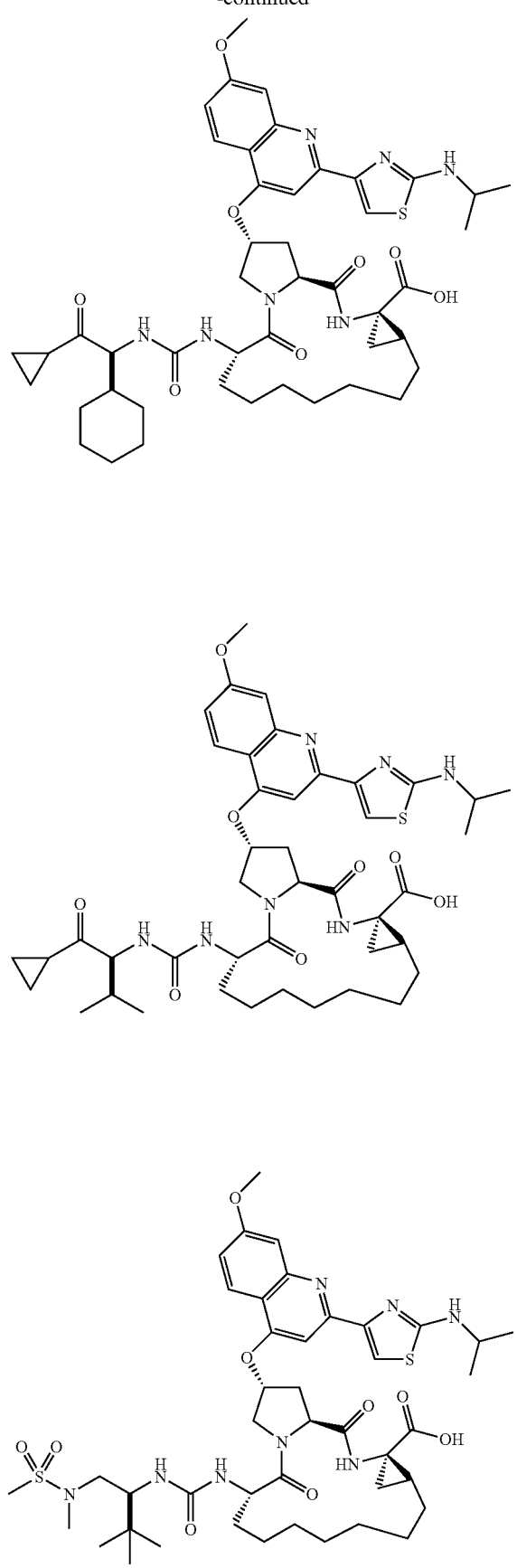

283
-continued
284
-continued
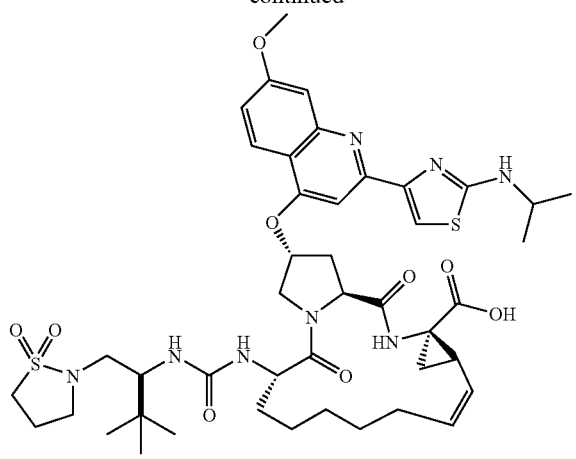
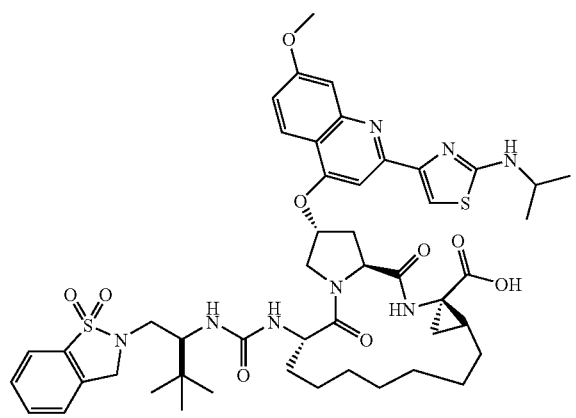
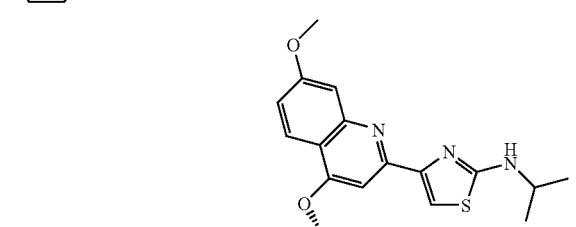
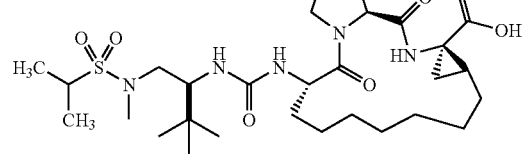
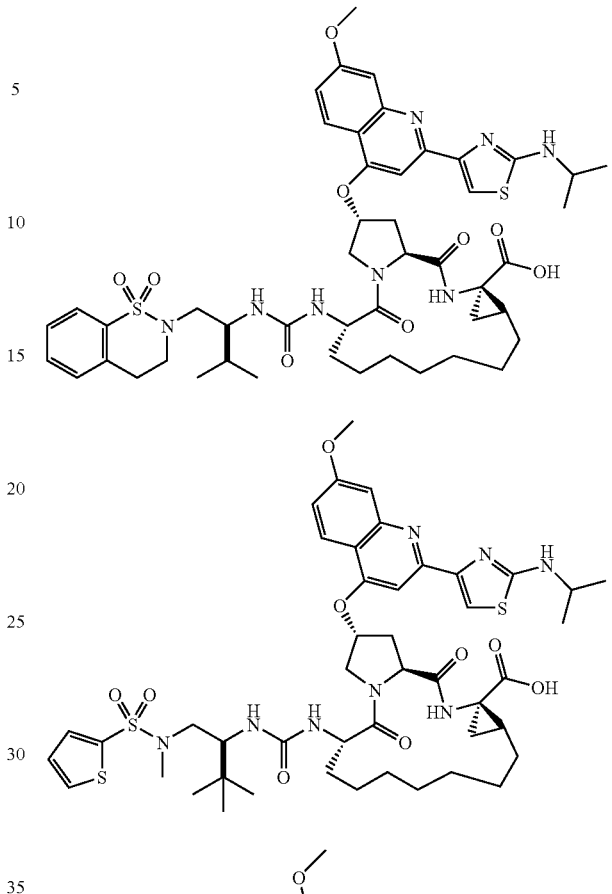
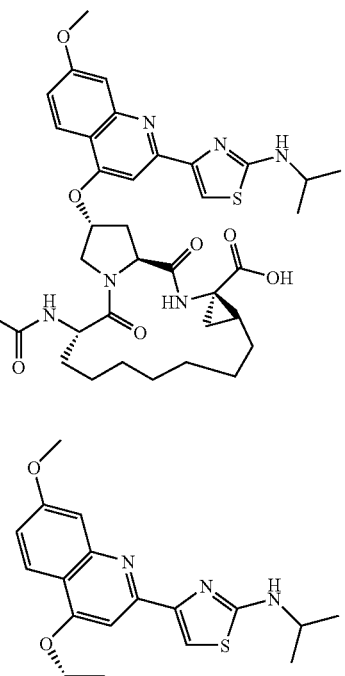
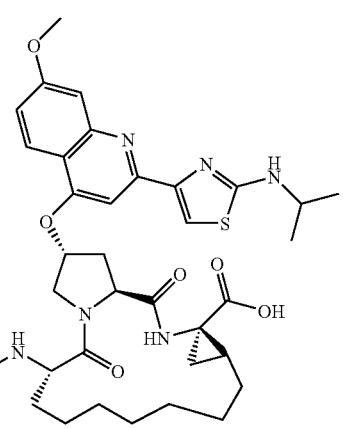
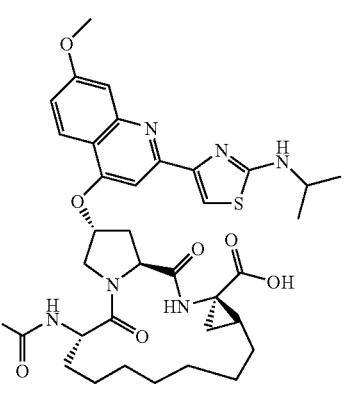

285
-continued
286
-continued
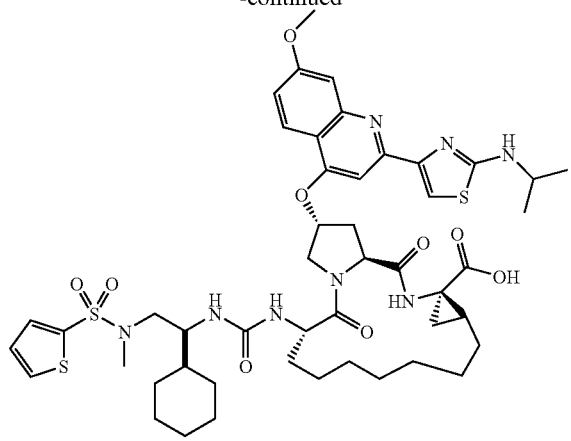
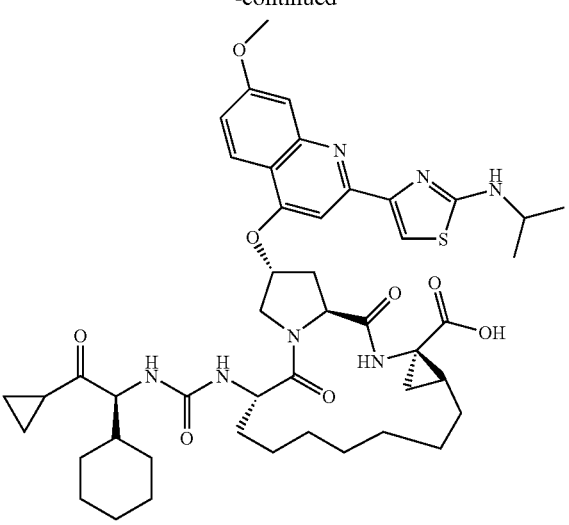
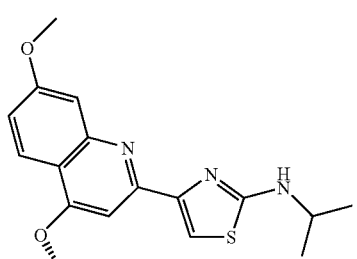
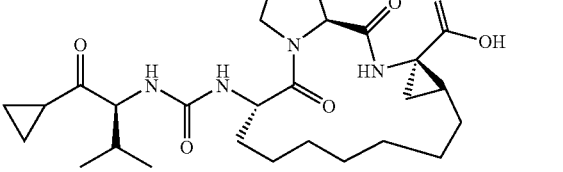
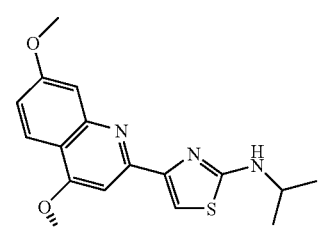
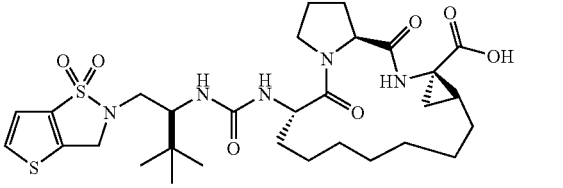

287
-continued
288
-continued
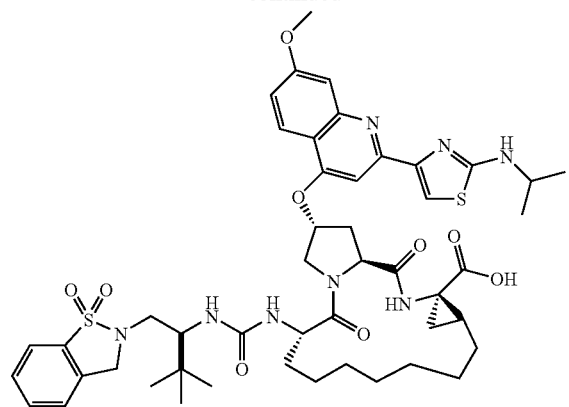
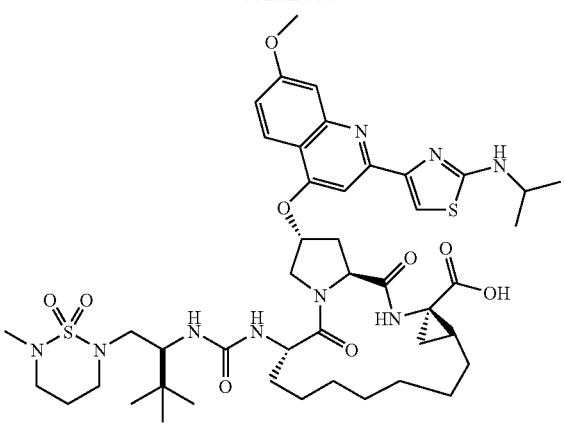

289
-continued
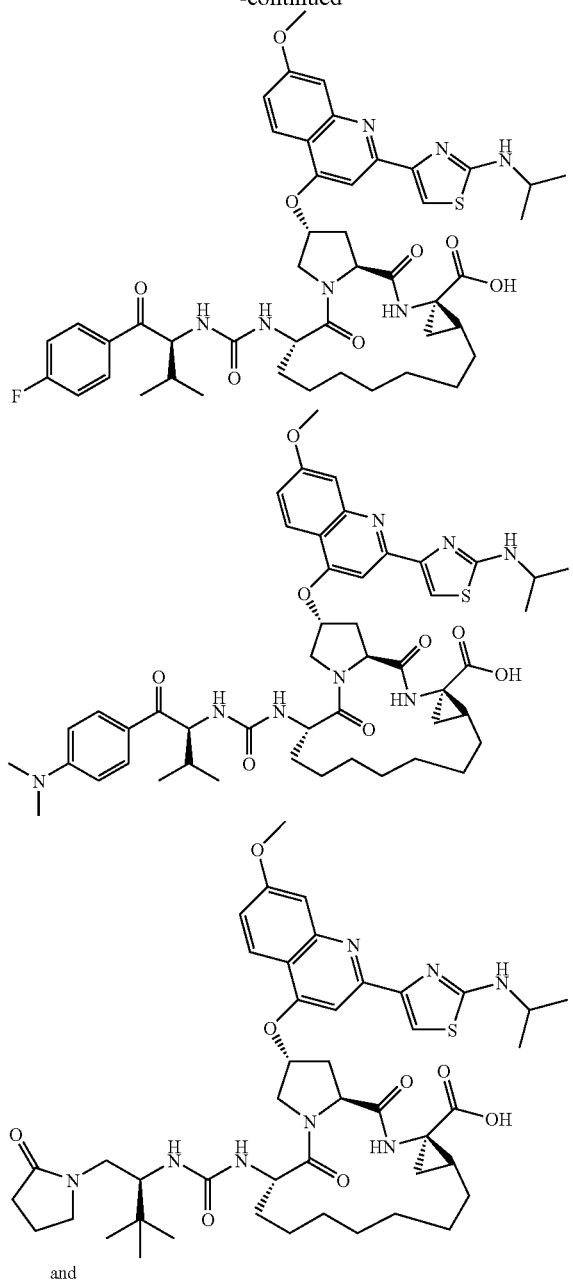
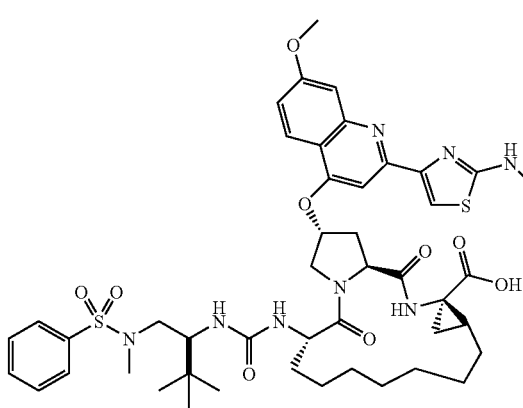
or a pharmaceutically acceptable salt, solvate or ester thereof.
Compounds of formula X are disclosed in U.S. patent application Ser. No. 11/065,572 filed Feb. 24, 2005 and the preparation of the compounds are detailed in the experimental section of this application set forth hereinbelow.
Non-limiting examples of certain compounds disclosed in U.S. patent application Ser. No. 11/065,572 filed Feb. 24, 2005 are:
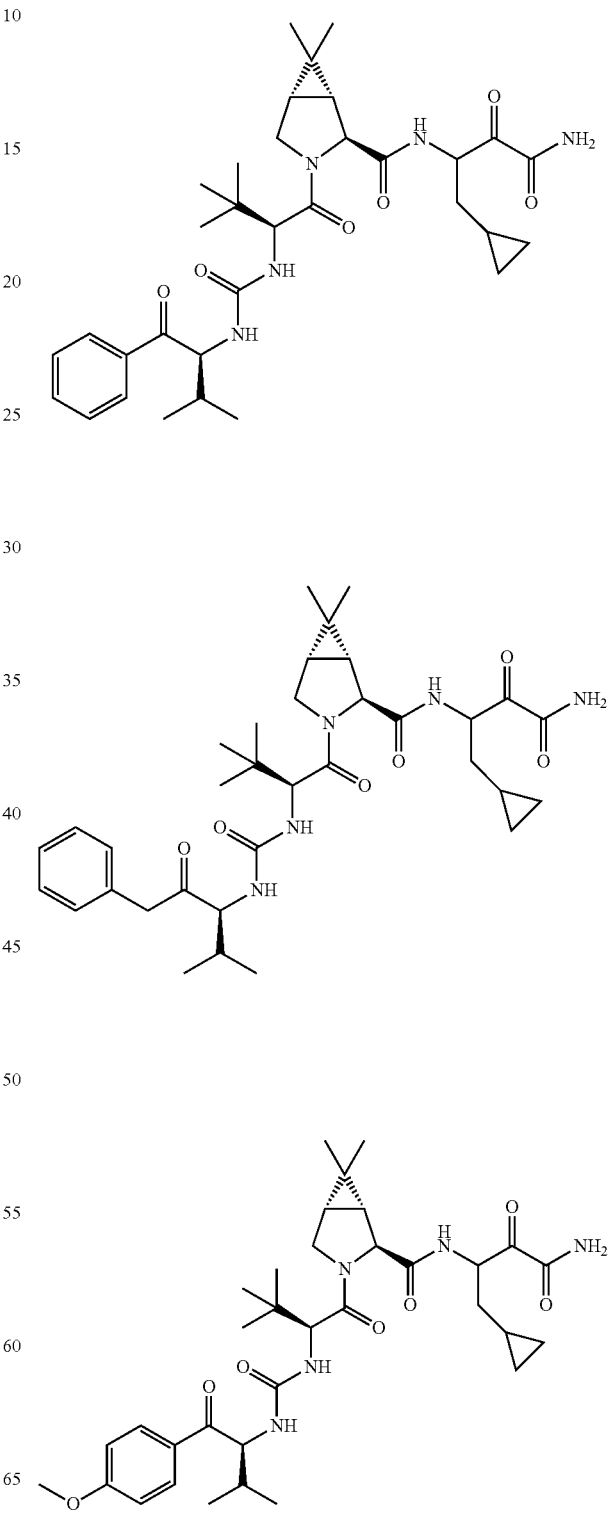

291
-continued
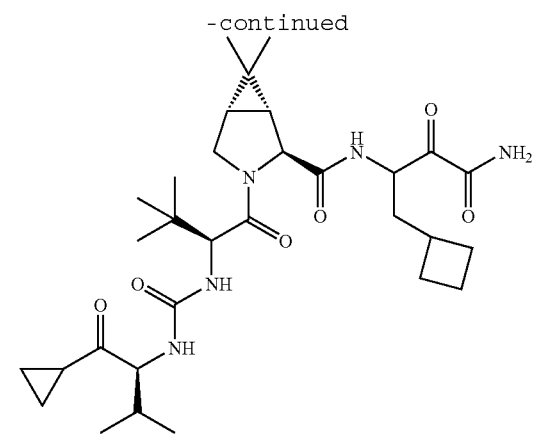
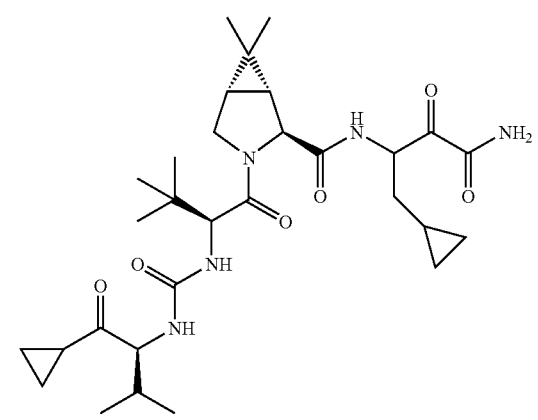
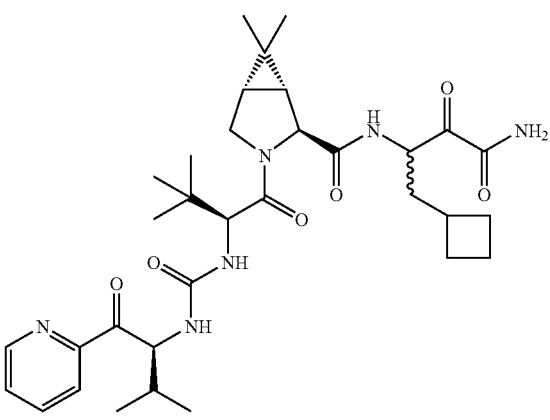

292
-continued
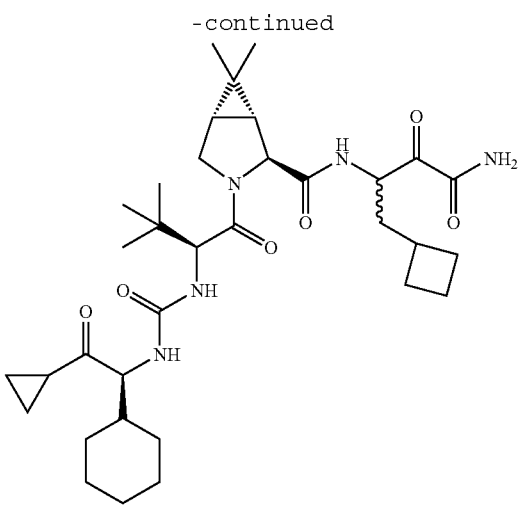

293
-continued
294
-continued
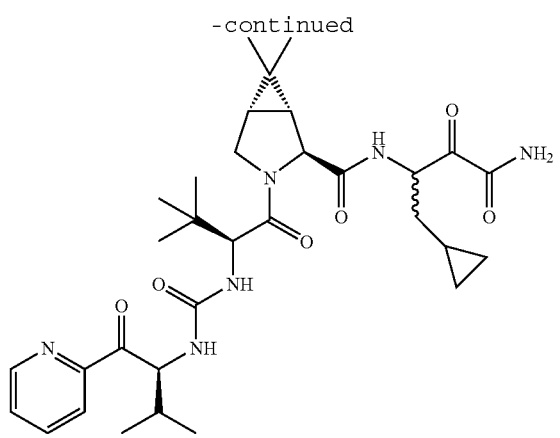
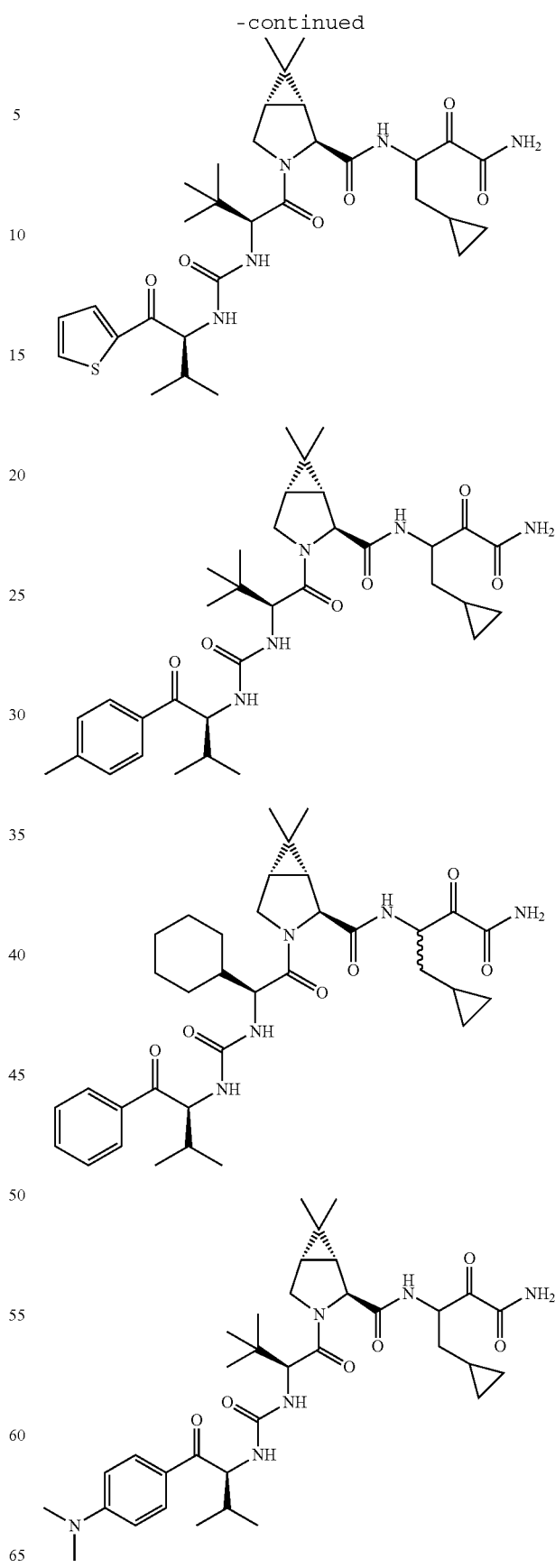

295
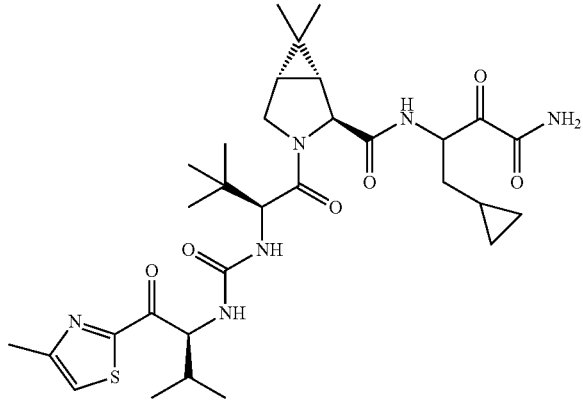
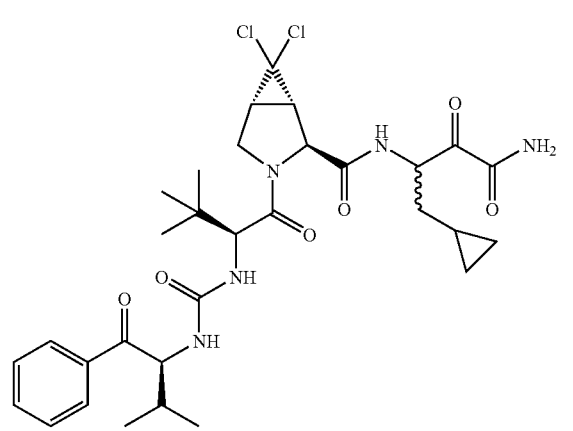
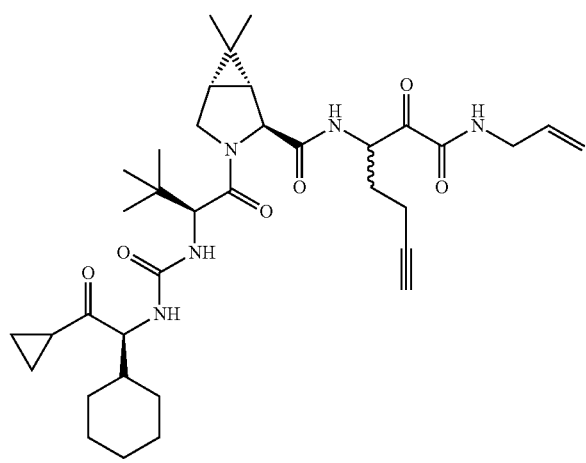
296
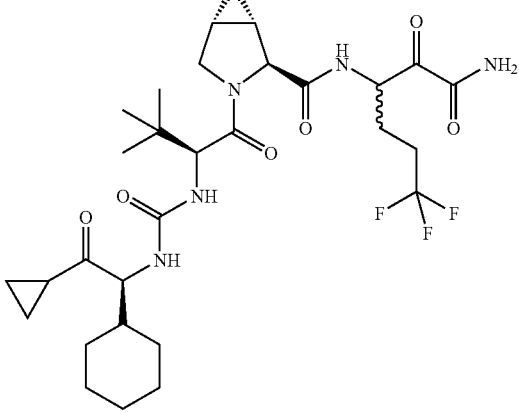
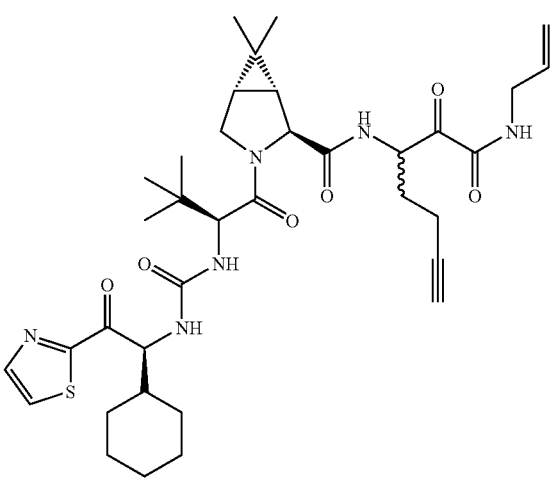
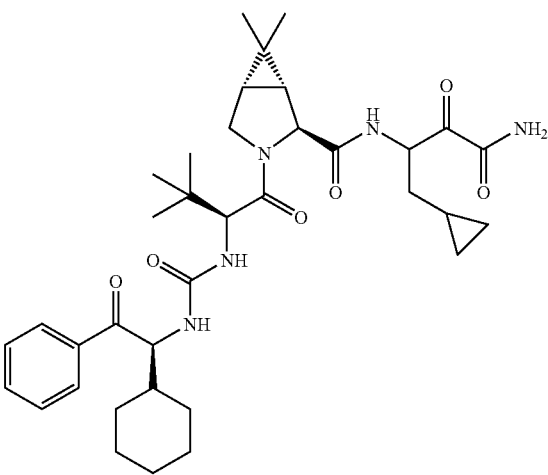

297
-continued
298
-continued
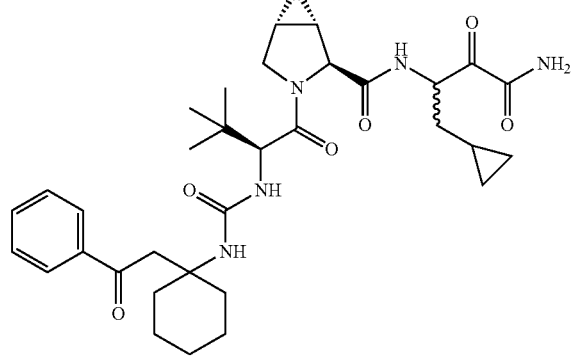
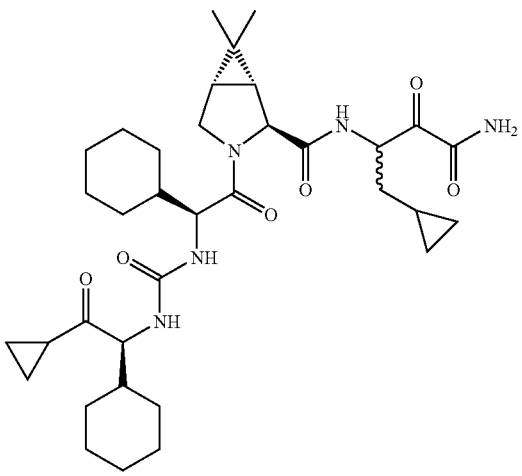
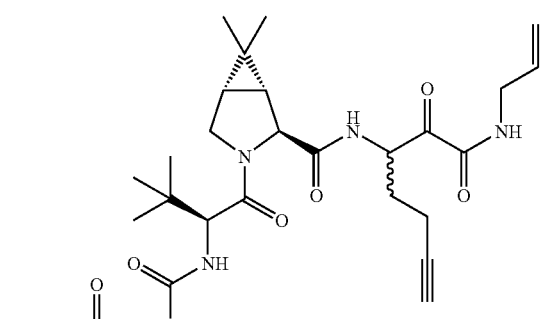
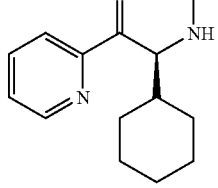
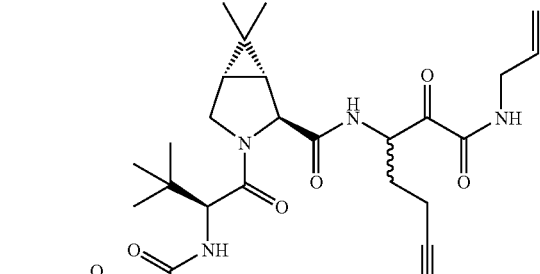
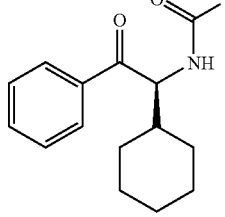

299
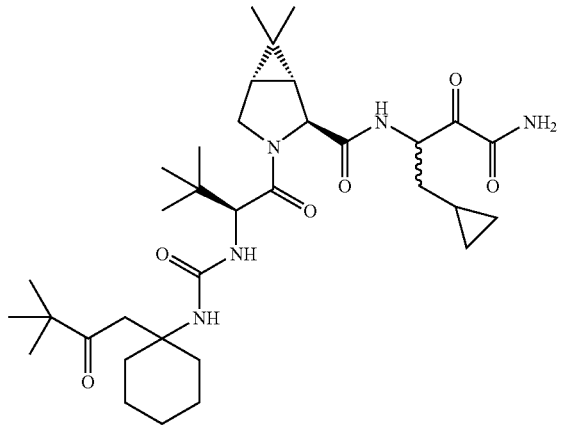
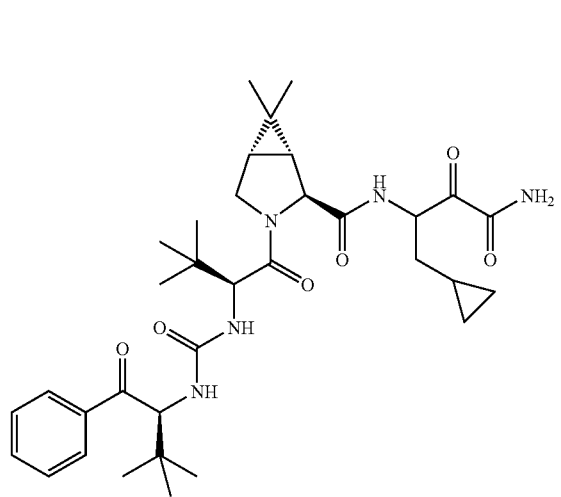
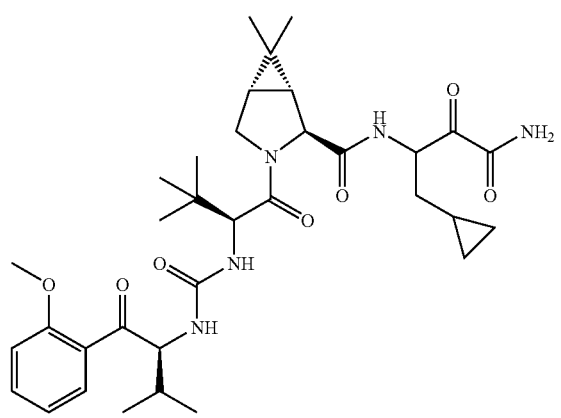
300
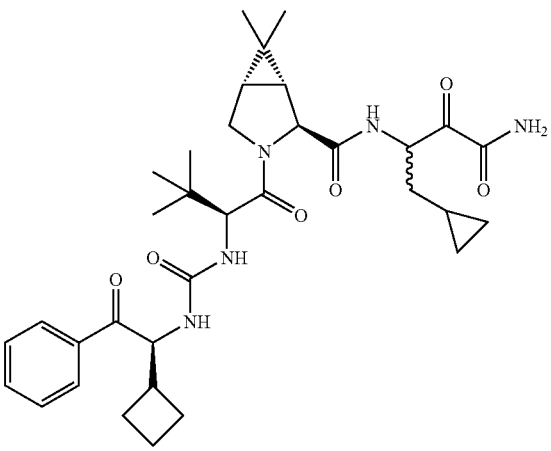
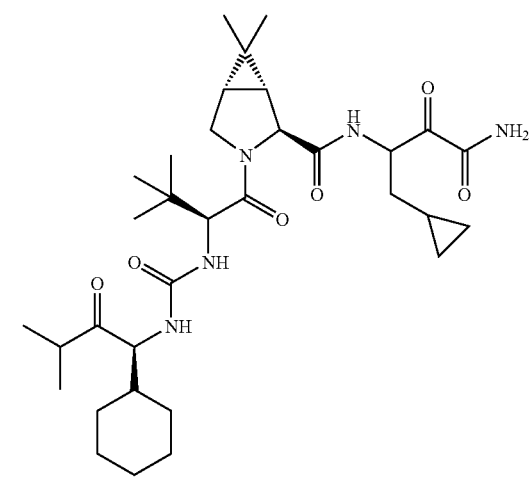
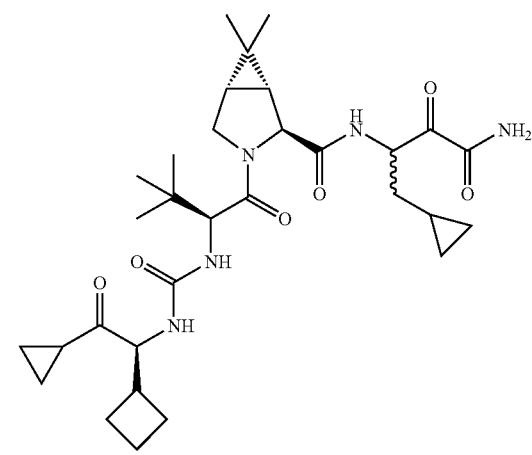

-continued
301
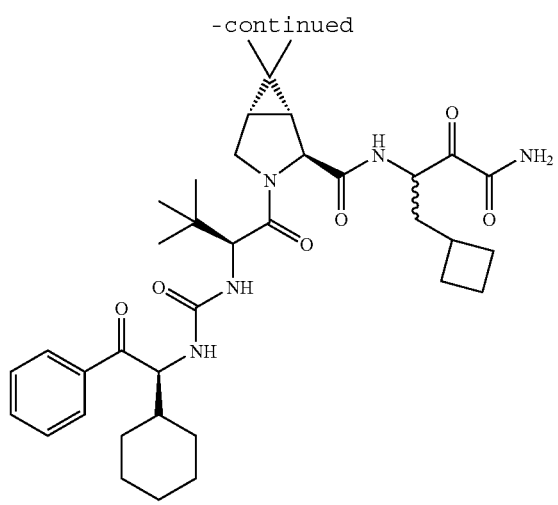
302
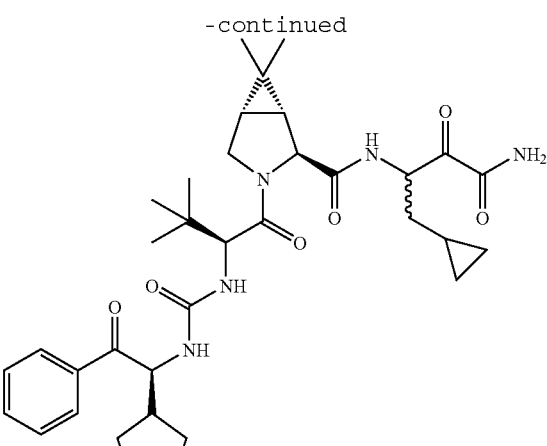
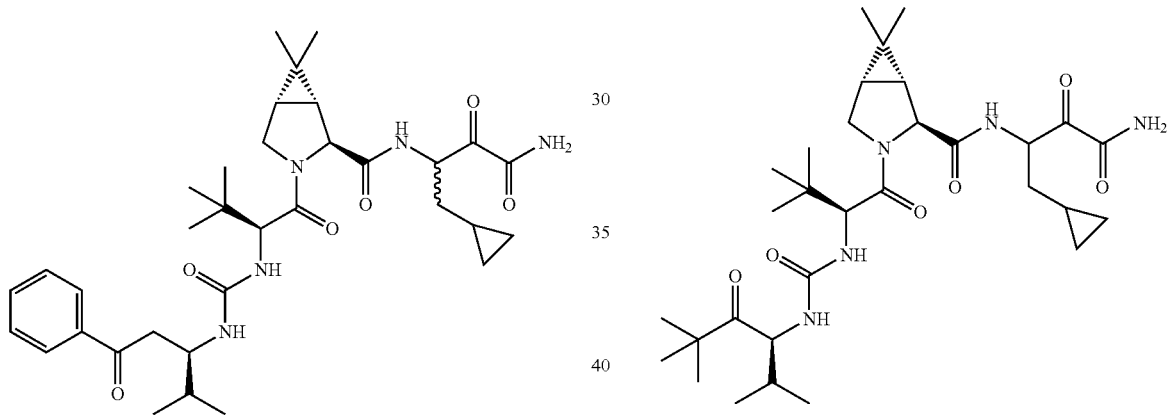
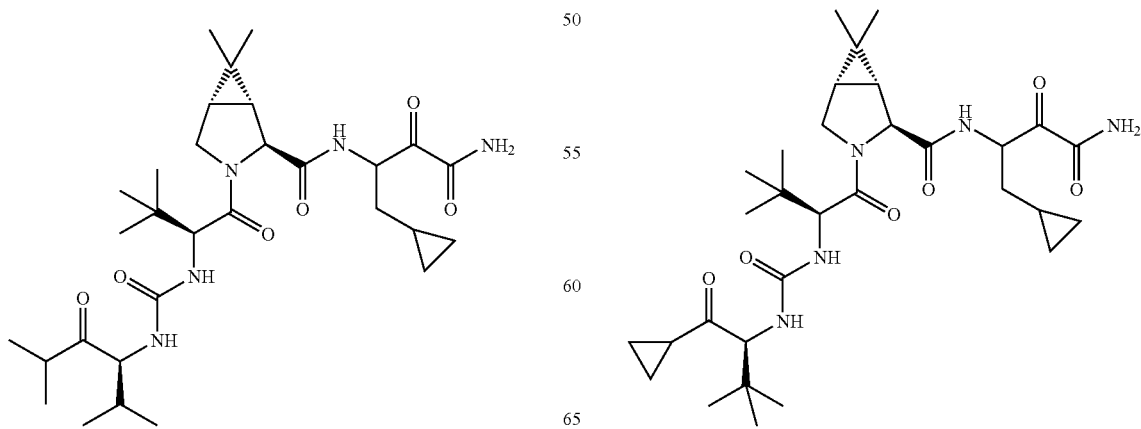

303                                    304
-continued                          -continued
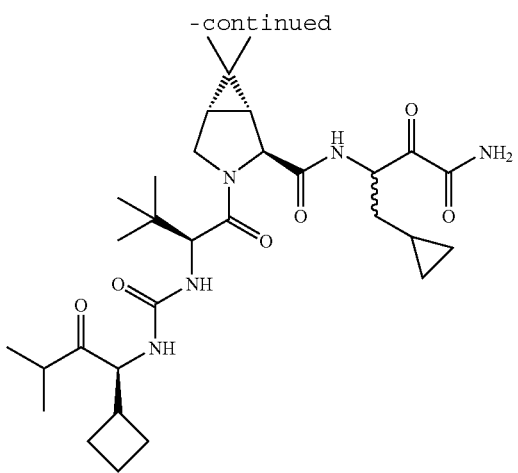
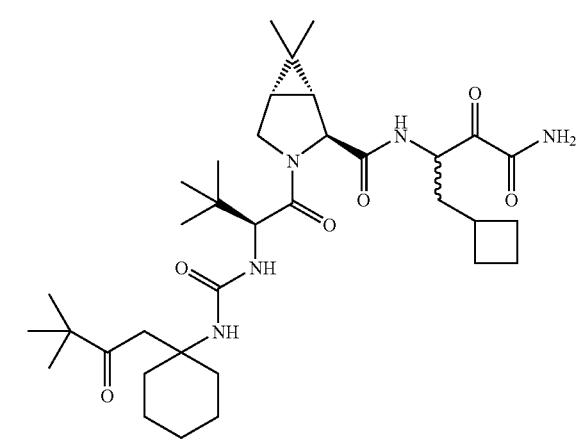
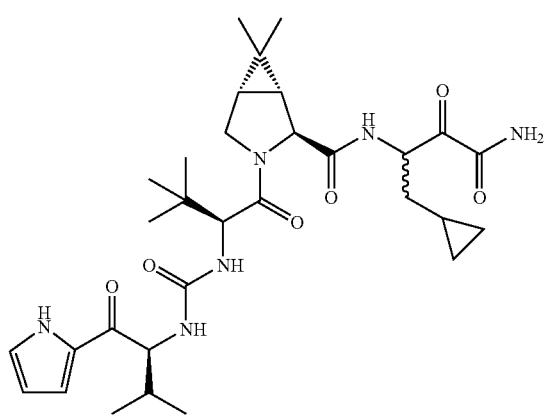
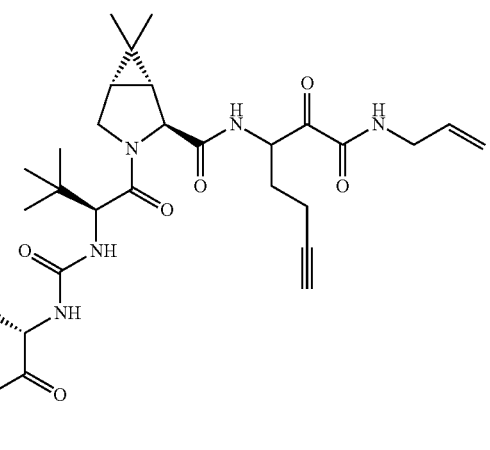
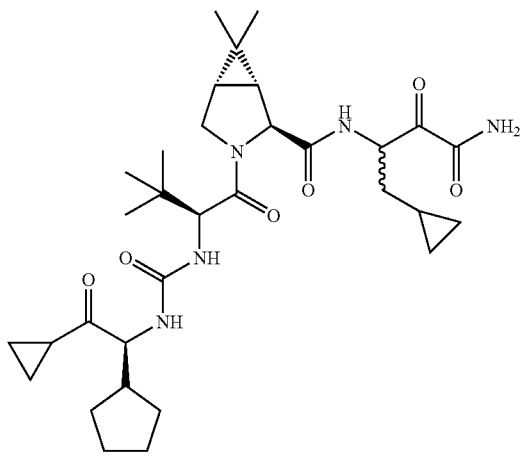
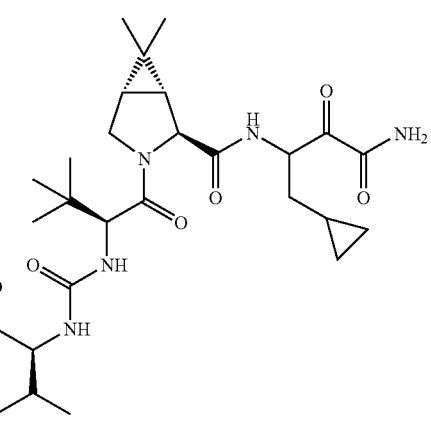

305
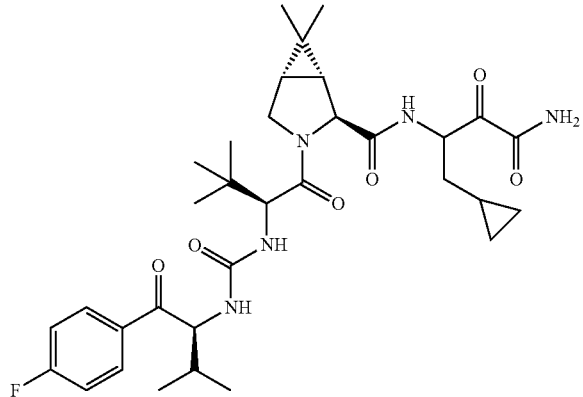
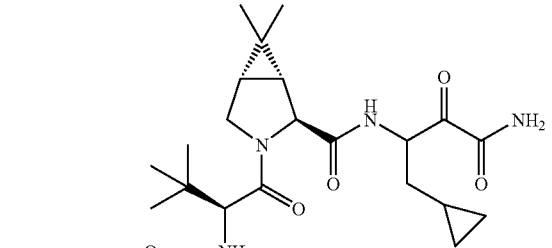
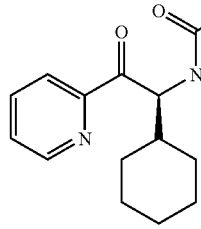
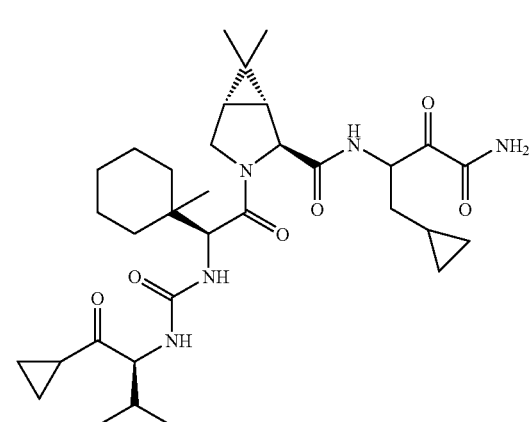
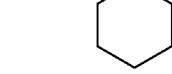
306
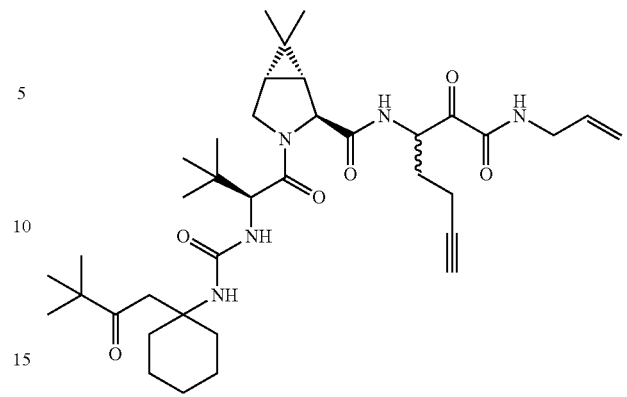
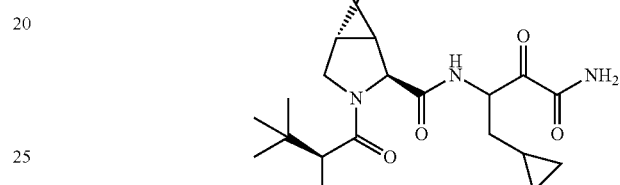
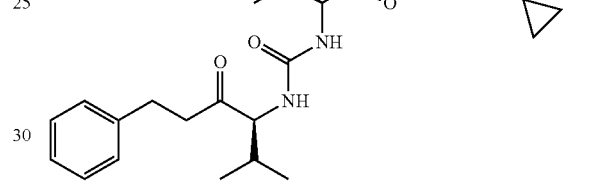
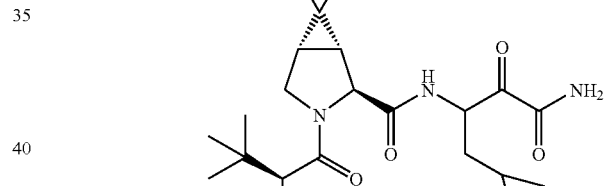
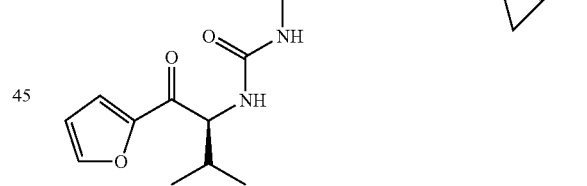
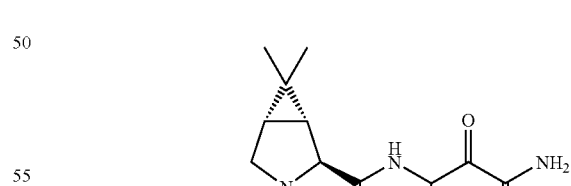

307                                   308
-continued                            -continued
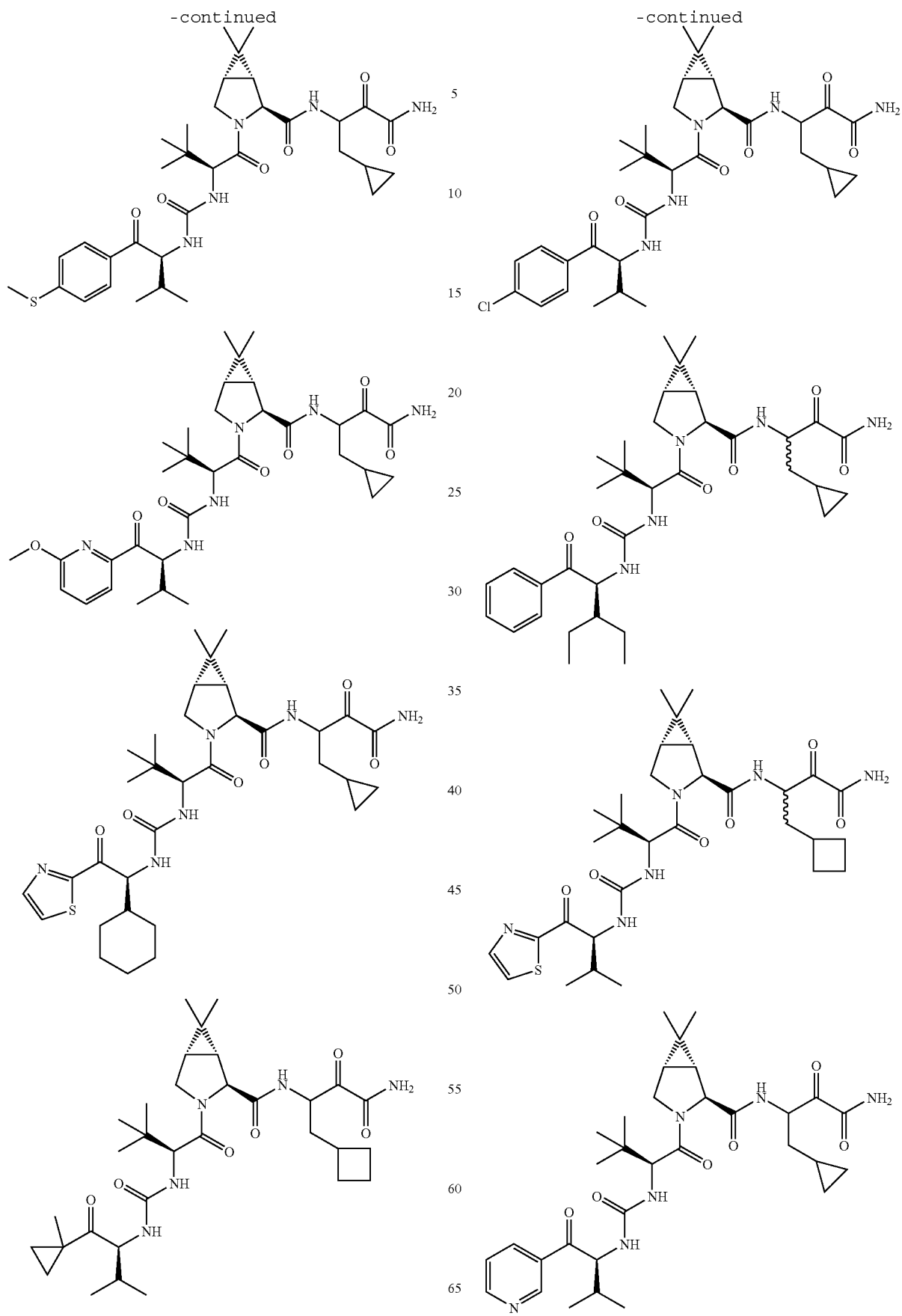

309
-continued
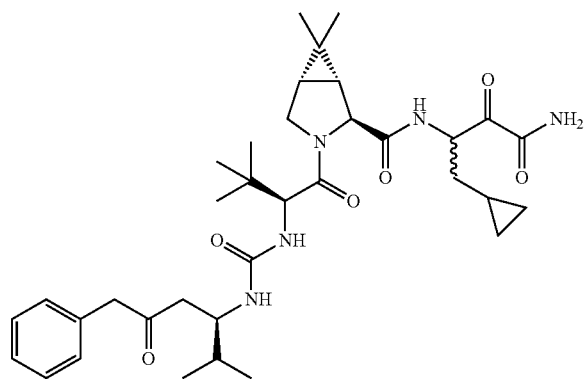
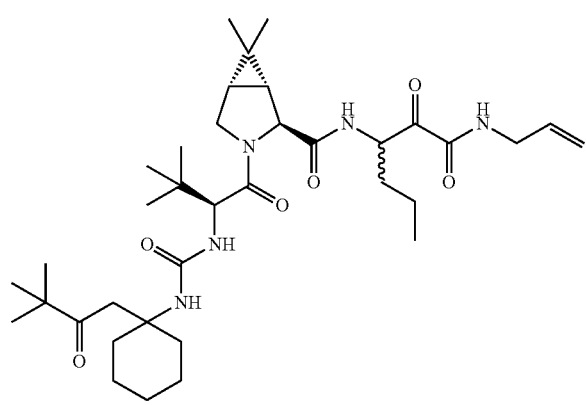
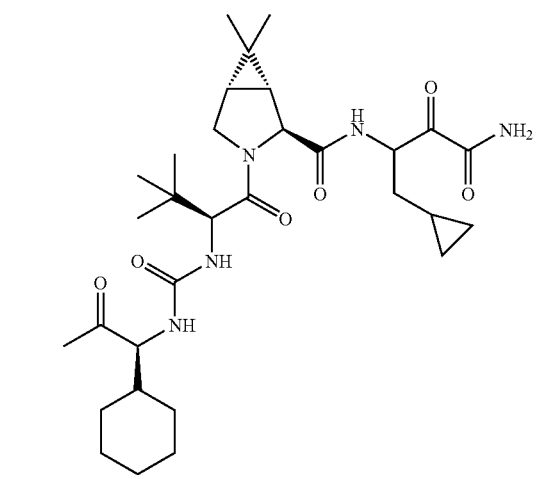
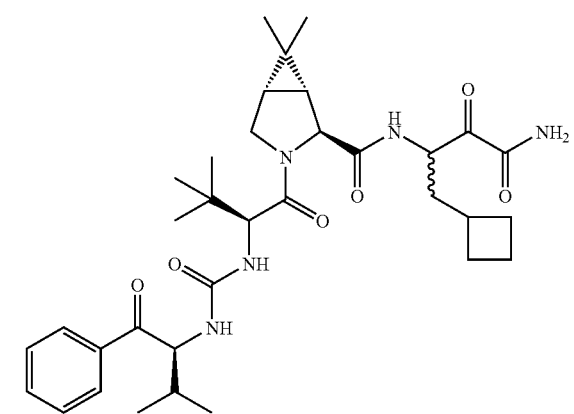
310
-continued
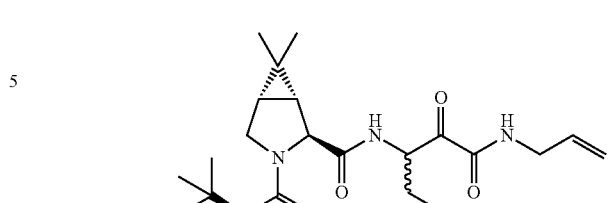
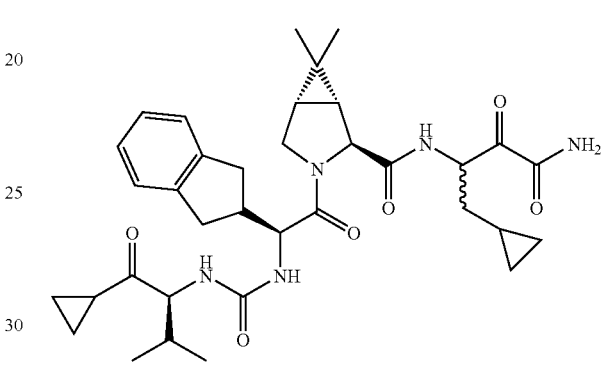
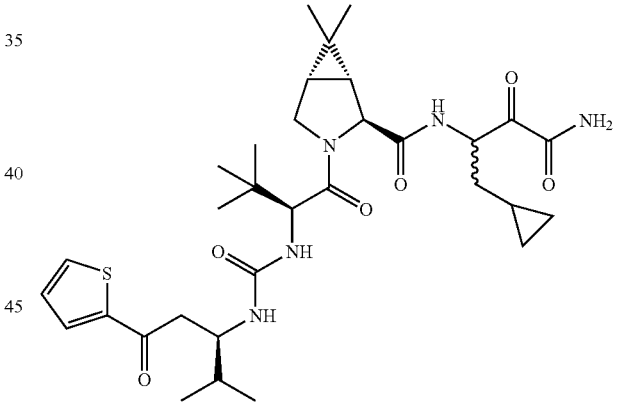
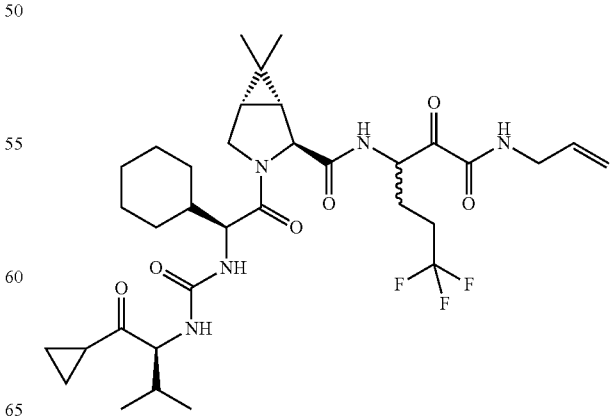

311                                     312
-continued                              -continued
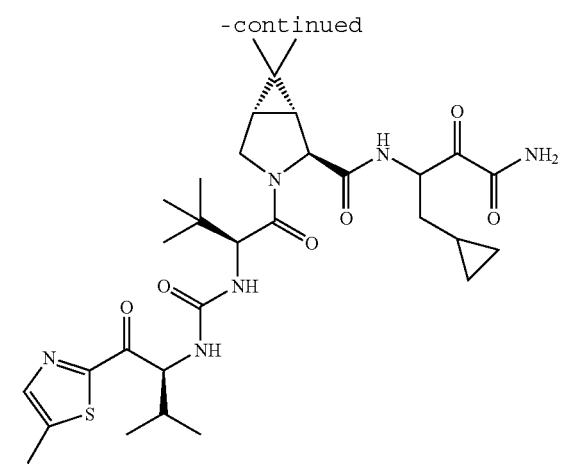
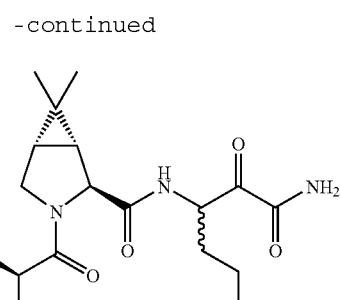
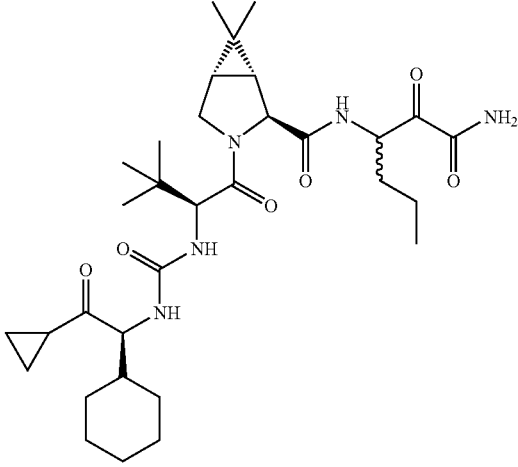
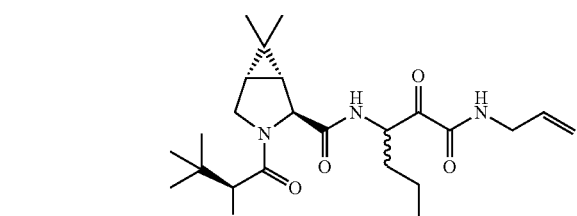
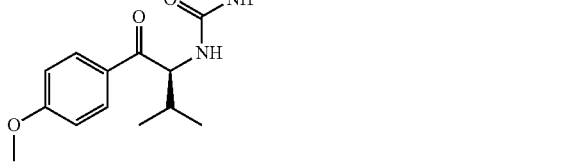
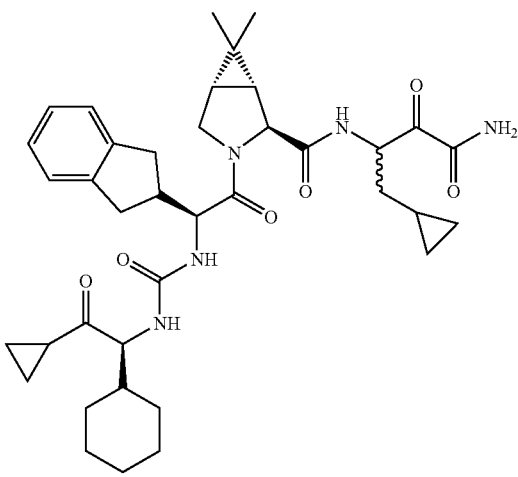
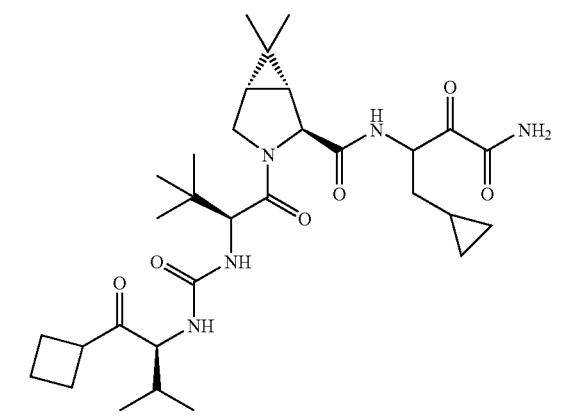
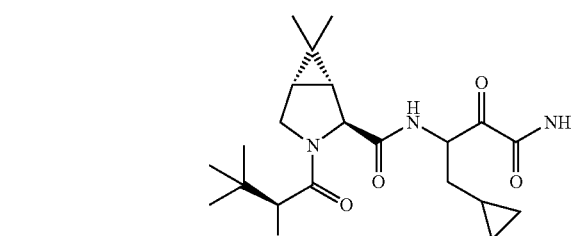
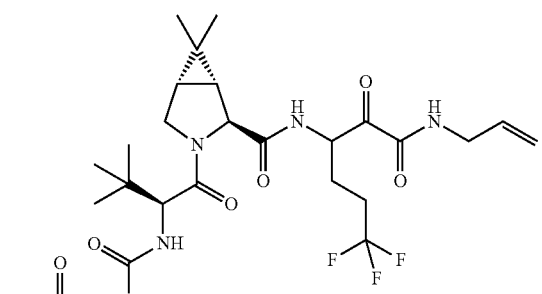
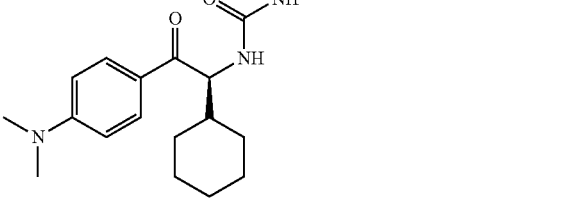

313
-continued
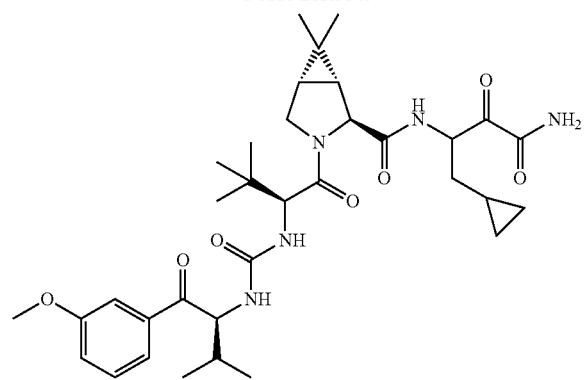
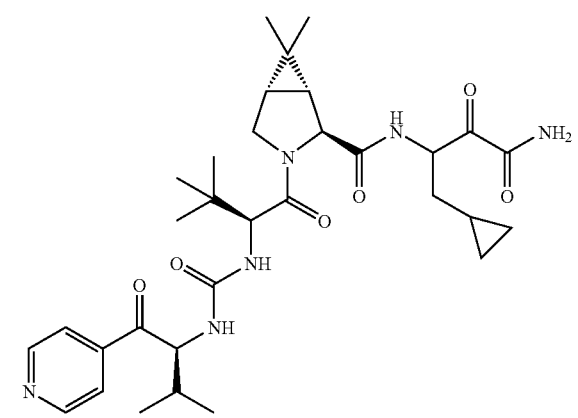
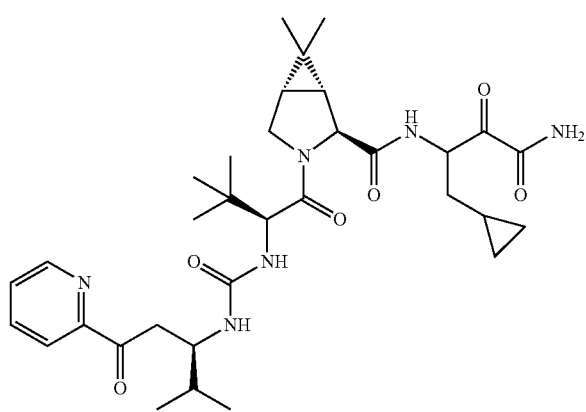
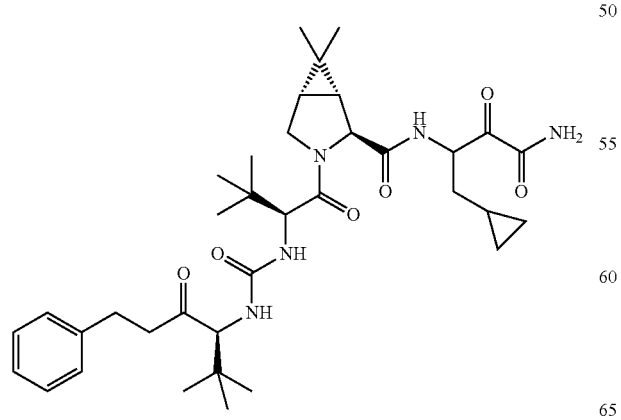
314
-continued
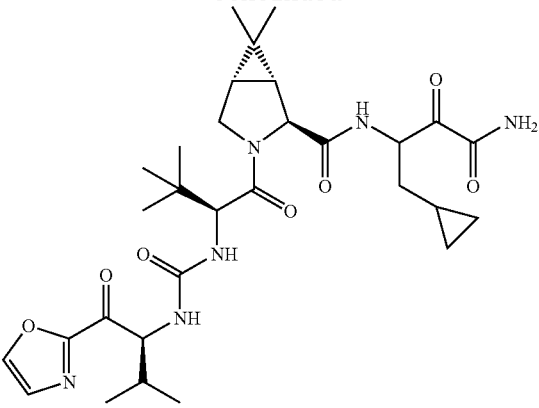
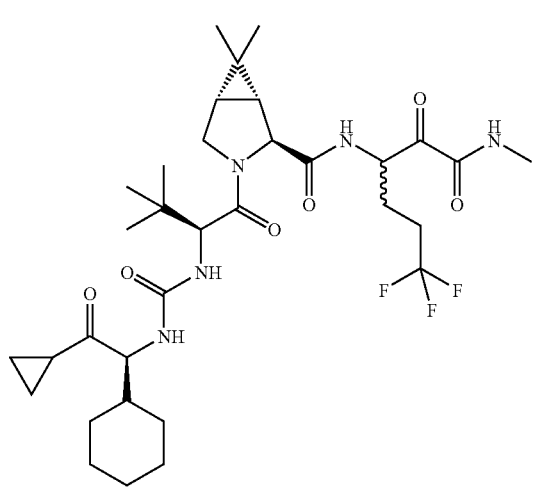
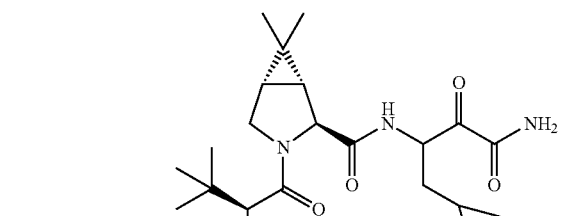
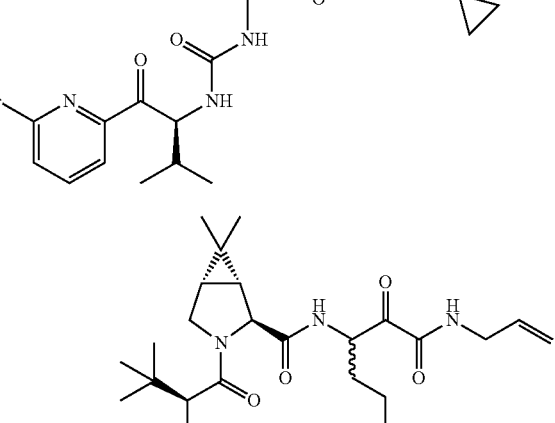
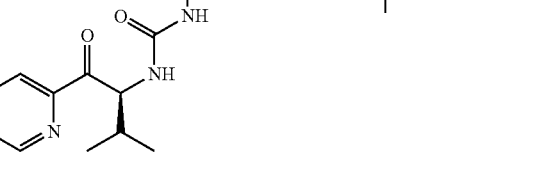

315
-continued
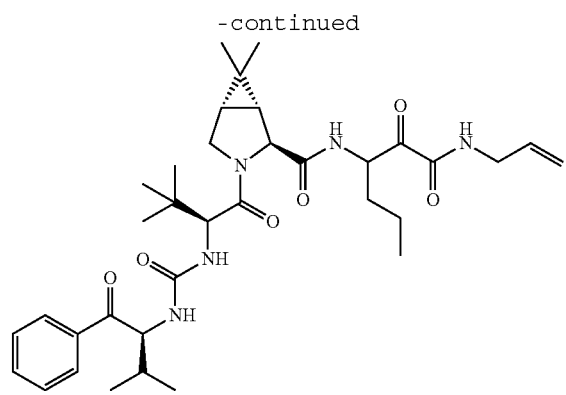
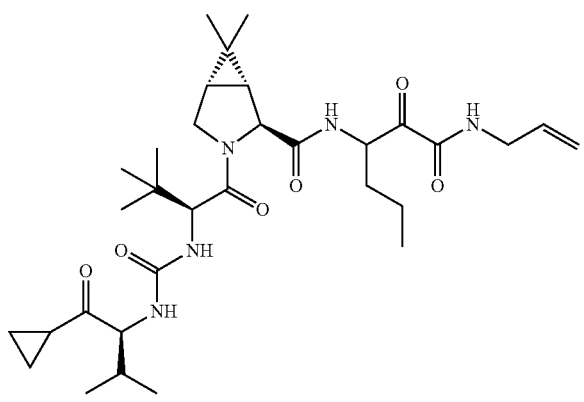
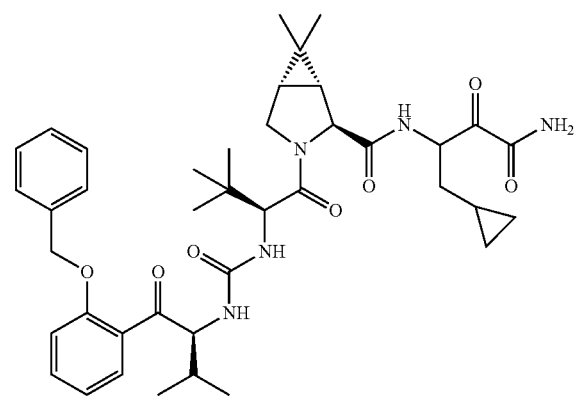
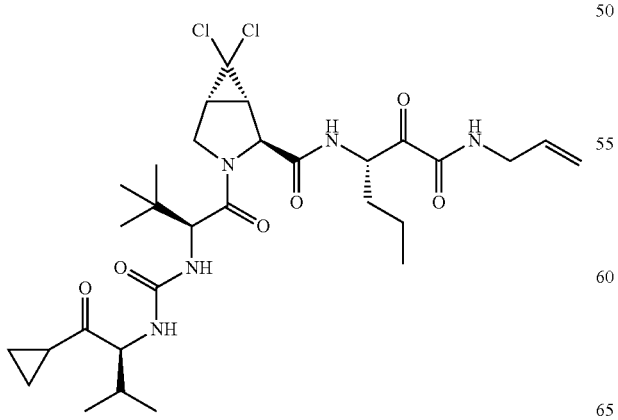
316
-continued
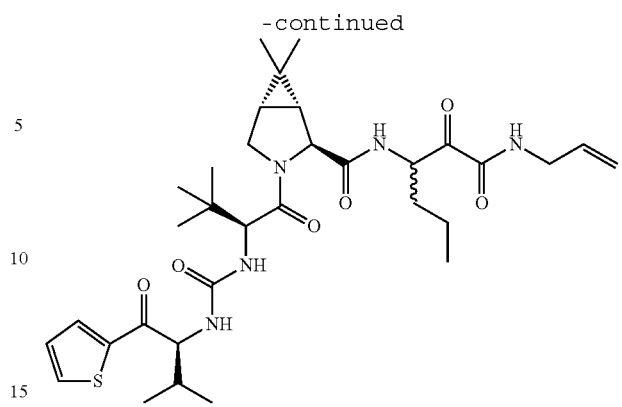
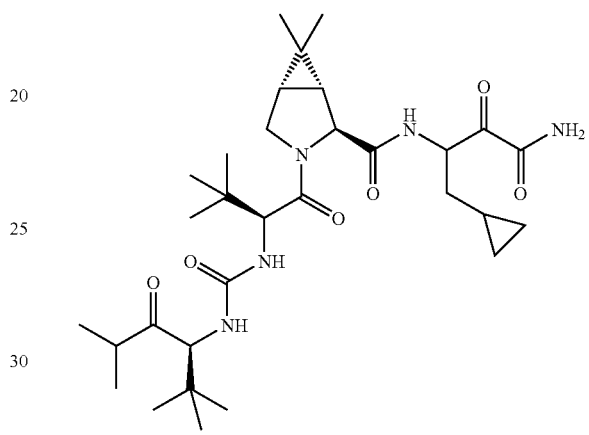
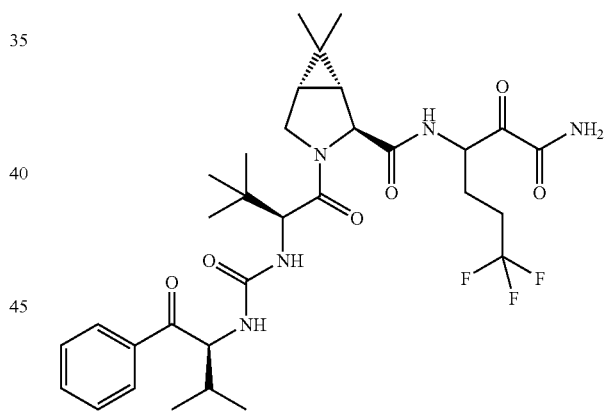
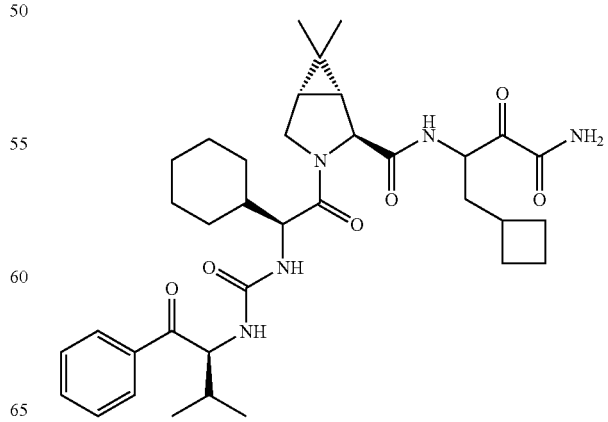

317
-continued
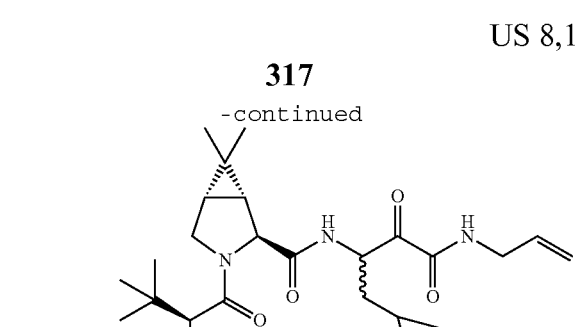
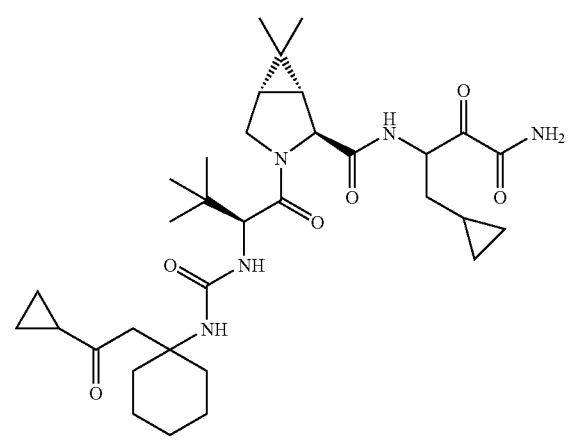
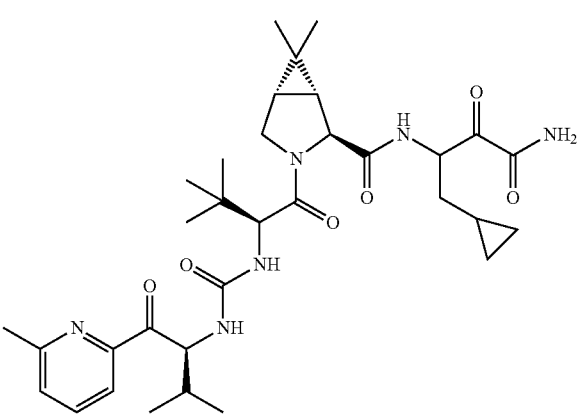
318
-continued
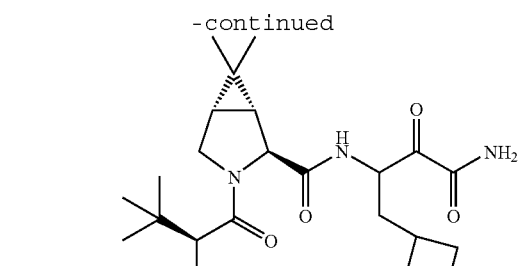
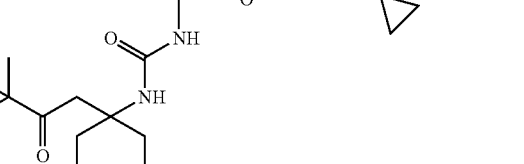
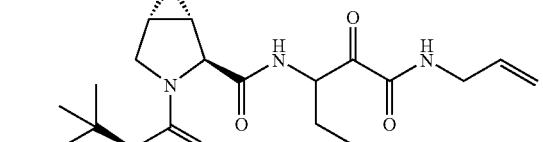

319
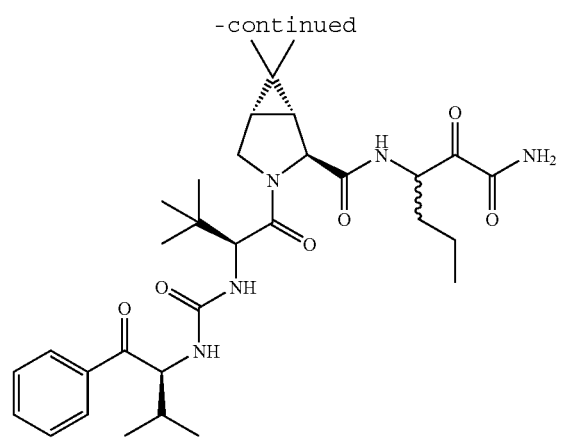
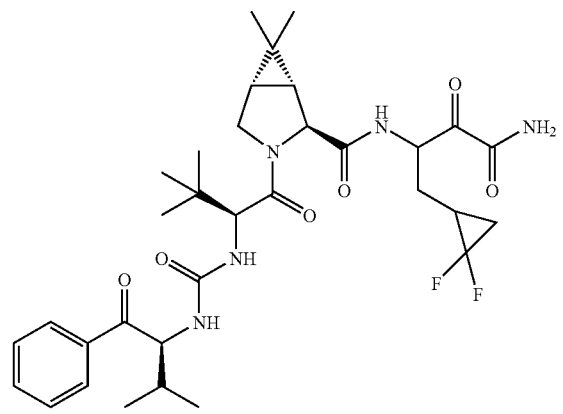
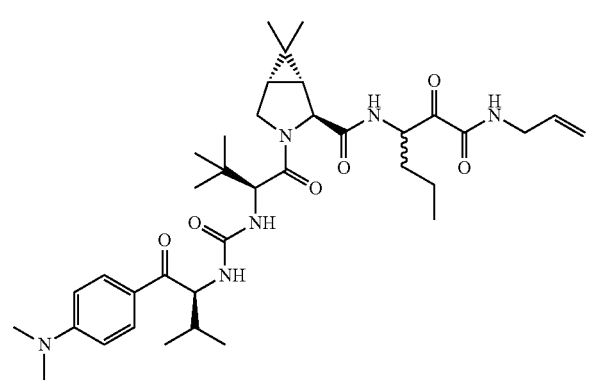
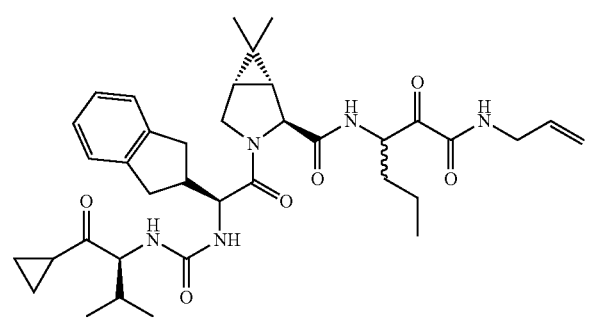
320
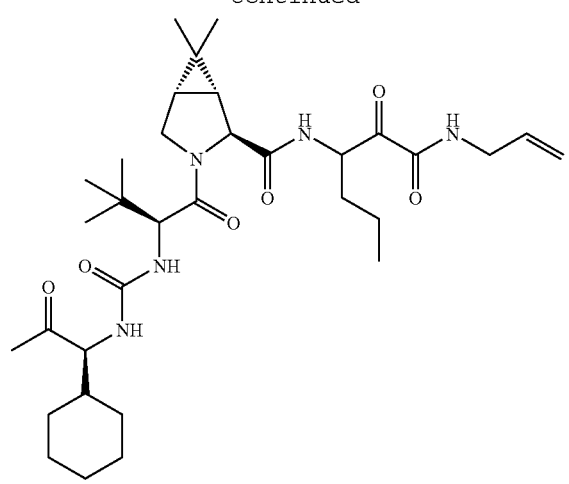
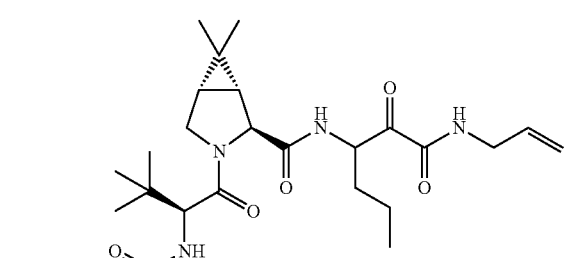
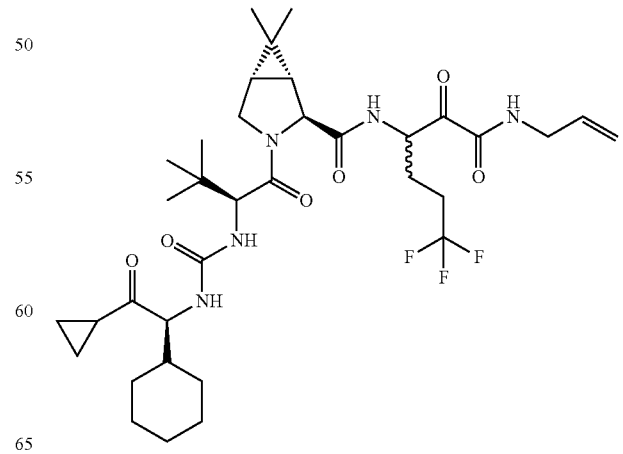

321
-continued
322
-continued
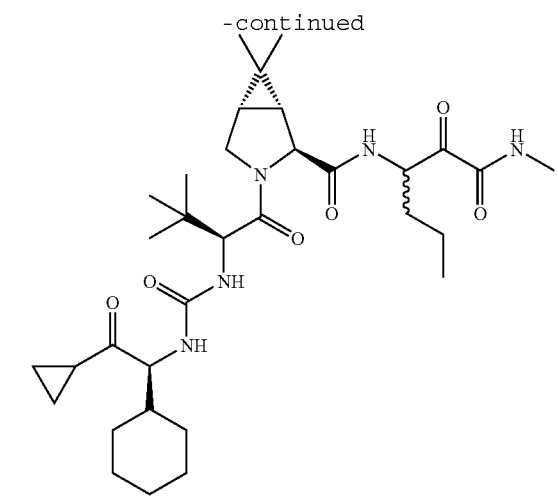
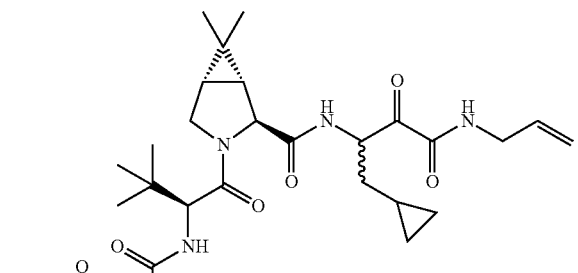
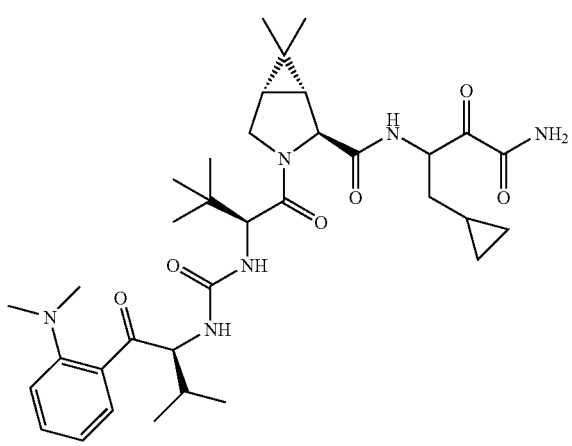
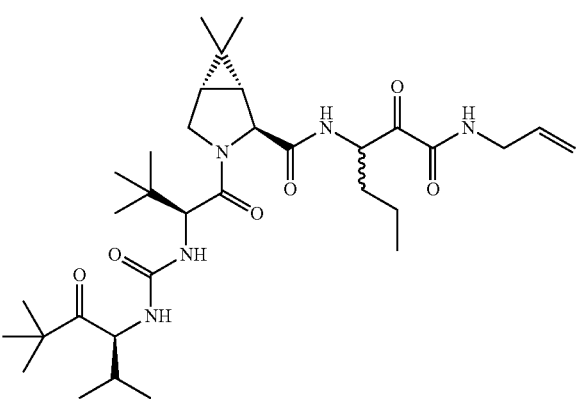
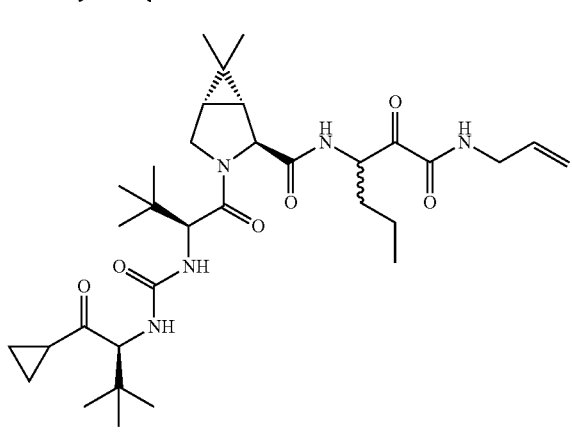

323
-continued
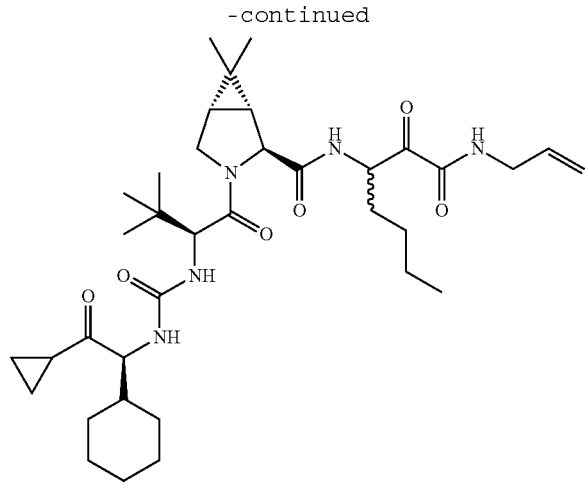
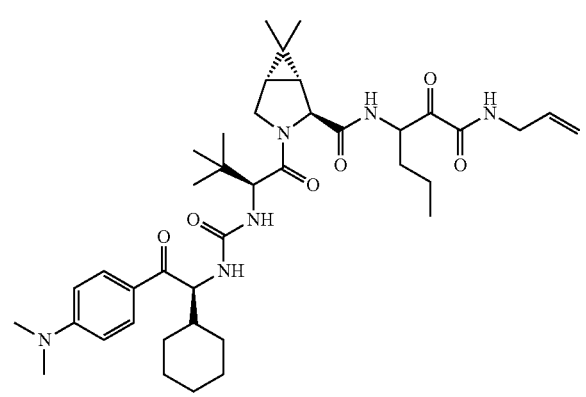
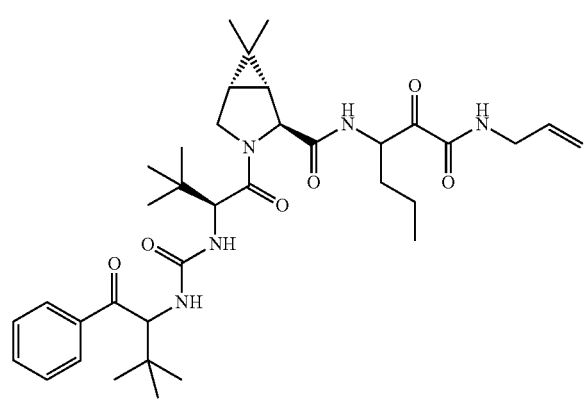
324
-continued
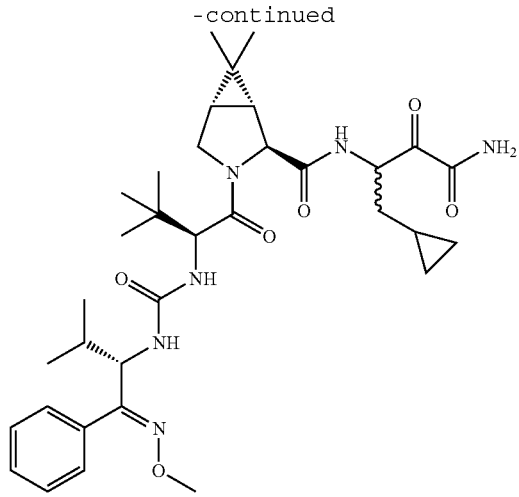
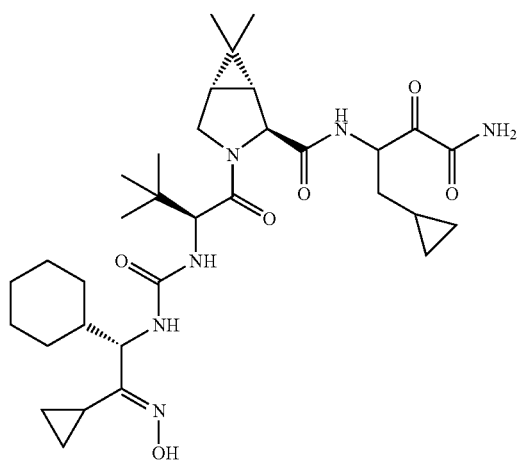
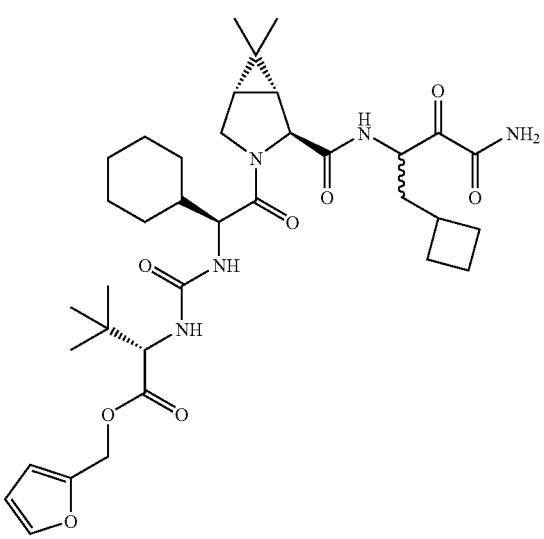

325
-continued
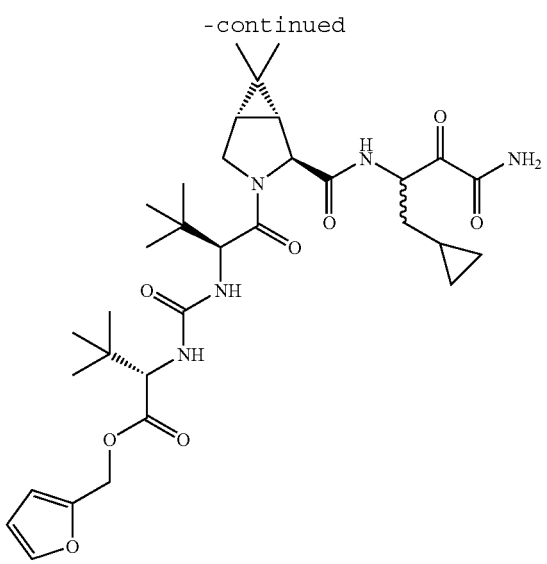
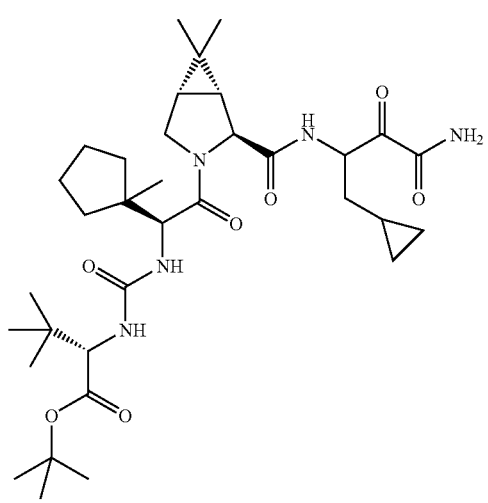
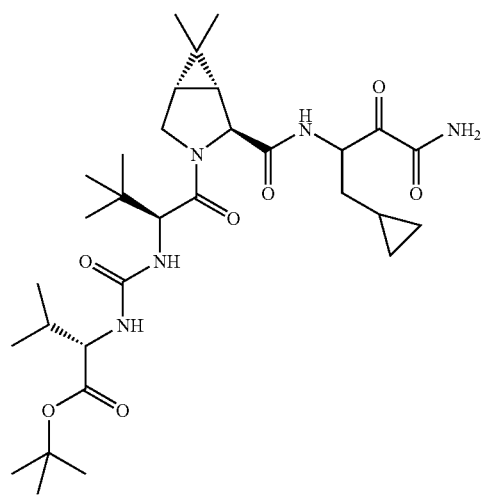
326
-continued
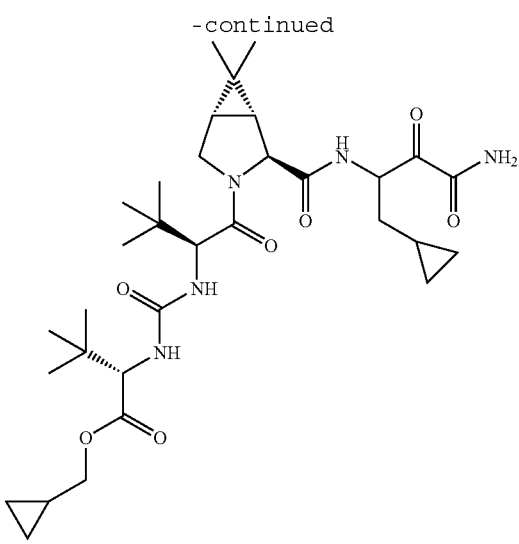
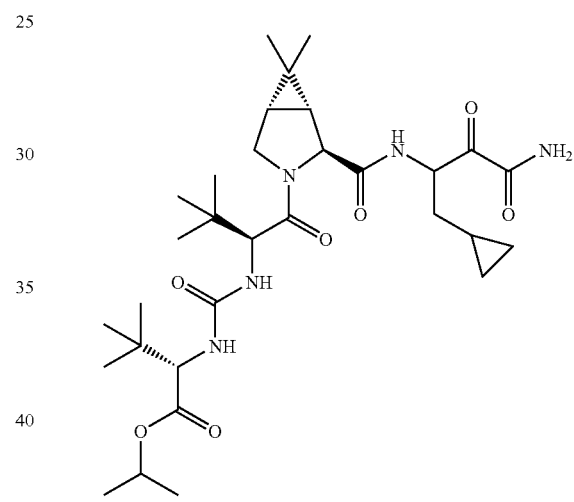
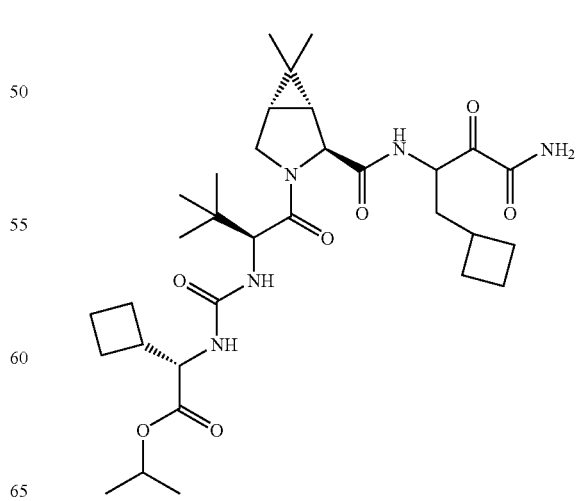

327
-continued
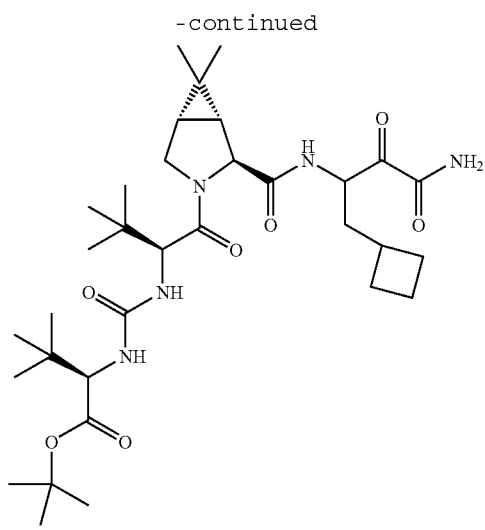
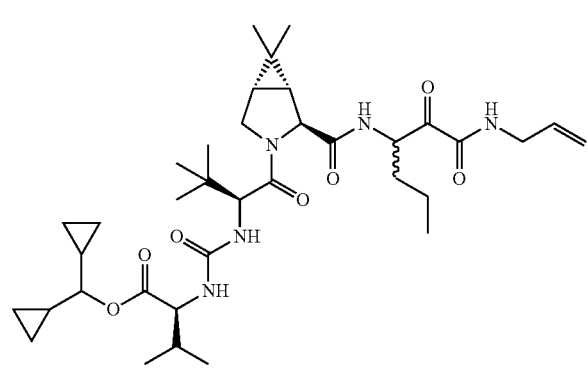
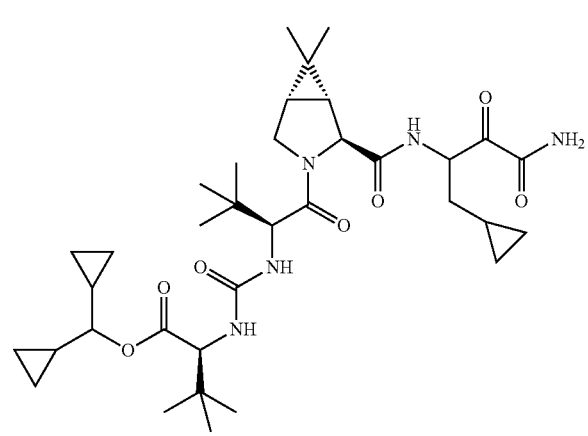
328
-continued
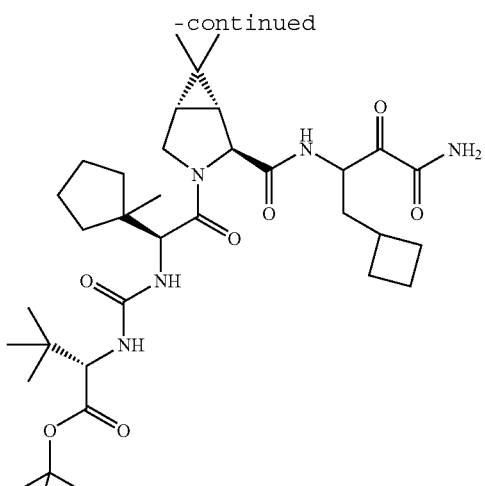
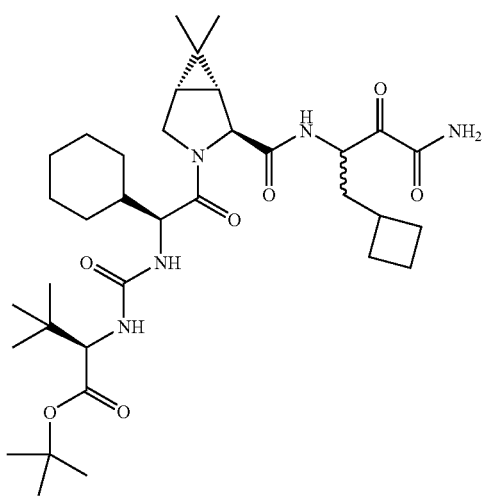
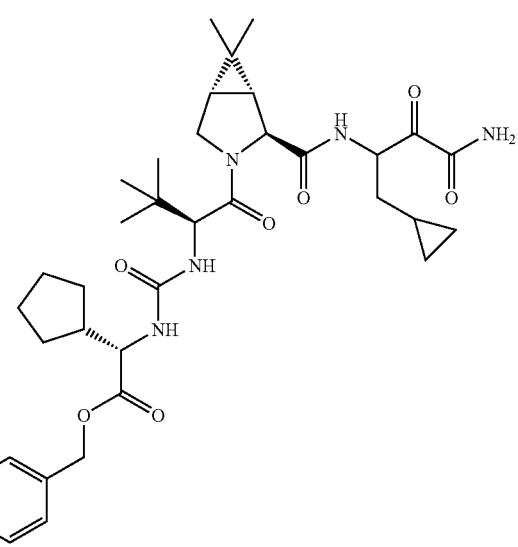

329
-continued
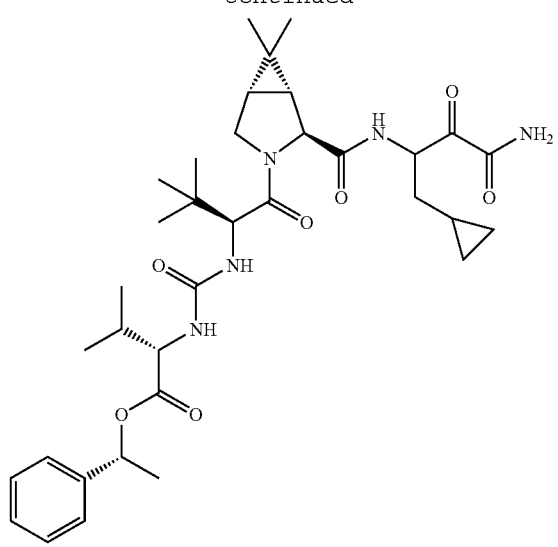
330
-continued
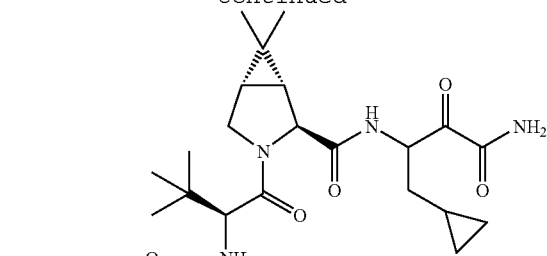
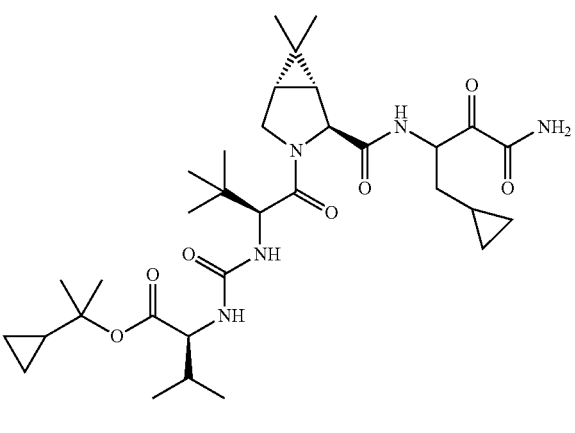
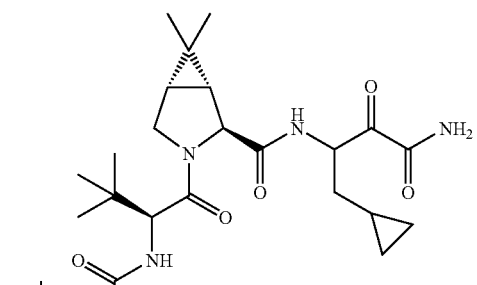
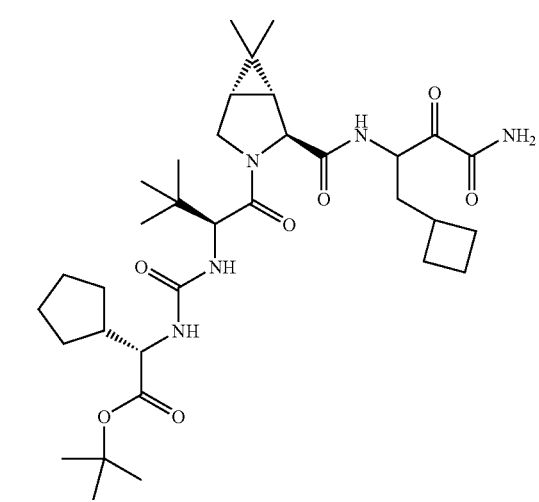
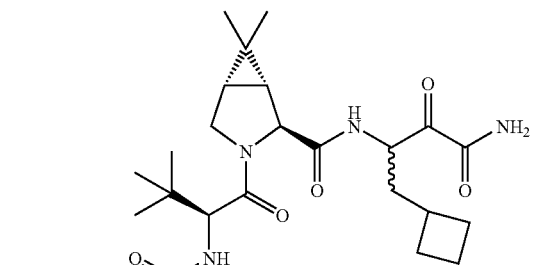

331
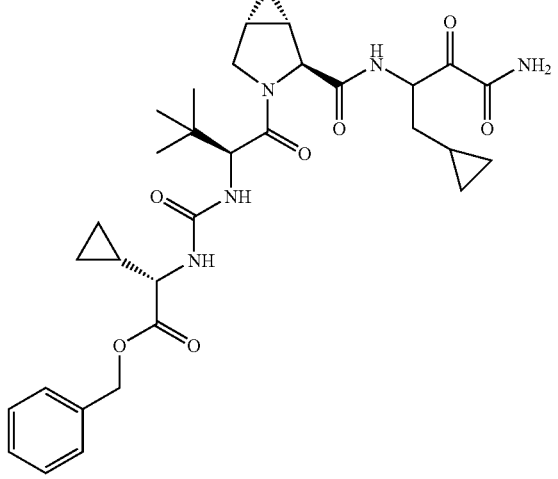
332
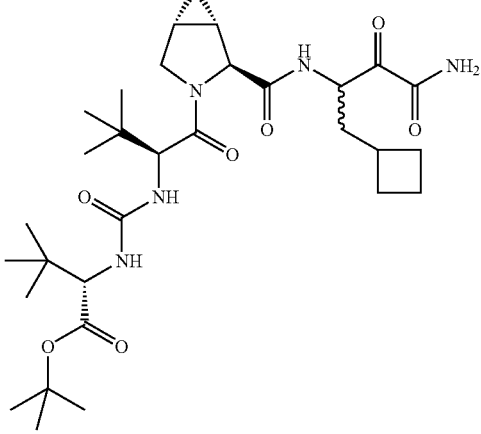

333
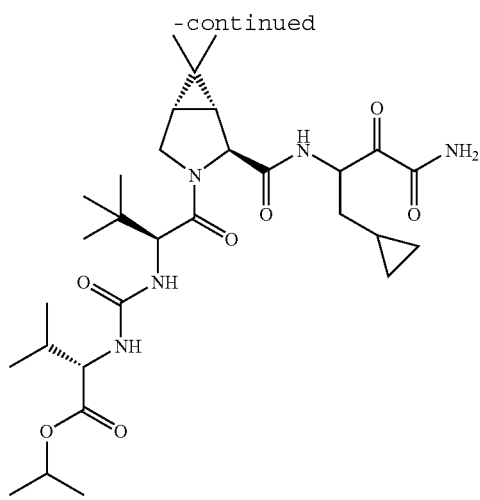
334
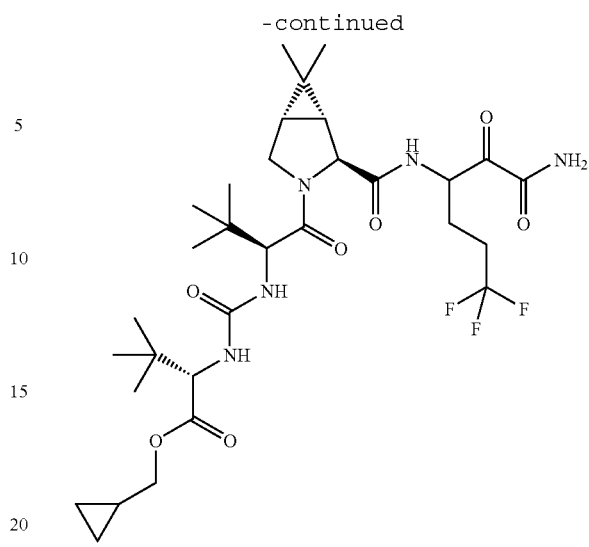
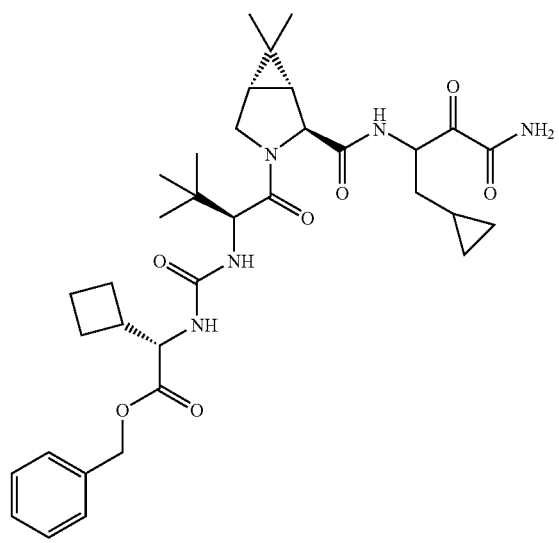
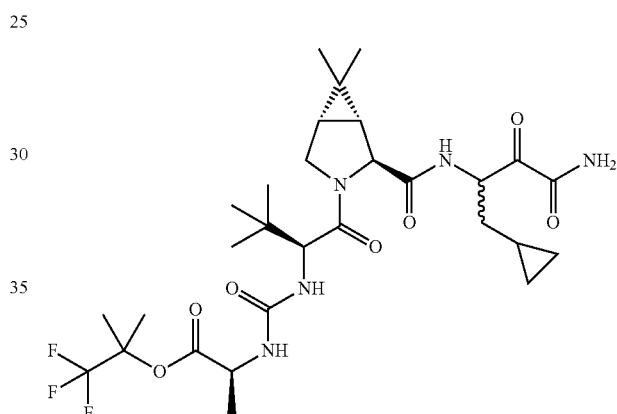
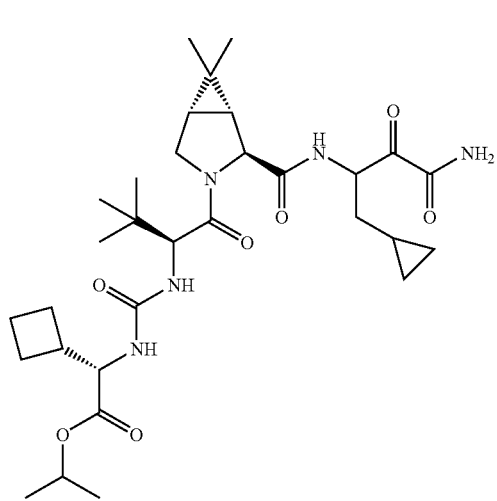
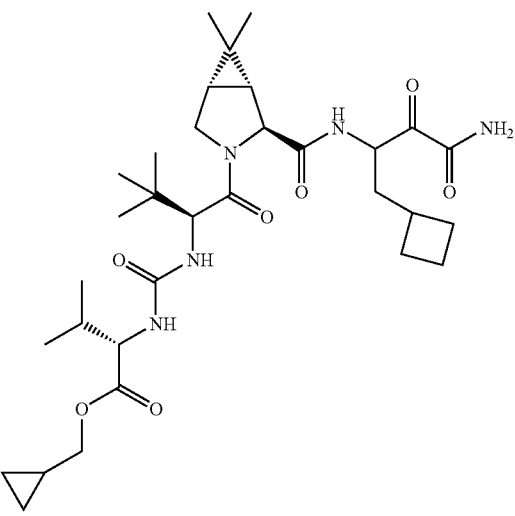

335
-continued
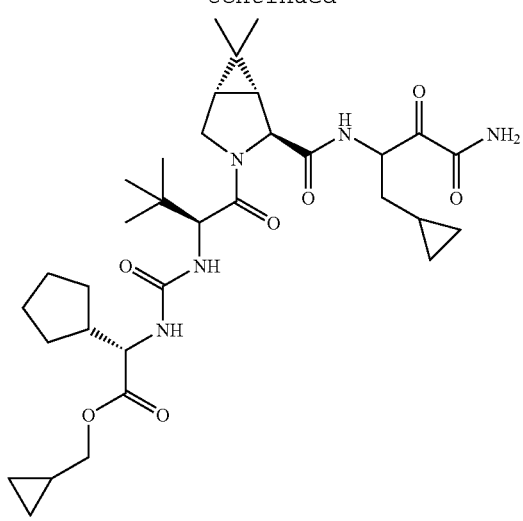
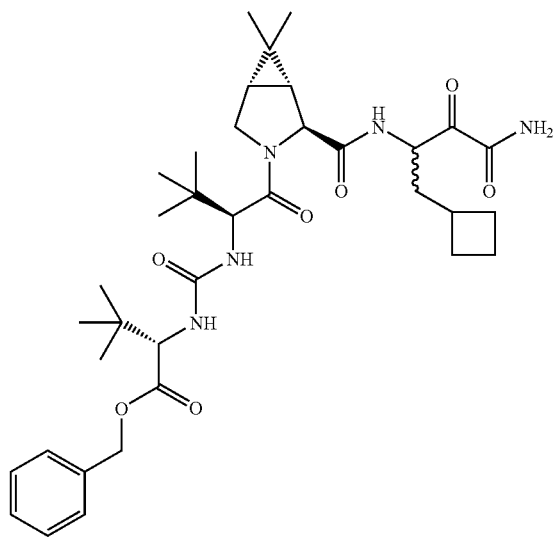
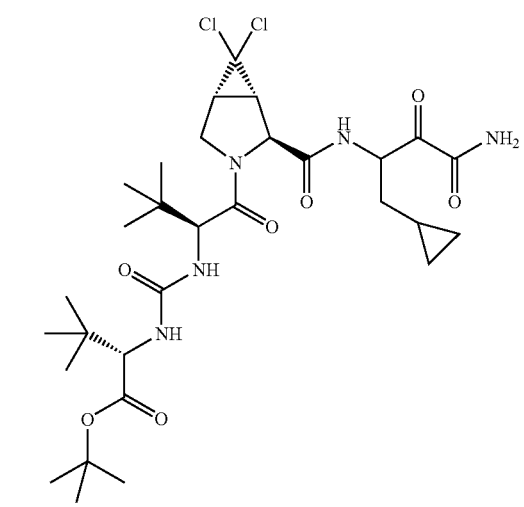
336
-continued
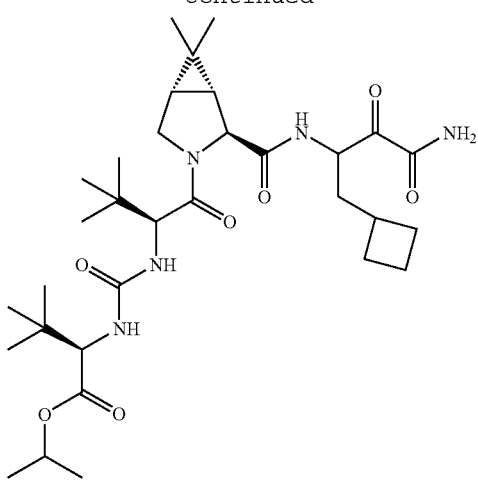
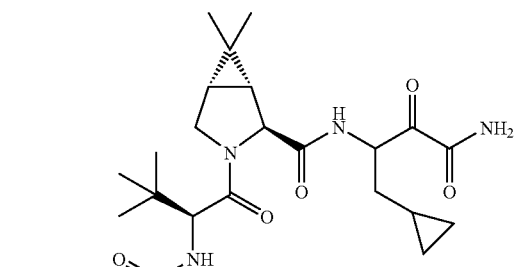
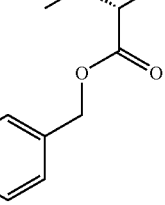
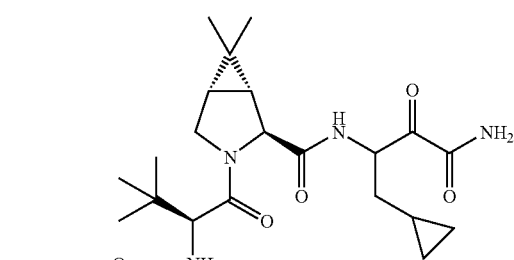
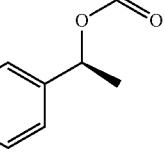

337
-continued
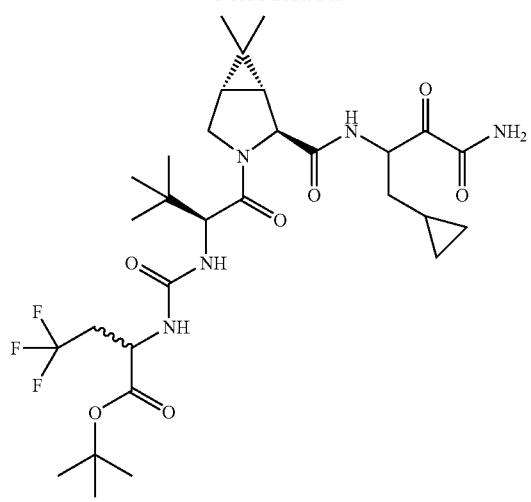
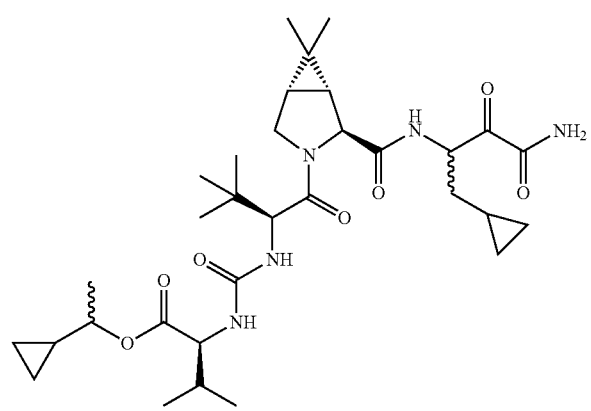
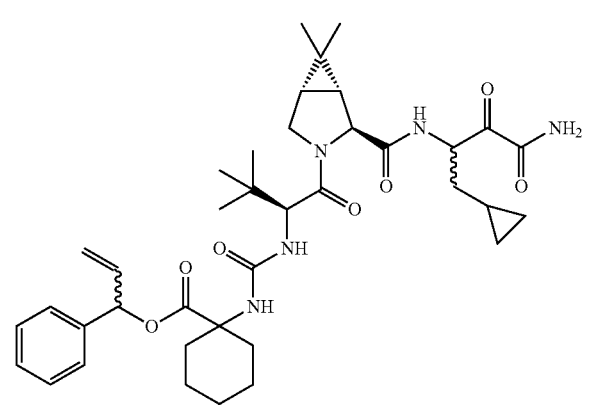
338
-continued
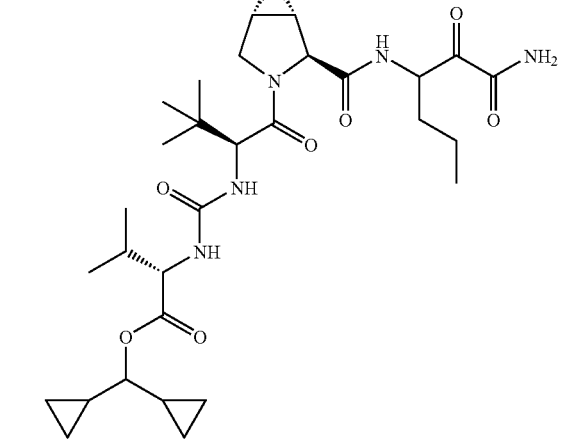
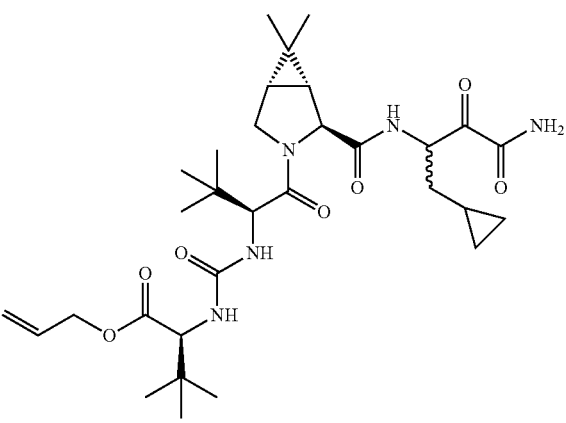
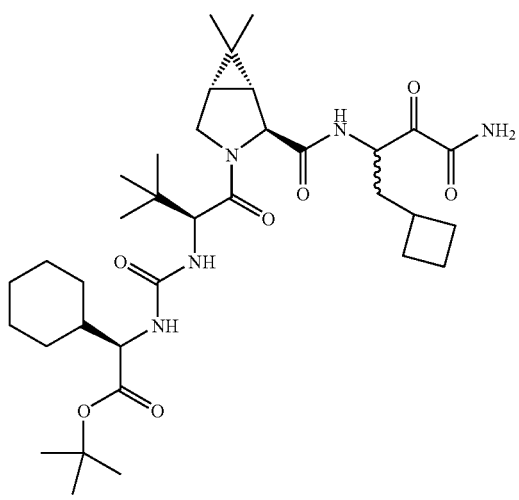

339
-continued
340
-continued
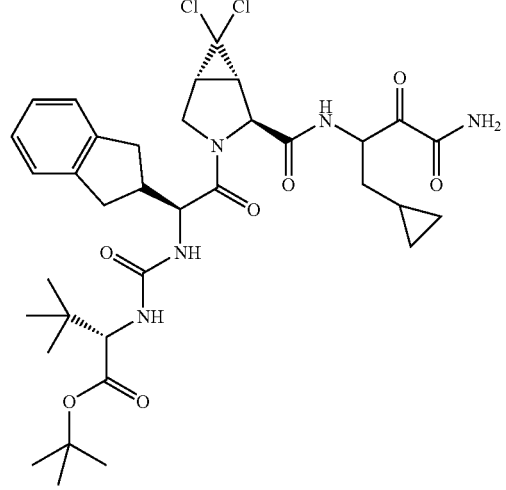
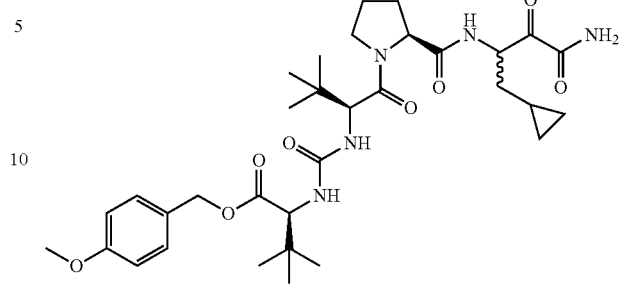
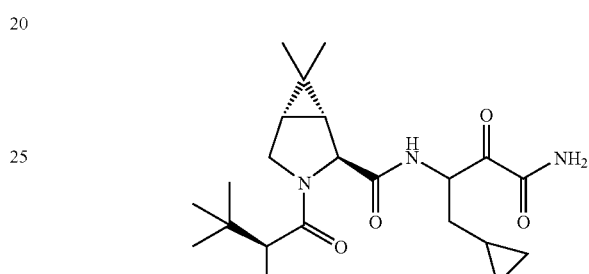
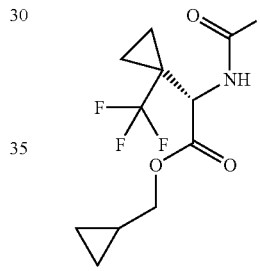
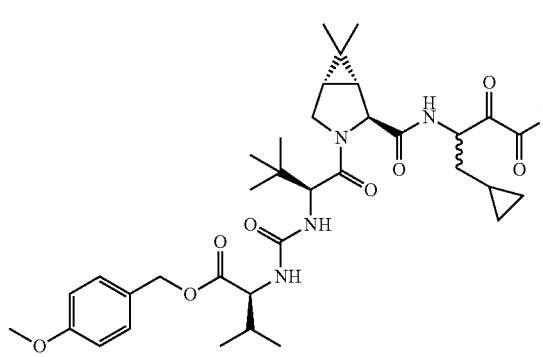
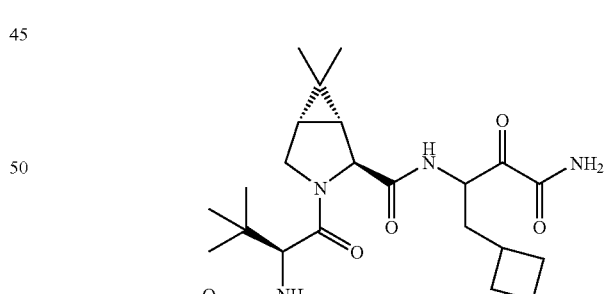
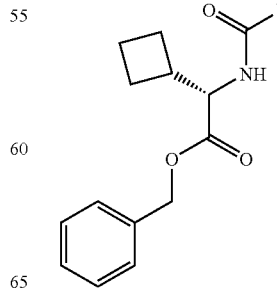

341
-continued
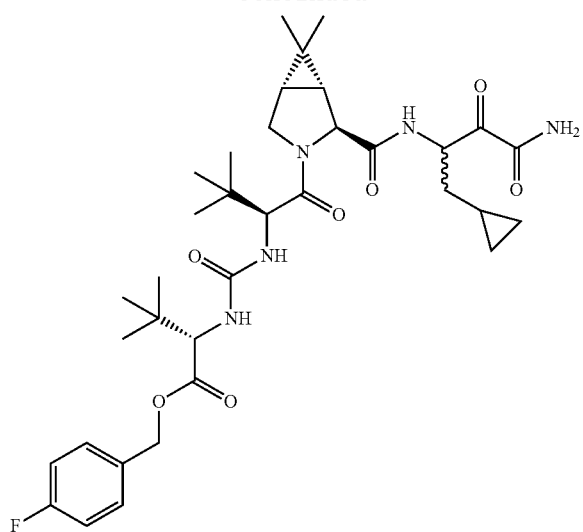
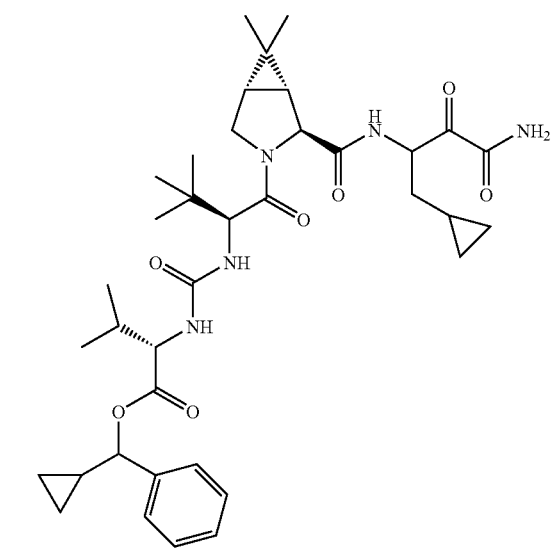
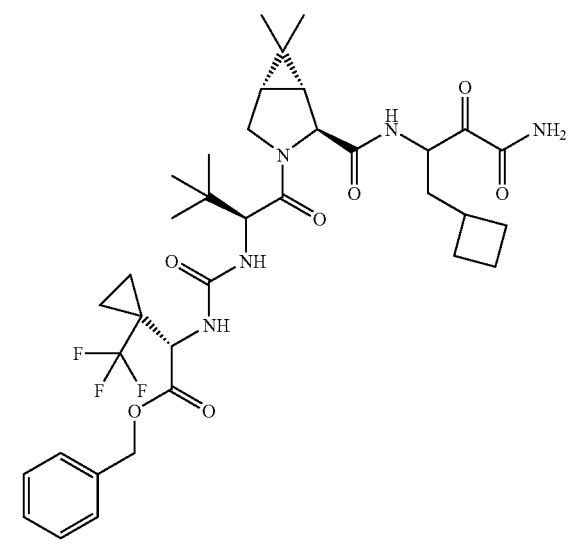
342
-continued
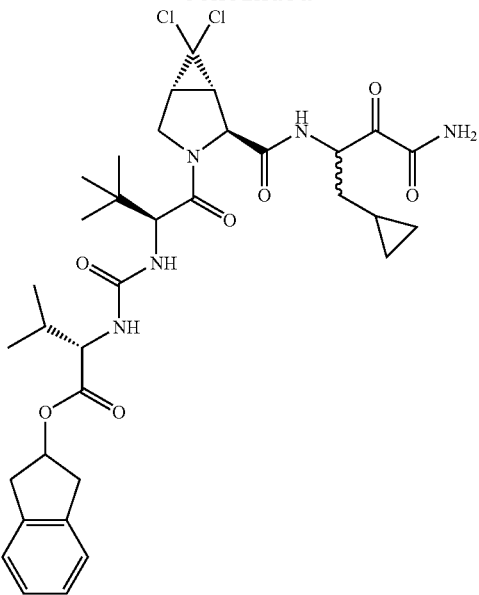
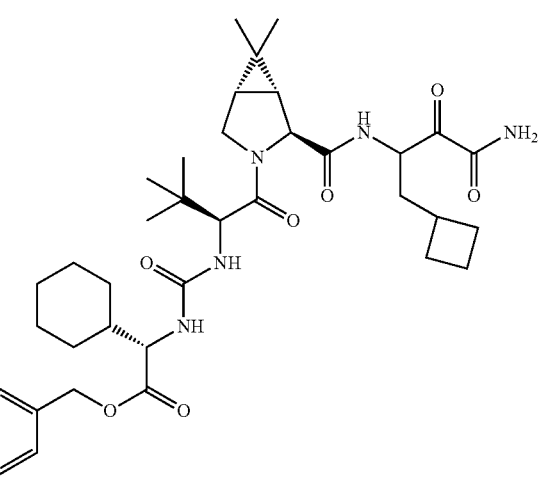
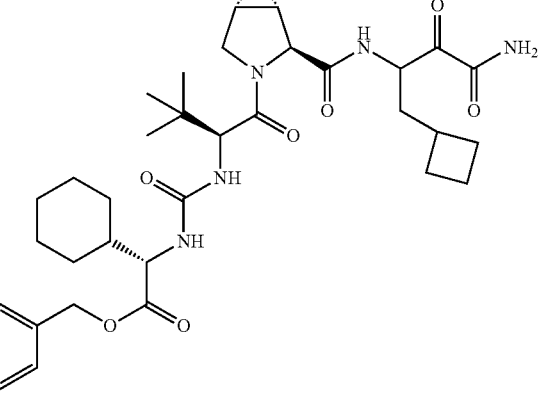

343
-continued
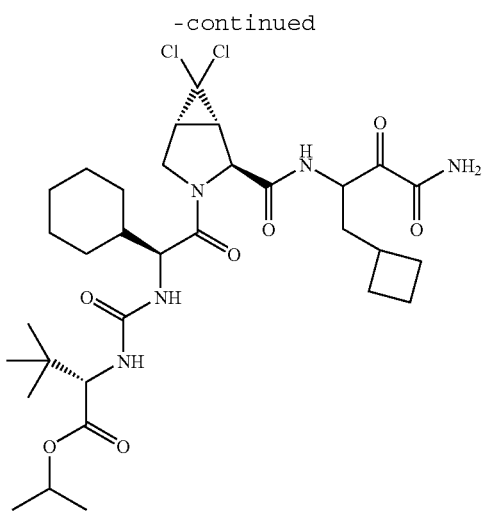
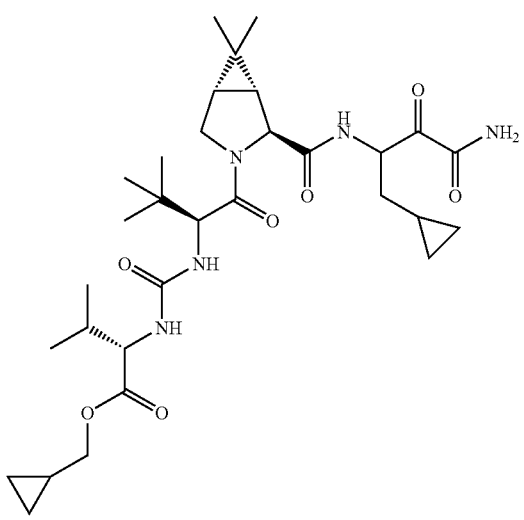
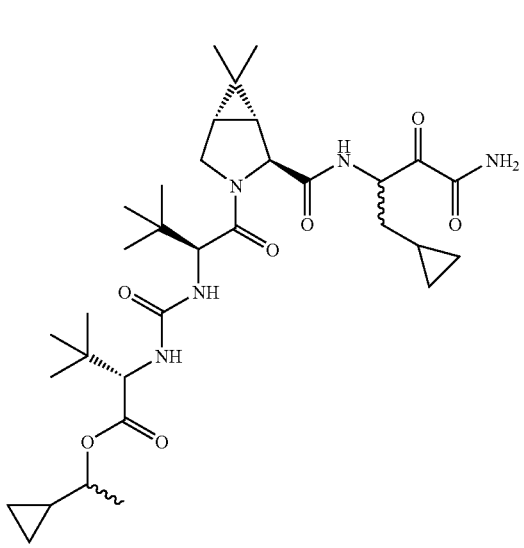
344
-continued
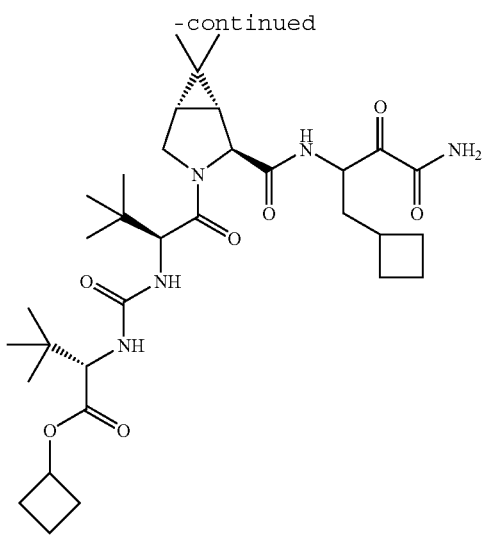
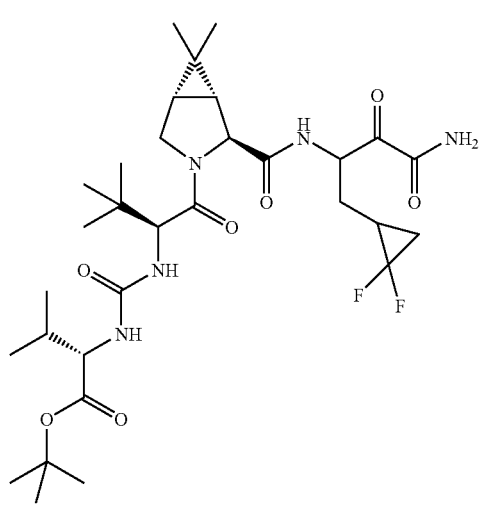
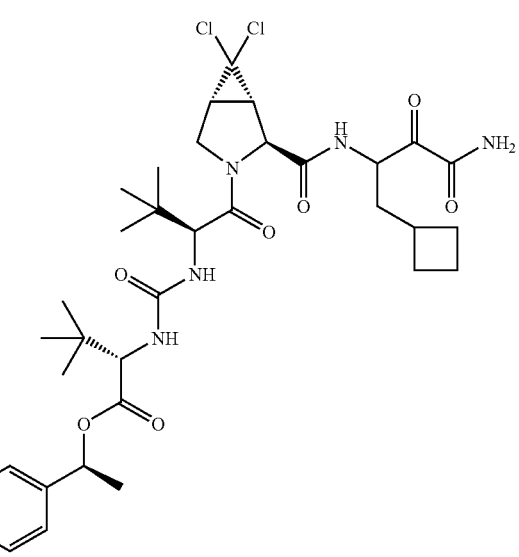

345
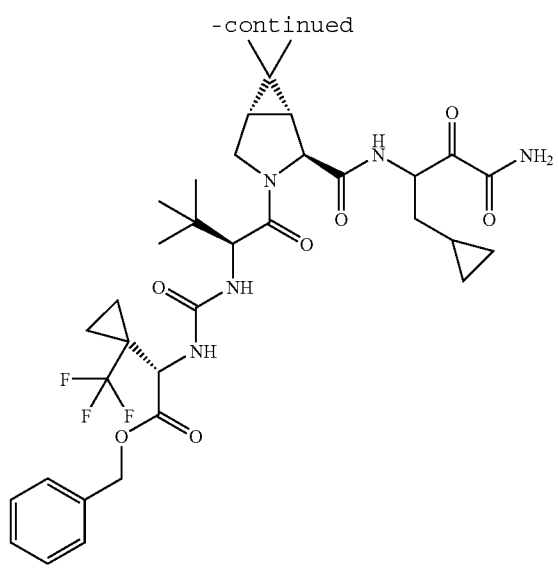
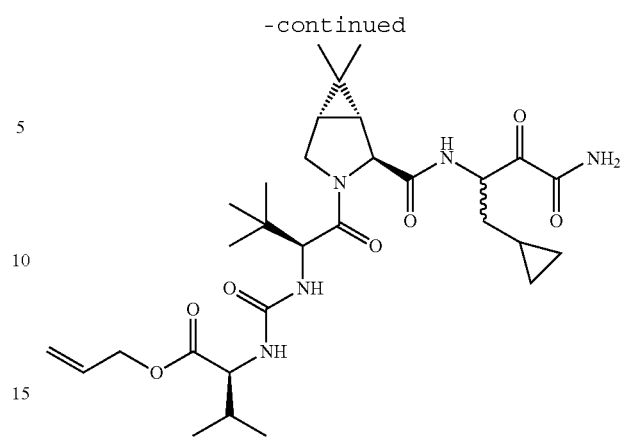
346
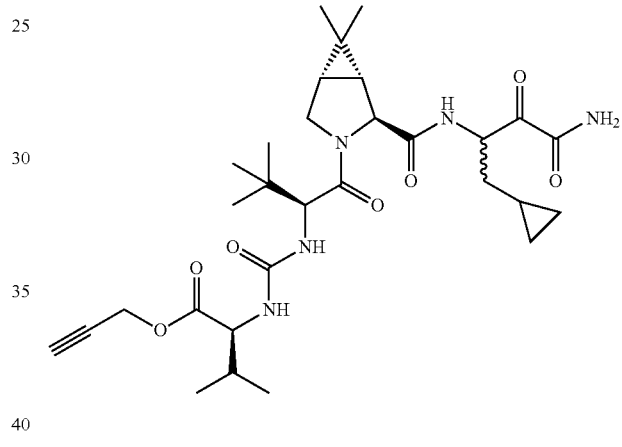
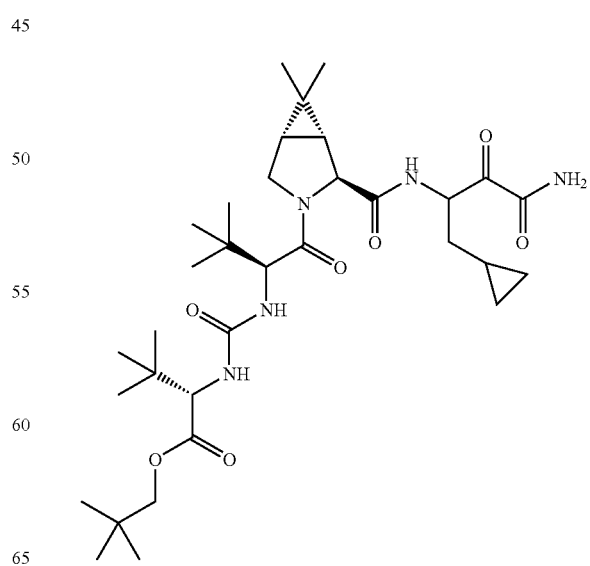

347
-continued
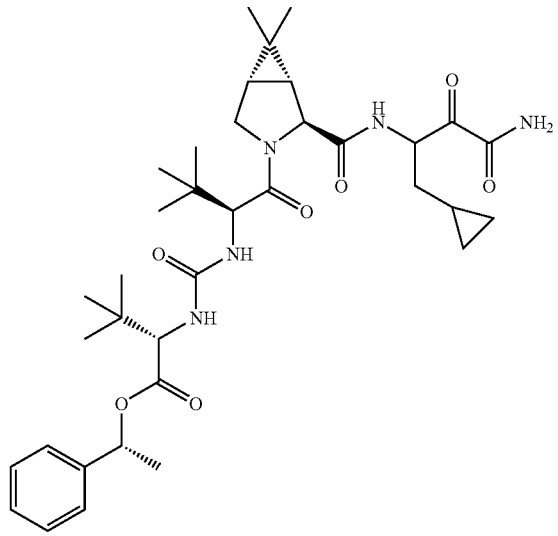
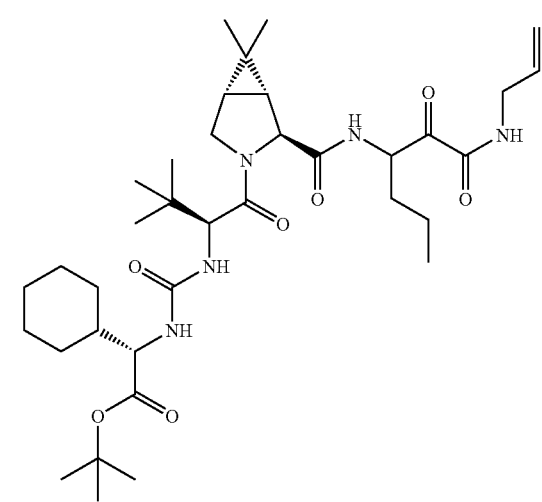
348
-continued
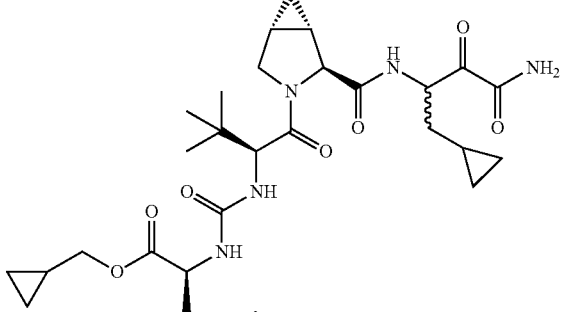
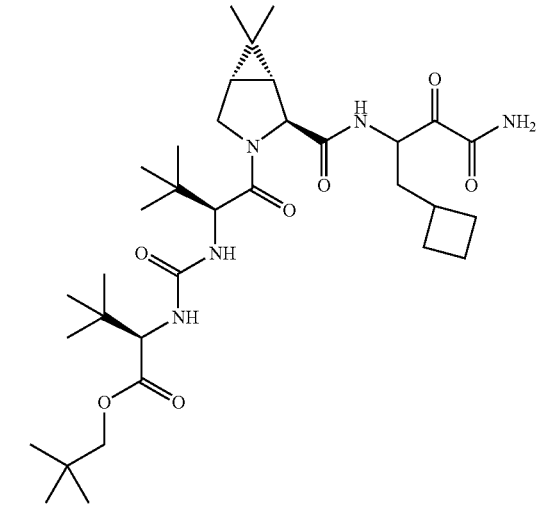
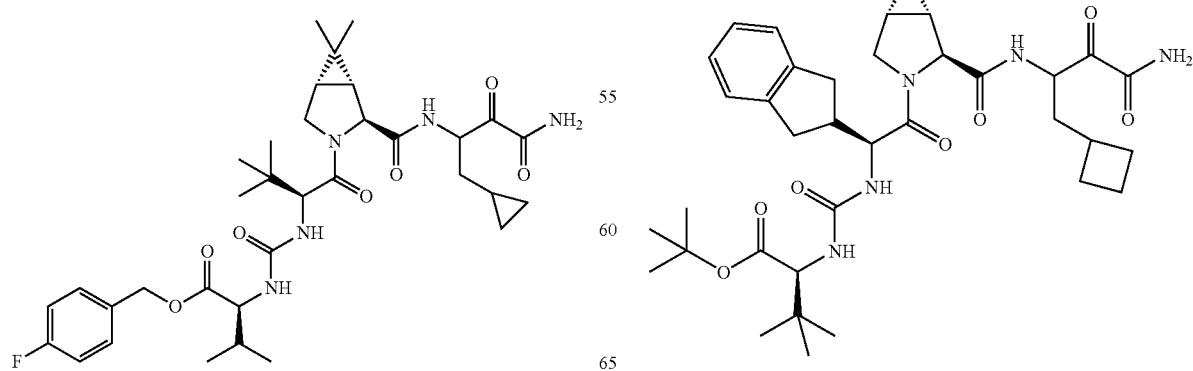

349
-continued
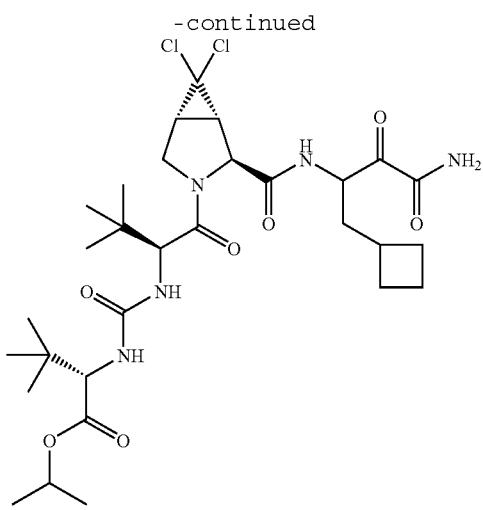
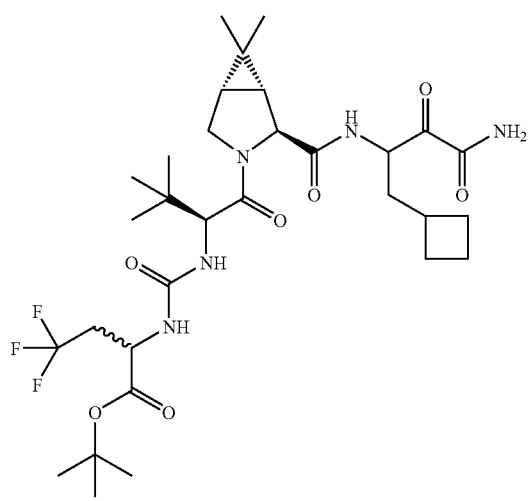
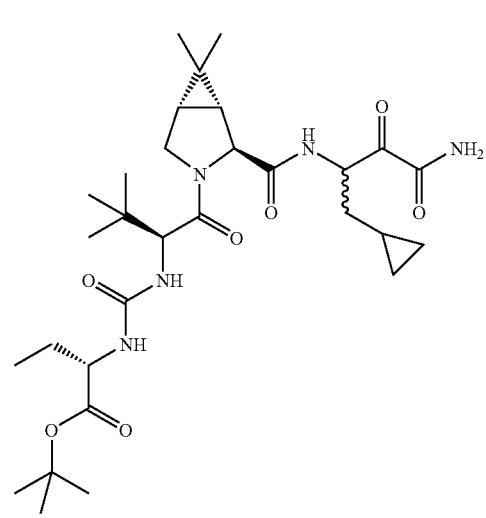
350
-continued
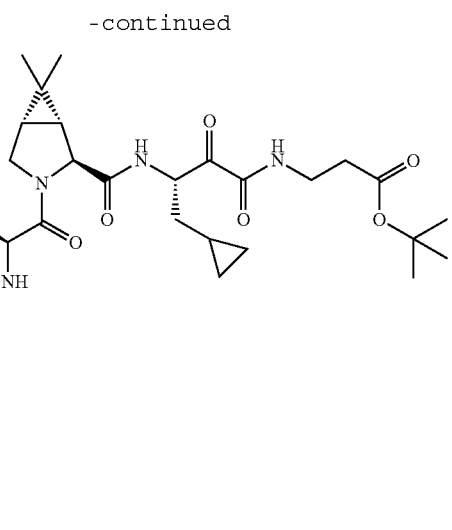
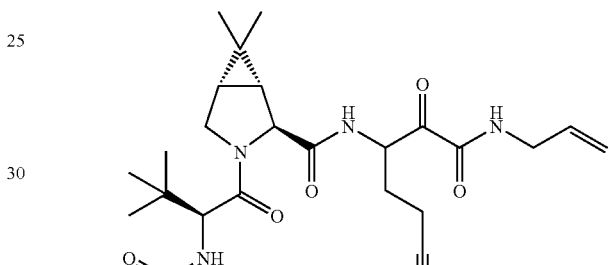
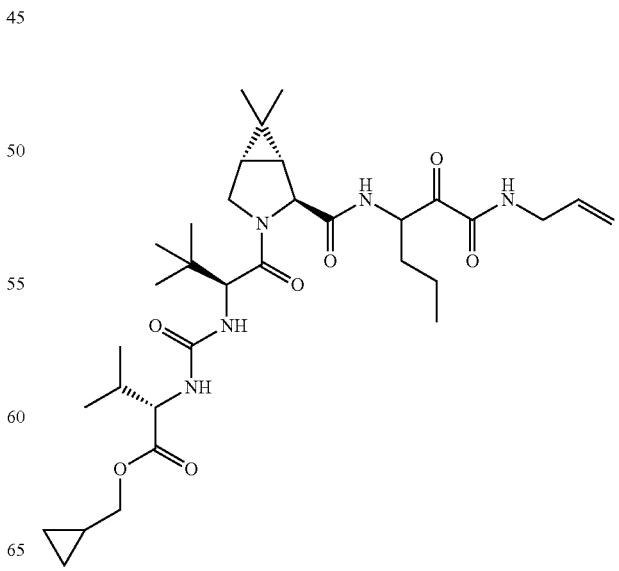

351
-continued
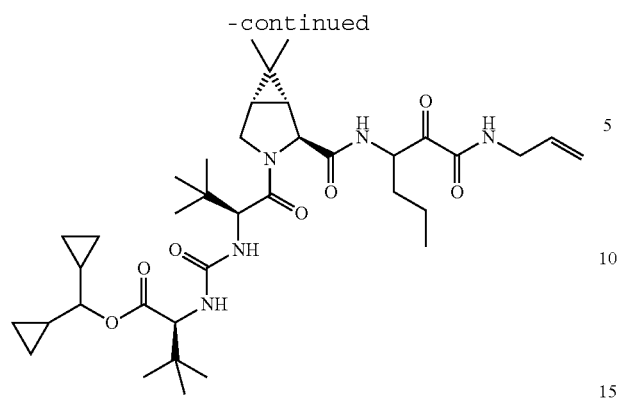
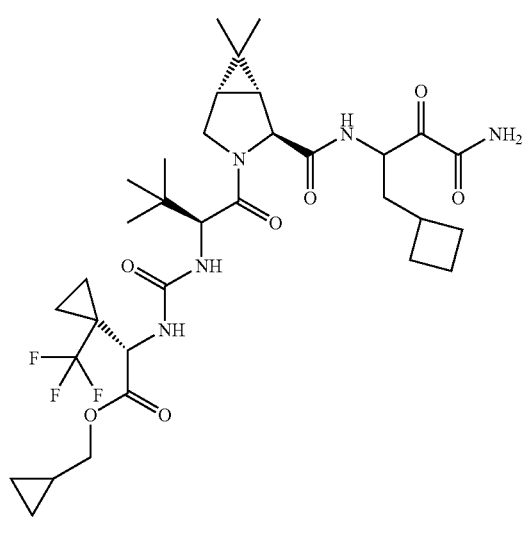
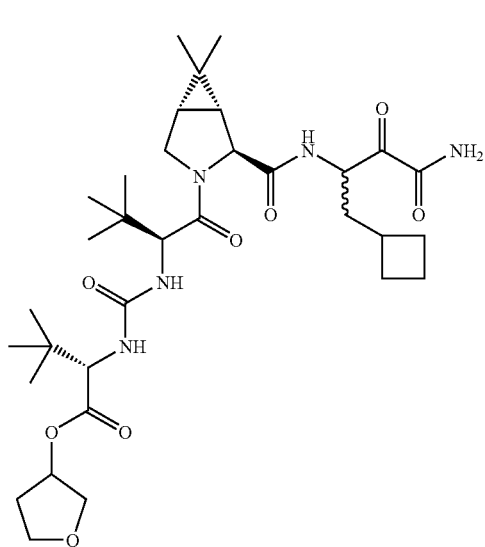
352
-continued
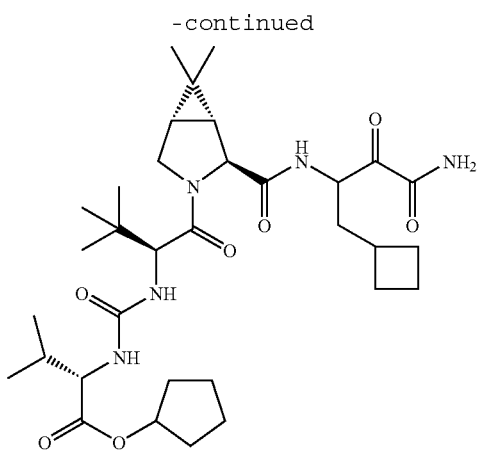
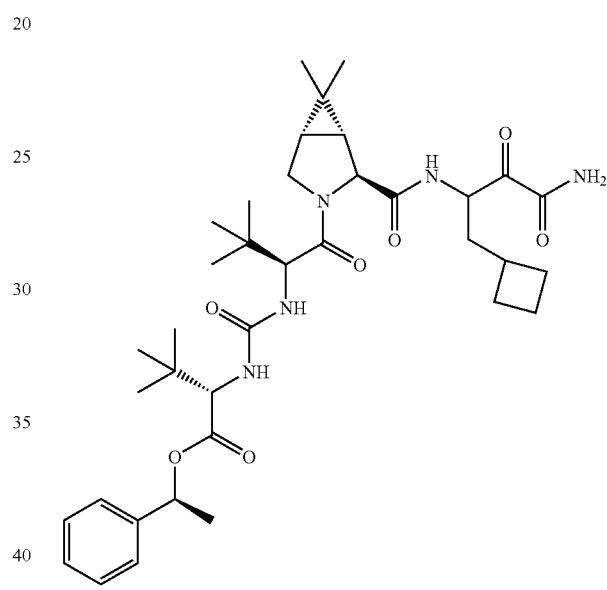
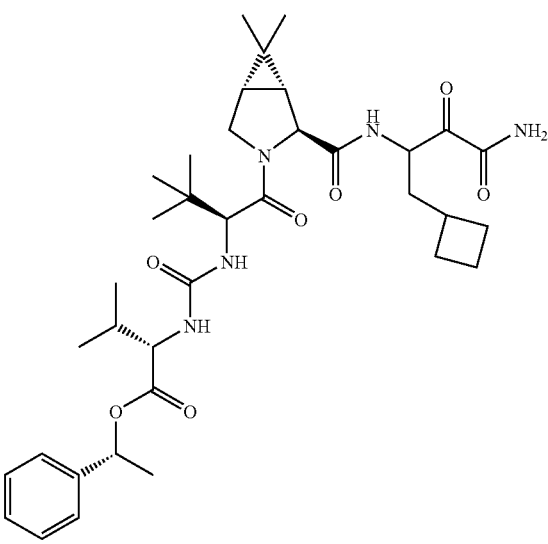

353
-continued
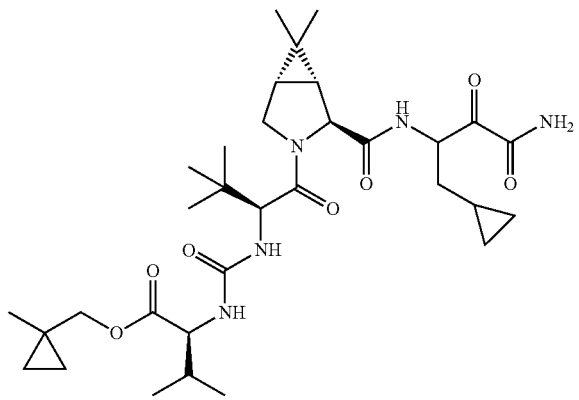
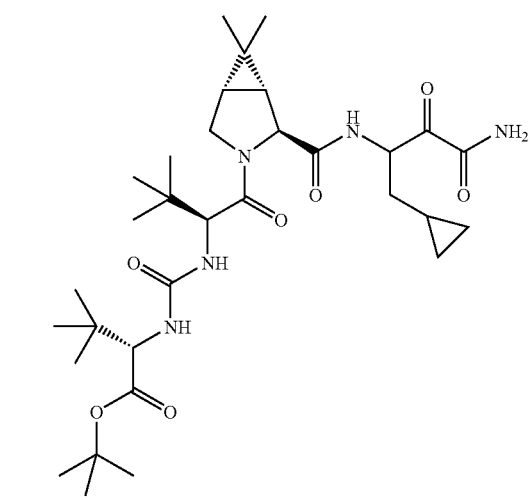
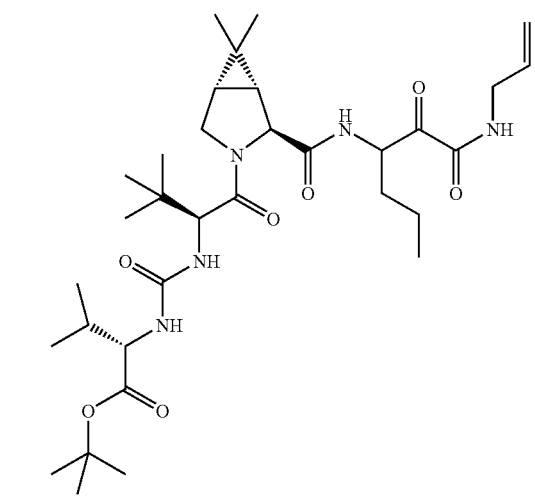
354
-continued
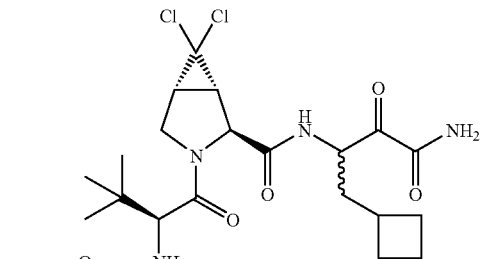
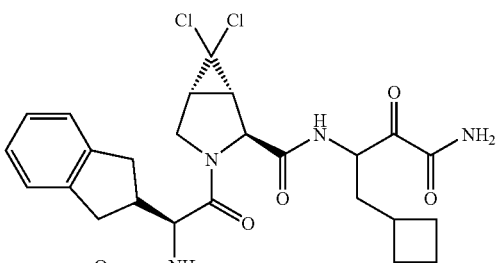
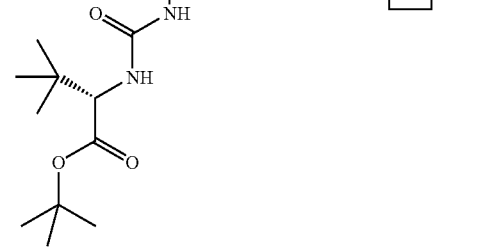
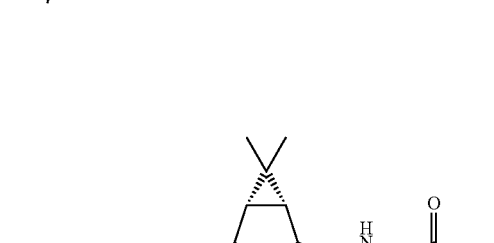

355
-continued
356
-continued
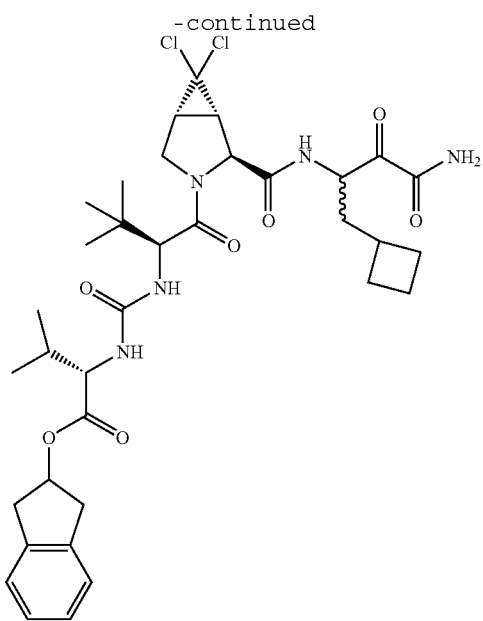
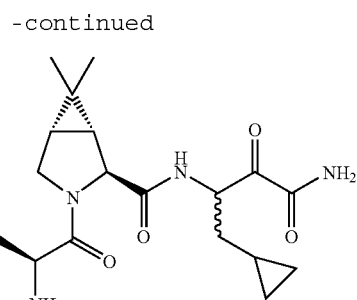
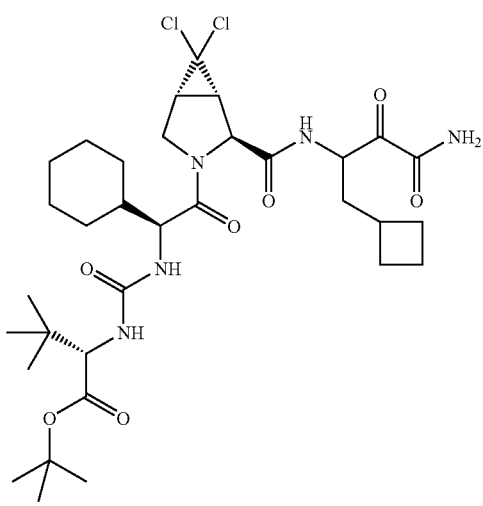
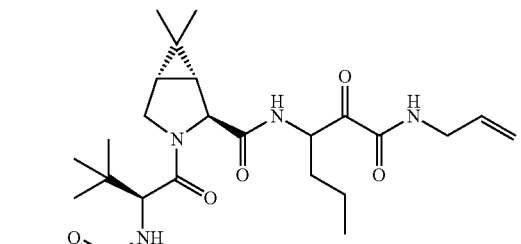
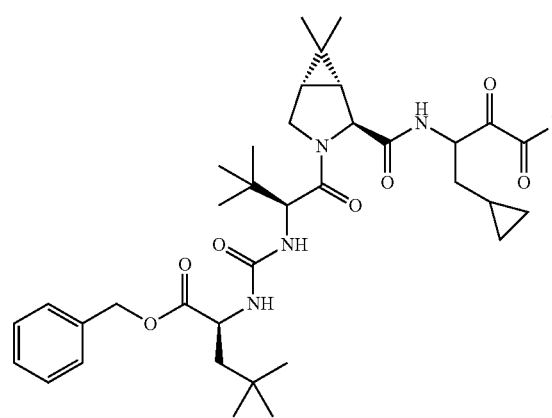
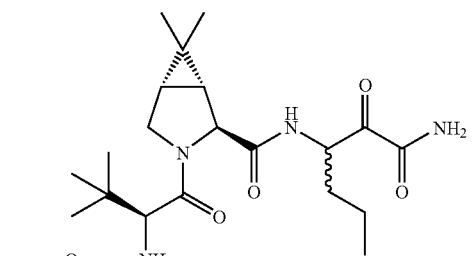
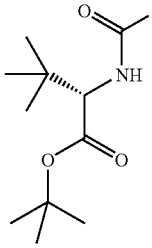

357 -continued
358 -continued
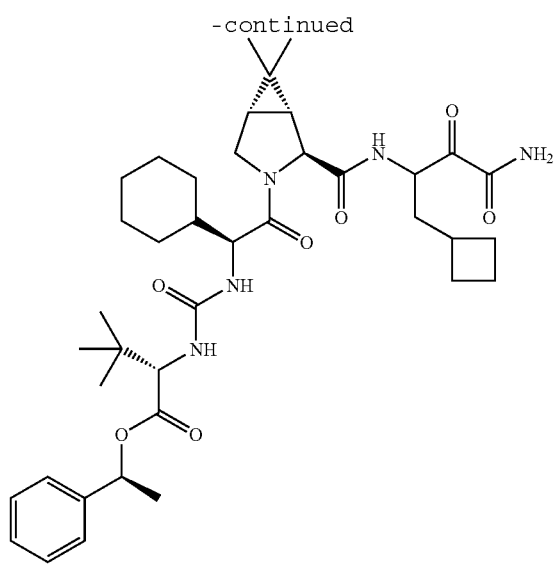
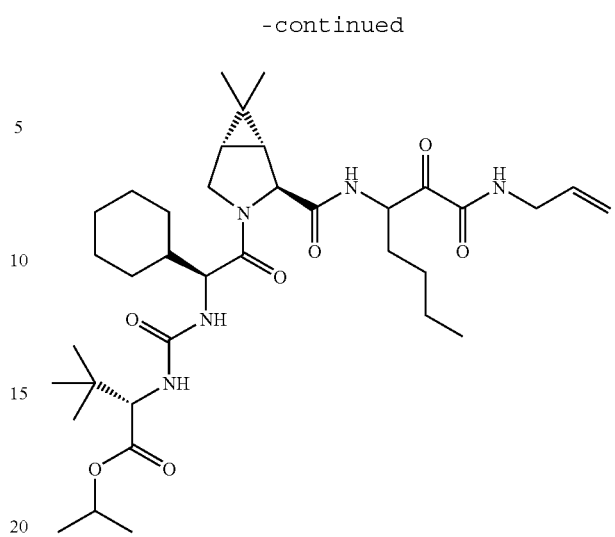
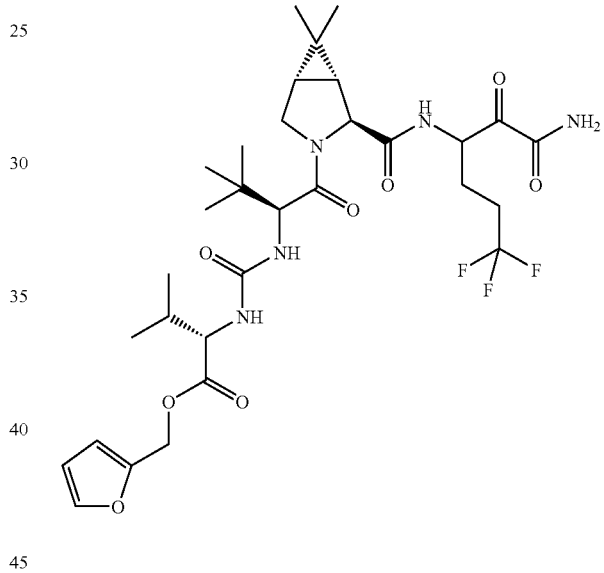
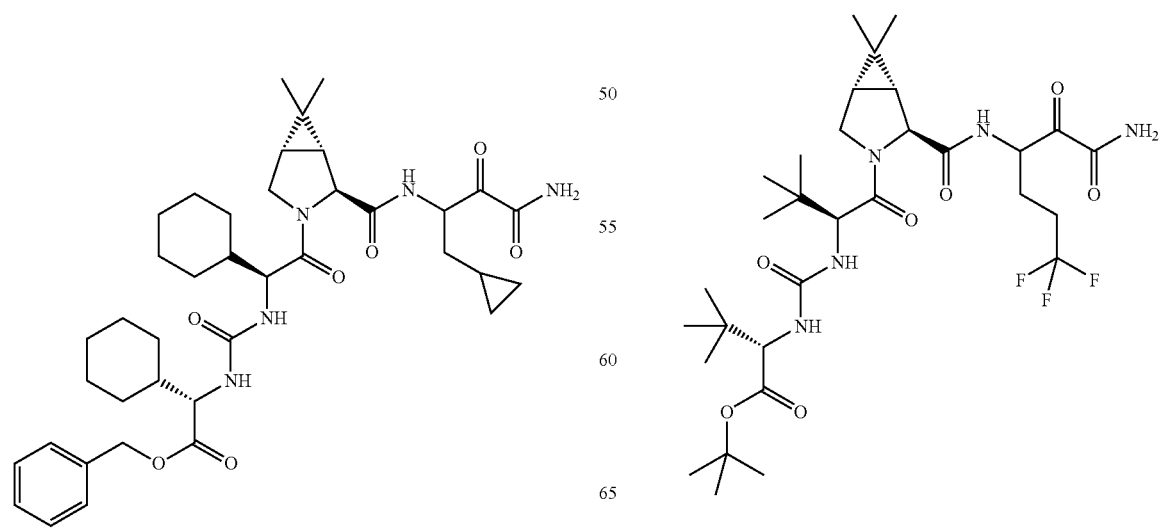

359
-continued
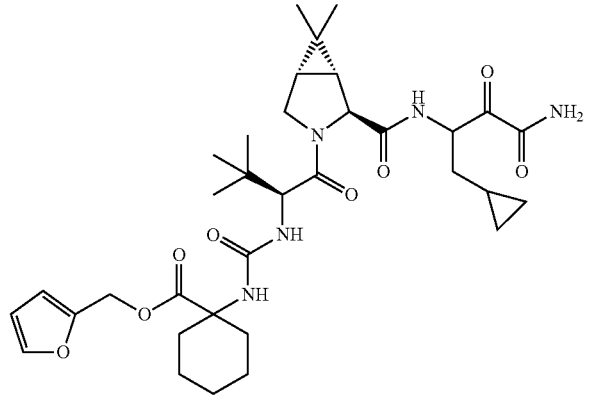
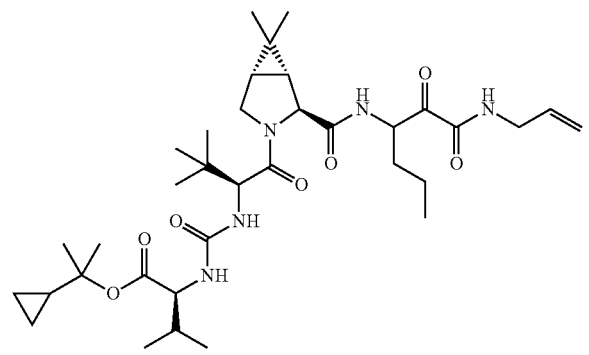
360
-continued
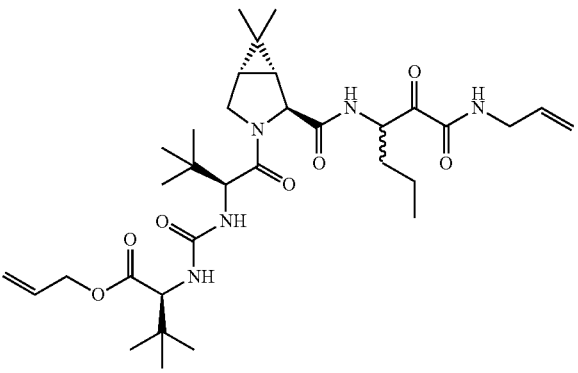
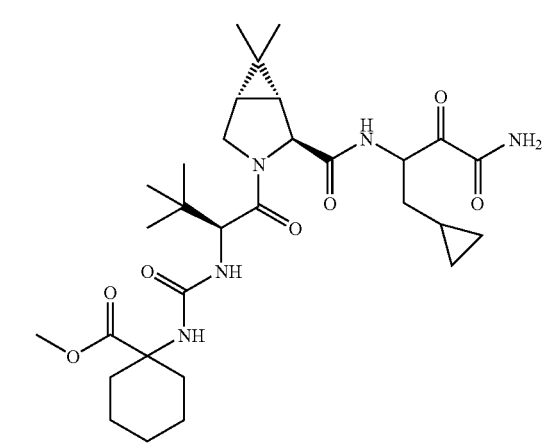

361
-continued
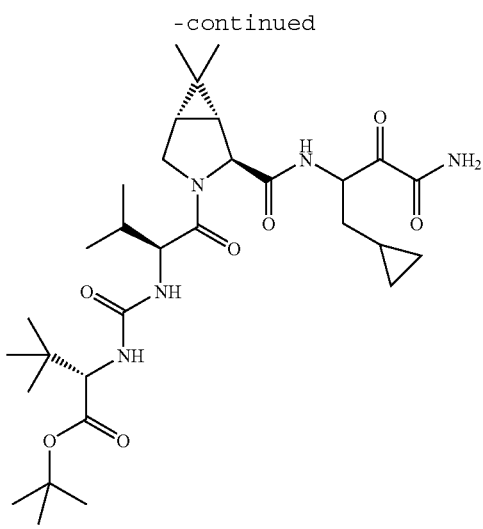
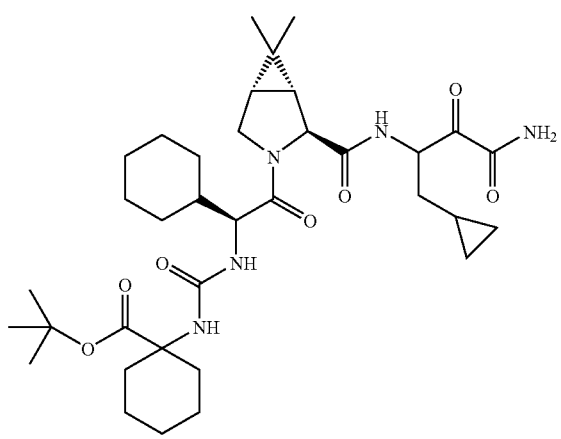
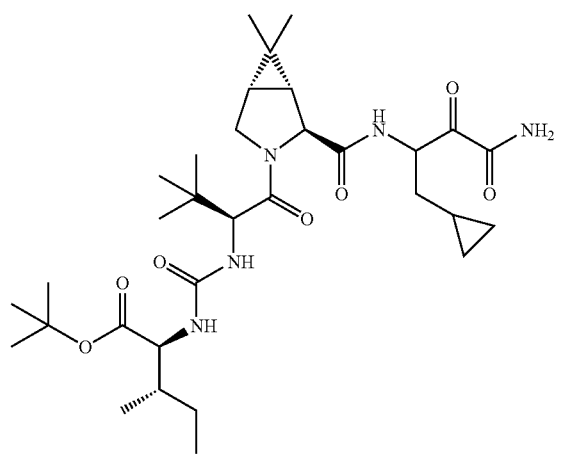
362
-continued
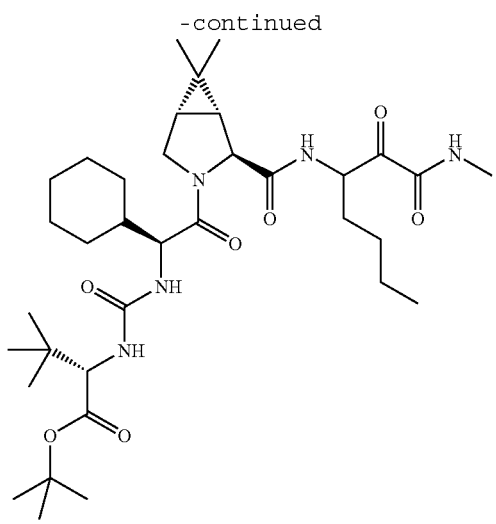
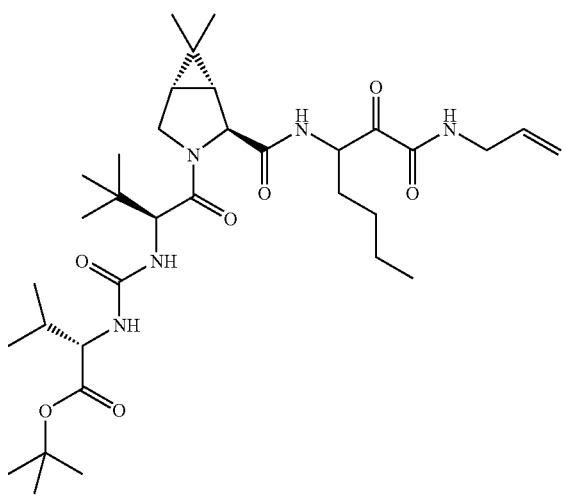
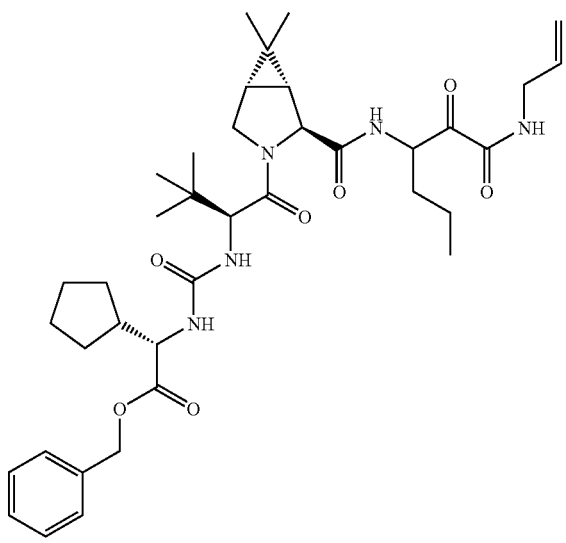

363
-continued
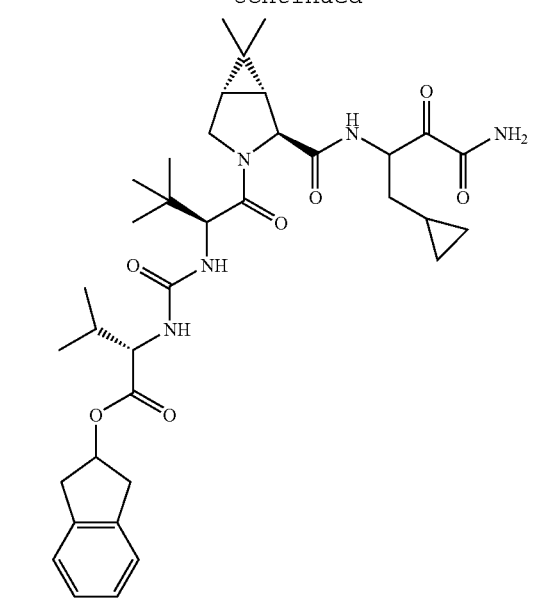
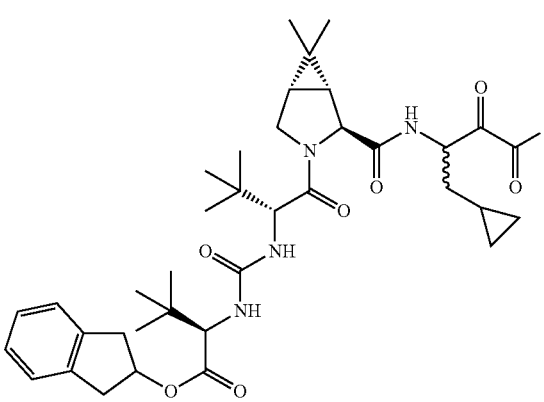
364
-continued
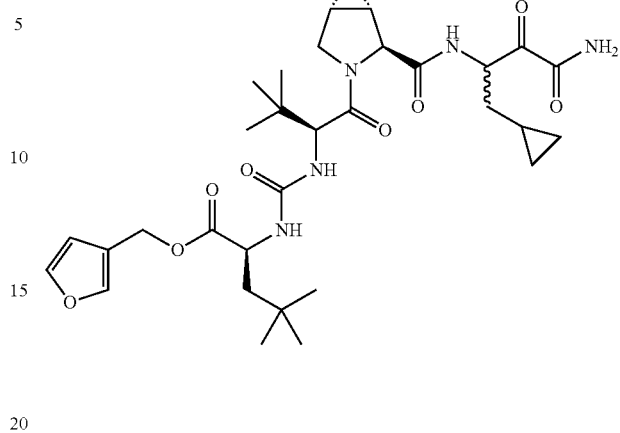
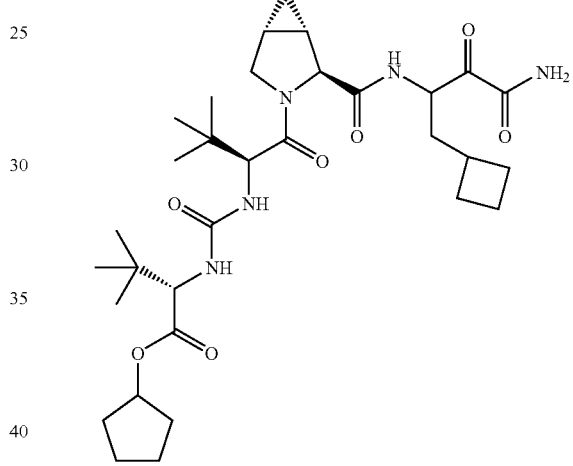
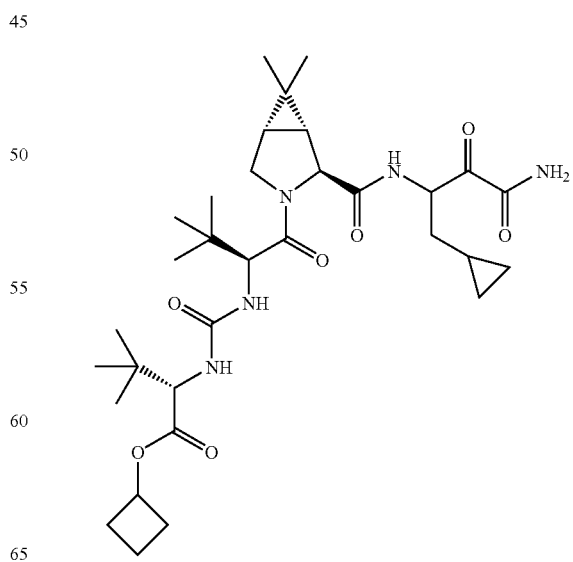

365 -continued
366 -continued
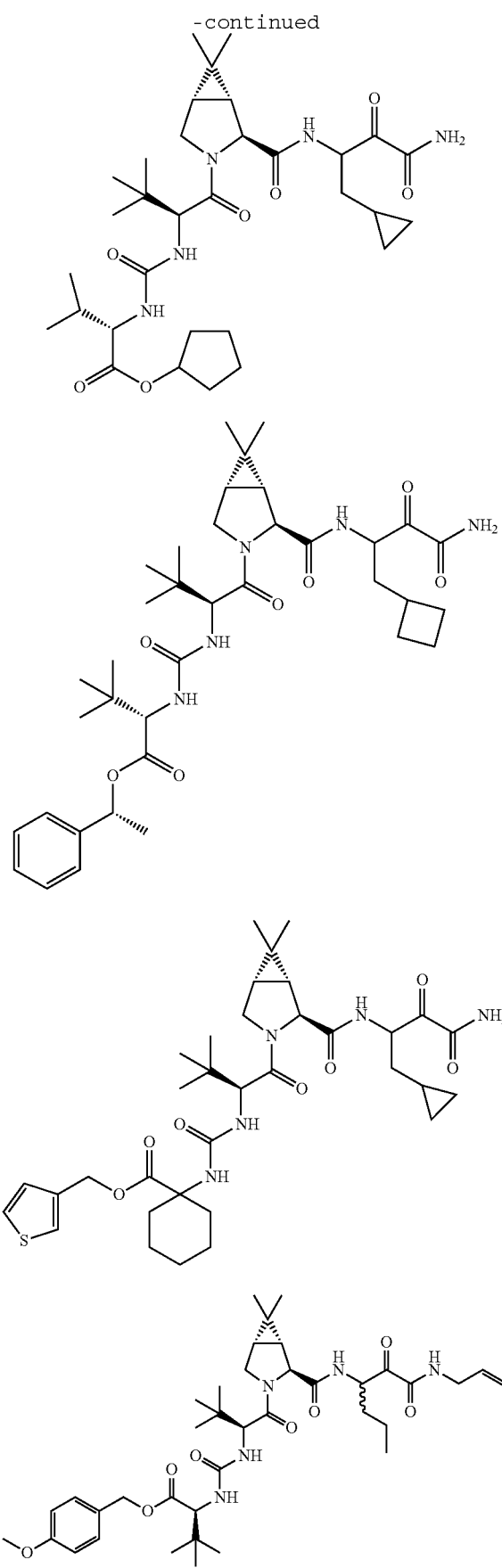
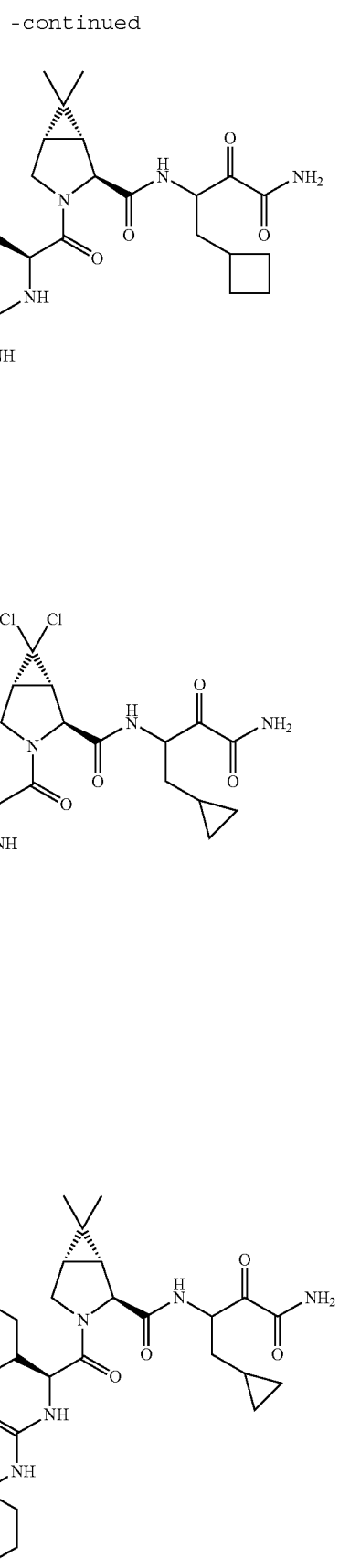

367
-continued
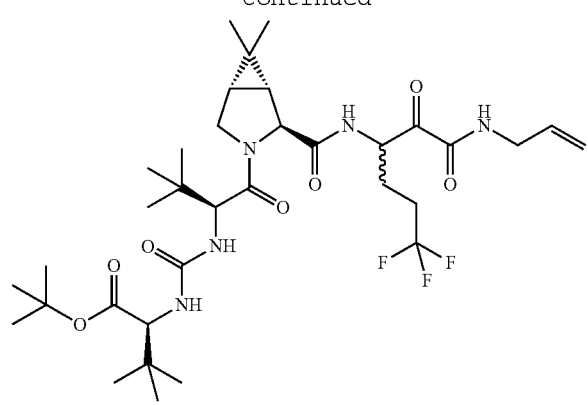
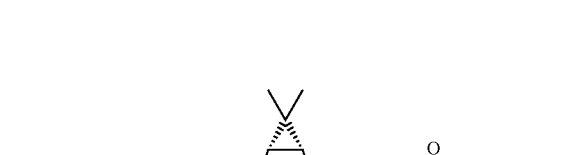
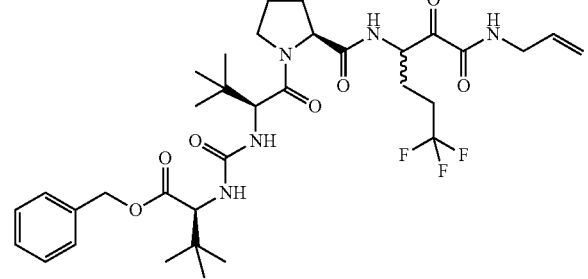
368
-continued
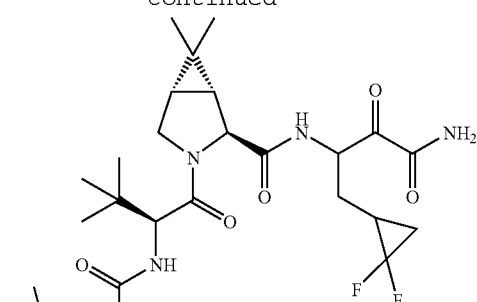
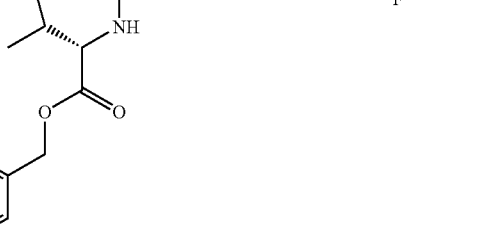
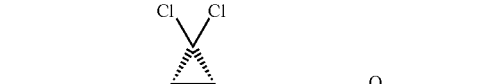

369
-continued
370
-continued
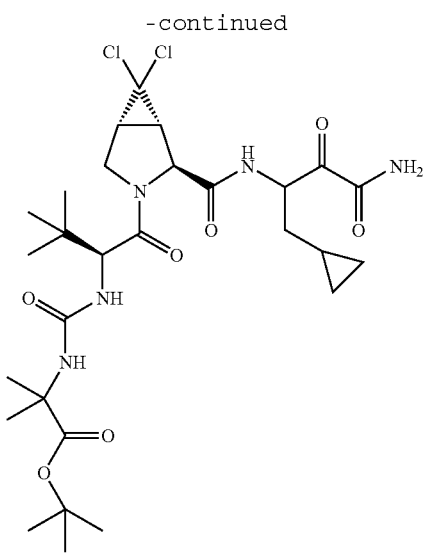
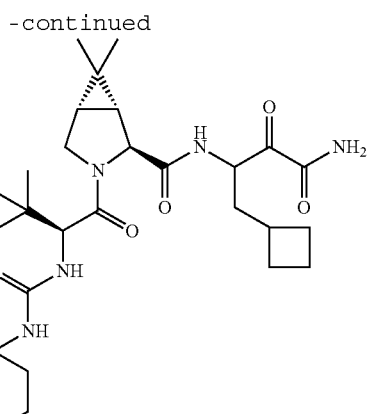
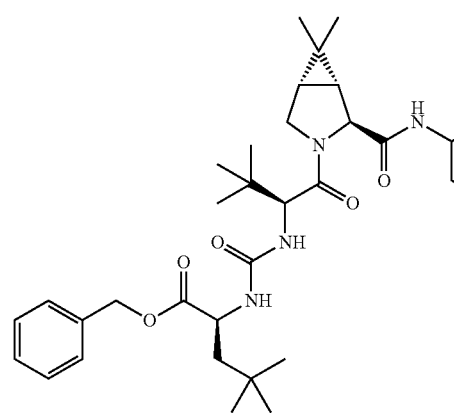
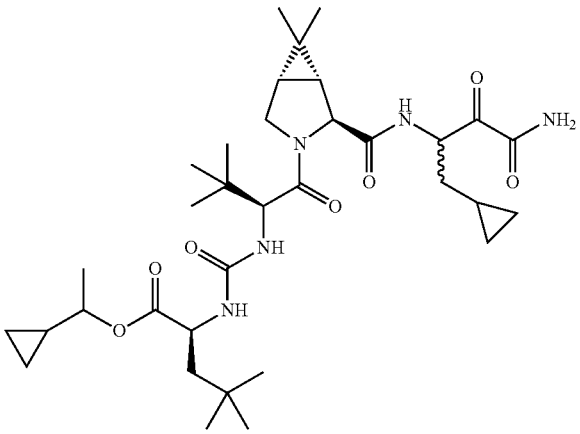

371
-continued
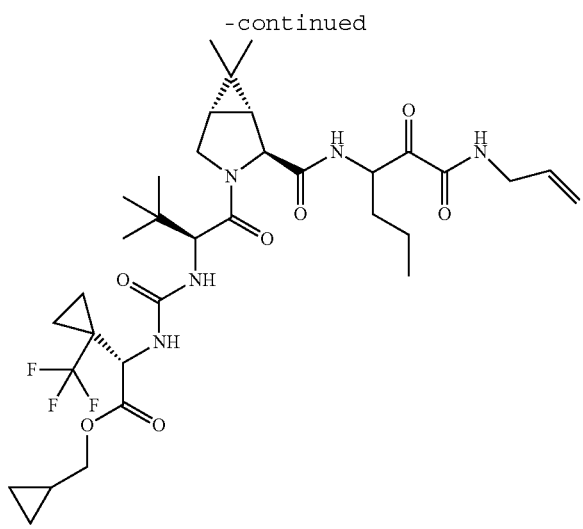
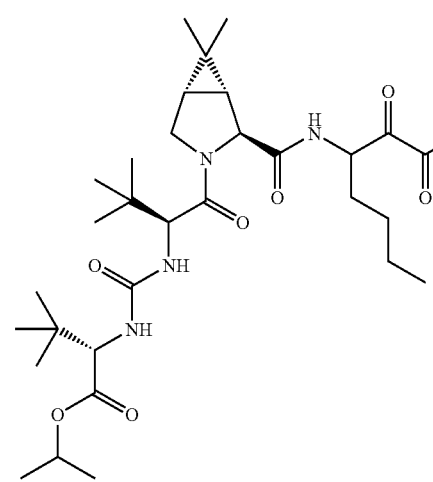
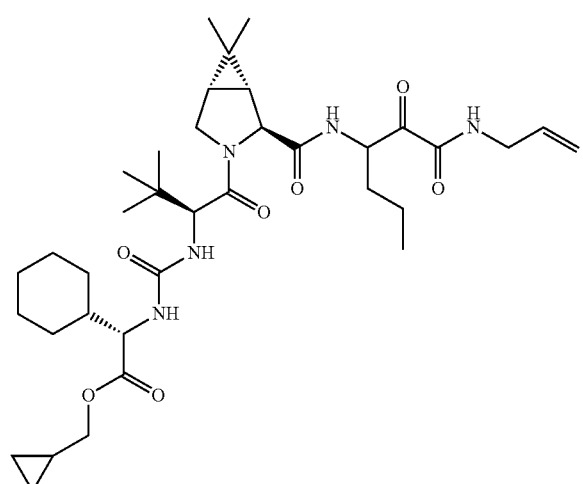
372
-continued
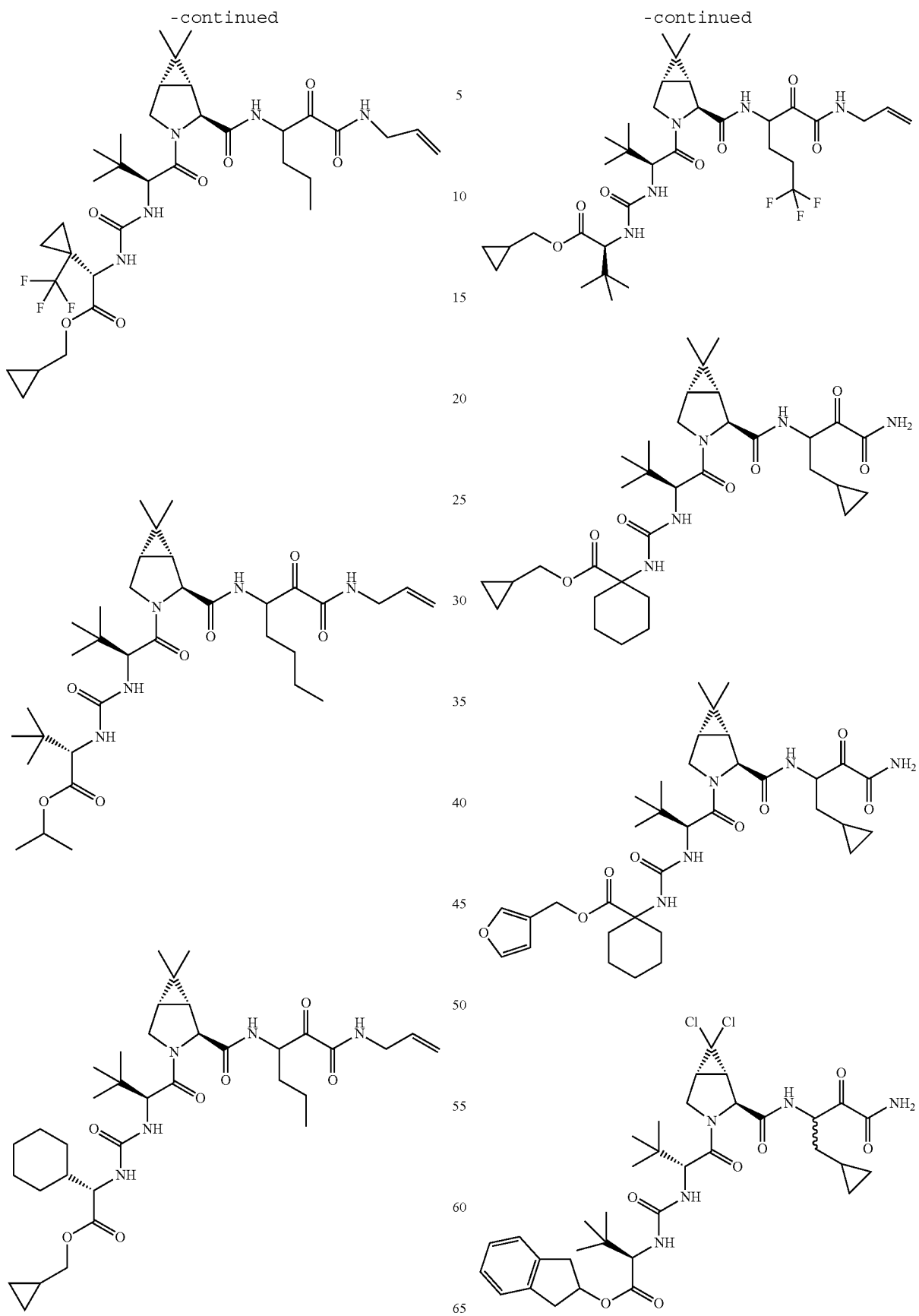

373
-continued
374
-continued
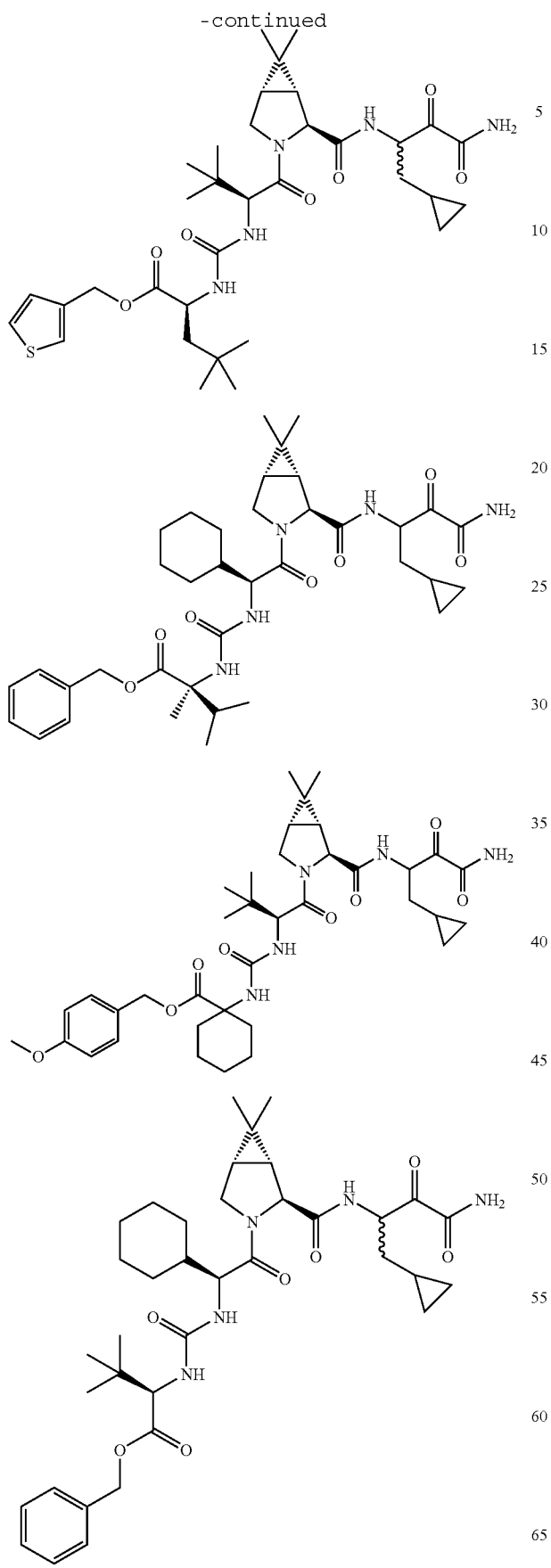
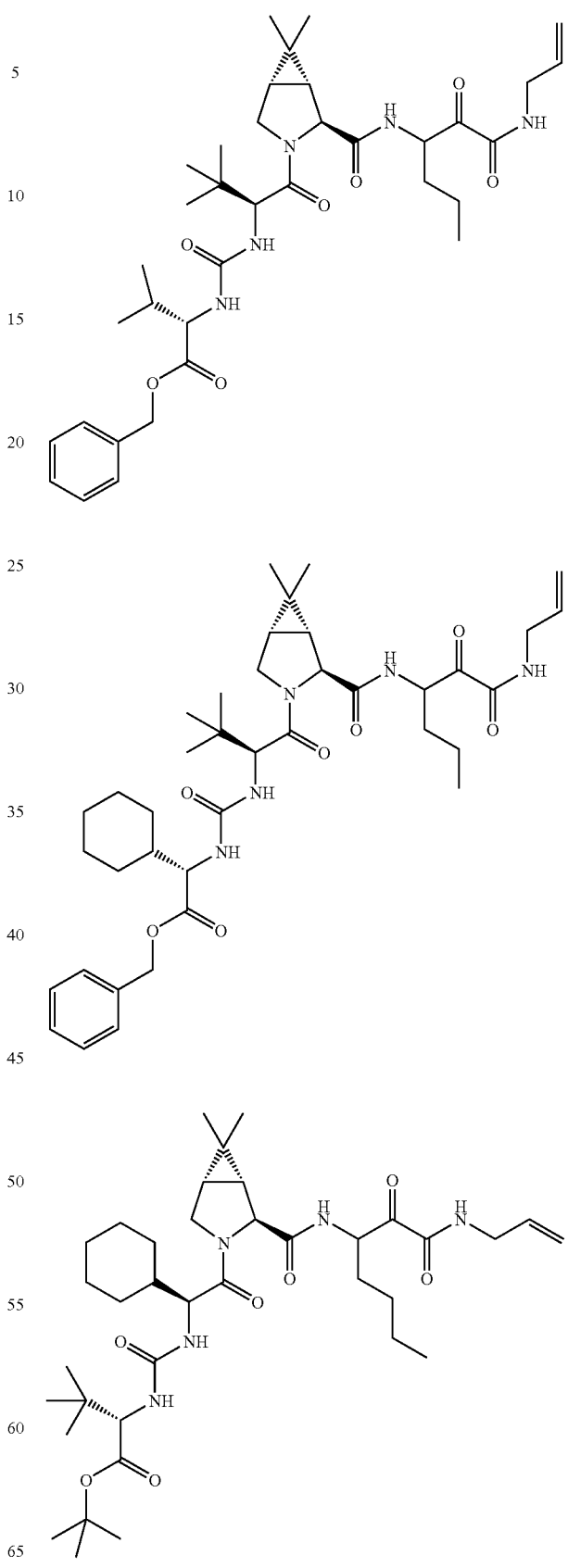

375
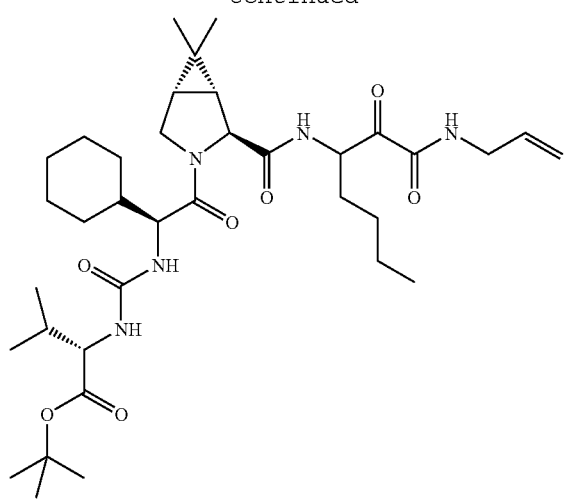
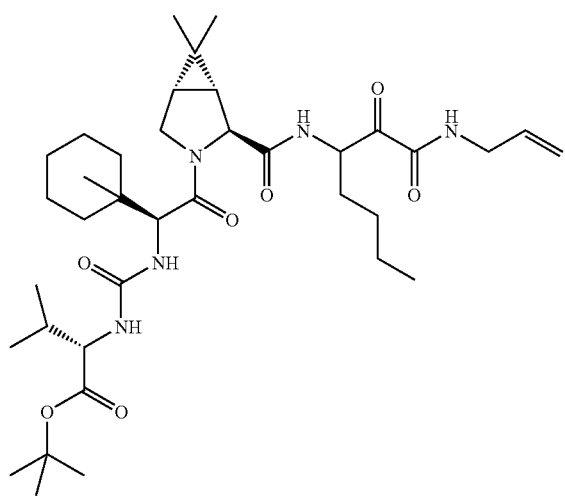
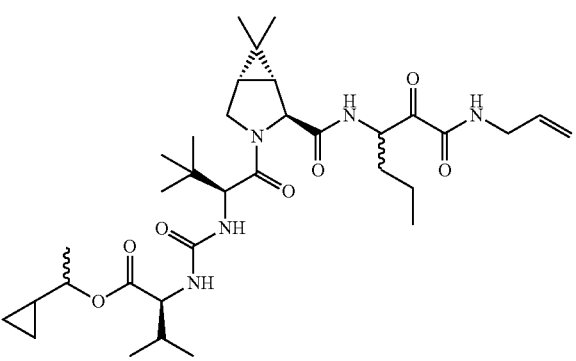
376
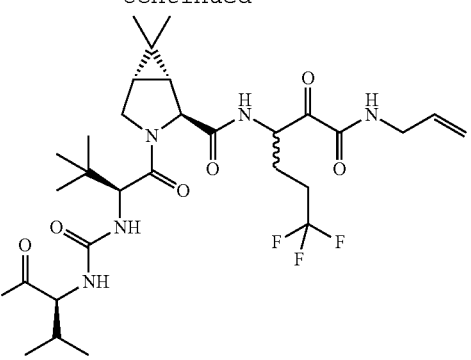
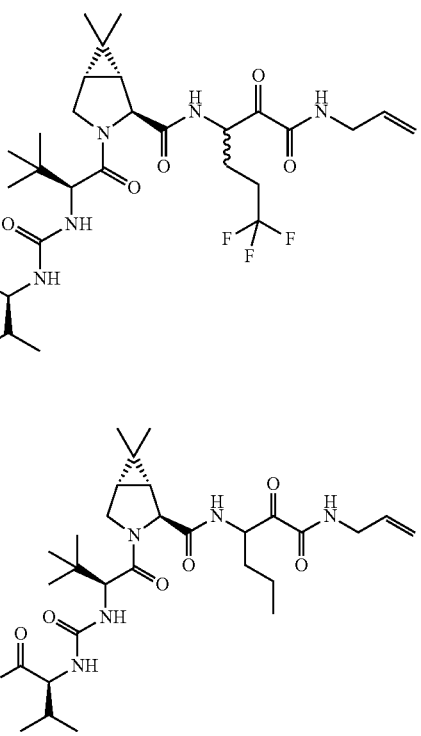
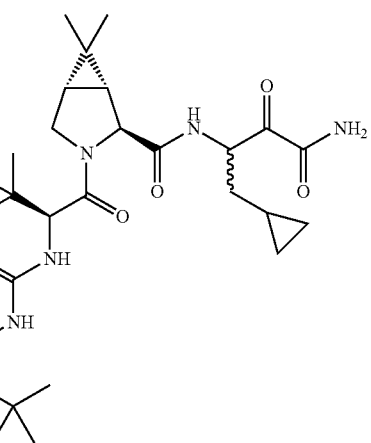

377       378
-continued   -continued
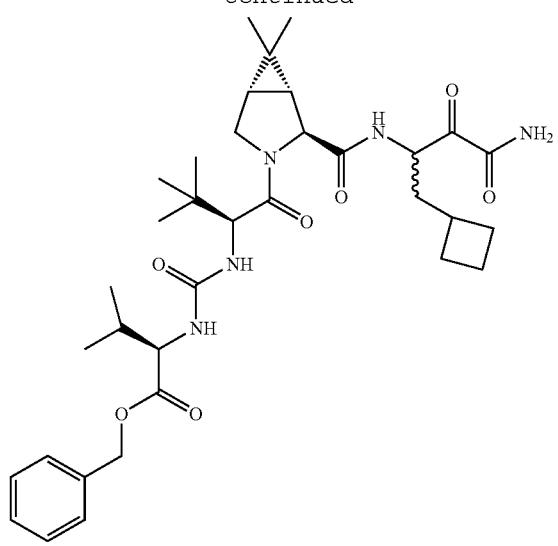
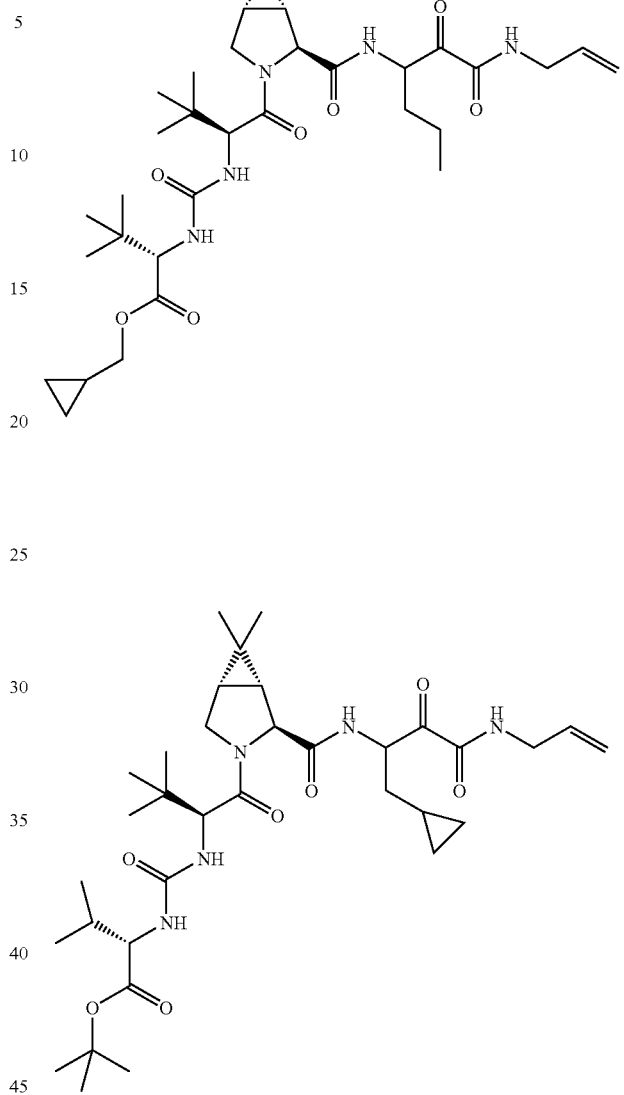
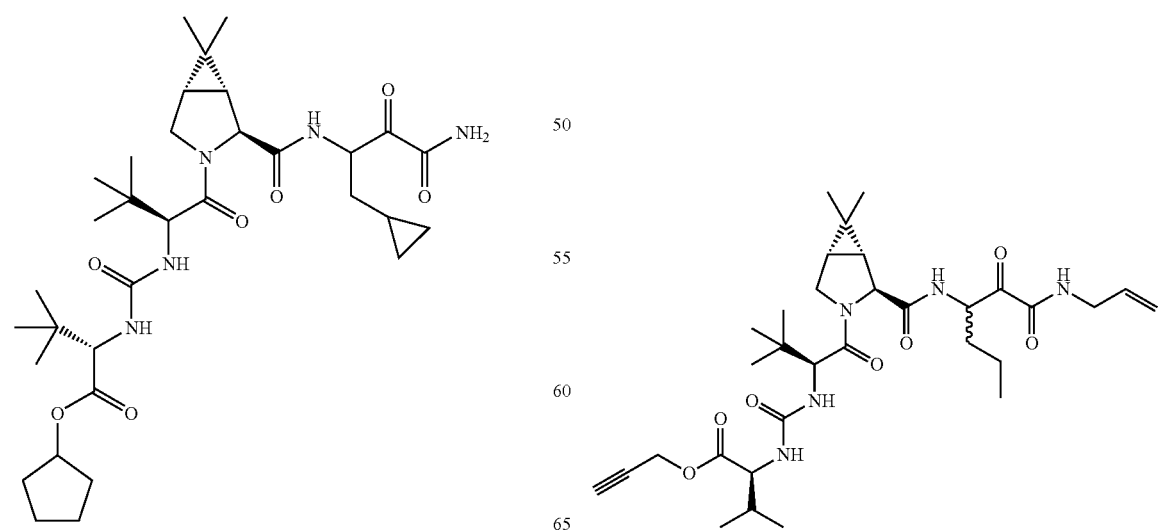

379 -continued
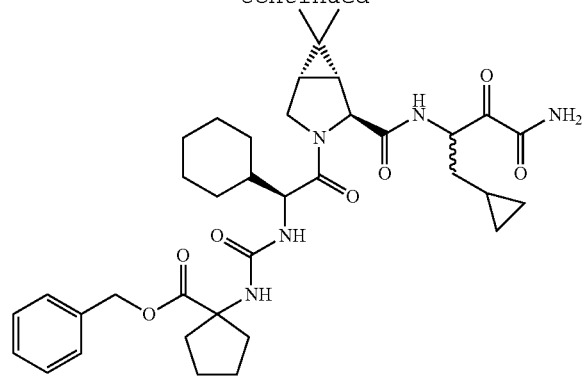
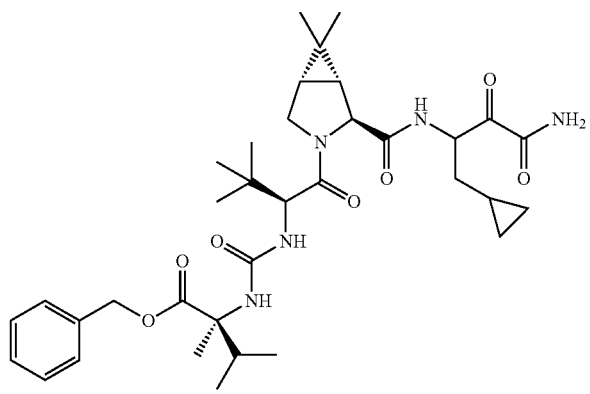
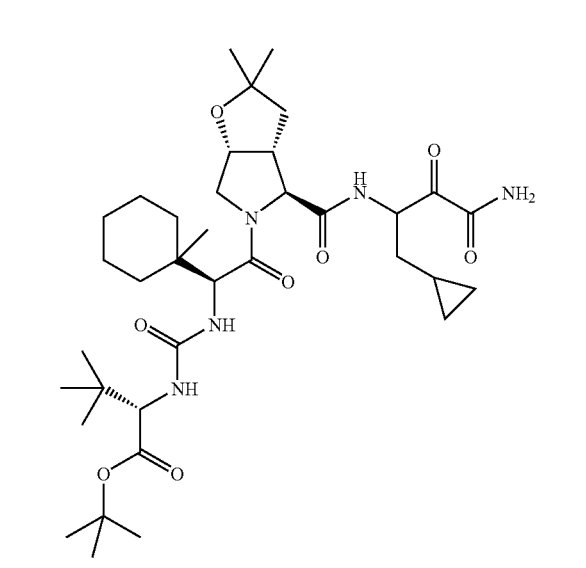
380 -continued
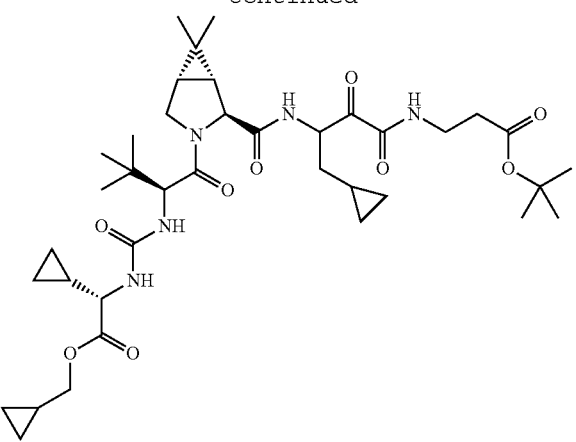
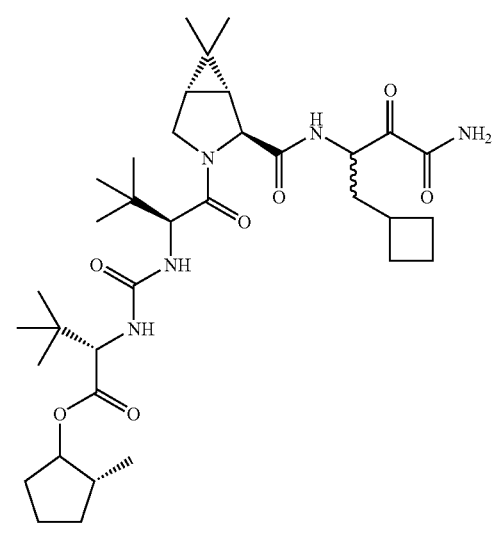

381
-continued
382
-continued
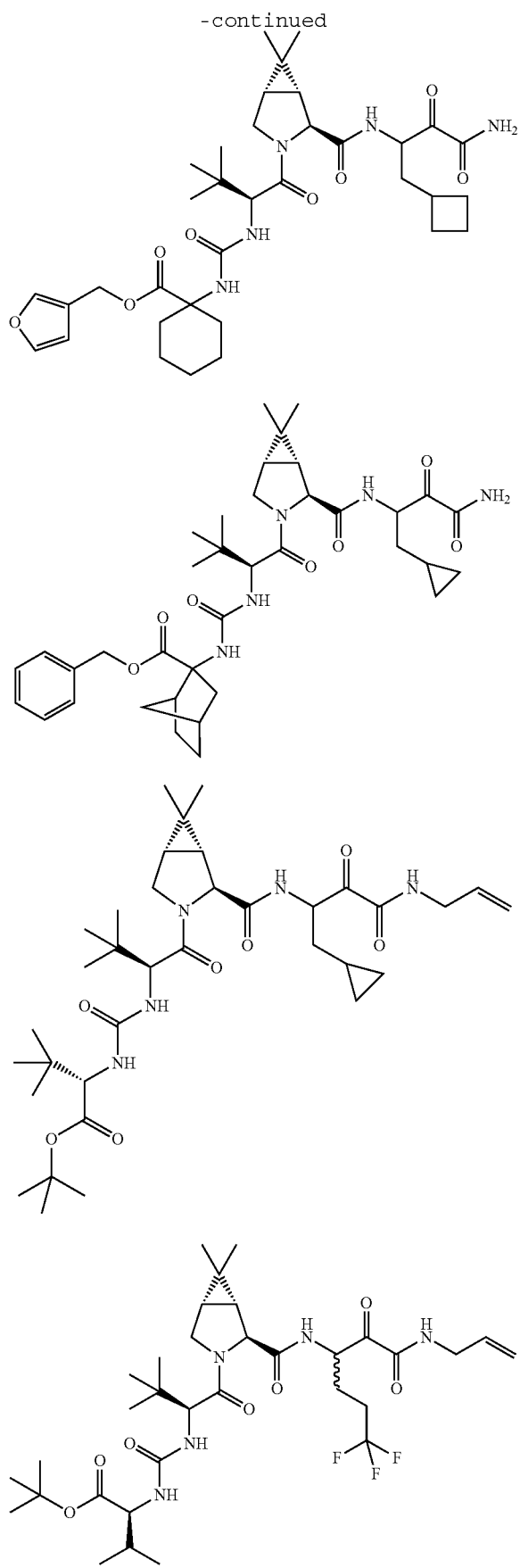
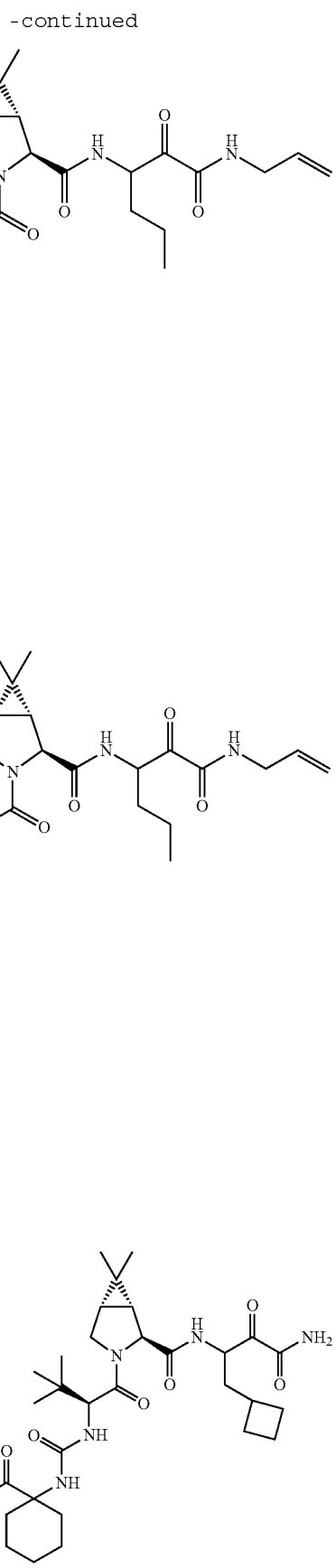

383
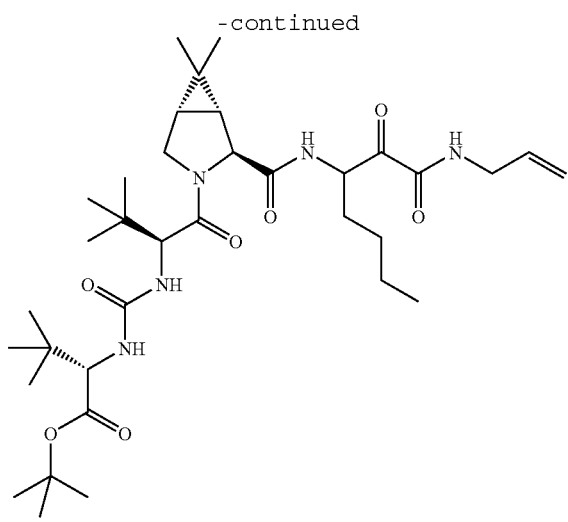
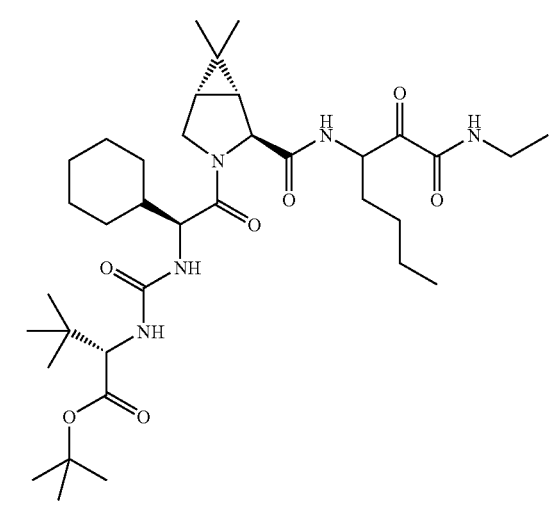
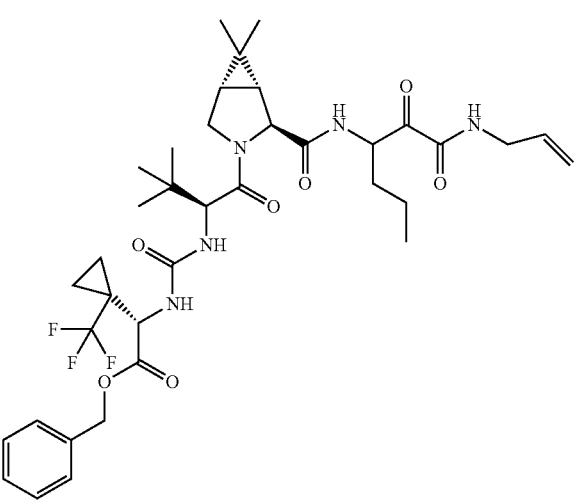
384
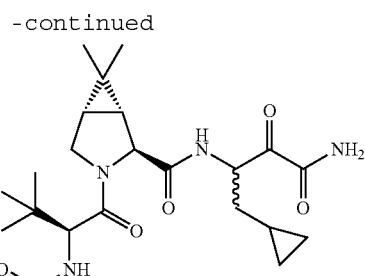
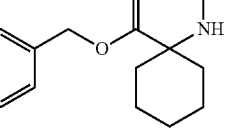
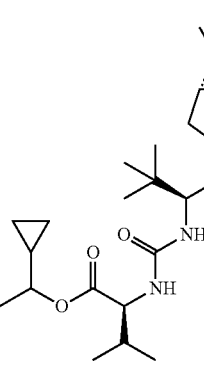
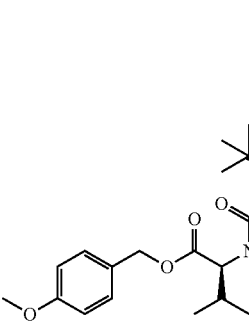
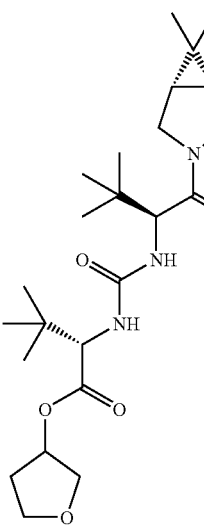

385
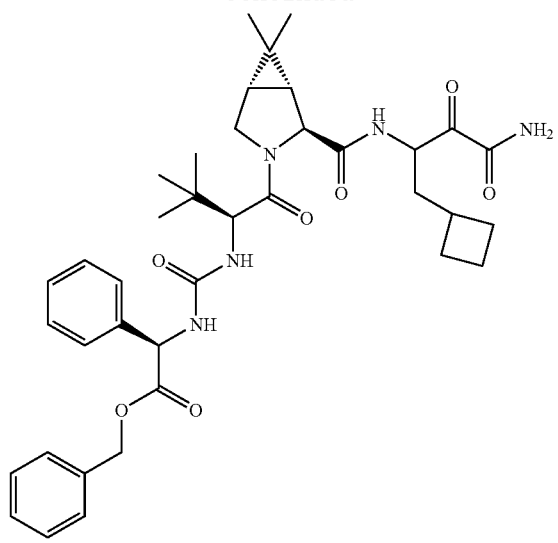
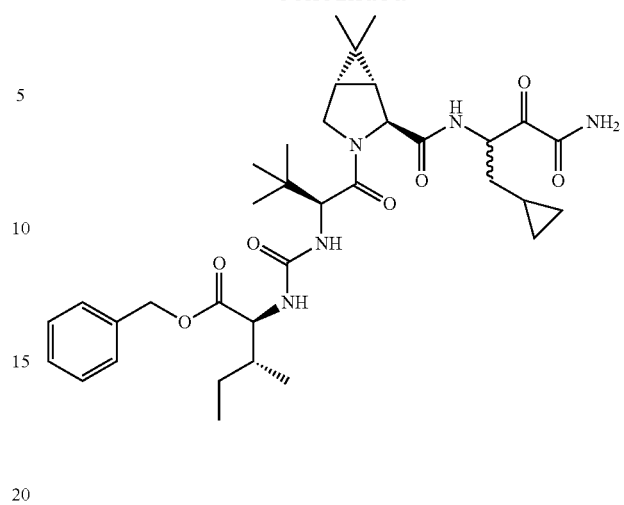
386
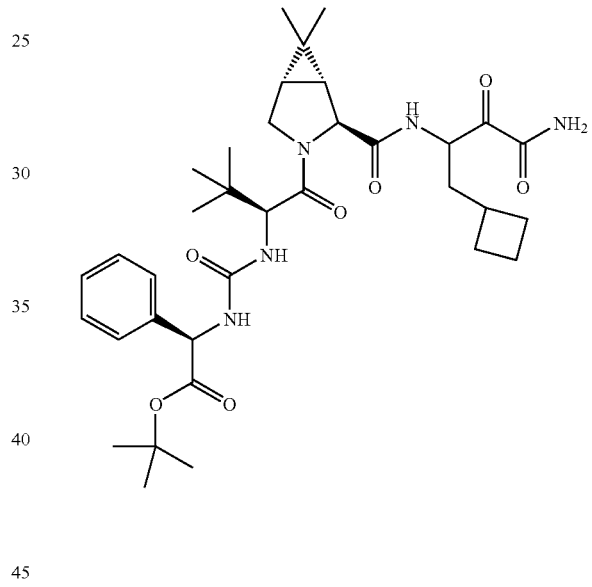
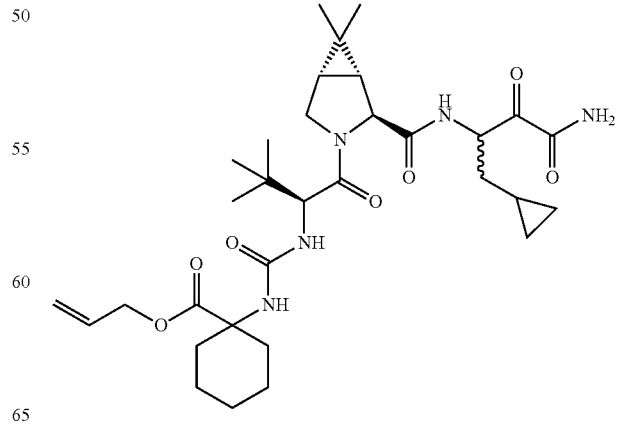

387                                        388
-continued                                 -continued
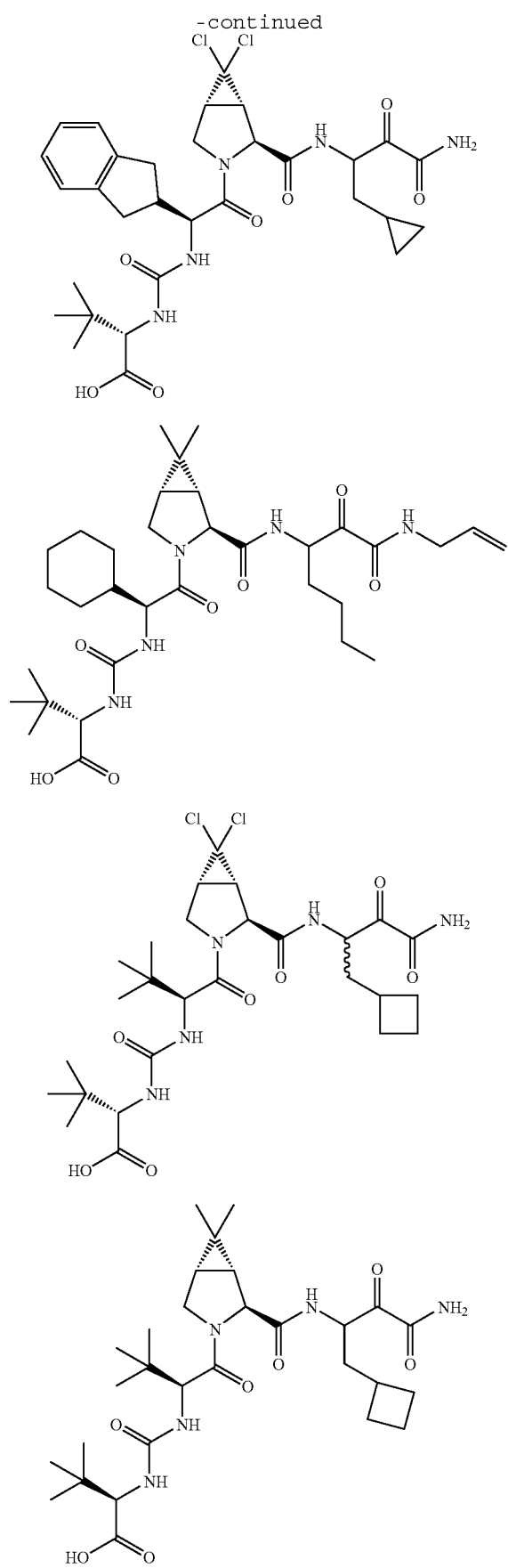
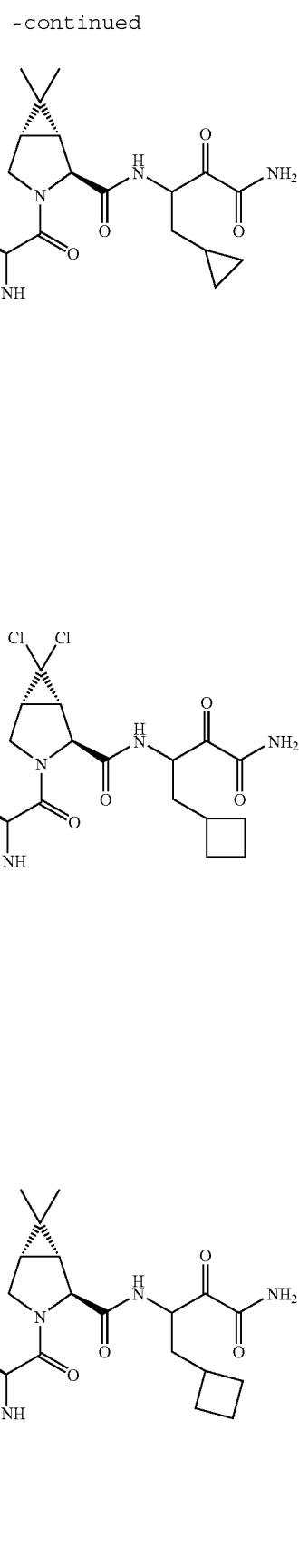

389                                    390
-continued                             -continued
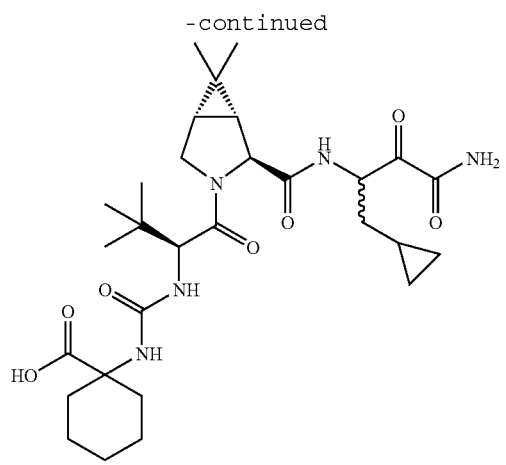
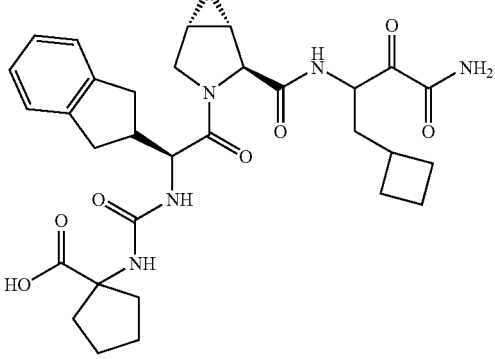
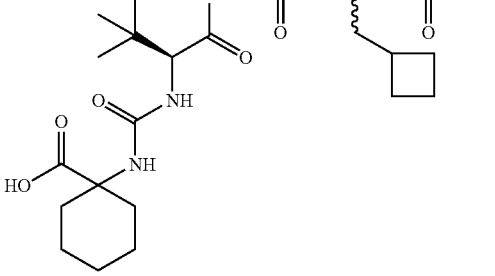
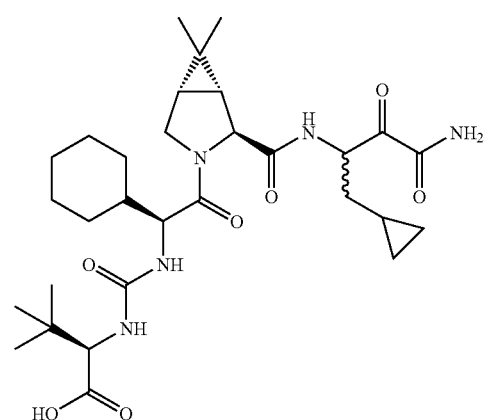

391
-continued
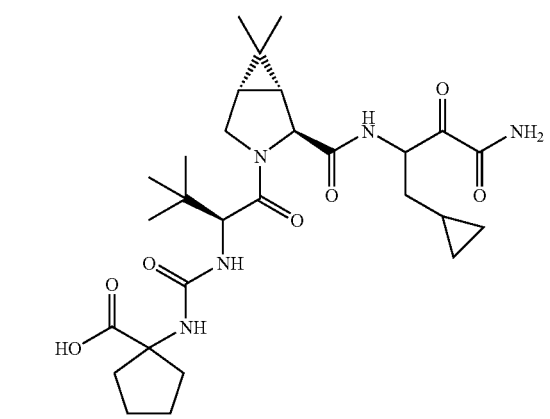
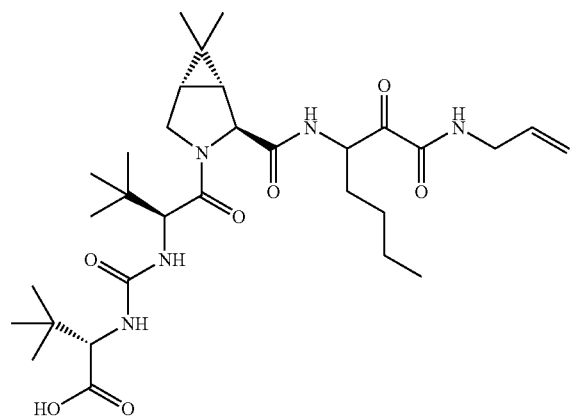
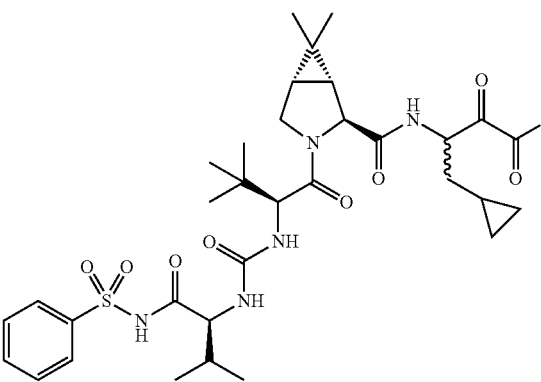
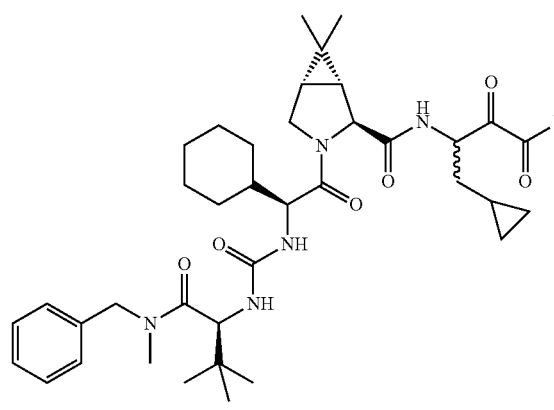
392
-continued
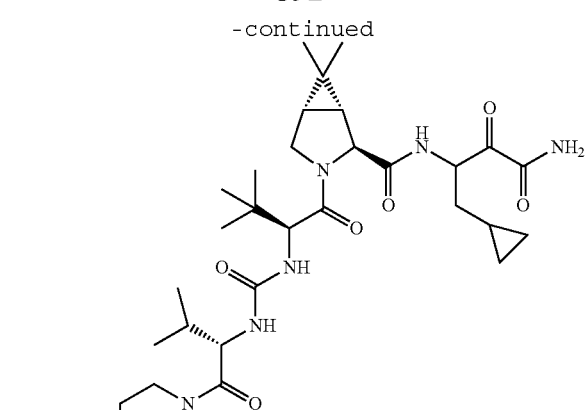
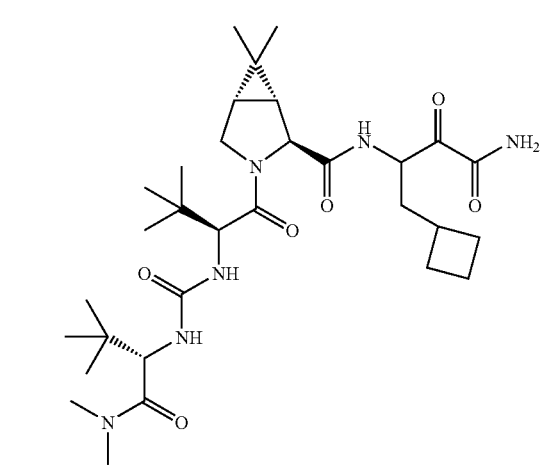
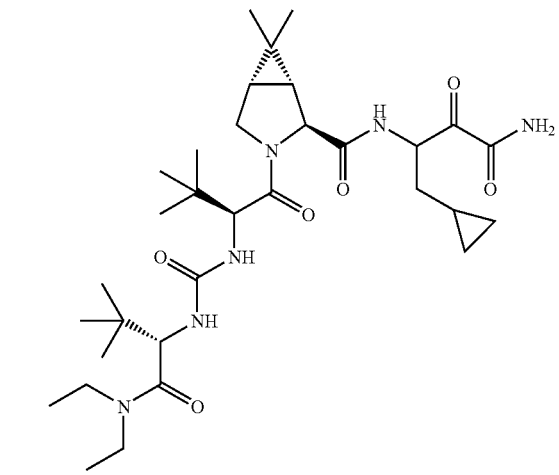

393
-continued
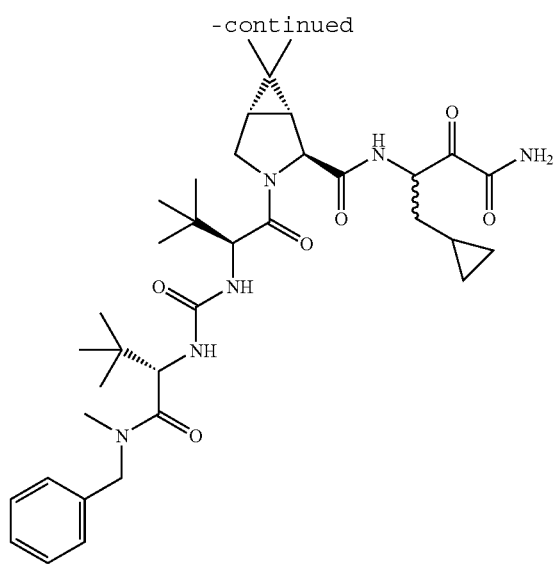
394
-continued
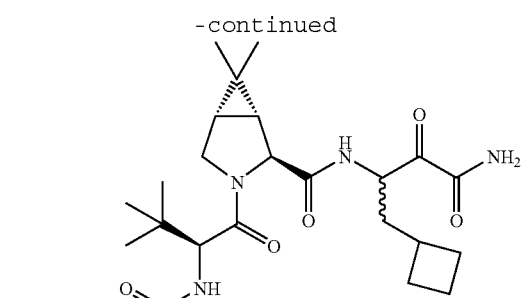
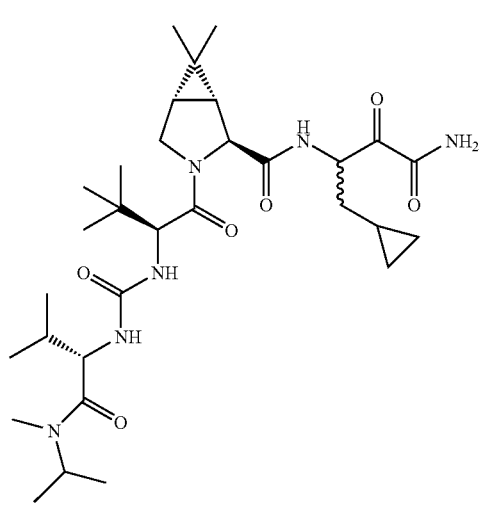
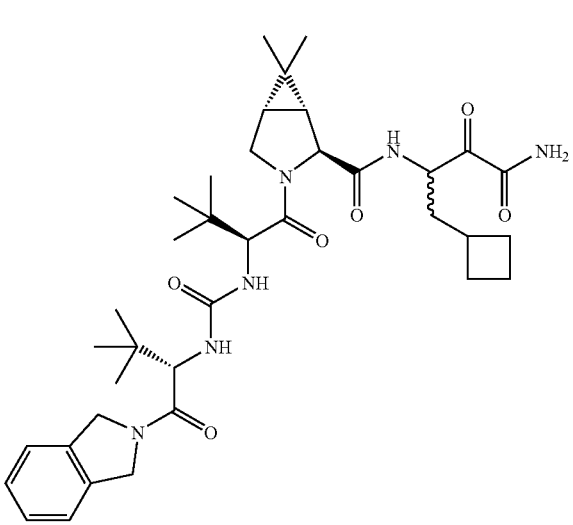
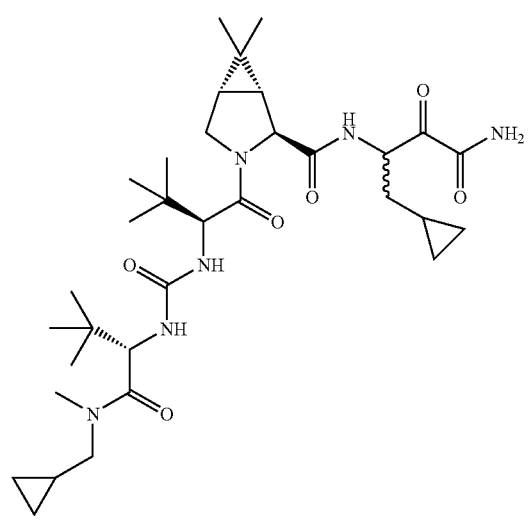
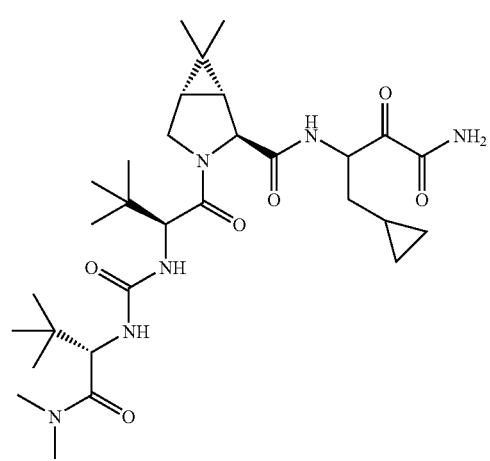

395
-continued
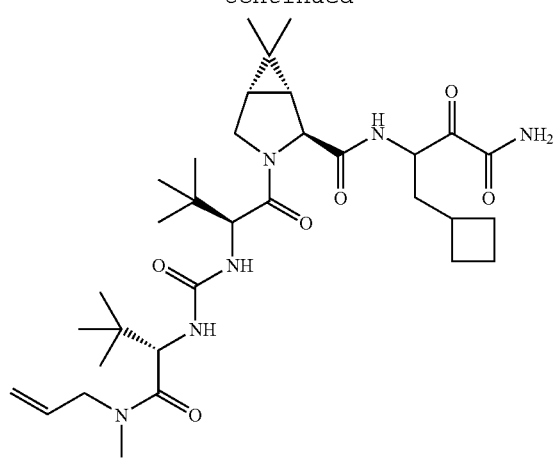
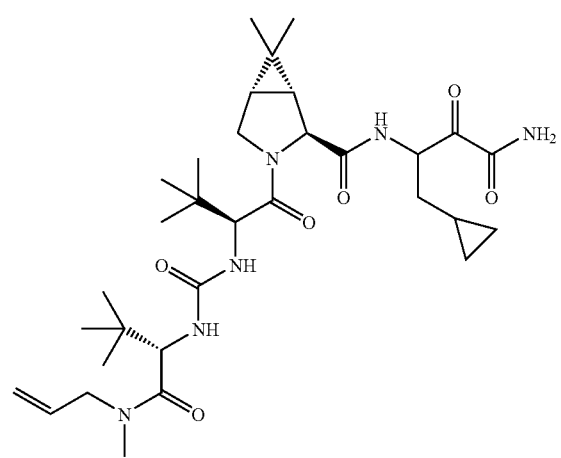
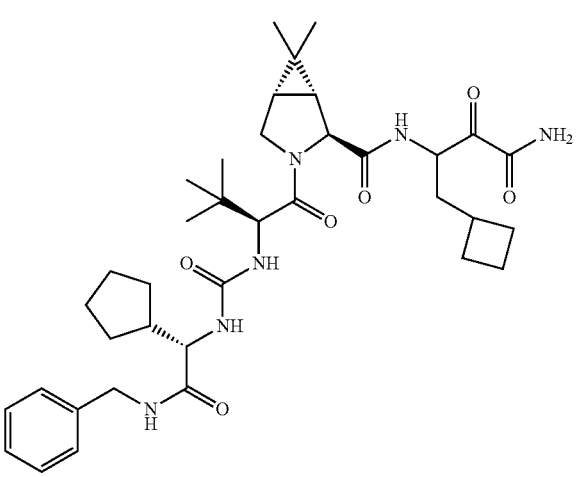
396
-continued
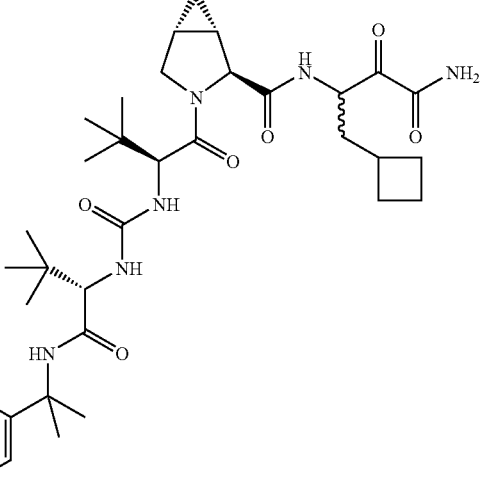
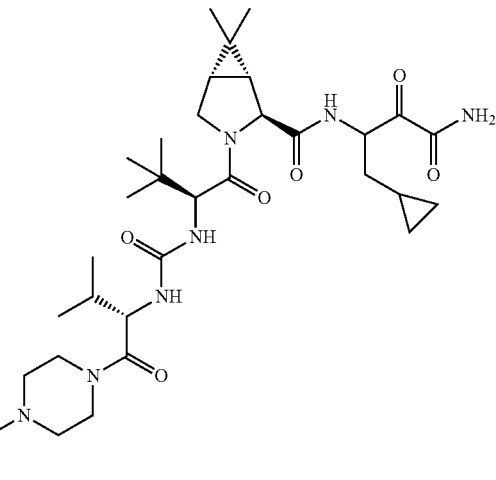

397
-continued
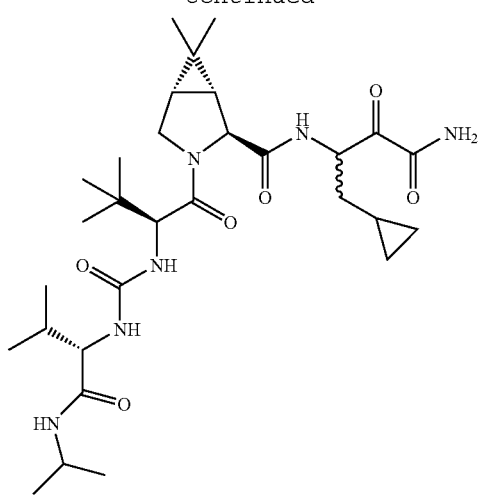
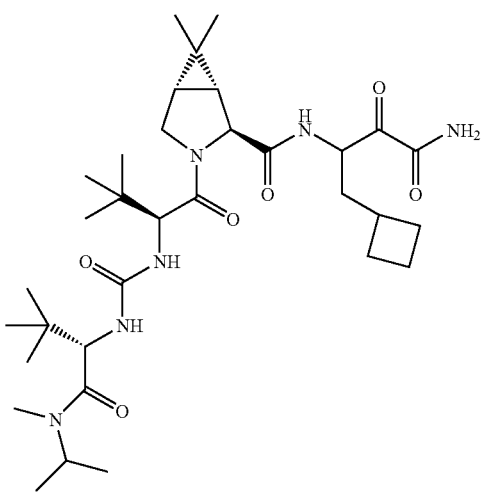
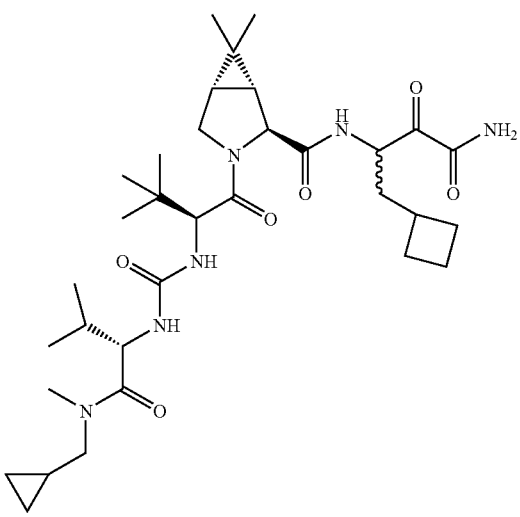
398
-continued
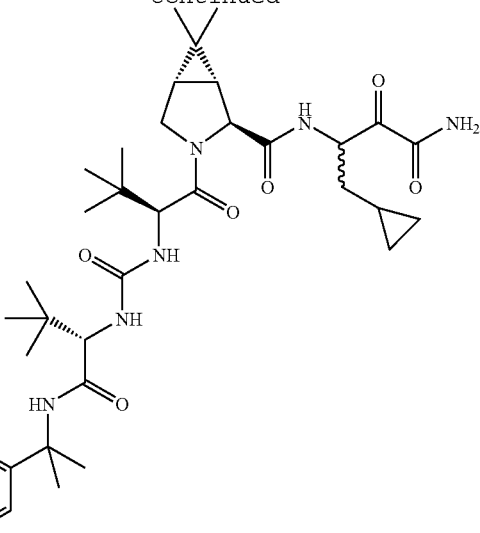
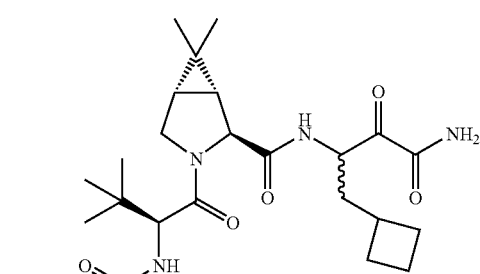
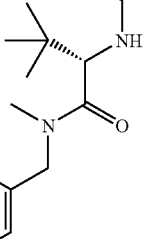
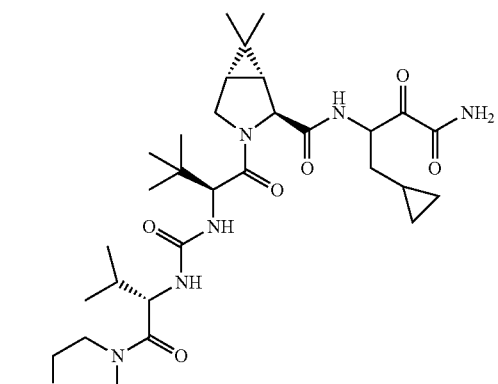

399 -continued
400 -continued
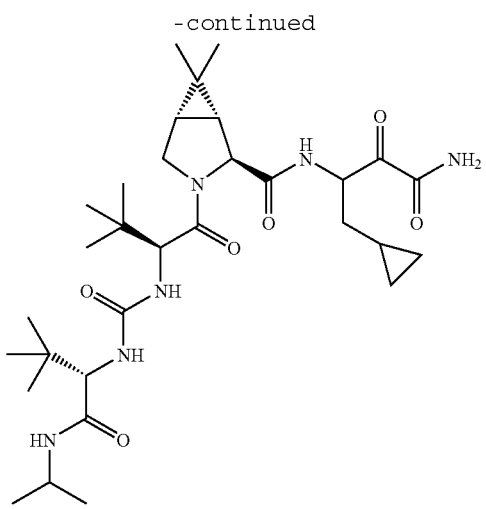
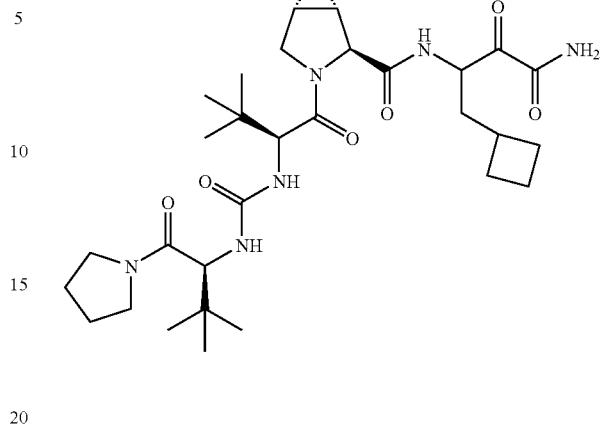
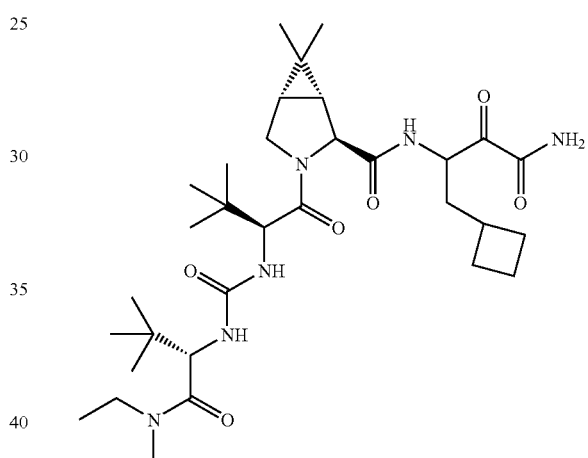
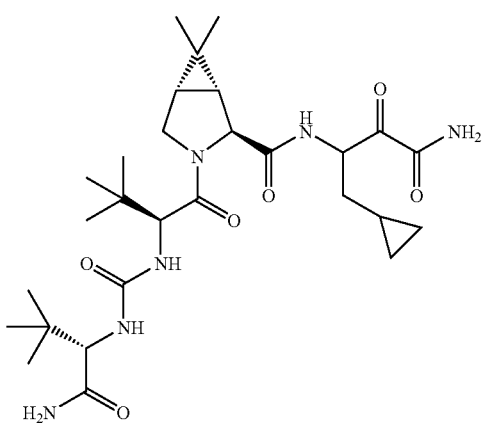
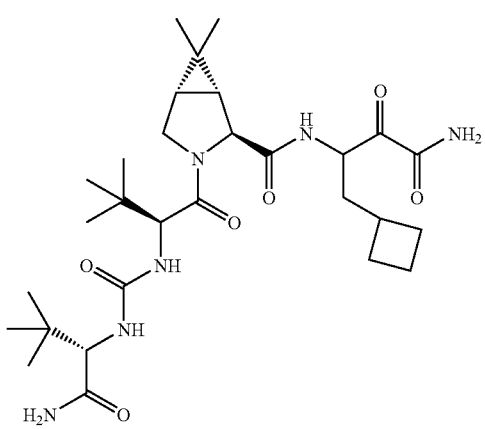

401
-continued
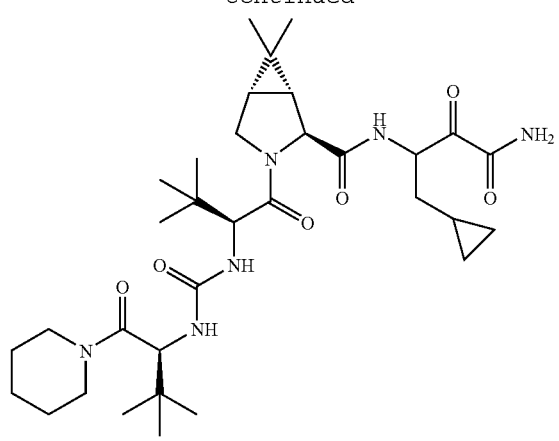
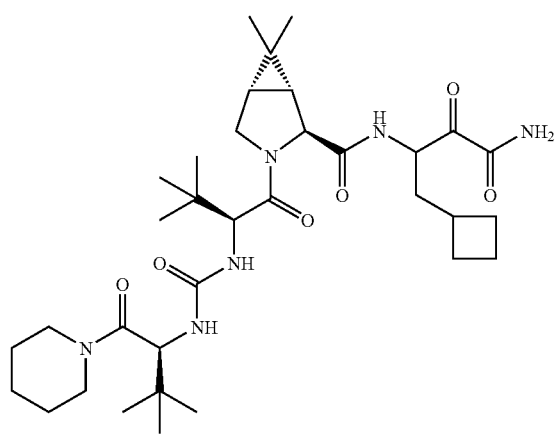
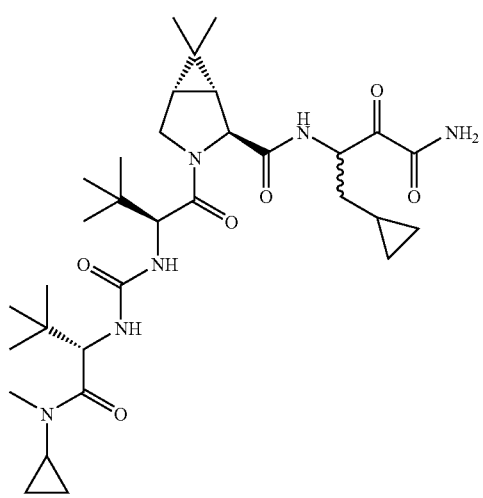
402
-continued
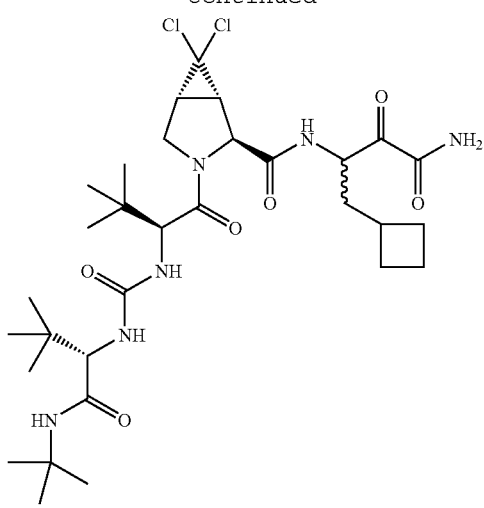
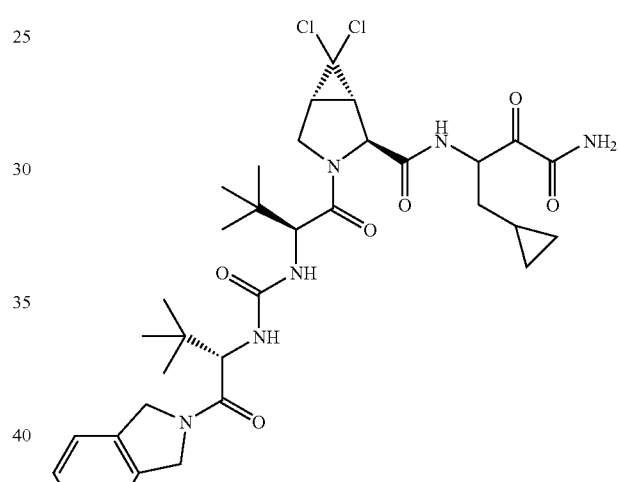
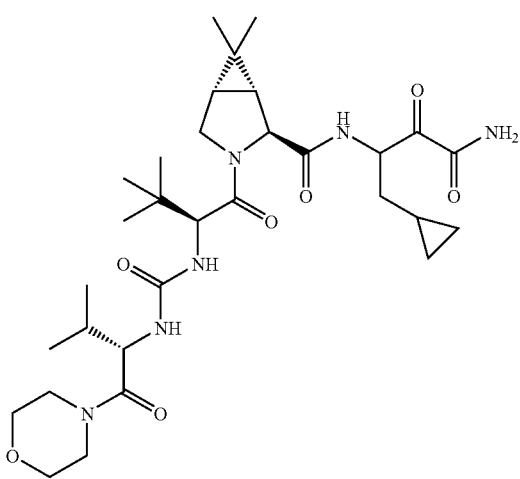

403                                    404
-continued                             -continued
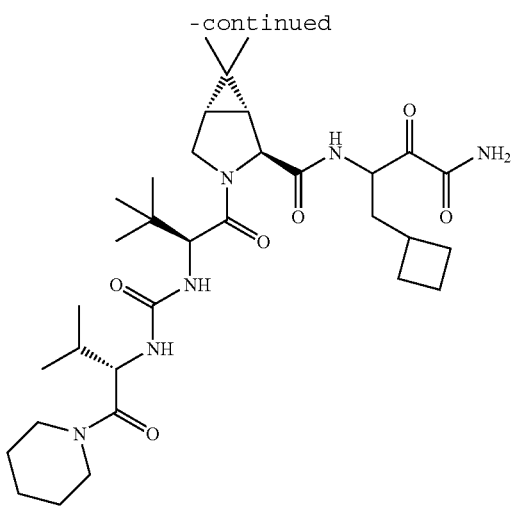 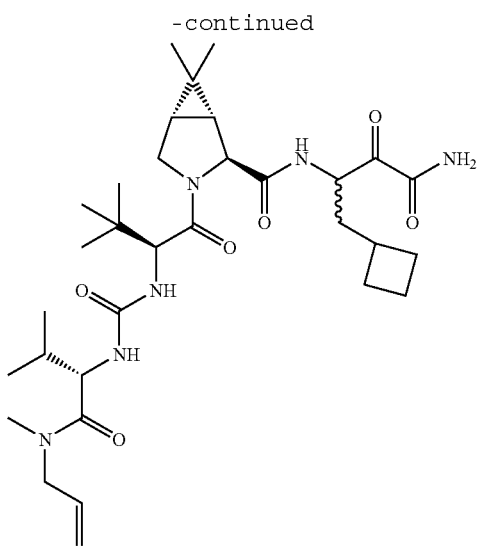
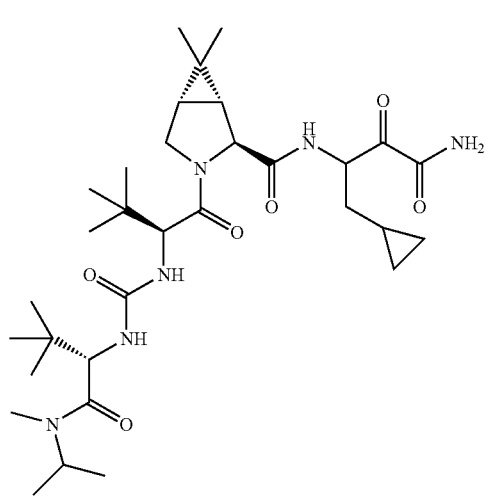 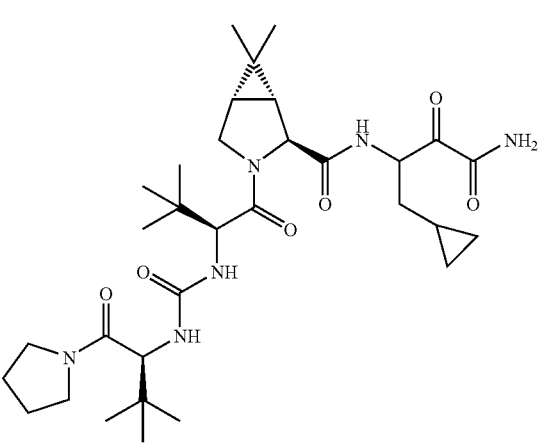
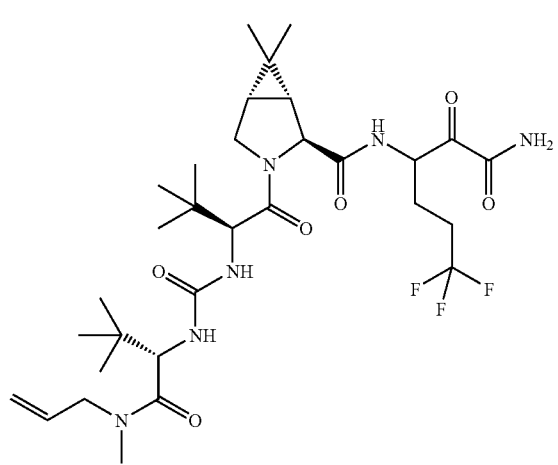 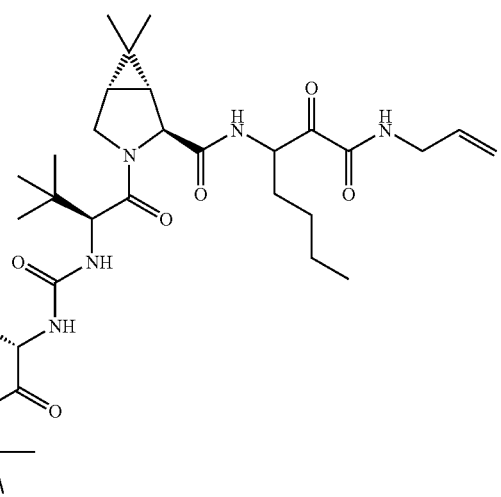

405
-continued
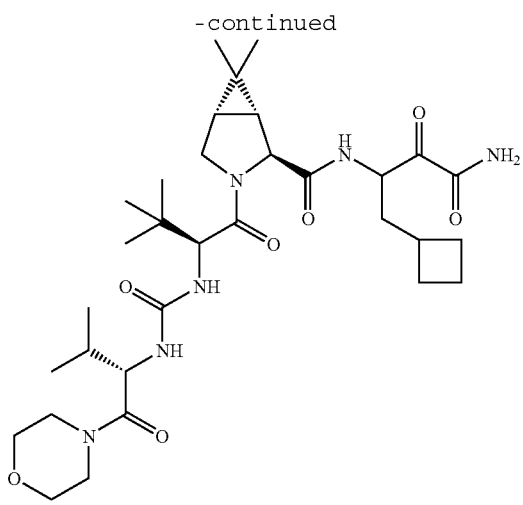
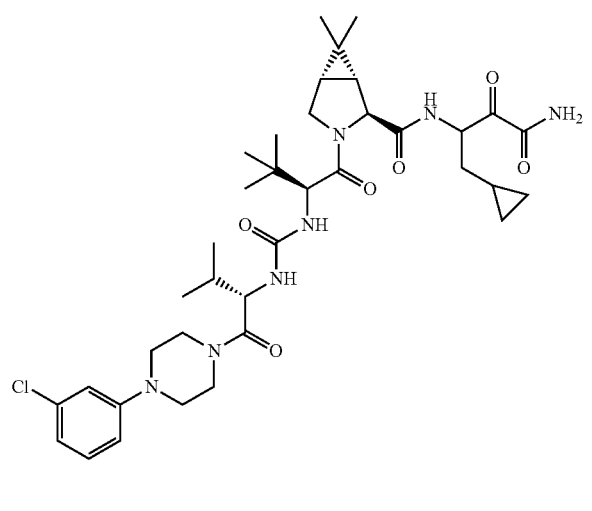
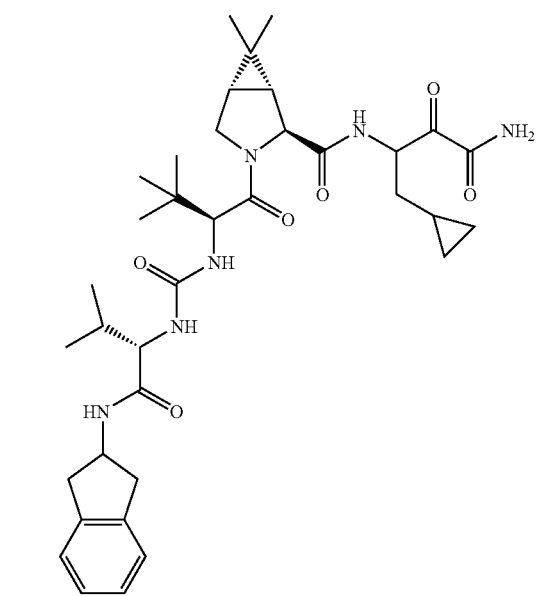
406
-continued
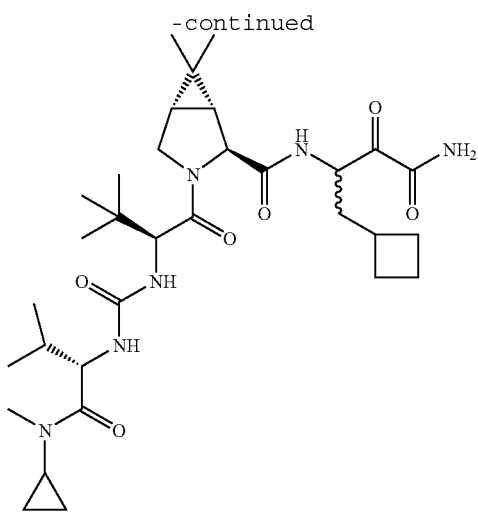
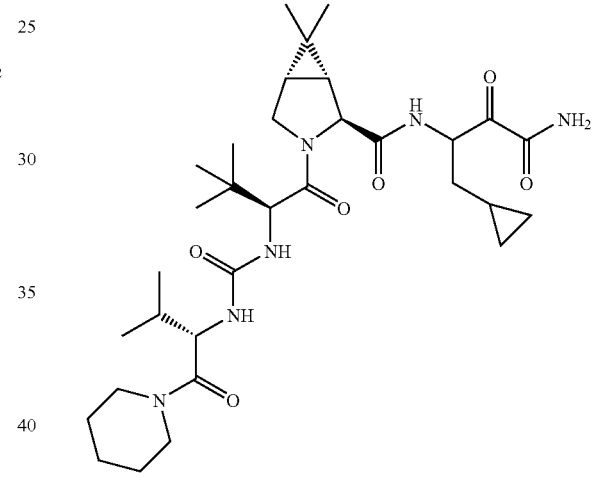

407
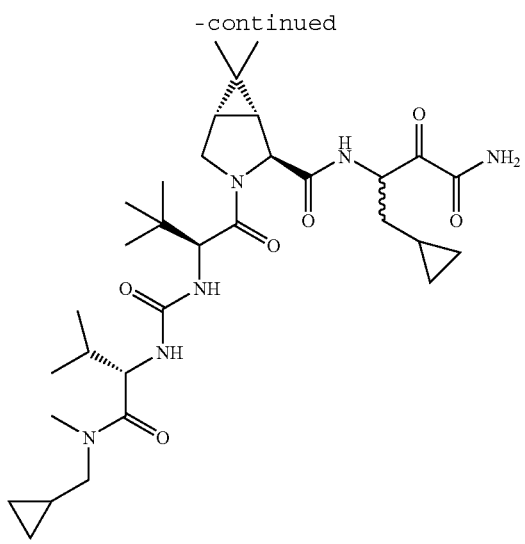
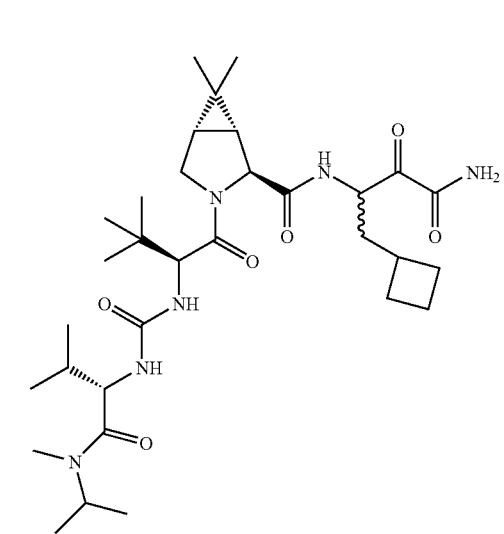
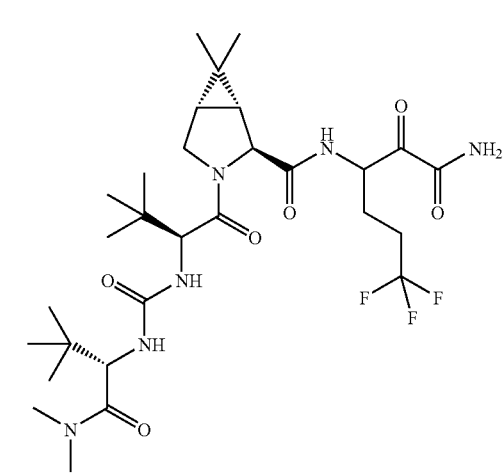
408
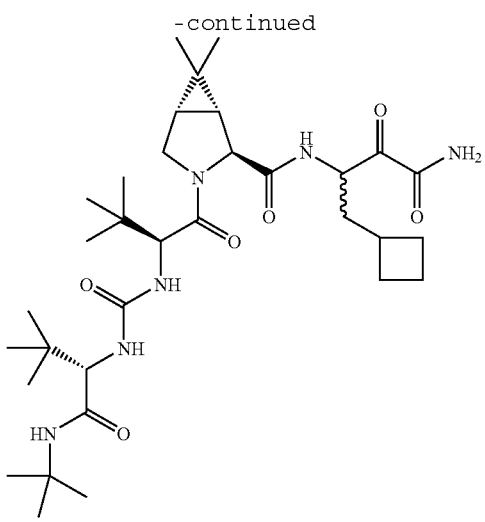
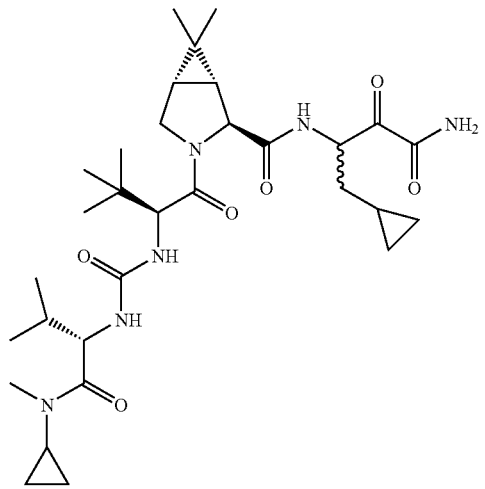

409
-continued
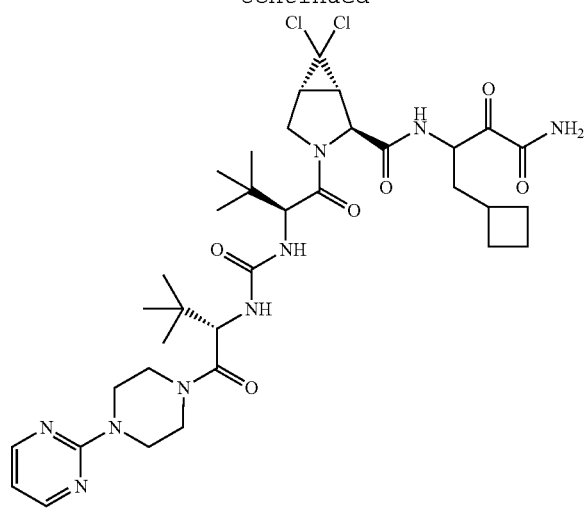
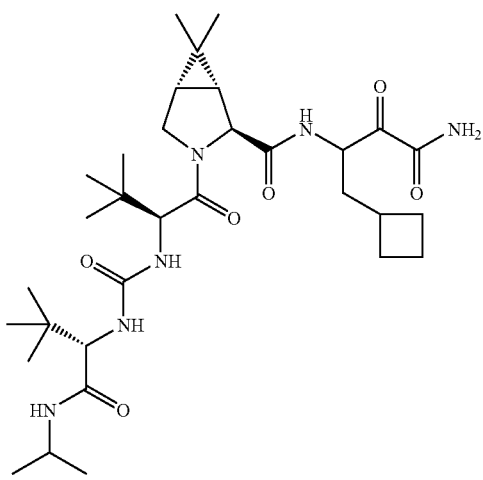
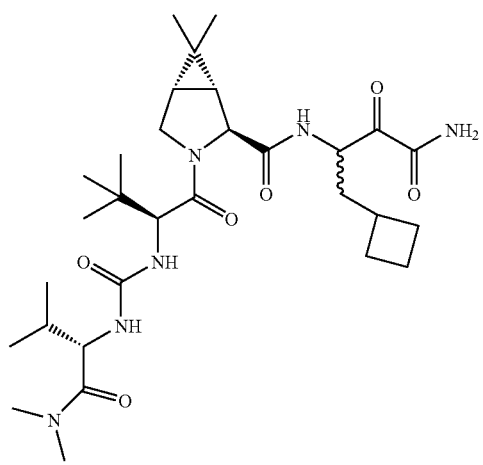
410
-continued
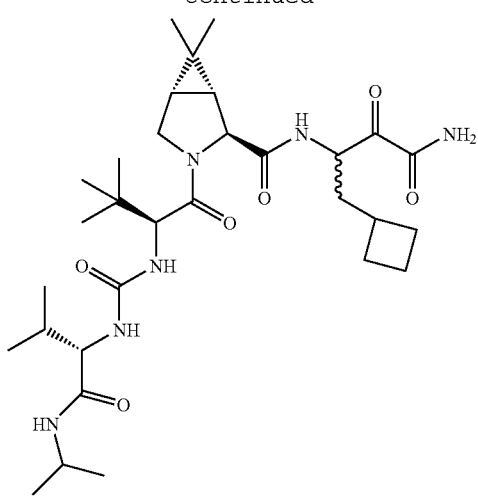
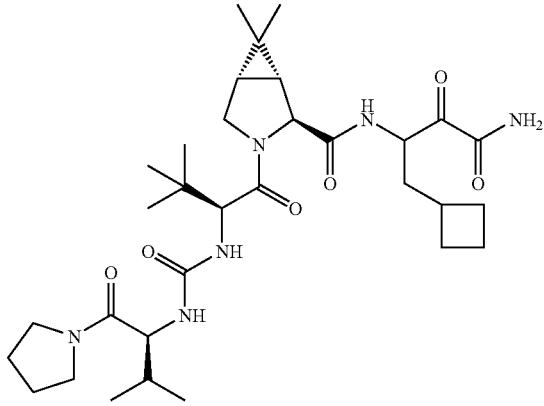
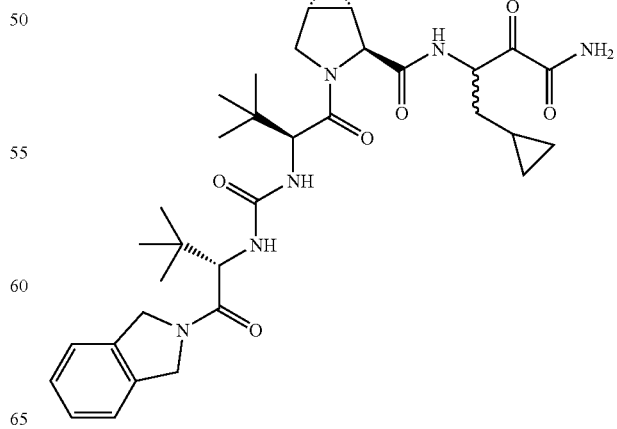

411
-continued
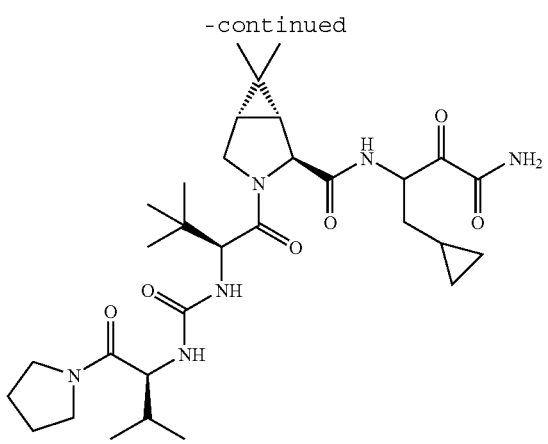
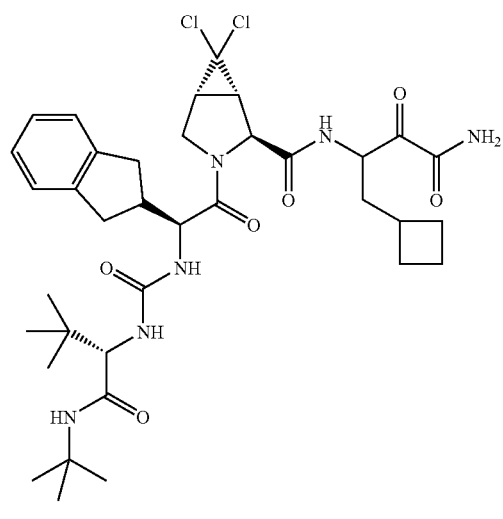
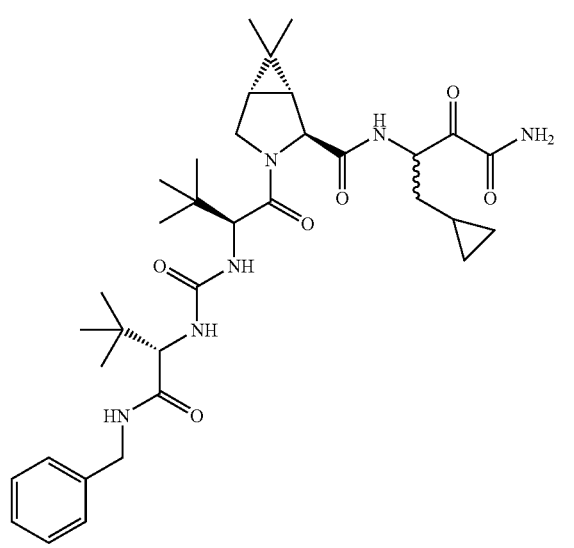
412
-continued
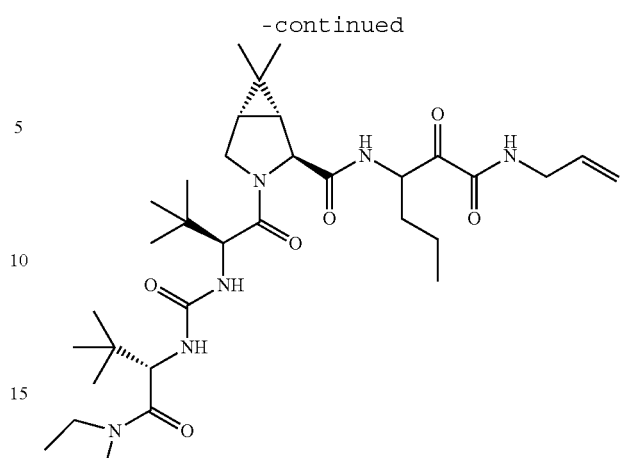
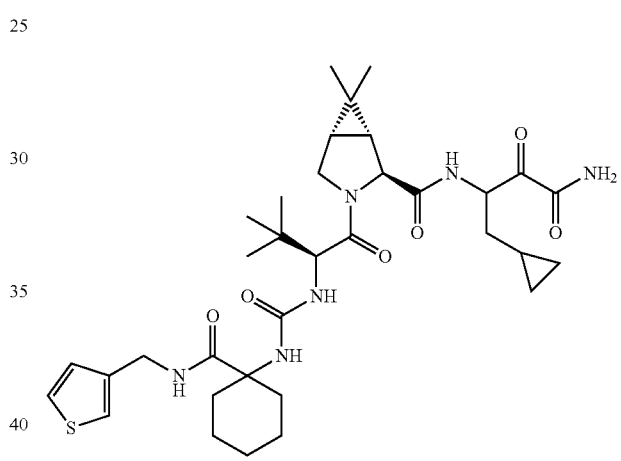
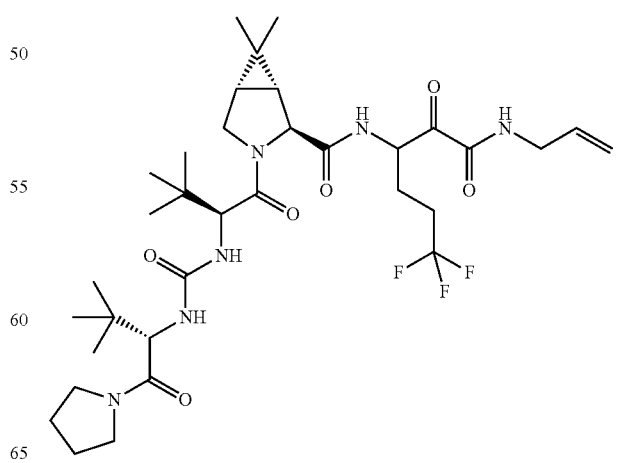

413                                           414
-continued                                   -continued
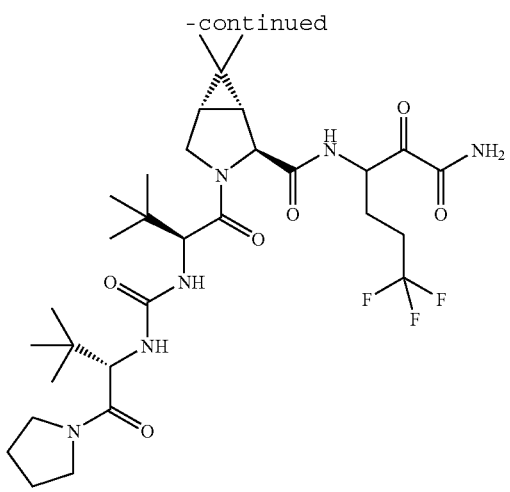
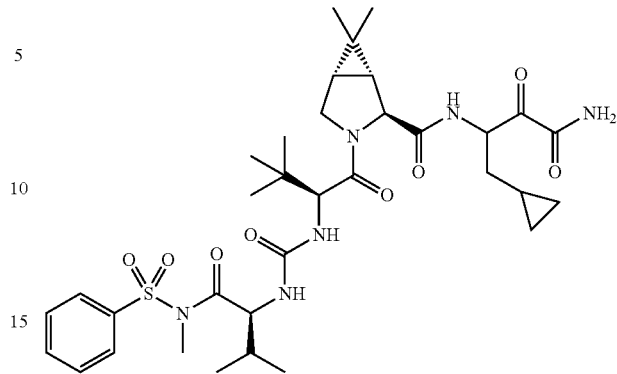
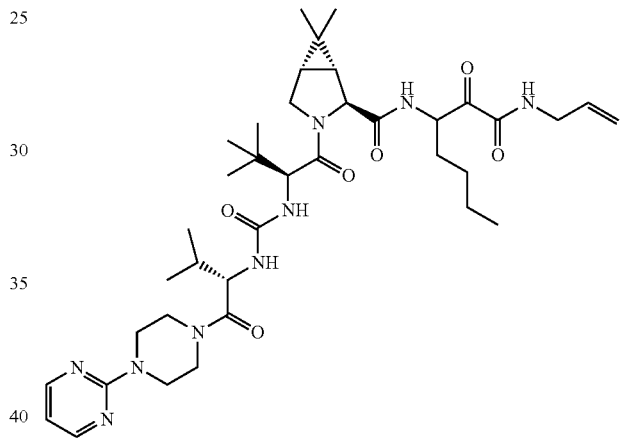
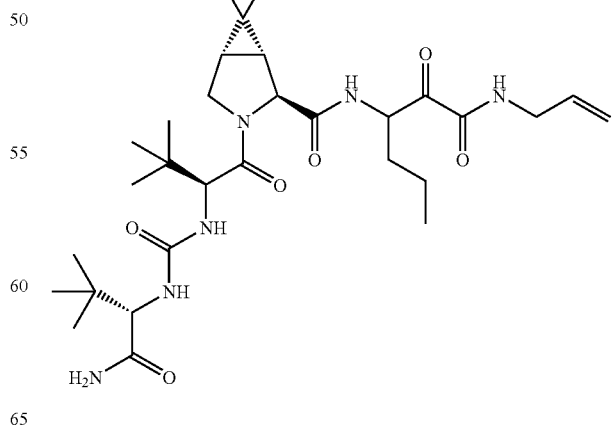

415
-continued
416
-continued
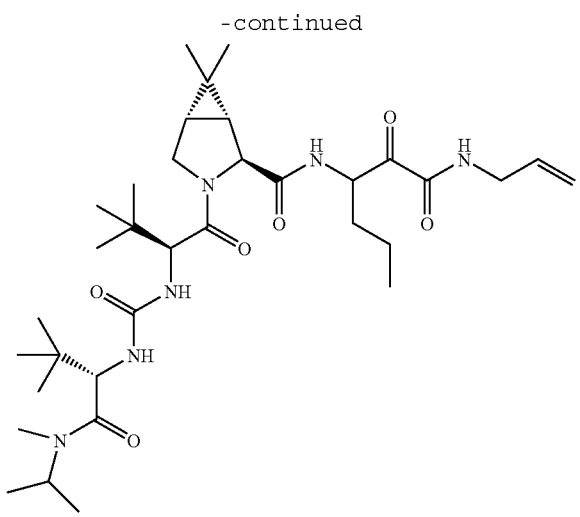
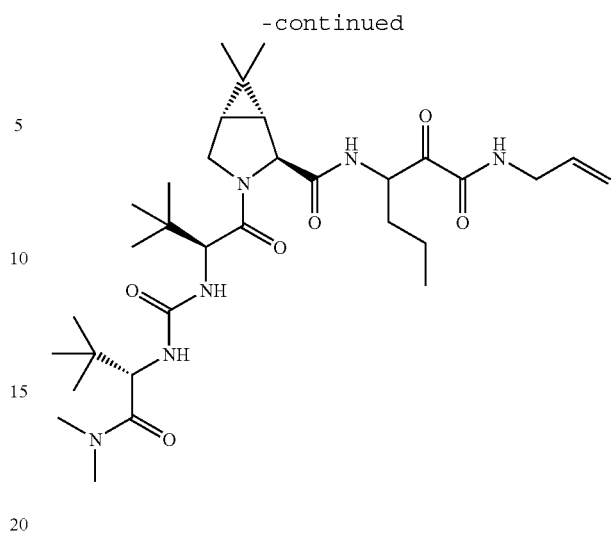
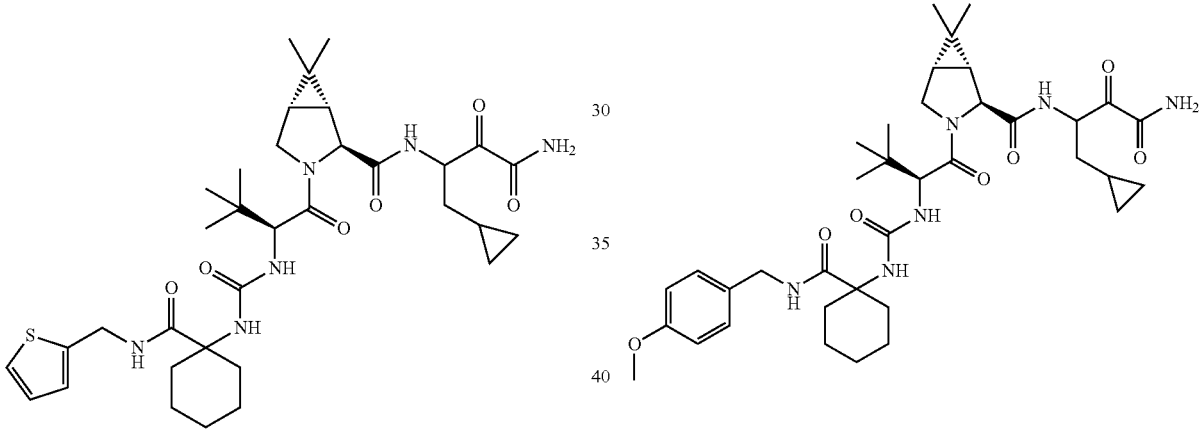
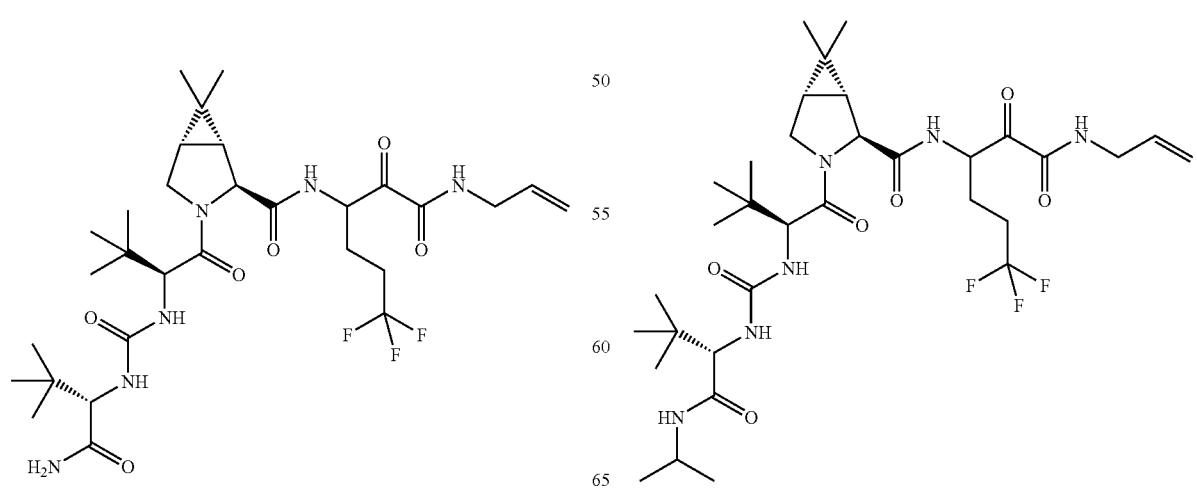

417
-continued
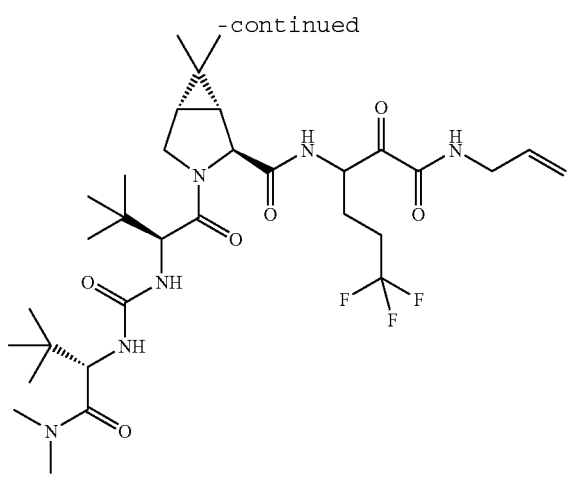
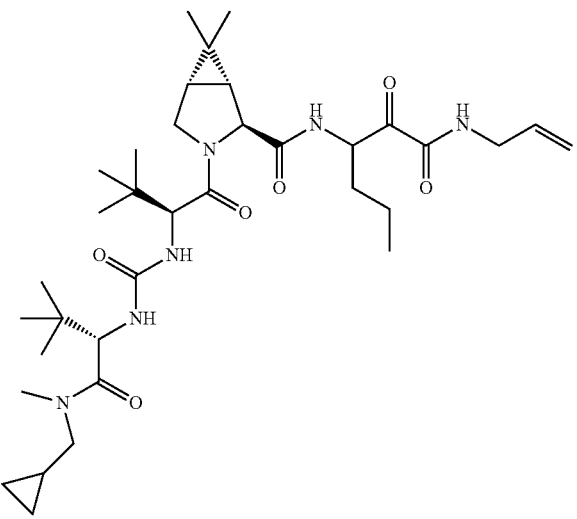
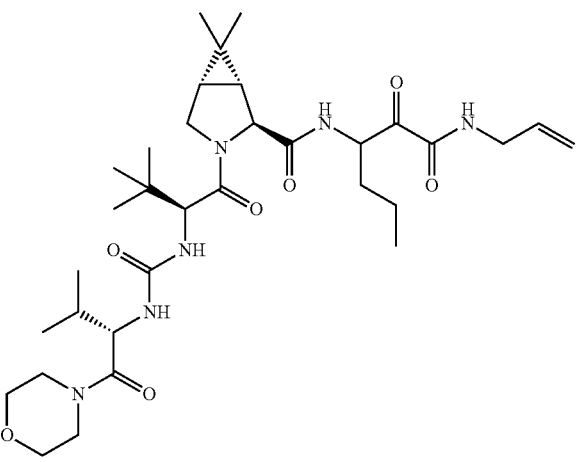
418
-continued
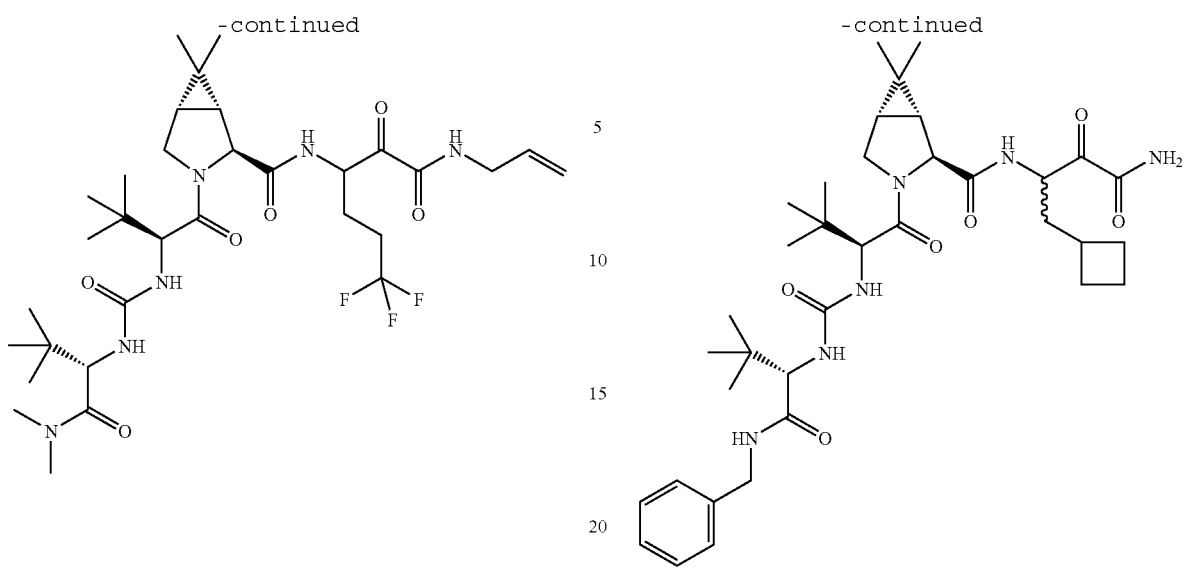
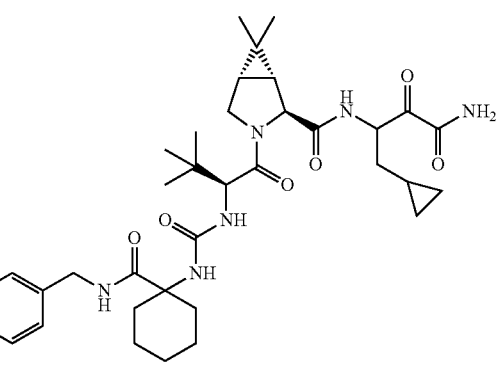
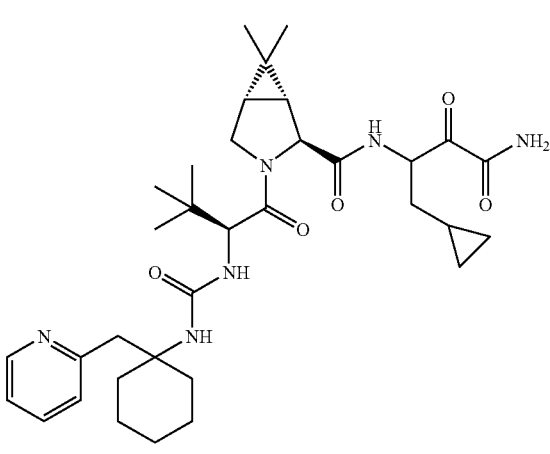

419
-continued
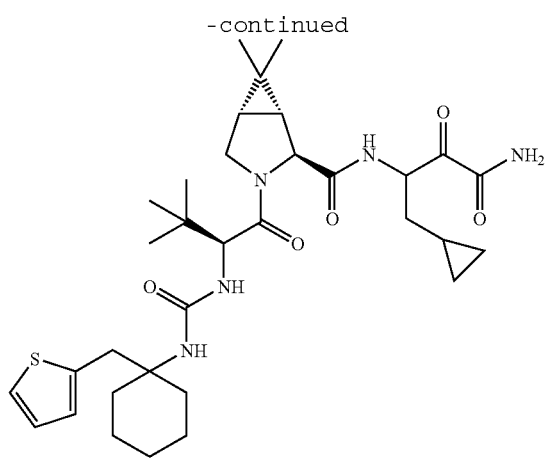
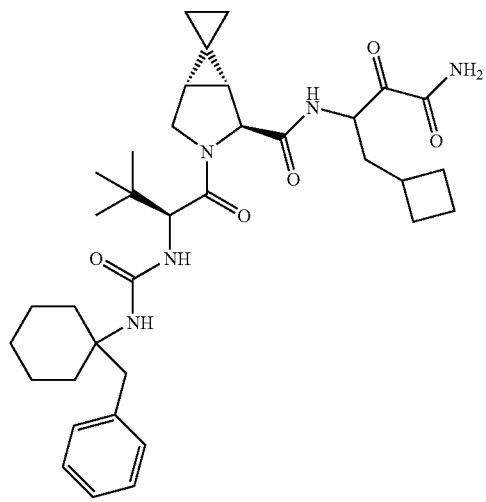
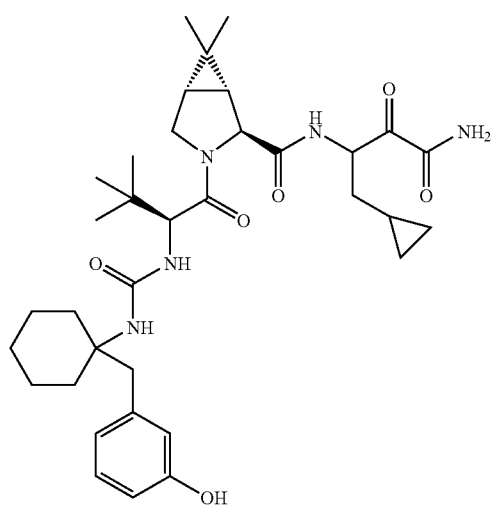
420
-continued
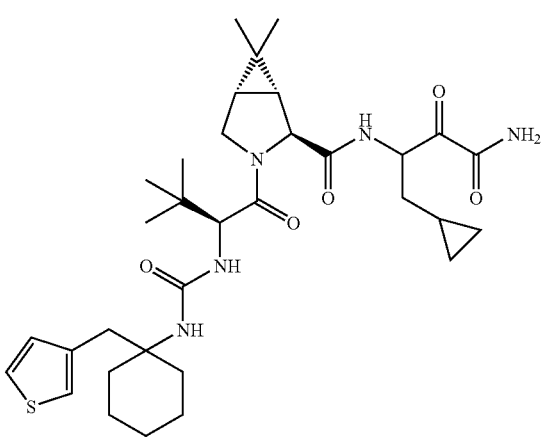
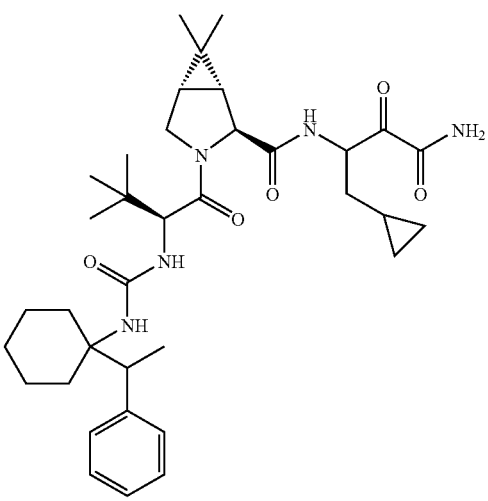
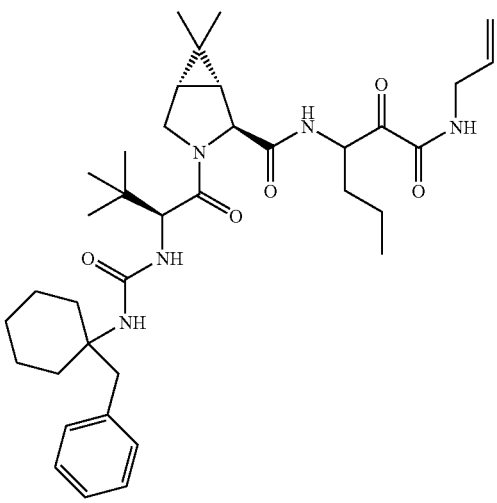

421
-continued
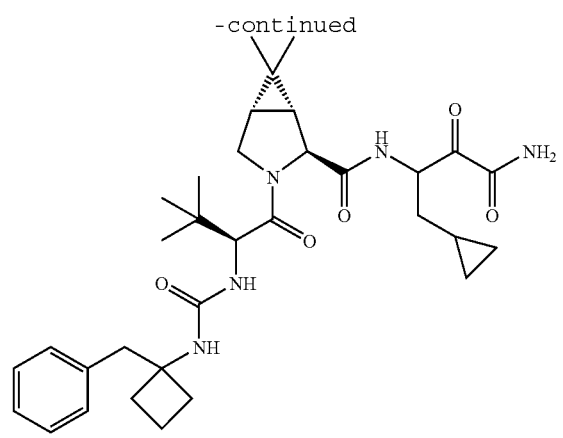
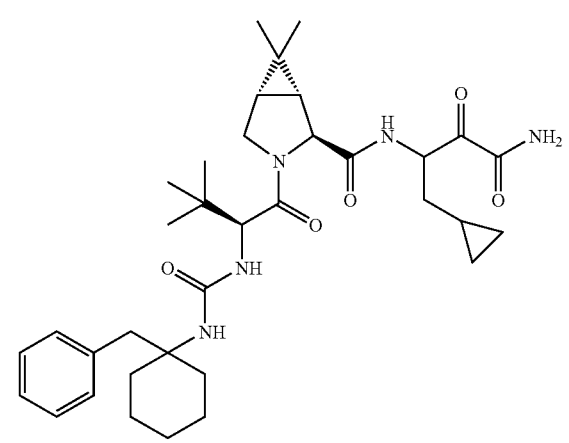
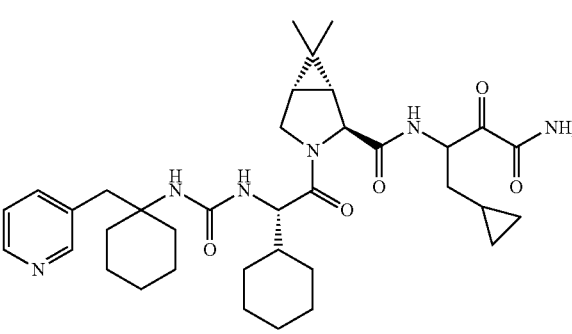
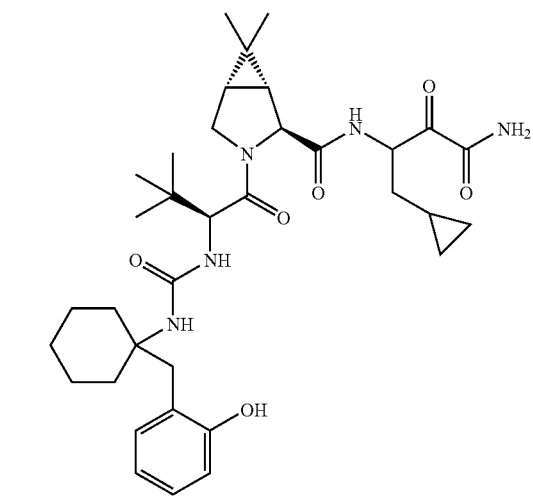
422
-continued
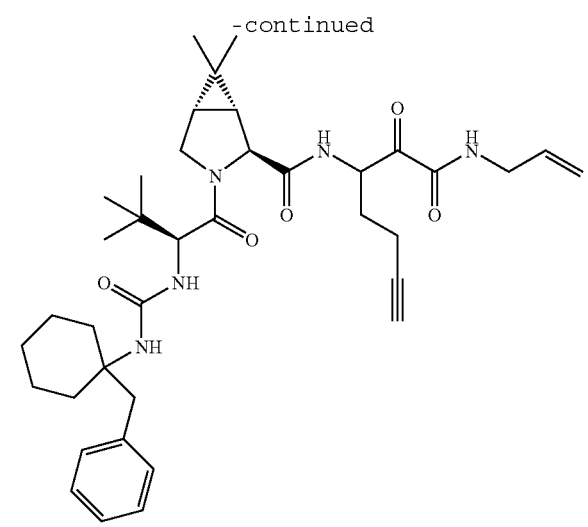
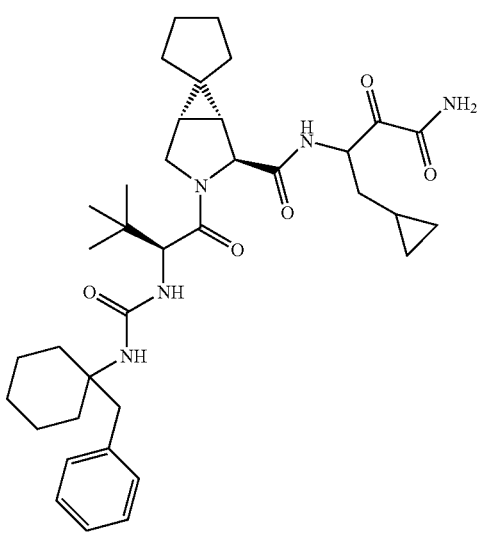
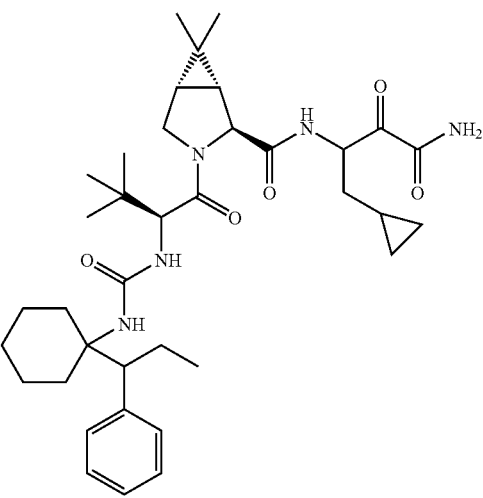

423 424
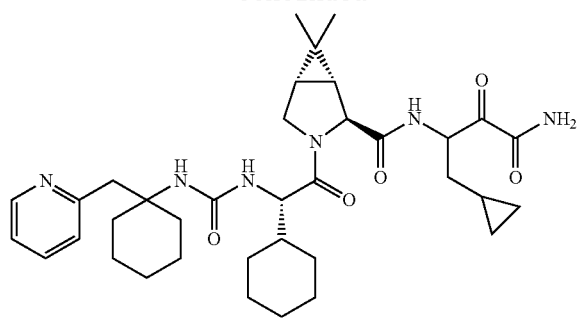
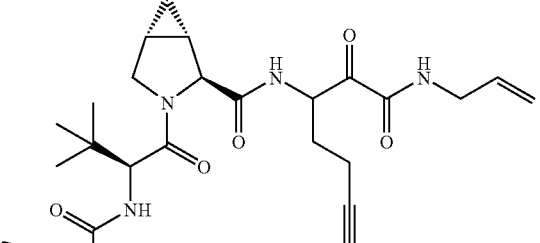
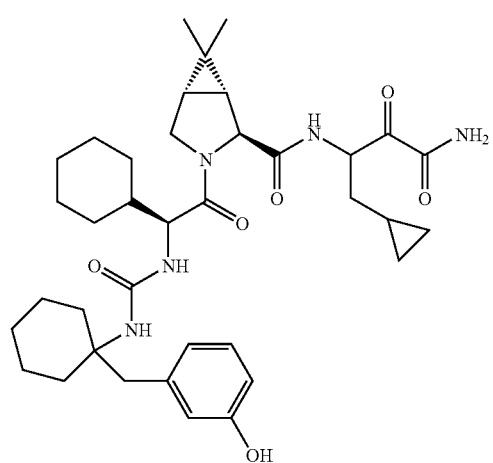
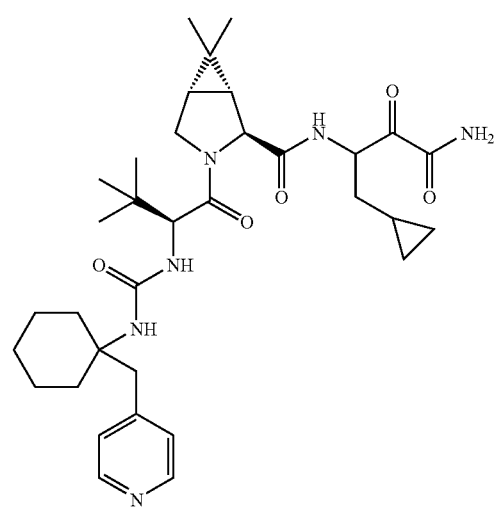
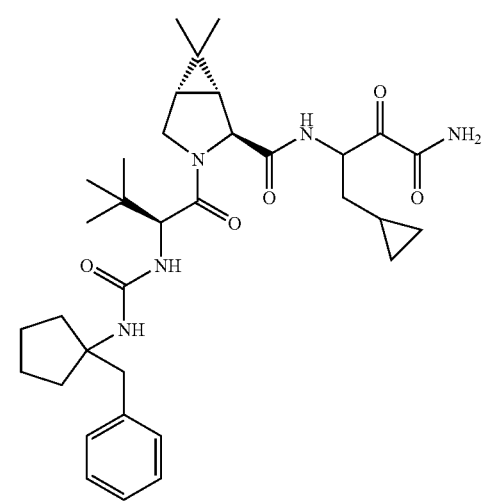
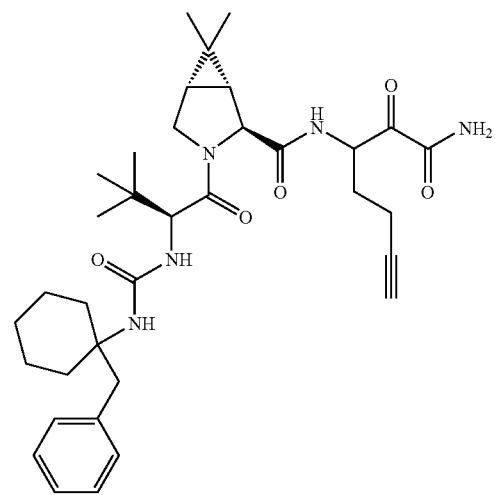

425 426
-continued -continued
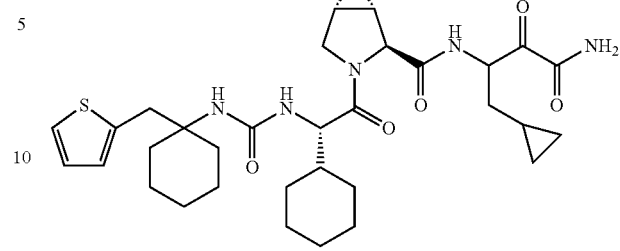
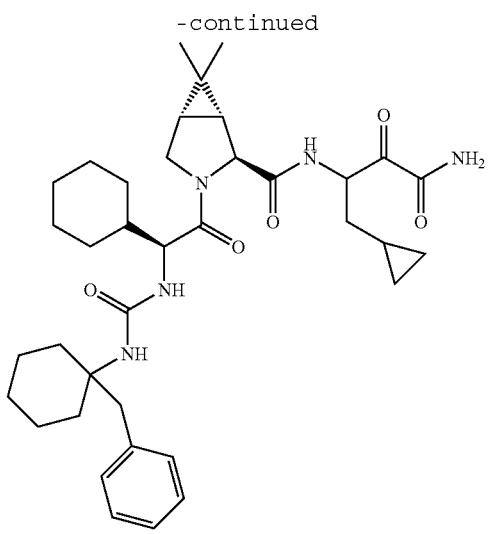
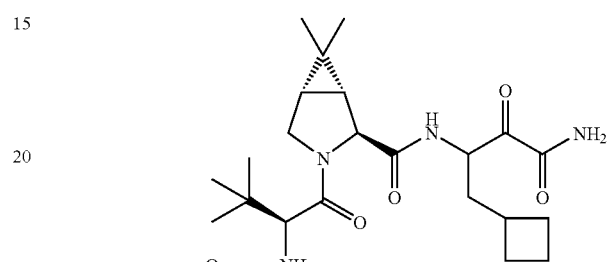
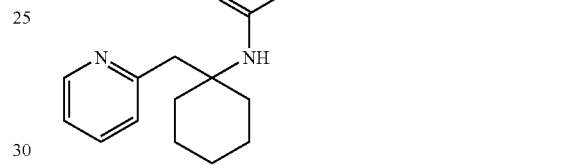
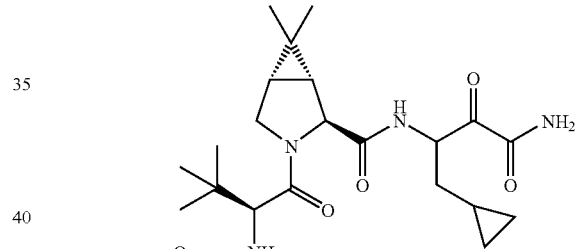
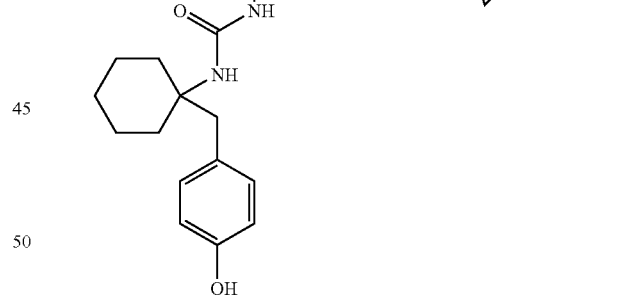
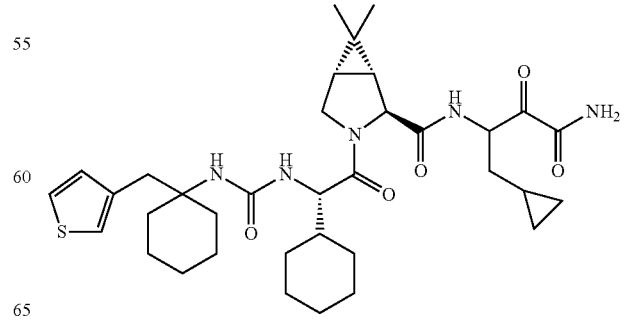

427
-continued
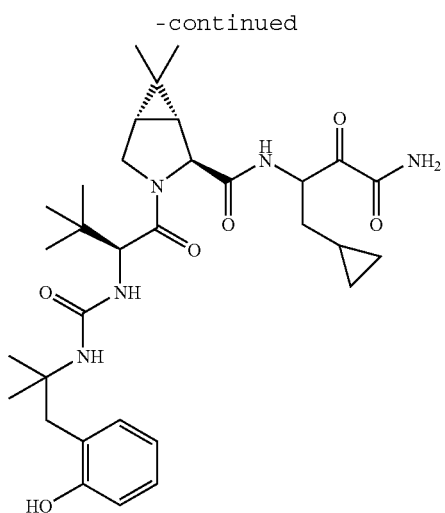
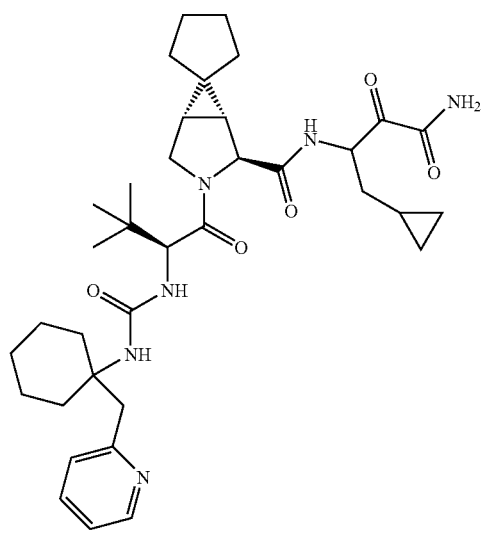
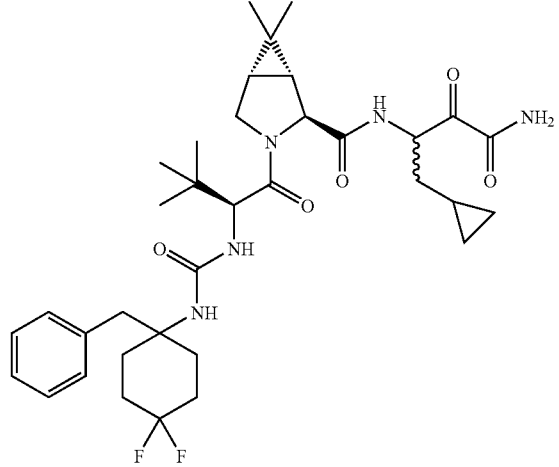
428
-continued
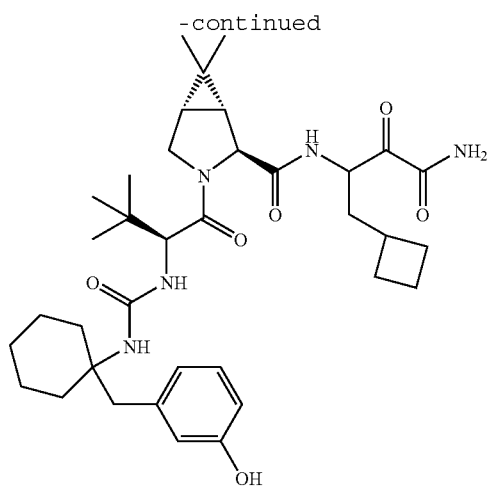
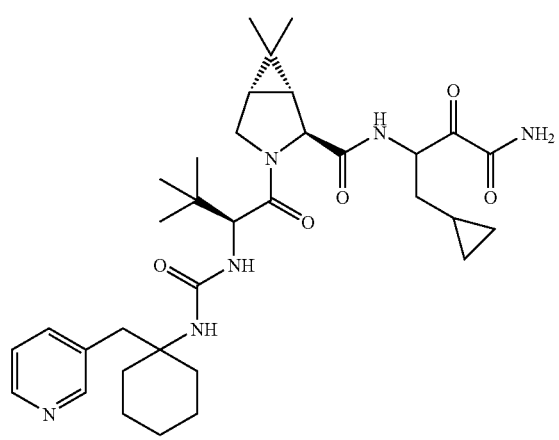
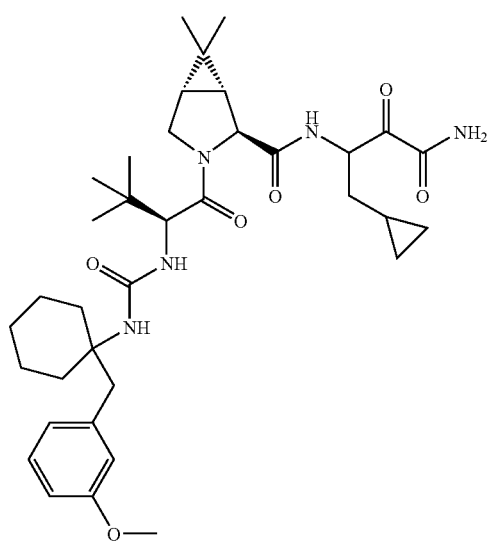

429                                          430
-continued                                  -continued
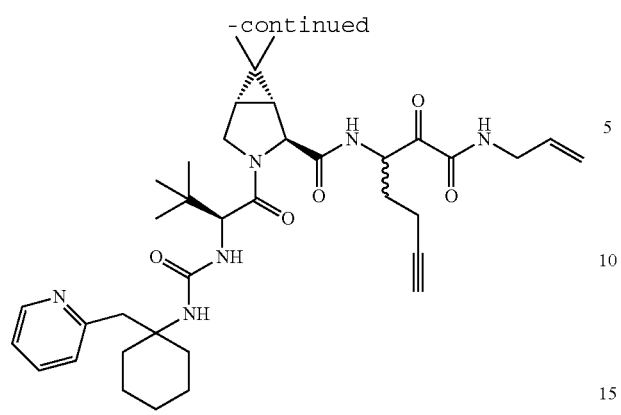
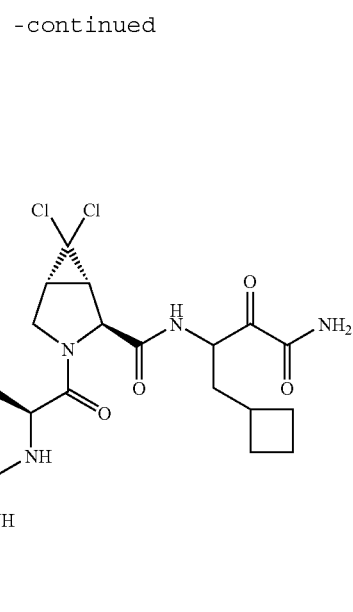
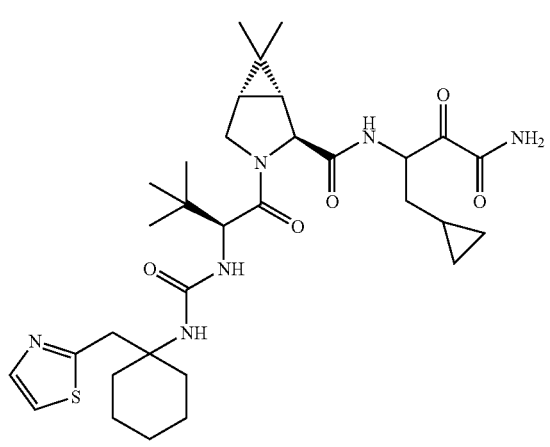
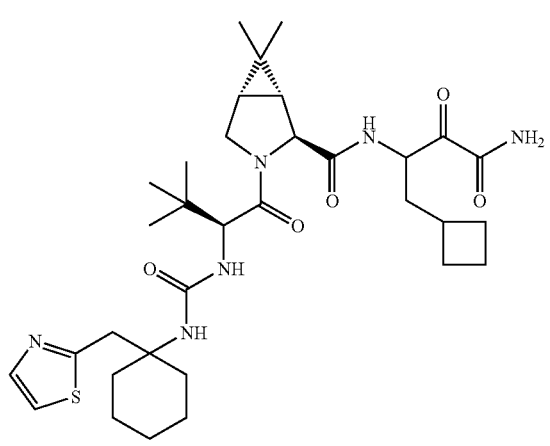
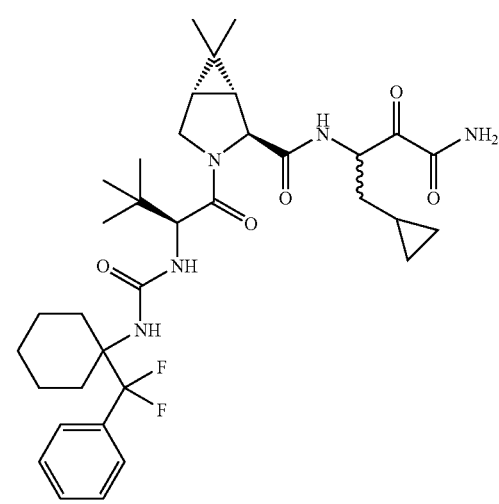
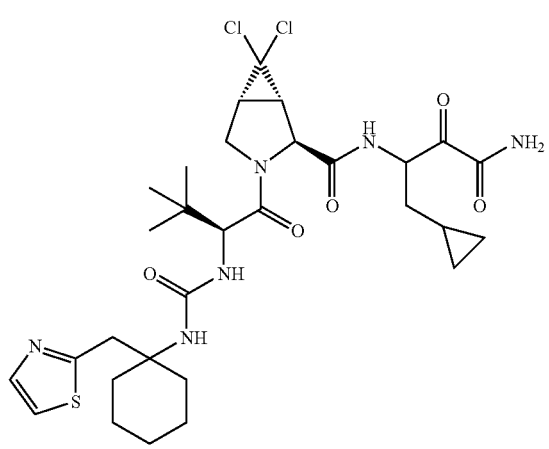
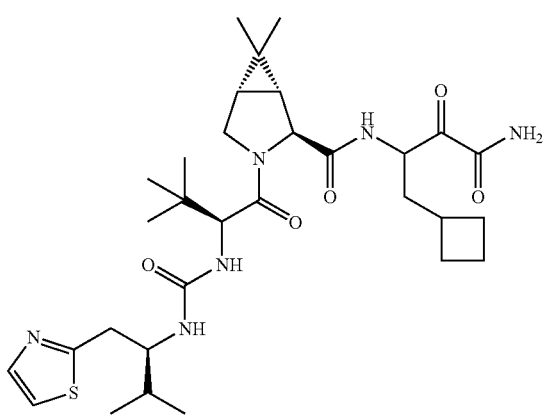

431
-continued
432
-continued
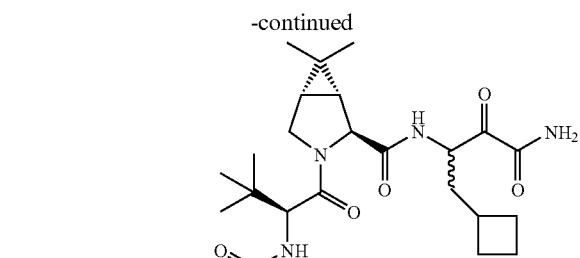
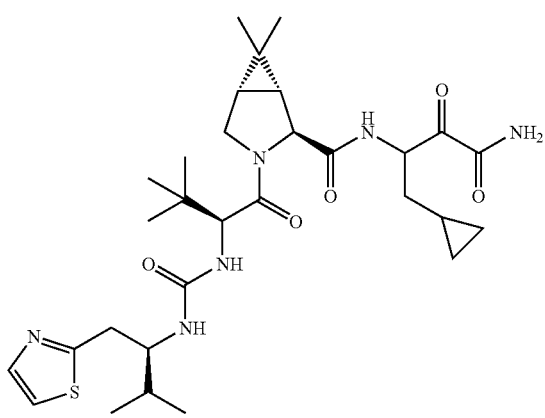
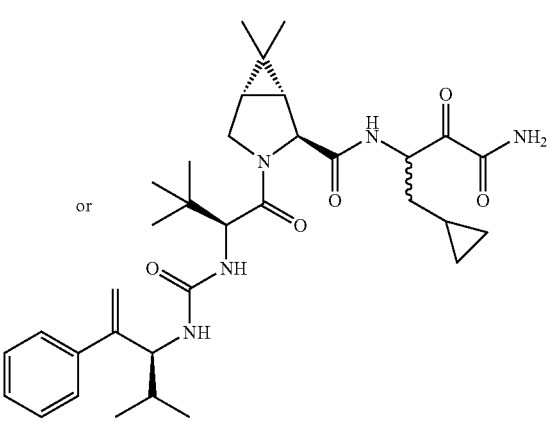
Compounds of formula XI are disclosed in U.S. application Ser. No. 11/065,509 filed Feb. 24, 2005. The preparation of these compounds is disclosed in the experimental section of this application set forth hereinbelow.
Non-limiting examples of certain compounds disclosed in U.S. application Ser. No. 11/065,509 are:
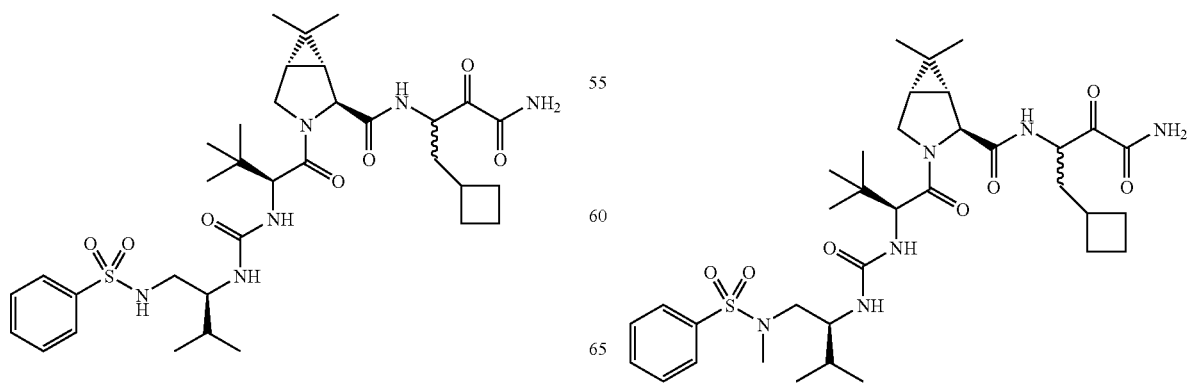

433
-continued
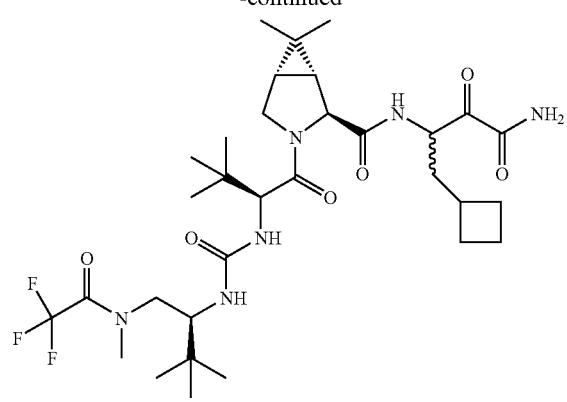
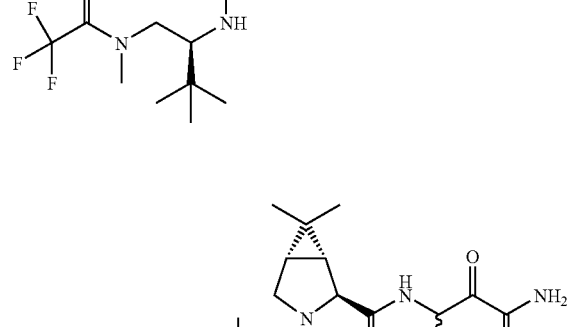
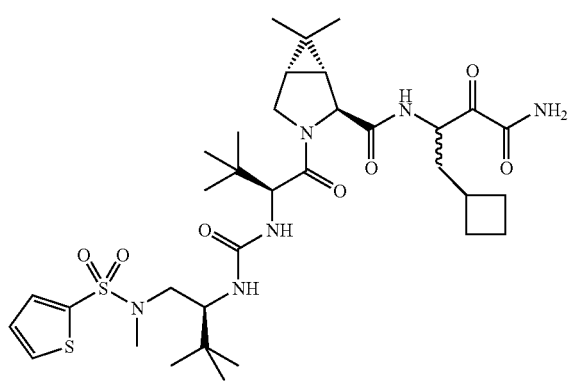
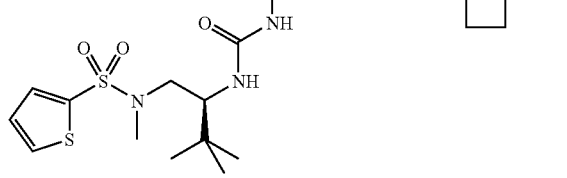
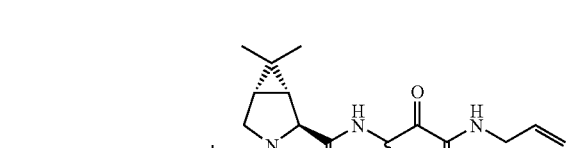
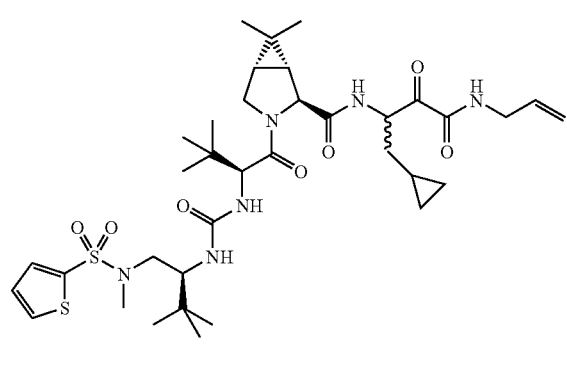
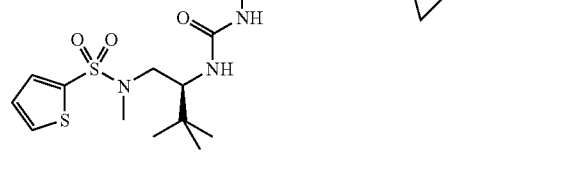
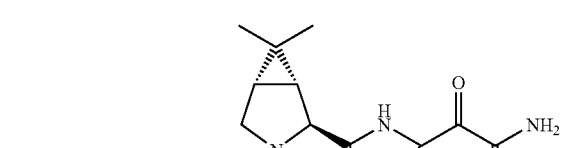
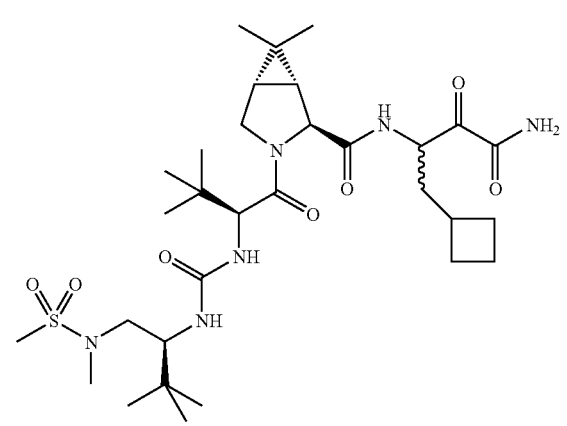
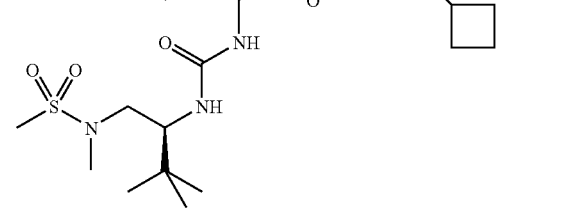
434
-continued
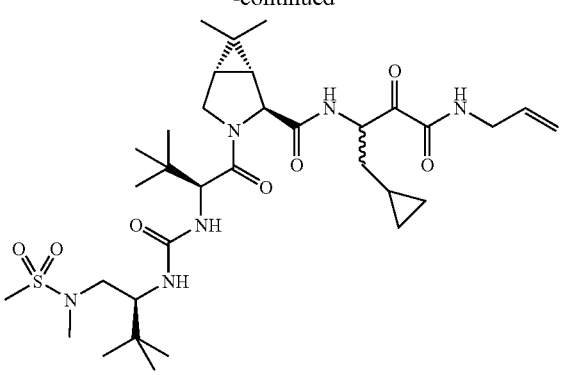
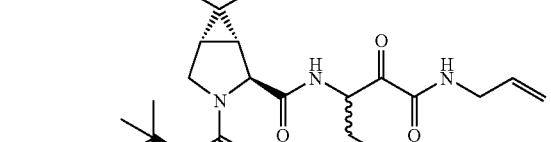
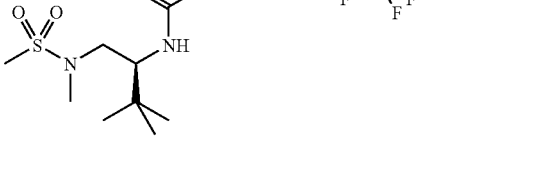
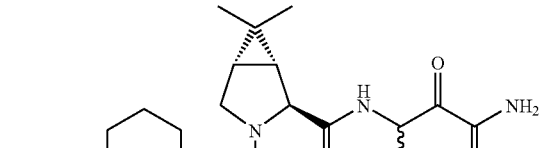
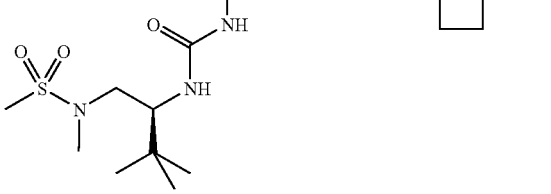
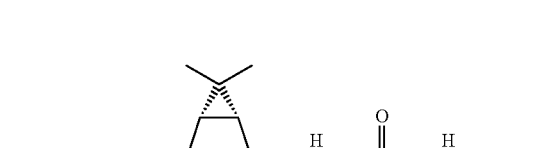
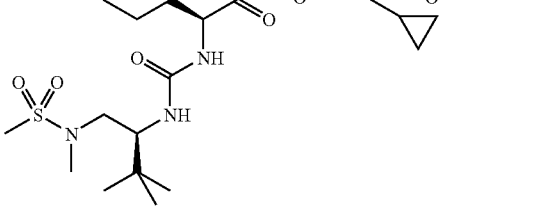

435
-continued
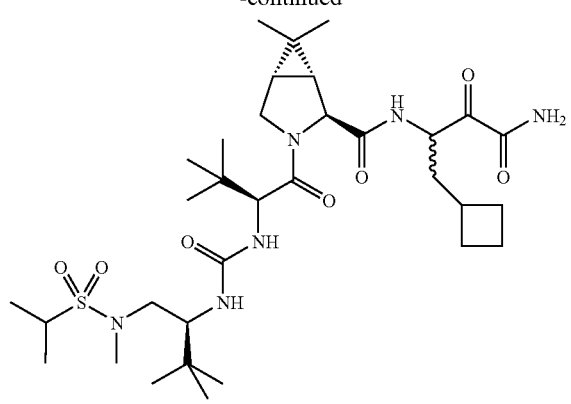
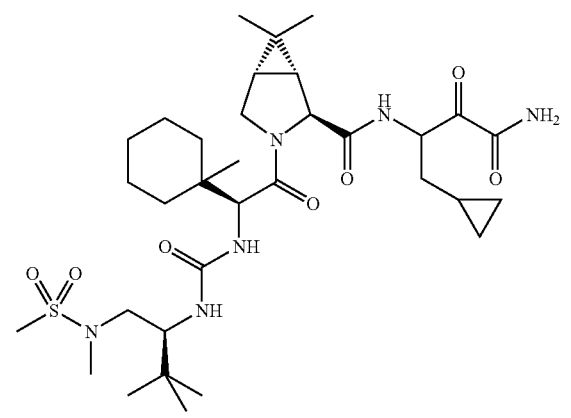
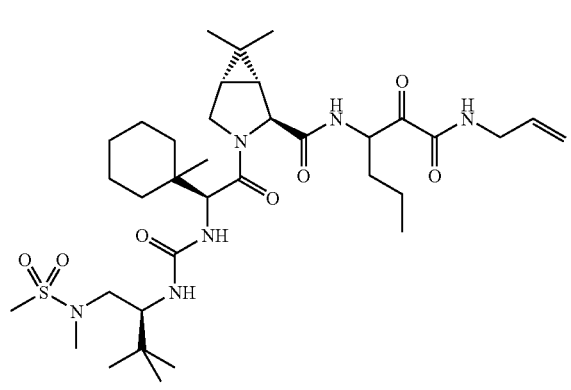
436
-continued
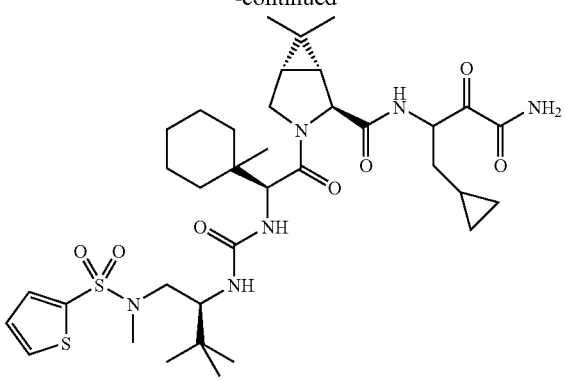
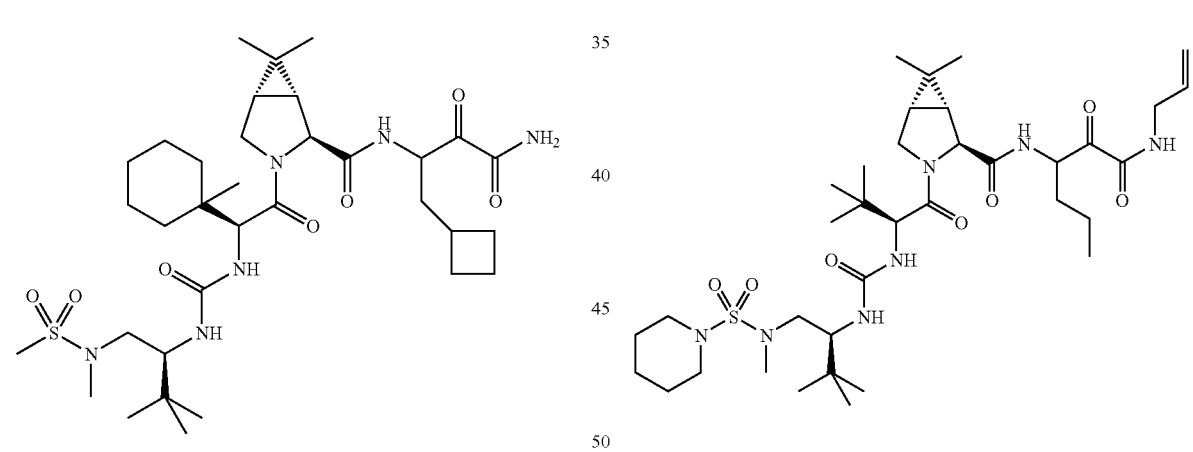
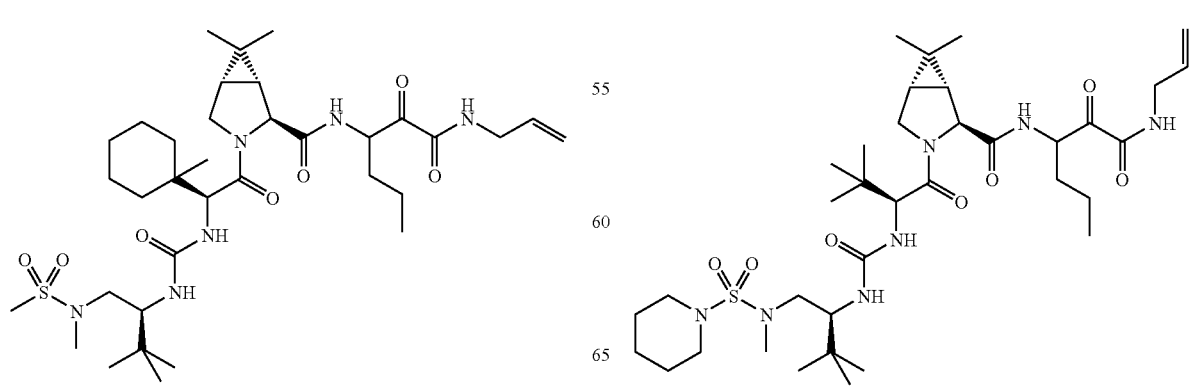
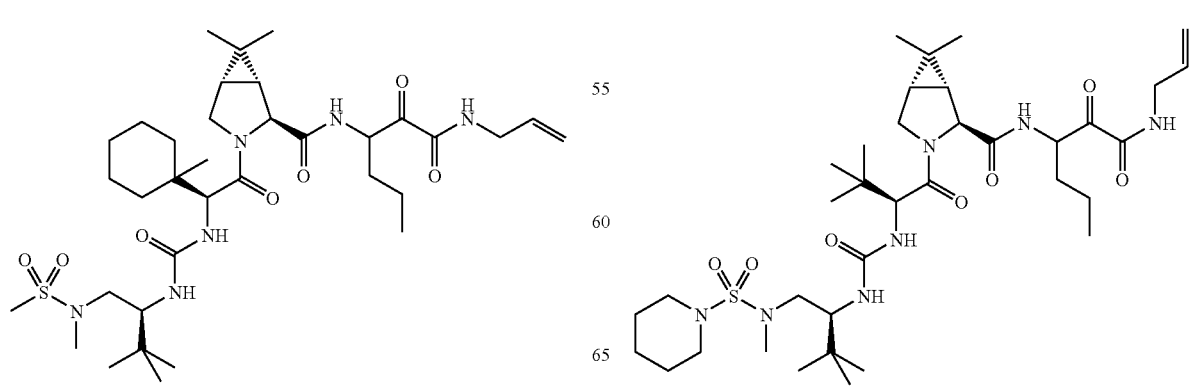

437
-continued
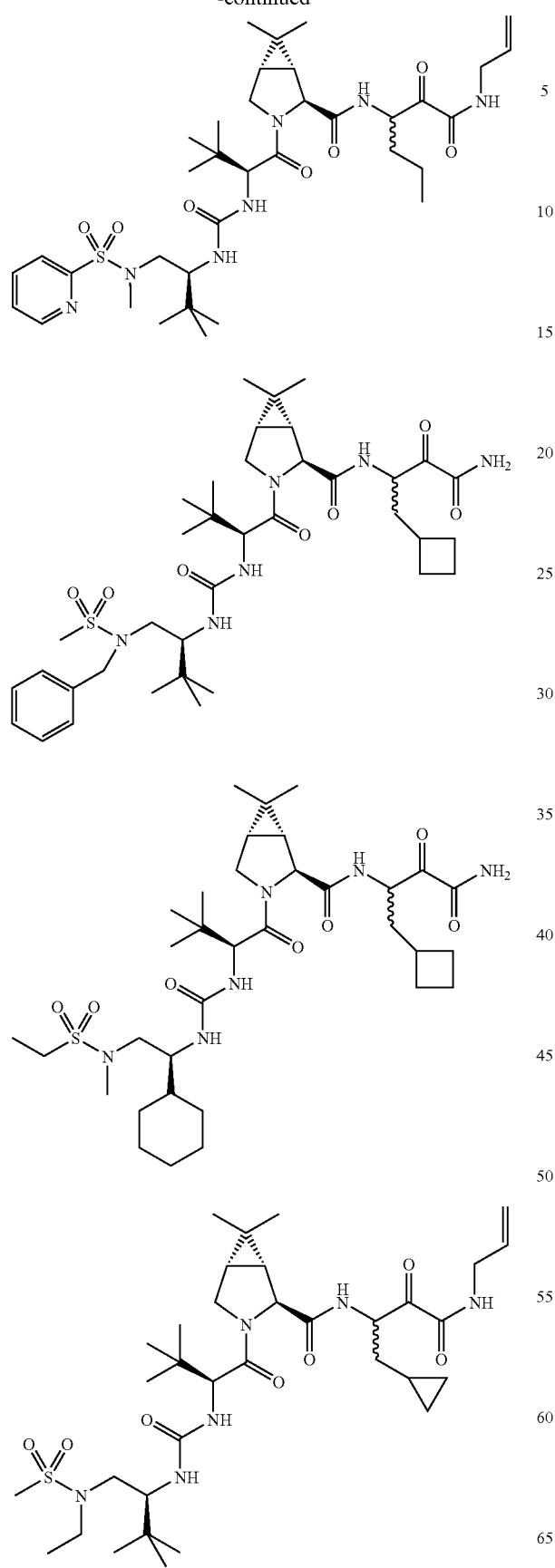
438
-continued
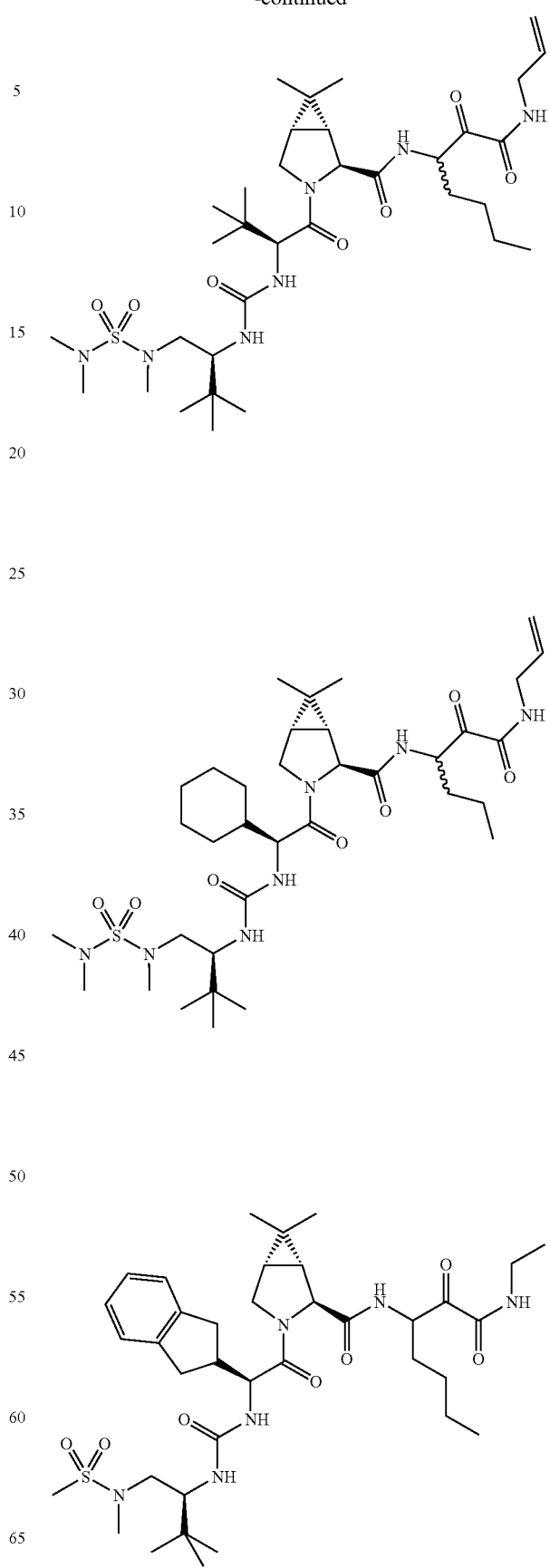

439
-continued
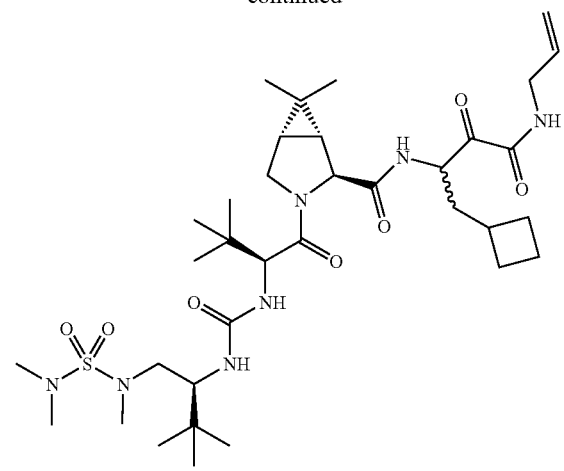
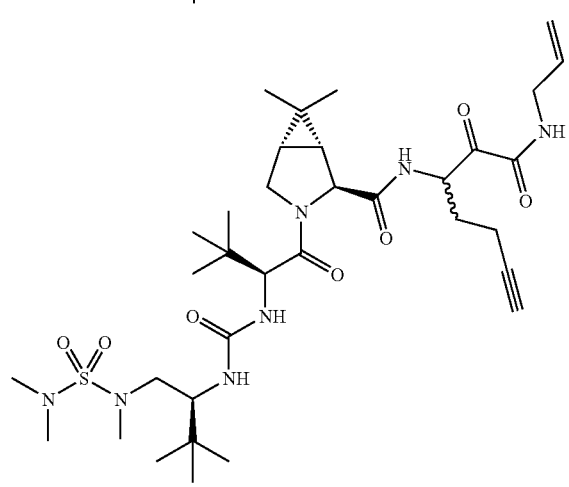
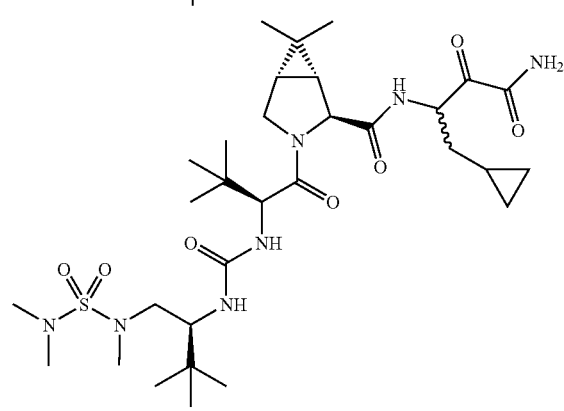
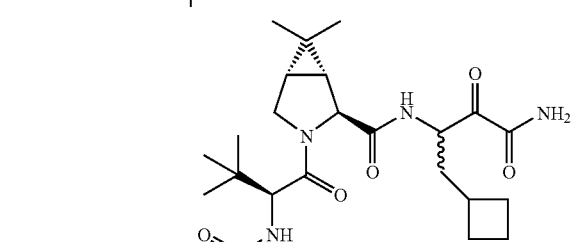
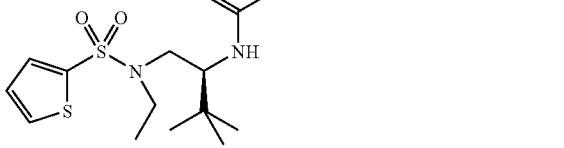
440
-continued
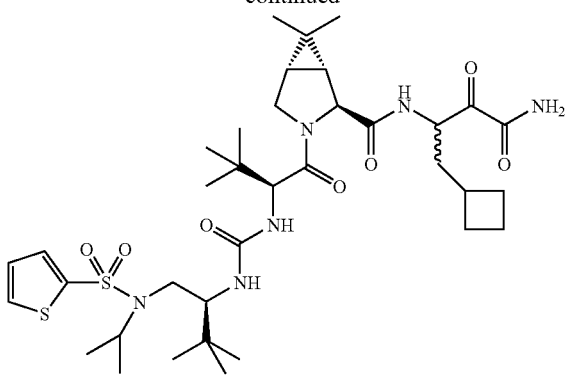
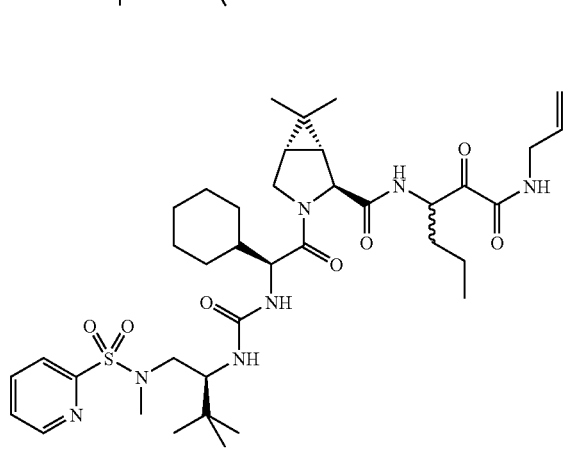
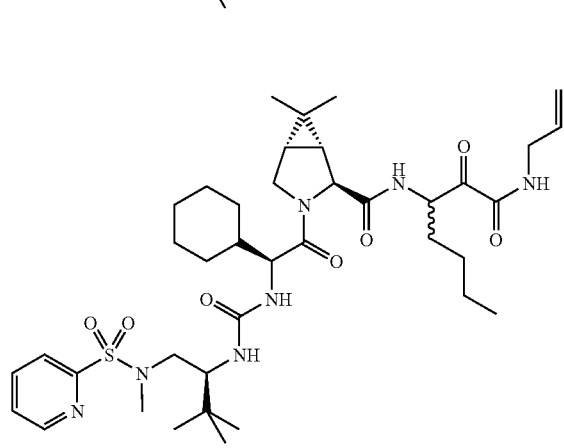
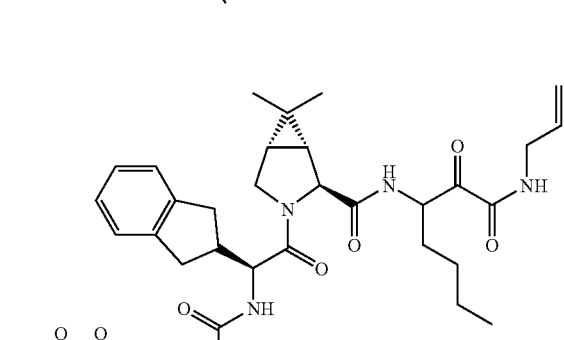
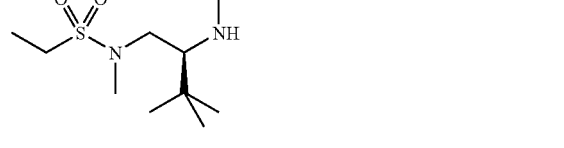

441
-continued
442
-continued
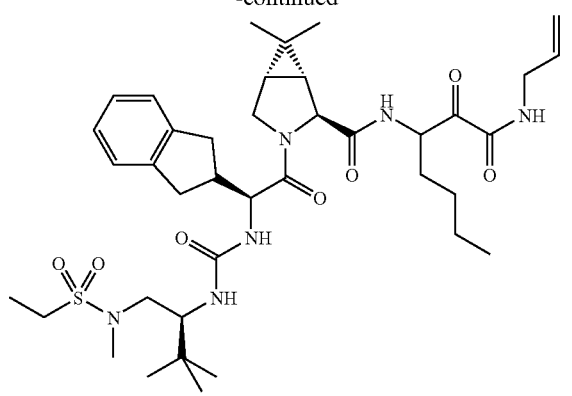
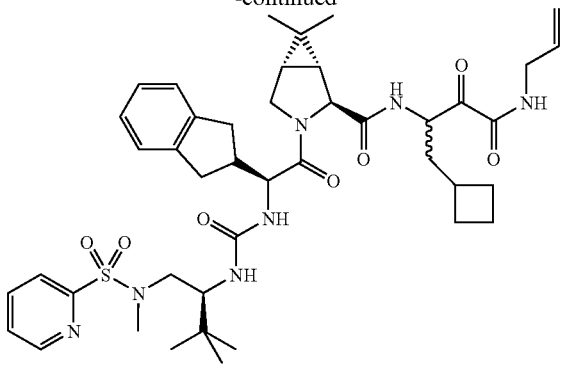

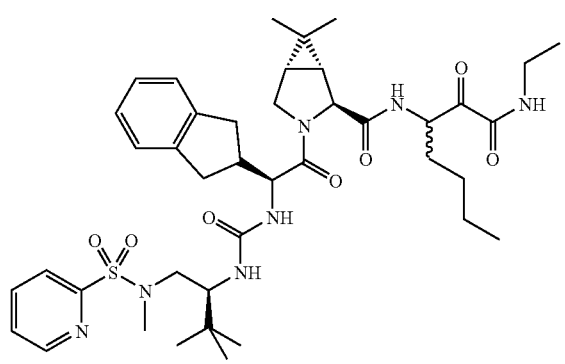
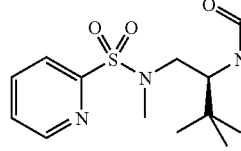
and
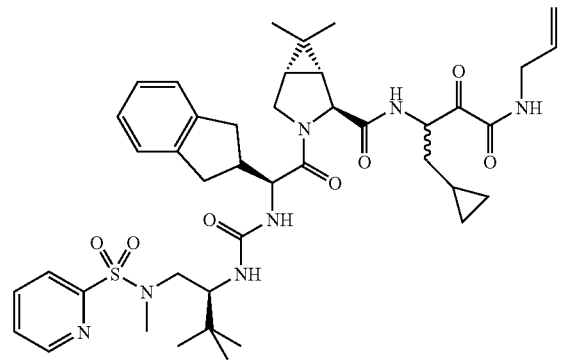
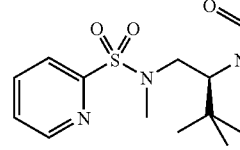
or a pharmaceutically acceptable salt, solvate or ester thereof.
Compounds of formula XII are disclosed in U.S. patent application Ser. No. 11/065,531 filed Feb. 24, 2005. The preparation of these compounds is disclosed in the experimental section of this application set forth hereinbelow.
Non-limiting examples of certain compounds disclosed in U.S. patent application Ser. No. 11/065,531 are:
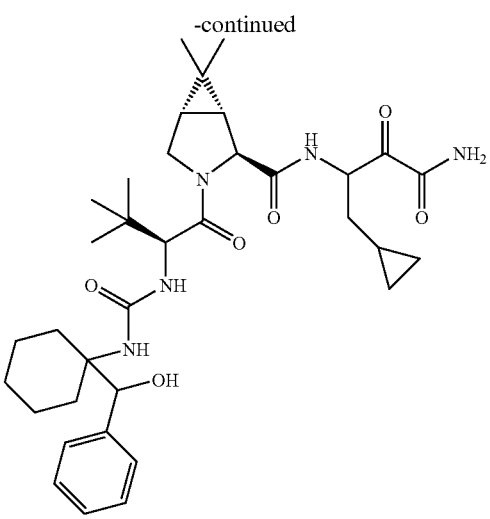
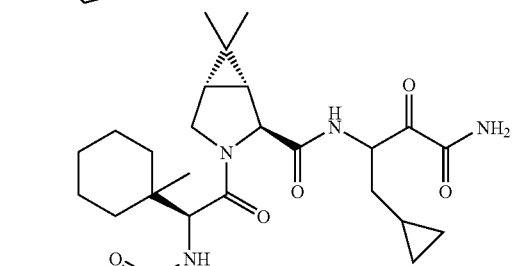
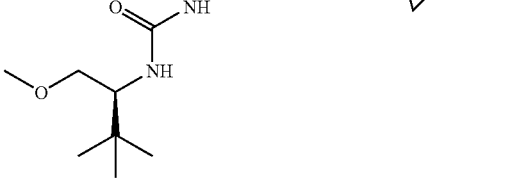
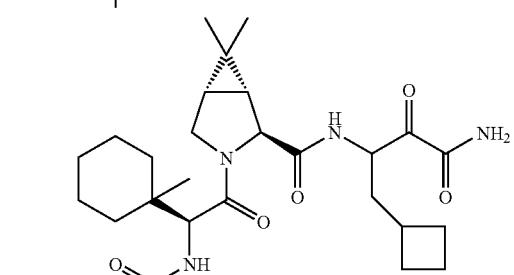
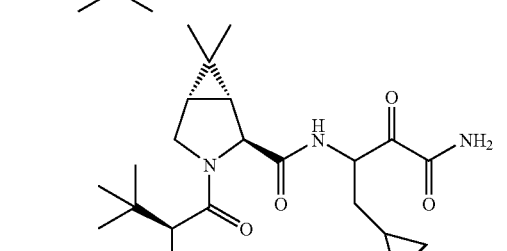
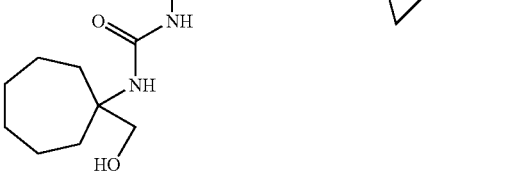

445
-continued
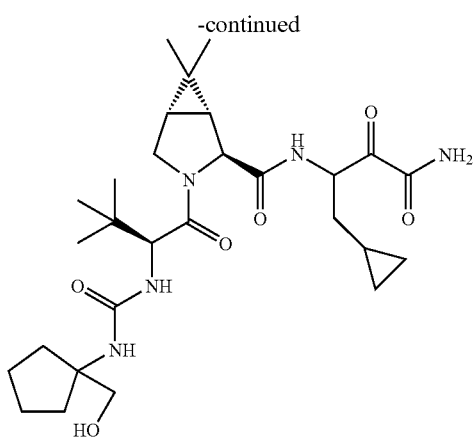
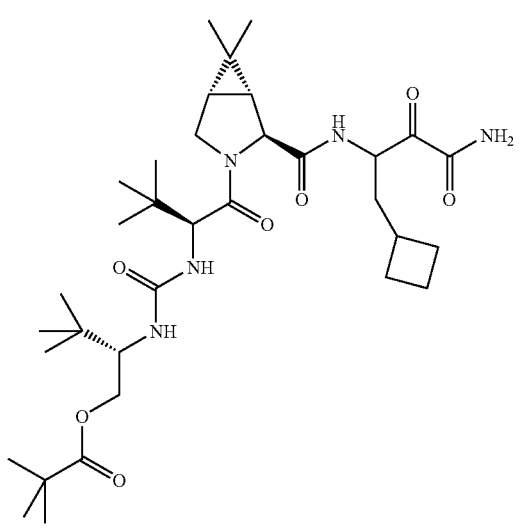
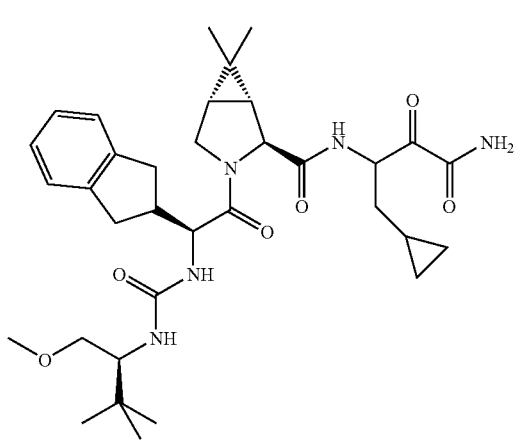
446
-continued
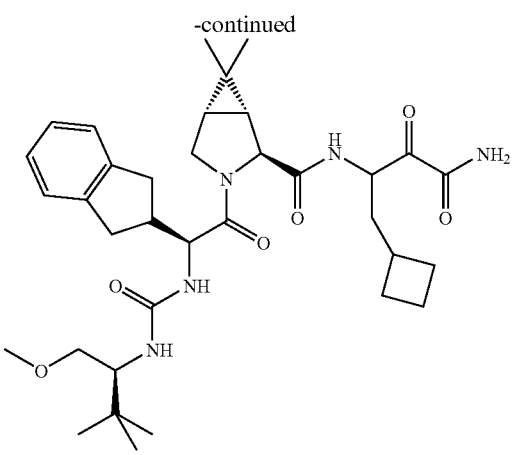
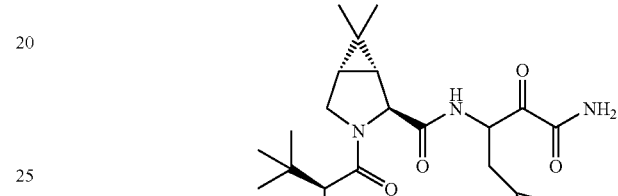
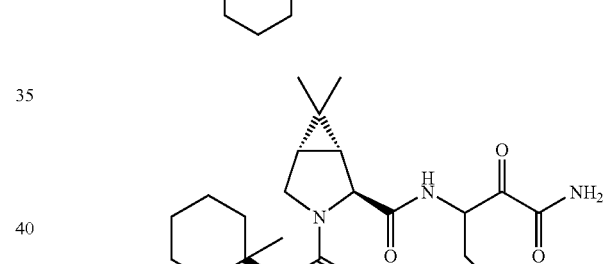
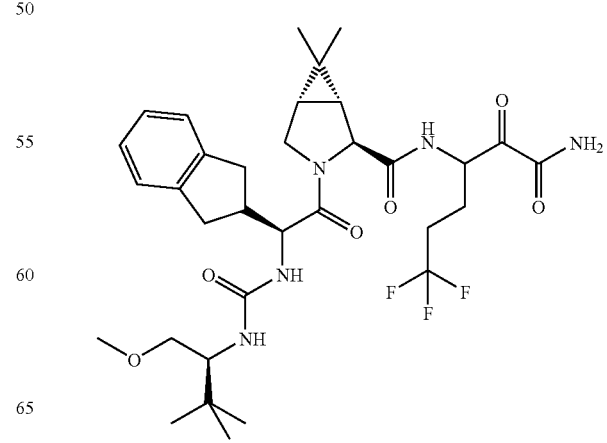

447
-continued
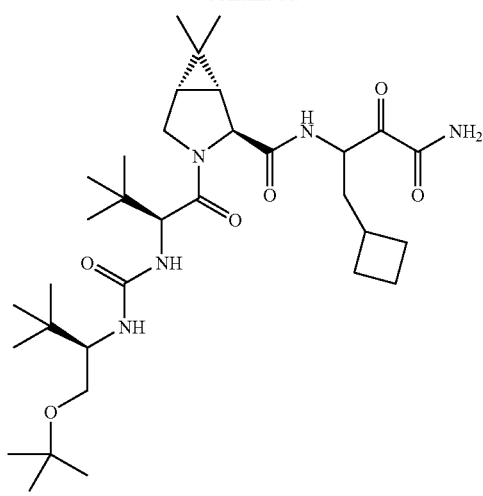
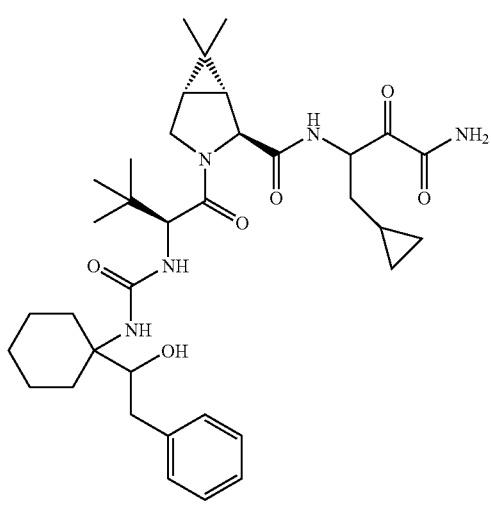
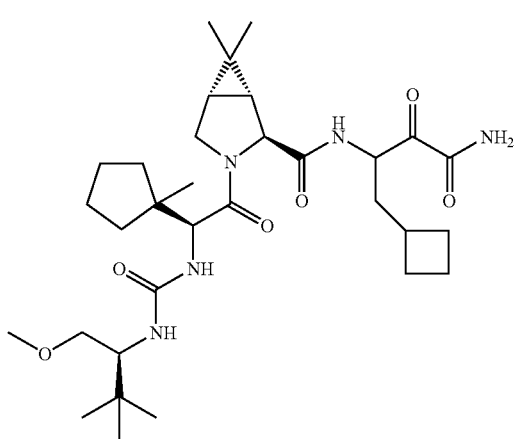
448
-continued
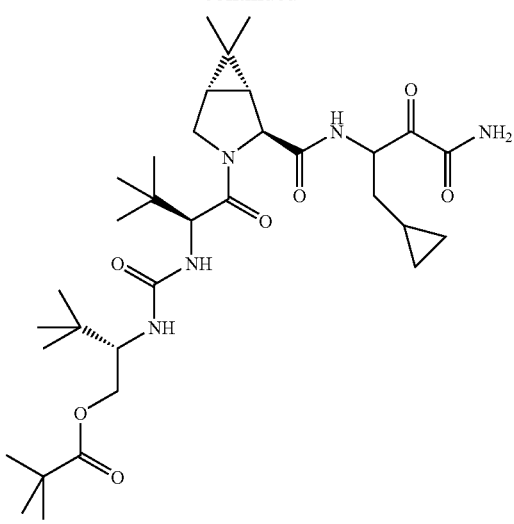
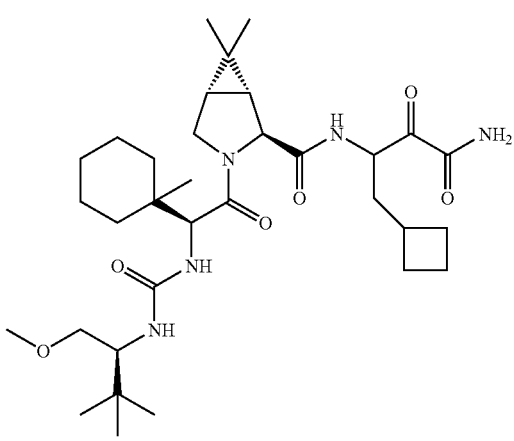
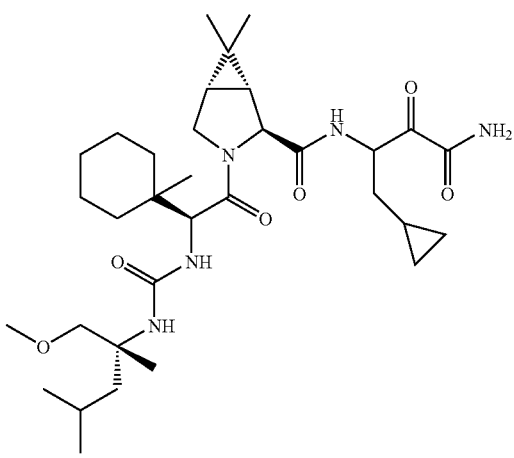

449
-continued
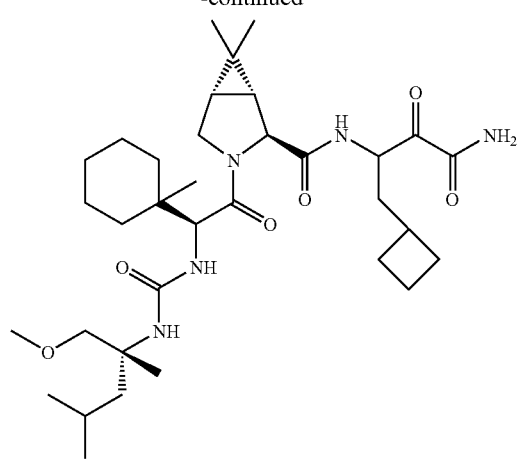
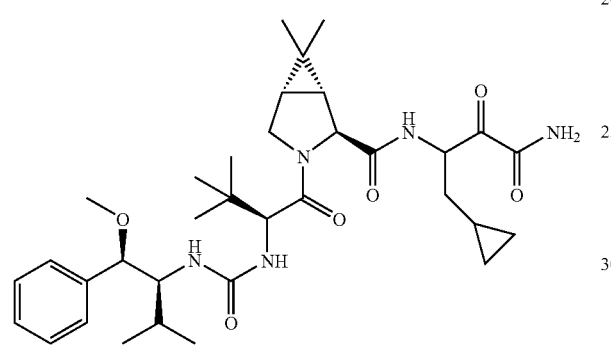
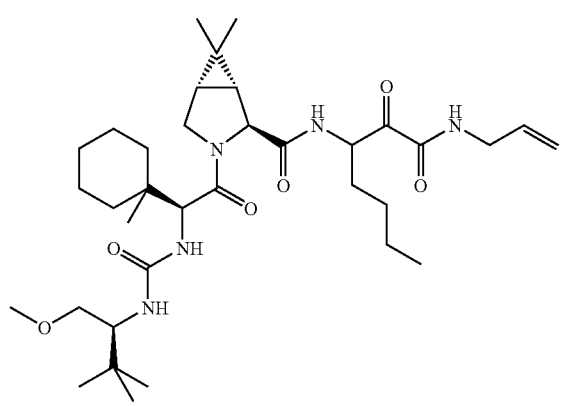
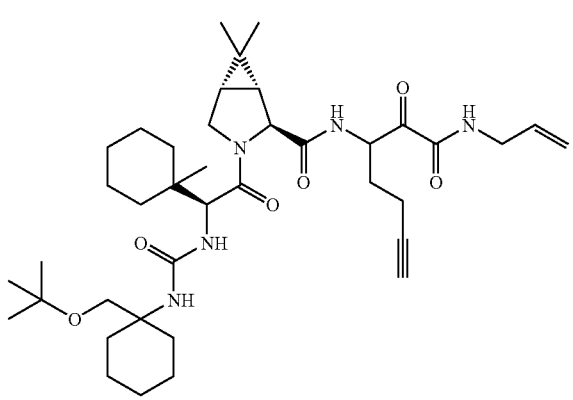
450
-continued
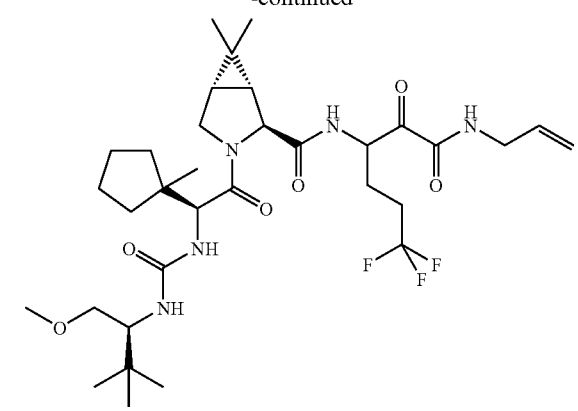
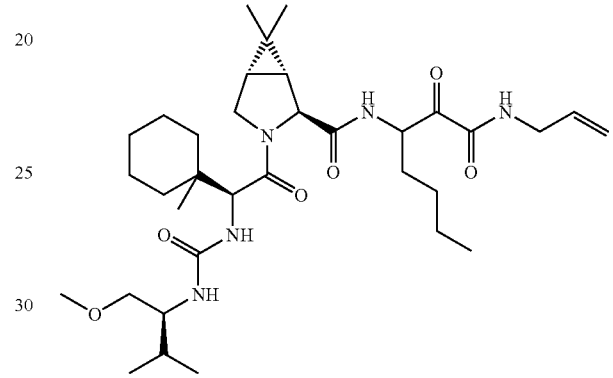
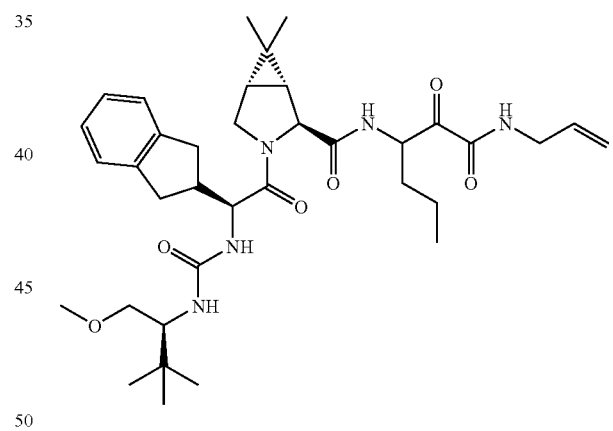
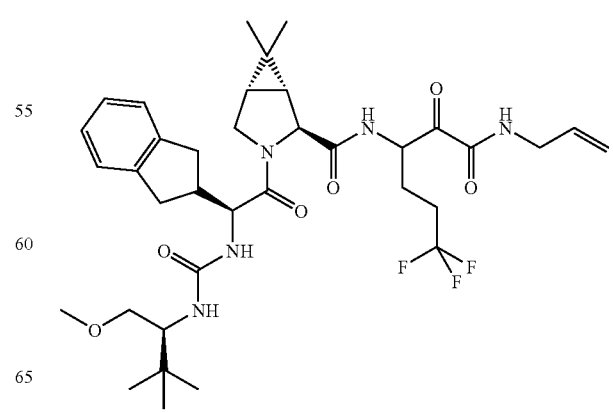

451
-continued
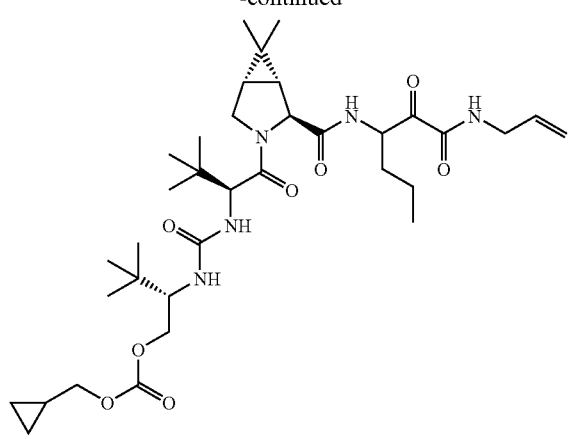
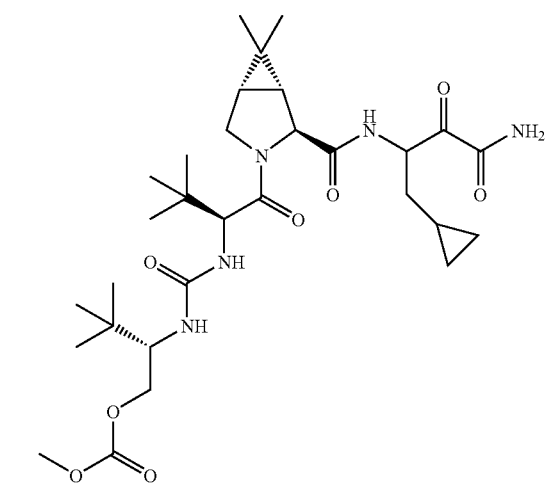
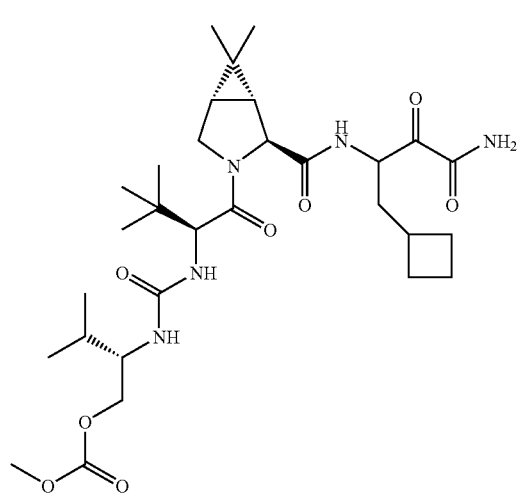
452
-continued
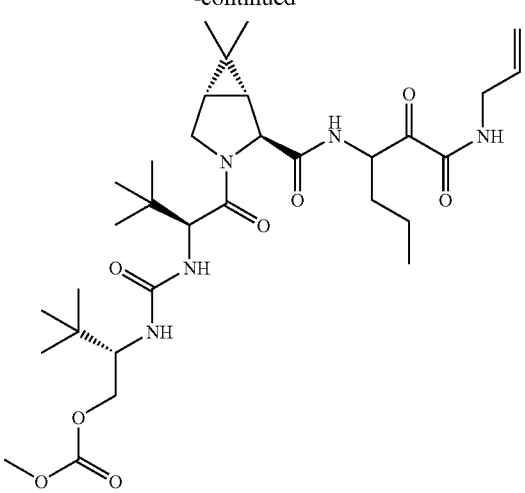
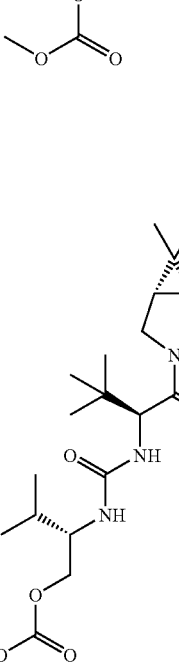
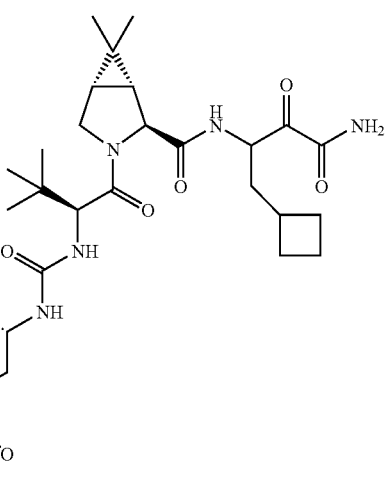

453
-continued
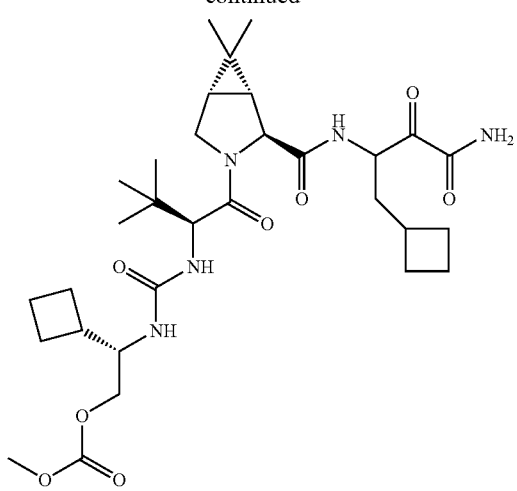
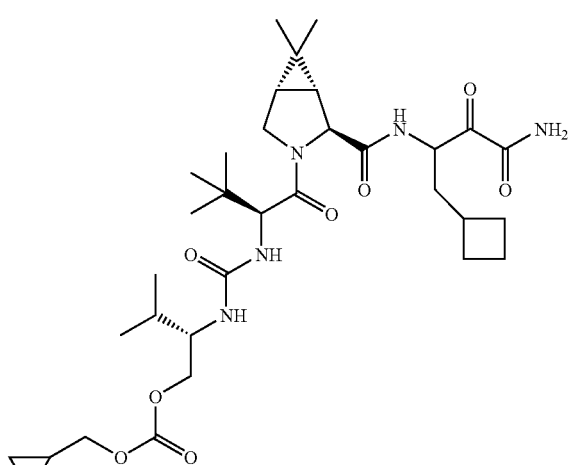
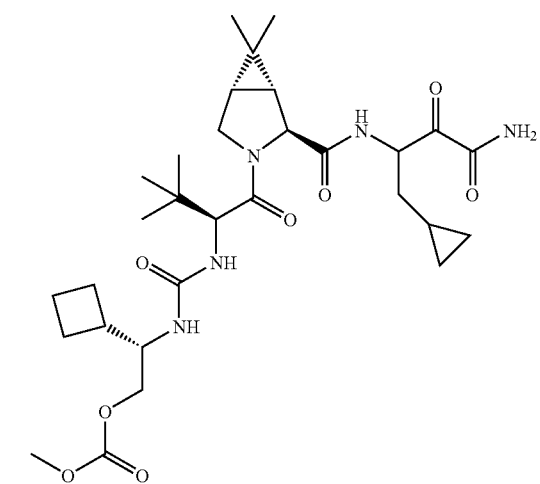
454
-continued
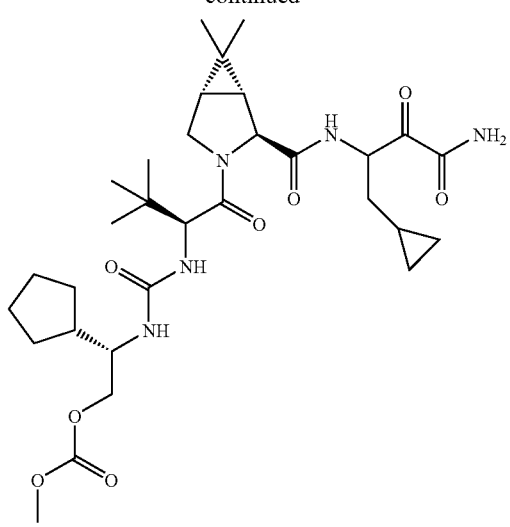
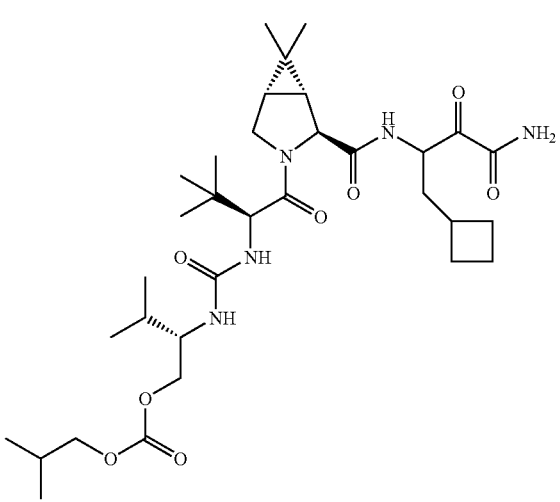
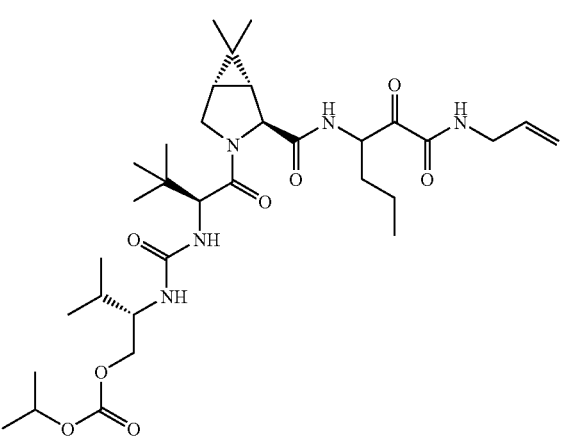

455
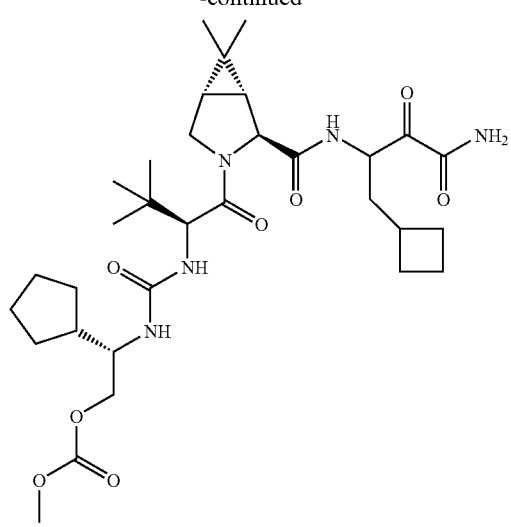
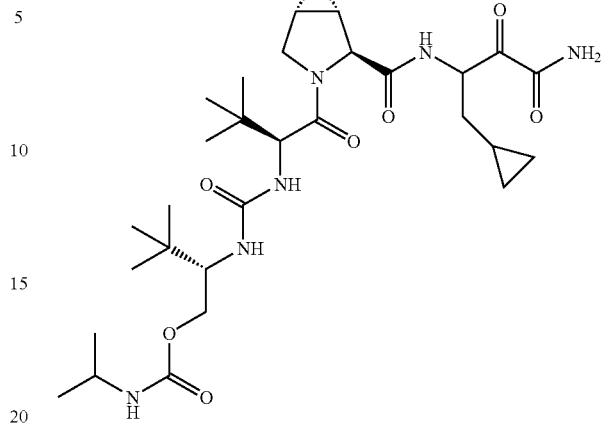
456
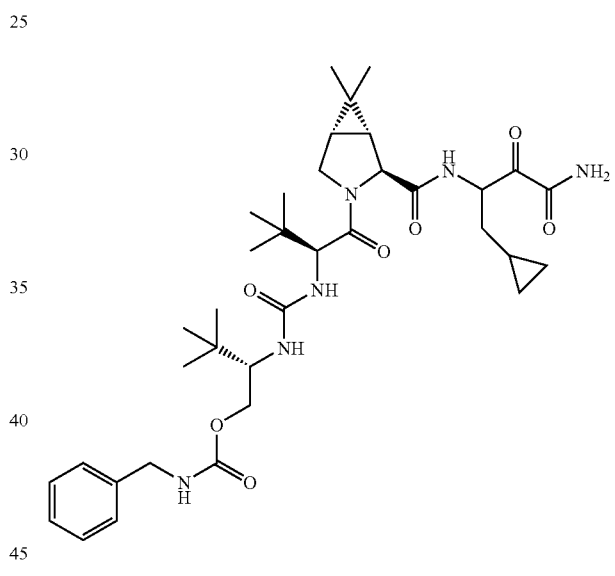
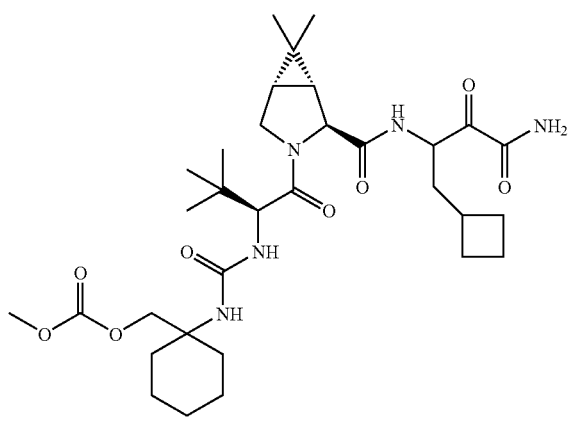
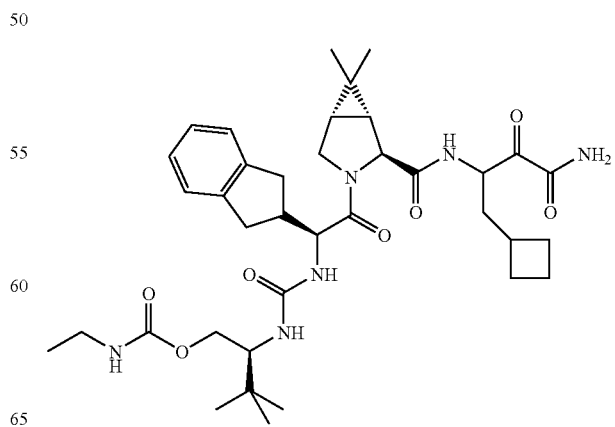

457
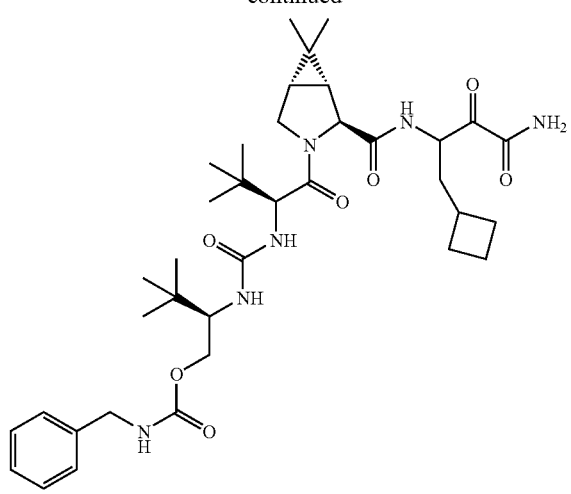
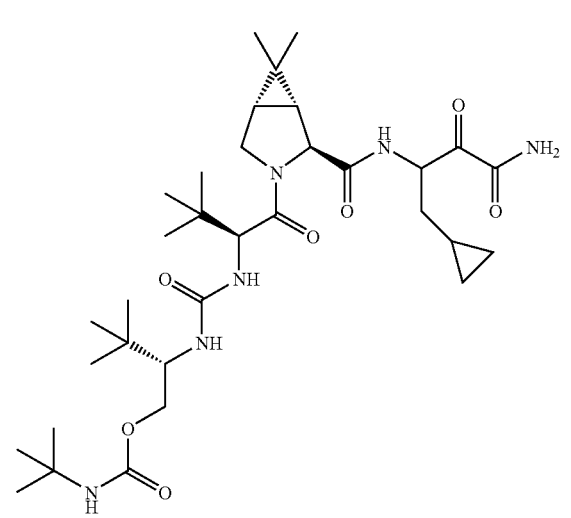
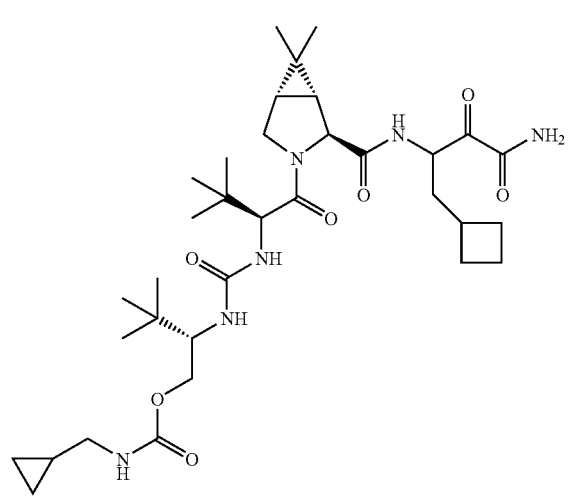
458
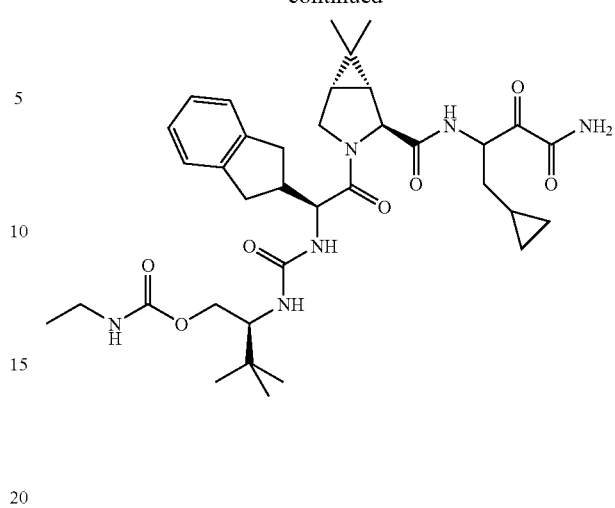
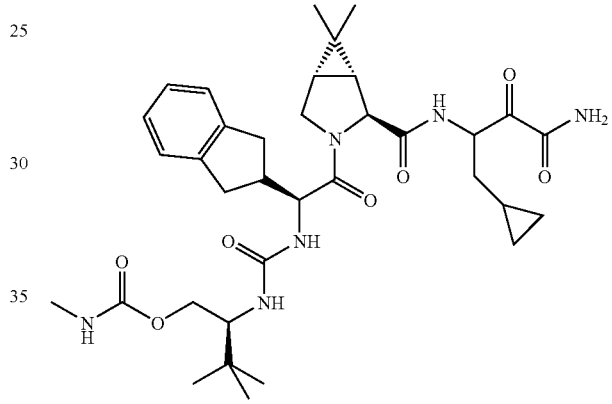
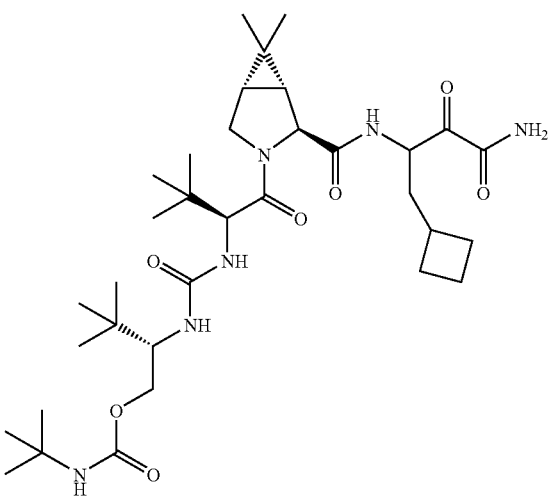

459 -continued
460 -continued
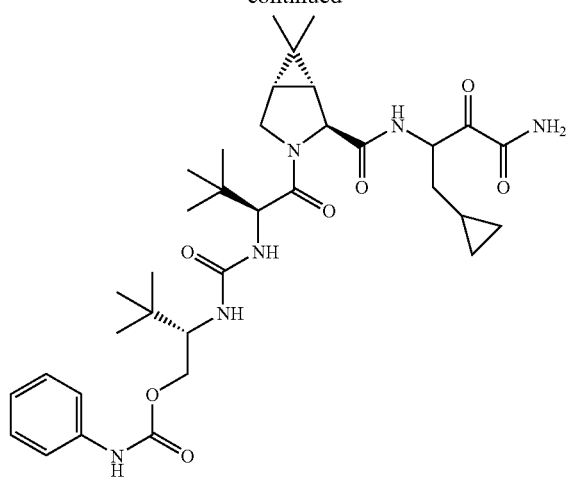
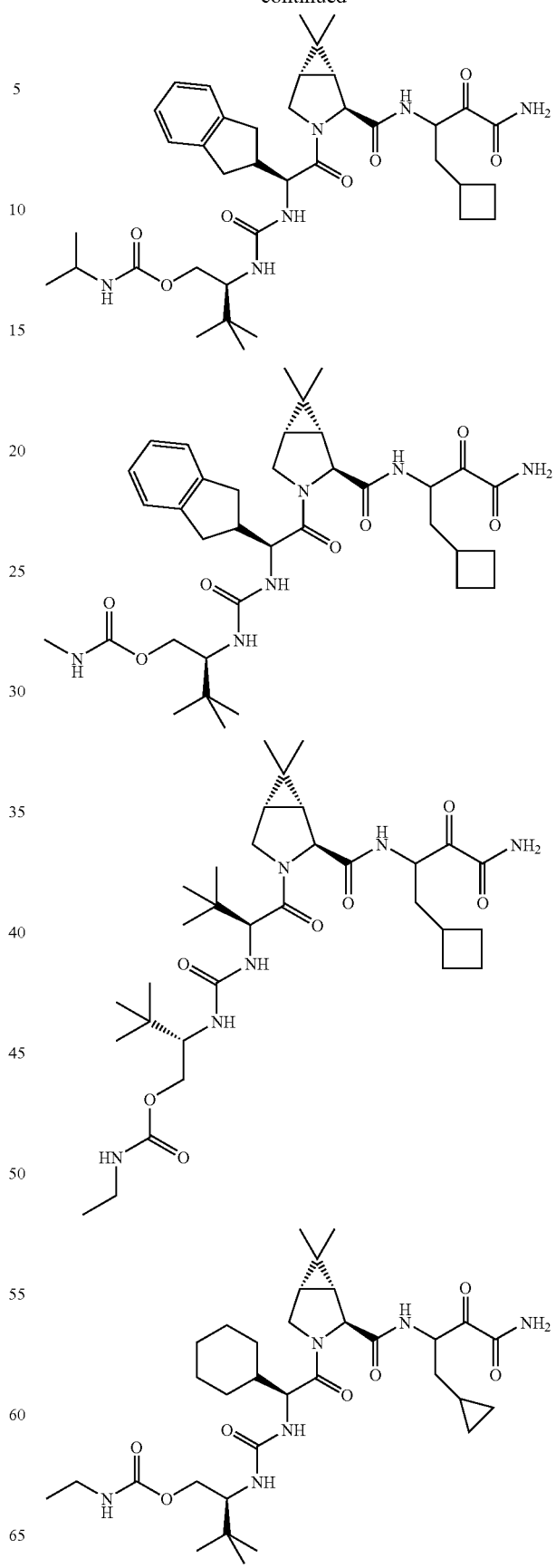

461
-continued
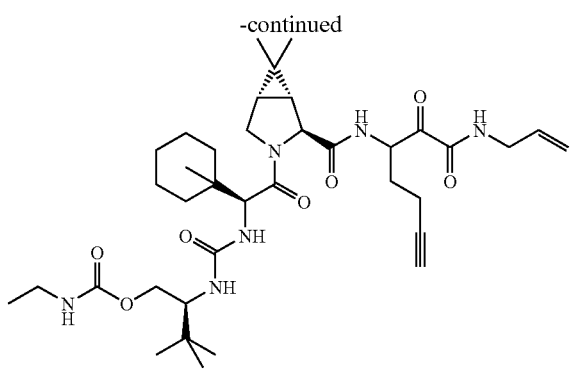
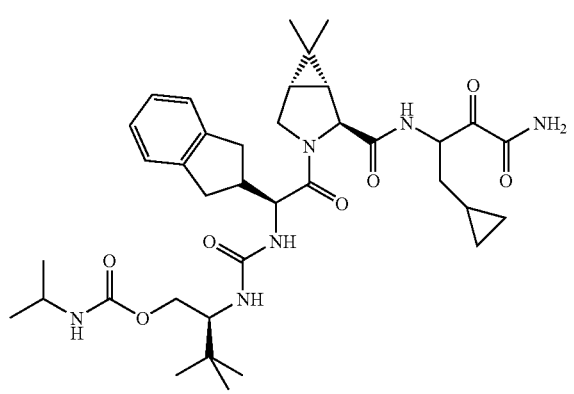
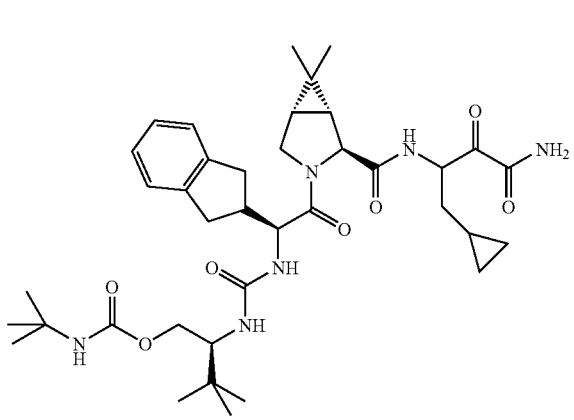
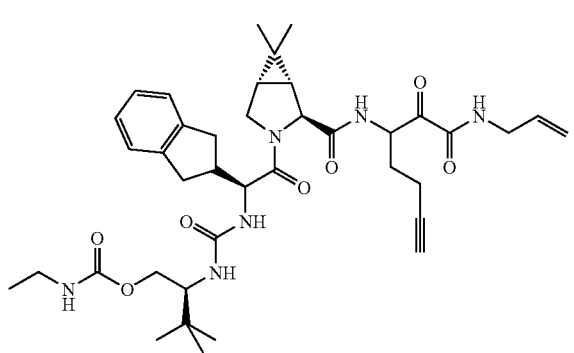
462
-continued
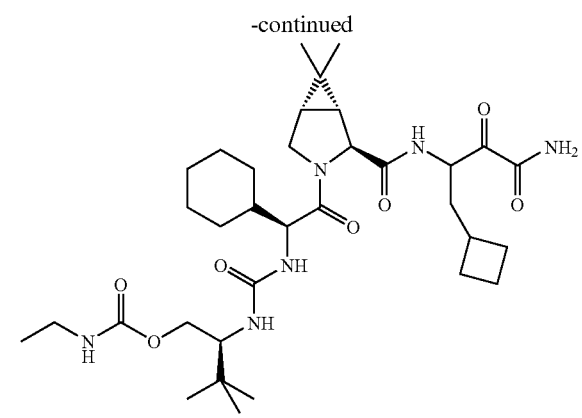
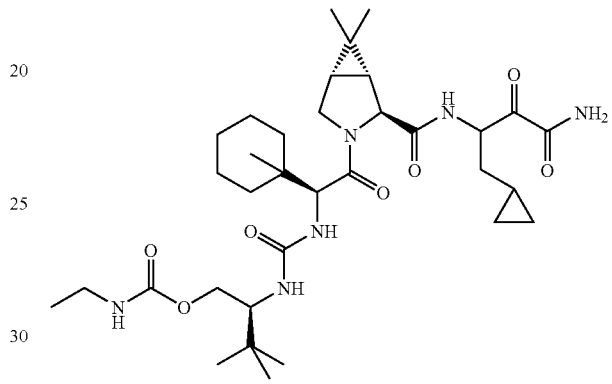
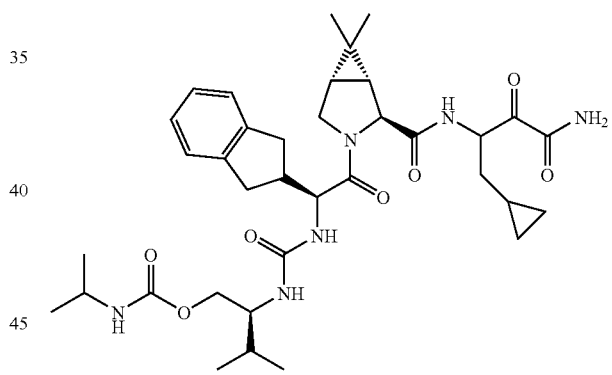
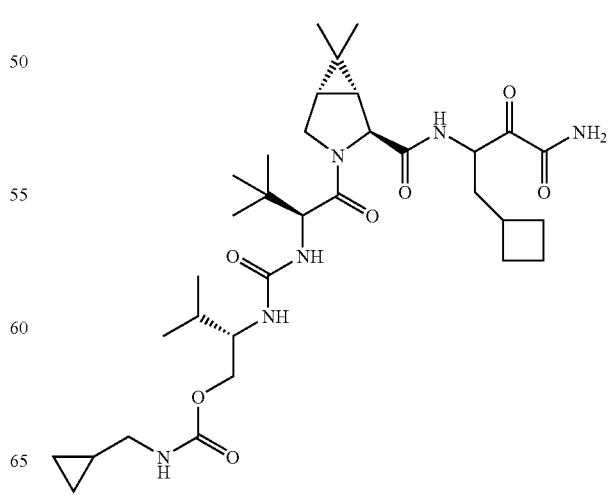

463
-continued
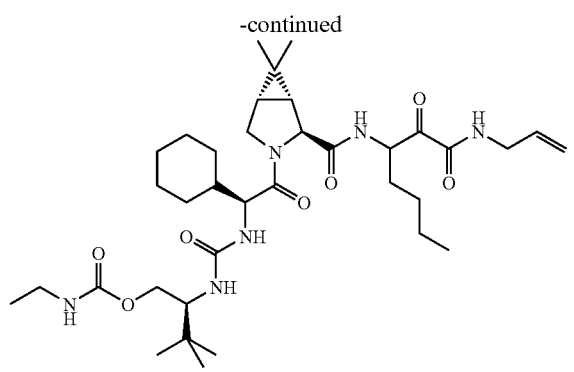
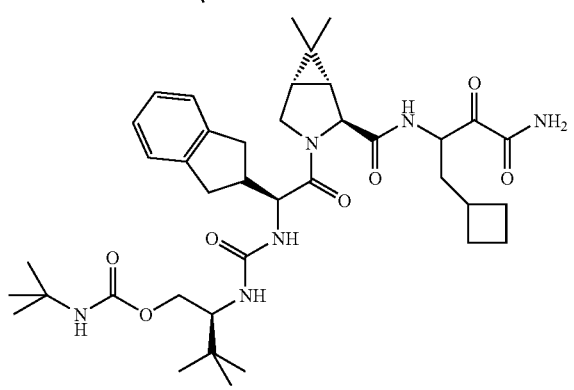
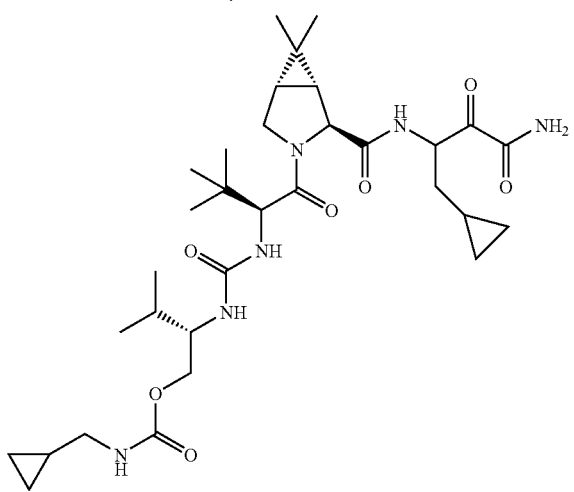
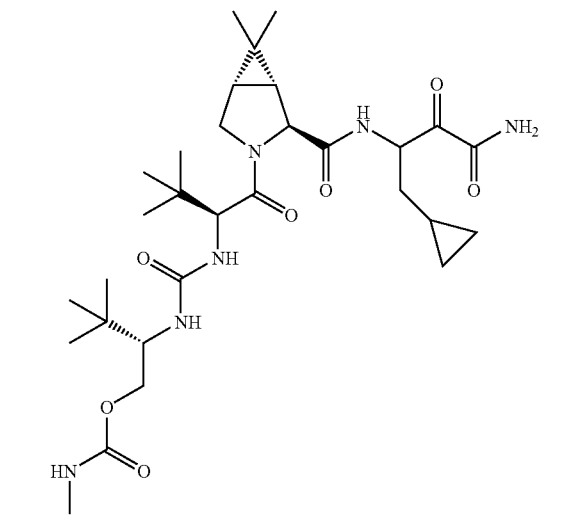
464
-continued
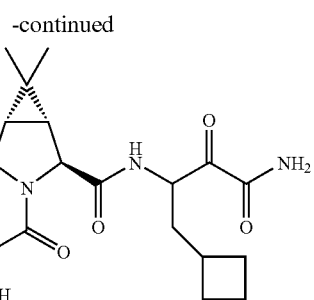
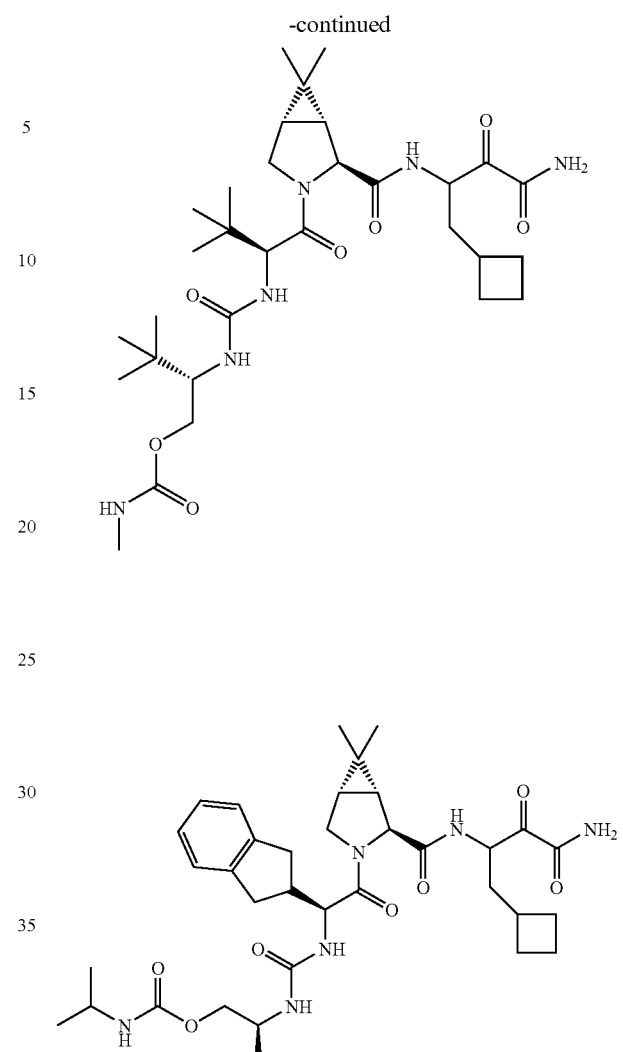
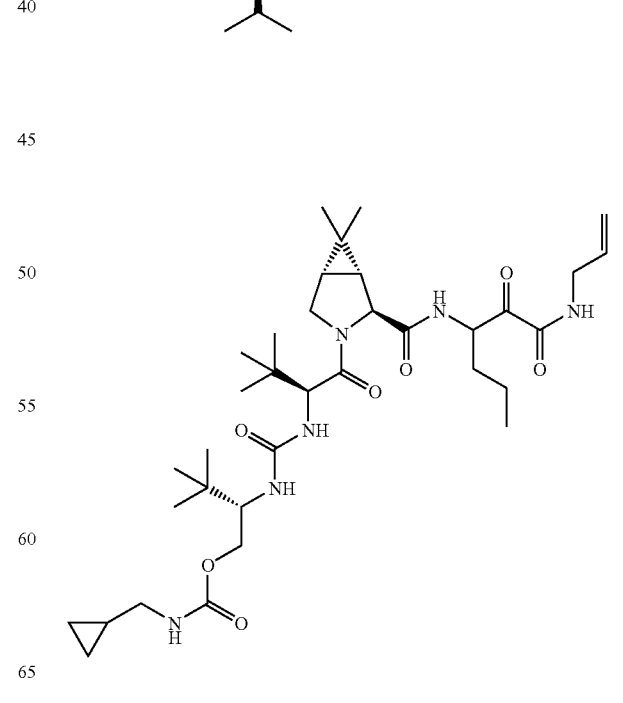

465
-continued
466
-continued
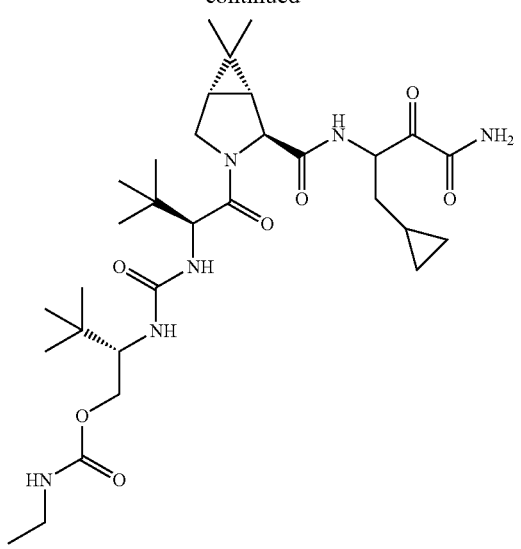
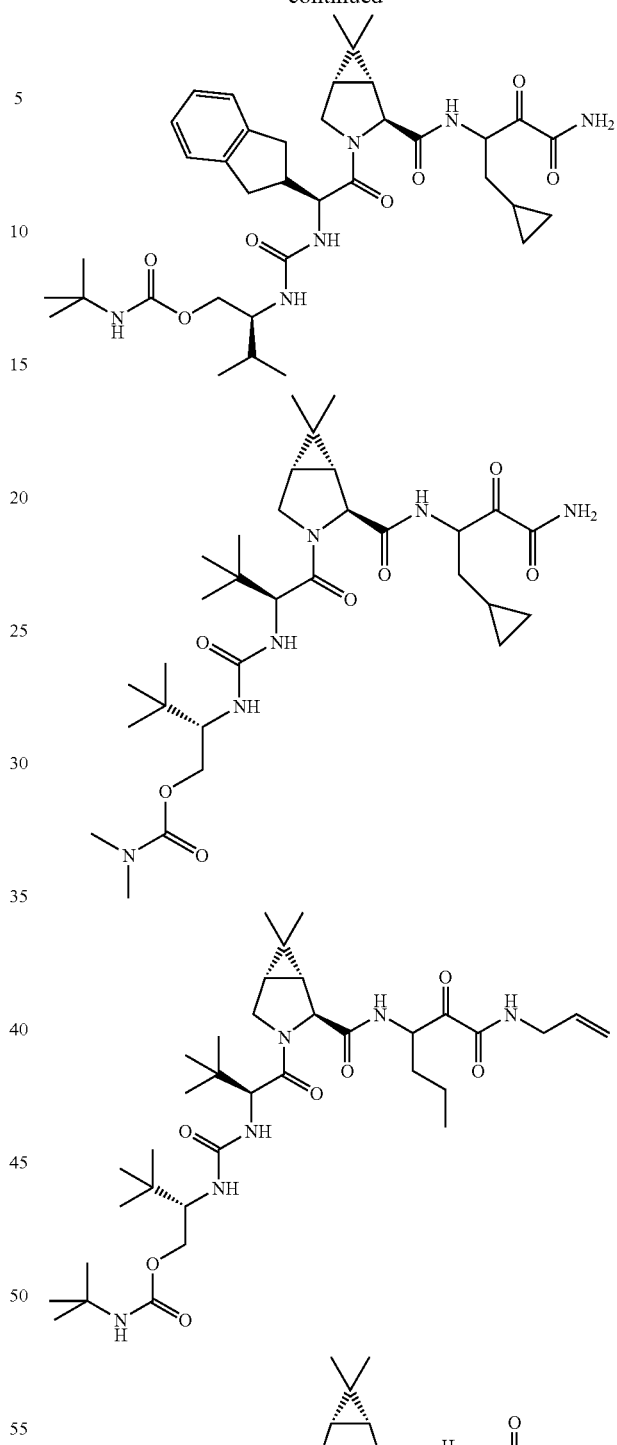
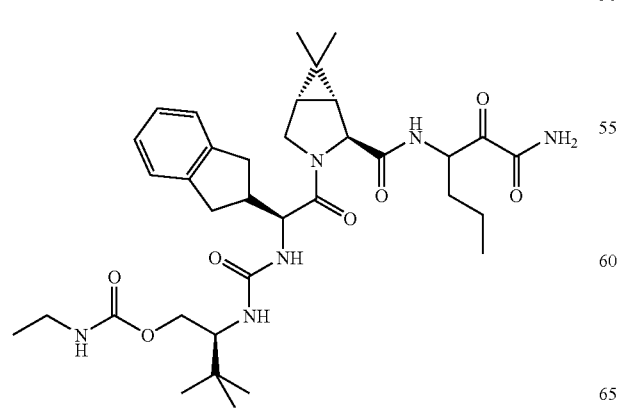

467
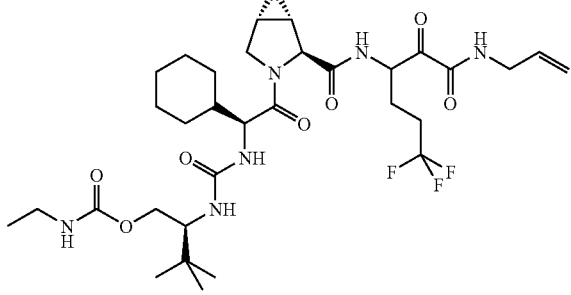
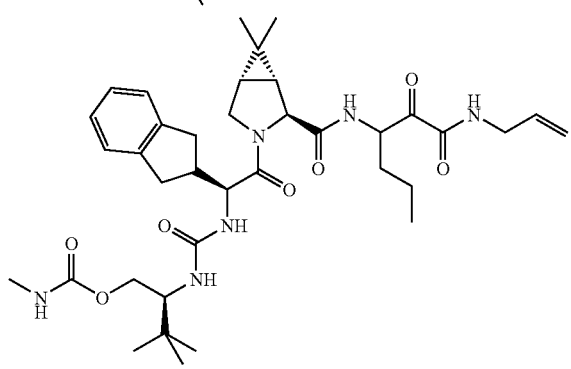
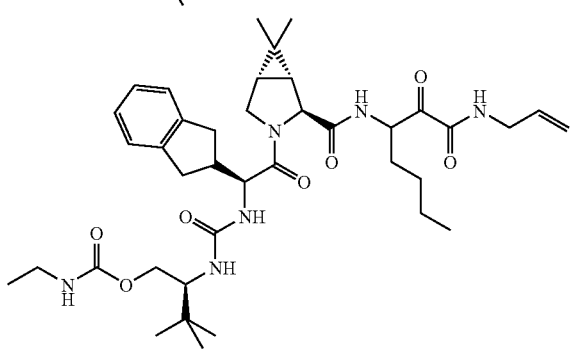
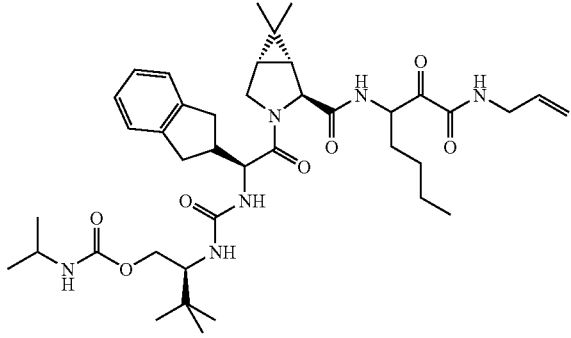
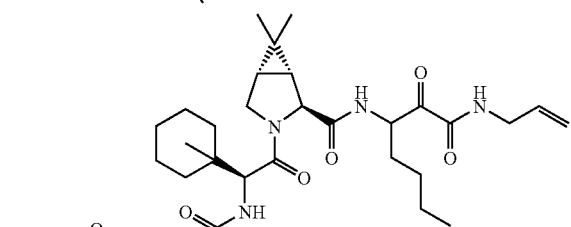
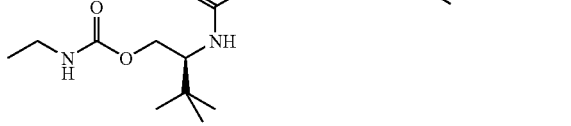
468
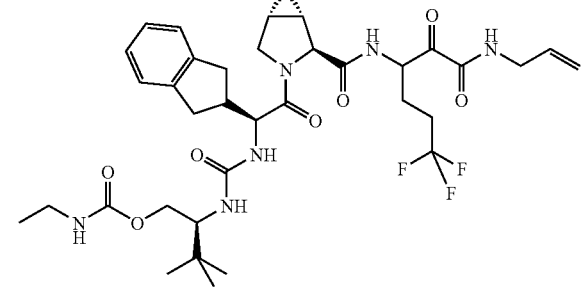
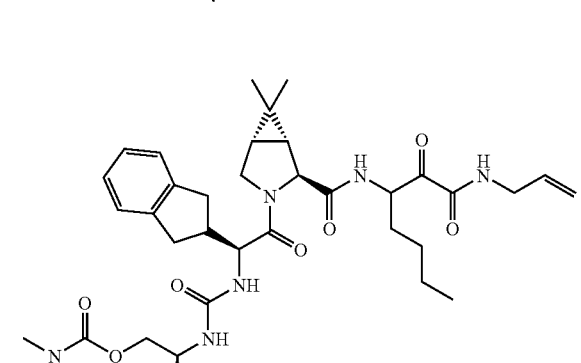
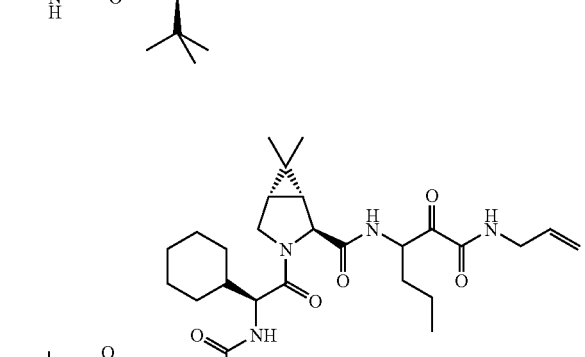
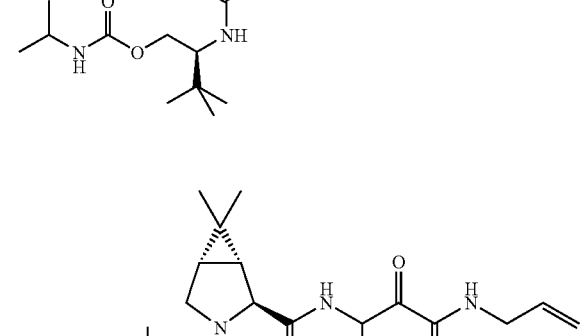
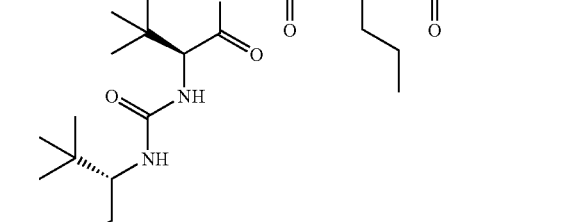

469
-continued
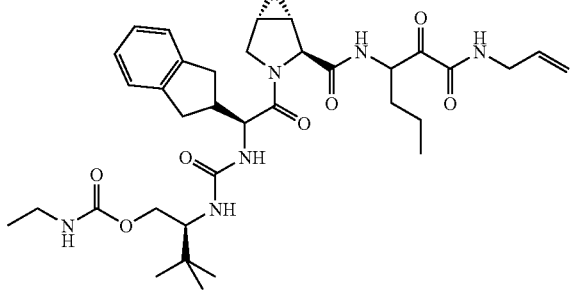
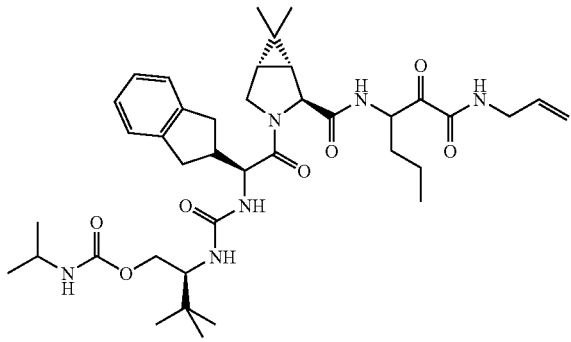
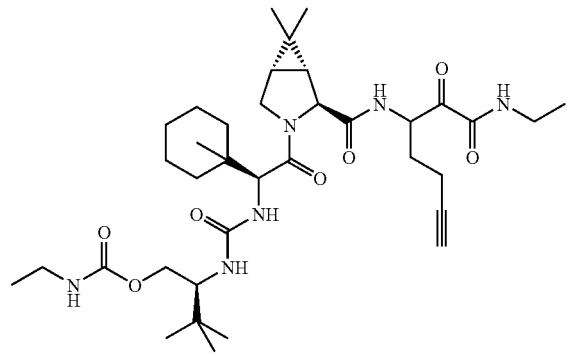
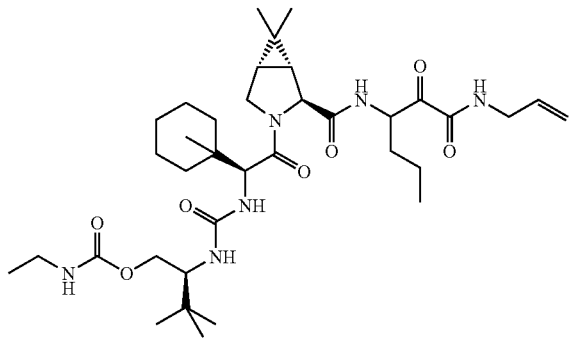
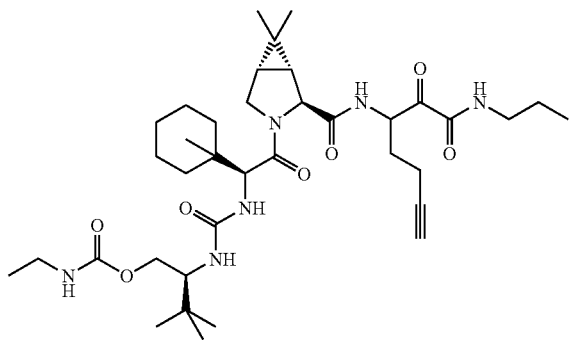
470
-continued
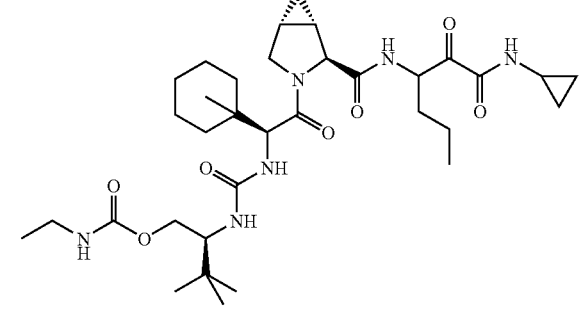
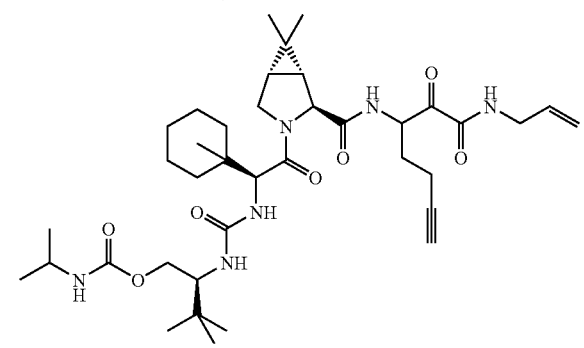
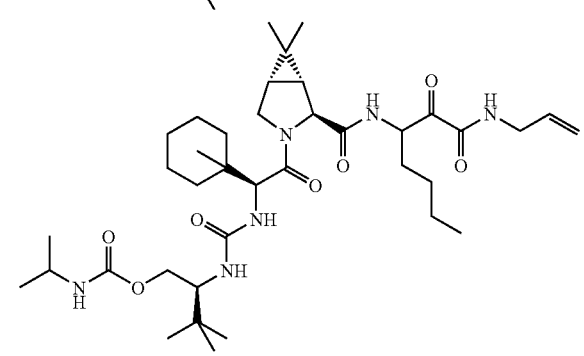
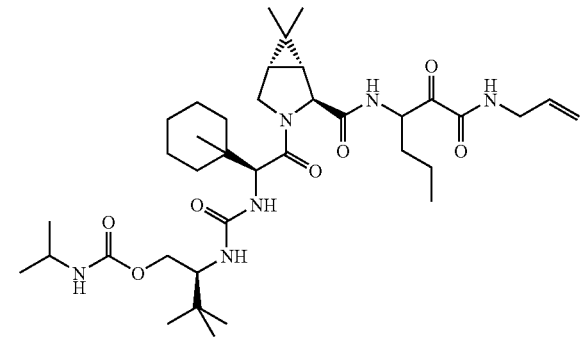
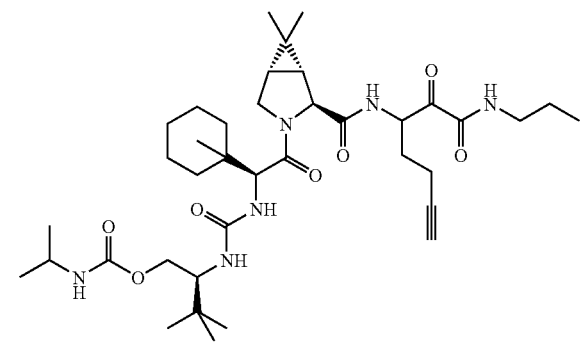

471
-continued
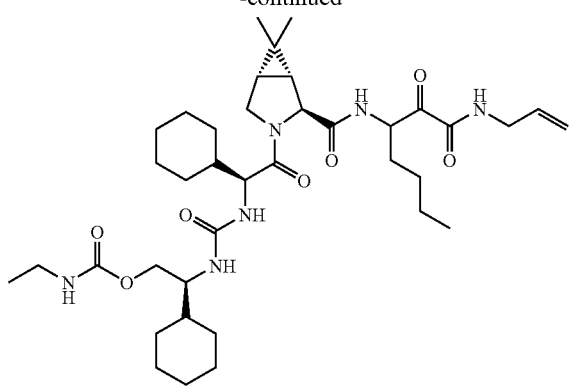
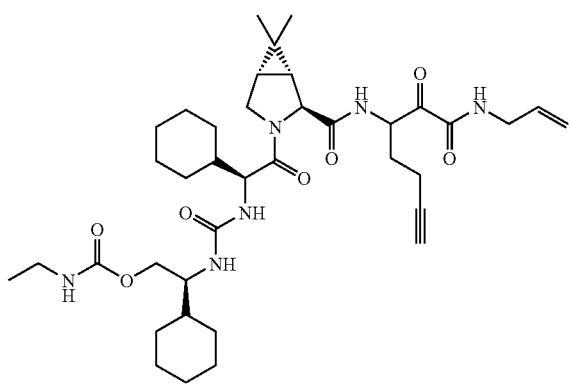

472
-continued
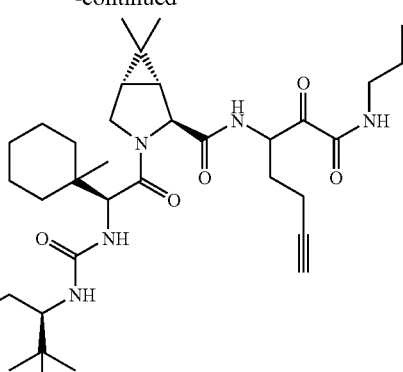
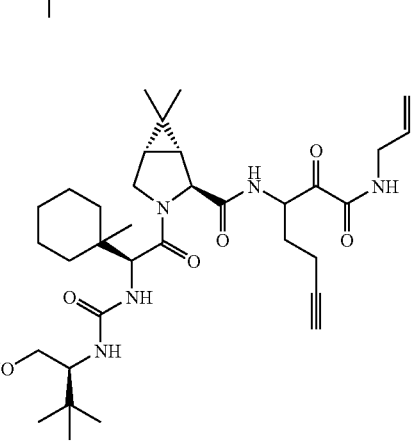
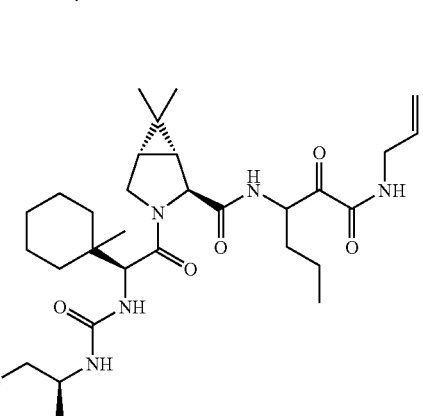
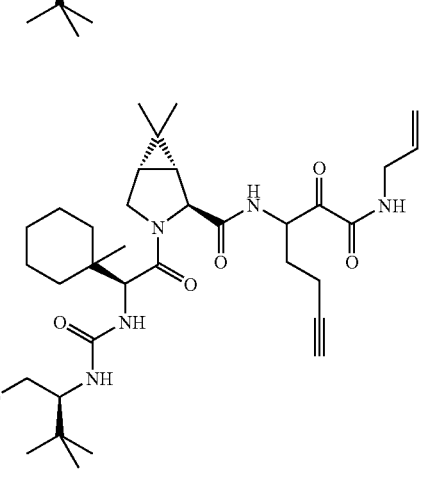

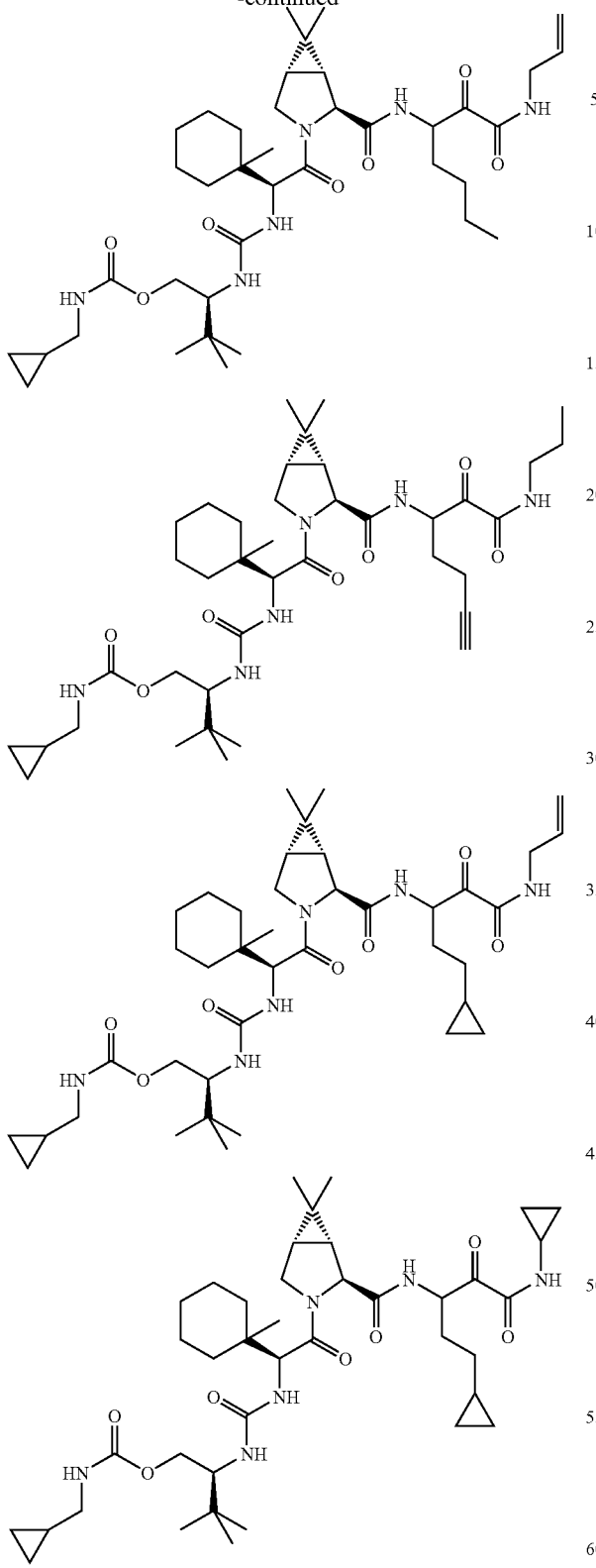
or a pharmaceutically acceptable salt, solvate or ester thereof.
Compounds of formula XIII are disclosed in U.S. patent application Ser. No. 11/065,647 filed Feb. 24, 2005. The preparation of these compounds is disclosed in the experimental section of this application set forth hereinbelow.
Non-limiting examples of certain compounds disclosed in U.S. patent application Ser. No. 11/065,647 are:
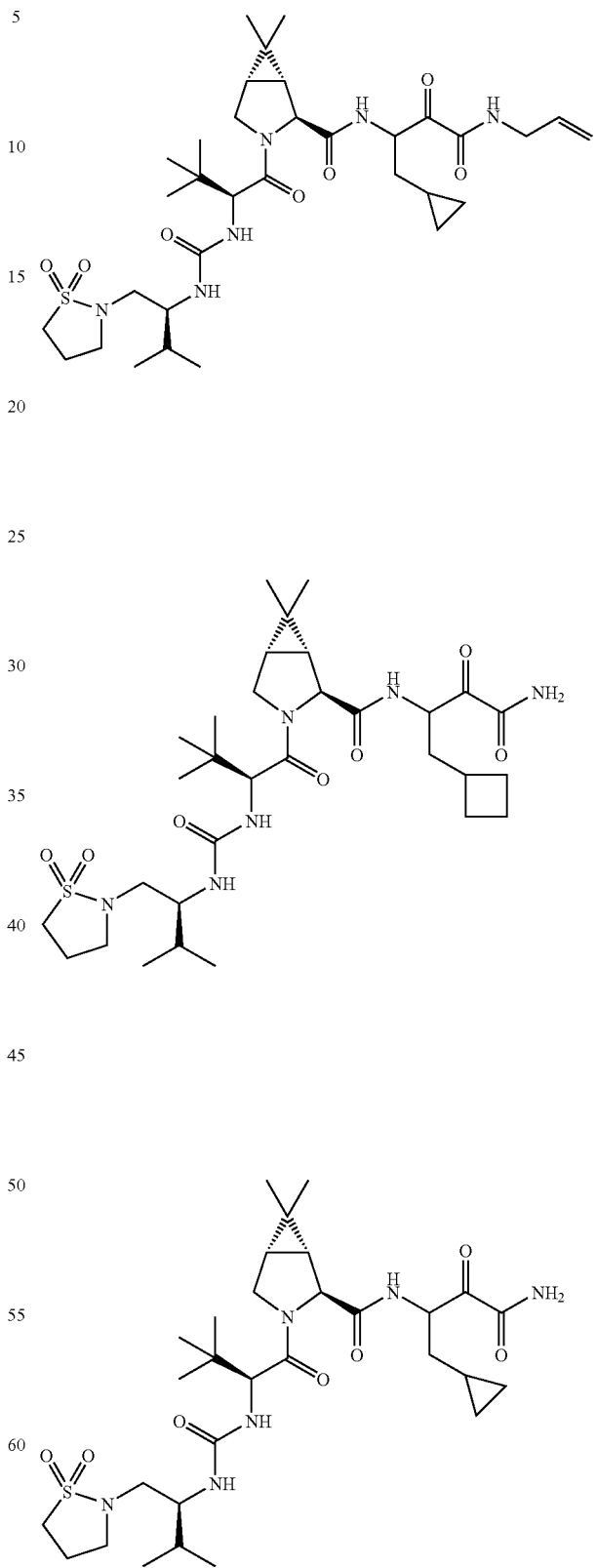

475
-continued
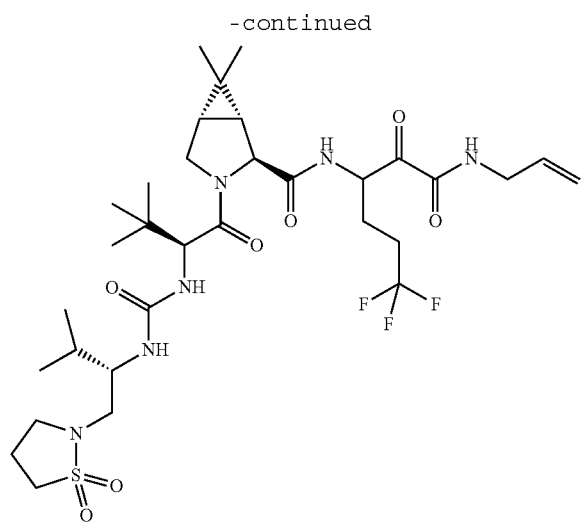
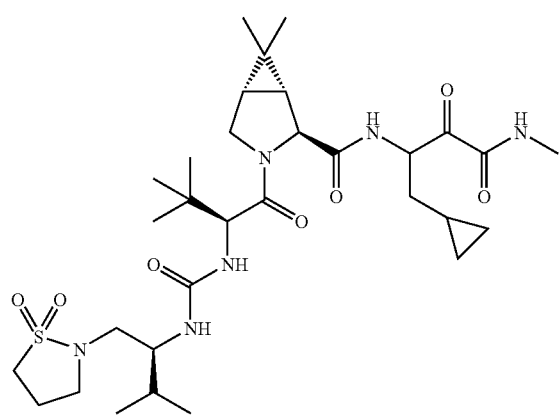
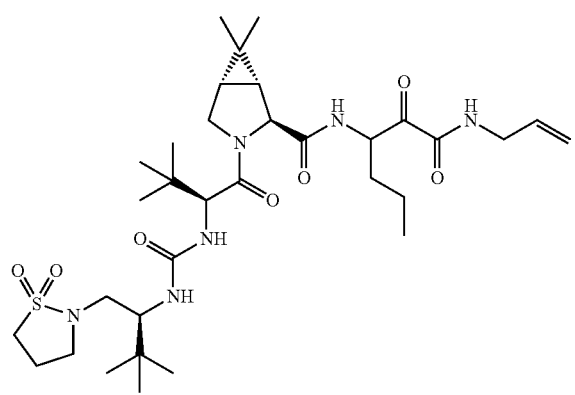
476
-continued
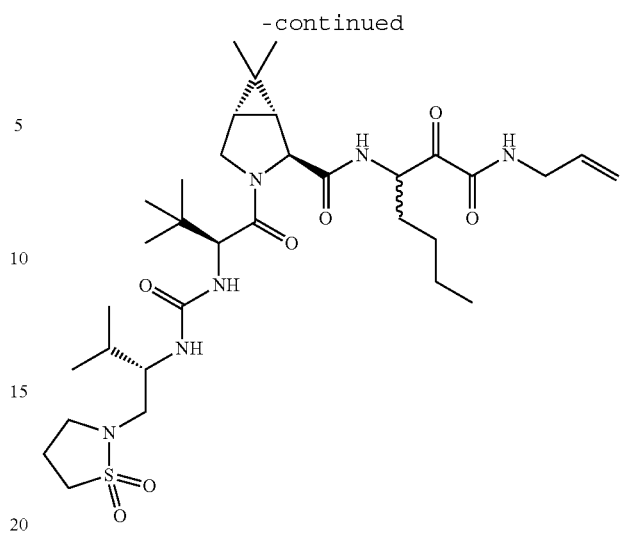
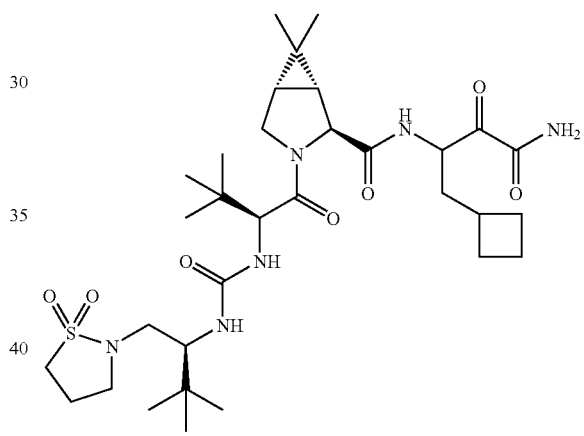
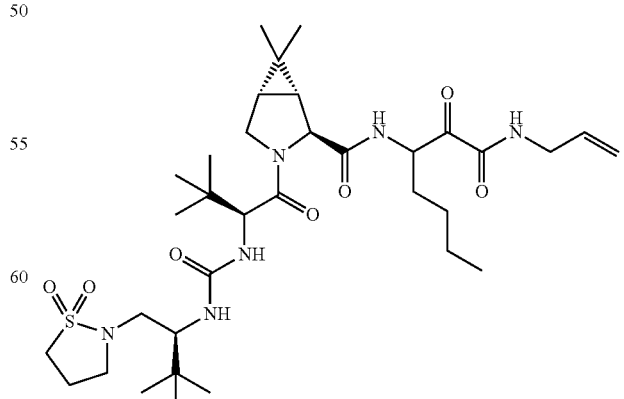

477
-continued
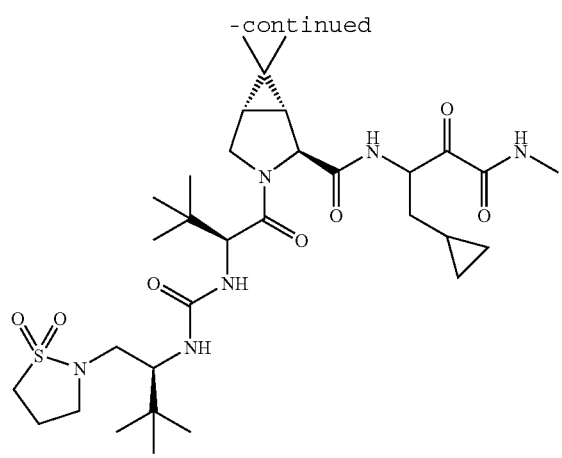
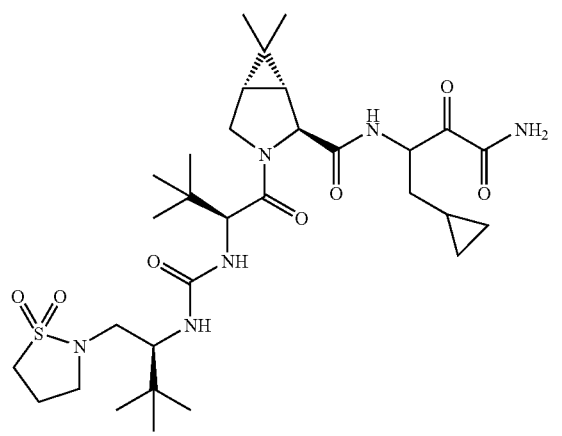
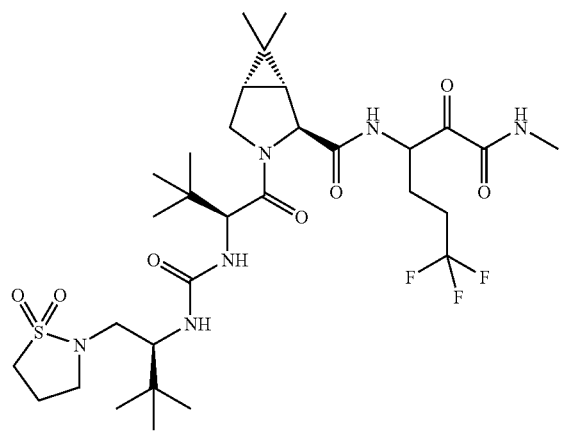
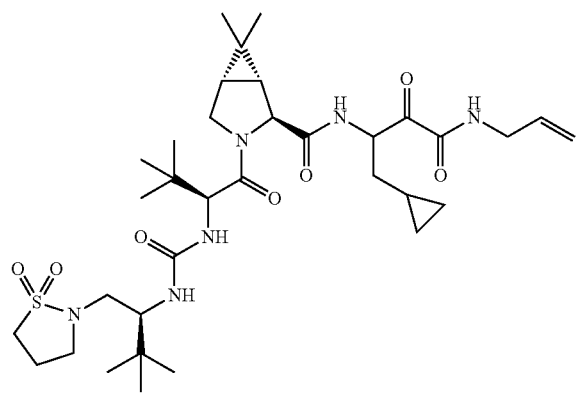
478
-continued
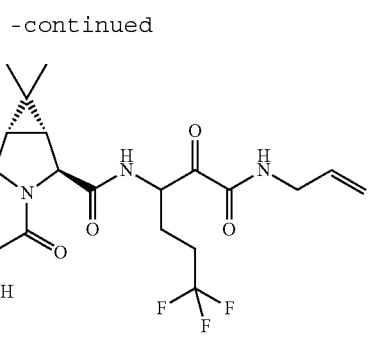
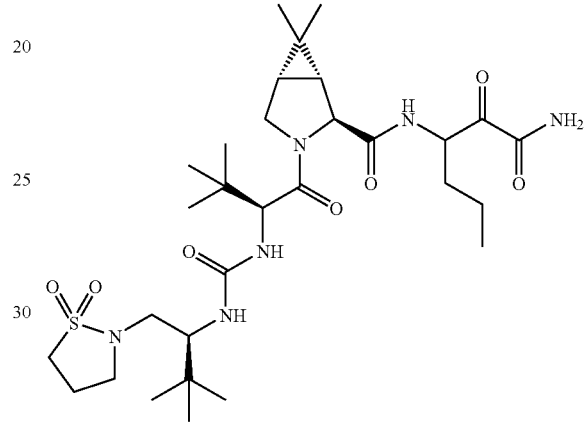
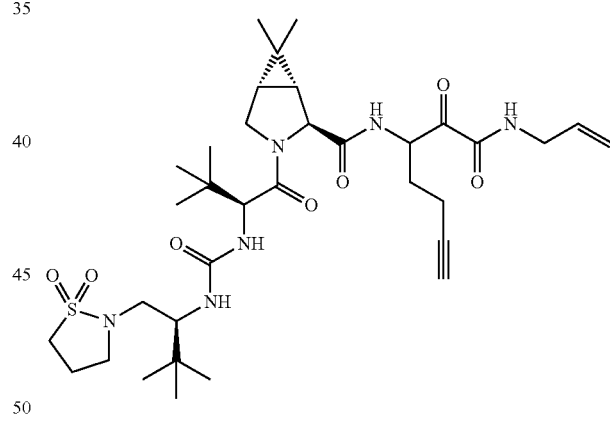
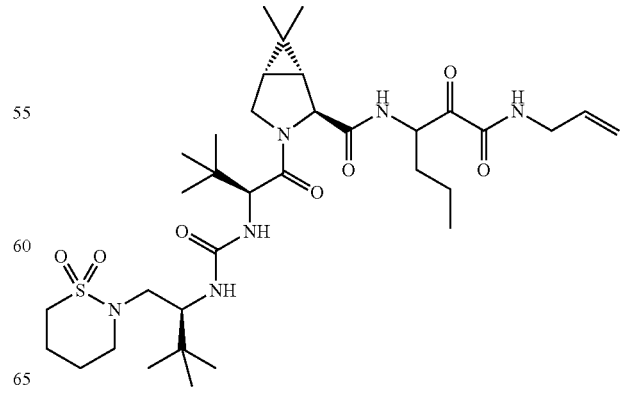

479          480
-continued     -continued
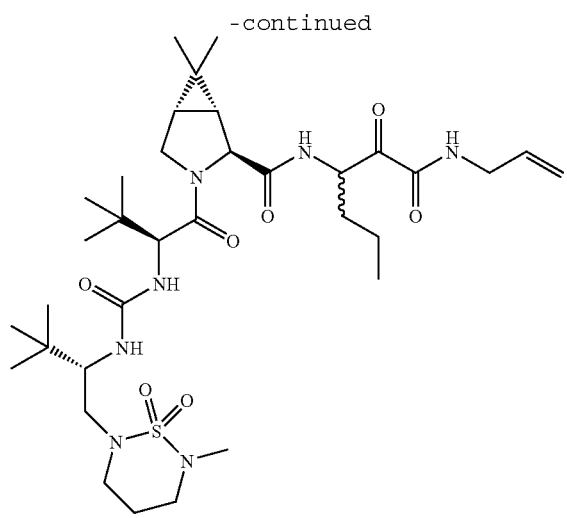 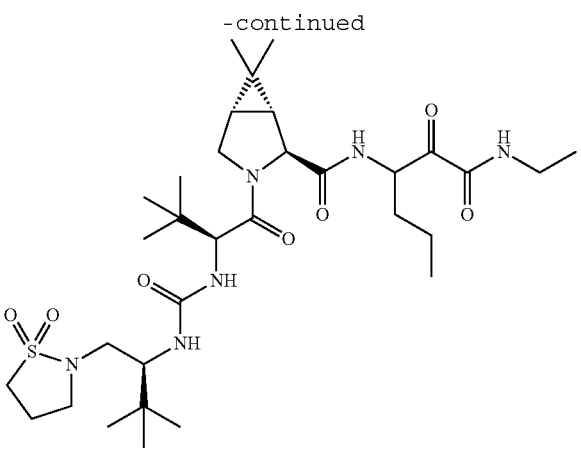
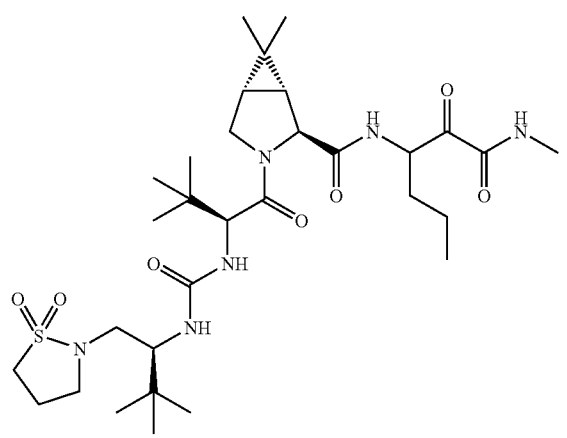 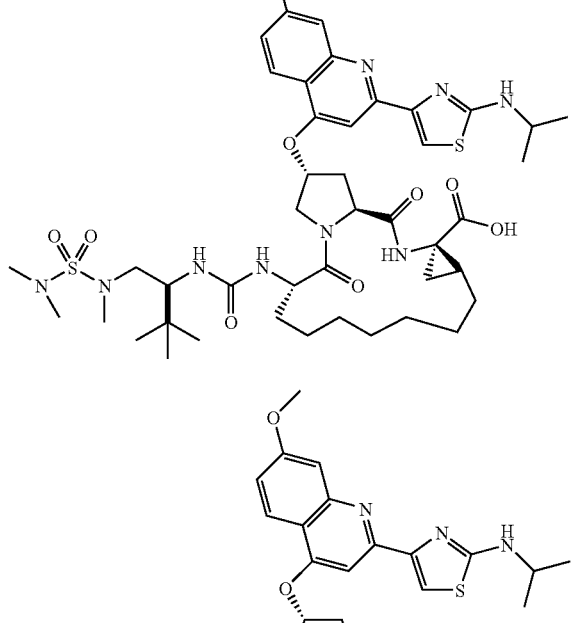
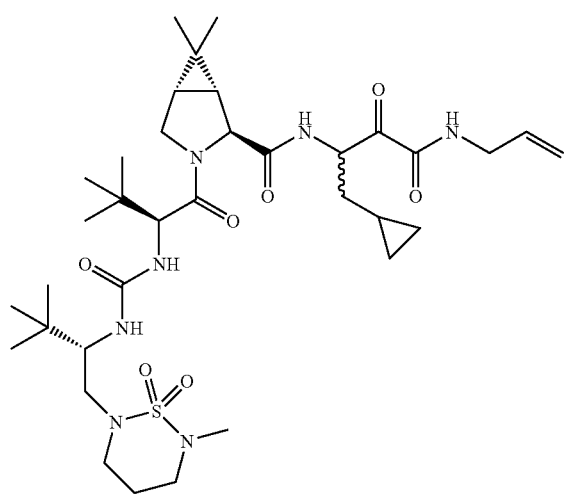 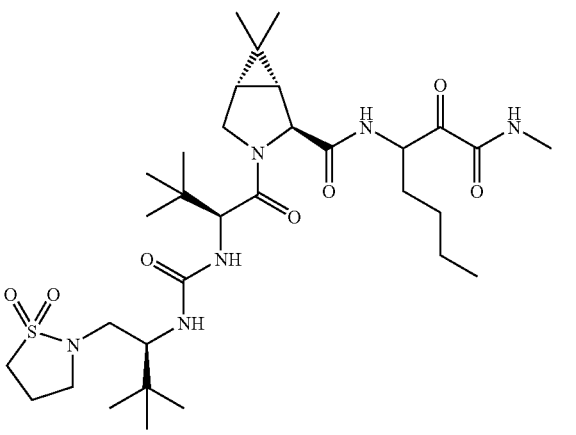

481
-continued
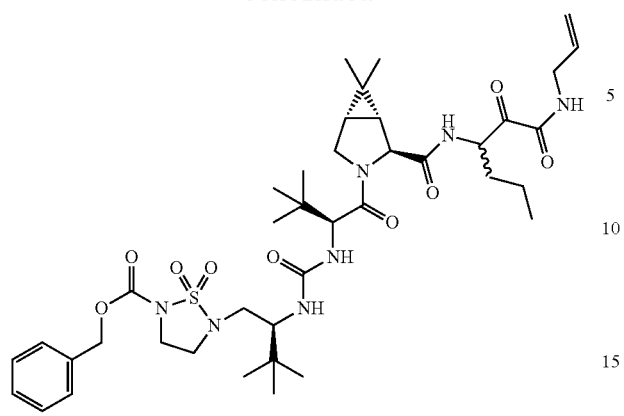
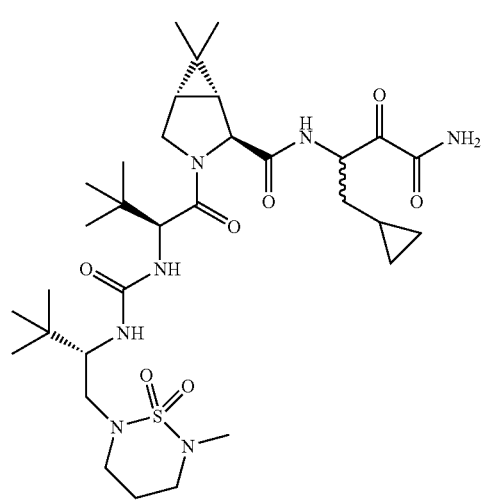
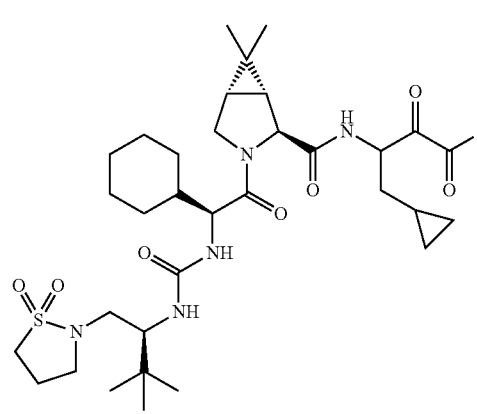
482
-continued
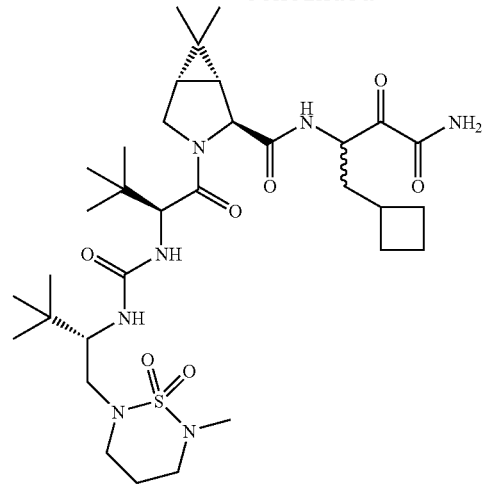
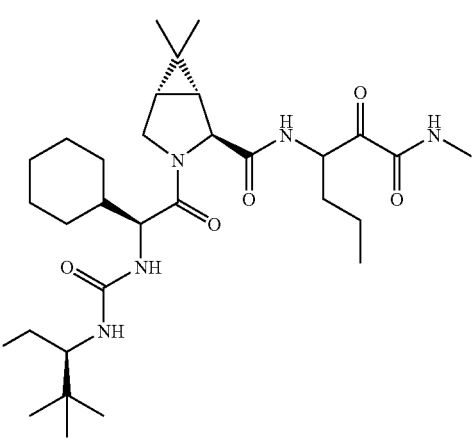
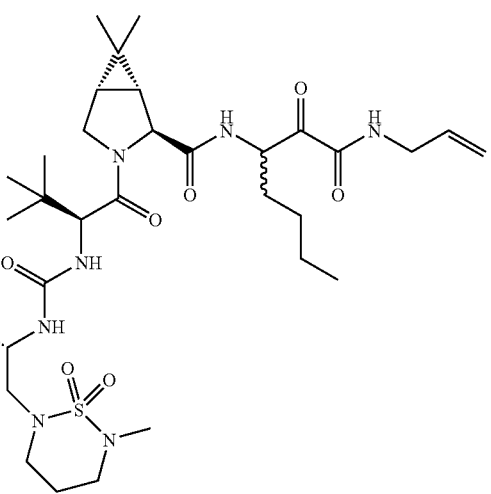

| 483 | 484 |
|---|---|
| -continued | -continued |
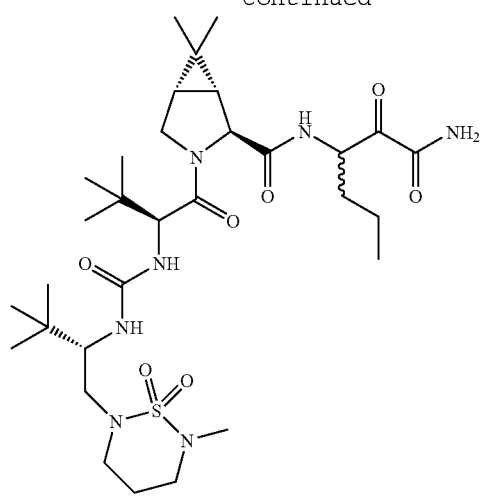
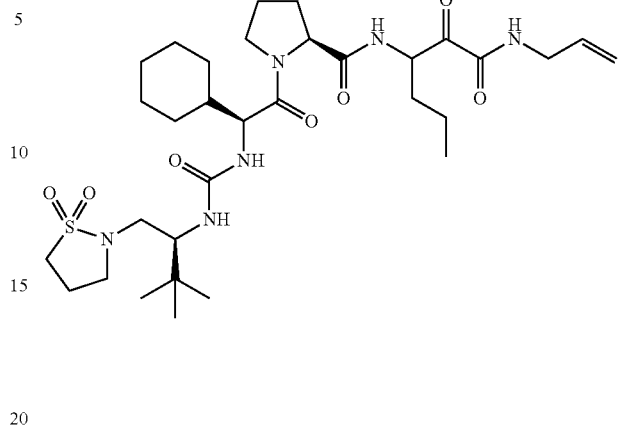
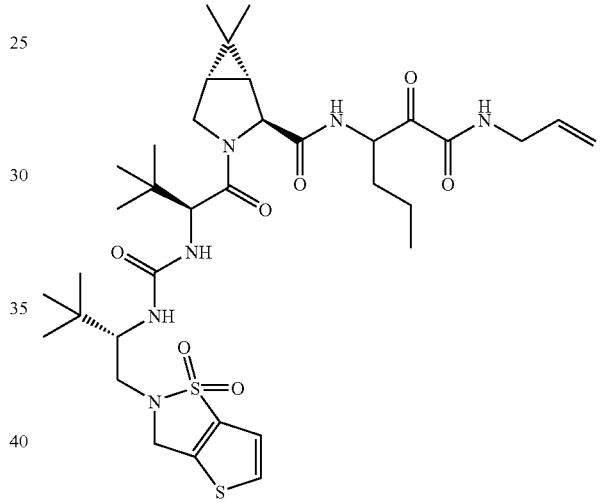
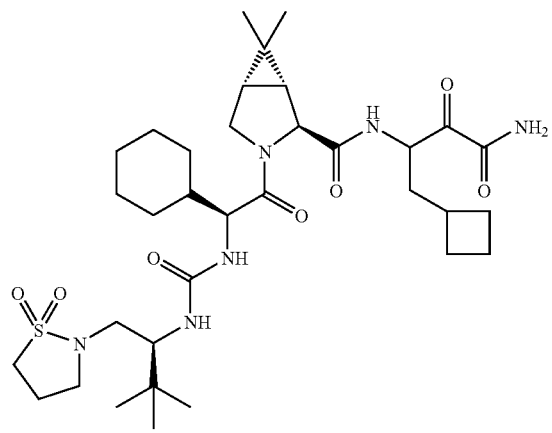

485
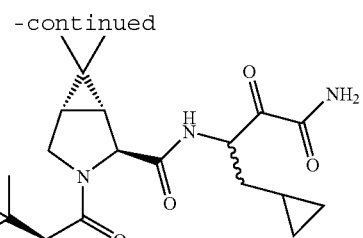
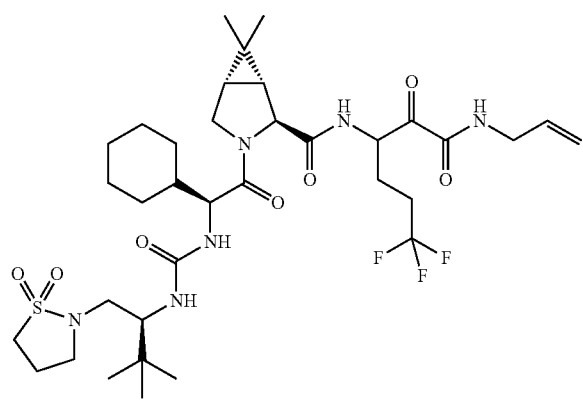
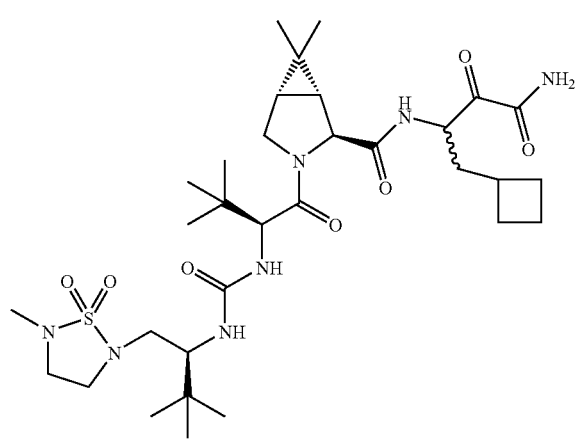
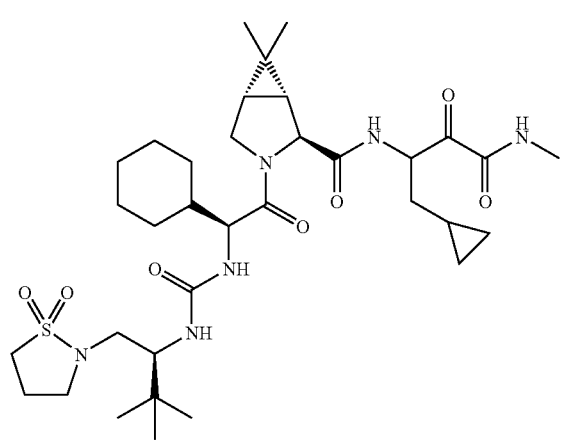
486
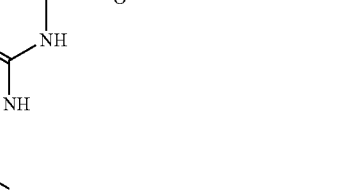
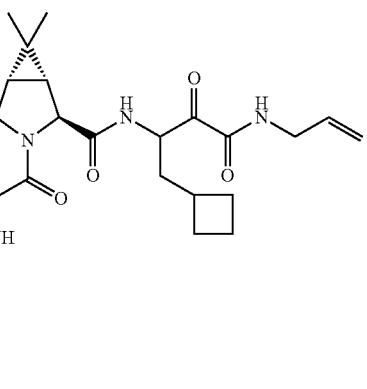
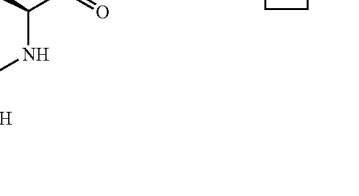
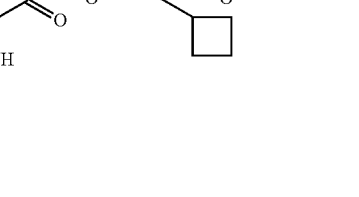

487 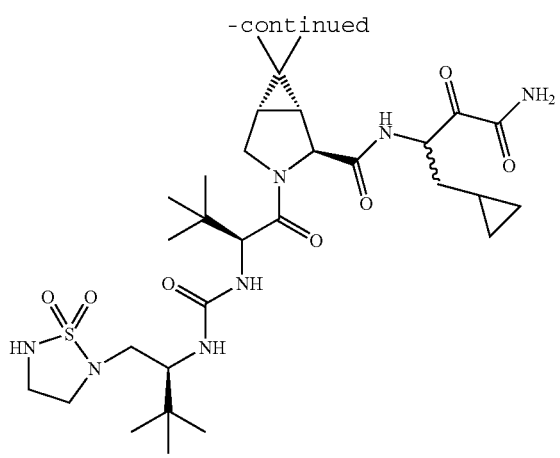 488 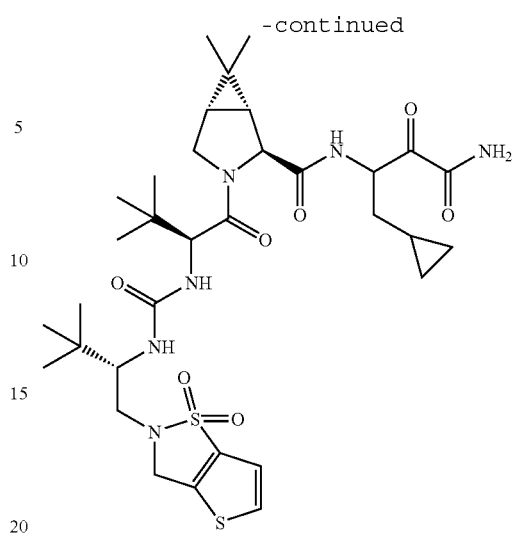
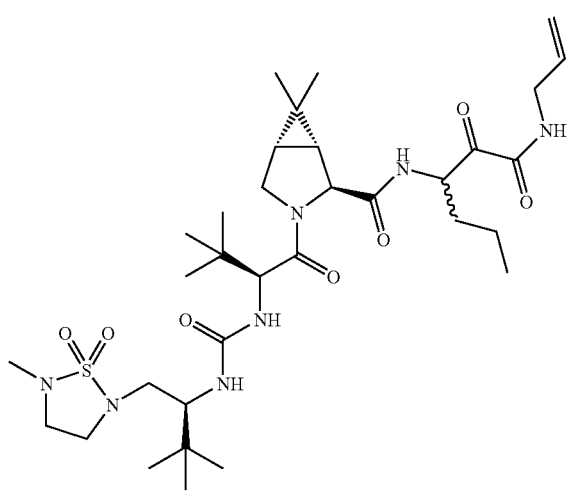 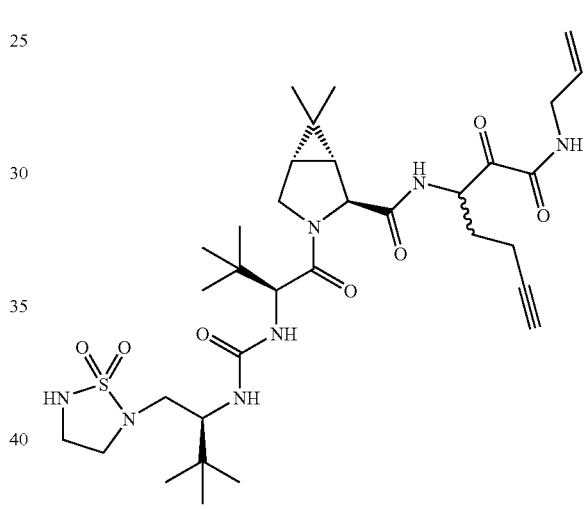
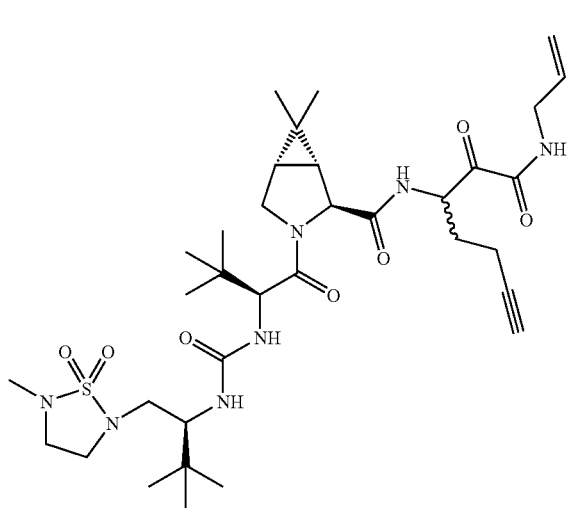 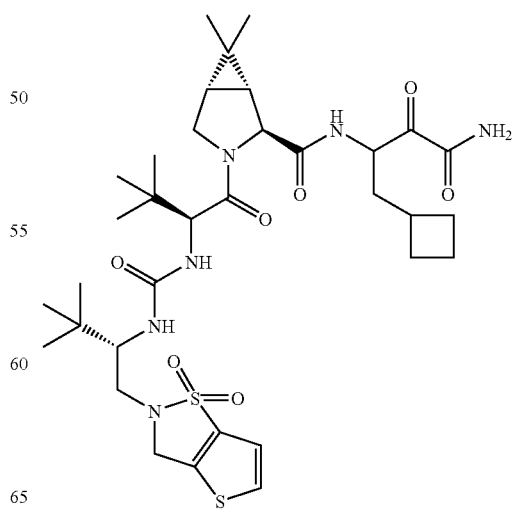

489
-continued
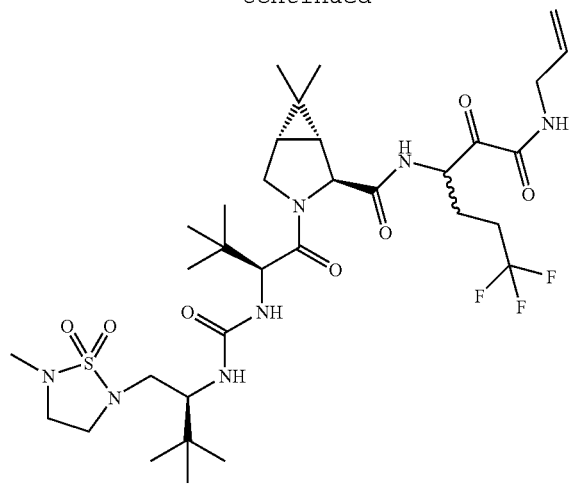
490
-continued
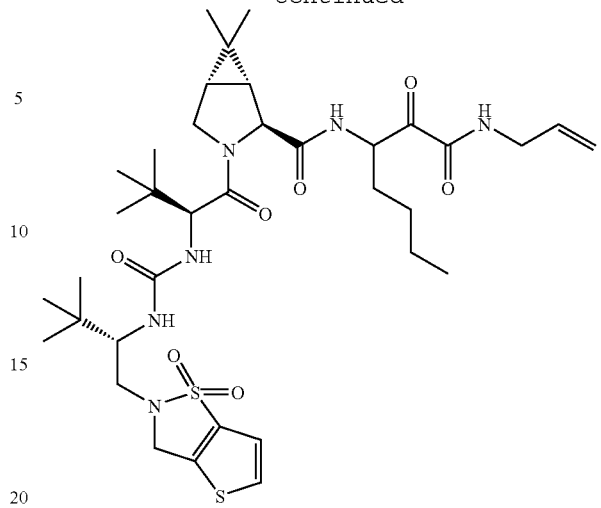
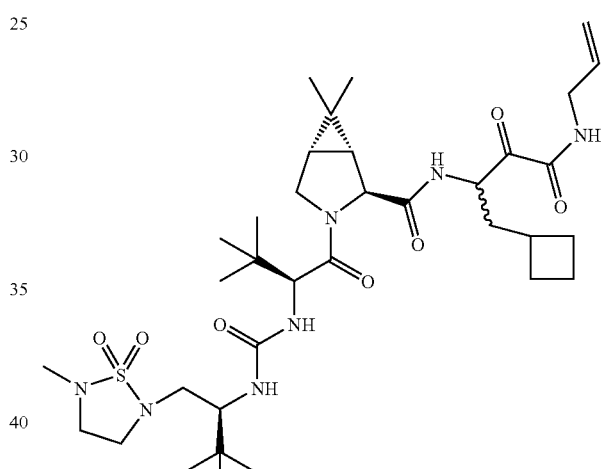
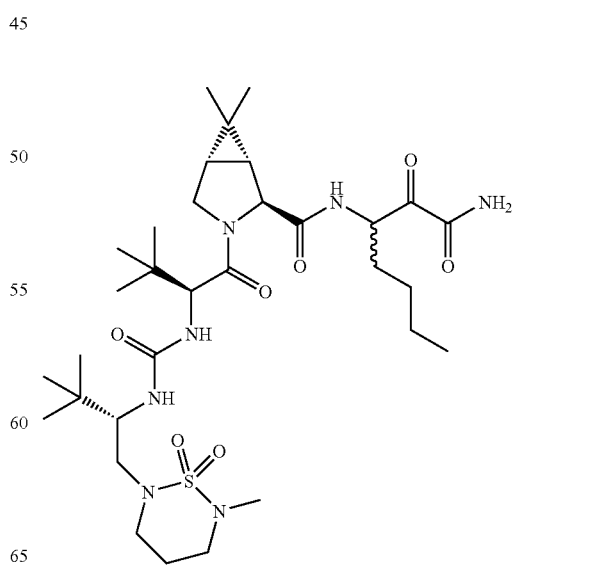

491
-continued
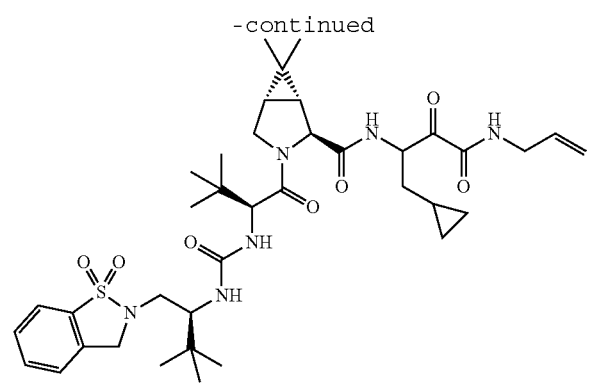
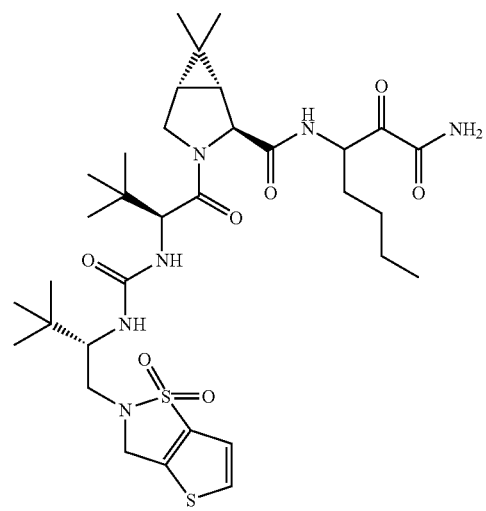
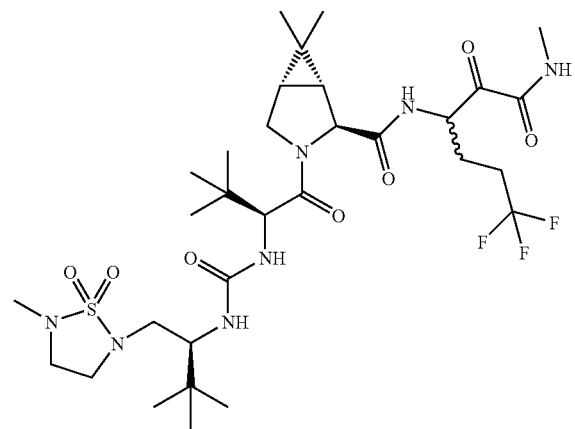
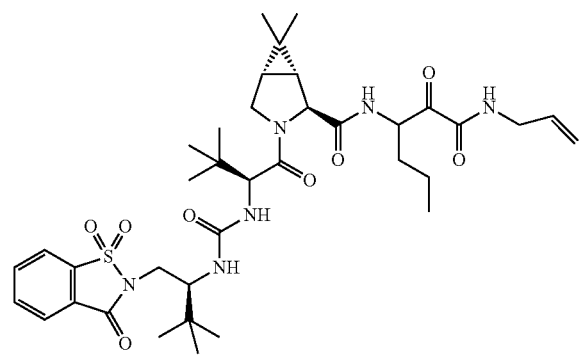
492
-continued
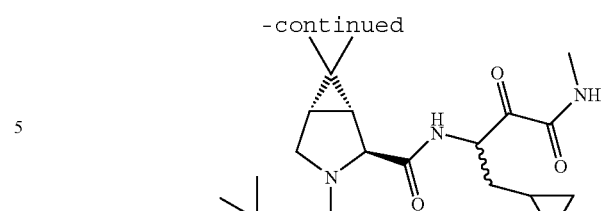
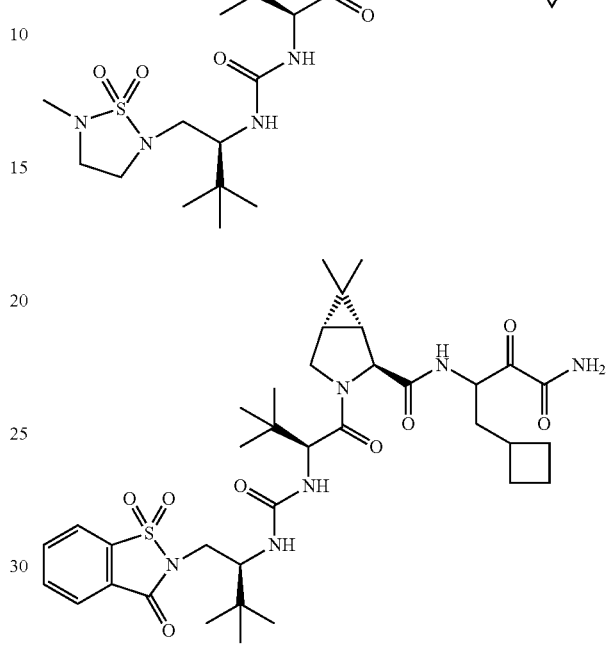
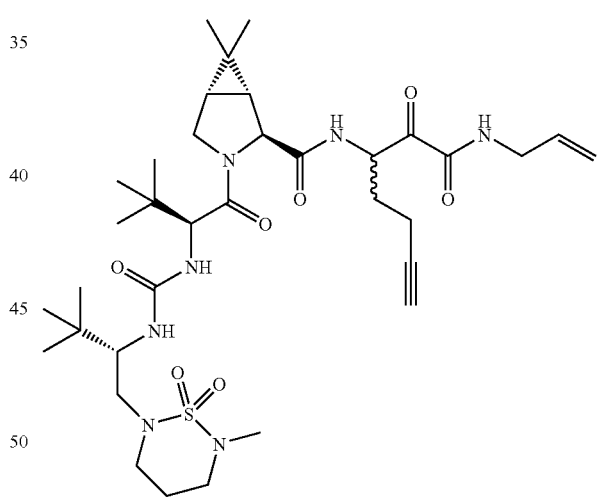
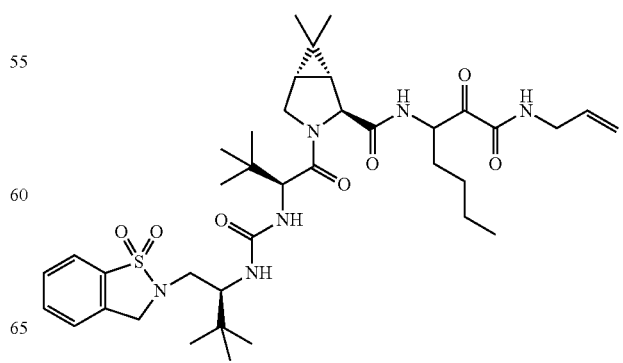

| 493 | 494 |
|---|---|
| -continued | -continued |
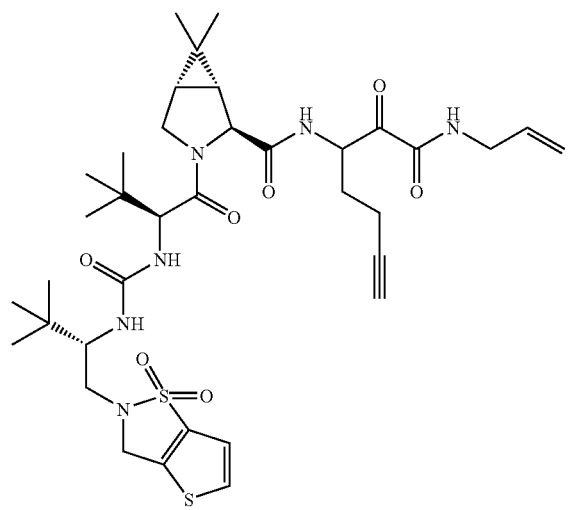
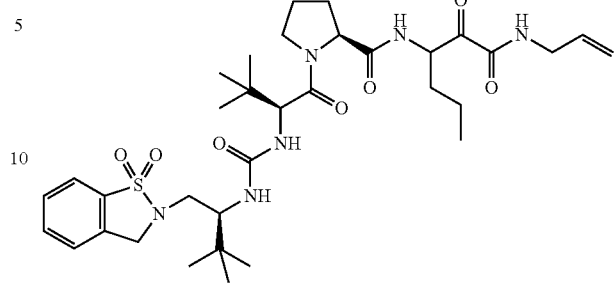
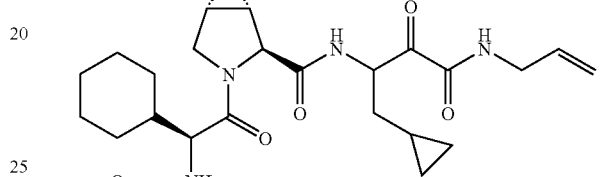
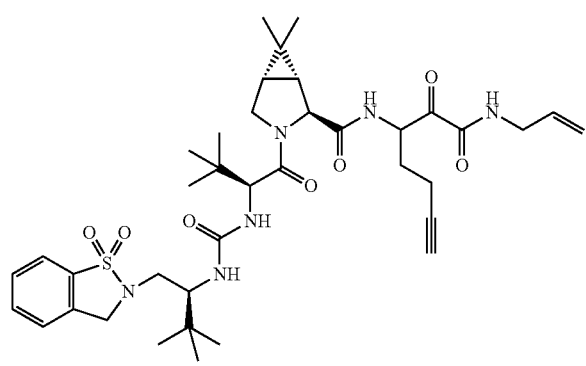
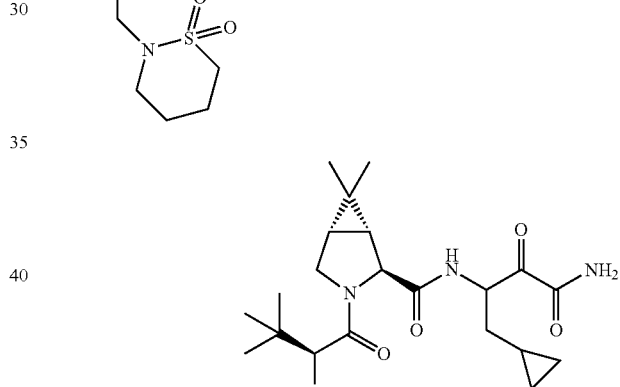
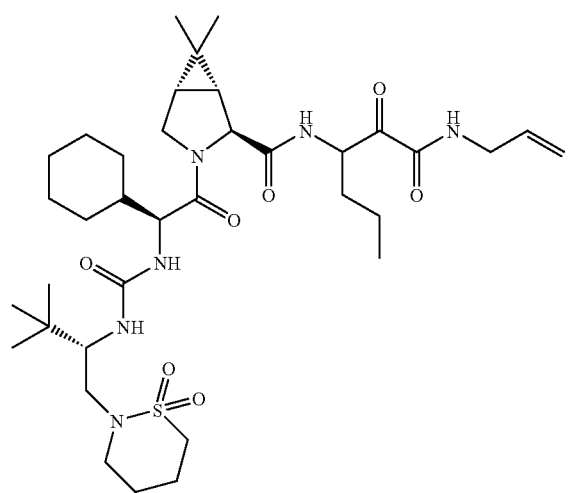
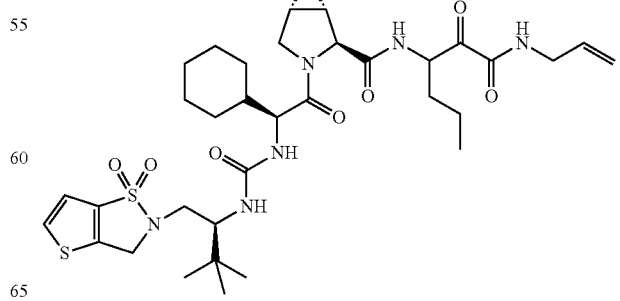

495
-continued
496
-continued
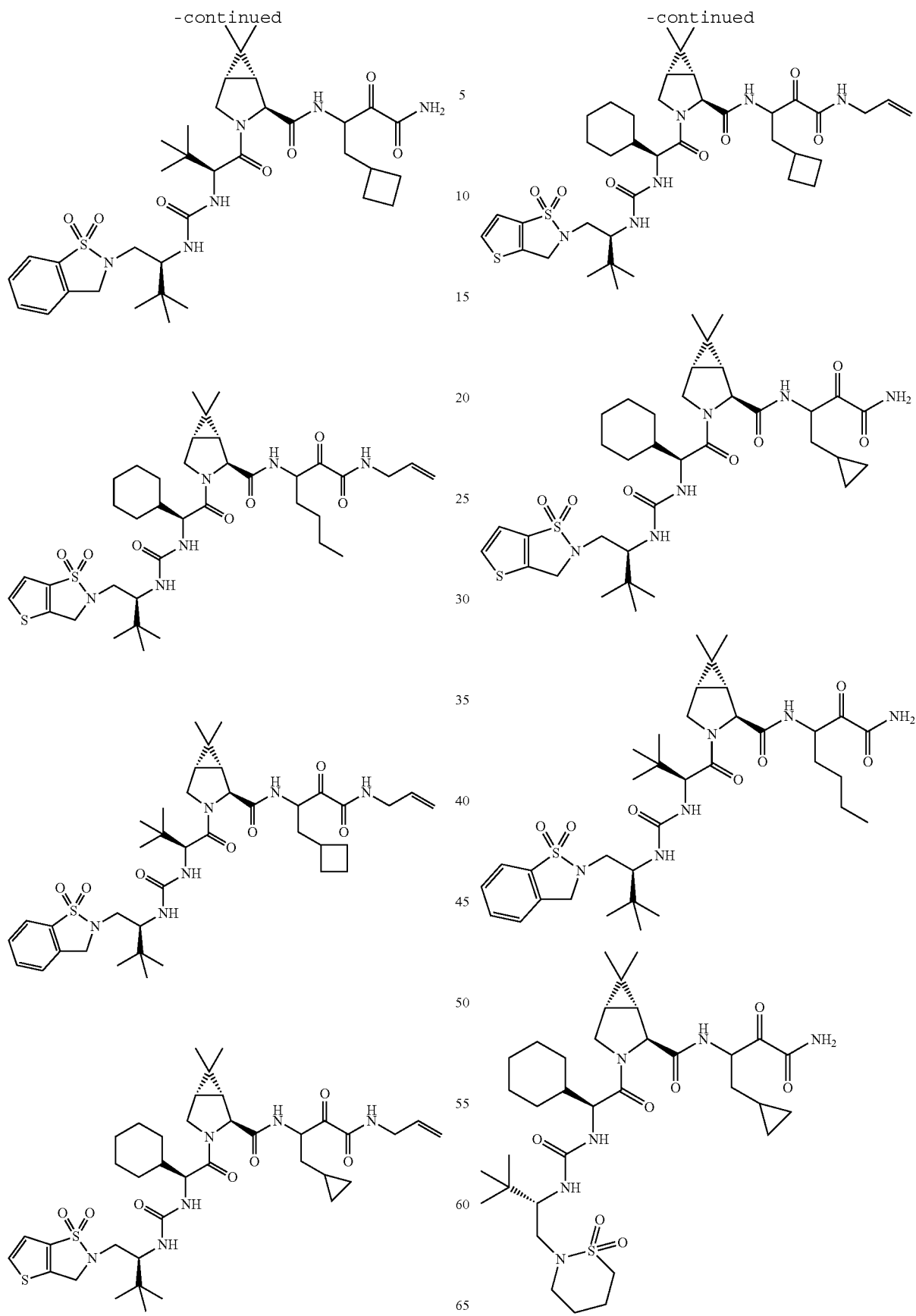

497
-continued
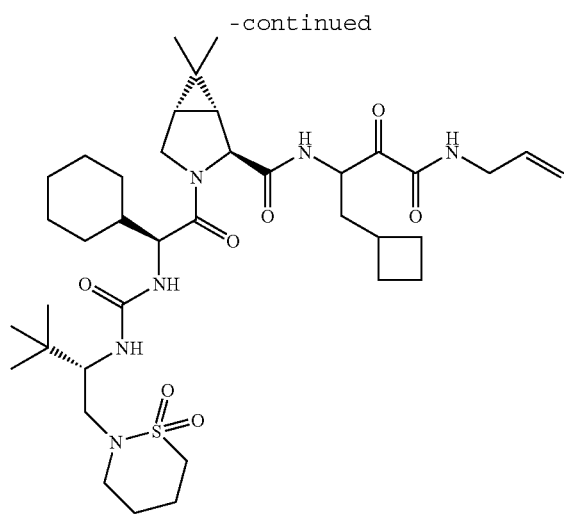
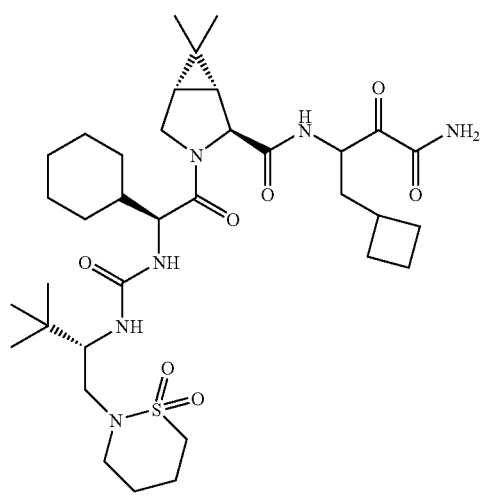
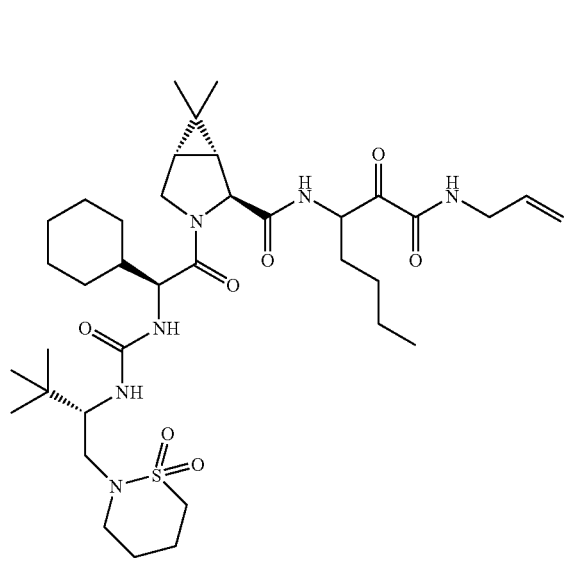
498
-continued
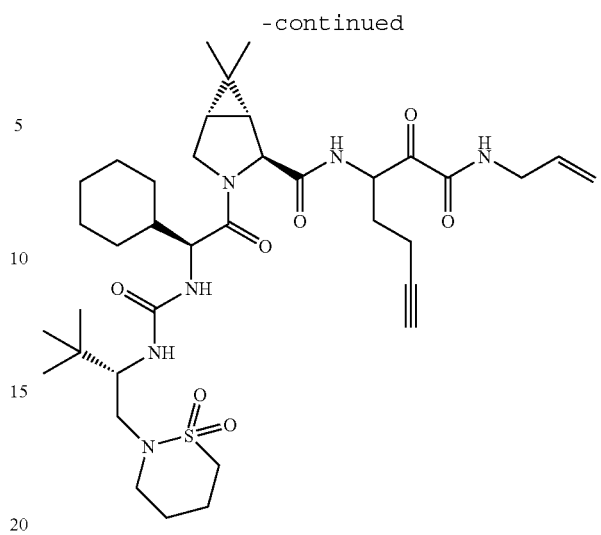
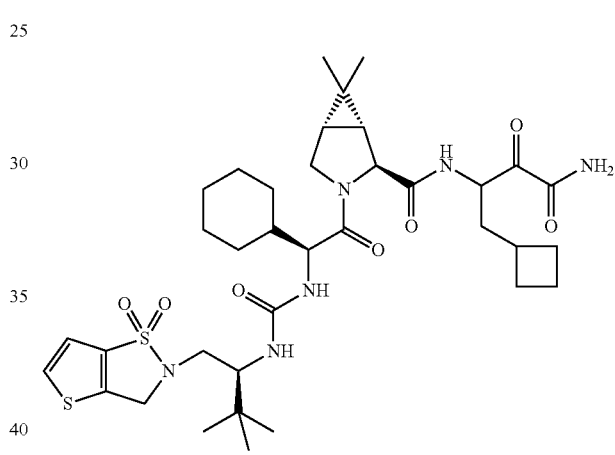
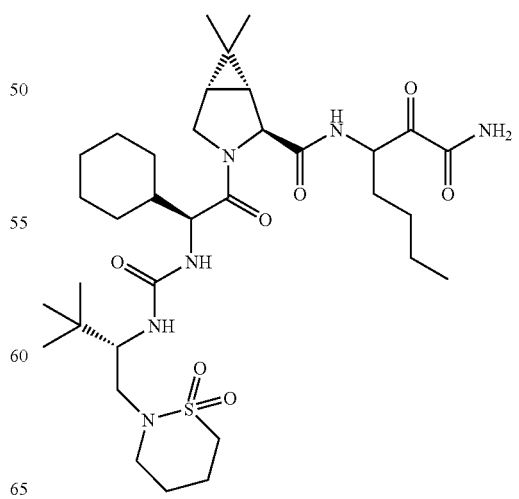

499
-continued
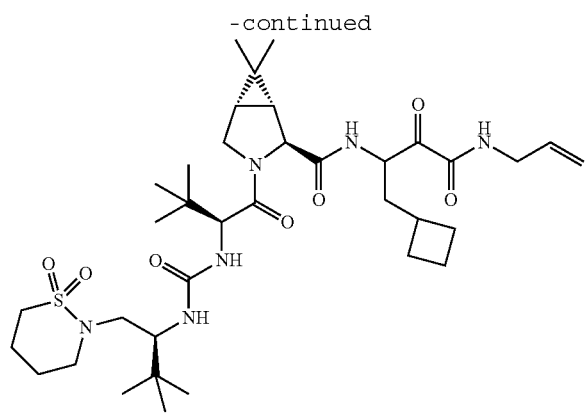
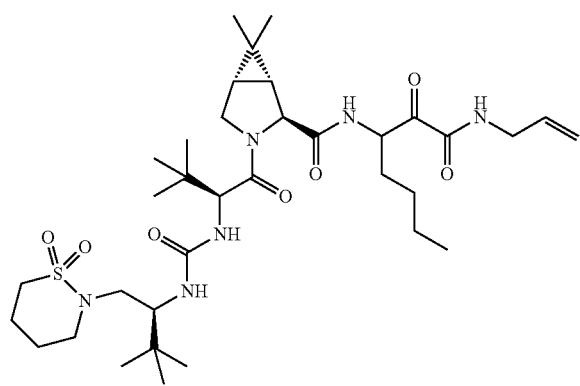
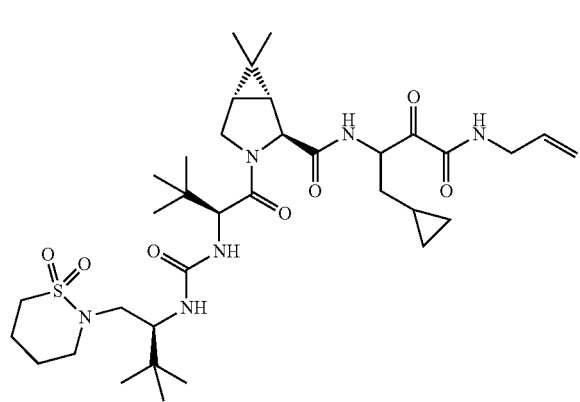
500
-continued
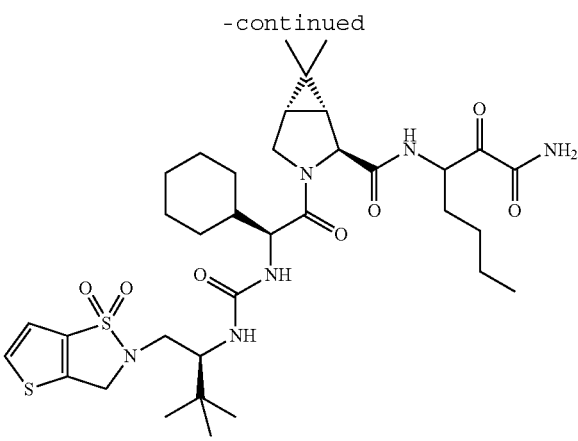
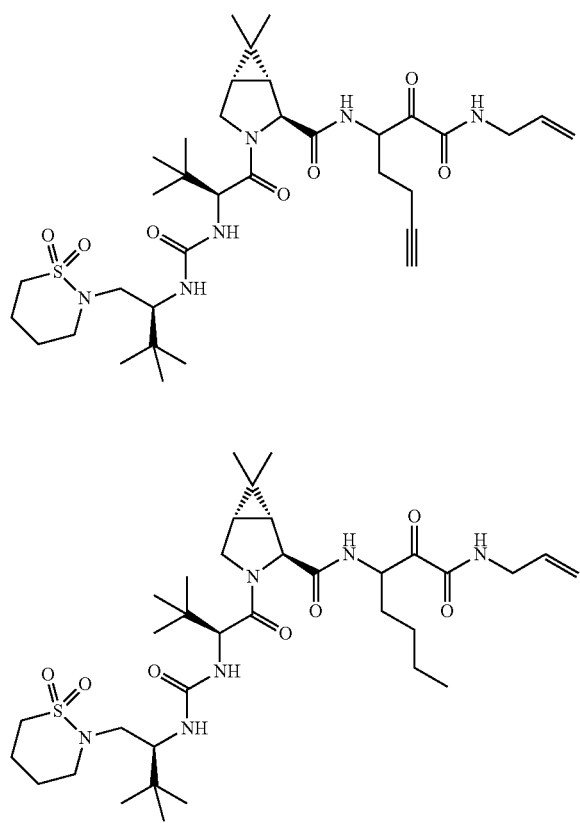
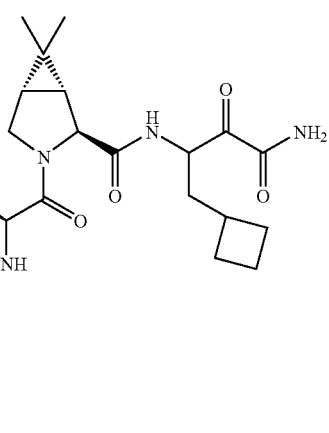

501
-continued
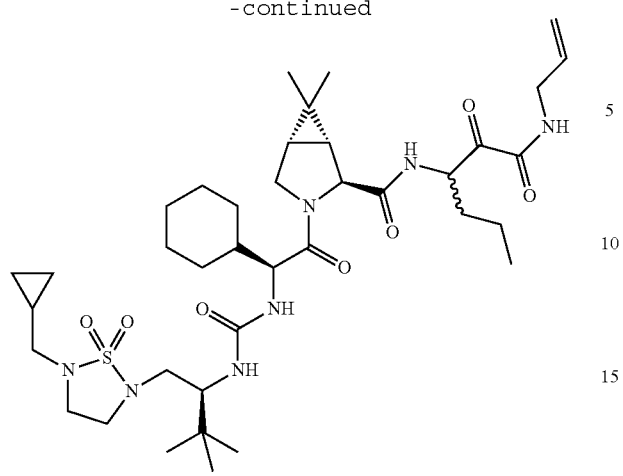
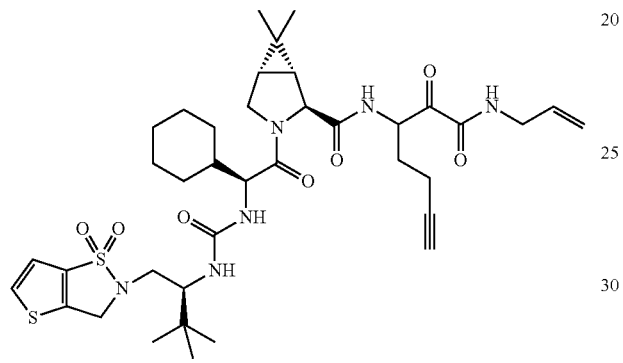
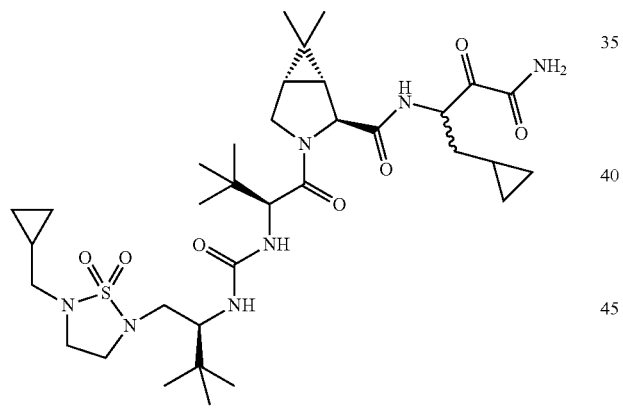
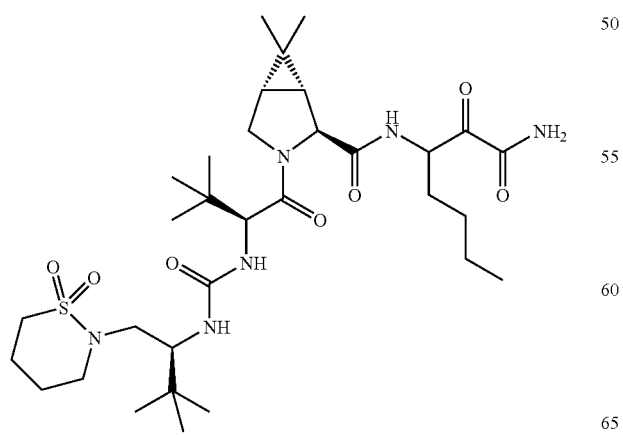
502
-continued
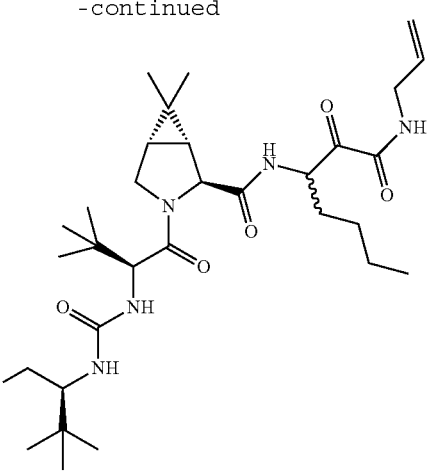
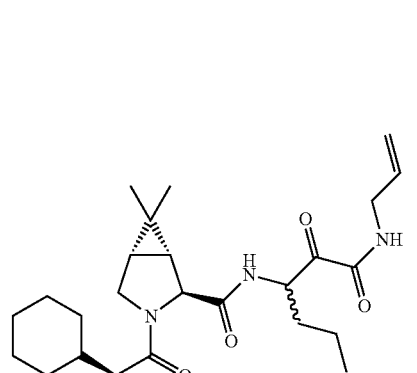
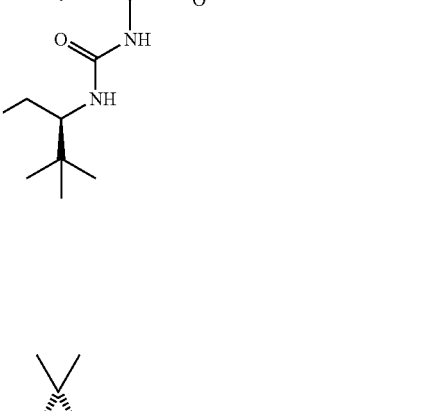
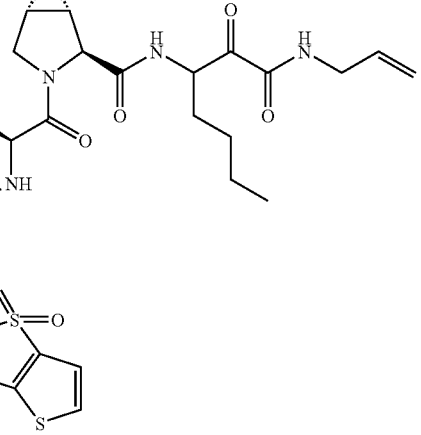

503                                    504
-continued                             -continued
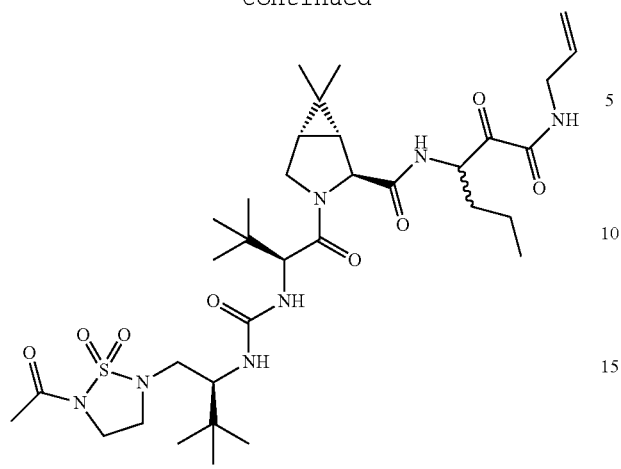 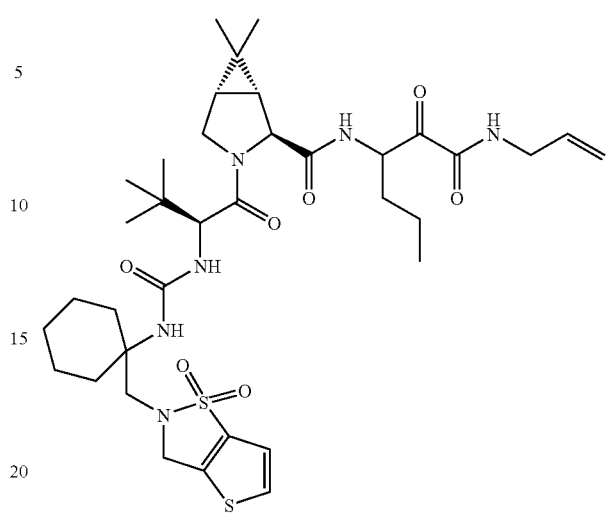
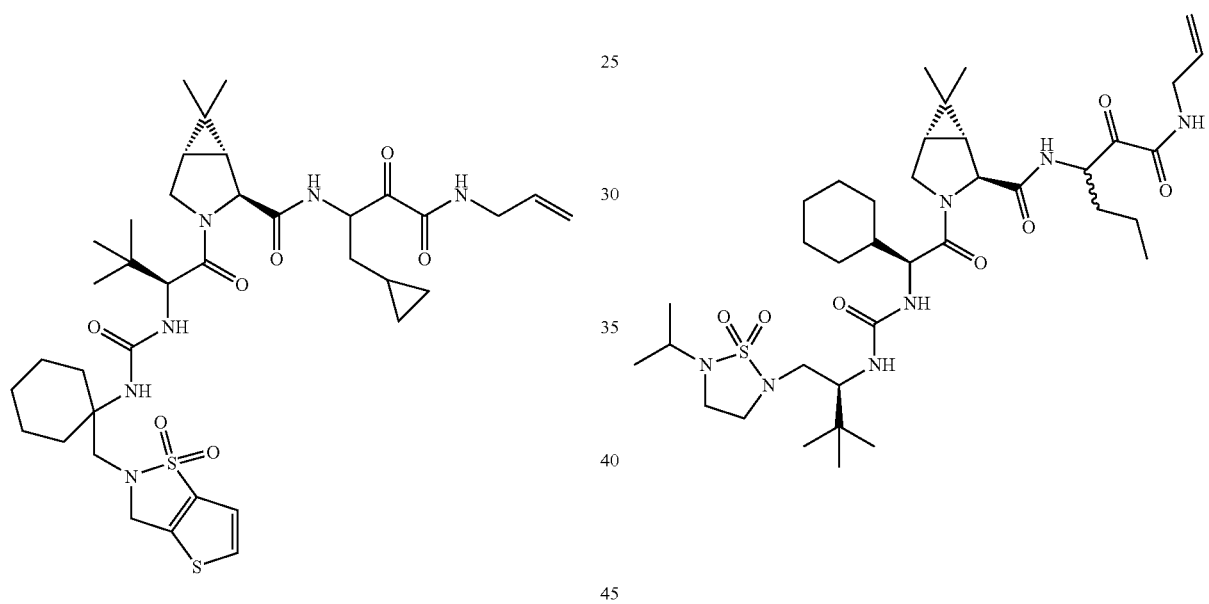
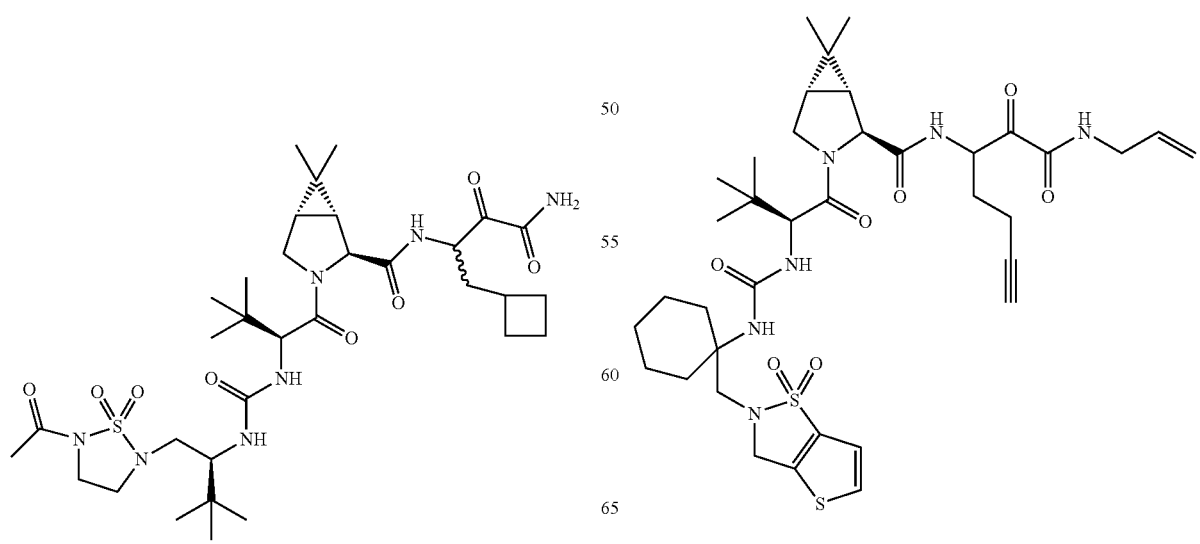

505 -continued
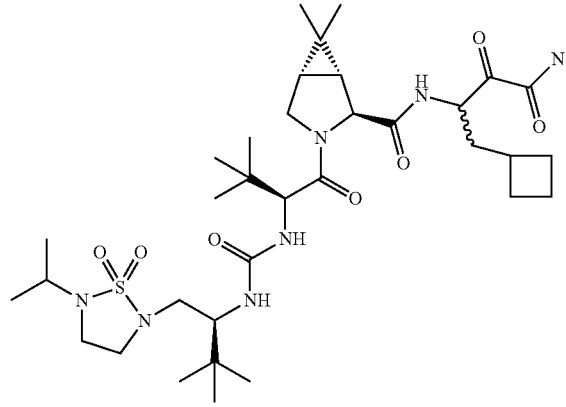
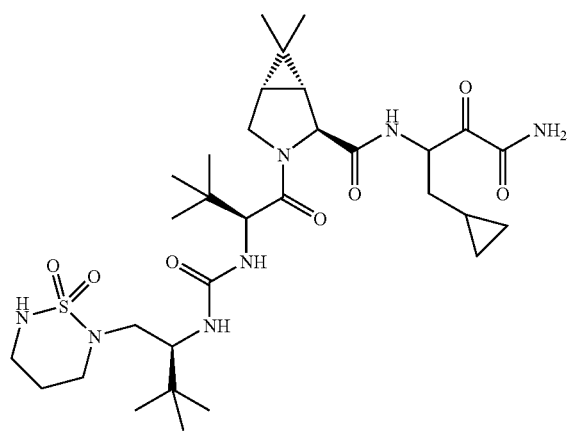
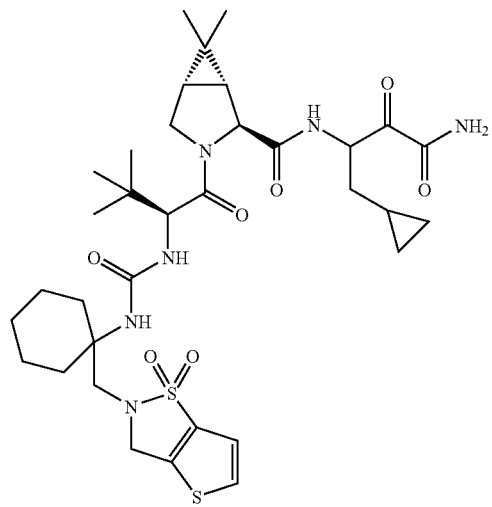
506 -continued
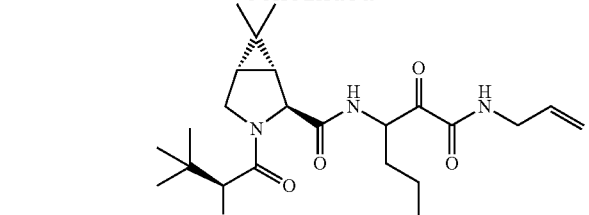
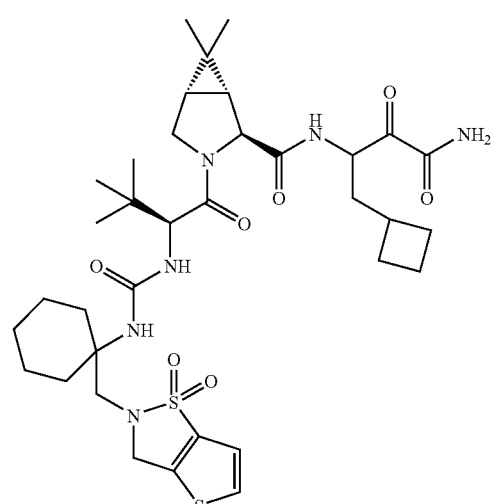
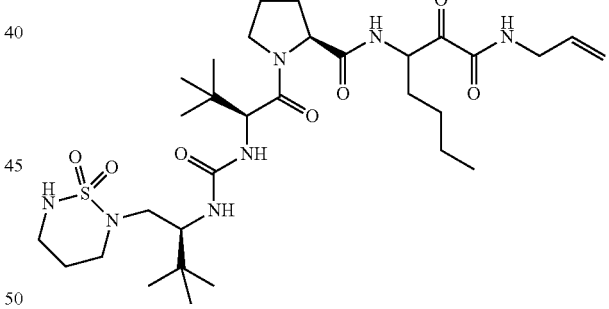
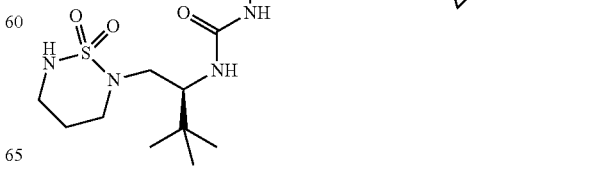

507
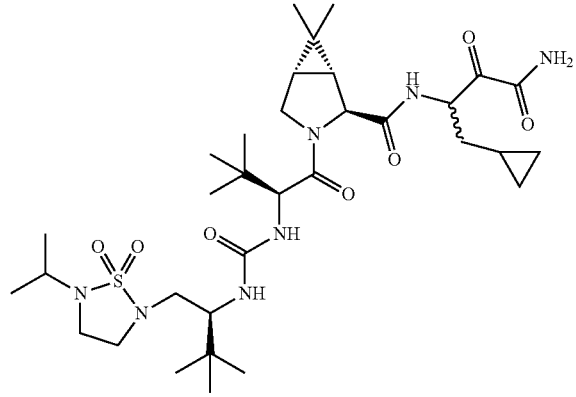
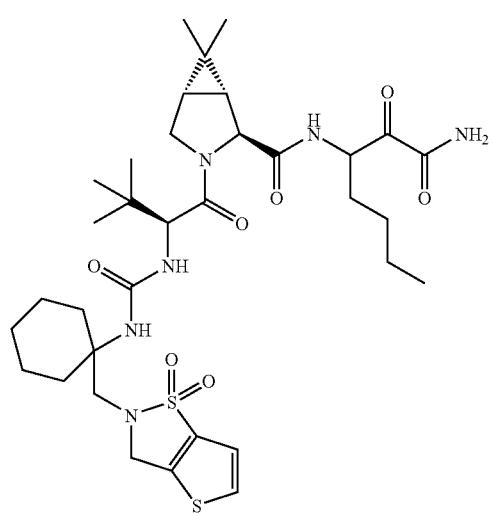
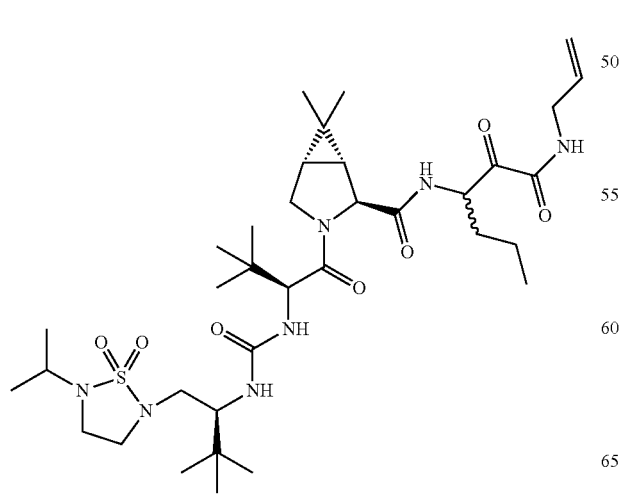
508
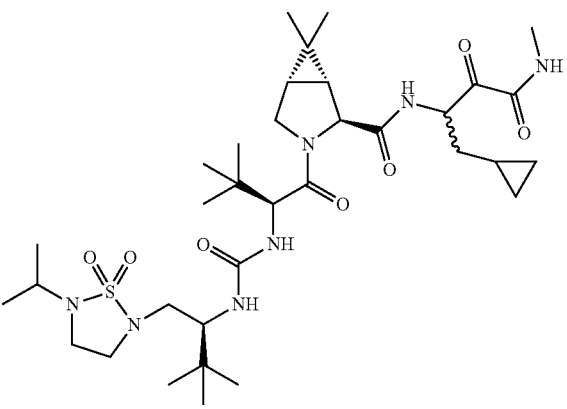
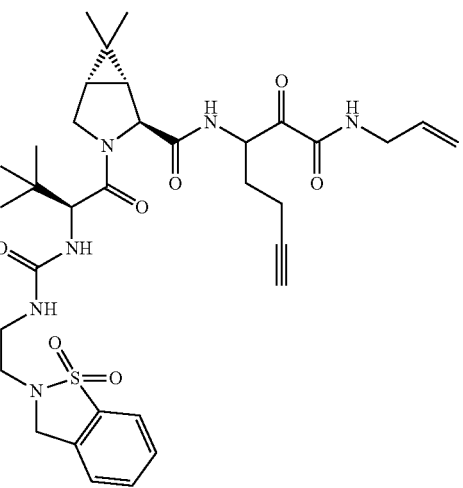

509 -continued
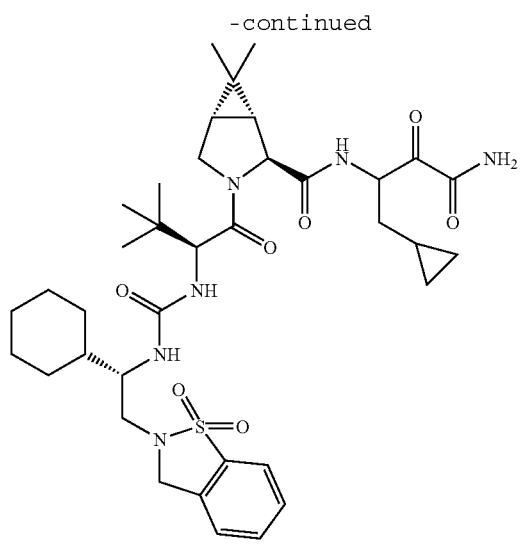
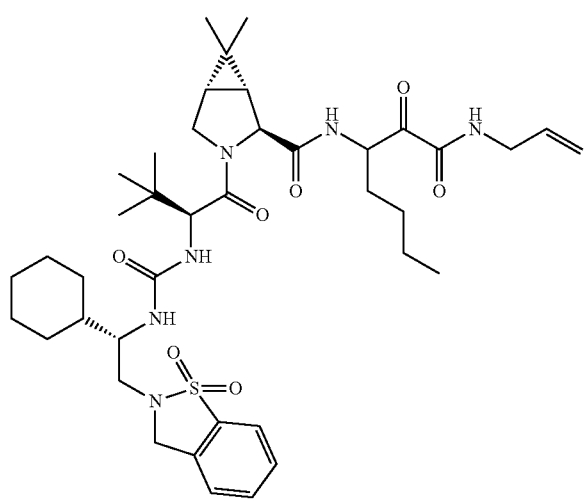
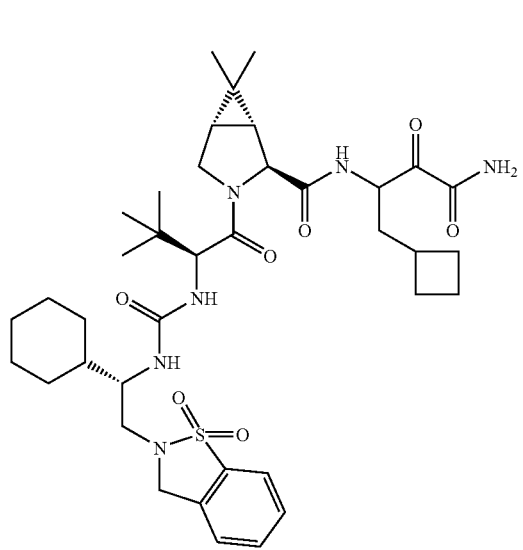
510 -continued
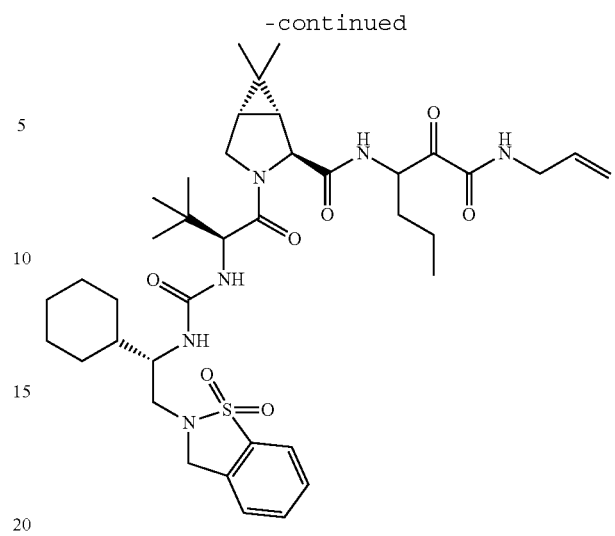
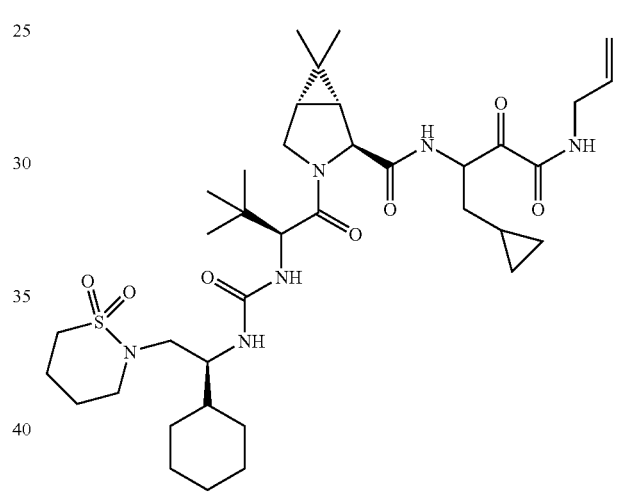
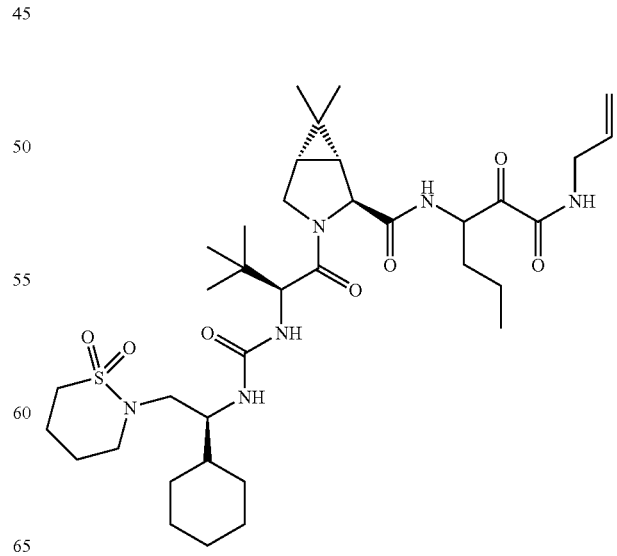

511
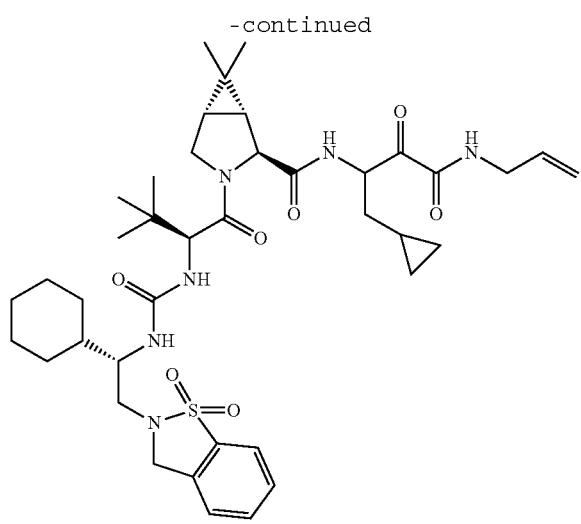
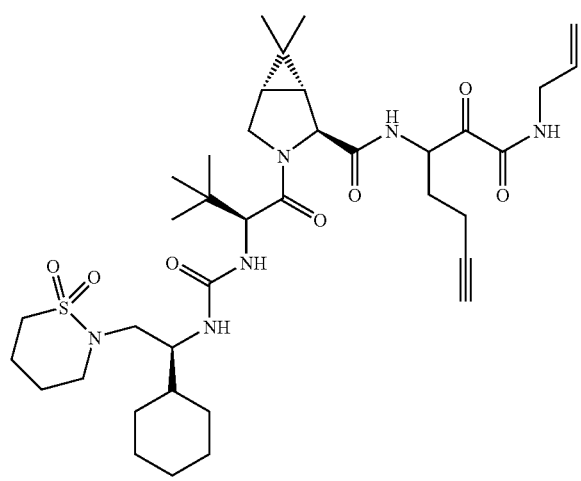
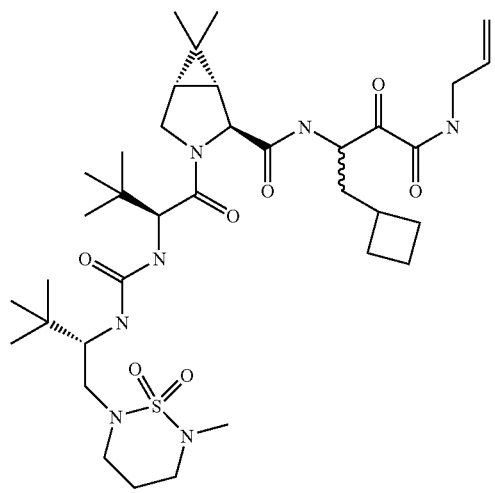
512
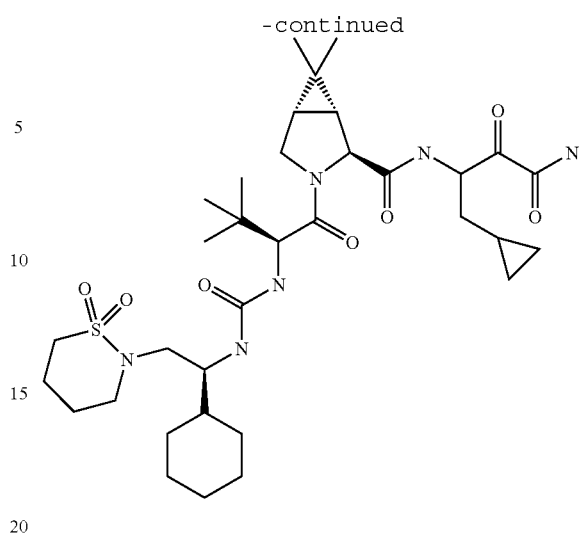
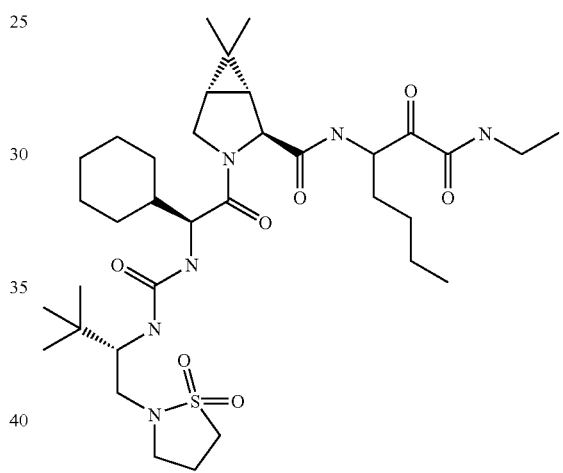
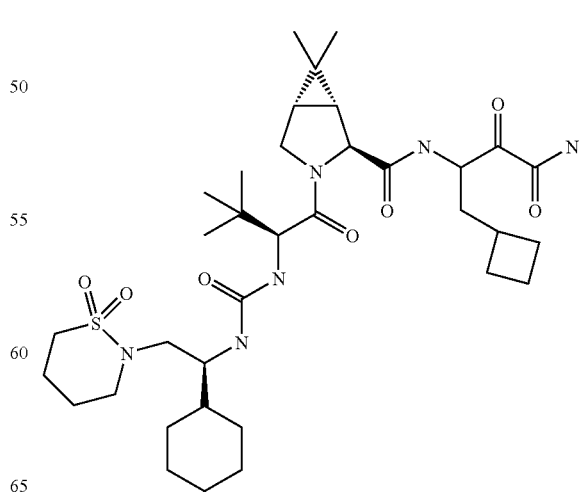

513
-continued
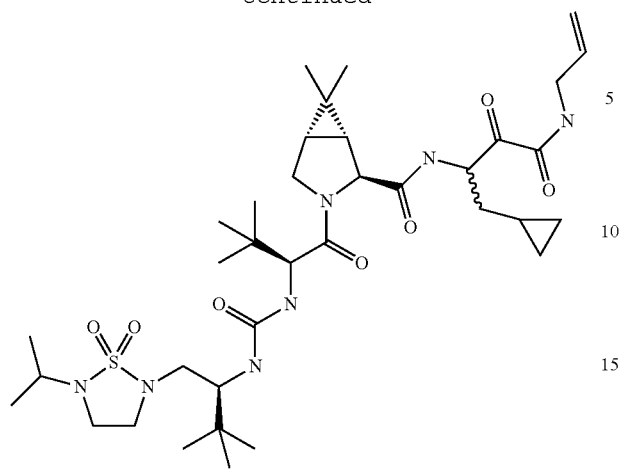
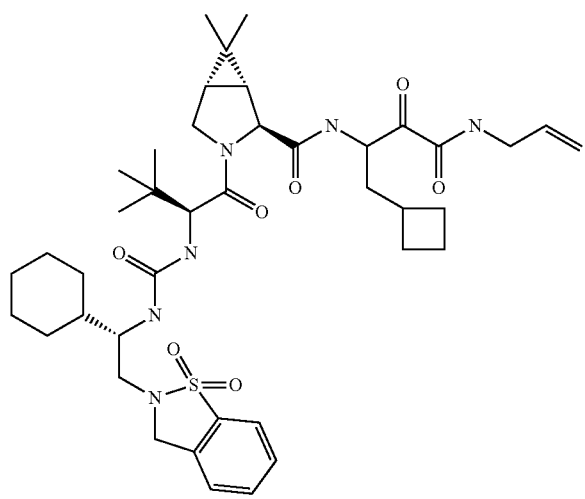
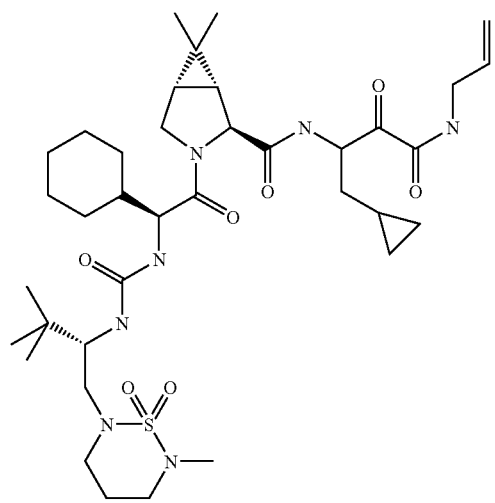
514
-continued
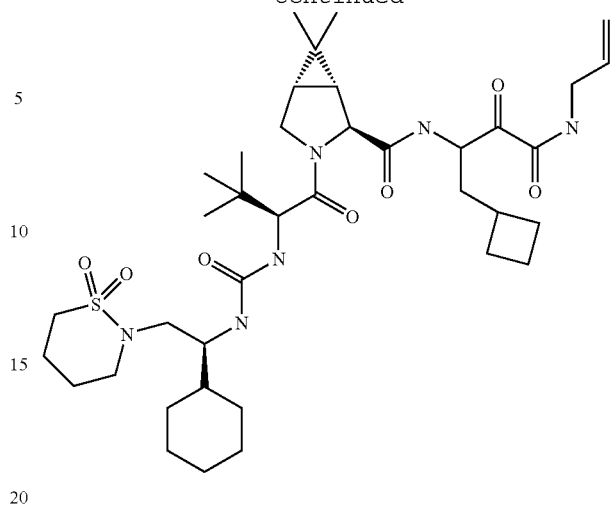
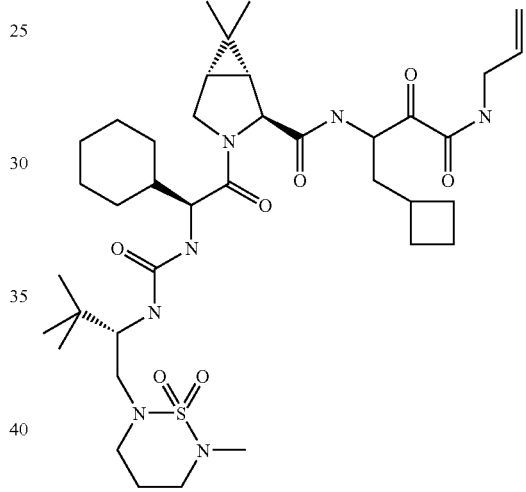
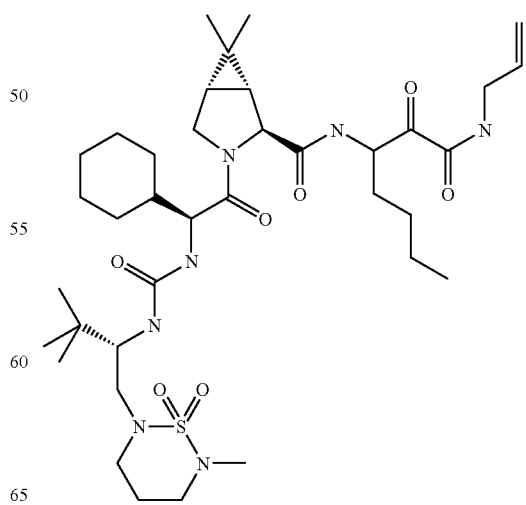

515
-continued
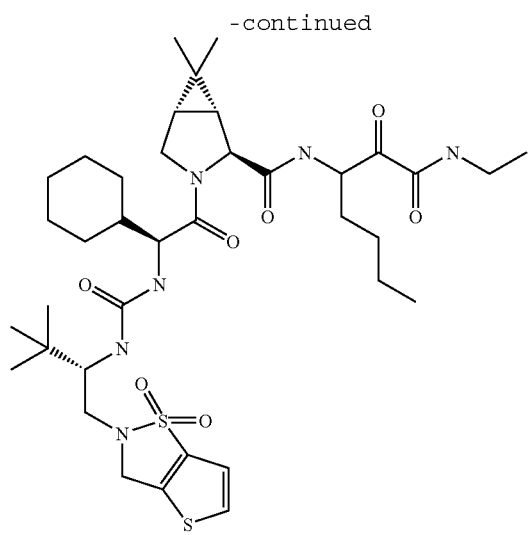
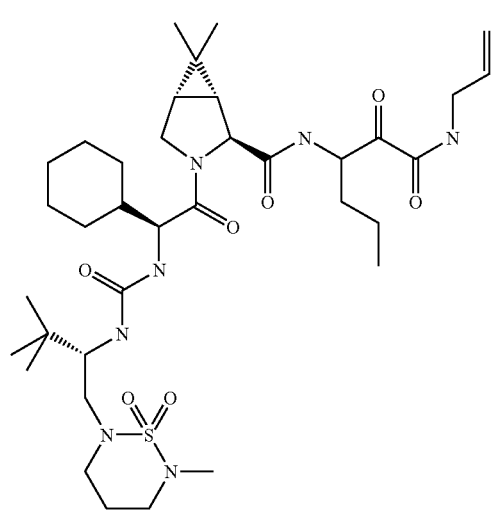
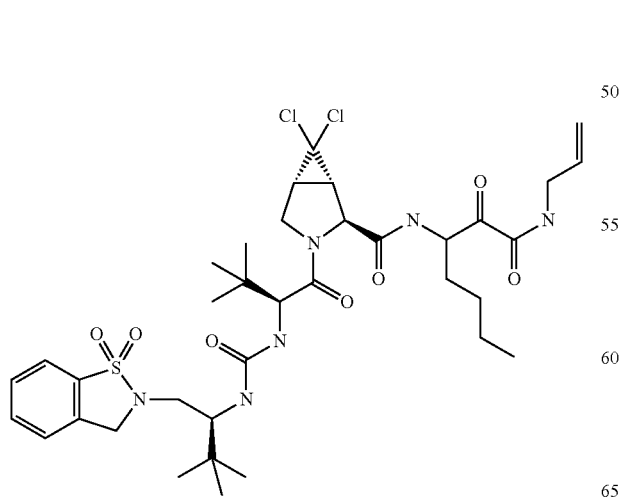
516
-continued
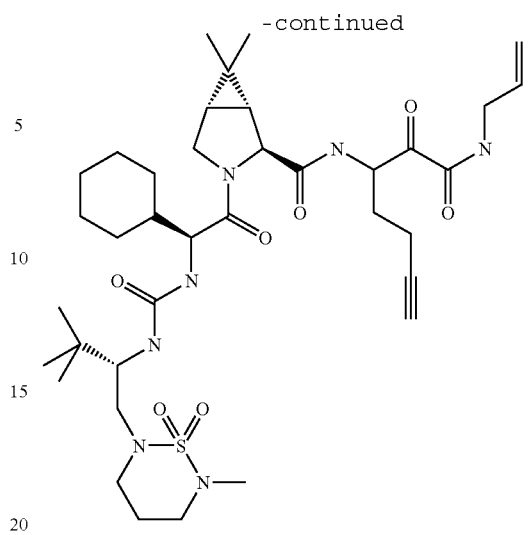
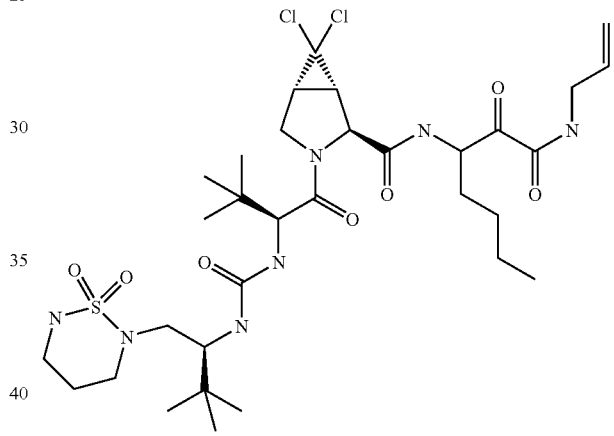
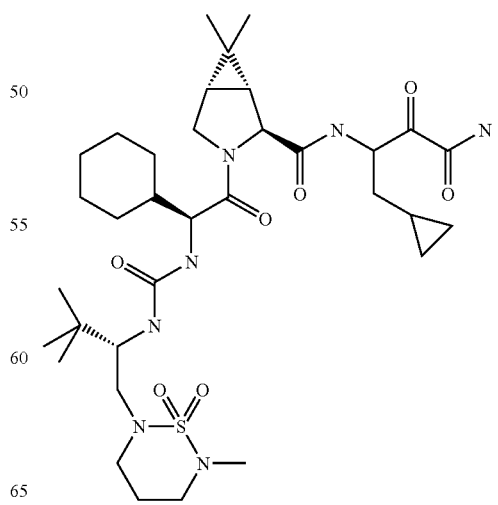

517 -continued
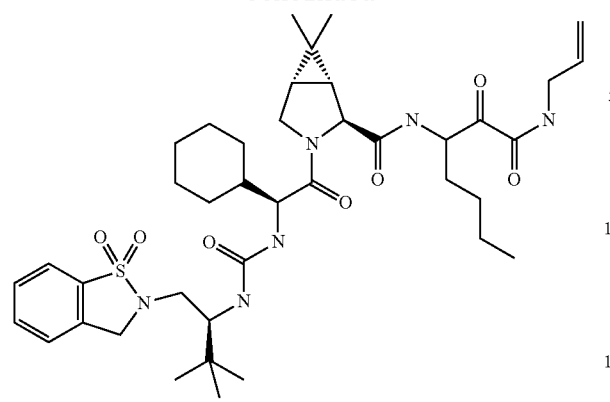
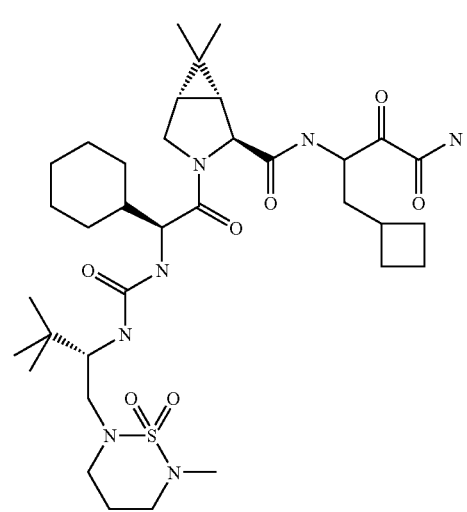
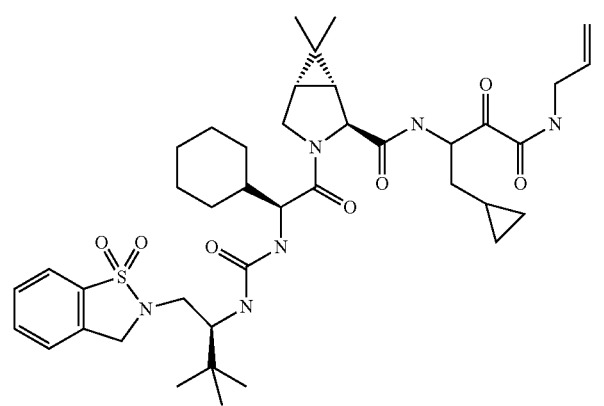
518 -continued
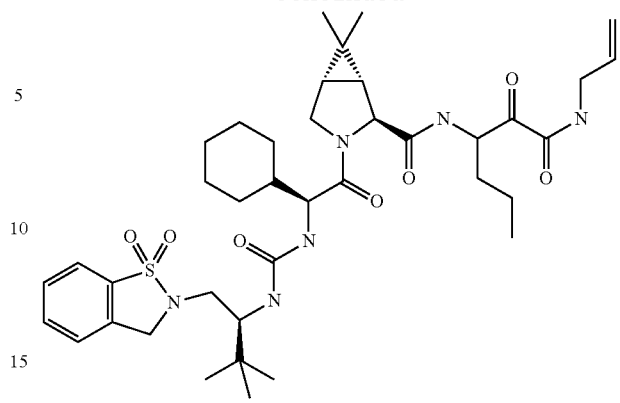
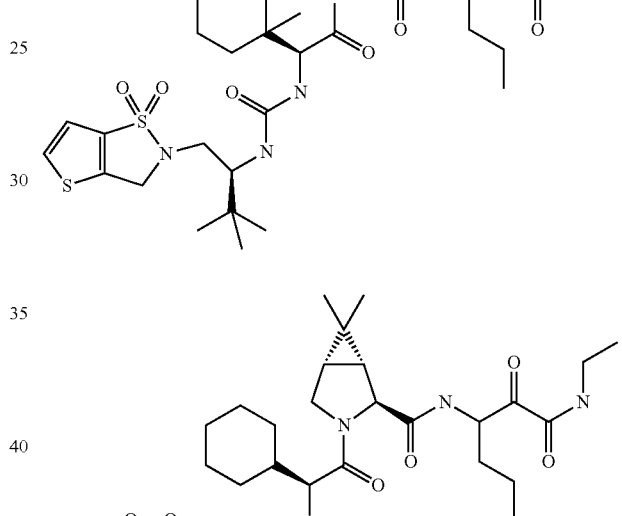
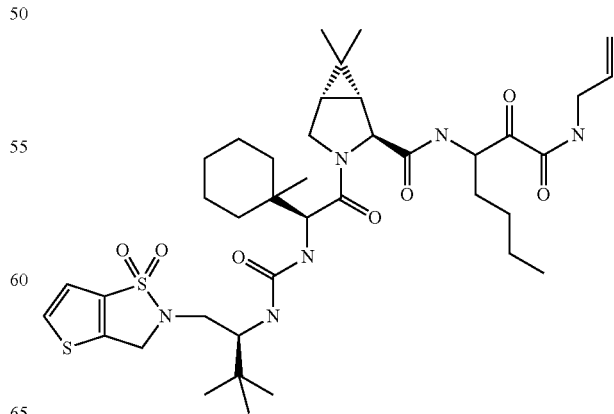

519
-continued
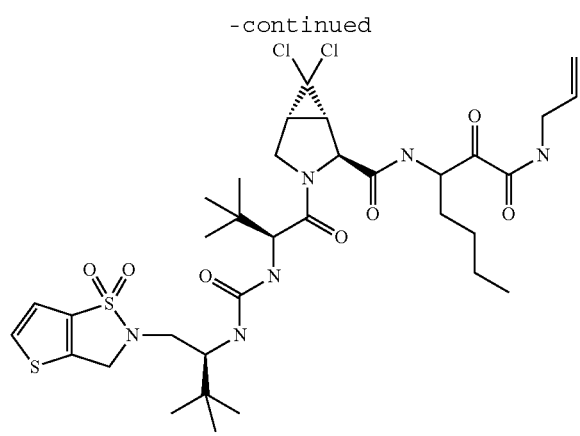
520
-continued
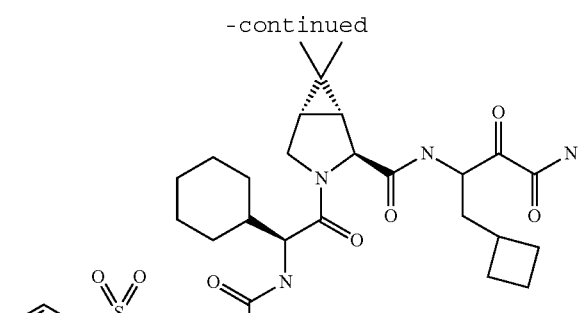
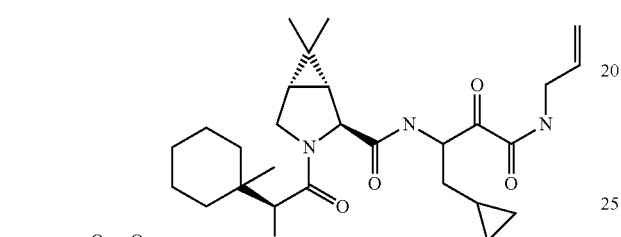
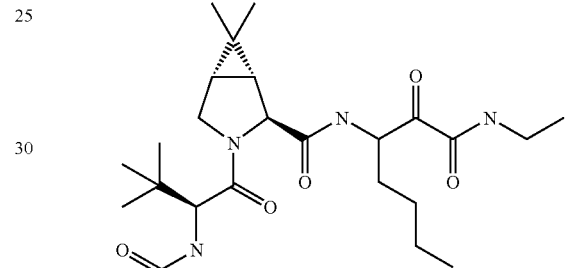
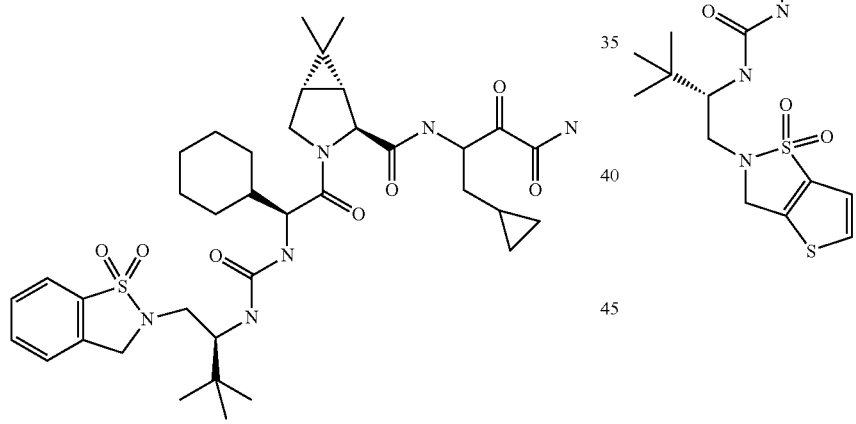
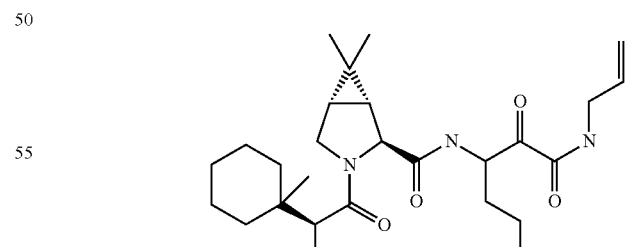
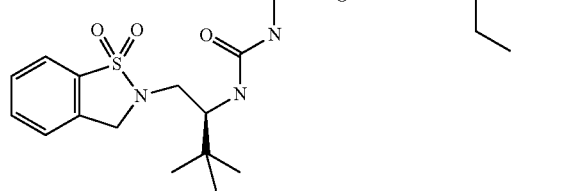
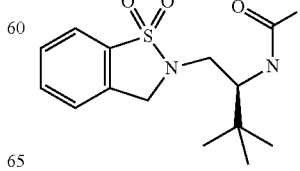

521
-continued
522
-continued
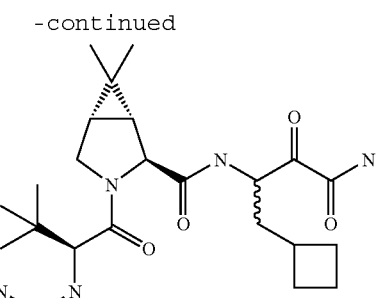
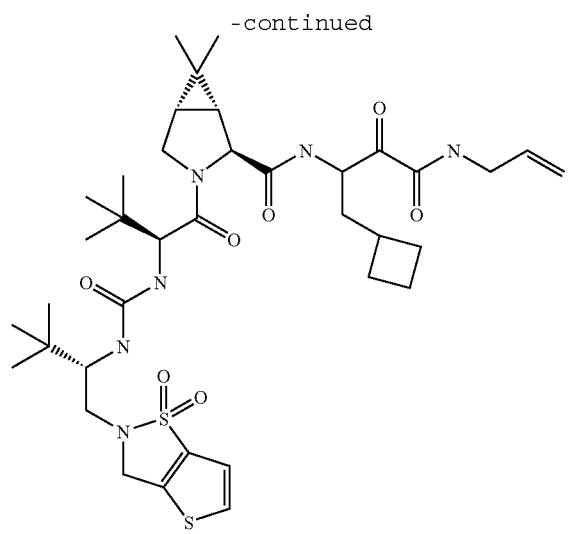
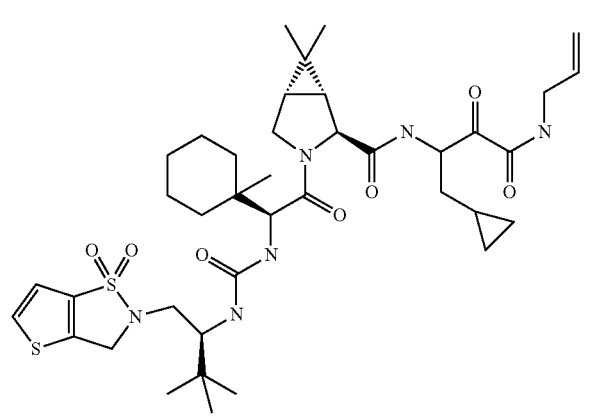
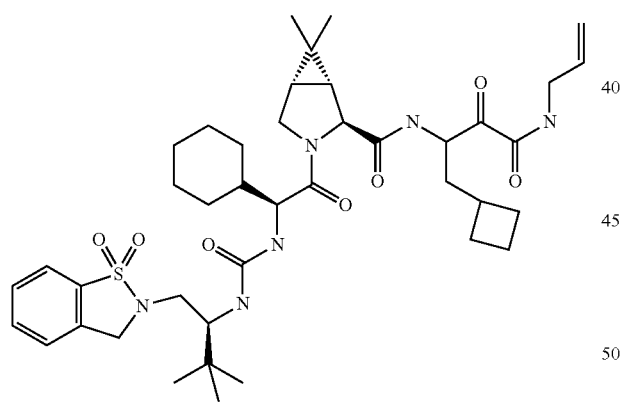
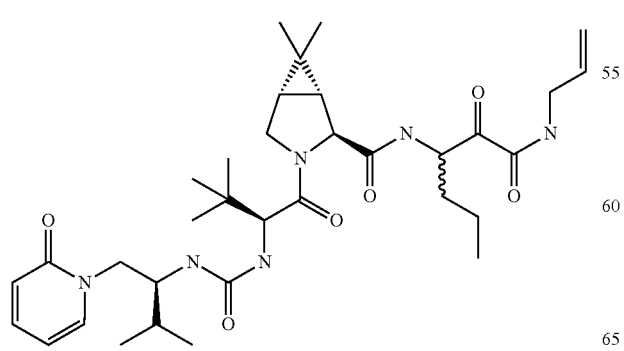

523
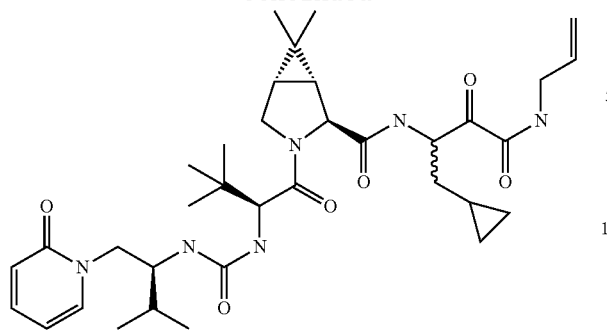
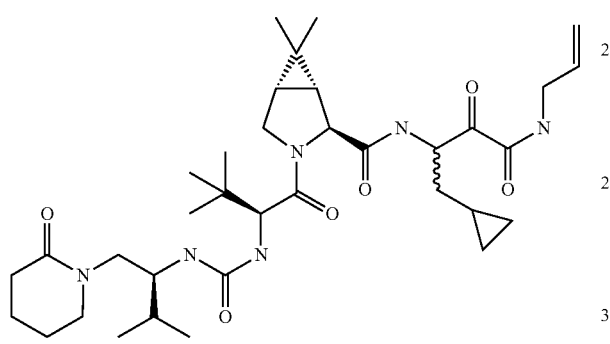
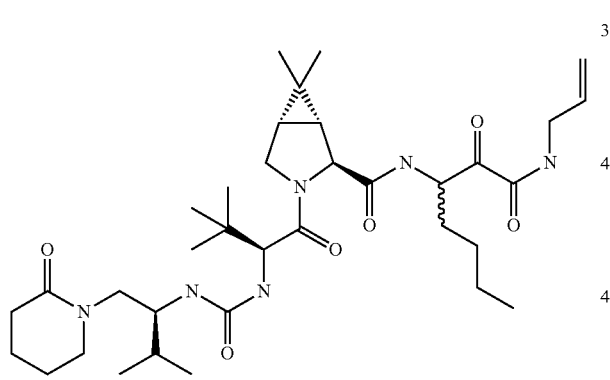
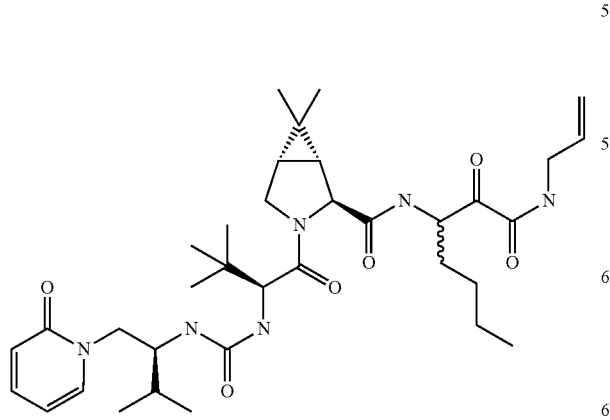
524
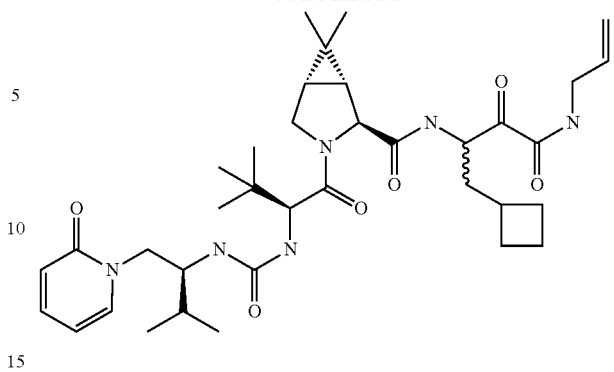
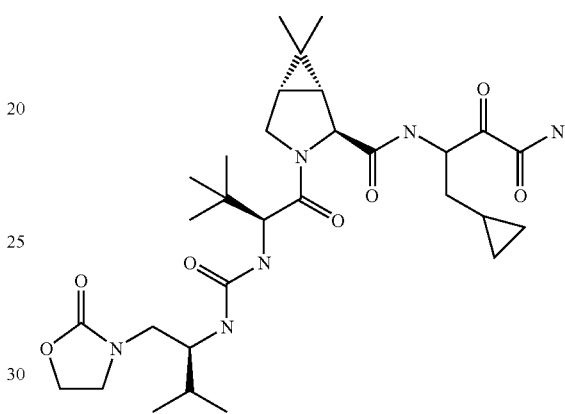
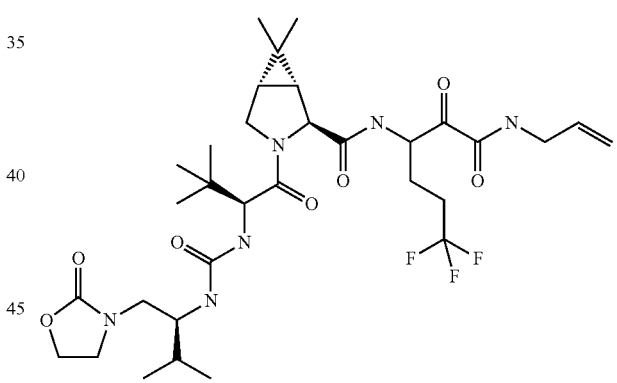
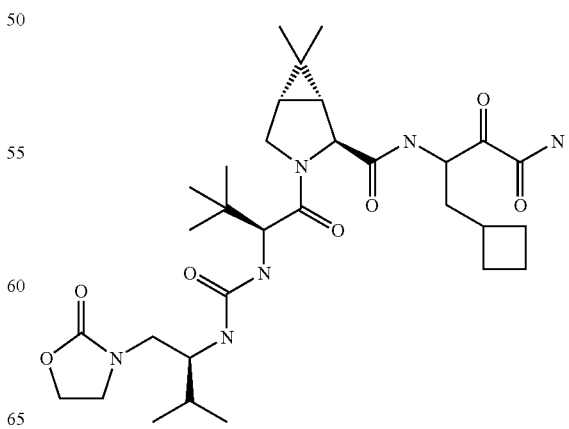

525
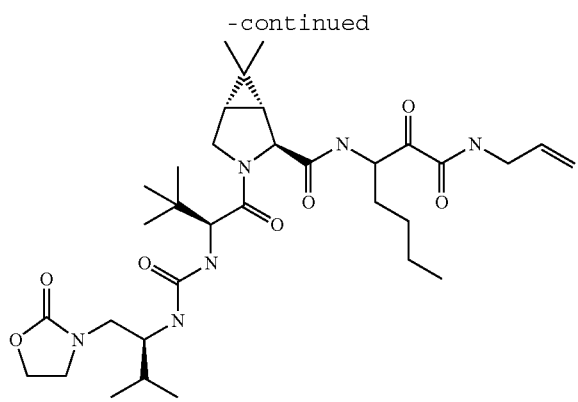
526
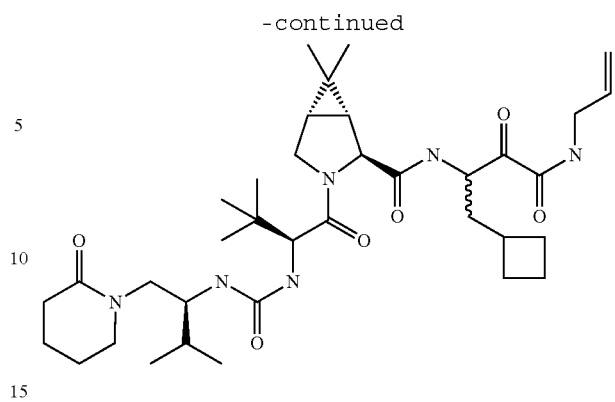
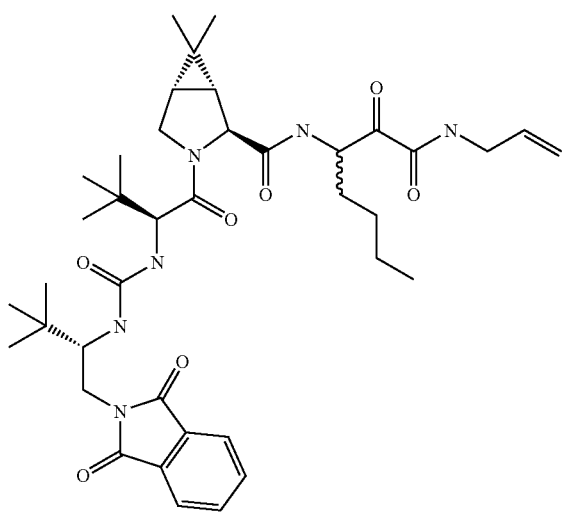
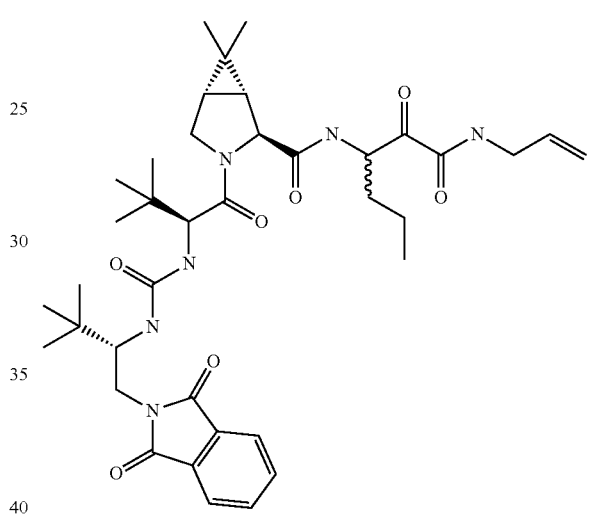
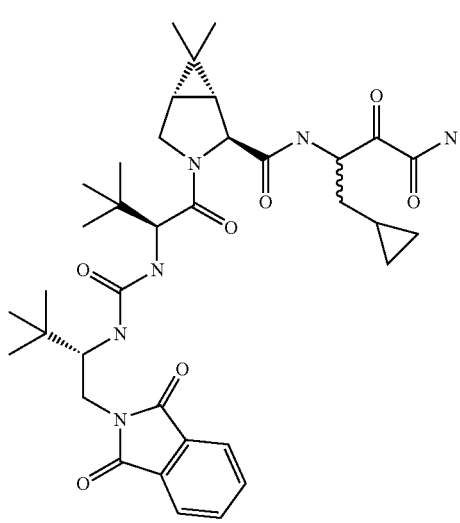
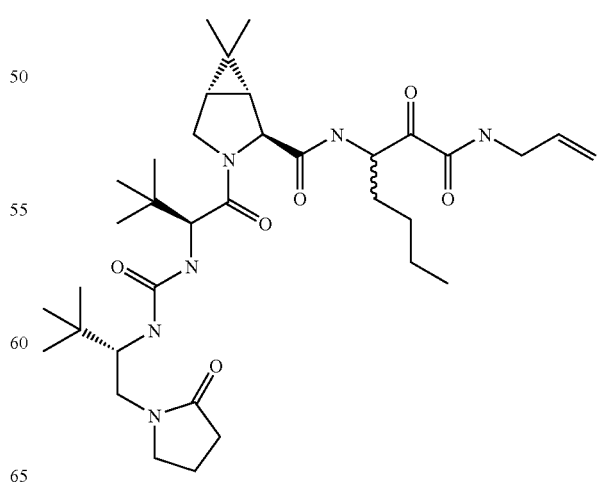

527
-continued
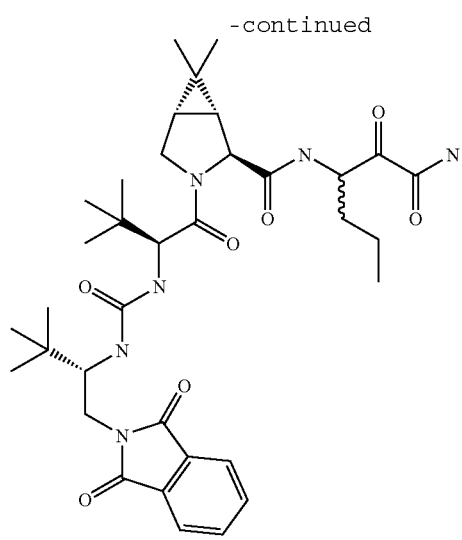
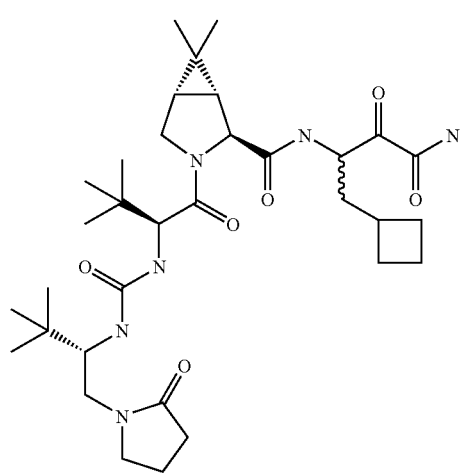
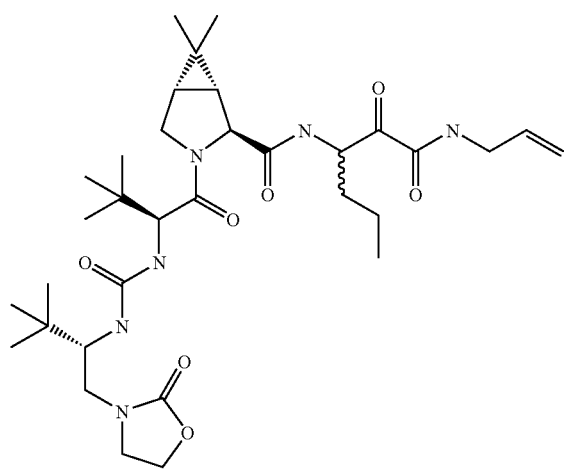
528
-continued
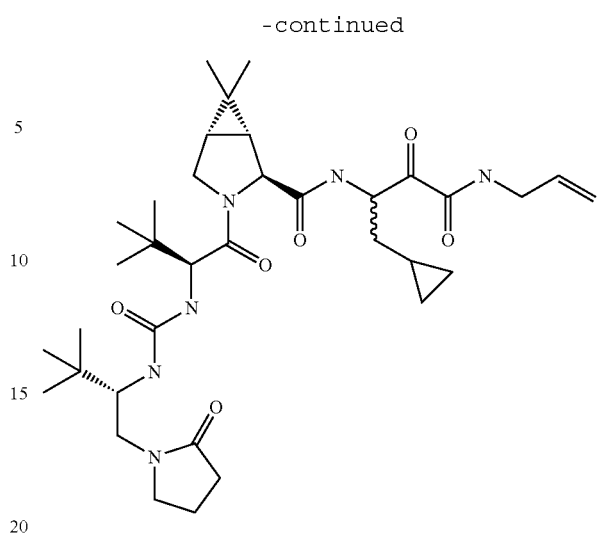
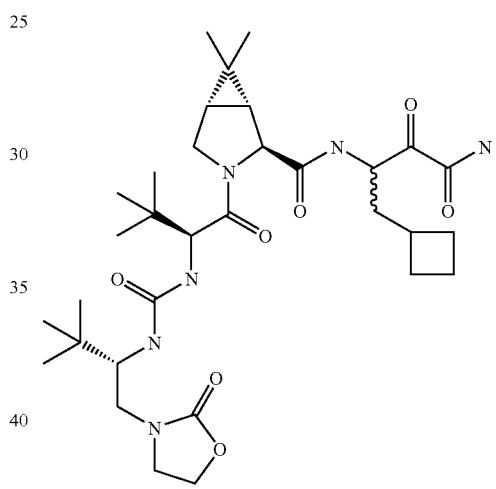
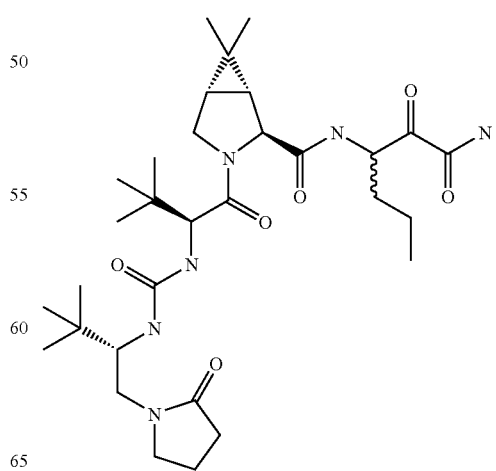

529
-continued
530
-continued
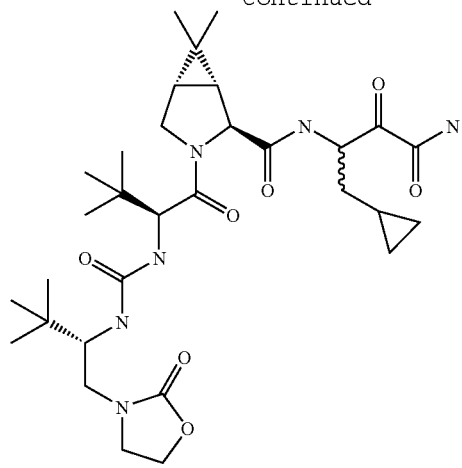
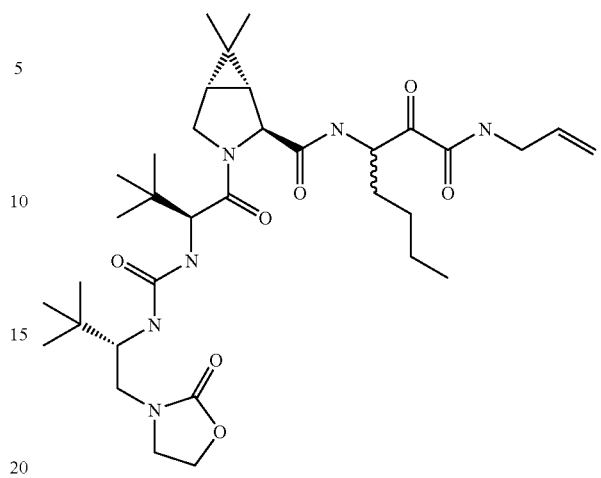
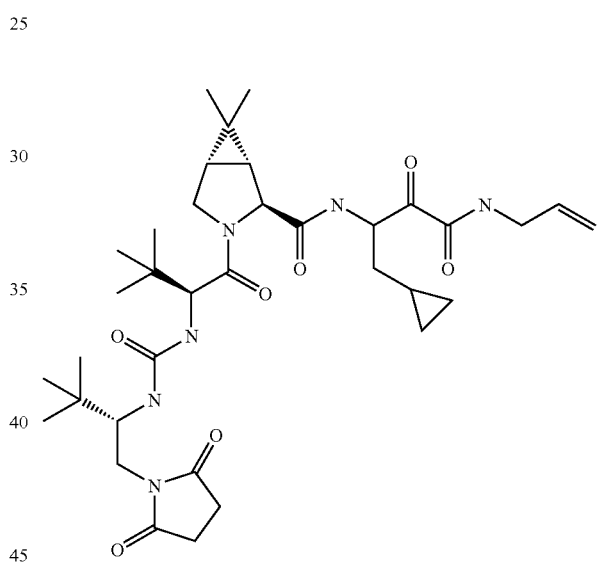
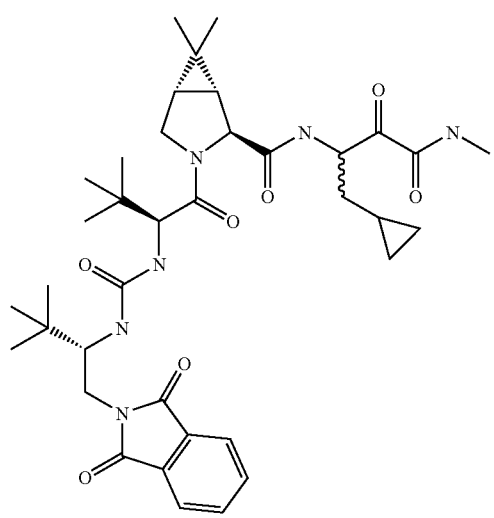
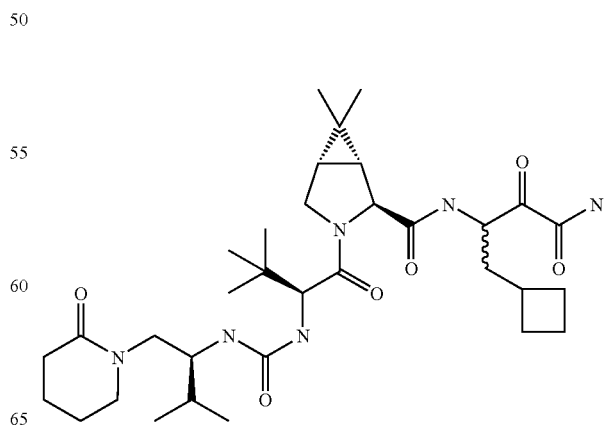

531
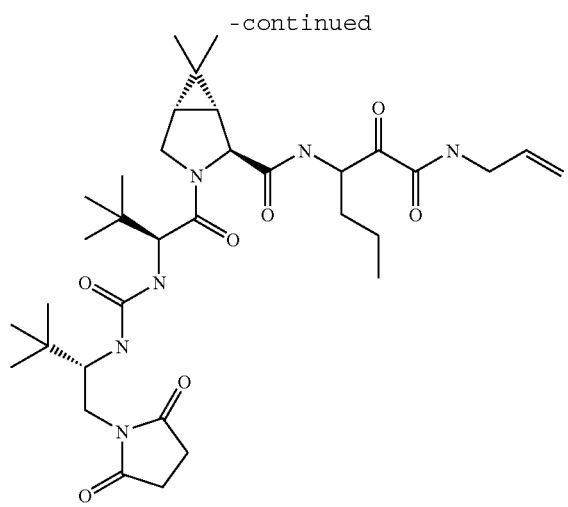
532
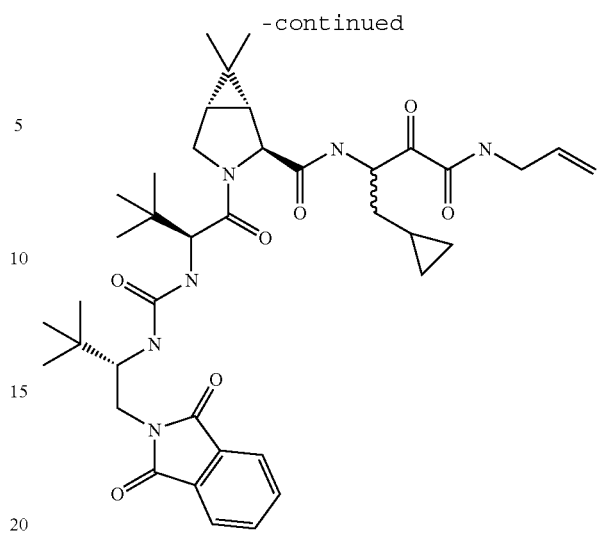
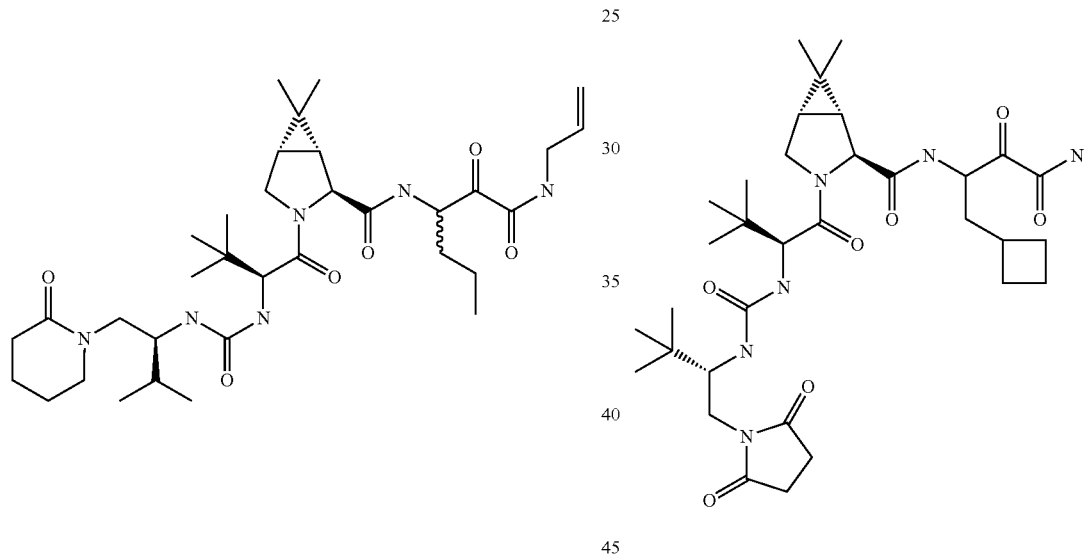
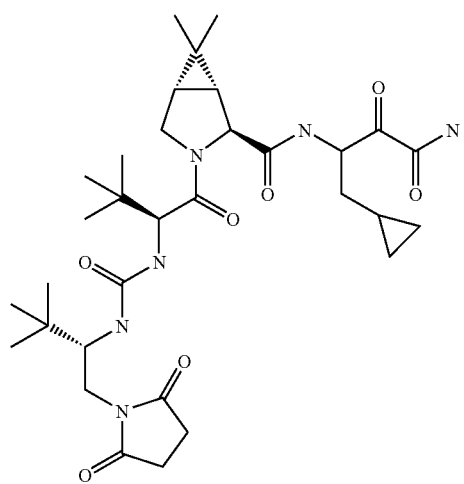
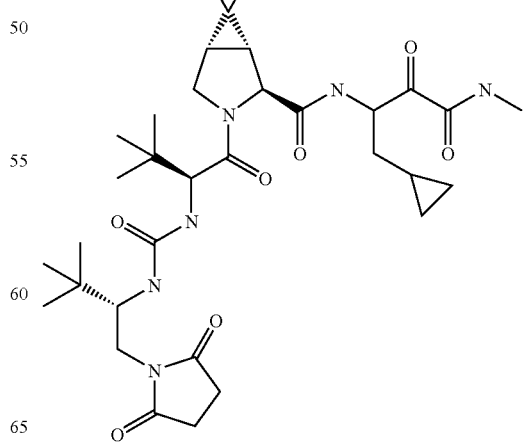

533
-continued
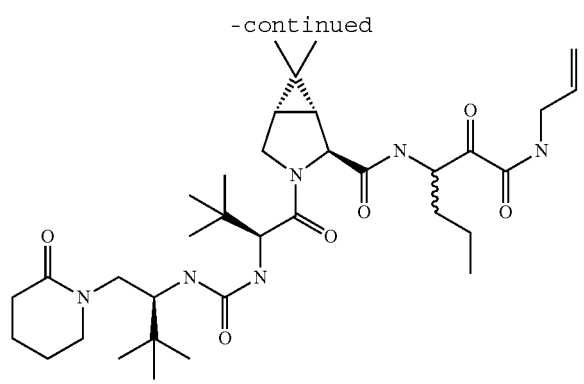
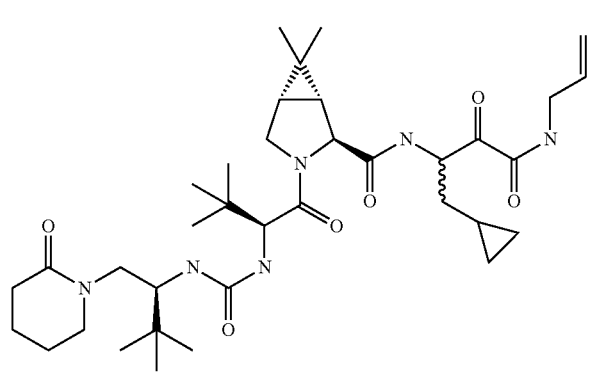
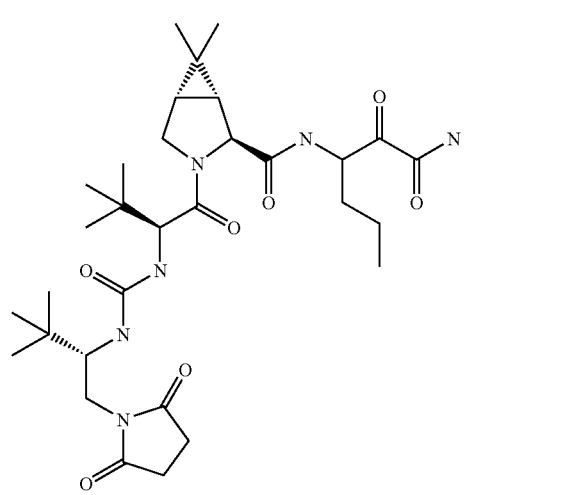
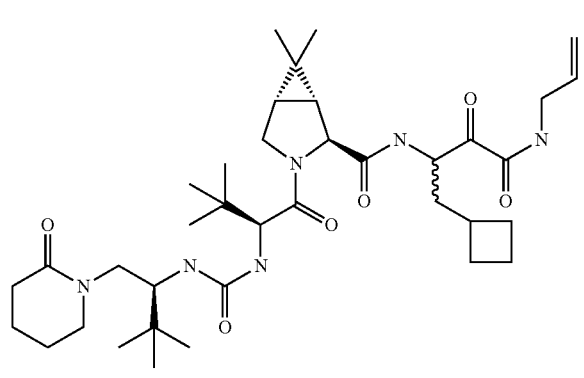
534
-continued
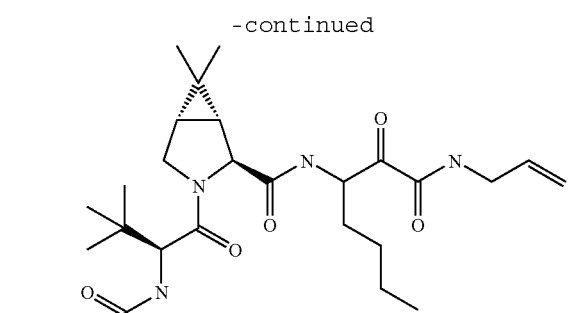
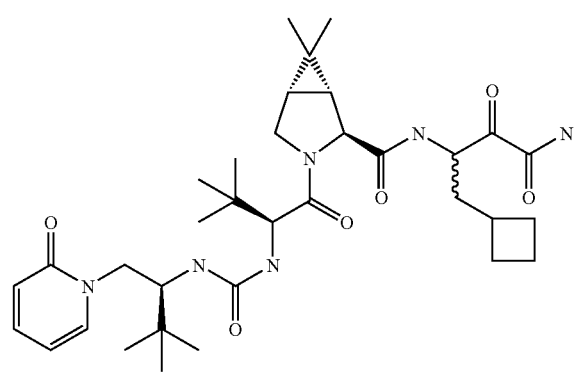
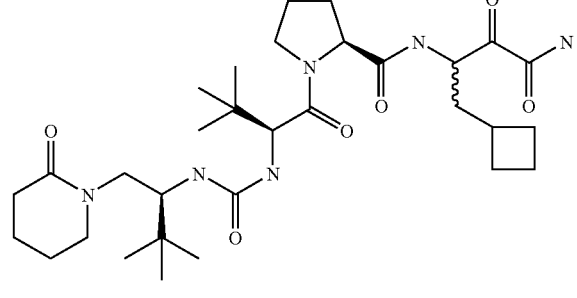

535
-continued
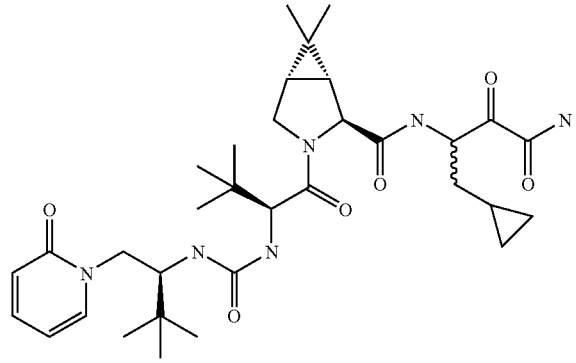
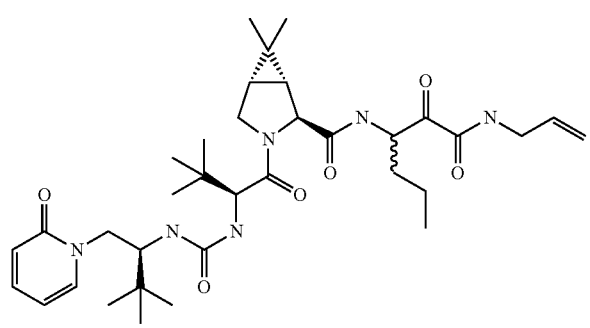
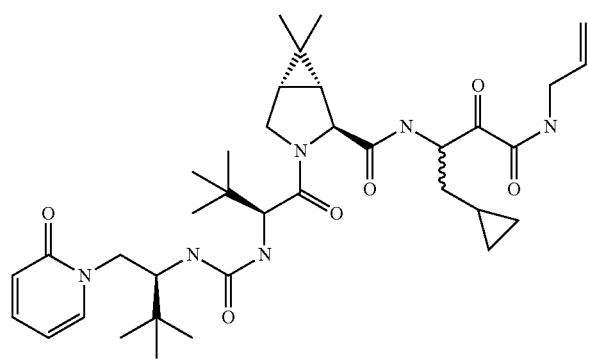
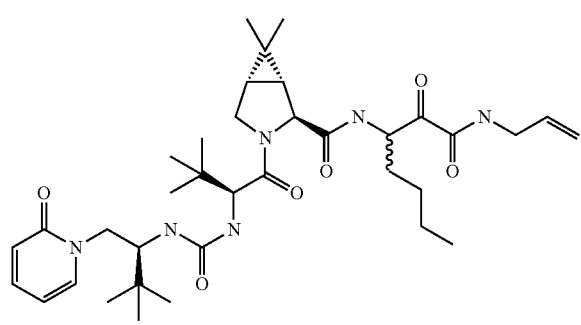
536
-continued
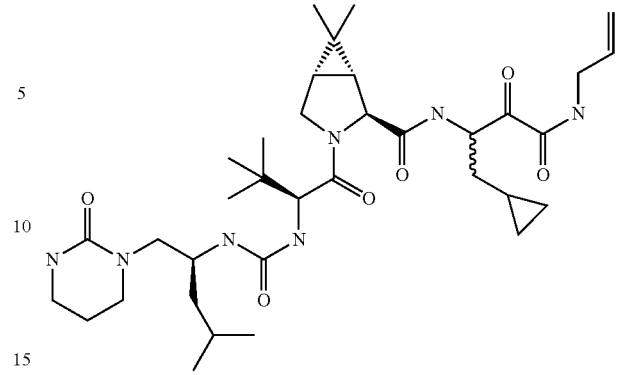
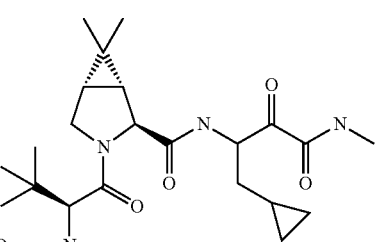

537
-continued

538
-continued

539
-continued
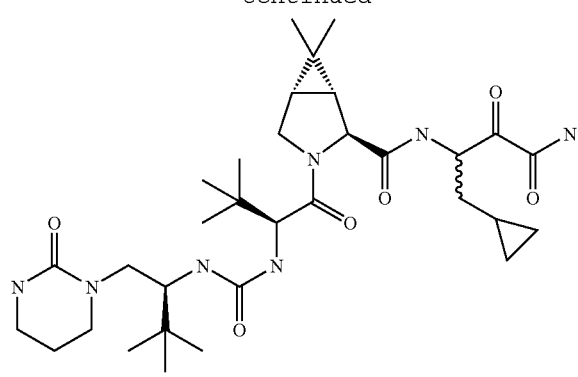
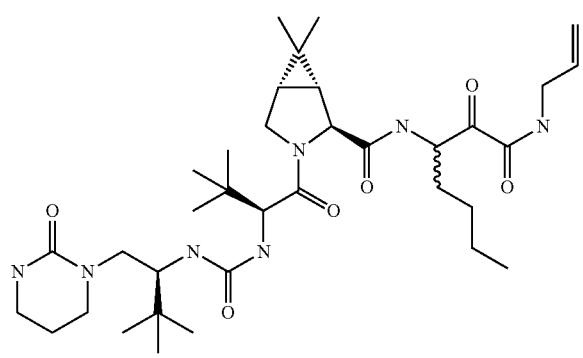
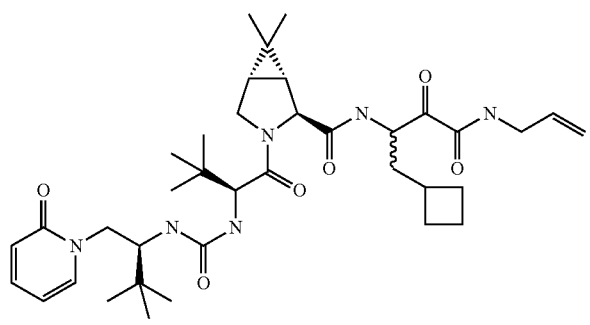
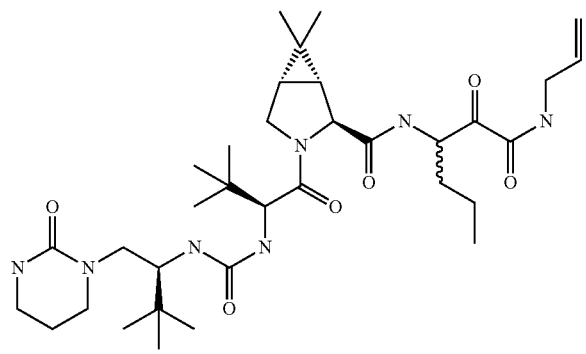
540
-continued
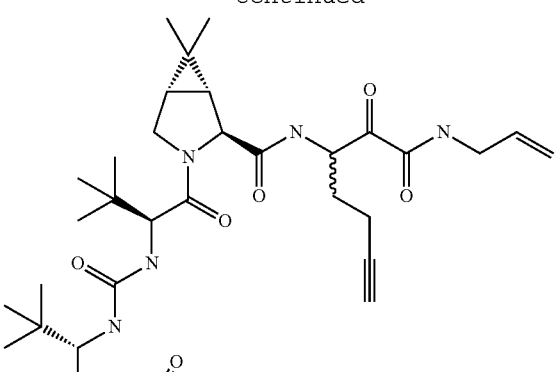

541
-continued
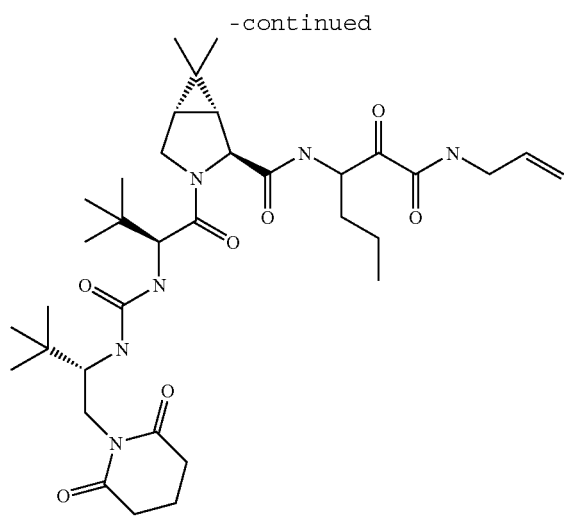
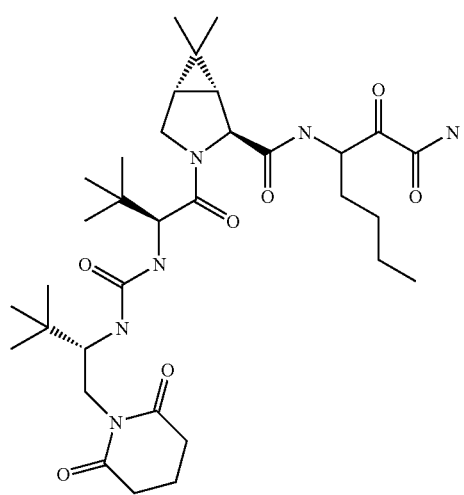
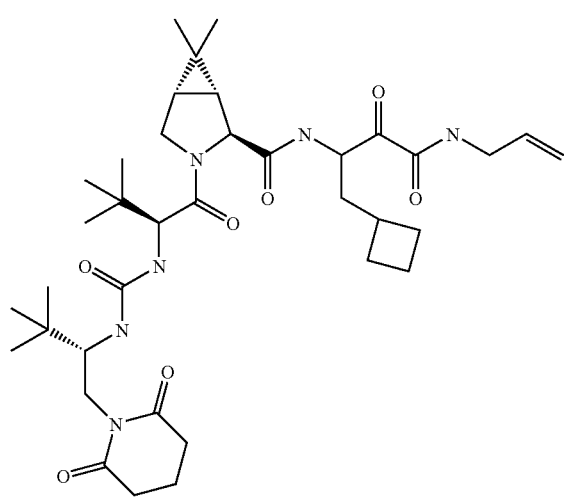
542
-continued
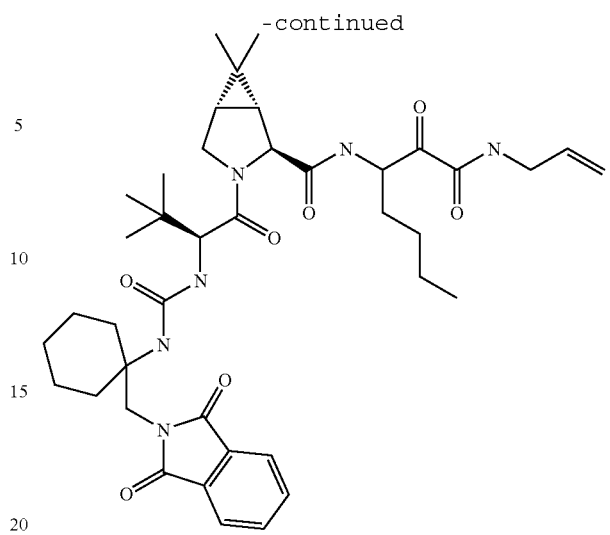
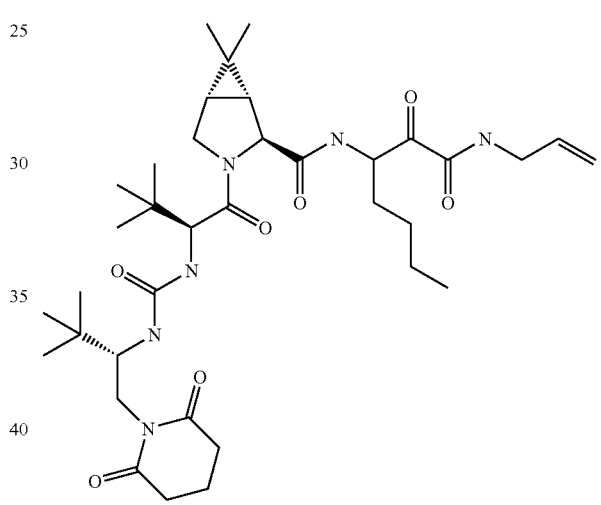
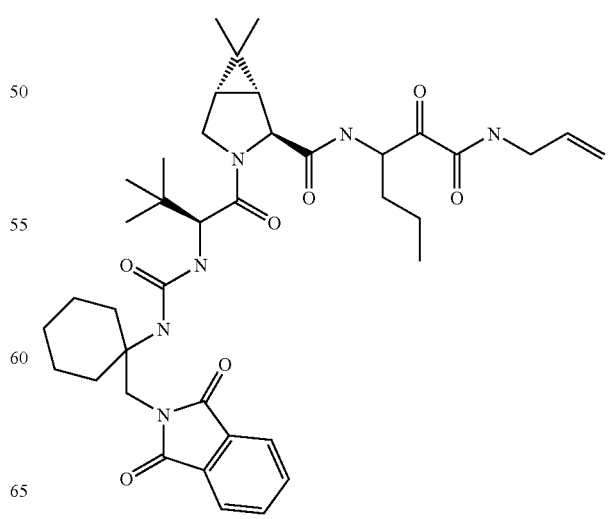

543
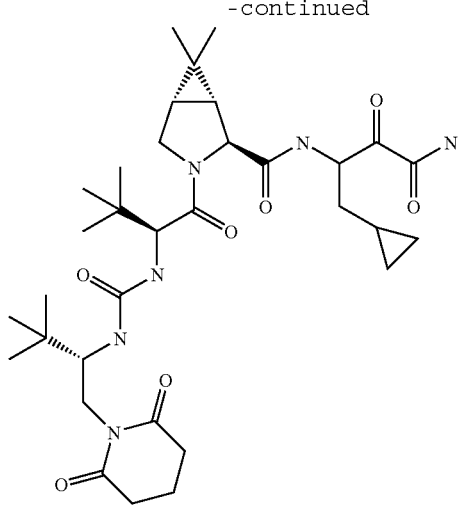
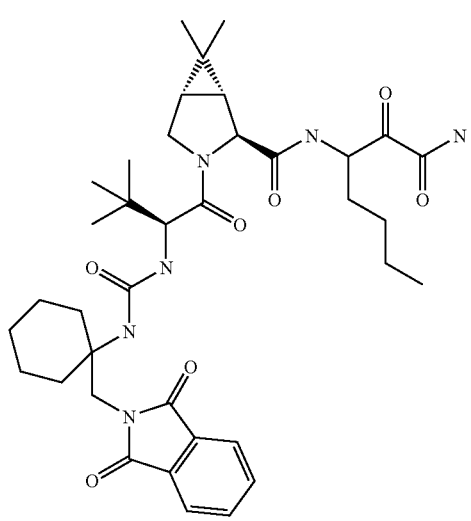
544
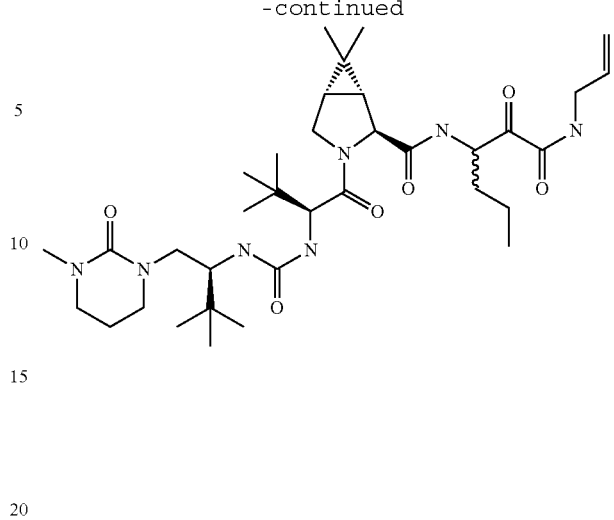
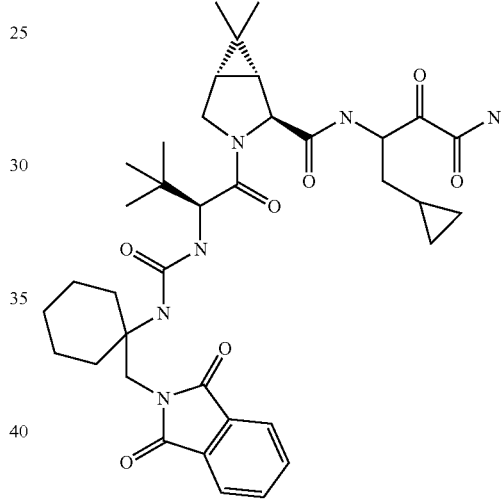
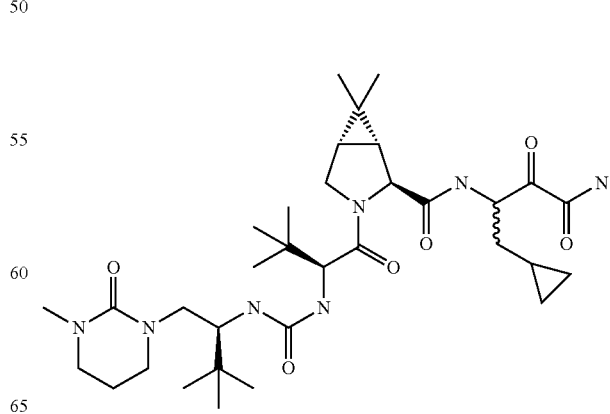

545
546
-continued
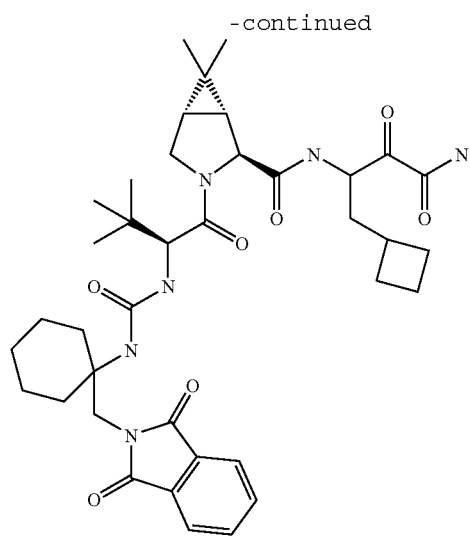
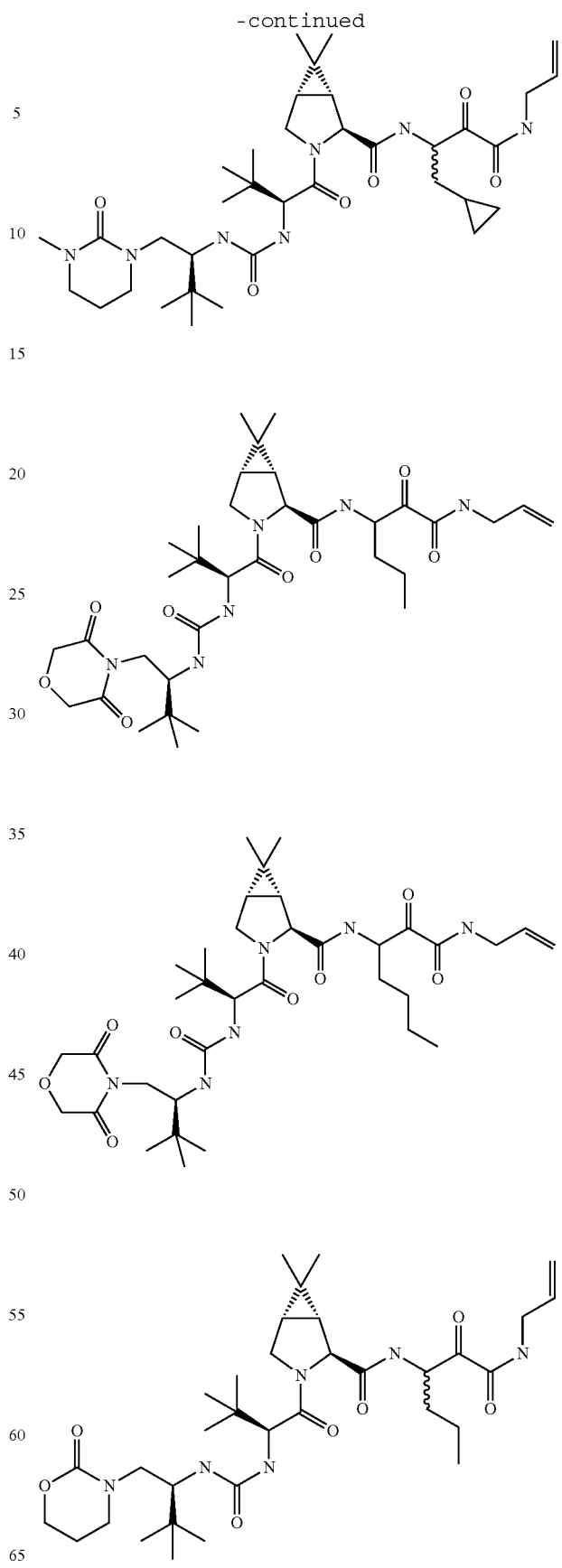

547
-continued
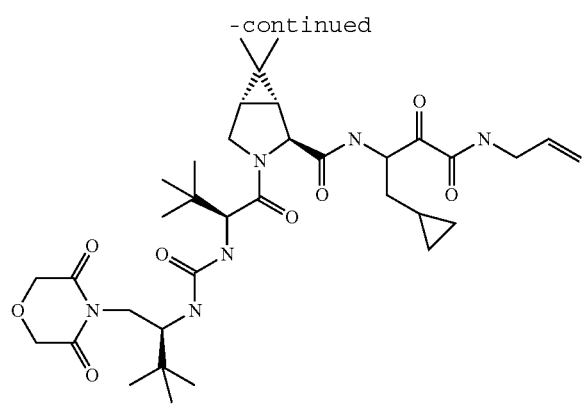
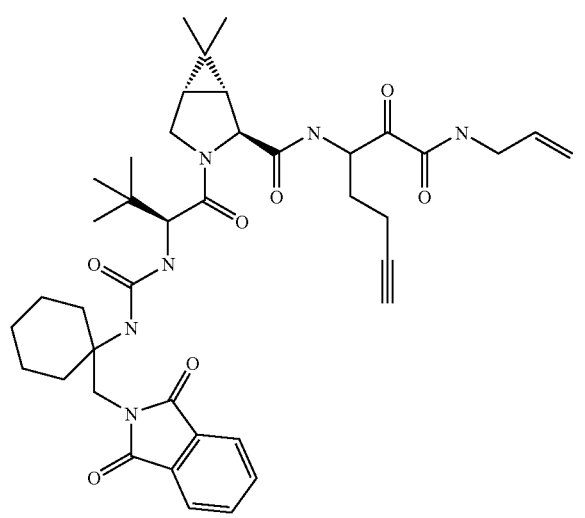
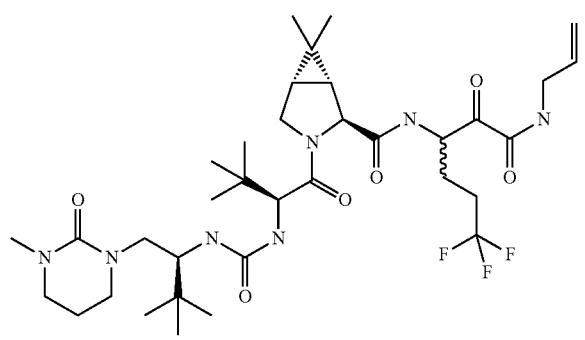
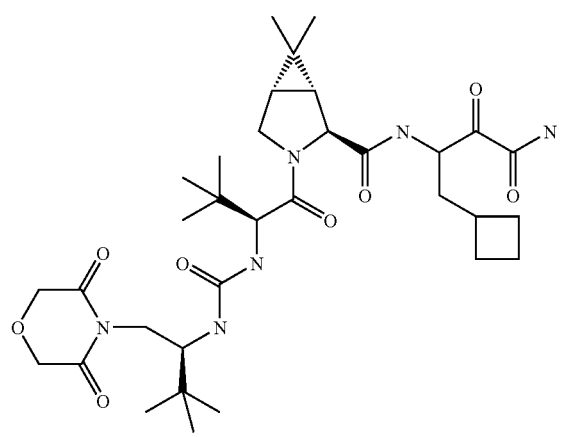
548
-continued
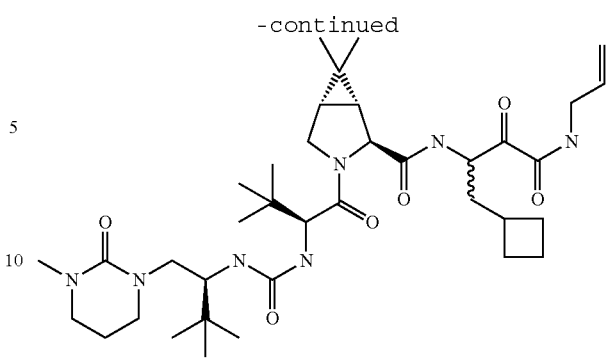

549
-continued
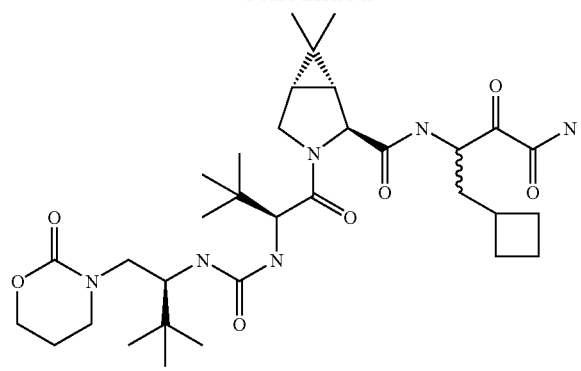
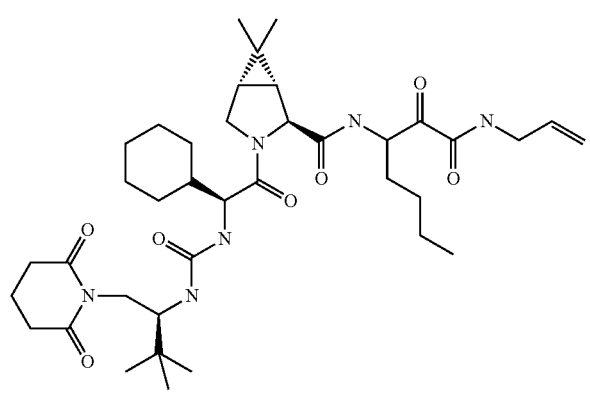
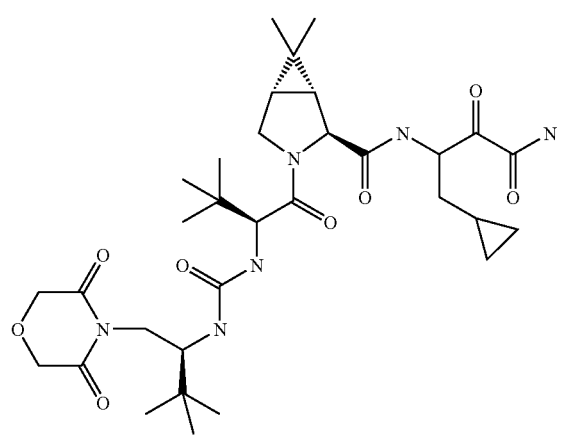
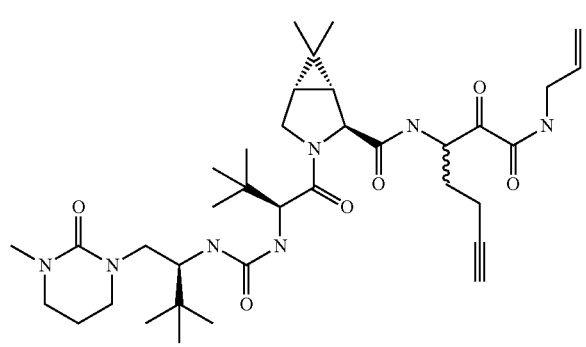
550
-continued
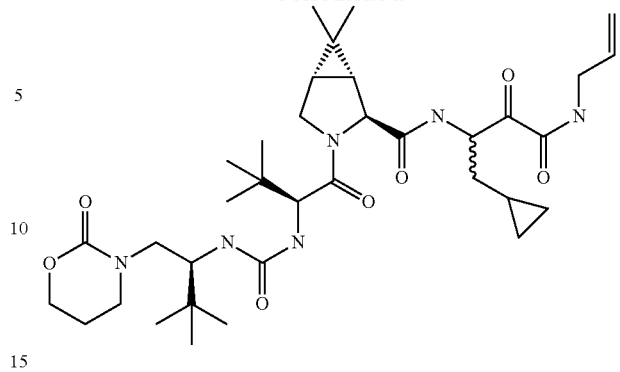
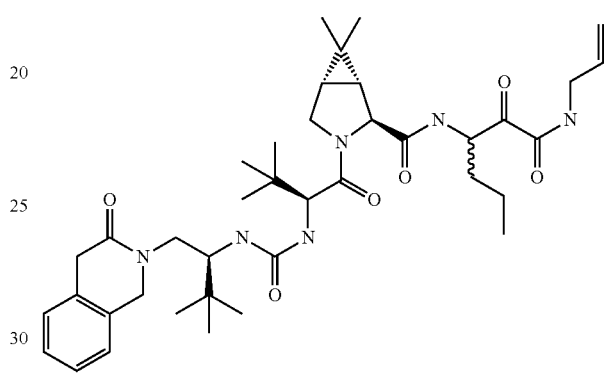
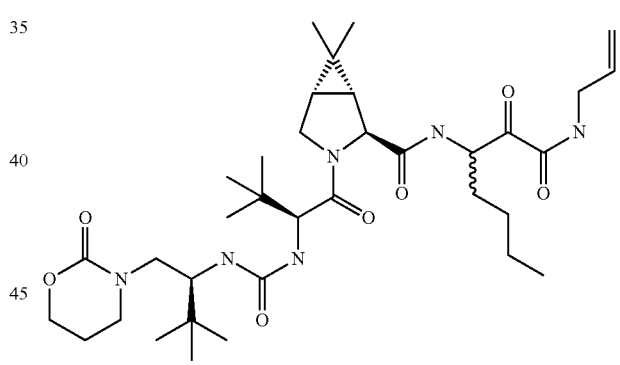
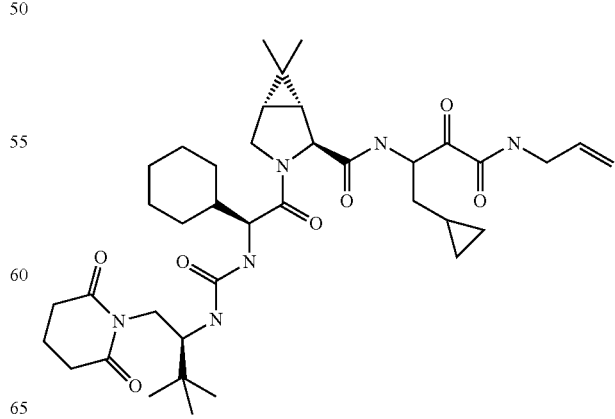

551                                           552
-continued                                    -continued
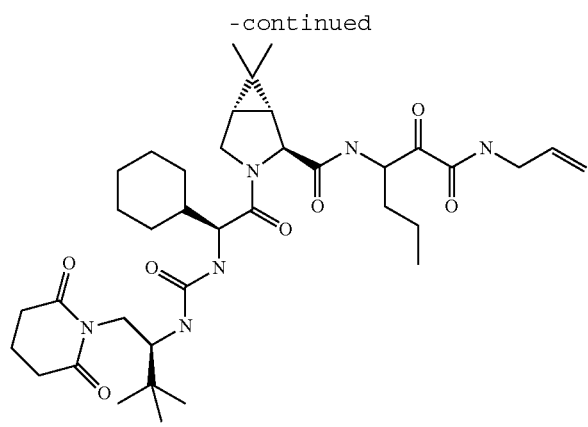
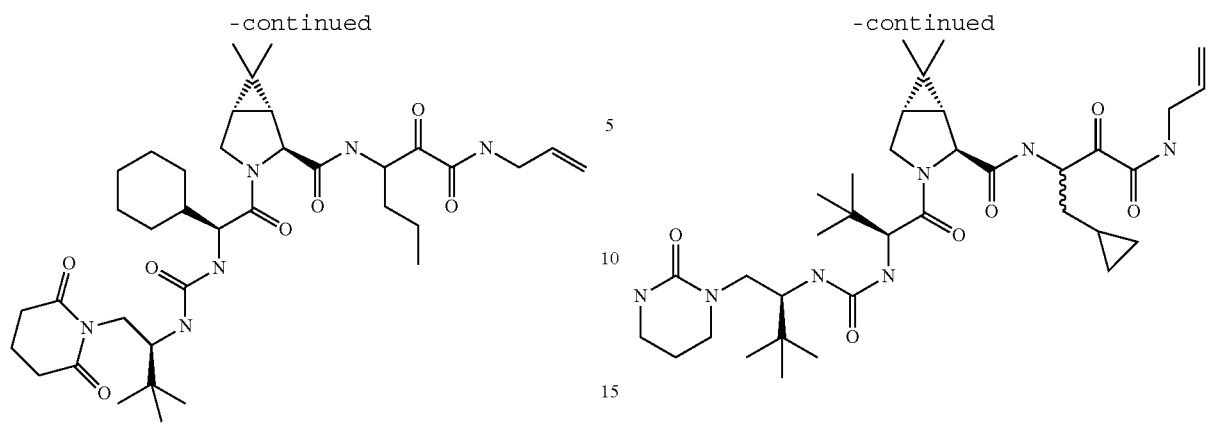
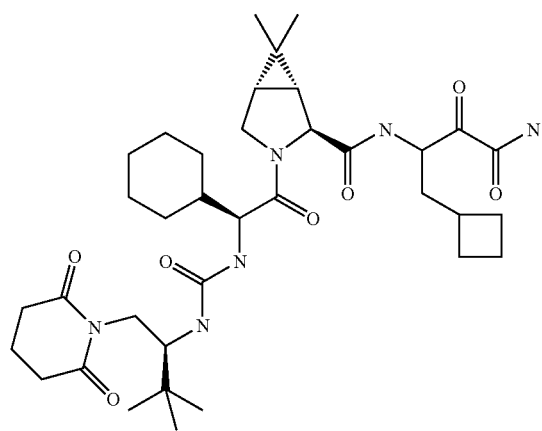
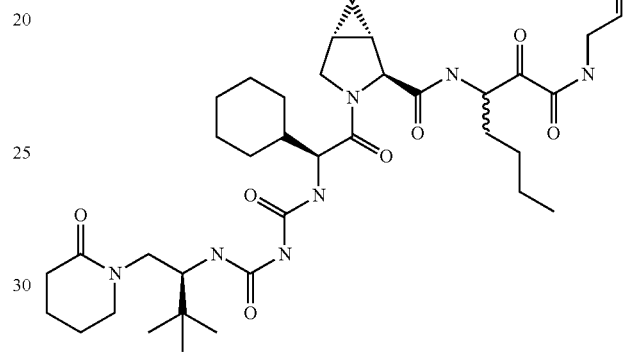
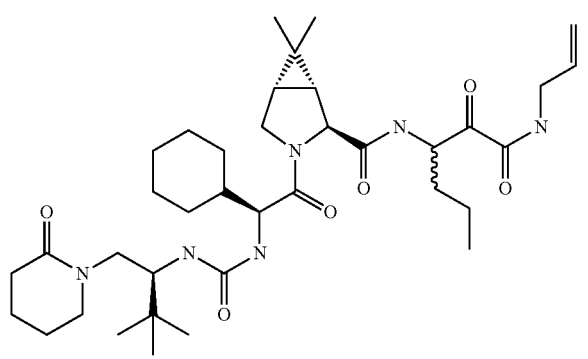
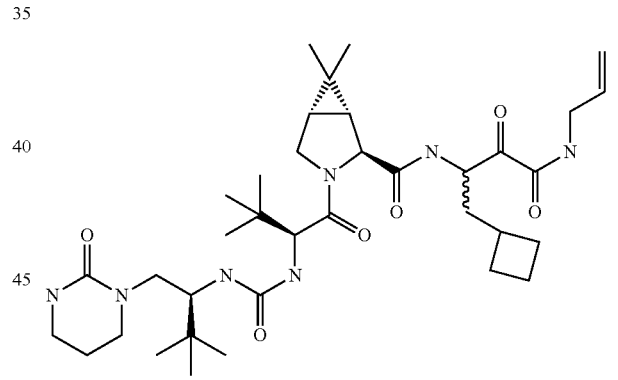
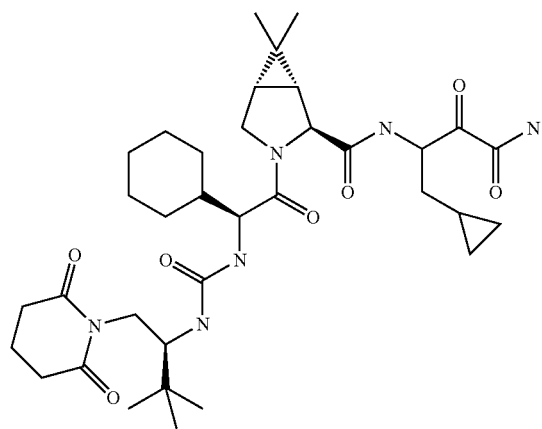
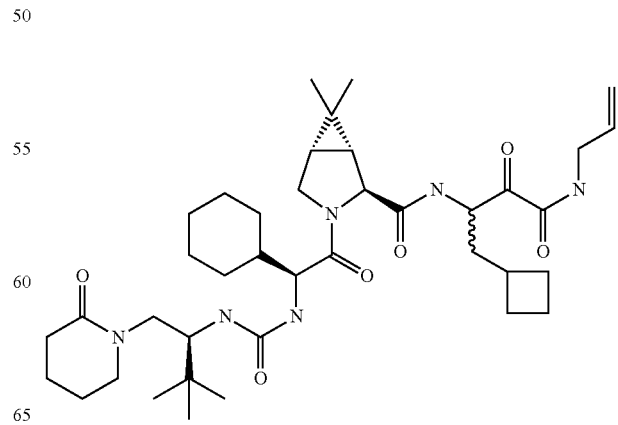

553 554
-continued -continued
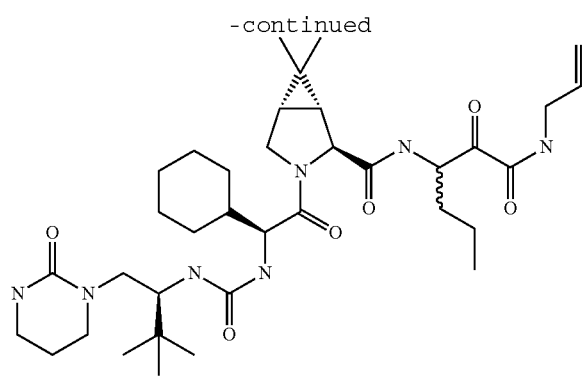
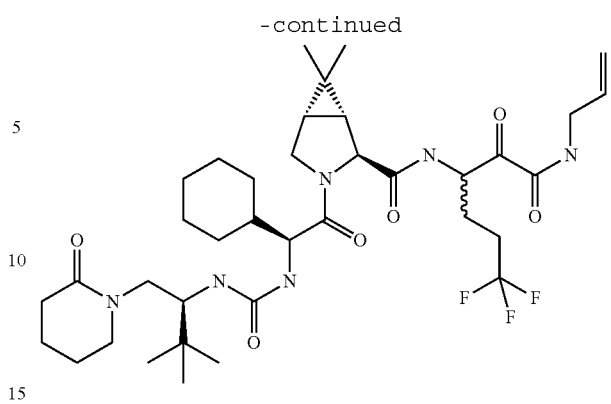
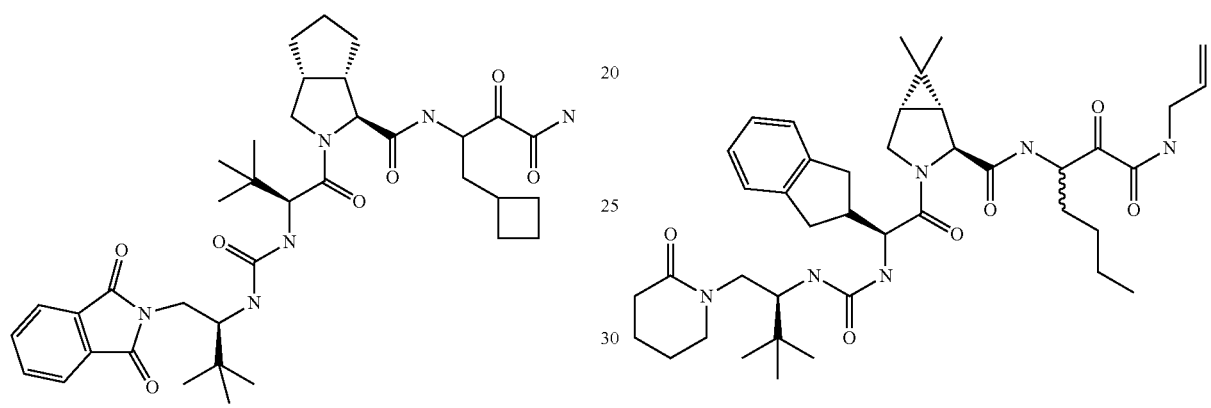
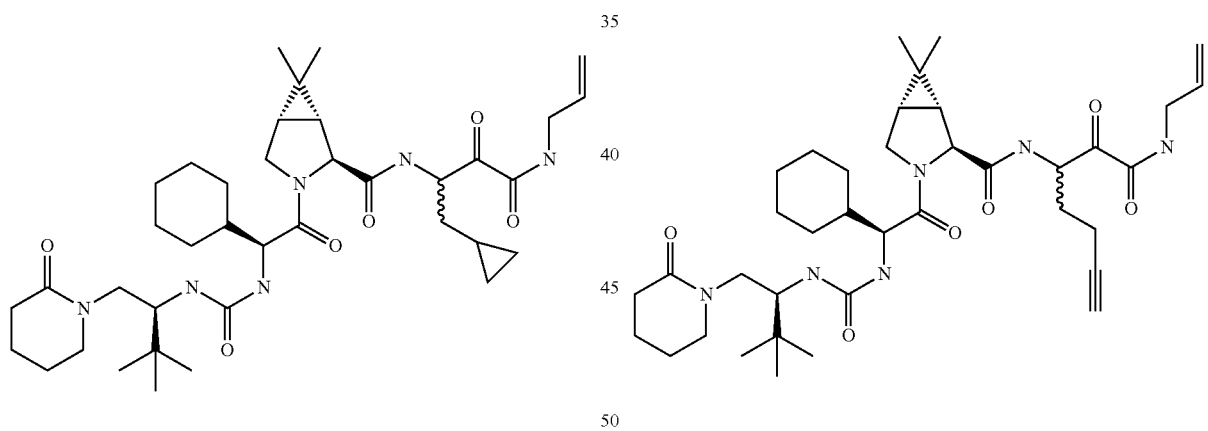
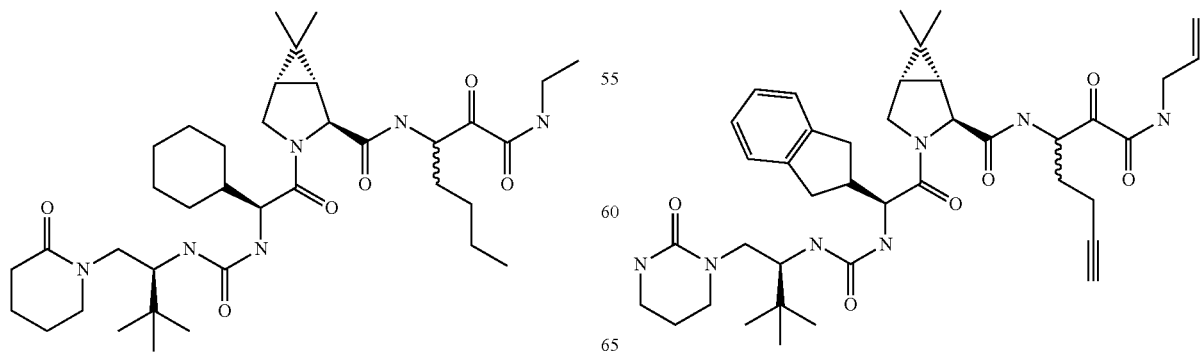

555
-continued
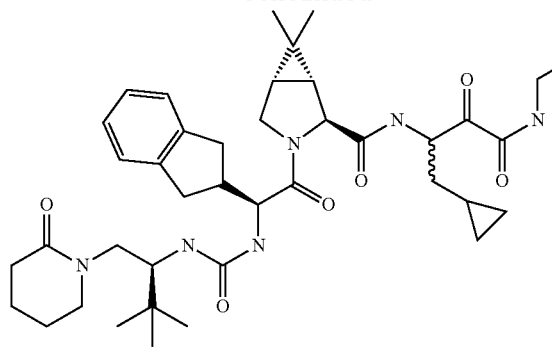
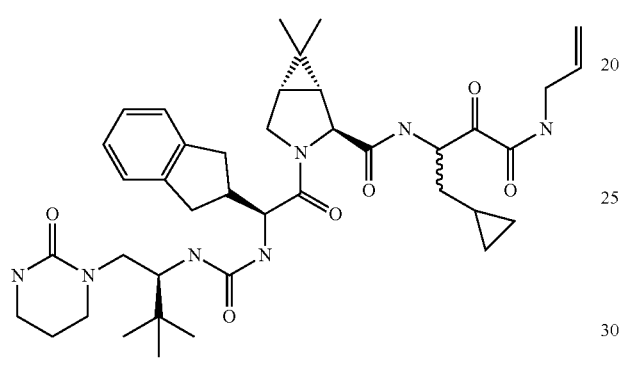
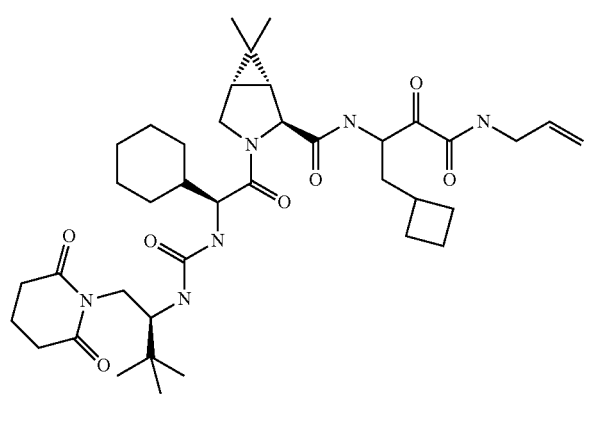
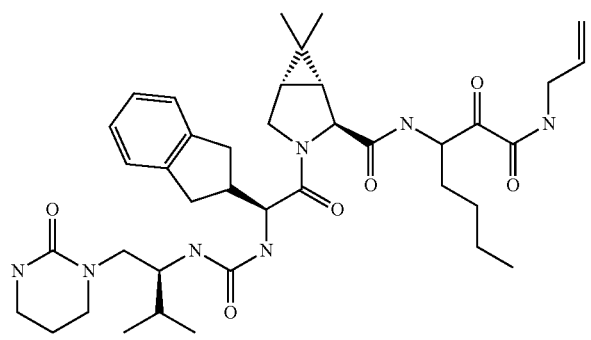
556
-continued
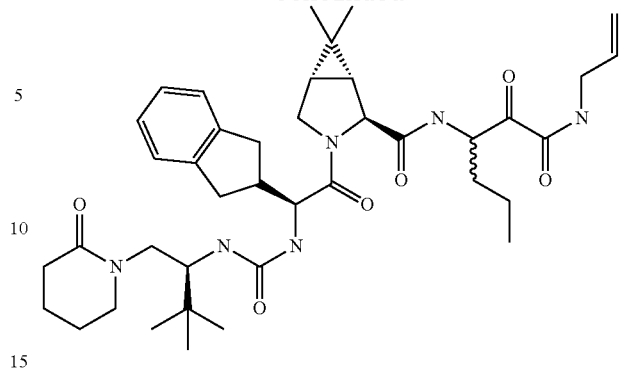
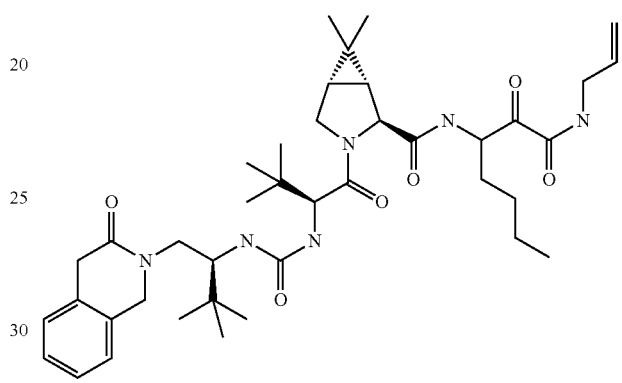

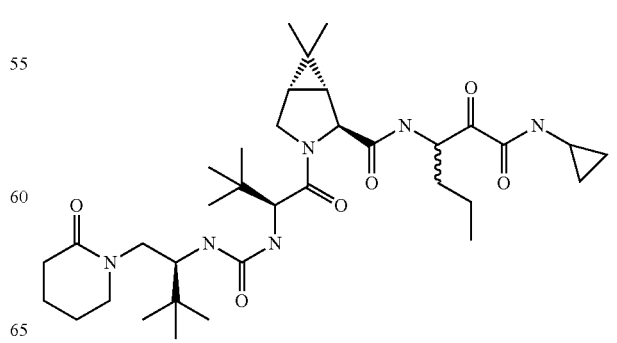

557
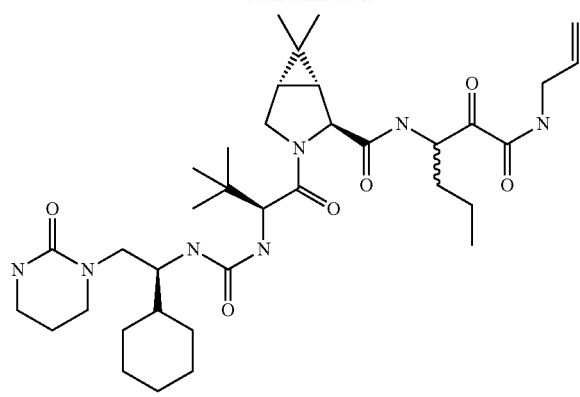
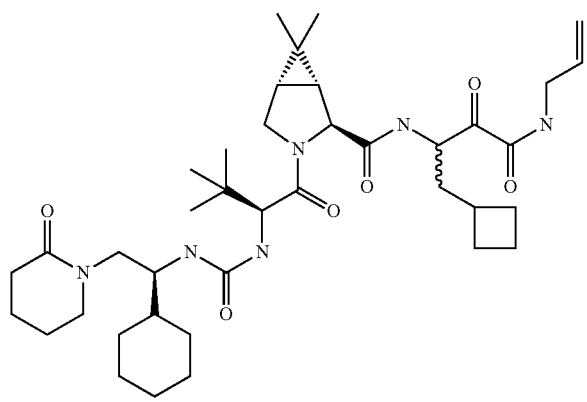
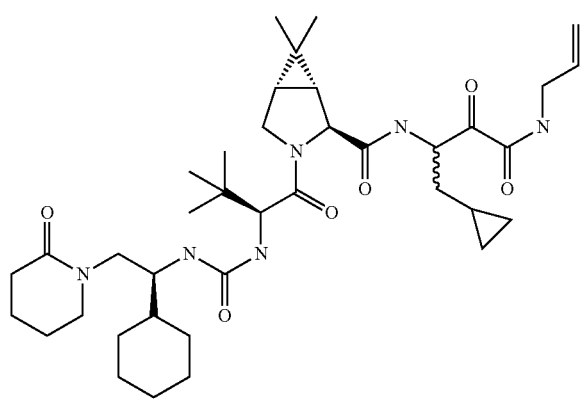
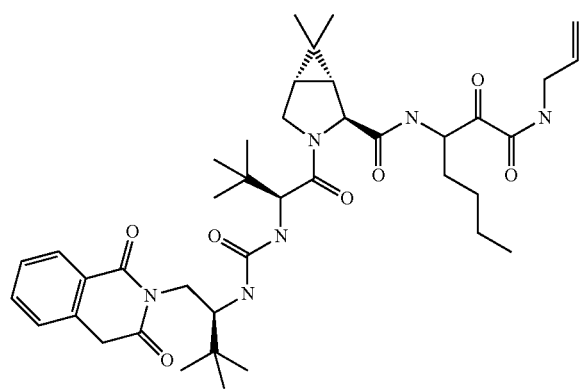
558
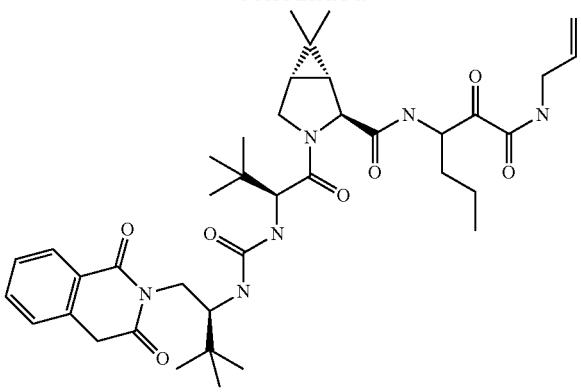
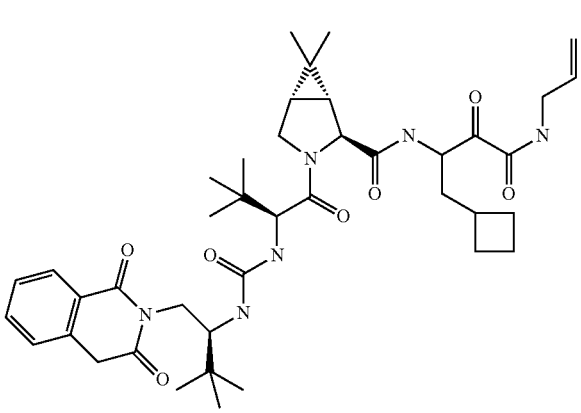
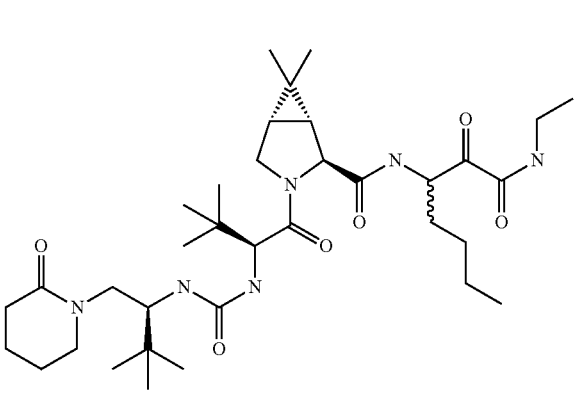
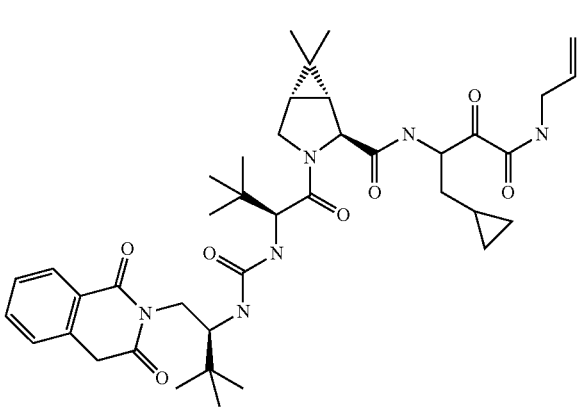

559
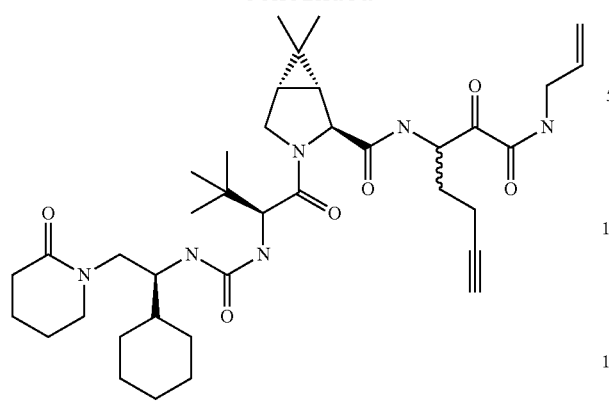
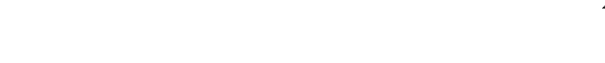
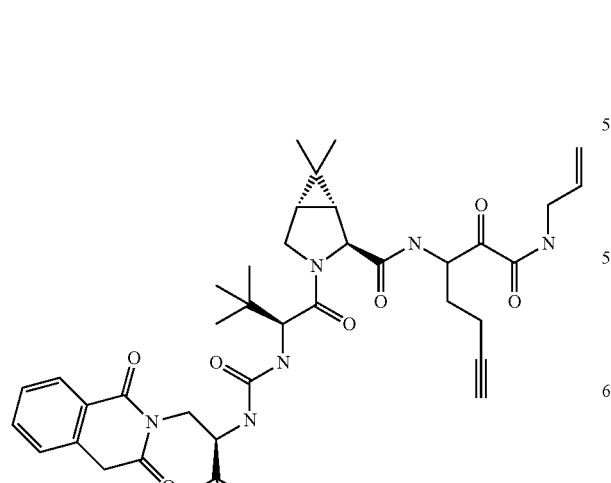
560
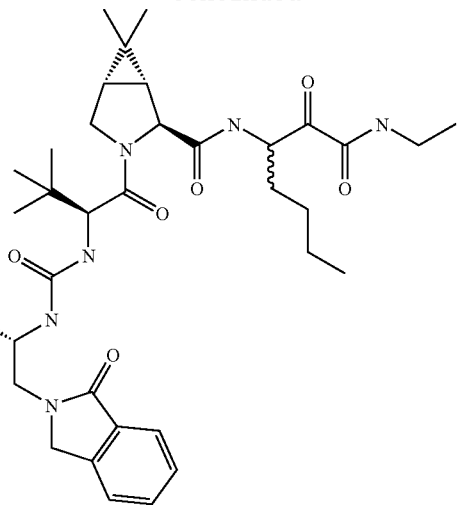
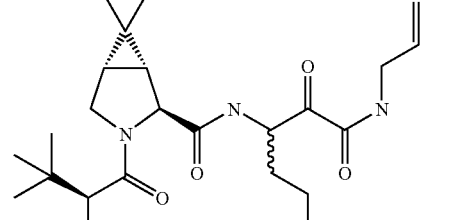
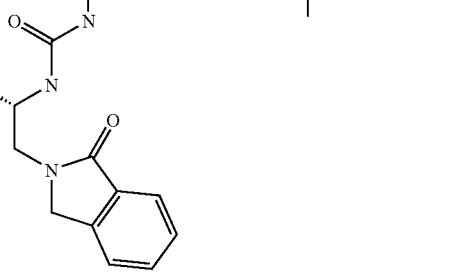
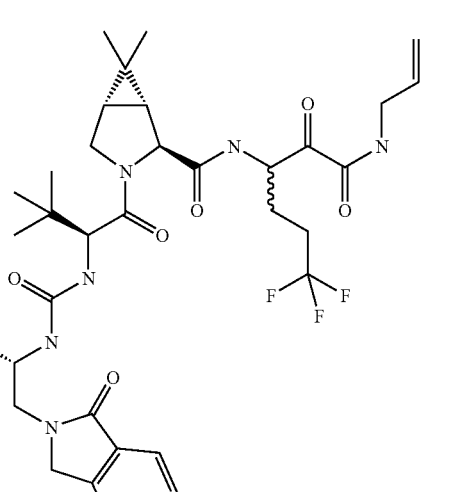

561 -continued
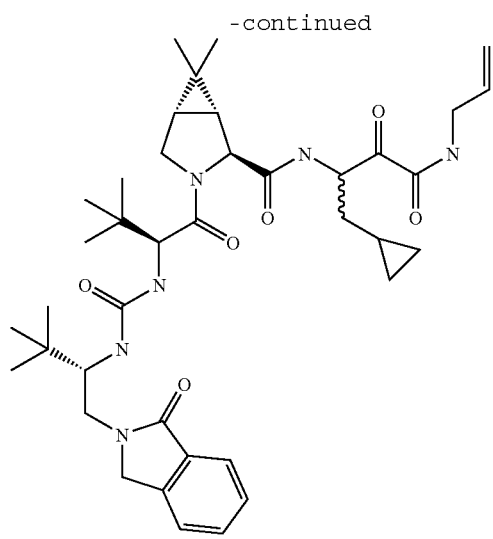
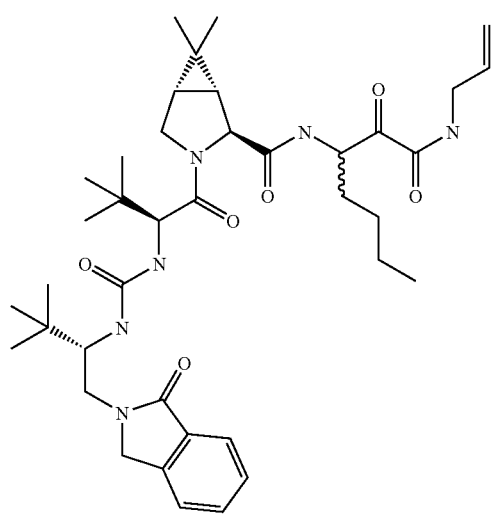
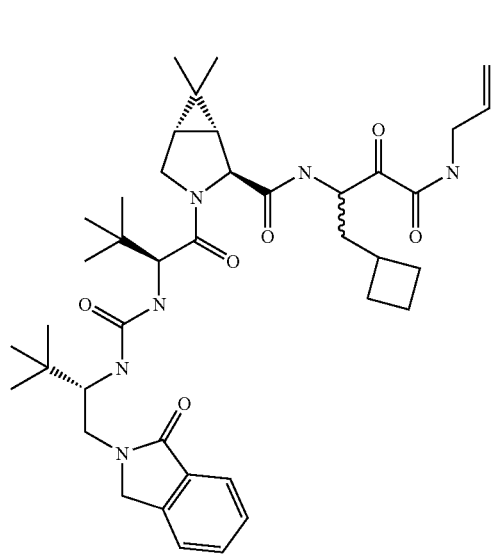
562 -continued
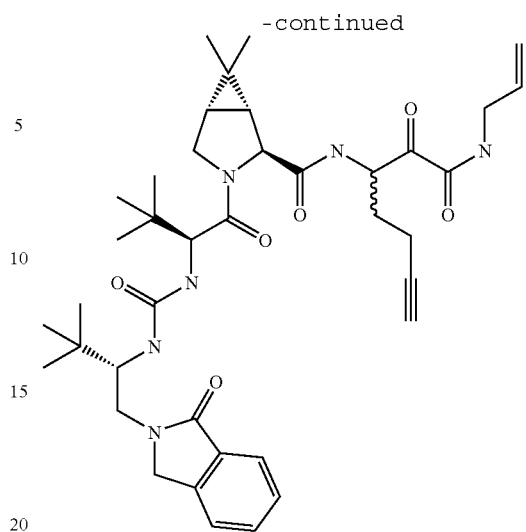
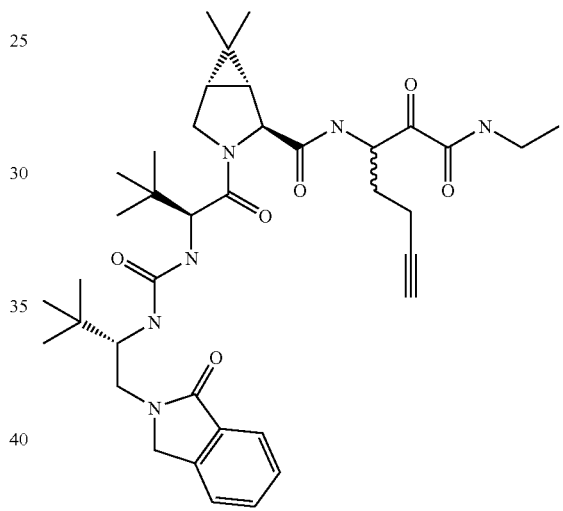
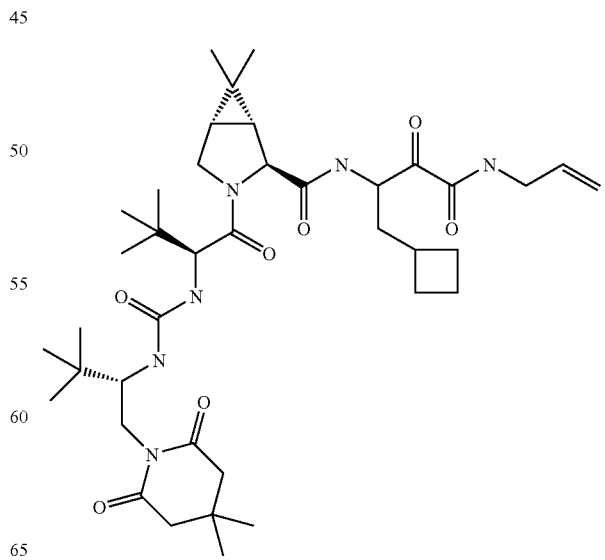

563
-continued
564
-continued
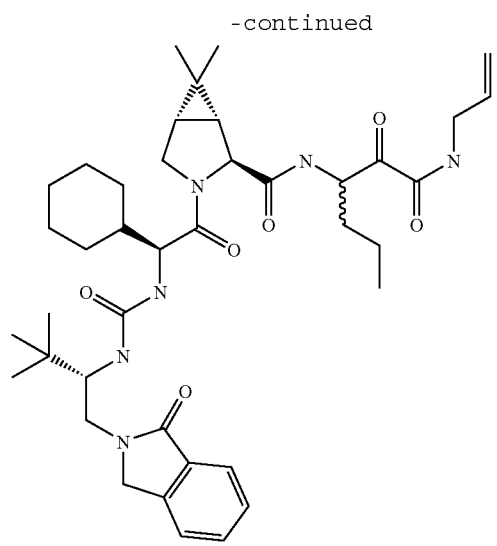
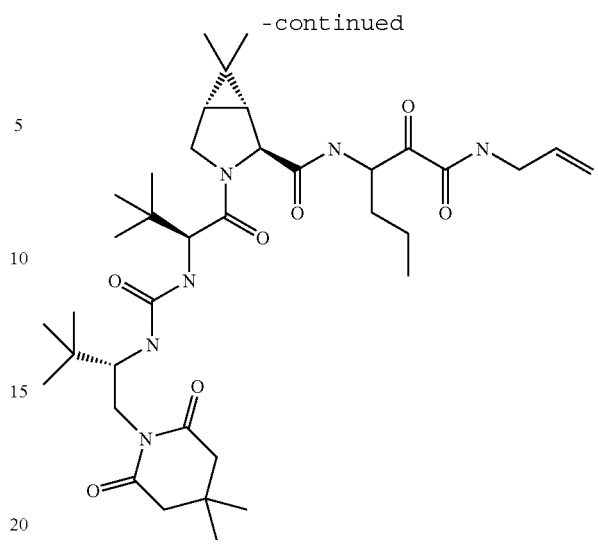
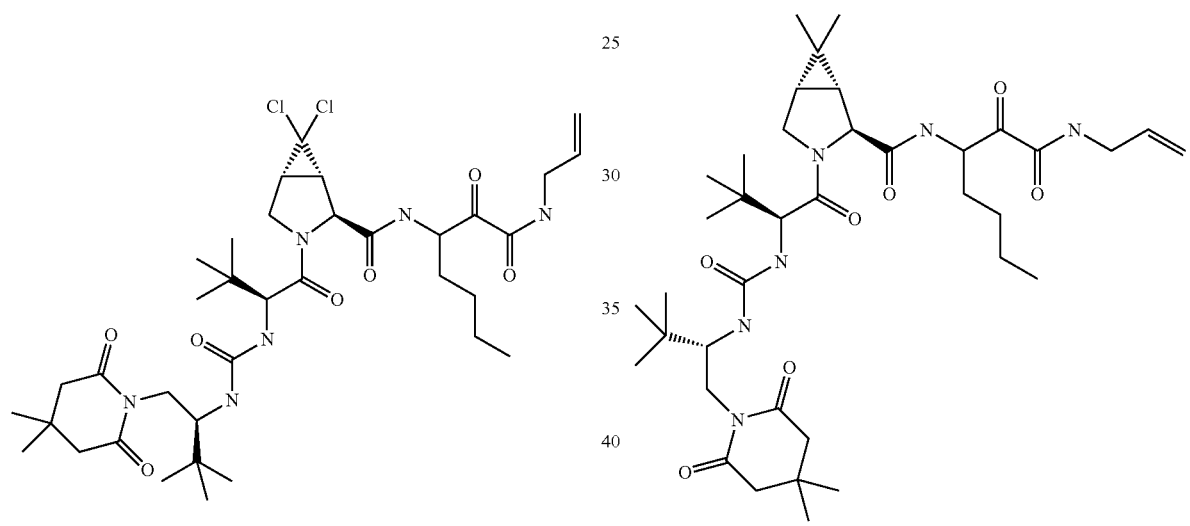
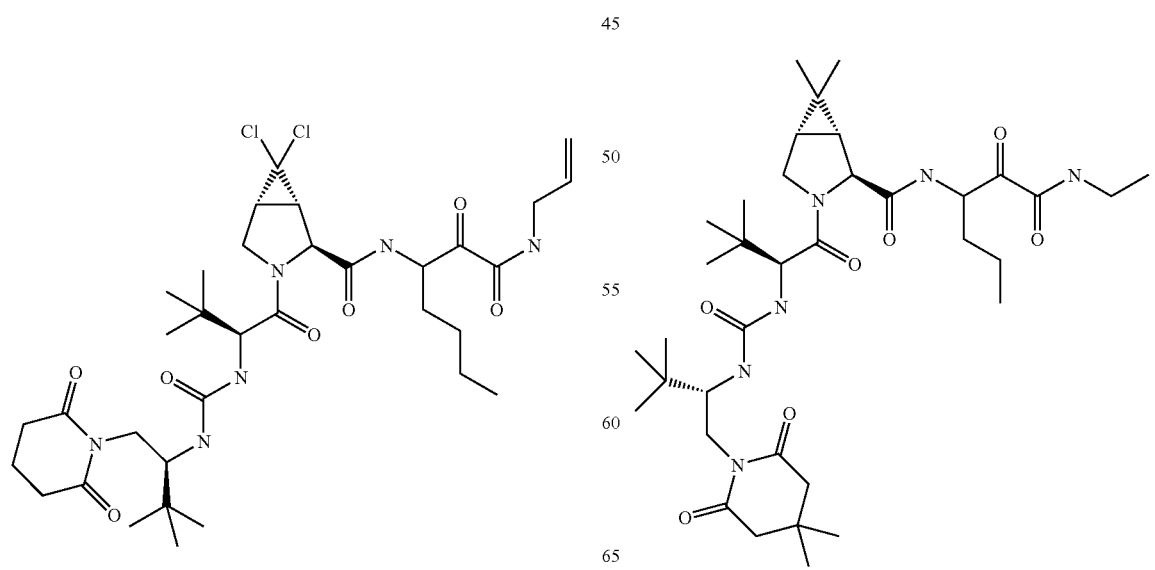

565
-continued
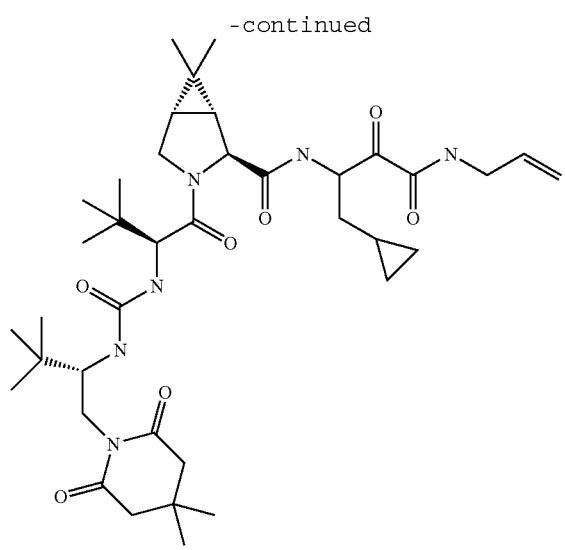
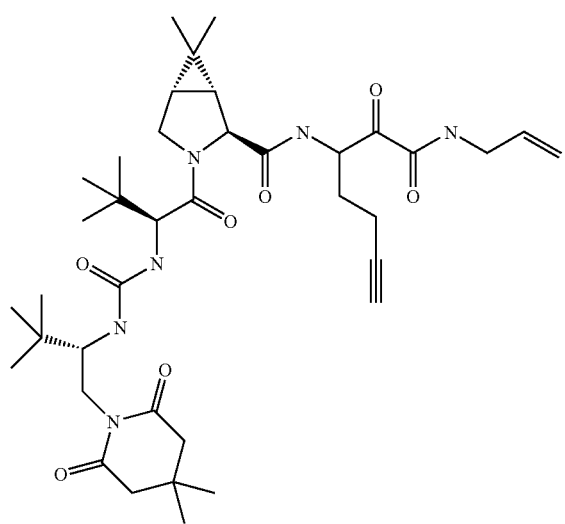
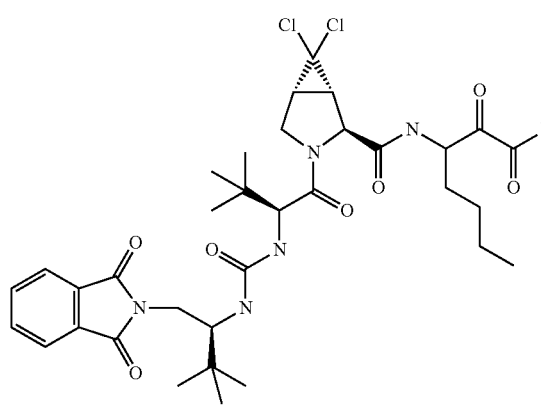
566
-continued
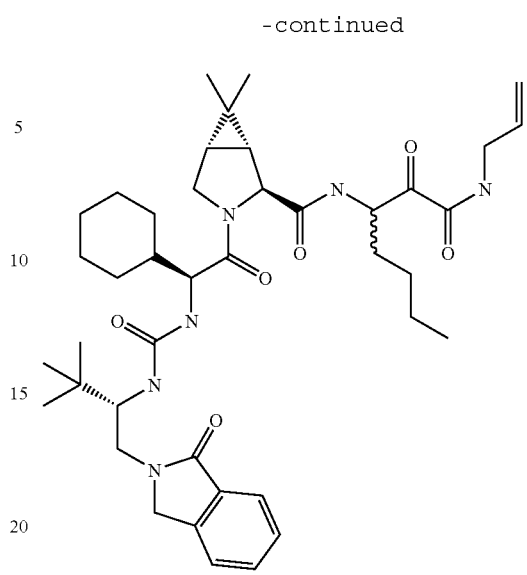
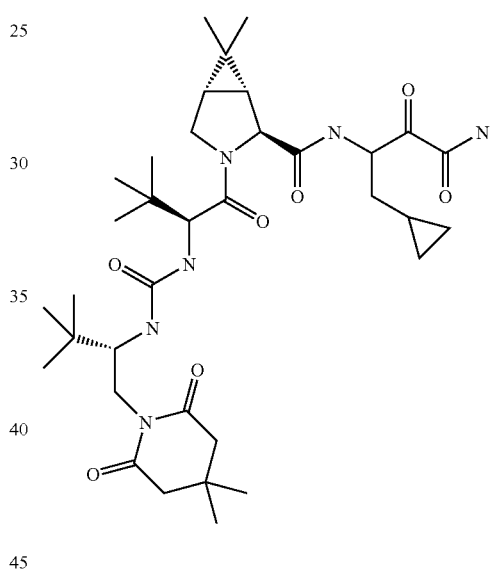
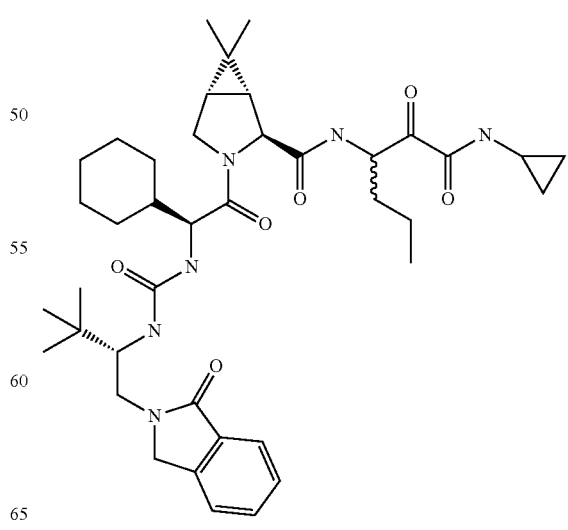

567
-continued
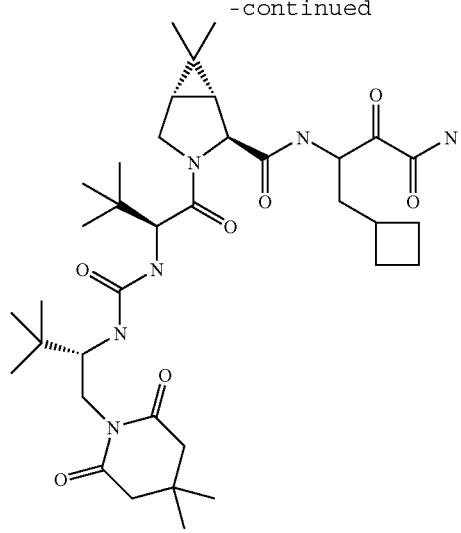
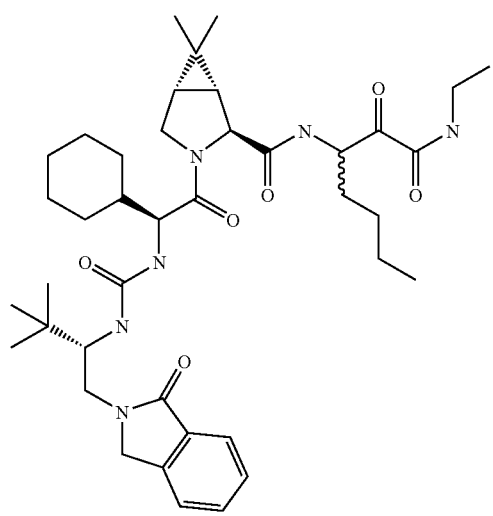
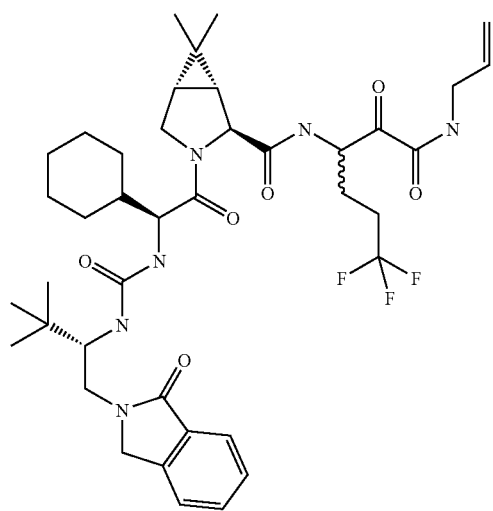
568
-continued
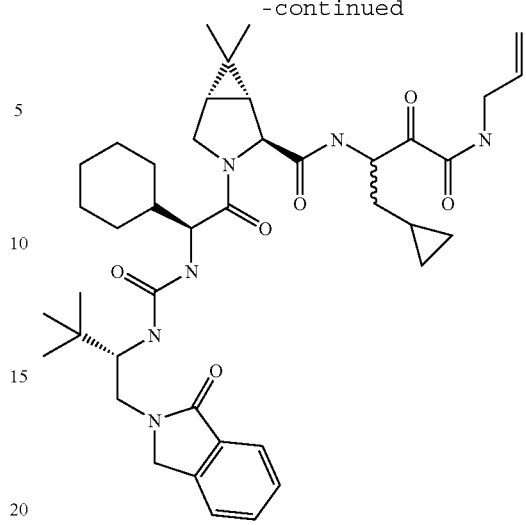
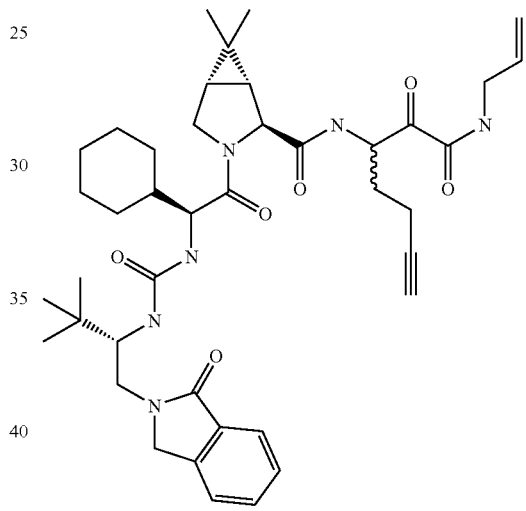
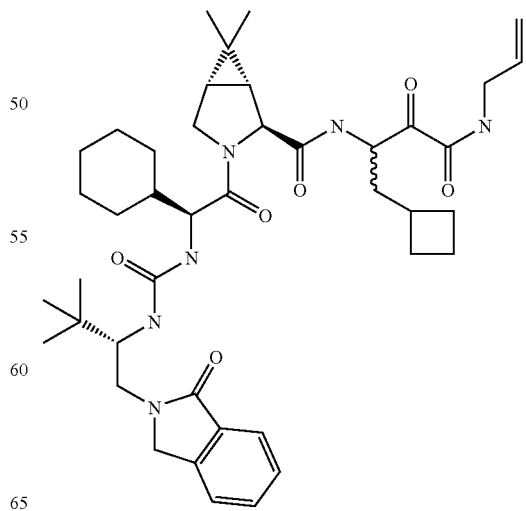

569
-continued
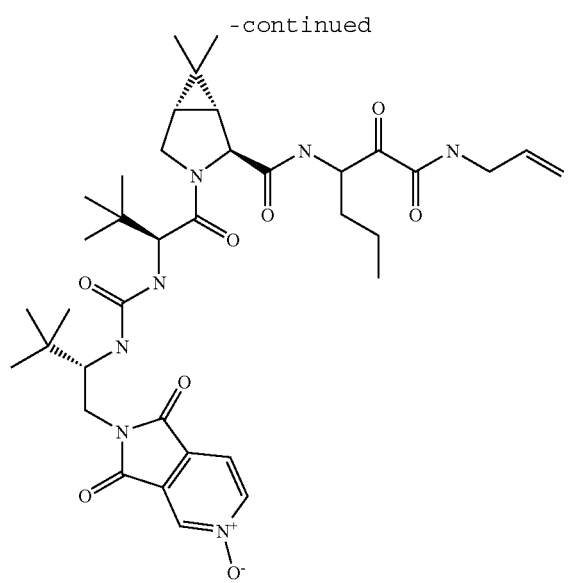
570
-continued
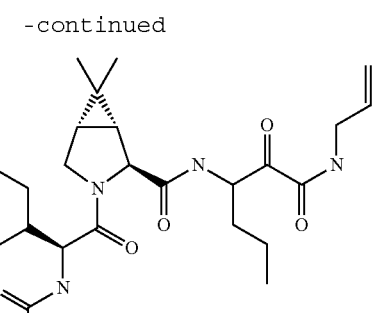
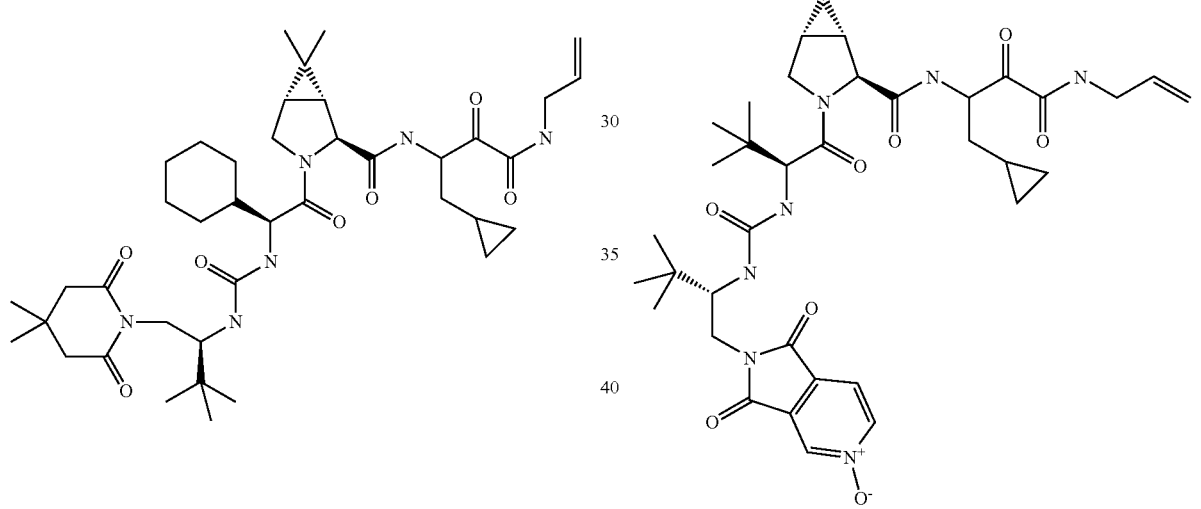
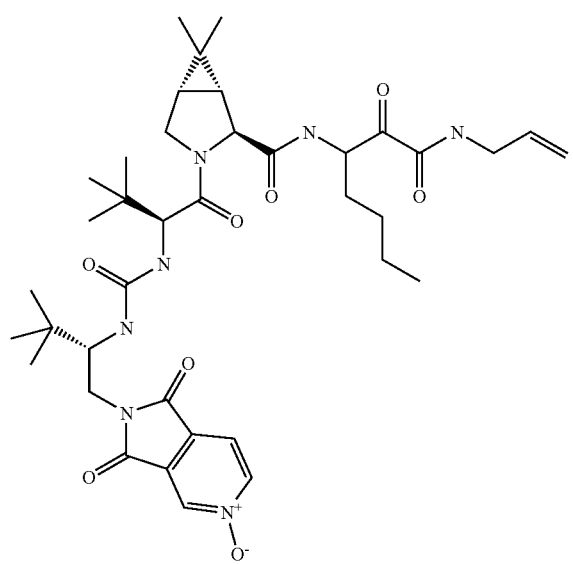
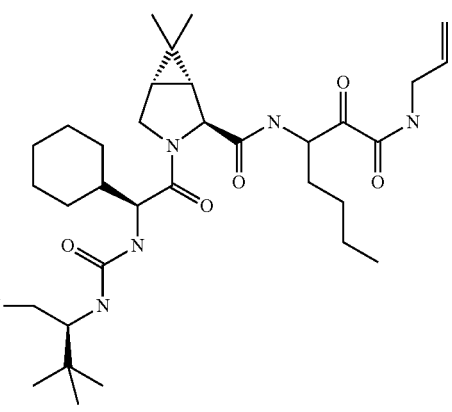

571
-continued
572
-continued
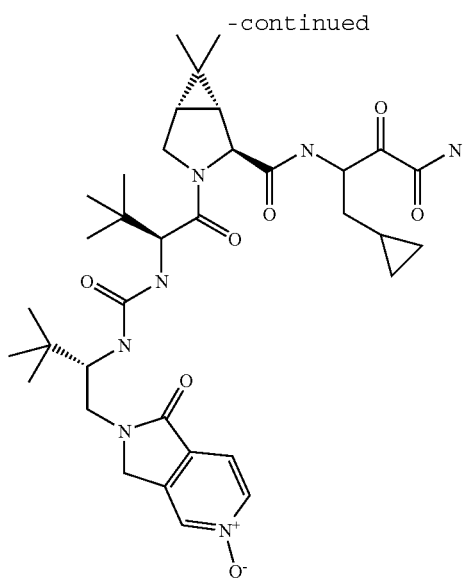
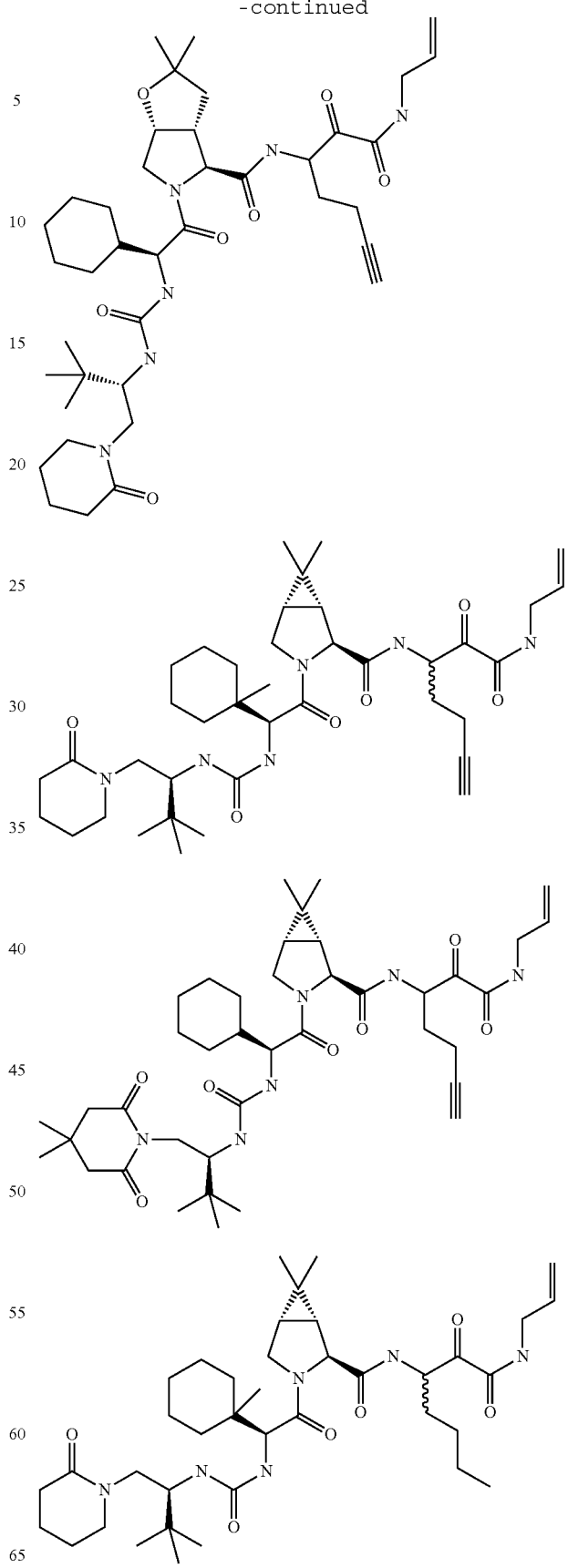

573
-continued
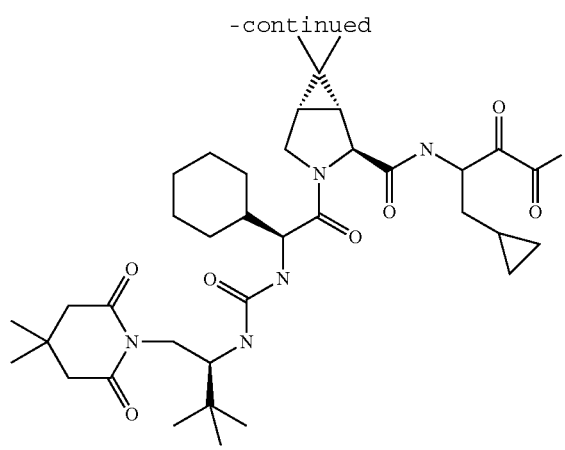
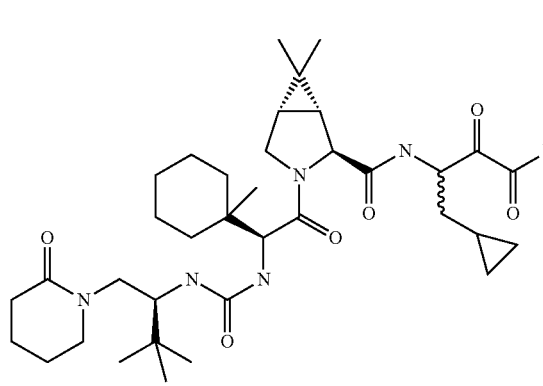
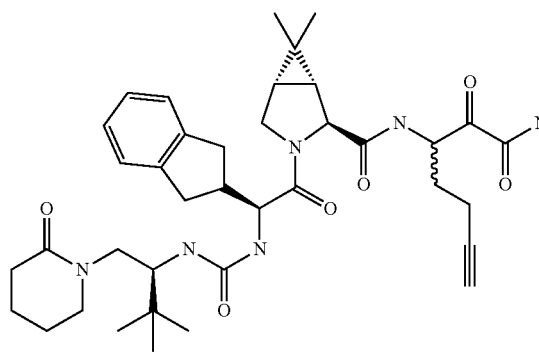
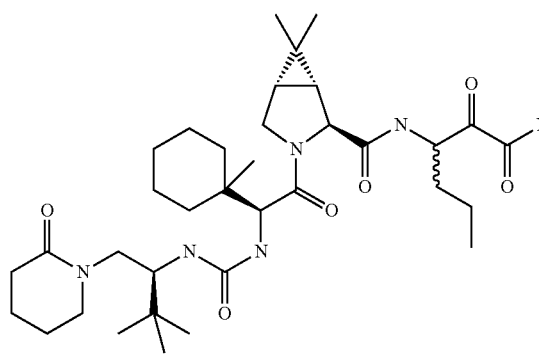
574
-continued
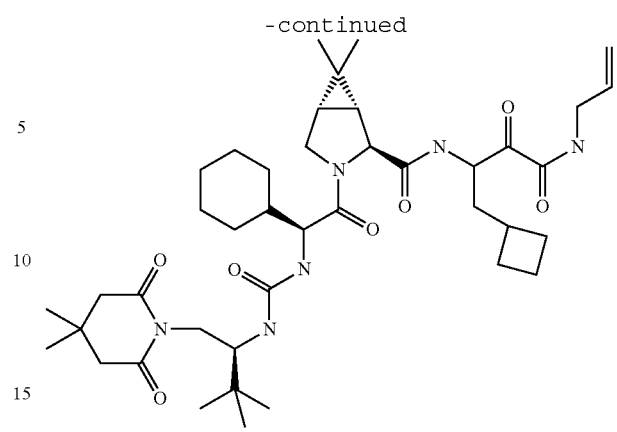
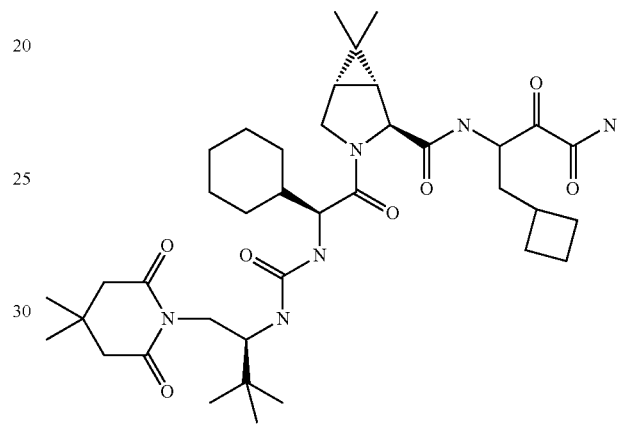
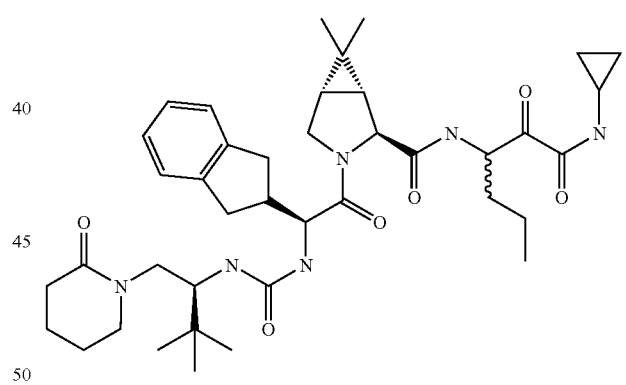
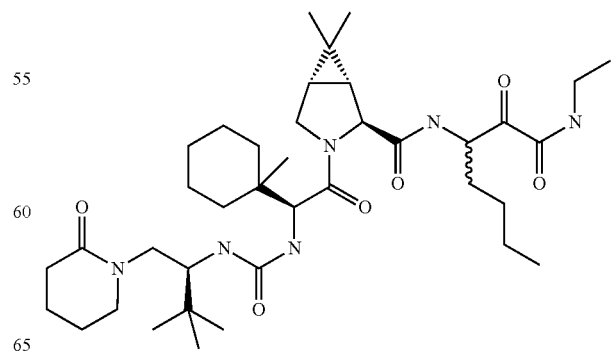

575
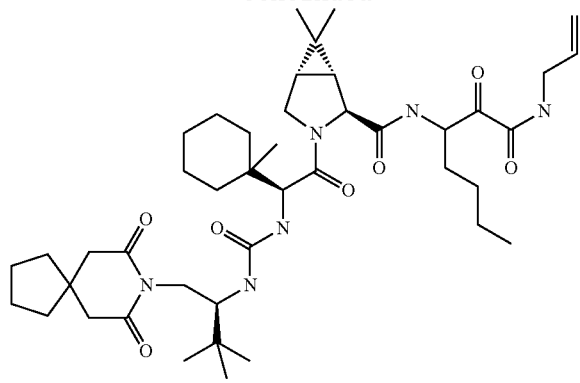
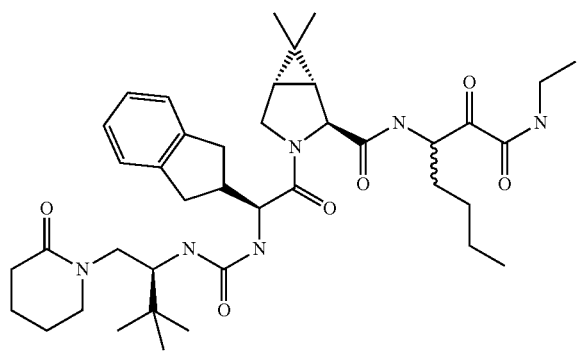
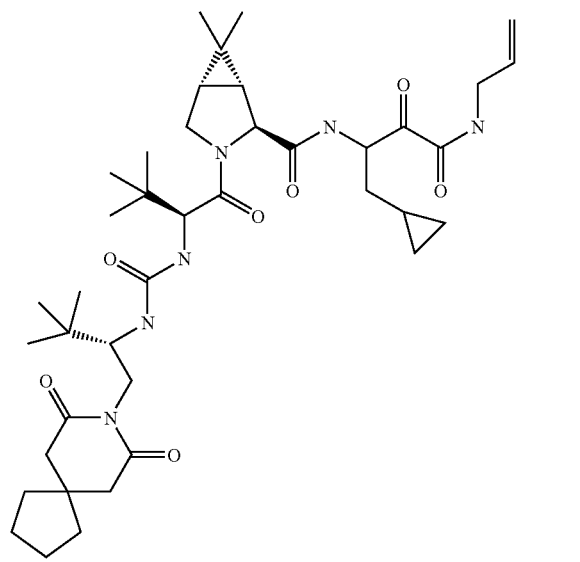
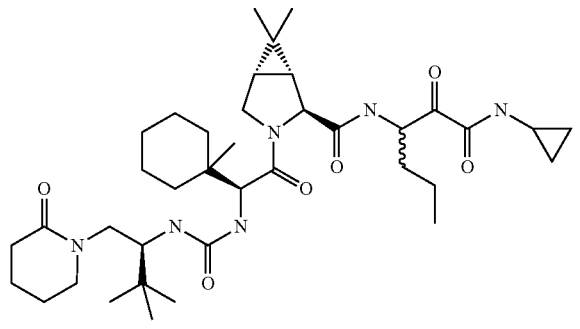
576
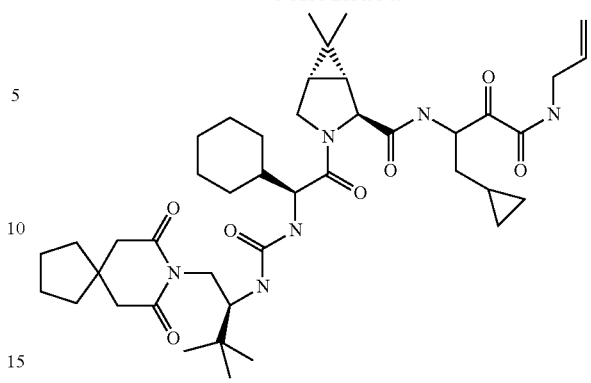
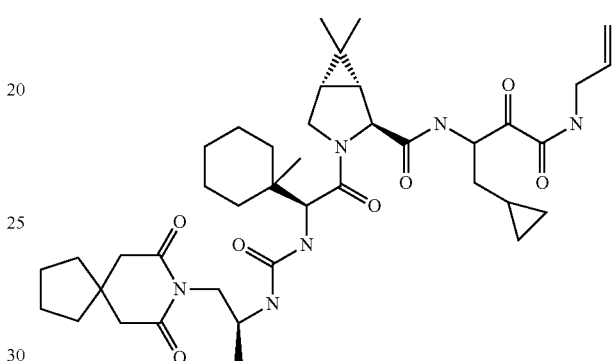
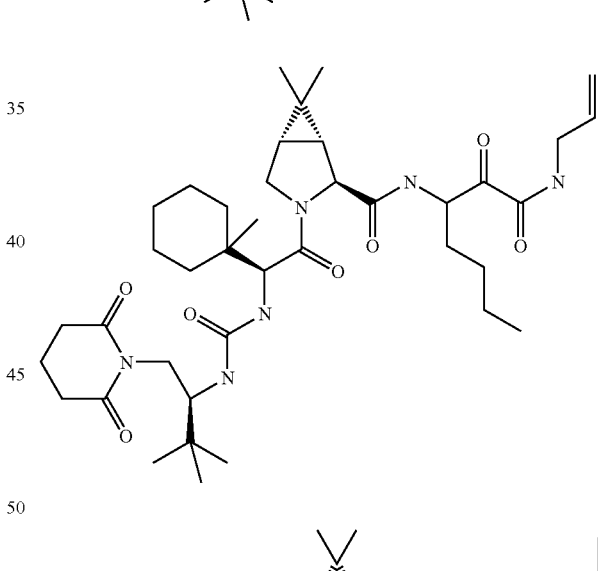
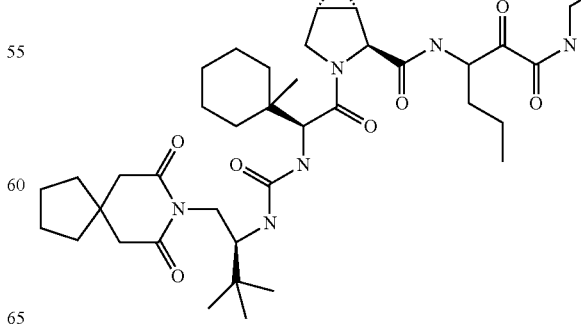

577
-continued
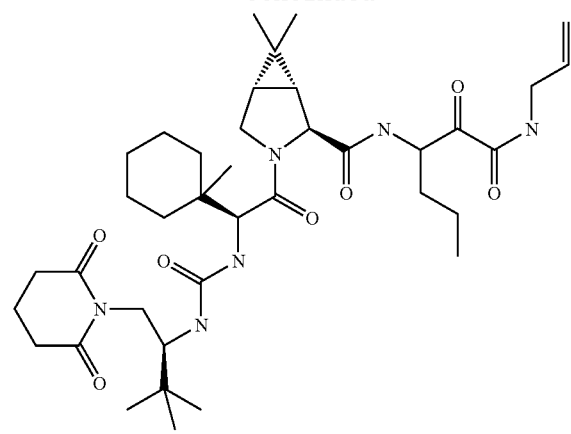
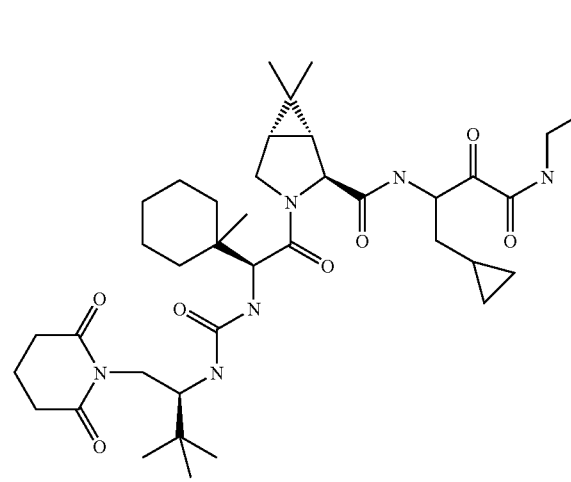
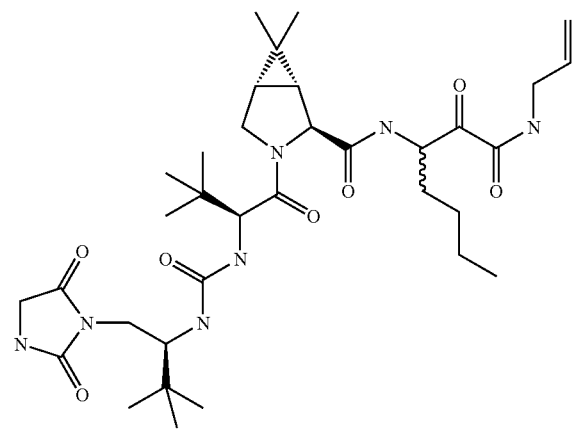
578
-continued
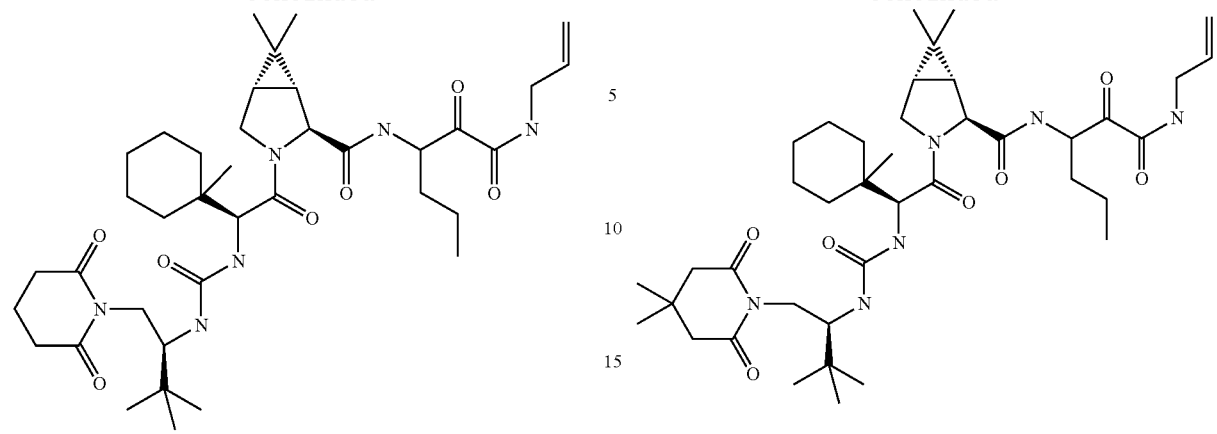
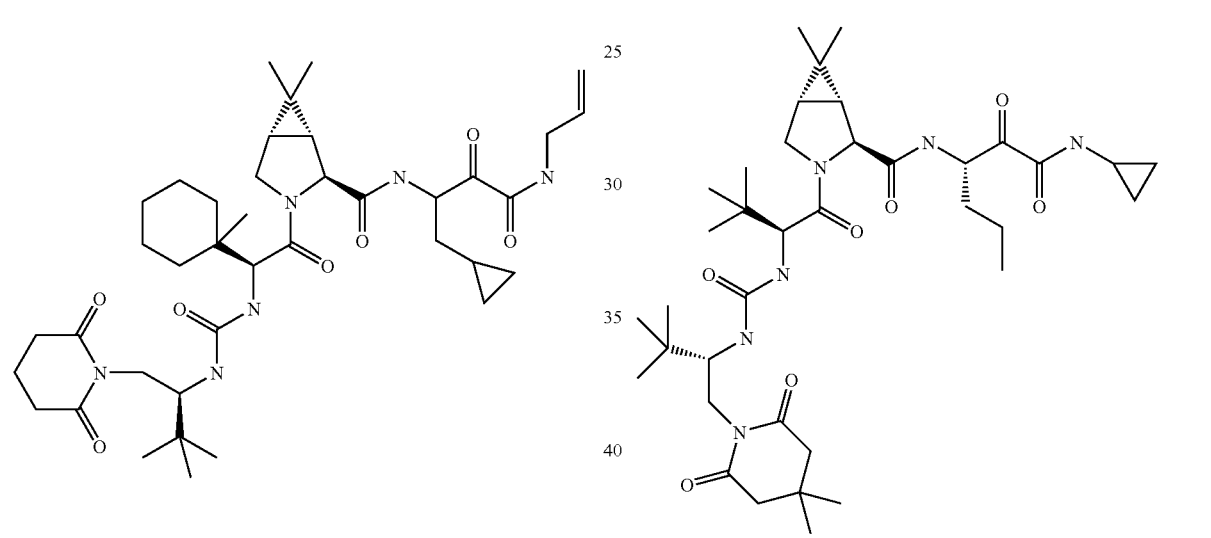
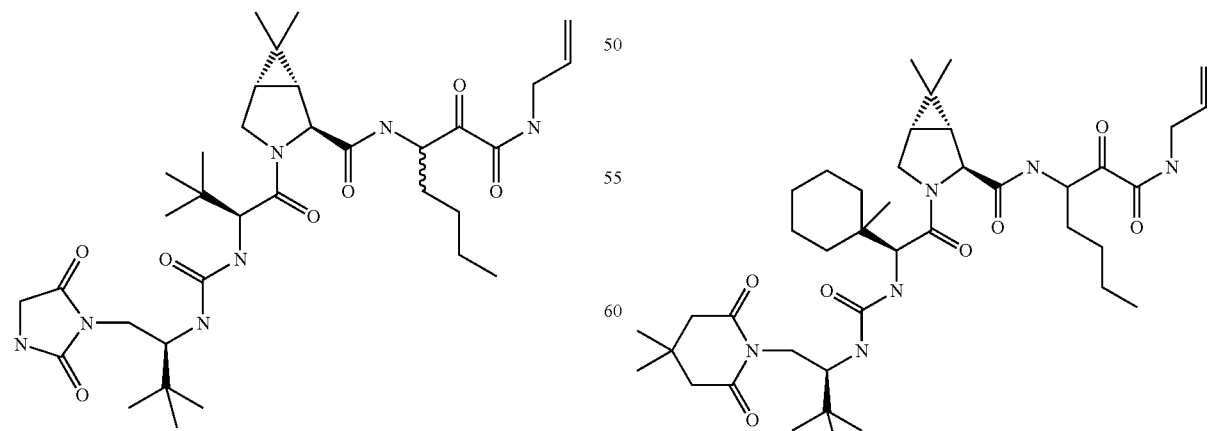

-continued
579
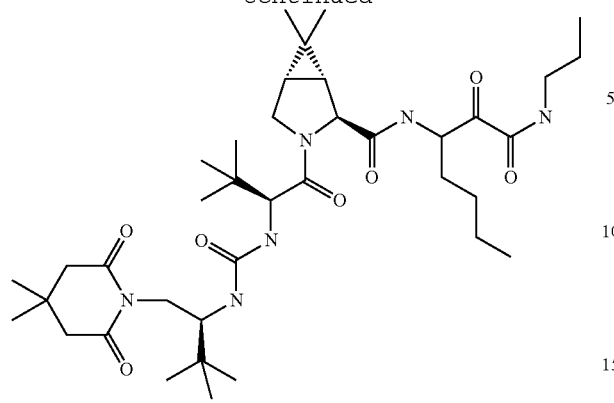
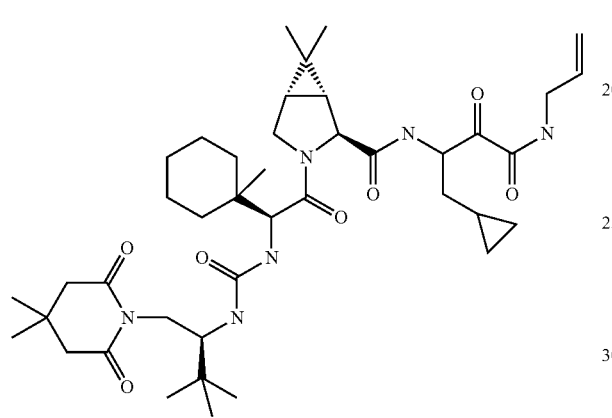
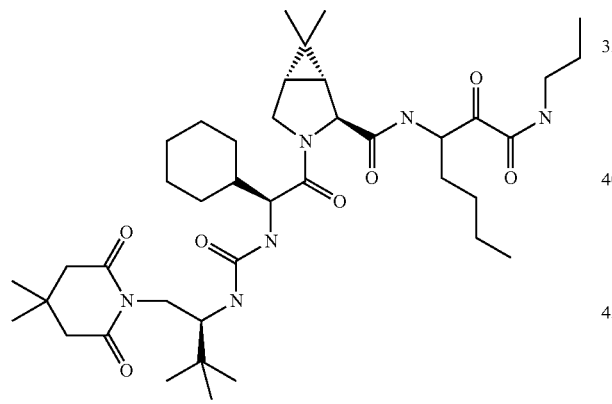
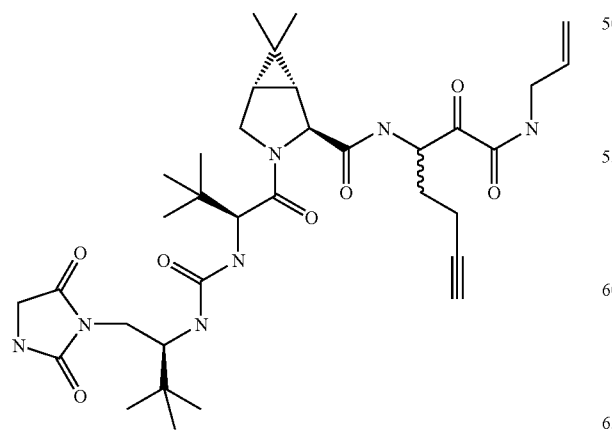
580
-continued
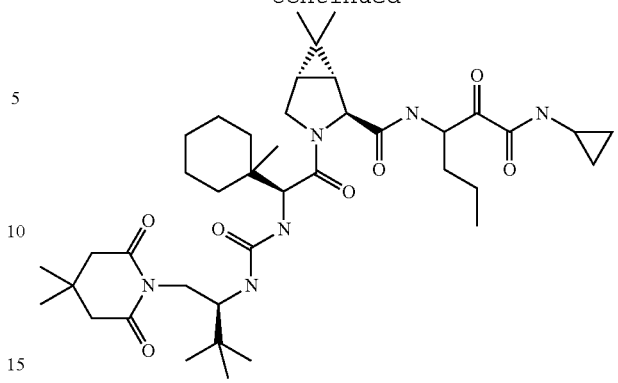
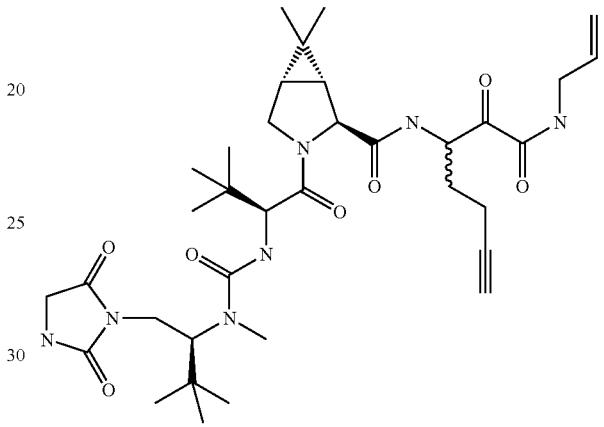
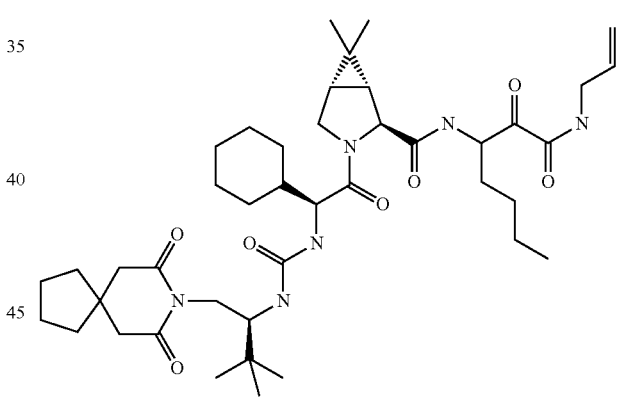
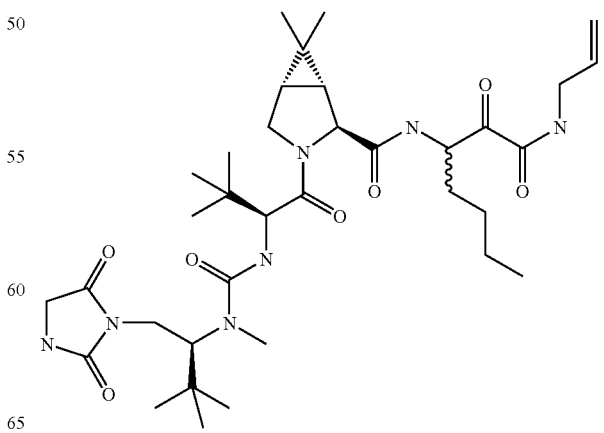

581
-continued
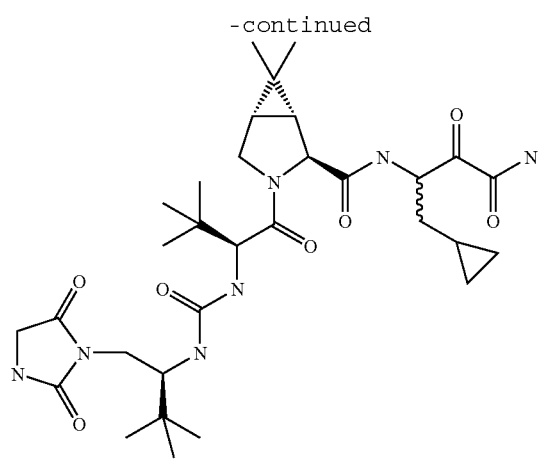
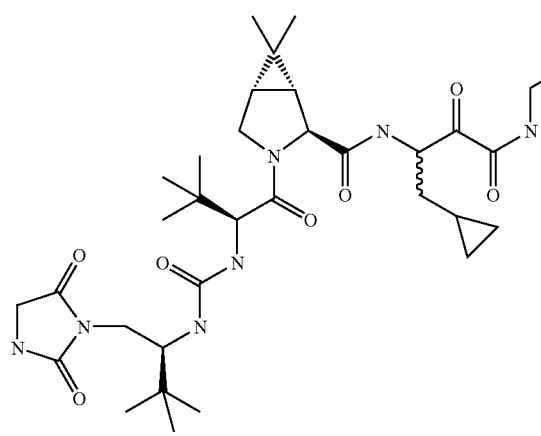
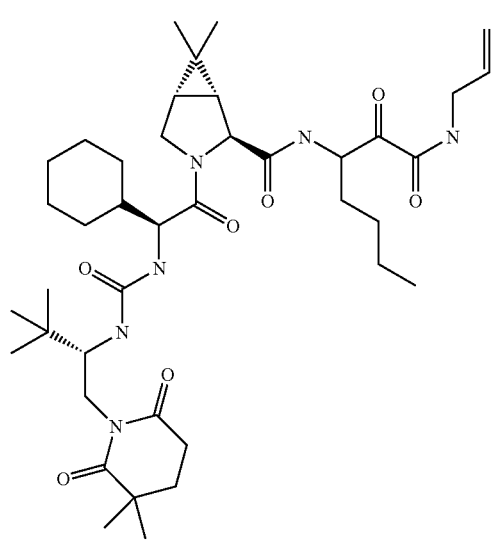
582
-continued
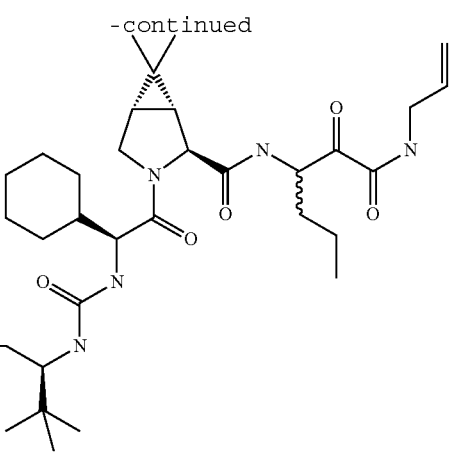
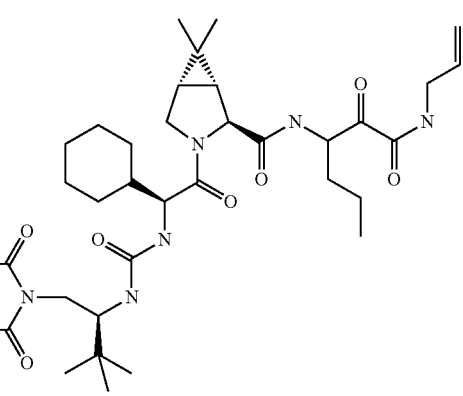
or a pharmaceutically acceptable salt, solvate or ester thereof.
Compounds of formula XIV are disclosed in U.S. patent application Ser. No. 11/064,673 filed Feb. 24, 2005. The preparation of these compounds is disclosed in the experimental section of this application set forth hereinbelow.
Non-limiting examples of certain compounds disclosed in U.S. patent application Ser. No. 11/064,673 are:

583
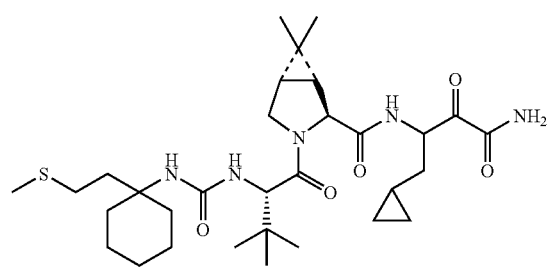
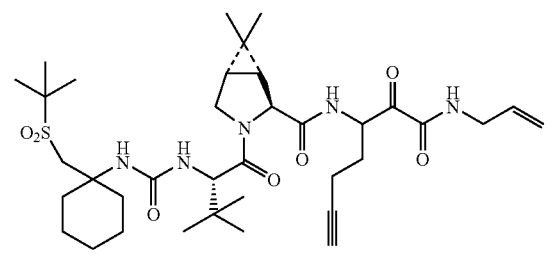
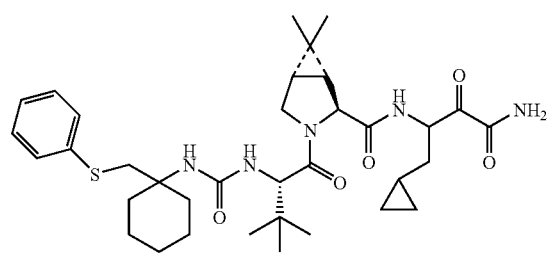
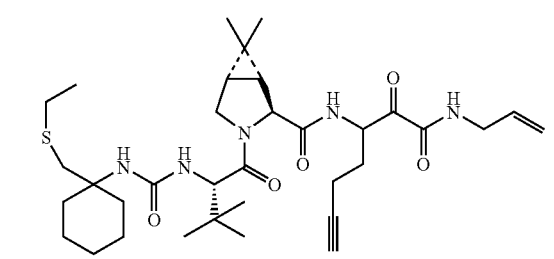
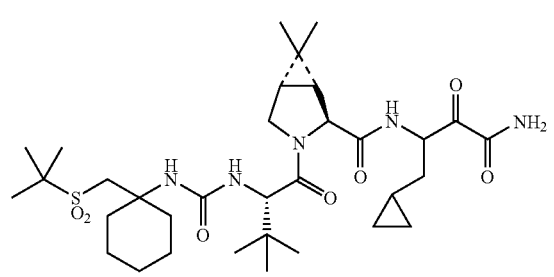
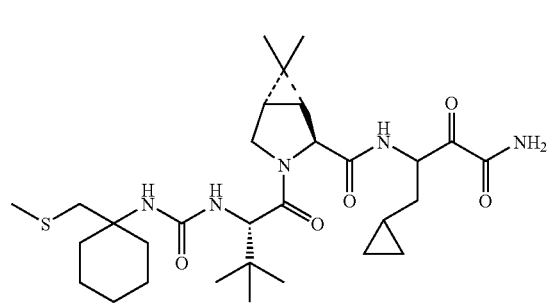
584
-continued
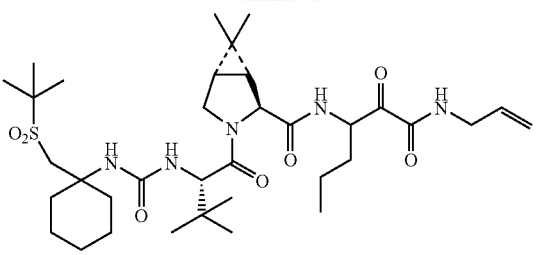
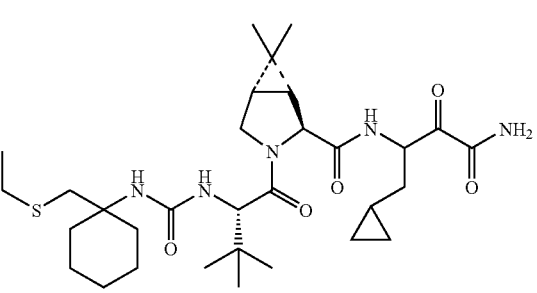
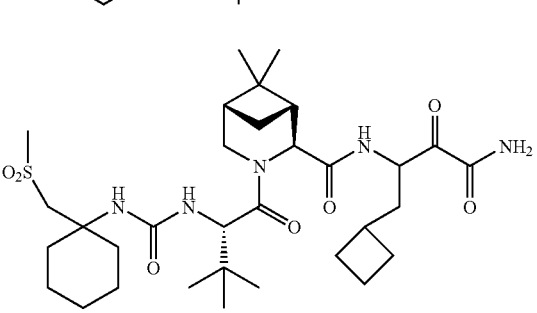
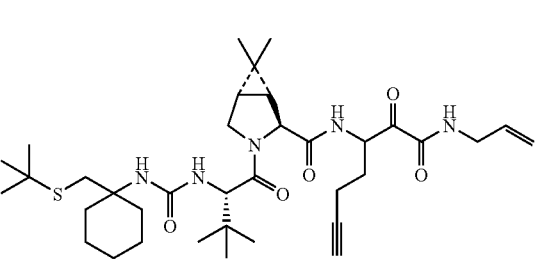
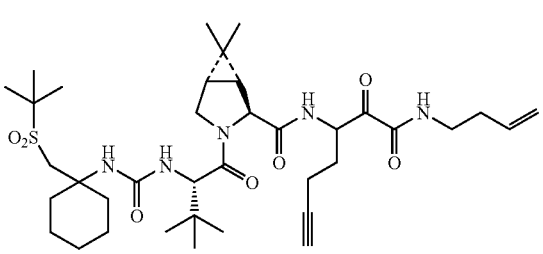
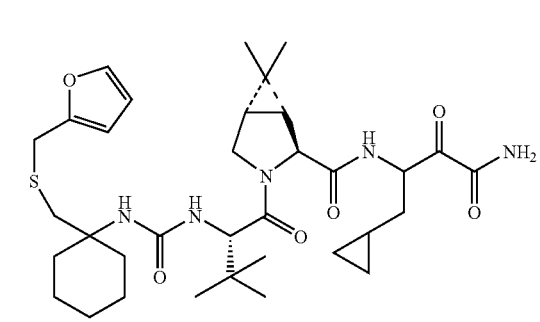

585
-continued
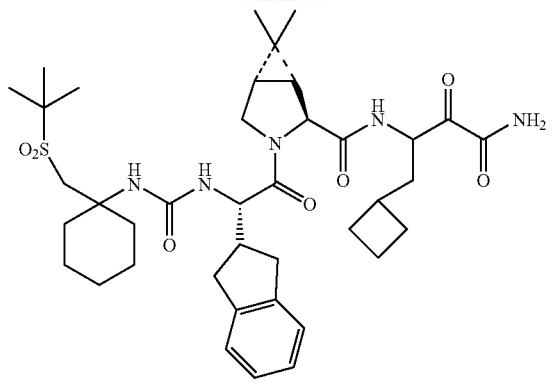
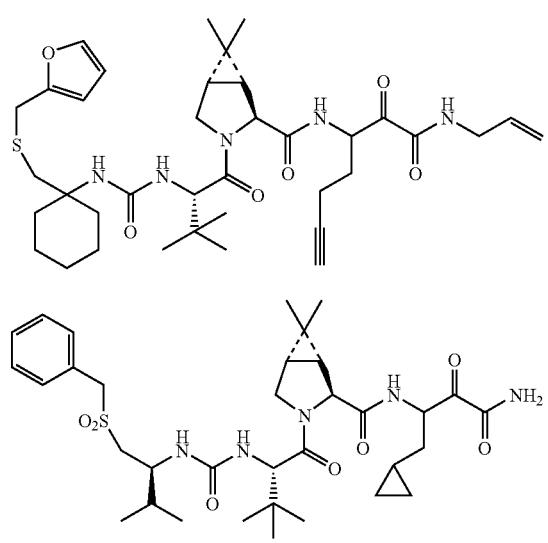
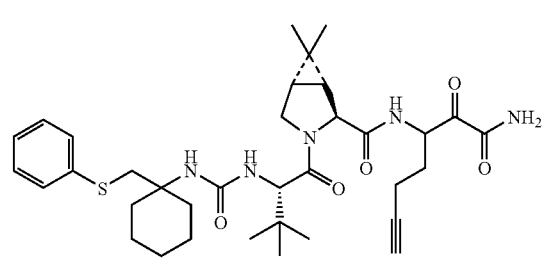
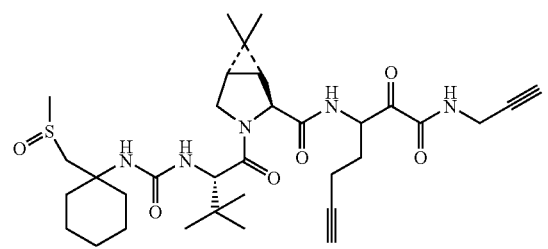
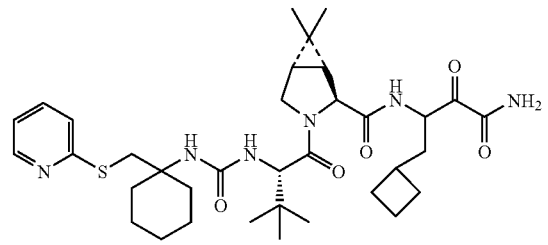
586
-continued
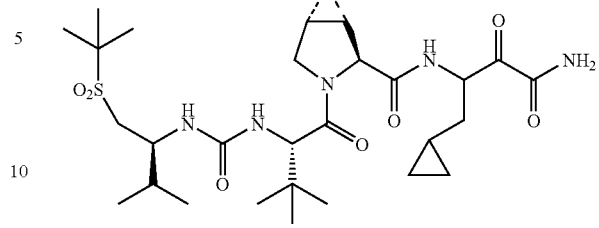
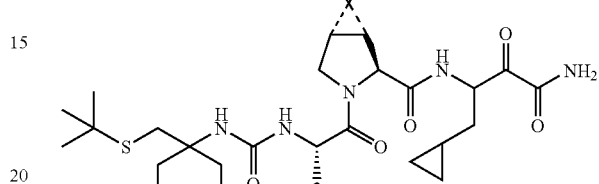
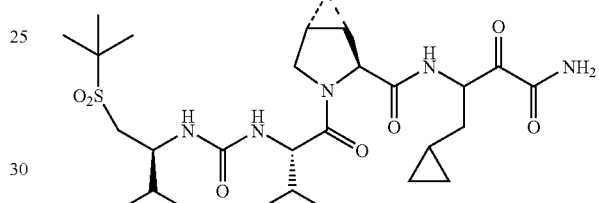
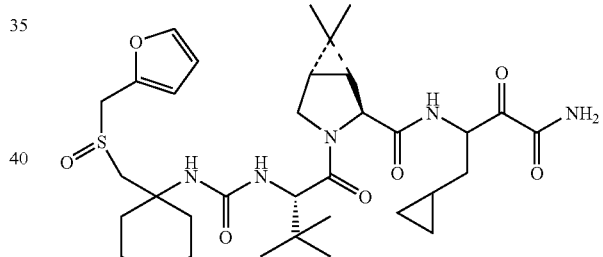
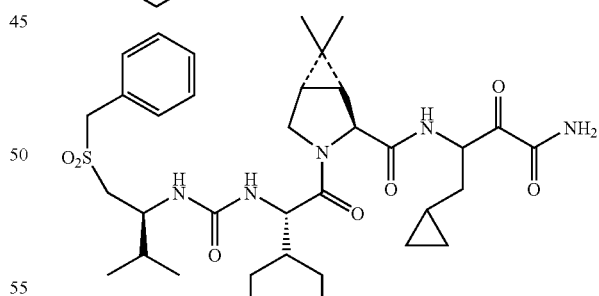
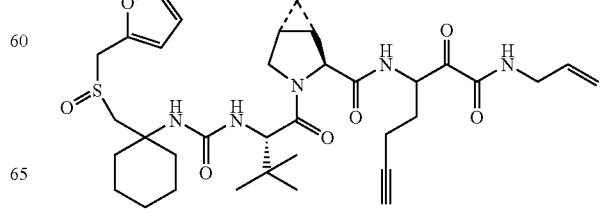

587
-continued
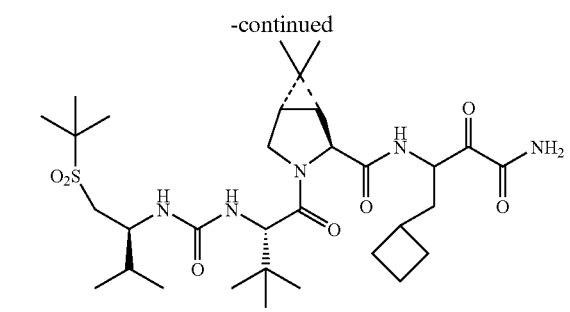
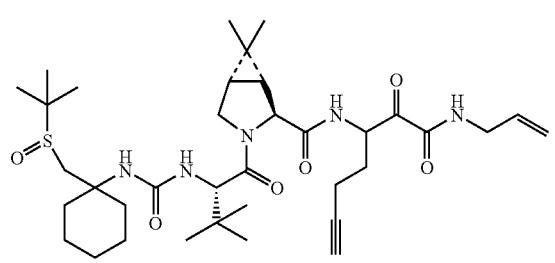
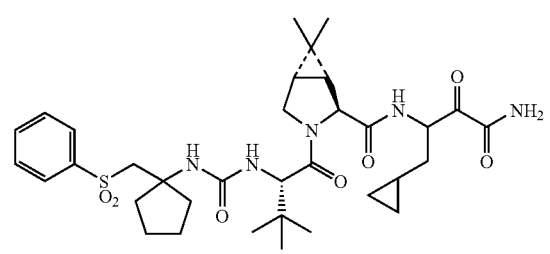
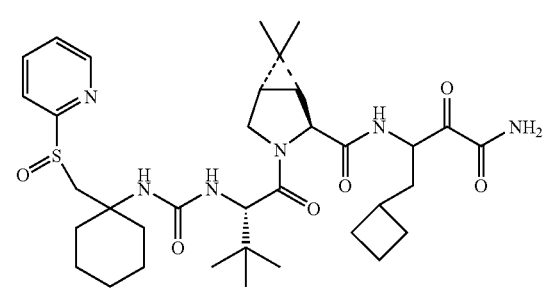
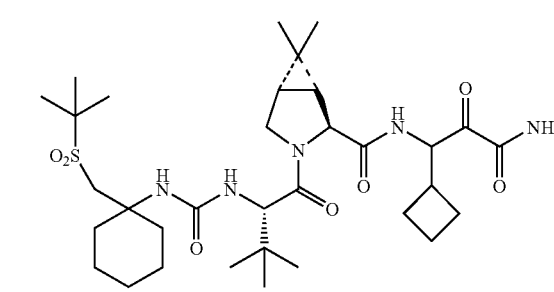
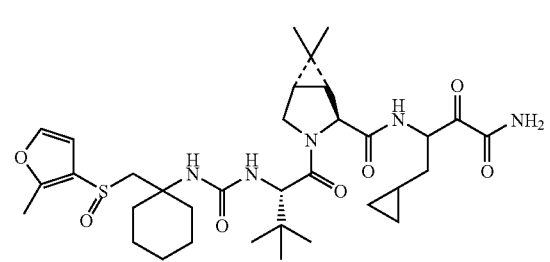
588
-continued
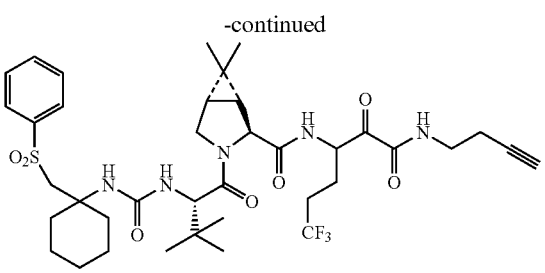
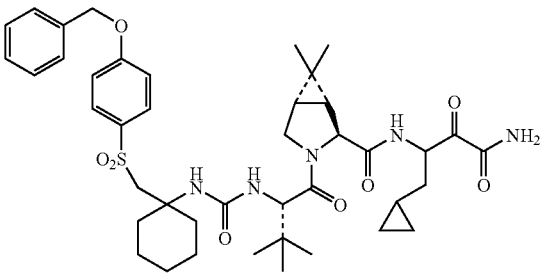
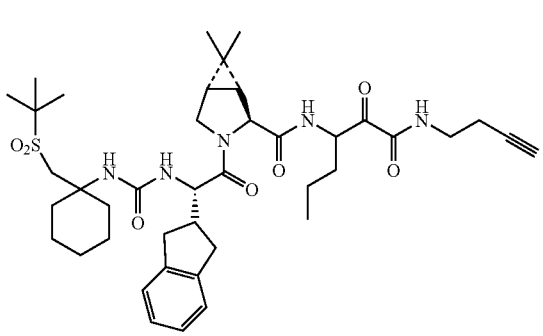
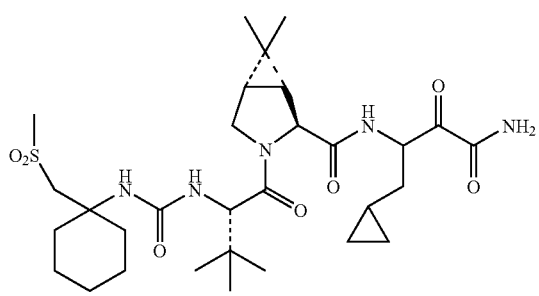
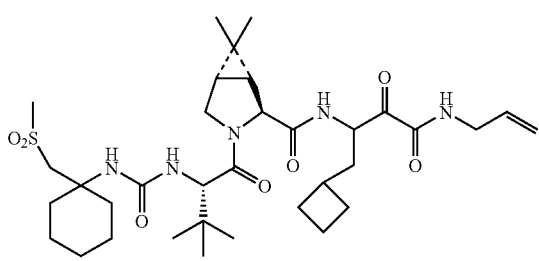
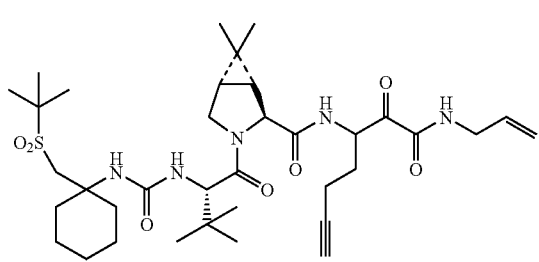

589 -continued
590 -continued
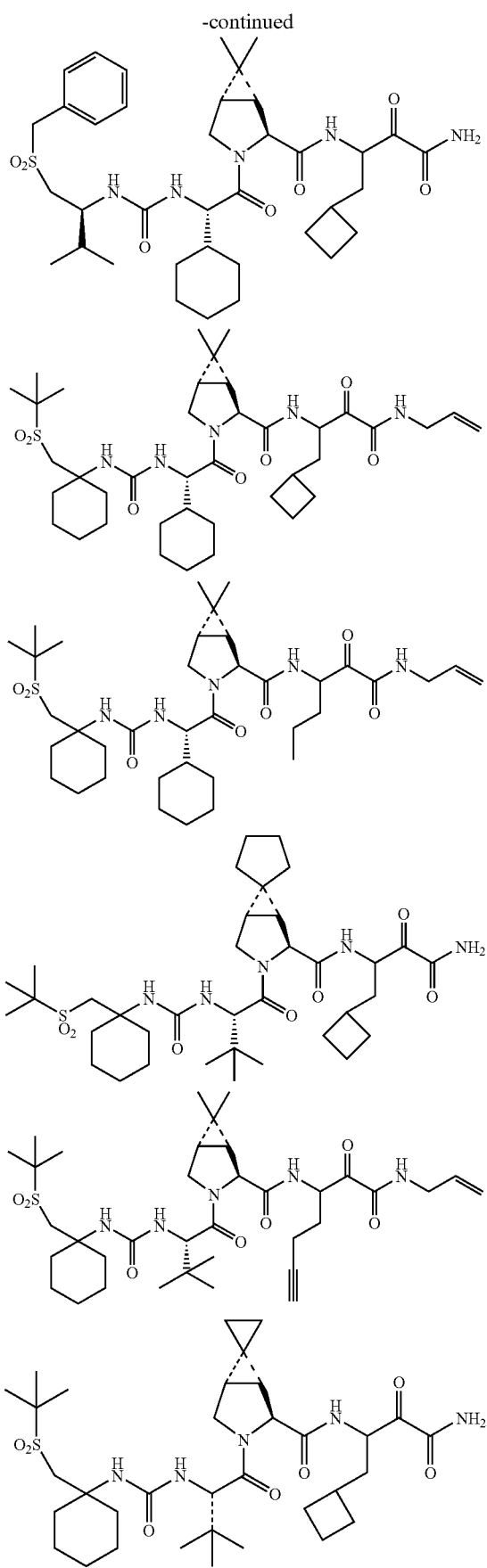
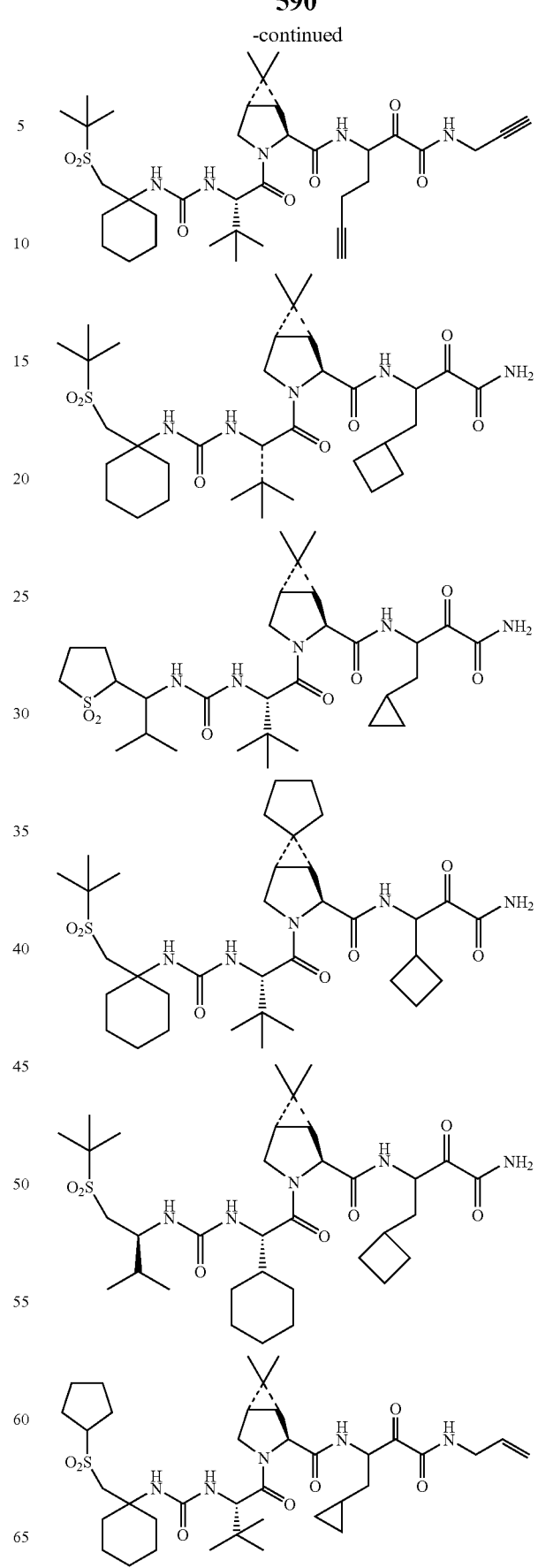

591 -continued
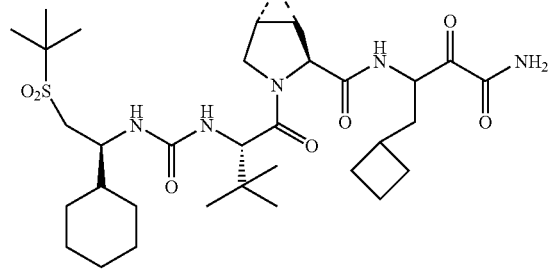
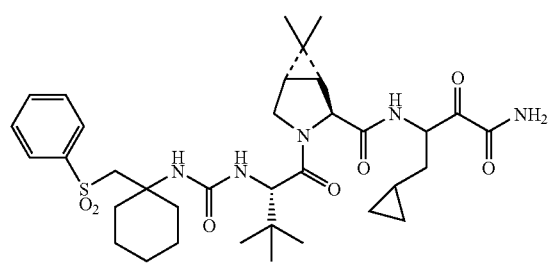
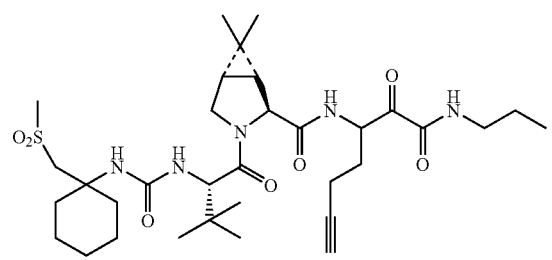
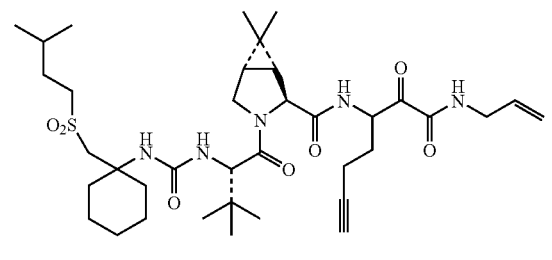
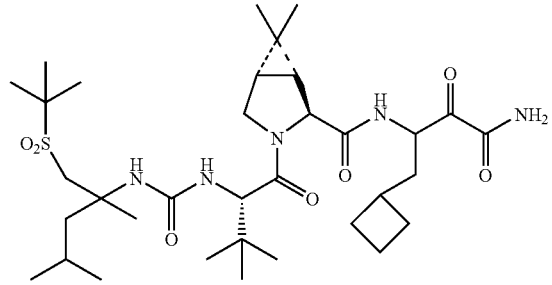
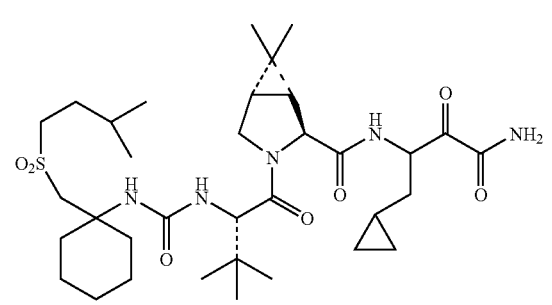
592 -continued
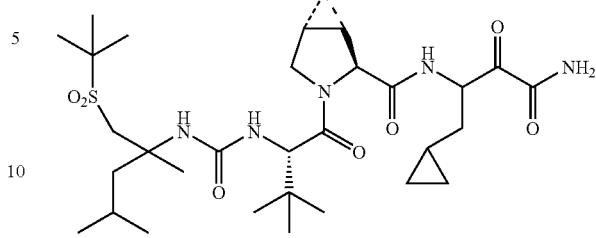
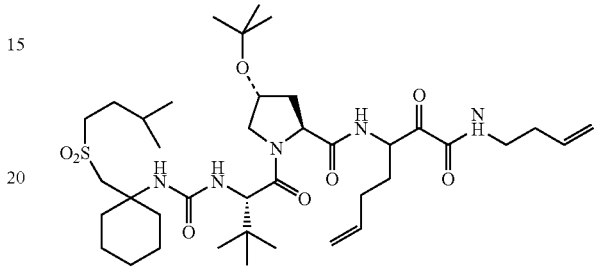
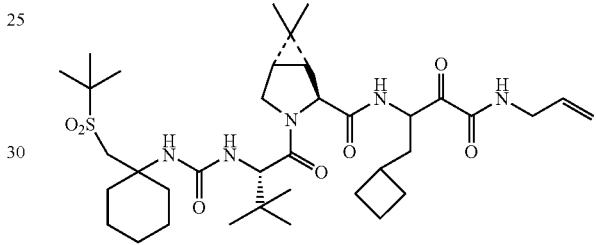

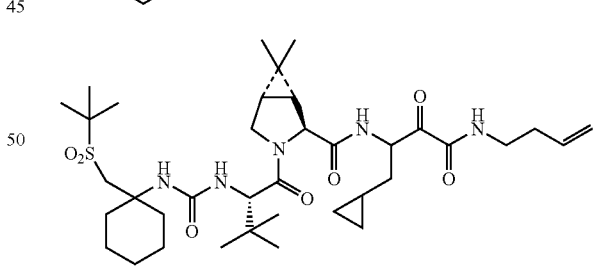
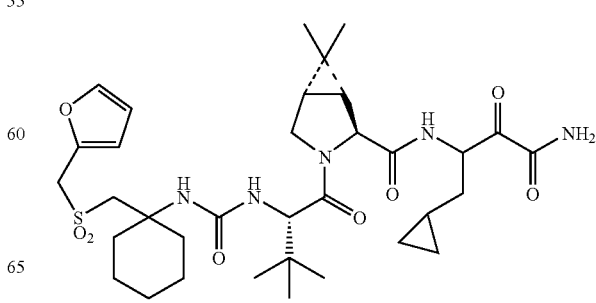

593
-continued
594
-continued
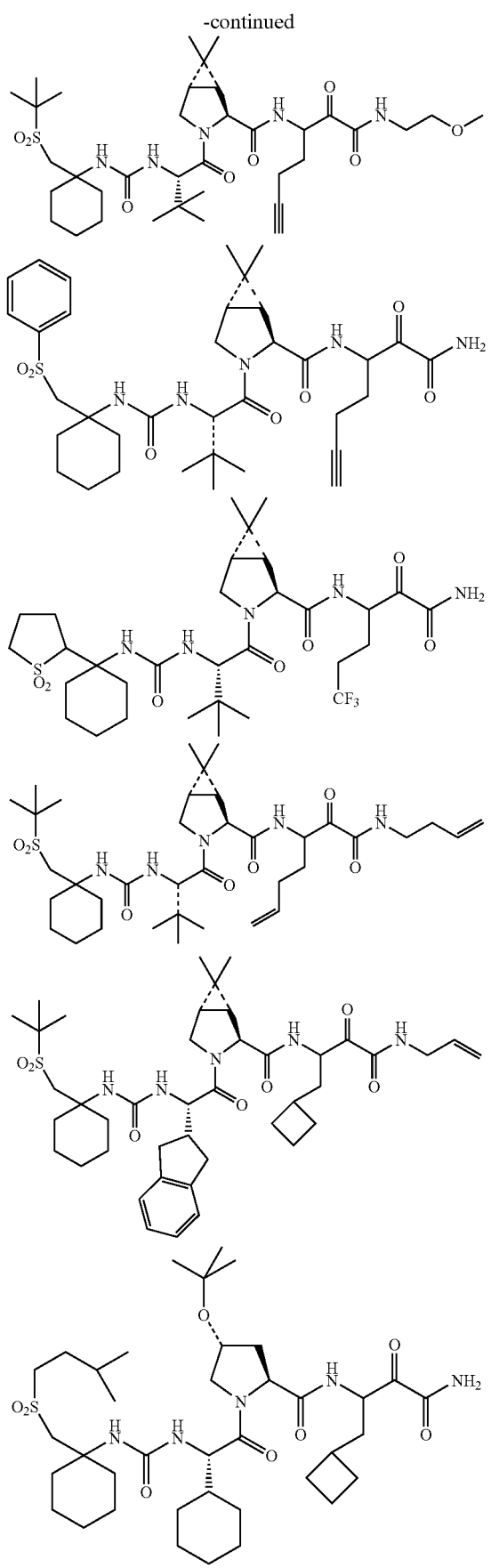
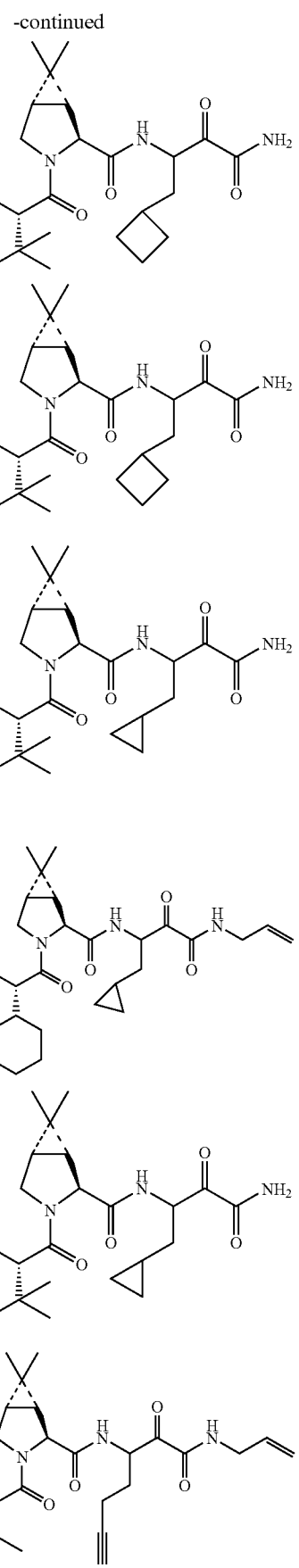

595
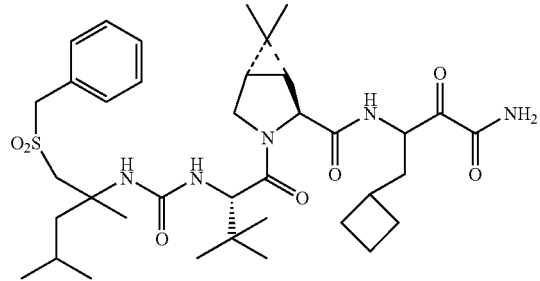
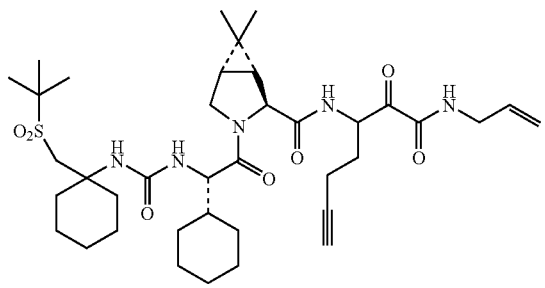
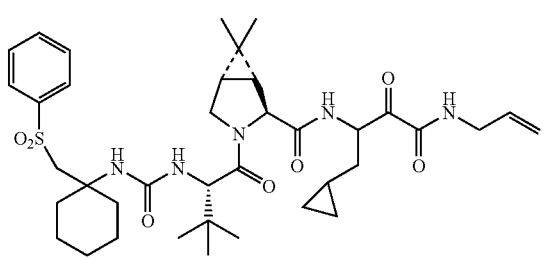
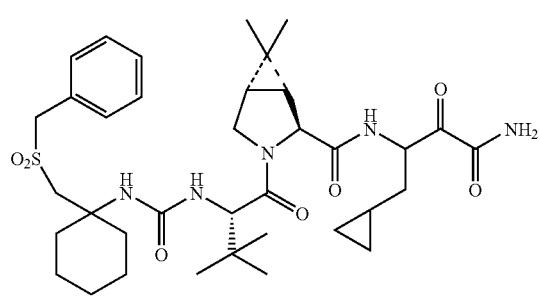
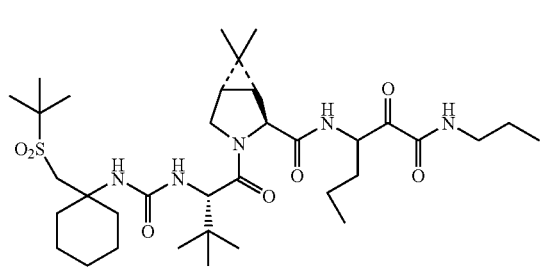
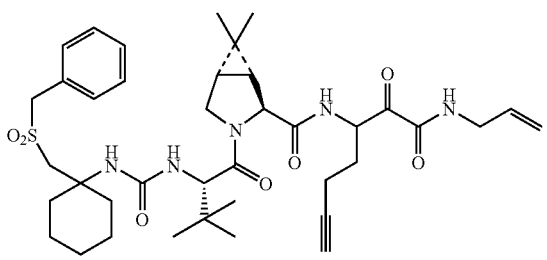
596
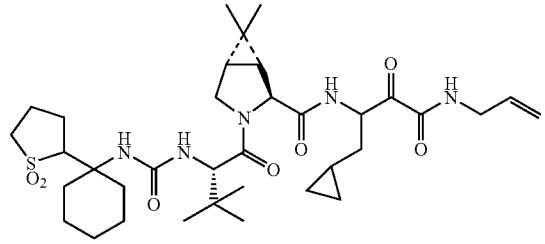
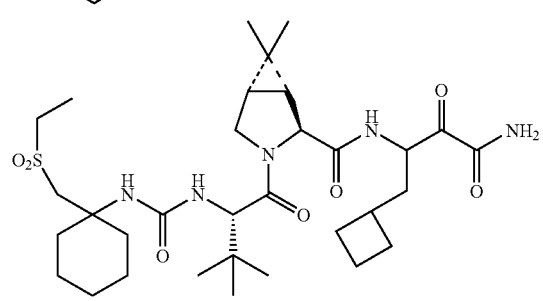
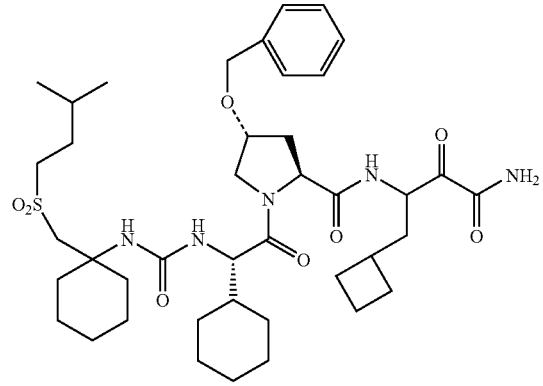
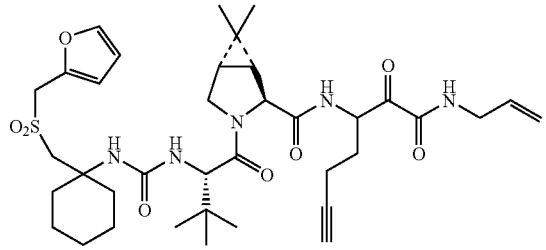
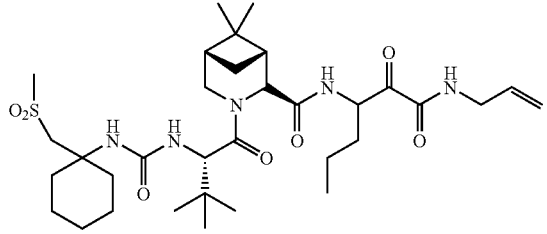
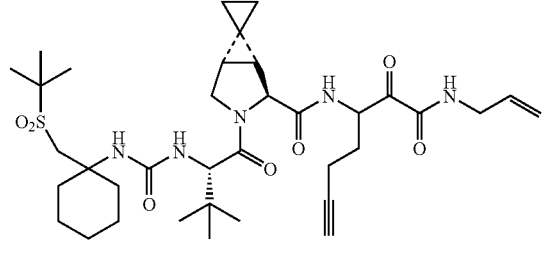

597
-continued
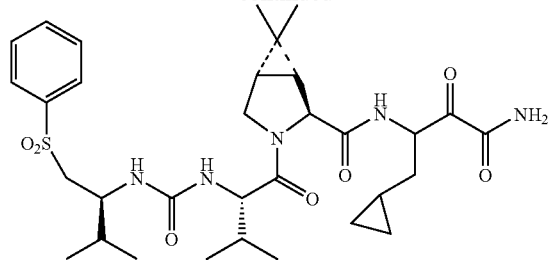
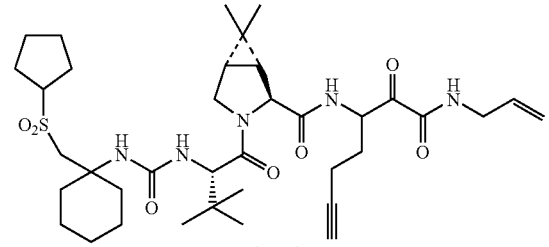
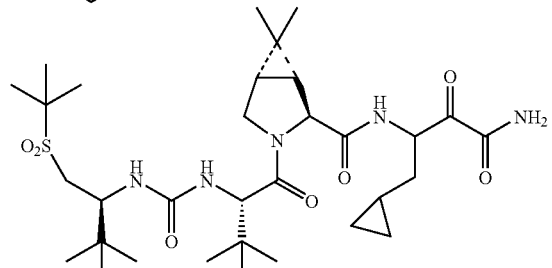
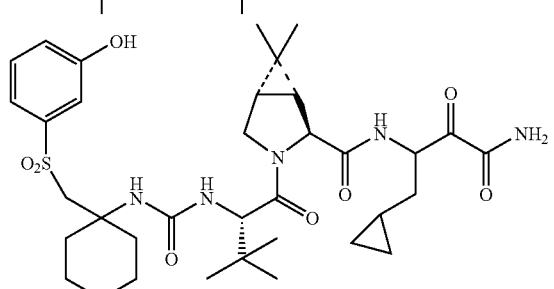
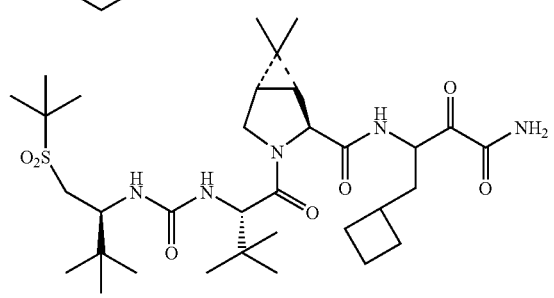
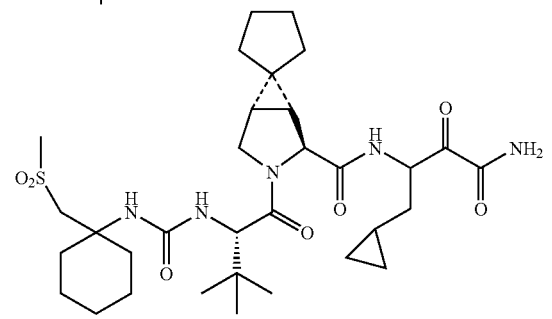
598
-continued
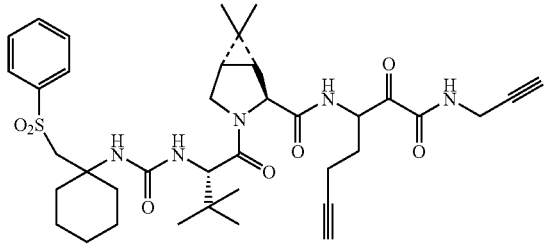
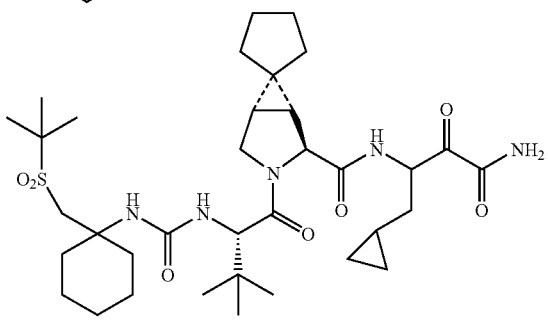
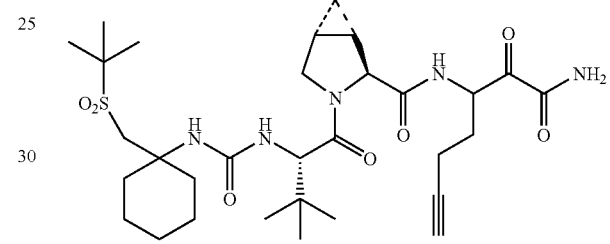
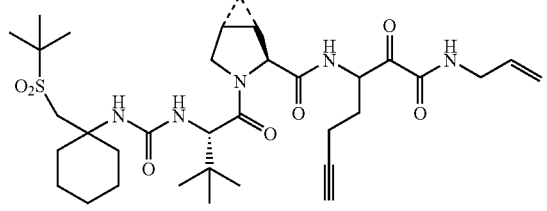
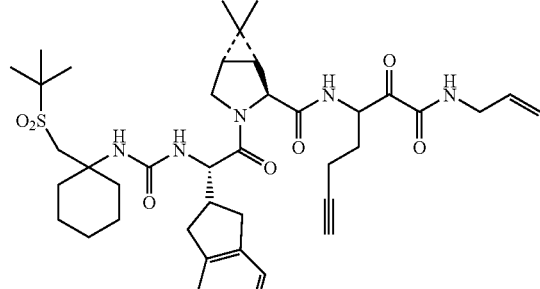
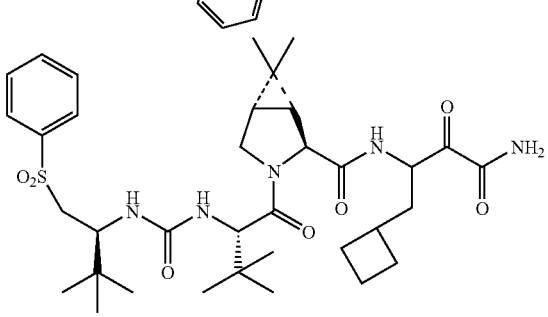

599
-continued
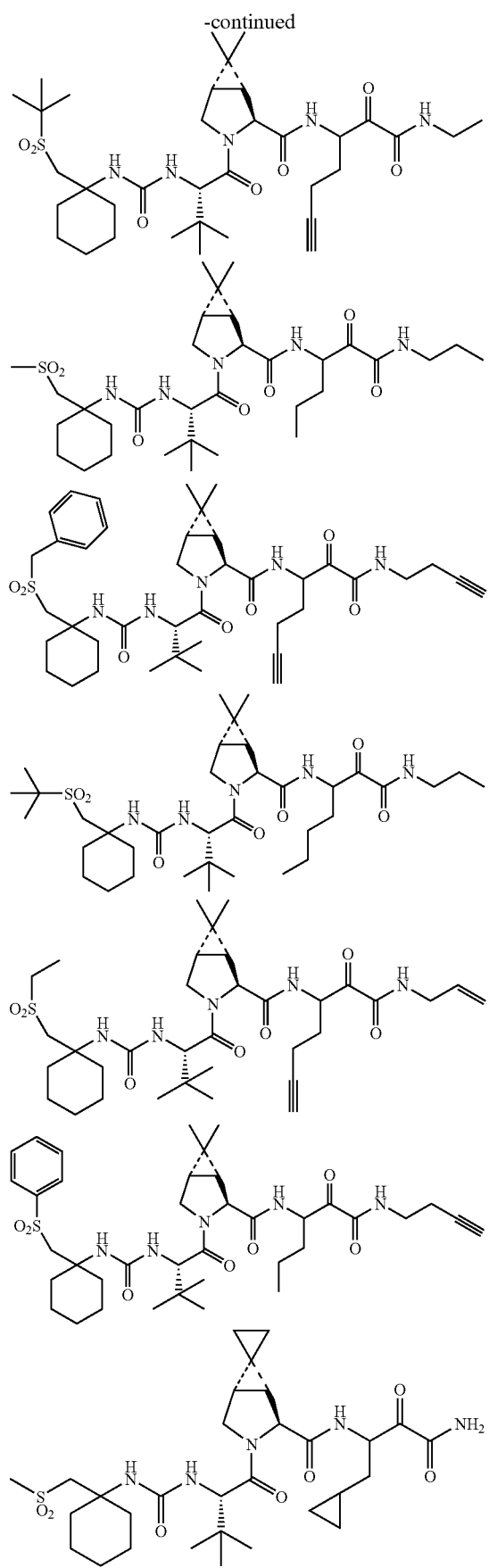
600
-continued
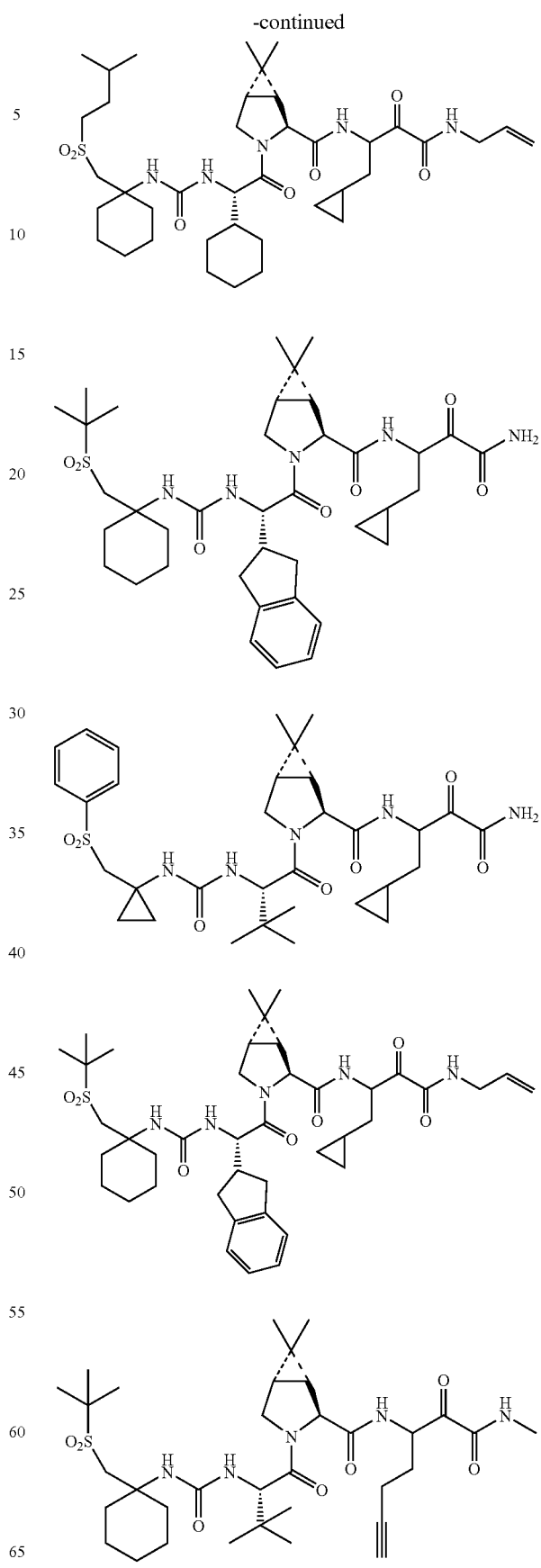

601
-continued
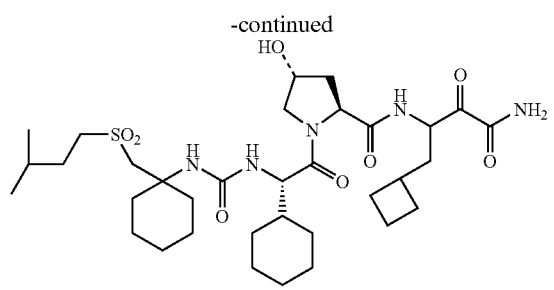
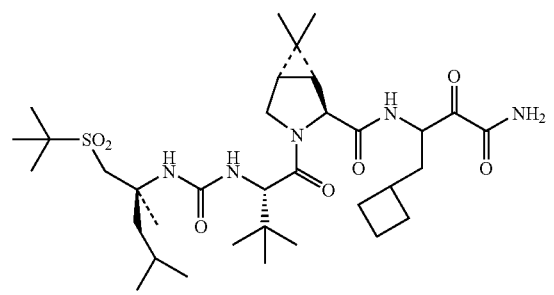
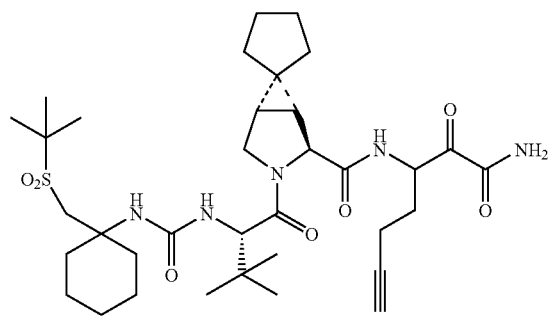
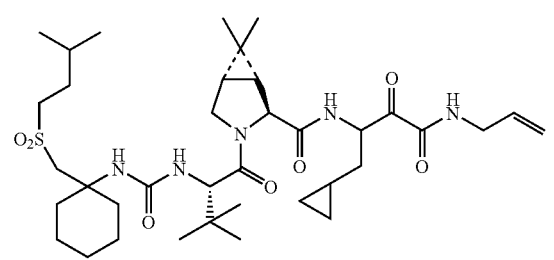
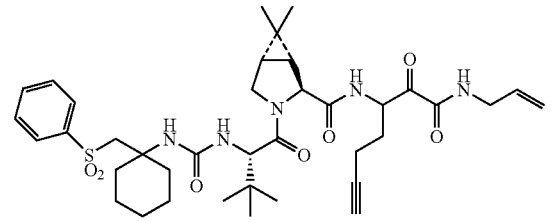
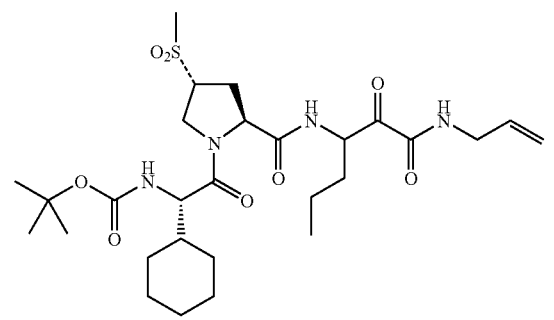
602
-continued
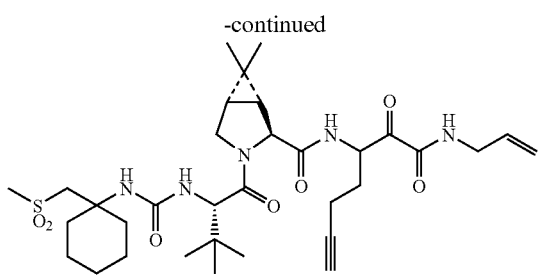
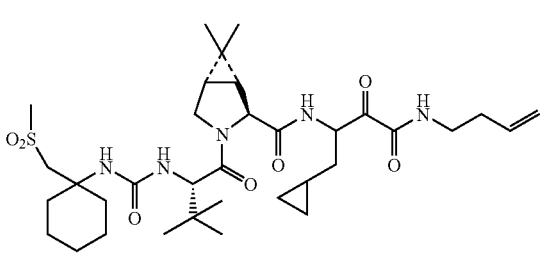
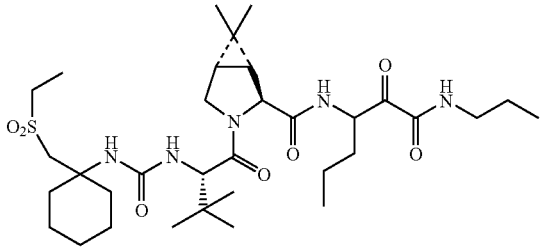
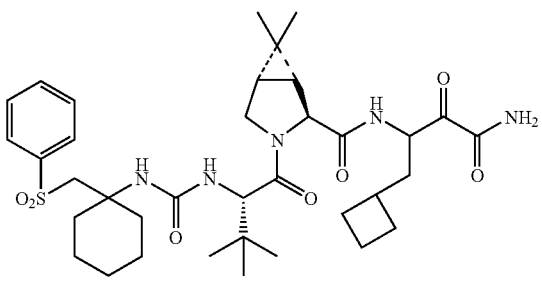
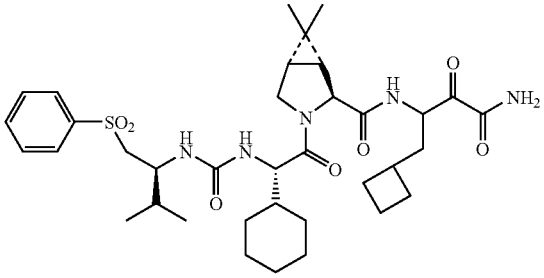
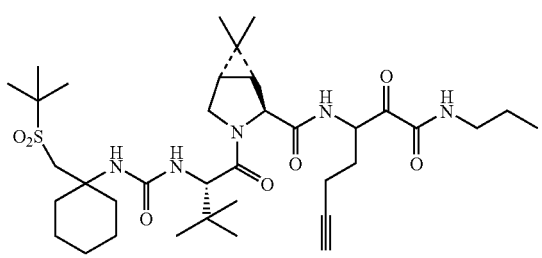

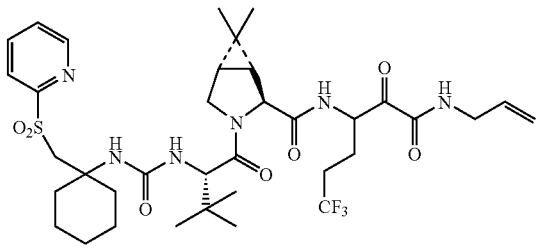
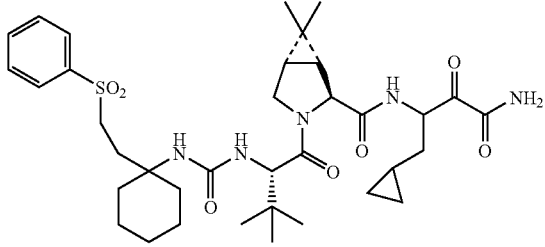
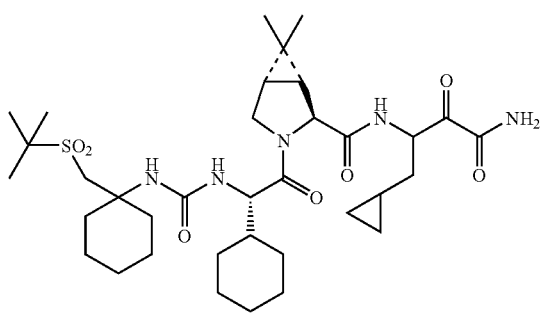
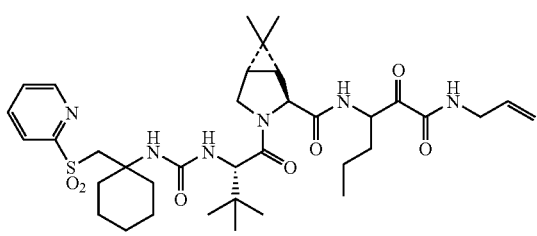
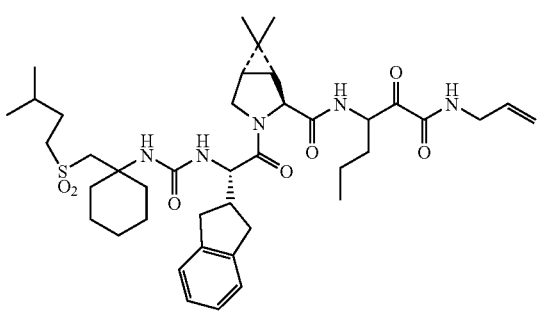
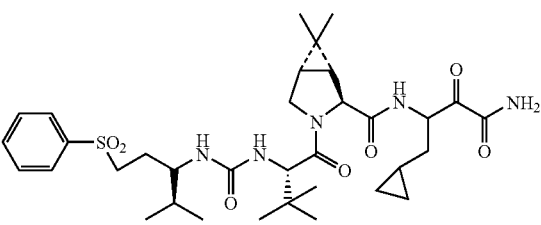
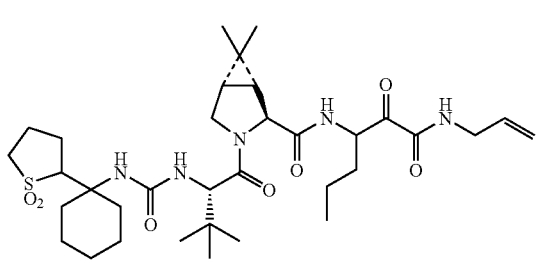

605
-continued
606
-continued
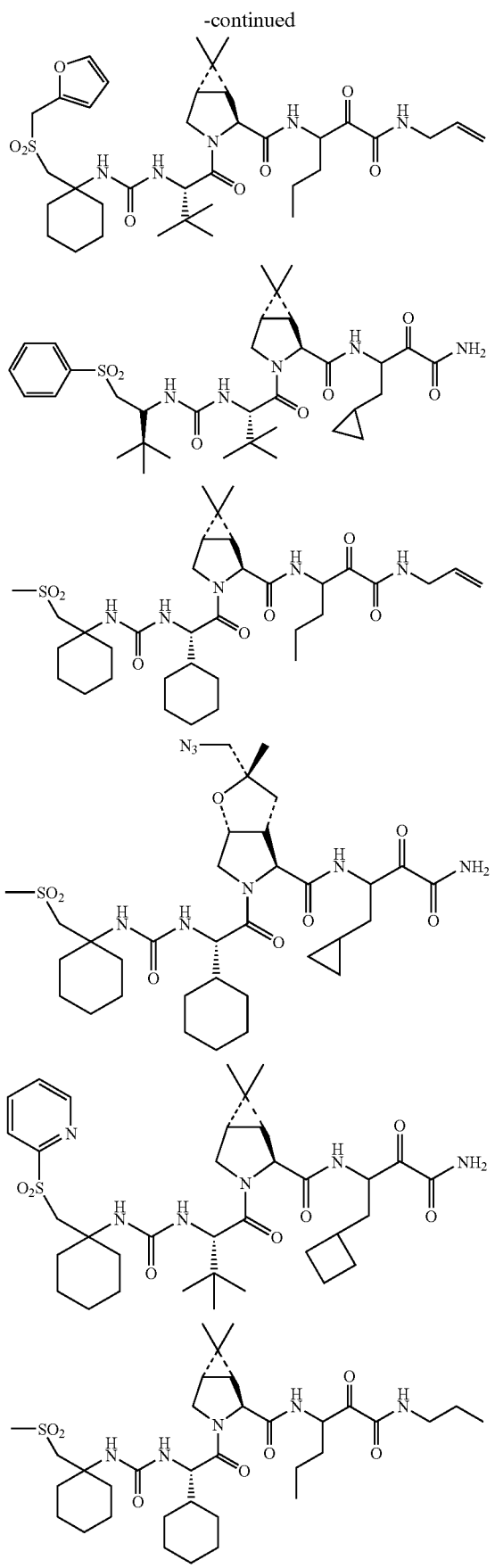
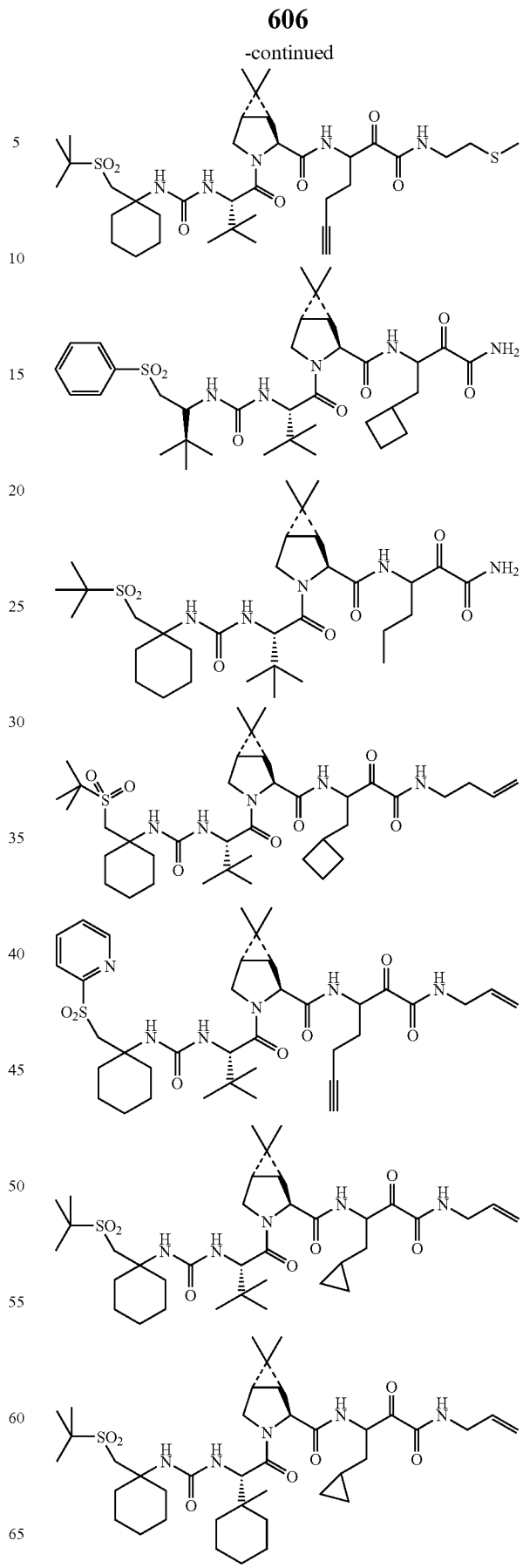

| 607 | 608 |
|---|---|
| -continued | -continued |
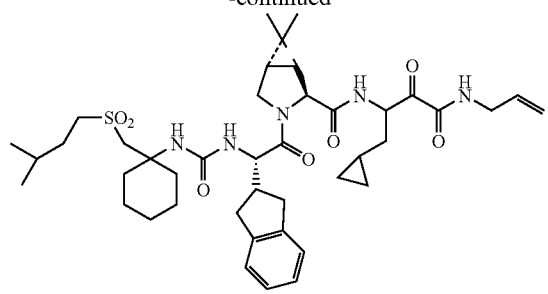
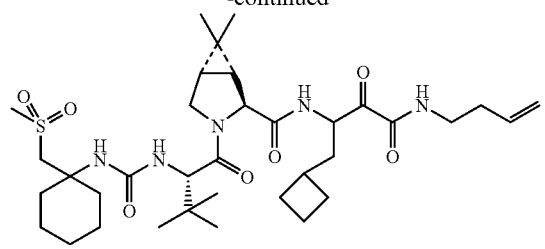
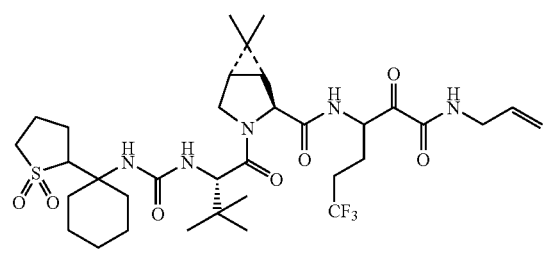
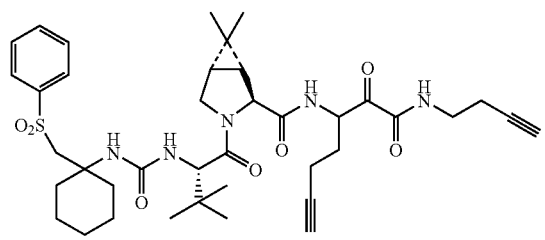
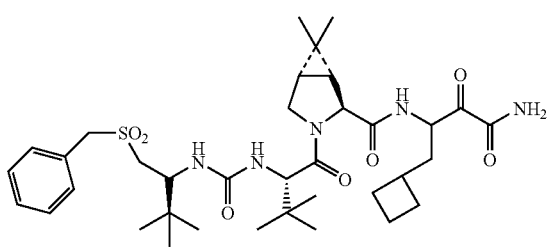
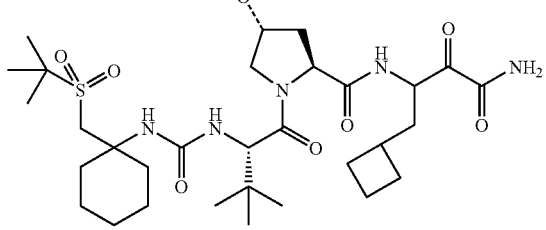
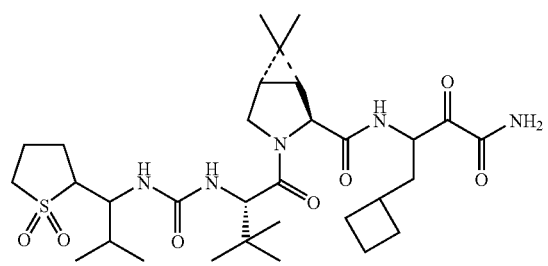
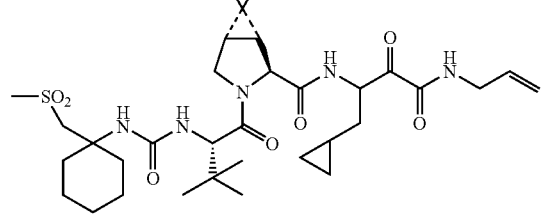
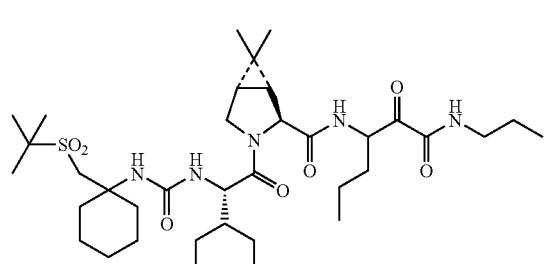
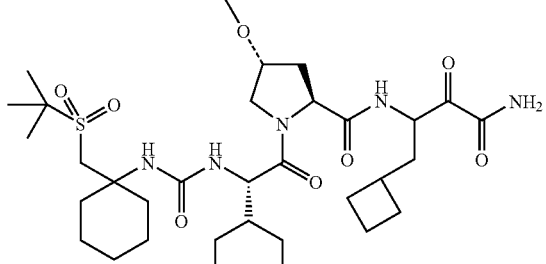
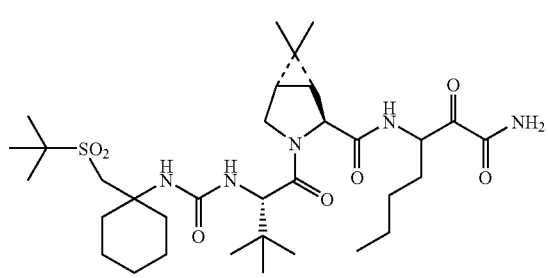
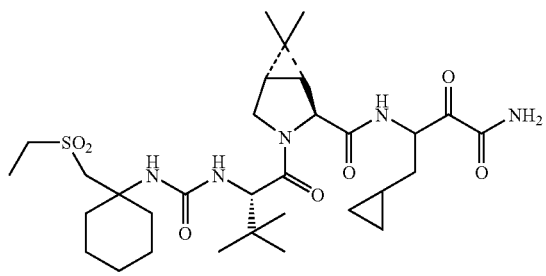

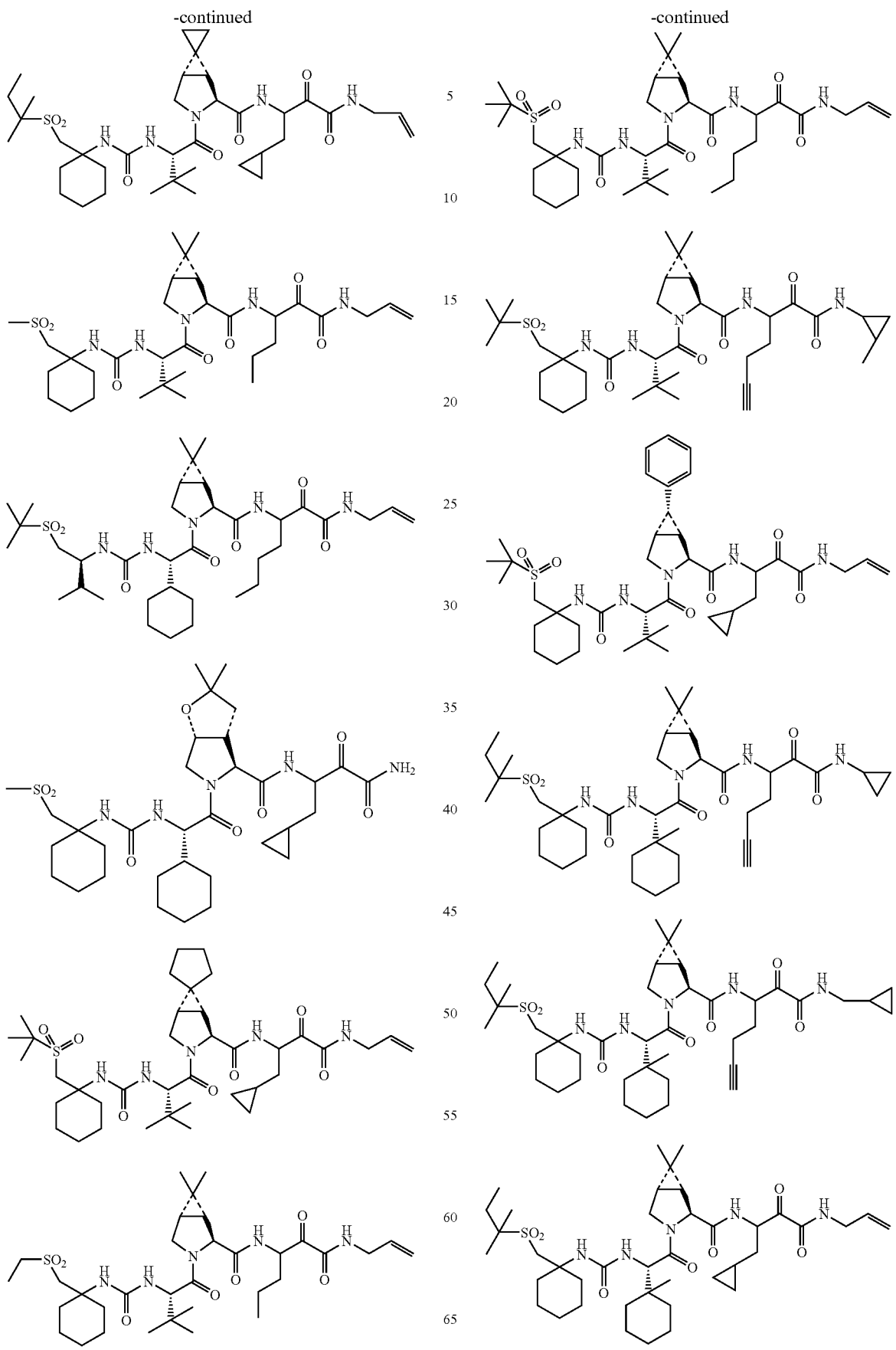

611
-continued
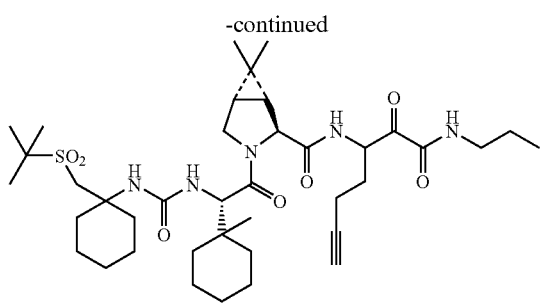
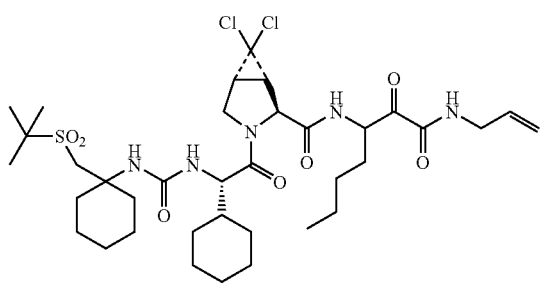
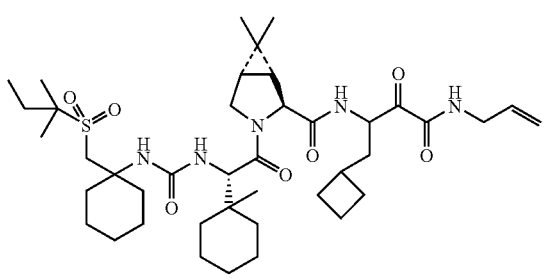
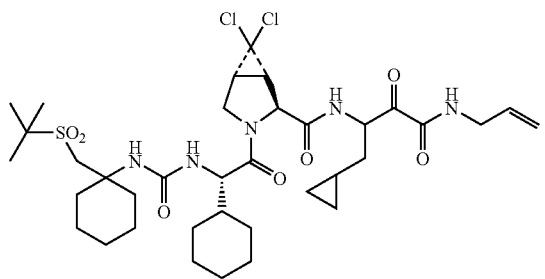
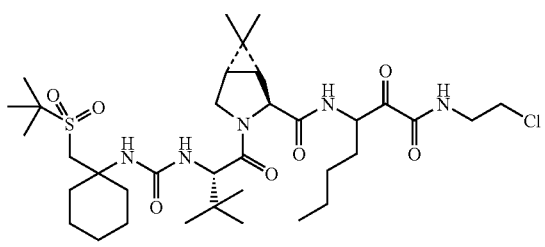
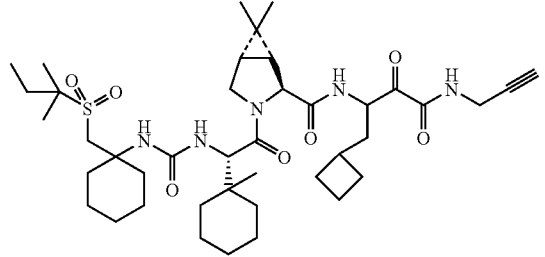
612
-continued
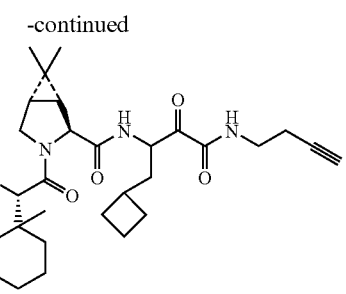
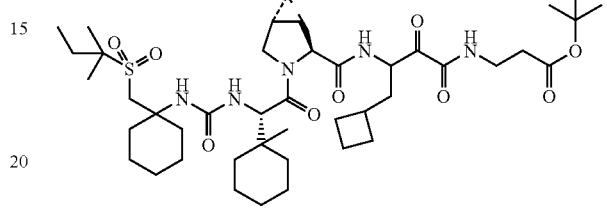
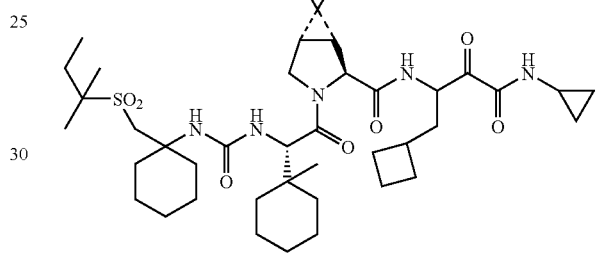
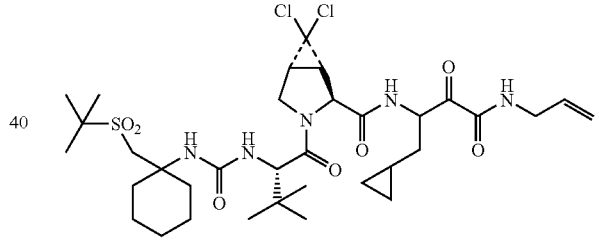
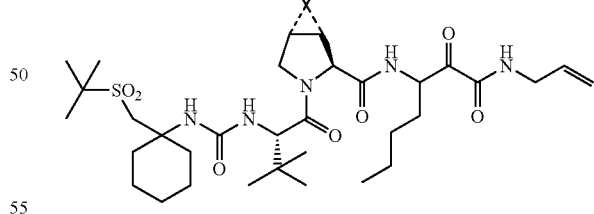
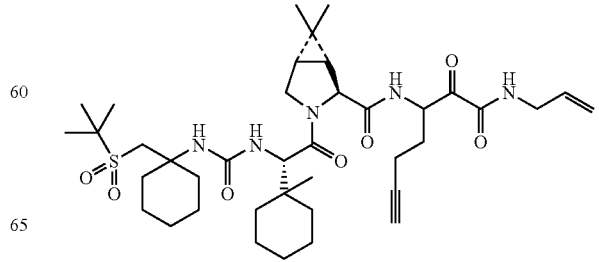

613
-continued
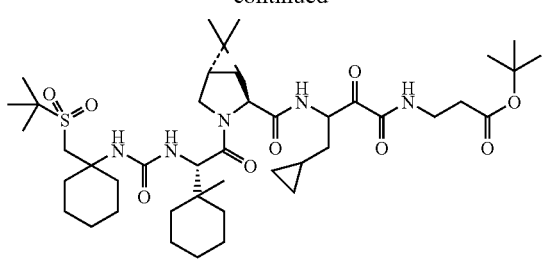
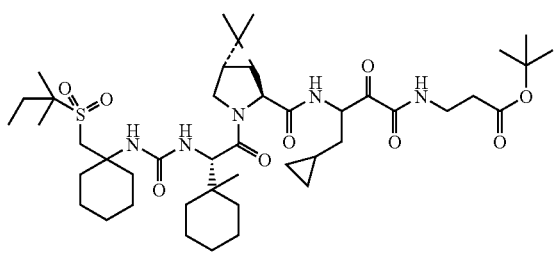
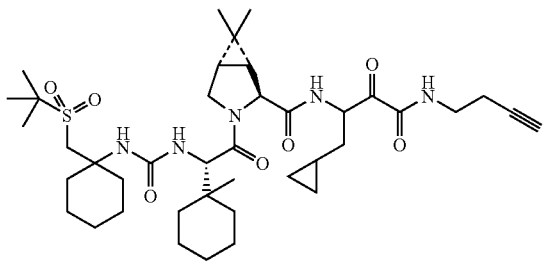
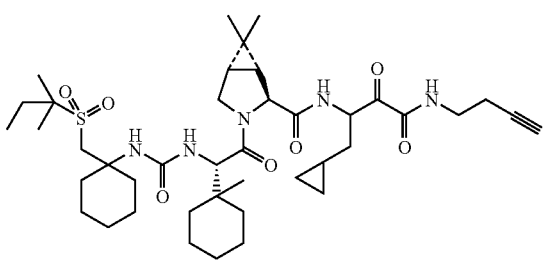
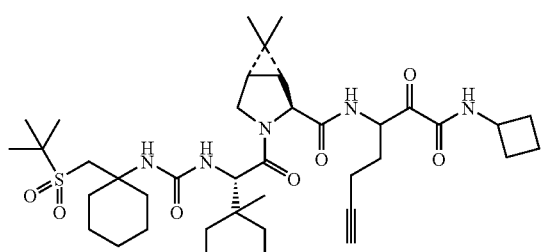
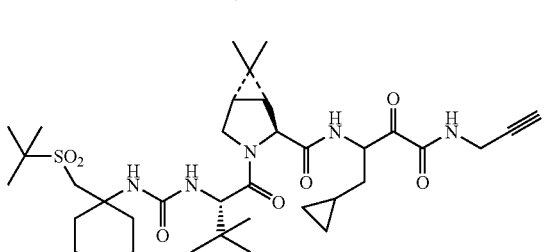
614
-continued
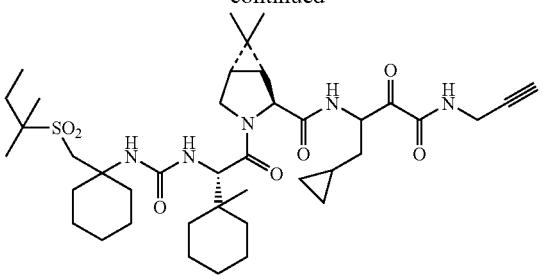
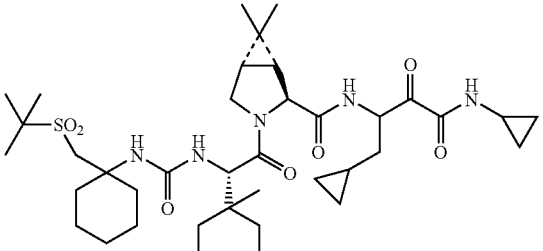
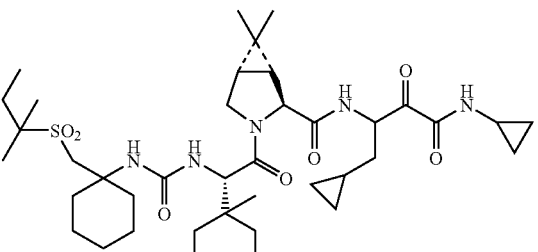
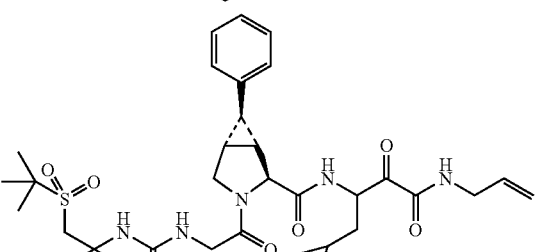
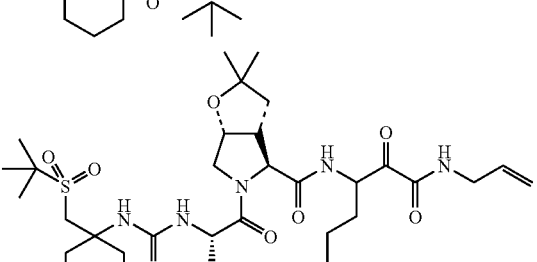
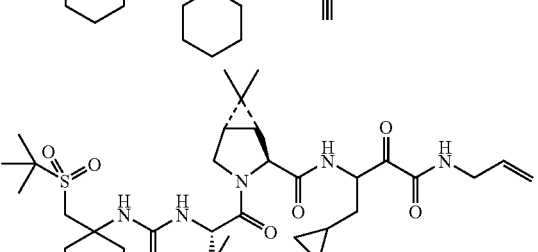

615
-continued
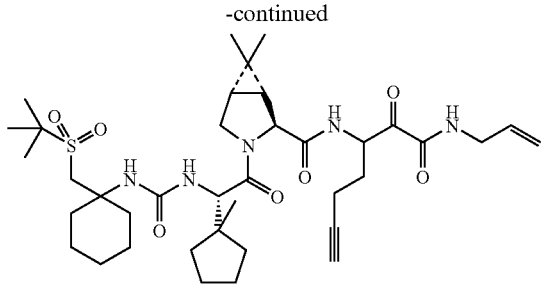
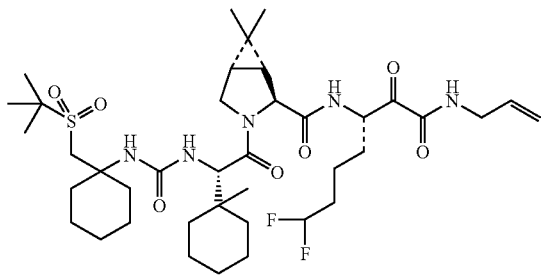
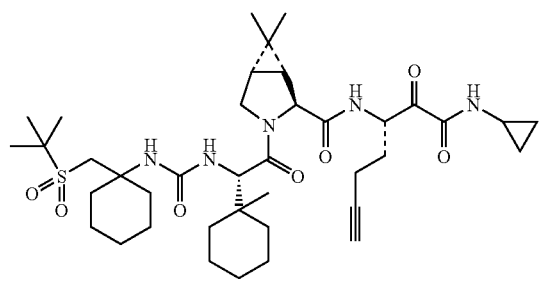
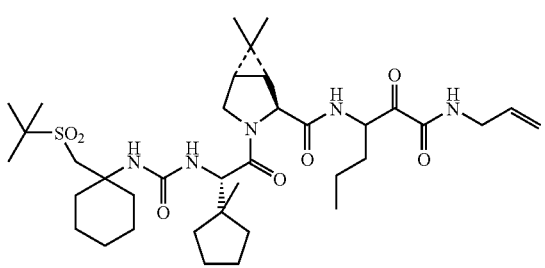
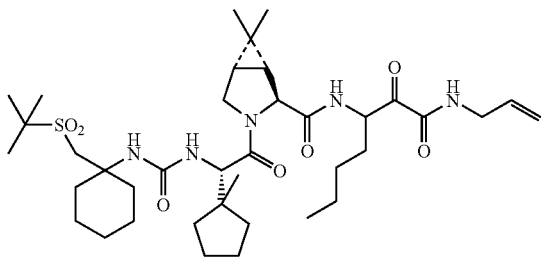
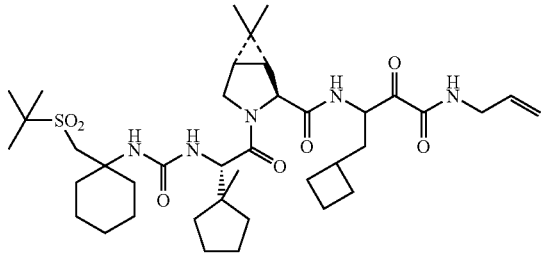
616
-continued
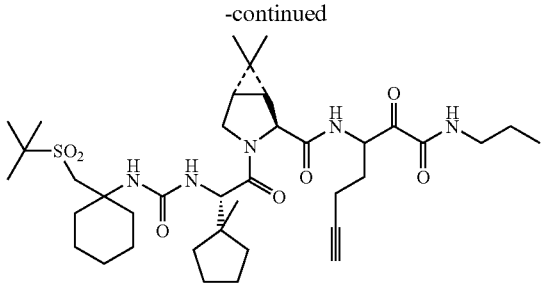
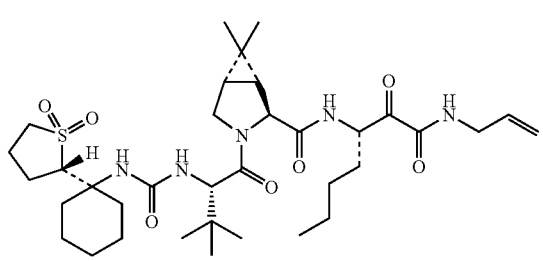
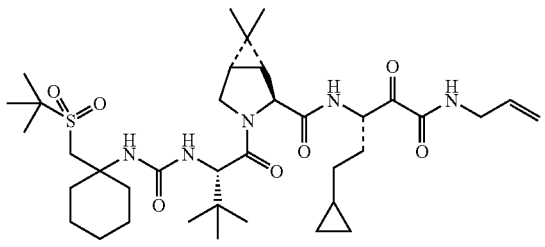
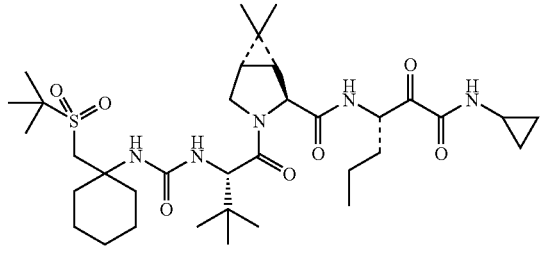
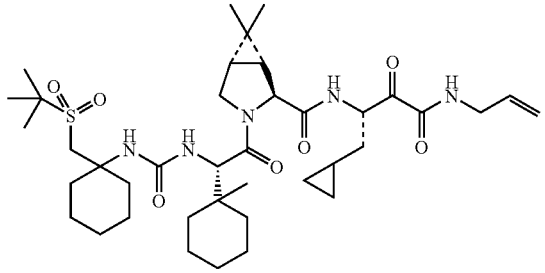
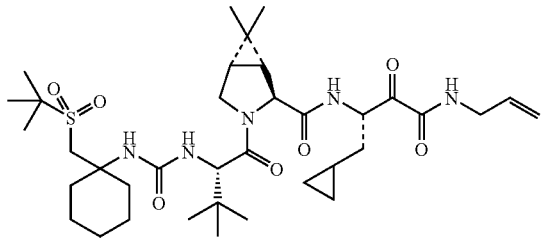

617
-continued
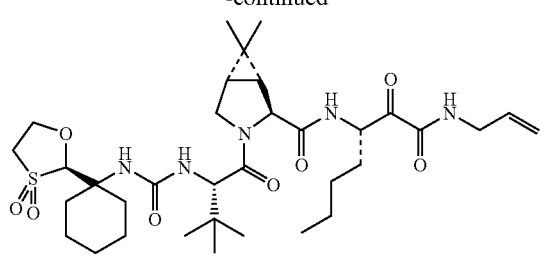
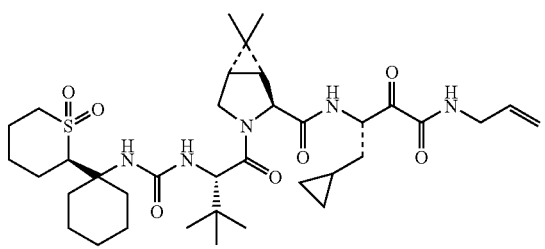
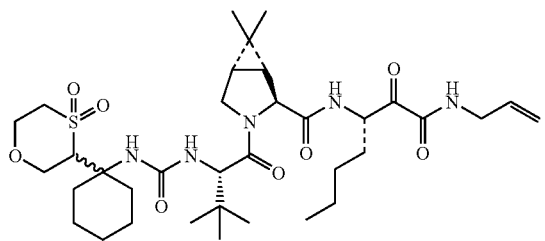
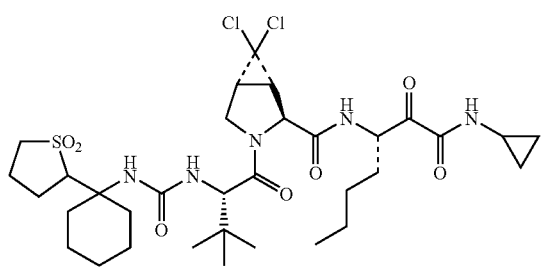
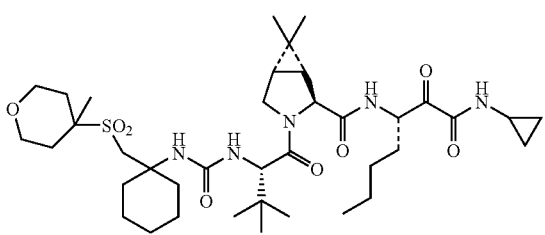
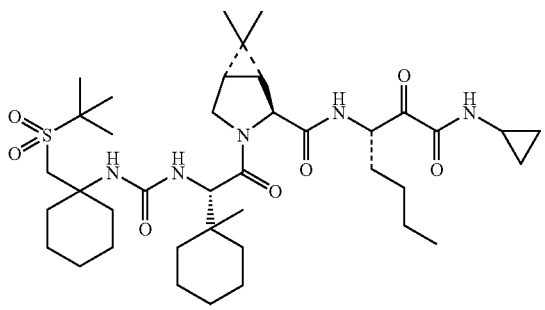
618
-continued
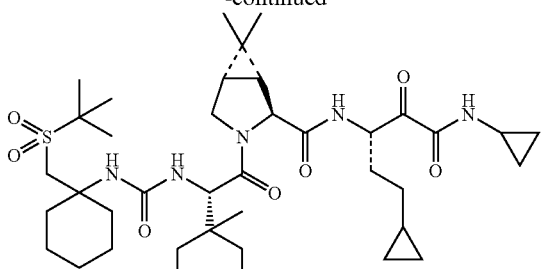
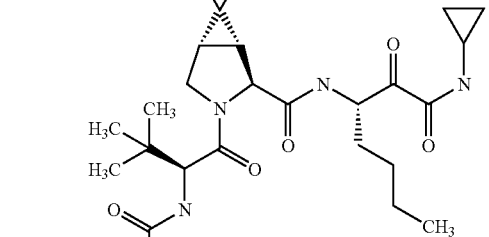
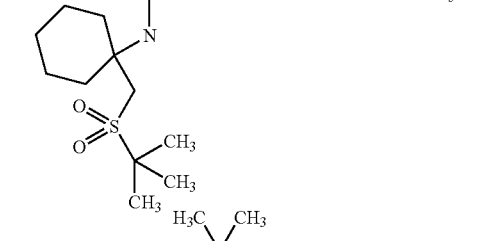
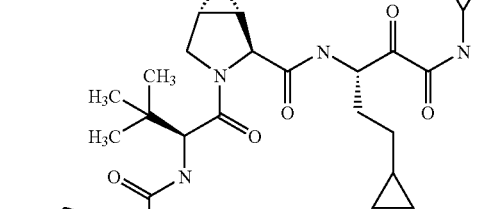
and
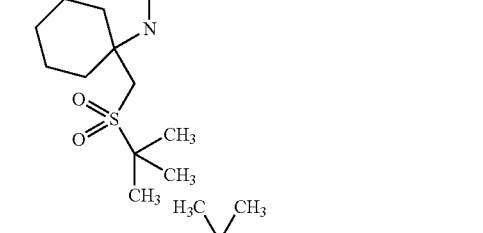
; or a
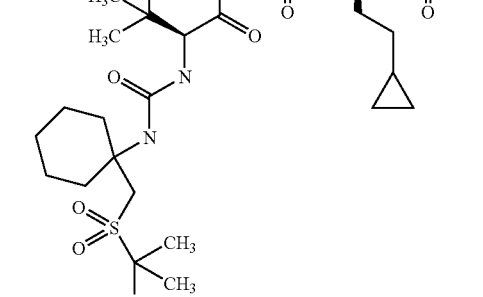
pharmaceutically acceptable salt, solvate or ester thereof.

Compounds of formula XV are disclosed in U.S. patent application Ser. No. 11/007,910 filed Dec. 9, 2004. The preparation of these compounds is disclosed in the experimental section of this application set forth hereinbelow.
Non-limiting examples of certain compounds disclosed in U.S. patent application Ser. No. 11/007,910 are:
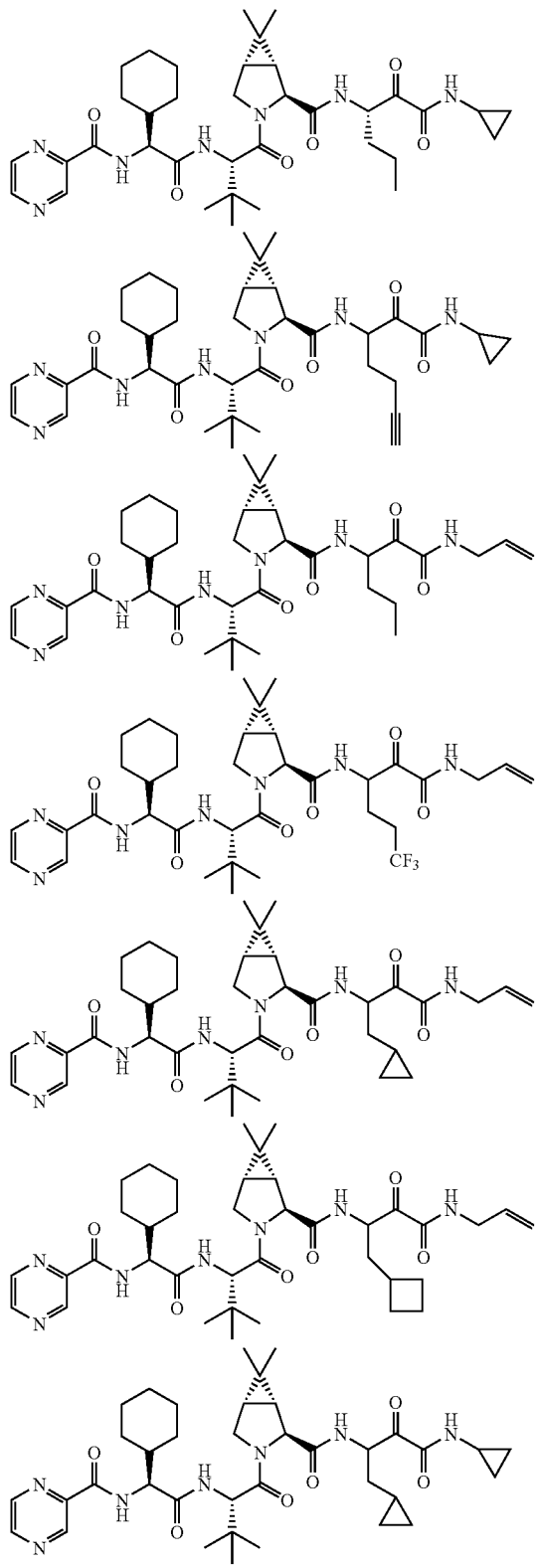
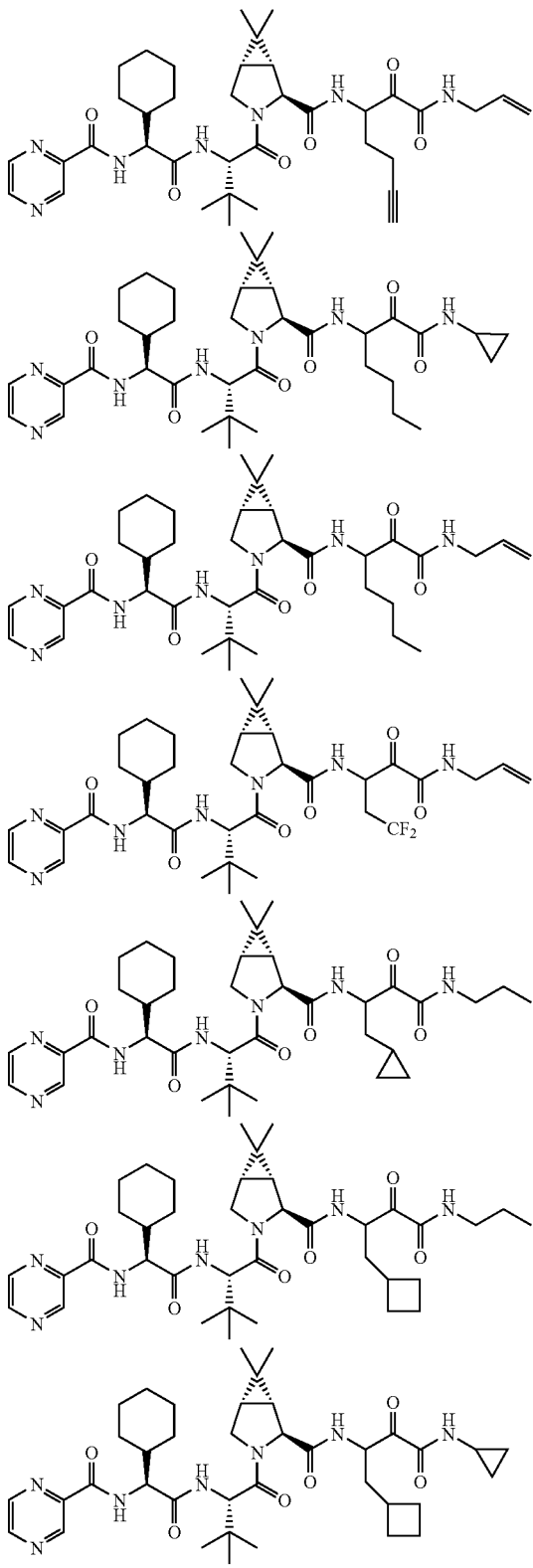

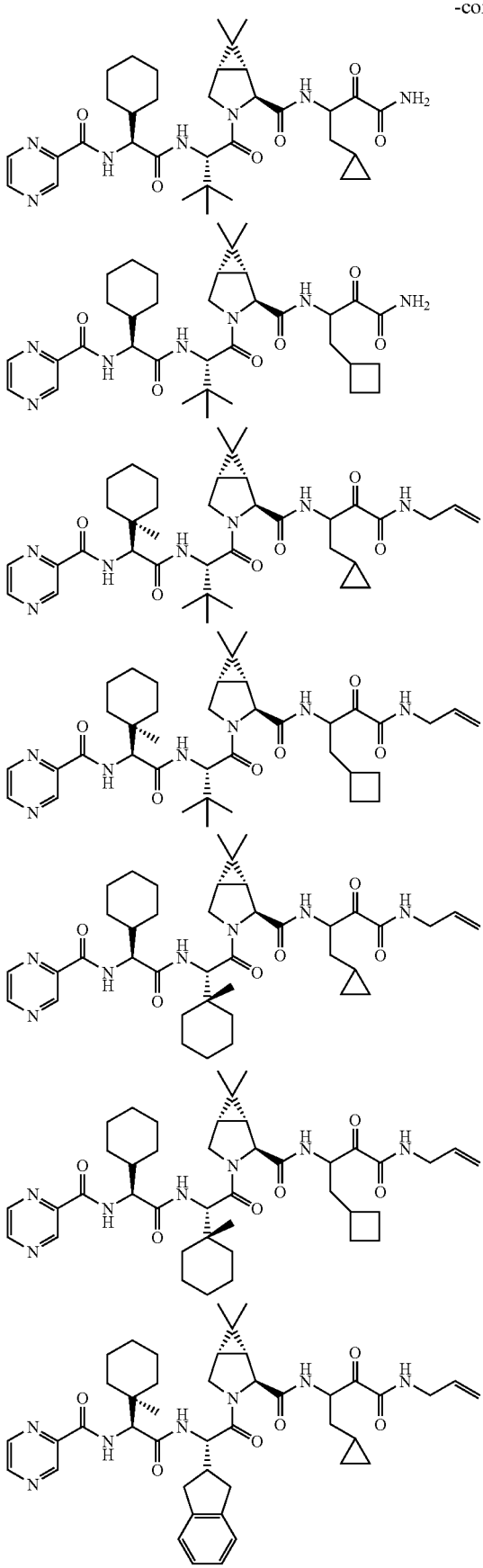

-continued
| 623 | 624 |
|---|---|
| 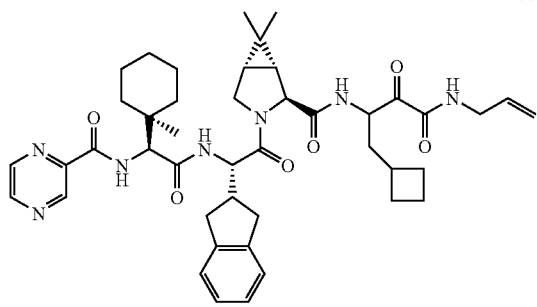 | 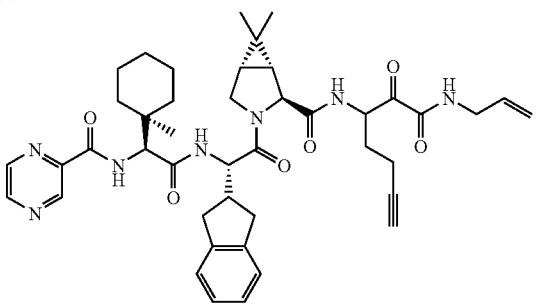 |
| 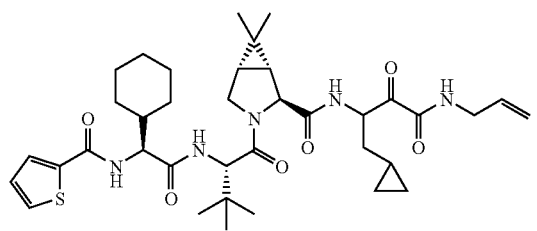 | 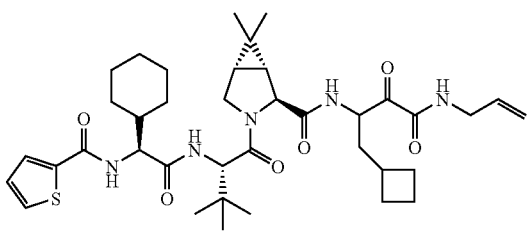 |
| 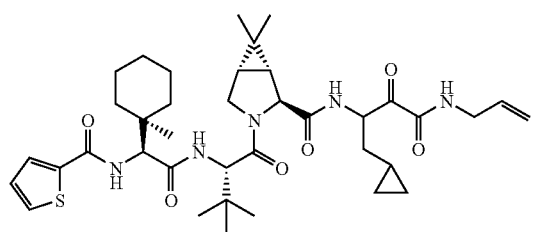 | 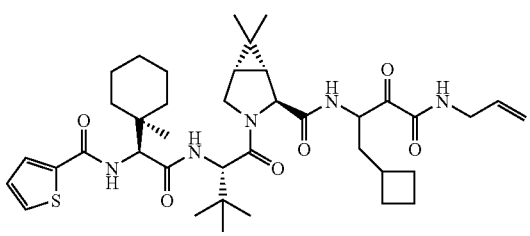 |
| 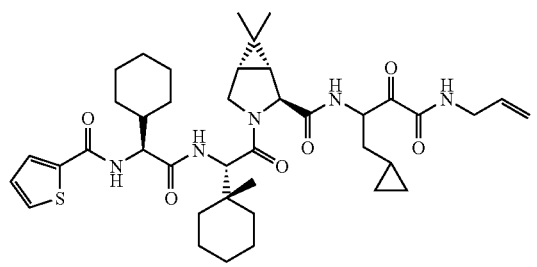 | 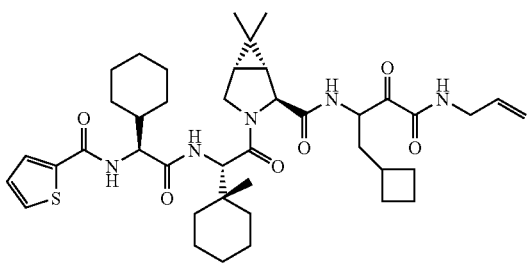 |
| 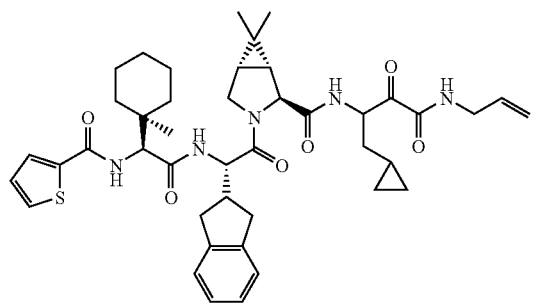 | 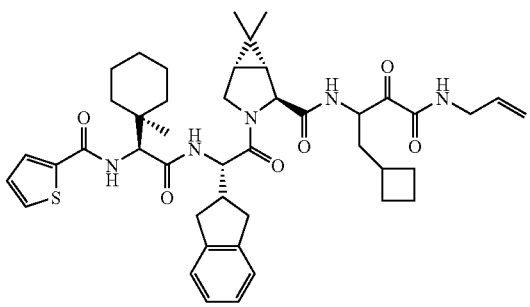 |
| 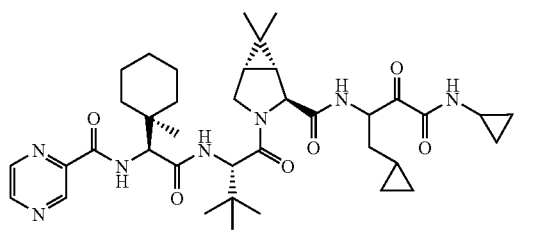 | 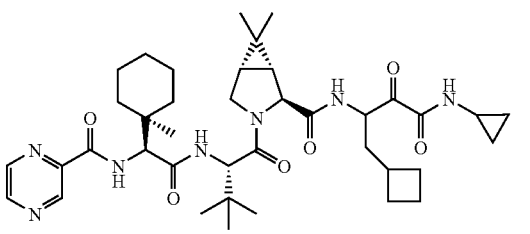 |

625 626
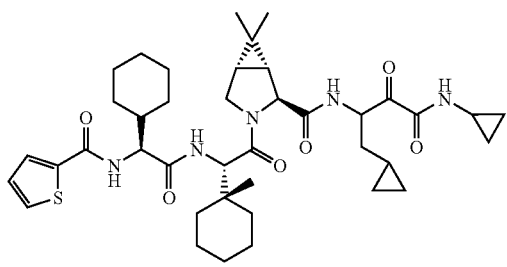 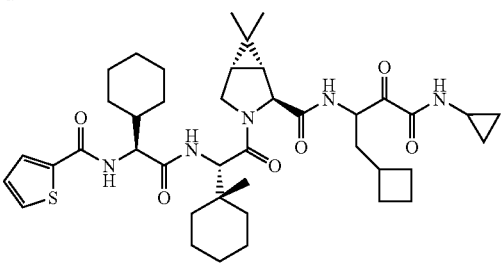
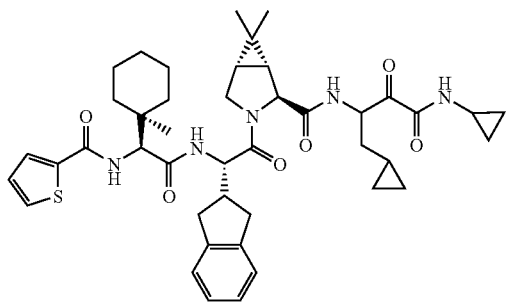 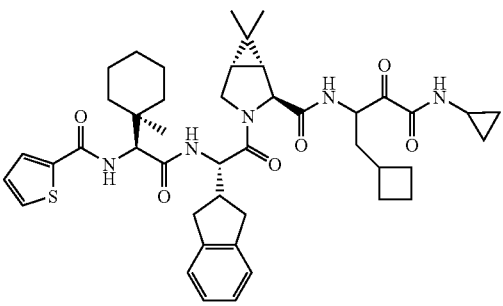
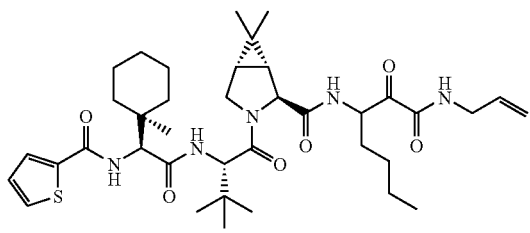 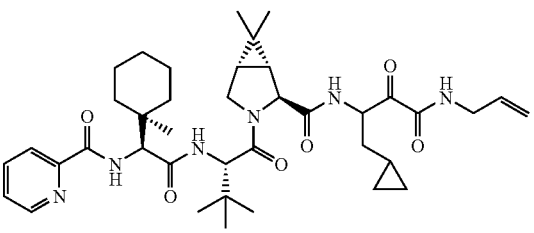
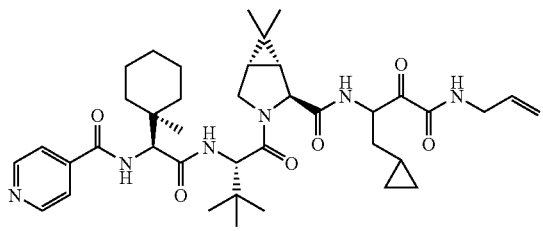 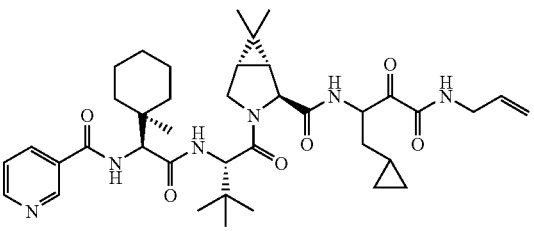
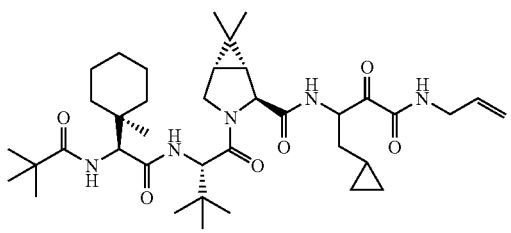 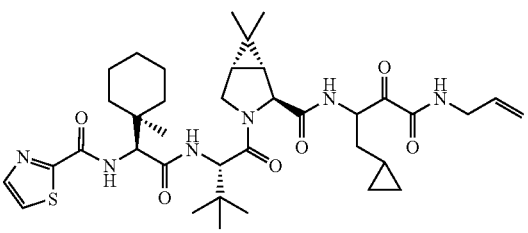
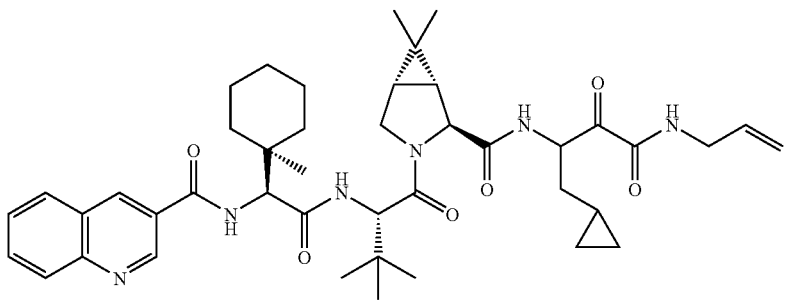

-continued
627
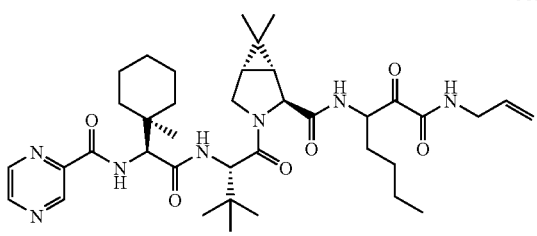
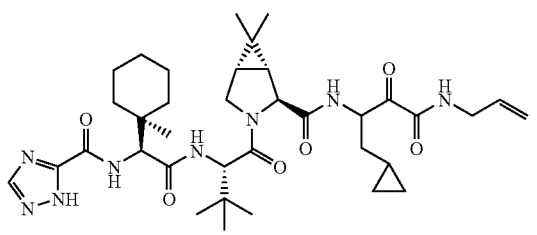
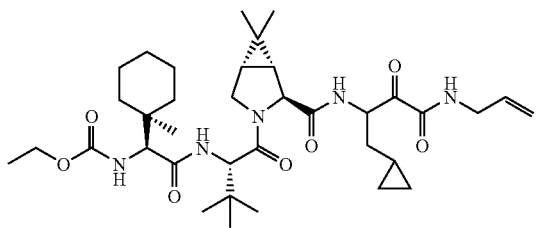
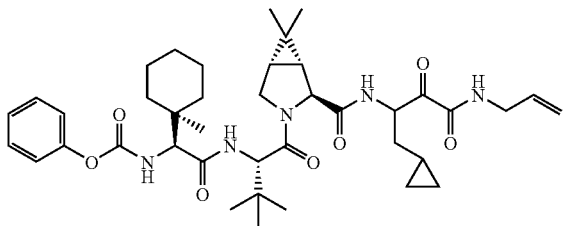
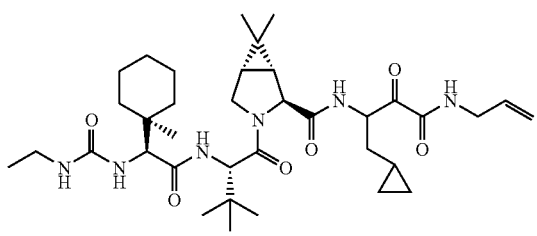
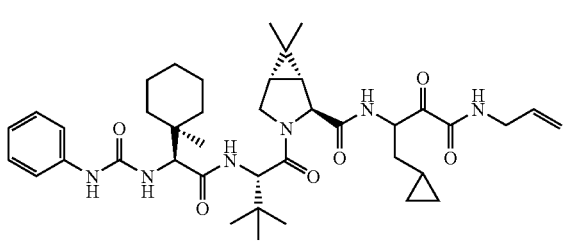
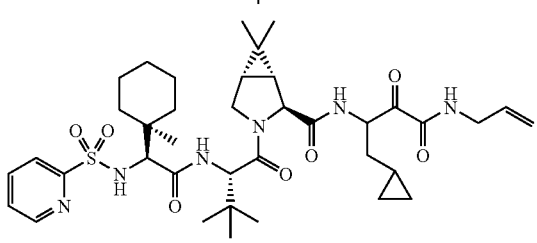
628
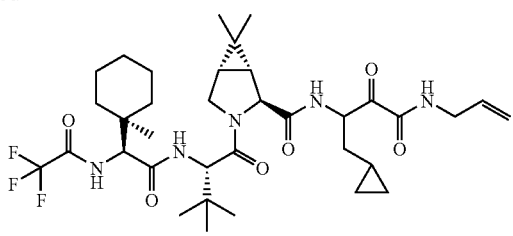
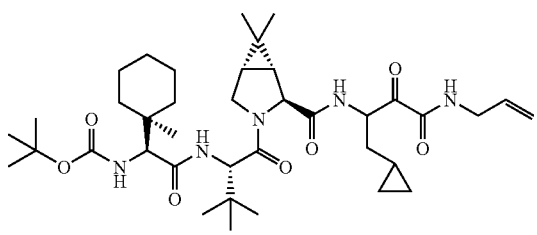
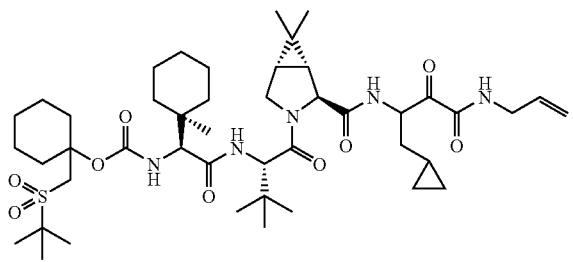
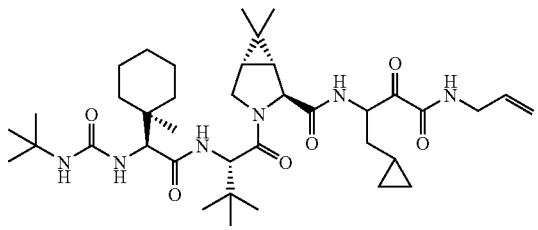
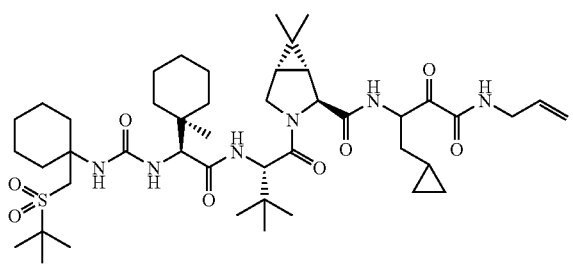
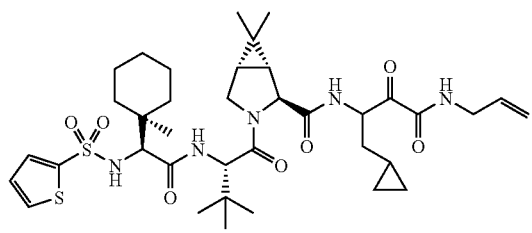
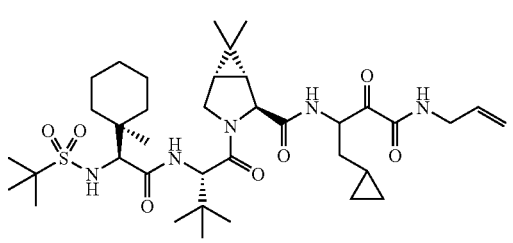

629 630
-continued
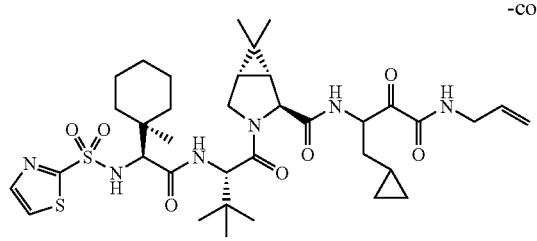 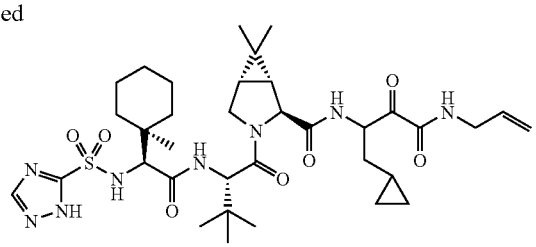
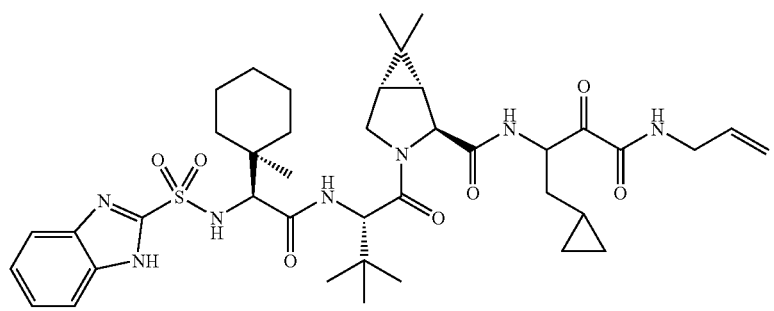
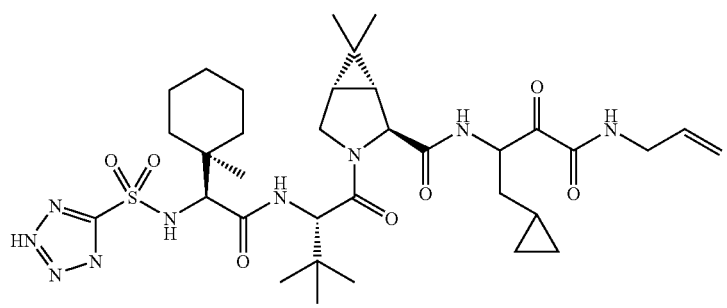
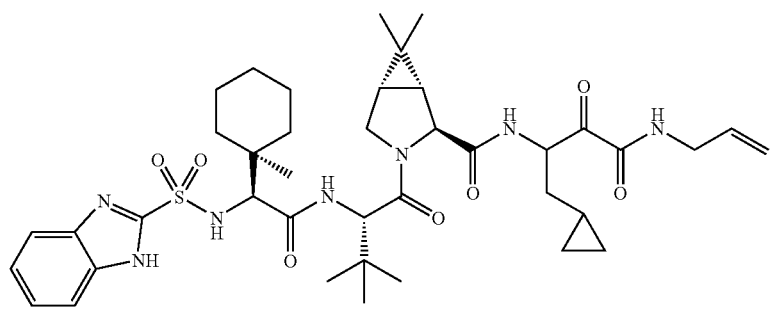
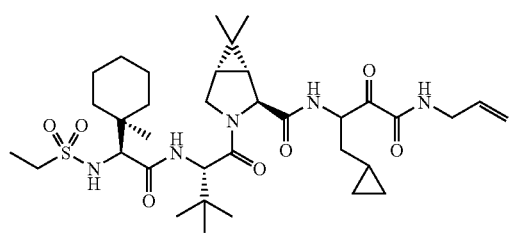 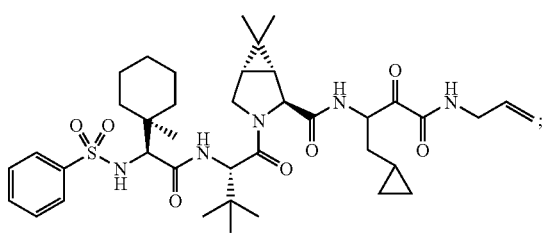
or a pharmaceutically acceptable salt, solvate or ester thereof.
Compounds of formula XVI are disclosed in U.S. patent application Ser. No. 11/064,757 filed Feb. 24, 2005. The preparation of these compounds is disclosed in the experimental section of this application set forth hereinbelow.
Non-limiting examples of certain compounds disclosed in U.S. patent application Ser. No. 11/064,757 are:

631
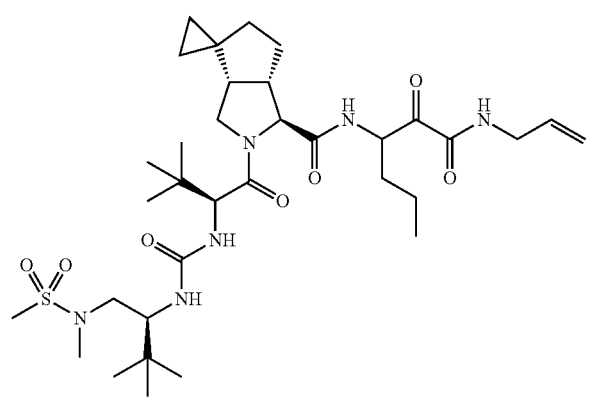
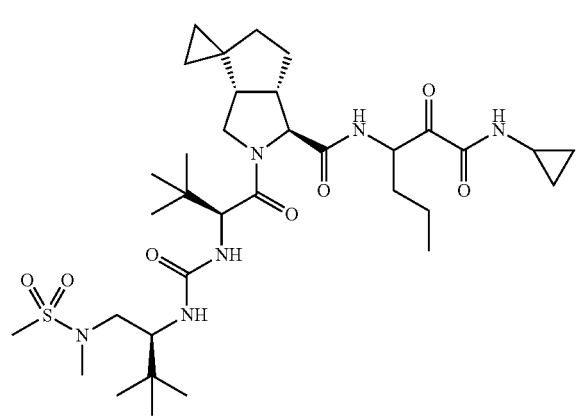
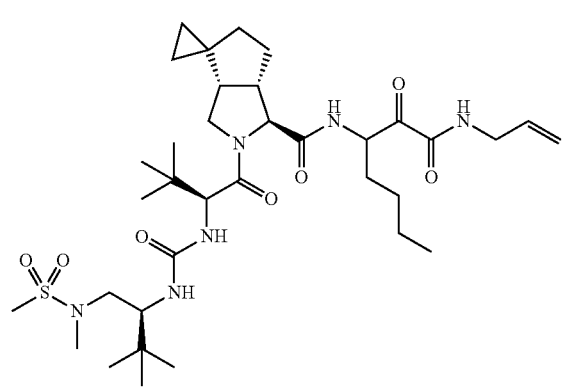
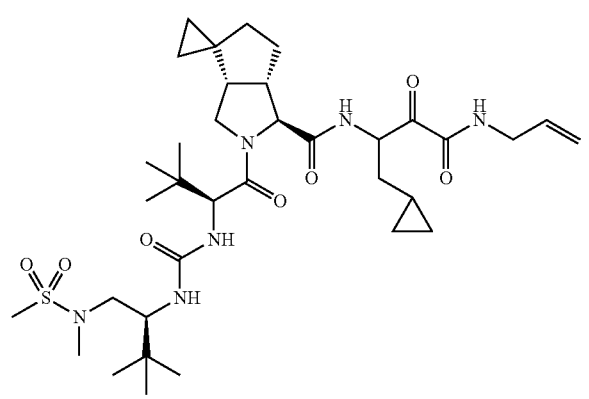
632
-continued
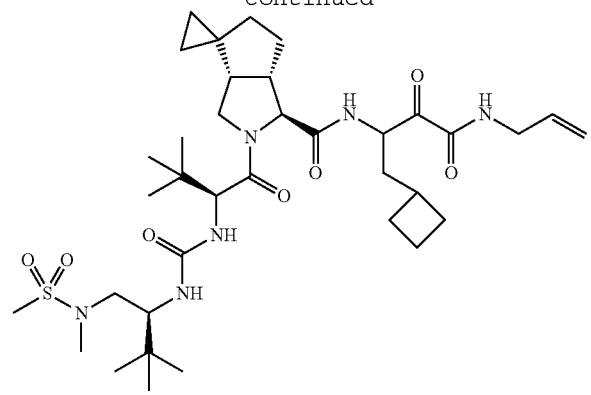
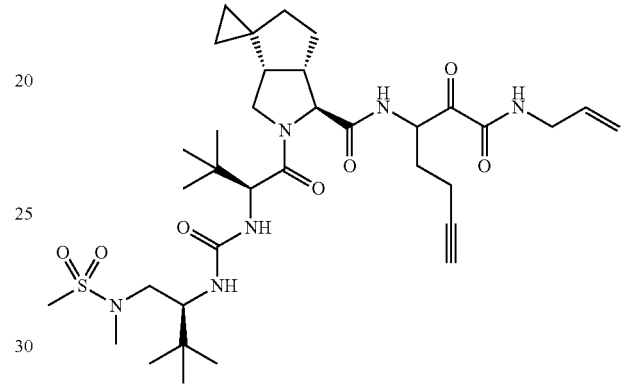
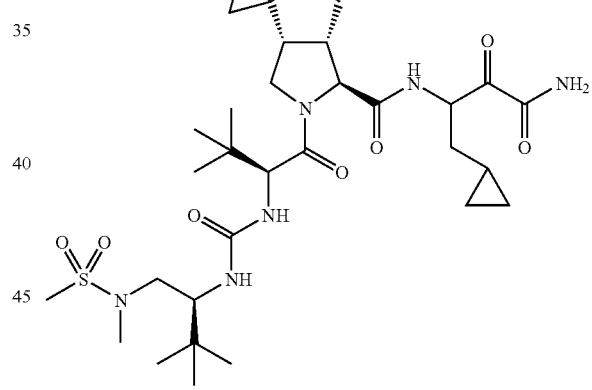
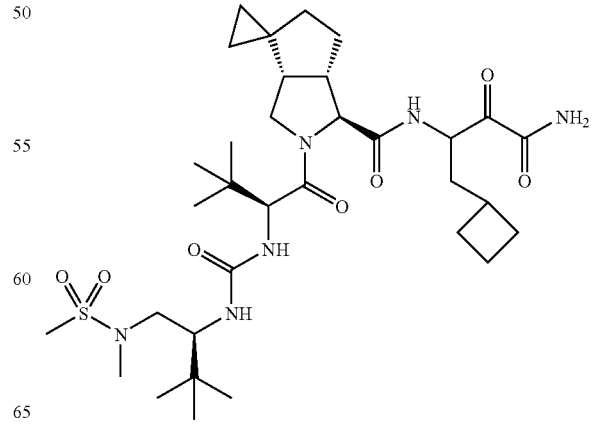

633 -continued
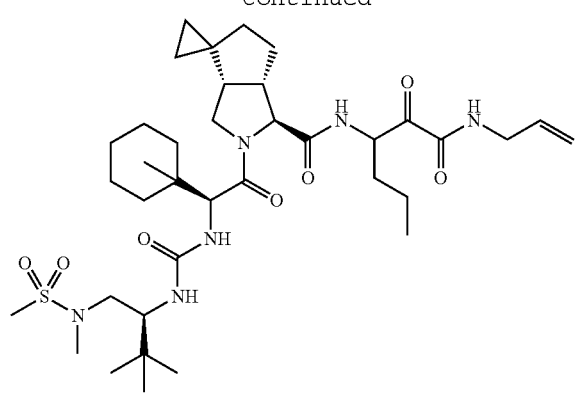
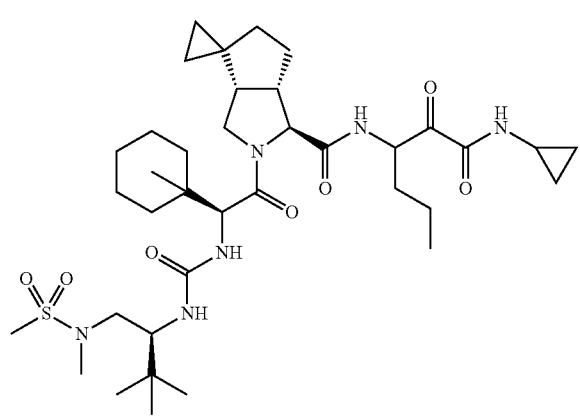
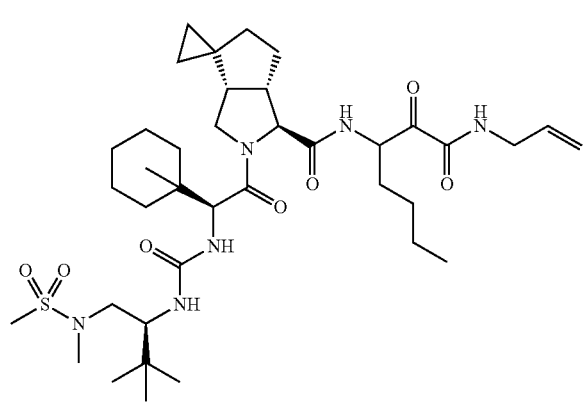
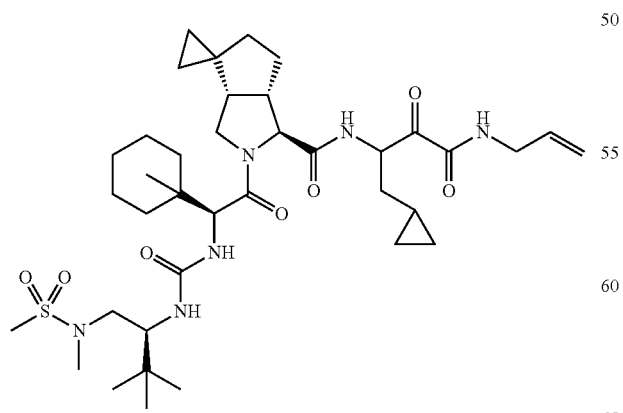
634 -continued
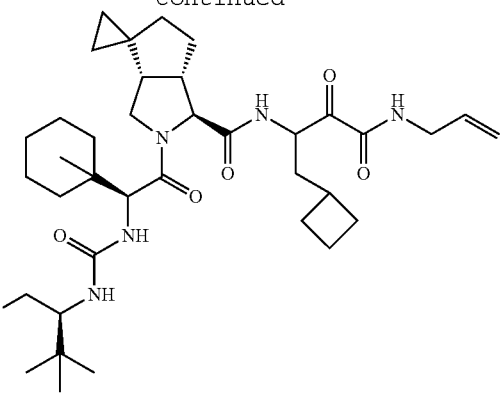
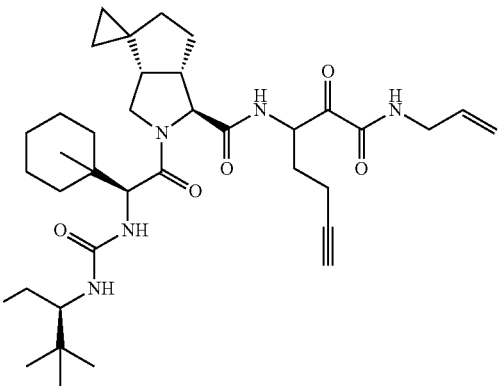
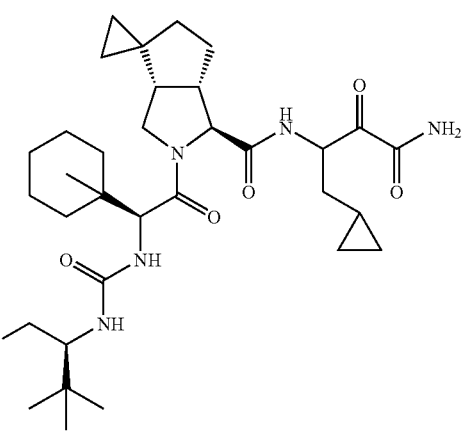
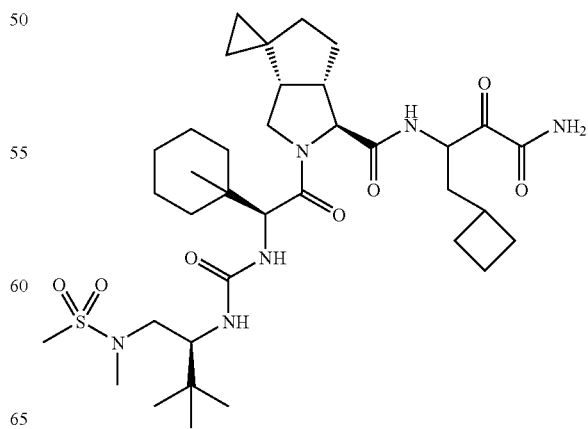

635
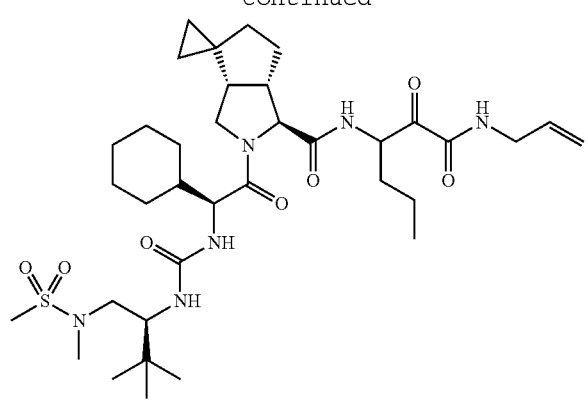
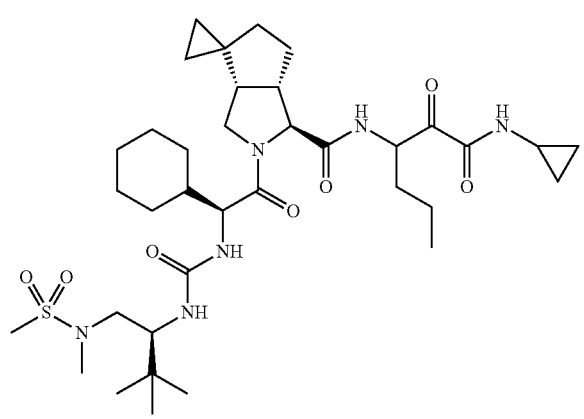
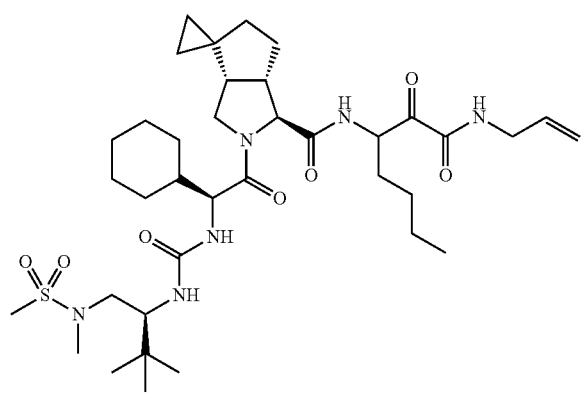
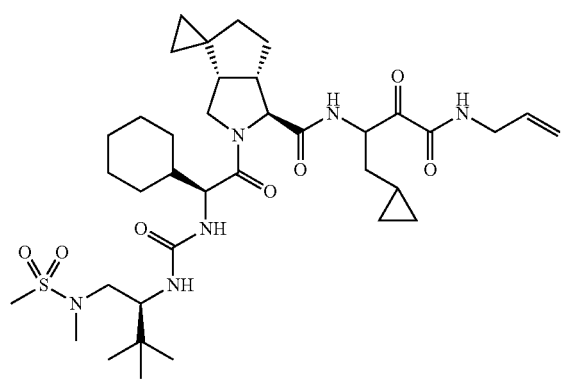
636
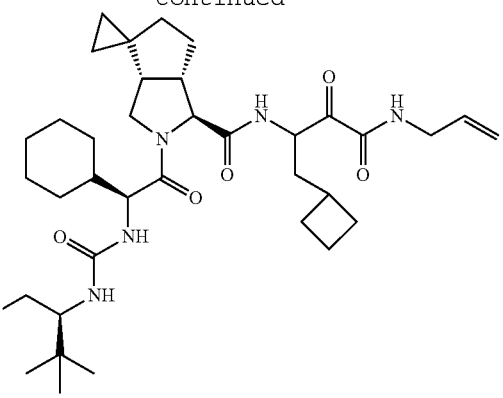
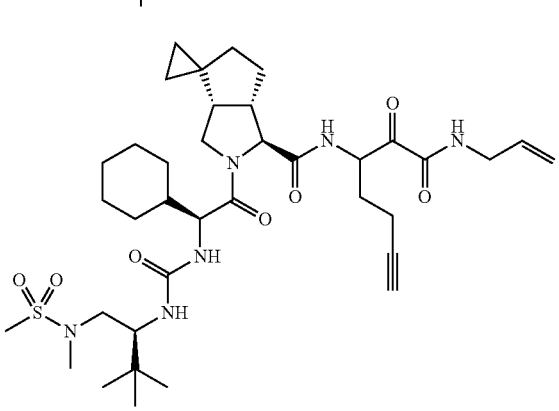
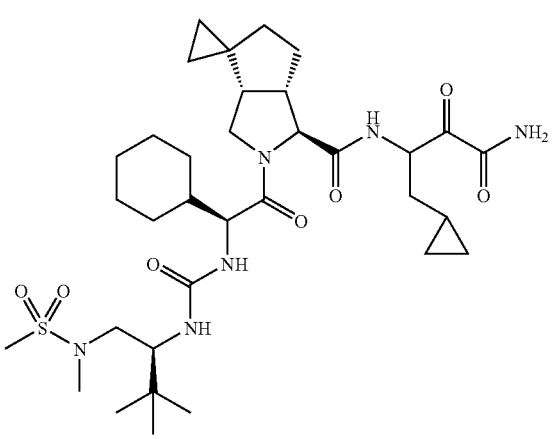
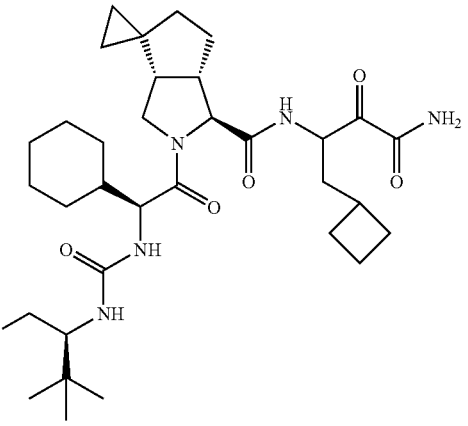

| 637 | 638 |
|---|---|
| -continued | -continued |
| 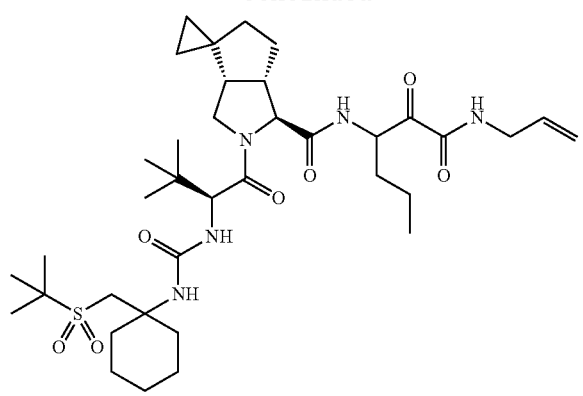 | 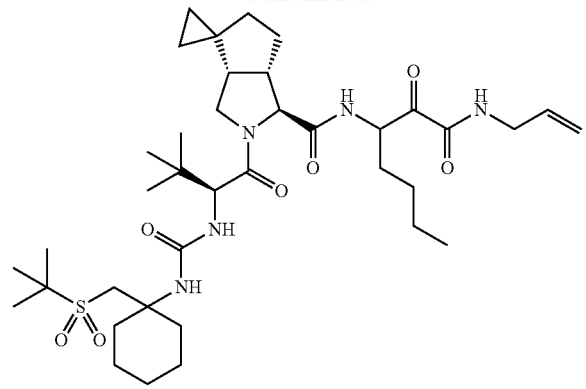 |
| 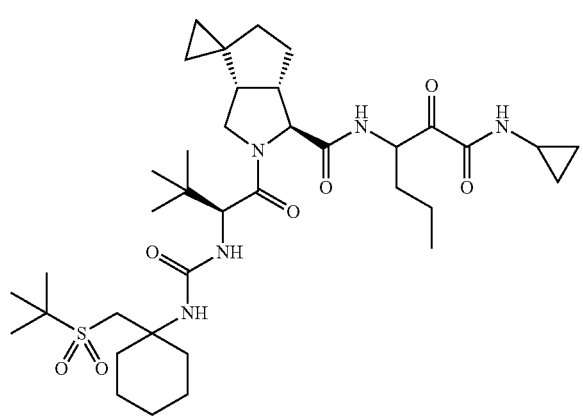 | 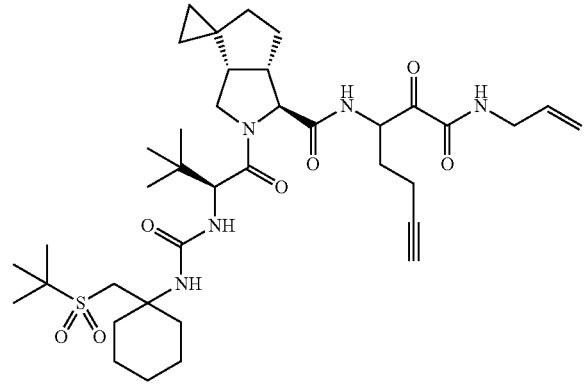 |
| 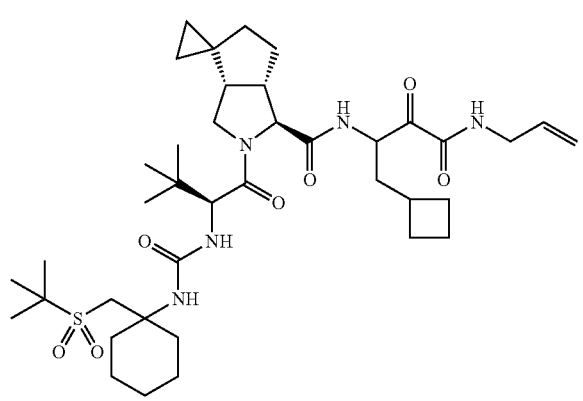 | 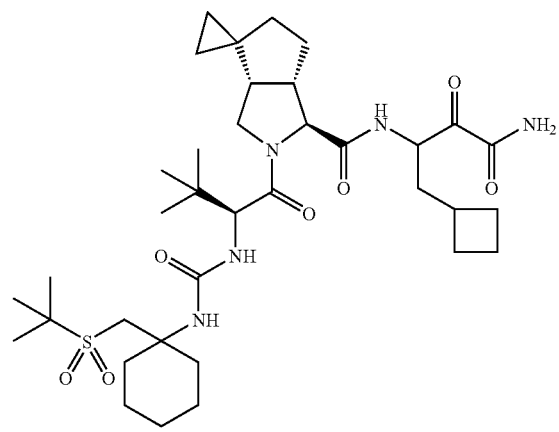 |
| 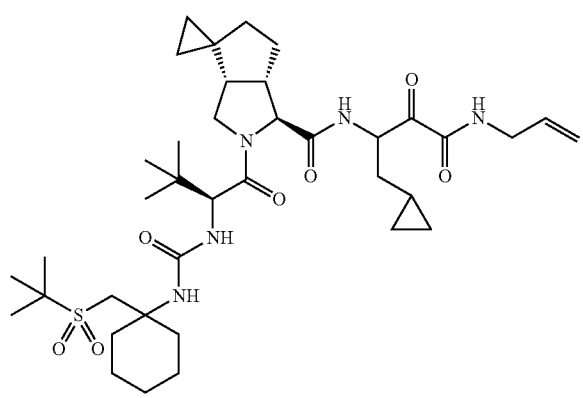 | 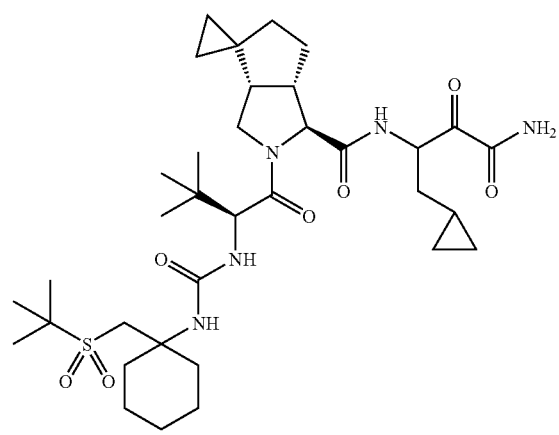 |

639
-continued
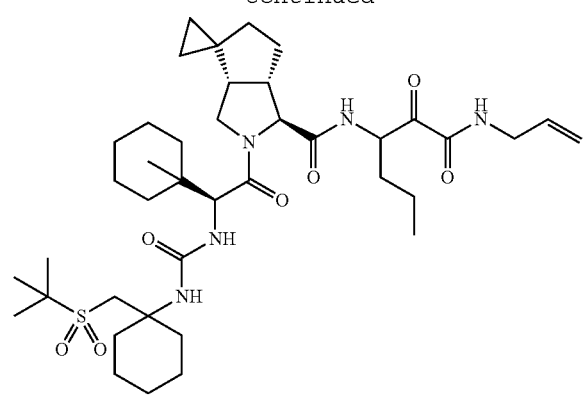
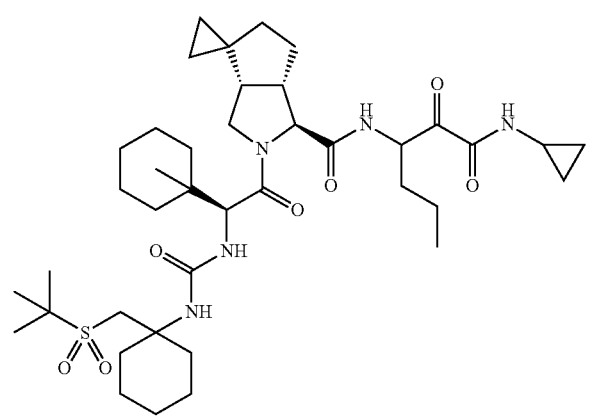
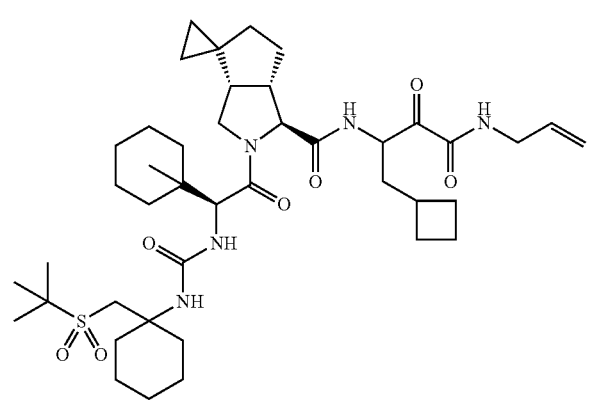
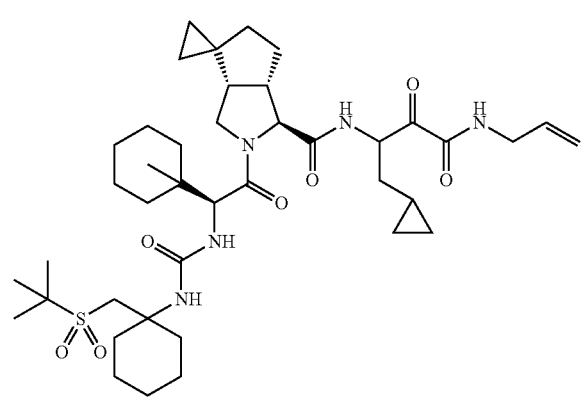
640
-continued
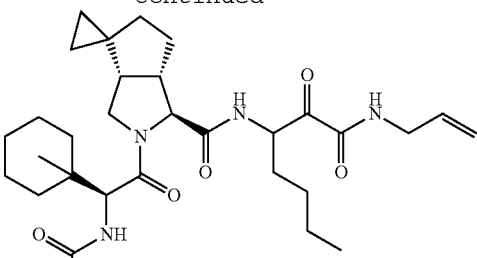
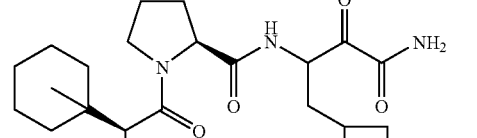
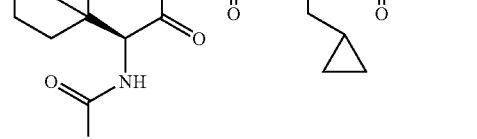

641
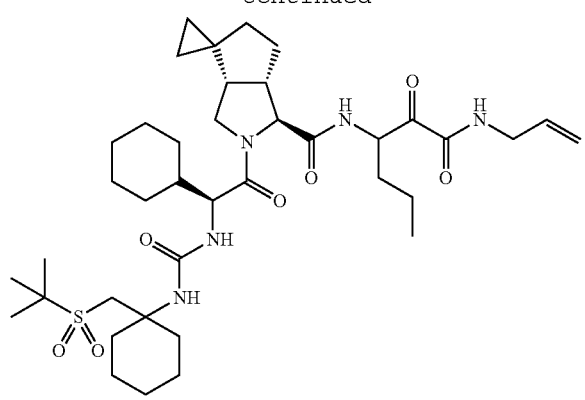
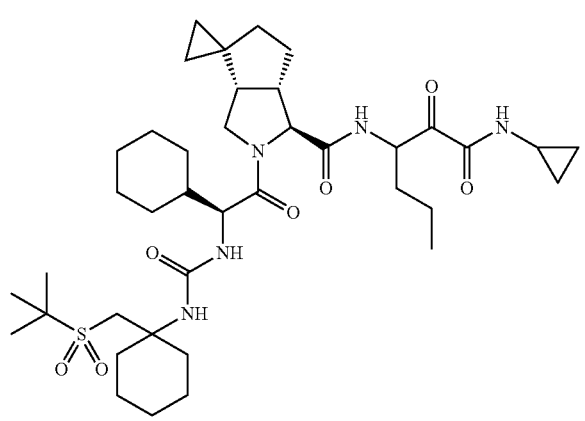
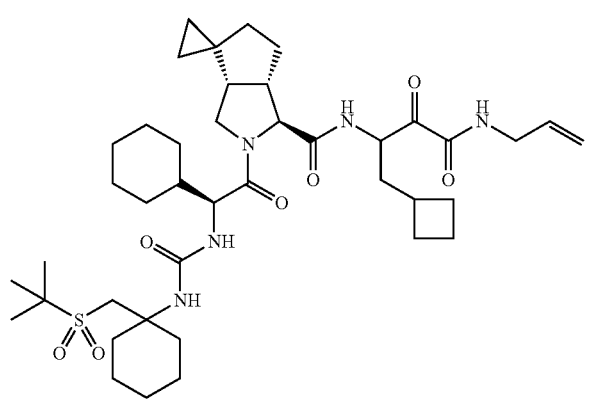
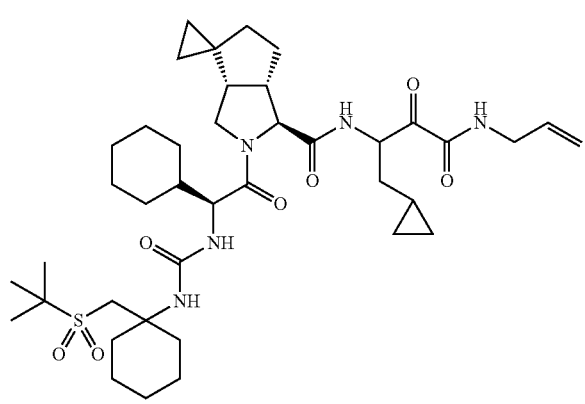
642
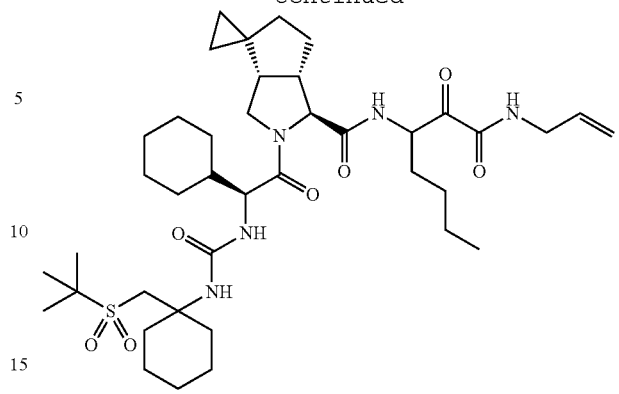
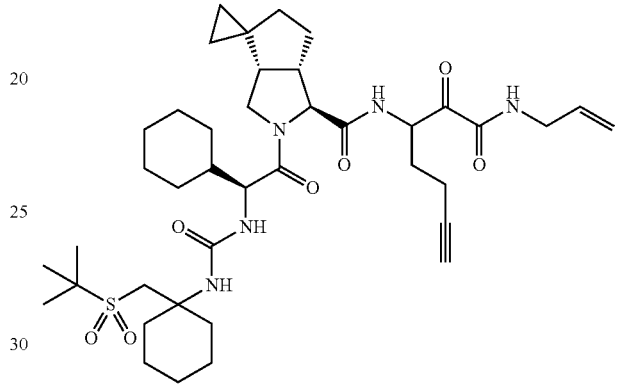
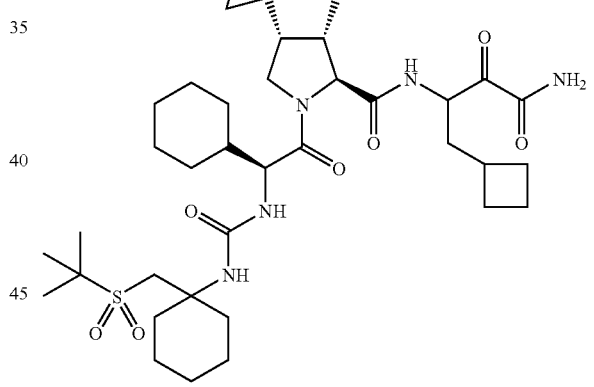
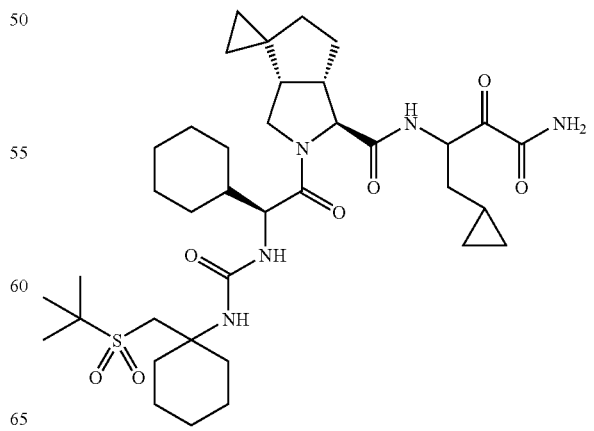

643
-continued
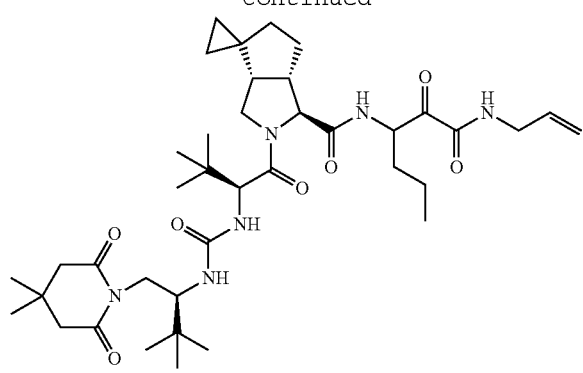
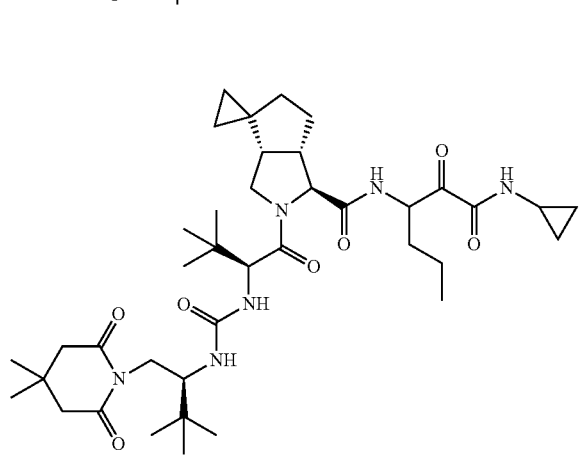
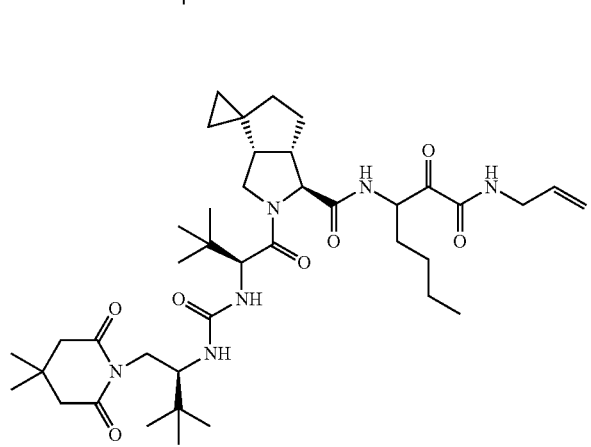
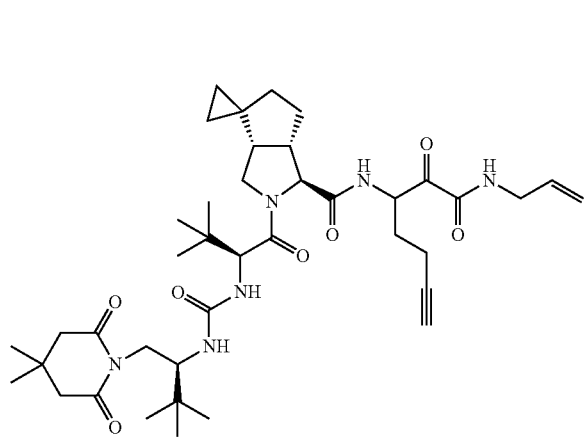
644
-continued
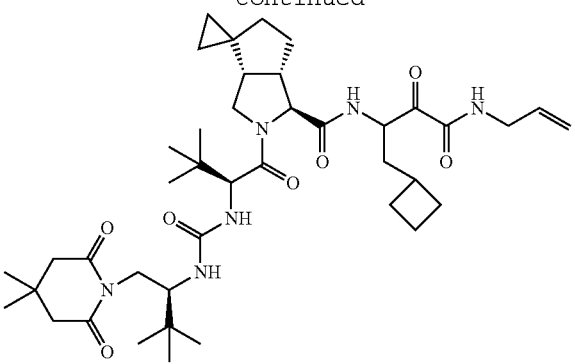
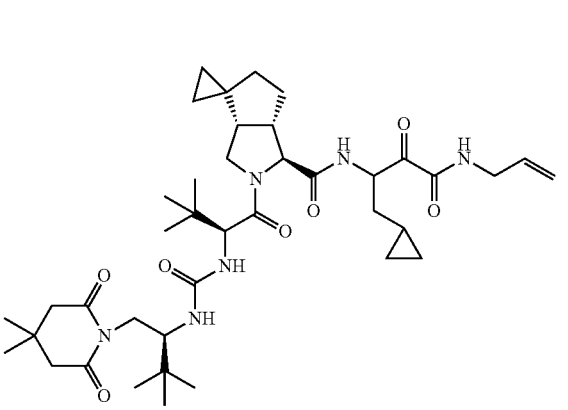
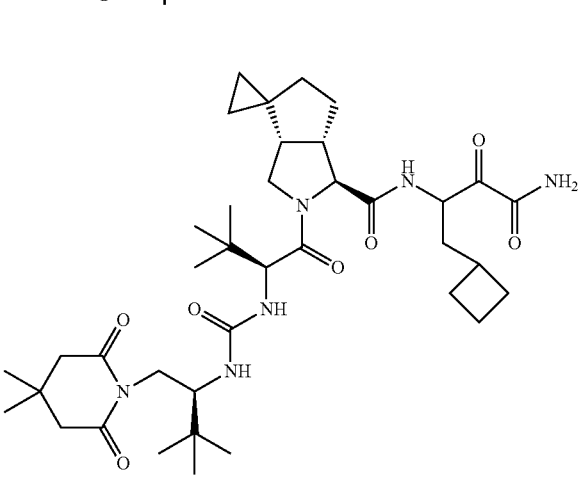
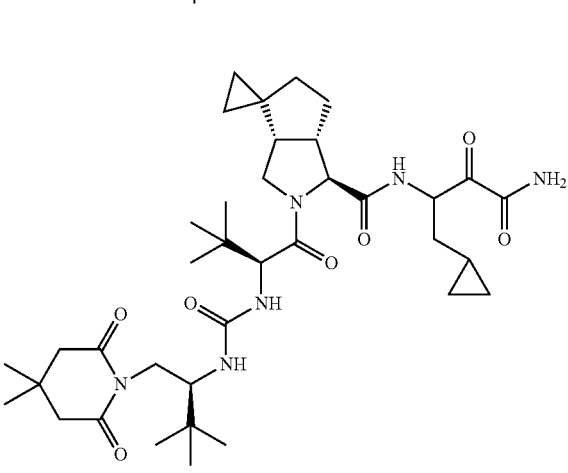

645 -continued
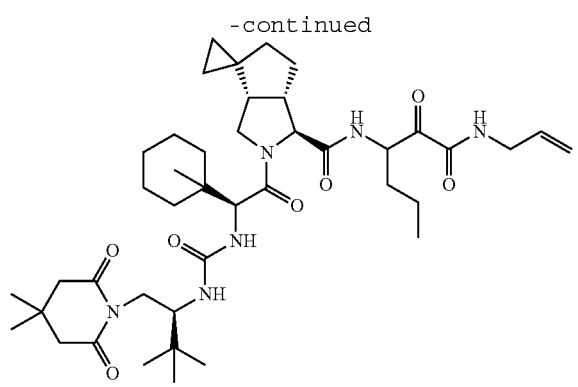
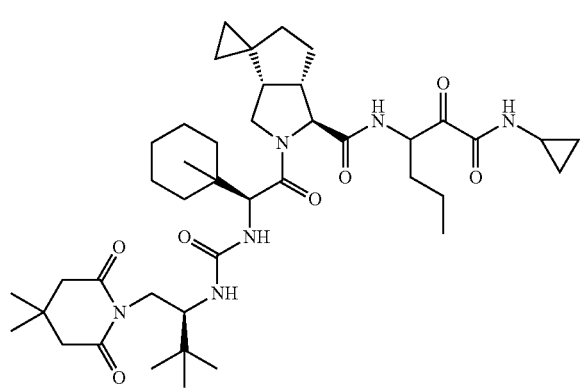
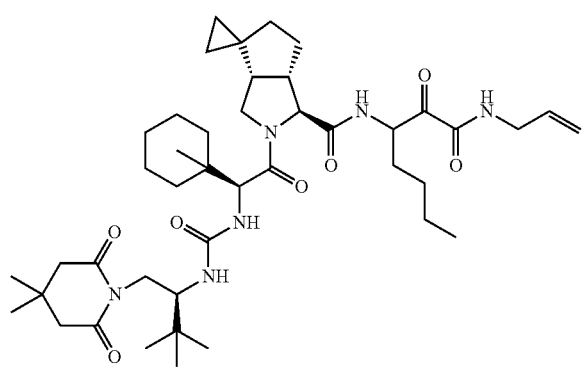
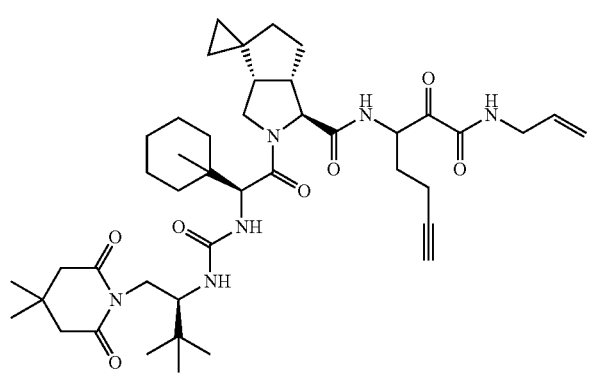
646 -continued
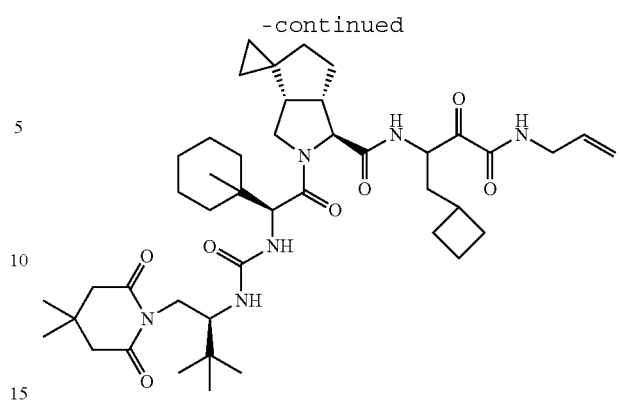
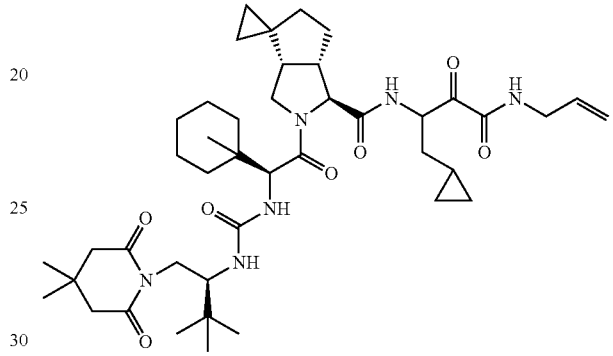
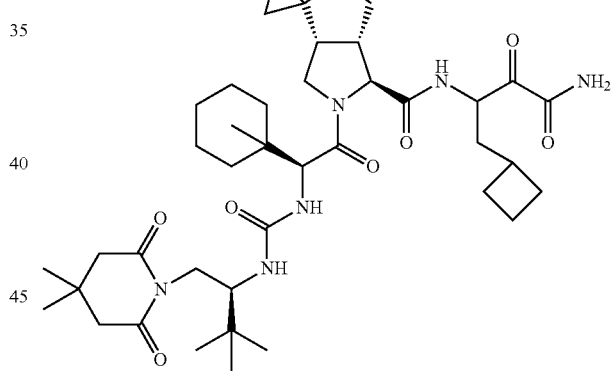
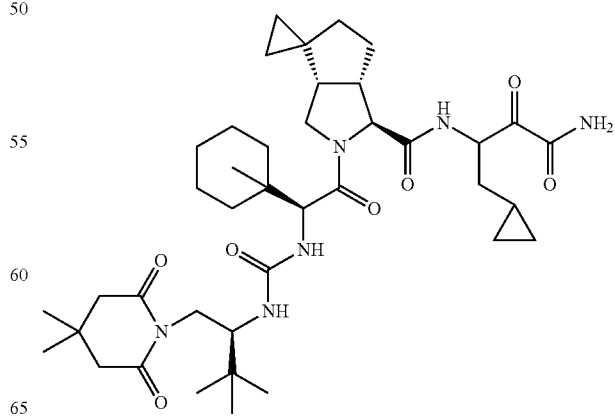

647 -continued
648 -continued
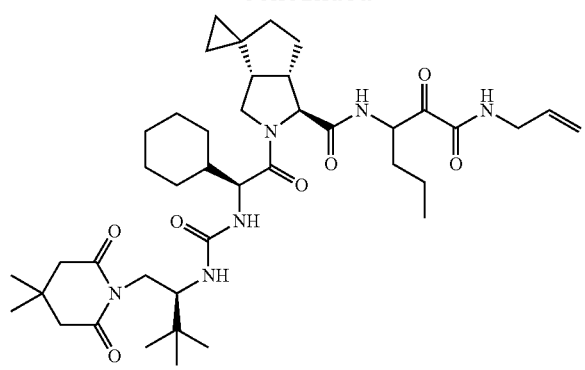
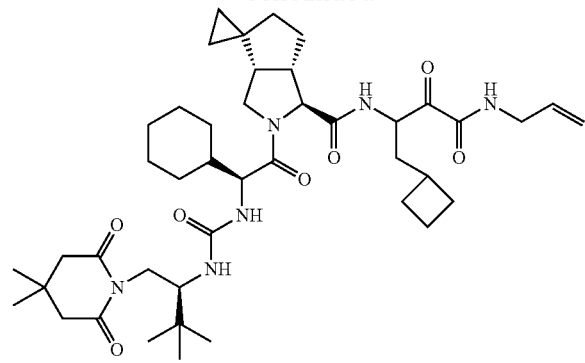

649
-continued
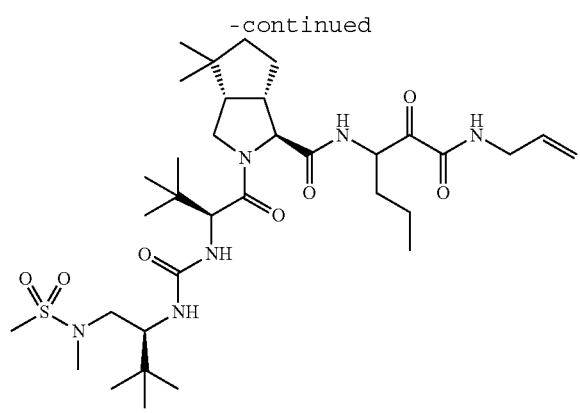
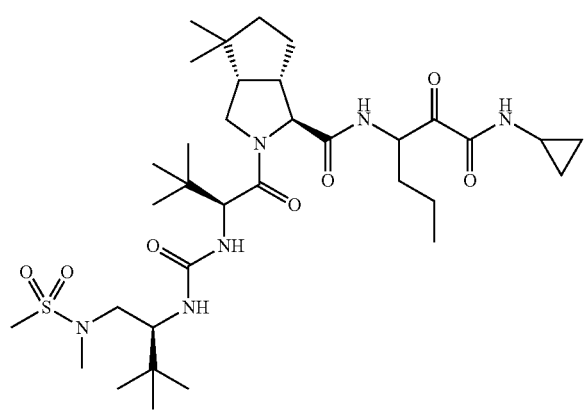
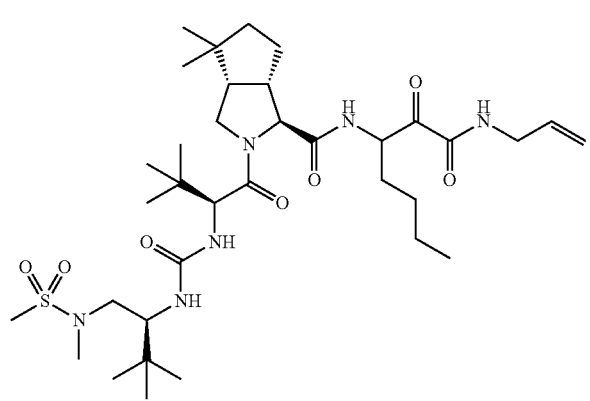
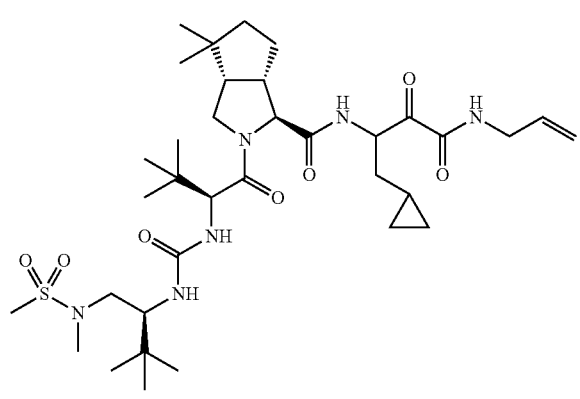
650
-continued
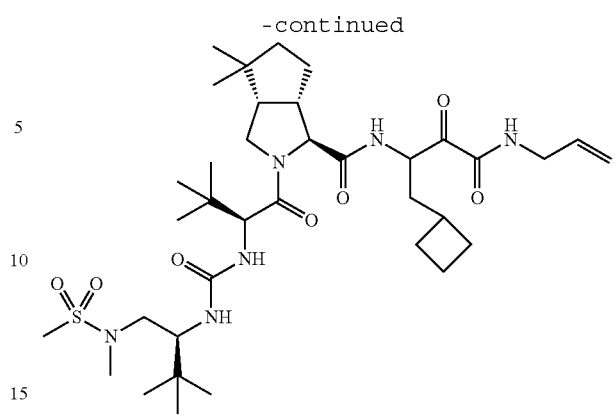
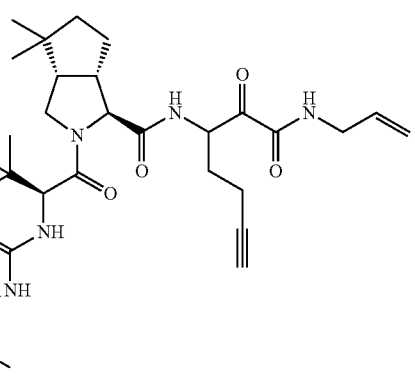
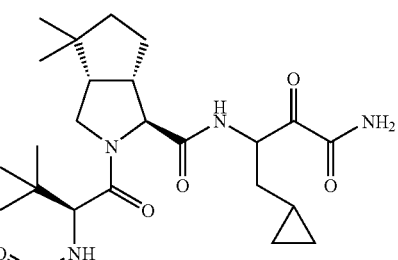
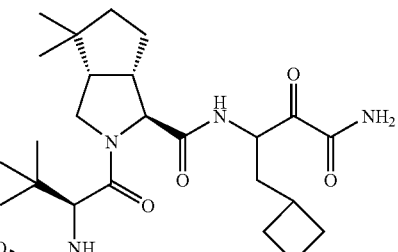

| 651 | 652 |
|---|---|
| -continued | -continued |
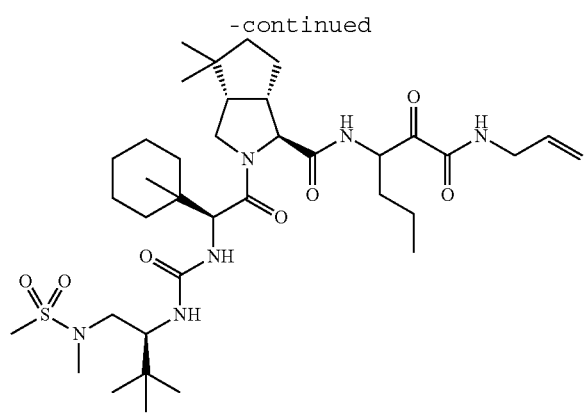
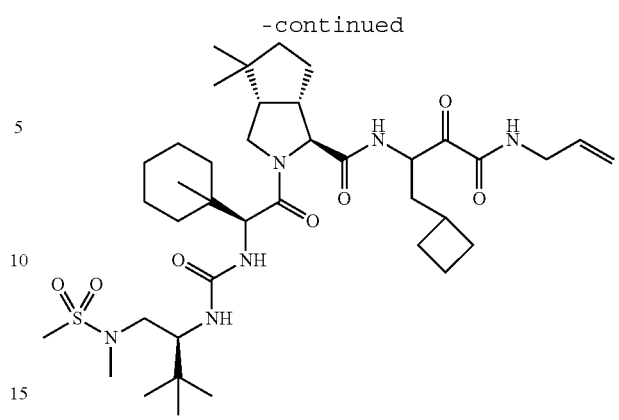
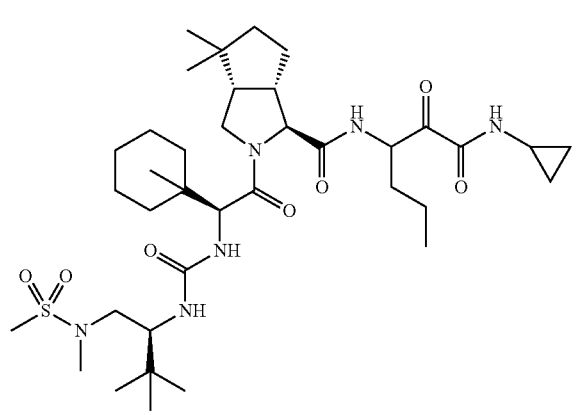
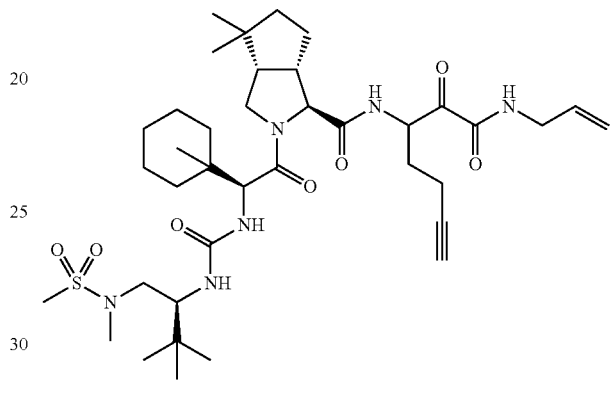
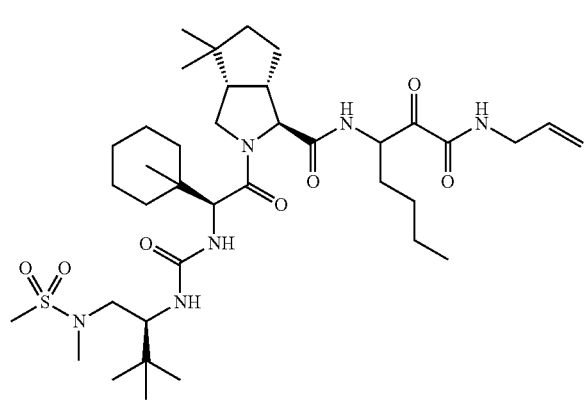
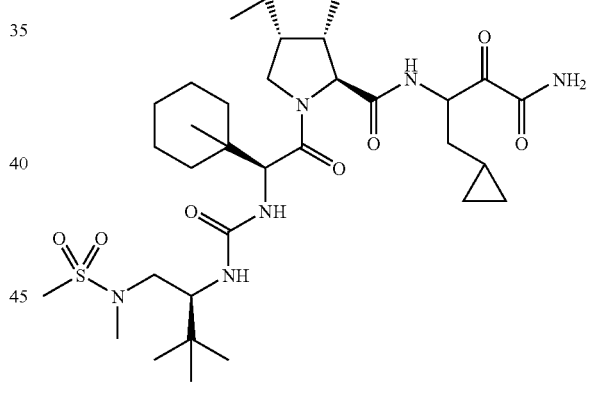
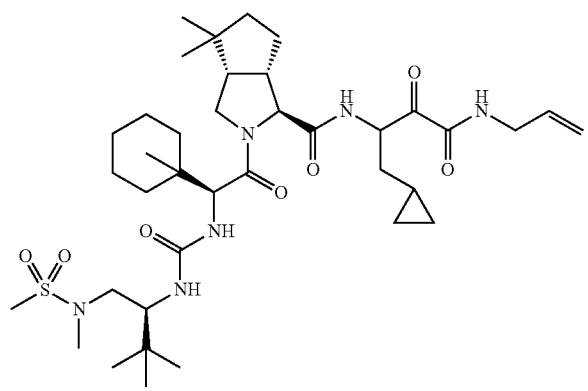
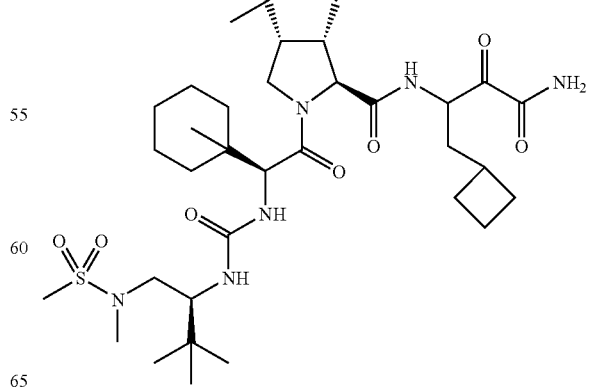

| 653 | 654 |
|---|---|
| -continued | -continued |
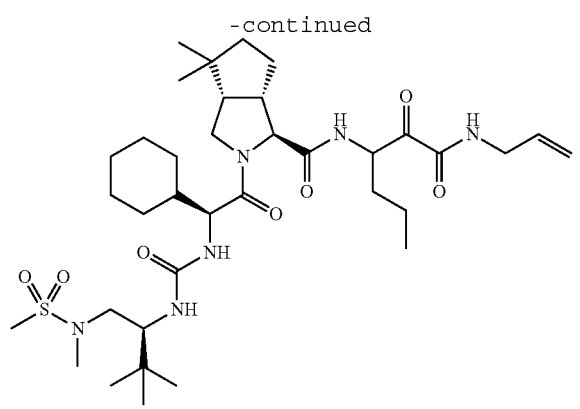
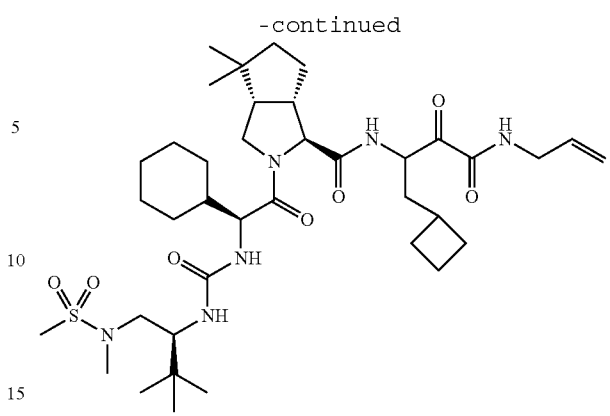
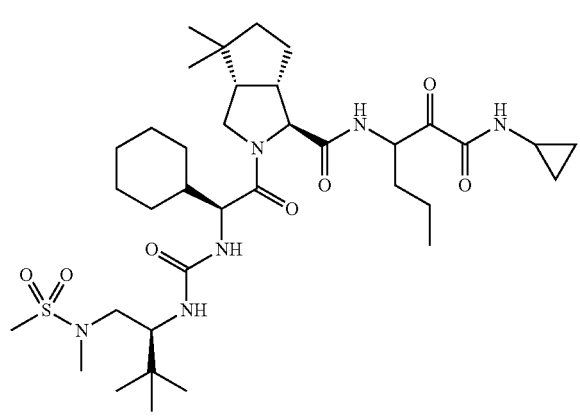
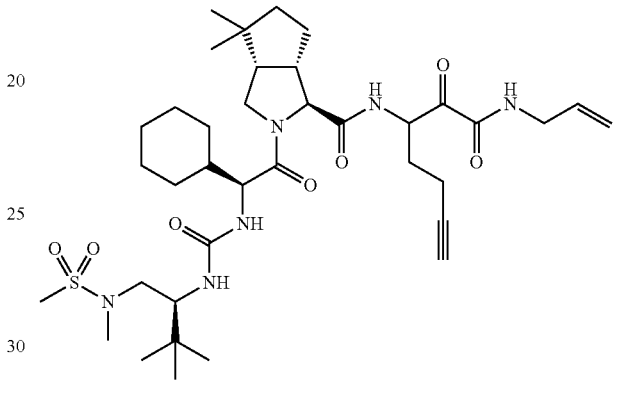
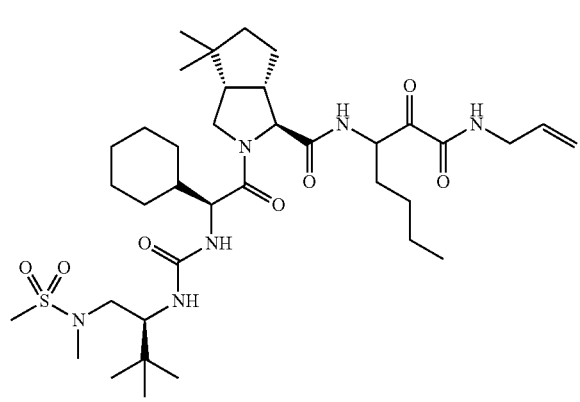
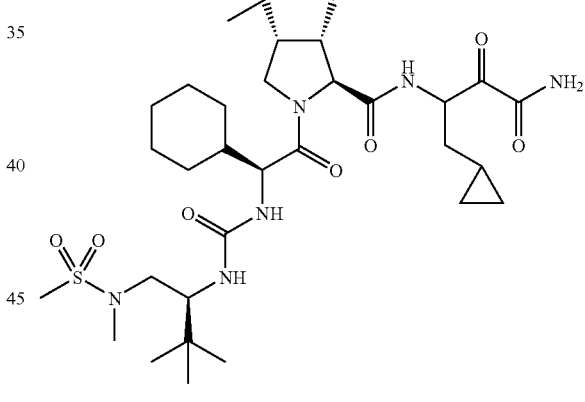
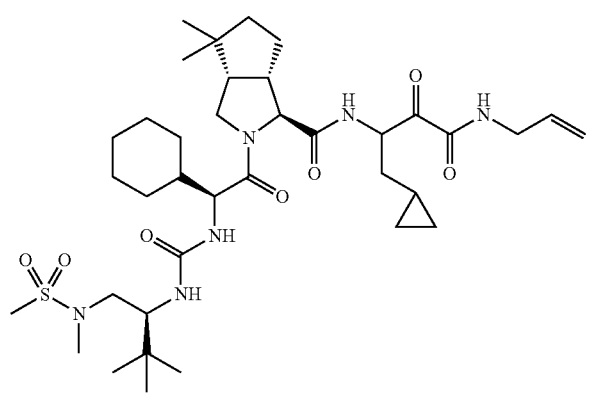
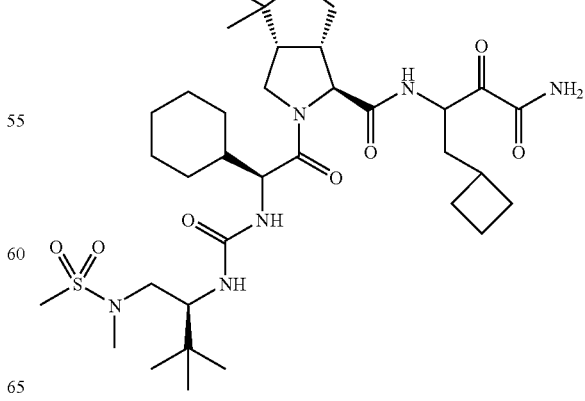

655
-continued
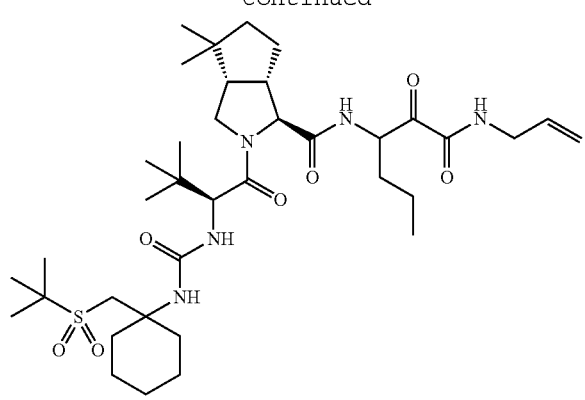
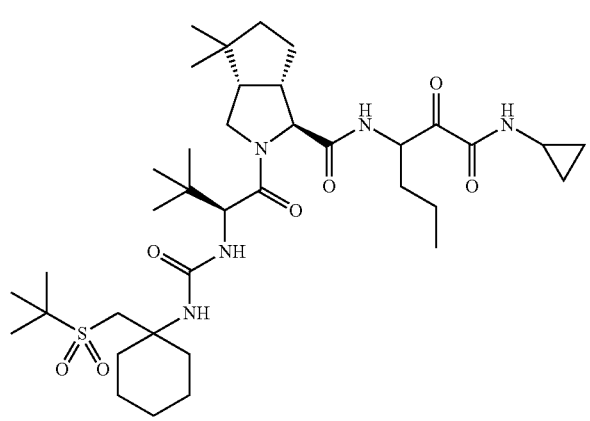
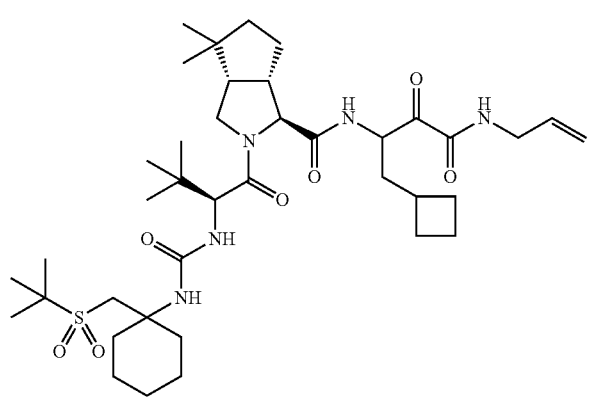
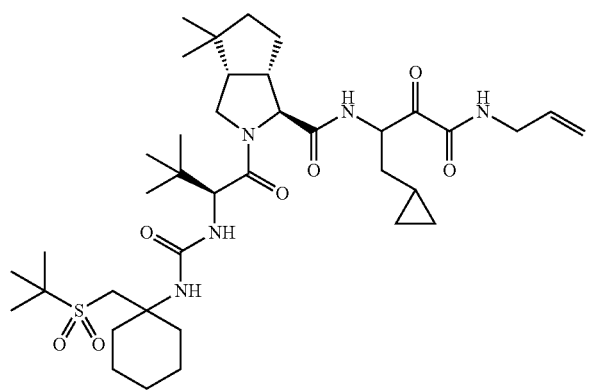
656
-continued
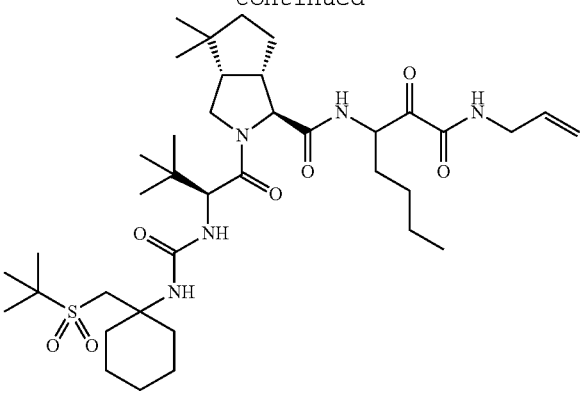
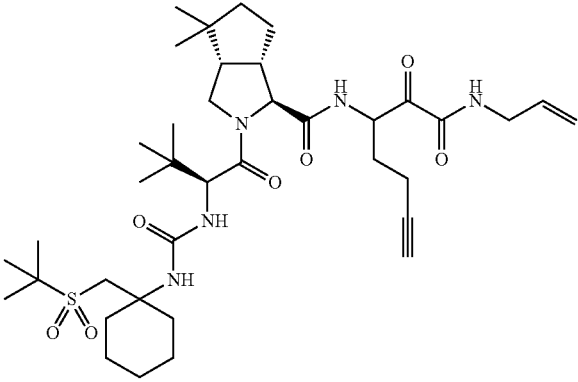
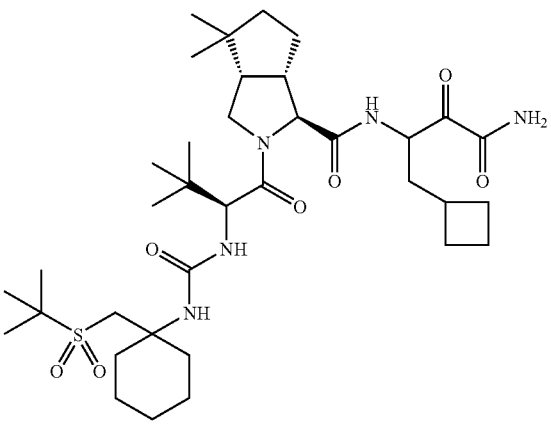
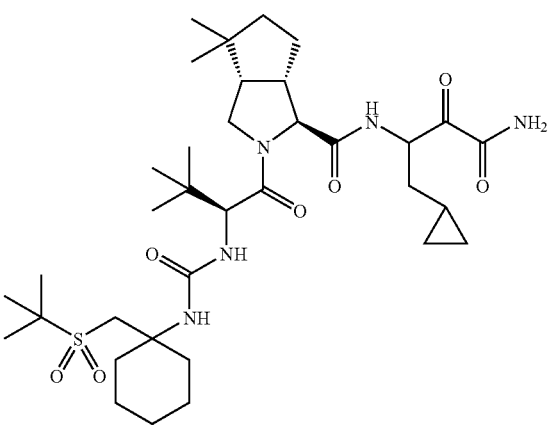

657 -continued
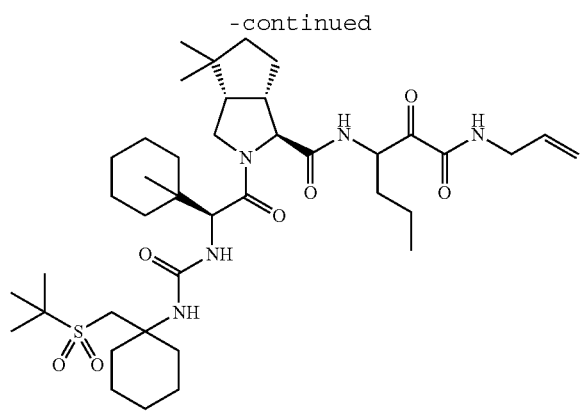
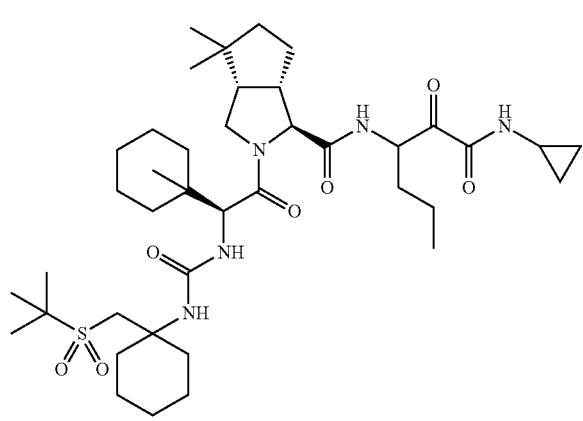
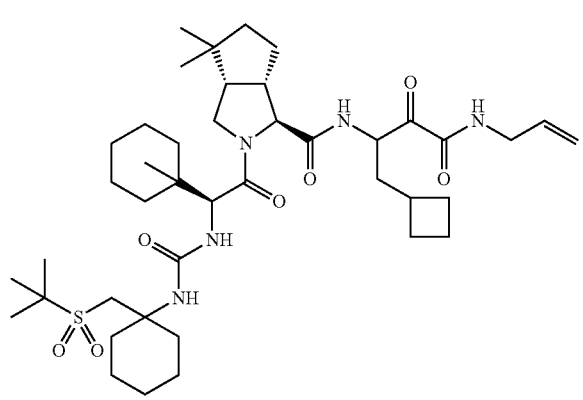
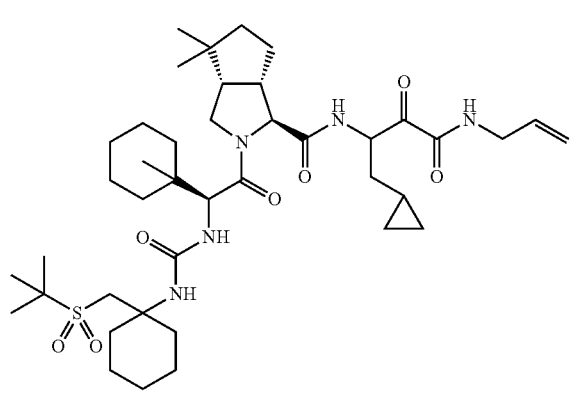
658 -continued
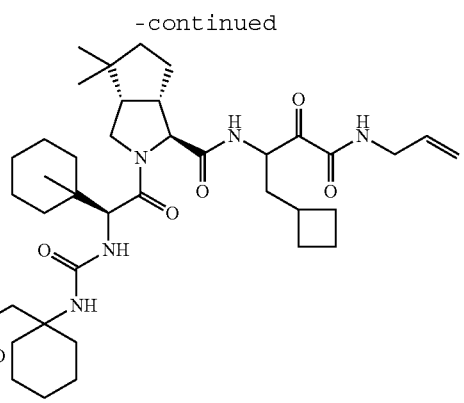
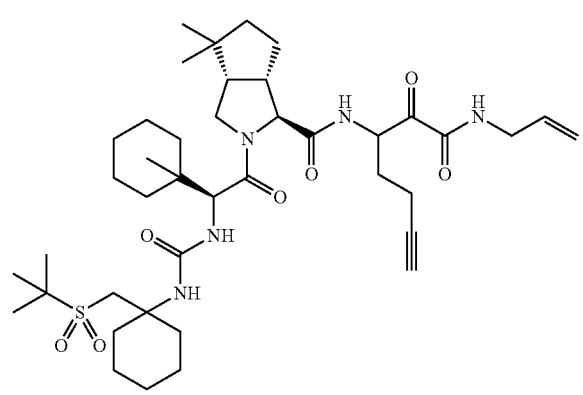
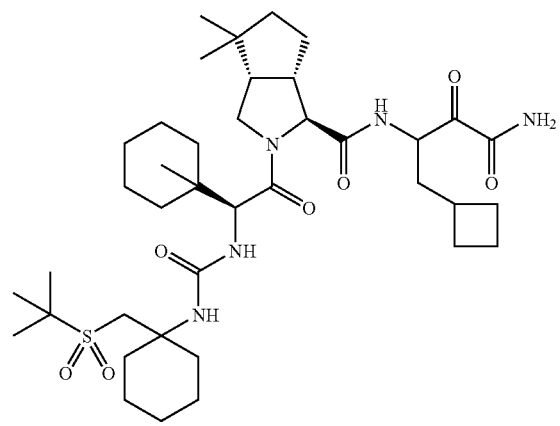
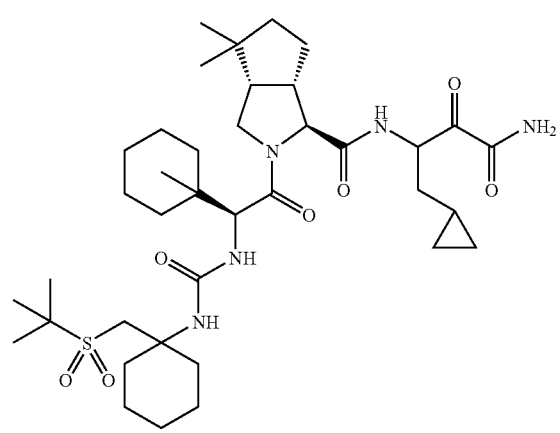

659
-continued
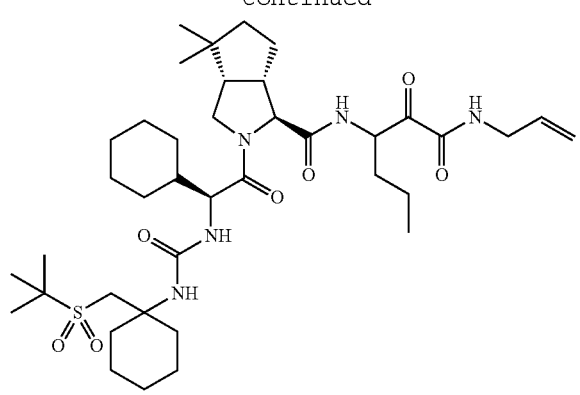
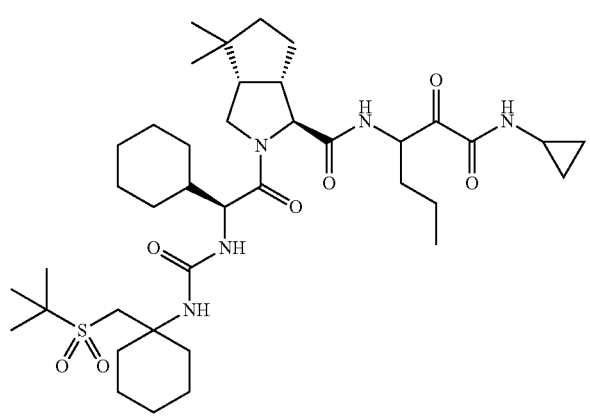
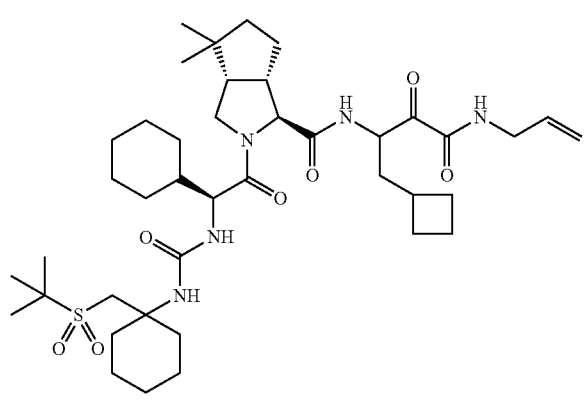
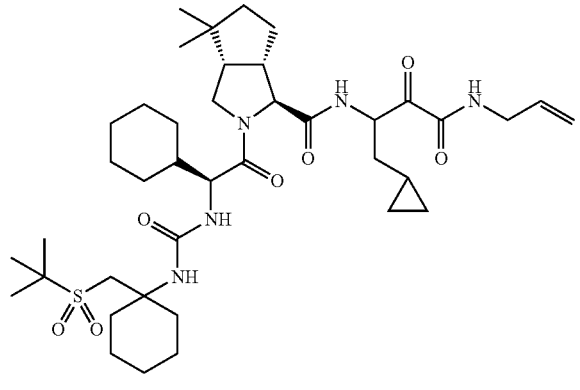
660
-continued
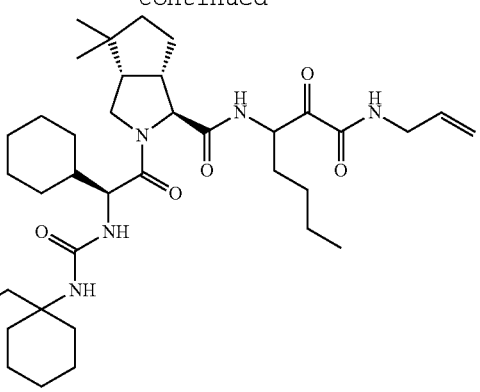
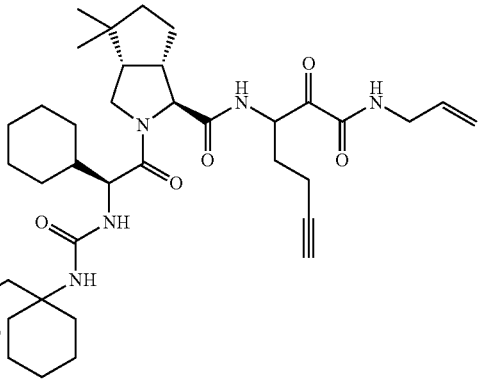
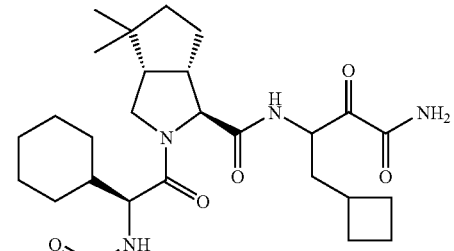
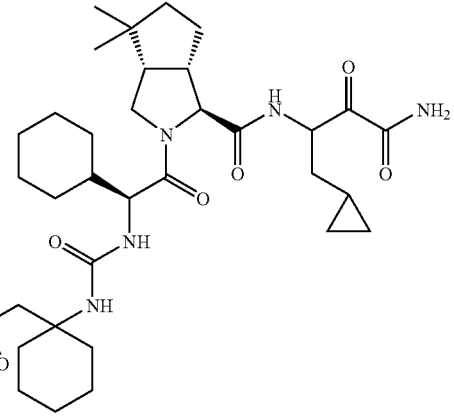

661 -continued
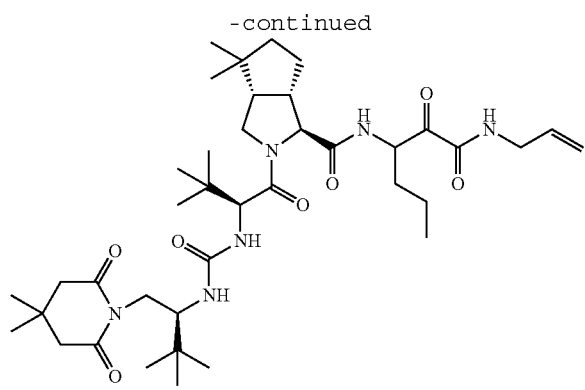
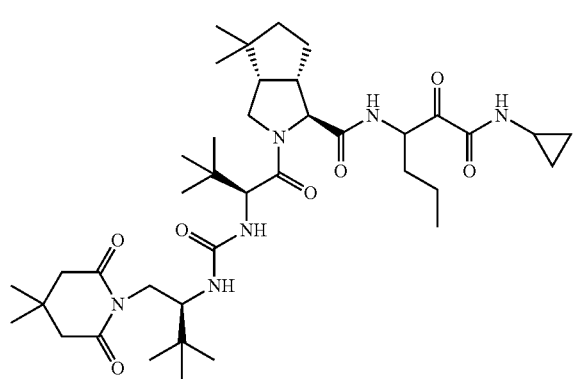
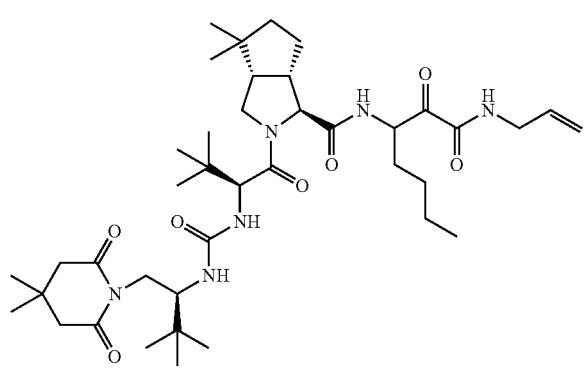
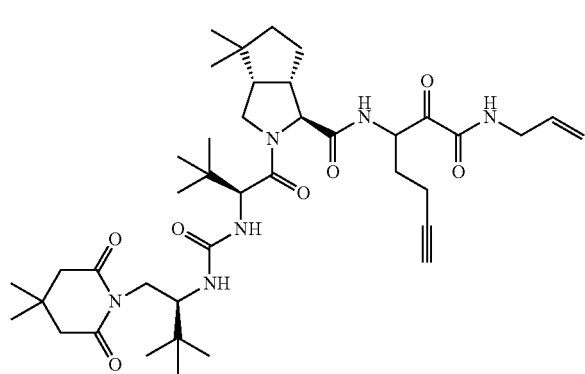
662 -continued
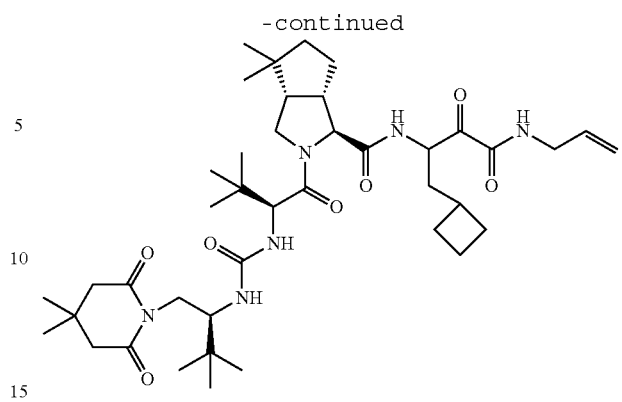
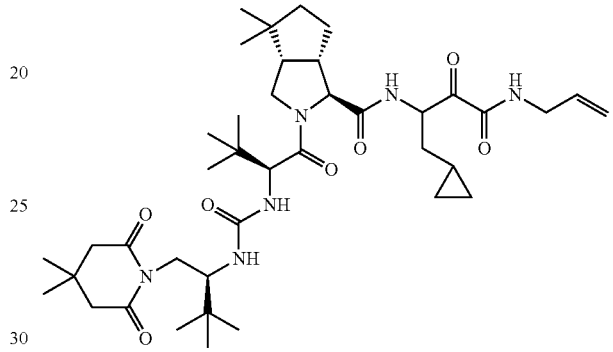
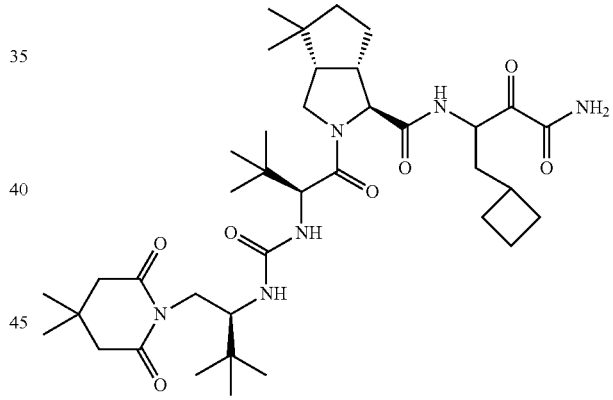
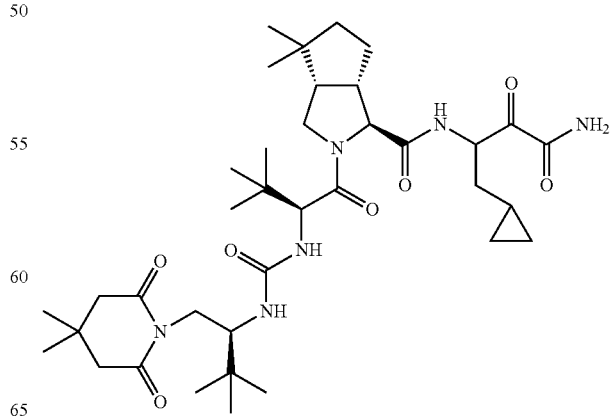

663
-continued
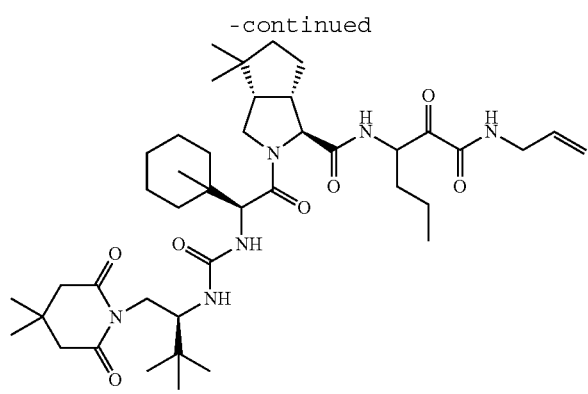
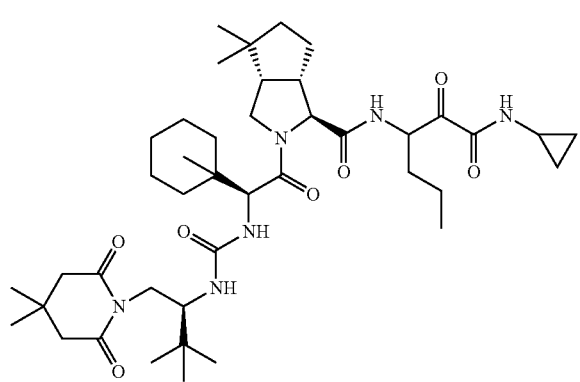
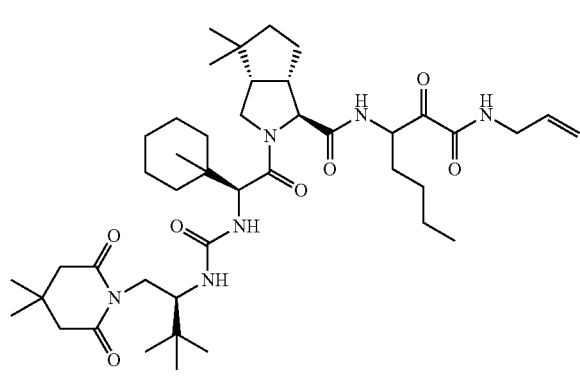
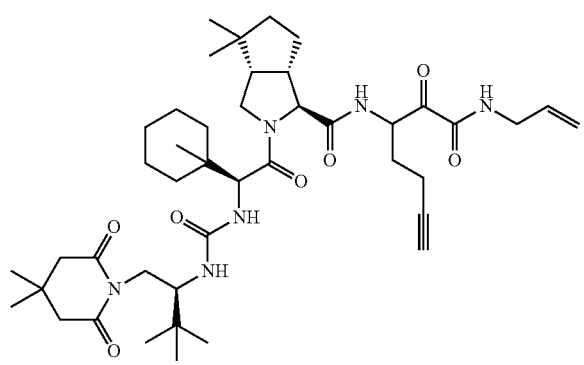
664
-continued
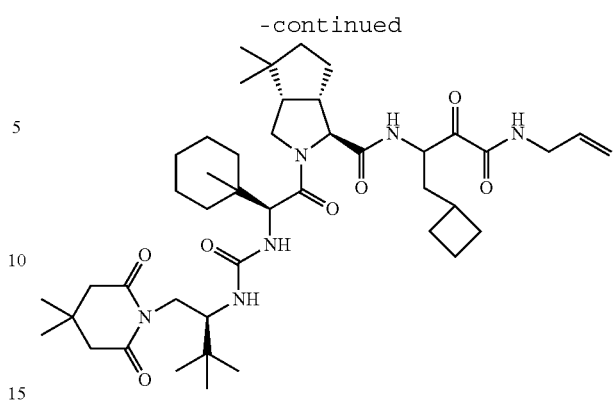
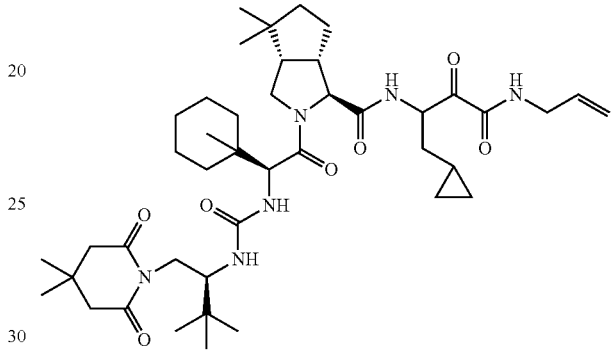
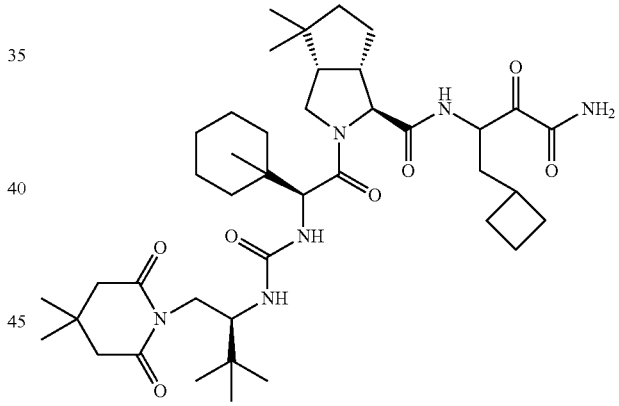
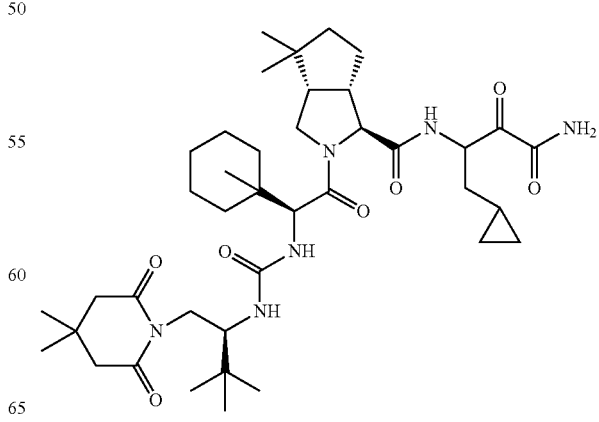

665
-continued
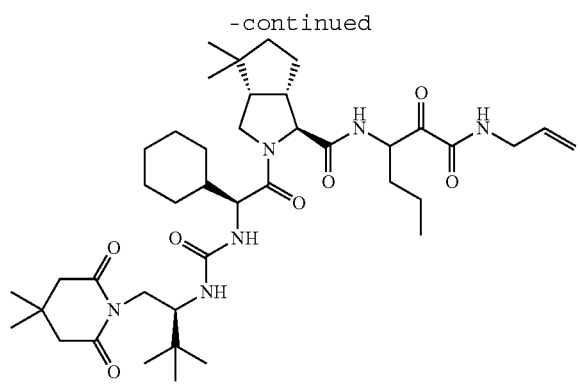
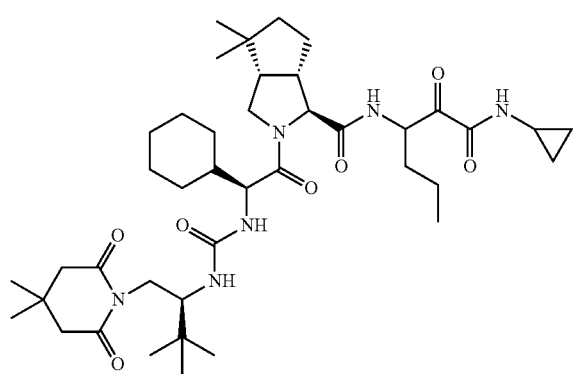
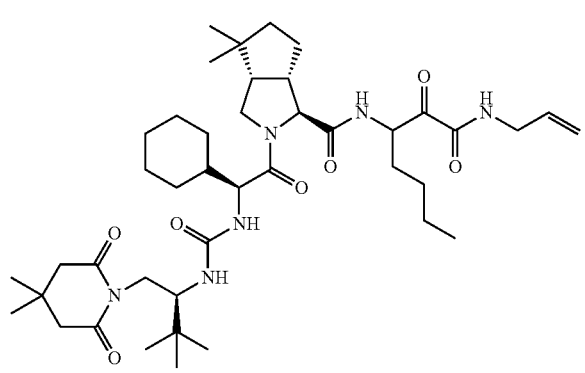
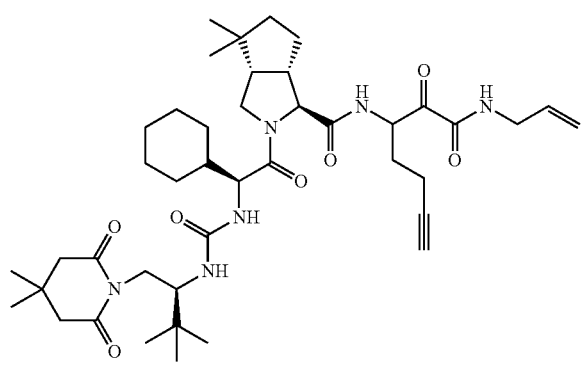
666
-continued
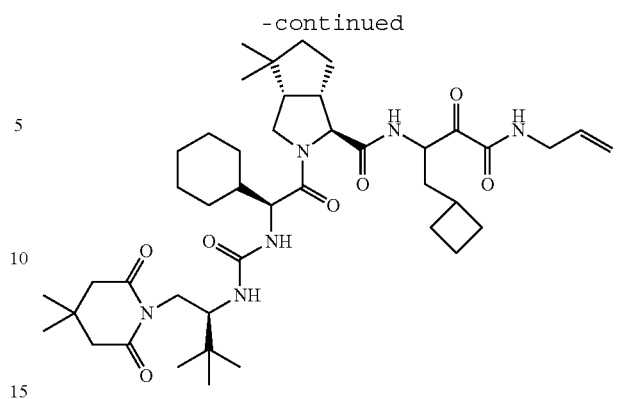
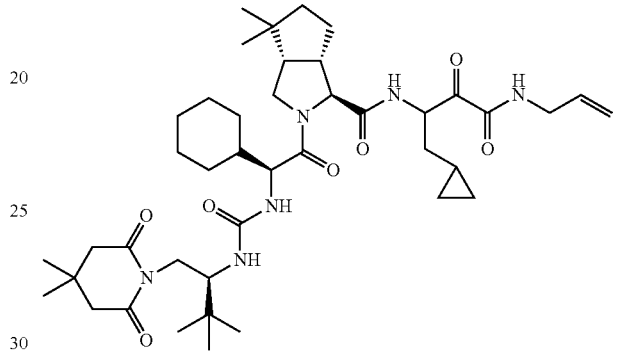
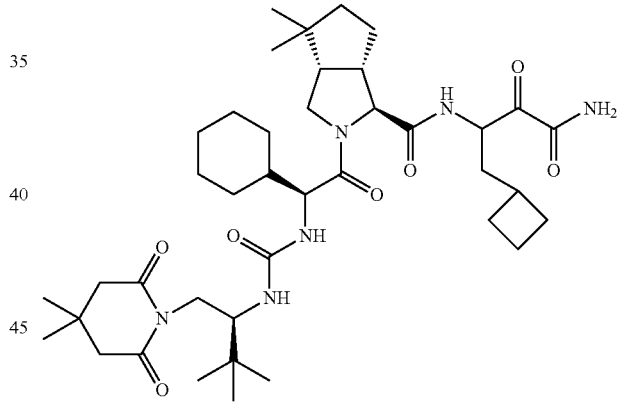
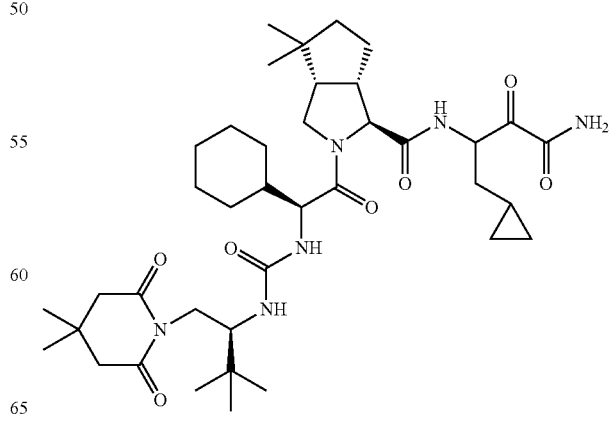

667 -continued
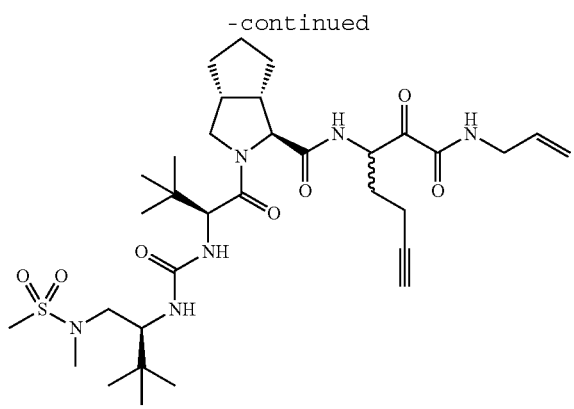
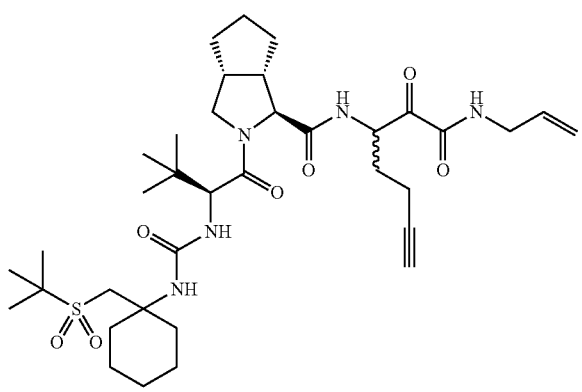
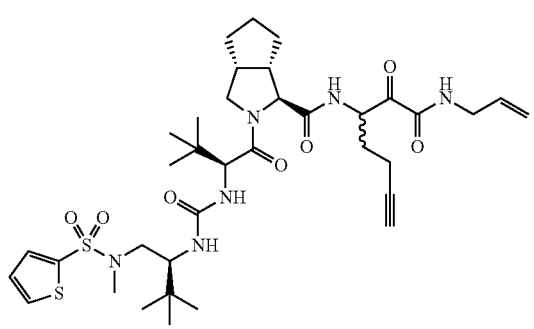
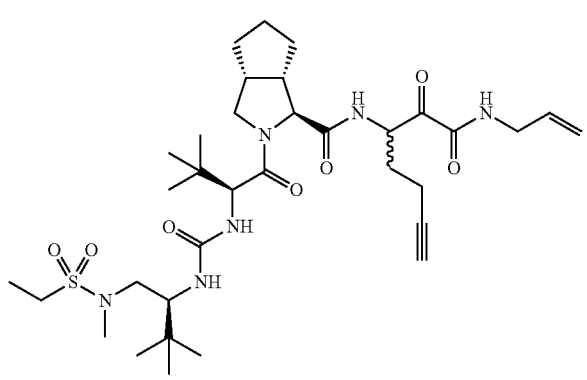
668 -continued
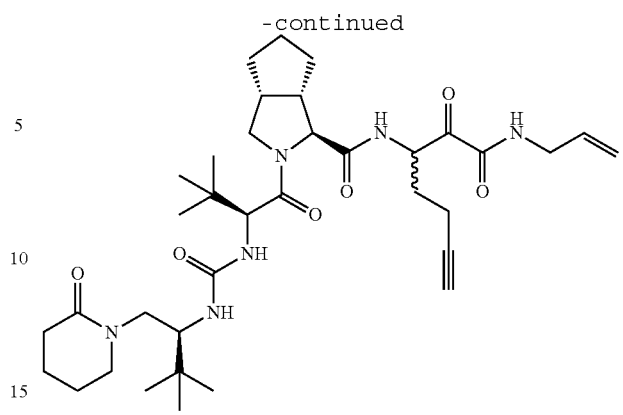
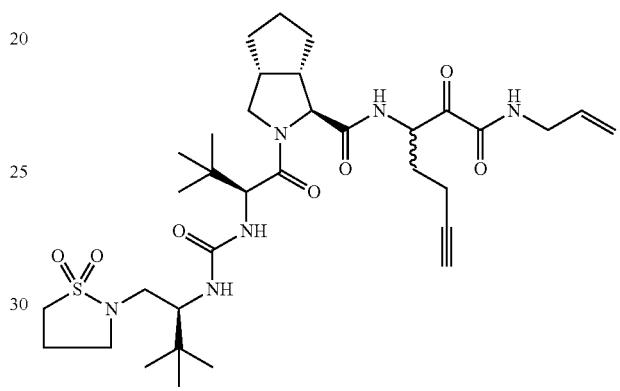
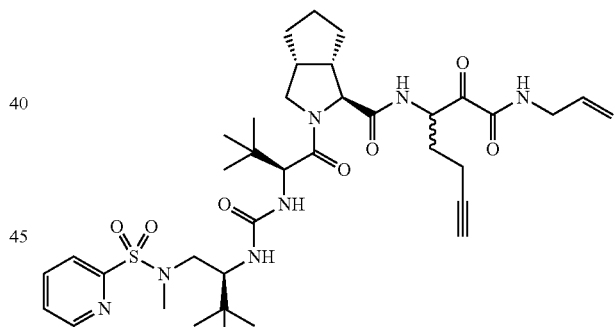
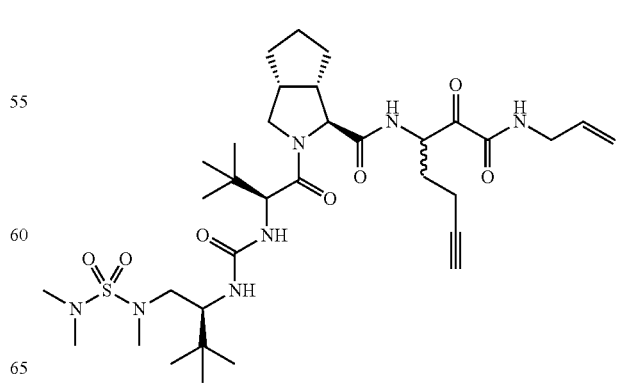

669
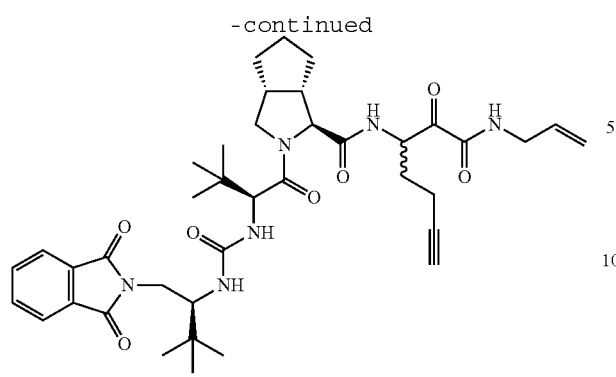
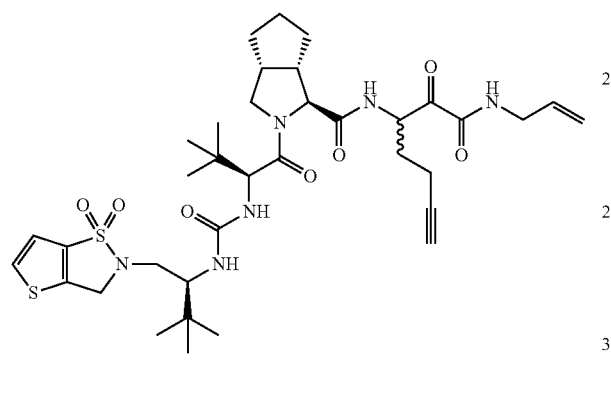
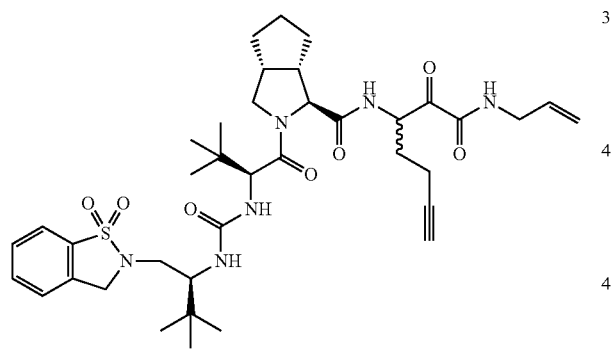
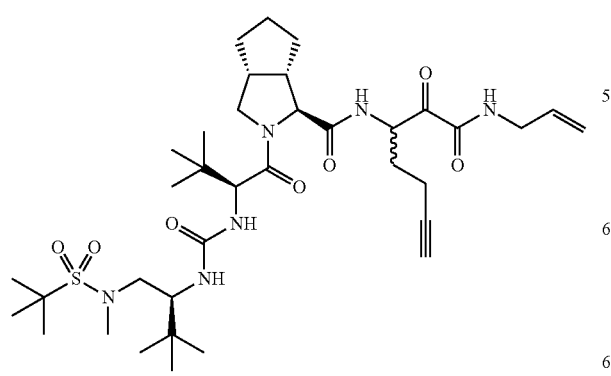
670
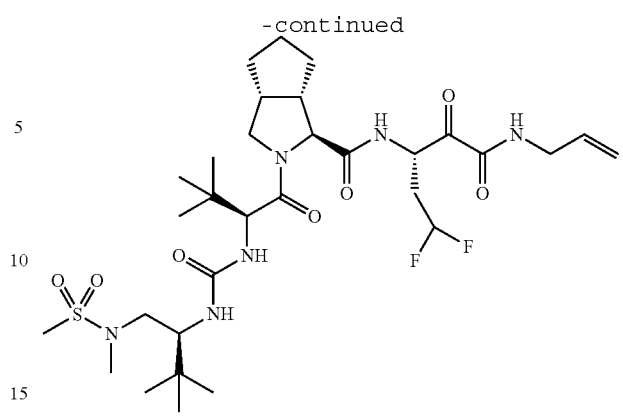
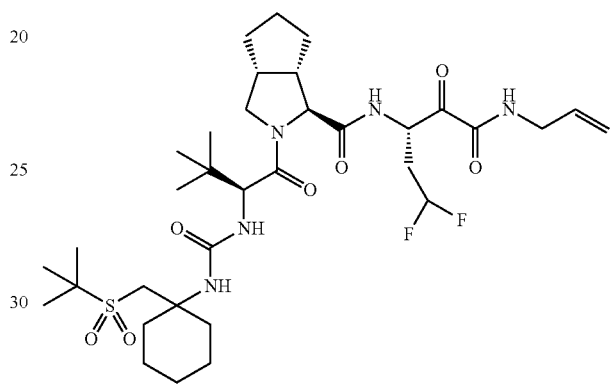
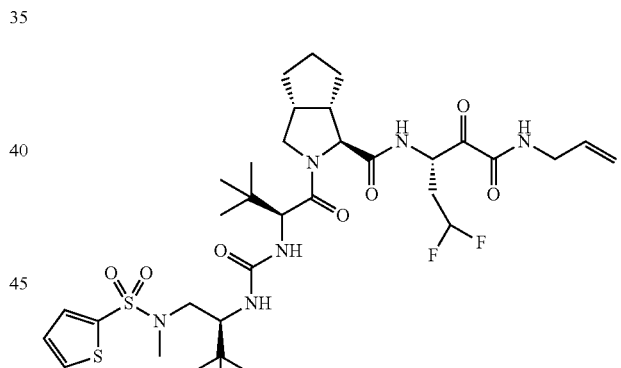
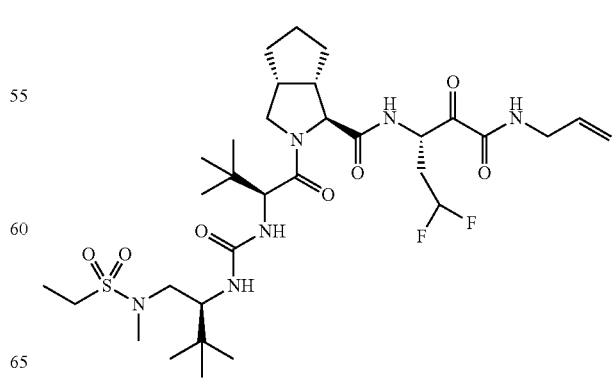

671
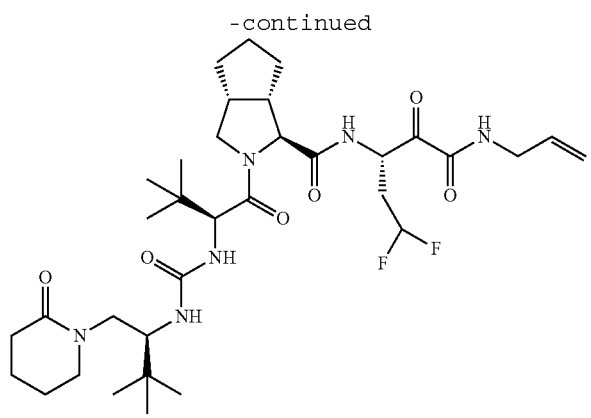
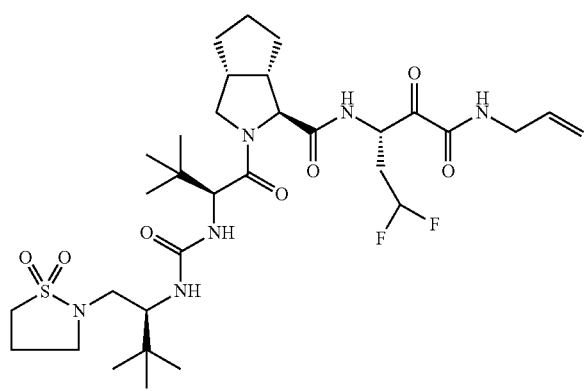
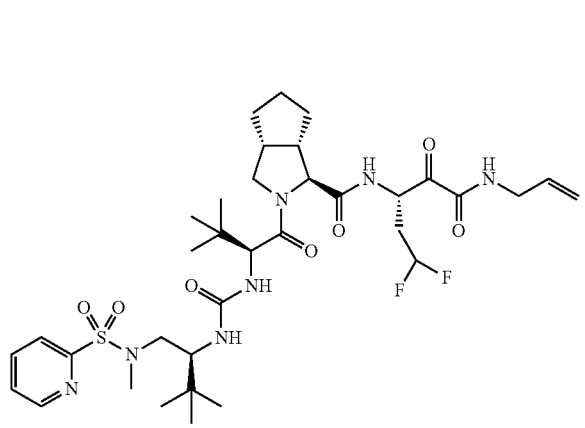
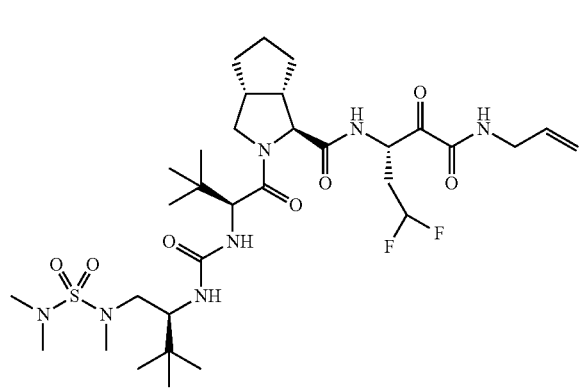
672
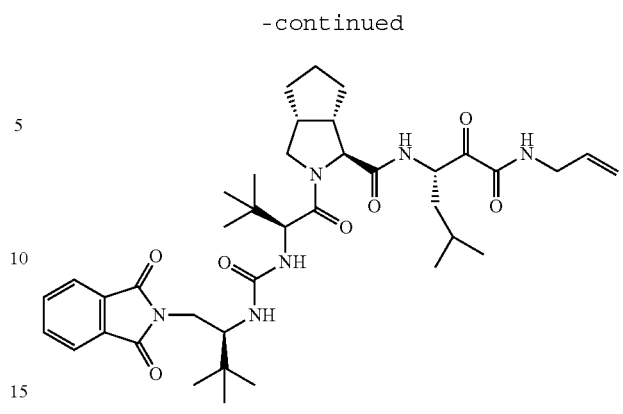
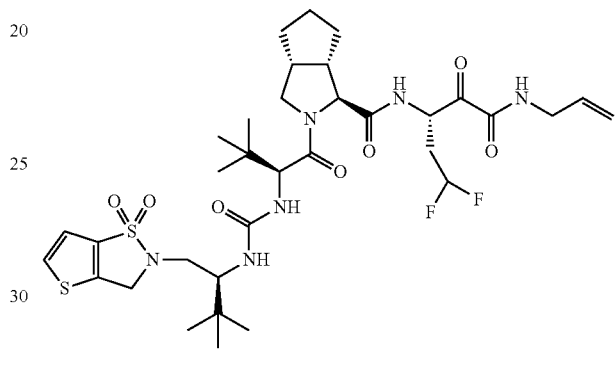
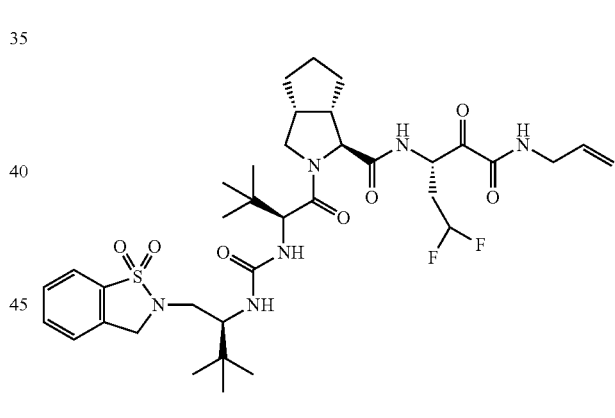
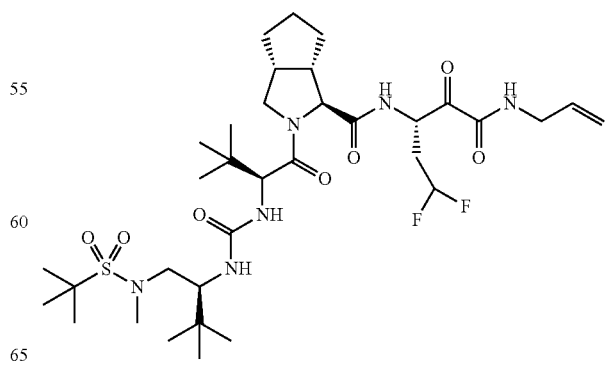

| 673 | 674 |
|---|---|
| 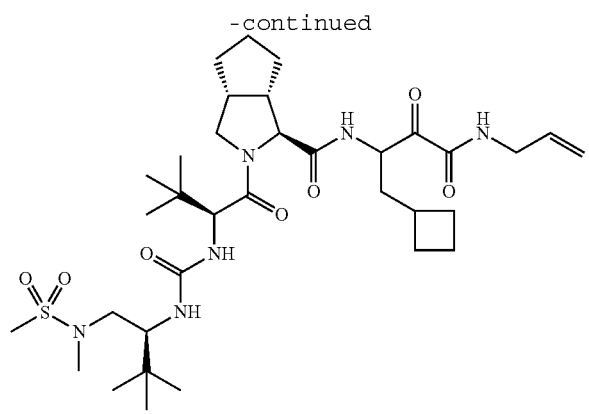 | 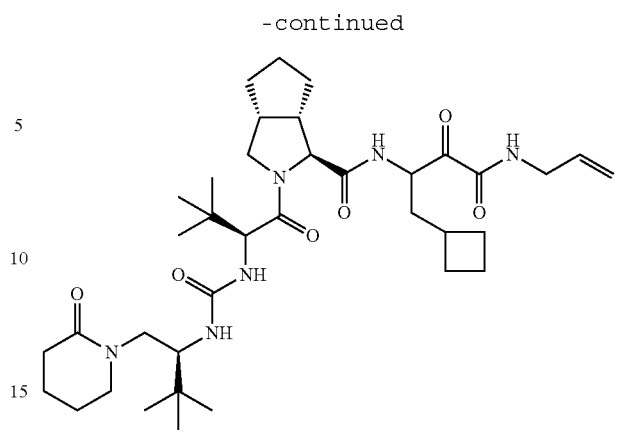 |
| 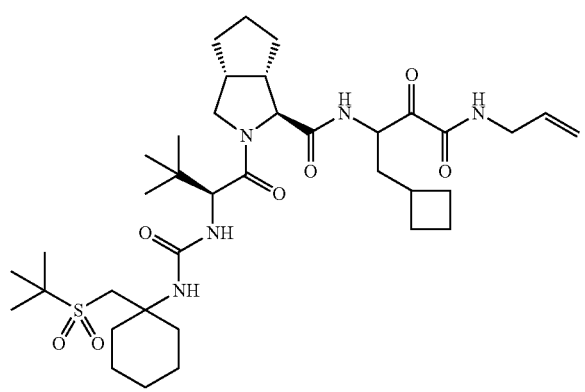 | 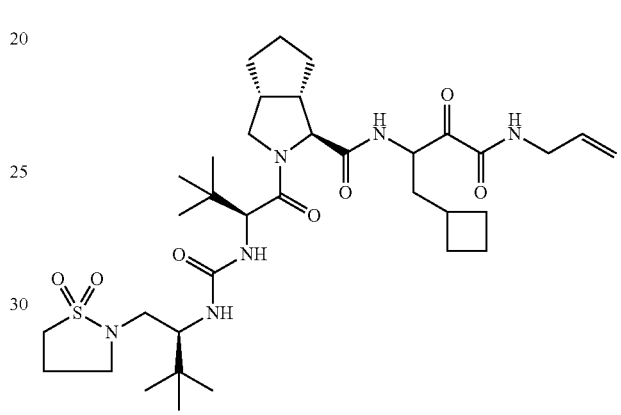 |
| 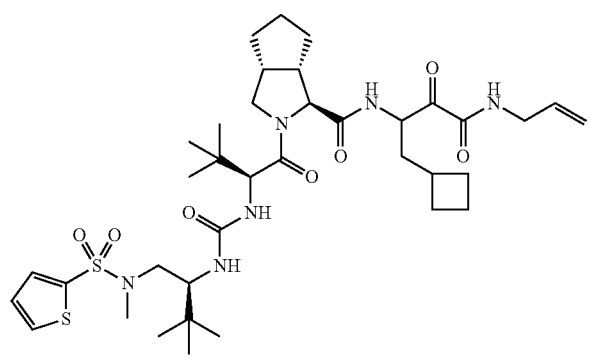 | 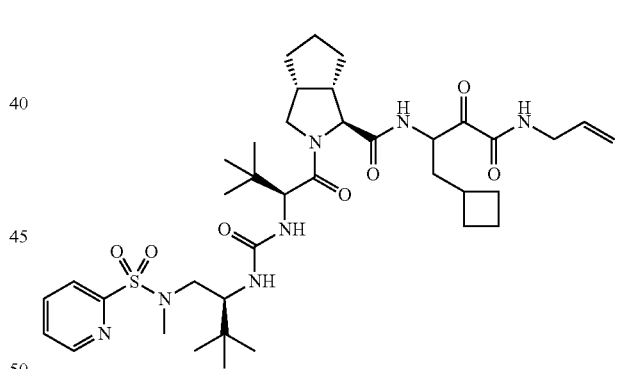 |
| 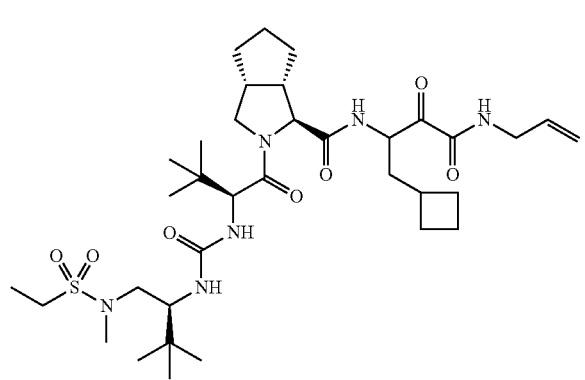 | 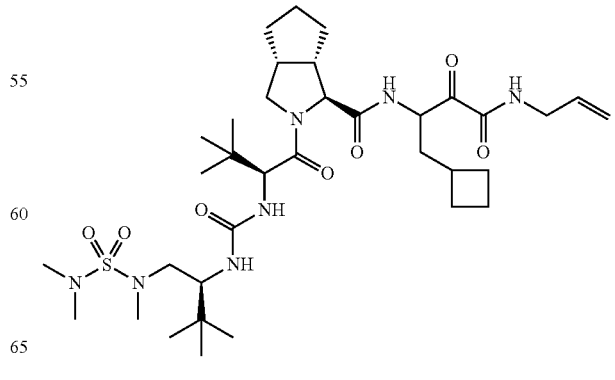 |

675 -continued
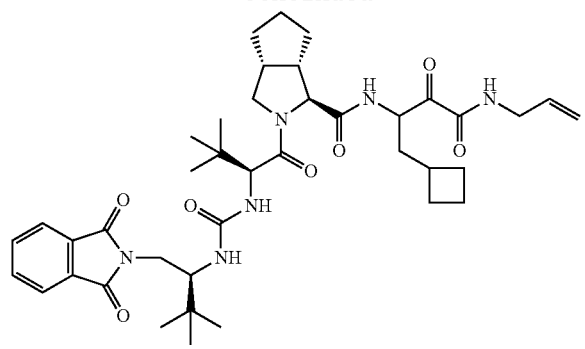
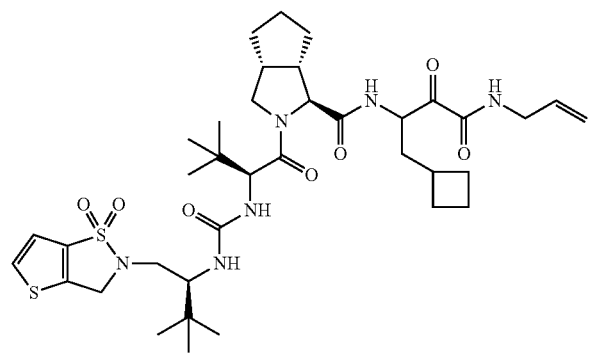
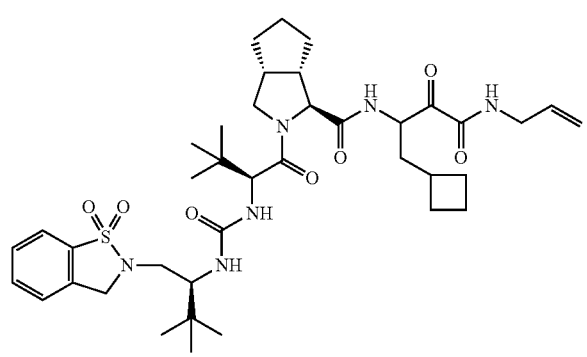
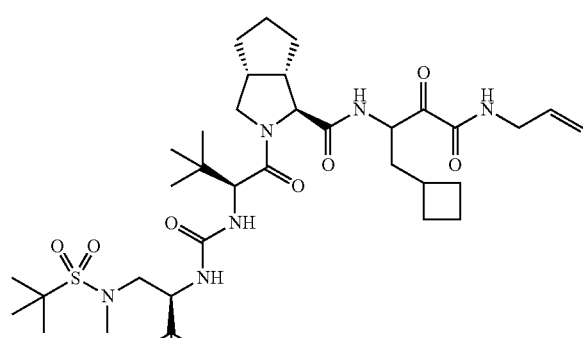
676 -continued
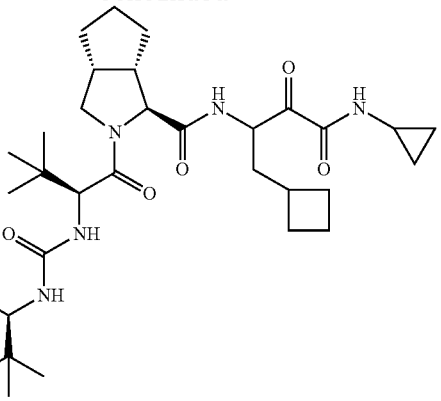
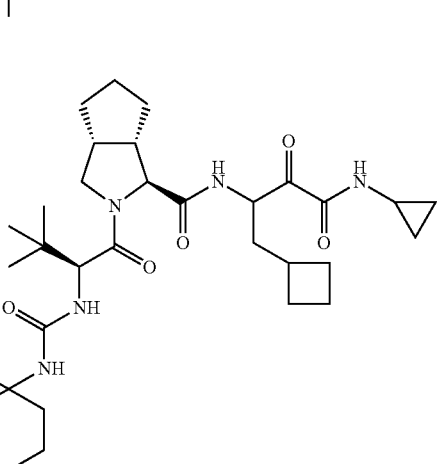
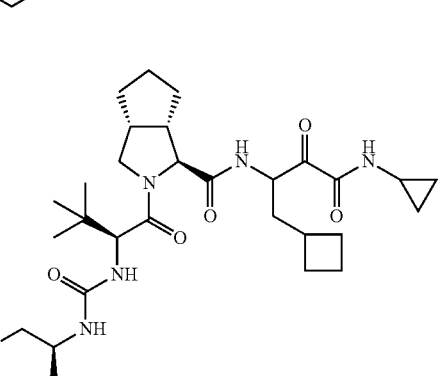
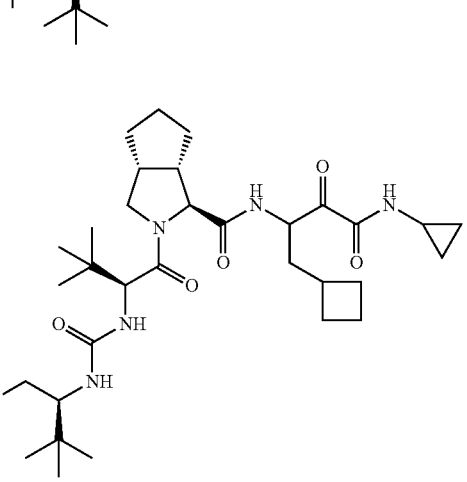

677 -continued
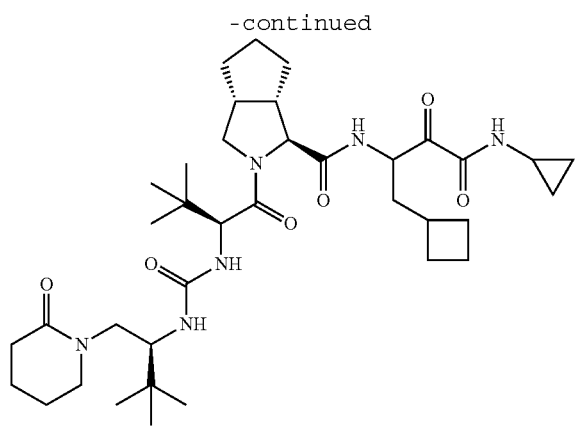
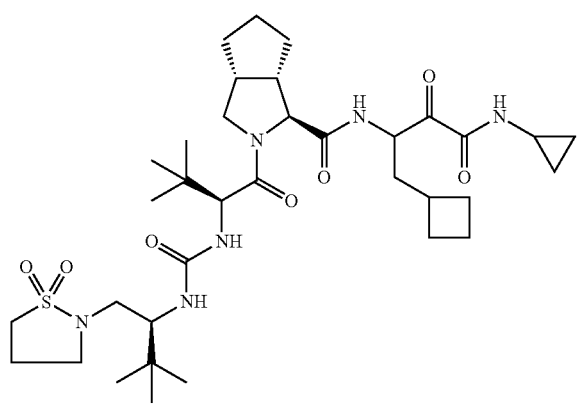
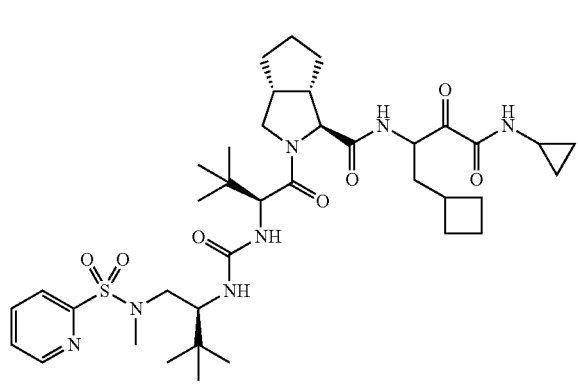
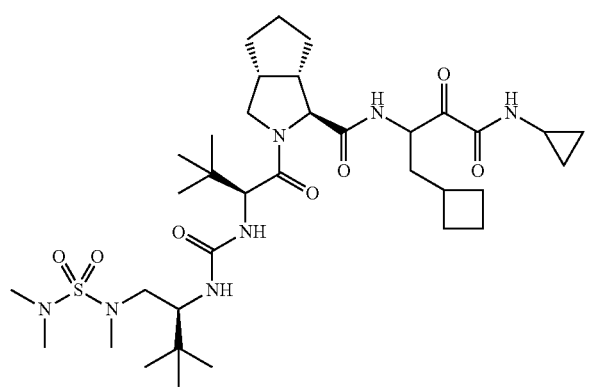
678 -continued
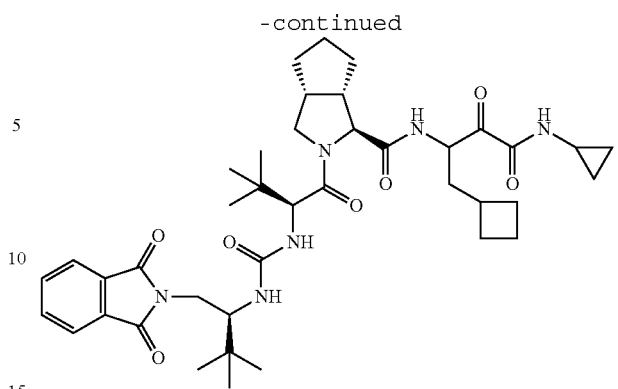
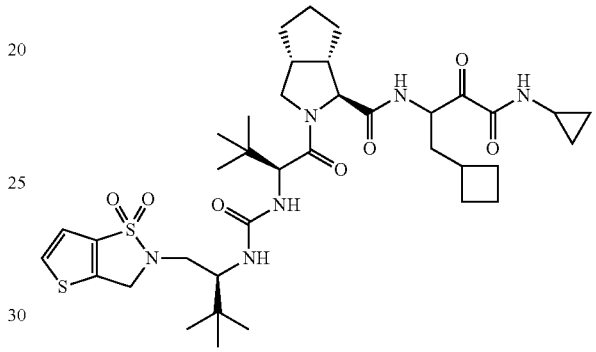
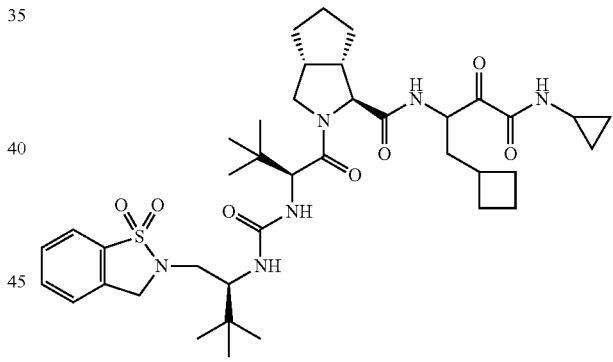
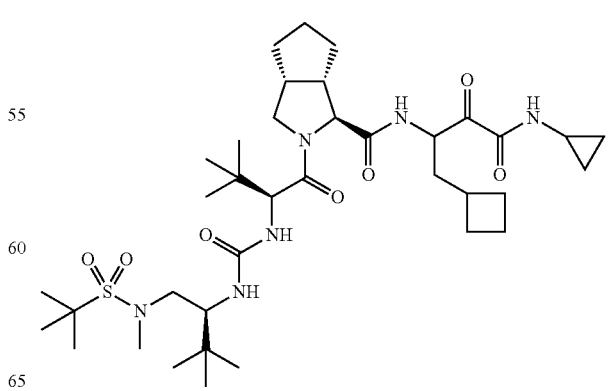

679
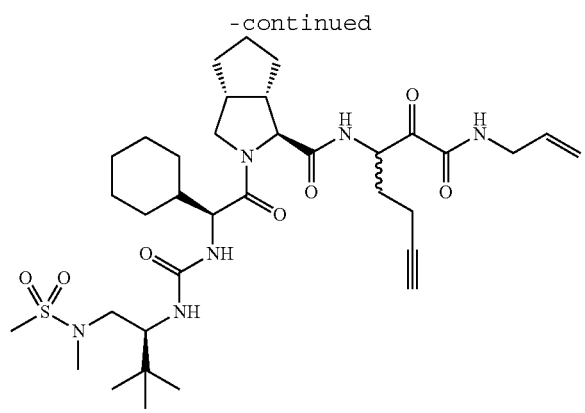
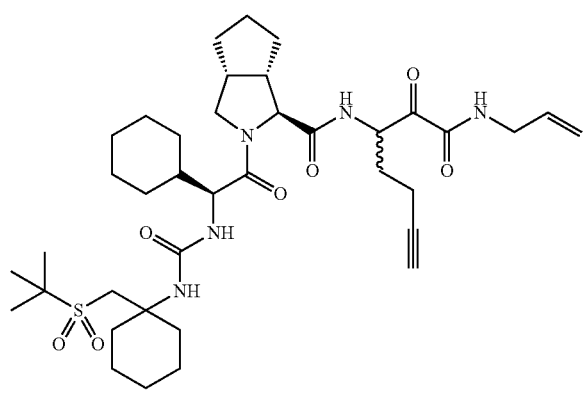
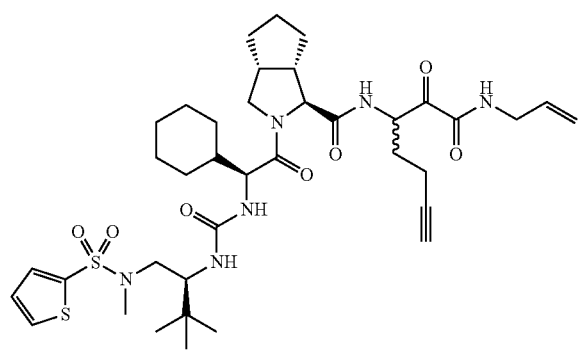
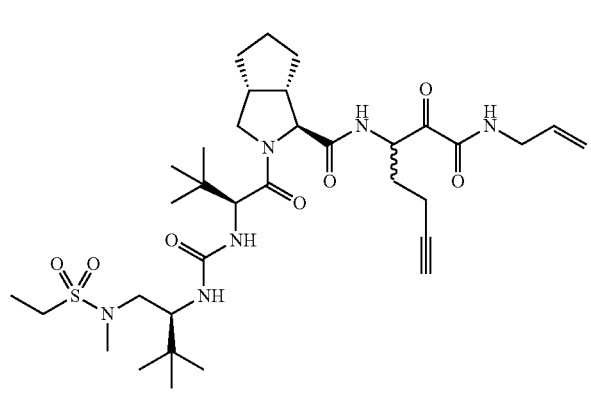
680
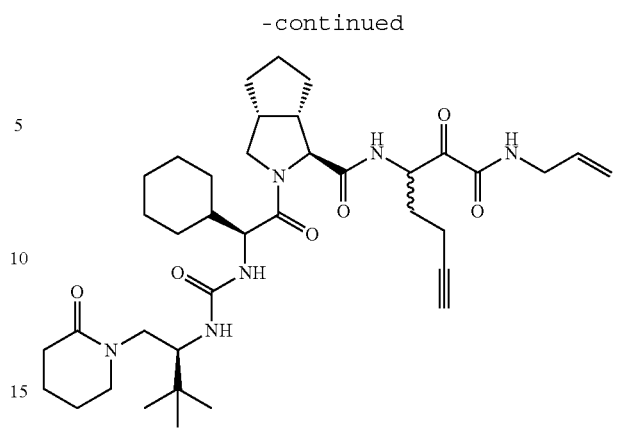
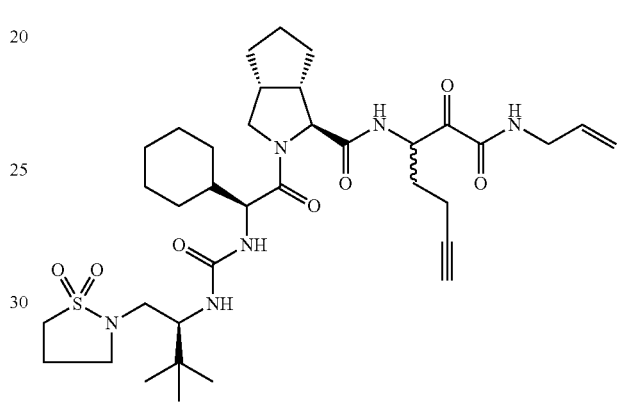
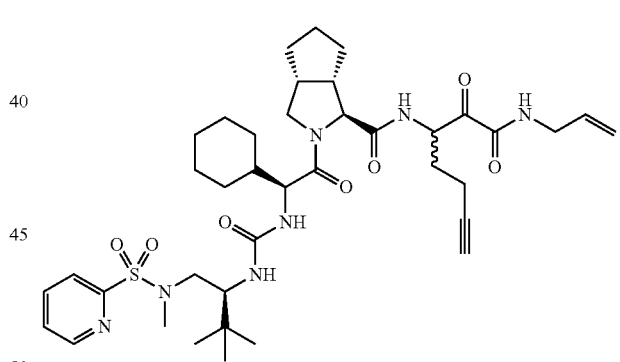
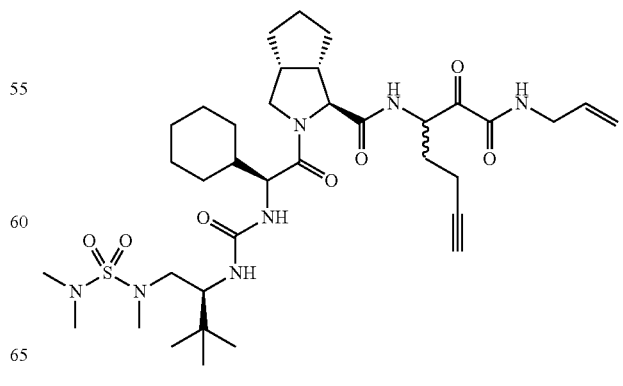

| 681 | 682 |
|---|---|
| 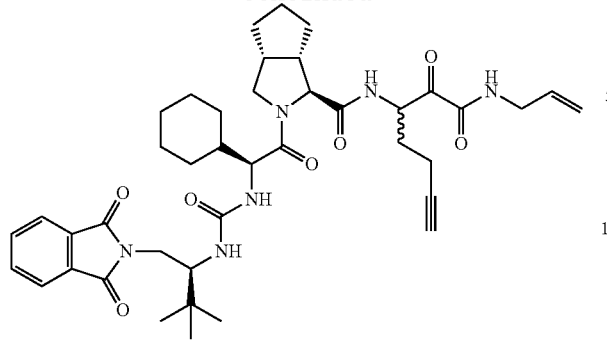 | 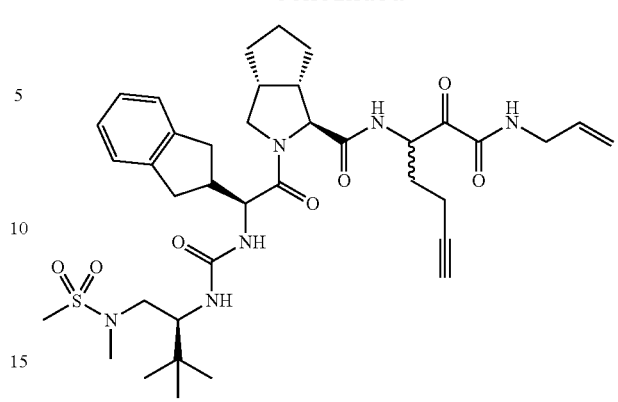 |
| 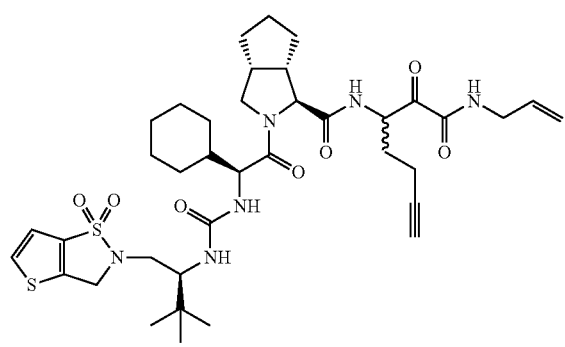 | 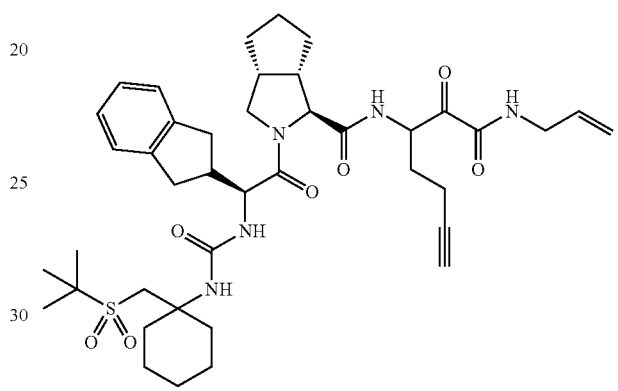 |
| 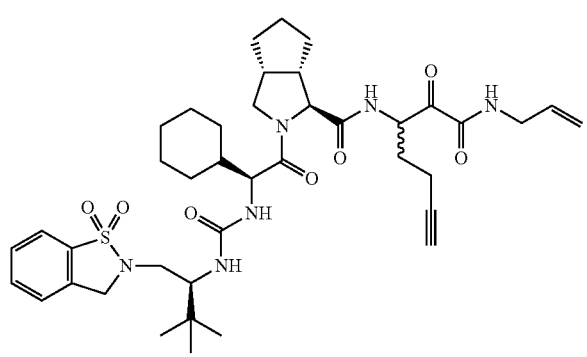 | 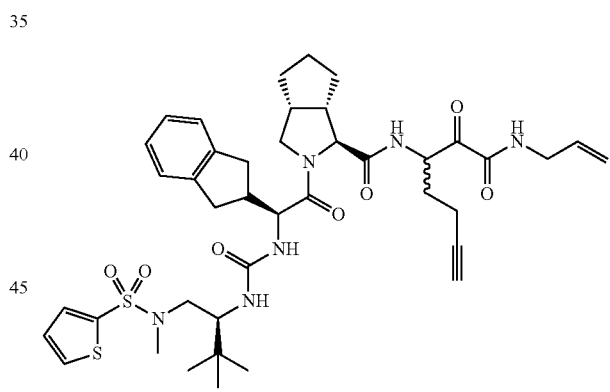 |
| 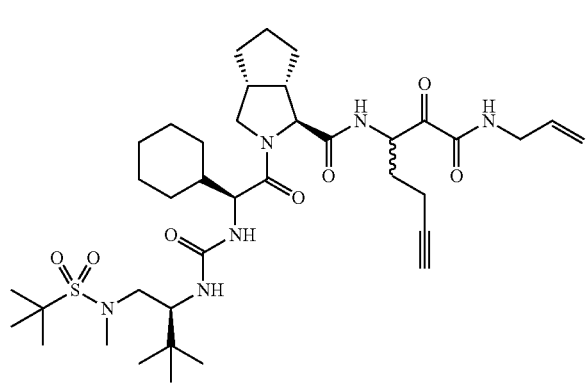 | 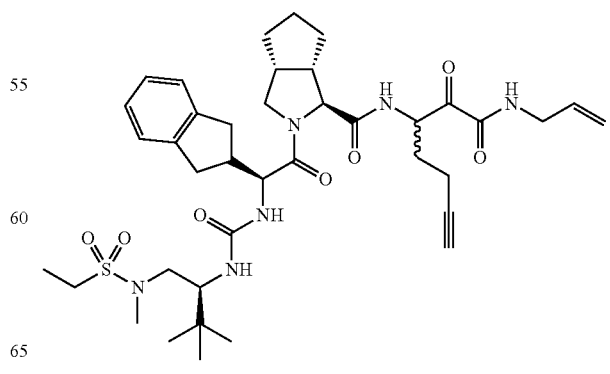 |

683
-continued
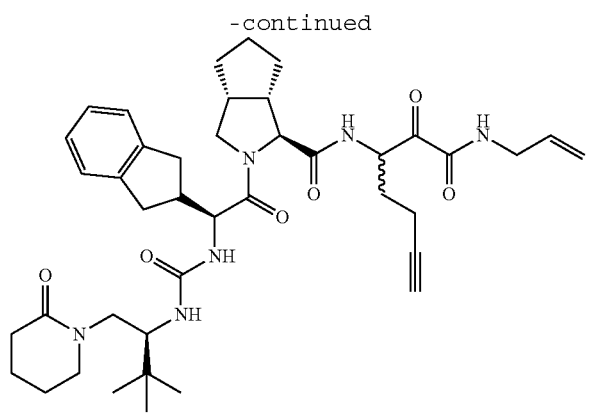
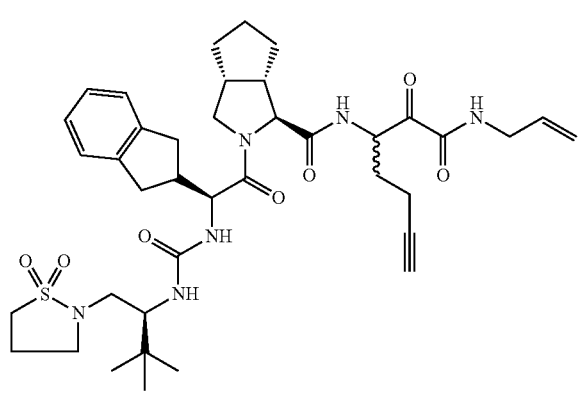
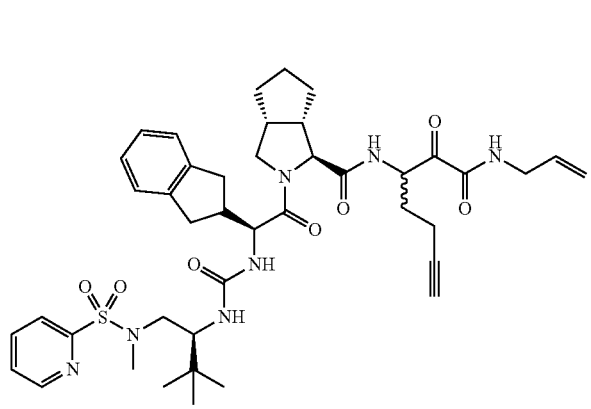
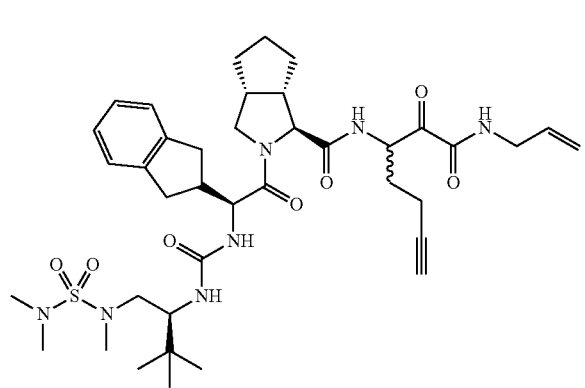
684
-continued
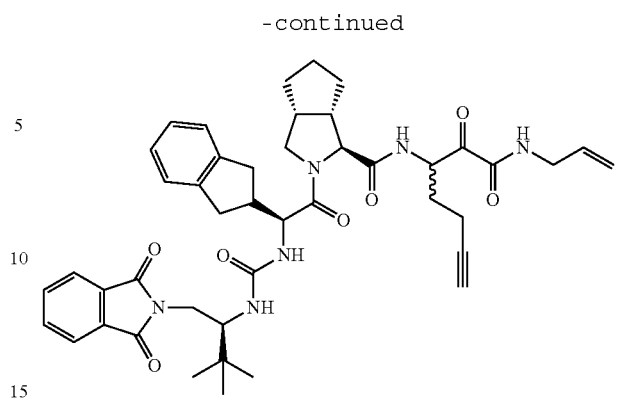
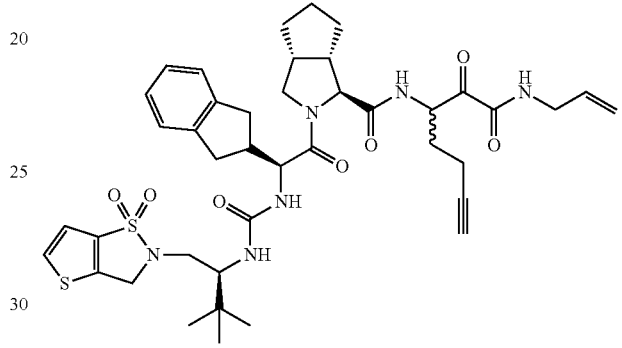
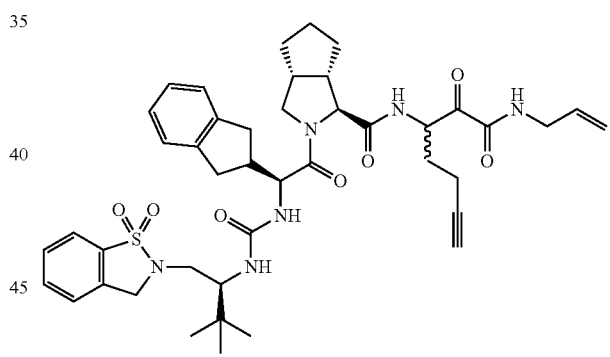
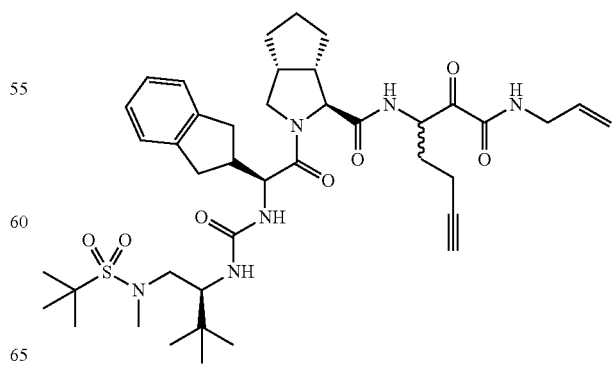

685 686
-continued -continued
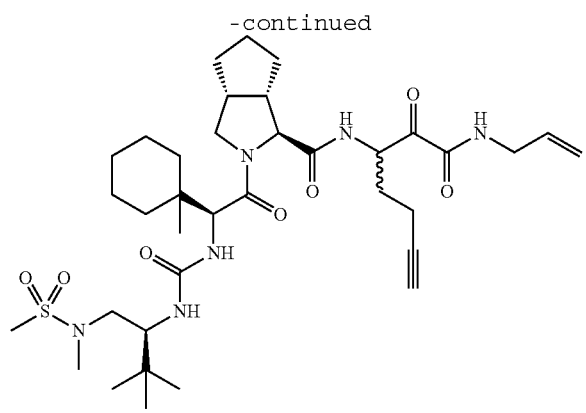 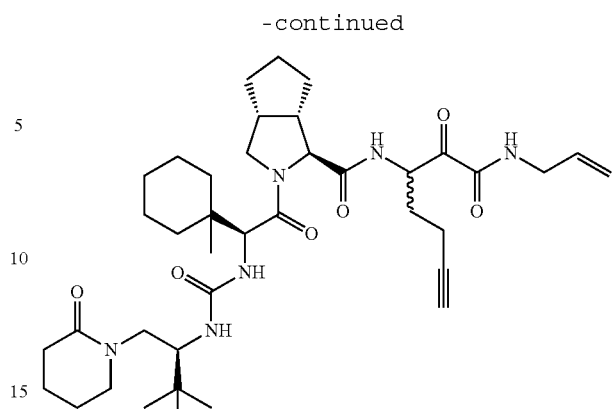
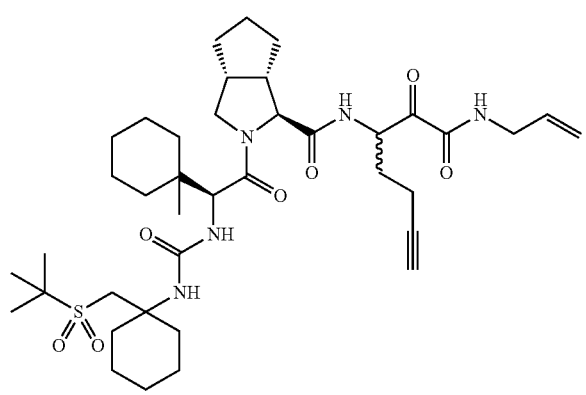 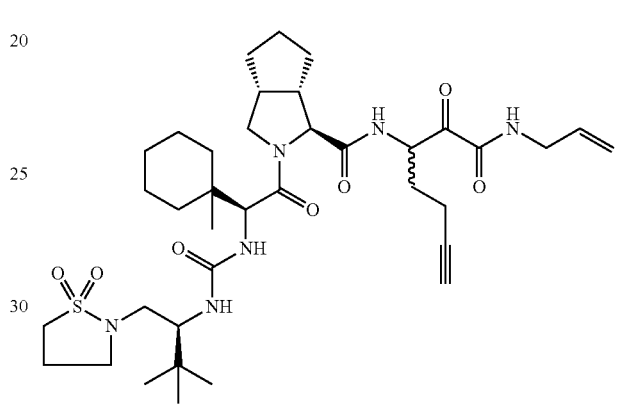
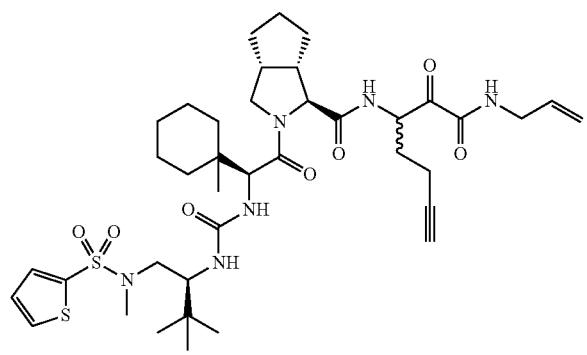 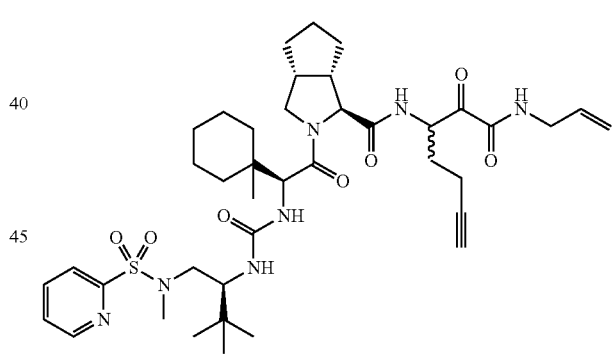
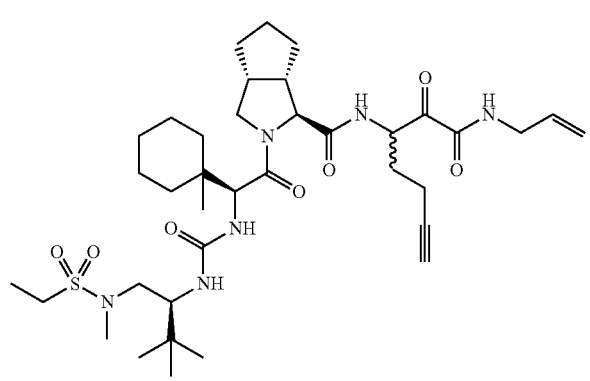 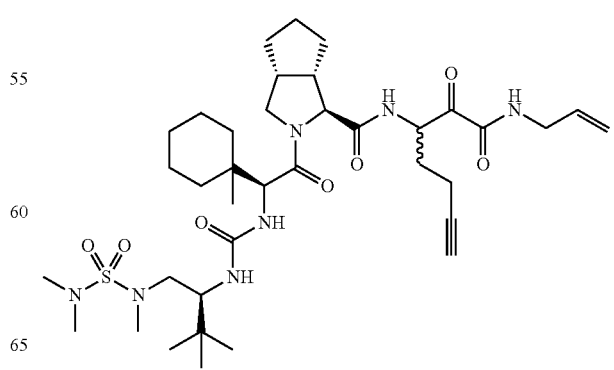

687
-continued
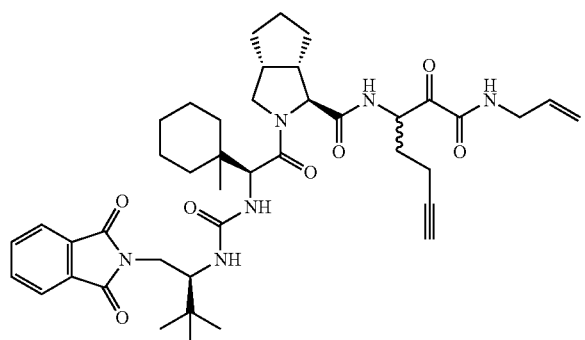
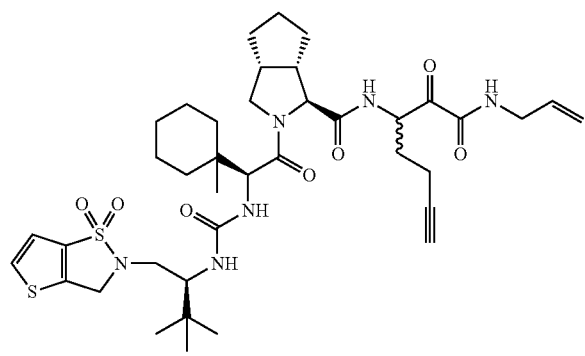
688
-continued
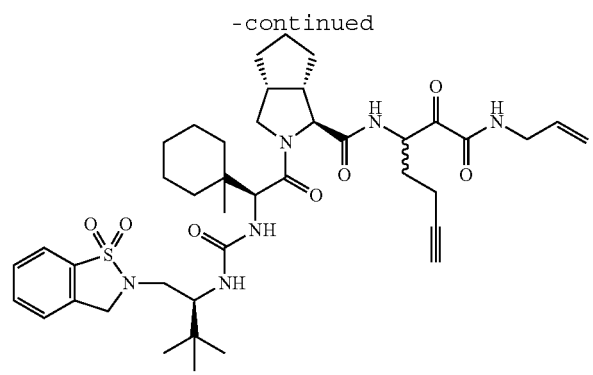
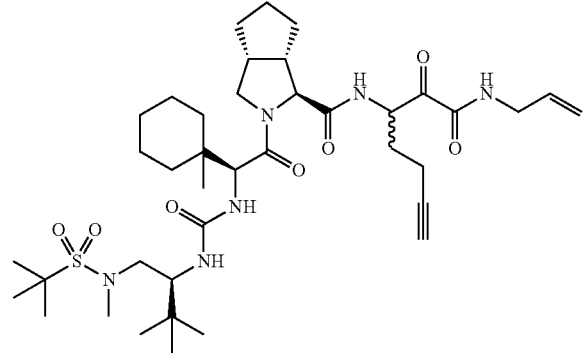
or a pharmaceutically acceptable salt, solvate or ester thereof.
Compounds of formula XVII are disclosed in U.S. patent application Ser. No. 11/064,574 filed Feb. 24, 2005. The preparation of these compounds is disclosed in the experimental section of this application set forth hereinbelow.
Non-limiting examples of certain compounds disclosed in U.S. patent application Ser. No. 11/064,574 are:
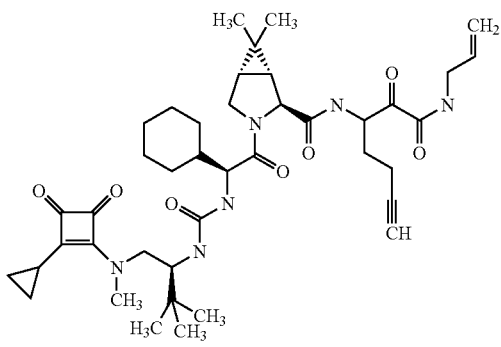
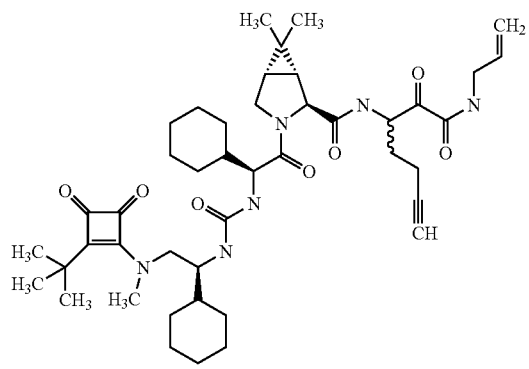
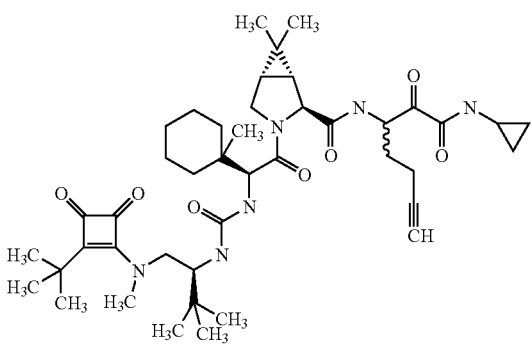
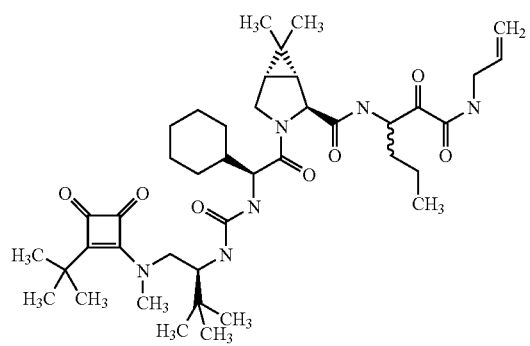

-continued
689
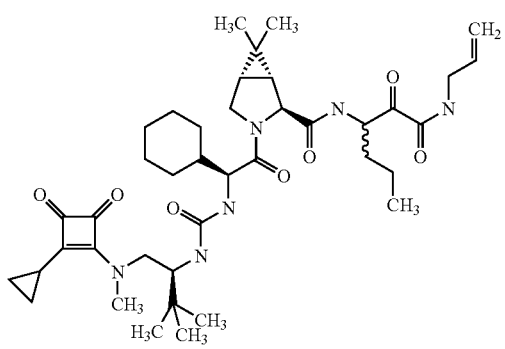
690
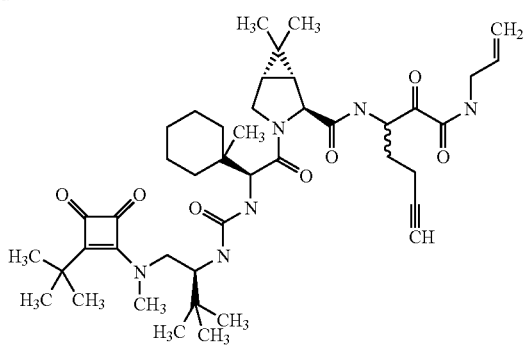
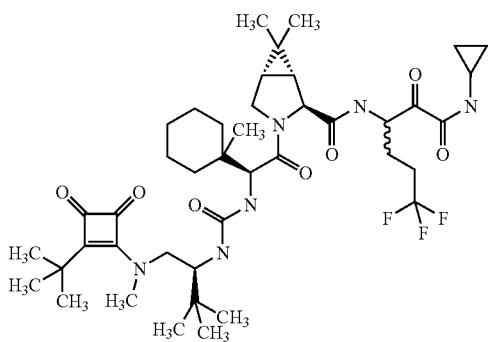
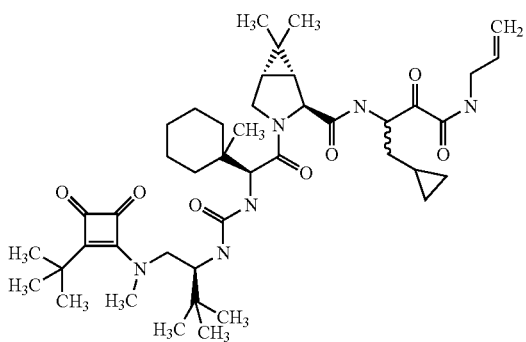
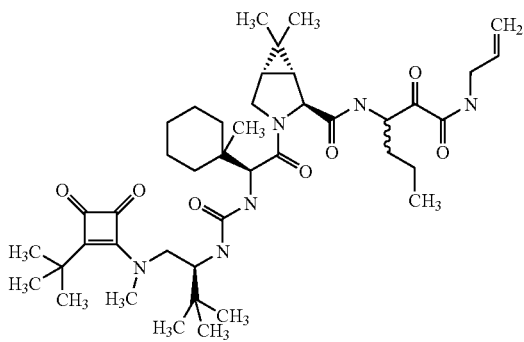
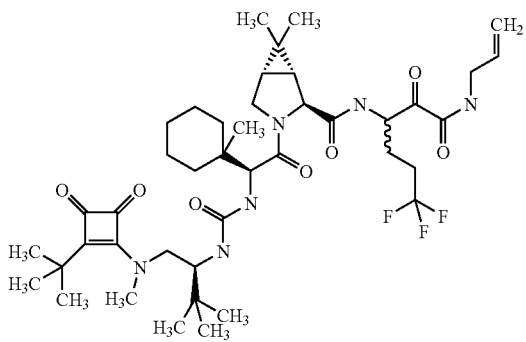
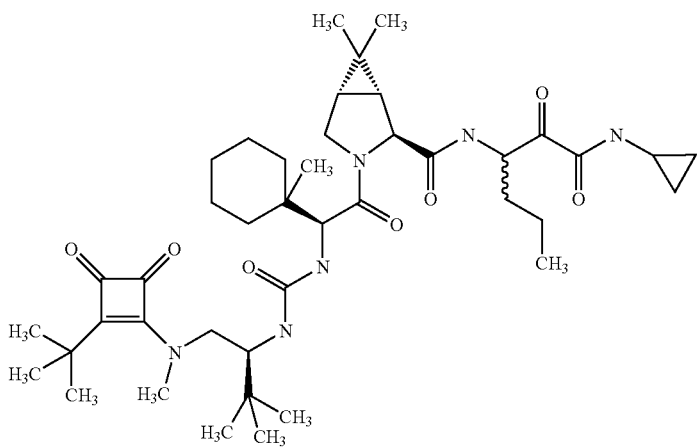 and

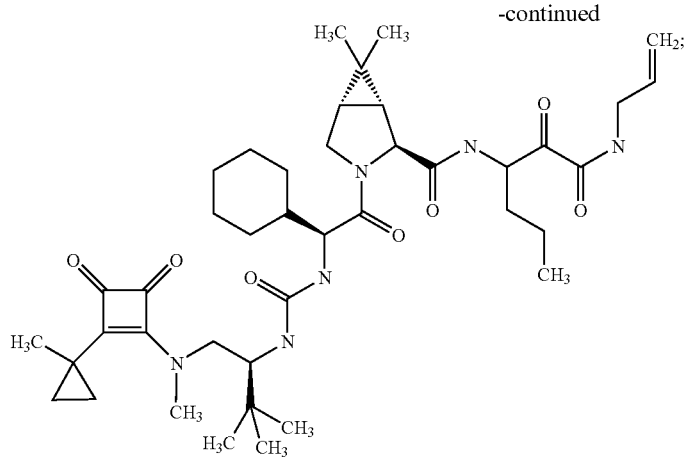

or a pharmaceutically acceptable salt, solvate or ester thereof.

Compounds of formula XVIII are disclosed in U.S. Provisional Patent Application Ser. No. 60/605,234 filed Aug. 27, 2004. The preparation of these compounds is disclosed in the experimental section of this application set forth hereinbelow.

Non-limiting examples of certain compounds disclosed in U.S. Provisional Patent Application Ser. No. 60/605,234 are:

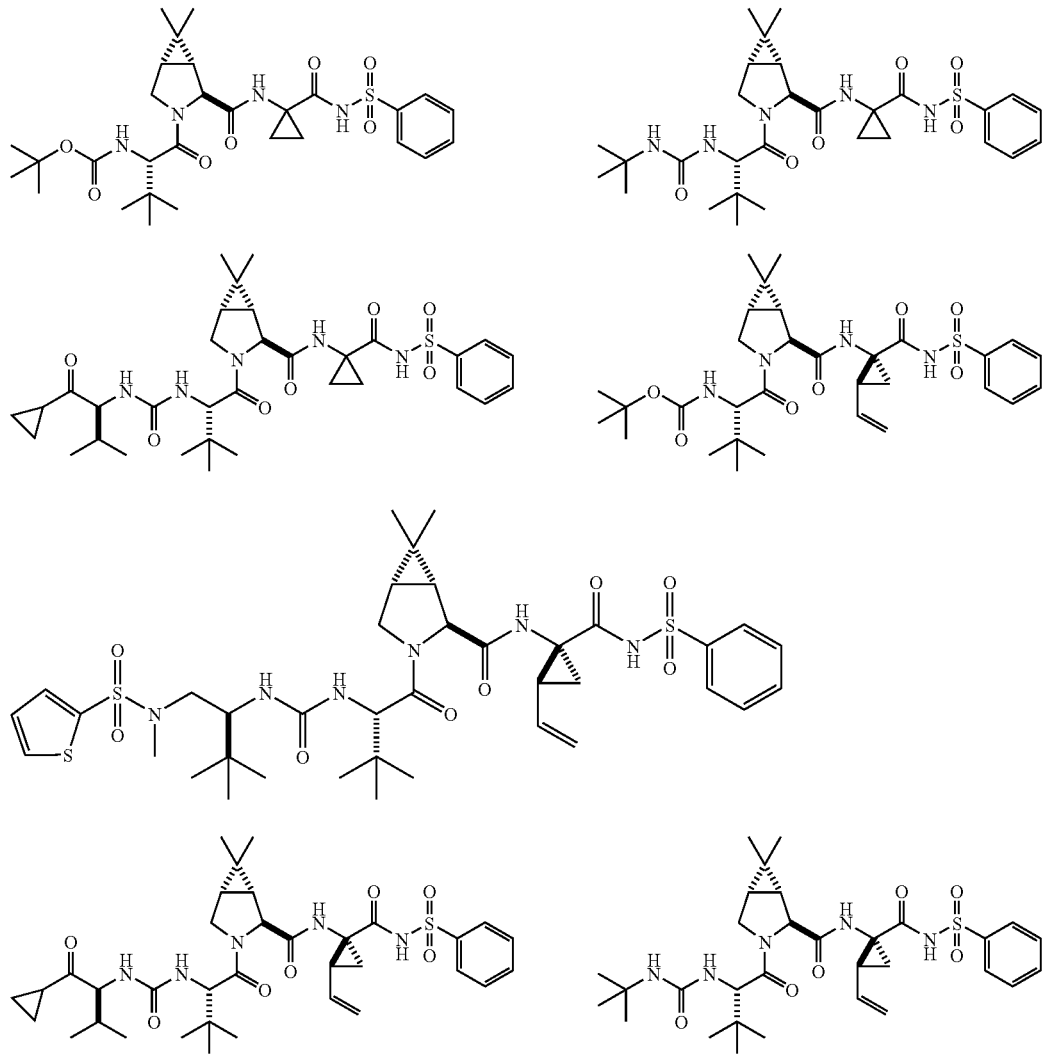

-continued
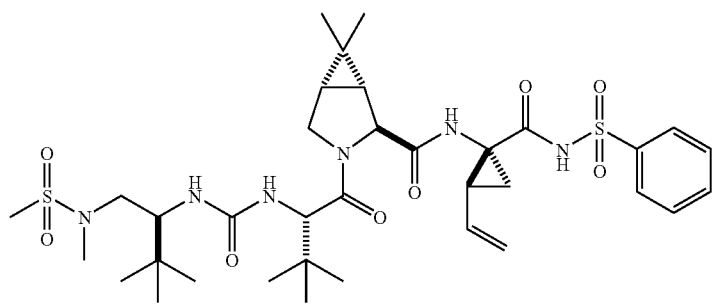
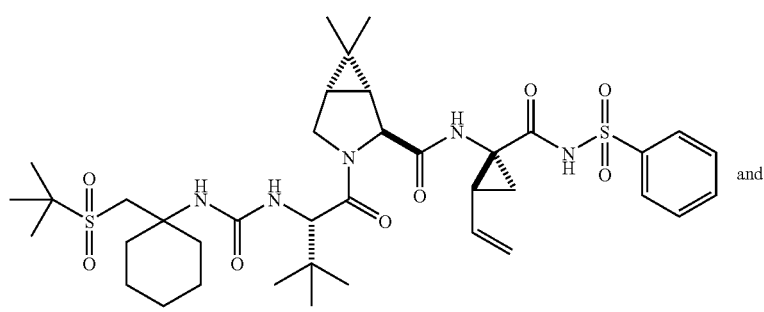
and
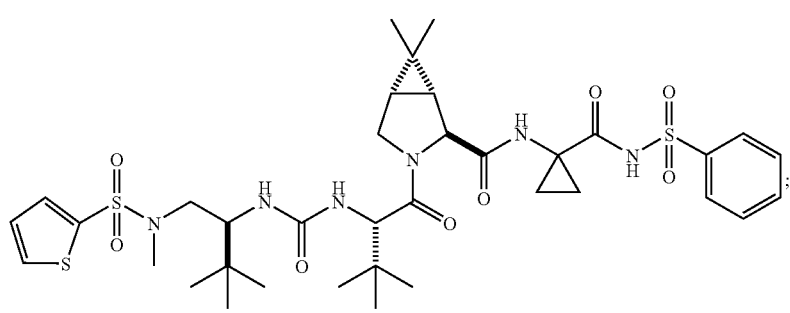
or a pharmaceutically acceptable salt, solvate or ester thereof.
Compounds of formula XIX are disclosed in U.S. Provisional Patent Application Ser. No. 60/573,191 filed May 20, 2004. The preparation of these compounds is disclosed in the experimental section of this application set forth hereinbelow.

Non-limiting examples of certain compounds disclosed in U.S. Provisional Patent Application Ser. No. 60/573,191 are:
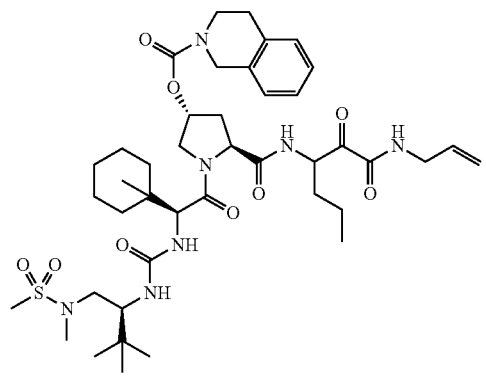
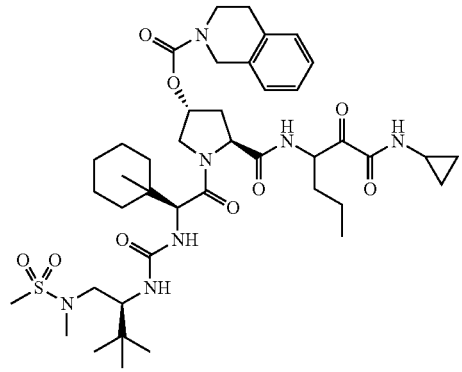
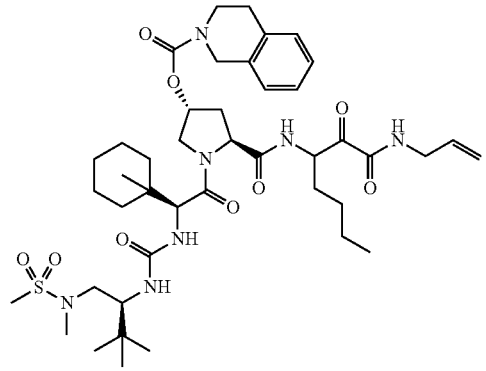
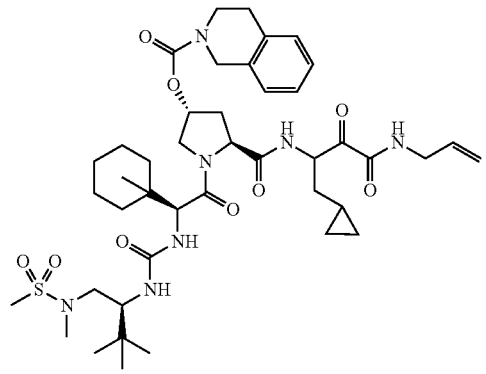
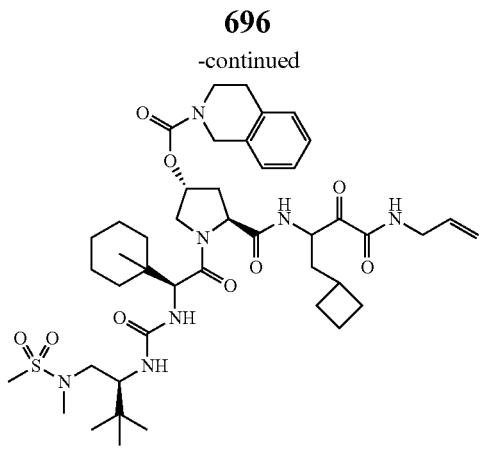
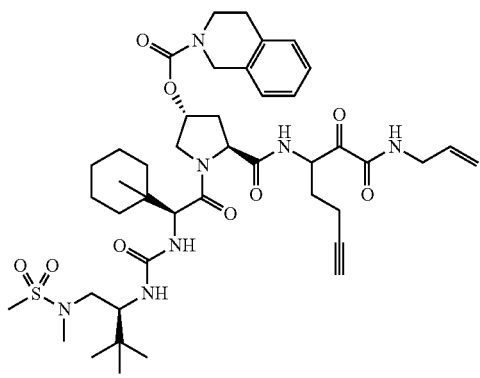
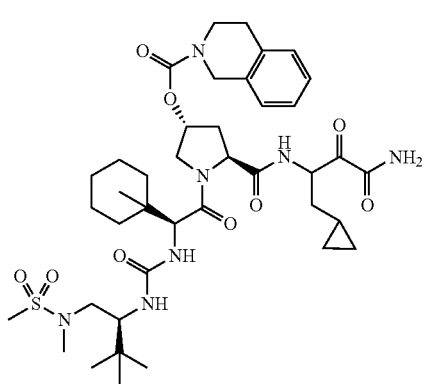
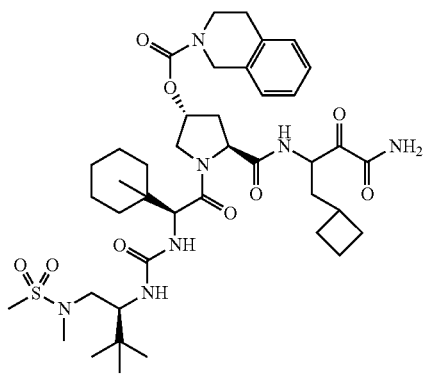

697
-continued
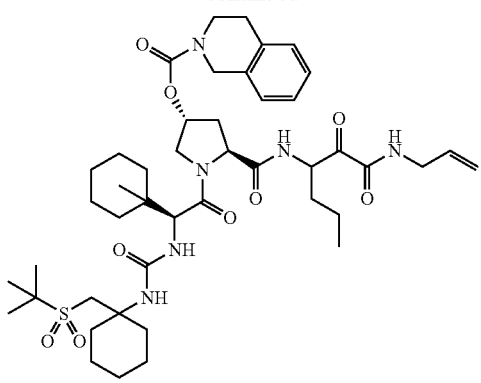
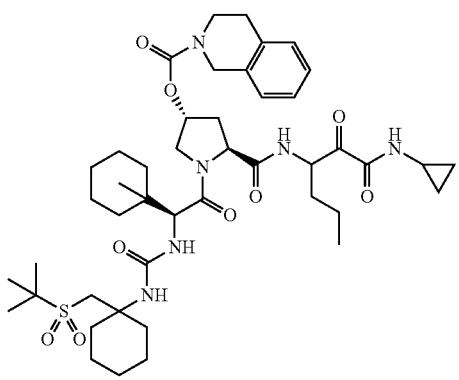
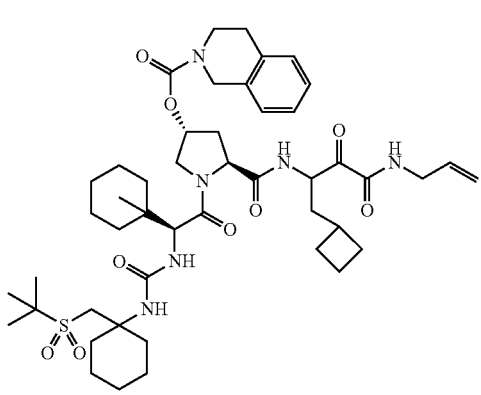
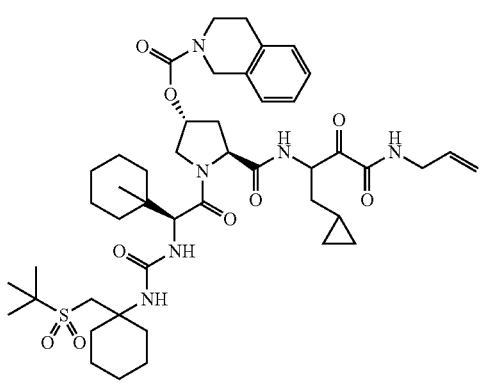
698
-continued
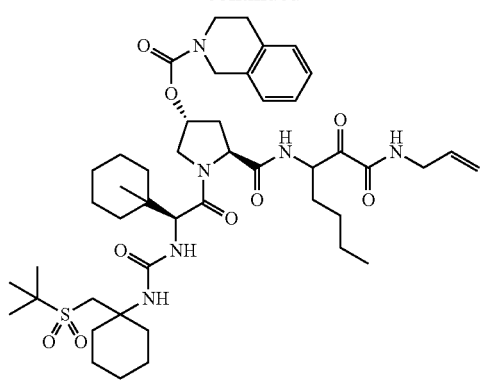
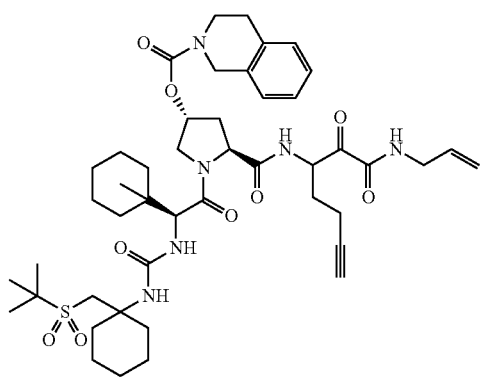
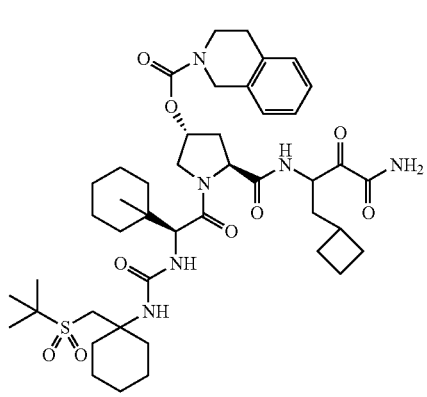

| 699 -continued | 700 -continued |
|---|---|
| 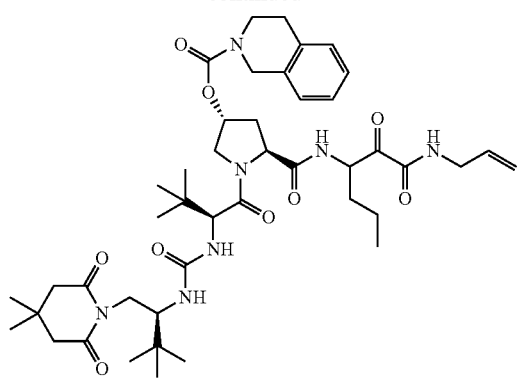 | 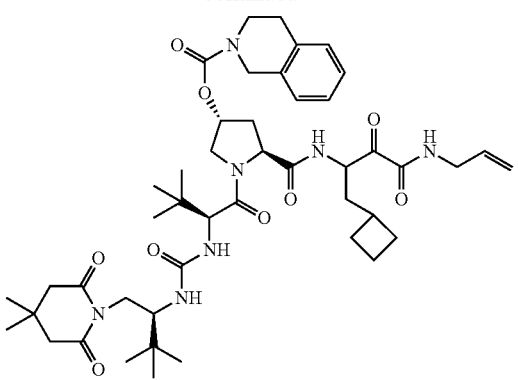 |
| 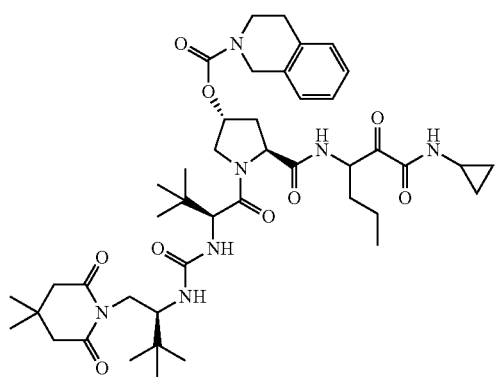 | 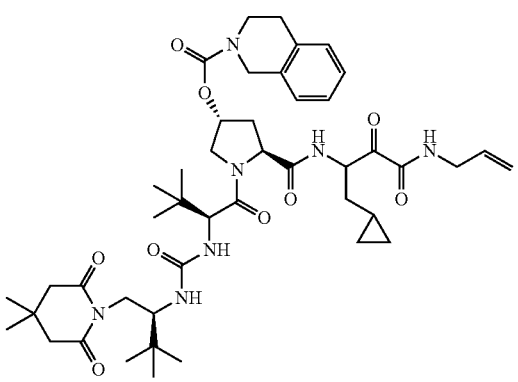 |
| 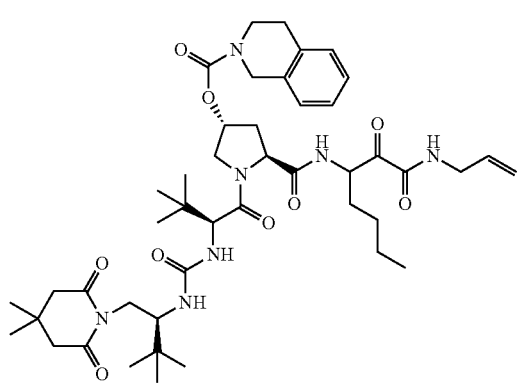 | 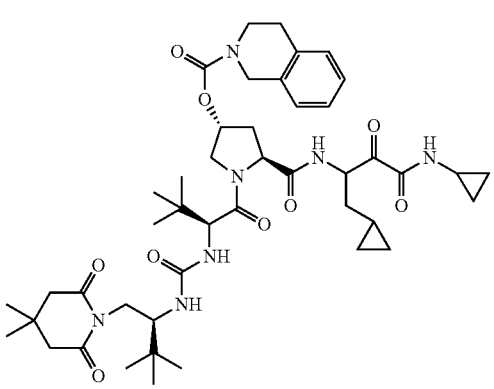 |
| 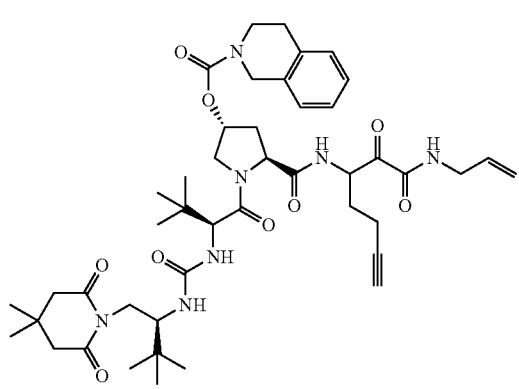 | 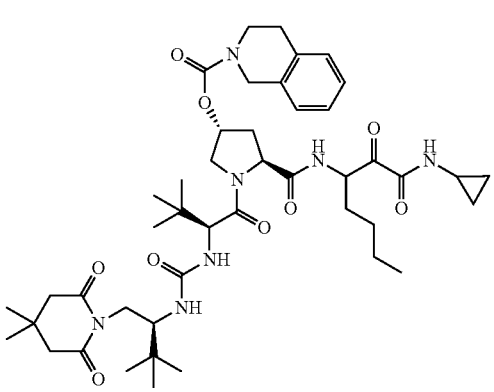 |

-continued
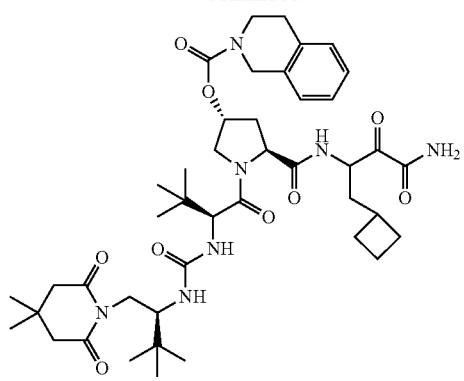
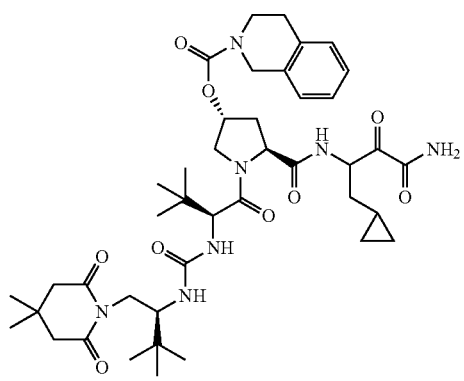
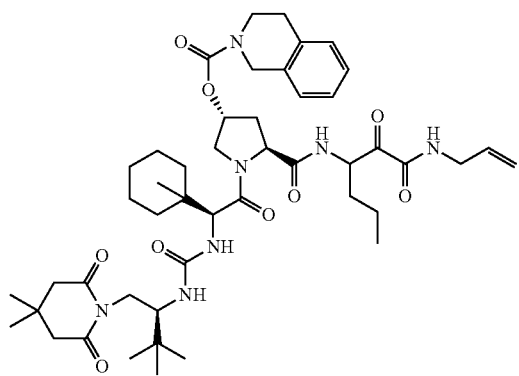
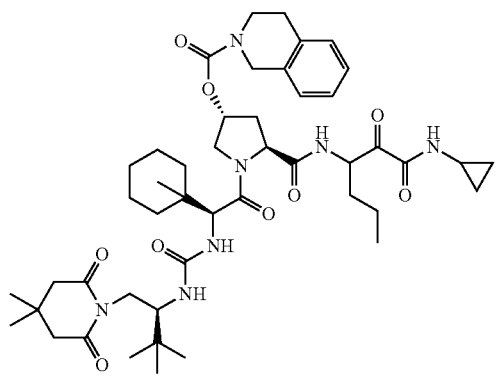
-continued
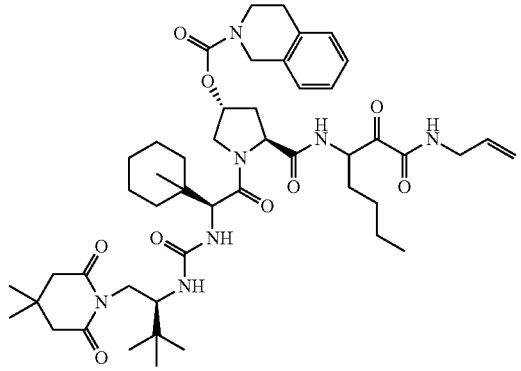
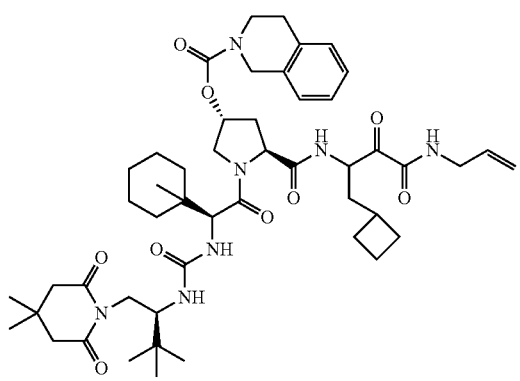
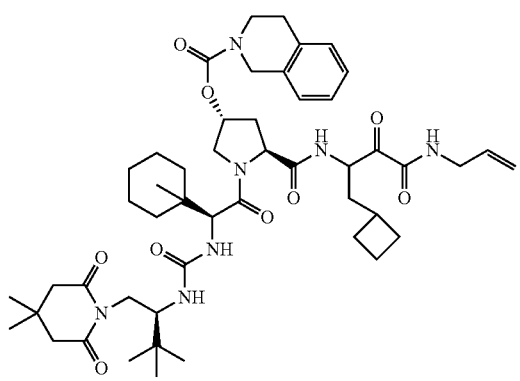
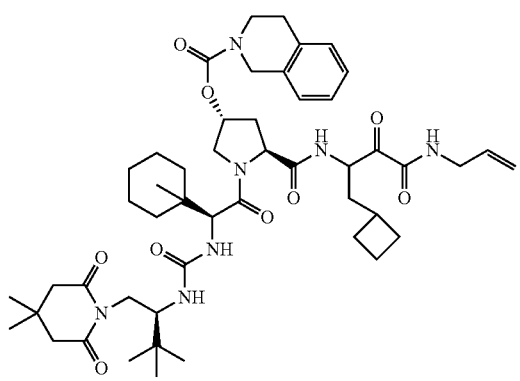

703
-continued
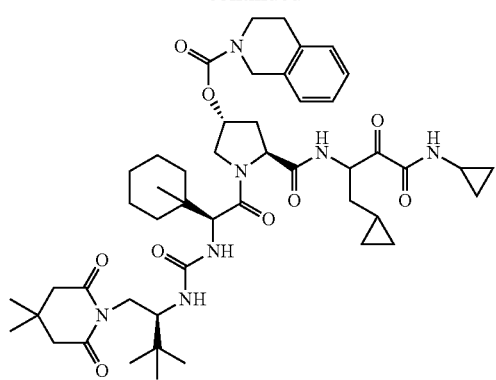
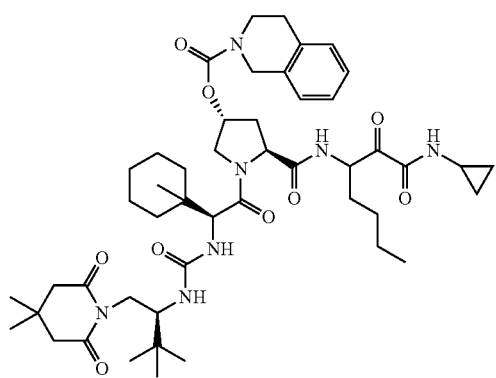
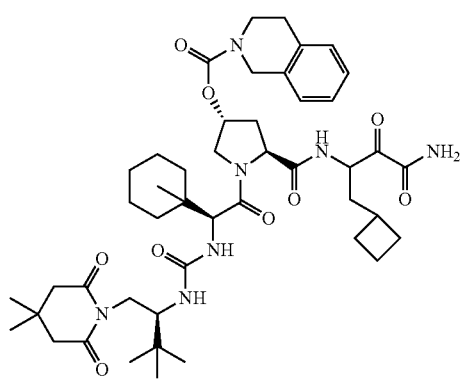
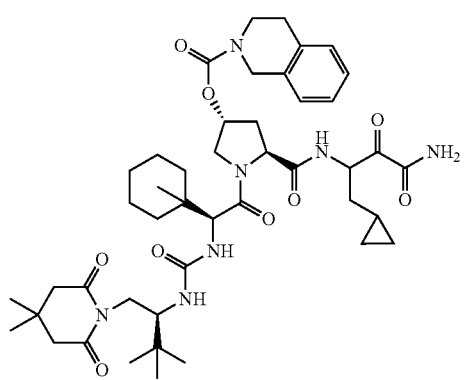
704
-continued
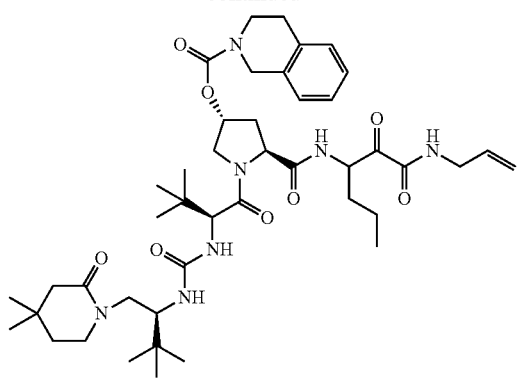
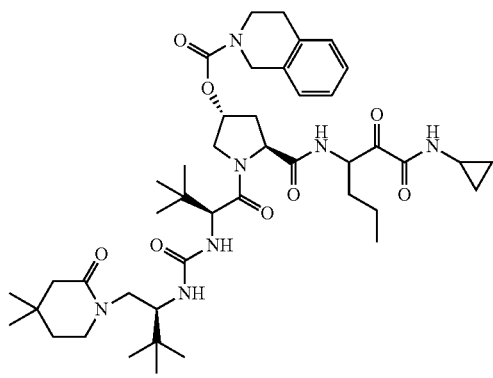
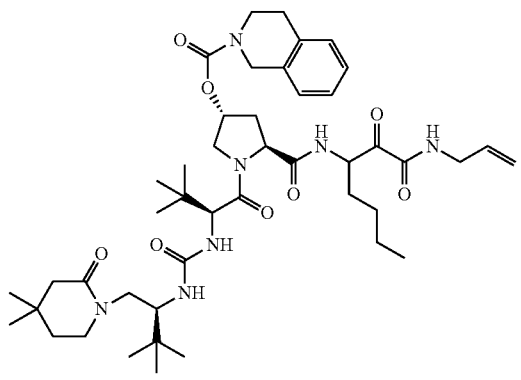
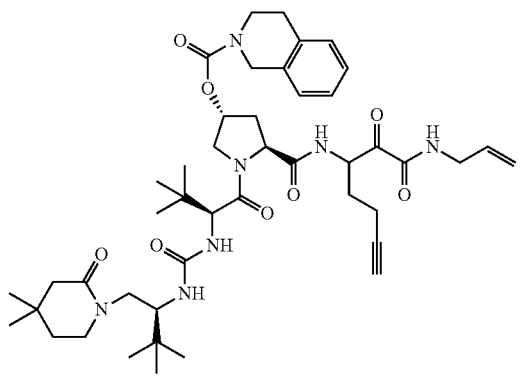

705
-continued
706
-continued
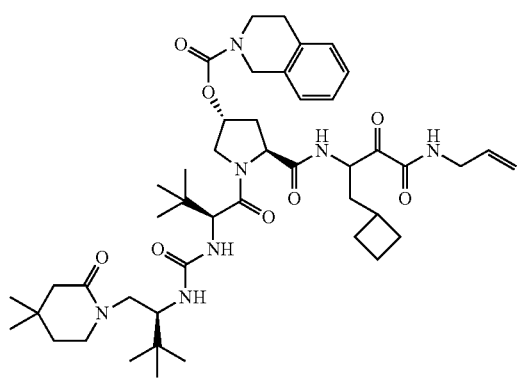
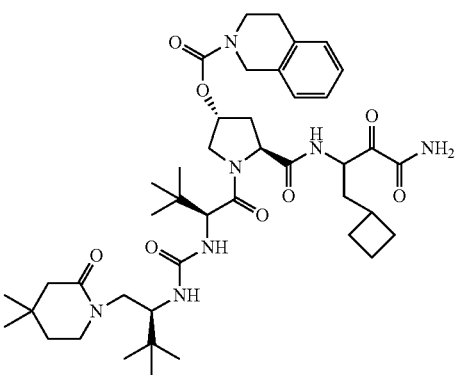

707
-continued
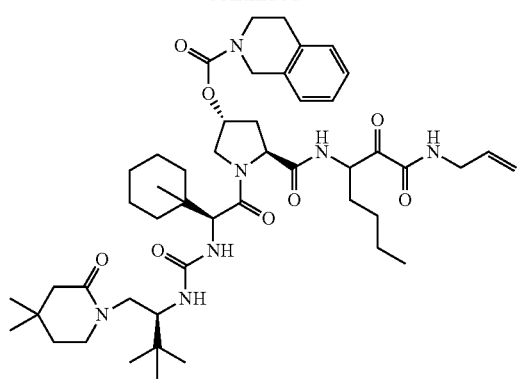
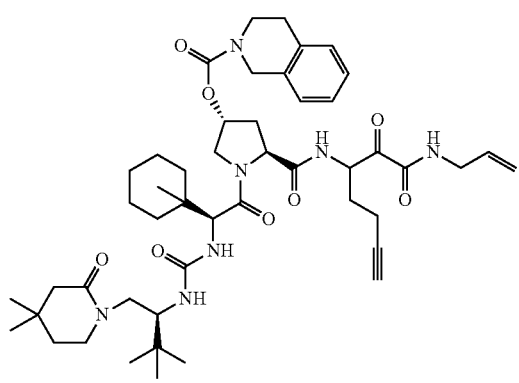
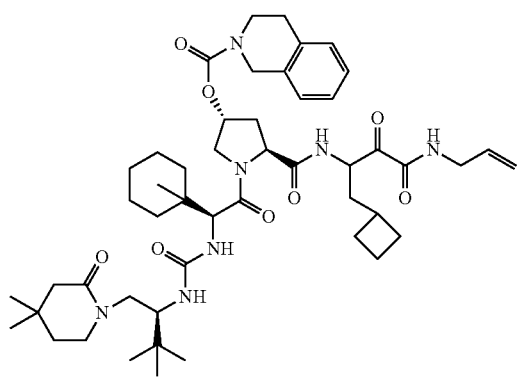
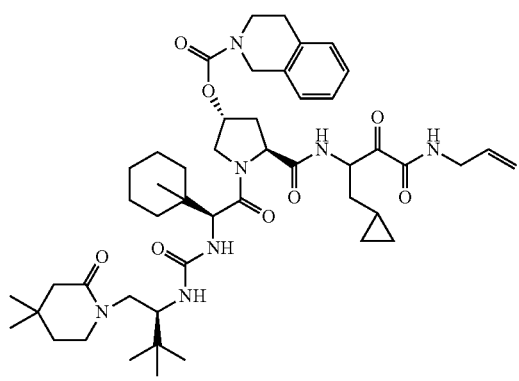
708
-continued
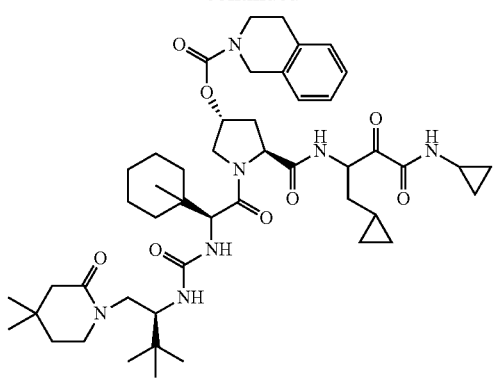
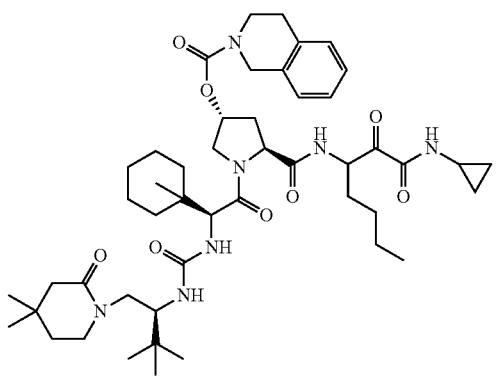
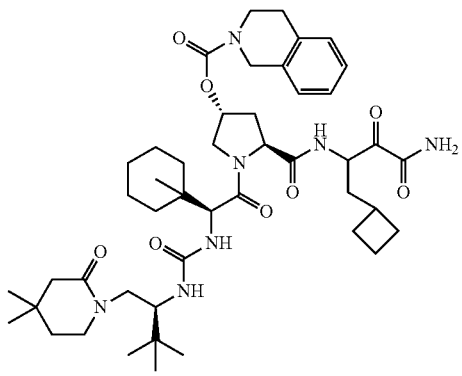
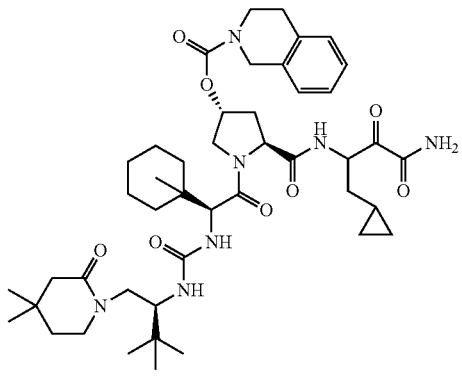

709

710

| 711 | 712 |
|---|---|
| -continued | -continued |
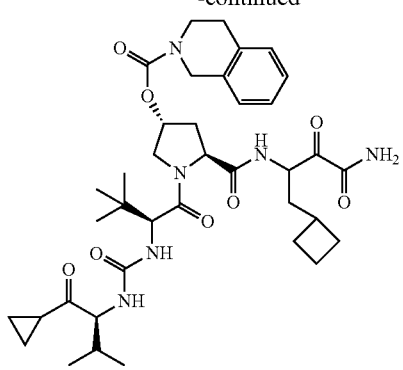 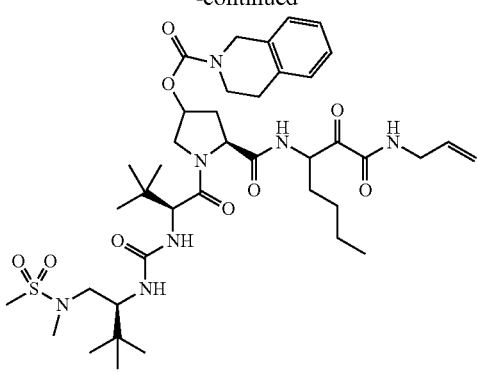
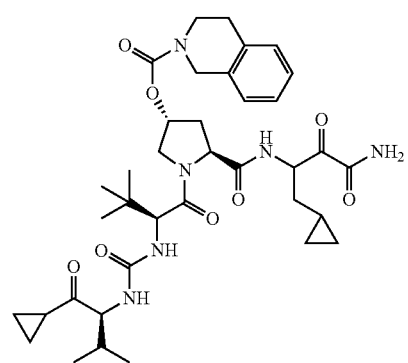 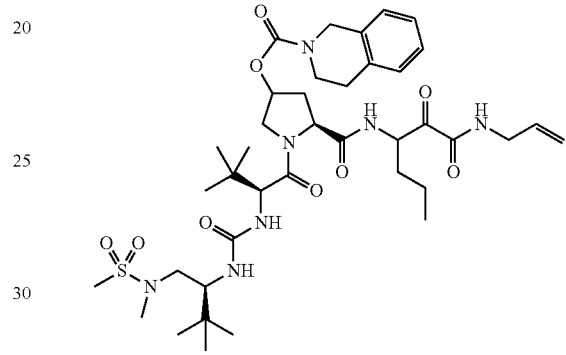
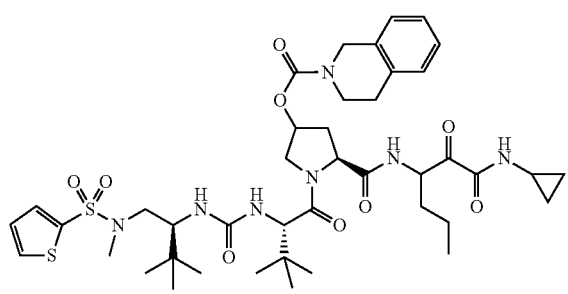
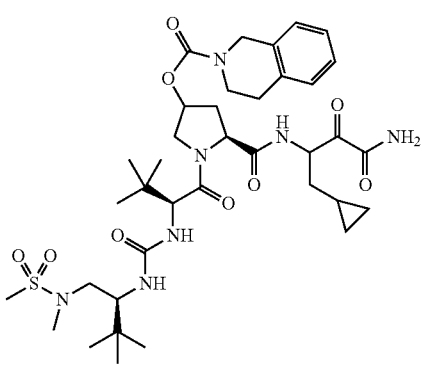
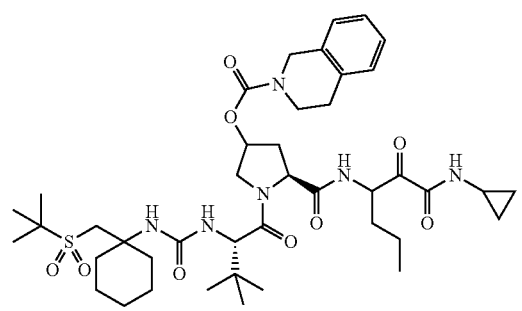
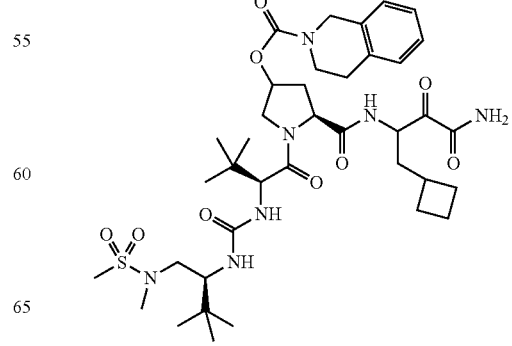

713
-continued
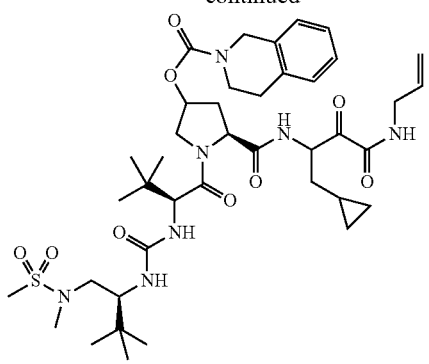
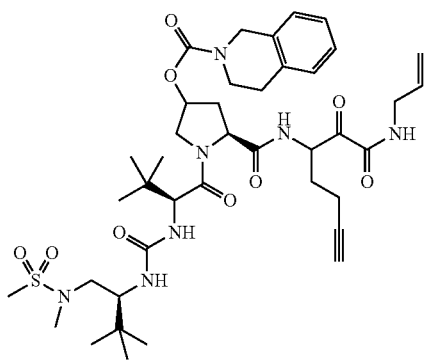
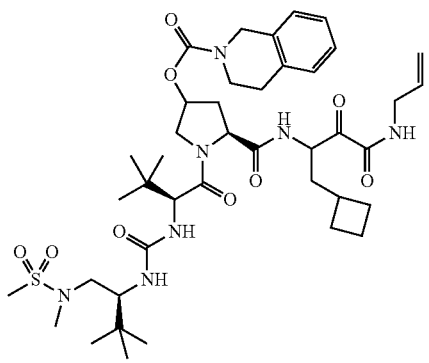
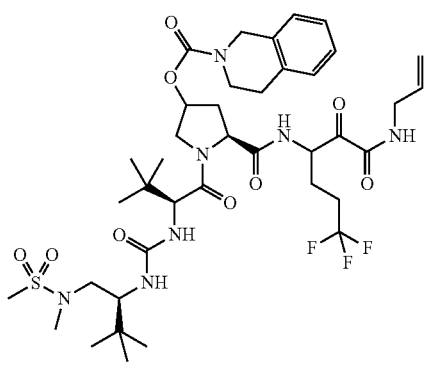
714
-continued
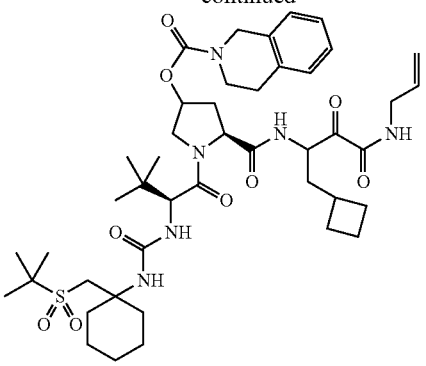
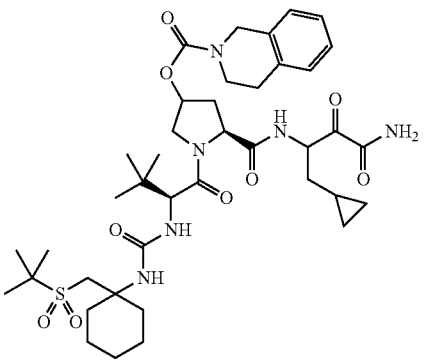
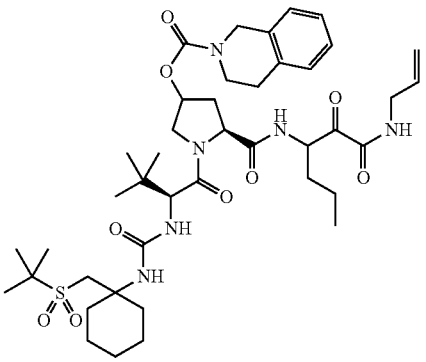
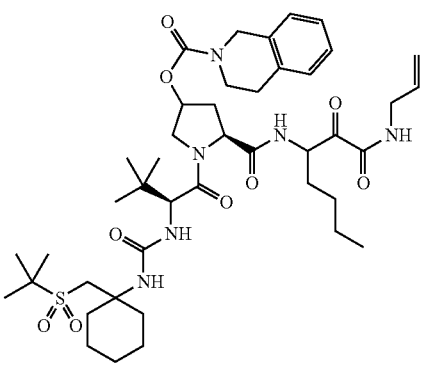

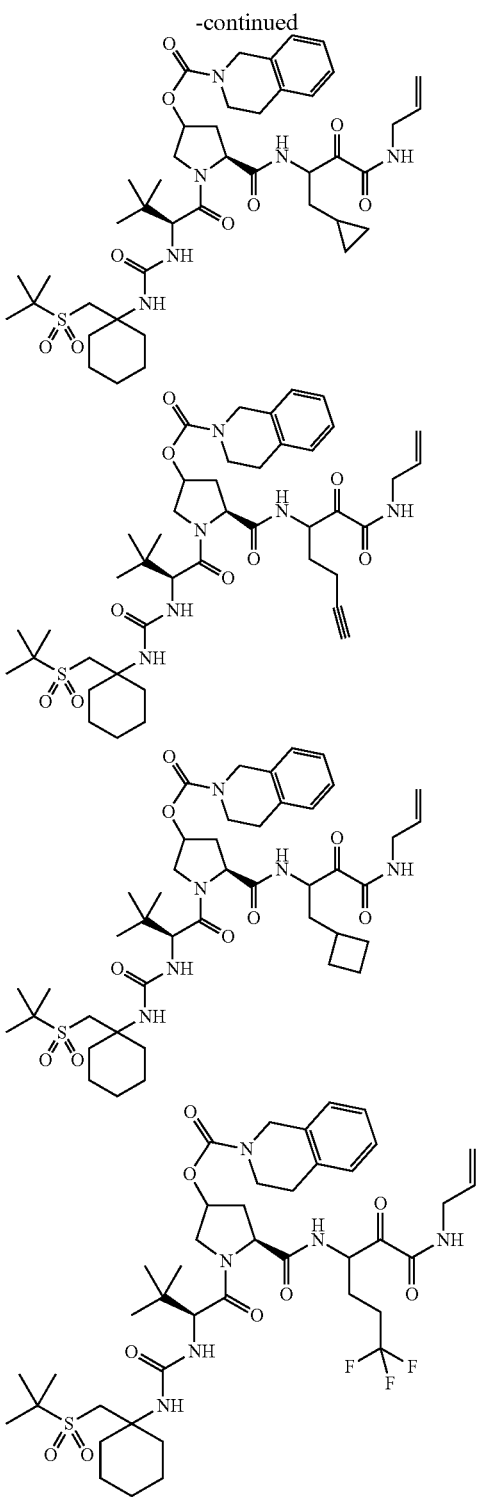

or a pharmaceutically acceptable salt, solvate or ester thereof.

Compounds of formula (XX) have been disclosed in U.S. Pat. No. 6,767,991 at col. 3, line 48 through col. 147, incorporated herein by reference.

Compounds of formula (XXI) have been disclosed in U.S. Patent Publication Nos. 2002/0016442, 2002/0037998 and U.S. Pat. Nos. 6,268,207, 6,323,180 at col. 3, line 28 through col. 141, line 60, U.S. Pat. No. 6,329,379 at col. 3, line 28 through col. 147, line 27, U.S. Pat. No. 6,329,417 at col. 3, line 25 through col. 147, line 30, U.S. Pat. No. 6,410,531 at col. 3, line 28 through col. 141, U.S. Pat. No. 6,534,523 at col. 3, line 34 through col. 139, line 29, and U.S. Pat. No. 6,420,380 at col. 3, line 28 through col. 141, line 65, each incorporated herein by reference.

Compounds of formula (XXII) have been disclosed in PCT International Patent Publication WO00/59929 published on Oct. 12, 2000, U.S. Patent Publication No. 2004/0002448 and U.S. Pat. No. 6,608,027 at col. 4 through col. 137, incorporated herein by reference.

Compounds of formula (XXIII) have been disclosed in PCT International Patent Publication WO02/18369 published on Mar. 7, 2002.

Compounds of formula (XXIV) have been disclosed U.S. Patent Publication Nos. 2002/0032175, 2004/0266731 and U.S. Pat. No. 6,265,380 at col. 3, line 35 through col. 121 and U.S. Pat. No. 6,617,309 at col. 3, line 40 through col. 121, each incorporated herein by reference.

Compounds of formula (XXV) have been disclosed U.S. Pat. No. 5,866,684 at col. 1 through col. 72 and U.S. Pat. No. 6,018,020 at col. 1 through col. 73, each incorporated herein by reference.

Compounds of formula (XXVI) have been disclosed in U.S. Pat. No. 6,143,715 at col. 3, line 6 through col. 62, line 20, incorporated herein by reference.

Isomers of the various compounds of the present invention (where they exist), including enantiomers, stereoisomers, rotamers, tautomers and racemates are also contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the present invention. Isomers may also include geometric isomers, e.g., when a double bond is present. Polymorphous forms of the compounds of the present invention, whether crystalline or amorphous, also are contemplated as being part of this invention. The (+) isomers of the present compounds are preferred compounds of the present invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are also within the scope of this invention.

It will be apparent to one skilled in the art that certain compounds of this invention may exist in alternative tautomeric forms. All such tautomeric forms of the present compounds are within the scope of the invention. Unless otherwise indicated, the representation of either tautomer is meant to include the other. For example, both isomers (1) and (2) are contemplated:

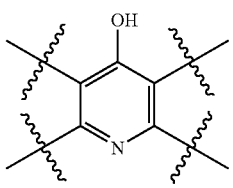

(1)

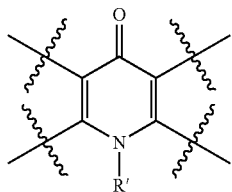

(2)

wherein R' is H or $C_{1-6}$ unsubstituted alkyl.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$alkyl and $Y^3$ is $(C_1-C_6)$alkyl, carboxy$(C_1-C_6)$alkyl, amino$(C_1-C_4)$alkyl or mono-N-or di-N,N—$(C_1-C_6)$alkylaminoalkyl, —$C(Y^4)Y^5$ wherein $Y^4$ is H or methyl and $Y^5$ is mono-N— or di-N,N-$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving a compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

"Effective amount" or "therapeutically effective amount" is meant to describe an amount of a compound or a composition of the present invention effective in inhibiting HCV protease and/or cathepsins, and thus producing the desired therapeutic, ameliorative, inhibitory or preventative effect in a suitable subject.

The compounds of the present invention form salts that are also within the scope of this invention. Reference to a compound of the present invention herein is understood to include reference to salts, esters and solvates thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the various formulae of the present invention may be formed, for example, by reacting a compound of the present invention with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217;

Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention. All acid and base salts, as well as esters and solvates, are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

In such esters, unless otherwise specified, any alkyl moiety present preferably contains from 1 to 18 carbon atoms, particularly from 1 to 6 carbon atoms, more particularly from 1 to 4 carbon atoms. Any cycloalkyl moiety present in such esters preferably contains from 3 to 6 carbon atoms. Any aryl moiety present in such esters preferably comprises a phenyl group.

In another embodiment, this invention provides pharmaceutical compositions comprising the inventive peptides as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

The nomenclature of Simmonds, P. et al. ("Classification of hepatitis C virus into six major genotypes and a series of subtypes by phylogenetic analysis of the NS-5 region," J. Gen. Virol., 74:2391-9, 1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3. (Lamballerie, X. et al., "Classification of hepatitis C variants in six major types based on analysis of the envelope 1 and nonstructural 5B genome regions and complete polyprotein sequences," J. Gen. Virol., 78:45-51, 1997). The major genotypes have been defined as having sequence similarities of between 55 and 72% (mean 64.5%), and subtypes within types as having 75%-86% similarity (mean 80%) when sequenced in the NS-5 region. (Simmonds, P. et al., "Identification of genotypes of hepatitis C by sequence comparisons in the core, E1 and NS-5 regions," J. Gen. Virol., 75:1053-61, 1994).

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

The compound of Formulae I-XXVI can be administered in combination with interferon alpha, PEG-interferon alpha conjugates or consensus interferon concurrently or consecutively at recommended dosages for the duration of HCV treatment in accordance with the methods of the present invention. The commercially available forms of interferon alpha include interferon alpha 2a and interferon alpha 2b and also pegylated forms of both aforementioned interferon alphas. The recommended dosage of INTRON-A interferon alpha 2b (commercially available from Schering-Plough Corp.) as administered by subcutaneous injection at 3 MIU (12 mcg)/0.5 mL/TIW is for 24 weeks or 48 weeks for first time treatment. The recommended dosage of PEG-INTRON interferon alpha 2b pegylated (commercially available from Schering-Plough Corp.) as administered by subcutaneous injection at 1.5 mcg/kg/week, within a range of 40 to 150 mcg/week, is for at least 24 weeks. The recommended dosage of ROFERON A interferon alpha 2a (commercially available from Hoffmann-La Roche) as administered by subcutaneous or intramuscular injection at 3 MIU (11.1 mcg/mL)/TIW is for at least 48 to 52 weeks, or alternatively 6 MIU/TIW for 12 weeks followed by 3 MIU/TIW for 36 weeks. The recommended dosage of PEGASUS interferon alpha 2a pegylated (commercially available from Hoffmann-La Roche) as administered by subcutaneous injection at 180 mcg/1 mL or 180 mcg/0.5 mL is once a week for at least 24 weeks. The recommended dosage of INFERGEN interferon alphacon-1 (commercially available from Amgen) as administered by subcutaneous injection at 9 mcg/TIW is for 24 weeks for first time treatment and up to 15 mcg/TIW for 24 weeks for non-responsive or relapse treatment. Optionally, Ribavirin, a synthetic nucleoside analogue with activity against a broad spectrum of viruses including HCV, can be included in combination with the interferon and the compound of Formulae I-XXVI. The recommended dosage of ribavirin is in a range from 600 to 1400 mg per day for at least 24 weeks (commercially available as REBETOL ribavirin from Schering-Plough or COPEGUS ribavirin from Hoffmann-La Roche).

In one embodiment, the compounds of the invention can be used to treat cellular proliferation diseases. Such cellular proliferation disease states which can be treated by the compounds, compositions and methods provided herein include, but are not limited to, cancer (further discussed below), hyperplasia, cardiac hypertrophy, autoimmune diseases, fungal disorders, arthritis, graft rejection, inflammatory bowel disease, immune disorders, inflammation, cellular proliferation induced after medical procedures, including, but not limited to, surgery, angioplasty, and the like. Treatment includes inhibiting cellular proliferation. It is appreciated that in some cases the cells may not be in a hyper- or hypoproliferation state (abnormal state) and still require treatment. For example, during wound healing, the cells may be proliferating "normally", but proliferation enhancement may be desired. Thus, in one embodiment, the invention herein includes application to cells or subjects afflicted or subject to impending affliction with any one of these disorders or states.

The methods provided herein are particularly useful for the treatment of cancer including solid tumors such as skin, breast, brain, colon, gall bladder, thyroid, cervical carcinomas, testicular carcinomas, etc. More particularly, cancers that may be treated by the compounds, compositions and methods of the invention include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic: blood (myeloid leukemia (acute and chronic), acute lymphoblastic leukemia, acute and chronic lymphocytic leukemia, myeloproliferative diseases, multiple myeloma, myelodysplastic syndrome), Hodgkin's disease, non-Hodgkin's lymphoma (malignant lymphoma), B-cell lymphoma, T-cell lymphoma, hairy cell lymphoma, Burkett's lymphoma, promyelocytic leukemia;

Skin: malignant melanoma, basal cell carcinoma, squamous cell carcinoma, Karposi's sarcoma, moles dysplastic nevi, lipoma, angioma, dermatofibroma, keloids, psoriasis;

Adrenal glands: neuroblastoma; and

Other tumors: including xenoderoma pigmentosum, keratoctanthoma and thyroid follicular cancer.

As used herein, treatment of cancer includes treatment of cancerous cells, including cells afflicted by any one of the above-identified conditions.

The compounds of the present invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The compounds of the present invention may also be useful in inhibiting tumor angiogenesis and metastasis.

The compounds of the present invention may also be useful as antifungal agents, by modulating the activity of the fungal members of the bimC kinesin subgroup, as is described in U.S. Pat. No. 6,284,480.

The present compounds are also useful in combination with one or more other known therapeutic agents and anti-cancer agents. Combinations of the present compounds with other anti-cancer or chemotherapeutic agents are within the scope of the invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The present compounds are also useful when co-administered with radiation therapy.

The phrase "estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-I-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-ydrazone, aid SH646.

The phrase "androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

The phrase "retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, a difluoromethylornithine, ILX23-7553, trans-N-(4'-hydroxyphenyl) retinamide, and N-4-carboxyphenyl retinamide.

The phrase "cytotoxic/cytostatic agents" refer to compounds which cause cell death or inhibit cell proliferation primarily by interfering directly with the cell's functioning or inhibit or interfere with cell mycosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, monoclonal antibody therapeutics, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide (TEMODARM™ from Schering-Plough Corporation, Kenilworth, N.J.), cyclophosphamide, heptaplatin, estramustine, improsulfan tosilate, trofosfamide, nimustine, dibrospidium chloride, pumitepa, lobaplatin, satraplatin, profiromycin, cisplatin, doxorubicin, irofulven, dexifosfamide, cis-aminedichloro(2-methyl-pyridine)platinum, benzylguanine, glufosfamide, GPX100, (trans,trans,trans)-bis-mu-(hexane-1,6-diamine)-mu-[diamine-platinum(II)]bis[diamine (chloro)platinum(II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deansino-3'-morpholino-13-deoxo-10-hydroxycarminomycin, annamycin, galarubicin, elinafide, MEN10755, 4-demethoxy-3-deamino-3-aziridinyl-4-methylsulphonyl-daunombicin (see WO 00/50032), methoxtrexate, gemcitabine, and mixture thereof.

An example of a hypoxia activatable compound is tirapazamine.

Examples of proteasome inhibitors include, but are not limited to, lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2-(diethylamino) ethylamino]-7-methoxy-9-oxo-9H-thioxanthen-4-ylmethyl] formamide,N-(2-(dimethylamino)ethyl)acridine-4-carboxamide, 6-[[2-(dimethylamino)ethyl]amino]-3-hydroxy-7H-indeno[2,1-c]quinolin-7-one, dimesna, and camptostar.

Other useful anti-cancer agents that can be used in combination with the present compounds include thymidilate synthase inhibitors, such as 5-fluorouracil.

In one embodiment, inhibitors of mitotic kinesins include, but are not limited to, inhibitors of KSP, inhibitors of MKLP1, inhibitors of CENP-E, inhibitors of MCAK, inhibitors of Kif14, inhibitors of Mphosph1 and inhibitors of Rab6-KIFL.

The phrase "inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

The phrase "antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 1'-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N-4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

Examples of monoclonal antibody therapeutics useful for treating cancer include Erbitux (Cetuximab).

The phrase "HMG-CoA reductase inhibitors" refers to inhibitors of 3-hydroxy-3-methylglutaryl-CoA reductase. Examples of HMG-CoA reductase inhibitors that may be used include but are not limited to lovastatin, simvastatin (ZOCOR®), pravastatin (PRAVACHOL®), fluvastatin and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open acid and lactone forms is included in the scope of this invention.

The phrase "prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO, 97/30053, WO 97/44350, WO 98/02436, and U.S. Pat. No. 5,532,359. For an example of the role of a prenyl-protein transferase inhibitor on angiogenesis see *European of Cancer*, Vol. 35, No. 9, pp. 1394-1401 (1999).

Examples of farnesyl protein transferase inhibitors include SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoehtyl]-1-piperidinecarboxamide from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.).

The phrase "angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α (for example Intron and Peg-Intron), interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med., Vol.* 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature,* 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor

[TAFIa]) (see *Thrombosis Res.* 101:329-354 (2001)). Examples of TAFIa inhibitors have been described in PCT Publication WO 03/013,526.

The phrase "agents that interfere with cell cycle checkpoints" refers to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

The phrase "inhibitors of cell proliferation and survival signaling pathway" refers to agents that inhibit cell surface receptors and signal transduction cascades downstream of those surface receptors. Such agents include inhibitors of EGFR (for example gefitinib and erlotinib), antibodies to EGFR (for example C225), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEEK (for example CI-1040 and PD-098059), inhibitors of mTOR (for example Wyeth CCI-779), and inhibitors of C-abl kinase (for example GLEEVEC™, Novartis Pharmaceuticals). Such agents include small molecule inhibitor compounds and antibody antagonists.

The phrase "apoptosis inducing agents" includes activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of IC50 for COX-2 over IC50 for COX-1 evaluated by cell or microsomal assays. Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5 pyridinyl)pyridine; or a pharmaceutically acceptable salt thereof.

Compounds that have been described as specific inhibitors of COX-2 and are therefore useful in the present invention include, but are not limited to, parecoxib, CELEBREX® and BEXTRA® or a pharmaceutically acceptable salt thereof.

Other examples of angiogenesis inhibitors include, but are not limited to, endostatin, ukrain, ranpimase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571 A, N-4-chlorophenyl-4-(4-pyridylmethyl)-1-phthalazinamine, and EMD121974.

Combinations with compounds other than anti-cancer compounds are also encompassed in the instant methods. For example, combinations of the present compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy)phenoxy)propoxy)-2-ethylchromane-2-carboxylic acid.

In one embodiment, useful anti-cancer (also known as anti-neoplastic) agents that can be used in combination with the present compounds include, but are not limited, to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methyl prednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, doxorubicin (adriamycin), cyclophosphamide (cytoxan), gemcitabine, interferons, pegylated interferons, Erbitux and mixtures thereof.

Another embodiment of the present invention is the use of the present compounds in combination with gene therapy for the treatment of cancer. For an overview of genetic strategies to treating cancer, see Hall et al (*Am J Hum Genet* 61:785-789,1997) and Kufe et al (*Cancer Medicine*, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8): 1105-13), and interferon gamma (*J Immunol* 2000; 164:217-222).

The present compounds can also be administered in combination with one or more inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

The present compounds can also be employed in conjunction with one or more anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with one or more other anti-emetic agents, especially neurokinin-1 receptor antagonists, 5HT3 receptor, antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or those as described in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In one embodiment, an anti-emesis agent selected from a neurokinin-1 receptor antagonist, a 5HT3 receptor antagonist and a corticosteroid is administered as an adjuvant for the treatment or prevention of emesis that may result upon administration of the present compounds.

Examples of neurokinin-1 receptor antagonists that can be used in conjunction with the present compounds are described in U.S. Pat. Nos. 5,162,339, 5,232,929, 5,242,930, 5,373,003, 5,387,595, 5,459,270, 5,494,926, 5,496,833, 5,637,699, and 5,719,147, content of which are incorporated herein by reference. In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl) morpholine, or a pharmaceutically acceptable salt thereof, which is described in U.S. Pat. No. 5,719,147.

A compound of the present invention may also be administered with one or more immunologic-enhancing drug, such as for example, levamisole, isoprinosine and Zadaxin.

Thus, the present invention encompasses the use of the present compounds (for example, for treating or preventing cellular proliferative diseases) in combination with a second compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an inhibitor of inherent multidrug resistance, an anti-emetic agent, an immunologic-enhancing drug, an inhibitor of cell proliferation and survival signaling, an agent that interfers with a cell cycle checkpoint, and an apoptosis inducing agent.

In one embodiment, the present invention emcompasses the composition and use of the present compounds in combination with a second compound selected from: a cytostatic agent, a cytotoxic agent, taxanes, a topoisomerase II inhibitor, a topoisomerase I inhibitor, a tubulin interacting agent, hormonal agent, a thymidilate synthase inhibitors, anti-metabolites, an alkylating agent, a farnesyl protein transferase inhibitor, a signal transduction inhibitor, an EGFR kinase inhibitor, an antibody to EGFR, a C-abl kinase inhibitor, hormonal therapy combinations, and aromatase combinations.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In one embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MW (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-(O-chloroacetylcarbonyl)-fumagillol, thalidomide, angiostatin, troponin-1, or an antibody to VEGF. In an embodiment, the estrogen receptor modulator is tamoxifen or raloxifene.

Also included in the present invention is a method of treating cancer comprising administering a therapeutically effective amount of at least one compound of the present invention in combination with radiation therapy and at least one compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an inhibitor of inherent multidrug resistance, an anti-emetic agent, an immunologic-enhancing drag, an inhibitor of cell proliferation and survival signaling, an agent that interfers with a cell cycle checkpoint, and an apoptosis inducing agent.

Yet another embodiment of the invention is a method of treating cancer comprising administering a therapeutically effective amount of at least one compound of the present invention in combination with paclitaxel or trastuzumab.

The present invention also includes a pharmaceutical composition useful for treating or preventing the various disease states mentioned herein cellular proliferation diseases (such as cancer, hyperplasia, cardiac hypertrophy, autoimmune diseases, fungal disorders, arthritis, graft rejection, inflammatory bowel disease, immune disorders, inflammation, and cellular proliferation induced after medical procedures) that comprises a therapeutically effective amount of at least one compound of the present invention and at least one compound selected from: an estrogen receptor modulator, an androgen receptor modulator, a retinoid receptor modulator, a cyto-toxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an inhibitor of cell proliferation and survival signaling, an agent that interfers with a cell cycle checkpoint, and an apoptosis inducing agent.

When the disease being treated by the cathepsin inhibitor compounds of the present invention is inflammatory disease, an embodiment of the present invention comprises administering: (a) a therapeutically effective amount of at least one compound of the present cathepsin inhibitors (e.g., a compound according to Formula I-XXVII) or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (non-limiting examples include methotrexate, cyclosporin, FK506); steroids; PDE IV inhibitors, anti-TNF-α compounds, TNF-alpha-convertase inhibitors, cytokine inhibitors, MMP inhibitors, glucocorticoids, chemokine inhibitors, CB2-selective inhibitors, p38 inhibitors, biological response modifiers; anti-inflammatory agents and therapeutics.

Another embodiment of the present invention is directed to a method of inhibiting or blocking T-cell mediated chemotaxis in a patient in need of such treatment the method comprising administering to the patient a therapeutically effective amount of at least one compound of the present cathepsin inhibitors (e.g., a compound according to formula I-XXVII) or a pharmaceutically acceptable salt, solvate or ester thereof.

Another embodiment of this invention is directed to a method of treating inflammatory bowel disease in a patient in need of such treatment comprising administering to the patient a therapeutically effective amount of at least one compound according to the present cathepsin inhibitors or a pharmaceutically acceptable salt, solvate or ester thereof.

Another embodiment of this invention is directed to a method of treating or preventing graft rejection in a patient in need of such treatment comprising administering to the patient a therapeutically effective amount of at least one compound according to the present cathepsin inhibitors, or a pharmaceutically acceptable salt, solvate or ester thereof.

Another embodiment of this invention is directed to a method comprising administering to the patient a therapeutically effective amount of: (a) at least one compound according to the present cathepsin inhibitors, or a pharmaceutically acceptable salt, solvate or ester thereof concurrently or sequentially with (b) at least one compound selected from the group consisting of: cyclosporine A, FK-506, FTY720, beta-Interferon, rapamycin, mycophenolate, prednisolone, azathioprine, cyclophosphamide and an antilymphocyte globulin.

Another embodiment of this invention is directed to a method of treating multiple sclerosis in a patient in need of such treatment the method comprising administering to the patient a therapeutically effective amount of: (a) at least one compound according to the present cathepsin inhibitors, or a pharmaceutically acceptable salt, solvate or ester thereof concurrently or sequentially with (b) at least one compound selected from the group consisting of: beta-interferon, glatiramer acetate, glucocorticoids, methotrexate, azothioprine, mitoxantrone, VLA-4 inhibitors and/or CB2-selective inhibitors.

Another embodiment of this invention is directed to a method of treating multiple sclerosis in a patient in need of such treatment the method comprising administering to the patient a therapeutically effective amount of: a) at least one compound according to the present cathepsin inhibitors, or a pharmaceutically acceptable salt, solvate or ester thereof concurrently or sequentially with (b) at least one compound selected from the group consisting of: methotrexate, cyclosporin, leflunimide, sulfasalazine, β-methasone, β-interferon, glatiramer acetate, prednisone, etonercept, and infliximab.

Another embodiment of this invention is directed to a method of treating rheumatoid arthritis in a patient in need of such treatment the method comprising administering to the patient a therapeutically effective amount of: (a) at least one compound according to the present cathepsin inhibitors or a pharmaceutically acceptable salt, solvate or ester thereof concurrently or sequentially with (b) at least one compound selected from the group consisting of: COX-2 inhibitors, COX inhibitors, immunosuppressives, steroids, PDE IV inhibitors, anti-TNF-α compounds, MMP inhibitors, glucocorticoids, chemokine inhibitors, CB2-selective inhibitors, caspase (ICE) inhibitors and other classes of compounds indicated for the treatment of rheumatoid arthritis.

Another embodiment of this invention is directed to a method of treating psoriasis in a patient in need of such treatment the method comprising administering to the patient a therapeutically effective amount of: a) at least one compound according to present cathepsin inhibitors, or a pharmaceutically acceptable salt, solvate or ester thereof concurrently or sequentially with (b) at least one compound selected from the group consisting of: immunosuppressives, steroids, and anti-TNF-α compounds.

Another embodiment of this invention is directed to a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, tuberculoid leprosy, type I diabetes, viral meningitis and tumors in a patient in need of such treatment, such method comprising administering to the patient an effective amount of at least one compound according to present cathepsin inhibitors, or a pharmaceutically acceptable salt, solvate or ester thereof.

Another embodiment of this invention is directed to a method of treating a disease selected from the group consisting of inflammatory disease, rheumatoid arthritis, multiple sclerosis, inflammatory bowel disease, graft rejection, psoriasis, fixed drug eruptions, cutaneous delayed-type hypersensitivity responses, tuberculoid leprosy and cancer in a patient in need of such treatment, such method comprising administering to the patient an effective amount of at least one compound according to the present cathepsin inhibitors, or a pharmaceutically acceptable salt, solvate or ester thereof.

Another embodiment of this invention is directed to a method of treating a disease selected from the group consisting of inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, type I diabetes, viral meningitis and cancer in a patient in need of such treatment, such method comprising administering to the patient an effective amount of (a) at least one compound according to the present cathepsin inhibitors, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives; steroids; PDE IV inhibitors, anti-TNF-α compounds, MMP inhibitors, glucocorticoids, chemokine inhibitors, CB2-selective inhibitors, biological response modifiers; anti-inflammatory agents and therapeutics.

When the present invention involves a method of treating a cardiovascular disease, in addition to administering the cathepsin inhibitors of the present invention, the method further comprises administering to the subject in need one or more pharmacological or therapeutic agents or drugs such as cholesterol biosynthesis inhibitors and/or lipid-lowering agents discussed below.

Non-limiting examples of cholesterol biosynthesis inhibitors for use in the compositions, therapeutic combinations and methods of the present invention include competitive inhibitors of HMG CoA reductase, the rate-limiting step in cholesterol biosynthesis, squalene synthase inhibitors, squalene epoxidase inhibitors and mixtures thereof. Non-limiting examples of suitable HMG CoA reductase inhibitors include statins such as lovastatin (for example MEVACOR® which is available from Merck & Co.), pravastatin (for example PRAVACHOL® which is available from Bristol Meyers Squibb), fluvastatin, simvastatin (for example ZOCOR® which is available from Merck & Co.), atorvastatin, cerivastatin, rosuvastatin, rivastatin (sodium 7-(4-fluorophenyl)-2,6-diisopropyl-5-methoxymethylpyridin-3-yl)-3,5-dihydroxy-6-heptanoate, CI-981 and pitavastatin (such as NK-104 of Negma Kowa of Japan); HMG CoA synthetase inhibitors, for example L-659,699 ((E,E)-11-[3'R-(hydroxymethyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride) and other sterol biosynthesis inhibitors such as DMP-565. Preferred HMG CoA reductase inhibitors include lovastatin, pravastatin and simvastatin.

In another embodiment, the method of treatment comprises administering the present cathepsin inhibitors in combination with one or more cardiovascular agents and one or more cholesterol biosynthesis inhibitors.

In another alternative embodiment, the method treatment of the present invention can further comprise administering nicotinic acid (niacin) and/or derivatives thereof coadministered with or in combination with the cardiovascular agent(s) and sterol absorption inhibitor(s) discussed above.

As used herein, "nicotinic acid derivative" means a compound comprising a pyridine-3-carboxylate structure or a pyrazine-2-carboxylate structure, including acid forms, salts, esters, zwitterions and tautomers, where available. Examples of nicotinic acid derivatives include niceritrol, nicofuranose and acipimox (5-methyl pyrazine-2-carboxylic acid 4-oxide). Nicotinic acid and its derivatives inhibit hepatic production of VLDL and its metabolite LDL and increases HDL and apo A-1 levels. An example of a suitable nicotinic acid product is NIASPAN® (niacin extended-release tablets) which are available from Kos.

In another alternative embodiment, the method of treatment of the present invention can further comprise administering one or more AcylCoA:Cholesterol O-acyltransferase ("ACAT") Inhibitors, which can reduce LDL and VLDL levels, coadministered with or in combination with the cardiovascular agent(s) and sterol absorption inhibitor(s) discussed above. ACAT is an enzyme responsible for esterifying excess intracellular cholesterol and may reduce the synthesis of VLDL, which is a product of cholesterol esterification, and overproduction of apo B-100-containing lipoproteins.

Non-limiting examples of useful ACAT inhibitors include avasimibe ([[2,4,6-tris(1-methylethyl)phenyl]acetyl]sulfamic acid, 2,6-bis(1-methylethyl)phenyl ester, formerly known as CI-1011), HL-004, lecimibide (DuP-128) and CL-277082 (N-(2,4-difluorophenyl)-N-[[4-(2,2-dimethylpropyl)phenyl]methyl]-N-heptylurea). See P. Chang et al., "Current, New and Future Treatments in Dyslipidaemia and Atherosclerosis", *Drugs* 2000 July; 60(1); 55-93, which is incorporated by reference herein.

In another alternative embodiment, the method of treatment of the present invention can further comprise administering probucol or derivatives thereof (such as AGI-1067 and other derivatives disclosed in U.S. Pat. Nos. 6,121,319 and 6,147,250), which can reduce LDL levels, coadministered with or in combination with the cardiovascular agent(s) and sterol absorption inhibitor(s) discussed above.

In another alternative embodiment, the method of treatment of the present invention can further comprise administering fish oil, which contains Omega 3 fatty acids (3-PUFA), which can reduce VLDL and triglyceride levels, coadministered with or in combination with the cardiovascular agent(s) and sterol absorption inhibitor(s) discussed above. Generally, a total daily dosage of fish oil or Omega 3 fatty acids can range from about 1 to about 30 grams per day in single or 24 divided doses.

In another alternative embodiment, the method of treatment of the present invention can further comprise administering natural water soluble fibers, such as psyllium, guar, oat and pectin, which can reduce cholesterol levels, coadministered with or in combination with the cardiovascular agent(s) and sterol absorption inhibitor(s) discussed above. Generally, a total daily dosage of natural water soluble fibers can range from about 0.1 to about 10 grams per day in single or 2-4 divided doses.

In another alternative embodiment, the method of treatment of the present invention can further comprise administering plant sterols, plant stanols and/or fatty acid esters of plant stanols, such as sitostanol ester used in BENECOL® margarine, which can reduce cholesterol levels, coadministered with or in combination with the cardiovascular agent(s) and sterol absorption inhibitor(s) discussed above. Generally, a total daily dosage of plant sterols, plant stanols and/or fatty acid esters of plant stanols can range from about 0.5 to about 20 grams per day in single or 2-4 divided doses.

In another alternative embodiment, the method of treatment of the present invention can further comprise administering antioxidants, such as probucol, tocopherol, ascorbic acid, β-carotene and selenium, or vitamins such as vitamin $B_6$ or vitamin $B_{12}$, coadministered with or in combination with the cardiovascular agent(s) and sterol absorption inhibitor(s) discussed above. Generally, a total daily dosage of antioxidants or vitamins can range from about 0.05 to about 10 grams per day in single or 2-4 divided doses.

In another alternative embodiment, the method of treatment of the present invention can further comprise administering one or more bile acid sequestrants (insoluble anion exchange resins), coadministered with or in combination with the cardiovascular agents and sterol absorption inhibitor(s) discussed above.

Bile acid sequestrants bind bile acids in the intestine, interrupting the enterohepatic circulation of bile acids and causing an increase in the faecal excretion of steroids. Use of bile acid sequestrants is desirable because of their non-systemic mode of action. Bile acid sequestrants can lower intrahepatic cholesterol and promote the synthesis of apo B/E (LDL) receptors which bind LDL from plasma to further reduce cholesterol levels in the blood.

Non-limiting examples of suitable bile acid sequestrants include cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl)alkylamines and poliglusam, insoluble quaternized polystyrenes, saponins and mixtures thereof. Other useful bile acid sequestrants are disclosed in PCT Patent Applications Nos. WO 97/11345 and WO 98/57652, and U.S. Pat. Nos. 3,692,895 and 5,703,188 which are incorporated herein by reference. Suitable inorganic cholesterol sequestrants include bismuth salicylate plus montmorillonite clay, aluminum hydroxide and calcium carbonate antacids.

Also useful with the present invention are methods of treatment that can further comprise administering at least one (one or more) activators for peroxisome proliferator-activated receptors (PPAR). These activators act as agonists for the peroxisome proliferator-activated receptors. Three subtypes of PPAR have been identified, and these are designated as peroxisome proliferator-activated receptor alpha (PPARα), peroxisome proliferator-activated receptor gamma (PPARγ) and peroxisome proliferator-activated receptor delta (PPARδ). It should be noted that PPARδ is also referred to in the literature as PPARβ and as NUC1, and each of these names refers to the same receptor.

PPARα regulates the metabolism of lipids. PPARα is activated by fibrates and a number of medium and long-chain fatty acids, and it is involved in stimulating β-oxidation of fatty acids. The PPARγ receptor subtypes are involved in activating the program of adipocyte differentiation and are not involved in stimulating peroxisome proliferation in the liver. PPARδ has been identified as being useful in increasing high density lipoprotein (HDL) levels in humans. See, e.g., WO 97/28149.

PPARα activator compounds are useful for, among other things, lowering triglycerides, moderately lowering LDL levels and increasing HDL levels. Useful examples of PPARα activators include the fibrates discussed above.

Other examples of PPARα activators useful with the practice of the present invention include suitable fluorophenyl compounds as disclosed in U.S. Pat. No. 6,028,109 which is incorporated herein by reference; certain substituted phenyl-propionic compounds as disclosed in WO 00/75103 which is incorporated herein by reference; and PPARα activator compounds as disclosed in WO 98/43081 which is incorporated herein by reference.

Non-limiting examples of PPARγ activator include suitable derivatives of glitazones or thiazolidinediones, such as, troglitazone (such as REZULIN® troglitazone (-5-[[4-[3,4-dihydro-6-hydroxy-2,5,7,8-tetramethyl-2H-1-benzopyran-2-yl)methoxy]phenyl]methyl]-2,4-thiazolidinedione) commercially available from Parke-Davis); rosiglitazone (such as AVANDIA® rosiglitazone maleate (-5-[[4-[2-(methyl-2-pyridinylamino)ethoxy]phenyl]methyl]-2,4-thiazolidinedione, (Z)-2-butenedioate) (1:1) commercially available from SmithKline Beecham) and pioglitazone (such as ACTOS™ pioglitazone hydrochloride (5-[[4-[2-(5-ethyl-2-pyridinyl) ethoxy]phenyl]methyl]-2,4-]thiazolidinedione monohydrochloride) commercially available from Takeda Pharmaceuticals). Other useful thiazolidinediones include ciglitazone, englitazone, darglitazone and BRL 49653 as disclosed in WO 98/05331 which is incorporated herein by reference; PPARγ activator compounds disclosed in WO 00/76488 which is incorporated herein by reference; and PPARγ activator compounds disclosed in U.S. Pat. No. 5,994,554 which is incorporated herein by reference.

Other useful classes of PPARγ activator compounds include certain acetylphenols as disclosed in U.S. Pat. No. 5,859,051 which is incorporated herein by reference; certain quinoline phenyl compounds as disclosed in WO 99/20275 which is incorporated herein by reference; aryl compounds as disclosed by WO 99/38845 which is incorporated herein by reference; certain 1,4-disubstituted phenyl compounds as disclosed in WO 00/63161; certain aryl compounds as disclosed in WO 01/00579 which is incorporated herein by reference; benzoic acid compounds as disclosed in WO 01/12612 & WO 01/12187 which are incorporated herein by reference; and substituted 4-hydroxy-phenylalconic acid compounds as disclosed in WO 97/31907 which is incorporated herein by reference.

PPARδ compounds are useful for, among other things, lowering triglyceride levels or raising HDL levels. Non-limiting examples of PPARδ activators include suitable thiazole and oxazole derivates, such as C.A.S. Registry No. 317318-32-4, as disclosed in WO 01/00603 which is incorporated herein by reference); certain fluoro, chloro or thio phenoxy phenylacetic acids as disclosed in WO 97/28149 which is incorporated herein by reference; suitable non-β-oxidizable fatty acid analogues as disclosed in U.S. Pat. No. 5,093,365 which is incorporated herein by reference; and PPARδ compounds as disclosed in WO 99/04815 which is incorporated herein by reference.

Moreover, compounds that have multiple functionality for activating various combinations of PPARα, PPARγ and PPARδ are also useful with the practice of the present invention. Non-limiting examples include certain substituted aryl compounds as disclosed in U.S. Pat. No. 6,248,781; WO 00/23416; WO 00/23415; WO 00/23425; WO 00/23445; WO 00/23451; and WO 00/63153, all of which are incorporated herein by reference, are described as being useful PPARα and/or PPARγ activator compounds. Other non-limiting examples of useful PPARα and/or PPARγ activator compounds include activator compounds as disclosed in WO 97/25042 which is incorporated herein by reference; activator compounds as disclosed in WO 00/63190 which is incorporated herein by reference; activator compounds as disclosed in WO 01/21181 which is incorporated herein by reference; biaryl-oxa(thia)zole compounds as disclosed in WO 01/16120 which is incorporated herein by reference; compounds as disclosed in WO 00/63196 and WO 00/63209 which are incorporated herein by reference; substituted 5-aryl-2,4-thiazolidinediones compounds as disclosed in U.S. Pat. No. 6,008,237 which is incorporated herein by reference; arylthiazolidinedione and aryloxazolidinedione compounds as disclosed in WO 00/78312 and WO 00/78313G which are incorporated herein by reference; GW2331 or (2-(4-[difluorophenyl]-1heptylureido)ethyl] phenoxy)-2-methylbutyric compounds as disclosed in WO 98/05331 which is incorporated herein by reference; aryl compounds as disclosed in U.S. Pat. No. 6,166,049 which is incorporated herein by reference; oxazole compounds as disclosed in WO 01/17994 which is incorporated herein by reference; and dithiolane compounds as disclosed in WO 01/25225 and WO 01/25226 which are incorporated herein by reference.

Other useful PPAR activator compounds include substituted benzylthiazolidine-2,4-dione compounds as disclosed in WO 01/14349, WO 01/14350 and WO/01/04351 which are incorporated herein by reference; mercaptocarboxylic compounds as disclosed in WO 00/50392 which is incorporated herein by reference; ascofuranone compounds as disclosed in WO 00/53563 which is incorporated herein by reference; carboxylic compounds as disclosed in WO 99/46232 which is incorporated herein by reference; compounds as disclosed in WO 99/12534 which is incorporated herein by reference; benzene compounds as disclosed in WO 99/15520 which is incorporated herein by reference; o-anisamide compounds as disclosed in WO 01/21578 which is incorporated herein by reference; and PPAR activator compounds as disclosed in WO 01/40192 which is incorporated herein by reference.

Also useful with the present invention are methods of treatment which further comprise administering hormone replacement agents and compositions. Useful hormone agents and compositions for hormone replacement therapy of the present invention include androgens, estrogens, progestins, their pharmaceutically acceptable salts and derivatives. Combinations of these agents and compositions are also useful.

The cathepsin inhibitors of the present invention are useful in the treatment of central nervous system diseases such as depression, cognitive function diseases and neurodegenerative diseases such as Parkinson's disease, senile dementia as in Alzheimer's disease, and psychoses of organic origin. In particular, the cathepsin inhibitors of the present invention can improve motor-impairment due to neurodegenerative diseases such as Parkinson's disease.

The other agents known to be useful in the treatment of Parkinson's disease which can be administered in combination with the cathepsin inhibitors of the present invention include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone.

A preferred dosage for the administration of a compound of the present invention is about 0.001 to 500 mg/kg of body weight/day of a compound of the present invention or a pharmaceutically acceptable salt or ester thereof. An especially preferred dosage is about 0.01 to 25 mg/kg of body weight/day of a compound of the present invention or a pharmaceutically acceptable salt or ester thereof.

The phrases "effective amount" and "therapeutically effective amount" mean that amount of a compound of the present invention, and other pharmacological or therapeutic agents described herein, that will elicit a biological or medical response of a tissue, a system, or a subject (e.g., animal or human) that is being sought by the administrator (such as a researcher, doctor or veterinarian) which includes alleviation of the symptoms of the condition or disease being treated and the prevention, slowing or halting of progression of one or more of the presently claimed diseases. The formulations or compositions, combinations and treatments of the present invention can be administered by any suitable means which produce contact of these compounds with the site of action in the body of, for example, a mammal or human.

For administration of pharmaceutically acceptable salts of the above compounds, the weights indicated above refer to the weight of the acid equivalent or the base equivalent of the therapeutic compound derived from the salt.

As described above, this invention includes combinations comprising an amount of at least one compound of the presently claimed methods or a pharmaceutically acceptable salt or ester thereof, and an amount of one or more additional therapeutic agents listed above (administered together or sequentially) wherein the amounts of the compounds/treatments result in desired therapeutic effect.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for illustration purposes, a compound of the present invention and an additional therapeutic agent may be present in fixed amounts (dosage amounts) in a single dosage unit (e.g., a capsule, a tablet and the like).

If formulated as a fixed dose, such combination products employ the compounds of this invention within the dosage range described herein and the other pharmaceutically active agent or treatment within its dosage range. Compounds of the present invention may also be administered sequentially with known therapeutic agents when a combination formulation is inappropriate. The invention is not limited in the sequence of administration; compounds of the present invention may be administered either prior to or after administration of the known therapeutic agent. Such techniques are within the skills of persons skilled in the art as well as attending physicians.

The pharmacological properties of the compounds of this invention may be confirmed by a number of pharmacological assays for measuring HCV viral activity or cathepsin activity, such as are well known to those skilled in the art.

Preferably, in the practice of the invention, the concentration of HCV-RNA is quantitatively measured by research-based reverse transcriptase polymerase chain reaction (RT-PCR) assay well known to the skilled clinician. Specifically, the Hepatitis C virus (HCV) RNA is measured by extracting total RNA from plasma or serum samples and using an in-house real-time reverse transcriptase polymerase chain reaction (RT-PCR) assay. The amplification target is the 5'-Untranslated region (UTR) of the HCV genome. An internal RNA control is added to each sample to assess the efficiency of RNA extraction. Appropriate negative and positive controls are added in each assay run. The assay method has been validated against the WHO International Standard for HCV. HCV RNA amount in a sample is reported as copies of HCV RNA per mL of sample and also as HCV IU per mL of sample. Results for samples at or above 100 copies of HCV RNA per mL are denoted as POS. On the other hand, ND stands for <100 copies of HCV RNA or <29 IU of HCV per mL of sample. The RT-PCR assay has a lower limit of detection of HCV-RNA viral load of 29 International Units (IU) per milliliter (ml) of plasma of a subject. The concentration of 29 IU/ml HCV-RNA is equal to a concentration of 100 copies of HCV RNA per milliliter of plasma. With respect to quantifying HCV RNA with the rt-PCR methodology referred to herein, one (1) copy of HCV RNA equals 0.29 IU, such that 100 copies of HCV RNA per milliliter of plasma is 29 International Units per milliliter of plasma. Serum HCV-RNA/qPCR testing and HCV genotype testing will be performed by a central laboratory. See also J. G. McHutchinson et al. (N. Engl. J. Med., 1998, 339:1485-1492), and G. L. Davis et al. (N. Engl. J. Med. 339:1493-1499). HCV genotype is determined by sequencing the PCR amplified DNA fragment of the 5'-UTR of the HCV genome. The sequence is then aligned with the published sequences of the HCV genotypes to arrive at a determination.

While it is possible for the active ingredient to be administered alone, it is preferable to present it as a pharmaceutical composition. The compositions of the present invention comprise at least one active ingredient, as defined above, together with one or more acceptable carriers, adjuvants or vehicles thereof and optionally other therapeutic agents. Each carrier, adjuvant or vehicle must be acceptable in the sense of being compatible with the other ingredients of the composition and not injurious to the mammal in need of treatment.

Accordingly, this invention also relates to pharmaceutical compositions comprising at least one compound utilized in the presently claimed methods, or a pharmaceutically acceptable salt or ester thereof and at least one pharmaceutically acceptable carrier, adjuvant or vehicle.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

In one embodiment, the adjuvant is at least one pharmaceutically acceptable surfactant or at least one pharmaceutically acceptable acidifying agent or both. When desired or needed, suitable carriers and other excipients (such as binders, glidents, lubricants, and disintegrants) may also be incorporated in the formulation. Surfactants may be present in the pharmaceutical formulations of the present invention in an amount of about 0.1 to about 10% by weight or about 1 to about 5% by weight. Acidifying agents may be present in the pharmaceutical formulations of the present invention in a total amount of about 0.1 to about 10% by weight or about 1 to 5% by weight.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally, intravenously or subcutaneously.

Preferably, the pharmaceutical preparation is in a unit dosage form. In such form, the preparation is subdivided into suitably sized unit doses containing appropriate quantities of the active components, e.g., an effective amount to achieve the desired purpose.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophilic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites;

and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

The term pharmaceutical composition is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a subject by administering a pharmaceutical composition of the present invention is also intended to encompass the administration of the afore-said bulk composition and individual dosage units.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the present invention and/or the pharmaceutically acceptable salts or esters thereof will be regulated according to the judgment of the attending clinician considering such factors as age, condition and size of the patient as well as severity of the symptoms being treated. A typical recommended daily dosage regimen for oral administration can range from about 50 mg/day to about 3,000 mg/day, preferably from about 50 mg/day to about 2,400 mg/day, more preferably from about 50 mg/day to about 1,200 mg/day, in two to four divided doses.

The pharmaceutical formulation in a unit dosage form may contain about 50 mg to about 1000 mg of the compound of Formulae I-XXVI. Other unit dosage forms may contain from about 50 mg to about 800 mg, or from about 50 mg to about 600 mg, or from about 50 mg to about 400 mg, or from about 50 mg to about 200 mg according to the particular application. In one embodiment, the unit dosage form is tablet containing about 400 mg of the active compound.

EXAMPLE

A single dose, randomized, two-treatment (fed vs. fasted) study was conducted to assess the effect of food on bioavailability of a compound of the present invention (SCH 503034 or Compound Ia). A single oral dose of 600 mg. of compound of Formula Ia was administered to two groups of healthy subjects. Group A received the dose after an overnight 10-hour fast; Group B received the dose about twenty minutes after consuming a high fat breakfast of 850 calories having 53.8 g fat (57% of calories from fat) or low fat breakfast of 451 calories. Blood samples were collected immediately prior to dosing (time zero) and at times 0.5, 1, 1.5, 2, 2.5, 3, 4, 6, 8, 12, 24, 36, 48, and 72 hours post dose. Results of measurement of mean maximum concentration ($C_{max}$) of compound of Formula Ia in serum in ng/ml are shown in Table 1 and FIG. 1 (graph of mean plasma concentration of the compound versus Time). Calculations of AUC(tf) (area under the curve at time final), AUC(I) (area under the curve extrapolated to infinity), t½ (time at which one-half of the compound has disappeared from the blood), Tmax (time at which maximum serum concentration is achieved), CL/F (clearance divided by bioavailability), and Vd/F (volume of distribution divided by bioavailability) are made according to standard formulas known to one skilled in the art of drug metabolism and pharmacokintics.

TABLE 1

Mean (CV %) Pharmacokinetic Parameters of SCH 503034 Under Fasted and Fed (with High Fat and Non Fat Diet) Conditions (Balanced Data)

| Parameter[a] | Fasted | | | Fed (High Fat Diet) | | | Fed (Non Fat Diet) | | |
|---|---|---|---|---|---|---|---|---|---|
| | n | Mean | CV (%) | n | Mean | CV (%) | n | Mean | CV (%) |
| Cmax | 11 | 502 | 38 | 11 | 1148 | 48 | 11 | 639 | 38 |
| AUC(tf) | 11 | 1557 | 28 | 11 | 5090 | 43 | 11 | 3036 | 11 |
| AUC(I) | 8 | 1627 | 29 | 8 | 4435 | 29 | 8 | 2749 | 8 |
| t½ | 8 | 7.61 | 72 | 8 | 2.01 | 47 | 8 | 3.2 | 8 |
| CL/F | 8 | 407 | 38 | 8 | 144.0 | 24 | 8 | 243 | 8 |
| Vd/F | 8 | 4577 | 76 | 8 | 418.5 | 54 | 8 | 1140 | 8 |
| Tmax[c] | 11 | 1.5 (1-2) | | 11 | 4 (2-12) | | 11 | 4 (2.5-11) | |

[a](unit): AUC-ng · hr/mL; Cmax-ng/mL; Tmax, t½-hr; CL/F-L/hr; Vd/F-L.
[c]Median (range).

As shown in FIG. 1, peak serum levels ($C_{max}$) in subjects dosed with food were delayed as compared to peak serum levels in fasting subjects. Additionally, a higher peak serum level was obtained in subjects dosed with food as compared with fasting subjects, indicating that dosing with food increases bioavailability of the compound of Formula Ia and increases serum levels of the compound of Formula Ia. The mean Cmax values were 502, 1148 and 639 ng/mL (balanced data) under fasted state and fed state with high fat and non fat diets, respectively, and were achieved at 1.5, 12 and 11 hours (median Tmax value), respectively. The SCH 503034 was absorbed more slowly in the fed state. In 8 of the 12 subjects who completed all three periods, there appeared to be an absorption lag time of 0.5 hour in the fed state with high fat diet and 7 subjects with non fat diet also had 0.5 hour absorption lag time.

The relative bioavailability of SCH 503034 under fed and fasted conditions are presented below:

Relative Bioavailability of SCH 503034 under Fed and fasted States: Balanced Data

| Parameters[a] | Compare | Ratio Estimate (%)[c] | 90% Confidence Interval |
|---|---|---|---|
| Cmax | — | — | — |
| | B/A | 223 | 169-293 |
| | C/A | 129 | 98-170 |
| AUC (tf) | — | — | — |
| | B/A | 317 | 266-377 |
| | C/A | 182 | 153-217 |
| AUC(I) | — | — | — |
| | B/A | 276 | 238-319 |
| | C/A | 167 | 145-194 |

[a](unit): AUC-ng · hr/mL; Cmax-ng/mL; Tmax, t½-hr; CL/F-L/hr; Vd/F-L.
[c]Median (range).

Based on ratio estimates, the mean AUCs were increased by over 200% for high fat diet and about 100% for non fat diet, respectively, relative to fasted state. The corresponding values for Cmax were increased by 123 and 29%, respectively.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Each document (including granted patents, published patent applications, and nonpatent publications such as journal articles) referred to in this application is incorporated in its entirety by reference for all purposes.

The Following Experimental Section Applies for the Preparation of the Compounds of Formula XI:

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCI: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazod icarboxylate
MeOH: Methanol
EtOH: Ethanol
$Et_2O$: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl 'Bu or Bu': tert-Butyl
Boc: tert-Butyloxycarbonyl
Cbz: Benzyloxycarbonyl
Cp: Cylcopentyldienyl
Ts: p-toluenesulfonyl
MCPBA: 3-chloroperbenzoic acid.
Me: Methyl
HATU: O-(7-azabenzotriazol-1-yl)-1,1,3,3-tetramethyluronium hexafluorophosphate
DMAP: 4-N,N-Dimethylaminopyridine
Bop: Benzotriazol-1-yl-oxy-tris(dimethylamino)hexafluorophosphate
PCC: Pyridiniumchlorochromate Other abbreviations are commonly used abbreviations Such as according to the guidelines published by *Journal of Organic Chemistry*.

General Schemes for Preparation of Target Compounds

Compounds of the present invention were synthesized using the general schemes (Methods A-E) described below.

Method A

Deprotection of the N-Boc functionality of 1.01 under acidic conditions provided the hydrochloride salt 1.02 which was subsequently coupled with N-Boc-tert-leucine under peptide coupling methodology (Louis A Carpino et al. "Preparation of uronium and immonium salts for peptide coupling", WO 2002094822, pp. 76) to afford 1.03. N-Boc deprotection followed by treatment with appropriate isocyanate gave the urea 1.05. Hydrolysis of the methyl ester provided the acid 1.06. Peptide coupling of the acid 1.06 with the appropriate $P_1$-$P'$ primary amide moiety afforded the hydroxyl amide 1.07. Oxidation (Moffatt, or Dess-Martin's) resulted in the target compound 1.08.

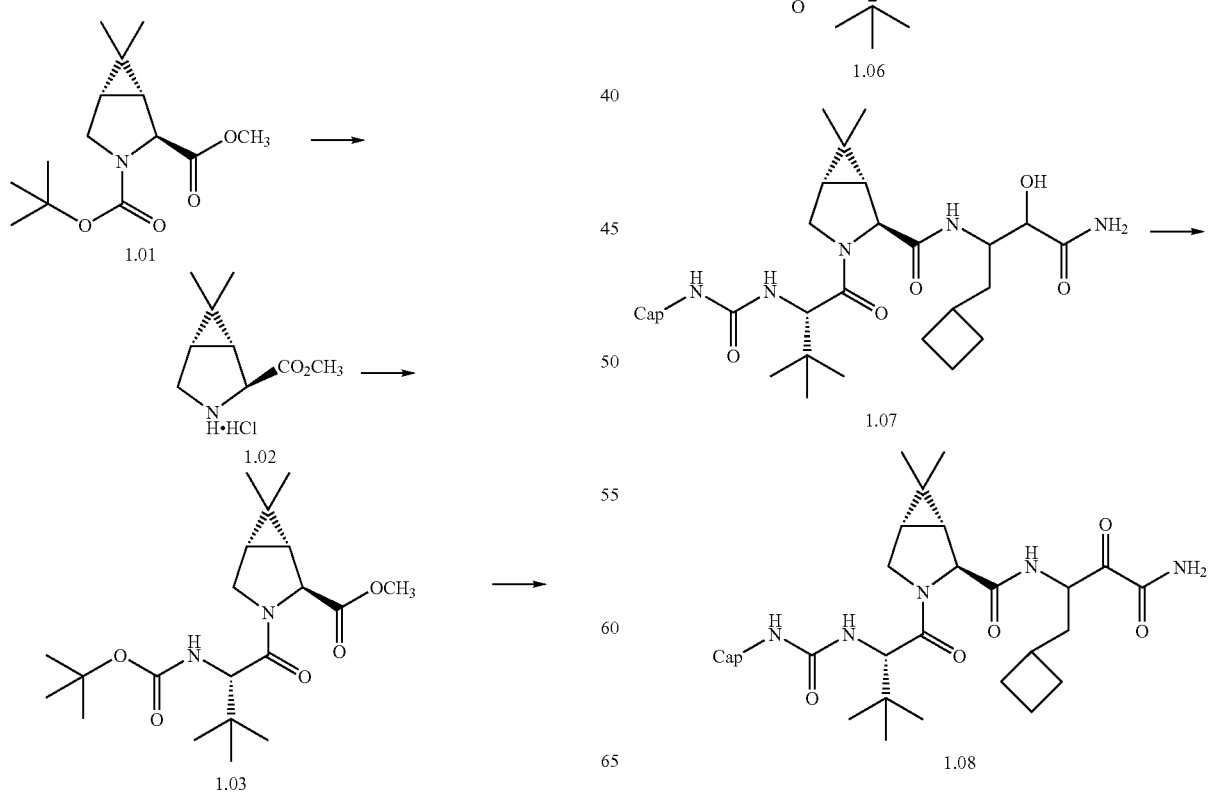

Method B

Peptide coupling of the acid 1.06 with the appropriate $P_1$-$P'$ secondary amide moiety afforded the hydroxylamide 1.09. Oxidation (Moffatt or Dess-Martin's) resulted in the target compound 1.10.

Method C

In another variation, peptide coupling of the N-Boc-P2-$P_3$-acid 1.03 with the appropriate $P_1$-$P'$ amide moiety afforded the hydroxylamide 1.11. Oxidation (Moffatt or Dess-Martin's) resulted in the keto-amide 1.12. Deprotection of the N-Boc using either formic acid or 4 M HCl in dioxane gave the formate or hydrochloride salt 1.13. Treatment with a suitable isocyanate (or isocyanate equivalent) resulted in the target compound 1.14.

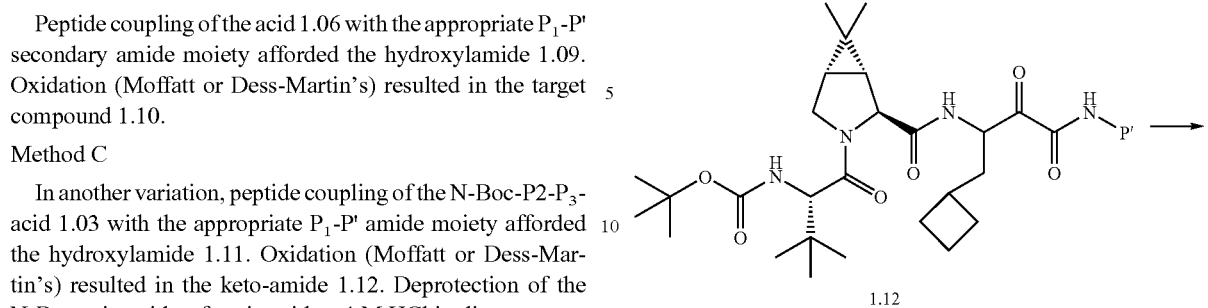

1.12

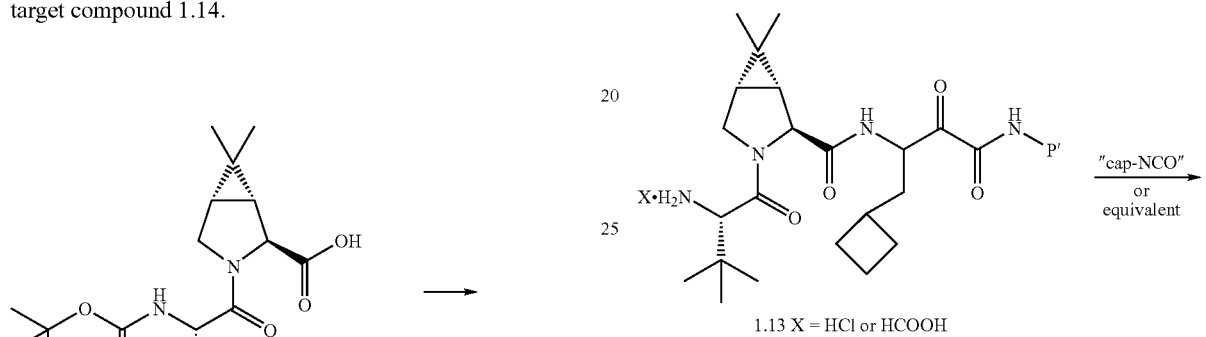

1.17

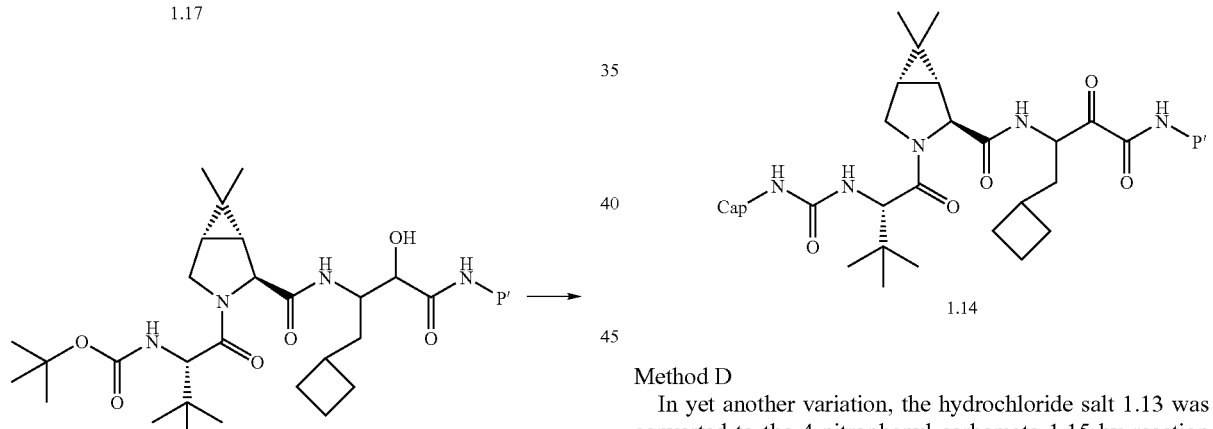

1.11

1.13 X = HCl or HCOOH 1.14

Method D

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

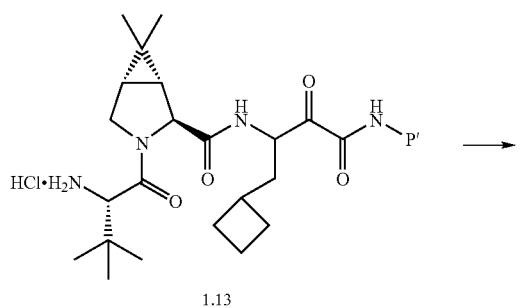

1.13

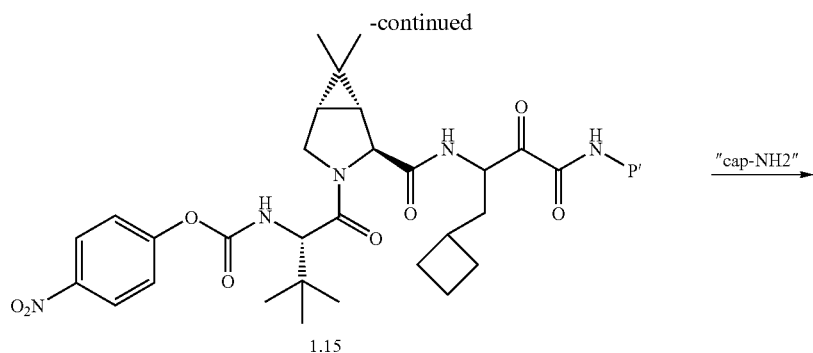

1.15

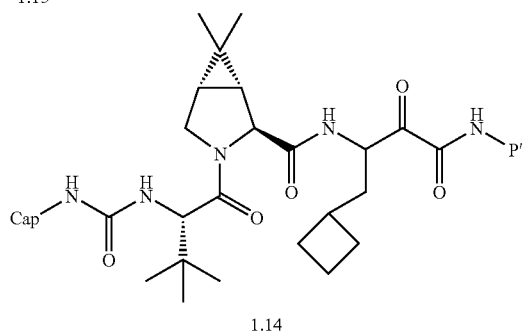

1.14

Method E

In yet another variation, the dipeptide hydrochloride salt 1.04 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

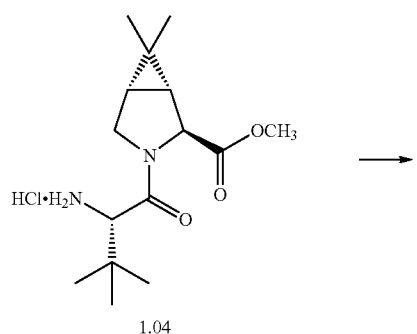

1.04

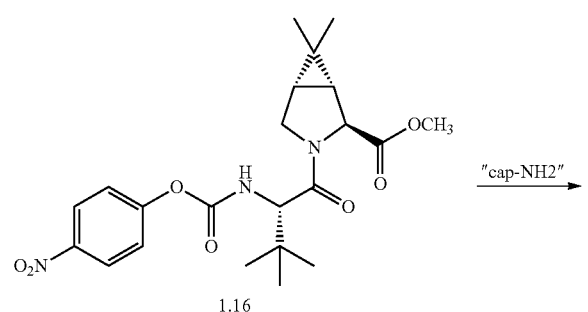

1.16

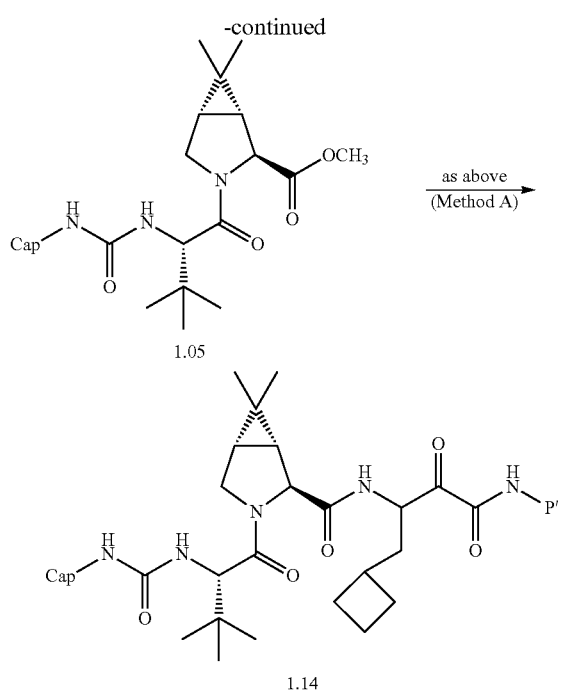

1.05

1.14

The Following Experimental Section Applies for the Preparation of the Compounds of Formula XII:

Abbreviations which are used in the descriptions of the schemes, preparations and the examples that follow are:

THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCI: 1-(3-dimethylaminopropyl)-3-ethylcarbodiimide hydrochloride NMM: N-Methylmorpholine
ADDP: 1,1'-(Azodicarbobyl)dipiperidine
DEAD: Diethylazodicarboxylate
MeOH: Methanol
EtOH: Ethanol
Et$_2$O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate General Schemes for Preparation of Target Compounds Compounds of the present invention were synthesized using the general schemes (Methods A-E) described below.

Method A:

Deprotection of the N-Boc functionality of 1.01 under acidic conditions provided the hydrochloride salt 1.02 which was subsequently coupled with N-Boc-tert-leucine under peptide coupling methodology to afford 1.03. N-Boc deprotection followed by treatment with appropriate isocyanate gave the urea 1.05. Hydrolysis of the methyl ester provided the acid 1.06. Peptide coupling of the acid 1.06 with the appropriate P$_1$-P' primary amide moiety afforded the hydroxylamide 1.07. Oxidation (Moffatt or related process—T. T. Tidwell, *Synthesis*, 1990, 857; or Dess-Martin's—*J. Org. Chem.*, 1983, 48, 4155) resulted in the target compound 1.08.

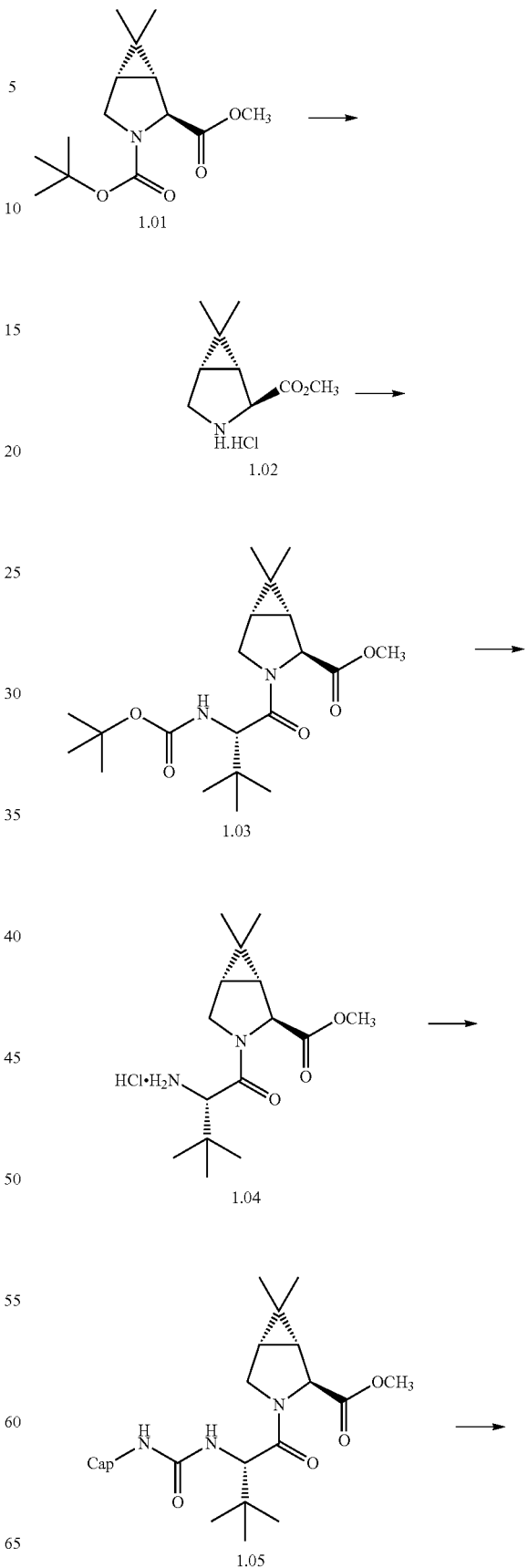

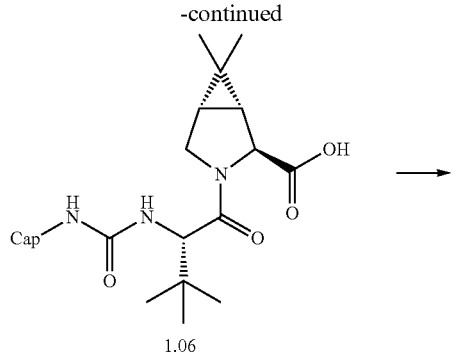

1.06

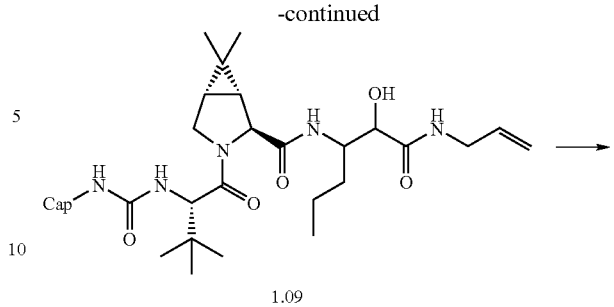

1.09

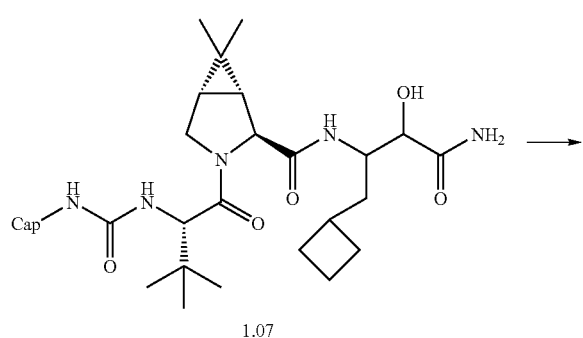

1.07

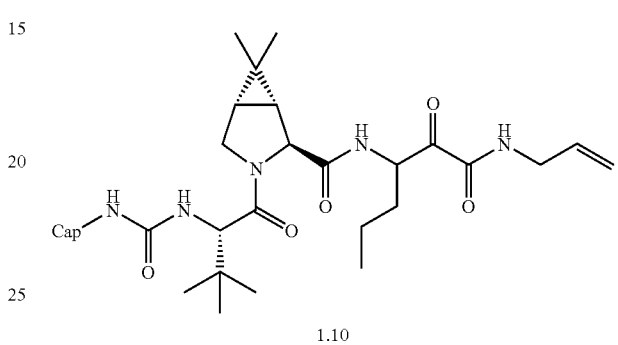

1.10

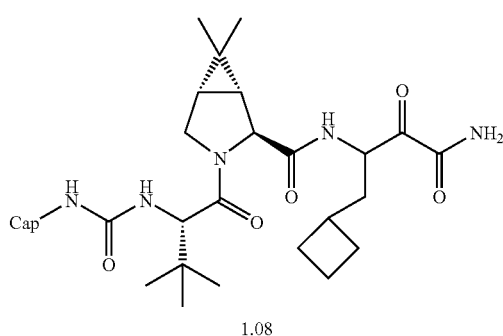

1.08

Method B

Peptide coupling of the acid 1.06 with the appropriate P$_1$-P' secondary amide moiety afforded the hydroxylamide 1.09. Oxidation (Moffatt or Dess-Martin's) resulted in the target compound 1.10.

Method C

In another variation, peptide coupling of the N-Boc-P$_2$-P$_3$-acid 1.17 with the appropriate P$_1$-P' amide moiety afforded the hydroxylamide 1.11. Oxidation (Moffatt or Dess-Martin's) resulted in the keto amide 1.12. Deprotection of the N-Boc functionality gave the hydrochloride salt 1.13. Treatment with a suitable isocyanate (or isocyanate equivalent) resulted in the target compound 1.14.

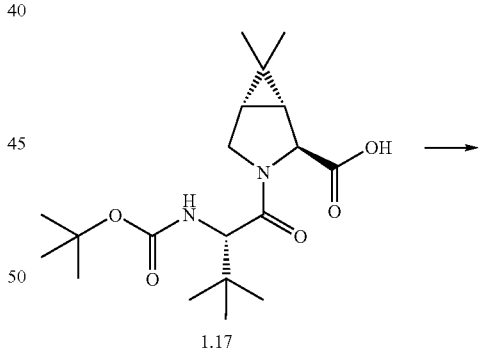

1.17

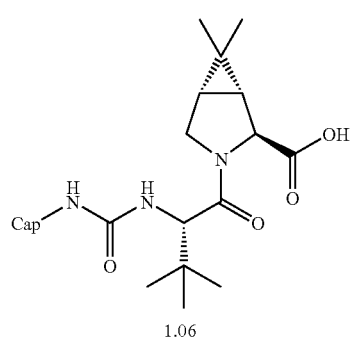

1.06

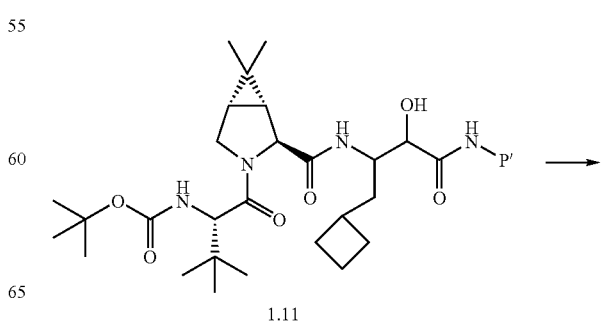

1.11

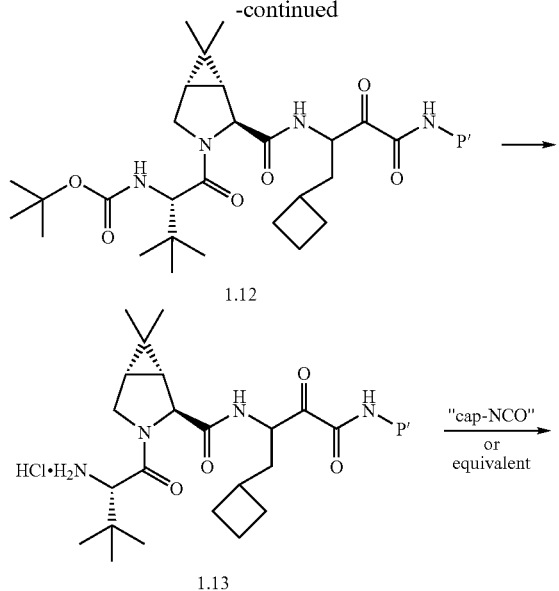
1.12
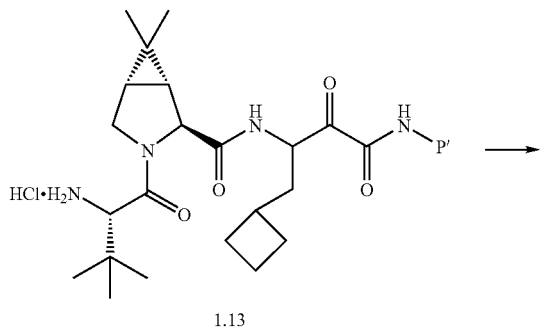
1.13
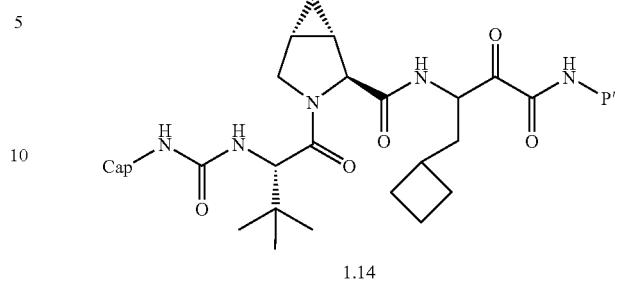
1.14
Method D
In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.
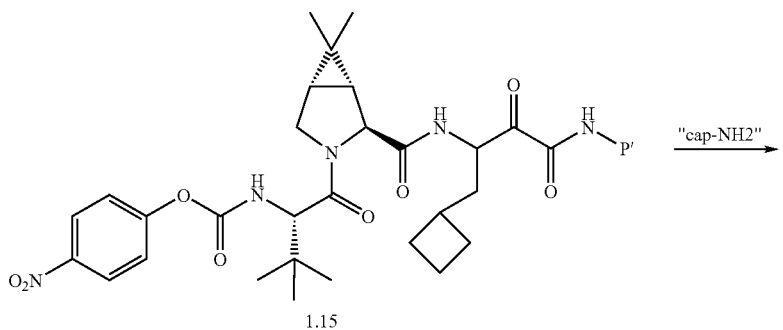
1.13
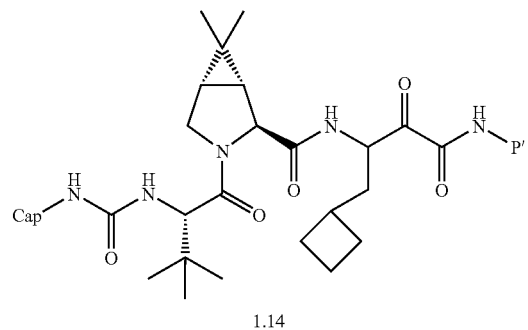
1.15
1.14

Method E

In yet another variation, the dipeptide hydrochloride salt 1.03 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

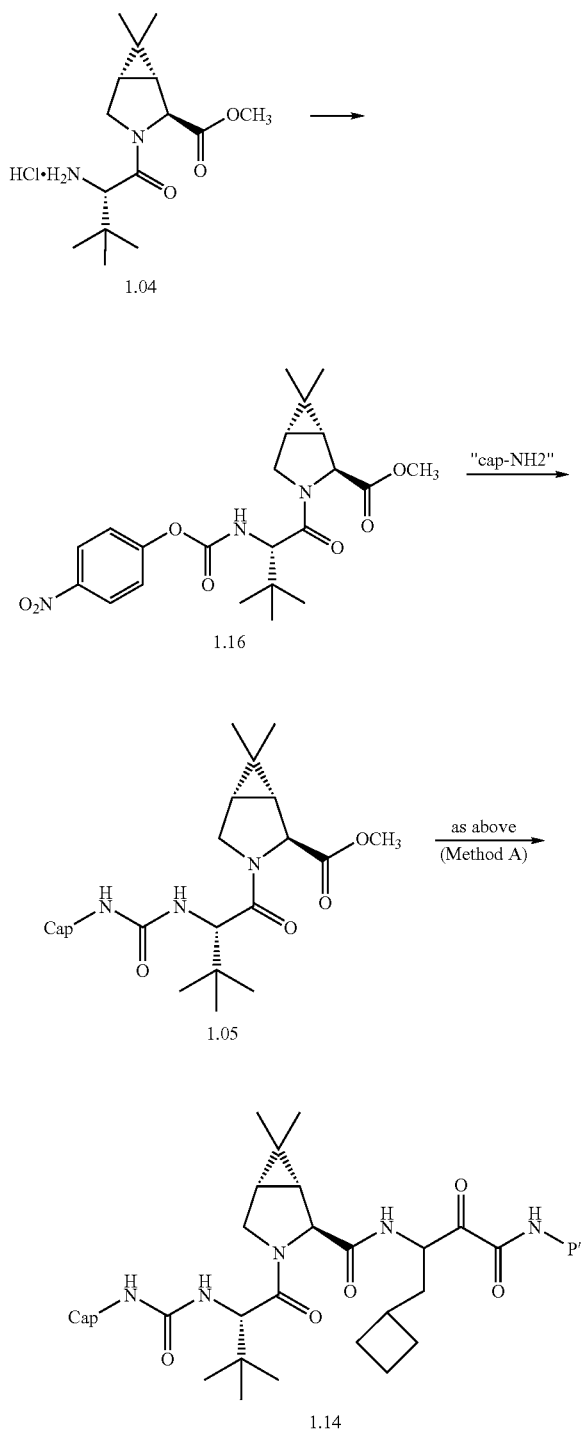

The following experimental section applies for the preparation of the compounds of Formula XIII:

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCI: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
DIAD: Diisopropylazodicarboxylate
MeOH: Methanol
EtOH: Ethanol
$Et_2O$: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bz: Benzyl
Et: Ethyl
Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
Ms or Mesyl: Methane sulfonyl
HATU: O-(7-azabenzotriazol-1-yl)-1,1,3,3-tetramethyluronium hexafluorophosphate
DMAP: 4-N,N-Dimethylaminopyridine
Bop: Benzotriazol-1-yl-oxy-tris(dimethylamino)hexafluorophosphate
PCC: Pyridiniumchlorochromate
DIBAL-H: diisopropyl aluminum hydride
rt or RT: Room temperature
quant.: Quantitative yield
h or hr: hour
min: minute
TFA: Trifluoroacetic acid General Schemes for Preparation of Target Compounds Compounds of the present invention were synthesized using the general schemes (Methods A-E) described below.

Method A

Deprotection of the N-Boc functionality of 1.01 under acidic conditions provided the hydrochloride salt 1.02 which was subsequently coupled with N-Boc-tert-leucine under peptide coupling methodology to afford 1.03. N-Boc deprotection followed by treatment with appropriate isocyanate gave the urea 1.05. Hydrolysis of the methyl ester provided the acid 1.06. Peptide coupling of the acid 1.06 with the appropriate P$_1$-P' primary amide moiety afforded the hydroxylamide 1.07. Oxidation (Moffatt or related process— T. T. Tidwell, *Synthesis*, 1990, 857; or Dess-Martin's periodinane (*J. Org. Chem.*, 1983, 48, 4155) resulted in the target compound 1.08.

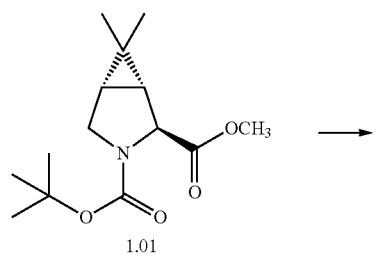
1.01

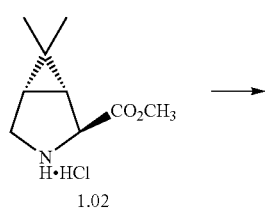
1.02

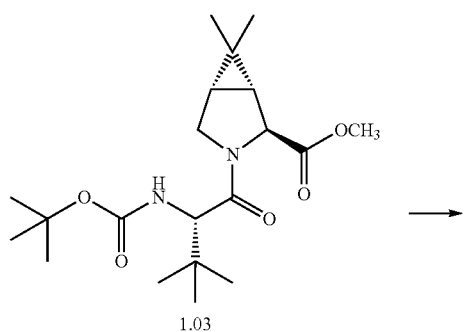
1.03

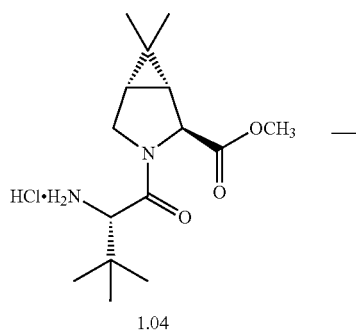
1.04

-continued

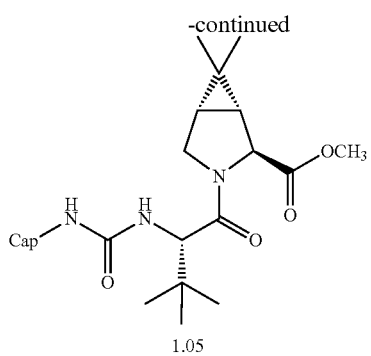
1.05

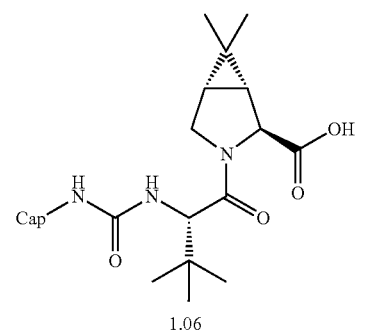
1.06

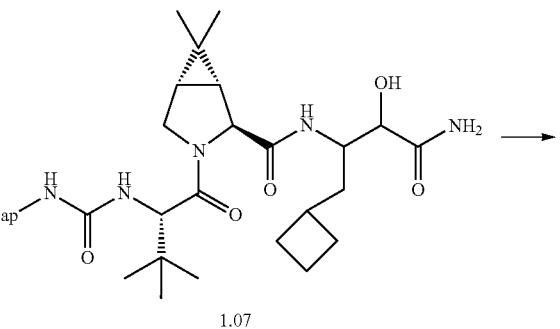
1.07

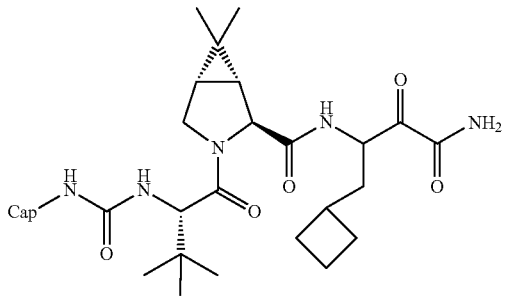
1.08

Method B

Peptide coupling of the acid 1.06 with the appropriate P$_1$-P' secondary amide moiety afforded the hydroxylamide 1.09. Oxidation (Moffatt or Dess-Martin's) resulted in the target compound 1.10.

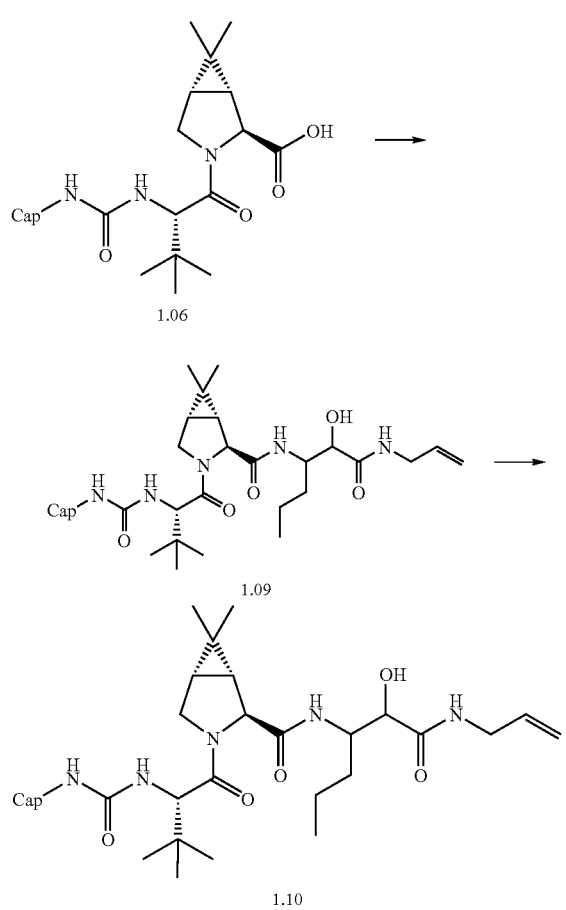

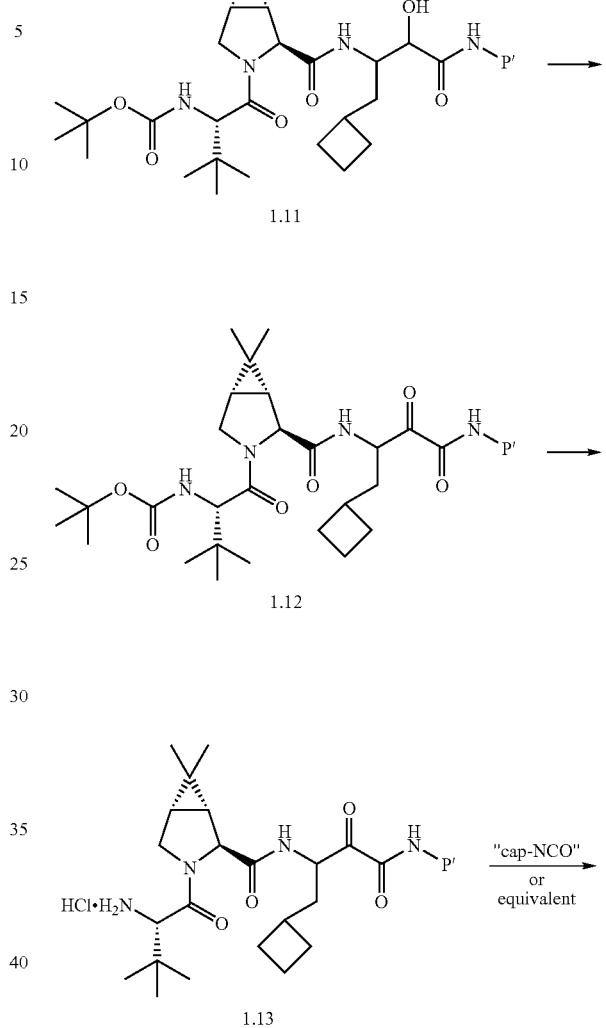

Method C

In another variation, peptide coupling of the N-Boc-P$_2$-P$_3$-acid 1.17 with the appropriate P$_1$-P' amide moiety afforded the hydroxylamide 1.11. Oxidation (Moffatt or Dess-Martin's) resulted in the keto amide 1.12. Deprotection of the N-Boc functionality gave the hydrochloride salt 1.13. Treatment with a suitable isocyanate (or isocyanate equivalent) resulted in the target compound 1.14.

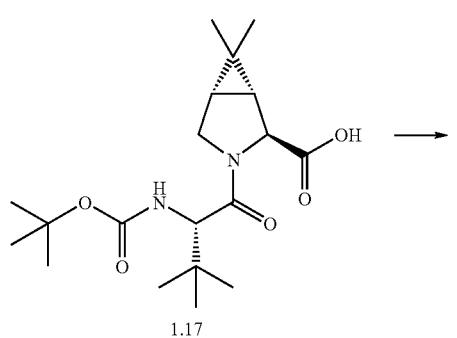

Method D

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

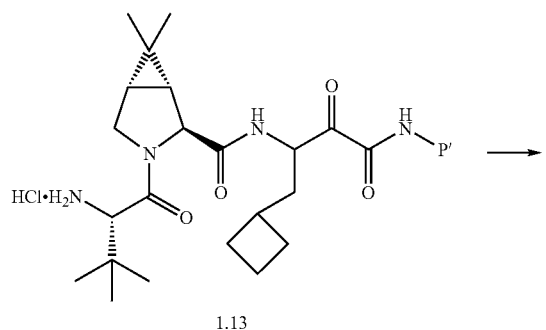
1.13
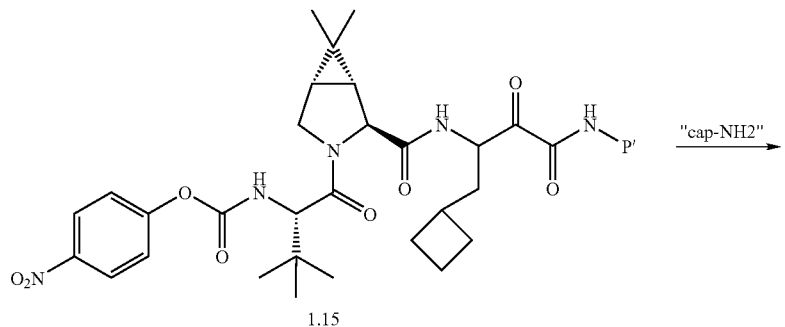
1.15
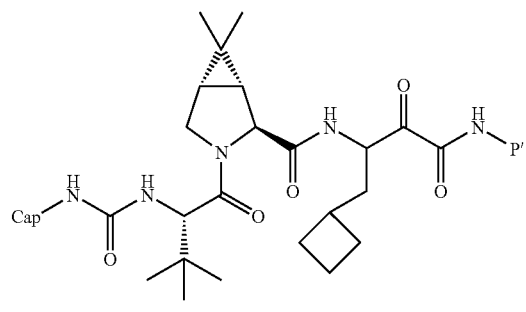
1.14
Method E
In yet another variation, the dipeptide hydrochloride salt 1.03 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.
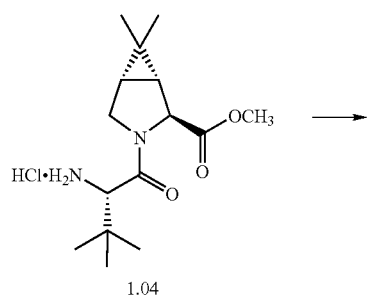
1.04
-continued
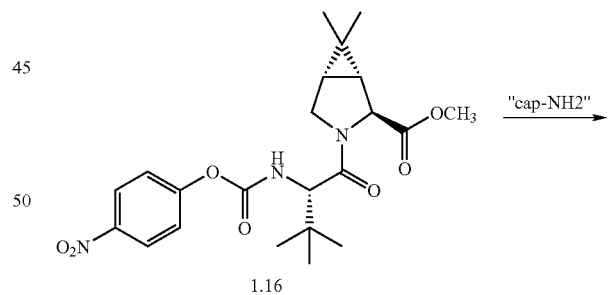
1.16
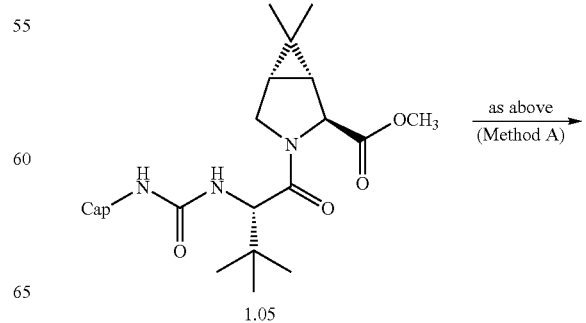
1.05

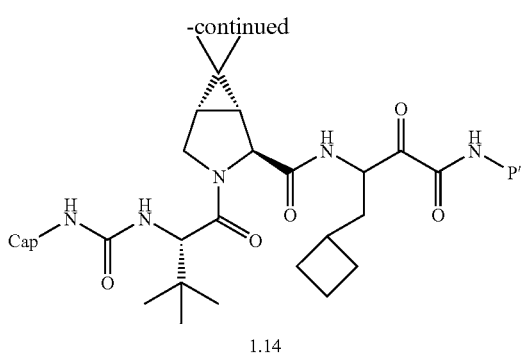

1.14

The Following Experimental Section Applies for the Preparation of the Compounds of Formula XIV:

For the procedures described below, the following abbreviations are used:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCI: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
DMF-DMA: N,N-Dimethylformamide-dimethylacetal
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis (trimethylsilylamide)
NaHMDS: Sodium Hexamethyldisilazide or Sodium bis(trimethylsilylamide)
LiHMDS: Lithium Hexamethyldisilazide or Lithium bis(trimethylsilylamide)
10% Pd/C: 10% Palladium on carbon (by weight).
TG: Thioglycerol General Schemes for Preparation of Target Compounds Compounds of the present invention were synthesized using the general schemes (Methods A-E) described below.

Method A

Deprotection of the N-Boc functionality of 1.01 under acidic conditions provided the hydrochloride salt 1.02 which was subsequently coupled with N-Boc-tert-leucine under peptide coupling methodology to afford 1.03. N-Boc deprotection followed by treatment with appropriate isocyanate gave the urea 1.05. Hydrolysis of the methyl ester provided the acid 1.06. Peptide coupling of the acid 1.06 with the appropriate P$_1$-P' primary amide moiety afforded the hydroxylamine 1.07. Oxidation (Moffatt oxidation or related process—see, T. T. Tidwell, *Synthesis,* 1990, 857), or Dess-Martin Periodinane—*J. Org. Chem.*, (1983) 48, 4155) resulted in the target compound 1.08.

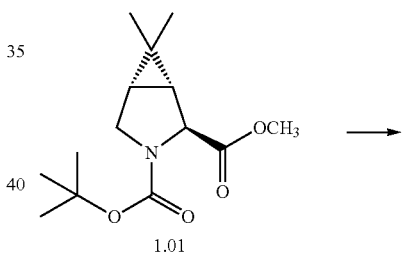

1.01

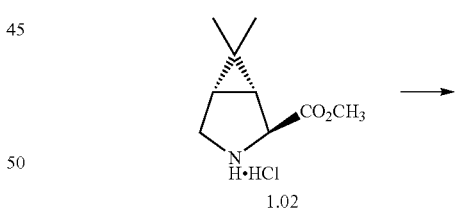

1.02

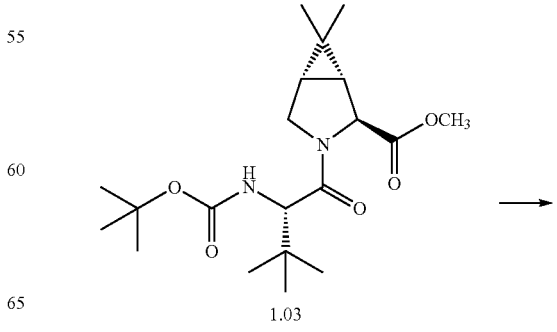

1.03

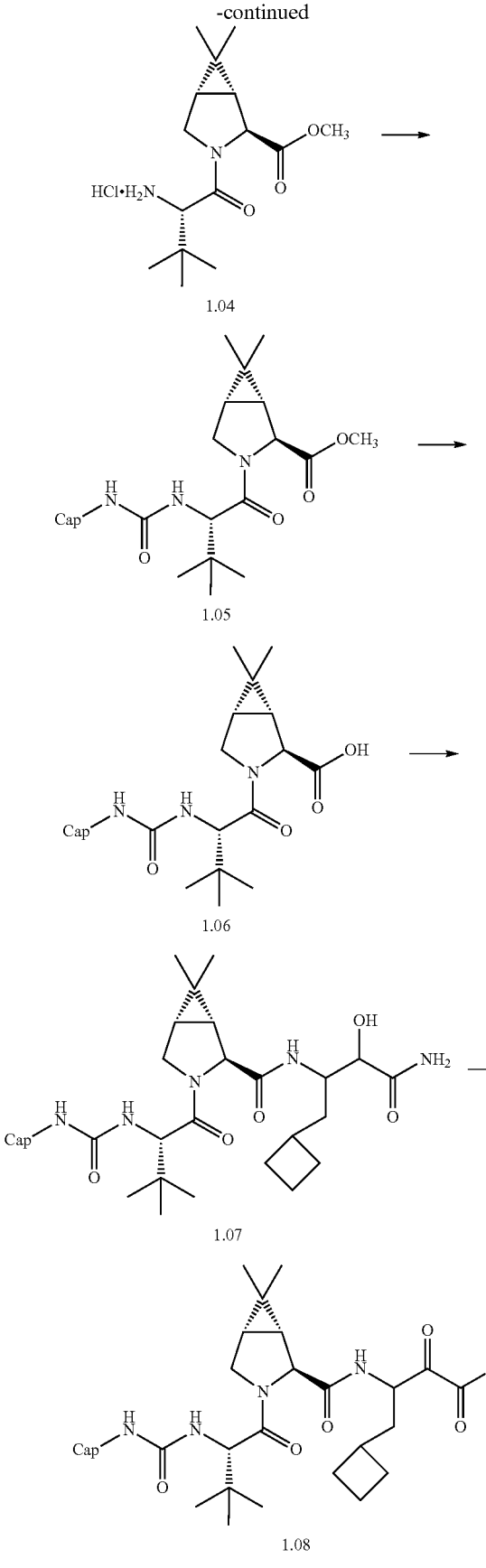

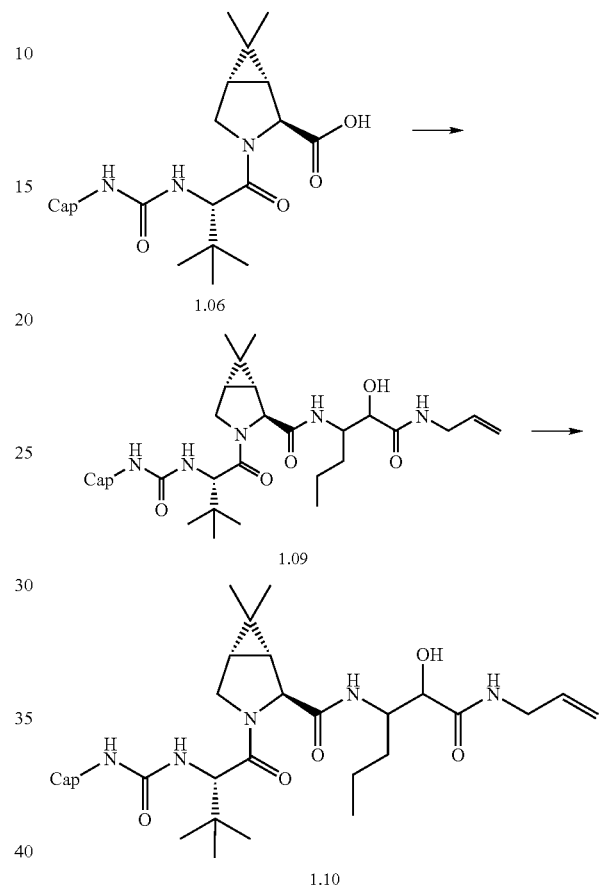

Method B

Peptide coupling of the acid 1.06 with the appropriate P₁-P' secondary amide moiety afforded the hydroxylamide 1.09. Oxidation (Moffatt or Dess-Martin's) resulted in the target compound 1.10.

Method C

In another variation, peptide coupling of the N-Boc-P2-P₃-acid 1.17 with the appropriate P₁-P' amide moiety afforded the hydroxylamide 1.11. Oxidation (Moffatt or Dess-Martin Periodinane) resulted in the keto amide 1.12. Deprotection of the N-Boc functionality gave the hydrochloride salt 1.13. Treatment with a suitable isocyanate (or isocyanate equivalent) resulted in the target compound 1.14.

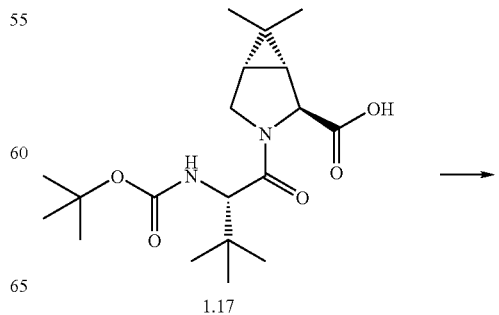

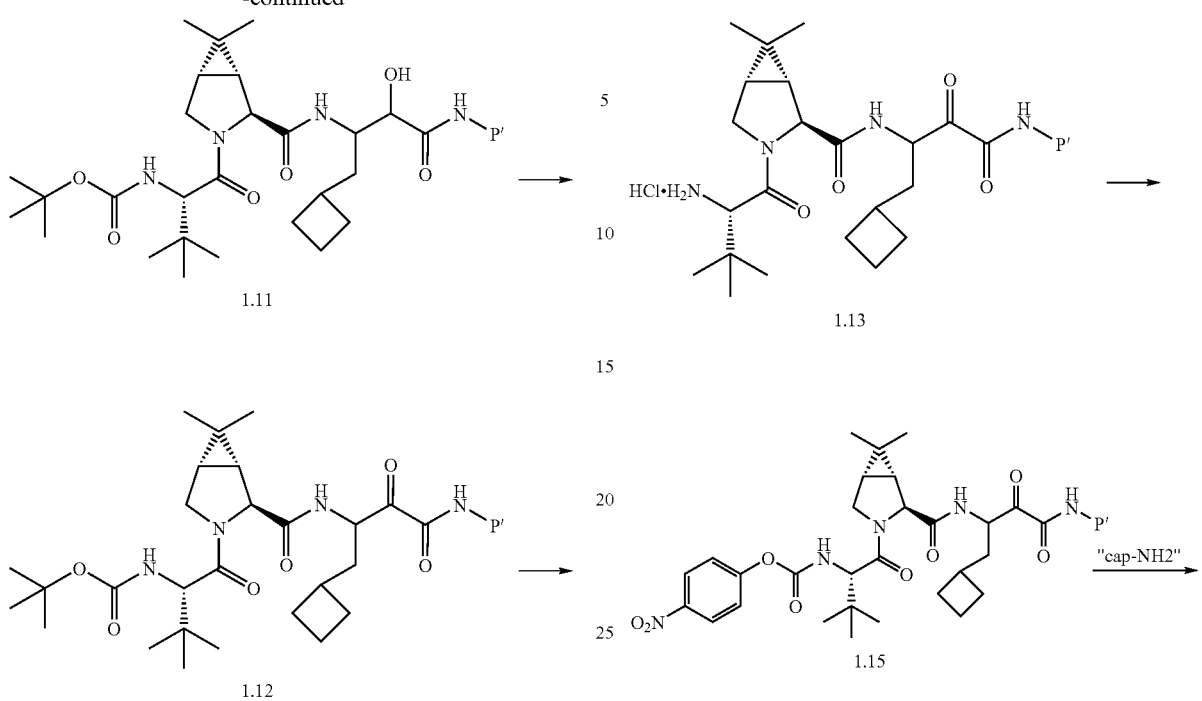

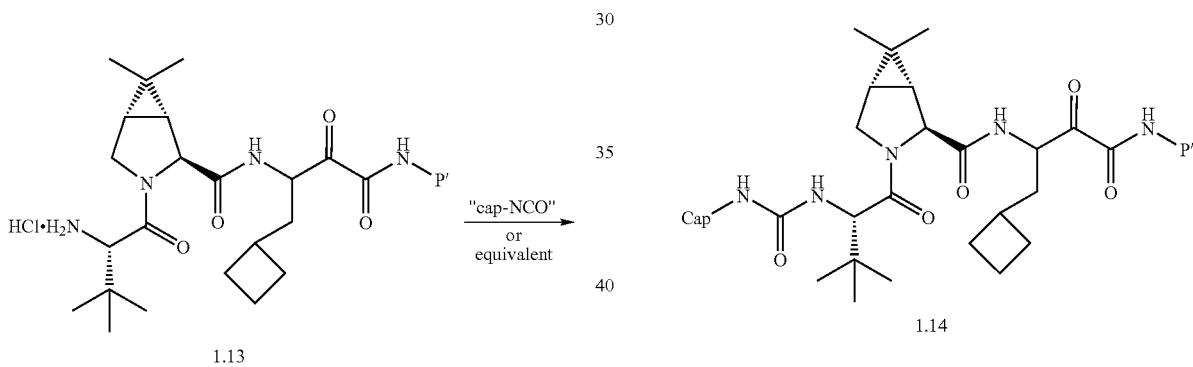

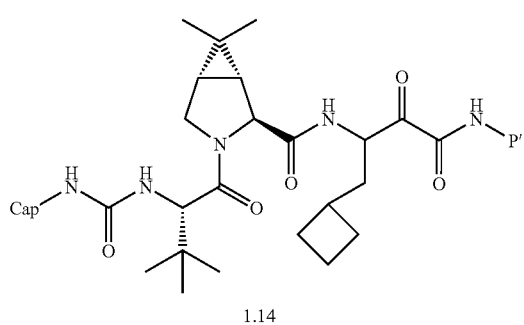

Method D

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

Method E

In yet another variation, the dipeptide hydrochloride salt 1.03 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

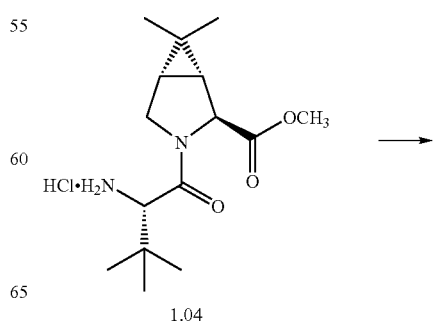

-continued

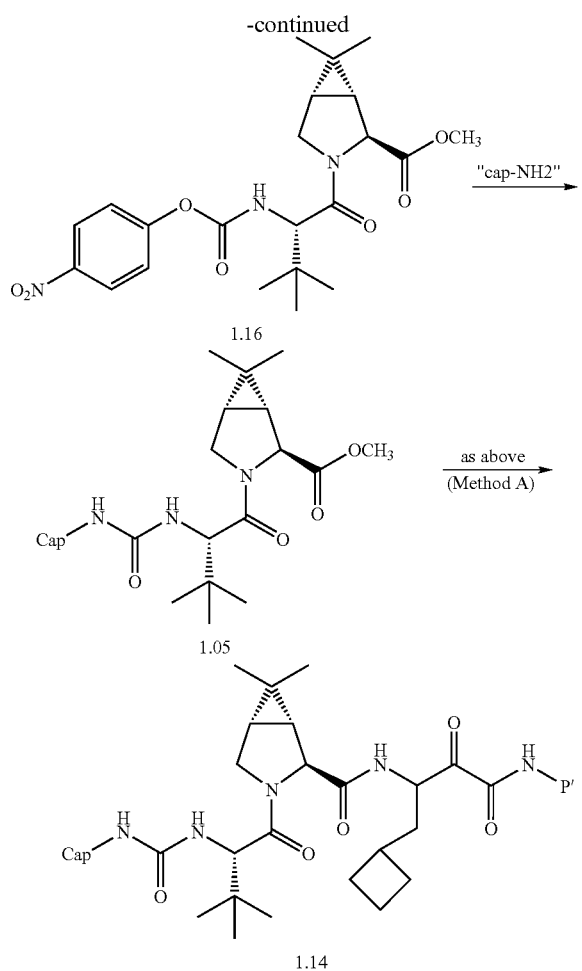

Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis(trimethylsilylamide)
NaHMDS: Sodium Hexamethyldisilazide or Sodium bis(trimethylsilylamide)
LiHMDS: Lithium Hexamethyldisilazide or Lithium bis(trimethylsilylamide)
10% Pd/C: 10% Palladium on carbon (by weight).

Preparative Example 1

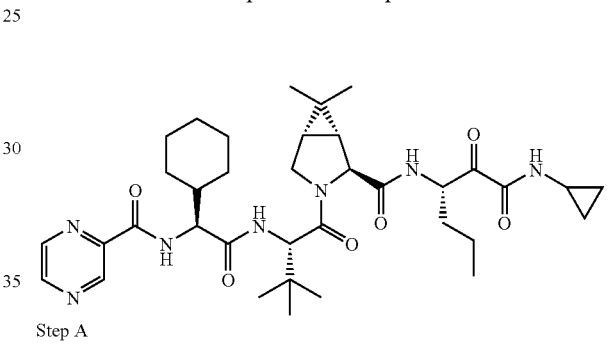

Step A

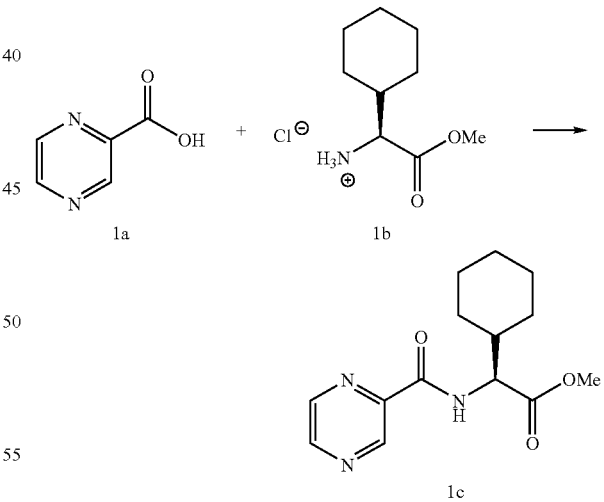

The Following Experimental Section Applies for the Preparation of the Compounds of Formula XV:

For the procedures described below, the following abbreviations are used:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCI: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl A solution of pyrazinecarboxylic acid 1a (3 g) in 150 mL of dry dichloromethane and 150 mL of dry DMF was stirred at 0° C. and treated with HATU (1.4 eq, 6.03 g). L-cyclohexylglycine hydrochloride 1b (1.2 eq, 6.03 g) was added in small portions. Then, N-methylmorpholine (4 eq, 10 mL, d 0.920) was added dropwise. The reaction mixture was gradually warmed to room temperature and stirred for 20 h. All the volatiles were removed under vacuum and the residue was dissolved in 500 mL of ethyl acetate. The organic layer was washed with water (100 mL), aqueous 1N HCl (100 mL), aqueous saturated sodium bicarbonate solution (100 mL), and brine (100 mL). The organic layer was dried over magnesium sulfate, filtered and concentrated under reduced pressure. The residue was chromatographed on silica gel (gradient: acetone/hexanes; 5:95 to 3:7) to afford the product 1c as a white solid.

Step B

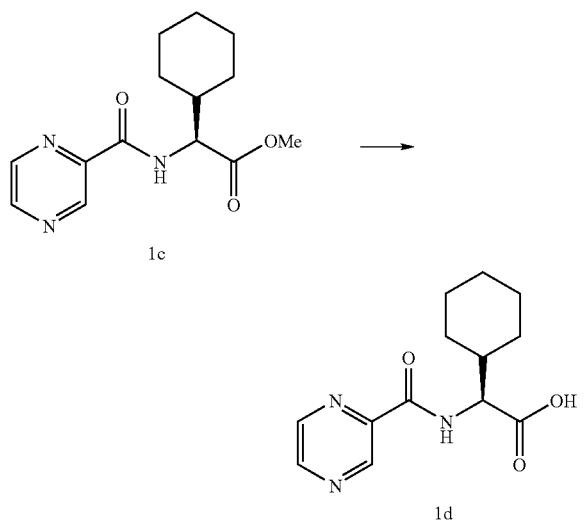

A solution of methyl ester 1c (6.5 g) in 270 mL of a 1:1:1 mixture of THF/MeOH/water was cooled to 0° C. and treated with lithium hydroxide monohydrate (2.5 eq, 2.45 g). The mixture was stirred and monitored by TLC (acetone/hexanes; 2:8). When all the starting material had been consumed, the reaction mixture was treated with 100 mL of aqueous 1N HCl and the mixture was concentrated on the rotavap. Dichloromethane (250 mL) was added and layers separated. The aqueous layer was extracted with dichloromethane (3×80 mL). The combined organic layers were dried over magnesium sulfate, filtered, and concentrated to afford the product 1d as a white solid.

Step C

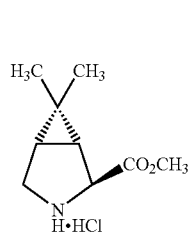

The amino ester 1e was prepared following the method of R. Zhang and J. S. Madalengoitia (*J. Org. Chem.* 1999, 64, 330), with the exception that the Boc group was cleaved by the reaction of the Boc-protected amino acid with methanolic HCl (4M HCl in dioxane was also employed for the deprotection).

(Note: In a variation of the reported synthesis, the sulfonium ylide was replaced with the corresponding phosphonium ylide).

Step D

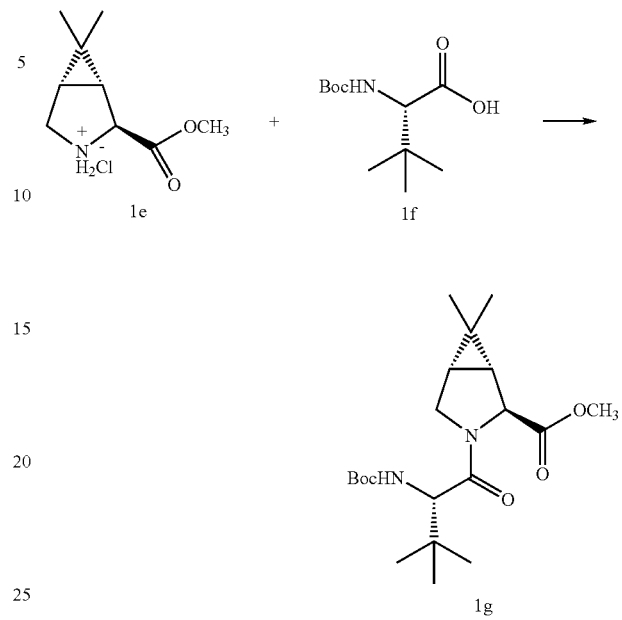

A solution of Boc-tert-Leu 1f (Fluka, 5.0 g, 21.6 mmol) in dry $CH_2Cl_2$/DMF (50 mL, 1:1) was cooled to 0° C. and treated with the amine hydrochloride 1e (5.3 g, 25.7 mmol), NMM (6.5 g, 64.8 mmol) and BOP reagent (11.6 g, 25.7 mmol). The reaction was stirred at rt. for 24 h, diluted with aqueous HCl (1 M) and extracted with $CH_2Cl_2$. The combined organic layers were washed with aqueous 1M HCl, saturated $NaHCO_3$, brine, dried ($MgSO_4$), filtered and concentrated in vacuo and purified by chromatography ($SiO_2$, Acetone/Hexane 1:5) to yield 1g as a colorless solid.

Step E

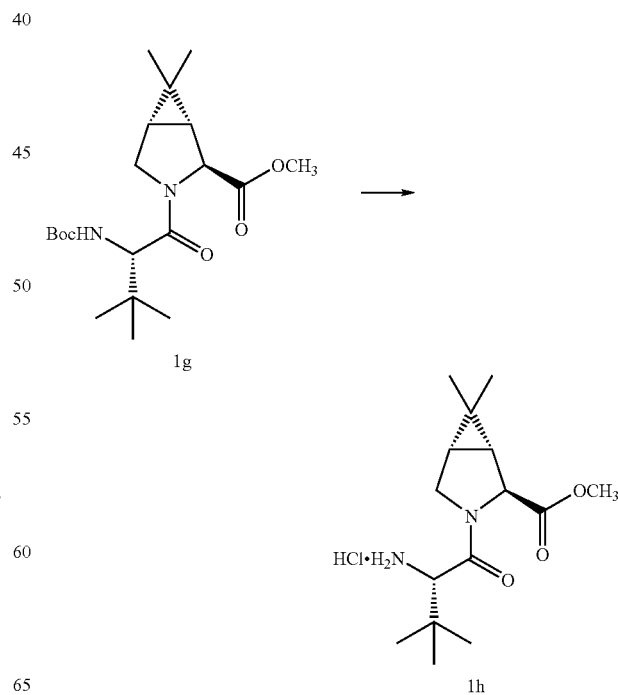

A solution of methyl ester 1g (4.0 g, 10.46 mmol) was dissolved in 4M HCl in dioxane and stirred at rt. for 3 h. The reaction mixture was concentrated in vacuo to obtain the amine hydrochloride salt, 1 h which was used without purification.

Step F

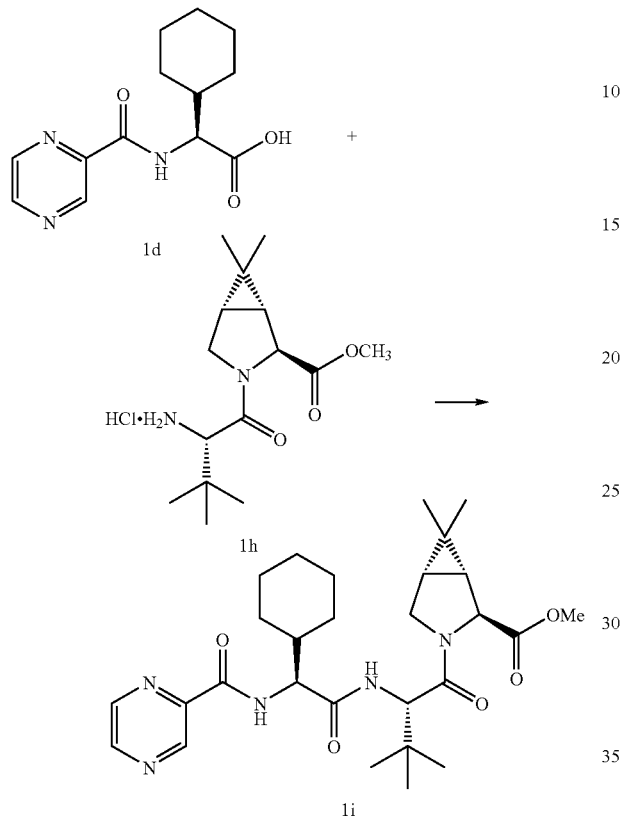

A solution of acid 1d (100 mg) in 5 mL of dry dichloromethane and 5 mL of dry DMF was stirred at 0° C. and treated with HATU (1.4 eq, 202 mg). The amine hydrochloride 1h (1.2 eq, 146 mg) was added. Then, N-methylmorpholine (4 eq, 0.17 mL, d 0.920) was also added. The reaction mixture was stirred at 0° C. overnight. All the volatiles were removed under vacuum and the residue was dissolved in 80 mL of ethyl acetate. The organic layer was washed with water (10 mL), aqueous 1N HCl (10 mL), aqueous saturated sodium bicarbonate solution (10 mL), and brine (10 mL). The organic layer was dried over magnesium sulfate, filtered and concentrated under reduced pressure. The residue was chromatographed on silica gel (gradient: acetone/hexanes; 1:9 to 4:6) to afford the product 1i as a white solid.

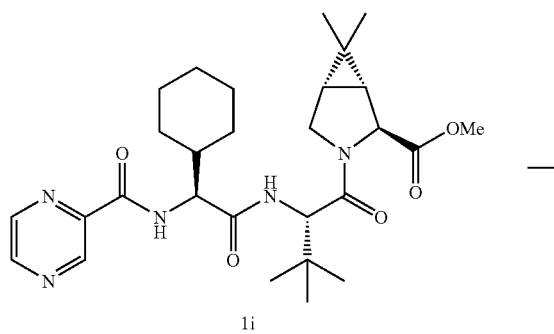

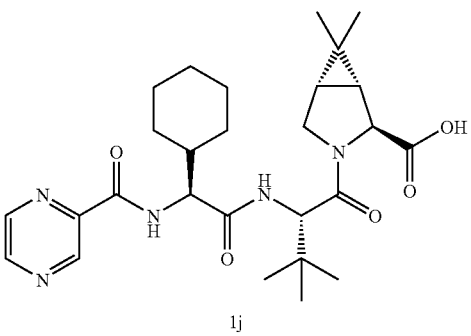

A solution of methyl ester 1i (180 mg) in 9 mL of a 1:1:1 mixture of THF/MeOH/water was cooled to 0° C. and treated with lithium hydroxide monohydrate (2.5 eq, 35 mg). The mixture was stirred and monitored by TLC (acetone/hexanes; 3:7). When all the starting material had been consumed, the reaction mixture was treated with 50 mL of aqueous 1N HCl and the mixture was concentrated on the rotavap. Dichloromethane (80 mL) was added and layers separated. The aqueous layer was extracted with dichloromethane (3×50 mL). The combined organic layers were dried over magnesium sulfate, filtered, and concentrated to afford the product 1j as a white solid.

Step H

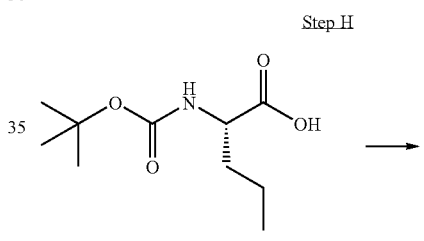

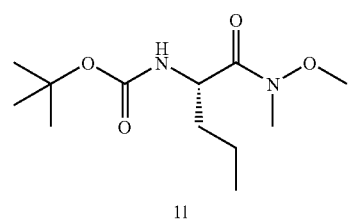

A solution of acid 1k (2 g) in 100 mL of dry dichloromethane and 5 mL of DMF was treated with N,O-dimethylhydroxylamine hydrochloride (1.1 eq, 986 mg), BOP reagent (1.1 eq, 4.47 g), and N-methylmorpholine (3.3 eq, 3.3 mL, d 0.920) in that order. The mixture was heated to 50° C. overnight. The reaction mixture was concentrated to half its volume and diluted with 400 mL of ethyl acetate. The organic layer was washed with water (80 mL), aqueous 1M HCl (80 mL), aqueous saturated sodium bicarbonate solution (80 mL), and brine (80 mL). The organic layer was dried over magnesium sulfate, filtered, and concentrated under reduced pressure. The residue was chromatographed on silica gel (gradient: acetone/hexanes; 5:95 to 3:7) to afford the product 1l as a clear oil.

Step I

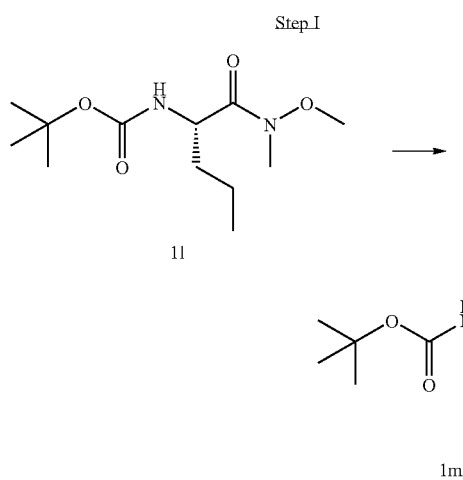

A solution of amide 11 (2.2 g) in 100 mL of dry THF was cooled to ° C. Lithium aluminum hydride solution (1.3 eq) was added dropwise. The cooling bath was removed after 5 min and the mixture was allowed to reach room temperature. TLC analysis (ethyl acetate/hexanes; 2:8) showed that all the starting material had been consumed. The excess LAH was carefully quenched by addition of drops of aqueous saturated sodium hydrogen sulfate. The mixture was diluted with 200 mL of ether and aqueous saturated sodium hydrogen sulfate was added in small portions until a white solid precipitated. The mixture was filtered thru celite and the filtrate was washed with 50 mL of brine. The organic layer was dried over magnesium sulfate, filtered and concentrated. The residue was chromatographed on silica gel (gradient: ethyl acetate/hexanes; 5:95 to 4:6) to afford the aldehyde product 1m as a colorless oil.

Step J

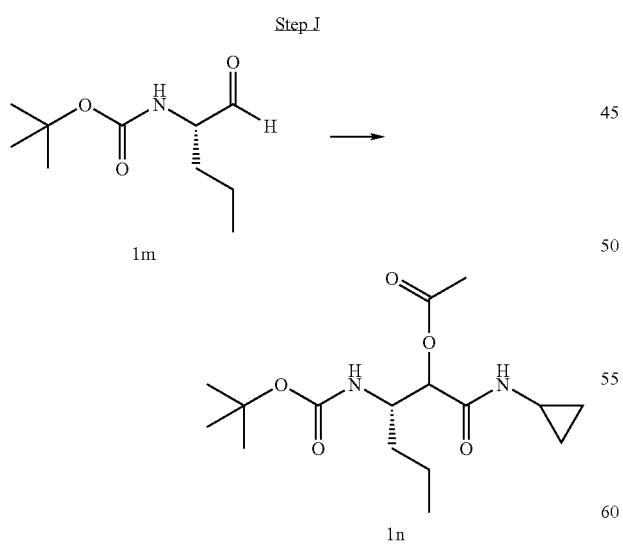

A solution of aldehyde 1m (1.8 g) in 100 mL of dry dichloromethane was treated with isonitrile (1.1 eq, 680 mg) and acetic acid (2 eq, 1.02 mL, d 1.0149). The mixture was stirred overnight. All the volatiles were removed under vacuum and the residue was chromatographed on silica gel (gradient: ethyl acetate/hexanes; 2:8 to 6:4) to afford the product 1n as a white solid.

Step K

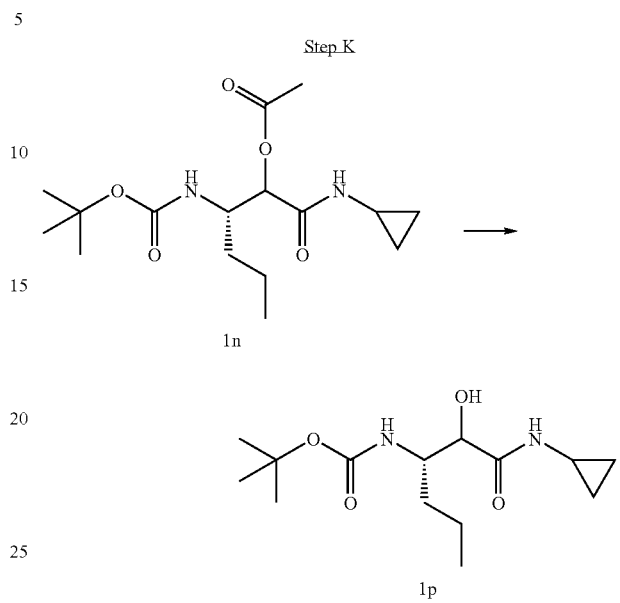

A solution of acetate 1n (1.6 g) in 60 mL of a 1:1:1 mixture of THF/MeOH/water was treated with lithium hydroxide monohydrate and stirred for approximately 1 h until all the starting material had been consumed as determined by TLC analysis (ethyl acetate/hexanes; 1:1). The volatiles were removed in rotavap and the residue was diluted with dichloromethane (150 mL). The layers were separated and the aqueous layer was diluted with 30 mL of aqueous saturated sodium bicarbonate solution and extracted with dichloromethane (3×80 mL). The combined organic layers were dried over magnesium sulfate, filtered and concentrated to afford the product 1p as a white solid.

Step L

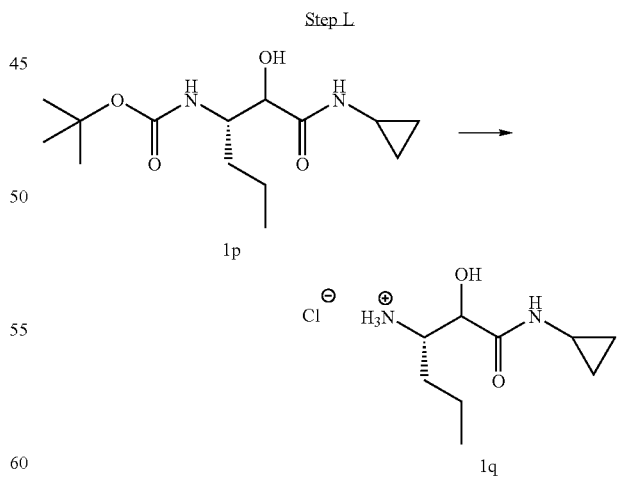

The N-Boc protected amine 1p (1.5 g) was dissolved in 20 mL of 4M HCl in dioxane. The reaction mixture was stirred for about 1 h until all the starting material had been consumed. All the volatiles were removed under vacuum to afford the product 1q as a white solid.

Step M

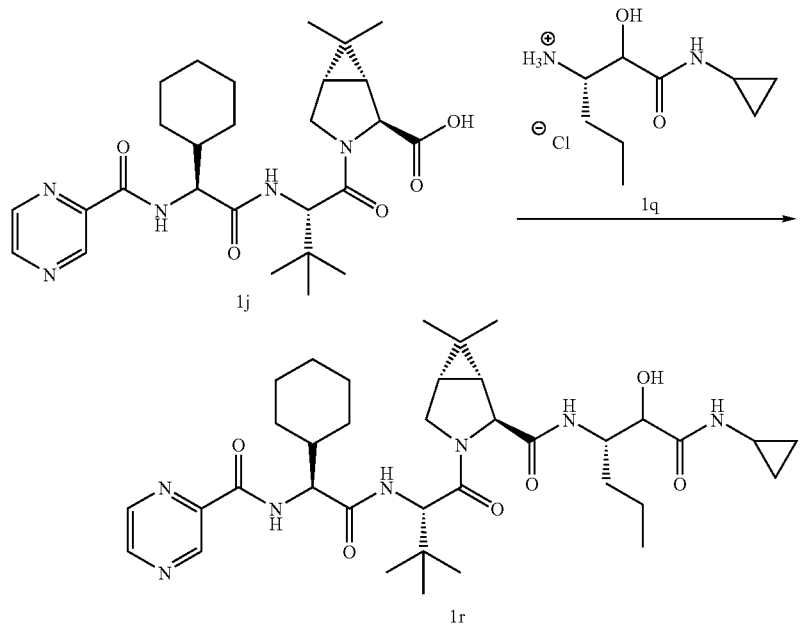

A solution of acid 1j (50 mg) in 2 mL of dry dichloromethane and 2 mL of dry DMF was stirred at 0° C. and treated with HATU (1.4 eq, 52 mg). The amine hydrochloride 1q (1.2 eq, 26 mg) was added. Then, N-methylmorpholine (4 eq, 0.042 mL, d 0.920) was also added. The reaction mixture was stirred at 0° C. overnight. All the volatiles were removed under vacuum and the residue was dissolved in 80 mL of ethyl acetate. The organic layer was washed with water (10 mL), aqueous 1N HCl (10 mL), aqueous saturated sodium bicarbonate solution (10 mL), and brine (10 mL). The organic layer was dried over magnesium sulfate, filtered and concentrated under reduced pressure. The product 1r was used without further purification.

Step N

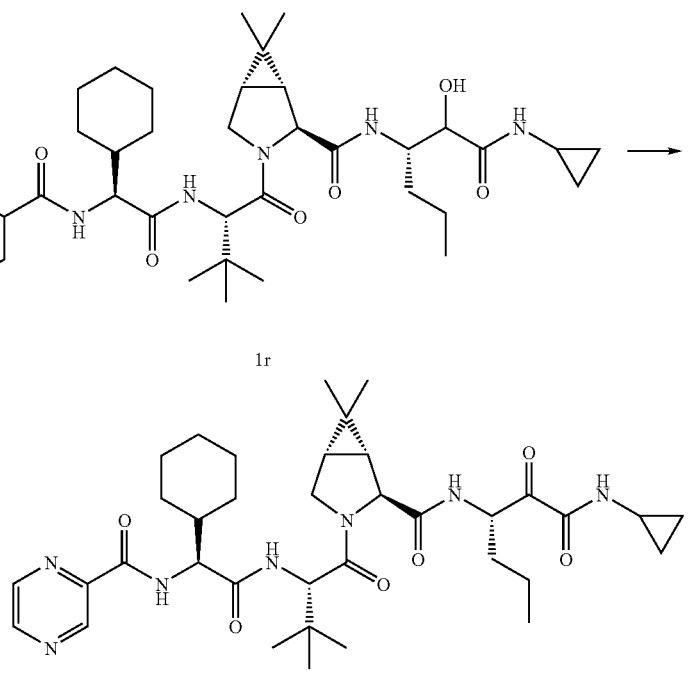

781

A solution of alcohol 1r (65 mg) in 5 mL of dry dichloromethane was treated with Dess-Martin periodinane (3 eq, 121 mg). Reaction mixture was stirred at room temperature for 45 min. The mixture was treated with aqueous 1M sodium thiosulfate solution (10 mL) and aqueous saturated sodium bicarbonate solution (10 mL) and stirred for 15 min. The mixture was extracted with dichloromethane (3×20 mL). The combined organic layers were dried over magnesium sulfate, filtered, and concentrated. The residue was chromatographed on silica gel (gradient: acetone/hexanes; 2:8 to 5:5) to afford the product 1 as a white solid.

One skilled in the art would understand that other suitable compounds of Formula XV can be prepared in a similar manner to that disclosed above.

The Following Experimental Section Applies for the Preparation of the Compounds of Formula XVI:

Preparative Example A

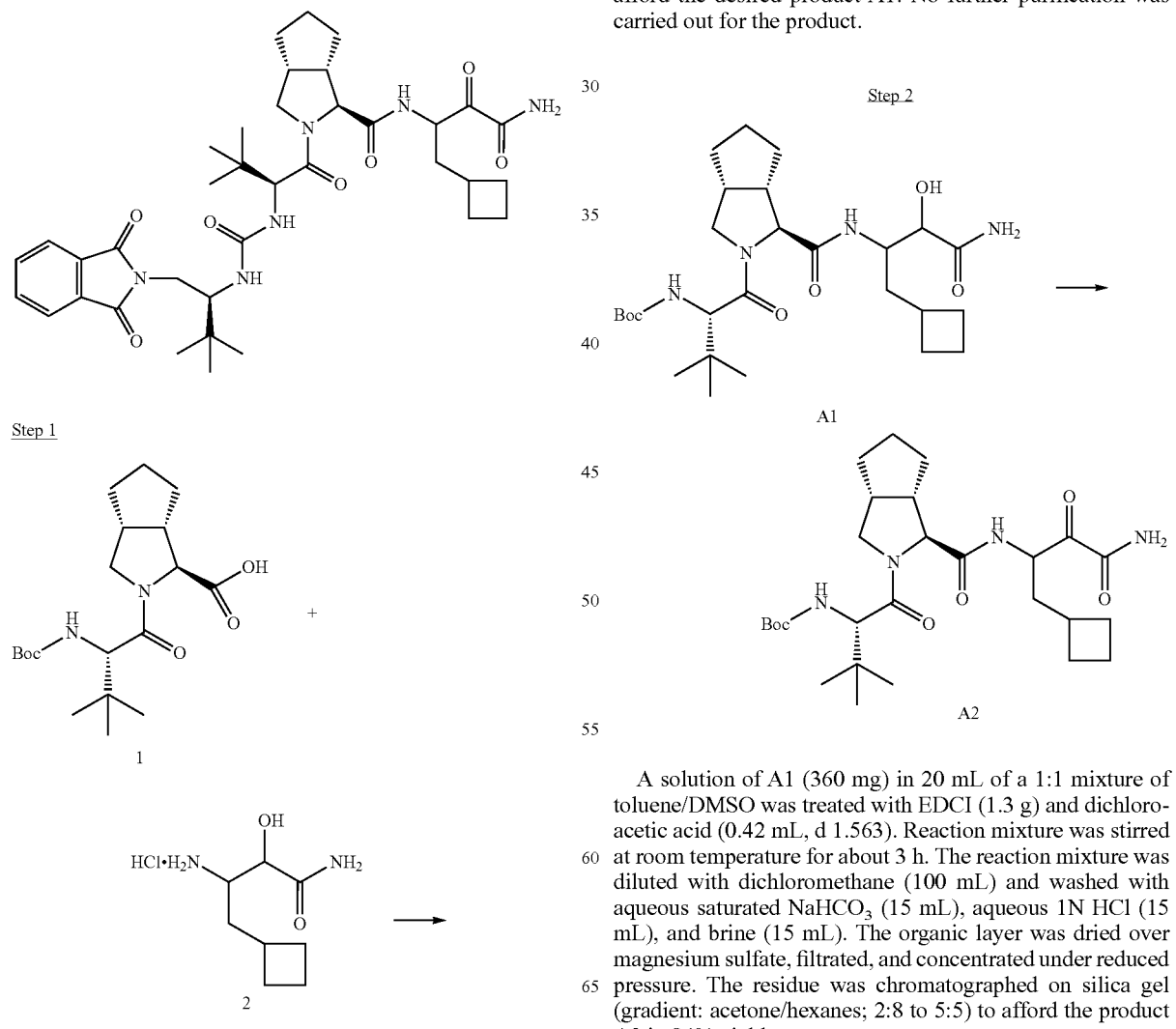

A solution of acid 1 (255 mg) in 5 mL of dry dichloromethane and 5 mL of dry DMF was stirred at 0° C. and treated with HATU (368 mg). The amine hydrochloride 2 (201 mg) was added followed by addition of N-methylmorpholine (0.42 mL). The reaction mixture was gradually warmed to room temperature and stirred overnight. All the volatiles were removed under vacuum and the residue was taken into 100 mL of ethyl acetate. The organic layer was washed with aqueous 1N HCl (15 mL), aqueous saturated NaHCO3 (15 mL), water (15 mL), brine (15 mL), dried over MgSO4, filtered, and concentrated under reduced pressure to afford the desired product A1. No further purification was carried out for the product.

A solution of A1 (360 mg) in 20 mL of a 1:1 mixture of toluene/DMSO was treated with EDCI (1.3 g) and dichloroacetic acid (0.42 mL, d 1.563). Reaction mixture was stirred at room temperature for about 3 h. The reaction mixture was diluted with dichloromethane (100 mL) and washed with aqueous saturated NaHCO₃ (15 mL), aqueous 1N HCl (15 mL), and brine (15 mL). The organic layer was dried over magnesium sulfate, filtrated, and concentrated under reduced pressure. The residue was chromatographed on silica gel (gradient: acetone/hexanes; 2:8 to 5:5) to afford the product A2 in 84% yield.

Step 3

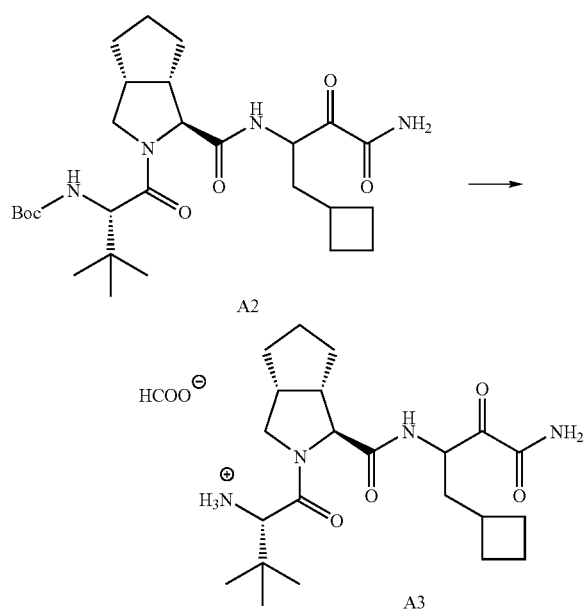

The N-Boc protected amine A2 was treated with 10 mL of formic acid. The resulting solution was stirred for 2 h. All the volatiles were removed under reduced pressure. No further purification was done for the product A3.

Step 4

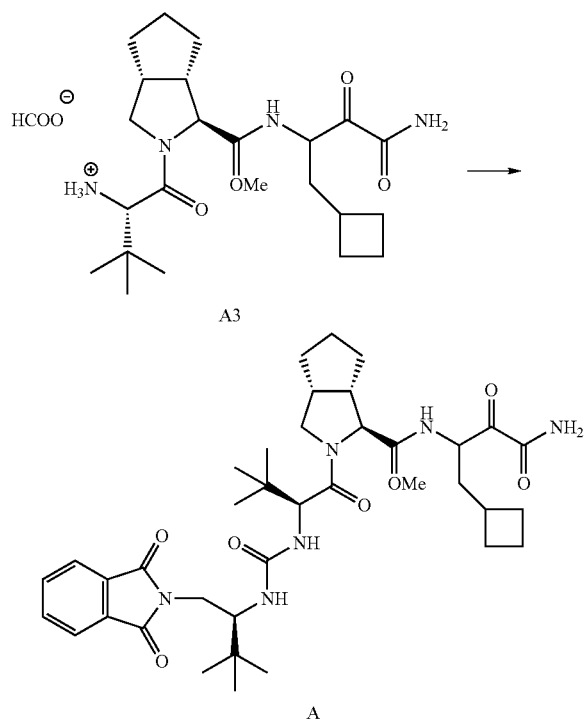

To a solution of the amine salt A3 in 1 mL of dry methylene chloride was added N-methylmorpholine (0.037 mL, d 0.920). The resulting solution was cooled in an ice-water bath and a solution of isocyanate in toluene (2.5 mL of a 0.135M soln) was slowly added. The mixture was stirred for 2 h (temp 0 to 25° C.). The reaction mixture was diluted with 60 mL of dichloromethane and washed with 15 mL of aqueous 1N HCl. Aqueous layer was back extracted with dichloromethane (2×20 mL). Combined organic layers were dried over magnesium sulfate, filtered and concentrated under reduced pressure. The residue was chromatographed on Silica gel (gradient: acetone/hexanes; 1:9 to 6:4) to give the product A (15 mg) as a white solid in 20% yield. HRMS (FAB) calcd for $C_{37}H_{53}N_6O_7$ [M+H] 693.3976; found 693.3987.

One skilled in the art would understand that other suitable compounds of Formula XVI can be prepared in a similar manner to that disclosed above.

The Following Experimental Section Applies for the Preparation of the Compounds of Formula XVII:

Abbreviations which are used in the descriptions of the schemes, preparations and the examples that follow are:

THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCI: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
$^tBu$ or $Bu^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis(trimethylsilylamide)
NaHMDS: Sodium Hexamethyldisilazide or Sodium bis(trimethylsilylamide)

LiHMDS: Lithium Hexamethyldisilazide or Lithium bis(tri-methylsilylamide)

10% Pd/C: 10% Palladium on carbon (by weight).

TG: Thioglycerol

General Schemes for Preparation of Target Compounds

Compounds of the present invention were synthesized using the general schemes (Methods A-E) described below.

Method A

Deprotection of the N-Boc functionality of 1.01 under acidic conditions provided the hydrochloride salt 1.02 which was subsequently coupled with N-Boc-tert-leucine under peptide coupling methodology to afford 1.03. N-Boc deprotection followed by treatment with appropriate isocyanate gave the urea 1.05. Hydrolysis of the methyl ester provided the acid 1.06. Peptide coupling of the acid 1.06 with the appropriate $P_1$-$P'$ primary amide moiety afforded the hydroxylamide 1.07. Oxidation (Moffatt oxidation or related process—see, T. T. Tidwell, *Synthesis,* 1990, 857), or Dess-Martin Periodinane—*J. Org. Chem.,* (1983) 48, 4155) resulted in the target compound 1.08.

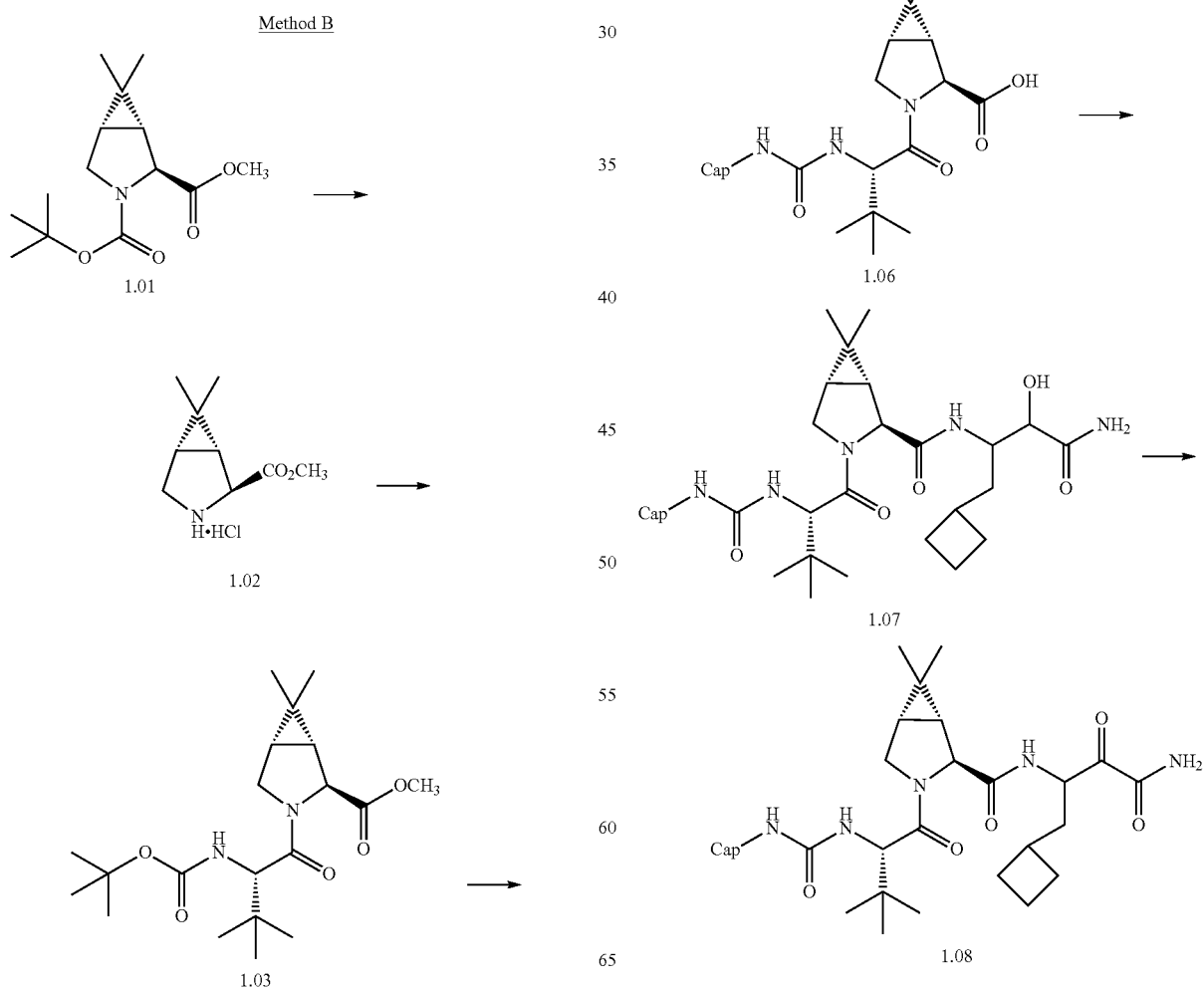

Peptide coupling of the acid 1.06 with the appropriate $P_1$-$P'$ secondary amide moiety afforded the hydroxylamide 1.09. Oxidation (Moffatt or Dess-Martin's) resulted in the target compound 1.10.

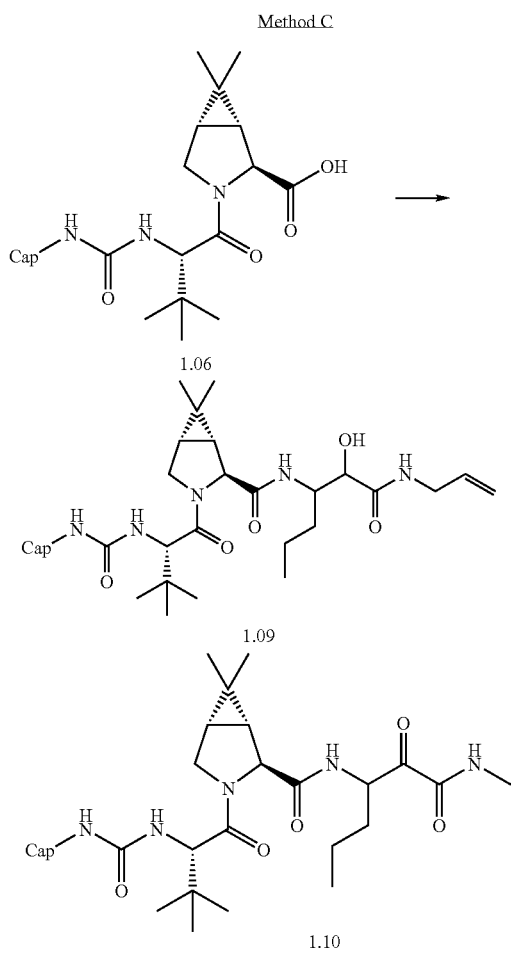

In another variation, peptide coupling of the N-Boc-P2-$P_3$-acid 1.17 with the appropriate $P_1$-$P'$ amide moiety afforded the hydroxylamide 1.11. Oxidation (Moffatt or Dess-Martin Periodinane) resulted in the keto amide 1.12. Deprotection of the N-Boc functionality gave the hydrochloride salt 1.13. Treatment with a suitable isocyanate (or isocyanate equivalent) resulted in the target compound 1.14.

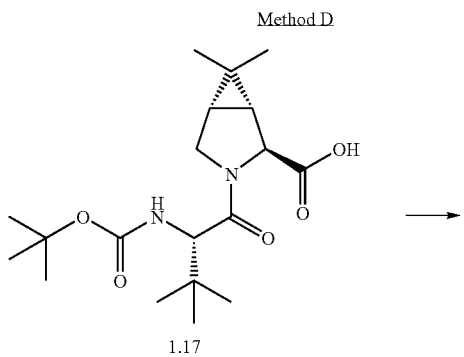

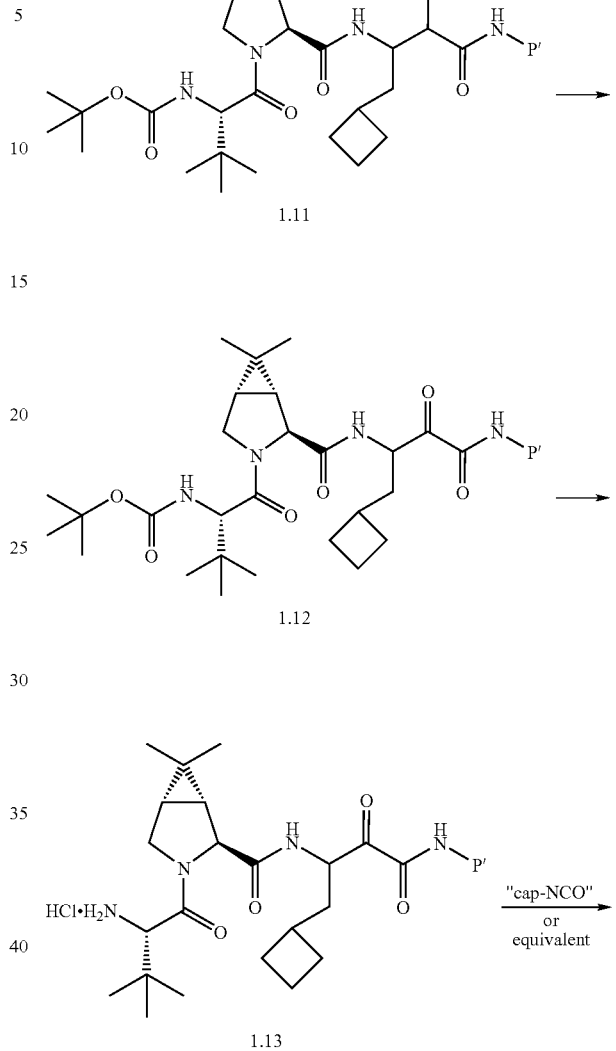

In yet another variation, the hydrochloride salt 1.13 was converted to the 4-nitrophenyl carbamate 1.15 by reaction with 4-nitrophenyl chloroformate. Subsequent treatment with an amine (or amine hydrochloride salt) of choice provided the target compound 1.14.

Method E

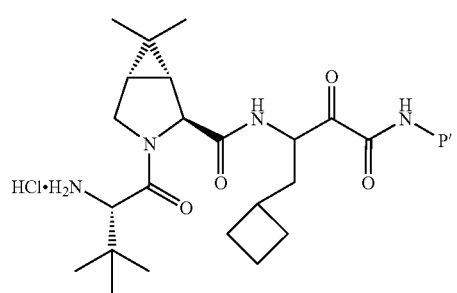

1.13

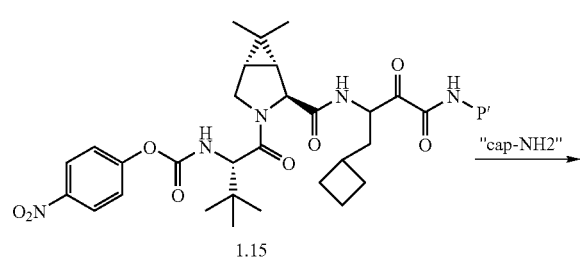

1.15

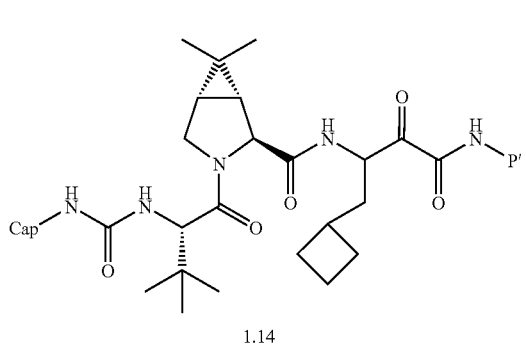

1.14

In yet another variation, the dipeptide hydrochloride salt 1.03 was converted to the 4-nitrophenyl carbamate as described above. Treatment with an amine (or amine hydrochloride salt) of choice provided the urea derivative 1.05. Hydrolysis and further elaboration as described in Methods A/B provided the target compounds 1.14.

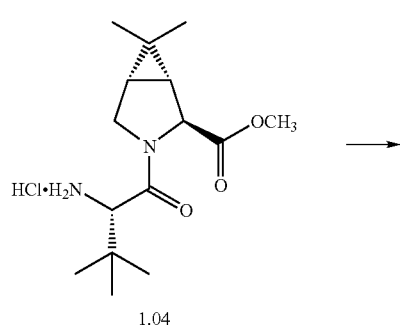

1.04

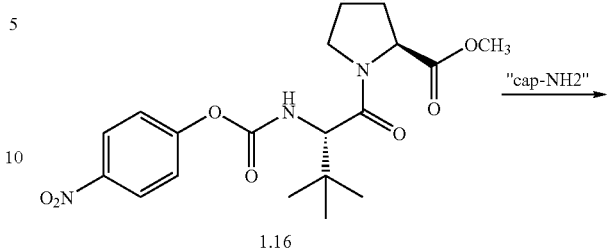

1.16

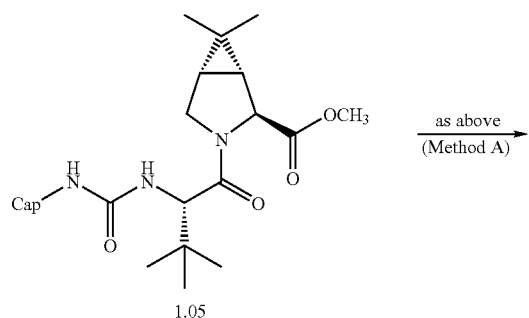

1.05

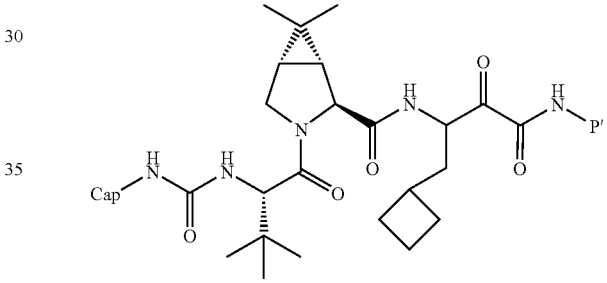

1.14

The Following Experimental Section Applies for the Preparation of the Compounds of Formula XVIII:

Example 3

Preparation of Compound of Formula 3

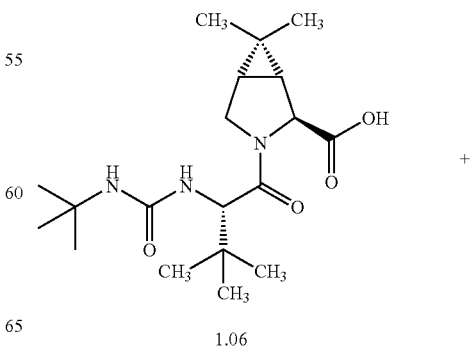

1.06

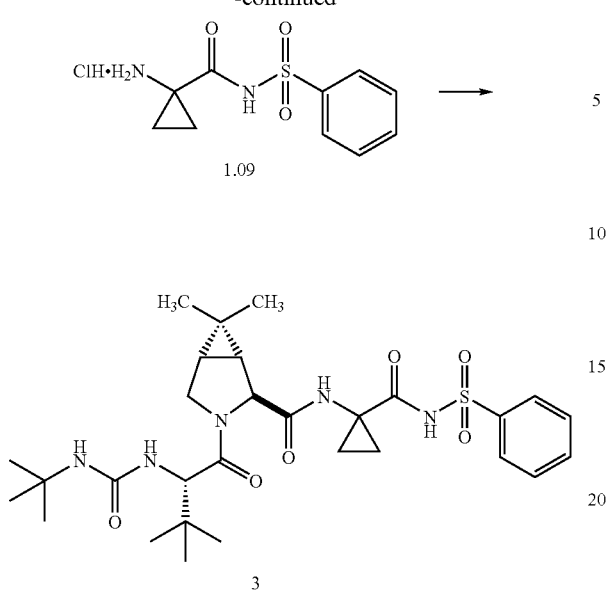

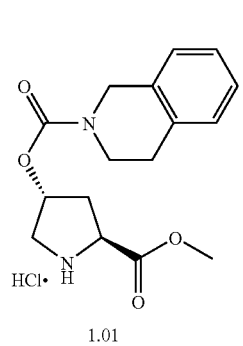

To a cooled solution (0° C.) of the intermediates 1.06 (75.0 mg, 0.2 mmol) and 1.09 (100.0 mg, 0.36 mmol) in DMF (5.0 mL) was added HATU (Aldrich, 76.05 mg, 0.20 mmol), followed by DIPEA (0.102 mL, 6 mmol). The reaction mixture was stirred for two days then warmed up to room temperature, diluted with ethyl acetate (40.0 mL), washed with 5% $KH_2PO_4$ containing 0.05 vol. of 1M $H_3PO_4$ and brine. Organic layer was dried over $MgSO_4$, filtered and concentrated to dryness. Residue was purified over silica gel using acetone-$CH_2Cl_2$ (1:9 to 1:1) to get 8.0 mg of product of formula 3 (6.5% yield); LCMS: (590.1).

One skilled in the art would understand that other suitable compounds of Formula XVIII can be prepared in a similar manner to that disclosed above.

The Following Experimental Section Applies for the Preparation of the Compounds of Formula XIX:

SYNTHESIS OF PREPARATIVE EXAMPLES

Synthesis of Example 101

Step 1

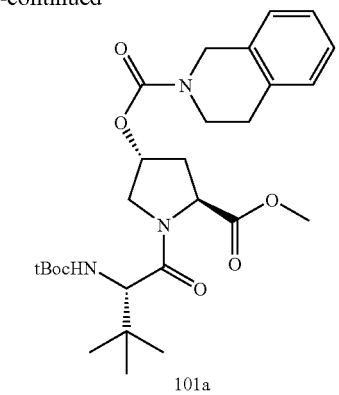

To a stirred solution of the proline derivative 1.01 (3.66 mmol, prepared as described above) in dichloromethane (20 mL) and DMF (15 mL) at 0° C. was added L-boc-tert-leucine (930 mg, 4.03 mmol), DIPEA (2.02 mL, 10.98 mmol) and HATU (1.8 g, 4.76 mmol). After 15 minutes at that temperature, the reaction flask was stored in the freezer (−20° C.), overnight (16 hr). The reaction mixture was diluted with dichloromethane (80 mL) and washed with saturated sodium bicarbonate solution (80 mL), 10% aq. citric acid solution (80 mL), brine (80 mL), dried ($Na_2SO_4$), filtered and concentrated. The crude material was purified by silica chromatography using 25/75 to 50/50 EtOAc/hexanes to provide 1.77 g of the required material, 101a. LC-MS: 518.1 $(M+H)^+$.

Step 2

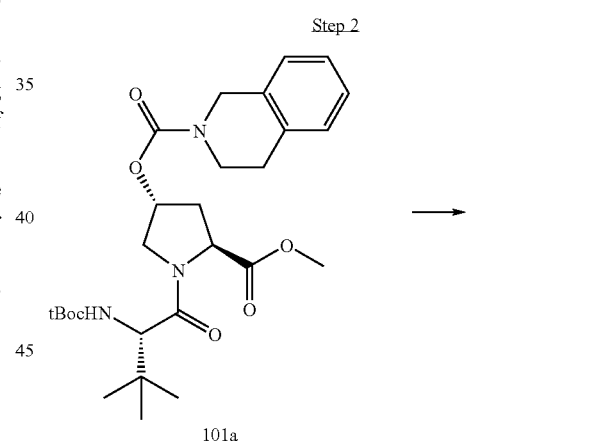

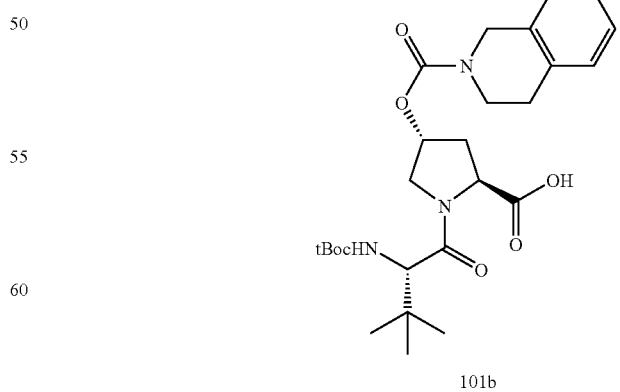

To a solution of the methyl ester 101a (1.21 g, 2.34 mmol) in THF (10 mL) and MeOH (5 mL) was added aq. 1M LiOH solution (5 mL). The reaction mixture was stirred at RT for 4 h. It was then concentrated, diluted with water (50 mL) and acidified with solid citric acid (pH approximately 3) when white solid material crashed out. This solid was filtered off, washed with water and dried in vacuo to afford 970 mg of 101b. LC-MS: 504.1 (M+H)⁺.

Step 3

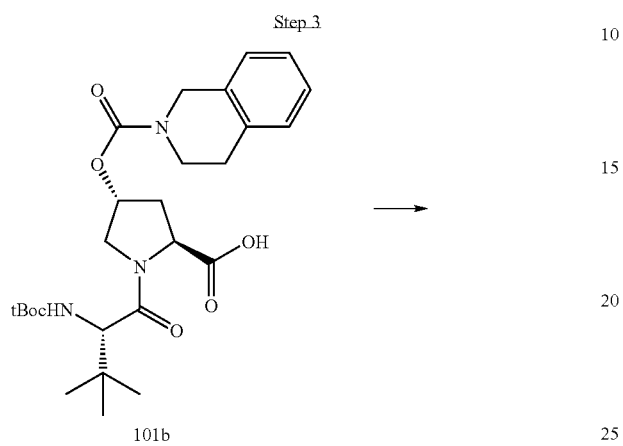

101b

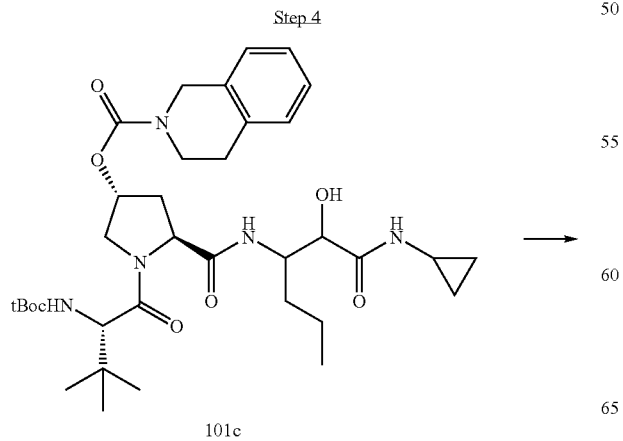

101c

The acid 101b (503 mg, 1 mmol) was coupled with intermediate 13.06 (334 mg, 1.5 mmol) using essentially procedure described above (Step 1, preparation of 101a) to provide 101c which was used without purification. MS: 672.37 (M+H)⁺.

Step 4

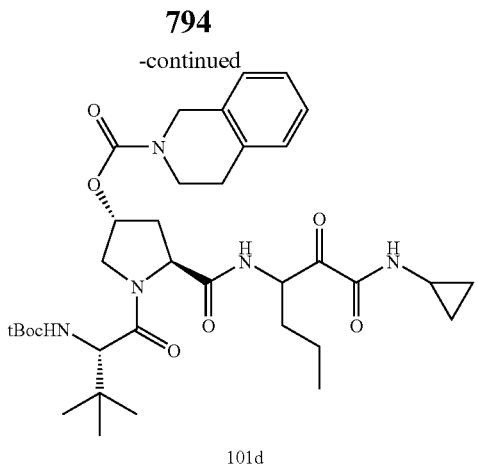

101d

To a solution of the hydroxyl compound 101c from above in dichloromethane (15 mL) was added Dess-Martin's periodinane (848 mg, 2 mmol) and the reaction mixture was stirred at RT for 5 h. At this time, the reaction mixture was diluted with dichloromethane (30 mL) and washed with 1:1 mixture of aq. 10% sodium thiosulfate solution and saturated sodium bicarbonate solution (2×25 mL each), brine (50 mL), dried (Na₂SO₄), filtered and concentrated. The crude material was purified by silica chromatography using 15/85 to 50/50 acetone/hexanes to provide 410 mg of the required material, 101d. LC-MS: 670.2 (M+H)⁺.

Step 5

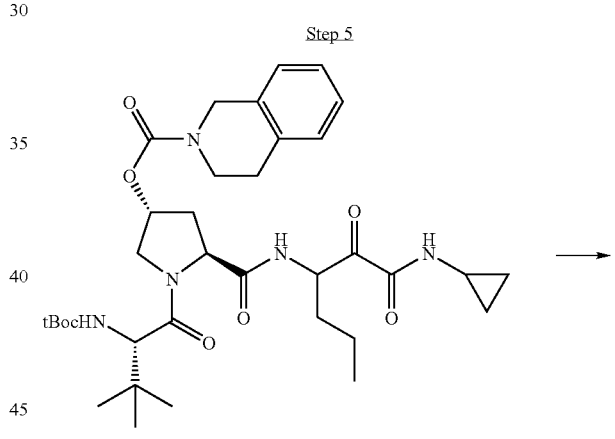

Deprotection of the N-boc functionality of 101d to provide the required material 101e was carried out as described for intermediate 1.01, Step 3 (reaction time=2 h). LC-MS: 570.1 (M+H)⁺.

Step 6

101e →

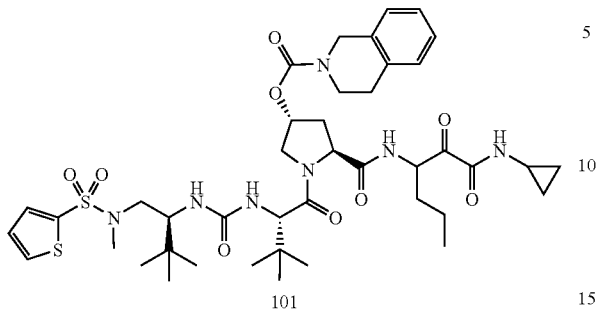

101

To a solution of the amine salt 101e (60 mg, 0.1 mmol) in dichloromethane (2 mL) at 0° C. was added DIPEA (0.06 mL, 0.3 mmol) followed by the isocyanate intermediate 65.01 (0.25 M solution in toluene, 0.8 mL, 0.2 mmol). After 15 minutes at that temperature, the reaction flask was stored in the freezer (−20° C.), overnight (16 hr). The reaction mixture was diluted with dichloromethane (20 mL) and washed with saturated ammonium chloride solution (20 mL), brine (20 mL), dried (Na$_2$SO$_4$), filtered and concentrated. The crude material was purified by silica chromatography using 15/85 to 50/50 acetone/hexanes to provide the required compound 101 (53 mg); LC-MS: 872.2 (M+H)$^+$.

One skilled in the art would understand that other suitable compounds of Formula XIX can be prepared in a similar manner to that disclosed above.

The Following Experimental Section Applies for the Preparation of the Compounds of Formulae Ia, Ib and Ic:

Abbreviations:

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4(3H)-one
EDCI: 1-(3-dimethylaminopropyl)-3-ethylcarbodiimide hydrochloride
NMM: N-Methylmorpholine
MeOH: Methanol
EtOH: Ethanol
Et2O: Diethyl ether
DMSO: Dimethylsulfoxide
K$^t$BuO: Potassium tert-butoxide
DCM: Dichloromethane
Chg: Cyclohexylglycine
Bn: Benzyl
Et: Ethyl
Ph: Phenyl
iPr: isopropyl
$^t$Bu or Bu$^t$: tert-Butyl
Boc: tert-Butyloxycarbonyl
Cbz: Benzyloxycarbonyl
HATU: O-(7-azabenzotriazol-1-yl)-1,1,3,3-tetramethyluronium hexafluorophosphate
BOP: Benzotriazol-1-yl-oxy-tris(dimethylamino)hexafluorophosphate
10% Pd/C: 10% Palladium on carbon (by weight).

EXAMPLE

Synthesis of (1R,5S)-N-[3-Amino-1-(Cyclobutylmethyl)-2,3-Dioxopropyl]-3-[2(S)-[[[(1,1-Dimethylethyl)Amino]Carbonyl]Amino]-3,3-Dimethyl-1-Oxobutyl]-6,6-Dimethyl-3-Azabicyclo[3.1.0]Hexan-2(S)-Carboxamide (Structure Ia)

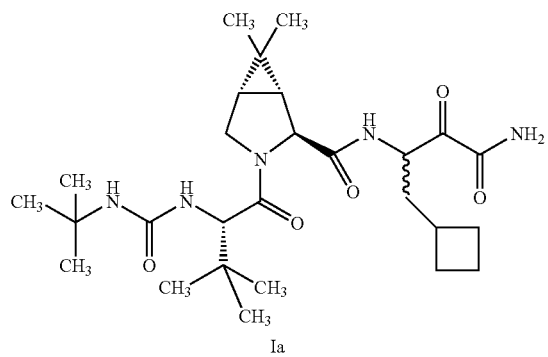

Ia

Step 1.

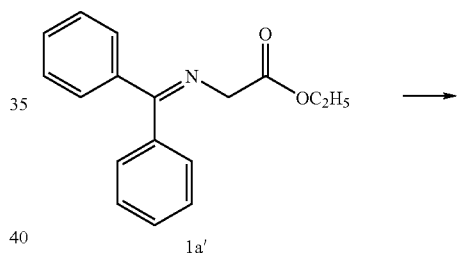

1a'

1b'

A stirred solution of the ketimime 1a' (50 g, 187.1 mmol, available from Aldrich Chemical Company, Milwaukee, Wis.) under N$_2$ in dry THF (400 mL) was cooled to −78° C. and treated with 1 M solution of K-$^t$BuO (220 mL, 1.15 equiv.) in THF. The reaction mixture was warmed to 0° C. and stirred for 1 h and treated with bromomethylcyclobutane (28 mL, 249 mmol). The reaction mixture was stirred at room temperature for 48 h and concentrated in vacuo. The residue was dissolved in Et$_2$O (300 mL) and treated with aq. HCl (2 M, 300 mL) The resulting solution was stirred at room temperature for 5 h and extracted with Et$_2$O (1 L). The aqueous layer was made basic to pH~12-14 with aq. NaOH (50%) and extracted with CH$_2$Cl$_2$ (3×300 mL). The combined organic layers were dried (MgSO$_4$), filtered, and concentrated to give pure amine (1b', 18 g) as a colorless oil.

Step 2.

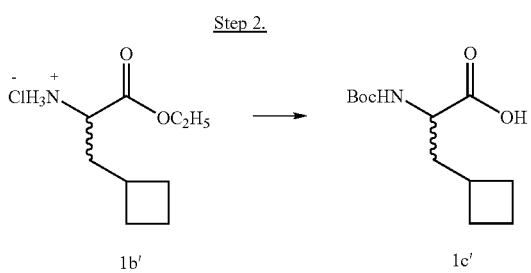

A solution of the amine 1b' (18 g, 105.2 mmol) at 0° C. in CH$_2$Cl$_2$ (350 mL) was treated with di-tert-butyldicarbonate (23 g, 105.4 mmol) and stirred at rt. for 12 h. After the completion of the reaction (TLC), the reaction mixture was concentrated in vacuo and the residue was dissolved in THF/H$_2$O (200 ml, 1:1) and treated with LiOH.H$_2$O (6.5 g, 158.5 mmol) and stirred at room temperature for 3 h. The reaction mixture was concentrated and the basic aqueous layer was extracted with Et$_2$O. The aqueous layer was acidified with conc. HCl to pH~1-2 and extracted with CH$_2$Cl$_2$. The combined organic layers were dried (MgSO$_4$), filtered, and concentrated in vacuo to yield 1c' as a colorless viscous oil which was used for next step without any further purification.

Step 3.

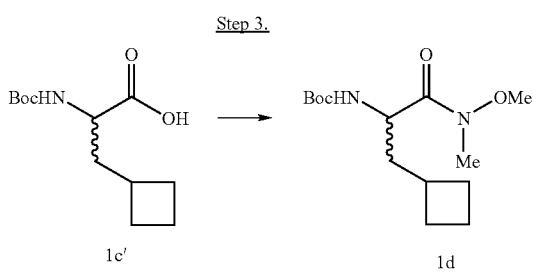

A solution of the acid 1c' (15.0 g, 62 mmol) in CH$_2$Cl$_2$ (250 mL) was treated with BOP reagent (41.1 g, 93 mmol), N-methylmorpholine (27 mL), N,O-dimethyl hydroxylamine hydrochloride (9.07 g, 93 mmol) and stirred overnight at rt. The reaction mixture was diluted with 1 N aq. HCl (250 mL), and the layers were separated and the aqueous layer was extracted with CH$_2$Cl$_2$ (3×300 ml). The combined organic layers were dried (MgSO$_4$), filtered, concentrated in vacuo and purified by chromatography (SiO$_2$, EtOAc/Hex 2:3) to yield the amide 1d (15.0 g) as a colorless solid.

Step 4.

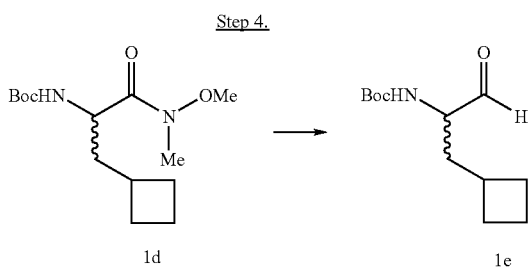

A solution of the amide 1d (15 g, 52.1 mmol) in dry THF (200 mL) was treated dropwise with a solution of LiAlH$_4$ (1M, 93 mL, 93 mmol) at 0° C. The reaction mixture was stirred at room temperature for 1 h and carefully quenched at 0° C. with a solution of KHSO$_4$ (10% aq.) and stirred for 0.5 h. The reaction mixture was diluted with aq. HCl (1 M, 150 mL) and extracted with CH$_2$Cl$_2$ (3×200 mL), The combined organic layers were washed with aq. HCl (1 M), saturated NaHCO$_3$, brine, and dried (MgSO$_4$). The mixture was filtered and concentrated in vacuo to yield 1e as viscous colorless oil (14 g).

Step 5.

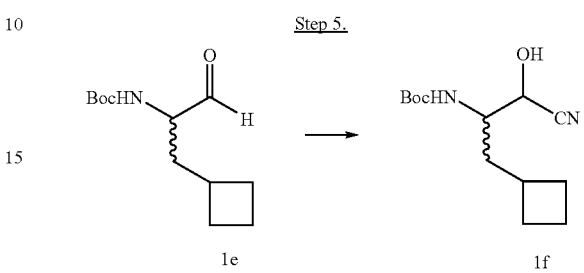

A solution of the aldehyde 1e (14 g, 61.6 mmol) in CH$_2$Cl$_2$ (50 mL), was treated with Et$_3$N (10.73 mL, 74.4 mmol), and acetone cyanohydrin (10.86 g, 127.57 mmol) and stirred at room temperature for 24 hrs. The reaction mixture was concentrated in vacuo and diluted with aq. HCl (1 M, 200 mL) and extracted into CH$_2$Cl$_2$ (3×200 mL). The combined organic layer were washed with H$_2$O, brine, dried (MgSO$_4$), filtered, concentrated in vacuo and purified by chromatography (SiO$_2$, EtOAc/Hex 1:4) to yield 1f (10.3 g) as a colorless liquid as a mixture of diastereomers.

Step 6.

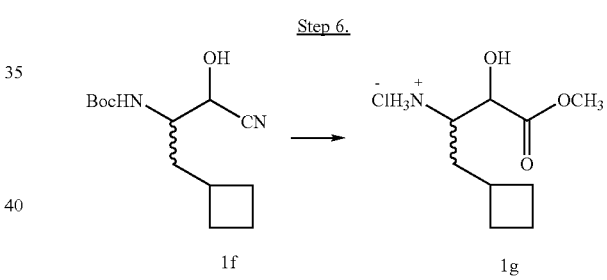

Methanol saturated with HCl*, prepared by bubbling HCl gas to CH$_3$OH (700 ml) at 0° C., was treated with cyanohydrin 1f and heated to reflux for 24 h. The reaction was concentrated in vacuo to yield 1g, which was used in the next step without purification.

*Alternatively 6M HCl prepared by addition of AcCl to dry methanol can also be used.

Step 7.

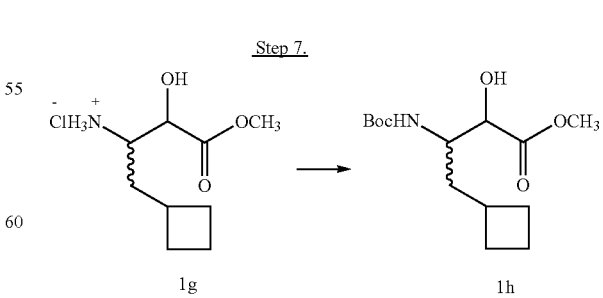

A solution of the amine hydrochloride 1g in CH$_2$Cl$_2$ (200 mL) was treated with Et$_3$N (45.0 mL, 315 mmol) and Boc$_2$O (45.7 g, 209 mmol) at −78° C. The reaction mixture was then stirred at room temperature overnight and diluted with HCl (2 M, 200 mL) and extracted into CH₂Cl₂. The combined organic layers were dried (MgSO₄) filtered, concentrated in vacuo and purified by chromatography (EtOAc/Hex 1:4) to yield hydroxy ester 1h.

Step 8.

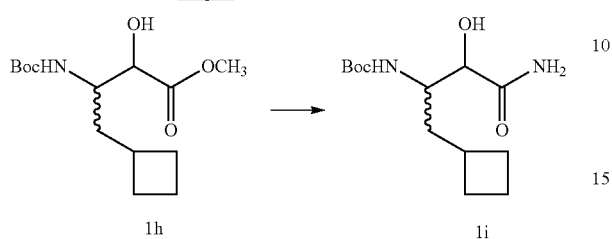

A solution of methyl ester 1h (3 g, 10.5 mmol) in THF/H₂O (1:1) was treated with LiOH.H₂O (645 mg, 15.75 mmol) and stirred at rt. for 2 h. The reaction mixture was acidified with aq HCl (1 M, 15 mL) and concentrated in vacuo. The residue was dried in vacuum.

A solution of the acid in CH₂Cl₂ (50 mL) and DMF (25 mL) was treated with NH₄Cl (2.94 g, 5.5 mmol), EDCI (3.15 g, 16.5 mmol), HOOBt (2.69 g, 16.5 mmol), and NMM (4.4 g, 44 mmol). The reaction mixture was stirred at room temperature for 3 d. The solvents were removed under vacuo and the residue was diluted with aq. HCl (250 mL) and extracted with CH₂Cl₂. The combined organic layers were washed with aq. saturated NaHCO₃, dried (MgSO₄) filtered concentrated in vacuo to obtain 1i, which was used as it is in the following steps. (Alternatively 1i can also be obtained directly by the reaction of 1f (4.5 g, 17.7 mmol) with aq. H₂O₂ (10 mL), LiOH.H₂O (820 mg, 20.8 mmol) at 0° C. in 50 mL of CH₃OH for 0.5 h.)

Step 9.

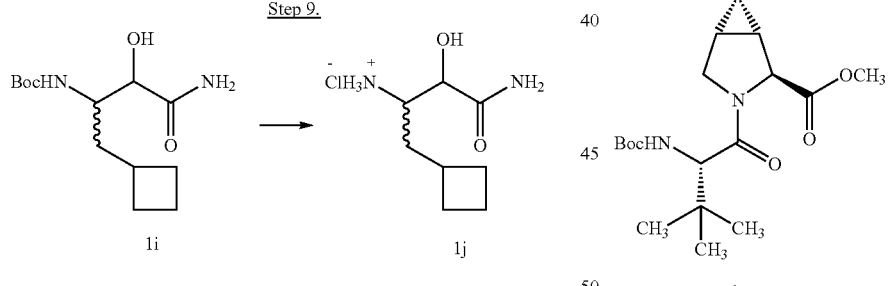

A solution of 1i obtained in the previous step was dissolved in 4 N HCl in dioxane and stirred at rt. for 2 h. The reaction mixture was concentrated in vacuo to give 1j as a solid, which was used without further purification.

Step 10.

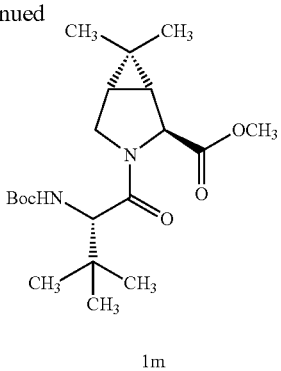

The amino ester 1l was prepared following the method of R. Zhang and J. S. Madalengoitia (*J. Org. Chem.* 1999, 64, 330), with the exception that the Boc group was cleaved by the reaction of the Boc-protected amino acid with methanolic HCl.

A solution of Boc-tert-Lue 1k (Fluka, 5.0 g 21.6 mmol) in dry CH₂Cl₂/DMF (50 mL, 1:1) was cooled to 0° C. and treated with the amine 11 (5.3 g, 25.7 mmol), NMM (6.5 g, 64.8 mmol) and BOP reagent (11.6 g, 25.7 mmol). The reaction was stirred at rt. for 24 hrs, diluted with aq. HCl (1 M) and extracted with CH₂Cl₂. The combined organic layers were washed with HCl (aq, 1 M), saturated NaHCO₃, brine, dried (MgSO₄), filtered and concentrated in vacuo and purified by chromatography (SiO₂, acetone/hexane 1:5) to yield 1m as a colorless solid.

Step 11.

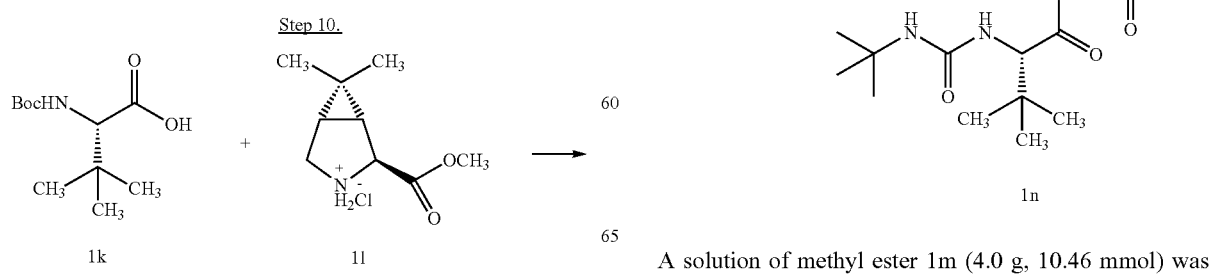

A solution of methyl ester 1m (4.0 g, 10.46 mmol) was dissolved in HCl (4 M solution in dioxane) and stirred at rt. for 3 h. The reaction mixture was concentrated in vacuo to obtain the amine hydrochloride salt used in the next step without further purification.

A solution of the amine hydrochloride salt (397 mg, 1.24 mmol) in CH$_2$Cl$_2$ (10 mL) was cooled to −78° C. and treated with tert-butyl isocyanate (250 mg, 2.5 mmol) and stirred at rt. overnight. The reaction mixture was concentrated in vacuo and the residue was diluted with aq. HCl (1M) and extracted with CH$_2$Cl$_2$. The combined organic layers were washed with aq. HCl (1M), saturated NaHCO$_3$ and brine. The organic layers were dried, filtered and concentrated in vacuo and the residue was purified by chromatography (SiO$_2$, acetone/Hex 1:4) to yield 1n as a colorless solid.

Step 12.

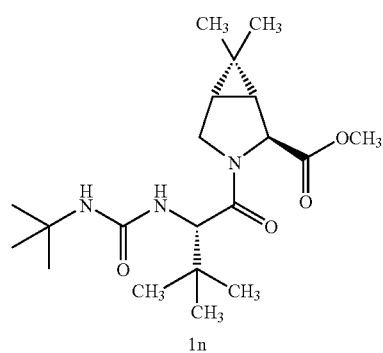

1n

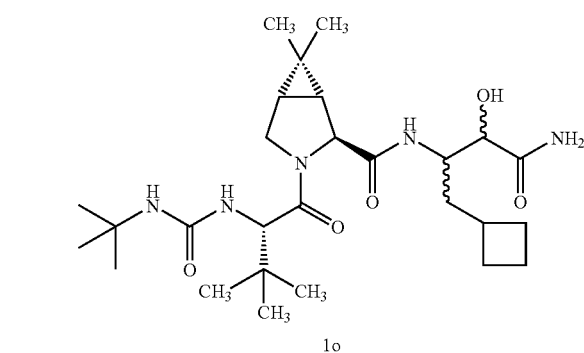

1o

A solution of methyl ester 1n (381 mg, 1.0 mmol) in THF/H$_2$O (1:1, 5 mL) was treated with LiOH.H$_2$O (62 mg, 1.5 mmol) and stirred at rt. for 3 h. The reaction mixture was acidified with aq. HCl and concentrated in vacuo to obtain the free acid.

A solution of acid (254.9 mg, 0.69 mmol) in DMF/CH$_2$Cl$_2$ (1:1, 5.0 mL) was treated with amine 1j (159 mg, 0.763 mmol), EDCI (199 mg, 1.04 mmol), HOOBt (169.5 mg, 1.04 mmol) and NMM (280 mg, 2.77 mmol) at −20° C. The reaction mixture was stirred at −20° C. for 48 h and concentrated in vacuo. The residue was diluted with aq. 1M HCl and extracted with EtOAc, The combined organic layers were extracted with aq. NaHCO$_3$, aq. HCl, brine, dried (MgSO$_4$) filtered, concentrated in vacuo to obtain 1o (470 mg) as a tan colored solid that was used in the next reaction without further purification.

Step 13.

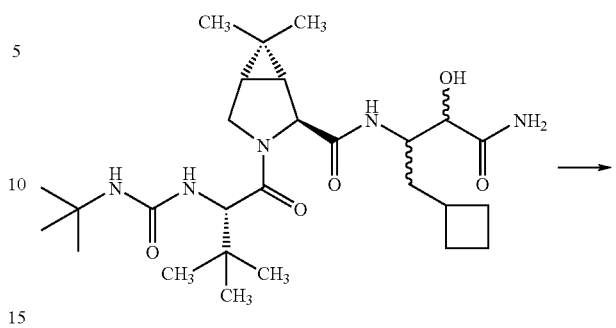

1o

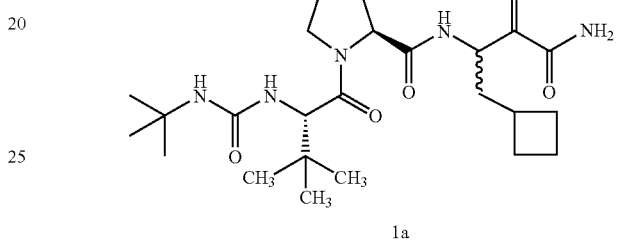

1a

A solution of amide 1o (470 mg, 0.9 mmol) in toluene and DMSO (1:1 20 mL) at 0° C. was treated with EDCI (1.72 g, 9.0 mmol) and dichloroacetic acid (0.37 mL, 4.5 mmol) and stirred at 0° C. for 4 hrs. The reaction mixture was diluted with CH$_2$Cl$_2$, and washed with saturated NaHCO$_3$, and brine. The organic layer was dried (MgSO$_4$), filtered, concentrated, in vacuo and purified by chromatography (SiO$_2$, acetone/hexanes 3:7) to yield 1a as a colorless solid.

Separation of the Compound of Formula 1 into Diastereomers of Formulas Ib and Ic:

Ib

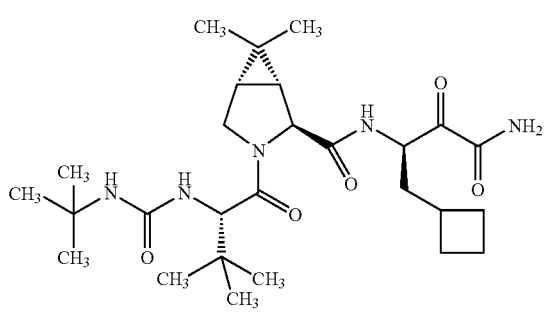

Ic

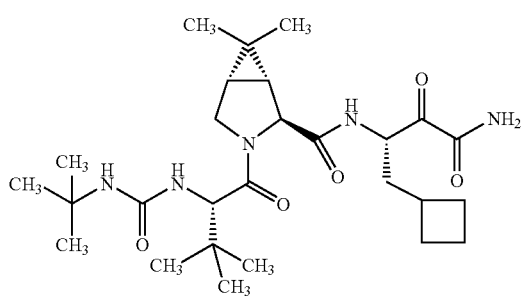

Preparative HPLC Condition for Separation

COLUMN USED: NORMAL PHASE YMC DIOL-NP COLUMN 120 Å, S-10/20; 50 mm×500 mm I.D/length
SOLVENT A: Hexanes
SOLVENT B: To make 4 L of solvent (1.7 L Isopropanol+300 mL of $CH_3CN$+2 L of $CH_2Cl_2$)
HPLC CONDITIONS: 12% of Solvent B/88% of Solvent A
FLOW: 120 mL/min
Procedure: 1 g of compound 1a was dissolved in 10 mL of $CH_2Cl_2$/25 mL of Hexanes and injected into the column. It was eluted with 120 mL/min and two peaks were independently collected and concentrated. The solid residue was further dried in high vacuum and analyzed by analytical HPLC. Since the polar (second isomer) contained 2.6% of nonpolar diastereomer (First isomer), it was purified once more to isolate the pure diastereomers.

Analytical Conditions for Analysis of Diastereomeric Purity

COLUMN USED: NORMAL PHASE YMC DIOL-NP COLUMN 200 Å, S-5 □M; 150 mm×3 mm length/I.D
SOLVENT A: Hexanes
SOLVENT B: To make 4 L of solvent (1.7 L Isopropanol+300 mL of $CH_3CN$+2 L of $CH_2Cl_2$)
HPLC CONDITIONS: 8.5% of Solvent B/91.5% of Solvent A
FLOW: 0.7 mL/min
Rt Nonpolar isomer (compound Ib)=13.2 min
  Polar isomer (compound Ic)=16.1 min
2.5 mg of compound in 1 mL was used and 20 μL was injected and analyzed with a U.V detector at λ=254 nm.
Analytical Data for Compounds 2 and 3.
Compound 3 [Polar Diastereomer]

$^1$H NMR ($d_6$-dmso, 500 MHz): δ 8.26 (d, 1 H, J=7.0 Hz), 8.00 (s, 1 H), 7.75 (s, 1 H), 5.96 (s, 1 H), 5.84 (d, 1 H, J=10 Hz), 4.96 (m, 1 H), 4.28 (s, 1H), 4.11 (d, 1 H, J=11 Hz), 3.94 (d, 1H, J=10 Hz), 3.73 (dd, 1 H, J=10 & 5 Hz), 2.48 (m, 1 H), 1.95 (m, 2 H), 1.61 (m, 1 H), 1.59 (m, 1 H), 1.77 (m, 1 H), 1.57 (m, 1 H), 1.74 (m, 2 H), 1.42 (dd, 1 H, J=7.5 & 5 Hz), 1.28 (d, 1 H, J=7.5 Hz), 1.17 (s, 9 H), 1.01 (s, 3 H), 0.90 (s, 9 H), 0.85 (s, 3 H). $^{13}$C NMR ($d_6$-dmso, 125 MHz): δ 197.8, 170.9, 170.8, 162.8, 157.4, 59.1, 56.8, 51.8, 48.9, 47.4, 36.7, 34.0, 32.0, 30.6, 29.1, 27.8, 27.3, 27.1, 26.4, 26.1, 18.5, 17.7, 12.5. MS [FAB] 520 (55), 421 (100), 308 (75), 213 (90). HRMS calcd for $C_{27}H_{46}O_5N_5$ $[M+1]^+$ 520.3499; observed: 520.3505.

Compound 2 [Non-polar Diastereomer]

$^1$H NMR ($d_6$-dmso, 500 MHz): □ 8.15 (d, 1 H, J=7.0 Hz), 7.96 (s, 1 H), 7.74 (s, 1 H), 5.96 (s, 1 H), 5.86 (d, 1 H, J=10 Hz), 4.85 (m, 1 H), 4.27 (s, 1H), 4.13 (d, 1 H, J=11.0 Hz), 3.97 (d, 1H, J=10 Hz), 3.76 (dd, 1 H, J=10 & 5 Hz), 2.36 (m, 1 H), 1.97 (m, 2 H), 1.60 (m, 2 H), 1.78 (m, 1 H), 1.64 (m, 1 H), 1.75 (m, 2 H), 1.44 (dd, 1 H, J=7.5 & 5 Hz), 1.27 (d, 1 H, J=7.5 Hz), 1.17 (s, 9 H), 1.00 (s, 3 H), 0.89 (s, 9 H), 0.82 (s, 3 H).

$^{13}$C NMR ($d_6$-dmso 125 MHz): δ197.1, 171.1, 170.7, 163.0, 157.3, 59.4, 56.9, 52.1, 48.9, 47.4, 36.6, 34.0, 32.1, 30.5, 29.1, 27.9, 27.4, 26.8, 26.4, 26.1, 18.5, 17.8, 12.4.

MS [FAB] 520 (40), 421 (100), 308 (60), 213 (65). HRMS calcd. for $C_{27}H_{46}O_5N_5$ $[M+1]^+$ 520.3499; observed: 520.3514.

Example 1

Subjects infected with HCV were put on various treatment regimens including 200 mg bid, 400 mg bid and 400 mg tid to determine dose and timing of dose on virus levels in serum. Blood samples were collected every [ ] hours and analyzed using reverse transcription PCR methods to determine viral load. Data on viral load is presented in FIG. 1. As shown in FIG. 1, overall viral load declined in all three regimens, with cyclical fluctuations in viral load corresponding to the subjects' sleep/wake cycle seen throughout the decline.

Example 2

Healthy subjects were dosed with two regimens of 400 mg. of a compound of Formula 1a, twice per day (bid) or three times per day (tid) for a period of two weeks. Blood samples were taken on day 14 in the morning at time zero (pre-dose) and at 12 hours post-dose (for the bid regimen) or 8 hours post-dose (for the tid regimen). Results are presented in FIG. 2. As shown in the box plots, with tid dosing a metabolism effect is observed. Serum levels of the drug are higher at time zero, 8 hours after the previous evening dose, as compared to serum levels of the drug when measured 8 hours following the morning dose.

What is claimed is:

1. A method of increasing the bioavailability of a compound in a subject in need thereof, comprising administering to the subject an effective amount of at least one of the following compounds

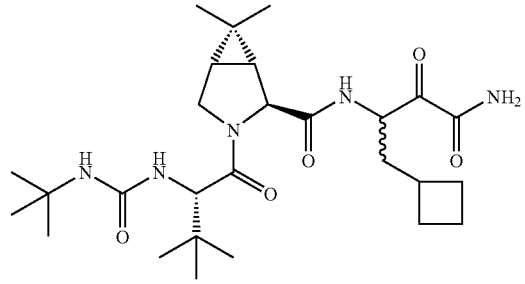

Formula Ia

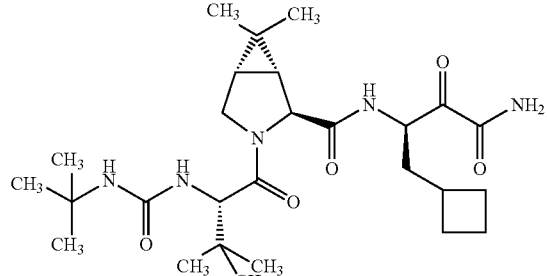

Formula Ib

-continued

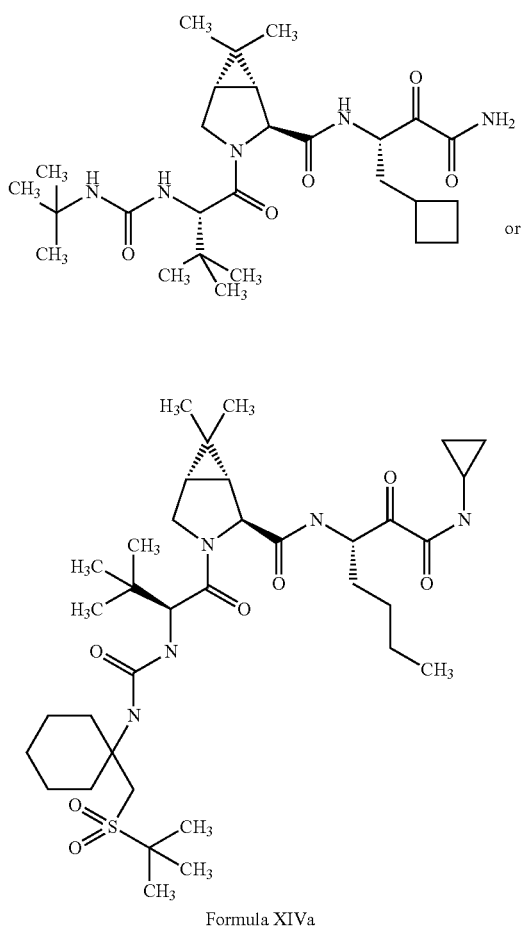

Formula Ic

Formula XIVa or a pharmaceutically acceptable salt thereof, in combination with food comprising high or low fat food, wherein said compound is administered concurrently with, up to ninety minutes after or up to 30 minutes before administration of said food and, wherein the bioavailability achieved is higher compared to that when the compound is administered without food.

2. The method of claim 1, wherein the total amount of the at least one compound administered over twenty-four hours is between 50 mg and 3,000 mg.

3. The method of claim 2, wherein the one or more discrete dosages are in oral dosage form.

4. The method of claim 1 wherein the at least one compound is administered in oral dosage form and is administered concurrently with consumption of food.

5. The method of claim 1 wherein the at least one compound is administered in oral dosage form and is administered up to thirty minutes before or up to thirty minutes after consumption of food.

6. The method of claim 1 wherein over 30% of the calories in the food are from fat.

7. The method of claim 1 wherein the at least one compound is administered in combination with at least one antiviral agent which is different from the at least one compound and/or an immunomodulatory agent.

8. A method of increasing bioavailability of the compound in a subject in need thereof of Formula Ia

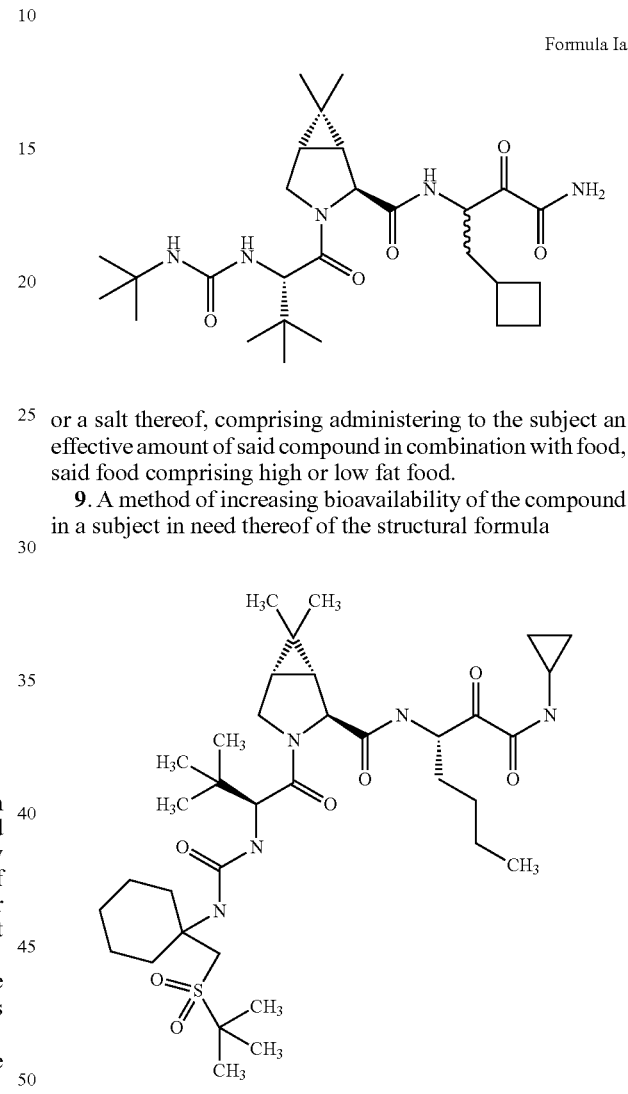

Formula Ia or a salt thereof, comprising administering to the subject an effective amount of said compound in combination with food, said food comprising high or low fat food.

9. A method of increasing bioavailability of the compound in a subject in need thereof of the structural formula or a salt thereof, comprising administering to the subject an effective amount of said compound in combination with food, said food comprising high or low fat food.

* * * * *